US012576156B2

(12) United States Patent
Woo et al.

(10) Patent No.: US 12,576,156 B2
(45) Date of Patent: Mar. 17, 2026

(54) COMPOUND COMPRISING SELF-IMMOLATIVE GROUP AND LIGAND-DRUG CONJUGATE COMPRISING SAME

(71) Applicant: TRIOAR, INC., Daejeon (KR)

(72) Inventors: Sung Ho Woo, Daejeon (KR); Su Ho Park, Daejeon (KR); Jong Un Cho, Daejeon (KR); Sang Hyeon Yun, Daejeon (KR); Gyoung Wook Min, Daejeon (KR); Ok Ku Park, Daejeon (KR); Hyun Mi Lee, Daejeon (KR)

(73) Assignee: TRIOAR, INC., Daejeon (KR)

( * ) Notice: Subject to any disclaimer, the term of this patent is extended or adjusted under 35 U.S.C. 154(b) by 0 days.

(21) Appl. No.: 18/957,012

(22) Filed: Nov. 22, 2024

(65) Prior Publication Data

US 2025/0121072 A1 Apr. 17, 2025

Related U.S. Application Data

(63) Continuation of application No. PCT/KR2023/008742, filed on Jun. 23, 2023.

(30) Foreign Application Priority Data

Jun. 27, 2022 (KR) ........................ 10-2022-0078448

(51) Int. Cl.

*A61K 47/54* (2017.01)
*A61K 47/68* (2017.01)
*C07D 409/14* (2006.01)
*C07H 15/26* (2006.01)
*C07H 17/02* (2006.01)

(52) U.S. Cl.

CPC ........ *A61K 47/549* (2017.08); *A61K 47/6889* (2017.08); *C07D 409/14* (2013.01); *C07H 15/26* (2013.01); *C07H 17/02* (2013.01)

(58) Field of Classification Search

CPC .......................... A61K 47/549; A61K 47/6889
See application file for complete search history.

(56) References Cited

U.S. PATENT DOCUMENTS

| | | | | |
|---|---|---|---|---|
| 5,635,483 A | 6/1997 | Pettit et al. | | |
| 6,531,609 B2 * | 3/2003 | Scalone | ............... | C07D 417/14 548/183 |
| 2009/0105461 A1 | 4/2009 | Kunz et al. | | |
| 2014/0031535 A1 | 1/2014 | Jeffrey | | |

FOREIGN PATENT DOCUMENTS

| | | | | |
|---|---|---|---|---|
| EP | 1 391 213 A1 | 2/2004 | | |
| KR | 10-2018-0077087 A | 7/2018 | | |
| WO | 2017/197056 A1 | 11/2017 | | |
| WO | 2018/124758 A2 | 7/2018 | | |
| WO | WO-2019236954 A1 * | 12/2019 | ......... | A61K 31/4745 |
| WO | 2021/016537 A1 | 1/2021 | | |

OTHER PUBLICATIONS

Yang, Xiaoxiao et al., Med. Res. Rev., "Making smart drugs smarter: the importance of linker chemistry in targeted drug delivery", 2020, vol. 40, No. 6, pp. 2382-2713 (Year: 2020).*
Beck et al., "The Next Generation of Antibody-drug Conjugates Comes of Age," *Discovery Medicine* 10(53):329-339, Oct. 16, 2010. (10 pages).
Chari, "Targeted Cancer Therapy: Conferring Specificity to Cytotoxic Drugs," *Accounts of Chemical Research* 41(1):98-107, Jan. 2008. (10 pages).
Hartley et al., "SG2285, a Novel C2-Aryl-Substituted Pyrrolobenzodiazepine Dimer Prodrug That Cross-links DNA and Exerts Highly Potent Antitumor Activity," *Cancer Res* 70(17): 6849-6858, Sep. 1, 2010. (10 pages).
Hinman et al., "Preparation and Characterization of Monoclonal Antibody Conjugates of the Calicheamicins: A Novel and Potent Family of Antitumor Antibiotics," *Cancer Research* 53:3336-3342, Jul. 15, 1993. (7 pages).
International Search Report and Written Opinion, dated Oct. 4, 2023, for International Application No. PCT/KR2023/008742. [w/ English Translation] (15 pages).
Kerr et al., "Listeriolysin O Potentiates Immunotoxin and Bleomycin Cytotoxicity," *Bioconjugate Chem.* 8(6):Nov./Dec. 1997. (4 pages).
Sanderson et al., "In vivo Drug-Linker Stability of an Anti-CD30 Dipeptide-Linked Auristatin Immunoconjugate," *Clinical Cancer Research* 11:843-852, Jan. 15, 2005. (10 pages).
Sato et al., "Design, Synthesis, and Utility of Defined Molecular Scaffolds," *Organics* 2:161-273, Jul. 11, 2021. (113 pages).
Anami et al., "Glutamic acid-valine-citrulline linkers ensure stability and efficacy of antibody-drug conjugates in mice," Nature Communications 9:2512, Jun. 2018. (10 pages).
Bargh et al., "Cleavable linkers in antibody-drug conjugates," Chem. Soc. Rev. 48:4361, 2019. [First published Jul. 11, 2019] (15 pages).
Bargh et al., "Sulfatase-cleavable linkers for antibody-drug conjugates," Chem. Sci. 11:2375-2380, 2020. [First published on Jan. 27, 2020] (6 pages).
Dwivedi et al., "Recent progress of enzyme cleavable linker in antibody-drug conjugates: sulfatase and phosphatase," J Radiopharm Mol Probes 7(1):33-40, Jun. 2021. (8 pages).
Gavriel et al., "Recent advances in self-immolative linkers and their applications in polymeric reporting systems," Polym. Chem. 13:3188-3269, 2022. [First published May 18, 2022] (82 pages).
Geurink et al., "A Cleavable Linker Based on the Levulinoyl Ester for Activity-Based Protein Profiling," Angew. Chem. Int. Ed. 49:6802-6805, 2010. [Published online: Aug. 16, 2010] (4 pages).
Johan et al., "Development of Photoremovable Linkers as a Novel Strategy to Improve the Pharmacokinetics of Drug Conjugates and Their Potential Application in Antibody-Drug Conjugates for Cancer Therapy," Pharmaceuticals 15:655, May 25, 2022. (26 pages).

(Continued)

*Primary Examiner* — Bahar Craigo
(74) *Attorney, Agent, or Firm* — Seed Intellectual Property Law Group LLP

(57) ABSTRACT

The present invention provides a compound comprising a self-immolative group and a ligand-drug conjugate comprising the same. According to the present invention, an active substance can be stably delivered to a target site, and the active substance can be rapidly released at the target site, thereby increasing the efficacy of the active substance, and the active substance can be inhibited from causing side effects at a location other than the target location.

20 Claims, 5 Drawing Sheets

(56) References Cited

OTHER PUBLICATIONS

Kikuchi et al., "Hydrogen peroxide-triggered conversion of boronic acid-appended insulin into insulin and its application as a glucose-responsive insulin formulation," Molecular Pharmaceutics 18(11):4224-4230, Oct. 8, 2021. (37 pages).
Li et al., "Novel antibody-drug conjugate with UV-controlled cleavage mechanism for cytotoxin release," Bioorganic Chemistry 111:104475, Jun. 2021. (23 pages).
Sharma et al., "Hypoxia-targeted drug delivery," Chem. Soc. Rev. 48:771-813, Feb. 4, 2019. [First Published Dec. 21, 2018] (43 pages).
Wang et al., "A molecular design strategy toward enzyme-activated probes with near-infrared I and II fluorescence for targeted cancer imaging," Chem. Sci. 10:7222, 2019. [First published: Jun. 14, 2019] (6 pages).
Wang et al., "Development and Properties of Valine-Alanine based Antibody-Drug Conjugates with Monomethyl Auristatin E as the Potent Payload," Int. J. Mol. Sci. 18(9):1860, Aug. 25, 2017. (19 pages).

* cited by examiner

【Figure 1】
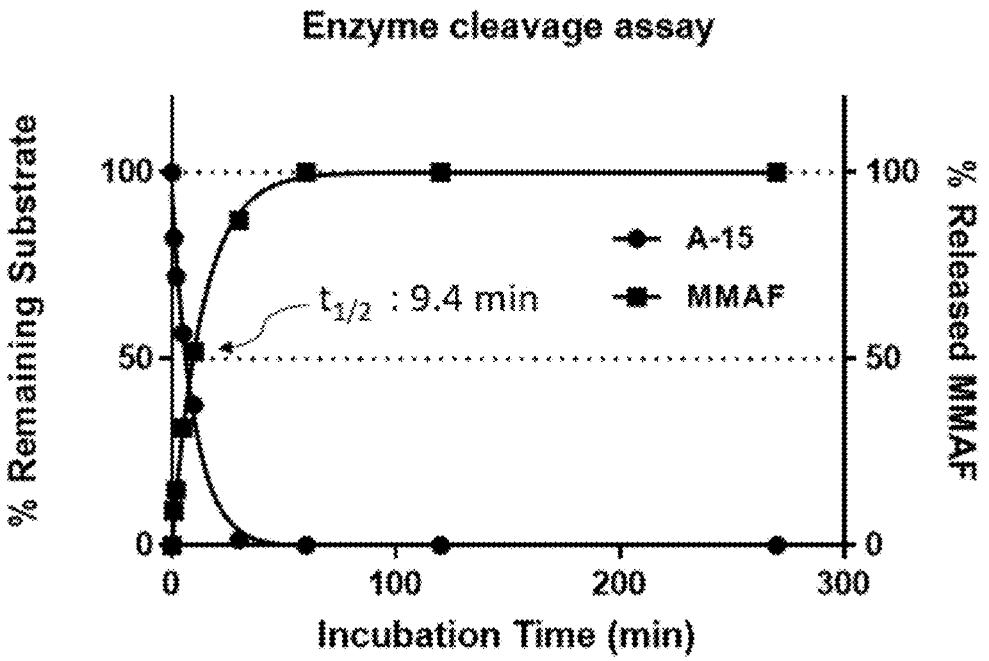
【Figure 2】
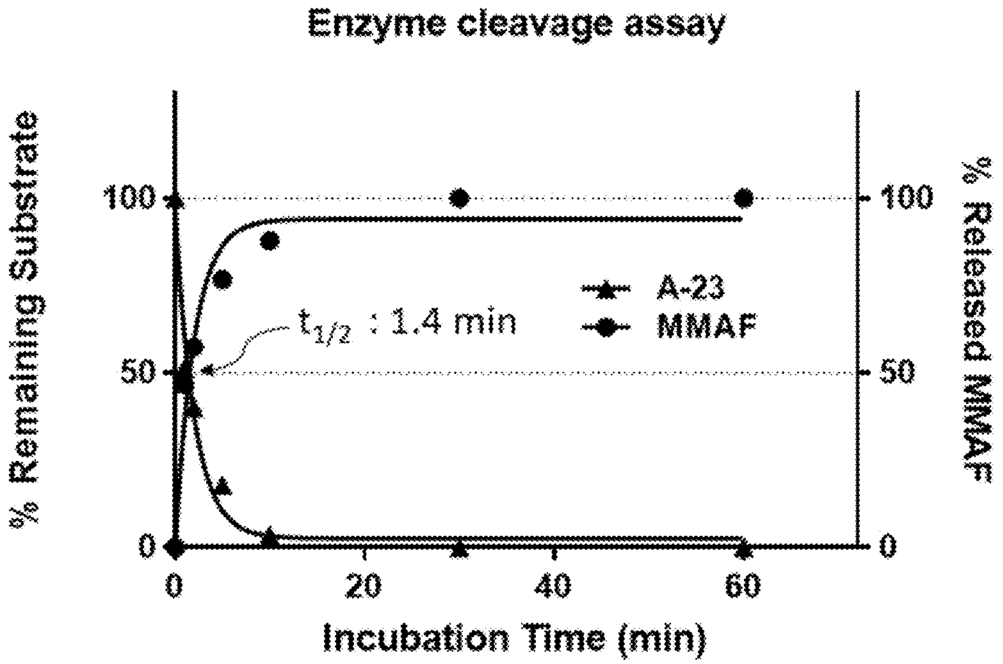

【Figure 3】
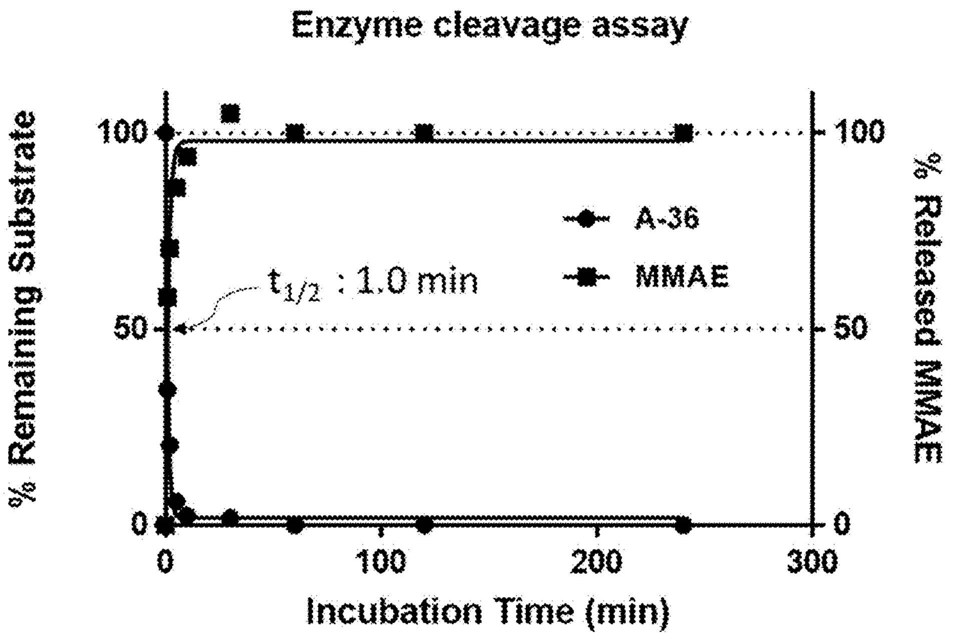
【Figure 4】
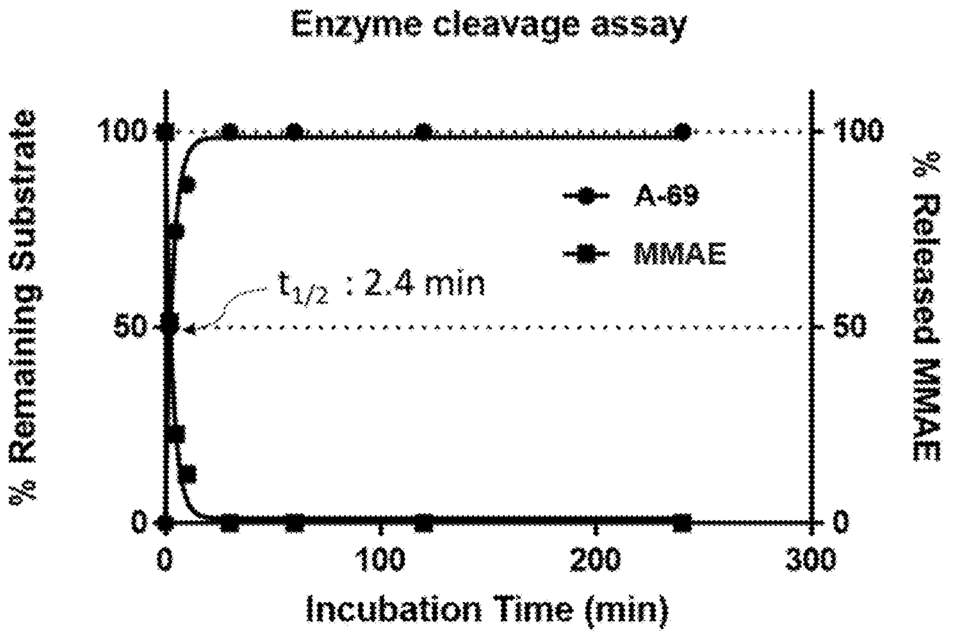

【Figure 5】
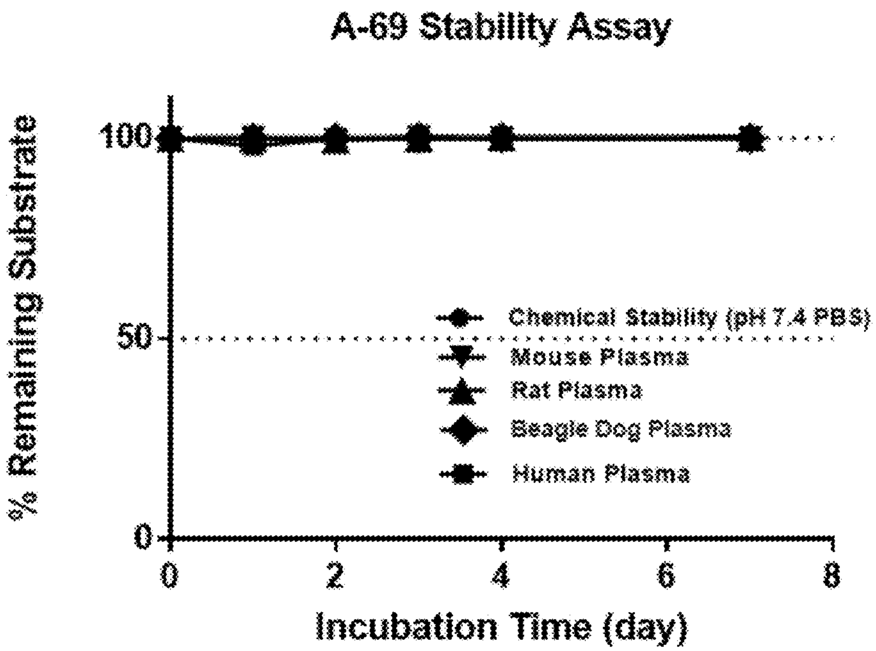
【Figure 6】
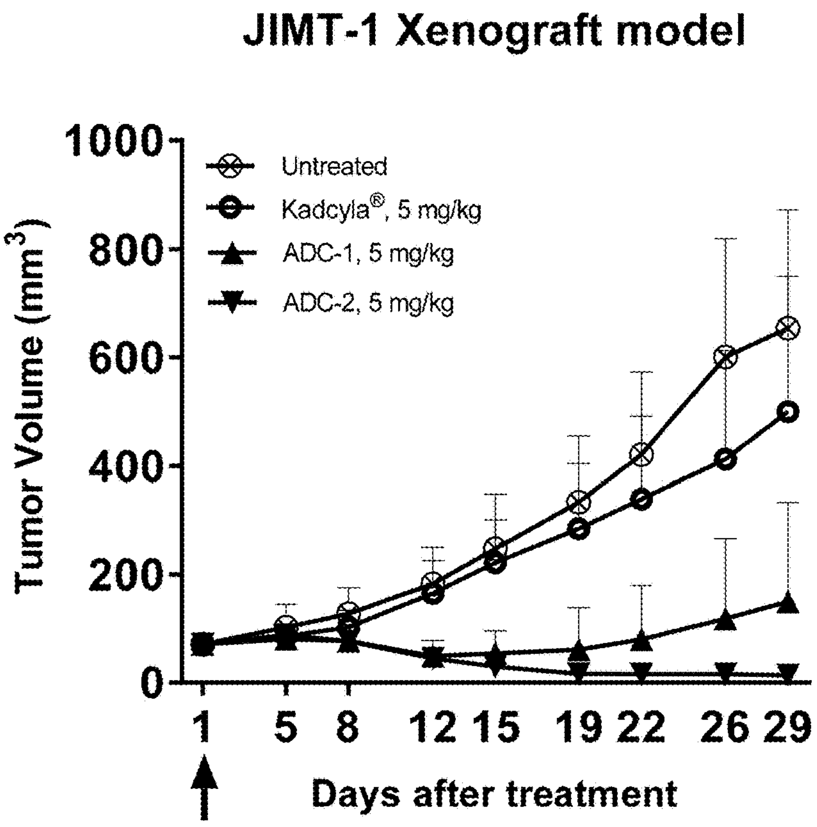

【Figure 7】
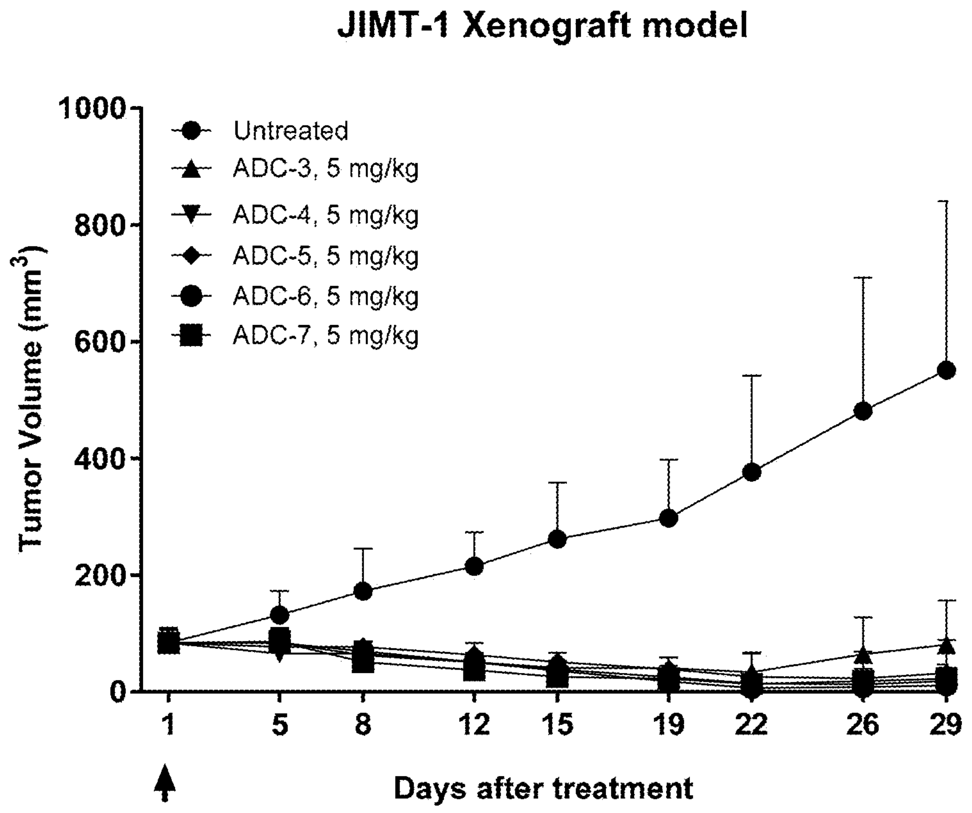

【Figure 8】
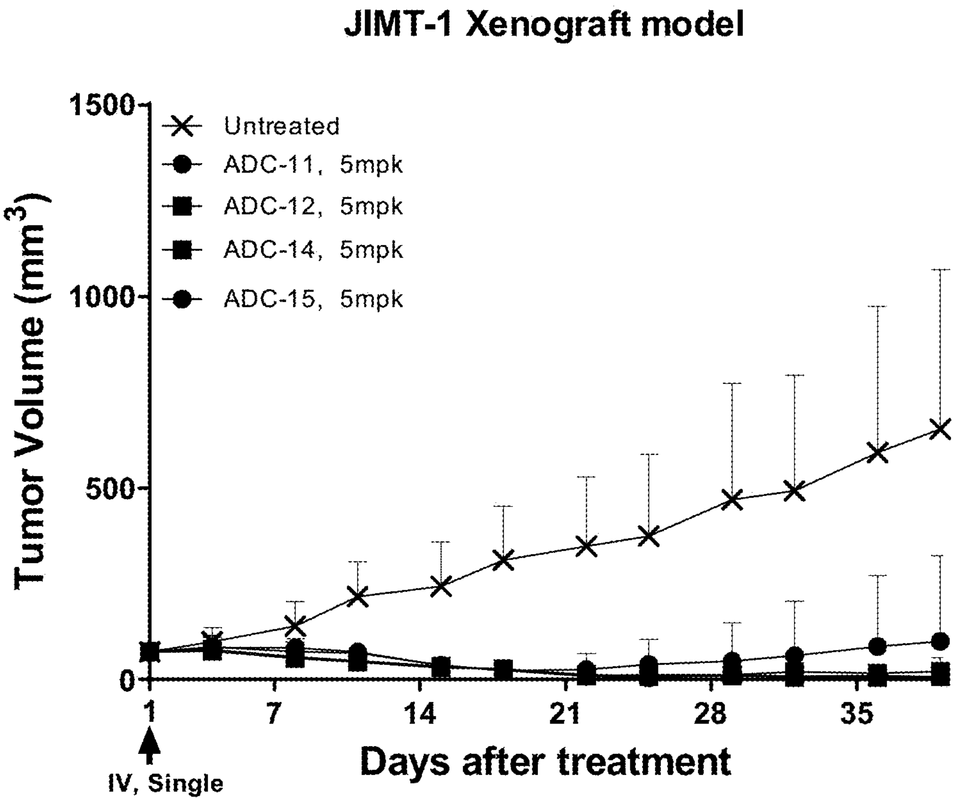

COMPOUND COMPRISING SELF-IMMOLATIVE GROUP AND LIGAND-DRUG CONJUGATE COMPRISING SAME

TECHNICAL FIELD

The present invention relates to a novel compound comprising a self-immolative group and a ligand-drug conjugate comprising the same, and specifically, relates to a compound comprising a self-immolative group of Formula 1 and a ligand-drug conjugate of Formula 2.

BACKGROUND ART

Bioactive substances such as drugs and diagnostic substances have target-specific activity in vivo. For example, drugs have an inhibitory or therapeutic effect on specific target cells, and diagnostic substances react with specific proteins in the body to perform diagnosis.

Meanwhile, since bioactive substances can be toxic to biomaterials other than the target, technologies have been proposed to suppress the side effects of the drug while allowing the drug effect to selectively appear on target cells.

For example, an antibody-drug conjugate (ADC) is a target-directed technology that binds a drug or toxin to an antibody that binds to an in vivo receptor and then selectively releases the drug or toxin from target cells to exhibit the desired drug effect. Because it releases a drug or toxin only under specific conditions and selectively delivers it to target cells while minimizing side effects on normal cells, it has better efficacy than antibody therapeutic agents and can greatly reduce the risk of side effects.

These antibody-drug conjugates consist of a general "antibody-linker-drug (toxin)" structure. The linker not only simply connects the antibody and the drug, but also allows the antibody-drug conjugate to stably reach the target cell during circulation in the body, and then the drug is separated by dissociation of the antibody-drug in the target cell (e.g., as a result of hydrolysis by enzymes), thereby selectively exerting its effect on the target cell. Therefore, the stability of the linker has a significant impact on the efficacy and systemic toxicity of the antibody-drug conjugate (Discovery Medicine 2010, 10(53): 329-39).

Linkers of antibody-drug conjugates can generally be classified into non-cleavable and cleavable types.

As a non-cleavable linker, thioether is mainly used. Instead of the bond between the drug and the linker dissociating within the cell, the bond between the linker and the antibody is dissociated, and the drug bound to the linker is separated from the antibody. A thiol-maleimide linker is mainly used, but has the disadvantages of low chemical and plasma stability and low potency.

As a cleavable linker, a linker that can be separated by a chemical method or hydrolyzed by an enzymatic reaction is mainly used.

As a linker having a chemical separation mechanism, a linker consisting of a disulfide, hydrazone, or oxime bond is typically used. However, a chemically separated linker can dissociate the drug at a location unrelated to the target site depending on conditions in the blood or cells, resulting in toxic side effects.

In order to solve this problem, linkers that are selectively hydrolyzed within target cells by enzymatic reactions are being developed. For example, a linker that is hydrolyzed by an enzymatic reaction is not directly linked to a drug, but is linked through a self-immolative group (SIG) interposed between the drug and the linker, and the drug is dissociated through a mechanism such as 1,6-elimination or cyclization after hydrolysis by an enzymatic reaction (Clinical Cancer Res. 2005, 11, 843-852).

However, there is still a need in the art for the development of a linker that has excellent plasma stability and chemical stability, can rapidly release the drug selectively within target cells, and has excellent versatility to form conjugates with various antibodies and drugs.

DETAILED DESCRIPTION OF INVENTION

Technical Problem

One object of the present invention is to provide a compound comprising a self-immolative group of Formula 1 or Formula 1-1 and a ligand-drug conjugate of Formula 2 or Formula 2-1.

Another object of the present invention is to provide a pharmaceutical composition, an imaging composition, or a composition for detection comprising a compound of Formula 1 or Formula 1-1, or a ligand-drug conjugate of Formula 2 or Formula 2-1.

Solution to Problem

Each description and embodiment disclosed in the present application may also be applied to each other description and embodiment. That is, all combinations of the various elements disclosed in the present application fall within the scope of the present application. In addition, the scope of the present application cannot be considered limited by the specific description described below.

In one aspect of the present invention, there is provided a compound comprising a self-immolative group represented by Formula 1 below, or a pharmaceutically acceptable salt thereof:

$A\text{-}(L^1)_k\text{-}U_j$ [Formula 1]

In addition, in another aspect of the present invention, there is provided a ligand-drug conjugate represented by Formula 2 below, or a pharmaceutically acceptable salt thereof:

[Formula 2]

$$E\text{—}[A'\text{—}(L^1)_k\text{—}U_j]_n$$

In Formula 1 or Formula 2 of the present invention, $L^1$ is a divalent or multivalent linking group, k is 0 or 1, and j is 1 to 10.

In Formula 1 or Formula 2 of the present invention, A is absent, H or a binding functional group, and A' is a divalent linking group derived from the binding functional group of A.

In Formula 2 of the present invention, n is a real number from 1 to 10, and E is a ligand or protein having a receptor binding property.

In Formula 1 or Formula 2 of the present invention, U is a moiety represented by Formula A below:

[Formula A]

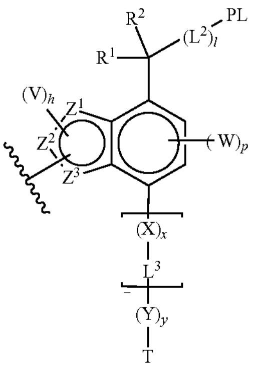

in Formula A, $R^1$ and $R^2$ are each independently H or $C_{1-8}$ saturated or unsaturated hydrocarbyl;

PL is an active agent linked to $L^2$ or the carbon atom to which $R^1$ and $R^2$ are bound by a heteroatom selected from N, O and S;

$L^2$ is a self-eliminating linker selected such that cleavage of the bond between $L^2$ and the carbon atom to which $R^1$ and $R^2$ are bound promotes cleavage of the bond between $L^2$ and PL; W is an optional substituent on the benzene ring;

one of $Z^1$ and $Z^3$ is selected from the group consisting of N, $NR^3$, O, S and Se, and the other one of$^{Z}$ and $Z^3$ and $Z^2$ are each independently CH or N, and $-(L^1)_k$-A, and if present $-(V)_h$, each independently replace H of NH or CH;

represents a bond with $A-(L^1)_k-$;

$R^3$ is H or $C_{1-8}$ hydrocarbyl;

V is an electron withdrawing group or an electron donating group;

T is a triggering group capable of initiating the release of PL, and if present $L^2$, by a 1,6-elimination reaction upon cleavage;

$L^3$ is an optional self-immolative spacer group that is cleaved sequentially upon cleavage of T, if present;

X and Y are each independently selected from —O—, —NH—, and S; and h, i, l, x and y are each independently 0 or 1, and p is an integer from 0 to 2.

Compounds Comprising a Self-Immolative Group of Formula 1

Fused-Ring Containing Core Unit U in Formula 1 ($A-(L^1)_k-U_j$) is represented by Formula A below:

[Formula A]

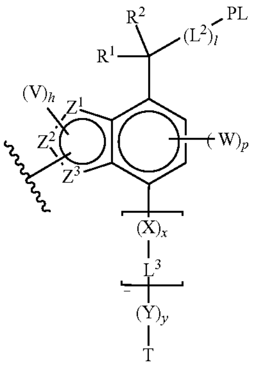

In Formula 1, if $L^1$ is a divalent linking group, then one side of $L^1$ binds to A and the other side binds to U. In this case, one U is bound to $L^1$. Alternatively, if $L^1$ comprises a branched structure or a dendrimeric structure (i.e., if $L^1$ is a multivalent linking group), multiple U's may bind to $L^1$. In this case, the number j of U's bound to $L^1$ may be 1 to 10. In one embodiment, j is 1 to 5. In one embodiment, j is 1.

In Formula A above, one of $Z^1$ and $Z^3$ is selected from the group consisting of N, $NR^3$, O, S and Se, and the other one of $Z^1$ and $Z^3$ and $Z^2$ are each independently CH or N. $-(L^1)_k$-A, and $-(V)_h$ if present, each independently replace H of NH or CH. In this case, $R^3$ is H or $C_{1-8}$ hydrocarbyl.

In Formula A above,

linked to the 5-membered ring comprising $Z^1$ to $Z^3$ represents a bond with $A-(L^1)_k-$ of Formula 1.

In one embodiment, one of $Z^1$ and $Z^3$ is selected from the group consisting of N, $NR^3$, O, S and Se, which is bound to $L^1$ or A, and the other one of $Z^1$ and $Z^3$ and $Z^2$ may be each independently C or N bound to H, V, $L^1$, or A. $R^3$ is H or $C_{1-8}$ alkyl. In one embodiment, $R^3$ may be H, $C_{1-4}$ alkyl or $C_{1-3}$ alkyl.

In one embodiment, any one of $Z^1$ to $Z^3$ may comprise a heteroatom selected from the group consisting of N, O, S and Se. In one embodiment, two or more of $Z^1$ to $Z^3$ may each independently comprise a heteroatom selected from the group consisting of N, O, S and Se.

In one embodiment, one of $Z^1$ and $Z^3$ may be N bound to A or $L^1$, and the other one and $Z^2$ may be CH. Alternatively, one of $Z^1$ and $Z^3$ may be selected from the group consisting of $NR^3$, O, S and Se, and the other one and $Z^2$ may be CH, or C bound to A or $L^1$. Alternatively, one of $Z^1$ and $Z^3$ may be selected from the group consisting of $NR^3$, O and S, and one of the other one and $Z^2$ may be N, and the other one of $Z^1$ to $Z^3$ may be CH, or C bound to A or $L^1$.

In one embodiment, V may be substituted on the carbon atom of CH when any one or more of $Z^1$ to $Z^3$ is CH. For example, when $Z^2$ is CH, V may be substituted on $Z^2$.

In one embodiment, the compound represented by Formula 1 may be a derivative of indole, benzothiophene, benzofuran, benzoselenophene, indazole, benzimidazole, benzoxazole, benzisoxazole or benzothiazole.

In one embodiment, the ring

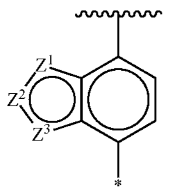

in Formula A may be selected from the

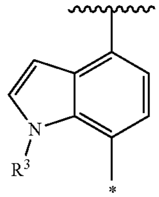 ; 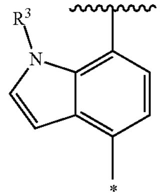 ; 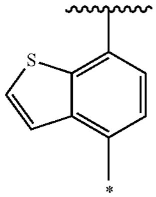 ;

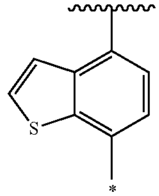 ; 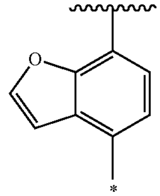 ; 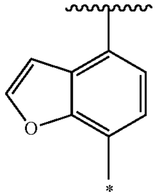 ;

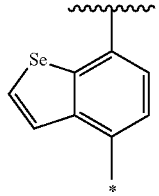 ; 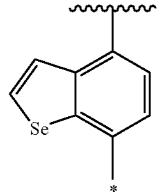 ; 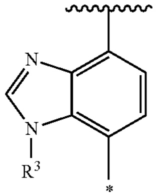 ;

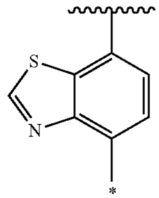 ; 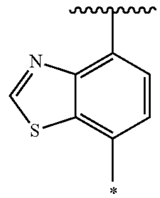 ; 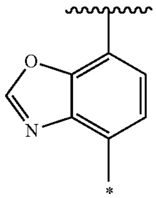 ;

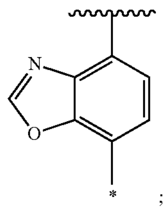 ; 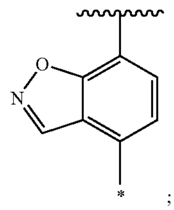 ;

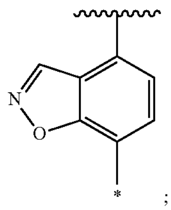 ; and 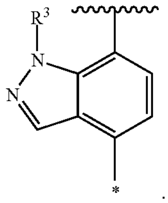 .

The benzene ring in the fused ring structure of Formula A above may be substituted with an optional substituent W as long as it does not have an undesirable effect on the 1,6-elimination reaction initiated from a triggering group T. In one embodiment, the substituent W on the benzene ring may be selected from the group consisting of H, $C_{1-12}$ saturated or unsaturated hydrocarbyl, halogen, halo-$C_{1-8}$ alkyl, CN, $NO_2$, OH, $C_{1-8}$ alkoxy, hydroxy-$C_{1-8}$ alkyl, $C_{1-8}$ alkoxy-$C_{1-8}$ alkyl, SH, $C_{1-8}$ alkylthio, mercapto-$C_{1-8}$ alkyl, amino, mono-$C_{1-8}$ alkylamino, di-$C_{1-8}$ alkylamino, amino-$C_{1-8}$ alkyl, $C_{1-8}$ monoalkylamino-$C_{1-8}$ alkyl, $C_{1-8}$ dialkylamino-$C_{1-8}$ alkyl, carboxy, $C_{1-8}$ alkoxycarbonyl, $C_{1-8}$ alkoxycarbonyloxy, carboxy-$C_{1-8}$ alkyl, $C_{1-8}$ alkoxycarbonyl-$C_{1-8}$ alkyl, carbamoyl, mono-$C_{1-8}$ alkylcarbamoyl, di-$C_{1-8}$ alkylcarbamoyl, carbamoyl-$C_{1-8}$ alkyl, mono-$C_{1-8}$ alkylcarbamoyl-$C_{1-8}$ alkyl and di-$C_{1-8}$ alkylcarbamoyl-$C_{1-8}$ alkyl. In Formula 1, p may be an integer from 0 to 2. In one embodiment, p may be 0.

In addition, the 5-membered ring comprising $Z^1$, $Z^2$ and $Z^3$ in the fused ring of Formula A above may be optionally substituted with V, an electron withdrawing group or an electron donating group. In Formula A, h is 0 or 1. In one embodiment, when A-$(L^1)_k$- is bound to $Z^2$, V may be absent (h is 0).

In some embodiments, V may be selected from the group consisting of halogen, CN, $NO_2$, formyl, $C_{1-8}$ alkylcarbonyl, carboxy, $C_{1-8}$ alkoxycarbonyl, carboxy-$C_{1-8}$ alkyl, carbamoyl, mono-$C_{1-8}$ alkylcarbamoyl, di-$C_{1-8}$ alkylcarbamoyl, $C_{1-8}$ alkyl, $C_{1-8}$ alkenyl, OH, $C_{1-8}$ alkoxy, SH, $C_{1-8}$ alkylsulfanyl, $NH_2$, mono-$C_{1-8}$ alkylamino, di-$C_{1-8}$ alkylamino and $C_{6-18}$ aryl. In some embodiments, V may be carboxy, carboxy-$C_{1-8}$ alkyl or $C_{1-8}$ alkoxycarbonyl. For example, V may be carboxy, methoxycarbonyl, ethoxycarbonyl, propoxycarbonyl, carboxymethyl, carboxyethyl or carboxypropyl.

In Formula A of the present invention, $R^1$ and $R^2$ are each independently H or $C_{1-8}$ saturated or unsaturated hydrocarbyl.

In one embodiment, $R^1$ and $R^2$ may be each independently H or $C_{1-8}$ alkyl or $C_{3-8}$ cycloalkyl. In one embodiment, $R^1$ and $R^2$ may be each independently H or a $C_{1-4}$ saturated or fully or partially unsaturated hydrocarbyl. For example, $R^1$ and $R^2$ may be each H. The unsaturated hydrocarbyl may include a partially unsaturated or fully unsaturated hydrocarbyl. The hydrocarbyl may be a straight-chain, branched or cyclic hydrocarbyl.

Self-Eliminating Linker

In Formula 1 of the present invention, $L^2$ is a self-eliminating linker selected such that cleavage of the bond between $L^2$ and the carbon atom to which $R^1$ and $R^2$ are bound promotes cleavage of the bond between $L^2$ and PL. 1 may be 0 or 1. When 1 is 0, PL may be directly bound to the carbon atom to which $R^1$ and $R^2$ are bound.

When a compound of Formula 1 comprises a self-eliminating linker, the $L^2$ group is cleaved from the carbon atom to which $R^1$ and $R^2$ are bound by a 1,6-elimination reaction triggered by the triggering group T, and PL- or PL-H may be released from $L^2$.

In one embodiment, $L^2$ is at least one linker selected from the group consisting of —OC(=O)—, —S(=O)$_2$—,

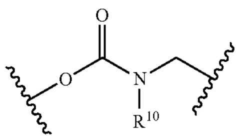 and

-continued

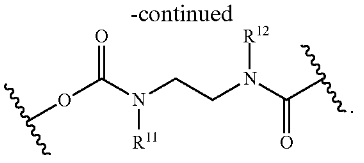

In this case, $R^{10}$ to $R^{12}$ may be each independently H, $C_{1-8}$ alkyl, amino-$C_{1-8}$ alkyl, $C_{1-8}$ alkyl substituted with mono- or di-($C_{1-8}$ alkyl)amino, or $—(CH_2CH_2O)_gR^{13}$. In this case, $R^3$ may be H or $C_{1-4}$ alkyl, and g may be an integer from 1 to 10. In one embodiment, $C_{1-8}$ alkyl may be $C_{1-6}$ alkyl, $C_{1-4}$ alkyl or $C_{1-3}$ alkyl. For example, $R^{10}$ to $R^{12}$ may each independently include H, methyl, ethyl, propyl, 2-aminoethyl, 2-(N-methylamino)ethyl, 2-(N,N-dimethylamino) ethyl, 2-(N-ethylamino)ethyl or 2-(N,N-diethylamino)ethyl. In one embodiment, the moiety of Formula A may include —OC(═O)— as $L^2$.

Active Agent (PL)

In Formula A of the present invention, PL is an active agent that exhibits the desired biological activity in target cells, and is linked to $L^2$ or the carbon atom to which $R^1$ and $R^2$ are bound by a heteroatom selected from N, O and S in the active agent. PL is released from the compound of Formula 1 by a 1,6-elimination reaction when T is cleaved by an enzymatic reaction or chemical reaction.

In one embodiment, PL may be at least one active agent selected from the group consisting of a drug, a toxin, a fluorophore, an affinity ligand, a diagnostic substance and a detection probe. Specifically, a heteroatom selected from N, O and S included in the drug, toxin, fluorophore, affinity ligand, diagnostic substance and detection probe may be bound to the carbon atom to which $R^1$ and $R^2$ are bound or to $L^2$. Therefore, as long as it contains a heteroatom selected from N, O and S which is capable of binding to the carbon atom to which $R^1$ and $R^2$ are bound or (if $L^2$ is present) $L^2$, or a functional group containing such a heteroatom can be additionally introduced thereto, it can be used as the PL of the present invention, and it should be noted that the PL of the present invention is not limited to the specific active agents exemplified herein. For example, PL may include a functional group where H of a primary or secondary amine group, H of a hydroxy group, and H of a carboxyl group are removed, a functional group where the lone pair of electrons of the nitrogen atom of a tertiary amine group is donated, or a functional group linked to a nitrogen atom through an addition reaction of an imine group.

The drug may be selected from, but is not limited thereto, the group consisting of erlotinib (TARCEVA; Genentech/OSI Pharm.); bortezomib (VELCADE; MilleniumPharm.); fulvestrant (FASLODEX; AstraZeneca); sutent (SU11248; Pfizer); letrozole (FEMARA; Novartis); imatinib mesylate (GLEEVEC; Novartis); PTK787/ZK 222584(Novartis); oxaliplatin (Eloxatin; Sanofi); 5-fluorouracil (5-FU); leucovorin; rapamycin (Sirolimus, RAPAMUNE; Wyeth); lapatinib (TYKERB, GSK572016; GlaxoSmithKline); lonafarnib (SCH 66336); sorafenib (BAY43-9006; Bayer Labs.); gefitinib (IRESSA; Astrazeneca); AG1478, AG1571 (SU 5271; Sugen); alkylating agents (e.g., thiotepa or CYTOXAN®; cyclophosphamide); alkyl sulfonates (e.g., busulfan, improsulfan or piposulfan); aziridine (e.g., benzodopa, carboquone, meturedopa or uredopa); ethylenimine, methylmelamine, altretamine, triethylenemelamine, triethylenephosphoramide, triethylenethiophosphoramide, trimethylolmelamine; acetogenins (e.g., bullatacin or bullatacinone); camptothecin including synthetic analogue topotecan; bryostatin; callystatin; CC-1065 (including adozelesin, carzelesin, or bizelesin synthetic analogues thereof); cryptophycins (e.g., cryptophycin 1 or cryptophycin 8); dolastatin; duocarmycin (including synthetic analogues, KW-2189 and CB1-TM1); eleutherobin; pancratistatin; sarcodictyin; spongistatin; nitrogen mustard (e.g., chlorambucil, chlornaphazine, cholophosphamide, estramustine, ifosfamide, mechlorethamine, mechlorethamine oxide hydrochloride, melphalan, novembichin, phenesterine, prednimustine, trofosfamide or uracil mustard); nitrousurea (e.g., carmustine, chlorozotocin, fotemustine, lomustine, nimustine or ranimnustine); antibiotics (e.g., as enediyne antibiotics, calicheamycin selected from calicheamycin gamma1 I and calicheamycin omegaI1 or dynemicin including dynemicin A); bisphosphonates (e.g., clodronate); esperamicin, neocarzinostatin chromophore or related chromoprotein enediyne antibiotic chromophores, aclacinomysins, actinomycin, antrmycin, azaserine, bleomycins, cactinomycin, carabicin, carninomycin, carzinophilin, chromomycins, dactinomycin, daunorubicin, detorubucin, 6-diazo-5-oxo-L-norleucine, ADRLIMYCIN; doxorubicin (ADRLIMYCIN) (e.g., morpholino-doxorubicin, cyanomorpholino-doxorubicin, 2-pyrrolino-doxorubucin, liposomal doxorubicin or deoxydoxorubicin), epirubicin, esorubicin, marcellomycin, mitomycins (e.g., mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin or zorubicin); anti-metabolites (e.g., 5-fluorouracil (5-FU)); folic acid analogues (e.g., denopterin, methotrexate, pteropterin or trimetrexate); purine analogs (e.g., fludarabine, 6-mercaptopurine, thiamiprine or thiguanine); pyrimidine analogs (e.g., ancitabine, azacitidine, 6-azauridine, carmofur, cytarabine, dideoxyuridine, doxifluridine, enocitabine or floxuridine); androgens (e.g., calusterone, dromostanolone propionate, epitiostanol, mepitiostane or testolactone); anti-adrenals (e.g., aminoglutethimide, mitotane or trilostane); folic acid replenishers (e.g., folinic acid); aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; epothilone; etoglucid; gallium nitrate; hydroxyurea; lentinan; lonidainine; maytansinoids (e.g., maytansine or ansamitocins); trichothecenes (e.g., T-2 toxin, verracurin A, roridin A or anguidine); mitoguazone; mitoxantrone; mopidanmol; nitraerine; pentostatin; phenamet; pirarubicin; losoxantrone; 2-ethylhydrazide; procarbazine; PSK®; polysaccharides; razoxane; rhizoxin; sizofiran; spirogermanium; tenuazonic acid; triaziquone; 2,2',2"-trichlorotriethylamine; trichothecenes (particularly, T-2 toxin, verracurin A, roridin A and anguidine); urethane; vindesine; dacarbazine; mannomustine; mitobronitol; mitolactol; pipobroman; gacytosine; arabinoside ('Ara-C'); cyclophosphamide; thiotepa; taxoids (e.g., TAXOL; paclitaxel (TAXOL; Bristol-Myers Squibb Oncology, Princeton, N.J.), ABRAXANE™ cremophor-free, albumin-engineered nanoparticle formulation of paclitaxel (American Pharmaceutical Partners, Schaumber, Ill.) or TAXOTERE; doxetaxel (TAXOTERE); chloranbucil; gemcitabine; 6-thioguanine; mercaptopurine; platinum analogs (e.g., cisplatin or carboplatin); vinblastine; platinum; etoposide, ifosfamide; mitoxantrone; vincristine; vinorelbine (NAVELBINE); novantrone; teniposide; edatrexate; daunomycin; aminopterin; xeloda; ibandronate; CPT-11; topoisomerase inhibitors RFS 2000; difluorometlhylornithine (DFMO); retinoids (e.g., retinoic acid); capecitabine; and a pharmaceutically acceptable salt, solvate, acid, or derivative thereof.

Additional drugs other than the aforementioned drug comprise, but are not limited thereto, (i) anti-hormones which modulates or inhibits hormone actions on tumors such as anti-estrogens and selective estrogen receptor modulators (SERM), including tamoxifen (NOLVADEX; including tamoxifen), raloxifene, droloxifene, 4-hydroxytamoxifen, trioxifene, keoxifene, LY117018, onapristone and FAREATON; toremifene; (ii) aromatase inhibitors which inhibits aromatase enzymes to modulate estrogen production in the adrenal glands, such as 4(5)-imidazole, aminoglutethimide, MEGASE; megestrol acetate, AROMASIN; exemestane, FEMARA; letrozole and ARIMIDEX; anastrozole; (iii) anti-androgens, such as flutamide, nilutamide, bicalutamide, leuprolid and goserelin; as well as troxacitabine (1,3-dioxolane nucleoside cytosine analog); (iv) aromatase inhibitors; (v) protein kinase inhibitors; (vi) lipid kinase inhibitors; (vii) antisense oligonucleotides, particularly those which inhibit gene expression in the signaling pathway associated with adherent cells, such as PKC-α, Raf, H-Ras; (viii) ribozymes, such as VEGF inhibitors, such as ANGIOZYME ribozymes and HER2 expression inhibitors; (ix) vaccines, such as gene therapy vaccines; ALLOVECTIN; vaccine, LEUVECTIN vaccine and VAXID vaccine; PROLEUKIN; rlL-2; LURTOTECAN; topoisomerase 1 inhibitors; ABARELIX; rmRH; (x) anti-angiogenic agents, such as bevacizumab (AVASTIN, Genentech); and (xi) a pharmaceutically acceptable salt, solvate, acid, or derivative thereof.

In one embodiment, the drug may be selected from cytokines, immunomodulatory compounds, anticancer agents, antiviral agents, antibacterial agents, antifungal agents, anthelmintic agents or a combination thereof.

The cytokines are small cell-signaling protein molecules that are secreted by numerous cells, which may be signaling molecules used extensively in intercellular communication. The cytokines include monokine, lympokine, traditional polypeptidehormone, etc. Exemplary cytokines may comprise, but are not limited to, growth hormone (e.g., human growth hormone, N-methionyl human growth hormone or bovine growth hormone); parathyroid hormone; thyroxine; insulin; proinsulin; relaxin; prorelaxin; glycoprotein hormone (e.g., follicle stimulating hormone (FSH), thyroid stimulating hormone (TSH) or luteinizing hormone (LH)); hepatic growth factor; fibroblast growth factor; prolactin; placental lactogen; tumor necrosis factor-a, tumor necrosis factor-0; mullerian-inhibiting substance; mouse gonadotropin-associated peptide; inhibin; activin; vascular endothelial growth factor; integrin, thrombopoietin (TPO); nerve growth factor (e.g., NGF-P); platelet-growth factor; transforming growth factor (TGF) (e.g., TGF-α or TGF-β); insulin-like growth factor-I, insulin-like growth factor-II; erythropoietin (EPO); osteoinductive factor; interferon (e.g., interferon-α, interferon-β or interferon-γ); colony stimulating factor (CSF) (e.g., macrophage-CSF (M-CSF), granulocyte-macrophage-CSF (GM-CSF) or granulocyte-CSF (G-CSF)); interleukin (IL) (e.g., IL-1, IL-1α, IL-2, IL-3, IL-4, IL-5, IL-6, IL-7, IL-8, IL-9, IL-10, IL-11 or IL-12); tumor necrosis factor (e.g., TNF-α or TNF-β); and polypeptide factor (e.g., LIF or kit ligand (KL)). In addition, the term "cytokine" also includes proteins from natural sources or from recombinant cell culture and biologically active equivalents of the native sequence cytokines.

The immunomodulatory compounds may be selected from the group consisting of aminocaproic acid, azathioprine, bromocriptine, chloroquine, chlorambucil, cyclosporine, cyclosporine A, danazol, DHEA (dehydroepiandrosterone), dexamethasone, etanercept, hydroxychloroquine, hydrocortisone, infliximab, meloxicam, methotrexate, cyclophosphamide, mycophenylate mofetil, prednisone, sirolimus and tacrolimus.

The anticancer agents may be selected from the group consisting of methotrexate, taxol, L-asparaginase, mercaptopurine, thioguanine, hydroxyurea, cytarabine, cyclophosphamide, ifosfamide, nitrosourea, cisplatin, carboplatin, mitomycin, dacarbazine, procarbazine, topotecan, nitrogen mustard, cytoxan, etoposide, 5-fluorouracil, BCNU (bischloroethylnitrosourea), irinotecan, camptothecin, exatecan, belotecan, bleomycin, doxorubicin, idarubicin, daunorubicin, dactinomycin, plicamycin, mitoxantrone, asparaginase, vinblastine, vincristine, vinorelbine, paclitaxel, docetaxel, chlorambucil, melphalan, carmustine, lomustine, busulfan, treosulfan, decarbazine, etoposide, teniposide, topotecan, 9-aminocamptothecin, crisnatol, mitomycin C, trimetrexate, mycophenolic acid, tiazofurin, ribavirin, EICAR (5-ethynyl-1-beta-D-ribofuranosylimidazole-4-carboxamide), hydroxyurea, deferoxamine, floxuridine, doxifluridine, raltitrexed, cytarabine (ara C), cytosine arabinoside, fludarabine, tamoxifen, raloxifene, megestrol, goserelin, leuprolide acetate, flutamide, bicalutamide, EB1089, CB1093, KH1060, verteporfin, phthalocyanine, photosensitizer Pe4, demethoxy-hypocrellin A, Interferon-a, Interferon-y, tumor necrosis factor, Gemcitabine, velcade, revamid, thalamid, lovastatin, 1-methyl-4-phenylpyridinium ion, staurosporine, actinomycin D, dactinomycin, bleomycin A2, bleomycin B2, peplomycin, epirubicin, pirarubicin, zorubicin, mitoxantrone, verapamil and thapsigargin.

The antiviral agents may be selected from the group consisting of pencicyclovir, valacyclovir, gancicyclovir, foscarnet, rivavirin, idoxuridine, vidarabine, trifluridine, acyclovir, famcicyclovir, amantadine, rimantadine, cidofovir, antisense oligonucleotide, immunoglobulin and interferon.

The antibacterial agents may be selected from the group consisting of chloramphenicol, vancomycin, metronidazole, trimethoprin, sulfamethazole, quinupristin, dalfopristin, rifampin, spectinomycin and nitrofurantoin.

The antifungal agents may be selected from the group consisting of amphotericin B, Candicidin, filipin, hamycin, natamycin, nystatin, rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, Micafungin, benzoic acid, ciclopirox, flucytosine, griseofulvin, haloprogin, tolnaftate, undecylenic acid, crystal violet, balsam of peru, Ciclopirox olamine, Piroctone olamine, Zinc pyrithione and Selenium sulfide. The anthelmintic agents may be selected from the group consisting of mebendazole, pyrantel pamoate, thiabendazole, diethylcarbamazine, ivermectin, niclosamide, praziquantel, albendazole, rifampin, amphotericin B, melarsoprol, eflornithine, metronidazole, tinidazole and miltefosine.

The "toxin" refers to a poisonous substance produced within living cells or organisms. Toxins can be small molecules, peptides or proteins that are capable of causing disease on contact with or absorption by body tissue interacting with biological macromolecules such as enzyme or cellular receptors. In addition, "toxin" comprises plant toxins and animal toxins. Exemplary animal toxins include, but are not limited to, diphtheria toxin, botulinum toxin, tetanus toxin, dysentery toxin, cholera toxin, tetrodotoxin, brevetoxin, ciguatoxin. Exemplary plant toxins include, but are not limited to, ricin and AM-toxin.

For example, small molecule toxins may include, but are not limited to, auristatin, tubulysin, geldanamycin (Kerr et al., 1997, Bioconjugate Chem. 8(6):781-784), maytansinoid (EP 1391213, ACR 2008, 41, 98-107), calicheamycin (US 2009105461, Cancer Res. 1993, 53, 3336-3342), daunomycin, doxorubicin, methotrexate, vindesine, SG2285 (Cancer Res. 2010, 70(17), 6849-6858), dolastatin, dolastatin analog, auristatin (U.S. Pat. No. 5,635,483), cryptophycin, camptothecin, rhizoxin derivative, CC-1065 analogues or derivatives, duocarmycin, enediyne antibiotics, esperamicin, epothilone, PBD (pyrrolobenzodiazepine) derivatives, α-amanitin and toxoid. Toxins may exhibit cytotoxicity and cell growth-inhibiting activity by tubulin binding, DNA binding, and topoisomerase inhibition, etc.

The affinity ligand may include a molecule capable of forming a complex with a target biomolecule. The affinity ligand may be a molecule that transmits a signal by binding to a predetermined position on the target protein. The affinity ligand may be a substrate, an inhibitor, a stimulant, a neurotransmitter, or a radioisotope.

"Detection probe" may refer to a substance or a portion of a substance that can be detected by spectroscopic, photochemical, biochemical, immunochemical, radioactive or chemical means. For example, useful detection probes may include $^{32}P$, $^{15}S$, fluorescent dyes, electron-dense reagents, enzymes (e.g., those commonly used in ELISA), biotin-streptavidin, dioxigenin, haptens, and proteins for which antisera or monoclonal antibodies are available, or nucleic acid molecules with a sequence complementary to a target. Detection probes are often capable of generating a measurable signal, such as a radioactive, chromogenic or fluorescent signal, which can be used to quantify the amount of bound detectable moiety in a sample. Quantification of the signal can be achieved, for example, by scintillation counting, densitometry, flow cytometry, ELISA, or direct analysis by mass spectrometry of intact or subsequently digested peptides (one or more peptides can be assayed).

The above detection probe may include (i) a substance capable of providing a detectable signal, (ii) a substance capable of altering a detectable signal provided by the first or second probe, such as fluorescence resonance energy transfer (FRET), by causing the first or second probe to react with each other, (iii) a substance capable of stabilizing an interaction with an antigen or a ligand or increasing binding affinity, (iv) a substance capable of affecting electrophoretic mobility or cell-invasiveness by physical parameters such as charge, hydrophobicity, and the like, and (v) a substance capable of modulating ligand affinity, antigen-antibody binding, or ionic complex formation.

In one embodiment, PL may be a moiety of an active agent selected from the group consisting of MMAF (monomethyl auristatin F), auristatin F, MMAE (monomethyl auristatin E), SN-38, p-nitrophenol, xanthenecarboxylic acid, abiraterone, gefitinib, PBD dimer, α-amanitin, seco-DUBA, doxorubicin, lapatinib, imatinib, erlotinib, exatecan, belotecan, and a compound represented by one of the following formulas:

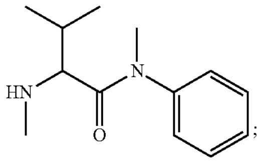

; and

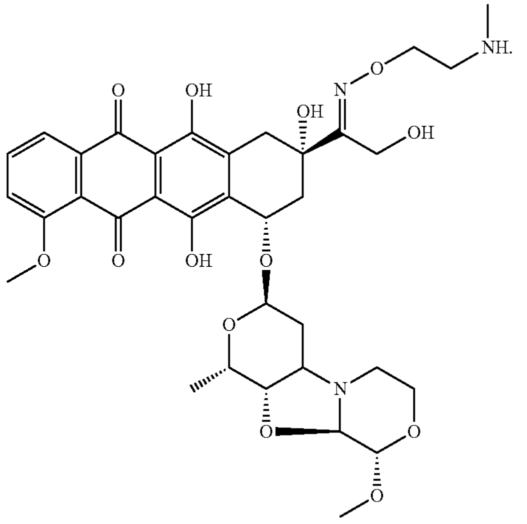

In one embodiment, PL may be selected from the group consisting of moieties represented by the following formulas:

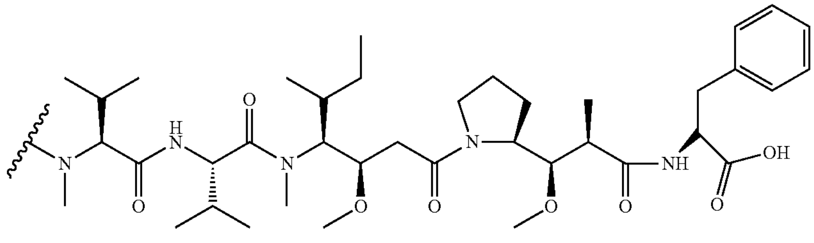

;

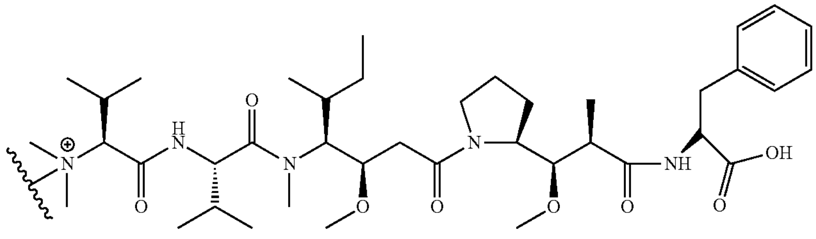

;

-continued
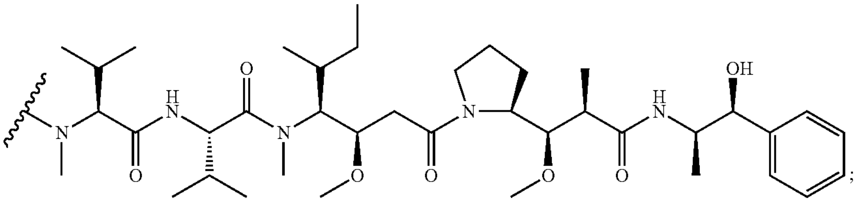
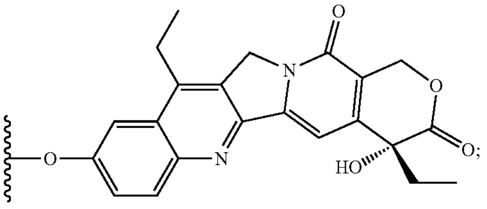
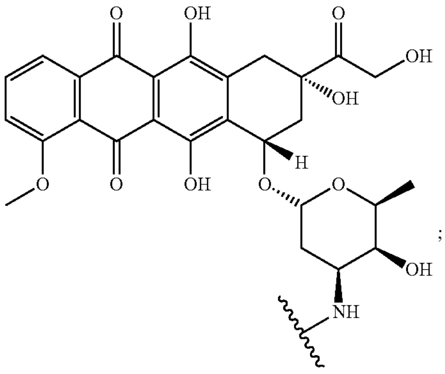
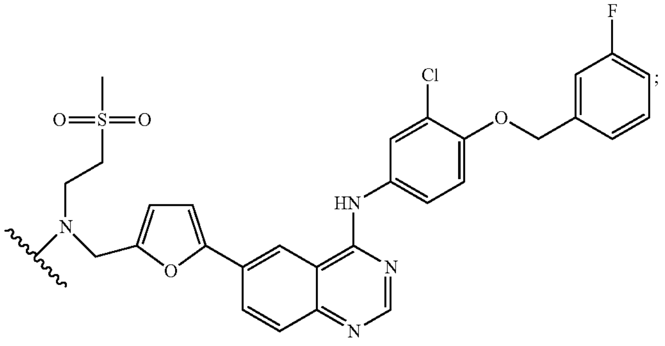
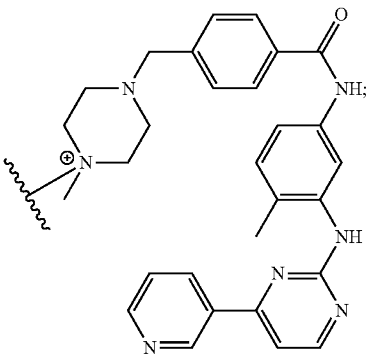
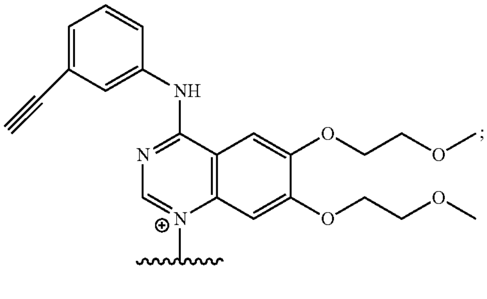
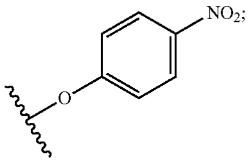
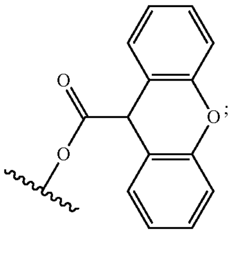

-continued
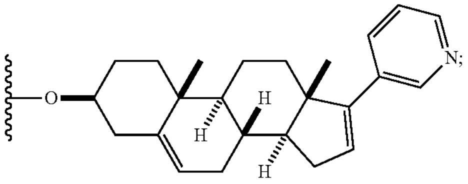
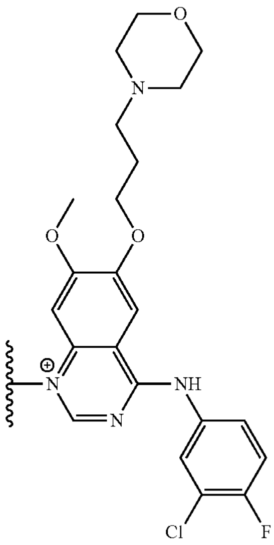
;
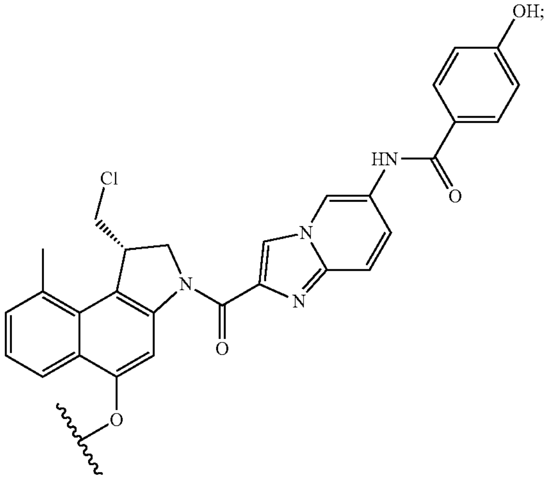
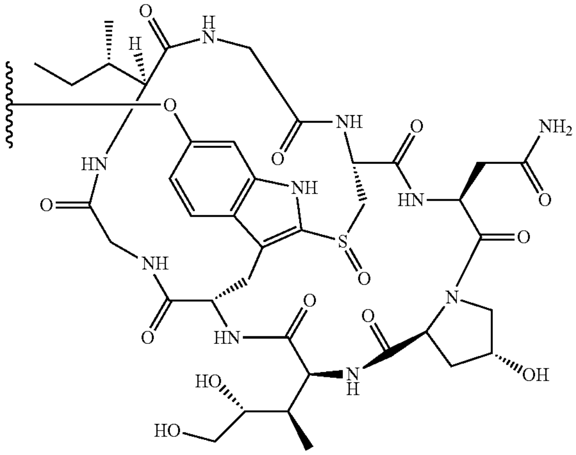
;
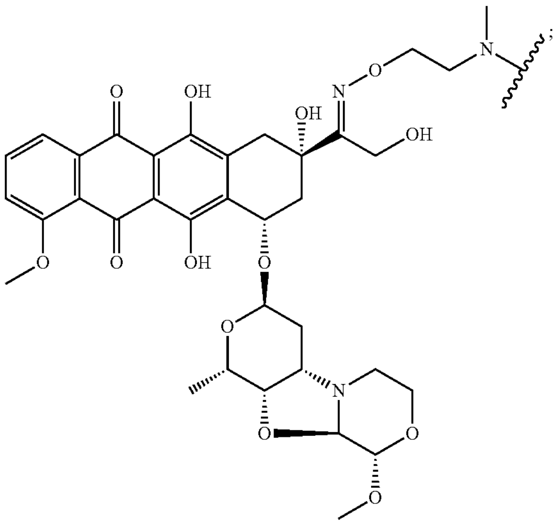
;
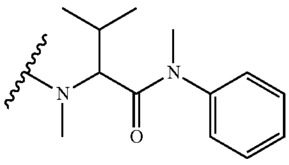
;

-continued

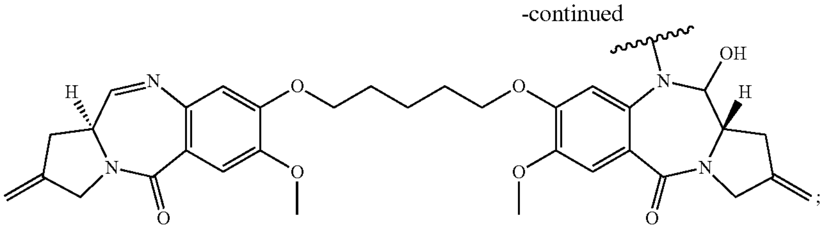

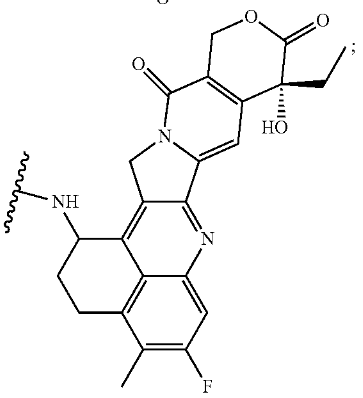

; and

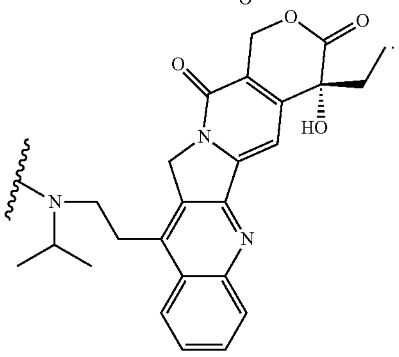

Triggering Unit

In Formula A of the present invention, T is a triggering group capable of initiating the release of PL, and if present $L^2$, by a 1,6-elimination reaction upon cleavage.

T can be selectively cleaved in vivo by chemical reaction or enzymatic reaction. That is, T (or the bond between Y and T if Y is present) can be selectively cleaved under specific conditions in vivo, thereby stably delivering PL to the target site, and selectively releasing PL at the target site.

In one embodiment, T may be linked to the benzene ring through a heteroatom such as an oxygen atom, a sulfur atom, or a nitrogen atom. That is, in Formula A, Y connecting the triggering group T to the compound moiety may be —O—, —NH—, and S.

In one embodiment, $-(Y)_y$-T may be selected from the group consisting of -β-galactoside, -β-glucuronide, —O—$SO_3^-$, —$NO_2$, -valine-citrulline derivative, -valine-alanine derivative, —$OC(O)(CH_2)_rCOR^{t1}$, —$O(CH_2)$—$Ar^1$—$NO_2$, —S—$C(O)(CH_2)_sCOR^2$, —$S(CH_2)$—$Ar^2$—$NO_2$ and —$BR^{t3}R^{t4}$.

The β-galactoside and β-glucuronide may be linked to the benzene ring through the oxygen atom bound to the $1^{st}$ carbon atom of the β-galactoside moiety and the β-glucuronide moiety. The valine-citrulline derivative and the valine-alanine derivative may be linked to the benzene ring through the nitrogen atom of the valine moiety. That is, the -β-galactoside, -β-glucuronide, -valine-citrulline derivative and -valine-alanine derivative herein may be moieties having the structure below.

-continued

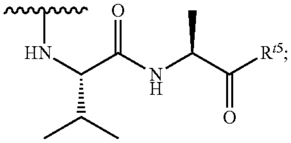

; and

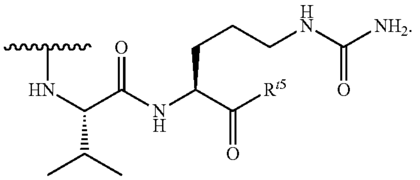

.

$R^{t1}$ and $R^{t2}$ may be each $C_1$-$C_5$ alkyl, $Ar^1$ and $Ar^2$ may be each $C_5$-$C_{20}$ arylene or heteroarylene, $R^3$ and $R^4$ may be each independently hydrogen, $C_1$-$C_5$ alkoxy or hydroxy, and r and s may be each an integer from 1 to 5. In one embodiment, the arylene may be phenyl or naphthyl. In one embodiment, the heteroarylene may contain 1 to 3 heteroatoms (N, O or S). For example, the heteroarylene may be furanyl, thiophenyl, or pyrrolyl.

$R^{t5}$ may be OH, mono-$C_{1-8}$ alkylamino, di-$C_{1-8}$ alkylamino or —$NH(CH_2CH_2O)_fR^{t6}$, wherein $R^{t6}$ may be H or $C_{1-4}$ alkyl, and f may be an integer from 1 to 10.

In one embodiment, $-(Y)_y$-T includes saccharides such as

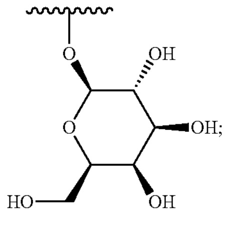

;

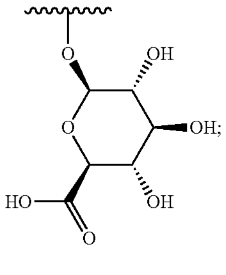

;

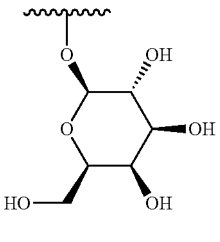

and

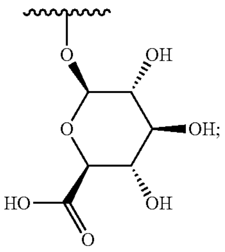

;

peptides such as

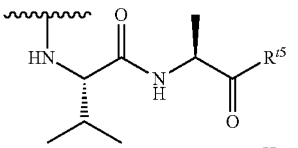

and

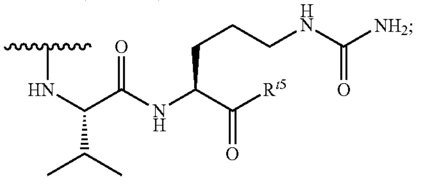

and $-O-SO_3^-$ functional group, which can be selectively hydrolyzed by specific enzymes in lysosomes. The above saccharides may include those in which the —OH is protected with a protecting group (e.g., acetyl) or substituted with an optional substituent. In addition, $-SC(O)(CH_2)_s COR^{t2}$, $-S(CH_2)-Ar^2-NO_2$, $-OC(O)(CH_2)_rCOR^{t1}$ and $-O(CH_2)-Ar^1-NO_2$ can be cleaved under reducing conditions.

For example, if Y is absent (y=0) and T is $-NO_2$ or $-BR^{t3}R^{t4}$, this can be cleaved under reducing conditions and protonolysis conditions, respectively.

Optional Self-Immolative Spacer Unit

In Formula A of the present invention, $L^3$ is an optional self-immolative spacer group that is cleaved sequentially upon cleavage of T, if present. The 1,6-elimination reaction triggered by the cleavage of the T under specific conditions in vivo separates $L^3$ from the moiety of the compound. Therefore, $L^3$ has a structure that can transfer electrons generated upon cleavage of T to the benzene ring of Formula A and PL.

In one embodiment, $-(X)_x-L^3-$ may be

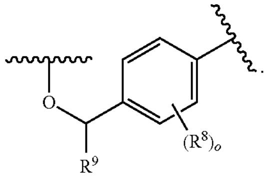

Here, $R^8$ and $R^9$ may be each independently selected from the group consisting of H, halogen, $C_{1-8}$ alkyl, CN and $NO_2$, and o may be an integer from 0 to 2. For example, $-(X)_x-L^3-$ may be derived from benzylhydroxide ($PhCH_2OH$) and a derivative thereof.

In one embodiment, one of $Z^1$ and $Z^3$ may be 0, and $-(X)_x-L^3-$ may be

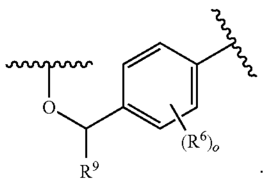

In Formula A of the present invention, i may be 0 or 1. In one embodiment, if i is 0, the self-immolative spacer group may be absent, and $-(Y)_y-T$ may be directly linked to the benzene ring.

Binding Unit

In Formula 1 of the present invention, A is absent, H or a binding functional group. If $L^1$ is present (k=1), A is H or a binding functional group, and when $L^1$ is absent (k=0), A is also absent.

The binding functional group may refer to, for example, a functional group that can be linked to, by reactions such as addition or substitution, a functional group included in a ligand or protein (E of Formula 2) or a functional group included in a linker precursor forming $L^1$ of Formula 1. That is, the binding functional group is any functional group that can provide binding between the ligand or protein (E) and $L^1$ of Formula 1, or (if $L^1$ is not present) U of Formula 1 and another linker. In the field of ligand-drug conjugates, various functional groups for binding between a ligand and a linker are known in the art. Therefore, those of ordinary skill in the art will be able to select an appropriate binding functional group considering the structure and properties of the ligand and linker, and it should be noted that the binding functional group of the present invention is not limited to the specific functional groups exemplified herein. For example, the binding functional group may bind to a ligand or protein (E) or a linker precursor having a receptor binding property by a click chemistry reaction. In one embodiment, when $L^1$ in Formula 1 is absent (i.e., k is 0), the binding functional group is further bound to a linker precursor and then may be bound to a ligand or protein (E) having a receptor binding property through the functional group included in the linker precursor. In this case, the compound of Formula 1 has the structure of "A-U", and the ligand-drug conjugate of Formula 2 has the structure of "E-linker-A-U". In another embodiment, even when $L^1$ in Formula 1 is present (i.e., k is 1), the binding functional group may be bound to an additional linker precursor to form an extended linker, which may then be bound to a ligand having a receptor binding property through the functional group included in the additional linker precursor.

Therefore, when A is a binding functional group, the compound according to Formula 1 of the present invention is intended for binding to an additional linker precursor or a ligand or protein (E) having a receptor binding property, and may be, for example, an intermediate for providing a ligand-drug conjugate. On the other hand, when A is absent or H, the compound according to Formula 1 of the present invention may be a complex comprising an active agent (PL) that is not assumed to bind to a ligand having a receptor binding property. The complex can be used for various purposes, such as changing the properties (e.g., water solubility) of the active agent, targeting, and the like.

In one embodiment, the binding functional group may comprise or consist of a functional group selected from the group consisting of halogen, OH, $C_{1-8}$ alkoxy, hydroxyamino, COH, $C_{1-8}$ alkylcarbonyl, carboxy, $C_{1-8}$ alkoxycarbonyl, tosyl, tosylate, amino, mono-$C_{1-8}$ alkylamino, di-$C_{1-8}$ alkylamino, $NHNH_2$, $N_3$, haloacetamide, maleimidyl, succinimidyl, SH, $SO_3H$, $C_{1-8}$ alkylsulfonyl,

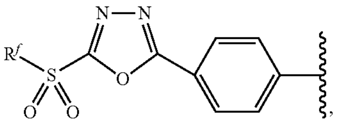

-continued

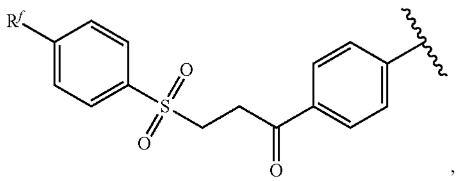
,

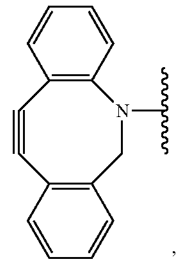
, $C_{1-8}$ alkoxysulfonyl, 2-pyridyl disulfide, $PO_3H_2$, $OPO_3H_2$, —N≡C, —NCS, $C_{4-10}$ dienyl, $C_{2-8}$ alkenyl, $C_{2-8}$ alkynyl, $C_{4-10}$ cycloalkynyl and $C_{2-8}$ alkynylcarbonyl. $R^f$ may be each independently H or $C_{1-8}$ alkyl.

In one embodiment, A may be maleimidyl, hydroxylamino, carboxy, amino, $N_3$, $C_{2-8}$ alkynyl, or

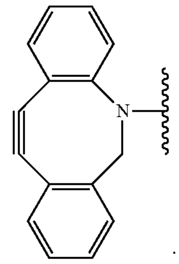
.

For example, maleimidyl may refer to a monovalent functional group in which the nitrogen atom of maleimide is linked to $L^1$ or U of Formula 1. In one embodiment, $C_{1-8}$ alkyl may be $C_{1-6}$ alkyl, $C_{1-4}$ alkyl or $C_{1-3}$ alkyl. In one embodiment, $C_{2-8}$ alkynyl may be ethynyl, propynyl (propargyl) or butynyl.

In Formula 1 of the present invention, $L^1$ is a linking group connecting A with the 5-membered ring comprising $Z^1$ to $Z^3$ of Formula A, and k is 0 or 1.

In one embodiment, when k in Formula A is 1 and $Z^1$ or $Z^3$ comprises a nitrogen atom, $L^1$ may be bound to the nitrogen atom of $Z^1$ or $Z^3$. In one embodiment, when k in Formula A is 1 and at least one of $Z^1$ to $Z^3$ comprises a carbon atom, $L^1$ may be bound to the carbon atom. For example, when $Z^2$ comprises a carbon atom, $L^1$ may be bound to the carbon atom of $Z^2$.

In one embodiment, A-$L^1$ in Formula 1 may be formed by binding between the precursor of A and the precursor of $L^1$. The binding between the precursor of A and the precursor of $L^1$ may be, but is not limited to, achieved through bond through a click chemistry reaction, amide bond, urea bond, ester bond, carbamate bond, disulfide bond, or maleimide bond.

For example, the precursor of A may include at least one functional group selected from the group consisting of hydroxy, amino, azido, alkynyl, conjugated dienyl, alkenyl, cyclooctynyl, maleimidyl, S02N3, alkoxysulfinyl, oxiranyl, aziridinyl, oxo, hydrazinyl, hydroxyamino, mercapto and 1,3-dicarbonyl. In addition, the precursor of $L^1$ may include a functional group that chemically reacts with the precursor of A to form an A-$L^1$ bond. Alternatively, a linker precursor having the structure A-$L^1$ may be bound to the remaining moiety of the compound of Formula 1.

In one embodiment, $L^1$ may be a $C_{1-200}$ alkylene optionally comprising a divalent or multivalent functional group selected from the group consisting of amide, sulfonamide, amino, ether, carbonyl, triazole, tetrazole, sugar-derived group, sulfo ester and dendrimer in the middle of the chain. The $C_{1-200}$ alkylene group may be $C_{1-150}$ alkylene group, $C_{1-100}$ alkylene group, $C_{1-80}$ alkylene group, $C_{1-60}$ alkylene group, $C_{1-50}$ alkylene group, $C_{1-40}$ alkylene group, $C_{1-30}$ alkylene group, $C_{1-20}$ alkylene group or $C_{1-10}$ alkylene group. The sugar-derived group refers to any chemical structure formed by a covalent bond between a sugar molecule and another group. For example, the sugar-derived group may include a glycosidic bond. The dendrimer refers to a well-ordered three-dimensional molecular structure having a branching unit centered on the core. In the field of ligand-drug conjugates, linkers of various dendrimeric structures are known (see, e.g., Lee, et al, Nat. Biotechnol. 2005, 23, 1517-26; Almutairi, et al; Proc. Natl. Acad. Sci. 2009, 106, 685-90), which may be advantageous, for example, to increase the ratio of ligand to drug.

In one embodiment, when $L^1$ comprises a multivalent functional group, that is, when $L^1$ comprises a branched structure or a dendrimeric structure, multiple U's may bind to $L^1$. In this case, the number of U bound to $L^1$ may be 1 to 10. In one embodiment, j may be 1 to 5. For example, j may be 1.

In one embodiment, when $Z^1$ or $Z^3$ in Formula A comprises a nitrogen atom, $L^1$ may be bound to the nitrogen atom.

In one embodiment, $L^1$ may be bound to any carbon atom of $Z^1$ to $Z^3$. For example, when $Z^2$ is a carbon atom, $L^1$ may be bound to the carbon atom of $Z^2$. In one embodiment, a functional group for the $L^1$-U bond (e.g., carboxyl group, aminocarbonyl group, amino group, etc.) may be required as a substituent for the carbon atom.

In one embodiment, $L^1$ may include $C_{1-10}$ alkylene, oxyethylene, amide, triazole ring, tetrazole ring, ether, carbonyl or a combination thereof.

In one embodiment, $L^1$ may include any one selected from the group consisting of $—(CH_2)_{na}—$; $—(CH_2CH_2O)_{ma}—$; $—(CH_2OCH_2)_{mb}—$; $—(OCH_2CH_2)_{mc}—$; —C(═O)—;

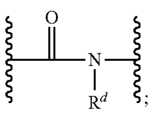
; 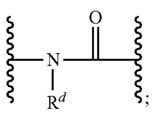
; 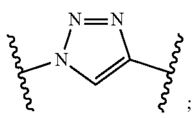
; and

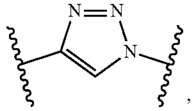
, or a combination thereof. Here, $R^d$ may be H or $C_{1-8}$ alkyl, and na and ma to me may be each independently an integer from 0 to 10. In one embodiment, na and ma to me may be each independently an integer from 1 to 8, an integer from 1 to 6, or an integer from 1 to 4. When two or more types of functional groups described above are combined with each other, the order of the functional groups is not limited.

In one embodiment, in Formula 1, k may be 1, and A-$L^1$- may be selected from the group consisting of $N_3$—$(CH_2)_{n1}$—; $N_3$—$(CH_2CH_2O)_{m1}$—$(CH_2)_{n2}$—; HO—$(CH_2CH_2O)_{m1}$—$(CH_2)_{n2}$—; $H_2N$—$(CH_2CH_2O)_{m1}$—$(CH_2)_{n2}$—; $H_2N$—O—$(CH_2CH_2O)_{m1}$—$(CH_2)_{n2}$—; $N_3$—$(CH_2CH_2O)_{m2}$—$(CH_2)_{n3}$—$NR^{d1}CO$—$(CH_2)_{n4}$—; $R^{a1}NH$—$(CH_2)_{n5}$—; $R^{b1}OC(=O)$—$(CH_2)_{n6}$—; $R^{c1}C\equiv C$—$(CH_2OCH_2)_{m3}$—$CONR^{d2}$—$(CH_2)_{n7}$—;

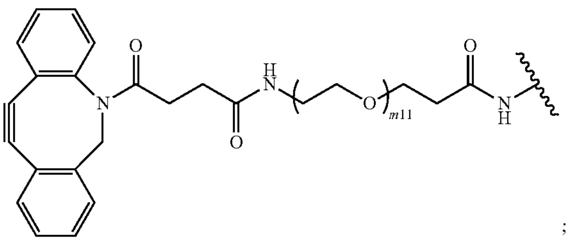

;

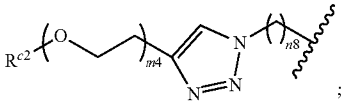

;

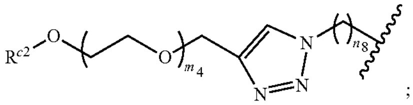

;

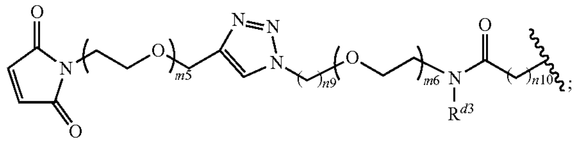

;

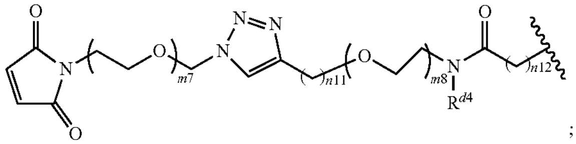

;

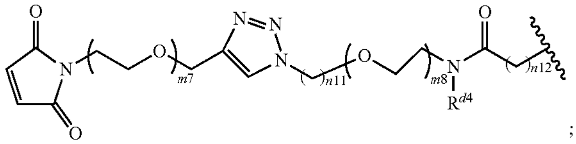

;

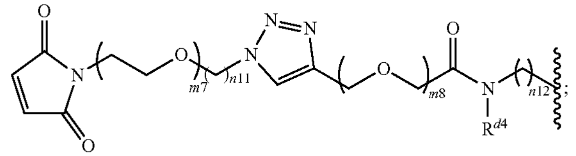

;

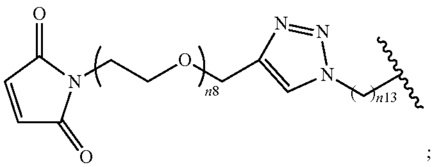

;

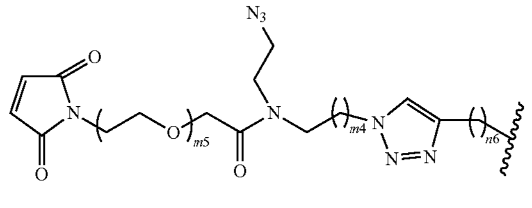

and

-continued

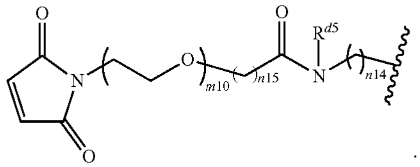

.

In this case $R^{a1}$, $R^{b1}$, $R^{c1}$, $R^{c2}$ and $R^{d1}$ to $R^{d2}$ may be each independently H or $C_{1-8}$ alkyl. In addition, n1 to n15 and m1 to m11 may be each independently an integer from 0 to 10. I n one embodiment, n1 to n15 and m11 to m11 may be each independently an integer from 0 to 8, an integer from 0 to 6, or an integer from 0 to 5. In one embodiment, n1 to n15 and m1 to m11 may be each independently an integer from 1 to 8, an integer from 1 to 6, or an integer from 1 to 5.

Exemplary Compounds of Formula 1

In one embodiment, the compound represented by Formula 1 of the present invention may be a compound represented by the following formula.

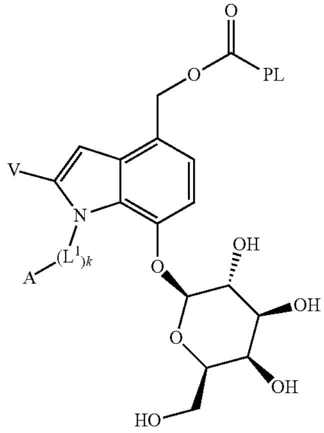

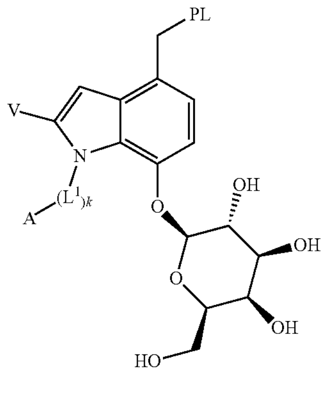

-continued
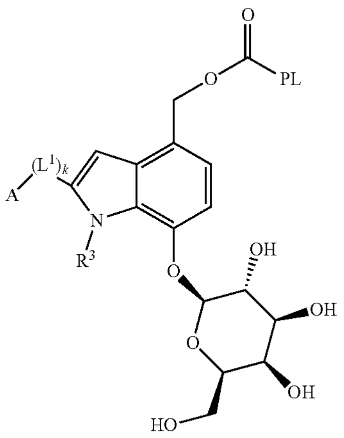
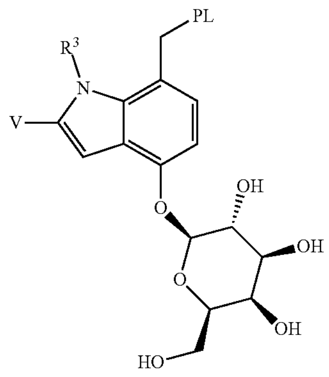
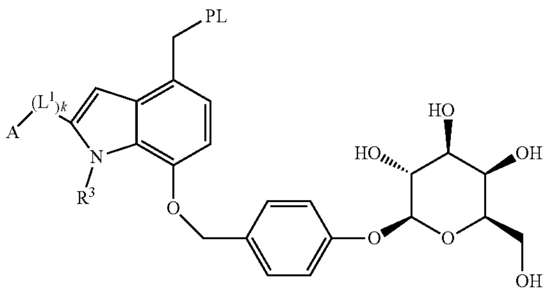
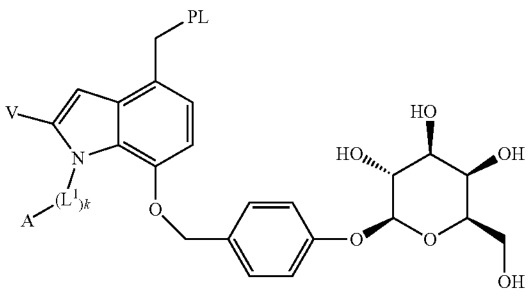
-continued
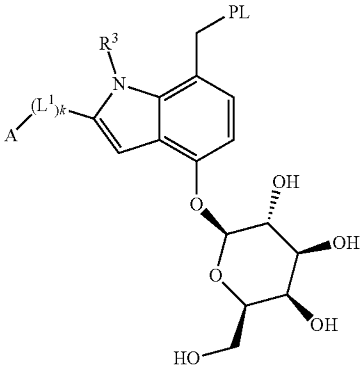
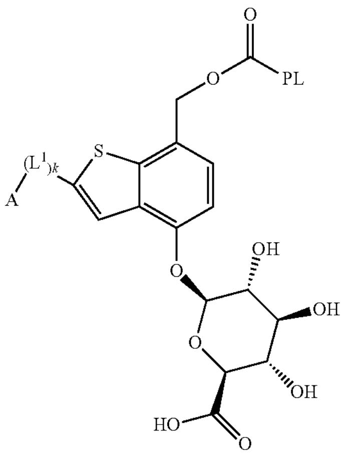
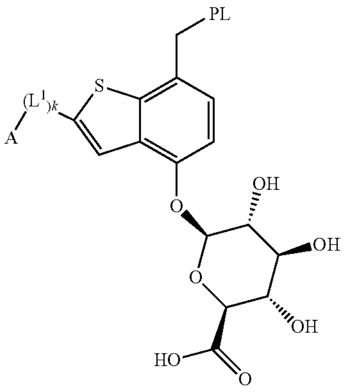
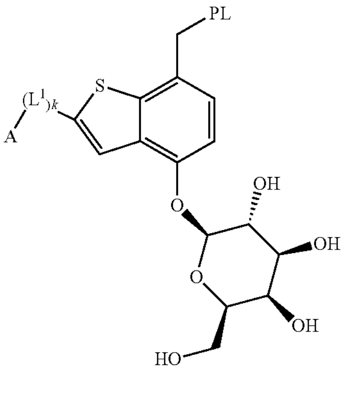

-continued
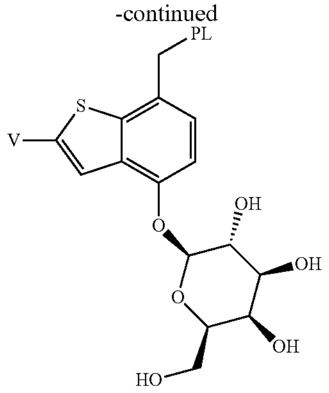
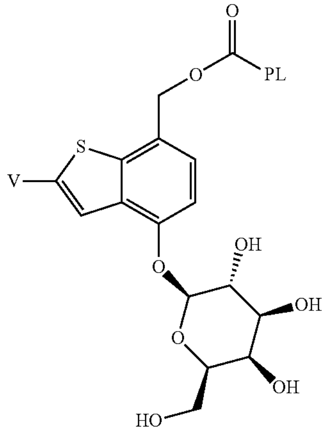
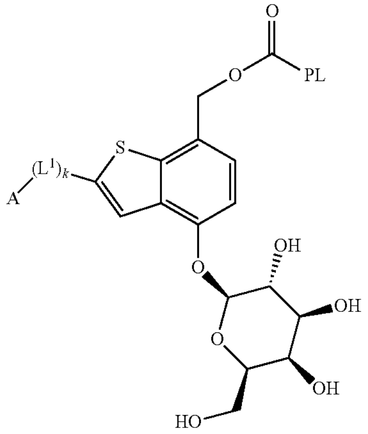
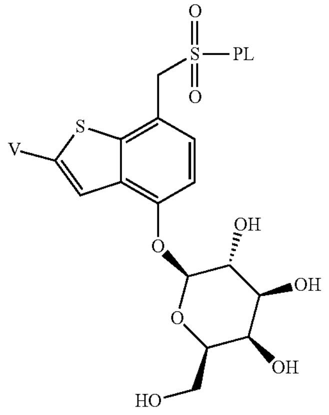
-continued
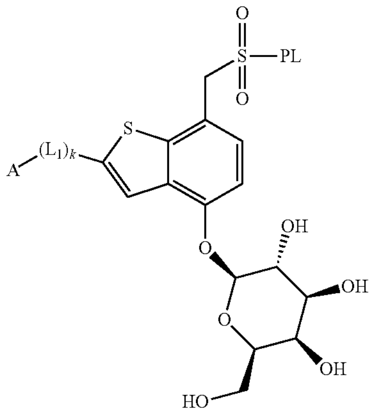
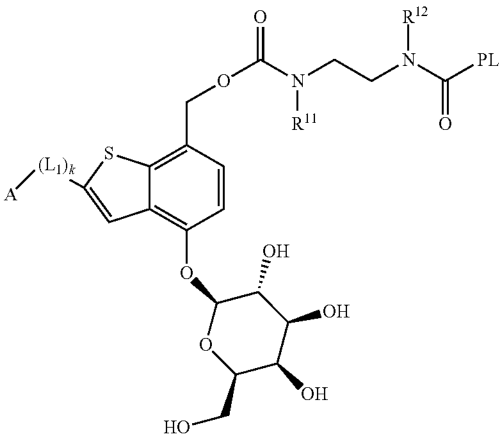
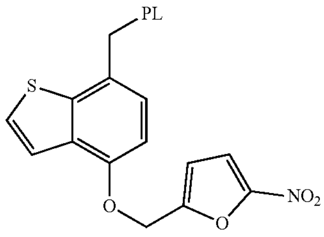
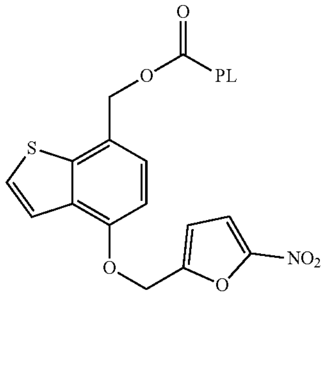

-continued
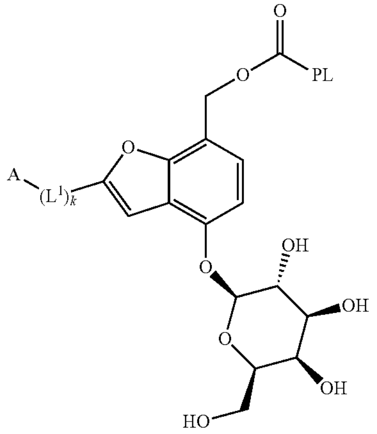
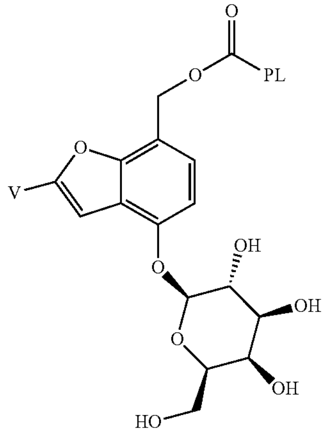
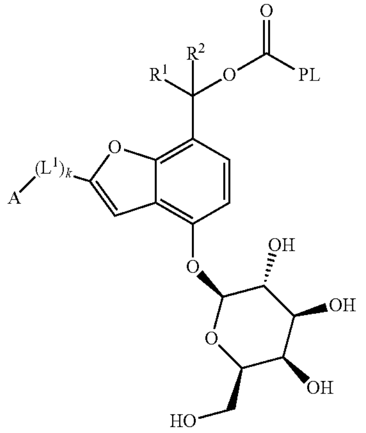
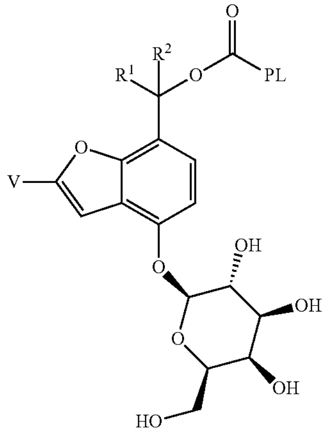
-continued
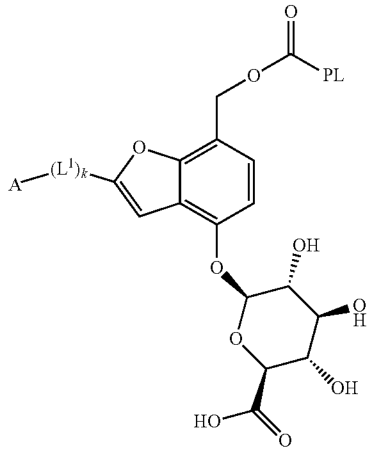
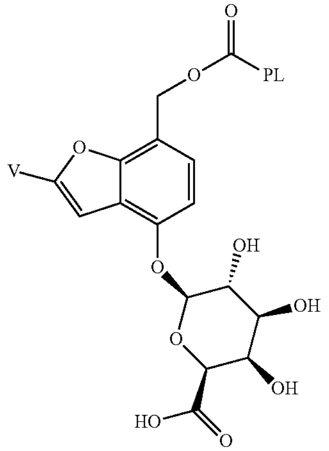
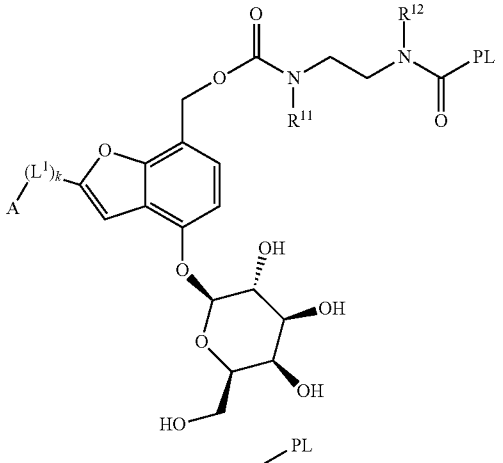
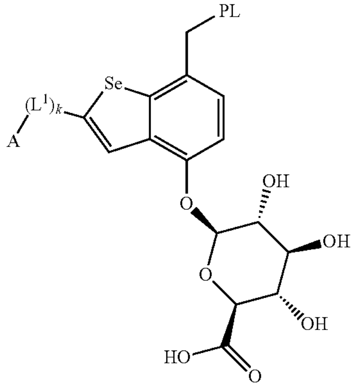

-continued
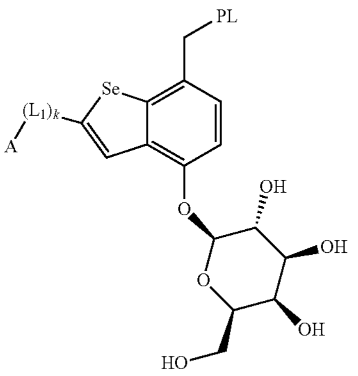
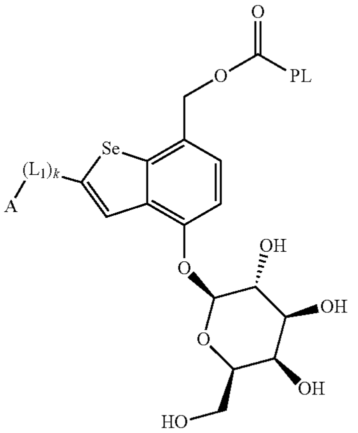
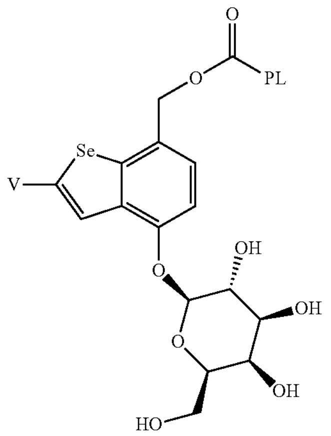
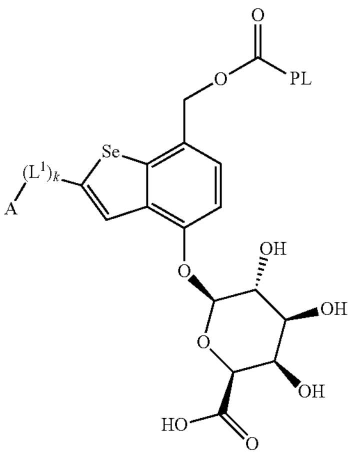
-continued
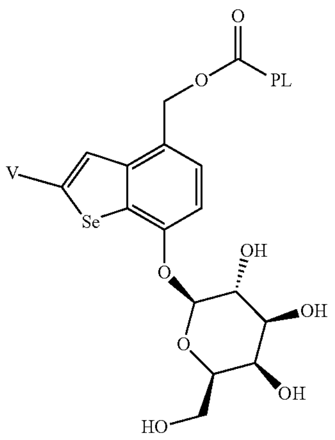
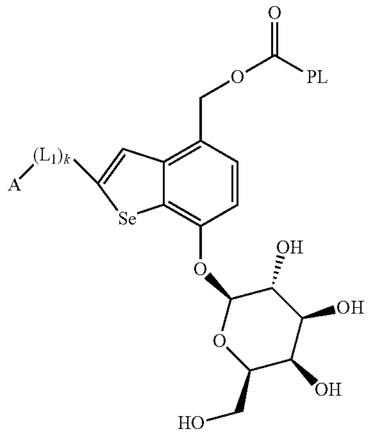
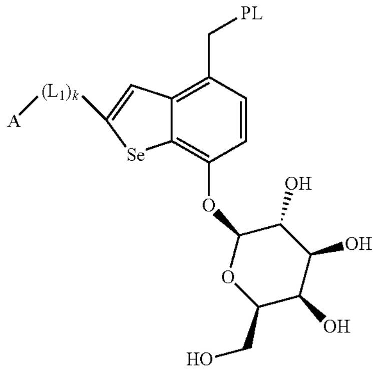
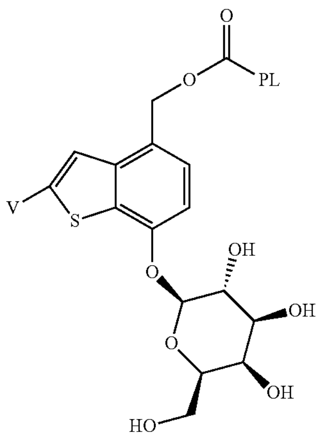

-continued

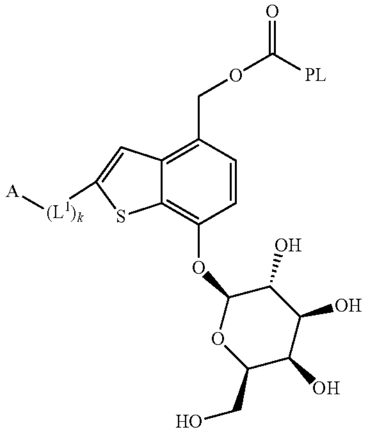

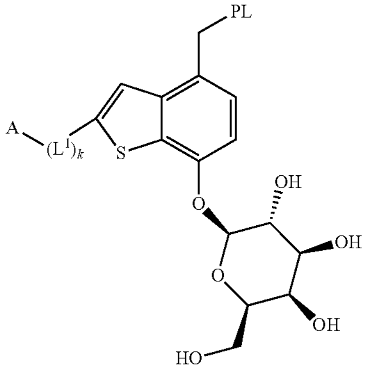

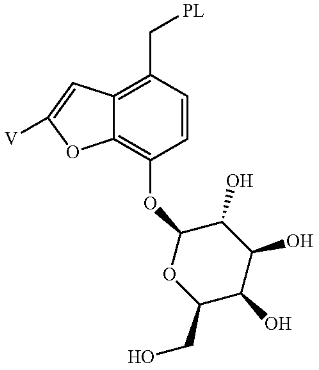

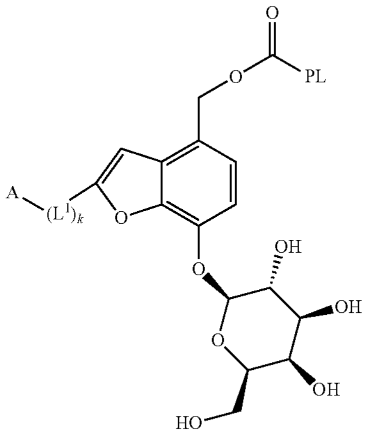

-continued

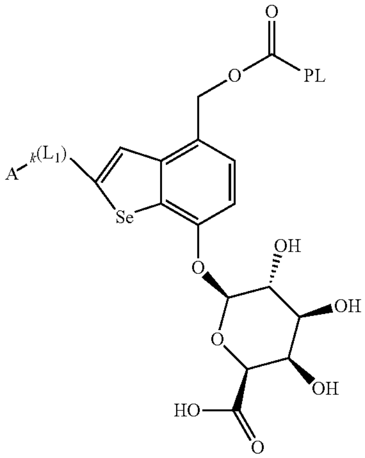

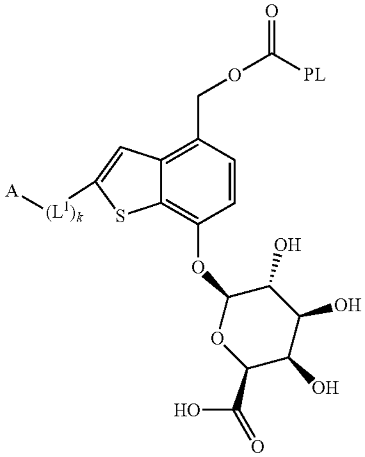

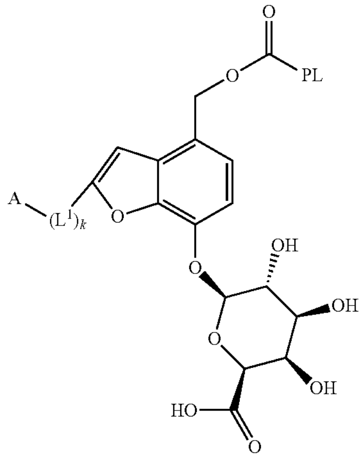

In the above formulas, A, $L^1$, k, V, $R^1$, $R^2$, $R^3$, $R^{11}$, $R^{12}$ and PL are as described above with respect to Formula 1.

The combinations of the structures A-$(L^1)_k$-, V, $L^2$, -$(X)_x$-$L^3$- and -$(Y)_y$-T- shown in the above formula are merely exemplary, and the compounds of Formula 1 having various combinations thereof can be easily prepared based on the examples described below and the disclosure of the present application. It should be understood that all such compounds fall within the scope of the present application.

In one embodiment, the compound represented by Formula 1 of the present invention may carry one PL. In this case, for example, the compound represented by Formula 1 may be selected from the group consisting of the compounds shown in Table A attached.

In one embodiment, a DAR2 type compound may include a functional group capable of forming a bond with a ligand, such as an antibody, for the preparation of a ligand-drug conjugate, such as a maleimide functional group. Examples of these compounds are shown in Table B attached.

DAR4 Type Compound (Formula 1-1)

In one embodiment, when the linking group $L^1$ of Formula 1 according to the present invention has a branched structure or a dendrimeric structure (i.e., when $L^1$ is a multivalent linking group), a compound of Formula 1 to which two or more active agents are bound can be provided.

In one embodiment, the compound represented by Formula 1 may be a compound represented by Formula 1-1 below.

[Formula 1-1]

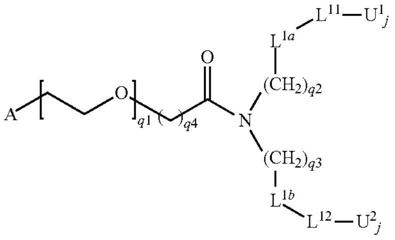

In Formula 1-1, A has the same meaning as in Formula 1.

In Formula 1-1, $U^1$ and $U^2$ each have the same meaning as U in Formula 1, wherein $U^1$ and $U^2$ may be the same or different from each other.

In Formula 1-1, $L^{11}$ and $L^{12}$ each have the same meaning as $L^1$ in Formula 1, wherein $L^{11}$ and $L^{12}$ may be the same or different from each other.

In Formula 1-1, j is 1 to 10. In one embodiment, j is 1 to 5. For example, j is 1.

With respect to Formula A, $L^1$ and U, the matters described in Formula 1 may be equally applied to A, $U^1$ and $U^2$, and $L^{11}$ and $L^{12}$ in Formula 1-1, respectively, if applicable.

In Formula 1-1, $L^{1a}$ and $L^{1b}$ may be each independently selected from a direct bond;

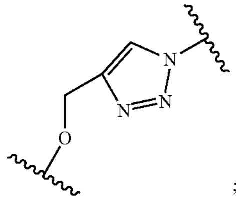 ; 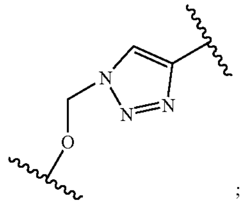 ;

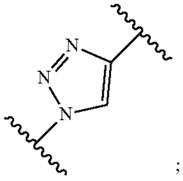 ; 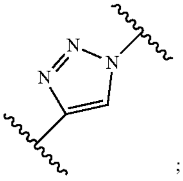 ;

-continued

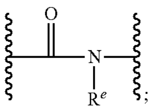 ; and 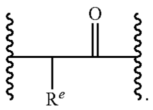 .

In this case, $R^e$ may be H or $C_{1-8}$ alkyl.

In Formula 1-1, q1, q2 and q3 may be each independently an integer from 0 to 10. In Formula 1-1, q4 may be an integer from 1 to 10. Further, if $L^{1a}$ is

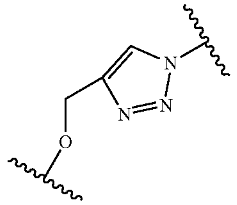 or 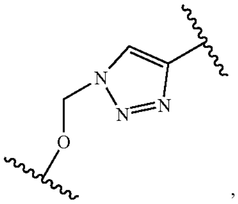 , q2 is not 0, and if $L^{1b}$ is

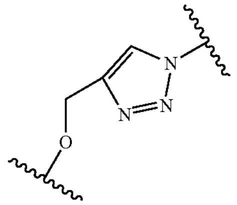 or 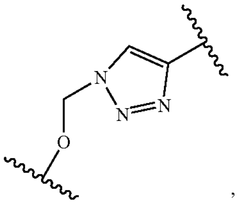 , q3 is not 0. In one embodiment, if $L^{1a}$ and/or $L^{1b}$ are a direct bond and q2 and q3 are 0, then a linker structure of $L^{11}$ and $L^{12}$, such as a $C_{1-200}$ alkylene optionally comprising a divalent or multivalent functional group selected from amide, sulfonamide, amino, ether, carbonyl, triazole, tetrazole, sugar-derived group, sulfoester and dendrimer in the middle of the chain may be directly bound to the central N atom.

In one embodiment, q1 may be an integer from 0 to 8, an integer from 1 to 8, or an integer from 1 to 6. In one embodiment, q2 and q3 may be each independently an integer from 0 to 8, an integer from 0 to 6, or an integer from 0 to 4. In one embodiment, q4 may be an integer from 1 to 8, an integer from 1 to 6, or an integer from 1 to 4.

In one embodiment,

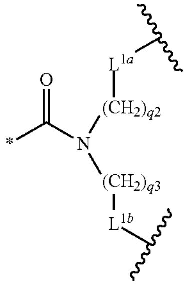

in Formula 1-1 above may be selected from the following structures:

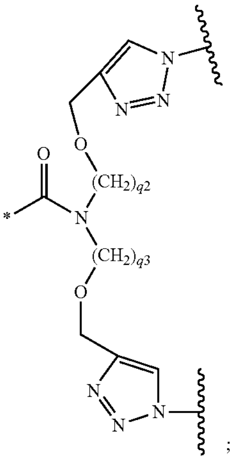
;
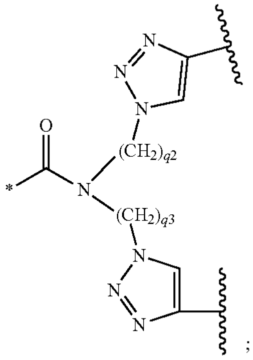
;
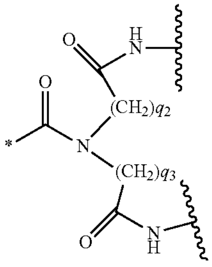
and
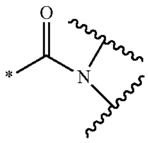

(where the definitions of q2 and q3 are as described above.)

In one embodiment, A in Formula 1-1 above may comprise or consist of a functional group selected from the group consisting of halogen, OH, $C_{1-8}$ alkoxy, hydroxylamino, COH, $C_{1-8}$ alkylcarbonyl, carboxy, $C_{1-8}$ alkoxycarbonyl, tosyl, tosylate, amino, mono-$C_{1-8}$ alkylamino, di-$C_{1-8}$ alkylamino, $NHNH_2$, $N_3$, haloacetamide, maleimidyl, succinimidyl, SH, $SO_3H$, $C_{1-8}$ alkylsulfonyl,

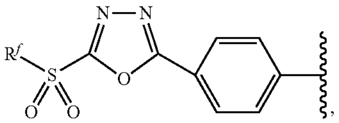
,
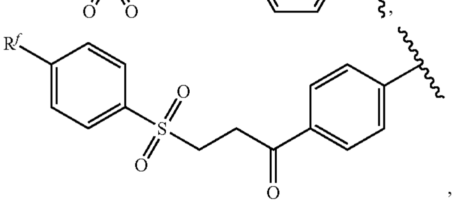
,
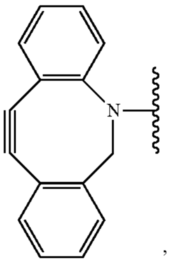
, $C_{1-8}$ alkoxysulfonyl, 2-pyridyl disulfide, $PO_3H_2$, $OPO_3H_2$, —N—C, —NCS, $C_{4-10}$ dienyl, $C_{2-8}$ alkenyl, $C_{2-8}$ alkynyl, $C_{4-10}$ cycloalkynyl and $C_{2-8}$ alkynylcarbonyl. R may be each independently H or $C_{1-8}$ alkyl. For example, A in Formula 1-1 may be maleimidyl, hydroxylamino, carboxy, amino, N3, alkynyl, or

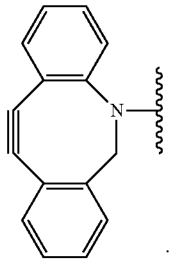 [SMILES: *N1Cc2ccccc2C#Cc2ccccc21]
.

In one embodiment, $L^{11}$ and $L^{12}$ may be each independently a $C_{1-200}$ alkylene optionally comprising a divalent or multivalent functional group selected from the group consisting of amide, sulfonamide, amino, ether, carbonyl, triazole, tetrazole, sugar-derived group, sulfo ester and dendrimer in the middle of the chain. The $C_{1-200}$ alkylene group may be a $C_{1-150}$ alkylene group, a $C_{1-100}$ alkylene group, a $C_{1-80}$ alkylene group, a $C_{1-60}$ alkylene group, a $C_{1-50}$ alkylene group, a $C_{1-40}$ alkylene group, a $C_{1-30}$ alkylene group, a $C_{1-20}$ alkylene group or a $C_{1-10}$ alkylene group.

In one embodiment, $L^{11}$ and $L^{12}$ may each independently include any one selected from the group consisting of $—(CH_2)_{na}—$; $—(CH_2CH_2O)_{ma}—$; $—(CH_2OCH_2)_{mb}—$; $—(OCH_2CH_2)_{mc}—$; —C(═O)—;

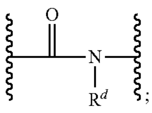
;
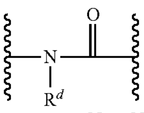
;
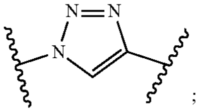
; and
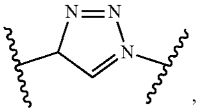
, or a combination thereof. Here, $R^d$, na, ma to me are as described above with respect to Formula 1.

In one embodiment, $L^{11}$ and $L^{12}$ may be each independently selected from $—(CH_2)_{n1}—$; $—(CH_2CH_2O)_{m1}—(CH_2)_{n2}—$; $—(CH_2CH_2O)_{m2}—(CH_2)_{n3}—NR^{d1}CO—(CH_2)_{n4}—$; $—(CH_2CH_2O)_{m10}—(CH_2)_{n15}—CONR^{d5}—(CH_2)_{n14}—$; and

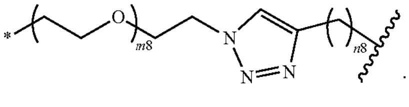
.

Here, n1, n2, n3, n4, n8, n14 and n15, and m1, m2, m8 and m10 may be each independently an integer from 1 to 8, an integer from 1 to 6 or an integer from 1 to 5. In addition, $R^{d1}$ and $R^{d5}$ are each independently H or $C_{1-8}$ alkyl.

In one embodiment, the compound represented by Formula 1-1 (where j is 1) may be a compound represented by the following formula:

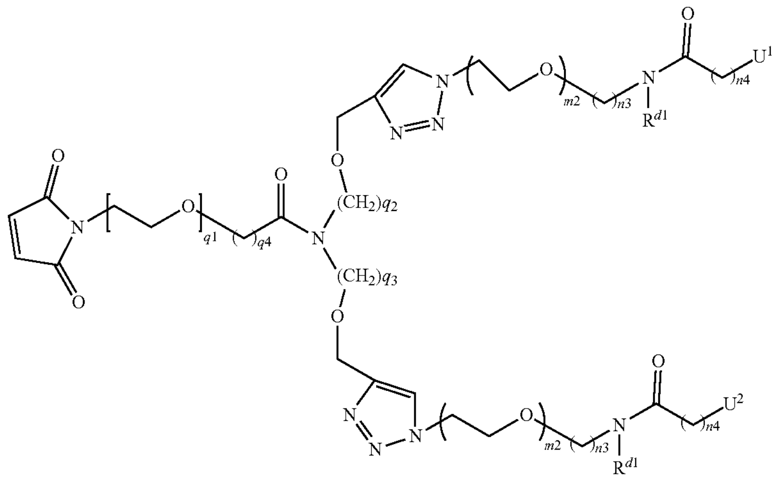
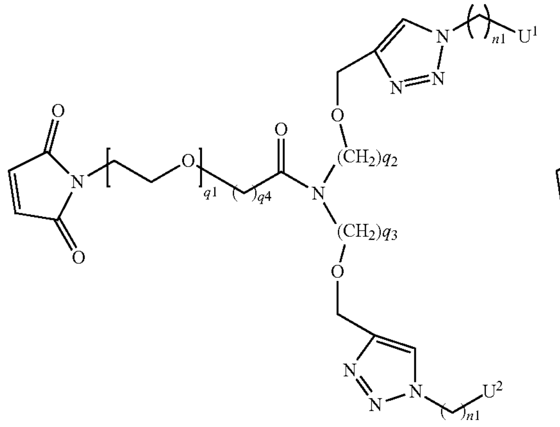
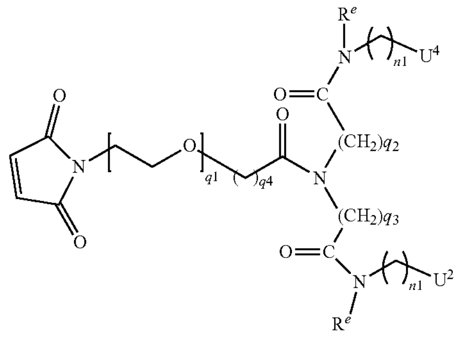
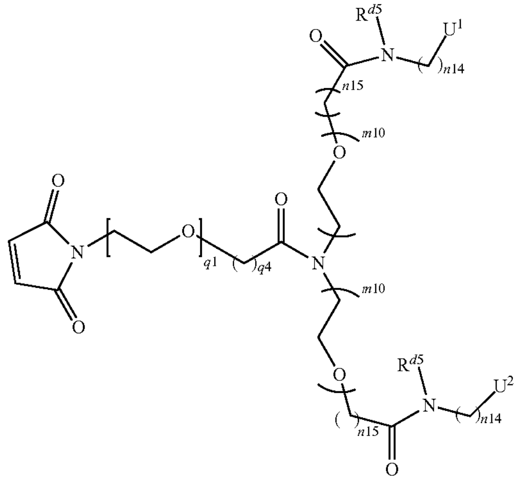
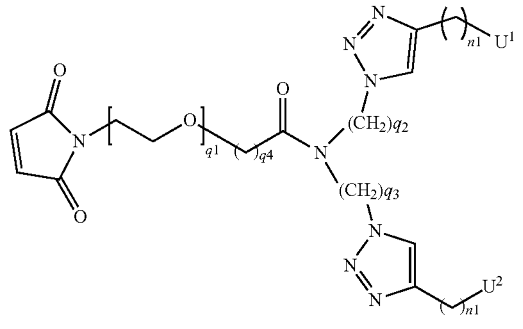

-continued
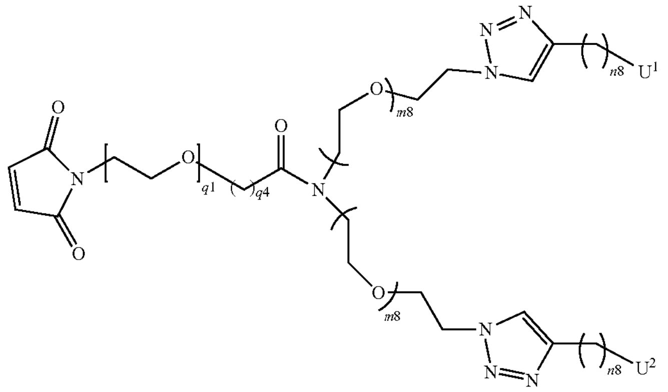
(in the above formulas, q1 to q4, $U^1$, $U^2$ n1, n3, n4, n8, n14 and n15, and m2, m8 and m10 are as described above with respect to Formula 1-1. In addition, $R^{d}$i Ras and $R^e$ are each independently H or $C_{1-8}$ alkyl.)
In one embodiment, the compound represented by Formula 1-1 may be a compound represented by the following formula:
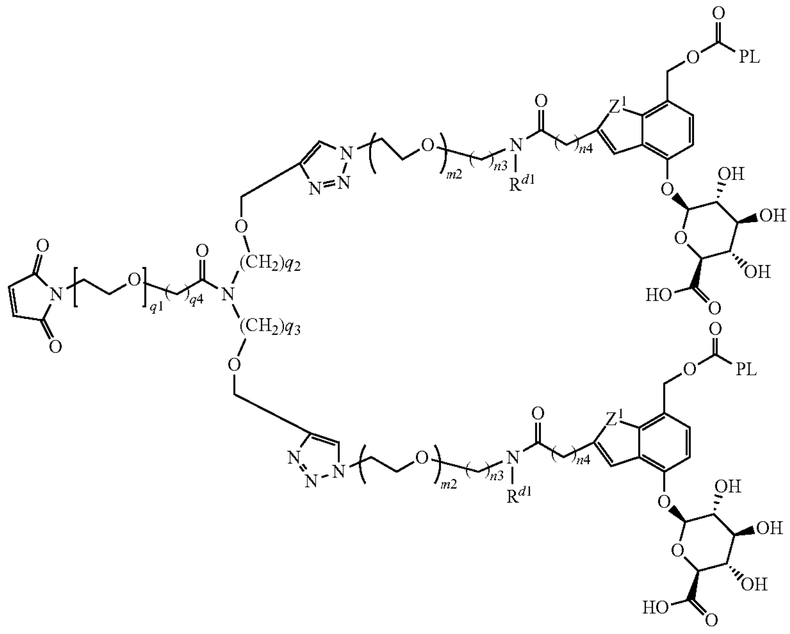

-continued
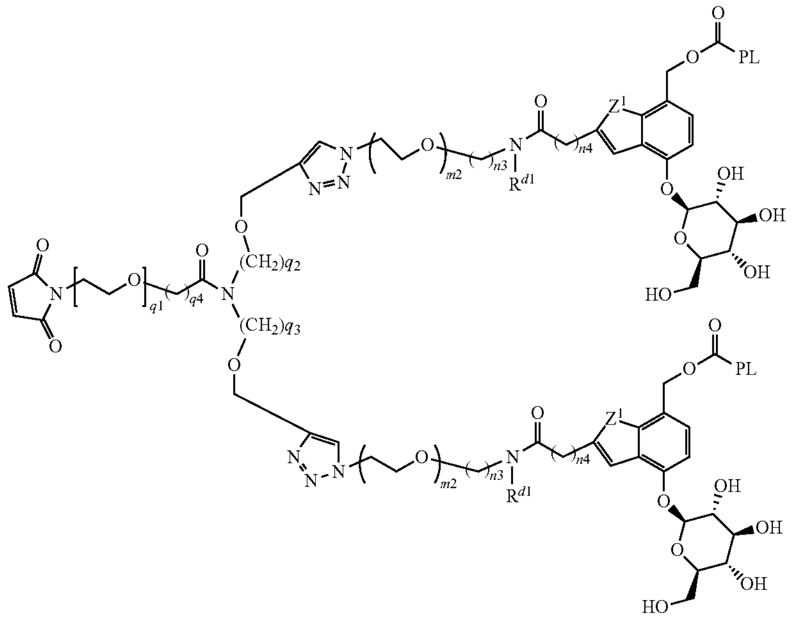
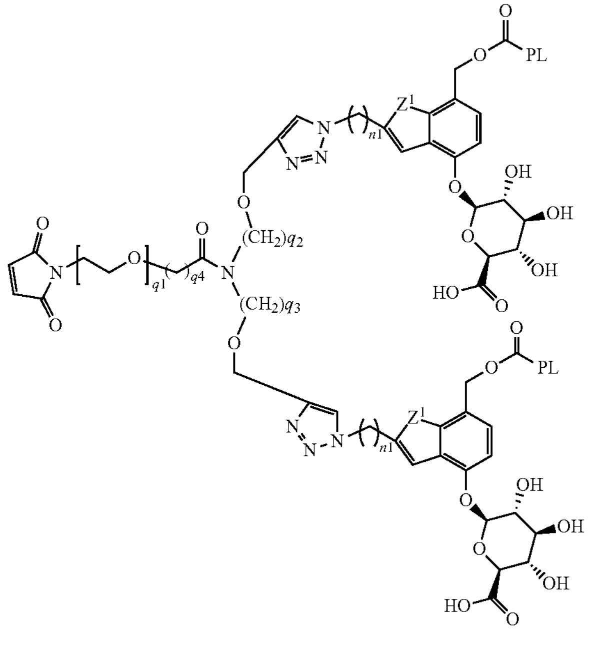
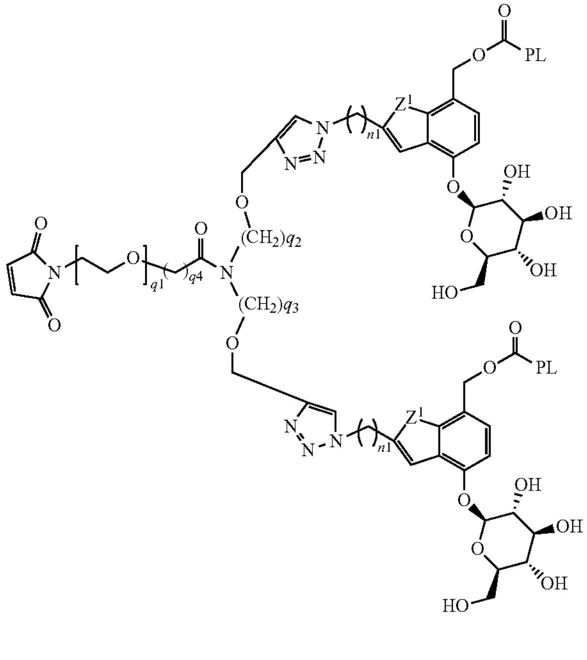

-continued

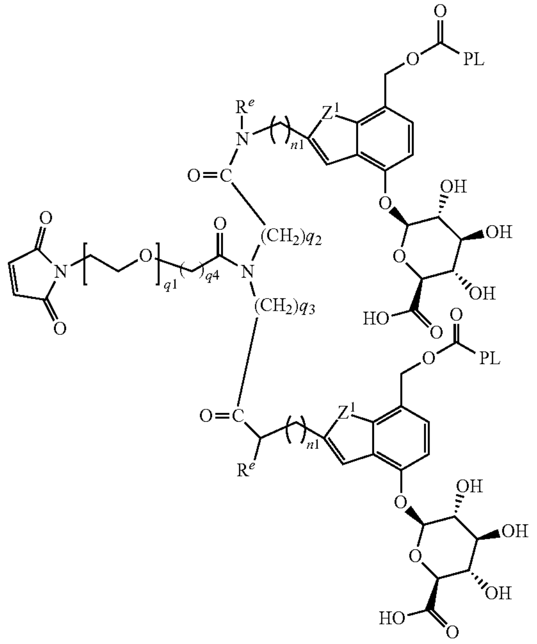

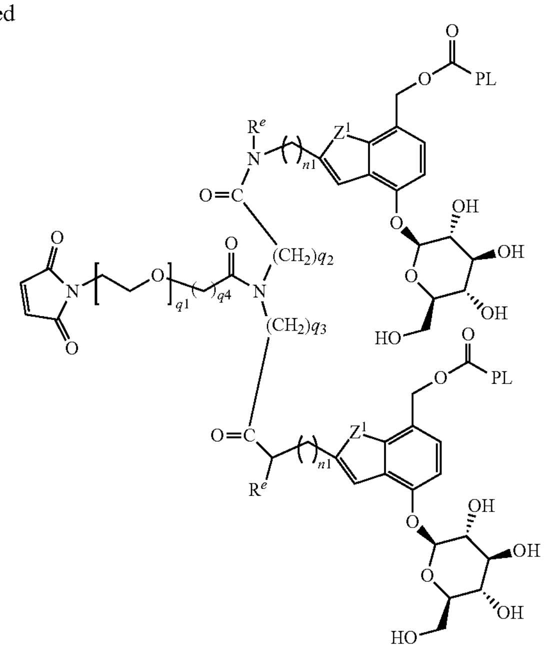

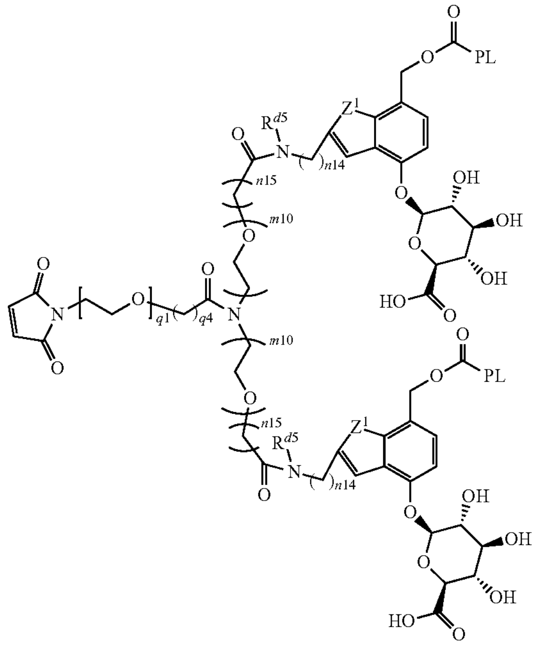

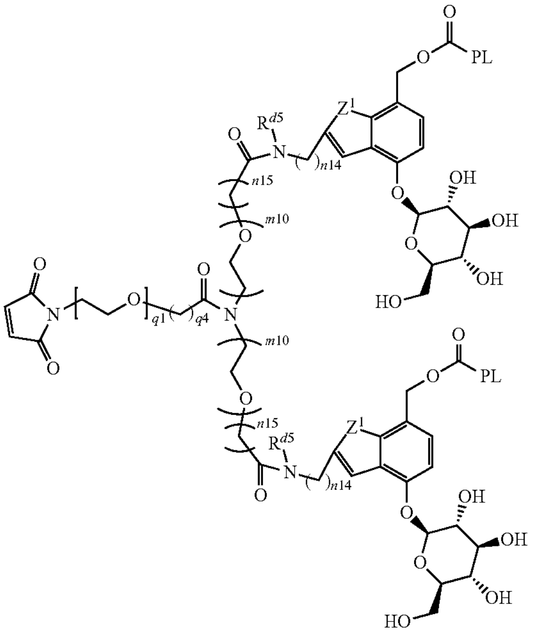

In the above formulas, q1 to q4, n1, n3, n4, n14 and n15, m2 and m10, $R^{d1}$, $R^{d5}$ and $R^e$ are as described above. In the above formulas, PL has the same meaning as PL in Formula 1. In the above formulas, $Z^1$ is a heteroatom selected from $NR^3$, O, S and Se. $R^3$ is H or $C_{1-8}$ hydrocarbyl.

In the above formulas, the —O—CO— group in the —O—CO-PL group is an optional self-immolative spacer group, and may be absent (i.e., the -PL group is directly linked to the —$CH_2$— group) or may be replaced with the functional groups described above with respect to an "optional self-immolative spacer group".

In one embodiment, the compound represented by Formula 1-1 may be selected from the compounds listed in Table C attached.

Method for Preparing a Compound of Formula 1

The compound comprising the self-immolative group of Formula 1 according to the present invention can be easily prepared by selecting an appropriate solvent, starting material, intermediate, reaction conditions, and the like based on the examples herein and the technical knowledge of those of ordinary skill in the art of organic synthesis.

In one embodiment, a compound of Formula 1 having an indole core and a β-galactoside triggering group can be prepared according to Reaction Scheme 1 below.

[Reaction Scheme 1]

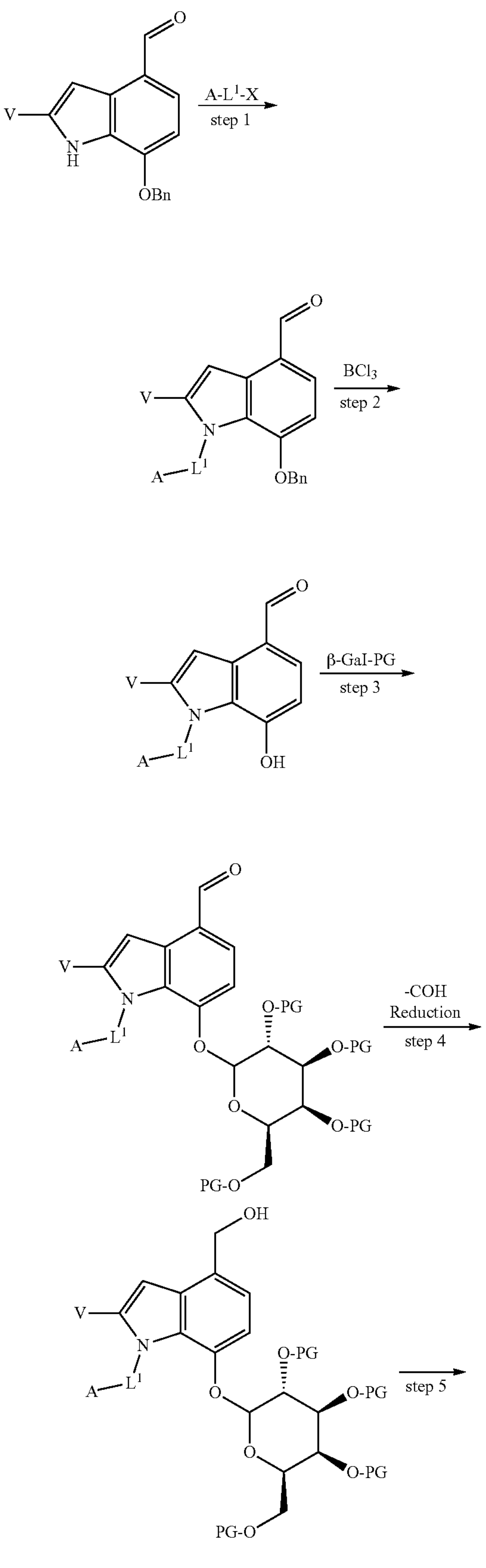

-continued

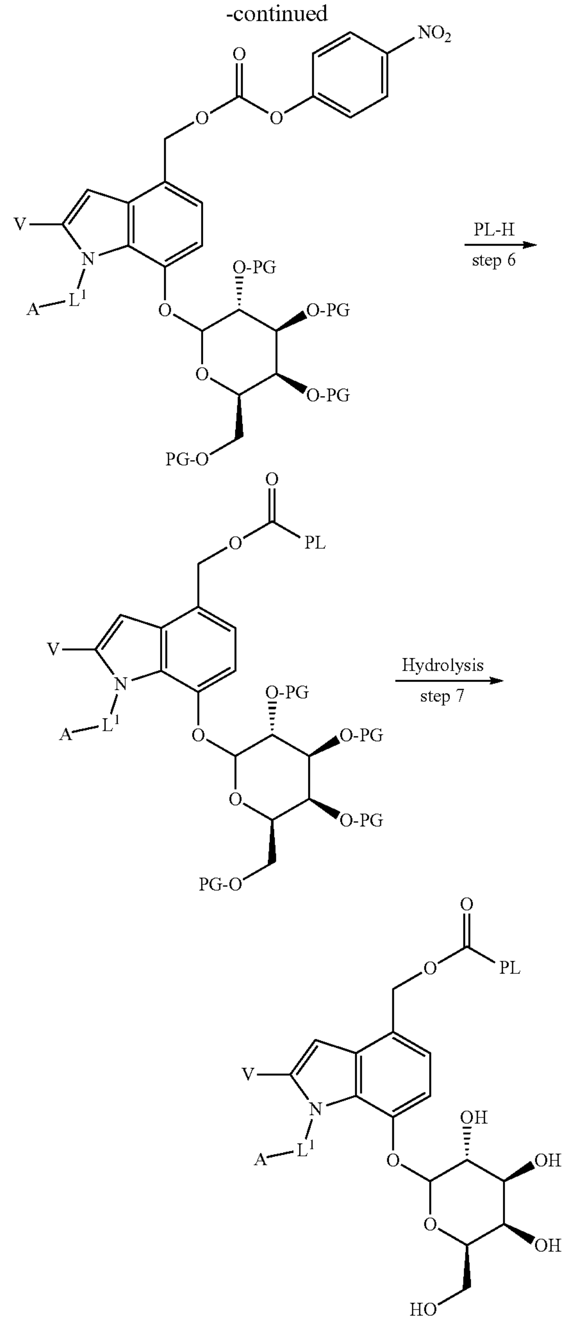

In Step 1 of Reaction Scheme 1, an indole starting material with COH and OBn substituted at the para position of the benzene ring can be prepared and reacted with A-$L^1$-X (where X is halogen: Cl, Br, etc.) to introduce A-$L^1$- to the nitrogen atom of the indole. In the reaction of Step 1, additives such as potassium carbonate can be used. Step 1 may be performed under temperature conditions of 40° C. to 100° C., 60° C. to 100° C., or 60° C. to 90° C.

In Step 2, OBn can be converted to OH using boron trichloride. Step 2 may be performed under low temperature conditions of, for example, −90° C. to 0° C., −90° C. to −10° C., −90° C. to −20° C., −80° C. to 0° C., −80° C. to −10° C., or −80° C. to −20° C.

In Step 3, galactose can be introduced where the hydroxyl group is protected with a protecting group (-PG). For example, a protected galactoside group such as an acetogalactoside group can be introduced through reaction with galactose into which a protecting group has been introduced, such as acetylated galactose or acetobromo-alpha-D-galactose. In the reaction of Step 3, additives such as benzyltributylammonium chloride, HOBt, pyridine, DIPEA, and the like may be used. In addition, additives such as silver oxide and molecular sieve may be used. Step 3 may be performed under temperature conditions of −40° C. to 40° C., −40° C. to 30° C., −20° C. to 40° C., −20° C. to 30° C., −10° C. to 40° C., or −10° C. to 30° C.

In Step 4, COH linked to the benzene ring can be reduced. The reduction reaction may be performed under low temperature conditions of −40° C. to 10° C., −40° C. to 0° C., −30° C. to 10° C., −30° C. to 0° C., −20° C. to 10° C., or −20° C. to 0° C. through a reducing agent such as sodium borohydride ($NaBH_4$).

In Step 5, the —OCO— self-eliminating linker structure can be introduced. As a precursor for the —OCO— linking group, bis(4-nitrophenyl) carbonate, 4-nitrophenyl chloroformate, and the like may be used. In the reaction of Step 5, additives such as DIPEA and pyridine may be used.

Step 5 may be performed under low temperature conditions of −40° C. to 10° C., −40° C. to 0° C., −30° C. to 10° C., −30° C. to 0° C., −20° C. to 10° C., or −20° C. to 0° C.

In Step 6, PL can be introduced. For example, PL can be introduced by replacing a precursor such as PL-H for a leaving group (e.g., p-nitrophenyl) linked to —OCO—. In the reaction of Step 6, additives such as HOBt, pyridine, and DIPEA may be used depending on the type of PL.

Step 6 may be performed under low temperature conditions of −40° C. to 10° C., −40° C. to 0° C., −30° C. to 10° C., −30° C. to 0° C., −20° C. to 10° C., or −20° C. to 0° C.

In Step 7, the protecting group of the protected galactoside can be deprotected through hydrolysis, thereby converting it to galactoside. Hydrolysis may be performed with an acid such as hydrochloric acid or a base such as potassium carbonate, sodium hydroxide, or lithium hydroxide. Step 7 may be performed under temperature conditions of −40° C. to 40° C., −40° C. to 30° C., −20° C. to 40° C., −20° C. to 30° C., −10° C. to 40° C., or −10° C. to 30° C.

Each step in Reaction Scheme 1 may be performed in an appropriate solvent selected from the group consisting of organic solvents such as methanol, DMF, MC, ACN, THF, EA, and distilled water. In addition, after the completion of the reaction at each step, the product may be purified through dilution, extraction, and chromatography using the appropriate solvent. In one embodiment, each step of Reaction Scheme 1 may be performed under a nitrogen atmosphere.

In one embodiment, depending on PL, A, $L^1$ and V, some steps in Reaction Scheme 1 may be omitted. For example, if PL can react with a hydroxymethyl group directly linked to the benzene ring even in the absence of —OCO— or can be bound to a methyl group, Step 5 may be omitted.

Ligand-Drug Conjugate Represented by Formula 2

In one aspect of the present invention, there is provided a ligand-drug conjugate represented by Formula 2 below, or a pharmaceutically acceptable salt thereof:

[Formula 2]

$$E\text{—}[A'\text{—}(L^1)_k\text{—}U_j]_n$$

in Formula 2, E is a ligand or protein having a receptor binding property.

The compound of Formula 1 according to the present invention can be bound to a ligand or protein (E) having a receptor binding property to provide a ligand-drug complex of Formula 2. The ligand or protein (E) may be optionally modified for binding to the binding functional group of compound of Formula 1. In one embodiment, when Ligand E is an antibody, a moiety such as —SH of cysteine, $-NH_2$ of lysine, $-C(=O)NH_2$ of glutamine, $-C_6H_4-OH$ of tyrosine, —SeH of selenocysteine, and $-N_3$ and $-\equiv$ of unnatural amino acids present at specific positions of the antibody and the binding functional group of the compound of Formula 1 may be bound to each other. In the field of ligand-drug complexes, the types and modifications of functional groups of a ligand for binding a linker-drug moiety to a ligand or protein are known in the art.

The ligand may be selected from the group consisting of peptides, tumor cell-specific peptides, tumor cell-specific aptamers, tumor cell-specific carbohydrates, tumor cell-specific monoclonal or polyclonal antibodies, and antibody fragments.

In one embodiment, the protein may be selected from the group consisting of $C_{1-20}$ hydrocarbyl, oligopeptide, polypeptide, antibody, fragment of antigenic polypeptide, and artificial antibody (Repebody). In one embodiment, the C-terminus of the protein may be the light or heavy chain of an antibody.

In one embodiment, the antibody may be selected from the group consisting of an intact polyclonal antibody, an intact monoclonal antibody, an antibody fragment, a single chain Fv (scFv) mutant, a multispecific antibody, a bispecific antibody, a chimeric antibody, a humanized antibody, a human antibody, a fusion protein comprising an antigen determination portion of an antibody, and other modified immunoglobulin molecules comprising an antigen recognition site.

In one embodiment, the antibody may be selected from the group consisting of Muromonab-CD3, Abciximab, Rituximab, Daclizumab, Palivizumab, Infliximab, Trastuzumab (herceptin), Etanercept, Basiliximab, Gemtuzumab, Alemtuzumab, Ibritumomab, Adalimumab, Alefacept, Omalizumab, Efalizumab, Tositumomob-I131, Cetuximab, Bevacizumab, Natalizumab, Ranibizumab, Panitumumab, Eculizumab, Rilonacept, Certolizumab pegol, Romiplostim, AMG-531 (Romiplostim), CNTO-148 (Golimumab), CNTO-1275 (Ustekinumab), ABT874 (Briakinumab), LEA-29Y (Belatacept), Belimumab, TACI-Ig (transmembrane active agent and calcium modulator and cyclophilin ligand interactor-immunoglobulin), second generation anti-CD20, ACZ-885 (Canakinumab), Tocilizumab, Atlizumab, Mepolizumab, Pertuzumab, Humax CD20 (Ofatumumab), Tremelimumab (CP-675 206), Ticilimumab, MDX-010 (Ipilimumab), IDEC-114 (Galiximab), Inotuzumab, HuMax EGFR (Zalutumumab), Aflibercept (VEGF Trap-Eye), HuMax-CD4 (Zanolimumab), Ala-Ala (hOKT3gamma1), Otelixizumab (ChAglyCD3; TRX4), Catumaxomab, MT-201 (Adecatumumab), Pregovomab, CH-14.18 (Dinutuximab), WXG250 (Girentuximab), AMG-162 (Denosumab), AAB-001 (Bapineuzumab), Motavizumab, MEDI524 (Motavizumab), Efumgumab, Aurograb®, Raxibacumab, third generation anti-CD20, LY2469298 (Ocaratuzumab), and Veltuzumab.

In one embodiment, the antibody may be a monoclonal antibody (mAb).

In Formula 2 above, A' is a divalent linking group derived from the binding functional group (A) of Formula 1. For example, A' may include a functional group formed by an addition reaction of a double bond included in the binding functional group. In one embodiment, when the binding functional group is maleimidyl, A' may be a functional group formed by participating in an addition reaction of a double bond in the 5-membered ring of the maleimidyl. The matters regarding the binding functional group (A) of Formula 1 described above may be equally applied to A', if applicable.

In one embodiment, Ligand E may be an antibody. For example, the antibody may include a functional group that binds to A in Formula 1 to form the E-A' binding structure in Formula 2.

If necessary, a functional group for the above binding can be introduced into the antibody, and the types of such functional groups and methods of introducing the functional groups are known in the art.

In one embodiment, the binding structure of Ligand E and A' may be represented by a moiety represented by one of the following formulas. In the formulas below, * may be the remaining moiety of the antibody. In the formulas below, the S, NH, CONH, $C_6H_3$—OH, Se and triazole ring moieties directly linked to * may be derived from a moiety such as —SH of cysteine, —$NH_2$ of lysine, —C(═O)$NH_2$ of glutamine, —$C_6H_4$—OH of tyrosine, —SeH of selenocysteine, and —$N_3$ and —≡ of unnatural amino acids present at specific positions of Ligand E.

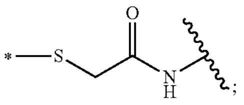
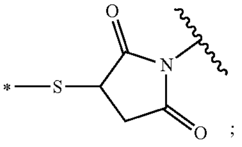
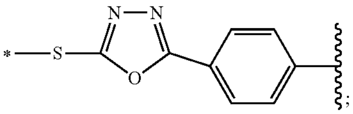
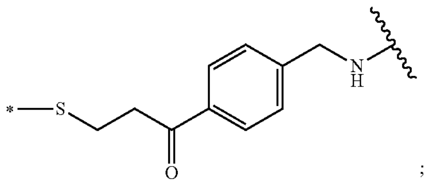
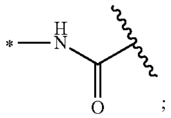
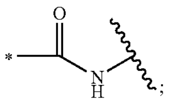
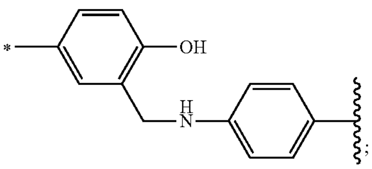

-continued

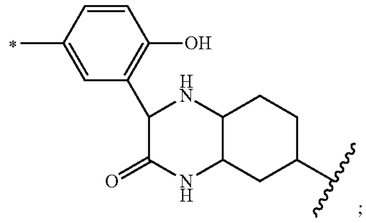
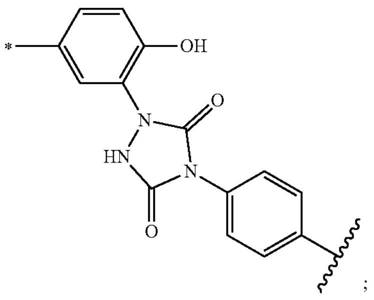
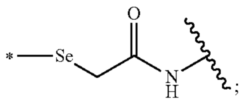
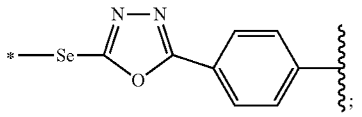
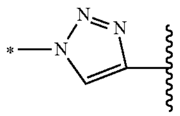
and
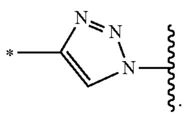

In Formula 2, n may be a real number from 1 to 10. For example, n may be a real number from 1 to 6, a real number from 1 to 4, or a real number from 1 to 2.

In Formula 2, U, $L^1$, k and j may be the same as U, $L^1$, k and j in Formula 1. The matters regarding U, $L^1$, k and j in Formula 1 described above may be equally applied to U, $L^1$, k and j in Formula 2, if applicable. In one embodiment, when E of Formula 2 above is an antibody and PL of U is a drug, the compound represented by Formula 2 may be provided as an antibody-drug conjugate.

In one embodiment, the conjugate represented by Formula 2 may be selected from the group consisting of conjugates represented by the following formulas:

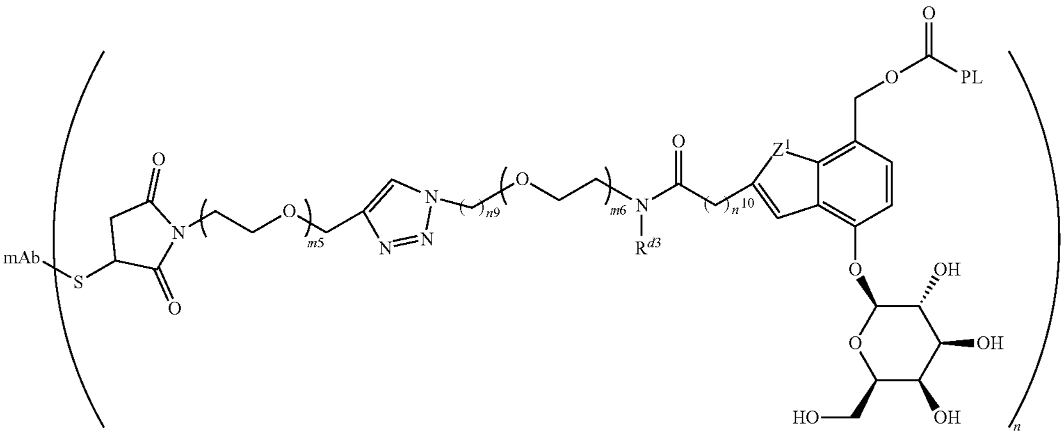
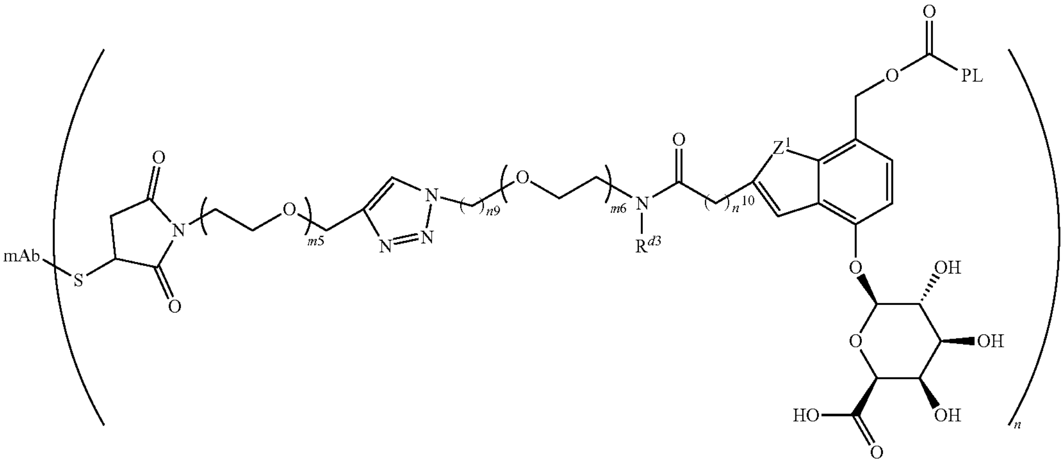
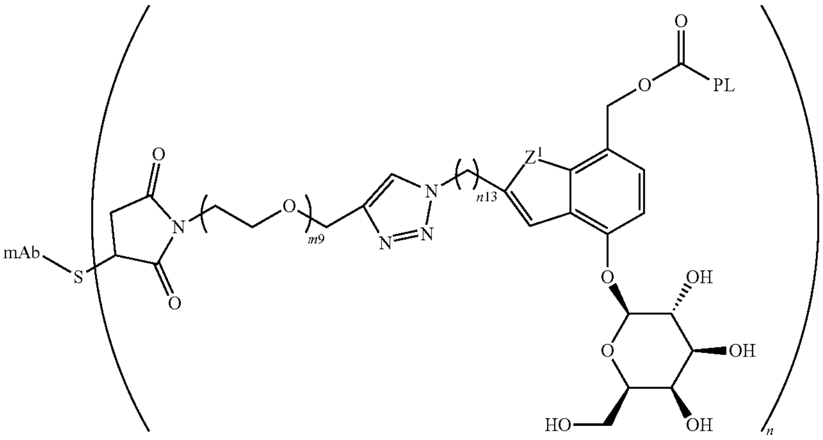

-continued

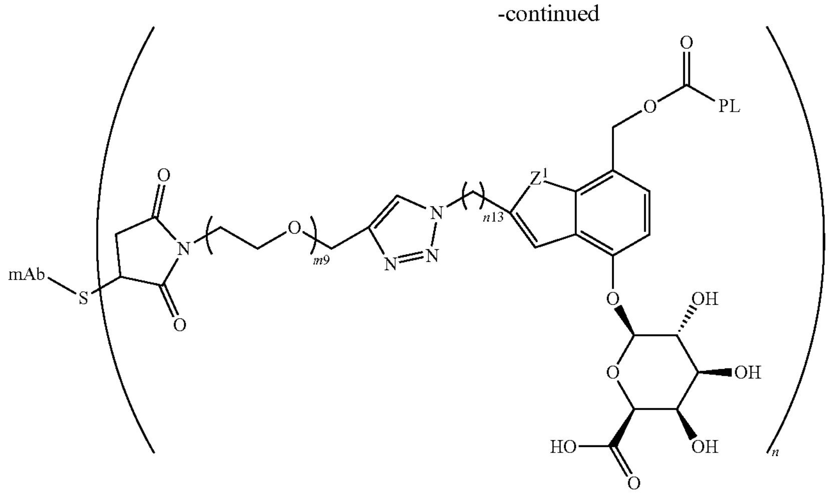

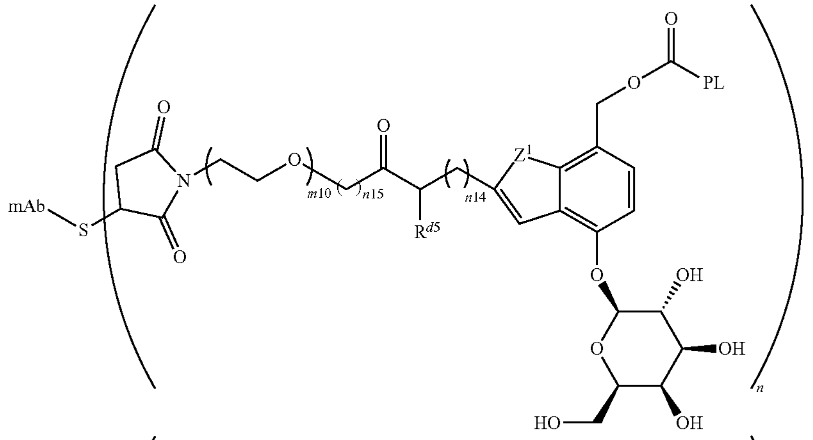

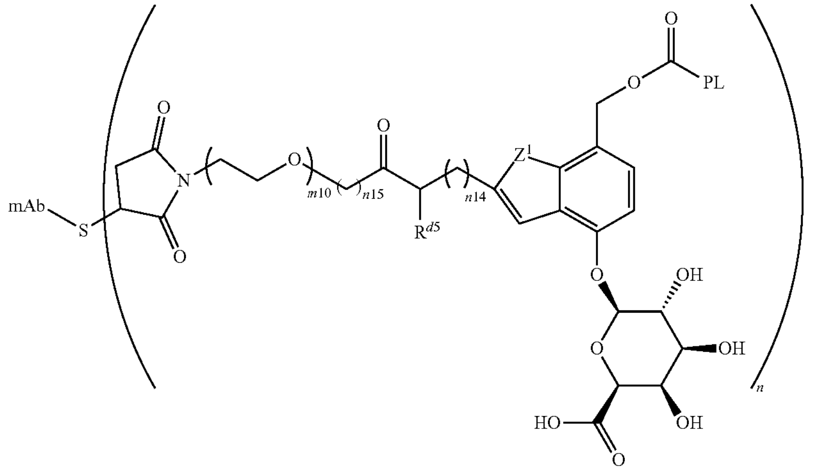

In the above formulas, mAb represents the moiety of the antibody. In the above formulas, m5, m6, m9, m10, n9, n10, n13, n14 and n15 may be each independently an integer from 1 to 10. In one embodiment, m5, m6, m9, m10, n9, n10, n13, n14, and n15 may be each independently an integer from 1 to 8, an integer from 1 to 6, an integer from 1 to 5, an integer from 1 to 4, or an integer from 1 to 3. In the above formulas, $R^{d3}$ and $R^{d5}$ are each independently H or $C_{1-8}$ alkyl.

In the above formulas, $Z^1$ is a heteroatom selected from $NR^3$, O, S and Se. $R^3$ is H or $C_{1-8}$ hydrocarbyl. In the above formulas, PL has the same meaning as PL in Formula 1. In the above formulas, the —O—CO— group in the —O—CO-PL group is an optional self-immolative spacer group, and may be absent (i.e., the -PL group is directly linked to the —$CH_2$— group) or may be replaced with —S(=O)$_2$—,

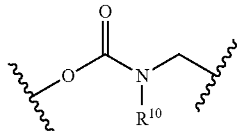

or

-continued

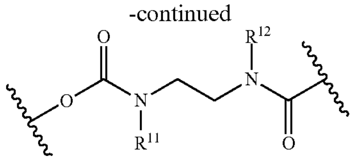

(in the above formulas, $R^{10}$ to $R^{12}$ are each independently H, $C_{1-8}$ alkyl, amino-$C_{1-8}$ alkyl, $C_{1-8}$ alkyl substituted with mono- or di-($C_{1-8}$ alkyl)amino, or $-(CH_2CH_2O)_gR^{13}$, $R^{13}$ is H or $C_{1-4}$ alkyl, and g is an integer from 1 to 10.)

In the above formulas, n is a real number from 1 to 10. In one embodiment, n may be a real number from 1 to 8, a real number from 1 to 6, a real number from 1 to 4, or a real number from 1 to 2.

In one embodiment, the conjugate represented by Formula 2 may be selected from the group consisting of conjugates represented by the following formulas:

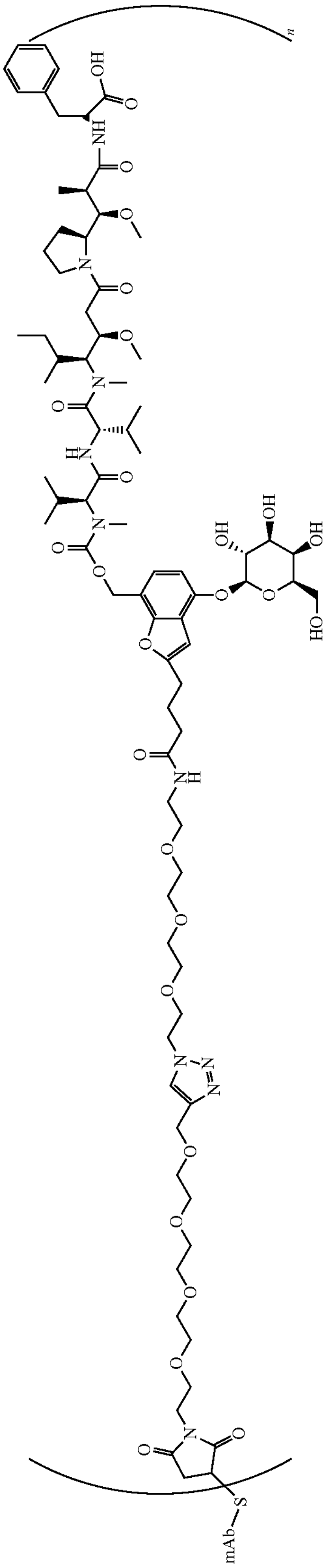
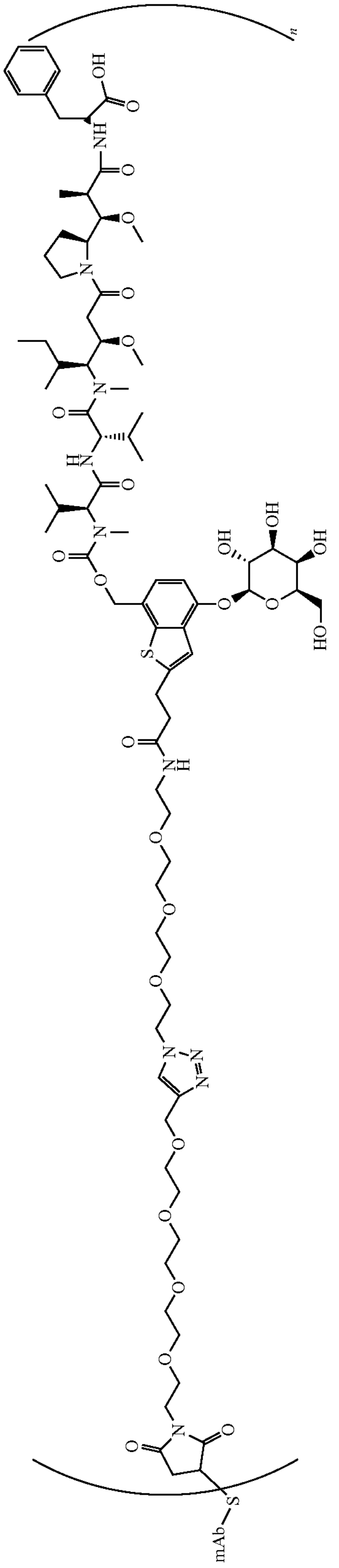

-continued
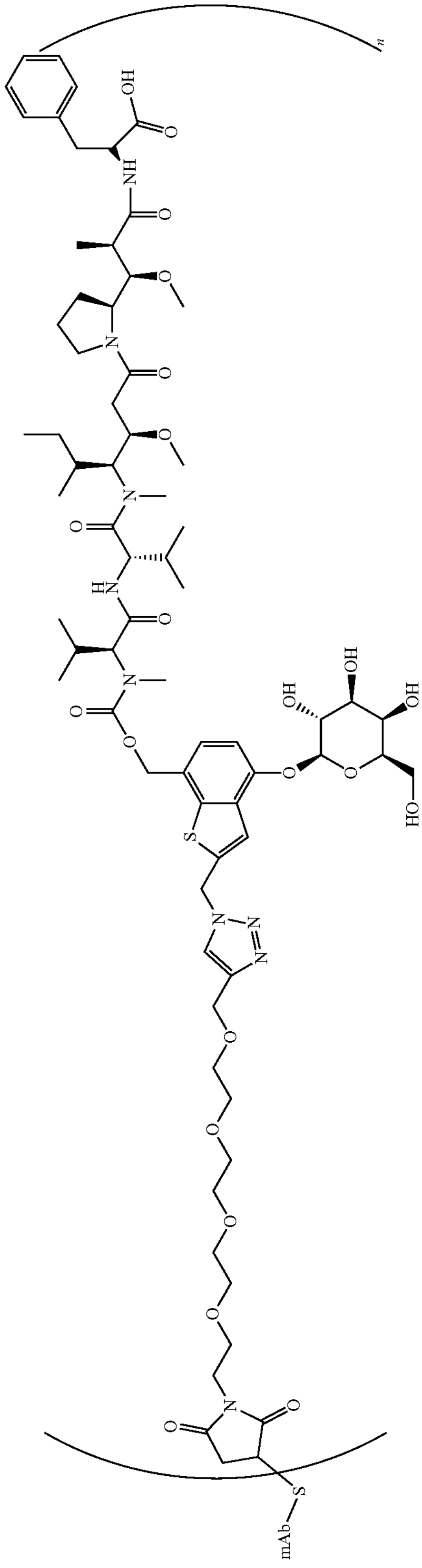
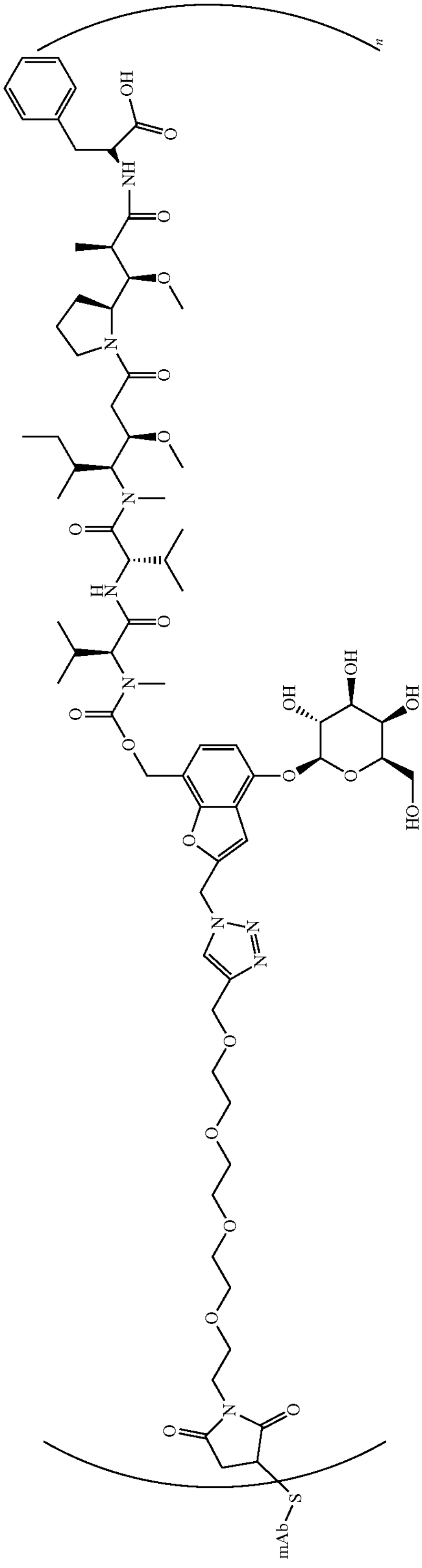

-continued
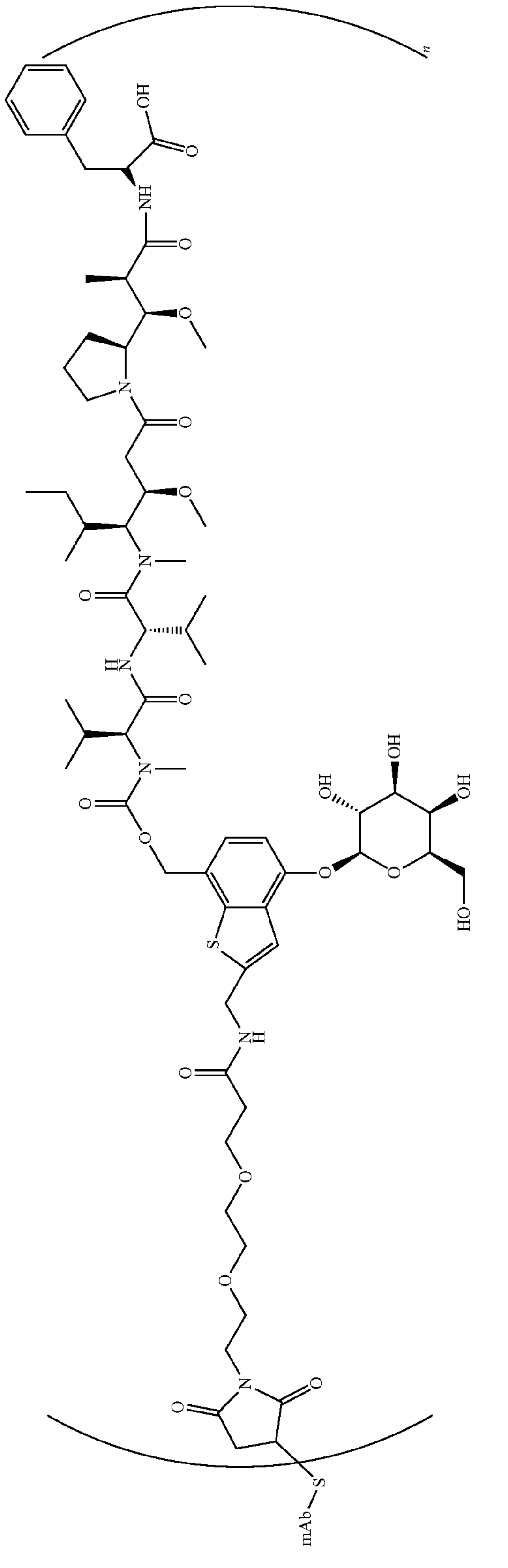
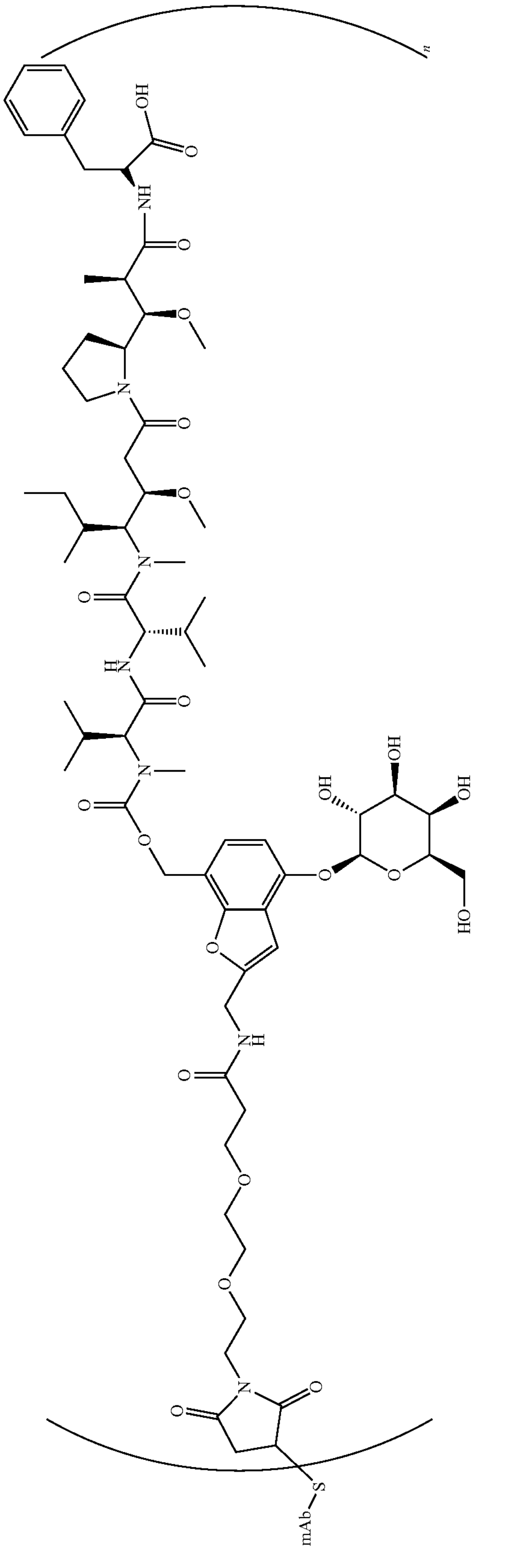

-continued
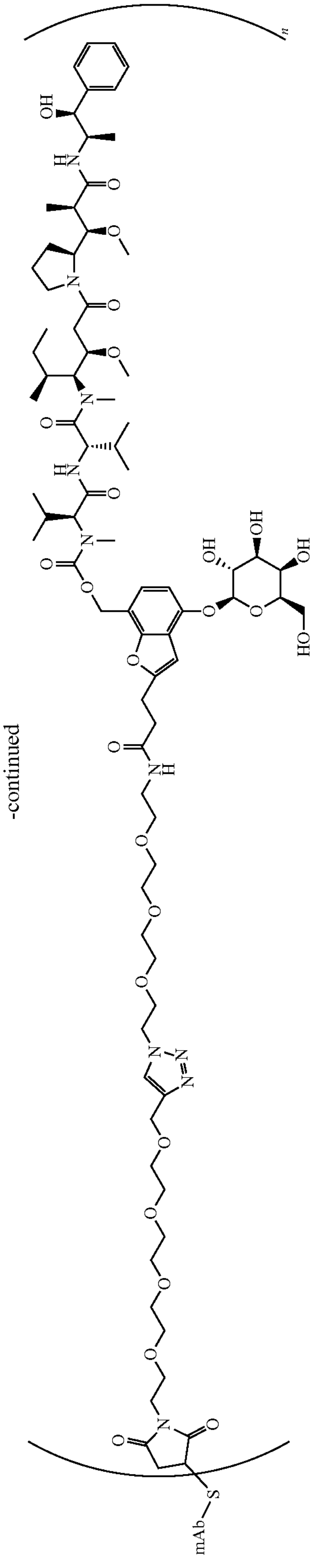
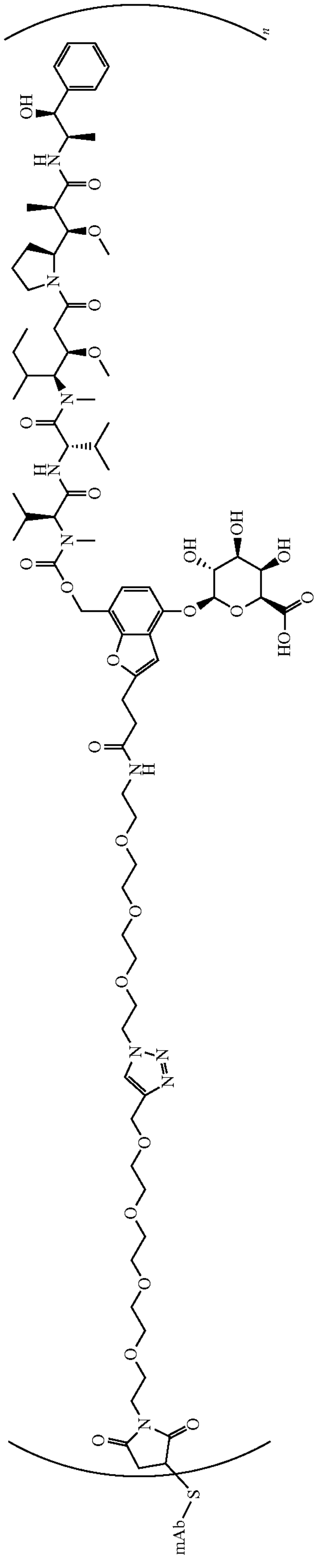

-continued
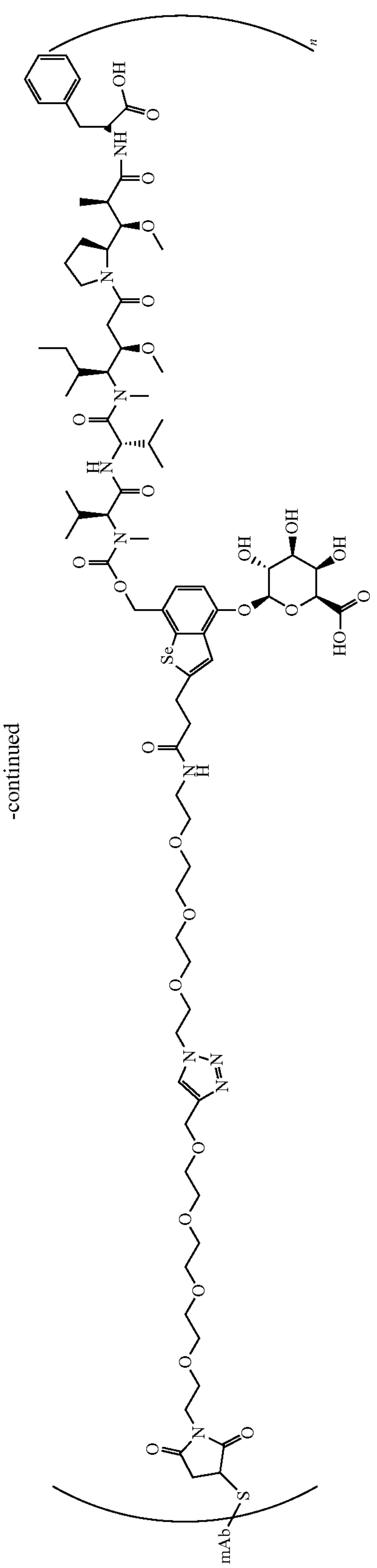
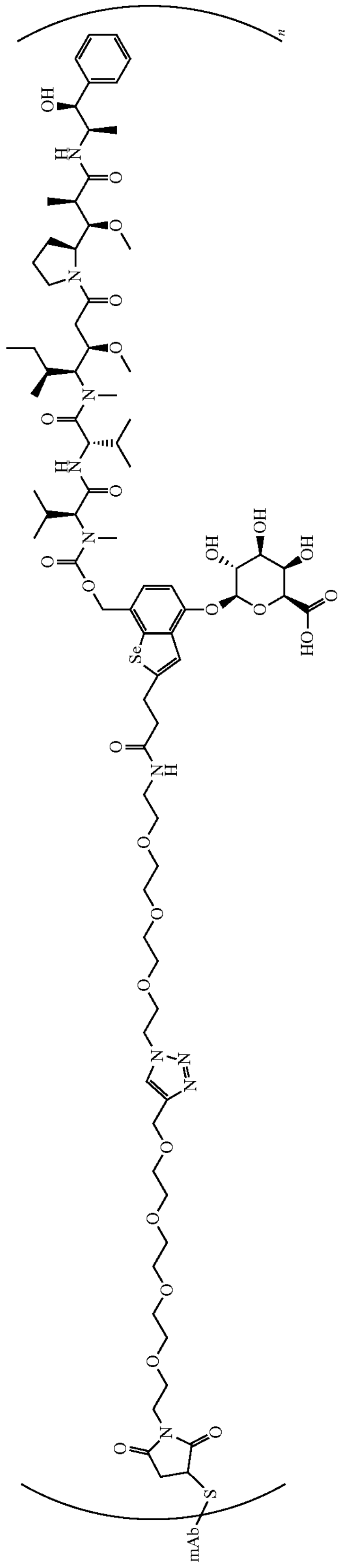

-continued
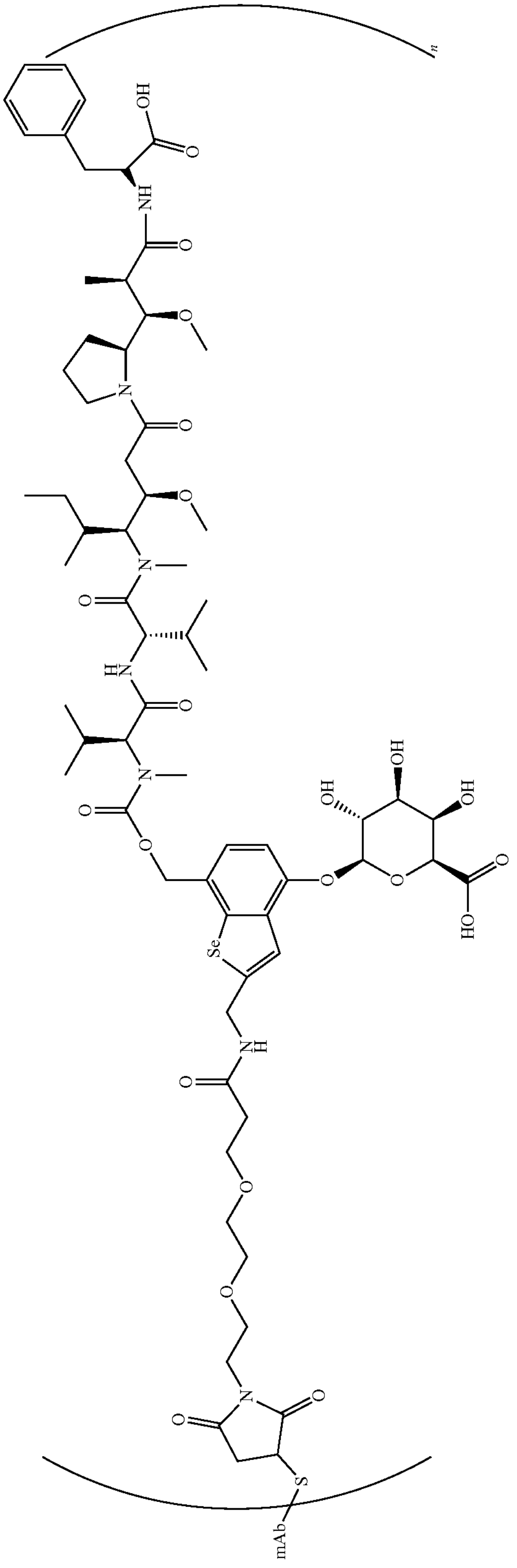
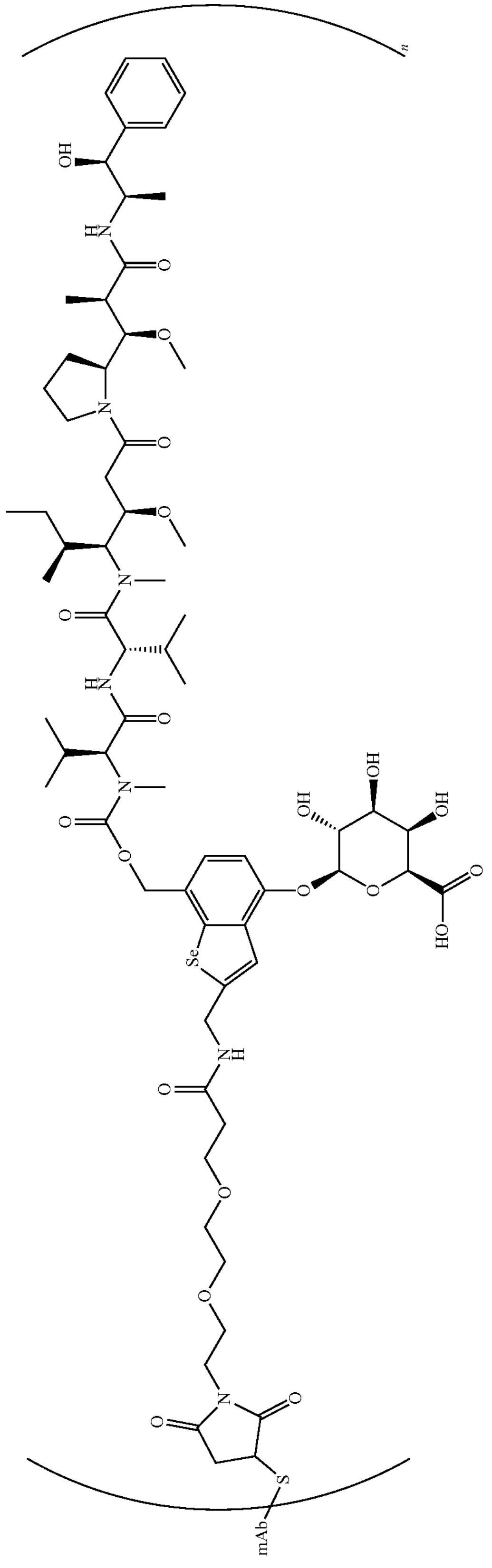

In the above formulas, mAb represents the moiety of the antibody. In the above formulas, n is a real number from 1 to 10. In one embodiment, n may be a real number from 1 to 8, a real number from 1 to 6, a real number from 1 to 4, or a real number from 1 to 2.

Exemplary DAR2 Type Ligand-Drug Conjugates

In one embodiment, the compound represented by Formula 2 may be selected from the compounds listed in Table D attached. The specific n values listed in Table D may vary in the real number range of 1 to 10. For example, n may be a real number from 1 to 8, a real number from 1 to 6, a real number from 1 to 4, or a real number from 1 to 2.

DAR4 Type Ligand-Drug Conjugate (Formula 2-1)

In one embodiment, when the linking group $L^1$ of Formula 2 according to the present invention has a branched structure or a dendrimeric structure (i.e., when $L^1$ is a multivalent linking group), a ligand-drug conjugate of Formula 2 to which a plurality of active agents are bound can be provided. In one embodiment, the compound represented by Formula 2 may be a ligand-drug conjugate represented by Formula 2-1 below:

[Formula 2-1]

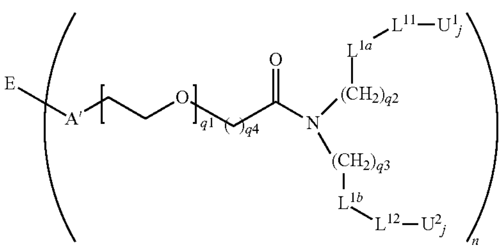

In Formula 2-1, E is a ligand or protein having a receptor binding property, and A' is a divalent linking group derived from the binding functional group (A) of Formula 1. With respect to E and A', the matters described in Formula 2 may also be equally applied to Formula 2-1.

In Formula 2-1, $U^1$ and $U^2$ each have the same meaning as U in Formula 1, wherein $U^1$ and $U^2$ may be the same or different from each other. In addition, $L^{11}$ and $L^{12}$ each have the same meaning as $L^1$ in Formula 1, wherein $L^{11}$ and $L^{12}$ may be the same or different from each other.

In Formula 2-1, j is 1 to 10. In one embodiment, j is 1 to 5. For example, j is 1.

With respect to Formula A, $L^1$ and U, the matters described in Formula 1 may be equally applied to A, $U^1$ and $U^2$, and $L^{11}$ and $L^{12}$ in Formula 2-1, respectively. In addition, with respect to $U^1$ and $U^2$, and $L^{11}$ and $L^{12}$, the matters described in Formula 1-1 may be equally applied in Formula 2-1, respectively.

In Formula 2-1, $L^{1a}$ and $L^{1b}$ may be each independently selected from a direct bond;

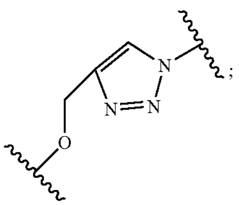

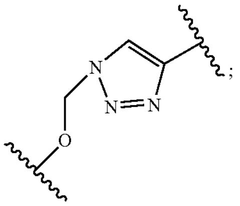

-continued

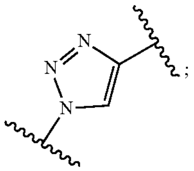

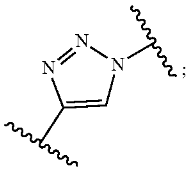

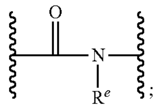

and

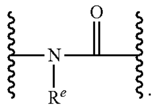

In this case, $R^e$ may be H or $C_{1-8}$ alkyl.

In Formula 2-1, q1, q2 and q3 may be each independently an integer from 0 to 10. In Formula 2-1, q4 may be an integer from 1 to 10. Further, if $L^{1a}$ is

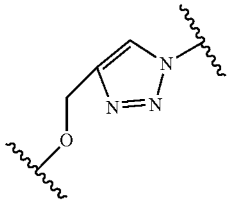

or

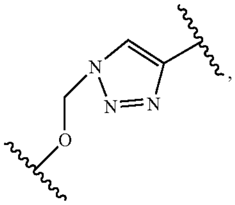

q2 is not 0, and if $L^{1b}$ is

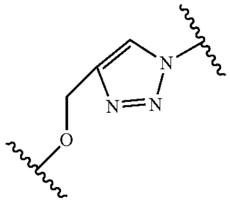

or

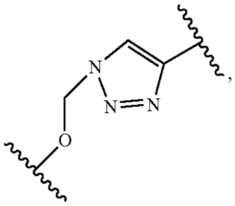

q3 is not 0.

In one embodiment, q1 may be an integer from 0 to 8, an integer from 1 to 8, or an integer from 1 to 6. In one embodiment, q2 and q3 may be each independently an integer from 0 to 8, an integer from 0 to 6, or an integer from 0 to 4. In one embodiment, q4 may be an integer from 1 to 8, an integer from 1 to 6, or an integer from 1 to 4.

With respect to $L^{1a}$ and $L^{1b}$, q1, q2, q3, q4, the matters described in Formula 1-1 may be equally applied in Formula 2-1, respectively.

In Formula 2-1, n is a real number from 1 to 10. In one embodiment, n may be a real number from 1 to 6, a real number from 1 to 4, or a real number from 1 to 2.

In one embodiment, the ligand-drug conjugate represented by Formula 2-1 may be conjugates represented by the following formulas:

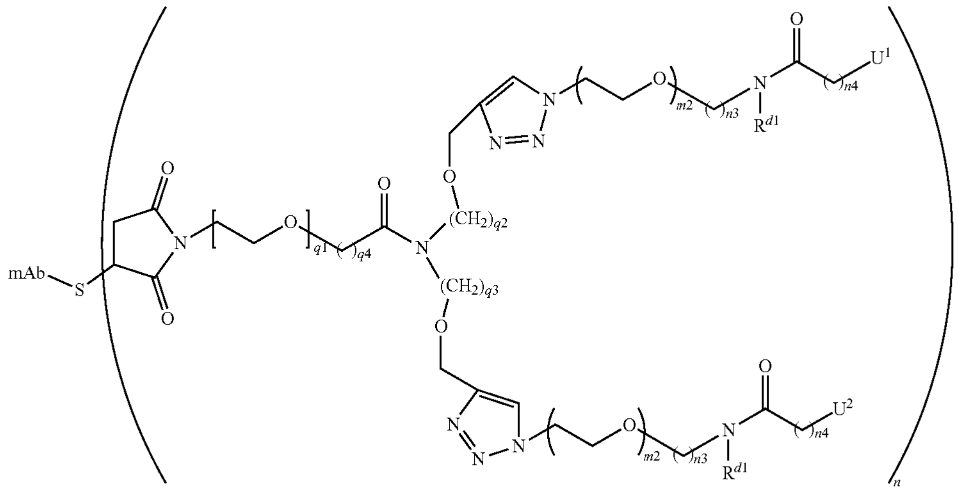
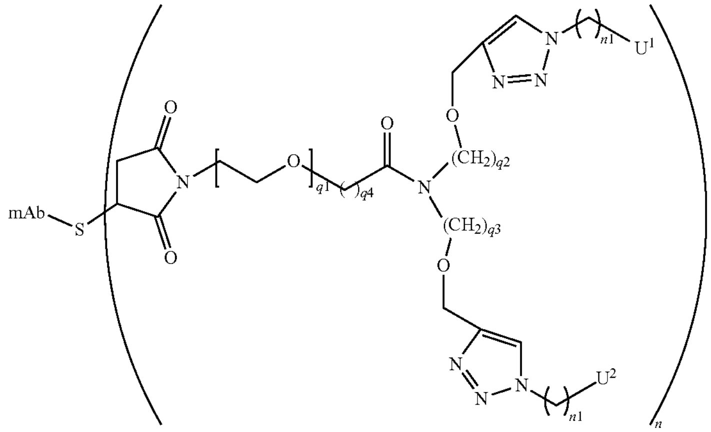
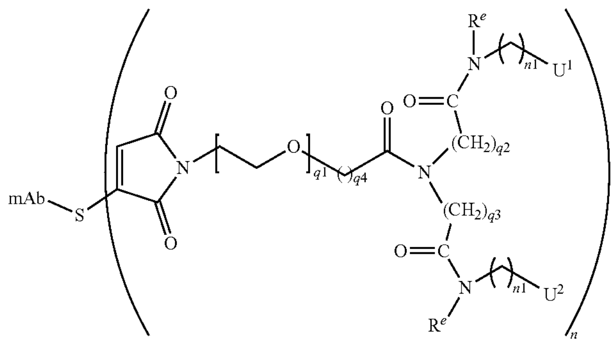

-continued
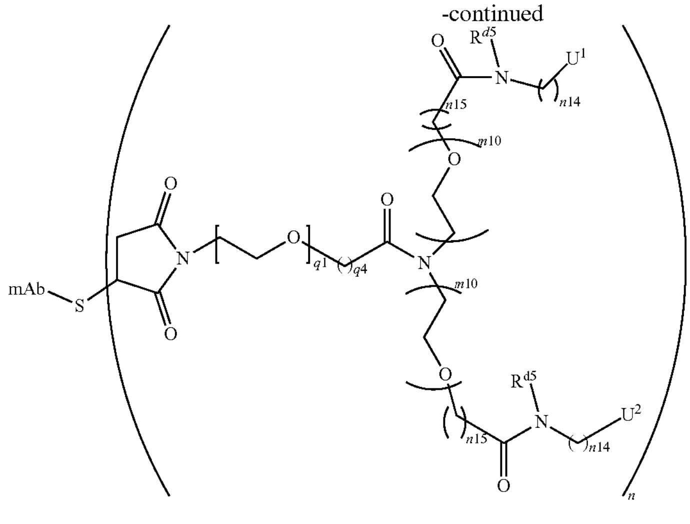
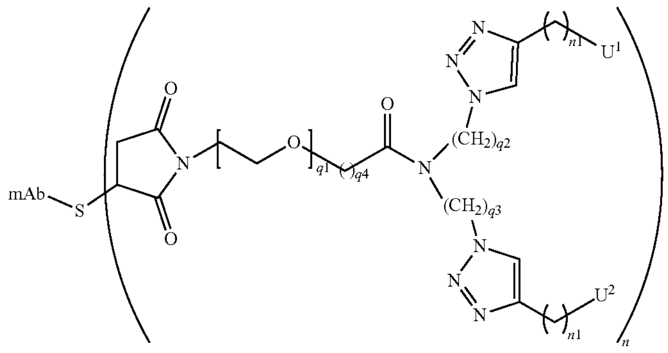
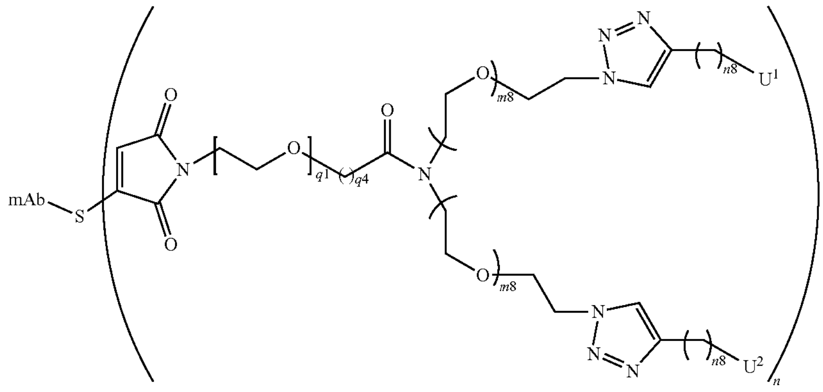
(In the above formulas, mAb is the moiety of the antibody. In the above formulas, q1 to q4, n, $U^1$ and $U^2$, $R^{d1}$, $R^{d5}$, $R^e$, n1, n3, n4, n8, n14 and n15, m2, m8 and m10 are as described above with respect to Formula 1-1 or Formula 2-1.)

In one embodiment, the ligand-drug conjugate represented by Formula 2-1 may be conjugates represented by the following formulas:
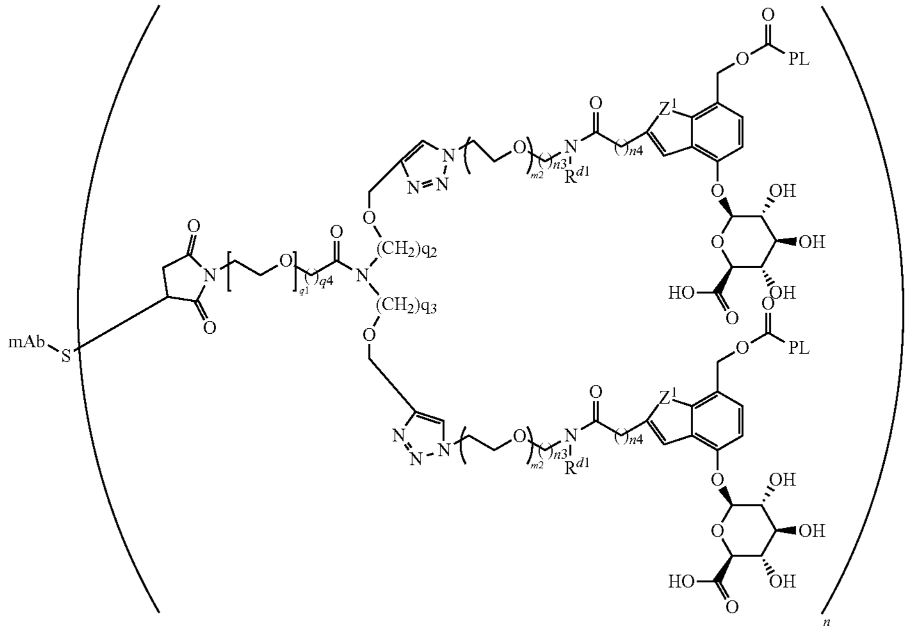
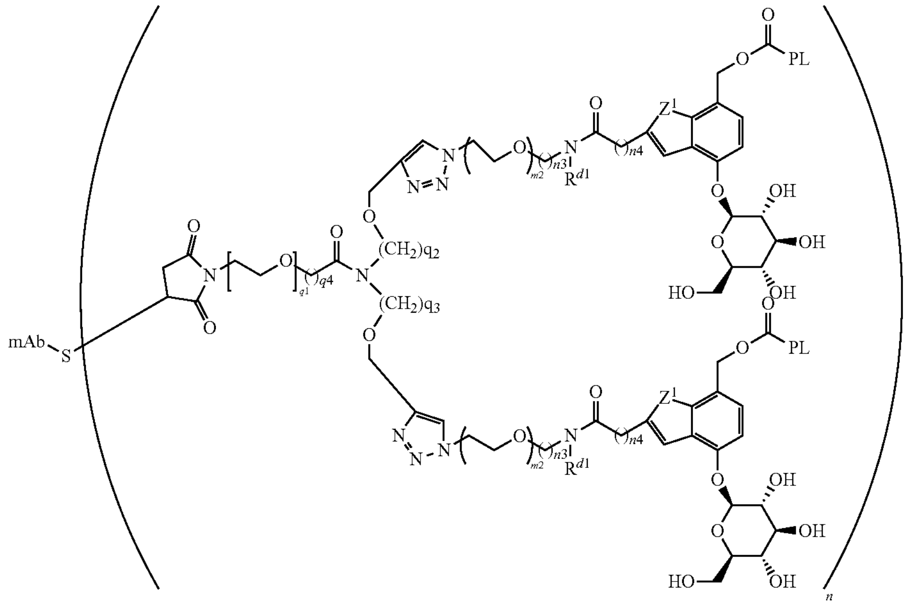

-continued
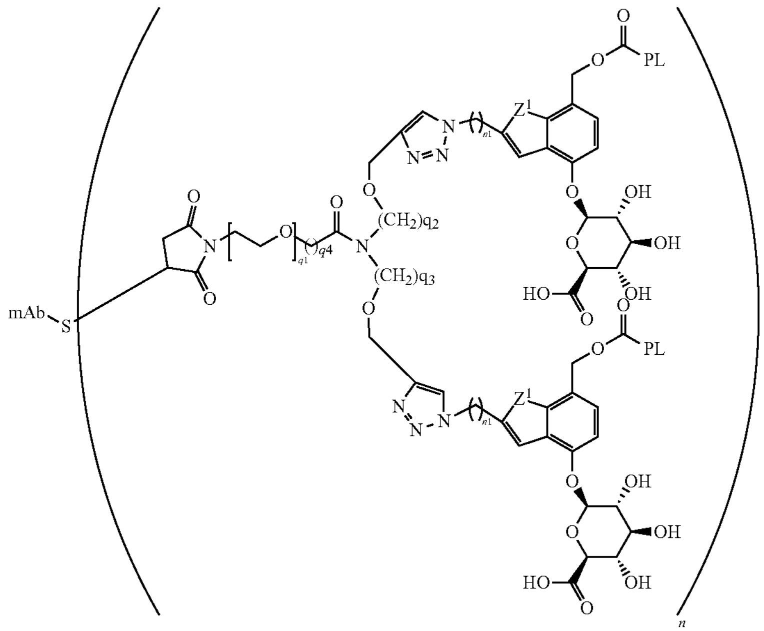
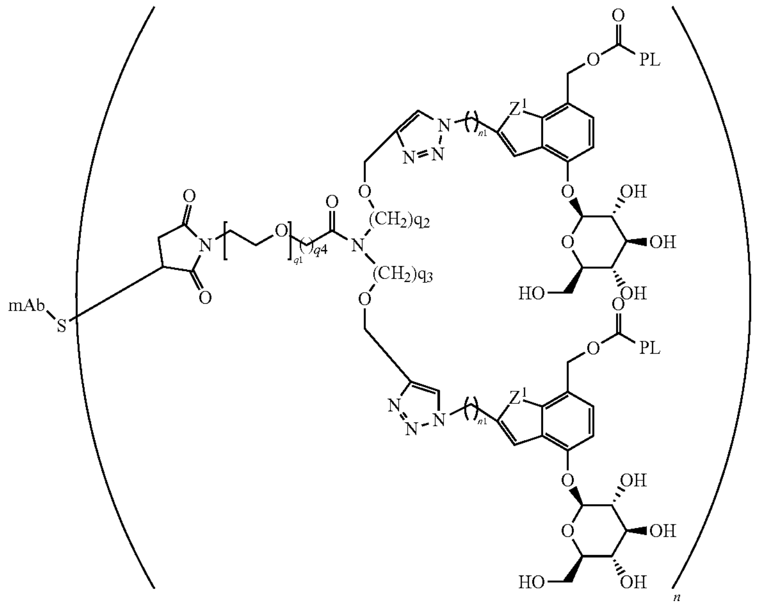

-continued
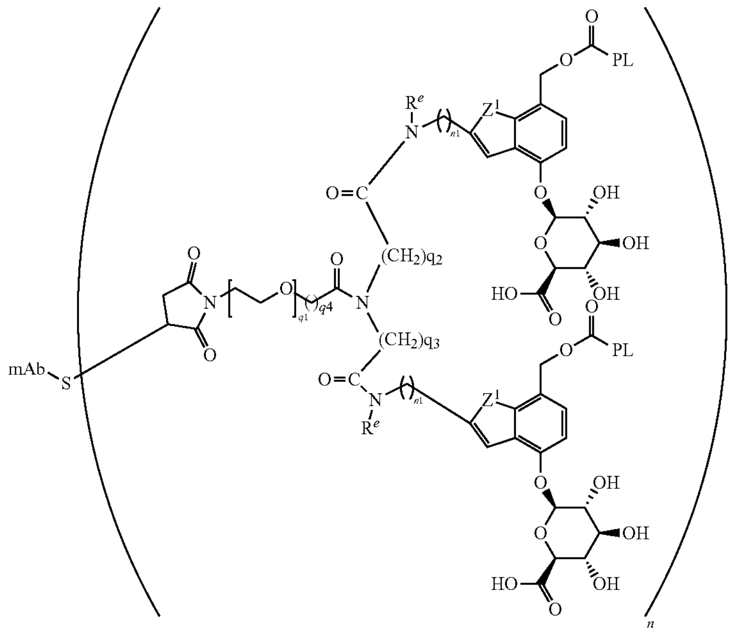
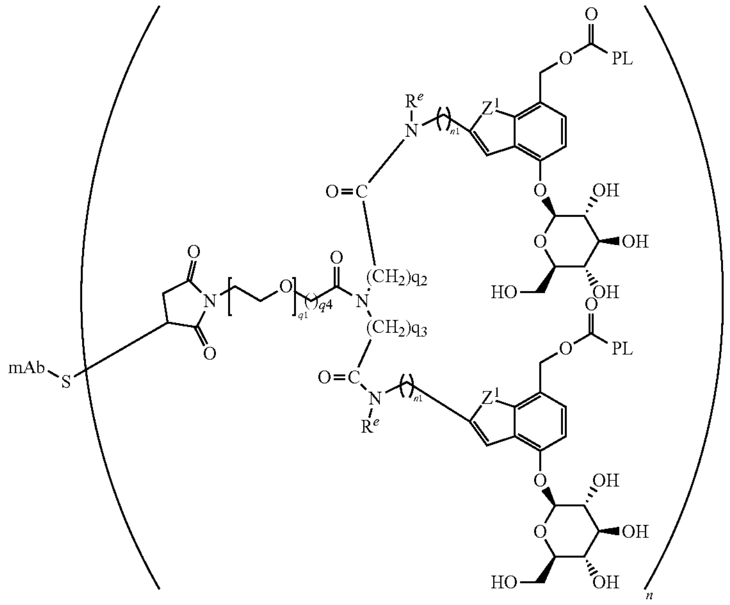

-continued

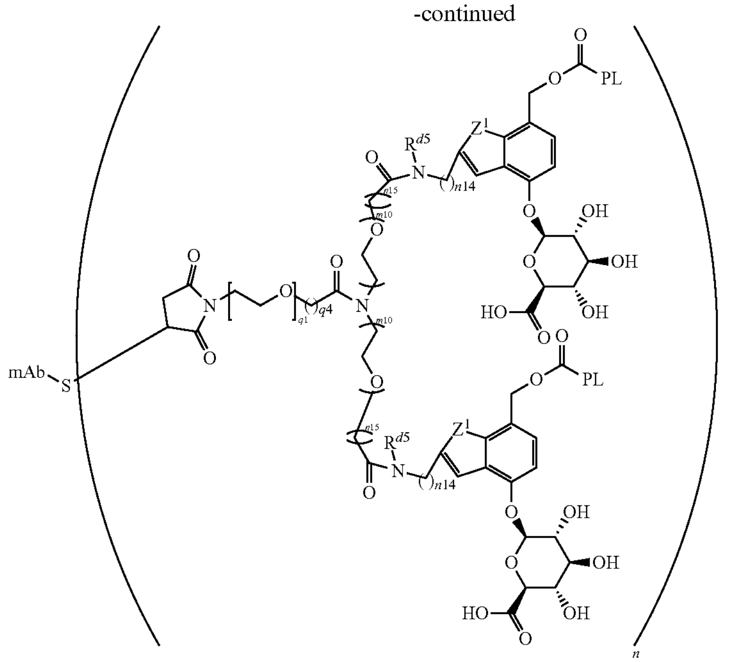

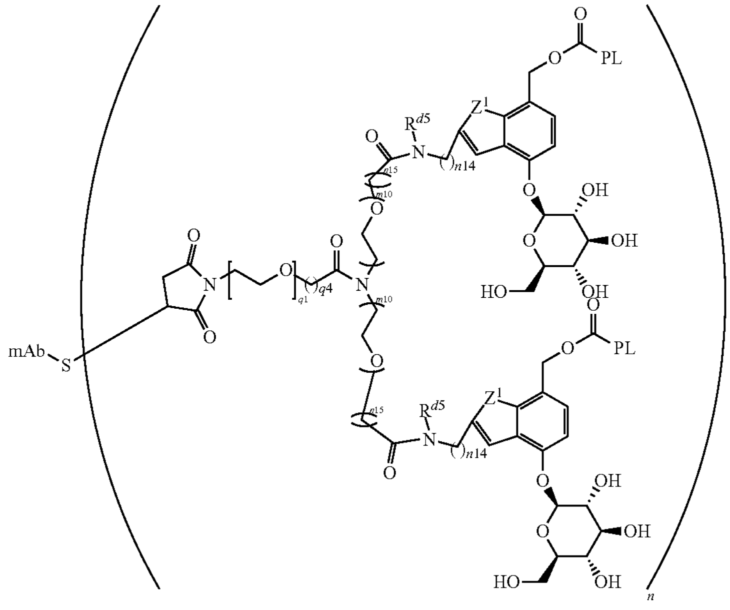

In the above formulas, mAb is the moiety of the antibody. In the above formulas, q1 to q4, n1, n3, n4, n14 and n15, m2 and m10, $R^{d1}$, $R^{d5}$ and $R^e$ are as described above with respect to Formula 1-1. In the above formulas, PL has the same meaning as PL in Formula 1. In the above formulas, $Z^1$ is a heteroatom selected from N, O, S and Se. In the above formulas, the —O—CO— group in the —O—CO-PL group is an optional self-immolative spacer group, which may be absent (i.e., the -PL group is directly linked to the —$CH_2$— group) or may be replaced with the functional groups described above with respect to an "optional self-immolative spacer group".

In one embodiment, the ligand-drug conjugate represented by Formula 2-1 may be selected from the compounds listed in Table E attached. The specific n values listed in Table E may vary in the real number range of 1 to 10. For example, n may be a real number from 1 to 6, a real number from 1 to 4, or a real number from 1 to 2.

Definition

As used herein, the term "hydrocarbyl" refers to a functional group consisting of carbon and hydrogen, and refers to a saturated, partially unsaturated or fully unsaturated straight-chain, branched or cyclic hydrocarbon. The hydrocarbyl may include alkyl, alkenyl, alkynyl, cycloalkyl, cycloalkenyl, cycloalkynyl, and the like. Non-limiting examples of the hydrocarbyl may include methyl, ethyl, propyl, butyl, ethenyl, propenyl, butenyl, ethynyl, propynyl, butynyl, and the like.

The term "alkyl" refers to a fully saturated branched or unbranched (or straight-chain or linear) hydrocarbon. The alkyl may be substituted or unsubstituted alkyl. The $C_{1-8}$ alkyl may be $C_1$ to $C_6$, $C_1$ to $C_5$, $C_1$ to $C_4$, $C_1$ to $C_3$, or $C_1$ to $C_2$ alkyl. Non-limiting examples of the alkyl may include methyl, ethyl, n-propyl, isopropyl, n-butyl, isobutyl, sec-butyl, n-pentyl, isopentyl, neopentyl, iso-amyl, or n-hexyl.

The term "alkenyl" includes straight-chain or branched alkenyl having 2 to 6 carbon atoms, 2 to 5 carbon atoms, or 2 to 4 carbon atoms with one or more double bonds at any position. For example, the alkenyl may include vinyl, propenyl, isopropenyl, butenyl, isobutenyl, prenyl, butadienyl, pentenyl, isopentenyl, pentadienyl, hexenyl, isohexenyl, hexadienyl, and the like.

The term "alkynyl" refers to a straight or branched hydrocarbon chain having at least one triple bond. The alkynyl is preferably a straight or branched chain having 2 to 8 carbon atoms, and examples of the alkynyl may include 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, and the like.

The term "alkoxy" refers to alkyl bound to an oxygen atom. For example, the $C_1$ to $C_8$ alkoxy may be $C_1$ to $C_6$, $C_1$ to $C_5$, $C_1$ to $C_4$, $C_1$ to $C_3$, or $C_1$ to $C_2$ alkoxy. The alkoxy may be methoxy, ethoxy, or propoxy.

The term "cycloalkyl" includes monocyclic or polycyclic saturated carbocycles containing 3 to 8 carbon atoms. Examples may include cyclopropyl, cyclobutyl, cyclopentyl, cyclohexyl, cycloheptyl, cyclooctyl, and the like.

The term "cycloalkenyl" includes non-aromatic monocyclic or polycyclic rings having 3 to 8 carbon atoms and containing at least one carbon-carbon double bond. Examples may include cyclopentenyl, cyclohexenyl, cycloheptenyl, cyclooctenyl, and the like.

The term "cycloalkynyl" refers to a monocyclic or polycyclic unsaturated hydrocarbon ring having 4 to 10 carbon atoms and containing at least one triple bond. Examples may include monocyclic alkynyl groups, such as cyclooctynyl group and cyclodecynyl group. "Cycloalkynyl" in its broadest sense includes structures in which one or more carbon atoms of a hydrocarbon ring containing at least one triple bond between carbon atoms are replaced by a heteroatom, such as N.

The term "dienyl" refers to an unsaturated branched or unbranched $C_{4-10}$ aliphatic substituent having two double bonds between two adjacent carbon atoms. Examples include 2,4-pentadienyl, 2,4-hexadienyl, 4-methyl-2,4-pentadienyl, and the like, but are not limited thereto.

The term "halogen" atom refers to an atom belonging to group 17 of the periodic table.

The halogen atom includes fluorine, chlorine, bromine, and iodine, etc.

The term "haloalkyl" refers to alkyl substituted with one or more halogen atoms.

The term "hydroxy" refers to the OH functional group (hydroxyl group).

The term "mercapto" refers to the SH functional group.

The term "cyano" is CN and refers to a functional group consisting of a triple bond between a carbon atom and a nitrogen atom.

The term "oxo" refers to =0, and "substituted with oxo" means that the carbon atom has a =O substituent in the form of —C(=O)—.

The term "nitro" refers to $NO_2$.

The term "amino" refers to $—NH_2$.

The term "alkylamino" refers to a functional group in which one or two hydrogen atoms of amino ($—NH_2$) are substituted with one or two of the alkyls mentioned above, and includes both mono-alkylamino and di-alkylamino, and the two alkyls in di-alkylamino may be the same or different.

Specifically, mono-$C_{1-8}$ alkylamino may be one in which one hydrogen atom of the amino ($—NH_2$) group is substituted with $C_{1-8}$ alkyl, and di-$C_{1-8}$ alkylamino may be one in which two hydrogen atoms of the amino ($—NH_2$) group are substituted with the same or different $C_{1-8}$ alkyl.

For example, mono-$C_{1-8}$ alkylamino ($—NH(C_{1-8}$ alkyl$)$) may include methylamino, ethylamino, propylamino, isopropylamino, butylamino, isobutylamino, sec-butylamino, tert-butylamino, pentylamino, hexylamino, and the like. Di-$C_{1-8}$ alkylamino ($—N(C_{1-8}$ alkyl$)_2$) may include, for example, dimethylamino, diethylamino, dipropylamino, methylethylamino, methylpropylamino, methylisopropylamino, methylbutylamino, methylisobutylamino, ethylpropylamino, ethylisopropylamino, ethylisobutylamino, isopropylisobutylamino, methylhexylamino, ethylhexylamino, and the like.

The term "carboxy" refers to —COOH.

The term "carbamoyl" refers to $—CONH_2$.

The terms "N-mono-$C_{1-8}$ alkylcarbamoyl" and "N,N-di-$C_{1-8}$ alkylcarbamoyl" refer to one in which one hydrogen atom or two hydrogen atoms bound to the nitrogen atom of carbamoyl ($—CONH_2$) are substituted with $C_{1-8}$ alkyl. In N,N-di-$C_{1-8}$ alkylcarbamoyl, the two $C_{1-8}$ alkyls may be the same or different from each other.

The term "alkanoyl" refers to alkyl as defined above, having the specified number of carbon atoms attached through a carbonyl bridge (i.e., —(C=O)-alkyl). For example, alkanoyl includes methanoyl (formyl: —COH), ethanoyl (acetyl: $—COCH_3$), propanoyl ($—COCH_2CH_3$), butanoyl ($—CO(CH_2)_2CH_3$), and the like.

The term "alkanoylamino" refers to an amino substituted with an alkanoyl group (i.e., —NH(C=O)-alkyl). The nitrogen atom of the alkanoylamino may be substituted with an additional substituent, for example an alkyl group. For example, alkanoylamino includes formylamino (—NHCOH), acetylamino ($—NHCOCH_3$), propanoylamino ($—NHCOCH_2CH_3$), butanoylamino ($—NHCO(CH_2)_2CH_3$), and the like.

The terms "cyano-$C_{1-8}$ alkyl", "halo-$C_{1-8}$ alkyl", "hydroxy-$C_{1-8}$ alkyl", "$C_{1-8}$ alkoxy-$C_{1-8}$ alkyl", "$C_{1-8}$ alkoxy-$C_{1-8}$ alkoxy-$C_{1-8}$ alkyl", "carboxy-$C_{1-8}$ alkyl", "amino-$C_{1-8}$ alkyl", "carbamoyl-$C_{1-8}$ alkyl", "N-mono-$C_{1-8}$ alkylcarbamoyl-$C_{1-8}$ alkyl" and "N,N-di-$C_{1-8}$ alkylcarbamoyl-$C_{1-8}$ alkyl" refer to $C_{1-8}$ alkyl substituted at the end or in the middle with cyano, halogen, hydroxy, alkoxy, carboxy, amino, carbamoyl. N-mono-$C_{1-8}$ alkylcarbamoyl and N,N-di-$C_{1-8}$ alkylcarbamoyl.

The term "glycosidyl" refers to a functional group formed by the condensation reaction of sugar molecules.

The term "heterocyclyl" refers to a saturated or partially unsaturated cyclic hydrocarbon containing at least one heteroatom. The heterocyclyl ring group may be monocyclic or bicyclic. The bicyclic heterocyclyl may be a spiro, bridged, or fused ring group. The heterocyclyl may contain 3 to 20 ring atoms, 3 to 10 ring atoms, 3 to 8 ring atoms, 3 to 7 ring atoms, 3 to 6 ring atoms, 4 to 9 ring atoms, 4 to 8 ring atoms, 4 to 7 ring atoms, or 4 to 6 ring atoms. The heteroatom may be any one or more selected from the group consisting of N, O and S. The heteroatom may be 1 to 3, 1, or 2 heteroatoms selected from the group consisting of N, O, and S.

Non-limiting examples of heterocyclyl may include aziridinyl, azetidinyl, pyrrolidinyl, piperidinyl, piperazinyl, dihydropyridinyl, tetrahydropyridinyl, oxetanyl, tetrahydrofuranyl, tetrahydropyranyl, dihydrofuranyl, dihydropyranyl, tetrahydrothiophenyl, morpholinyl, thiomorpholinyl, azepanyl, diazepanyl, oxazepanyl, thiazepanyl, and the like.

The term "heterocyclyloxy" refers to a functional group in which an oxygen atom is directly linked to the ring of the heterocycle.

The term "heteroaryl" or "heteroarylene" refers to a monocyclic or bicyclic aromatic moiety that contains one or more heteroatoms selected from the group consisting of N, O, and S, and the remaining ring atoms being carbon. The heteroaryl group may contain, for example, 1 to 4 heteroatoms, 1 to 3 heteroatoms, or 1 or 2 heteroatoms. The heteroaryl group may contain 5 to 10 ring elements, 5 to 7 ring elements, or 5 or 6 ring elements. The heteroaryl may be a 5- to 6-membered heteroaryl containing one or two N, O or S. The heteroaryl group may be a one-ring group, a two-ring group, or a three-ring group. The two-ring group may be a spiro-ring group, a bridged-ring group, and a fused-ring group.

Non-limiting examples of "heteroaryl" may include pyrrolyl, imidazolyl, pyrazolyl, pyridazinyl, furanyl, pyranyl, thienyl, thiophenyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, 2-pyrazin-2-yl, pyrazin-4-yl, pyrazin-5-yl, 2-pyrimidin-2-yl, 4-pyrimidin-2-yl, 5-pyrimidin-2-yl, indolyl, and the like.

The term "binding functional group" refers to a functional group that can form a covalent bond through addition, substitution, condensation reactions, and the like with a functional group included in a ligand or protein, or a functional group included in a linker precursor.

As used herein, the term "moiety" refers to a portion of the compound that corresponds to the parent compound of the moiety when the parent compound is bound to the compound of Formula 1 or the conjugate of Formula 2. Even when a portion of an entire compound is referred to herein as a compound or an active agent, it will be understood from the context that it refers to a "moiety" of the compound or active agent.

In the present invention, "precursor" refers to a compound as a reactant that ultimately provides the desired moiety through a chemical reaction, etc.

In the present invention, "linker precursor" refers to a compound that forms the desired linker structure or a part thereof through a chemical reaction. For example, as a PEG linker, various substances such as hydroxy-PEG linker, alkynyl-PEG linker, bromo-PEG linker, DBCO-PEG linker, azido-PEG linker, amino-PEG linker, maleimide-PEG linker are known. In addition, linker compounds such as aminooxy-PEG linker, tetrazine-PEG linker, tosylate-PEG linker, thiol-PEG linker, aldehyde-PEG linker, phosphonate-PEG linker, hydrazide-PEG linker, iodo-PEG linker, carboxyl-PEG linker are also widely used in the related art. As another example, as a linker having a DBCO (dibenzocyclooctyne) group, various substances such as amine reactive DBCO (DBCO-NHS, DBCO-sulfo-NHS ester, DBCO-PEG-NHS ester, DBCO-NHCO-PEG-NHS ester, etc.), carboxyl/carbonyl reactive DBCO (DBCO-amine, DBCO-PEG-amine, etc.), —SH group reactive DBCO (DBCO-maleimide, DBCO-PEG-maleimide, etc.), DBCO-PEG-t-butyl ester, DBCO-alcohol, DBCO-PEG-alcohol, DBCO-PEG-DBCO, Bis-DBCO-PEG are known. The linker precursor of the present invention includes a variety of linkers known in the field of ligand-conjugates and is not limited to the linker structures exemplified herein. Available linker precursors, preparation methods, reaction conditions, and the like are well known in the related art.

The term "dendrimer" refers to a well-ordered three-dimensional molecular structure with branching units centered on a core.

The term "1,6-elimination reaction" refers to a reaction in which cleavage of a covalent bond occurs at a specific position in the molecular structure of a compound, leading to cleavage of the covalent bond at a position 5 atoms away (1,6-position relationship).

In one embodiment, a compound of Formula 1 having an indole core and a β-galactoside triggering group can release $PL^-$ or PL-H through a 1,6-elimination reaction when β-galactose is separated by galactosidase.

[Reaction Scheme A]

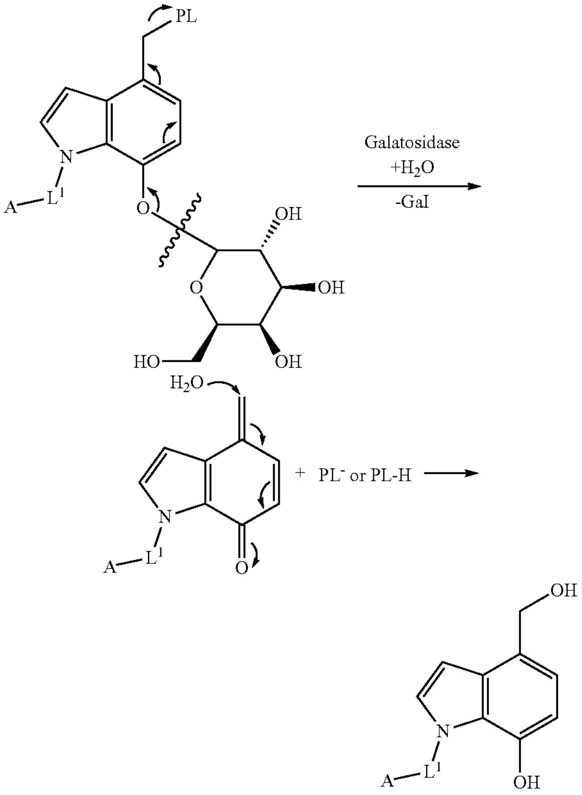

In addition, when the compound of Formula 1 comprises an optional self-immolative group T, β-galactose and 4-hydroxybenzyl alcohol can be separated to release $PL^-$ or PL-H, for example, by a 1,6-elimination reaction as shown in Reaction Scheme B below.

[Reaction Scheme B]

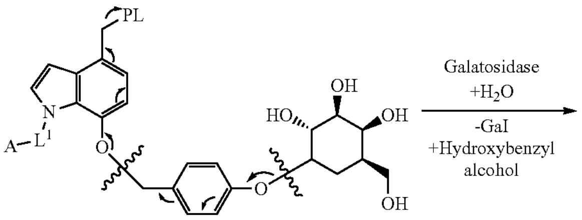

-continued

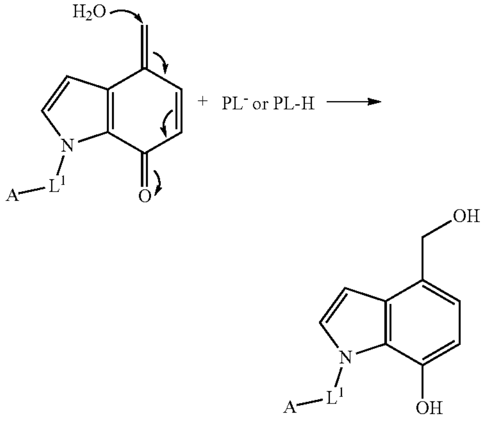

In addition, when the compound of Formula 1 comprises a self-eliminating linker, such as —OCO—, β-galactose and $CO_2$ can be separated to release $PL^-$ or PL-H, for example, by a 1,6-elimination reaction as shown in Reaction Scheme C below.

[Reaction Scheme C]

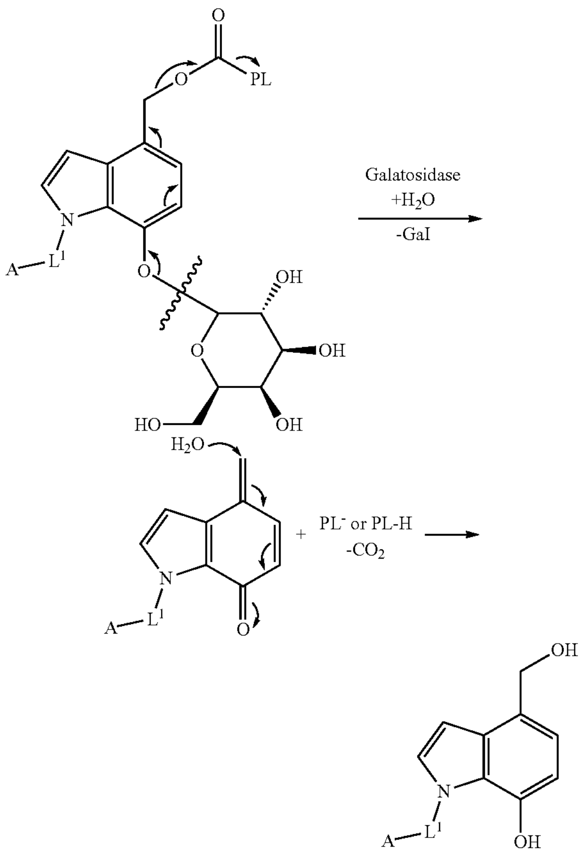

In the present application, the term "click chemistry reaction" refers to a general term for molecular assembly reactions using modular reactants that specifically react with each other even under mild conditions such as room temperature and room pressure, and the types of click chemistry reactions and the functional groups involved in click chemistry reactions are generally well known. For example, the click chemistry reaction includes [3+2]cycloadditions, thiol-ene reaction, Diels-Alder reaction, inverse electron demand Diels-Alder reaction, [4+1]cycloadditions, and the like, but is not limited thereto. More specifically, the click chemistry reaction includes copper (I)-catalyzed azide-alkyne cycloaddition (CuAAC), strain-promoted azide-alkyne cycloaddition (SPAAC), strain-promoted alkyne-nitrone cycloaddition (SPANC), [3+2]cycloaddition of alkenes and azides, inverse-demand Diels-Alder of alkenes and tetrazines, photoclick reaction of alkenes and tetrazoles, and Huisgen cycloaddition of azides and alkynes, but is not limited thereto. The click chemistry functional group includes alkyne, cycloalkyne, cyclooctyne and cyclononyne (e.g., cycloalkyne such as bicyclo[6.1.0]-non-4-yn-9-yl methanol), trans-cyclooctene, nitrone, nitrile oxide, azide, Conjugated Diene, dienophile, and cycloalkyne such as cyclooctyne, cyclononyne, dibenzocyclooctyne (DIBO), BARAC (biarylazacyclooctynone), ALO (aryl-less octyne), DIFO (difluorinated cyclooctyne), MOFO (monofluorinated), DIBAC (dibenzo-aza-cyclooctyne) and DIMAC (dimethoxyazacylooctyne), but is not limited thereto. For example, the click chemistry functional group may include acetylene, transcyclooctene, cyclooctyne, diarylcyclooctyne, methyl ester phosphine, norbornene, tetrazine, methylcyclopropene, azetine, cyanide, azide, dibenzocyclooctyne, and the like.

Medical Uses and Pharmaceutical Compositions

The compound of Formula 1 or the ligand-drug conjugate of Formula 2 of the present invention can have excellent stability in various blood environments. In other words, the active agent can maintain a stable binding state in the plasma environment of mice, rats, dogs, and humans, thereby minimizing blood toxicity.

In addition, the compound of Formula 1 or the ligand-drug conjugate of Formula 2 of the present invention can exhibit excellent target cell selectivity and excellent active agent release property. The compound and conjugate of the present invention can rapidly dissociate and release the active agent by reacting with enzymes such as galactosidase and glucuronidase under pH 4 to 5 conditions. Therefore, the compound of the present invention can effectively release the active agent in the environment within the target cells (e.g., tumor lysosomes).

In one aspect of the present invention, there are provided a pharmaceutical composition comprising a compound comprising a self-immolative group of Formula 1 or Formula 1-1 or a ligand-drug conjugate of Formula 2 or Formula 2-1, or a pharmaceutically acceptable salt thereof, and a pharmaceutically acceptable carrier or excipient.

In another aspect of the present invention, there is provided an imaging composition or a composition for detection comprising a compound comprising a self-immolative group of Formula 1 or Formula 1-1 or a ligand-drug conjugate of Formula 2 or Formula 2-1, or a pharmaceutically acceptable salt thereof.

The compound comprising the self-immolative group of Formula 1 or Formula 1-1 and the ligand-drug conjugate of Formula 2 or Formula 2-1 according to the present invention may be mixed with a solvent and provided as a composition.

The composition may be prepared in an injectable form as a liquid solution or as a suspension. In addition, the composition may be prepared in a solid form suitable for injection as an emulsion or a polypeptide encapsulated in liposomes. The compound or ligand-drug conjugate of the present invention can be combined with a pharmaceutically acceptable carrier, including any carrier that does not induce the production of antibodies harmful to the subject receiving the carrier. Suitable carriers may typically include slowly metabolized macromolecules such as proteins, polysaccharides, polylactic acid, polyglycolic acid, polymeric amino acids, amino acid copolymers, lipid aggregates, and the like. Proteins may be formulated into a vaccine in a neutral or salt form.

The composition may contain a diluent such as water, saline, glycerol, ethanol, and the like. Auxiliary substances such as wetting or emulsifying agents, pH buffers, and the like may be added to the composition. The composition may be administered parenterally by injection, or may be administered via subcutaneous or intramuscular injection. Additional formulations may be provided, for example, as suppositories or oral preparations. Oral compositions may be provided as solutions, suspensions, tablets, pills, capsules, or sustained-release formulations.

The composition may be administered in a manner that is compatible with the dosage form. The composition comprises a therapeutically effective amount of the compound or the ligand-drug conjugate according to the present invention. The therapeutically effective amount refers to a single dose or a dose in a multiple dose schedule that is effective in treating or preventing a disease or disorder. The administered dose will be determined depending on the type of an active agent included in the compound or ligand-drug conjugate of the present invention, and/or the type of a ligand or protein that binds to a receptor. In addition, the administered dose may vary depending on the health and physical condition of the subject being treated, the desired degree of protection, and other related factors.

For example, a therapeutically effective amount of the compound or ligand-drug conjugate of the present invention or a pharmaceutical composition comprising the same can be used for the treatment or prevention of proliferative diseases, autoimmune diseases, or infectious diseases.

For example, the composition can be used for the treatment of cancer or tumors. For example, the composition can be administered to a patient to treat or prevent infection by pathogens (e.g., viruses, bacteria, fungi, parasites, etc.). These methods comprise administering to a mammal a therapeutic or prophylactic amount of a compound or conjugate sufficient to treat the disease or disorder or symptoms thereof, under conditions such that the disease or disorder is prevented or treated.

In the above composition, the compound or conjugate of the present invention may be administered in the form of a pharmaceutically acceptable salt, hydrate, or solvate thereof. In one embodiment, it may be administered with a pharmaceutically acceptable carrier, a pharmaceutically acceptable excipient and/or a pharmaceutically acceptable additive. The pharmaceutically effective amount and the types of pharmaceutically acceptable salts or solvates, excipients and additives can be determined using standard methods (see: Remington's Pharmaceutical Sciences, Mack Publishing Co., Easton, PA, 18th edition, 1990).

As used herein, the term "pharmaceutically acceptable salt" includes organic salts and inorganic salts. Examples may include, but are not limited to, hydrochloride, hydrobromide, hydroiodide, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantonate, bitartrate, ascorbate, succinate, maleate, genticinate, fumarate, gluconate, glucuronate, saccharate, formate, benzoate, glutamate, methane sulfonate, ethane sulfonate, benzene sulfonate, p-toluene sulfonate and pamoate (i.e., 1,1'-methylene-bis(2-hydroxy-3-naphthoate)). Pharmaceutically acceptable salts may comprise another molecule (e.g., acetate ion, succinate ion, and other counterions, etc.), and may also comprise one or more charged atoms or one or more counter ions.

Exemplary solvates that can be used for pharmaceutically acceptable solvates of the above compounds include, but are not limited to, solvates of water, isopropanol, ethanol, methanol, DMSO, ethyl acetate, acetic acid, or ethanol amine.

Effects of Invention

The compound or ligand-drug conjugate of the present invention can stably deliver an active agent such as a drug, a toxin, a fluorophore, an affinity ligand, a diagnostic substance, or a detection probe to a target site, and can rapidly release the active agent in a specific environment of the target site.

The compound or ligand-drug conjugate of the present invention can have excellent stability at blood temperature and neutral conditions, and can rapidly release the active agent under acidic conditions, for example, under the tumor microenvironment.

BRIEF DESCRIPTION OF DRAWINGS

FIGS. 1 to 4 show the results of measuring the enzyme cleavage rate using *E. coli-p*-galactosidase or *E. coli* β-glucuronidase for Compounds A-15, A-23, A-36 and A-69, respectively.

FIG. 5 shows the results of measuring the chemical stability and plasma stability for Compound A-69.

FIGS. 6 to 8 show the results of in vivo activity analysis for ADC-1 to ADC-7 and ADC-11 to ADC-15.

DETAILED DESCRIPTION FOR CARRYING OUT THE INVENTION

Hereinafter, the present invention will be described in more detail through examples. However, these examples are provided for illustrative purposes only and the scope of the present invention is not limited to these examples.

The abbreviations used in this specification are as follows, and abbreviations not listed in the abbreviation list below have meanings commonly used in the field of organic synthesis:

AcO: acetyl
AcOH: acetic acid
EA: ethyl acetate
MC: methylene chloride
DMF: dimethylformamide
EDCI: 1-ethyl-3-(3-dimethylaminopropyl)carbodiimide
EDC: N-(3-dimethylaminopropyl)-N'-ethylcarbodiimide hydrochloride
HOBt: 1-hydroxybenzotriazole hydrate
ACN: acetonitrile
THE: tetrahydrofuran
DCC: N,N'-dicyclohexylcarbodiimide
DMAP: 4-dimethylaminopyridine
NHS: N-hydroxysuccinimide
DIPEA: diisopropylethylamine
TEA: triethylamine
Boc: tert-butyloxycarbonyl
LAH: lithium aluminium hydride
TFA: trifluoroacetic acid
AgOTf: silver trifluoromethanesulfonate
KO$^t$Bu: potassium tert-butoxide
MMAF-OMe: monomethyl auristatin F methyl ester
PPTS: pyridinium p-toluenesulfonate
TBAI: tetrabutylammonium iodide Preparation Example 1: Preparation of Linker P-1

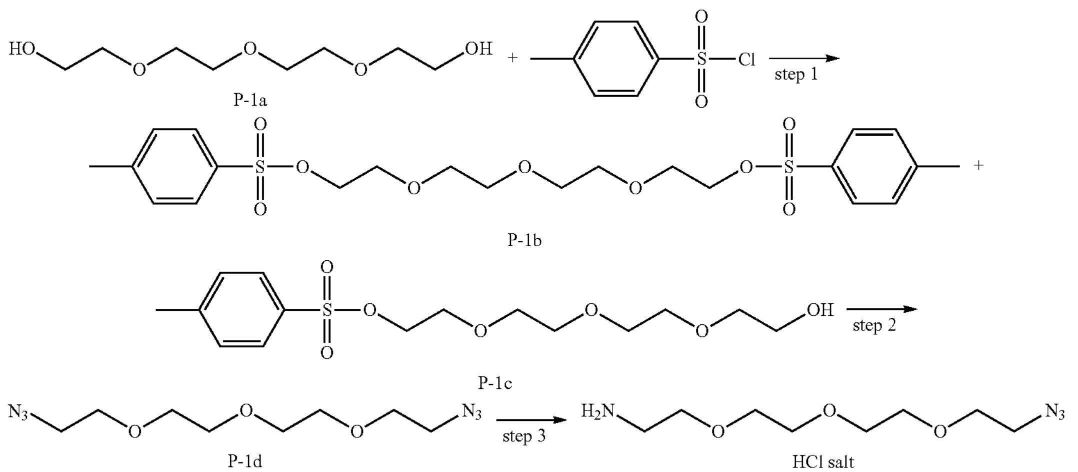

P-1a
P-1b
P-1c
P-1d
HCl salt
P-1

Step 1: Preparation of Compounds P-1b and P-1c

Compound P-1a (tetraethylene glycol, Daejung Chemicals & Metals, CAS NO. 112-60-7, 30 g, 154.46 mmol) was dissolved in MC (300 mL) under a nitrogen atmosphere at 0° C., and then 4-methylbenzenesulfonyl chloride (14.7 g, 77.23 mmol) and potassium hydroxide (4.3 g, 77.23 mmol) were added, and the mixture was stirred at room temperature for 16 hours. After completion of the reaction, MC (500 mL) and distilled water (500 mL) were added to extract the organic layer twice. The obtained organic layer was dried over anhydrous magnesium sulfate, filtered, and then concentrated under reduced pressure. The residue was subjected to column chromatography to obtain Compounds P-1b and P-1c, respectively, in the form of a colorless oil (P-1b: 4.4 g, 11%, P-1c: 15.1 g, 56%).

P-1b: $^1$H-NMR (400 MHz, $CDCl_3$) δ 7.79 (d, J=8.4 Hz, 4H), 7.34 (d, J=8.0 Hz, 4H), 4.16-4.14 (m, 4H), 3.69-3.66 (m, 4H), 3.57-3.55 (m, 8H), 2.44 (s, 6H).

P-1c: $^1$H-NMR (400 MHz, $CDCl_3$) δ 7.80 (d, J=8.4 Hz, 2H), 7.34 (d, J=8.0 Hz, 2H), 4.18-4.15 (m, 2H), 3.72-3.59 (m, 14H), 2.45 (s, 3H).

Step 2: Preparation of Compound P-1d

Compound P-1b (8.78 g, 17.48 mmol) was dissolved in DMF (50 mL) under a nitrogen atmosphere at room temperature, and then sodium azide (3.41 g, 52.44 mmol) was added, and the mixture was stirred at 60° C. for 16 hours. After completion of the reaction, the mixture was cooled to room temperature, and EA (500 mL) and saturated aqueous sodium bicarbonate solution (500 mL) were added to extract the organic layer twice. The obtained organic layer was dried over anhydrous magnesium sulfate, filtered, and then concentrated under reduced pressure. The residue was subjected to column chromatography to obtain Compound P-1d in the form of a colorless liquid (4.17 g, 97%).

$^1$H-NMR (400 MHz, $CDCl_3$) δ 3.69-3.66 (m, 12H), 3.40-3.37 (m, 4H).

Step 3: Preparation of Linker P-1

Compound P-1d (4.17 g, 17.06 mmol) was dissolved in EA (32 mL), diethyl ether (32 mL) and 5% hydrochloric acid aqueous solution (64 mL) under a nitrogen atmosphere at 0° C., and then triphenylphosphine (4.47 g, 17.06 mmol) was added, and the mixture was stirred at room temperature for 16 hours. After completion of the reaction, the mixture was concentrated under reduced pressure to remove the organic layer, and then the process of adding MC (100 mL) to the aqueous layer and washing the aqueous layer was repeated three times. The obtained aqueous layer was concentrated under reduced pressure to obtain Linker P-1 in the form of a colorless liquid (4.12 g, 95%).

$^1$H-NMR (400 MHz, $CDCl_3$) δ 8.27 (brs, 2H), 3.86-3.83 (m, 2H), 3.72-3.68 (m, 10H), 3.47-3.45 (m, 2H), 3.26-3.24 (m, 2H).

Preparation Example 2: Preparation of Linker P-2

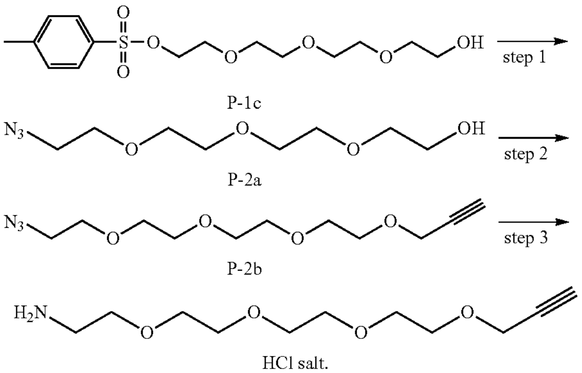

P-1c
P-2a
P-2b
HCl salt.
P-2

Step 1: Preparation of Compound P-2a

Compound P-1c (15.1 g, 43.34 mmol) prepared in Step 1 of Preparation Example 1 was dissolved in DMF (100 mL) under a nitrogen atmosphere at room temperature, and then sodium azide (4.2 g, 65.01 mmol) was added, and the mixture was stirred at 60° C. for 16 hours. After completion of the reaction, the mixture was cooled to room temperature, and EA (800 mL) and distilled water (800 mL) were added to extract the organic layer 5 times. The obtained organic layer was dried over anhydrous magnesium sulfate, filtered, and then concentrated under reduced pressure. The residue was subjected to column chromatography to obtain Compound P-2a in the form of a colorless liquid (6.11 g, 64%).

$^1$H-NMR (400 MHz, $CDCl_3$) δ 3.73-3.66 (m, 12H), 3.62-3.60 (m, 2H), 3.41-3.39 (m, 2H).

Step 2: Preparation of Compound P-2b

Compound P-2a (3.82 g, 17.44 mmol) was dissolved in THF (50 mL) under a nitrogen atmosphere at 0° C., and then KO$^t$Bu (2.93 g, 26.16 mmol) was added, and the mixture was stirred at 0° C. for 20 minutes. Then, propargyl bromide (5.2 g, 34.88 mmol) was added, and the mixture was stirred for 16 hours while slowly raising the temperature from 0° C. to room temperature. After completion of the reaction, the reaction solution was diluted with EA (200 mL) and extracted by adding distilled water (250 mL) to the solution, which was filtered using a Celite filter. The obtained organic layer was dried over anhydrous magnesium sulfate, filtered, and then concentrated under reduced pressure. The resulting residue was subjected to column chromatography to obtain Compound P-2b in the form of an orange liquid (2.97 g, 66%).

$^1$H-NMR (400 MHz, $CDCl_3$) δ 4.21 (d, J=2.4 Hz, 2H), 3.70-3.67 (m, 14H), 3.40-3.38 (m, 2H), 2.43 (t, J=2.4 Hz, 1H).

Step 3: Preparation of Linker P-2

Compound P-2b (2.97 g, 11.54 mmol) was dissolved in EA (24 mL), diethyl ether (24 mL) and 5% hydrochloric acid aqueous solution (48 mL) under a nitrogen atmosphere at 0° C., and then triphenylphosphine (3.03 g, 11.54 mmol) was added, and the mixture was stirred for 16 hours while slowly raising the temperature from 0° C. to room temperature. After completion of the reaction, the reaction solution was concentrated under reduced pressure to remove the organic solvent, and then the organic layer was extracted and removed by adding MC (100 mL) to the remaining aqueous solution, and the obtained aqueous layer was concentrated under reduced pressure to obtain Linker P-2 in the form of a yellow liquid (2.66 g, 86%).

$^1$H-NMR (400 MHz, DMSO-$d_6$) δ 7.93 (brs, 2H), 4.14 (d, J=2.4 Hz, 2H), 3.62-3.52 (m, 14H), 3.44 (t, J=2.4 Hz, 1H), 2.96-2.95 (m, 2H).

Preparation Example 3: Preparation of Linker P-3

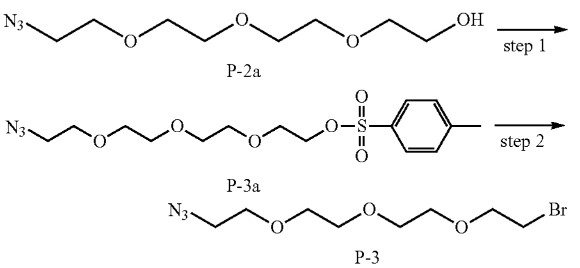

P-2a

P-3a

P-3

Step 1: Preparation of Compound P-3a

Compound P-2a (2.27 g, 10.35 mmol) prepared in Step 1 of Preparation Example 2 was dissolved in MC (52 mL) under a nitrogen atmosphere at room temperature, and then TEA (4.3 mL, 31.06 mmol) and 4-methylbenzenesulfonyl chloride (3.95 g, 20.71 mmol) were added, and the mixture was stirred at room temperature for 16 hours. After completion of the reaction, MC (100 mL) and distilled water (100 mL) were added to extract the organic layer three times. The obtained organic layer was dried over anhydrous magnesium sulfate, filtered, and then concentrated under reduced pressure. The residue was subjected to column chromatography to obtain Compound P-3a in the form of a yellow liquid (2.52 g, 65%).

$^1$H-NMR (400 MHz, $CDCl_3$) δ 7.80 (d, J=8.0 Hz, 2H), 7.34 (d, J=8.0 Hz, 2H), 4.16 (t, J=4.8 Hz, 2H), 3.70-3.59 (m, 12H), 3.37 (t, J=4.8 Hz, 2H), 2.45 (s, 3H).

Step 2: Preparation of Linker P-3

Compound P-3a (2.52 g, 6.76 mmol) was dissolved in THF (33 mL) under a nitrogen atmosphere at room temperature, and then lithium bromide (1.76 g, 20.29 mmol) was added, and the mixture was refluxed and stirred for 3 hours. After completion of the reaction, the mixture was cooled to room temperature, and EA (150 mL) and sodium bicarbonate aqueous solution (150 mL) were added to extract the organic layer twice. The obtained organic layer was dried over anhydrous magnesium sulfate, filtered, and then concentrated under reduced pressure. The residue was subjected to column chromatography to obtain Compound P-3 in the form of a yellow liquid (1.8 g, 94%).

$^1$H-NMR (400 MHz, $CDCl_3$) δ 3.81 (t, J=6.4 Hz, 2H), 3.69-3.67 (m, 10H), 3.47 (t, J=6.4 Hz, 2H), 3.39 (m, 2H).

Preparation Example 4: Preparation of Linker P-4

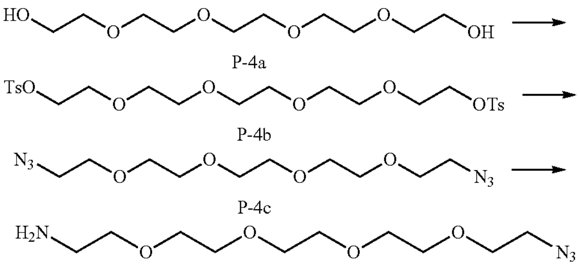

P-4a

P-4b

P-4c

HCl salt.
P-4

Step 1: Preparation of Compound P-4b

Compound P-4a (pentaethylene glycol, Merck, CAS NO. 4792-15-8, 10 g, 41.97 mmol) was dissolved in MC (60 mL) under a nitrogen atmosphere at 0° C., and then 4-methylbenzenesulfonyl chloride (17.60 g, 92.33 mmol) and lithium hydroxide monohydrate (8.80 g, 209.85 mmol) were added, and the mixture was stirred at room temperature for 12 hours. After completion of the reaction, MC (200 mL) and distilled water (200 mL) were added to extract the organic layer twice. The obtained organic layer was dried over anhydrous magnesium sulfate, filtered, and then concentrated under reduced pressure. The residue was subjected to column chromatography to obtain Compound P-4b in the form of a colorless oil (22.5 g, 98%).

$^1$H-NMR (400 MHz, $CDCl_3$) δ 7.79 (d, J=8.0 Hz, 4H), 7.34 (d, J=8.0 Hz, 4H), 4.14 (t, J=4.8 Hz, 4H), 3.68 (t, J=4.8 Hz, 4H), 3.60 (s, 4H), 3.58 (s, 8H), 2.44 (s, 6H).

Step 2: Preparation of Compound P-4c

Compound P-4b (22.5 g, 41.16 mmol) was dissolved in ACN (200 mL) under a nitrogen atmosphere at room temperature, and then sodium azide (6.69 g, 102.89 mmol) was added, and the mixture was stirred at 80° C. for 15 hours. After completion of the reaction, the mixture was cooled to room temperature, and the precipitate was removed by filtration using diethyl ether (100 mL), and the remaining filtrate was concentrated under reduced pressure. The residue was subjected to column chromatography to obtain Compound P-4c in the form of a colorless liquid (8.72 g, 73.5%).

$^1$H-NMR (400 MHz, $CDCl_3$) δ 3.69-3.66 (m, 16H), 3.39 (t, J=4.8 Hz, 4H).

Step 3: Preparation of Linker P-4

Compound P-4c (8.72 g, 30.25 mmol) was dissolved in EA (48 mL) and diethyl ether (48 mL) under a nitrogen atmosphere at 0° C., and then 5% hydrochloric acid aqueous solution (96 mL) and triphenylphosphine (8.73 g, 33.28 mmol) were sequentially and slowly added dropwise. The reaction solution was stirred for 15 hours while slowly raising the temperature from 0° C. to room temperature. After completion of the reaction, the organic layer was removed, and the remaining aqueous layer was washed again with EA (50 mL), and the obtained aqueous layer was concentrated under reduced pressure to obtain Linker P-4 in the form of a colorless oil (7.8 g, 86.3%).

$^1$H-NMR (400 MHz, $CDCl_3$) 8.21 (brs, 2H), 3.90 (t, J=4.8 Hz, 2H), 3.74-3.66 (m, 14H), 3.51 (t, J=4.8 Hz, 2H), 3.21 (m, 2H).

Preparation Example 5: Preparation of Linker P-5

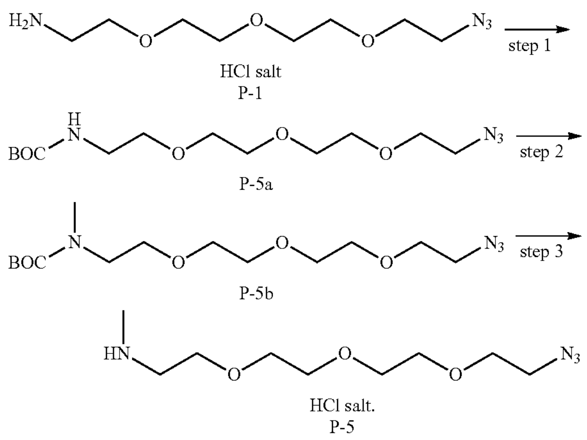

Step 1: Preparation of Compound P-5a

Linker P-1 (3.36 g, 13.19 mmol) was dissolved in 1,4-dioxane (44 mL) under a nitrogen atmosphere at 0° C., and then sodium bicarbonate (2.21 g, 26.38 mmol) and di-tert-butyl dicarbonate (Boc anhydride, 3.45 g, 15.83 mmol), which were dissolved in distilled water (22 mL), were added, and the mixture was stirred at room temperature for 5 hours. After completion of the reaction, EA (350 mL) and distilled water (300 mL) were added to extract the organic layer. The obtained organic layer was dried over anhydrous magnesium sulfate, filtered, and then concentrated under reduced pressure. The residue was subjected to column chromatography to obtain Compound P-5a in the form of a colorless liquid (3.68 g, 87%).

$^1$H-NMR (400 MHz, $CDCl_3$) δ 5.02 (brs, 1H), 3.70-3.60 (m, 10H), 3.54 (t, J=5.2 Hz, 2H), 3.39 (t, J=5.2 Hz, 2H), 3.32-3.31 (m, 2H), 1.44 (s, 9H).

Step 2: Preparation of Compound P-5b

THE (70 mL) was added dropwise to sodium hydride (60% dispersion in mineral oil, 924 mg, 23.10 mmol) under a nitrogen atmosphere at 0° C., and Compound P-5a (3.68 g, 11.55 mmol), which was dissolved in THE (30 mL), was slowly added to the reaction solution, and then the mixture was stirred at 0° C. for 30 minutes. Iodomethane (7.19 mL, 115.52 mmol) was slowly added to the reaction solution, and the mixture was stirred for 30 minutes and then stirred for an additional 16 hours while slowly raising the temperature to room temperature. After completion of the reaction, the mixture was cooled to 0° C., and distilled water (350 mL) and EA (350 mL) were added to extract the organic layer. The obtained organic layer was dried over anhydrous magnesium sulfate, filtered, and then concentrated under reduced pressure. The residue was subjected to column chromatography to obtain Compound P-5b in the form of a yellow liquid (3.74 g, 97%).

$^1$H-NMR (400 MHz, $CDCl_3$) δ 3.69-3.62 (m, 12H), 3.41-3.38 (m, 4H), 2.91 (s, 3H), 1.45 (s, 9H).

Step 3: Preparation of Linker P-5

Compound P-5b (3.74 g, 11.27 mmol) was dissolved in MC (20 mL) under a nitrogen atmosphere at 0° C., and then 4M-hydrochloric acid solution (4M HCl in 1,4-dioxocane, 40 mL) was added, and the mixture was stirred at room temperature for 1.5 hours. After completion of the reaction, the mixture was concentrated under reduced pressure to obtain Linker P-5 in the form of a yellow liquid (3.33 g, 99%).

$^1$H-NMR (400 MHz, $CDCl_3$) δ 9.45 (brs, 1H), 3.91 (t, J=5.2 Hz, 2H), 3.72-3.68 (m, 10H), 3.44 (t, J=5.2 Hz, 2H), 3.20-3.17 (m, 2H), 2.76 (t, J=5.2 Hz, 3H).

Preparation Example 6: Preparation of Linker P-6

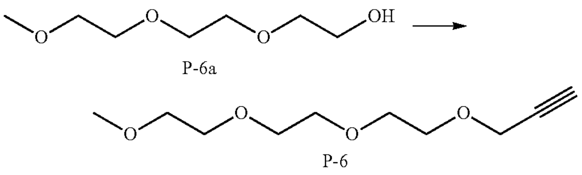

Compound P-6a (triethylene glycol monomethyl ether, TCI, CAS No. 112-35-6, 1 g, 6.09 mmol) was dissolved in THE (10 mL) under a nitrogen atmosphere at 0° C., and then KO$^t$Bu (1 g, 9.13 mmol) was added, and the mixture was stirred at 0° C. for 20 minutes. Propargyl bromide (1.3 mL, 12.18 mmol) was added to the reaction solution, and the mixture was stirred for 16 hours while slowly raising the temperature from 0° C. to room temperature. After completion of the reaction, the reaction solution was diluted with EA (200 mL) and extracted by adding distilled water (250 mL) to the solution, which was filtered using Celite. The obtained organic layer was dried over anhydrous magnesium sulfate, filtered, and then concentrated under reduced pressure. The resulting residue was subjected to column chromatography to obtain Linker P-6 (820 mg, 66%).

$^1$H-NMR (400 MHz, $CDCl_3$) δ 4.21 (d, J=2.4 Hz, 2H), 3.71-3.63 (m, 10H), 3.56-3.54 (m, 2H), 3.38 (s, 3H), 2.42 (t, J=2.4 Hz, 1H).

Preparation Example 7: Preparation of Linker P-7

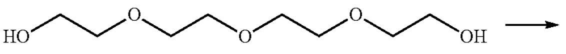

p-7a

-continued

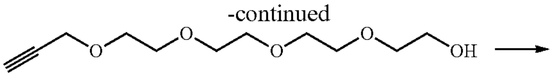

P-7b

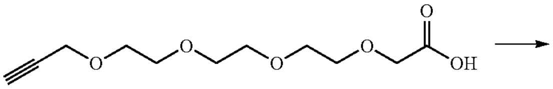

P-7c

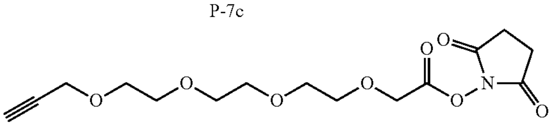

P-7

Step 1: Preparation of Compound P-7b

Sodium hydride (60% dispersion in mineral oil, 411 mg, 10.29 mmol) was added to THE (10 mL) under a nitrogen atmosphere at 0° C., and Compound P-7a (tetraethylene glycol, Merck, CAS NO. 112-60-7, 6.0 g, 30.89 mmol) was dissolved in THE (20 mL) and slowly added dropwise, and then the mixture was stirred for 5 minutes. Propargyl bromide (80% in toluene, 1.146 mL, 10.29 mmol) was added to the reaction solution, and the mixture was stirred at 0° C. for an additional 2 hours. After completion of the reaction, MC (200 mL) and distilled water (100 mL) were added to extract the organic layer. The obtained organic layer was dried over anhydrous magnesium sulfate, filtered, and then concentrated under reduced pressure. The resulting residue was subjected to column chromatography to obtain Compound P-7b in the form of an oil (1.9 g, 79.8%).

$^1$H-NMR (400 MHz, $CDCl_3$) δ 4.21 (d, J=2.4 Hz, 2H), 3.72-3.67 (m, 14H), 3.61 (t, J=4.4 Hz, 2H), 2.61 (brs, 1H), 2.43 (t, J=2.4 Hz, 1H).

Step 2: Preparation of Compound P-7c

Compound P-7b (1.0 g, 4.3 mmol) was dissolved in acetone (30 mL), then Jones reagent (Merck, CAS NO. 65272-70-0, 3 mL) was slowly added at −5° C., and the mixture was stirred at room temperature for 3 hours. After completion of the reaction, the green inorganic salt was removed by filtration, and the remaining filtrate was extracted with MC (100 mL) and distilled water (50 mL), and the obtained organic layer was dried over anhydrous magnesium sulfate, filtered, and then concentrated under reduced pressure. The resulting residue was subjected to column chromatography to obtain Compound P-7c (630 mg, 59.4%).

$^1$H-NMR (400 MHz, DMSO-$d_6$) δ 4.20 (d, J=2.4 Hz, 2H), 4.12 (s, 2H), 3.73-3.67 (m, 12H), 2.44 (t, J=2.4 Hz, 1H); EI-MS m/z: 246 $[M+H]^+$.

Step 3: Preparation of Linker P-7

Compound P-7c (90 mg, 0.365 mmol) was dissolved in MC (5 mL) under a nitrogen atmosphere at 0° C., and then NHS (46.2 mg, 0.40 mmol) and DCC (83 mg, 0.40 mmol) were added, and the mixture was stirred for 16 hours. After completion of the reaction, EA/n-pentane (1:1 volume ratio, 20 mL) was added, and the resulting precipitate was removed by filtration. The filtrate was concentrated, and then the EA/n-pentane (1:1 volume ratio, 20 mL) solution was added once again, and the resulting precipitate was removed, and the filtrate was concentrated under reduced pressure, and the obtained Linker P-7 was used in the next reaction without an additional purification process (100 mg, 80%).

$^1$H-NMR (400 MHz, $CDCl_3$) δ 4.53 (s, 2H), 4.20 (d, J=2.4 Hz, 2H), 3.81-3.79 (m, 2H), 3.75-3.67 (m, 10H), 2.85 (s, 4H), 2.43 (t, J=2.4 Hz, 1H); EI-MS m/z: 366 $[M+Na]^+$.

Preparation Example 8: Preparation of Linker P-8

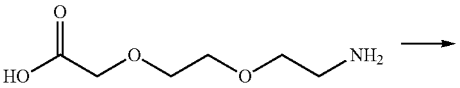

P-8a

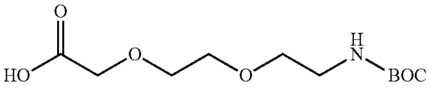

P-8

P-8a (2-[2-(2-aminoethoxy)ethoxy]acetic acid, TCI, CAS No. 134978-97-5, 1.28 g, 7.87 mmol) was dissolved in 1,4-dioxane (30 mL) under a nitrogen atmosphere at 0° C., and then sodium bicarbonate (1.32 g, 15.74 mmol) and di-tert-butyl dicarbonate (Boc anhydride, 2.06 g, 9.44 mmol), which were dissolved in distilled water (15 mL), were sequentially added, and the mixture was stirred for 16 hours while slowly raising the temperature from 0° C. to room temperature. After completion of the reaction, EA (200 mL), distilled water (150 mL), and 2N-hydrochloric acid aqueous solution (50 mL) were added to extract the organic layer 5 times. The obtained organic layer was dried over anhydrous magnesium sulfate, filtered, and then concentrated under reduced pressure to obtain Linker P-8 in the form of a colorless liquid (2.32 g, quantitatively obtained).

$^1$H-NMR (400 MHz, $CDCl_3$) δ 4.93 (brs, 1H), 4.17 (s, 2H), 3.78-3.76 (m, 2H), 3.68-3.65 (m, 2H), 3.62-3.56 (m, 2H), 3.38-3.32 (m, 2H), 1.45 (s, 9H).

Preparation Example 9: Preparation of Auristatin F-OMe

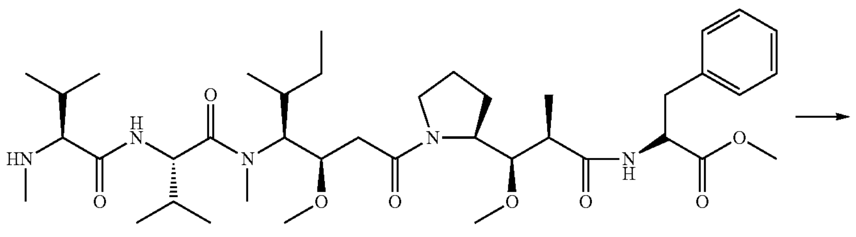

MMAF-OMe

-continued

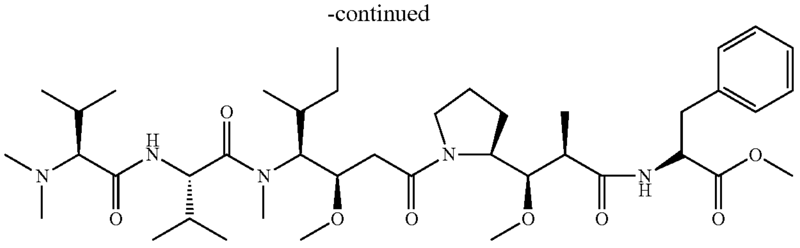

Auristatin F-OMe

The compound MMAF-OMe (CAS NO. 863971-12-4, 1 g, 1.34 mmol) was dissolved in DMF (7 mL) under a nitrogen atmosphere at room temperature, and then 37% formaldehyde aqueous solution (37 wt. % in $H_2O$, 299 μL, 4.02 mmol) and acetic acid (1.53 mL, 26.81 mmol) were sequentially added, and the mixture was stirred at room temperature for 30 minutes. Sodium cyanoborohydride ($NaCNBH_3$, 168.5 mg, 2.68 mmol) was added to the reaction solution, and the mixture was stirred for 2.5 hours at room temperature. After completion of the reaction, a saturated aqueous sodium bicarbonate solution was slowly added dropwise until the pH of the reaction solution reached 9, and EA (100 mL) was added to extract the organic layer. The obtained organic layer was dried over anhydrous magnesium sulfate, filtered, and then concentrated under reduced pressure. The resulting residue was subjected to column chromatography to obtain auristatin F-OMe in the form of a white solid (892 mg, 88%); EI-MS m/z: 761.0 $[M+H]^+$.

Preparation Example 10: Preparation of Compound L3-1

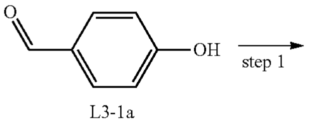

L3-1a

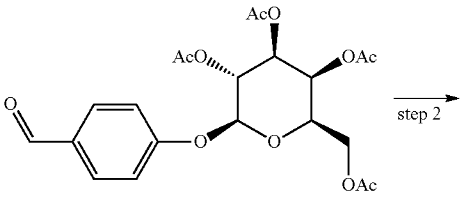

L3-1b

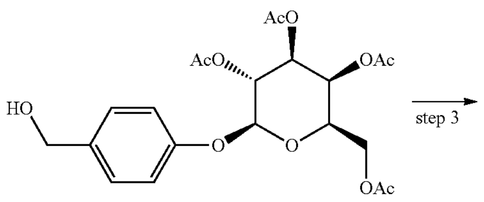

L3-1c

-continued

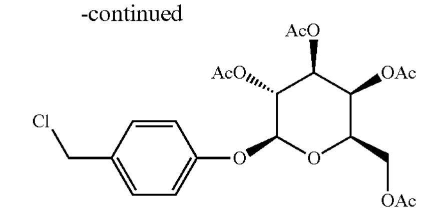

L3-1

Step 1: Preparation of Compound L3-1b

Compound L3-1a (4-hydroxybenzaldehyde, CAS NO. 123-08-0, 300 mg, 2.46 mmol) was dissolved in ACN (10 mL) under a nitrogen atmosphere at 0° C., and then aceto-bromo-alpha-D-galactose (Merck, CAS No. 3068-32-4, 1.1 g, 2.70 mmol), a molecular sieve (100 mg) and silver oxide (I) (1.42 g, 6.14 mmol) were sequentially added, and the mixture was stirred at room temperature for 3 hours. After completion of the reaction, the reaction solution was diluted with EA (100 mL), filtered using Celite, and concentrated under reduced pressure. The resulting residue was subjected to column chromatography to obtain Compound L3-1b in the form of a white solid (951 mg, 86%).

$^1$H-NMR (400 MHz, $CDCl_3$) δ 9.93 (s, 1H), 7.86 (d, J=8.4 Hz, 2H), 7.11 (d, J=8.4 Hz, 2H), 5.47 (m, 2H), 5.15 (m, 2H), 4.17 (m, 3H), 2.19 (s, 3H), 2.07 (s, 6H), 2.02 (s, 3H).

Step 2: Preparation of Compound L3-1c

Compound L3-1b (951 mg, 2.1 mmol) was dissolved in THE (20 mL) under a nitrogen atmosphere at 0° C., and then sodium borohydride (159 mg, 4.2 mmol) was added, and the mixture was stirred at room temperature for 3 hours. After completion of the reaction, distilled water (100 mL) was added to terminate the reaction, and EA (100 mL) was added to extract the organic layer three times. The obtained organic layer was dried over anhydrous magnesium sulfate, filtered, and then concentrated under reduced pressure. The resulting residue was subjected to column chromatography to obtain Compound L3-1c in the form of a white solid (695 mg, 73%).

$^1$H-NMR (400 MHz, $CDCl_3$) 7.31 (d, J=8.8 Hz, 2H), 7.00 (d, J=8.8 Hz, 2H), 5.46 (m, 2H), 5.04 (m, 2H), 4.66 (s, 2H), 4.17 (m, 3H), 2.19 (s, 3H), 2.07 (s, 6H), 2.01 (s, 3H).

Step 3: Preparation of Compound L3-1

Compound L3-1c (800 mg, 1.76 mmol) was dissolved in MC (10 mL) under a nitrogen atmosphere at 0° C., and then thionyl chloride (191 μL, 2.64 mmol) was added, and the mixture was stirred for 2 hours while raising the temperature from 0° C. to room temperature. After completion of the reaction, the mixture was diluted by adding MC (10 mL) and then concentrated under reduced pressure. The organic layer of the residue obtained by concentration under reduced pressure was extracted twice with EA (50 mL) and distilled water (50 mL). The obtained organic layer was dried over anhydrous magnesium sulfate, filtered, and then concentrated under reduced pressure to obtain Compound L3-1 in the form of a colorless sticky oil (831 mg, 99%).

$^1$H-NMR (400 MHz, $CDCl_3$) 7.32 (d, J=8.8 Hz, 2H), 6.98 (d, J=8.8 Hz, 2H), 5.51-5.45 (m, 2H), 5.11 (dd, J=10.4, 3.6 Hz, 1H), 5.04 (d, J=7.6 Hz, 1H), 4.56 (s, 2H), 4.25-4.14 (m, 3H), 2.18 (s, 3H), 2.06 (s, 6H), 2.01 (s, 3H).

Preparation Example 11: Preparation of Compound PL-1

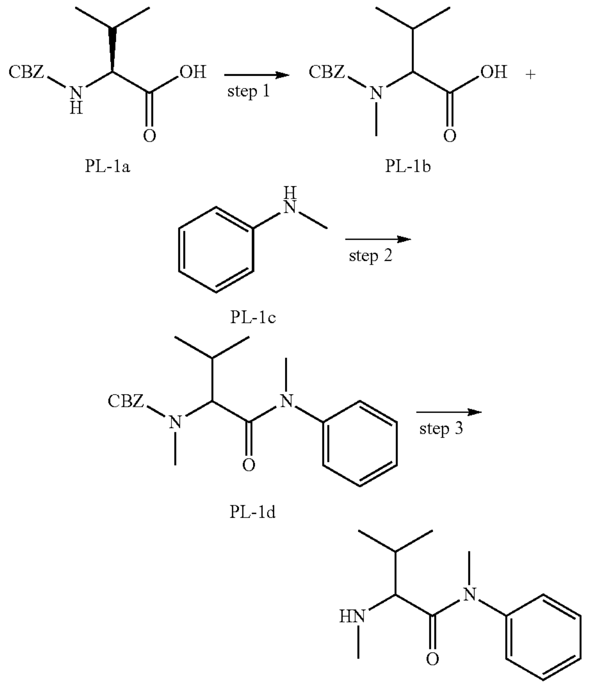

PL-1a PL-1b PL-1c PL-1d

PL-1

Step 1: Preparation of Compound PL-1b

A solution of Compound PL-1a (carbobenzyloxy-L-valine, Z-Val-OH, Merck, CAS No. 1149-26-4, 5 g, 19.9 mmol) dissolved in THE (20 mL) was slowly added to a reaction solution in which THE (50 mL) was added to 60% sodium hydride (60% dispersion in mineral oil, 3.4 g, 85.56 mmol) under a nitrogen atmosphere at 0° C., and the mixture was stirred at 0° C. for 20 minutes. Then, iodomethane (12.38 mL, 198.98 mmol) was slowly added, and the mixture was stirred at room temperature for 20 hours. The reaction solution was cooled to 0° C., and then distilled water (150 mL) was added to terminate the reaction, and EA (200 mL) and 2N-hydrochloric acid aqueous solution (50 mL) were added to extract the organic layer twice. The obtained organic layer was dried over anhydrous magnesium sulfate, filtered, and then concentrated under reduced pressure. The residue was subjected to column chromatography to obtain Compound PL-1b (3.7 g, 70%).

$^1$H-NMR (400 MHz, DMSO-$d_6$) δ 7.36-7.30 (m, 5H), 5.11 (s, 2H), 4.22-412 (m, 1H), 2.84-81 (m, 3H), 2.11 (m, 1H), 0.95 (m, 3H), 0.82 (m, 3H).

Step 2: Preparation of Compound PL-1d

Compound PL-1b (600 mg, 2.26 mmol) and Compound PL-1c (N-methylaniline, Merck, CAS No. 100-61-8, 361 mg, 3.39 mmol) were dissolved in MC (12 mL) under a nitrogen atmosphere at 0° C., and then DCC (700 mg, 3.39 mmol), DMAP (55.2 mg, 0.46 mmol) and DIPEA (0.78 mL, 4.52 mmol) were sequentially added, and the mixture was stirred at 0° C. for 20 minutes. The reaction mixture was stirred for an additional 16 hours. After completion of the reaction, the reaction solution was diluted with EA (100 mL) and extracted by adding 2N-hydrochloric acid aqueous solution (100 mL) to the filtered solution. The obtained organic layer was extracted once more by adding 2N-sodium hydroxide aqueous solution (100 mL), and then washed by adding a saturated aqueous sodium chloride solution (100 mL). The obtained organic layer was dried over anhydrous magnesium sulfate, filtered, and then concentrated under reduced pressure. The resulting residue was subjected to column chromatography to obtain Compound PL-1d in the form of a colorless oil (429 mg, 53%).

$^1$H-NMR (400 MHz, $CDCl_3$) δ 7.41-7.24 (m, 6H), 7.09-7.02 (m, 4H), 5.01-4.96 (m, 2H), 4.40-4.28 (m, 1H), 3.25 (s, 3H), 2.91-2.87 (m, 3H), 2.33 (m, 1H), 0.90 (d, J=6.8 Hz, 3H), 0.74-0.65 (m, 3H).

Step 3: Preparation of Compound PL-1

Compound PL-1d (429 mg, 1.21 mmol) was dissolved in methanol (50 mL) under a nitrogen atmosphere at room temperature, and then 5% palladium charcoal (5% Pd/C, 150 mg) was added, and the mixture was stirred for 2 hours under a hydrogen environment. After completion of the reaction, the reaction solution was diluted with EA (100 mL) and filtered using a Celite filter, and the solution was concentrated under reduced pressure to obtain Compound PL-1 in the form of a colorless oil (264.3 mg, 99%).

$^1$H-NMR (400 MHz, $CDCl_3$) δ 7.45-4.41 (m, 2H), 7.37-7.34 (m, 1H), 7.02-7.18 (m, 2H), 3.31 (s, 3H), 2.85 (d, J=6.4 Hz, 1H), 2.31 (s, 3H), 1.71 (m, 1H), 0.85 (d, J=6.8 Hz, 3H), 0.80 (d, J=6.8 Hz, 3H).

Preparation Example 12: Preparation of Compound PL-2

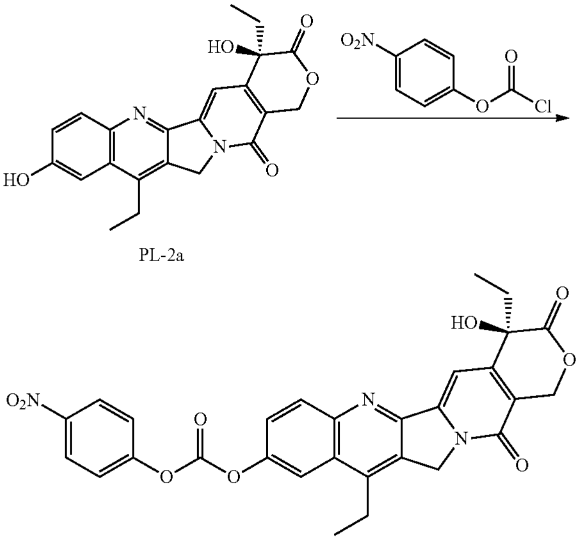
PL-2a

PL-2

Compound PL-2a (SN-38, 7-ethyl-10-hydroxycamptothecin, ASTATECH, CAS No. 86639-52-3, 30.0 mg, 0.076 mmol) was dissolved in MC (6.0 mL) under a nitrogen atmosphere, and then 4-nitrophenyl chloroformate (23.1 mg, 0.114 mmol) and DIPEA (13.3 μL, 0.076 mmol) and pyridine (18.4 μL, 0.229 mmol) were sequentially added, and the mixture was stirred at room temperature for 16 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound PL-2 in the form of a white solid (7.5 mg, 17%); EI-MS m/z: 558 $[M+H]^+$.

Preparation Example 13: Preparation of Compound PL-3

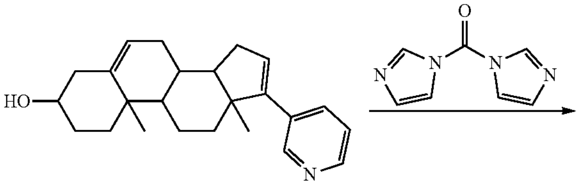

PL-3a

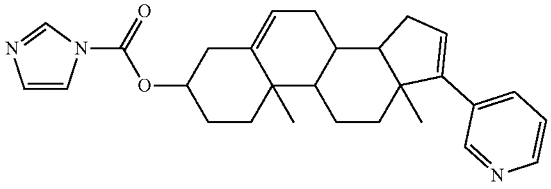

PL-3

Compound PL-3a (Abiraterone, TCI, CAS No. 154229-19-3, 30.0 mg, 0.086 mmol) was dissolved in THE (3.0 mL) under a nitrogen atmosphere, and then carbonyldiimidazole (CDI, Alfa Aesar, CAS No. 530-62-1, 17.2 mg, 0.105 mmol) was added, and the mixture was stirred at room temperature for 16 hours. After completion of the reaction, EA (10 mL) and distilled water (10 mL) were added to extract the organic layer. The obtained organic layer was dried over anhydrous magnesium sulfate, filtered, and then concentrated under reduced pressure. The resulting residue was subjected to column chromatography to obtain Compound PL-3 in the form of a white solid (16.0 mg, 42%).

$^1$H-NMR (400 MHz, $CDCl_3$) δ 8.62 (s, 1H), 8.46 (d, J=4.8 Hz, 1H), 8.13 (s, 1H), 8.13 (s, 1H), 7.65 (d, J=8.0 Hz, 1H), 7.42 (s, 1H), 7.22 (dd, J=8.0 Hz, J=4.8 Hz, 1H), 7.06 (s, 1H), 6.00 (s, 1H), 5.49 (d, J=4.8 Hz, 1H), 4.85-4.83 (m, 1H), 2.54-2.52 (m, 2H), 2.29-2.25 (m, 1H), 2.08-2.04 (m, 4H), 1.97-1.81 (m, 1H), 1.80-1.48 (m, 9H), 1.26-1.22 (m, 1H), 1.13 (s, 3H), 1.06 (s, 3H).

Preparation Example 14: Preparation of Core C-1

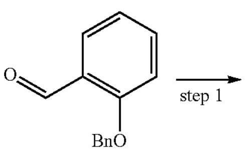

C-1a

-continued

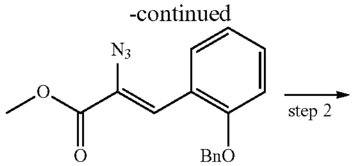

C-1b

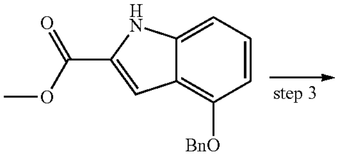

C-1c

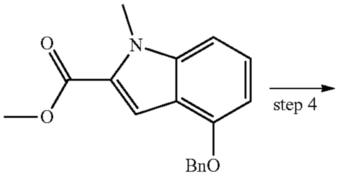

C-1d

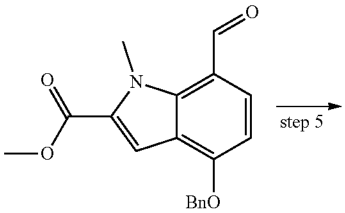

C-1e

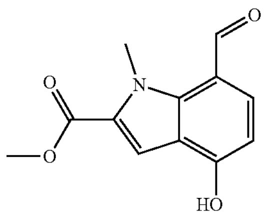

C-1

Step 1: Preparation of Compound C-1b

Compound C-1a (2-benzyloxybenzaldehyde, CAS NO. 5896-17-3, 5.48 g, 25.8 mmol) was dissolved in methanol (55 mL) under a nitrogen atmosphere at −30° C., and then ethyl azidoacetate (CAS NO. 637-81-0, TCI, 28.2 mL, 258.20 mmol) and sodium methoxide (25 wt % in MeOH, 44.6 mL, 206.4 mmol) were slowly added. The mixture was stirred at −30° C. for 3 hours, and then distilled water (100 mL) was slowly added dropwise to terminate the reaction, and EA (100 mL) was added to extract the organic layer. The obtained organic layer was dried over anhydrous magnesium sulfate, filtered, and then concentrated under reduced pressure to obtain Compound C-1b (7.74 g, 97%). The obtained Compound C-1b was used in the next reaction without an additional purification process.

Step 2: Preparation of Compound C-1c

Compound C-1b (7.74 g, 25.02 mmol) was dissolved in xylene (200 mL) under a nitrogen atmosphere at room temperature, and then the mixture was stirred at 150° C. for 3 hours. After completion of the reaction, the mixture was cooled to room temperature and concentrated under reduced pressure. The resulting residue was subjected to column chromatography to obtain Compound C-1c (510.8 mg, 22.7%).

$^1$H-NMR (400 MHz, $CDCl_3$) δ 8.82 (brs, 1H), 7.51-7.49 (m, 2H), 7.42-7.33 (m, 4H), 7.22 (t, J=8 Hz, 1H), 7.02 (d, J=8 Hz, 1H), 6.58 (d, J=8 Hz, 1H), 5.22 (s, 2H), 3.92 (s, 3H).

Step 3: Preparation of Compound C-1d

Compound C-1c (1.14 g, 4.05 mmol) was dissolved in DMF (35 mL) under a nitrogen atmosphere at room temperature, and then potassium carbonate (1.68 g, 12.15 mmol) and iodomethane (0.65 mL, 10.53 mmol) were sequentially added, and the mixture was stirred for 12 hours. After completion of the reaction, EA (100 mL) and distilled water (100 mL) were added to extract the organic layer. Distilled water (300 mL) was added to extract the obtained organic layer again, and the organic layer was dried over anhydrous magnesium sulfate, filtered, and then concentrated under reduced pressure. The resulting residue was subjected to column chromatography to obtain Compound C-1d (912.7 mg, 76%).

$^1$H-NMR (400 MHz, $CDCl_3$) δ 7.50-7.47 (m, 3H), 7.42-7.33 (m, 3H), 7.25 (m, 1H), 6.99 (d, J=8 Hz, 1H), 6.57 (d, J=8 Hz, 1H), 5.22 (s, 2H), 4.06 (s, 3H), 3.89 (s, 3H).

Step 4: Preparation of Compound C-1e

C-1d (800 mg, 2.70 mmol) was dissolved in MC (40 mL) under a nitrogen atmosphere at −50° C., and then dichloromethyl methyl ether (735 μL, 8.10 mmol) and titanium tetrachloride solution (1M-$TiCl_4$ in MC, 8.1 mL, 8.1 mmol) were sequentially and slowly added, and the mixture was stirred for 2 hours while maintaining the temperature. After completion of the reaction, cooled distilled water (100 mL) was slowly added dropwise to terminate the reaction, and EA (100 mL) was added to extract the organic layer. The obtained organic layer was dried over anhydrous magnesium sulfate, filtered, and then concentrated under reduced pressure. The resulting residue was subjected to column chromatography to obtain Compound C-1e (392 mg, 44.8%).

$^1$H-NMR (400 MHz, $CDCl_3$) δ 10.10 (s, 1H), 7.81 (d, J=8.4 Hz, 1H), 7.44 (s, 1H), 7.49-7.47 (m, 2H), 7.44-7.36 (m, 3H), 6.69 (d, J=8.4 Hz, 1H), 5.39 (s, 2H), 4.36 (s, 3H), 3.90 (s, 3H).

Step 5: Preparation of Core C-1

Compound C-1e (393.2 mg, 1.22 mmol) was dissolved in MC (20 mL) under a nitrogen atmosphere at −50° C., and then boron trichloride solution (1M-$BCl_3$ in MC, 6 mL, 6.08 mmol) was slowly added, and the mixture was stirred for 1.5 hours while slowly raising the temperature to -30° C. After completion of the reaction, distilled water (100 mL) was slowly added dropwise to terminate the reaction, and 2N-sodium hydroxide aqueous solution was added at 0° C. to neutralize it. MC (100 mL) was added to the mixture to extract the organic layer four times. The obtained organic layer was dried over anhydrous magnesium sulfate, filtered, and then concentrated under reduced pressure. The resulting residue was subjected to column chromatography to obtain Core C-1 in the form of a pale orange solid (239.7 mg, 84%).

$^1$H-NMR (400 MHz, DMSO-$d_6$) δ 9.99 (s, 1H), 7.79 (m, 1H), 7.43 (s, 1H), 6.55 (m, 1H), 4.22 (s, 3H), 3.84 (s, 3H).

Preparation Example 15: Preparation of Core C-2

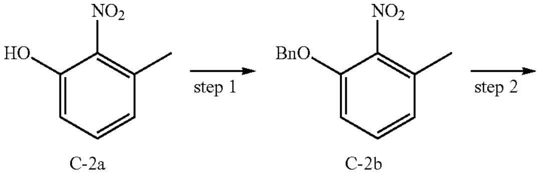

C-2a C-2b

-continued

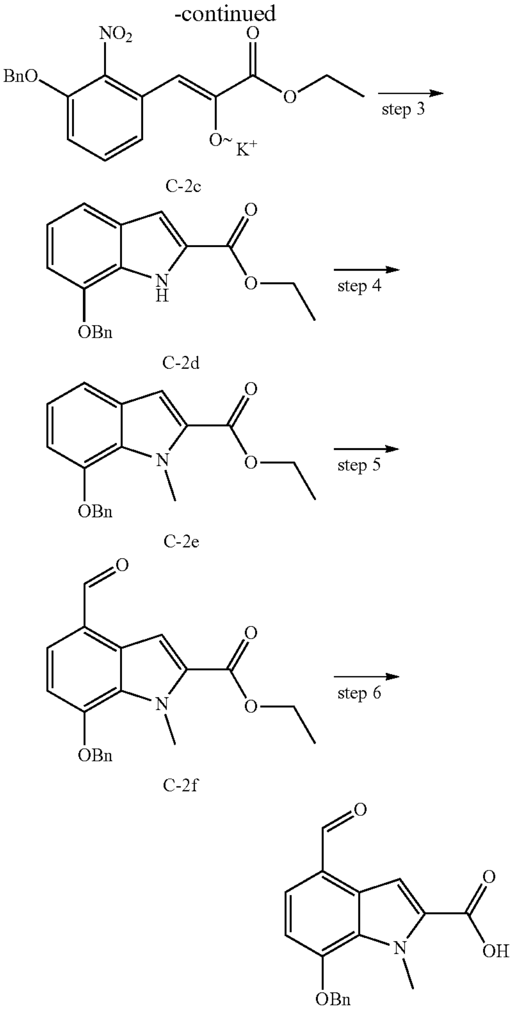

C-2c C-2d C-2e C-2f C-2

Step 1: Preparation of Compound C-2b

Compound C-2a (2-nitro-m-cresol, TCI, CAS NO. 4920-77-8, 20 g, 130.59 mmol) was dissolved in ACN (250 mL) under a nitrogen atmosphere at 0° C., and then benzyl chloride (15.78 mL, 137.12 mmol) and potassium carbonate (22.56 g, 163.24 mmol) were added, and the mixture was stirred at 80° C. for 16 hours. After completion of the reaction, EA (200 mL) and distilled water (300 mL) were added to extract the organic layer. The obtained organic layer was dried over anhydrous magnesium sulfate, filtered, and then concentrated under reduced pressure. The residue was subjected to column chromatography to obtain Compound C-2b in the form of a light yellow oil (31.76 g, 99%).

$^1$H-NMR (400 MHz, $CDCl_3$) δ 7.37-7.31 (m, 5H), 7.24 (m, 1H), 6.89-6.83 (m, 2H), 5.15 (s, 2H), 2.31 (s, 3H).

Step 2: Preparation of Compound C-2c

KO$^t$Bu (15.35 g, 136.82 mmol) was dissolved in THF (100 mL) and diethyl ether (300 mL) under a nitrogen atmosphere at room temperature, and diethyl oxalate (Merck, CAS NO. 95-92-1, 19.46 mL, 143.34 mmol) was added, and then the mixture was stirred for 15 minutes. Compound C-2c (31.7 g, 31.7 mmol) dissolved in THF (50 mL) was slowly added to the above reaction solution, and then the mixture was stirred at room temperature for 19 hours and stirred at 80° C. for an additional 3 hours. After completion of the reaction, the reaction solution was cooled to room temperature, diethyl ether (200 mL) was added dropwise, and the resulting precipitate was filtered, washed with diethyl ether (100 mL), and then dried to obtain Compound C-2c in the form of a light orange solid (41.5 g, 83%).

$^1$H-NMR (400 MHz, DMSO-$d_6$) δ 8.66 (d, J=8 Hz, 1H), 7.40-7.30 (m, 5H), 7.04 (t, J=8 Hz, 1H), 6.50 (d, J=8 Hz, 1H), 5.15 (s, 1H), 5.10 (s, 2H), 3.99 (q, J=7.2 Hz, 2H), 1.17 (t, J=7.2 Hz, 3H).

Step 3: Preparation of Compound C-2d

Iron powder (57.1 g, 1.02 mol) was slowly added to acetic acid (200 mL) under a nitrogen atmosphere at room temperature, and while stirring, Compound C-2c (39 g, 102.24 mmol) dissolved in acetic acid (150 mL) was added, and the mixture was stirred at 80° C. for 6 hours. After completion of the reaction, the temperature of the reaction solution was lowered to 45° C., and EA (500 mL) was added dropwise, and then the mixture was stirred for an additional 30 minutes, and the filtrate obtained through Celite filtration was concentrated under reduced pressure. EA (300 mL) was added to the concentrate thus obtained, and the resulting precipitate was filtered once again. The filtrate was concentrated under reduced pressure. The resulting residue was subjected to column chromatography to obtain Compound C-2d in the form of a light yellow solid (22.18 g, 73%).

$^1$H-NMR (400 MHz, CD30D-$d_4$) 7.57-7.55 (m, 2H), 7.43-7.39 (m, 2H), 7.36-7.32 (m, 1H), 7.23 (d, J=8 Hz, 1H), 7.15 (s, 1H), 6.98 (t, J=8 Hz, 1H), 6.83 (d, J=7.6 Hz, 1H), 5.29 (s, 2H), 4.39 (q, J=7.2 Hz, 2H), 1.42 (t, J=7.2 Hz, 3H).

Step 4: Preparation of Compound C-2e

Compound C-2d (6 g, 20.31 mmol) was dissolved in DMF (30 mL) under a nitrogen atmosphere at 0° C., and then potassium carbonate (4.21 g, 30.46 mmol) and iodomethane (1.64 mL, 26.40 mmol) were sequentially added, and the mixture was stirred at 0° C. for 1 hour. The reaction temperature was raised to room temperature, and the mixture was stirred for 12 hours, and then the mixture was stirred for an additional 3 hours at 60° C. to complete the reaction. The temperature of the reaction solution was cooled to room temperature, and EA (200 mL) and distilled water (400 mL) were added to extract the organic layer. Distilled water (300 mL) was added to extract the obtained organic layer again, and the extracted organic layer was dried over anhydrous magnesium sulfate, filtered, and then concentrated under reduced pressure. The obtained C-2e was used in the next reaction without an additional purification process (6.28 g, 99%).

$^1$H-NMR (400 MHz, $CDCl_3$) δ 7.49-7.47 (m, 2H), 7.42-7.39 (m, 2H), 7.37-7.33 (m, 1H), 7.25-7.23 (m, 2H), 6.99 (t, J=8 Hz, 1H), 6.77 (d, J=7.6 Hz, 1H), 5.18 (s, 2H), 4.37 (s, 3H), 4.35 (q, J=7.2 Hz, 2H), 1.40 (t, J=7.2 Hz, 3H).

Step 5: Preparation of Compound C-2f

Compound C-2e (500 mg, 1.61 mmol) was dissolved in MC (20 mL) under a nitrogen atmosphere at −30° C., and then dichloromethyl methyl ether (Merck, CAS NO. 4885-02-3, 438 μL, 4.83 mmol) and titanium tetrachloride solution (1M-$TiCl_4$ in MC, 4.85 mL, 4.83 mmol) were sequentially and slowly added, and the mixture was stirred for 1 hour while maintaining the temperature. After completion of the reaction, cooled distilled water (100 mL) was slowly added dropwise to terminate the reaction, and EA (100 mL) was added to extract the organic layer. The obtained organic layer was dried over anhydrous magnesium sulfate, filtered, and then concentrated under reduced pressure. The resulting residue was subjected to column chromatography to obtain Compound C-2f (495 mg, 94%).

$^1$H-NMR (400 MHz, CD30D-$d_4$) δ 9.96 (s, 1H), 7.91 (s, 1H), 7.67 (d, J=8 Hz, 1H), 7.57-7.55 (m, 2H), 7.47-7.37 (m, 3H), 7.08 (d, J=8 Hz, 1H), 5.37 (s, 2H), 4.39-4.36 (m, 5H), 1.42 (t, J=7.2 Hz, 3H).

Step 6: Preparation of Core C-2

Compound C-2f (300 mg, 0.89 mmol) was dissolved in ethanol (8 mL) and THE (4 mL) at room temperature, and then lithium hydroxide monohydrate (75 mg, 1.78 mmol) dissolved in distilled water (3 mL) was slowly added dropwise, and the mixture was stirred at 50° C. for 30 minutes. The reaction solution was cooled, and then 1N-hydrochloric acid aqueous solution (10 mL) and distilled water (50 mL) and EA (100 mL) were added to extract the organic layer, and the obtained organic layer was dried over anhydrous magnesium sulfate, filtered, and then concentrated under reduced pressure to obtain Core C-2, which was used in the next reaction without an additional purification process (275 mg, 99%).

$^1$H-NMR (400 MHz, Aceton-$d_4$) δ 10.06 (s, 1H), 8.03 (s, 1H), 7.71 (d, J=8 Hz, 1H), 7.65-7.63 (m, 2H), 7.49-7.38 (m, 3H), 7.15 (d, J=8 Hz, 1H), 5.45 (s, 2H), 4.41 (s, 3H).

Preparation Example 16: Preparation of Core C-3

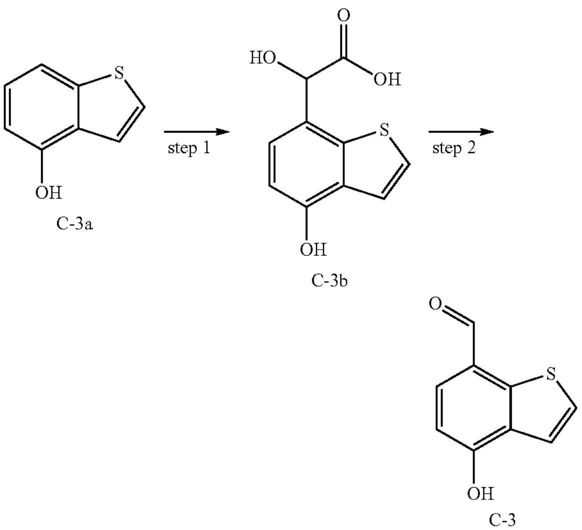

C-3a C-3b C-3

Step 1: Preparation of Compound C-3b

Compound C-3a (benzo[b]thiophene-4-ol, Ambeed, CAS NO. 3610-02-4, 500 mg, 3.35 mmol) was dissolved in 10% potassium hydroxide aqueous solution (410 mg in 4 mL $H_2O$) under a nitrogen atmosphere at 0° C., and then glyoxylic acid monohydrate (300 mg) was added, and the mixture was stirred for 7 hours. After completion of the reaction, the mixture was diluted by adding distilled water (2 mL), and 2N-hydrochloric acid aqueous solution was slowly added dropwise to adjust the pH of the reaction solution to 7. The organic layer was extracted and removed using diethyl ether (10 mL), and 2N-hydrochloric acid aqueous solution was slowly added dropwise to the aqueous layer to adjust the pH to 2, and extracted three times using diethyl ether (100 mL). The organic layer was collected, dried over anhydrous magnesium sulfate, filtered, and then concentrated under reduced pressure to obtain Compound C-3b (460 mg, 61.6%).

$^1$H-NMR (400 MHz, $CDCl_3$) δ 7.51 (d, J=5.6 Hz, 1H), 7.36 (d, J=5.6 Hz, 1H), 7.24 (d, J=8 Hz, 1H), 6.72 (d, J=8 Hz, 1H), 5.41 (s, 1H).

Step 2: Preparation of Core C-3

Compound C-3b (450 mg, 2.0 mmol) was dissolved in ethanol (0.8 mL) under a nitrogen atmosphere at room temperature, and then ferric sulfate hydrate (923 mg, 2.3 mmol) and 0.4N-sulfuric acid aqueous solution (3.8 mL) were sequentially added, and the mixture was stirred at 60° C. for 1 hour. After completion of the reaction, the reaction temperature was lowered to room temperature, and the reaction solution was filtered using EA (100 mL). Distilled water (100 mL) was added to the filtrate to extract the organic layer, and the organic layer was dried over anhydrous magnesium sulfate, filtered, and then concentrated under reduced pressure. The resulting residue was subjected to column chromatography to obtain Core C-3 (210 mg, 58%).

$^1$H-NMR (400 MHz, $CDCl_3$) δ 10.01 (s, 1H), 7.74 (d, J=8 Hz, 1H), 7.60 (d, J=5.6 Hz, 1H), 7.52 (d, J=5.6 Hz, 1H), 6.88 (d, J=8 Hz, 1H).

Preparation Example 17: Preparation of Core C-4

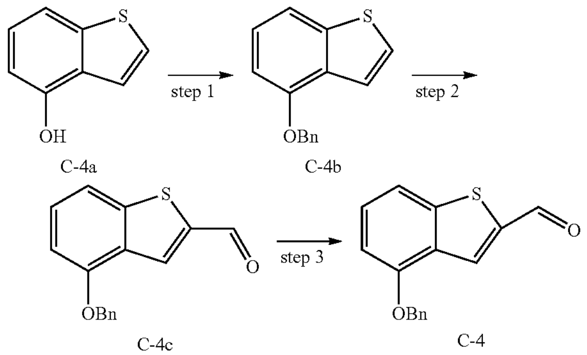

C-4a C-4b C-4c C-4

Step 1: Preparation of Compound C-4b

Compound C-4a (benzo[b]thiophene-4-ol, Ambeed, CAS NO. 3610-02-4, 1.14 g, 7.63 mmol) was dissolved in ACN (50 mL) under a nitrogen atmosphere at 0° C., and then potassium carbonate (2.63 g, 19.07 mmol) and benzyl bromide (1 mL, 8.39 mmol) were slowly added, and the mixture was stirred at 0° C. for 30 minutes. The reaction temperature was raised to room temperature, and the mixture was stirred for an additional 16 hours. After completion of the reaction, EA (350 mL) and distilled water (350 mL) were added to extract the organic layer. The obtained organic layer was dried over anhydrous magnesium sulfate, filtered, and then concentrated under reduced pressure. The residue was subjected to column chromatography to obtain Compound C-4b in the form of a light orange oil (1.87 g, 99%).

$^1$H-NMR (400 MHz, $CDCl_3$) δ 7.57 (d, J=5.6 Hz, 1H), 7.50-7.47 (m, 3H), 7.42-7.38 (m, 2H), 7.35-7.32 (m, 2H), 7.27-7.23 (m, 1H), 6.81 (d, J=8 Hz, 1H), 5.22 (s, 2H).

Step 2: Preparation of Compound C-4c

Compound C-4b(1.87 g, 7.8 mmol) was dissolved in THE (60 mL) under a nitrogen atmosphere at room temperature. The solution was cooled to −78° C., and then n-butyl lithium solution (2.5M n-BuLi in hexane, 1.42 mL, 3.56 mmol) was slowly added dropwise, and the mixture was stirred at the same temperature for 30 minutes. DMF (0.78 mL) was slowly added to the mixture, and the mixture was stirred at the same temperature for an additional 30 minutes. Distilled water (300 mL) was added to the mixture at the same temperature to terminate the reaction, and then EA (300 mL) was added to extract the organic layer. The obtained organic layer was dried over anhydrous magnesium sulfate, filtered, and then concentrated under reduced pressure. The residue was subjected to column chromatography to obtain Compound C-4c in the form of a light yellow oil (1.36 g, 65%).

$^1$H-NMR (400 MHz, $CDCl_3$) δ 10.06 (s, 1H), 8.25 (s, 1H), 7.50-7.37 (m, 7H), 6.85 (d, J=7.6 Hz, 1H), 5.24 (s, 2H).

Step 3: Preparation of Core C-4

Compound C-4c (300 mg, 1.11 mmol) was dissolved in MC (20 mL) under a nitrogen atmosphere at −78° C., and then boron trichloride solution (1M-$BCl_3$ in MC, 2.2 mL, 2.20 mmol) was slowly added, and the mixture was stirred for 30 minutes. After completion of the reaction, EA (10 mL) and distilled water (10 mL) were slowly added dropwise at −50° C. to terminate the reaction, and EA (100 mL) and distilled water (100 mL) were added at room temperature to extract the organic layer. The obtained organic layer was dried over anhydrous magnesium sulfate, filtered, and then concentrated under reduced pressure. The resulting residue was subjected to column chromatography to obtain Core C-4 in the form of a light yellowish brown solid (174 mg, 87.4%).

$^1$H-NMR (400 MHz, DMSO-$d_6$) δ 10.62 (brs, 1H), 8.41 (s, 1H), 7.46 (d, J=8 Hz, 1H), 7.39 (t, J=8 Hz, 1H), 6.82 (d, J=8 Hz, 1H).

Preparation Example 18: Preparation of Core C-5

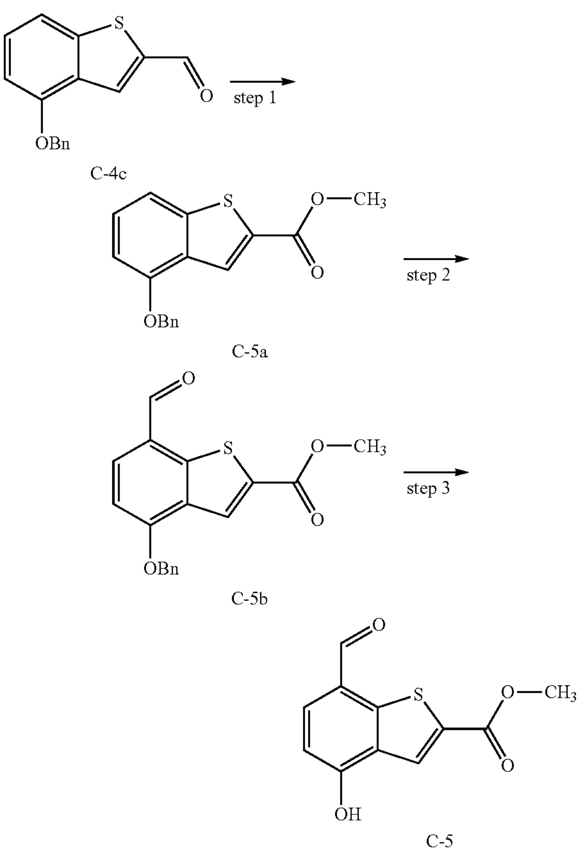

C-4c C-5a C-5b C-5

Step 1: Preparation of Compound C-5a

Compound C-4c (1.36 g, 5.09 mmol) prepared in Step 2 of Preparation Example 17 was dissolved in methanol (65 mL) under a nitrogen atmosphere at 0° C., and then potassium hydroxide (713 mg, 12.72 mmol) dissolved in methanol (15 mL) and iodine (1.67 g, 6.61 mmol) dissolved in methanol (15 mL) were sequentially and slowly added, and then the mixture was stirred at room temperature for 1 hour. After completion of the reaction, the organic layer was extracted with EA (500 mL) and distilled water (500 mL). The obtained organic layer was dried over anhydrous magnesium sulfate, filtered, and then concentrated under reduced pressure. The resulting residue was subjected to column chromatography to obtain Compound C-5a in the form of an ivory solid (1.43 g, 94%).

$^1$H-NMR (400 MHz, $CDCl_3$) δ 8.28 (s, 1H), 7.49-7.47 (m, 2H), 7.44-7.34 (m, 5H), 6.82 (d, J=7.6 Hz, 1H), 5.21 (s, 2H), 3.93 (s, 3H).

Step 2: Preparation of Compound C-5b

Compound C-5a (240 mg, 0.80 mmol) was dissolved in MC (15 mL) under a nitrogen atmosphere at −78° C., and then dichloromethyl methyl ether (218 μL, 2.41 mmol) and titanium tetrachloride solution (1M-$TiCl_4$ in MC, 2.41 mL, 2.41 mmol) were sequentially and slowly added, and the mixture was stirred for 1 hour while maintaining the temperature. After completion of the reaction, distilled water (100 mL) was slowly added dropwise to terminate the reaction, and EA (100 mL) was added to extract the organic layer twice. The obtained organic layer was dried over anhydrous magnesium sulfate, filtered, and then concentrated under reduced pressure. The resulting residue was subjected to column chromatography to obtain Compound C-5b (206.7 mg, 79%).

$^1$H-NMR (400 MHz, $CDCl_3$) δ 10.07 (s, 1H), 8.34 (s, 1H), 7.93 (d, J=8 Hz, 1H), 7.50-7.39 (m, 5H), 7.00 (d, J=8 Hz, 1H), 5.34 (s, 2H), 3.95 (s, 3H).

Step 3: Preparation of Core C-5

Compound C-5b (82.5 mg, 0.25 mmol) was dissolved in MC (5 mL) under a nitrogen atmosphere at −78° C., and then boron trichloride solution (1M-$BCl_3$ in MC, 2.78 mL, 2.78 mmol) was slowly added, and the mixture was stirred for 5 hours while slowly raising the temperature to −30° C. After completion of the reaction, distilled water (50 mL) was slowly added dropwise to terminate the reaction, and 2N-sodium hydroxide aqueous solution was added at 0° C. to neutralize it. MC (50 mL) was added to the mixture to extract the organic layer three times. The obtained organic layer was dried over anhydrous magnesium sulfate, filtered, and then concentrated under reduced pressure. The resulting residue was subjected to column chromatography to obtain Core C-5 in the form of an ivory solid (32.8 mg, 55%).

$^1$H-NMR (400 MHz, DMSO-$d_6$) δ 10.01 (s, 1H), 8.23 (s, 1H), 8.12 (d, J=8 Hz, 1H), 7.02 (d, J=8 Hz, 1H), 3.90 (s, 3H).

Preparation Example 19: Preparation of Core C-6

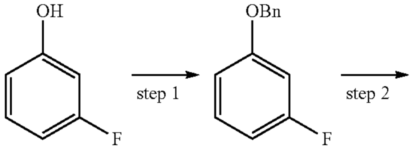

C-6a C-6b

-continued

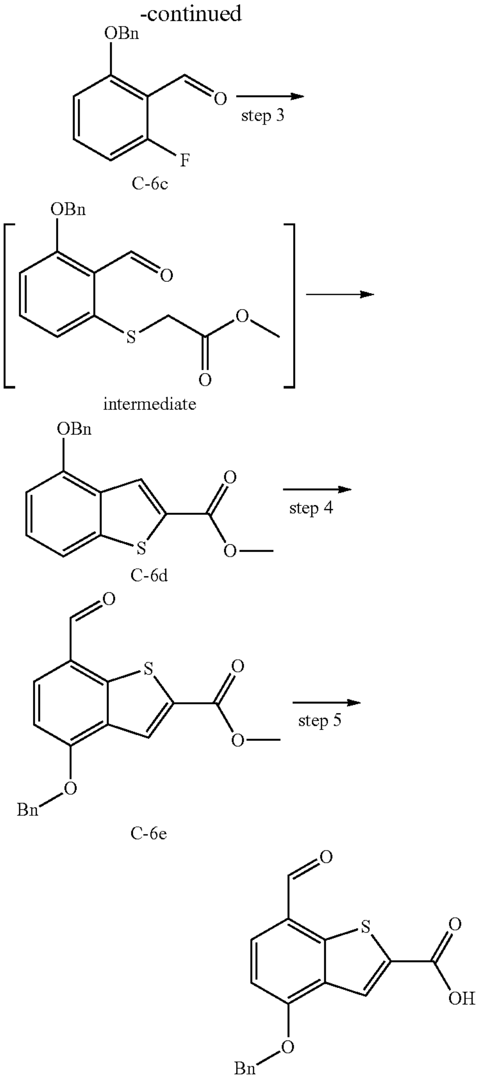

C-6c intermediate

C-6d

C-6e

C-6

Step 1: Preparation of Compound C-6b

Compound C-6a (3-fluorophenol, TCI, CAS NO. 372-20-3, 10 g, 89.2 mmol) was dissolved in anhydrous ACN (200 mL) under a nitrogen atmosphere at 0° C., and then benzyl bromide (12.7 mL, 107 mmol) and potassium carbonate (18.5 g, 7.98 mmol) were added, and the mixture was stirred at room temperature for 20 hours. After completion of the reaction, the organic layer was extracted twice with EA (350 mL) and distilled water (350 mL). The obtained organic layer was dried over anhydrous magnesium sulfate, filtered, and then concentrated under reduced pressure. The residue was subjected to column chromatography to obtain Compound C-6b in the form of a white solid (15 g, 83%).

$^1$H-NMR (400 MHz, $CDCl_3$) δ 7.43-7.37 (m, 4H), 7.35-7.32 (m, 1H), 7.25-7.19 (m, 1H), 6.75 (dd, J=8.4, 2.4 Hz, 1H), 6.71-6.64 (m, 2H), 5.04 (s, 2H).

Step 2: Preparation of Compound C-6c

Compound C-6b (15 g, 74.1 mmol) was added to THF (495 mL) under a nitrogen atmosphere at room temperature, the mixture was cooled to −78° C., and then n-butyl lithium solution (2.5M n-BuLi in hexane, 35.6 mL, 89.0 mmol) was slowly added dropwise. The mixture was stirred for 30 minutes while maintaining −78° C., and then DMF (17.2 mL) was slowly added dropwise, and the mixture was stirred for an additional 30 minutes. After 30 minutes, the temperature was slowly raised, and then the mixture was stirred at 0° C. for 1 hour. After completion of the reaction, the mixture was cooled again to −20° C., and distilled water (300 mL) was added dropwise to terminate the reaction. The reaction solution was extracted twice with EA (500 mL), and the obtained organic layer was dried over anhydrous magnesium sulfate, filtered, and then concentrated under reduced pressure. The residue was subjected to column chromatography to obtain Compound C-6c in the form of a white solid (14.5 g, 85%).

$^1$H-NMR (400 MHz, $CDCl_3$) δ 10.51 (s, 1H), 7.44-7.40 (m, 6H), 6.83 (d, J=8.4 Hz, 1H), 6.74 (t, J=8.4 Hz, 1H), 5.20 (s, 2H).

Step 3: Preparation of Compound C-6d

Compound C-6c (14.5 g, 62.9 mmol) was dissolved in DMF (150 mL) under a nitrogen atmosphere at room temperature, and then methyl thioglycolate (Merck, CAS NO. 2365-48-2, 8.44 mL, 94.4 mmol) and triethylamine (22.1 mL, 157.4 mmol) were added, and the mixture was stirred at 100° C. for 16 hours. After completion of the reaction, the temperature of the reaction solution was cooled to room temperature, and then the organic layer was extracted twice with EA (400 mL) and distilled water (400 mL). The obtained organic layer was washed by adding an aqueous sodium chloride solution. The washed organic layer was dried over anhydrous magnesium sulfate, filtered, and then concentrated under reduced pressure. The residue was subjected to column chromatography to obtain Compound C-6d in the form of a white solid (7.2 g, 38%).

$^1$H-NMR (400 MHz, $CDCl_3$) δ 8.28 (s, 1H), 7.49-7.47 (m, 2H), 7.45-7.29 (m, 5H), 6.81 (d, J=7.6 Hz, 1H), 5.21 (s, 2H), 3.92 (s, 3H).

Step 4: Preparation of Compound C-6e

Compound C-6d (1 g, 3.35 mmol) was dissolved in MC (65 mL) under a nitrogen atmosphere at −78° C., and then dichloromethyl methyl ether (Merck, CAS NO. 4885-02-3, 910 μL, 10.05 mmol) and titanium tetrachloride solution (1M-$TiCl_4$ in MC, 10.05 mL, 10.05 mmol) were sequentially and slowly added, and the mixture was stirred for 3 hours while maintaining the temperature. After completion of the reaction, distilled water (250 mL) was slowly added dropwise to terminate the reaction, and MC (250 mL) was added to extract the organic layer twice. The obtained organic layer was dried over anhydrous magnesium sulfate, filtered, and then concentrated under reduced pressure. The resulting residue was subjected to column chromatography to obtain Compound C-6e (733 mg, 67%).

$^1$H-NMR (400 MHz, $CDCl_3$) δ 10.07 (s, 1H), 8.34 (s, 1H), 7.93 (d, J=8 Hz, 1H), 7.50-7.39 (m, 5H), 7.00 (d, J=8 Hz, 1H), 5.34 (s, 2H), 3.95 (s, 3H).

Step 5: Preparation of Core C-6

Compound C-6e (1.37 g, 4.19 mmol) was dissolved in ethanol (45 mL) and THE (45 mL) under a nitrogen atmosphere at room temperature, and then lithium hydroxide monohydrate (352.2 mg, 8.39 mmol) dissolved in distilled water (17 mL) was slowly added dropwise, and the mixture was stirred at room temperature for 1 hour. The mixture was stirred at 60° C. for an additional 3 hours. After completion of the reaction, EA (300 mL) and 2N-hydrochloric acid aqueous solution (250 mL) were added to extract the organic layer. The obtained organic layer was dried over anhydrous magnesium sulfate, filtered, and then concentrated under reduced pressure to obtain Core C-6 (1.3 g, 99%).

$^1$H-NMR (400 MHz, DMSO-$d_6$) δ 10.08 (s, 1H), 8.26 (d, J=8.4 Hz, 1H), 8.09 (s, 1H), 7.56 (m, 2H), 7.46-7.35 (m, 4H), 5.47 (s, 2H).

Preparation Example 20: Preparation of Core C-7

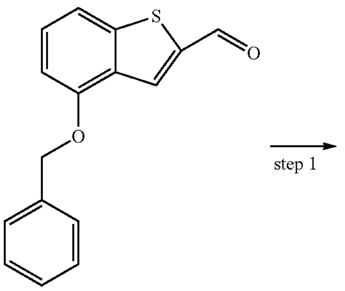

C-4c

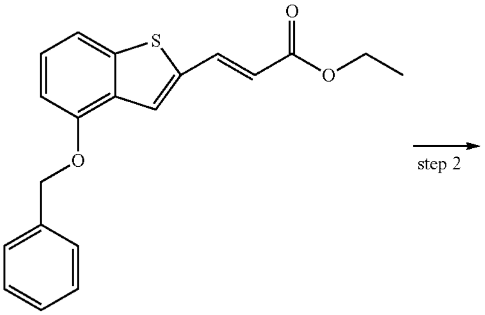

C-7a

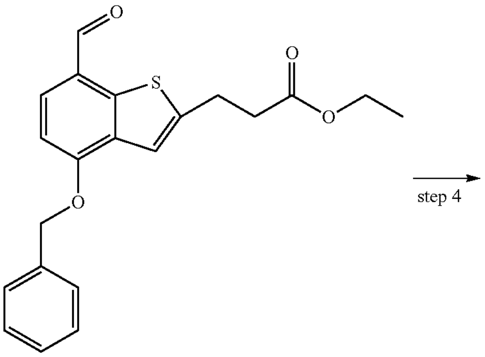

C-7c

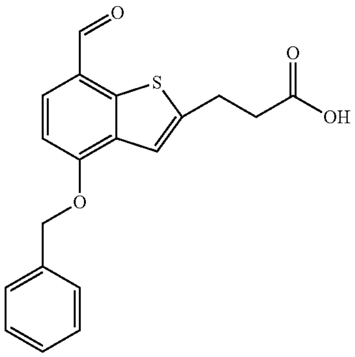

C-7

Step 1: Preparation of Compound C-7a

Compound C-4c (2.1 g, 7.82 mmol) prepared in Step 2 of Preparation Example 17 was dissolved in MC (40 mL) under a nitrogen atmosphere at room temperature, and then ethyl (triphenylphosphoranylidene)acetate (5.45 g, 15.6 mmol)

was added, and the mixture was stirred at room temperature for 16 hours. After completion of the reaction, the organic layer was extracted twice with MC (100 mL) and distilled water (100 mL). The obtained organic layer was dried over anhydrous magnesium sulfate, filtered, and then concentrated under reduced pressure. The residue was subjected to column chromatography to obtain Compound C-7a in the form of a white solid (2.5 g, 95%).

$^1$H-NMR (400 MHz, $CDCl_3$) δ 7.85 (d, J=15.6 Hz, 1H), 7.69 (s, 1H), 7.48-7.46 (m, 2H), 7.43-7.35 (m, 4H), 7.31-7.27 (m, 1H), 6.79 (d, J=7.6 Hz, 1H), 6.25 (d, J=15.6 Hz, 1H), 5.21 (s, 2H), 4.26 (q, J=7.2 Hz, 2H), 1.33 (t, J=7.2 Hz, 3H).

Step 2: Preparation of Compound C-7b

Compound C-7a (4.7 g 13.3 mmol) was dissolved in THE (150 mL) and methanol (500 mL) under a nitrogen atmosphere at room temperature, and 5% palladium charcoal (5% Pd/C, 5.67 g) was added, and then the mixture was reacted under hydrogen atmosphere for 1 hour. After completion of the reaction, the solution was filtered using Celite and concentrated under reduced pressure. The resulting residue was subjected to column chromatography to obtain Compound C-7b in the form of a white solid (4.3 g, 91%).

$^1$H-NMR (400 MHz, $CDCl_3$) δ 7.48-7.41 (m, 1H), 7.42-7.34 (m, 4H), 7.26-7.25 (m, 1H), 7.18 (t, J=8 Hz, 1H), 6.77 (d, J=7.6 Hz, 1H), 5.19 (s, 2H), 4.15 (q, J=7.2 Hz, 2H), 3.22 (t, J=8.0 Hz, 2H), 2.74 (t, J=8.0 Hz, 2H), 1.25 (t, J=7.2 Hz, 3H).

Step 3: Preparation of Compound C-7c

Compound C-7b (485 mg, 1.42 mmol) was dissolved in MC (30 mL) under a nitrogen atmosphere at −78° C., and then dichloromethyl methyl ether (Merck, CAS NO. 4885-02-3, 400 μL, 4.27 mmol) and titanium tetrachloride solution (1M-$TiCl_4$ in MC, 4.3 mL, 4.27 mmol) were sequentially and slowly added, and the mixture was stirred for 2 hours while maintaining the temperature. After completion of the reaction, distilled water (250 mL) was slowly added dropwise to terminate the reaction, and MC (250 mL) was added to extract the organic layer twice. The obtained organic layer was dried over anhydrous magnesium sulfate, filtered, and then concentrated under reduced pressure. The resulting residue was subjected to column chromatography to obtain Compound C-7c (290 mg, 55%).

$^1$H-NMR (400 MHz, $CDCl_3$) δ 10.03 (s, 1H), 7.74 (d, J=8.4 Hz, 1H), 7.49-7.35 (m, 6H), 6.94 (d, J=8.4 Hz, 1H), 5.30 (s, 2H), 4.15 (q, J=7.2 Hz, 2H), 3.27 (t, J=7.6 Hz, 2H), 2.78 (t, J=7.6 Hz, 2H), 1.24 (t, J=7.2 Hz, 3H).

Step 4: Preparation of Core C-7

Compound C-7c (290 mg, 0.79 mmol) was dissolved in ethanol (5 mL) and THE (5 mL) under a nitrogen atmosphere at room temperature, and then lithium hydroxide monohydrate (66 mg, 1.57 mmol) dissolved in distilled water (2.5 mL) was slowly added dropwise, and the mixture was stirred at room temperature for 2 hours. After completion of the reaction, EA (300 mL) and 2N-hydrochloric acid aqueous solution (250 mL) were added to extract the organic layer. The obtained organic layer was dried over anhydrous magnesium sulfate, filtered, and then concentrated under reduced pressure to obtain Core C-7 (278 mg, 99%).

$^1$H-NMR (400 MHz, $CDCl_3$) δ 10.03 (s, 1H), 7.75 (d, J=8.4 Hz, 1H), 7.49-7.35 (m, 6H), 6.94 (d, J=8.4 Hz, 1H), 5.31 (s, 2H), 3.28 (t, J=7.6 Hz, 2H), 2.85 (t, J=7.6 Hz, 2H); EI-MS m/z: 341(M*).

Preparation Example 21: Preparation of Core C-8

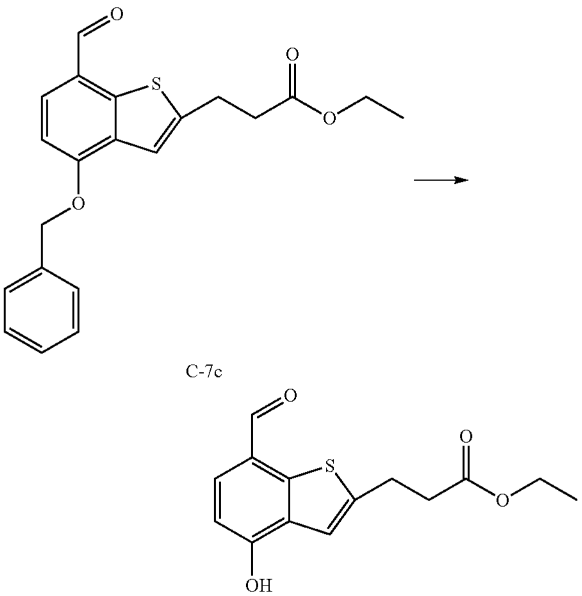

C-7c

C-8

Compound C-7c (279 mg, 0.81 mmol) was dissolved in MC (16 mL) under a nitrogen atmosphere at −78° C., and then boron trichloride solution (1M-$BCl_3$ in MC, 2.44 mL, 2.44 mmol) was slowly added, and the mixture was stirred for 1.5 hours. After completion of the reaction, the temperature was raised to −50° C., and then distilled water (15 mL) was added dropwise to terminate the reaction. The temperature was raised to 0° C., and 2N-sodium hydroxide aqueous solution (5 mL) was added dropwise. The organic layer was extracted twice from the mixture using MC (30 mL). The obtained organic layer was dried over anhydrous magnesium sulfate, filtered, and then concentrated under reduced pressure. The resulting residue was subjected to column chromatography to obtain Core C-8 in the form of a white solid (150 mg, 66%).

$^1$H-NMR (400 MHz, $CDCl_3$) δ 10.02 (s, 1H), 7.67 (d, J=7.6 Hz, 1H), 6.84 (d, J=8 Hz, 1H), 5.94 (s, 1H), 4.16 (q, J=6.8 Hz, 2H), 3.29 (t, J=7.6 Hz, 2H), 2.79 (t, J=7.6 Hz, 2H), 1.26 (t, J=7.2 Hz, 3H).

Preparation Example 22: Preparation of Core C-9

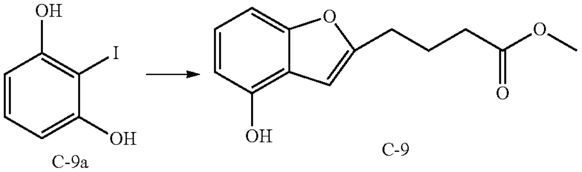

C-9a C-9

Compound C-9a (2-iodoresorcinol, CAS NO. 41046-67-7, TCI, 1 g, 4.23 mmol) was dissolved in ACN (150 mL) under a nitrogen atmosphere at 0° C., and then methyl 5-hexynoate (CAS NO. 77758-51-1, Thermoscientific, 600 μL), $PdCl_2(TPP)_2$ (100 mg), CuI (40 mg) and TEA (5.9 mL, 42.3 mmol) were sequentially added, and the mixture was stirred at room temperature for 1 hour. The mixture was stirred at 60° C. for an additional 16 hours, and then EA (100 mL) and 2N-hydrochloric acid aqueous solution (100 mL) were added to extract the organic layer, and the obtained organic layer was dried over anhydrous magnesium sulfate, filtered, and then concentrated under reduced pressure. The resulting residue was subjected to column chromatography to obtain Core C-9 (340 mg, 34.2%).

$^1$H-NMR (400 MHz, $CDCl_3$) δ 7.08-7.01 (m, 2H), 6.59 (m, 1H), 6.47 (s, 1H), 5.15 (s, 1H), 3.67 (s, 3H), 2.82 (t, J=7.2 Hz, 2H), 2.41 (t, J=7.2 Hz, 2H), 2.08 (m, 2H).

Preparation Example 23: Preparation of Core C-10

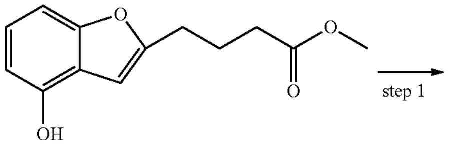

C-9

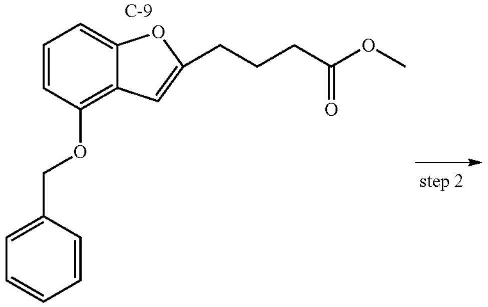

C-10a

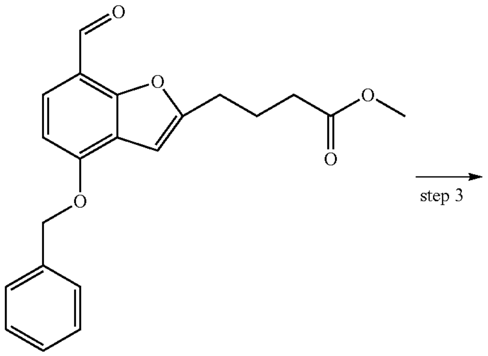

C-10b

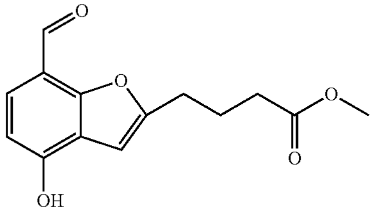

C-10

Step 1: Preparation of Compound C-10a

Core C-9 (690 mg, 2.94 mmol) was dissolved in ACN (20 mL) under a nitrogen atmosphere at 0° C., and then potassium carbonate (1.01 g, 7.36 mmol) and benzyl bromide (420 L, 3.53 mmol) were slowly added, and the mixture was stirred at 0° C. for 30 minutes, and then the mixture was stirred at room temperature for 16 hours. After completion of the reaction, EA (300 mL) and distilled water (300 mL) were added to extract the organic layer. The obtained organic layer was dried over anhydrous magnesium sulfate, filtered, and then concentrated under reduced pressure. The residue was subjected to column chromatography to obtain Compound C-10a in the form of a yellow oil (894 mg, 93%).

$^1$H-NMR (400 MHz, $CDCl_3$) δ 7.48-7.46 (m, 2H), 7.41-7.32 (m, 3H), 7.13-7.04 (m, 2H), 6.69 (d, J=8 Hz, 1H), 6.55 (s, 1H), 5.18 (s, 2H), 3.66 (s, 3H), 2.81 (t, J=7.2 Hz, 2H), 2.41 (t, J=7.2 Hz, 2H), 2.07 (p, J=7.2 Hz, 2H).

Step 2: Preparation of Compound C-10b

Compound C-10a (894 mg, 2.75 mmol) was dissolved in MC (50 mL) under a nitrogen atmosphere at −78° C., and then dichloromethyl methyl ether (748 μL, 8.27 mmol) and titanium tetrachloride solution (1M-$TiCl_4$ in MC, 8.27 mL, 8.27 mmol) were sequentially and slowly added, and the mixture was stirred for 1.5 hours while maintaining the temperature. After completion of the reaction, distilled water (250 mL) was slowly added dropwise to terminate the reaction, and MC (250 mL) was added to extract the organic layer twice. The obtained organic layer was dried over anhydrous magnesium sulfate, filtered, and then concentrated under reduced pressure. The resulting residue was subjected to column chromatography to obtain Compound C-10b in the form of a yellow oil (511 mg, 53%).

$^1$H-NMR (400 MHz, $CDCl_3$) δ 10.25 (s, 1H), 7.68 (d, J=8.4 Hz, 1H), 7.47-2.27 (m, 5H), 6.81 (d, J=8.4 Hz, 1H), 6.61 (s, 1H), 5.27 (s, 2H), 3.67 (s, 3H), 2.89 (t, J=7.2 Hz, 2H), 2.43 (t, J=7.2 Hz, 2H), 2.11 (p, J=7.2 Hz, 2H).

Step 3: Preparation of Core C-10

Compound C-10b (511 mg, 1.45 mmol) was dissolved in MC (30 mL) under a nitrogen atmosphere at −78° C., and then boron trichloride solution (1M-$BCl_3$ in MC, 4.35 mL, 4.35 mmol) was slowly added, and the mixture was stirred for 1.5 hours. After completion of the reaction, distilled water (150 mL) was slowly added dropwise to terminate the reaction, and 2N-sodium hydroxide aqueous solution was added at 0° C. to neutralize it. MC (150 mL) was added to the mixture to extract the organic layer twice. The obtained organic layer was dried over anhydrous magnesium sulfate, filtered, and then concentrated under reduced pressure. The resulting residue was subjected to column chromatography to obtain Core C-10 in the form of a white solid (200.2 mg, 5 2%).

$^1$H-NMR (400 MHz, DMSO-$d_6$) δ 10.04 (s, 1H), 7.61 (d, J=8.4 Hz, 1H), 6.74 (d, J=8.4 Hz, 1H), 6.71 (s, 1H), 3.58 (s, 3H), 2.82 (t, J=7.2 Hz, 2H), 2.43 (t, J=7.2 Hz, 2H), 1.95 (p, J=7.2 Hz, 2H).

Preparation Example 24: Preparation of Core C-11

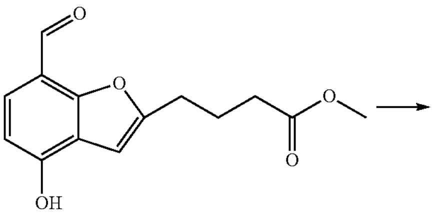

C-9

-continued

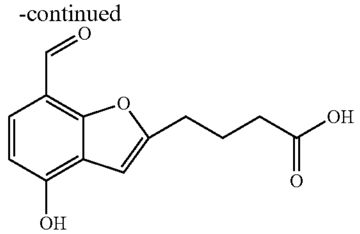

C-11

Core C-9 (200.2 mg, 0.76 mmol) was dissolved in ethanol (5 mL) and THE (5 mL) under a nitrogen atmosphere at room temperature, and then lithium hydroxide monohydrate (64 mg, 1.53 mmol) dissolved in distilled water (2.5 mL) was slowly added dropwise, and the mixture was stirred at room temperature for 2.5 hours. After completion of the reaction, EA (150 mL) and 2N-hydrochloric acid aqueous solution (150 mL) were added to extract the organic layer twice. The obtained organic layer was dried over anhydrous magnesium sulfate, filtered, and then concentrated under reduced pressure to obtain Core C-11 in the form of a black solid (210 mg, 99%).

$^1$H-NMR (400 MHz, DMSO-$d_6$) δ 11.08 (s, 1H), 10.05 (s, 1H), 7.61 (d, J=8.4 Hz, 1H), 6.74 (d, J=8.4 Hz, 1H), 6.71 (s, 1H), 2.82 (t, J=7.2 Hz, 2H), 2.33 (t, J=7.2 Hz, 2H), 1.90 (p, J=7.2 Hz, 2H).

Preparation Example 25: Preparation of Core C-12

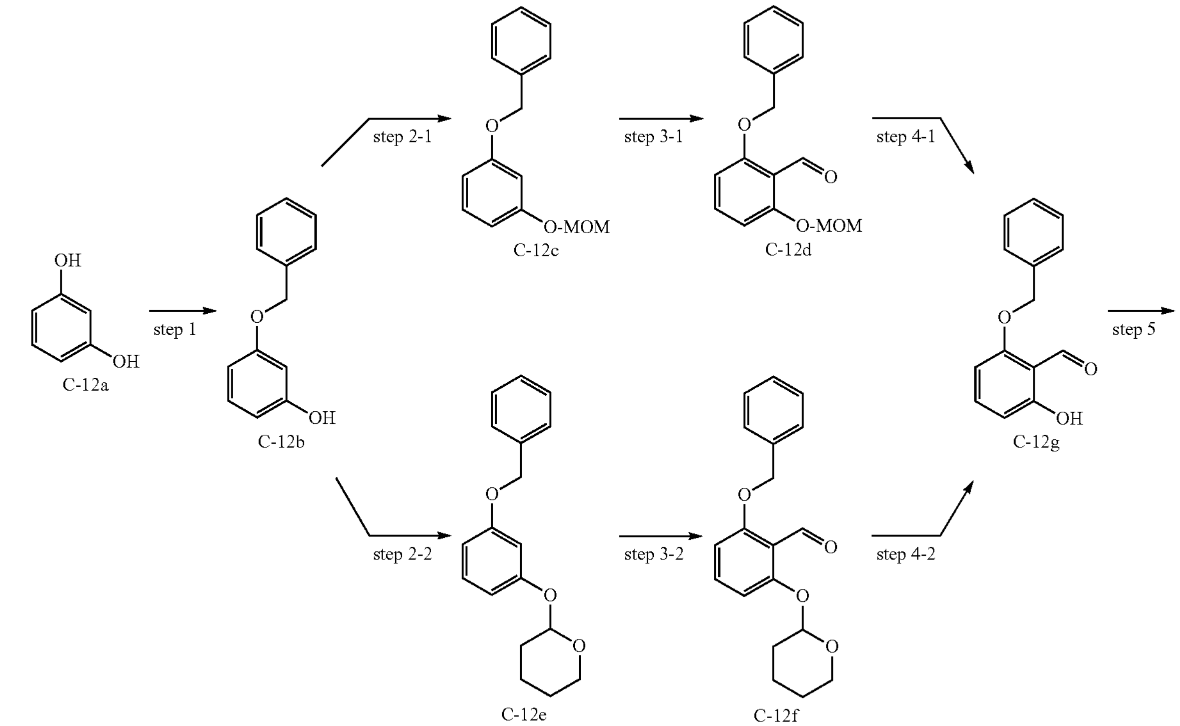

C-12a C-12b C-12c C-12d C-12e C-12f C-12g

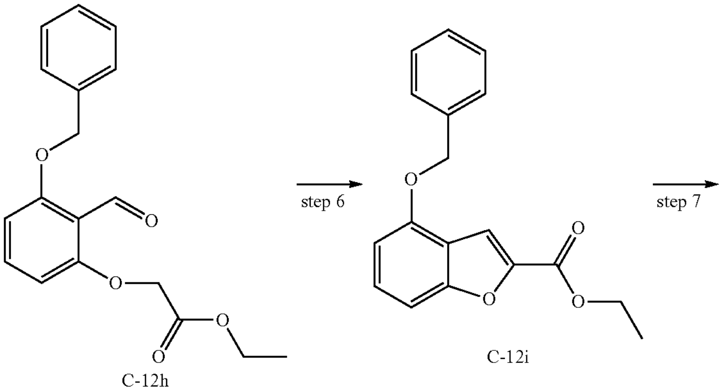

C-12h C-12i

-continued

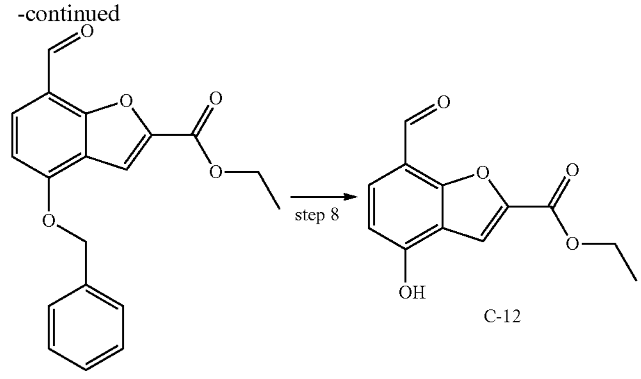

C-12j

C-12

Step 1: Preparation of Compound C-12b

Compound C-12a (10 g, 90.8 mmol) was dissolved in ACN (200 mL) under a nitrogen atmosphere at room temperature, and then benzyl bromide (7.18 mL, 60.5 mmol) was added, and then the mixture was cooled to 0° C. Potassium carbonate (20.9 g, 151.2 mmol) was added, and the mixture was stirred at room temperature for 20 hours. After completion of the reaction, the organic layer was extracted twice with EA (400 mL) and distilled water (500 mL). The obtained organic layer was dried over anhydrous magnesium sulfate, filtered, and then concentrated under reduced pressure. The residue was subjected to column chromatography to obtain Compound C-12b in the form of a yellow solid (6.6 g, 54%).

$^1$H-NMR (400 MHz, $CDCl_3$) δ 7.43-7.36 (m, 4H), 7.34-7.32 (m, 1H), 7.13 (t, J=8.4 Hz, 1H), 6.56 (dd, J=2.4, 0.8 Hz, 1H), 6.48 (t, J=2.4 Hz, 1H), 6.43 (dd, J=2.4, 0.8 Hz, 1H), 5.03 (s, 2H), 4.97 (s, 1H).

Step 2-1: Preparation of Compound C-12c

Compound C-12b (1.0 g, 4.99 mmol) was dissolved in ACN (25 mL) under a nitrogen atmosphere at room temperature, and then chloromethyl methyl ether (CAS NO. 107-30-2, 7.18 mL, 5.99 mmol) and potassium carbonate (1.37 g, 9.98 mmol) were added, and the mixture was stirred at room temperature for 16 hours. After completion of the reaction, the organic layer was extracted twice with EA (100 mL) and distilled water (100 mL). The obtained organic layer was dried over anhydrous magnesium sulfate, filtered, and then concentrated under reduced pressure. The residue was subjected to column chromatography to obtain Compound C-12c in the form of a white solid (908 mg, 74%).

$^1$H-NMR (400 MHz, $CDCl_3$) δ 7.44-7.42 (m, 2H), 7.39-7.36 (m, 2H), 7.33-7.31 (m, 1H), 7.18 (t, J=8.4 Hz, 1H), 6.70-6.69 (m, 1H), 6.66-6.62 (m, 2H), 5.15 (s, 2H), 5.04 (s, 2H), 3.47 (s, 3H).

Step 3-1: Preparation of Compound C-12d

Compound C-12c (900 mg, 3.68 mmol) was added to THE (30 mL) under a nitrogen atmosphere at room temperature, and the mixture was cooled to −40° C., and then n-butyl lithium solution (2.5M n-BuLi in hexane, 1.76 mL, 4.42 mmol) was slowly added dropwise. The temperature of the mixture was raised to −20° C., and then DMF (0.85 mL) was slowly added dropwise, and the temperature was slowly raised to room temperature, and then the mixture was stirred for 1 hour. After completion of the reaction, distilled water (30 mL) was added dropwise to terminate the reaction. The organic layer was extracted twice from the reaction solution using EA (30 mL), and the obtained organic layer was dried over anhydrous magnesium sulfate, filtered, and then concentrated under reduced pressure. The residue was subjected to column chromatography to obtain Compound C-12d in the form of a white solid (300 mg, 30%).

$^1$H-NMR (400 MHz, $CDCl_3$) δ 10.60 (s, 1H), 7.46-7.45 (m, 2H), 7.41-7.34 (m, 3H), 7.32-7.30 (m, 1H), 6.80 (d, J=8.4 Hz, 1H), 6.67 (d, J=8.4 Hz, 1H), 5.26 (s, 2H), 5.18 (s, 2H), 3.50 (s, 3H).

Step 4-1: Preparation of Compound C-12g (Method 1)

Compound C-12d (300 mg, 1.10 mmol) was dissolved in ethanol (10 mL) under a nitrogen atmosphere at room temperature, and then 2N-hydrochloric acid aqueous solution (1.1 mL) was added, and the mixture was stirred for 16 hours. After completion of the reaction, distilled water (50 mL) was added dropwise to terminate the reaction, and the organic layer was extracted twice with EA (50 mL). The obtained organic layer was dried over anhydrous magnesium sulfate, filtered, and then concentrated under reduced pressure. The residue was subjected to column chromatography to obtain Compound C-12g in the form of a white solid (150 mg, 60%).

$^1$H-NMR (400 MHz, $CDCl_3$) δ 11.95 (s, 1H), 10.41 (s, 1H), 7.41-7.35 (m, 6H), 6.54 (d, J=8.4 Hz, 1H), 6.45 (d, J=8.4 Hz, 1H), 5.14 (s, 2H), 3.88 (td, J=10.8, 3.2 Hz, 1H), 3.63-3.60 (m, 1H), 2.05-1.98 (m, 1H), 1.97-1.86 (m, 2H), 1.73-1.60 (m, 3H).

Step 2-2: Preparation of Compound C-12e

Compound C-12b (22 g, 109.8 mmol) was dissolved in MC (200 mL) under a nitrogen atmosphere at room temperature, and then 3,4-dihydro-2H-pyran (CAS NO. 110-87-2, 12.0 mL, 131.8 mmol) and PPTS (2.76 g, 10.9 mmol) were added, and the mixture was stirred at room temperature for 16 hours. After completion of the reaction, the organic layer was extracted twice with MC (500 mL) and distilled water (500 mL). The obtained organic layer was dried over anhydrous magnesium sulfate, filtered, and then concentrated under reduced pressure. The residue was subjected to column chromatography to obtain Compound A-24e in the form of a white solid (23.9 g, 76%).

$^1$H-NMR (400 MHz, $CDCl_3$) δ 7.44-7.42 (m, 2H), 7.40-7.36 (m, 2H), 7.33-7.29 (m, 1H), 7.17 (t, J=8.4 Hz, 1H), 6.72 (t, J=2.4 Hz, 1H), 6.66 (dd, J=2.4, 0.8 Hz, 1H), 6.61 (dd, J=2.4, 0.8 Hz, 1H), 5.39 (t, J=3.6 Hz, 1H), 5.04 (s, 2H), 3.94-3.88 (m, 1H), 3.62-3.57 (m, 1H), 2.04-1.95 (m, 1H), 1.86-1.82 (m, 2H), 1.69-1.53 (m, 3H).

Step 3-2: Preparation of Compound C-12f

Compound C-12e (7.7 g, 27.0 mmol) was dissolved in THE (200 mL) under a nitrogen atmosphere at room temperature, and then the mixture was cooled to 0° C., and then n-butyl lithium solution (2.5M n-BuLi in hexane, 13.0 mL, 32.4 mmol) was slowly added dropwise. The reaction solution was stirred for 30 minutes, and then DMF (6.3 mL) was slowly added dropwise, and the temperature was slowly raised to room temperature, and then the mixture was stirred for an additional 1 hour. After completion of the reaction, distilled water (500 mL) was added dropwise to terminate the reaction. The organic layer was extracted twice from the reaction solution using EA (500 mL), and the obtained organic layer was dried over anhydrous magnesium sulfate, filtered, and then concentrated under reduced pressure. The residue was subjected to column chromatography to obtain Compound C-12f in the form of a white solid (2.5 g, 27%).

$^1$H-NMR (400 MHz, $CDCl_3$) δ 10.62 (s, 1H), 7.47-7.46 (m, 2H), 7.40-7.36 (m, 3H), 7.35-7.31 (m, 1H), 6.82 (d, J=8.4 Hz, 1H), 6.64 (d, J=8.4 Hz, 1H), 3.88 (td, J=10.8, 3.2 Hz, 1H), 3.63-3.60 (m, 1H), 2.05-1.98 (m, 1H), 1.97-1.86 (m, 2H), 1.73-1.60 (m, 3H).

Step 4-2: Preparation of Compound C-12g (Method 2)

Compound C-12f (3.98 g, 12.7 mmol) was dissolved in ethanol (80 mL) under a nitrogen atmosphere at room temperature, and then PPTS (2.76 g, 10.9 mmol) was added. The mixture was stirred at 60° C. for 2 hours. After completion of the reaction, distilled water (300 mL) was added dropwise to terminate the reaction. EA (300 mL) was added to the reaction solution to extract the organic layer twice, and the obtained organic layer was dried over anhydrous magnesium sulfate, filtered, and then concentrated under reduced pressure. The residue was subjected to column chromatography to obtain Compound C-12g in the form of a white solid (2.6 g, 89%).

$^1$H-NMR (400 MHz, $CDCl_3$) δ 11.97 (s, 1H), 10.41 (s, 1H), 7.42-7.38 (m, 6H), 6.54 (d, J=8.4 Hz, 1H), 6.45 (d, J=8.4 Hz, 1H), 5.14 (s, 2H), 3.88 (td, J=10.8, 3.2 Hz, 1H), 3.63-3.60 (m, 1H), 2.05-1.98 (m, 1H), 1.97-1.86 (m, 2H), 1.73-1.60 (m, 3H).

Step 5: Preparation of Compound C-12h

Compound C-12g (2.5 g, 10.9 mmol) was dissolved in DMF (50 mL) under a nitrogen atmosphere at room temperature, and then ethyl chloroacetate (1.40 mL, 13.1 mmol) and potassium carbonate (3.02 g, 21.9 mmol) were added, and the mixture was stirred at 80° C. for 2 hours. After completion of the reaction, distilled water (300 mL) was added dropwise to terminate the reaction. EA (300 mL) was added to the reaction solution to extract the organic layer twice, and an aqueous sodium chloride solution was added to the obtained organic layer to extract the organic layer again. The washed organic layer was dried over anhydrous magnesium sulfate, filtered, and then concentrated under reduced pressure. The residue was subjected to column chromatography to obtain Compound C-12h in the form of a white solid (2.7g mg, 77%).

$^1$H-NMR (400 MHz, $CDCl_3$) δ 10.63 (s, 1H), 7.46-7.45 (m, 2H), 7.40-7.36 (m, 3H), 7.33-7.32 (m, 1H), 6.68 (d, J=8.4 Hz, 1H), 6.45 (d, J=8.4 Hz, 1H), 5.18 (s, 2H), 4.72 (s, 2H), 4.26 (q, J=7.2 Hz, 2H), 1.28 (d, J=7.2 Hz, 3H).

Step 6: Preparation of Compound C-12i

Compound C-12h (2.7 g, 8.59 mmol) was dissolved in DMF (50 mL) under a nitrogen atmosphere at room temperature, and then potassium carbonate (1.78 g, 12.9 mmol) was added, and the mixture was stirred at 100° C. for 2 hours. After completion of the reaction, distilled water (200 mL) was added dropwise to terminate the reaction. The organic layer was extracted twice from the reaction solution using EA (300 mL), and the obtained organic layer was washed by adding an aqueous sodium chloride solution. The washed organic layer was dried over anhydrous magnesium sulfate, filtered, and then concentrated under reduced pressure. The residue was subjected to column chromatography to obtain Compound C-12i in the form of a white solid (2.1g mg, 82%).

$^1$H-NMR (400 MHz, $CDCl_3$) δ 7.67 (s, 1H), 7.48-7.46 (m, 2H), 7.43-7.39 (m, 2H), 7.37-7.32 (m, 2H), 7.20 (d, J=8.4 Hz, 1H), 6.75 (d, J=8.4 Hz, 1H), 5.21 (s, 2H), 4.42 (q, J=7.2 Hz, 2H), 1.42 (t, J=7.2 Hz, 3H).

Step 7: Preparation of Compound C-12j

Compound C-12i (910 mg, 3.07 mmol) was dissolved in MC (60 mL) under a nitrogen atmosphere at −78° C., and then dichloromethyl methyl ether (833 μL, 9.21 mmol) and titanium tetrachloride solution (1M-$TiCl_4$ in MC, 9.2 mL, 9.21 mmol) were sequentially and slowly added, and the mixture was stirred for 2 hours while maintaining the temperature. After completion of the reaction, distilled water (100 mL) was slowly added dropwise to terminate the reaction, and EA (100 mL) was added to extract the organic layer. The obtained organic layer was dried over anhydrous magnesium sulfate, filtered, and then concentrated under reduced pressure. The resulting residue was subjected to column chromatography to obtain Compound C-12j (270 mg, 26.7%).

$^1$H-NMR (400 MHz, $CDCl_3$) δ 10.43 (s, 1H), 7.95 (d, J=8.4 Hz, 1H), 7.71 (s, 1H), 7.47-7.38 (m, 5H), 6.88 (d, J=8.4 Hz, 1H), 5.30 (s, 2H), 4.44 (q, J=7.2 Hz, 2H), 1.42 (t, J=7.2 Hz, 3H).

Step 8: Preparation of Core C-12

Compound C-12j (250 mg, 0.77 mmol) was dissolved in MC (15 mL) under a nitrogen atmosphere at −78° C., and then boron trichloride solution (1M-$BCl_3$ in MC, 4.3 mL, 4.3 mmol) was slowly added, and the mixture was stirred for 1 hour. After completion of the reaction, distilled water (50 mL) was slowly added dropwise at −50° C. to terminate the reaction, and EA (100 mL) and distilled water (100 mL) were further added at room temperature to extract the organic layer. The obtained organic layer was dried over anhydrous magnesium sulfate, filtered, and then concentrated under reduced pressure. The resulting residue was subjected to column chromatography to obtain Core C-12 in the form of a white solid (150 mg, 83%).

$^1$H-NMR (400 MHz, $CDCl_3$) δ 10.37 (s, 1H), 7.85 (d, J=8.4 Hz, 1H), 7.76 (s, 1H), 6.81 (d, J=8.4 Hz, 1H), 4.44 (q, J=7.2 Hz, 2H), 1.43 (t, J=7.2 Hz, 3H).

Preparation Example 26: Preparation of Core C-13

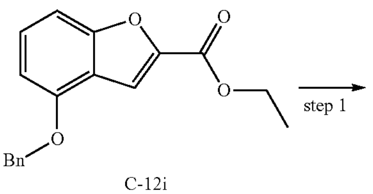

C-12i

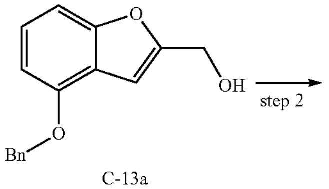

C-13a

-continued

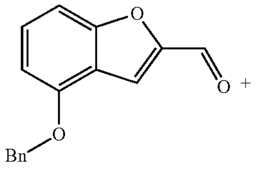

C-13b

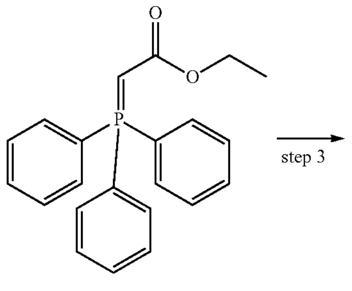

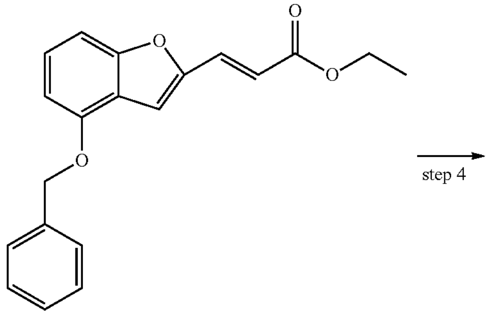

C-13c

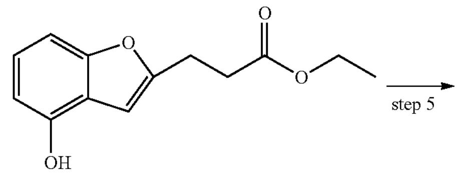

C-13d

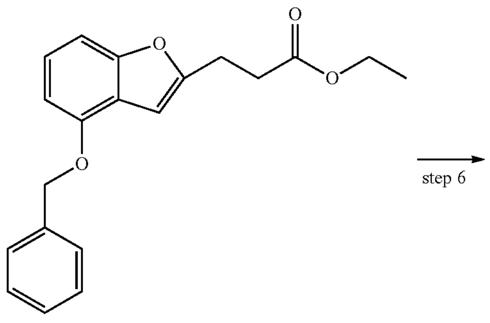

C-13e

-continued

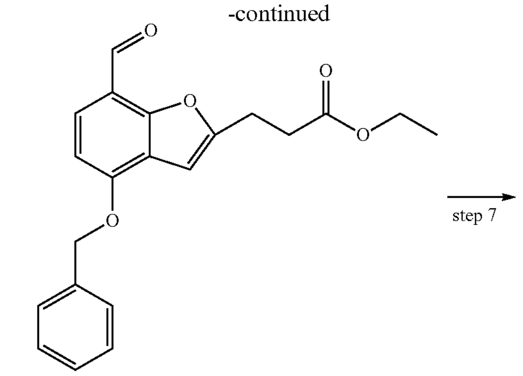

C-13f

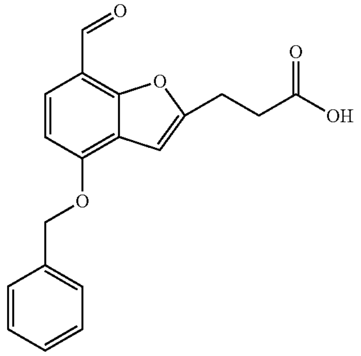

C-13

Step 1: Preparation of Compound C-13a

LAH (2.65 g, 69.77 mmol) was added to THE (350 mL) under a nitrogen atmosphere at 0° C., and then Compound C-12i (8.27 g, 27.91 mmol) prepared in Step 6 of Preparation Example 25 was dissolved in THE (50 mL) and slowly added, and the mixture was stirred at 0° C. for 1 hour. After completion of the reaction, distilled water (300 mL) was added to terminate the reaction, and the reaction solution was diluted with EA (300 mL) and filtered using Celite. The obtained solution was concentrated under reduced pressure to remove the organic layer, and then EA (500 mL) was added to extract the organic layer twice. The obtained organic layer was dried over anhydrous magnesium sulfate, filtered, and then concentrated under reduced pressure. The resulting residue was subjected to column chromatography to obtain C-13a in the form of a white solid (6.99 g, 98%).

$^1$H-NMR (400 MHz, $CDCl_3$) δ 7.47-7.45 (m, 2H), 7.41-7.37 (m, 2H), 7.35 (m, 1H), 7.18 (t, J=8 Hz, 1H), 7.10 (d, J=8 Hz, 1H), 6.80 (s, 1H), 6.71 (d, J=8 Hz, 1H), 5.19 (s, 2H), 4.73 (d, J=6 Hz, 2H), 1.88 (t, J=6 Hz, 1H).

Step 2: Preparation of Compound C-13b

Dess-Martin Periodinane (CAS NO. 87413-09-0, 7.02 g, 16.56 mmol) was added to MC (25 mL) under a nitrogen atmosphere at 0° C., and then Compound C-13a (3.5 g, 13.80 mmol) dissolved in MC (10 mL) was slowly added, and the mixture was stirred at 0° C. for 30 minutes. The mixture was stirred for an additional 3 hours while raising the temperature to room temperature. After completion of the reaction, the reaction solution was diluted with MC (200 mL) and filtered using Celite, and then distilled water (200 mL) was added to extract the organic layer twice. The obtained organic layer was dried over anhydrous magnesium sulfate, filtered, and then concentrated under reduced pressure. The resulting residue was subjected to column chromatography to obtain C-13b in the form of a pale yellow solid (3.31 g, 95%).

$^{1}$H-NMR (400 MHz, $CDCl_3$) δ 9.80 (s, 1H), 7.71 (s, 1H), 7.48-7.36 (m, 6H), 7.20 (d, J=8 Hz, 1H), 6.77 (d, J=8 Hz, 1H), 5.22 (s, 2H).

Step 3: Preparation of Compound C-13c

Compound C-13b (3.31 g, 13.12 mmol) was dissolved in MC (65 mL) under a nitrogen atmosphere at room temperature, and then (carbethoxymethylene)triphenylphosphorane (Merck, CAS No. 1099-45-2, 9.14 g, 26.24 mmol) was added, and the mixture was stirred at room temperature for 16 hours. After completion of the reaction, the reaction solution was concentrated under reduced pressure. The resulting residue was subjected to column chromatography to obtain Compound C-13c in the form of a white solid (4.24 g, 99%).

Cis-form: $^{1}$H-NMR (400 MHz, $CDCl_3$) δ 8.03 (s, 1H), 7.48-7.46 (m, 2H), 7.41-7.33 (m, 3H), 7.23 (m, 1H), 7.07 (d, J=8 Hz, 1H), 6.85 (d, J=13.2 Hz, 1H), 6.68 (d, J=8 Hz, 1H), 5.92 (d, J=13.2 Hz, 1H), 5.21 (s, 2H), 4.28 (q, J=7.2 Hz, 2H), 1.34 (t, J=7.2 Hz, 3H); EI-MS m/z: 323 $[M+H]^+$.

Trans-form: $^{1}$H-NMR (400 MHz, $CDCl_3$) δ 7.52 (d, J=15.6 Hz, 1H), 7.48-7.45 (m, 2H), 7.42-7.35 (m, 3H), 7.24 (m, 1H), 7.10 (d, J=8 Hz, 1H), 7.07 (s, 1H), 6.71 (d, J=8 Hz, 1H), 6.53 (d, J=15.6 Hz, 1H), 5.20 (s, 2H), 4.27 (q, J=7.2 Hz, 2H), 1.34 (t, J=7.2 Hz, 3H); EI-MS m/z: 323 $[M+H]^+$.

Step 4: Preparation of Compound C-13d

Compound C-13c (4.24 g, 13.15 mmol) was dissolved in THE (160 mL) and methanol (480 mL) under a nitrogen atmosphere at room temperature, and then 5% palladium charcoal (5% Pd/C, 2.1 g) was added, and the mixture was stirred under a hydrogen environment for 3 hours. After completion of the reaction, the reaction solution was diluted with EA (350 mL) and filtered using Celite. The filtered solution was concentrated under reduced pressure. The resulting residue was subjected to column chromatography to obtain Compound C-13d in the form of a white solid (2.93 g, 95%).

$^{1}$H-NMR (400 MHz, $CDCl_3$) δ 7.08-7.00 (m, 2H), 6.59 (dd, J=7.6, 0.8 Hz, 1H), 6.49 (d, J=0.8 Hz, 1H), 5.41 (s, 1H), 4.16 (q, J=7.2 Hz, 2H), 3.10 (t, J=7.2 Hz, 2H), 2.75 (t, J=7.2 Hz, 2H), 1.26 (t, J=7.2 Hz, 3H); EI-MS m/z: 235 $[M+H]^+$.

Step 5: Preparation of Compound C-13e

Compound C-13d (2.93 g, 12.51 mmol) was dissolved in ACN (100 mL) under a nitrogen atmosphere at room temperature, and then potassium carbonate (4.3 g, 31.27 mmol) and benzyl bromide (1.9 mL, 16.26 mmol) were added, and the mixture was stirred at 80° C. for 16 hours. After completion of the reaction, EA (500 mL) and distilled water (450 mL) and 2N-hydrochloric acid aqueous solution (50 mL) were added to extract the organic layer. The obtained organic layer was dried over anhydrous magnesium sulfate, filtered, and then concentrated under reduced pressure. The residue was subjected to column chromatography to obtain Compound C-13e in the form of a colorless oil (3.99 g, 98%).

$^{1}$H-NMR (400 MHz, $CDCl_3$) δ 7.47-7.45 (m, 2H), 7.41-7.37 (m, 2H), 7.33 (m, 1H), 7.12 (t, J=8 Hz, 1H), 7.05 (d, J=8 Hz, 1H), 7.68 (d, J=8 Hz, 1H), 6.57 (s, 1H), 5.18 (s, 2H), 4.16 (q, J=7.2 Hz, 2H), 3.10 (t, J=7.2 Hz, 2H), 2.74 (t, J=7.2 Hz, 2H), 1.25 (t, J=7.2 Hz, 3H); EI-MS m/z: 325 $[M+H]^+$.

Step 6: Preparation of Compound C-13f

Compound C-13e (3.99 g, 12.3 mmol) was dissolved in MC (240 mL) under a nitrogen atmosphere at −78° C., and then dichloromethyl methyl ether (3.3 mL, 36.9 mmol) and titanium tetrachloride solution (1M-$TiCl_4$ in MC, 36.9 mL, 36.9 mmol) were sequentially and slowly added, and the mixture was stirred for 1.5 hours while maintaining the temperature. After completion of the reaction, distilled water (500 mL) was slowly added dropwise to terminate the reaction, and MC (350 mL) was added to extract the organic layer twice. The obtained organic layer was dried over anhydrous magnesium sulfate, filtered, and then concentrated under reduced pressure. The resulting residue was subjected to column chromatography to obtain Compound C-13f in the form of a yellow solid (2.3 g, 53%).

$^{1}$H-NMR (400 MHz, $CDCl_3$) δ 10.24 (s, 1H), 7.68 (d, J=8.4 Hz, 1H), 7.46-7.34 (m, 5H), 6.80 (d, J=8.4 Hz, 1H), 6.62 (s, 1H), 5.26 (s, 2H), 4.17 (q, J=7.2 Hz, 2H), 3.18 (t, J=7.2 Hz, 2H), 2.78 (t, J=7.2 Hz, 2H), 1.25 (t, J=7.2 Hz, 3H).

Step 7: Preparation of Core C-13

Compound C-13f (2.3 g, 6.53 mmol) was dissolved in ethanol (40 mL) and THE (40 mL) under a nitrogen atmosphere at 0° C., and then lithium hydroxide monohydrate (821 mg, 19.58 mmol) dissolved in distilled water (20 mL) was slowly added dropwise, and the mixture was stirred at room temperature for 1.5 hours. After completion of the reaction, the organic layer was extracted with EA (300 mL) and 2N-hydrochloric acid aqueous solution (200 mL). The obtained organic layer was dried over anhydrous magnesium sulfate, filtered, and then concentrated under reduced pressure. The resulting residue was subjected to column chromatography to obtain Core C-13 in the form of a green solid (2.4 g, 99%).

$^{1}$H-NMR (400 MHz, DMSO-$d_6$) δ 10.11 (s, 1H), 7.76 (d, J=8.4 Hz, 1H), 7.53-7.51 (m, 2H), 7.44-7.36 (m, 3H), 7.08 (d, J=8.4 Hz, 1H), 6.74 (s, 1H), 5.37 (s, 2H), 3.04 (t, J=7.2 Hz, 2H), 2.71 (t, J=7.2 Hz, 2H).

Preparation Example 27: Preparation of Core C-14

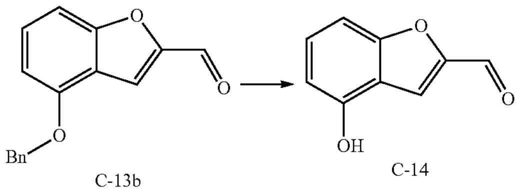

C-13b C-14

Compound C-13b (1 g, 3.96 mmol) prepared in Step 2 of Preparation Example 26 was dissolved in MC (80 mL) under a nitrogen atmosphere at −78° C., and then boron trichloride solution (1M-$BCl_3$ in MC, 11.89 mL, 11.89 mmol) was slowly added, and the mixture was stirred at −78° C. for 2 hours. After completion of the reaction, distilled water (250 mL) was slowly added dropwise to terminate the reaction, and 2N-sodium hydroxide aqueous solution was added at 0° C. to neutralize it. MC (250 mL) was added to the mixture to extract the organic layer three times. The obtained organic layer was dried over anhydrous magnesium sulfate, filtered, and then concentrated under reduced pressure. The resulting residue was subjected to column chromatography to obtain Core C-14 in the form of a yellow solid (580 mg, 90%).

$^{1}$H-NMR (400 MHz, DMSO-$d_6$) δ 10.61 (brs, 1H), 9.78 (s, 1H), 7.97 (s, 1H), 7.38 (t, J=8.4 Hz, 1H), 7.12 (d, J=8.4 Hz, 1H), 6.71 (d, J=8.4 Hz, 1H).

Preparation Example 28: Preparation of Core C-15

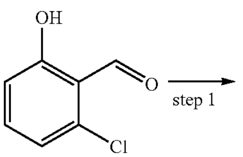

C-15a

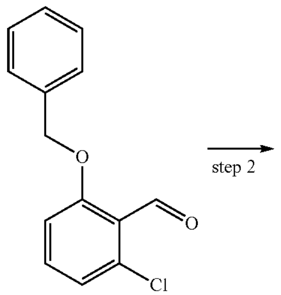

C-15b

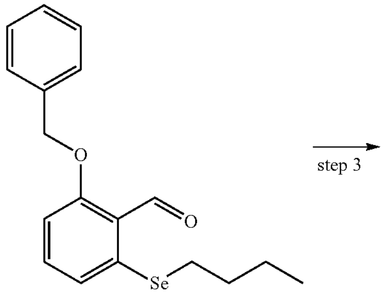

C-15c

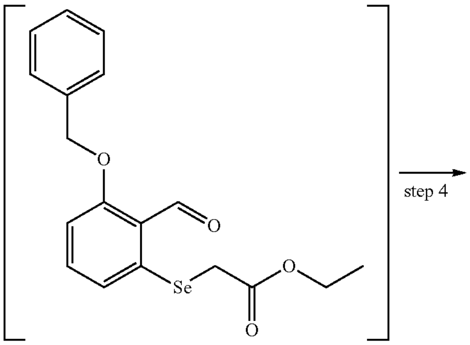

In -sit u
C-15d

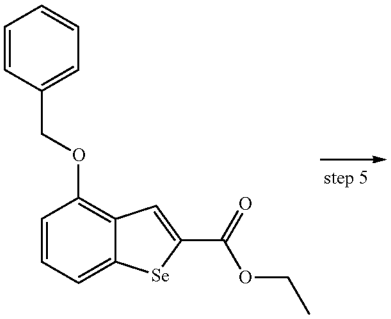

C-15e

-continued

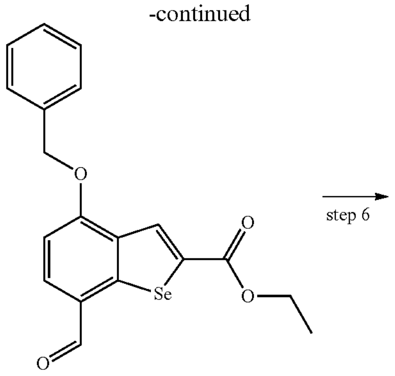

C-15f

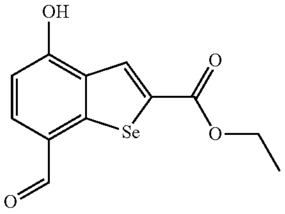

C-15

Step 1: Preparation of Compound C-15b

Compound C-15a (2-chloro-6-hydroxybenzaldehdye, Merck, CAS NO. 18362-30-6, 500 mg, 3.19 mmol) was dissolved in ACN (10 mL) under a nitrogen atmosphere at 0° C., and then benzyl bromide (400 μL, 3.35 mmol) and potassium carbonate (1.1 g, 7.98 mmol) were added, and the mixture was stirred at room temperature for 16 hours. After completion of the reaction, EA (100 mL) and distilled water (100 mL) were added to extract the organic layer. The obtained organic layer was dried over anhydrous magnesium sulfate, filtered, and then concentrated under reduced pressure. The residue was subjected to column chromatography to obtain Compound C-15b in the form of a white solid (750 mg, 95%).

$^1$H-NMR (400 MHz, $CDCl_3$) δ 10.57 (s, 1H), 7.45-7.34 (m, 6H), 7.04 (d, J=8 Hz, 1H), 6.96 (d, J=8.8 Hz, 1H), 5.19 (s, 2H)

Step 2: Preparation of Compound C-15c

Selenium powder (256 mg, 3.24 mmol) was added to THE (10 mL) under a nitrogen atmosphere at room temperature, and the mixture was cooled to 0° C., and then n-butyl lithium solution (2.5M n-BuLi in hexane, 1.42 mL, 3.56 mmol) was slowly added dropwise. The mixture was stirred at 0° C. for 40 minutes, and then Compound C-15b (800 mg, 3.24 mmol) dissolved in DMF (2 mL) was added, and the mixture was stirred for 12 hours at room temperature. After completion of the reaction, the mixture was cooled to 0° C., and distilled water (100 mL) was slowly added dropwise to terminate the reaction. EA (100 mL) was added to the reaction solution, and then the reaction solution was extracted, and the obtained organic layer was dried over anhydrous magnesium sulfate, filtered, and then concentrated under reduced pressure. The residue was subjected to column chromatography to obtain Compound C-15c in the form of a light yellow solid (900 mg, 80%).

$^1$H-NMR (400 MHz, $CDCl_3$) δ 10.70 (s, 1H), 7.42-7.33 (m, 6H), 7.04 (d, J=8 Hz, 1H), 6.81 (d, J=8.8 Hz, 1H), 5.18 (s, 2H), 2.85 (t, J=7.6 Hz, 2H), 1.75 (qui, J=7.6 Hz, 2H), 1.51 (m, 2H), 0.95 (t, J=7.6 Hz, 3H).

Step 3: Preparation of Compound C-15d

Compound C-15c (900 mg, 2.59 mmol) was dissolved in DMF (10 mL) under a nitrogen atmosphere at room temperature, and then ethyl bromoacetate (574 μL, 6.48 mmol) was added, and the mixture was stirred at 120° C. for 12 hours. After completion of the reaction, the temperature of the reaction solution was cooled to room temperature, which was used in the next reaction without an additional purification process.

Step 4: Preparation of Compound C-15e

Potassium carbonate (716 mg, 6.48 mmol) was added to the reaction solution under a nitrogen atmosphere, and the mixture was stirred at 120° C. for 2.5 hours. After completion of the reaction, EA (100 mL) and distilled water (200 mL) were added to extract the organic layer. The organic layer was further washed by adding distilled water (200 mL) to the obtained organic layer again, and the organic layer was dried over anhydrous magnesium sulfate, filtered, and then concentrated under reduced pressure. The residue was subjected to column chromatography to obtain Compound C-15e in the form of a white solid (840 mg, 90%).

$^1$H-NMR (400 MHz, $CDCl_3$) δ 8.55 (s, 1H), 7.49-7.47 (m, 3H), 7.43-7.29 (m, 4H), 6.84 (d, J=8 Hz, 1H), 5.21 (s, 2H), 4.37 (q, J=7.2 Hz, 2H), 1.39 (t, J=7.2 Hz, 3H); EI-MS m/z: 361 $[M+H]^+$.

Step 5: Preparation of Compound C-15f

Compound C-15e (400 mg, 1.11 mmol) was dissolved in MC (30 mL) under a nitrogen atmosphere at −78° C., and then dichloromethyl methyl ether (300 μL, 3.33 mmol) and titanium tetrachloride solution (1M-$TiCl_4$ in MC, 3.33 mL, 3.33 mmol) were sequentially and slowly added, and the mixture was stirred for 2 hours while maintaining the temperature. After completion of the reaction, distilled water (100 mL) was slowly added dropwise to terminate the reaction, and EA (100 mL) was added to extract the organic layer. The obtained organic layer was dried over anhydrous magnesium sulfate, filtered, and then concentrated under reduced pressure. The resulting residue was subjected to column chromatography to obtain Compound C-15f (310 mg, 72%).

$^1$H-NMR (400 MHz, $CDCl_3$) δ 10.09 (s, 1H), 8.62 (s, 1H), 7.89 (d, J=8 Hz, 1H), 7.49-7.38 (m, 5H), 7.03 (d, J=8 Hz, 1H), 5.34 (s, 2H), 4.39 (q, J=7.2 Hz, 2H), 1.41 (t, J=7.2 Hz, 3H); EI-MS m/z: 388 $[M+H]^+$.

Step 6: Preparation of Core C-15

Compound C-15f (300 mg, 0.77 mmol) was dissolved in MC (15 mL) under a nitrogen atmosphere at −78° C., and then boron trichloride solution (1M-$BCl_3$ in MC, 4.62 mL, 4.62 mmol) was slowly added, and the mixture was stirred for 1.5 hours. After completion of the reaction, distilled water (100 mL) was slowly added dropwise to terminate the reaction, and EA (100 mL) was added to extract the organic layer. The obtained organic layer was dried over anhydrous magnesium sulfate, filtered, and then concentrated under reduced pressure. The resulting residue was subjected to column chromatography to obtain Core C-15 in the form of a white solid (185 mg, 80%).

$^1$H-NMR (400 MHz, DMSO-$d_6$) δ 10.05 (s, 1H), 8.47 (s, 1H), 8.09 (d, J=8 Hz, 1H), 7.05 (d, J=8 Hz, 1H), 4.33 (q, J=7.2 Hz, 2H), 1.34 (t, J=7.2 Hz, 3H).

Preparation Example 29: Preparation of Core C-16

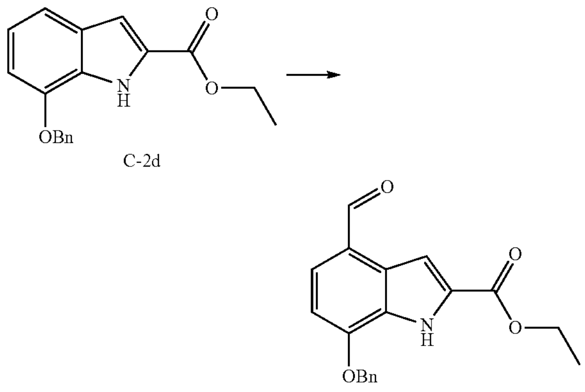

C-2d

C-16

Compound C-2d (3.0 g, 10.15 mmol) was dissolved in MC (180 mL) under a nitrogen atmosphere at −30° C., and then dichloromethyl methyl ether (Merck, CAS NO. 4885-02-3, 2.76 mL, 30.45 mmol) and titanium tetrachloride solution (1M-$TiCl_4$ in MC, 30.45 mL, 30.45 mmol) were sequentially and slowly added, and the mixture was stirred for 2 hours while maintaining the temperature. After completion of the reaction, cooled distilled water (100 mL) was slowly added dropwise to terminate the reaction, and EA (300 mL) was added to extract the organic layer. The obtained organic layer was dried over anhydrous magnesium sulfate, filtered, and then concentrated under reduced pressure. The resulting residue was subjected to column chromatography to obtain Core C-16 (2.76 g, 84%).

$^1$H-NMR (400 MHz, $CDCl_3$) δ 10.07 (S, 1H), 9.28 (brs, 1H), 7.94 (d, J=2.0 Hz, 1H), 7.61 (d, J=8 Hz, 1H), 7.49-7.40 (m, 5H), 6.90 (d, J=8 Hz, 1H), 5.31 (s, 2H), 4.41 (q, J=7.2 Hz, 2H), 1.41 (t, J=7.2 Hz, 3H).

Preparation Example 30: Preparation of Linker Q-1

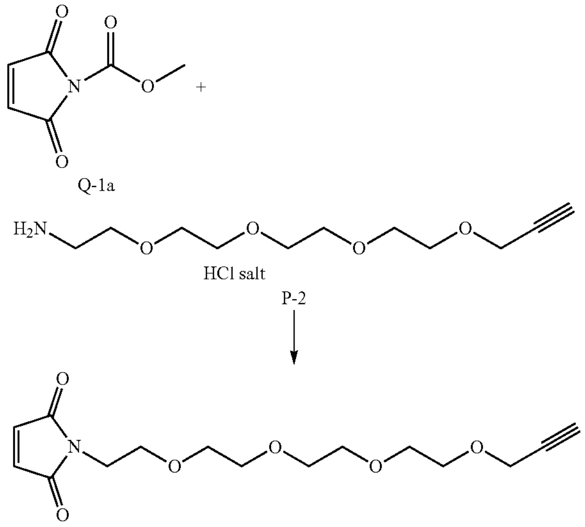

Q-1a

Q-1

Linker P-2 (172 mg, 0.64 mmol) was dissolved in a saturated sodium bicarbonate aqueous solution (3.5 mL) under a nitrogen atmosphere at 0° C., and then the mixture was stirred at 0° C. for 15 minutes. Q-1a (N-methoxycarbonylmaleimide, TCI, CAS No. 55750-48-6, 100 mg, 0.64 mmol) was slowly added to the mixture, and the mixture was stirred at the same temperature for 1.5 hours. After completion of the reaction, EA (50 mL) and distilled water (50 mL) were added to extract the organic layer twice. The obtained organic layer was dried over anhydrous magnesium sulfate, filtered, and then concentrated under reduced pressure at a temperature of 20° C. or lower. The residue thus obtained was subjected to column chromatography to obtain Linker Q-1 in the form of a colorless oil (137.3 mg, 68%).

$^1$H-NMR (400 MHz, $CDCl_3$) δ 6.70 (s, 2H), 4.20 (d, J=2.4 Hz, 2H), 3.74-3.59 (m, 16H), 2.42 (t, J=2.4 Hz, 1H).

Preparation Example 31: Preparation of Linker 0-2

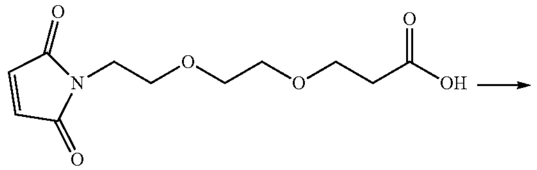

Q-2a

-continued

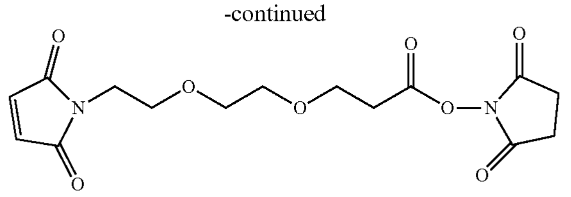

Q-2

Compound Q-2a (Mal-PEG2-acid, CAS NO. 1374666-32-6, TCI, 100 mg, 0.388 mmol) was dissolved in MC (5 mL) under a nitrogen atmosphere at 0° C., and then NHS (49.2 mg, 0.427 mmol) and DCC (88.2 mg, 0.427 mmol) were added, and the mixture was stirred for 15 hours. After completion of the reaction, EA/n-hexane (1:1 volume ratio, 20 mL) was added, and the resulting precipitate was removed by filtration. The filtrate was concentrated, and then EA/n-hexane (1:1 volume ratio, 20 mL) was added once again, and the resulting precipitate was removed, and the filtrate was concentrated under reduced pressure to obtain Linker Q-2 (139 mg, 99%).

$^1$H-NMR (400 MHz, $CDCl_3$) δ 6.70 (s, 2H), 3.81 (t, J=6.4 Hz, 2H), 3.72 (m, 2H), 3.65-3.58 (m, 6H), 2.87 (t, J=6.4 Hz, 2H), 2.84 (s 4H); EI-MS m/z: 355 $[M+H]^+$.

Preparation Example 32: Preparation of Linker Q-3

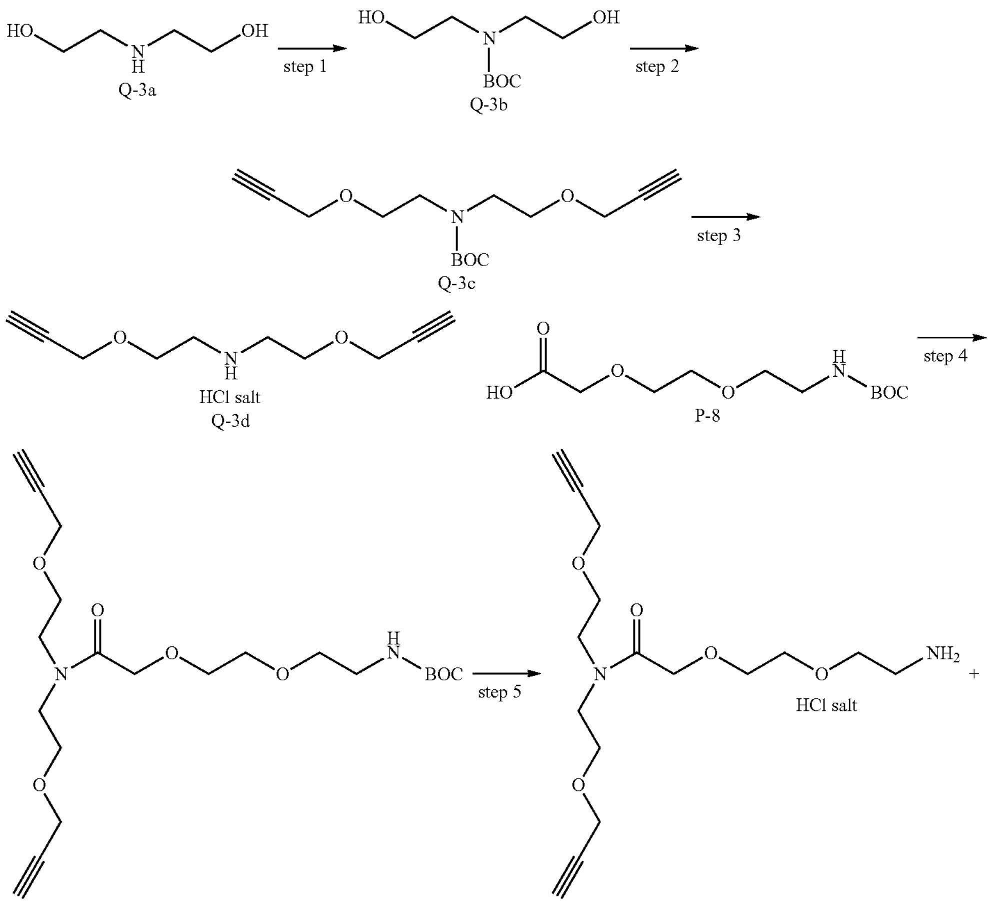

Q-3a Q-3b Q-3c Q-3d P-8 Q-3e Q-3f

-continued

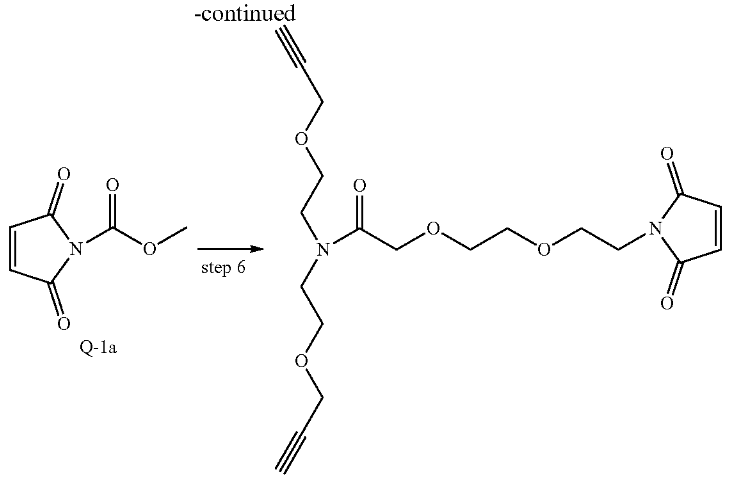

Q-1a

Q-3

Step 1: Preparation of Compound Q-3b

Compound Q-3a (diethanolamine, Daejung Chemicals & Metals, CAS No. 111-42-2, 10 g, 95.12 mmol) was dissolved in 1,4-dioxane (320 mL) under a nitrogen atmosphere at 0° C., and then sodium bicarbonate (16 g, 190.24 mmol) and di-tert-butyl dicarbonate (Boc anhydride, 25 g, 114.14 mmol), which were dissolved in distilled water (160 mL), were sequentially added, and the mixture was stirred for 48 hours while slowly raising the temperature from 0° C. to room temperature. After completion of the reaction, EA (500 mL), distilled water (400 mL), and 2N-hydrochloric acid aqueous solution (100 mL) were added to extract the organic layer 5 times. The obtained organic layer was dried over anhydrous magnesium sulfate, filtered, and then concentrated under reduced pressure to obtain Compound Q-3b in the form of a colorless liquid (17.89 g, 91%).

$^1$H-NMR (400 MHz, DMSO-$d_6$) δ 4.67 (brs, 2H), 3.49-3.42 (m, 4H), 3.25-3.19 (m, 4H), 1.38 (s, 9H).

Step 2: Preparation of Compound Q-3c

Compound Q-3b (1.02 g, 4.97 mmol) was dissolved in DMF (16 mL) under a nitrogen atmosphere at 0° C., and then propargyl bromide (2.2 mL, 19.88 mmol) and potassium hydroxide (1.11 g, 19.88 mmol) were added, and the mixture was stirred for 16 hours while slowly raising the temperature from 0° C. to room temperature. After completion of the reaction, EA (250 mL), distilled water (150 mL), and 2N-hydrochloric acid aqueous solution (100 mL) were added to extract the organic layer twice. The obtained organic layer was washed by adding a saturated aqueous sodium chloride solution (250 mL). The obtained organic layer was dried over anhydrous magnesium sulfate, filtered, and then concentrated under reduced pressure. The resulting residue was subjected to column chromatography to obtain Compound Q-3c in the form of a light yellow liquid (806 mg, 57%).

$^1$H-NMR (400 MHz, $CDCl_3$) δ 4.14 (d, J=2 Hz, 4H), 3.67-3.61 (m, 4H), 3.51-3.43 (m, 4H), 2.43-2.40 (m, 2H), 1.46 (s, 9H).

Step 3: Preparation of Compound Q-3d

Compound Q-3c (806 mg, 2.86 mmol) was dissolved in dichloromethane (5 mL) under a nitrogen atmosphere at 0° C., and then 4N-hydrochloric acid solution (4M-HCl in dioxane, 10 mL) was added, and the mixture was stirred at 0° C. for 1 hour, and then the mixture was stirred at room temperature for 4 hours. After completion of the reaction, the mixture was concentrated under reduced pressure to obtain Compound Q-3d in the form of an ivory solid (618 mg, 99%).

$^1$H-NMR (400 MHz, $CDCl_3$) δ 9.46 (brs, 1H), 4.26 (d, J=2.4 Hz, 4H), 3.98 (t, J=5.2 Hz, 4H), 3.38-3.30 (m, 4H), 2.50 (t, J=2.4 Hz, 2H).

Step 4: Preparation of Compound Q-3e

Compound Q-3d (618 mg, 2.84 mmol) and Linker P-8 (747 mg, 2.84 mmol) were dissolved in DMF (15 mL) under a nitrogen atmosphere at 0° C., and then EDCI hydrochloride (816 mg, 4.26 mmol), HOBt (384 mg, 2.84 mmol), DMAP (35 mg, 0.28 mmol) and DIPEA (1.48 mL, 8.51 mmol) were sequentially added, and the mixture was stirred for 16 hours while slowly raising the temperature from 0° C. to room temperature. After completion of the reaction, the organic layer was extracted twice with EA (150 mL) and distilled water (100 mL) and 2N-hydrochloric acid aqueous solution (50 mL). A saturated aqueous sodium chloride solution (200 mL) was added to the obtained organic layer, and the organic layer was washed. The obtained organic layer was dried over anhydrous magnesium sulfate, filtered, and then concentrated under reduced pressure. The resulting residue was subjected to column chromatography to obtain Q-3e in the form of a yellow oil (887 mg, 73%).

$^1$H-NMR (400 MHz, $CDCl_3$) δ 5.08 (brs, 1H), 4.30 (s, 2H), 4.16-4.11 (m, 4H), 3.73-3.68 (m, 4H), 3.68-3.63 (m, 4H), 3.62-3.58 (m, 4H), 3.57-3.52 (m, 2H), 3.35-3.29 (m, 2H), 2.45-2.40 (m, 2H), 1.44 (s, 9H); EI-MS m/z: 427(M*).

Step 5: Preparation of Compound Q-3f

Compound Q-3e (887 mg, 2.08 mmol) was dissolved in dichloromethane (4 mL) under a nitrogen atmosphere at 0° C., and then 4N-hydrochloric acid solution (4M-HCl in dioxane, 8 mL) was added, and the mixture was stirred at 0° C. for 1 hour, and then the mixture was stirred at room temperature for 4 hours. After completion of the reaction, the mixture was concentrated under reduced pressure to obtain Compound Q-3f in the form of an ivory solid (824 mg, quantitatively obtained).

$^1$H-NMR (400 MHz, $CDCl_3$) δ 8.42 (brs, 2H), 4.35 (s, 2H), 4.18-4.14 (m, 4H), 3.92 (t, J=4.8 Hz, 2H), 3.76-3.73 (m, 2H), 3.72-3.64 (m, 6H), 3.58 (t, J=4.8 Hz, 2H), 3.50 (t, J=4.8 Hz, 2H), 3.29-3.23 (m, 2H), 2.52-2.48 (m, 2H); EI-MS m/z: 327 $[M+H]^+$.

Step 6: Preparation of Compound Q-3

Compound Q-3f (147 mg, 0.40 mmol) was dissolved in a saturated sodium bicarbonate aqueous solution (sodium bicarbonate, 2 mL) under a nitrogen atmosphere at 0° C., and then the mixture was stirred at 0° C. for 15 minutes. Q-1a (N-methoxycarbonylmaleimide, TCI, CAS No. 55750-48-6, 63 mg, 0.40 mmol) was slowly added to the mixture, and the mixture was stirred at the same temperature for 1.5 hours. After completion of the reaction, EA (50 mL) and distilled water (50 mL) were added to extract the organic layer three times. The obtained organic layer was dried over anhydrous magnesium sulfate, filtered, and then concentrated under reduced pressure at a temperature of 15° C. or lower. The residue thus obtained was subjected to column chromatography to obtain Q-3 in the form of a colorless oil (55.1 mg, 33%).

$^1$H-NMR (400 MHz, $CDCl_3$) δ 6.69 (s, 2H), 4.27 (s, 2H), 4.16-4.11 (m, 4H), 3.75-3.68 (m, 4H), 3.67-3.62 (m, 8H), 3.61-3.57 (m, 4H), 2.45-2.41 (m, 2H); EI-MS m/z: 407 $[M+H]^+$.

Preparation Example 33: Preparation of Linker Q-4

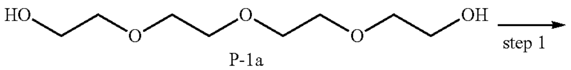

P-1a

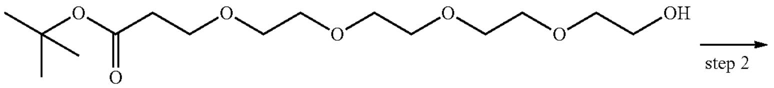

Q-4a

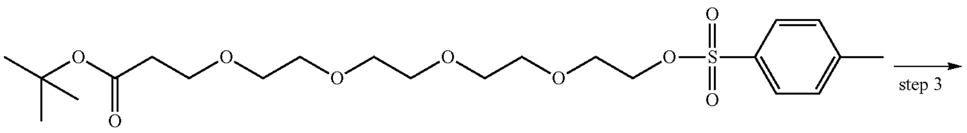

Q-4b

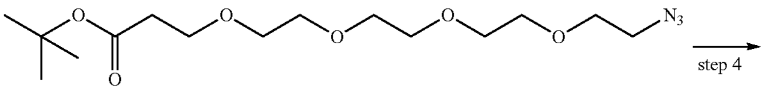

Q-4c

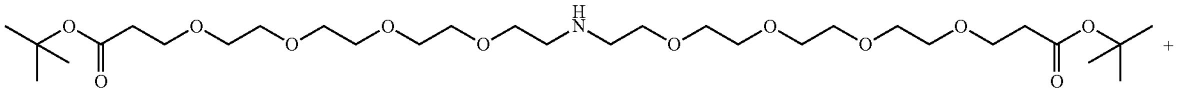

Q-4d

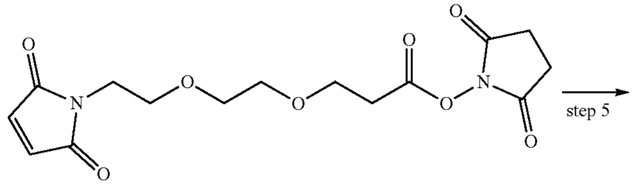

Q-2

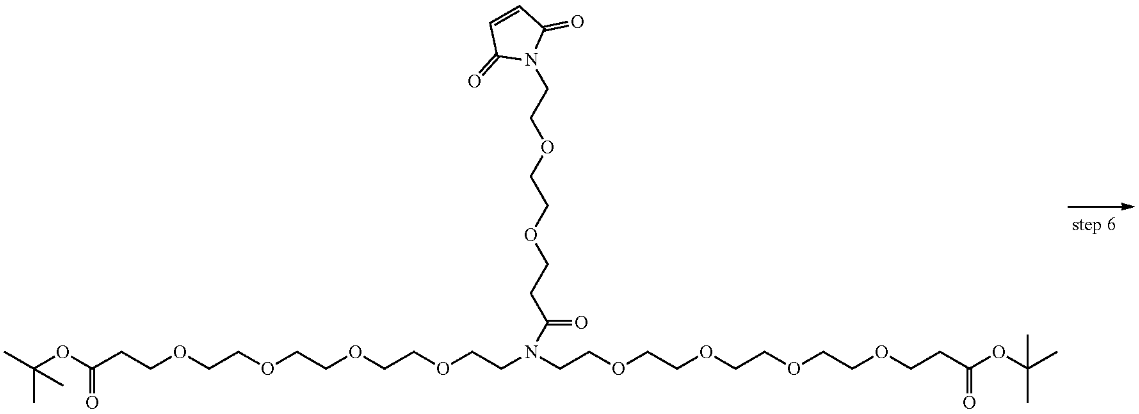

Q-4e

-continued

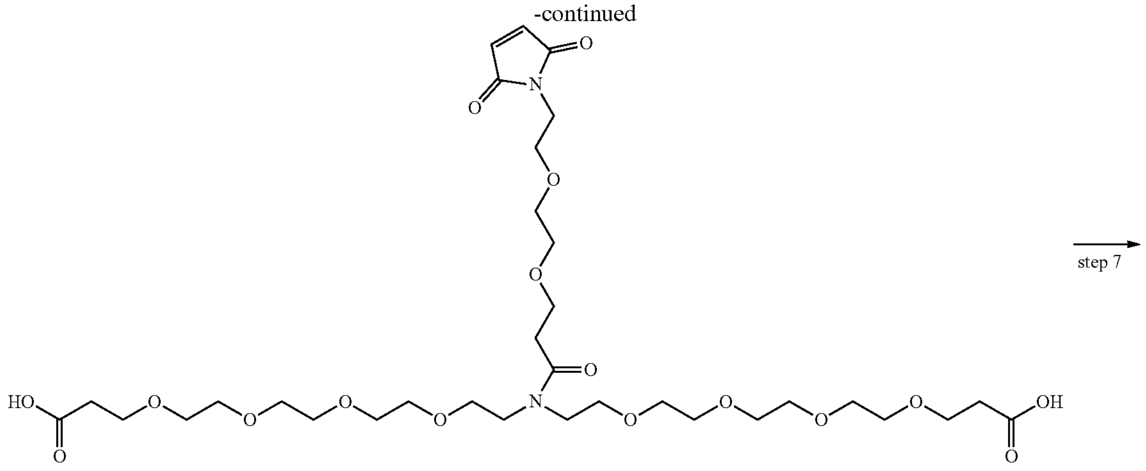

Q-4f

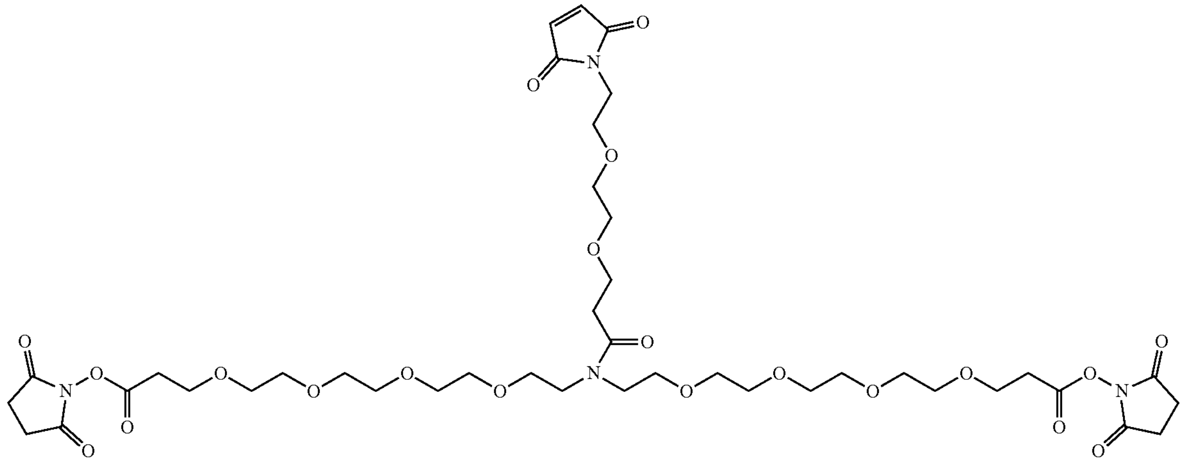

Q-4

Step 1: Preparation of Compound Q-4a

Compound P-1a (tetraethylene glycol, Daejung Chemicals & Metals, CAS NO. 112-60-7, 5 g, 25.74 mmol) was dissolved in THF (60 mL) under a nitrogen atmosphere at room temperature, and then sodium hydride (NaH 60% dispersion in mineral oil, 16.5 mg, 0.41 mmol) was added, and the mixture was stirred at room temperature for 30 minutes. Tert-butyl acrylate (Merck, CAS NO. 1663-39-4, 1.5 mL, 10.30 mmol) was slowly added to the reaction solution for 2 hours, and the mixture was stirred at room temperature for 3 hours. After completion of the reaction, a saturated aqueous sodium chloride solution (20 mL) was added to terminate the reaction, and the reaction organic solvent was removed by concentration under reduced pressure. MC (60 mL) was added to the remaining aqueous sodium chloride solution to extract the organic layer, and then the obtained organic layer was dried over anhydrous magnesium sulfate, filtered, and concentrated under reduced pressure. The residue was subjected to column chromatography to obtain Compound Q-4a in the form of a pink oil (1.39 g, 42%).

$^1$H-NMR (400 MHz, $CDCl_3$) δ 3.75-3.60 (m, 18H), 2.69 (t, J=6.4 Hz, 1H), 2.50 (t, J=6.4 Hz, 2H), 1.45 (s, 9H); EI-MS m/z: 345 $[M+Na]^+$.

Step 2: Preparation of Compound Q-4b

Compound Q-4a (1.39 g, 4.31 mmol) was dissolved in ACN (7.5 mL) under a nitrogen atmosphere at 0° C., and then pyridine (4 mL) was slowly added. Then, a solution of 4-methylbenzenesulfonyl chloride (p-toluenesulfonyl chloride, 1.1 g, 5.77 mmol) dissolved in ACN (10.5 mL) was slowly added for 30 minutes, and the mixture was stirred at room temperature for 6.5 hours. After completion of the reaction, EA (200 mL) and distilled water (150 mL) and 2N-hydrochloric acid aqueous solution (50 mL) were added to extract the organic layer twice. The obtained organic layer was dried over anhydrous magnesium sulfate, filtered, and then concentrated under reduced pressure. The residue was subjected to column chromatography to obtain Compound Q-4b in the form of a colorless oil (1.78 g, 86%).

$^1$H-NMR (400 MHz, $CDCl_3$) δ 7.80 (d, J=8 Hz, 2H), 7.34 (d, J=8 Hz, 2H), 4.16 (t, J=4.8 Hz, 2H), 3.73-3.65 (m, 4H), 3.65-3.57 (m, 12H), 2.50 (t, J=6.4 Hz, 2H), 2.45 (s, 3H), 1.44 (s, 9H); EI-MS m/z: 499 $[M+Na]^+$.

Step 3: Preparation of Compound Q-4c Compound Q-4b (1.78 g, 3.73 mmol) was dissolved in DMF (20 mL) under a nitrogen atmosphere at room temperature, and then sodium azide ($NaN_3$, 364 mg, 5.60 mmol) was added, and the mixture was stirred at 60° C. for 16 hours. After completion of the reaction, the mixture was cooled to room temperature, and EA (200 mL) and distilled water (200 mL) were added to extract the organic layer twice. The obtained organic layer was washed three times by adding a saturated aqueous sodium chloride solution (200 mL). The obtained organic layer was dried over anhydrous magnesium sulfate, filtered, and then concentrated under reduced pressure. The residue was subjected to column chromatography to obtain Compound Q-4c in the form of a colorless oil (1.25 g, 96%).

$^1$H-NMR (400 MHz, $CDCl_3$) δ 3.73-3.60 (m, 16H), 3.39 (t, J=4.8 Hz, 2H), 2.50 (t, J=6.4 Hz, 2H), 1.44 (s, 9H); EI-MS m/z: 348 $[M+H]^+$.

Step 4: Preparation of Compound Q-4d

Compound Q-4c (500 mg, 1.44 mmol) was dissolved in 1,4-dioxane (8 mL) under a nitrogen atmosphere at room temperature, and then 5% palladium charcoal (5% Pd/C, 153 mg, 0.07 mmol) was added, and then the mixture was stirred under a hydrogen environment at 60° C. for 4 hours. After completion of the reaction, the reaction solution was diluted with EA (50 mL) and filtered using a Celite filter, and the solution was concentrated under reduced pressure. The obtained residue was subjected to column chromatography to obtain Compound Q-4d in the form of a colorless oil (92.5 mg, 20%).

$^1$H-NMR (400 MHz, $CDCl_3$) δ 3.71 (t, J=6.4 Hz, 4H), 3.65-3.56 (m, 28H), 2.81 (t, J=5.6 Hz, 4H), 2.50 (t, J=6.4 Hz, 4H), 1.44 (s, 18H); EI-MS m/z: 626 $[M+H]^+$.

Step 5: Preparation of Compound Q-4e

Compound Q-4d (92.5 mg, 0.15 mmol) was dissolved in MC (2 mL) under a nitrogen atmosphere at 0° C., and then Linker Q-2 (68.1 mg, 0.19 mmol), pyridine (11.9 μL) and DIPEA (5.1 μL) were sequentially added dropwise, and the mixture was stirred for 2 hours at room temperature. After completion of the reaction, it was subjected to column chromatography without extraction to obtain Compound Q-4e in the form of an orange oil (83.6 mg, 65%).

$^1$H-NMR (400 MHz, $CDCl_3$) δ 6.70 (s, 2H), 3.76-3.69 (m, 8H), 3.65-3.54 (m, 38H), 2.66 (t, J=6.8 Hz, 2H), 2.50 (t, J=6.4 Hz, 4H), 1.44 (s, 18H); EI-MS m/z: 866 $[M+H]^+$.

Step 6: Preparation of Compound Q-4f

Compound Q-4e (92.5 mg, 0.15 mmol) was dissolved in MC (3 mL) under a nitrogen atmosphere at 0° C., and then TFA (0.3 mL) was slowly added, and the mixture was stirred for 6 hours while slowly raising the temperature from 0° C. to 15° C. After completion of the reaction, the mixture was diluted by adding MC (20 mL), and then concentrated under reduced pressure at low temperature to obtain Compound Q-4f in the form of a colorless oil (41.2 mg, 99%).

$^1$H-NMR (400 MHz, $CDCl_3$) δ 6.71 (s, 2H), 3.80-3.70 (m, 8H), 3.67-3.54 (m, 38H), 2.71 (t, J=6.8 Hz, 2H), 2.63-2.58 (m, 4H); EI-MS m/z: 753 $[M+H]^+$.

Step 7: Preparation of Compound Q-4

Compound Q-4f (40.5 mg, 0.054 mmol) was dissolved in MC (3 mL) under a nitrogen atmosphere at 0° C., and then NHS (13 mg, 0.113 mmol) and DCC (24.4 mg, 0.118 mmol) were added, and the mixture was stirred for 16 hours while slowly raising the temperature from 0° C. to room temperature. After completion of the reaction, EA/n-hexane (1:1 volume ratio, 20 mL) was added, and the resulting precipitate was removed by filtration. The filtrate was concentrated, and then EA/n-hexane (1:1 volume ratio, 20 mL) was added once again, and the resulting precipitate was removed, and the filtrate was concentrated under reduced pressure to obtain Linker Q-4 (17.4 mg, 43%).

$^1$H-NMR (400 MHz, $CDCl_3$) δ 6.70 (s, 2H), 3.85 (t, J=6.4 Hz, 4H), 3.76-3.69 (m, 4H), 3.66-3.52 (m, 38H), 2.90 (t, J=6.4 Hz, 4H), 2.85-2.80 (m, 8H), 2.66 (t, J=6.8 Hz, 2H); EI-MS m/z: 947 $[M+H]^+$.

Preparation Example 34: Preparation of Linker Q-5

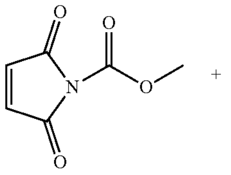

Q-1a

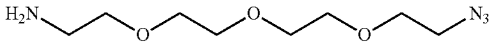

HCl salt
P-1

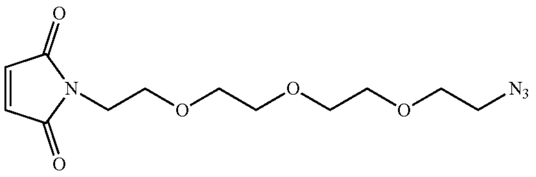

Q-5

Linker P-1 (164 mg, 0.64 mmol) was dissolved in a saturated sodium bicarbonate aqueous solution (3.5 mL) under a nitrogen atmosphere at 0° C., and then the mixture was stirred at 0° C. for 20 minutes. Q-1a (N-methoxycarbonylmaleimide, TCI, CAS No. 55750-48-6, 100 mg, 0.64 mmol) was slowly added to the mixture, and the mixture was stirred at the same temperature for 1.5 hours. EA (50 mL) and distilled water (50 mL) were added to extract the organic layer three times. The obtained organic layer was dried over anhydrous magnesium sulfate, filtered, and then concentrated under reduced pressure at a temperature of 10° C. or lower. The residue thus obtained was subjected to column chromatography to obtain Linker Q-5 in the form of a colorless oil (77 mg, 40%).

$^1$H-NMR (400 MHz, $CDCl_3$) δ 6.70 (s, 2H), 3.76-3.71 (m, 2H), 3.69-3.60 (m, 12H), 3.39 (t, J=5.2 Hz, 2H).

Preparation Example 35: Preparation of Linker 0-6

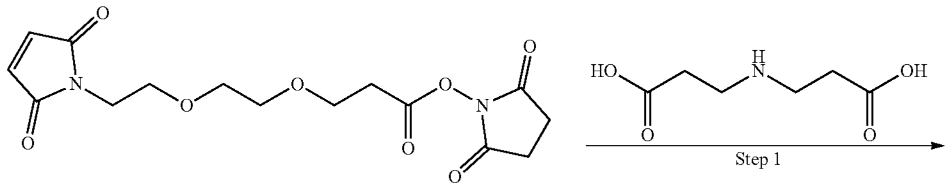

Q-2

-continued

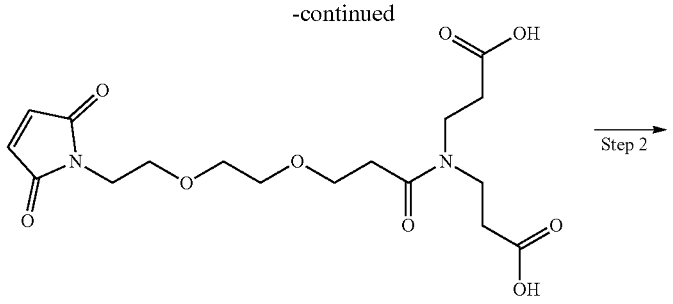

Q-6a

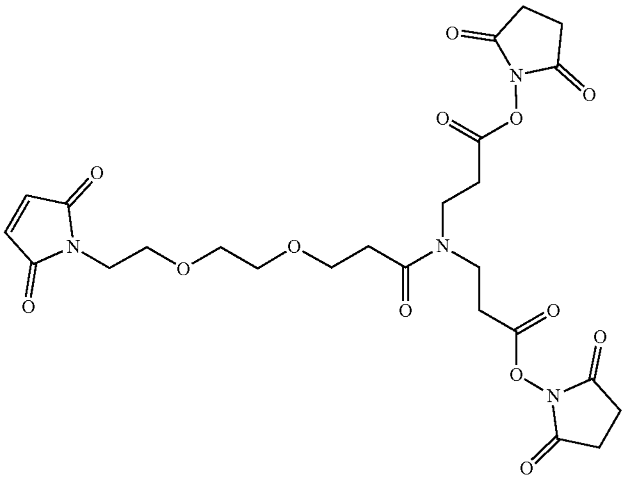

Q-6

Step 1: Preparation of Compound Q-6a

Linker Q-2 (70 mg, 0.198 mmol) was dissolved in THE (3 mL) under a nitrogen atmosphere at 0° C., and then 3,3'-iminodipropionic acid (TCI, CAS No. 505-47-5, 28.6 mg, 0.177 mmol), distilled water (300 μL) and DIPEA (41.3 μL) were sequentially added dropwise, and the mixture was stirred for 12 hours at room temperature. After completion of the reaction, the reaction solution was diluted with ACN (1 mL) containing 0.1% formic acid and distilled water (1 mL), separated and purified using Preparative-HPLC, and then freeze-dried to obtain Compound Q-6a (3 mg, 4%); MS m/z: 401 $[M+H]^+$.

Step 2: Preparation of Compound Q-6

Compound Q-6a (3 mg, 0.0074 mmol) was dissolved in MC (1 mL) under a nitrogen atmosphere at 0° C., and then NHS (1.9. mg, 0.0148 mmol) and DCC (3.24 mg, 0.0155 mmol) were added, and the mixture was stirred for 2 hours. After completion of the reaction, EA/n-hexane (1:1 volume ratio, 20 mL) was added, and the resulting precipitate was removed by filtration. The filtrate was concentrated, and then EA/n-hexane (1:1 volume ratio, 20 mL) was added once again, and the resulting precipitate was removed, and the filtrate was concentrated under reduced pressure to obtain Linker Q-6 (4.5 mg, 99%); EI-MS m/z: 595 $[M+H]^+$.

Preparation Example 36: Preparation of Linker 0-7

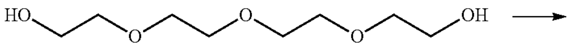

P-1a

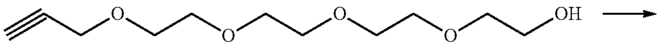

Q-7a

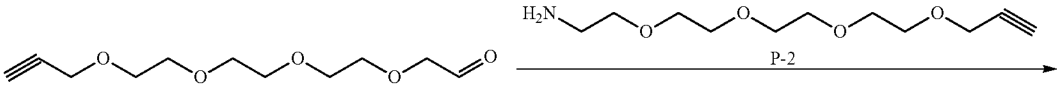

P-2

Q-7b

-continued

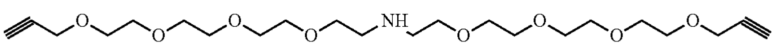

Q-7c

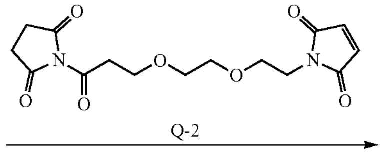

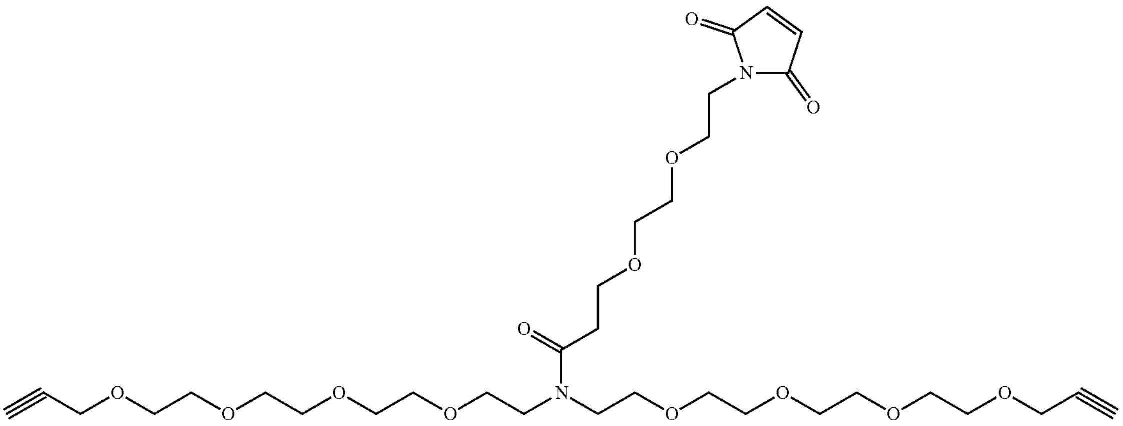

Q-7

Step 1: Preparation of Compound Q-7a

Compound P-1a (20 g, 102.97 mmol) was dissolved in ethanol THF (80 mL) under a nitrogen atmosphere at 0° C., and then sodium hydride (NaH 60% dispersion in mineral oil, 823 mg, 34.3 mmol) was added, and then the mixture was stirred at 0° C. for 20 minutes. Propargyl bromide (1.96 mL, 20.6 mmol) was added, and then the mixture was stirred at 0° C. for 1 hour, and then the mixture was stirred at room temperature for 16 hours. After completion of the reaction, it was extracted with EA (100 mL) and distilled water (100 mL) and a saturated aqueous sodium chloride solution (50 mL). The organic layer was dried over anhydrous magnesium sulfate, filtered, and then concentrated under reduced pressure. The resulting residue was subjected to column chromatography to obtain Q-7a in the form of a yellow oil (3.5 g, 74%).

$^1$H-NMR (400 MHz, $CDCl_3$) δ 4.20 (d, J=2.0 Hz, 2H), 3.72-3.67 (m, 15H), 3.62-3.60 (m, 2H), 2.51 (s, 1H), 2.42 (t, J=2.0 Hz, 1H).

Step 2: Preparation of Compound Q-7b

Compound Q-7a (1.0 g, 4.30 mmol) was dissolved in MC (50 mL) under a nitrogen atmosphere at room temperature, and then DMP (Dess-Martin periodinane, 2.73 g, 6.45 mmol) was added, and the mixture was stirred at room temperature for 16 hours. After completion of the reaction, it was extracted with MC (100 mL), sodium thiosulfate aqueous solution (50 mL) and sodium bicarbonate aqueous solution (50 mL). The obtained organic layer was dried over anhydrous magnesium sulfate, filtered, and then concentrated under reduced pressure. The resulting residue was subjected to column chromatography to obtain Q-7b in the form of a colorless oil (570 mg, 57%).

$^1$H-NMR (400 MHz, $CDCl_3$) δ 9.73 (s, 1H), 4.20 (d, J=2.0 Hz, 2H), 4.15 (s, 2H), 3.74-3.66 (m, 12H), 2.42 (t, J=2.0 Hz, 1H).

Step 3: Preparation of Compound Q-7c

Compound Q-7b (1.23 g, 5.34 mmol) was dissolved in methanol (100 mL) under a nitrogen atmosphere at room temperature, and then Compound P-2 (1.23 g, 5.34 mmol) and acetic acid (0.3 mL, 5.34 mmol) were added, and the mixture was stirred for 10 minutes. Sodium cyanoborohydride (671 mg, 10.68 mmol) was added, and the mixture was stirred for 3 hours. After completion of the reaction, the mixture was concentrated under reduced pressure. The residue was subjected to column chromatography to obtain Compound Q-7c in the form of a colorless oil (90 mg, 3.8%).

$^1$H-NMR (400 MHz, $CDCl_3$) δ 4.20 (d, J=2.0 Hz, 4H), 3.78-3.66 (m, 29H), 2.87 (t, J=5.2 Hz, 4H), 2.43 (t, J=2.0 Hz, 2H); EI-MS m/z: 446 $[M+H]^+$.

Step 4: Preparation of Compound Q-7

Compound Q-7c (40 mg, 0.089 mmol) was dissolved in MC (5 mL) under a nitrogen atmosphere at room temperature, and then Compound Q-2 (47.7 mg, 0.134 mmol), DIPEA (7.7 L, 0.044 mmol), and pyridine (7.3 μL, 0.089 mmol) were sequentially added, and the mixture was stirred at room temperature for 4 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound Q-7 in the form of a colorless oil (10.9 mg, 17%).

Example I-1: Preparation of Compounds A-1 and A-2
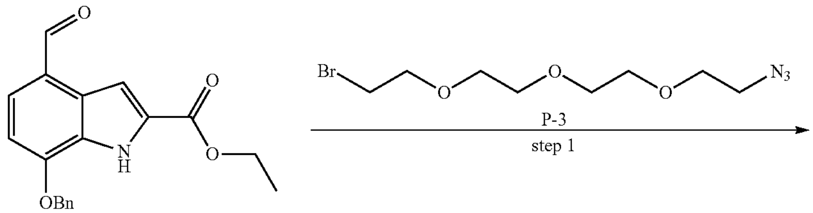
C-16
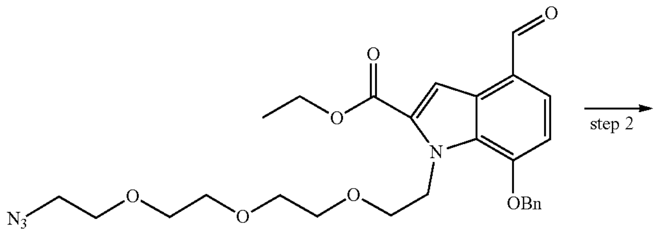
A-1a
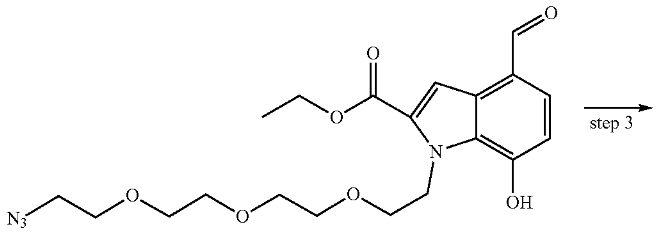
A-1b
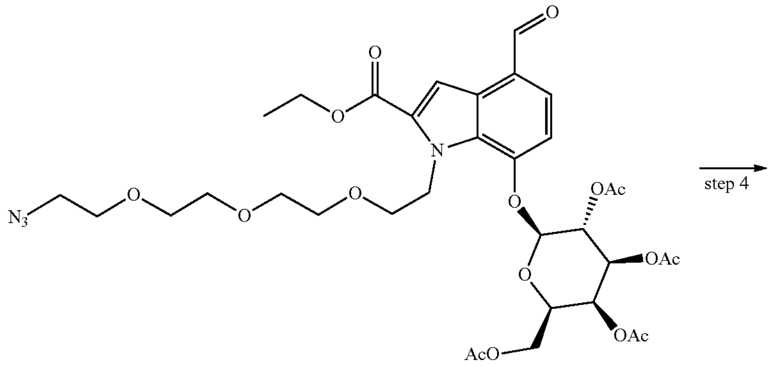
A-1c
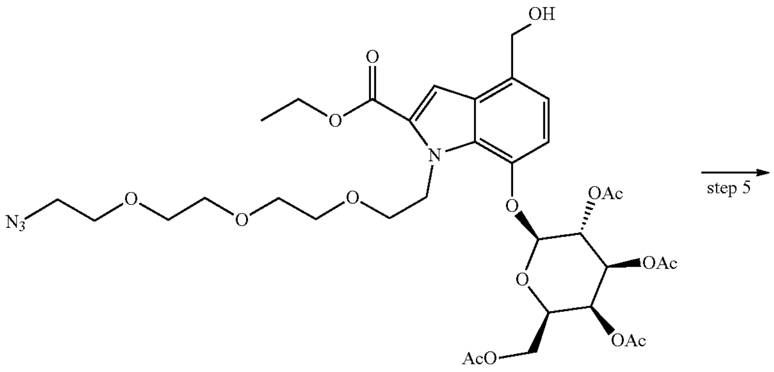
A-1d -continued
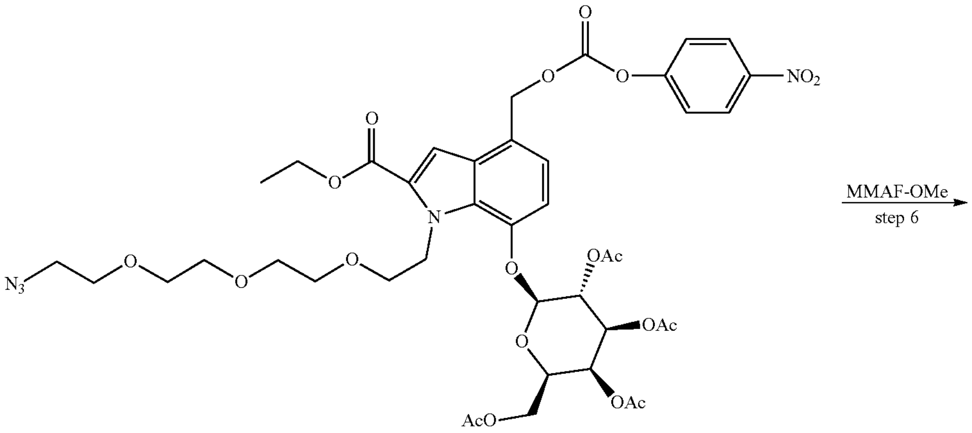
A-1e
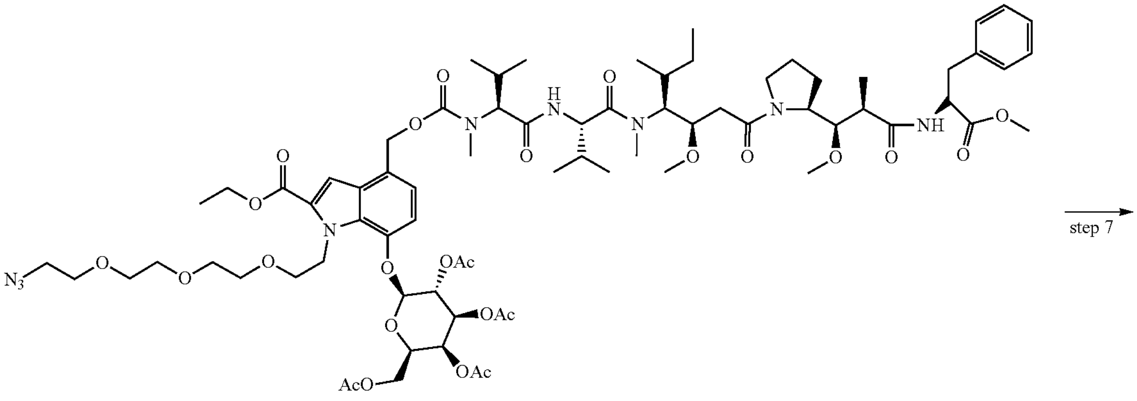
A-1f
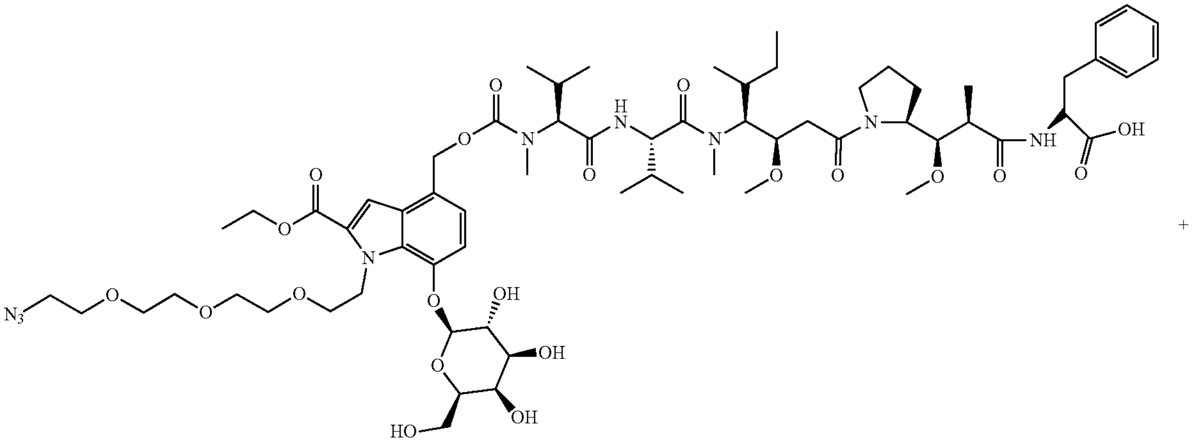
A-1

-continued

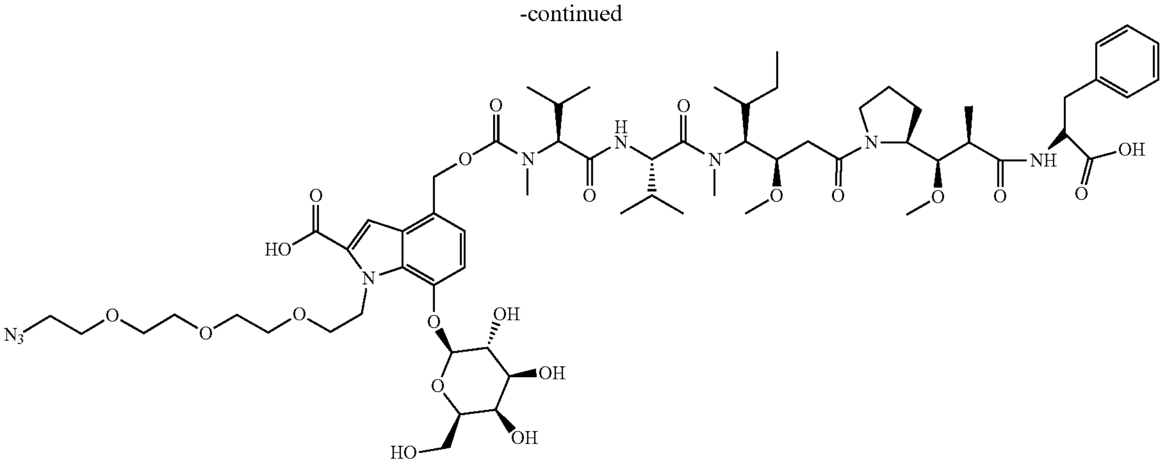

A-2

Step 1: Preparation of Compound A-1a

Core C-16 (1.76 g, 5.46 mmol) was dissolved in DMF (27 mL) under a nitrogen atmosphere at room temperature, and then Linker P-3 (1.8 g, 6.38 mmol) and potassium carbonate (2.26 g, 16.38 mmol) were added, and the mixture was stirred at 80° C. for 16 hours. After completion of the reaction, EA (250 mL) and 2N-hydrochloric acid aqueous solution (250 mL) were added to extract the organic layer twice. The obtained organic layer was dried over anhydrous magnesium sulfate, filtered, and then concentrated under reduced pressure. The residue was subjected to column chromatography to obtain Compound A-1a in the form of a yellow liquid (2.86 g, 99%).

$^1$H-NMR (400 MHz, $CDCl_3$) δ 10.05 (s, 1H), 8.04 (s, 1H), 7.57 (d, J=8 Hz, 1H), 7.50-7.36 (m, 5H), 6.90 (d, J=8 Hz, 1H), 5.17-5.13 (m, 2H), 4.36 (q, J=7.2 Hz, 2H), 3.71-3.67 (m, 2H), 3.59 (t, J=4.8 Hz, 2H), 3.53-3.38 (m, 8H), 3.33 (t, J=5.2 Hz, 2H), 1.41 (t, J=7.2 Hz, 3H).

Step 2: Preparation of Compound A-1b

Compound A-1a (2.83 g, 5.39 mmol) was dissolved in MC (95 mL) under a nitrogen atmosphere at −78° C., and then boron trichloride solution (1M-$BCl_3$ in MC, 43.15 mL, 43.15 mmol) was slowly added, and the mixture was stirred for 8 hours while slowly raising the temperature to −50° C. After completion of the reaction, distilled water (300 mL) was slowly added dropwise to terminate the reaction, and 2N-sodium hydroxide aqueous solution was added at 0° C. to neutralize it. MC (300 mL) was added to the mixture to extract the organic layer three times. The obtained organic layer was dried over anhydrous magnesium sulfate, filtered, and then concentrated under reduced pressure. The resulting residue was subjected to column chromatography to obtain Compound A-1b in the form of a brown liquid (1.68 mg, 71%).

$^1$H-NMR (400 MHz, $CDCl_3$) δ 10.03 (s, 1H), 9.24 (brs, 1H), 8.12 (s, 1H), 7.56 (d, J=8 Hz, 1H), 6.94 (d, J=7.6 Hz, 1H), 4.95-4.92 (m, 2H), 4.37 (q, J=7.2 Hz, 2H), 4.15-4.09 (m, 2H), 3.73-3.71 (m, 2H), 3.61-3.58 (m, 4H), 3.57-3.51 (m, 4H), 3.33 (t, J=5.2 Hz, 2H), 1.42 (t, J=7.2 Hz, 3H).

Step 3: Preparation of Compound A-1c

Compound A-1b (1.68 g, 3.87 mmol) was dissolved in MC (130 mL) under a nitrogen atmosphere at 0° C., and then acetobromo-alpha-D-galactose (183 mg, 0.44 mmol) and benzyltributylammonium chloride (1.2 g, 3.87 mmol) were added. 5N-sodium hydroxide aqueous solution (2.32 mL, 11.60 mmol) was slowly added to this reaction solution, and the mixture was stirred at room temperature for 16 hours. After completion of the reaction, MC (150 mL) and distilled water (150 mL) were added to extract the organic layer three times. The obtained organic layer was dried over anhydrous magnesium sulfate, filtered, and then concentrated under reduced pressure. The resulting residue was subjected to column chromatography to obtain Compound A-1c in the form of a brown sticky gum (1.9 g, 64%).

$^1$H-NMR (400 MHz, $CDCl_3$) δ 10.10 (s, 1H), 8.02 (s, 1H), 7.57 (d, J=8.4 Hz, 1H), 6.97 (d, J=8.4 Hz, 1H), 5.59 (dd, J=10.4, 8 Hz, 1H), 5.50 (d, J=3.2 Hz, 1H), 5.43 (d, J=8 Hz, 1H), 5.21-5.17 (m, 2H), 5.01 (m, 1H), 4.37 (q, J=7.2 Hz, 2H), 4.23-4.11 (m, 3H), 3.69-3.67 (m, 2H), 3.58 (t, J=5.2 Hz, 2H), 3.50-3.47 (m, 2H), 3.43-3.32 (m, 8H), 2.21 (s, 3H), 2.19 (s, 3H), 2.14 (s, 3H), 2.04 (s, 3H), 1.42 (t, J=7.2 Hz, 3H).

Step 4: Preparation of Compound A-1d

Compound A-1c (1.9 g, 2.49 mmol) was dissolved in THE (40 mL) under a nitrogen atmosphere at 0° C., and then sodium borohydride (188.6 mg) was added, and the mixture was stirred for 2.5 hours. After completion of the reaction, distilled water (200 mL) was added to terminate the reaction, and then EA (200 mL) was added to extract the organic layer twice. The obtained organic layer was dried over anhydrous magnesium sulfate, filtered, and then concentrated under reduced pressure. The resulting residue was subjected to column chromatography to obtain Compound A-1d in the form of a yellow solid (1.55 g, 81%).

$^1$H-NMR (400 MHz, $CDCl_3$) δ 7.38 (s, 1H), 7.01 (d, J=7.6 Hz, 1H), 6.86 (d, J=8 Hz, 1H), 5.55 (dd, J=10.4, 8 Hz, 1H), 5.48 (d, J=3.2 Hz, 1H), 5.31 (d, J=8 Hz, 1H), 5.21-5.14 (m, 2H), 5.01-4.95 (m, 1H), 4.90 (d, J=5.2 Hz, 2H), 4.35 (q, J=7.2 Hz, 2H), 4.23-4.09 (m, 3H), 3.71-3.66 (m, 2H), 3.58 (t, J=5.2 Hz, 2H), 3.51-3.34 (m, 10H), 2.21 (s, 3H), 2.07 (s, 3H), 2.05 (s, 3H), 2.02 (s, 3H), 1.76 (t, J=5.6 Hz, 1H), 1.41 (t, J=7.2 Hz, 3H).

Step 5: Preparation of Compound A-1e

Compound A-1d (160 mg, 0.2 mmol) was dissolved in DMF (4 mL) under a nitrogen atmosphere at 0° C., and then bis(4-nitrophenyl) carbonate (127 mg, 0.4 mmol) and DIPEA (54.5 L, 0.3 mmol) were sequentially added, and the mixture was stirred for 1 hour. The reaction mixture was stirred at room temperature for an additional 5 hours and then extracted with EA (50 mL) and distilled water (50 mL). The obtained organic layer was dried over anhydrous magnesium sulfate, filtered, and then concentrated under reduced pressure. The resulting residue was subjected to column chromatography to obtain Compound A-1e in the form of a light yellow oil (162 mg, 83%).

$^1$H-NMR (400 MHz, $CDCl_3$) δ 8.27 (d, J=9.2 Hz, 2H), 7.37 (d, J=9.2 Hz, 2H), 7.35 (s, 1H), 7.13 (d, J=8 Hz, 1H), 6.87 (d, J=8 Hz, 1H), 5.56 (dd, J=10.4, 8 Hz, 1H), 5.52 (s, 2H), 5.49 (d, J=3.2 Hz, 1H), 5.34 (d, J=8 Hz, 1H), 5.21-5.15 (m, 2H), 5.03-4.98 (m, 1H), 4.38 (q, J=7.2 Hz, 2H), 4.24-4.10 (m, 3H), 3.71-3.68 (m, 2H), 3.60 (t, J=5.2 Hz, 2H), 3.54-3.42 (m, 8H), 3.35 (m, 2H), 2.21 (s, 3H), 2.07 (s, 3H), 2.05 (s, 3H), 2.03 (s, 3H), 1.42 (t, J=7.2 Hz, 3H); EI-MS m/z: 795 $[M+H]^+$.

Step 6: Preparation of Compound A-1f

Compound A-1e (30 mg, 0.032 mmol) was dissolved in DMF (0.2 mL) under a nitrogen atmosphere at room temperature, and then MMAF-OMe (24 mg, 0.032 mmol), HOBt (6.5 mg, 0.048 mmol) and DIPEA (14 μL, 0.08 mmol) were sequentially added, and the mixture was stirred at room temperature for 16 hours. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and freeze-dried to obtain Compound A-if in the form of a white solid (12.1 mg, 24%); EI-MS m/z: 1539 $[M+H]^+$.

Step 7: Preparation of Compounds A-1 and A-2

Compound A-1f (12.1 mg, 0.008 mmol) was dissolved in methanol (1 mL) at 0° C., and then lithium hydroxide monohydrate (4.3 mg, 0.1 mmol) dissolved in distilled water (250 μL) was slowly added dropwise, and the mixture was stirred at room temperature for 1.5 hours. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and freeze-dried to obtain Compounds A-1 and A-2 in the form of a white solid (A-1: 1.4 mg, 13%, A-2: 1.8 mg, 17%); EI-MS m/z: A-1: 1357 $[M+H]^+$, A-2: 1328 $[M+H]^+$.

Example I-2: Preparation of Compound A-3

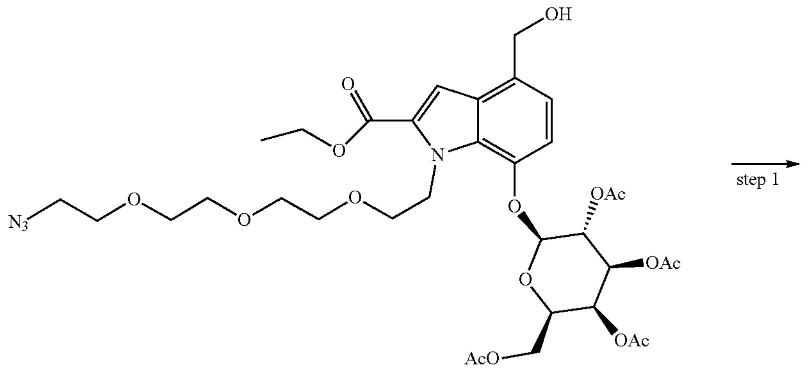

A-1d

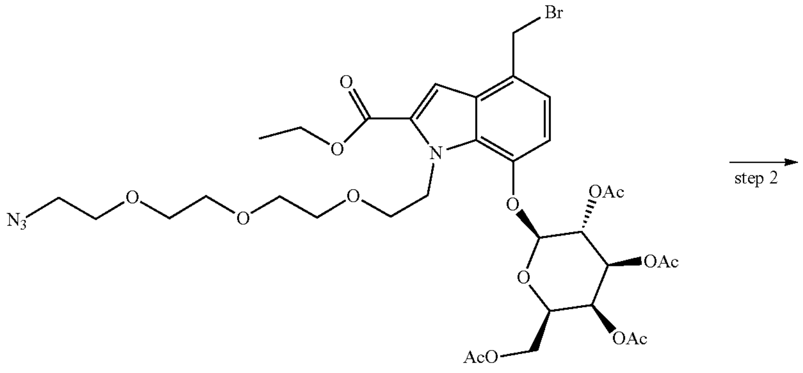

A-3a

-continued

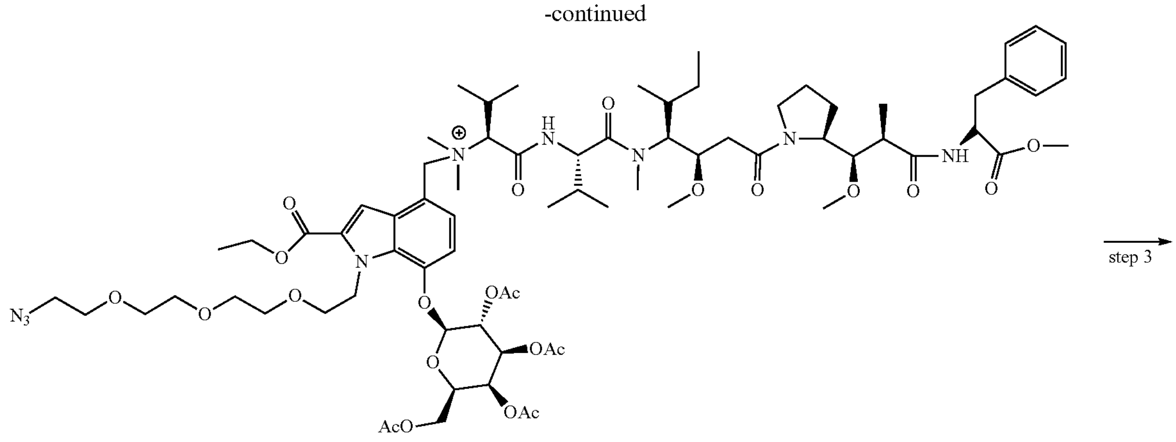

A-3b

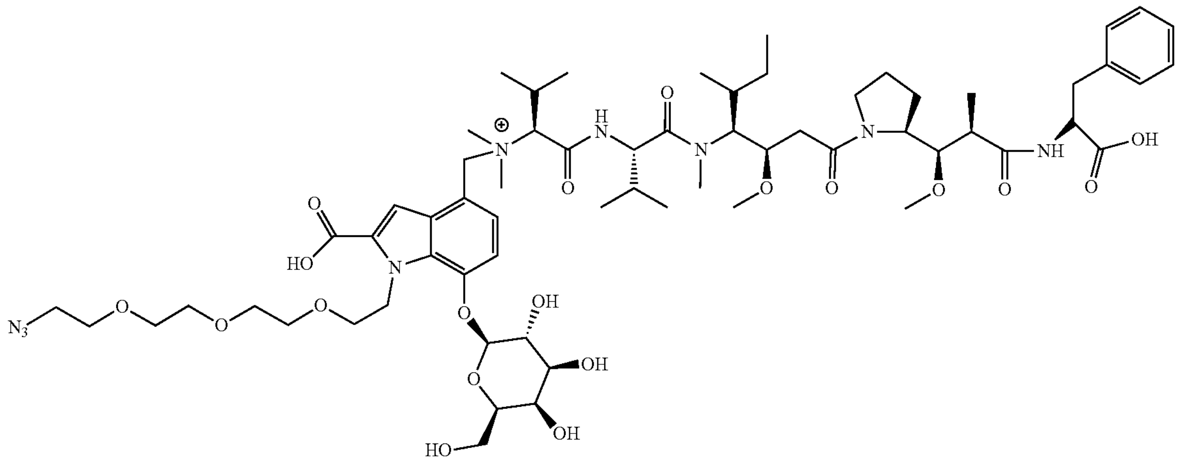

A-3

Step 1: Preparation of Compound A-3a

Triphenylphosphine (65.6 mg, 0.24 mmol) and carbon tetrabromide ($CBr_4$, 173 mg, 0.50 mmol) were dissolved in MC (5 mL) under a nitrogen atmosphere at 0° C., and then the mixture was stirred for 30 minutes. Compound A-1d (160 mg, 0.20 mmol) prepared in Step 4 of Example I-1, which was dissolved in MC (2 mL), was added to the above reaction solution, and the mixture was stirred for 1 hour. After completion of the reaction, EA (100 mL) and distilled water (100 mL) were added to extract the organic layer, and the obtained organic layer was dried over anhydrous magnesium sulfate, filtered, and then concentrated under reduced pressure. The residue was subjected to column chromatography to obtain Compound A-3a (30 mg, 17%); EI-MS m/z: 761 $[M+H]^+$.

Step 2: Preparation of Compound A-3b

Compound A-3a (30 mg, 0.036 mmol) was dissolved in DMF (2 mL) under a nitrogen atmosphere at 0° C., and then auristatin F-OMe (30 mg, 0.04 mmol) prepared in Preparation Example 9 and DIPEA (18.9 μL, 0.11 mmol) were sequentially added, and the mixture was stirred at 60° C. for 3 hours. After completion of the reaction, the reaction solution was cooled to room temperature, and the reaction solution containing Compound A-3b was used in the next reaction without an additional process; EI-MS m/z: 1509 $[M+H]^+$.

Step 3: Preparation of Compound A-3

Lithium hydroxide monohydrate (15.2 mg, 0.36 mmol) was slowly added dropwise to the above reaction solution, and the mixture was stirred for 3 hours. After completion of the reaction, 2N-hydrochloric acid aqueous solution (0.1 mL) was slowly added dropwise to terminate the reaction, and the reaction solution was diluted with ACN (1 mL) and distilled water (1 mL), then separated and purified using Preparative-HPLC, and freeze-dried to obtain Compound A-3 in the form of a white solid (7.9 mg, 16%); EI-MS m/z: 1299 $[M+H]^+$.

Example I-3: Preparation of Compound A-4
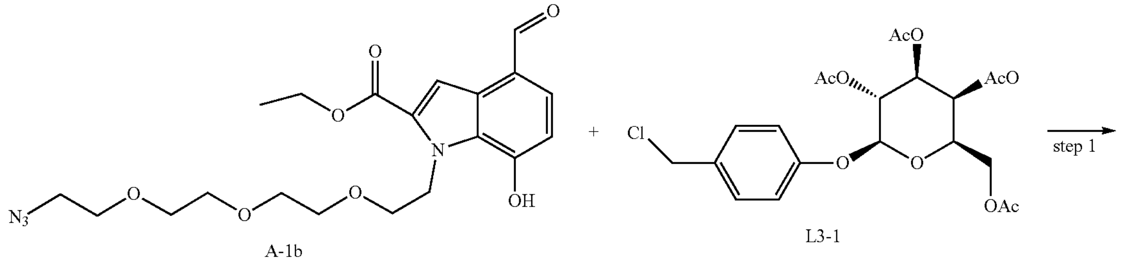
A-1b L3-1
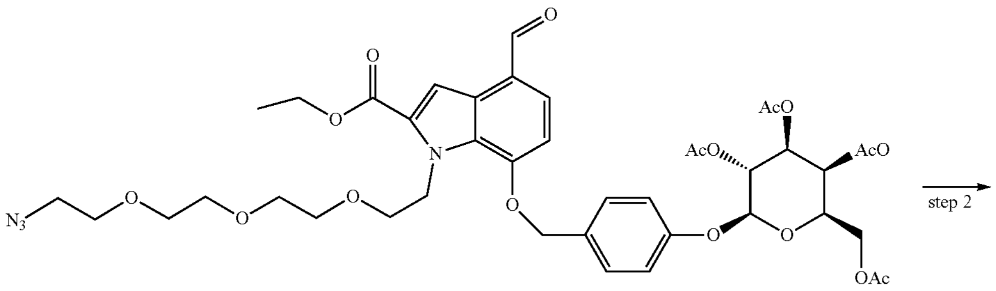
A-4a
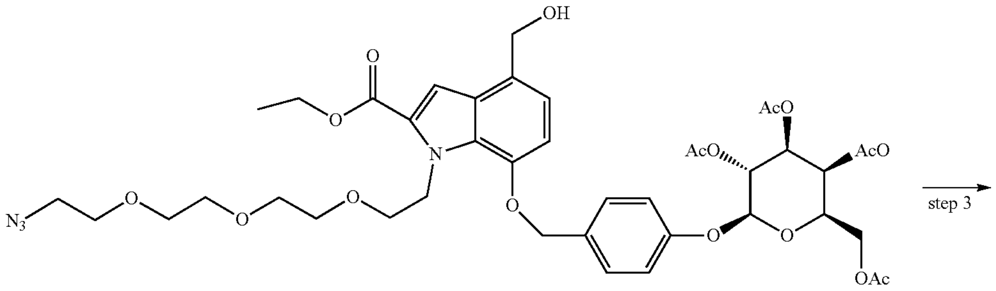
A-4b
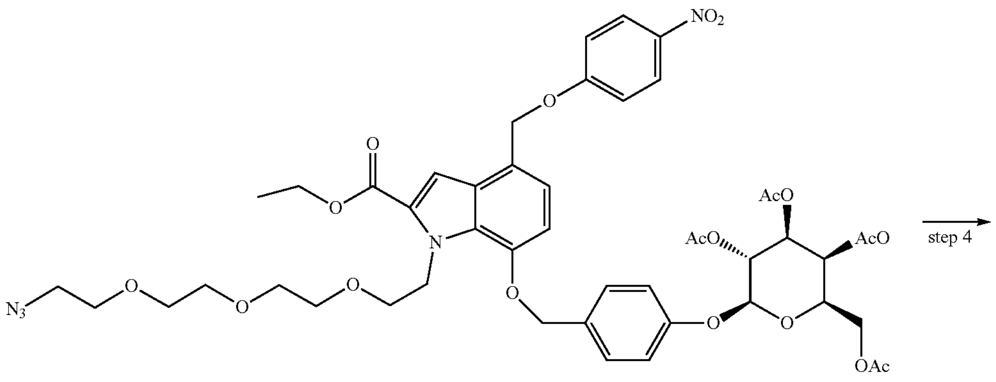
A-4c -continued

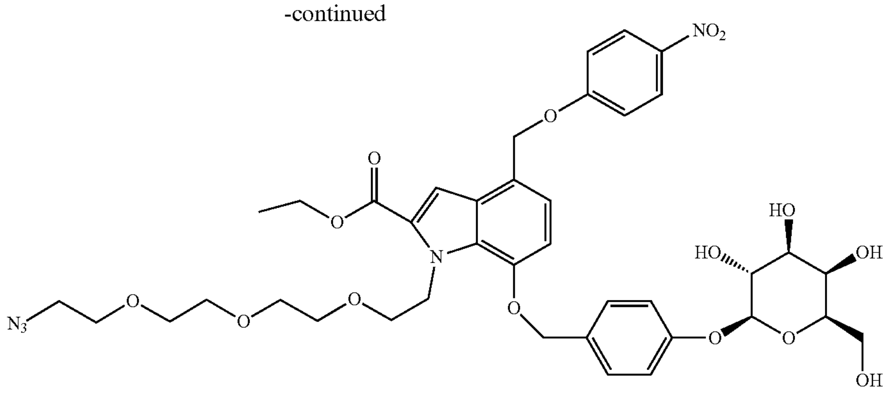

A-4

Step 1: Preparation of Compound A-4a

Compound A-1b (300 mg, 0.69 mmol) prepared in Step 2 of Example I-1 was dissolved in DMF (5 mL) under a nitrogen atmosphere at room temperature, and then potassium carbonate (286 mg, 2.07 mmol) and Compound L3-1 (424 mg, 0.90 mmol) prepared in Preparation Example 10 were sequentially added, and the mixture was stirred at 70° C. for 4 hours. After completion of the reaction, the temperature of the reaction solution was lowered to room temperature, and EA (100 mL) and distilled water (200 mL) were added to extract the organic layer. Distilled water (300 mL) was added to extract the obtained organic layer again, and the extracted organic layer was dried over anhydrous magnesium sulfate, filtered, and then concentrated under reduced pressure. The resulting residue was subjected to column chromatography to obtain Compound A-4a in the form of a light yellow oil (580 mg, 96%).

$^1$H-NMR (400 MHz, $CDCl_3$) δ 10.05 (s, 1H), 8.04 (s, 1H), 7.57 (d, J=8 Hz, 1H), 7.43 (d, J=8.8 Hz, 2H), 7.05 (d, J=8.8 Hz, 2H), 6.88 (d, J=8 Hz, 1H), 5.52 (m. 2H), 5.25 (s, 2H), 5.15-5.08 (m, 4H), 4.36 (q, J=7.2 Hz, 2H), 4.26-4.22 (m, 1H), 4.19-4.07 (m, 2H), 3.69 (t, J=6 Hz, 2H), 3.59 (m, 2H), 3.53-3.51 (m, 2H), 3.48-3.43 (m, 4H), 3.41-3.39 (m, 2H), 3.44 (m, 2H), 2.19 (s, 3H), 2.08 (s, 3H), 2.05 (s, 3H), 2.02 (s, 3H), 1.41 (t, J=7.2 Hz, 3H).

Step 2: Preparation of Compound A-4b

Compound A-4a (580 mg, 0.66 mmol) was dissolved in THE (10 mL) under a nitrogen atmosphere at 0° C., and then sodium borohydride (63 mg, 1.65 mmol) was added, and the mixture was stirred for 3 hours. After completion of the reaction, distilled water (100 mL) was added to terminate the reaction, and EA (100 mL) was added to extract the organic layer. The obtained organic layer was dried over anhydrous magnesium sulfate, filtered, and then concentrated under reduced pressure. The resulting residue was subjected to column chromatography to obtain Compound A-4b (370 mg, 63%).

$^1$H-NMR (400 MHz, $CDCl_3$) δ 7.42-7.40 (m, 3H), 7.04-6.98 (m, 3H), 6.73 (d, J=8 Hz, 1H), 5.52-5.47 (m, 2H), 5.15-5.07 (m, 6H), 4.89 (m, 2H), 4.35 (q, J=7.2 Hz, 2H), 4.23 (m, 1H), 4.17 (m, 1H), 4.09 (m, 1H), 3.70 (m, 2H), 3.59 (m, 2H), 3.53-3.41 (m, 8H), 3.33 (m, 2H), 2.19 (s, 3H), 2.08 (s, 3H), 2.05 (s, 3H), 2.02 (s, 3H), 1.40 (t, J=7.2 Hz, 3H).

Step 3: Preparation of Compound A-4c

Compound A-4b (150 mg, 0.17 mmol) was dissolved in DMF (3 mL) under a nitrogen atmosphere at 0° C., and then bis(4-nitrophenyl) carbonate (104.5 mg, 0.34 mmol) and DIPEA (60 L, 0.34 mmol) were sequentially added, and the mixture was stirred at room temperature for 2 hours. After completion of the reaction, the organic layer was diluted with EA (50 mL), and distilled water (50 mL) and 2N-hydrochloric acid aqueous solution (10 mL) were added to extract the organic layer, and the extracted organic layer was dried over anhydrous magnesium sulfate, filtered, and then concentrated under reduced pressure. The residue thus obtained was subjected to column chromatography to obtain Compound A-4c (115 mg, 67%).

$^1$H-NMR (400 MHz, $CDCl_3$) δ 8.20 (d, J=8 Hz, 2H), 7.41 (d, J=8.8 Hz, 2H), 7.29 (s, 1H), 7.07-7.02 (m, 5H), 6.75 (d, J=8 Hz, 1H), 5.52-5.46 (m, 2H), 5.34 (s, 2H), 5.16 (s, 2H), 5.14-5.07 (m, 4H), 4.35 (q, J=7.2 Hz, 2H), 4.23 (m, 1H), 4.19-4.08 (m, 2H), 3.72 (m, 2H), 3.61 (t, J=7.2 Hz, 2H), 3.52-3.42 (m, 8H), 3.43 (m, 2H), 2.19 (s, 3H), 2.08 (s, 3H), 2.05 (s, 3H), 2.02 (s, 3H), 1.39 (t, J=7.2 Hz, 3H); EI-MS m/z: 1016 $[M+Na]^+$.

Step 4: Preparation of Compound A-4

Compound A-4c (22.3 mg, 0.022 mmol) was dissolved in methanol (1 mL) and THE (1 mL) at 0° C., and then lithium hydroxide monohydrate (4.7 mg, 0.112 mmol) dissolved in distilled water (200 μL) was slowly added dropwise, and the mixture was stirred at 0° C. for 10 minutes. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and freeze-dried to obtain Compound A-4 in the form of an ivory solid (8.9 mg, 48%).

$^1$H-NMR (400 MHz, DMSO-$d_6$) δ 8.24 (d, J=9.2 Hz, 2H), 7.49 (d, J=8.8 Hz, 2H), 7.34 (s, 1H), 7.28 (d, J=9.2 Hz, 2H), 7.20 (d, J=7.6 Hz, 1H), 7.08 (d, J=8.8 Hz, 2H), 6.99 (d, J=7.6 Hz, 1H), 5.48 (s, 2H), 5.21 (s, 2H), 5.18 (m, 1H), 5.03-5.01 (m, 2H), 4.89-4.84 (m, 2H), 4.67 (m, 1H), 4.53 (m, 1H), 4.32 (q, J=7.2 Hz, 2H), 3.73 (m, 1H), 3.62-3.39 (m, 15H), 1.33 (t, J=7.2 Hz, 3H); EI-MS m/z: 848 $[M+Na]^+$.

Example I-4: Preparation of Compound A-5

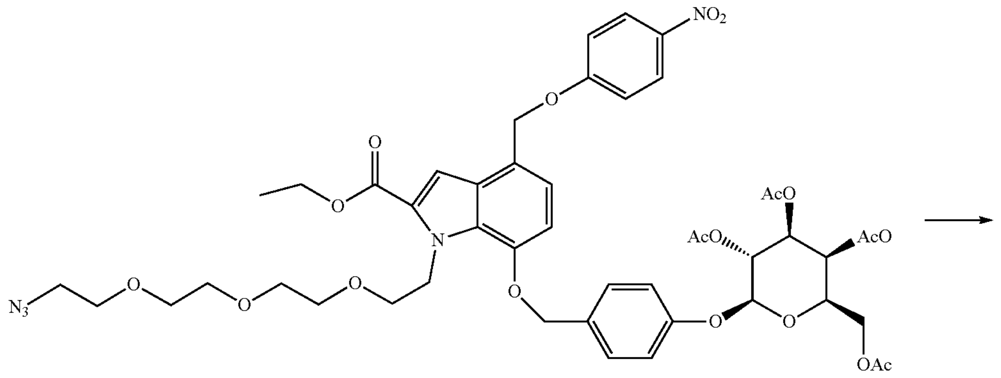

A-4c

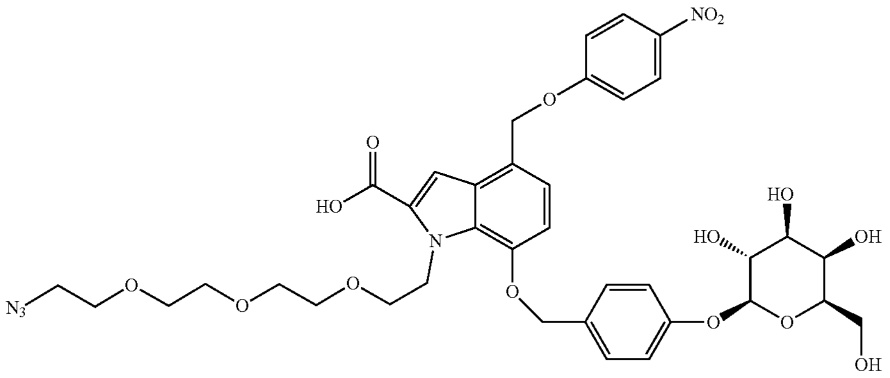

A-5

Compound A-4c (23.5 mg, 0.024 mmol) prepared in Step 3 of Example I-3 was dissolved in methanol (1.5 mL) and THE (0.4 mL) at 0° C., and then lithium hydroxide monohydrate (24.8 mg, 0.59 mmol) dissolved in distilled water (500 μL) was slowly added dropwise, and the mixture was stirred at 0° C. for 1 hour. The reaction mixture was stirred at room temperature for an additional 2 hours. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and freeze-dried to obtain Compound A-5 in the form of a white solid (10 mg, 53%).

$^1$H-NMR (400 MHz, DMSO-$d_6$) δ 8.21 (d, J=9.2 Hz, 2H), 7.47 (d, J=8.4 Hz, 2H), 7.26 (d, J=9.2 Hz, 2H), 7.18 (s, 1H), 7.12 (d, J=8 Hz, 1H), 7.06 (d, J=8.4 Hz, 2H), 6.91 (d, J=8 Hz, 1H), 5.43 (s, 2H), 5.19 (s, 2H), 5.17 (m, 1H), 5.03-5.01 (m, 2H), 4.90-4.83 (m, 2H), 4.65 (m, 1H), 4.51 (m, 1H), 3.71 (m, 1H), 3.61-3.46 (m, 15H); EI-MS m/z: 820 $[M+Na]^+$.

Example I-5: Preparation of Compound A-6

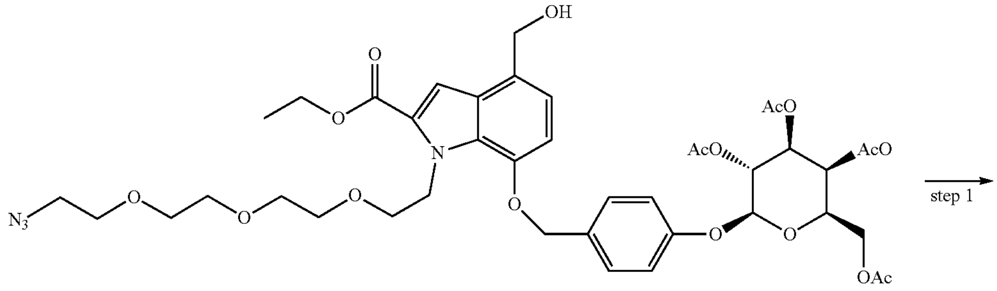

A-4b

-continued

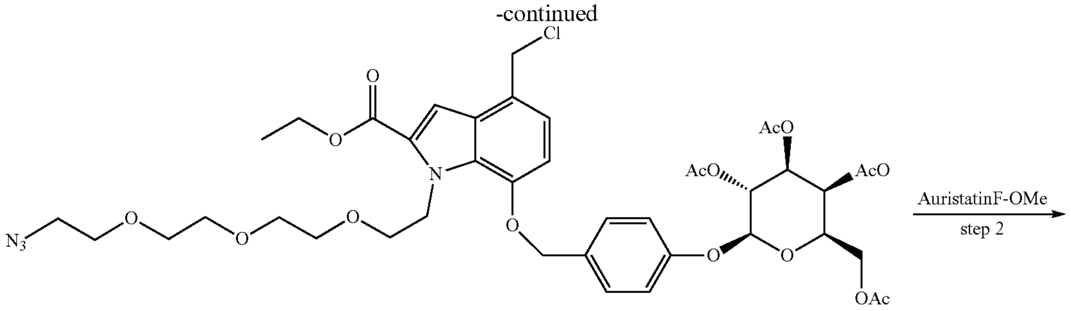

A-6a

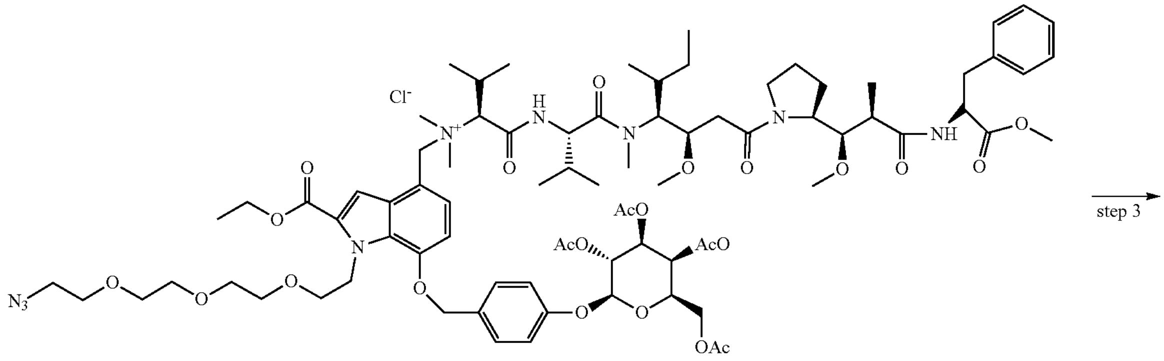

A-6b

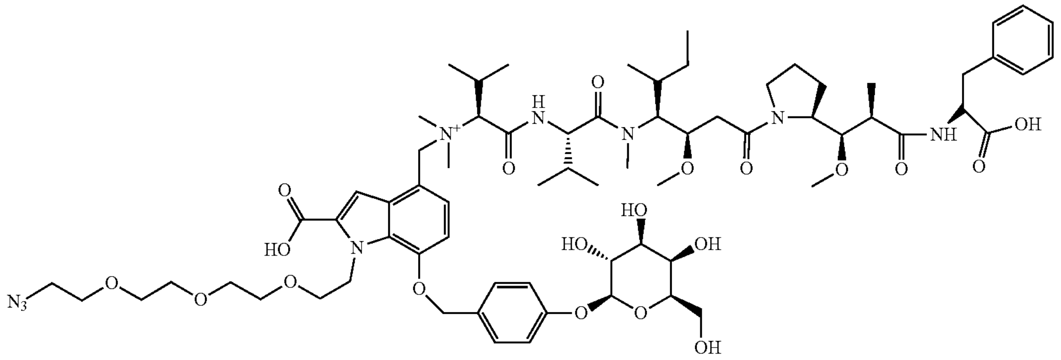

A-6

Step 1: Preparation of Compound A-6a

Compound A-4b (50 mg, 0.057 mmol) prepared in Step 2 of Example I-3 was dissolved in MC (2.5 mL) under a nitrogen atmosphere at 0° C., and then thionyl chloride (5 μL, 0.069 mmol) was added, and the mixture was stirred for 3 hours at 0° C. After completion of the reaction, EA (50 mL) and distilled water (50 mL) were added to extract the organic layer, and the obtained organic layer was dried over anhydrous magnesium sulfate, filtered, and then concentrated under reduced pressure. The residue was subjected to column chromatography to obtain Compound A-6a (50 mg, 98%); EI-MS m/z: 891 $[M+H]^+$.

Step 2: Preparation of Compound A-6b

Compound A-6a (50 mg, 0.056 mmol) was dissolved in DMF (2 mL) under a nitrogen atmosphere at 0° C., and then auristatin F-OMe (46.9 mg, 0.061 mmol) prepared in Preparation Example 9, DIPEA (24.4 μL, 0.14 mmol) and TBAI (2 mg, 0.005 mmol) were sequentially added, and the mixture was stirred at 40° C. for 15 hours to prepare Compound A-6b; EI-MS m/z: 1615 $[M+H]^+$.

Step 3: Preparation of Compound A-6

The reaction solution containing Compound A-6b obtained in Step 2 above was cooled to room temperature, and methanol (1 mL) was added. 6N-sodium hydroxide aqueous solution (0.1 mL) and distilled water (1 mL) were sequentially added at 0° C., and the mixture was stirred for 30 minutes and then stirred at room temperature for an additional 2 hours. 2N-hydrochloric acid aqueous solution (0.1 mL) was slowly added dropwise to terminate the reaction, and the reaction solution was diluted with ACN (1 mL) and distilled water (1 mL), then separated and purified using Preparative-HPLC, and freeze-dried to obtain Compound A-6 (2 mg, 2%); EI-MS m/z: 1405 $[M+H]^+$.

Example I-6: Preparation of Compound A-7

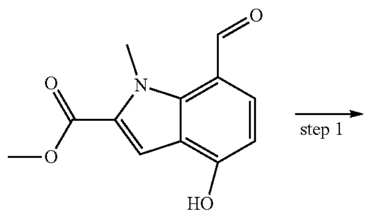

C-1

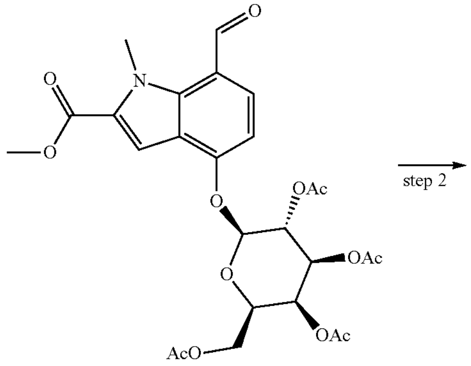

A-7a

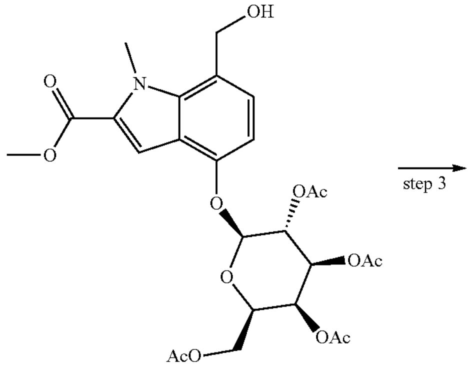

A-7b

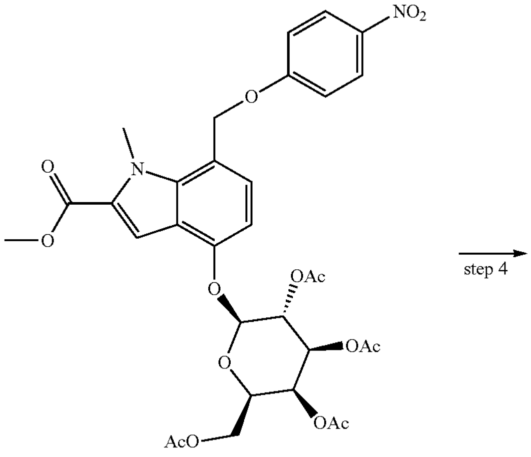

A-7c

-continued

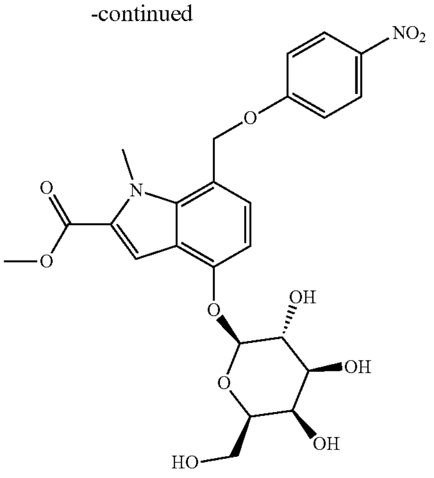

A-7

Step 1: Preparation of Compound A-7a

Core C-1 (99.1 mg, 0.42 mmol) was dissolved in MC (15 mL) under a nitrogen atmosphere at 0° C., and then aceto-bromo-alpha-D-galactose (192 mg, 0.46 mmol) and benzyl-tributylammonium chloride (132 mg, 0.42 mmol) were added. 5N-sodium hydroxide aqueous solution (255 μL, 1.27 mmol) was slowly added to this reaction solution, and the mixture was stirred at room temperature for 16 hours. After completion of the reaction, MC (50 mL) and distilled water (50 mL) were added to extract the organic layer three times. The obtained organic layer was dried over anhydrous magnesium sulfate, filtered, and then concentrated under reduced pressure. The resulting residue was subjected to column chromatography to obtain Compound A-7a in the form of an ivory solid (131.3 mg, 55%).

$^{1}$H-NMR (400 MHz, $CDCl_3$) δ 10.19 (s, 1H), 7.82 (d, J=8 Hz, 1H), 7.38 (s, 1H), 6.80 (d, J=8 Hz, 1H), 5.64 (dd, J=10.4, 8 Hz, 1H), 5.50 (d, J=3.2 Hz, 1H), 5.29 (d, J=8 Hz, 1H), 5.16 (dd, J=10.4, 3.2 Hz, 1H), 4.34 (s, 3H), 4.26-4.09 (m, 3H), 3.93 (s, 3H), 2.21 (s, 3H), 2.08 (s, 3H), 2.06 (s, 3H), 2.05 (s, 3H).

Step 7: Preparation of Compound A-7b

Compound A-7a (131.3 mg, 0.23 mmol) was dissolved in THE (3 mL) under a nitrogen atmosphere at 0° C., and then sodium borohydride (26.5 mg, 0.70 mmol) was added, and the mixture was stirred at room temperature for 2 hours. After completion of the reaction, distilled water (50 mL) was added to terminate the reaction, and EA (50 mL) was added to extract the organic layer twice. The obtained organic layer was dried over anhydrous magnesium sulfate, filtered, and then concentrated under reduced pressure. The resulting residue was subjected to column chromatography to obtain Compound A-7b in the form of a yellow solid (101.5 mg, 77%).

$^{1}$H-NMR (400 MHz, $CDCl_3$) δ 7.32 (s, 1H), 7.12 (d, J=8 Hz, 1H), 6.63 (d, J=8 Hz, 1H), 5.61 (dd, J=10.4, 8 Hz, 1H), 5.48 (d, J=2.8 Hz, 1H), 5.16-5.12 (m, 2H), 4.99-4.97 (m, 2H), 4.41 (s, 3H), 4.28-4.08 (m, 3H), 3.91 (s, 3H), 2.20 (s, 3H), 2.07 (s, 3H), 2.06 (s, 3H), 2.04 (s, 3H).

Step 8: Preparation of Compound A-7c

Compound A-7b (101.5 mg, 0.18 mmol) was dissolved in MC (5 mL) under a nitrogen atmosphere at 0° C., and then 4-nitrophenyl chloroformate (108.5 mg, 0.54 mmol) and DIPEA (156 L, 0.89 mmol) were sequentially added, and the mixture was stirred for 20 hours. After completion of the reaction, EA (30 mL) and distilled water (30 mL) were added to extract the organic layer. The obtained organic layer was dried over anhydrous magnesium sulfate, filtered, and then concentrated under reduced pressure. The resulting residue was subjected to column chromatography to obtain Compound A-7c (44.1 mg, 36%).

$^1$H-NMR (400 MHz, $CDCl_3$) δ 8.25 (d, J=9.2 Hz, 2H), 7.35 (s, 1H), 7.23 (d, J=8 Hz, 1H), 7.08 (d, J=9.2 Hz, 2H), 6.69 (d, J=8 Hz, 1H), 5.62 (dd, J=10.4, 8 Hz, 1H), 5.49 (d, J=2.8 Hz, 1H), 5.44 (m, 2H), 5.18 (d, J=8 Hz, 1H), 5.15 (dd, J=10.4, 3.6 Hz, 1H), 4.27 (m, 1H), 4.24 (s, 3H), 4.20-4.09 (m, 2H), 3.91 (s, 3H), 2.21 (s, 3H), 2.06 (m, 6H), 2.04 (s, 3H).

Step 9: Preparation of Compound A-7

Compound A-7c (37.2 mg, 0.054 mmol) was dissolved in methanol (1.5 mL) and ACN (1.5 mL) under a nitrogen atmosphere at 0° C., and then potassium carbonate (52.4 mg, 0.38 mmol) was added, and the mixture was stirred for 1.5 hours while raising the temperature from 0° C. to room temperature. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and freeze-dried to obtain Compound A-7 in the form of a white solid (5 mg, 18%).

$^1$H-NMR (400 MHz, DMSO-$d_6$) δ 8.25 (d, J=9.2 Hz, 2H), 7.47 (s, 1H), 7.38 (d, J=8 Hz, 1H), 7.32 (d, J=9.2 Hz, 2H), 6.76 (d, J=8 Hz, 1H), 5.59 (s, 2H), 5.33 (m, 1H), 4.94-4.92 (m, 2H), 4.68 (m, 1H), 4.57 (m, 1H), 4.18 (s, 3H), 3.85 (s, 3H), 3.73 (m, 1H), 3.64 (m, 1H).

Example I-7: Preparation of Compound A-8

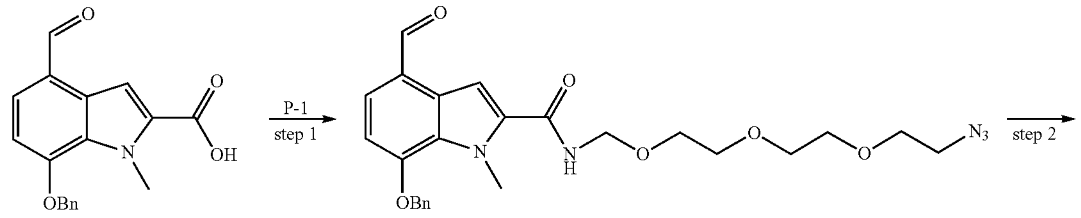

C-2 A-8a

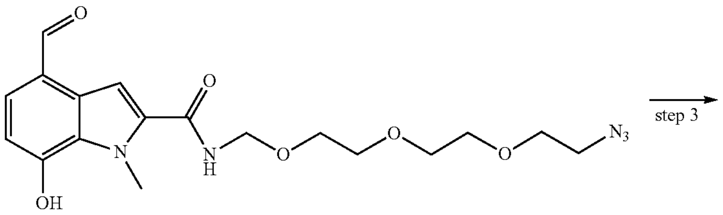

A-8b

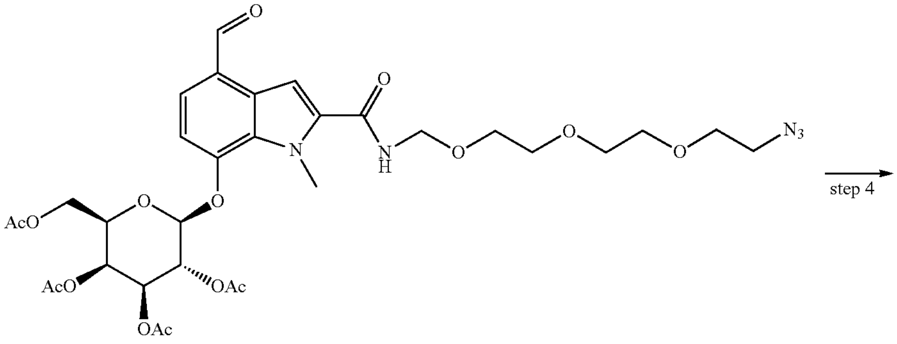

A-8c

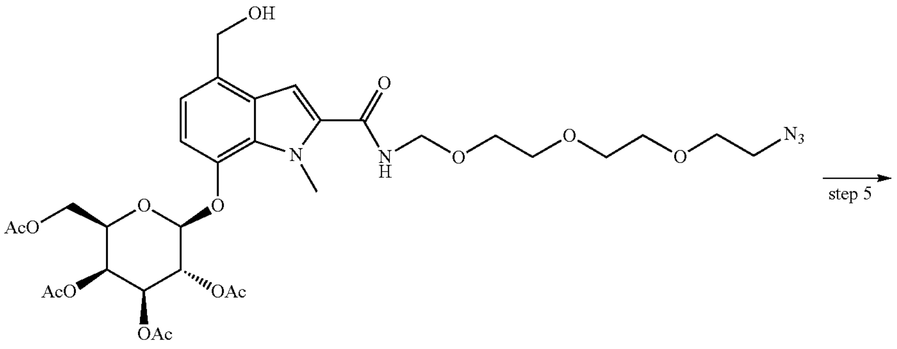

A-8d

-continued
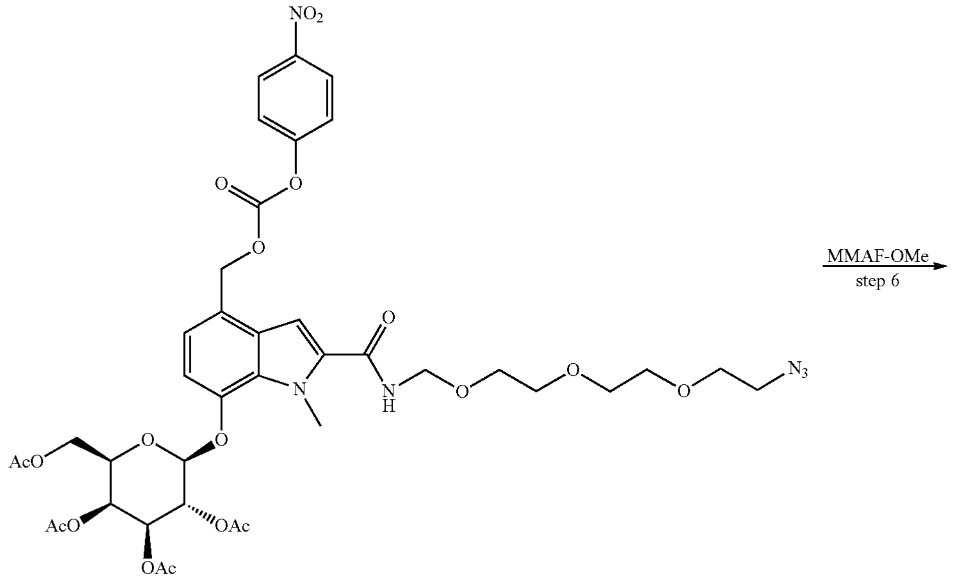
A-8e
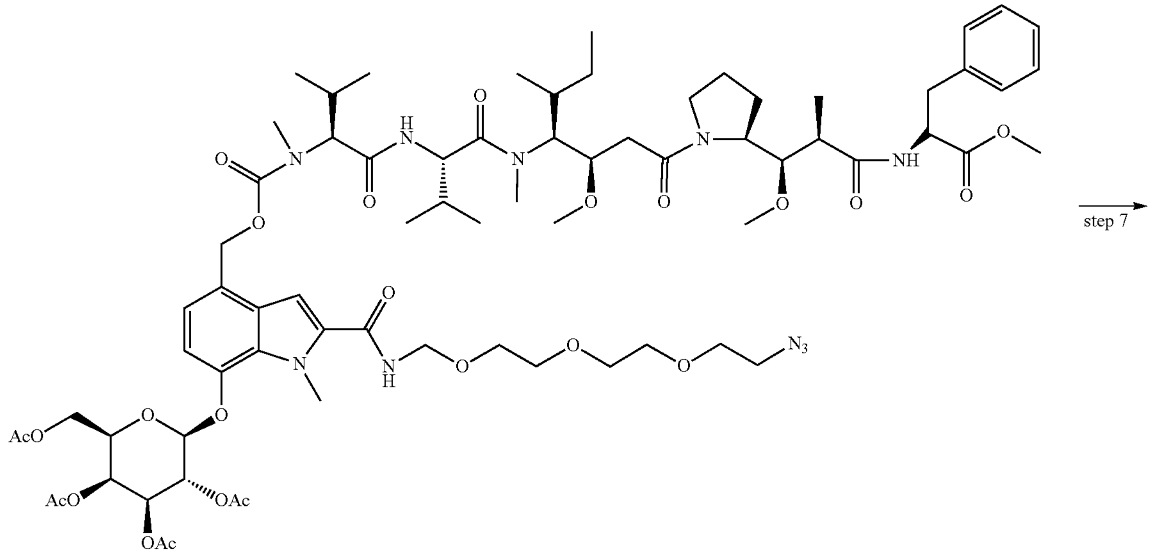
A-8f

-continued

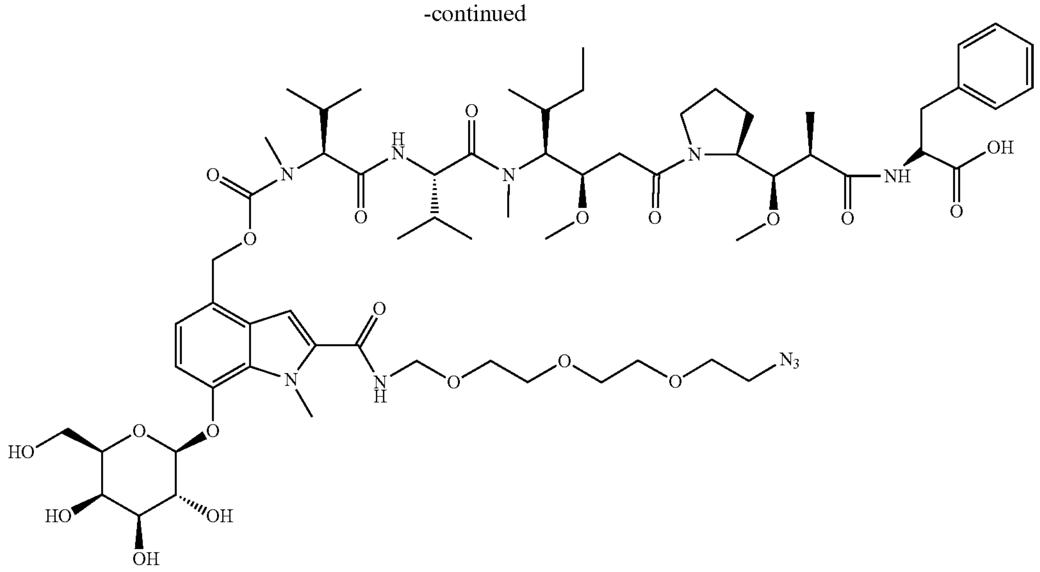

A-8

Step 1: Preparation of Compound A-8a

Core C-2 (2.4 g, 7.75 mmol) was dissolved in DMF (25 mL) under a nitrogen atmosphere at 0° C., and then EDC (CAS NO. 25952-53-8, 2.23 g, 11.63 mmol), HOBt (1.05 g, 8.14 mmol), DMAP (95 mg, 0.77 mmol), DIPEA (4 mL, 23.25 mmol) and Linker P-1 (1.98 g, 7.75 mmol) were sequentially added, and the mixture was stirred for 30 minutes. The reaction mixture was stirred at room temperature for an additional 16 hours and then extracted with EA (300 mL) and 1N-hydrochloric acid aqueous solution (400 mL). 1N-sodium hydroxide aqueous solution (5 mL) and distilled water (300 mL) were added to the obtained organic layer to extract it, and the organic layer was dried over anhydrous magnesium sulfate, filtered, and then concentrated under reduced pressure. The resulting residue was subjected to column chromatography to obtain Compound A-8a in the form of a light yellow oil (2.57 g, 65%).

$^1$H-NMR (400 MHz, $CDCl_3$) δ 10.01 (s, 1H), 7.67 (s, 1H), 7.54 (d, J=8 Hz, 1H), 7.48-7.37 (m, 5H), 6.88-6.84 (m, 2H), 5.30 (s, 2H), 4.33 (s, 3H), 3.71-3.60 (m, 14H), 3.32 (t, J=5.2 Hz, 2H); EI-MS m/z: 510 $[M+H]^+$.

Step 2 to Step 7: Preparation of Compound A-8

Compound A-8 was obtained in the form of a white solid using Compound A-8a as a starting material in the same manner as in Steps 2 to 7 of Example I-1 (3.1 mg, 39%); EI-MS m/z: 1341 $[M+H]^+$.

Example I-8: Preparation of Compound A-9

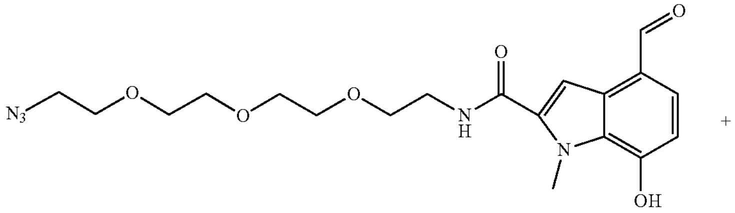

A-8a

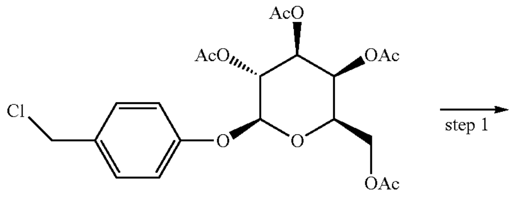

L3-1

-continued
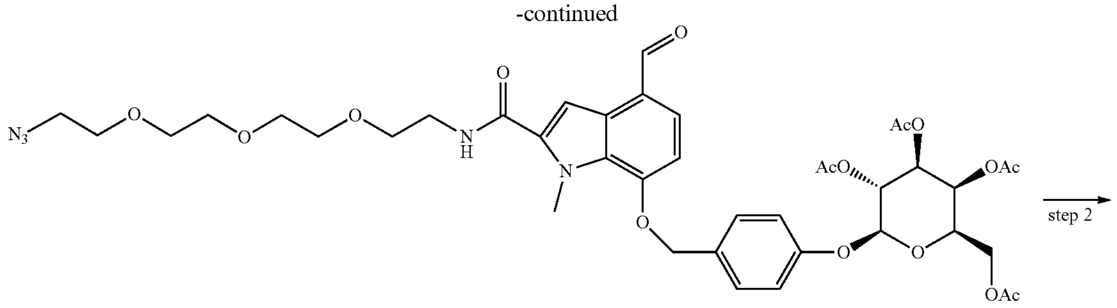
A-9a
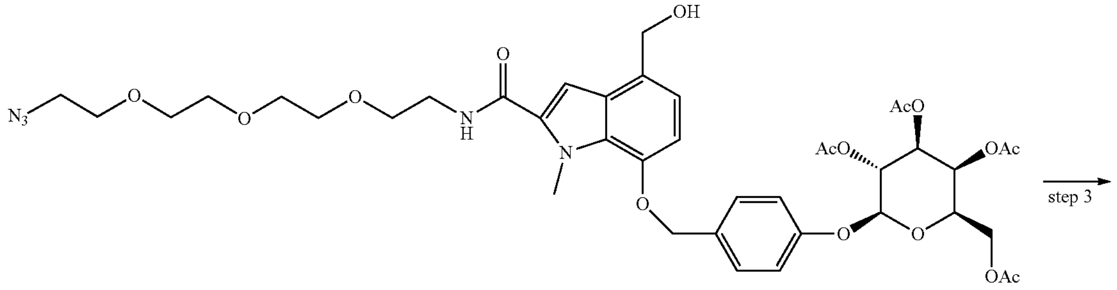
A-9b
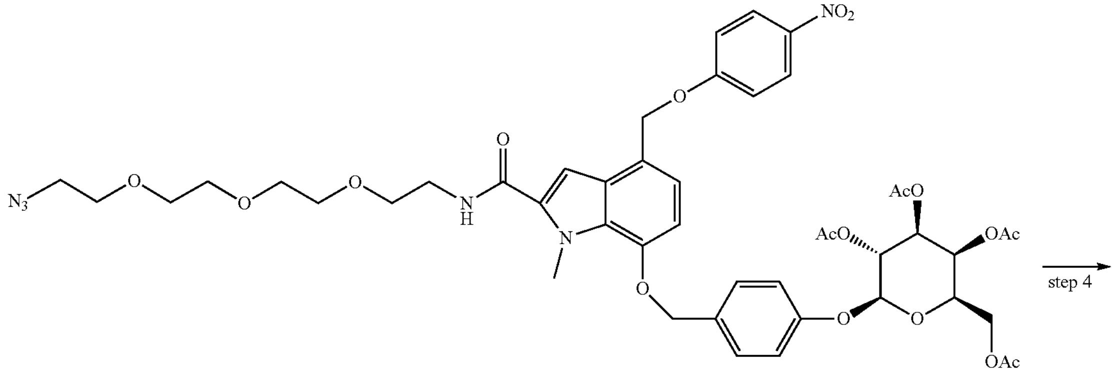
A-9c
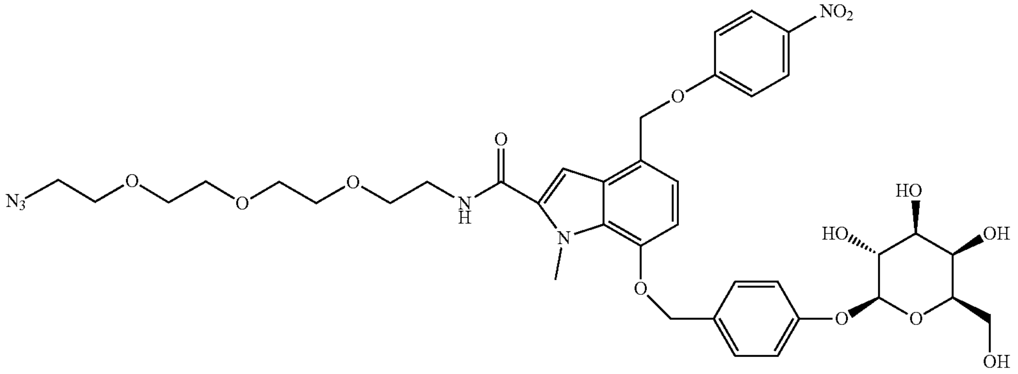
A-9
Compound A-9 was obtained in the form of an ivory solid using Compound A-8b as a starting material in the same manner as in Example I-3 (21.5 mg, 72%).
$^1$H-NMR (400 MHz, DMSO-$d_6$) δ 8.50 (t, J=5.2 Hz, 1H), 8.22 (d, J=9.2 Hz, 2H), 7.45 (d, J=8.8 Hz, 2H), 7.26 (d, J=9.2 Hz, 2H), 7.13-7.11 (m, 2H), 7.06 (d, J=8.8 Hz, 2H), 6.87 (d, J=8 Hz, 1H), 5.38 (s, 2H), 5.18 (s, 2H), 5.16 (m, 1H), 4.84-4.82 (m, 2H), 4.64 (m, 1H), 4.51 (m, 1H), 4.20 (s, 3H), 3.70 (m, 1H), 3.56-3.51 (m, 15H), 3.40 (m, 2H).

Example I-9: Preparation of Compound A-10

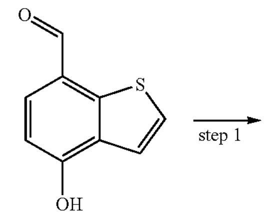

C-3

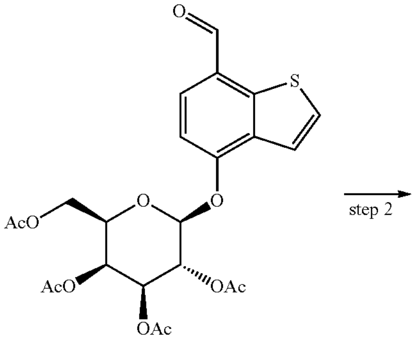

A-10a

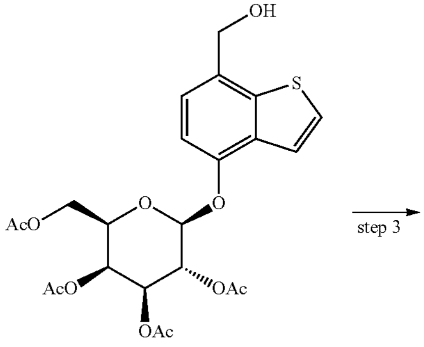

A-10b

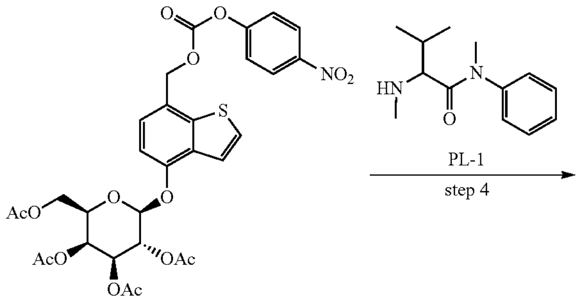

A-10c

-continued

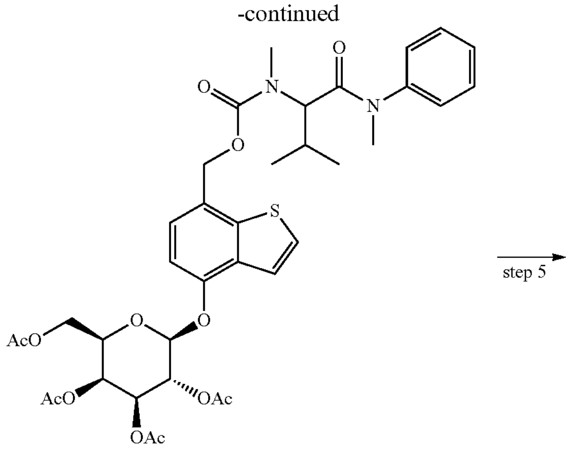

A-10d

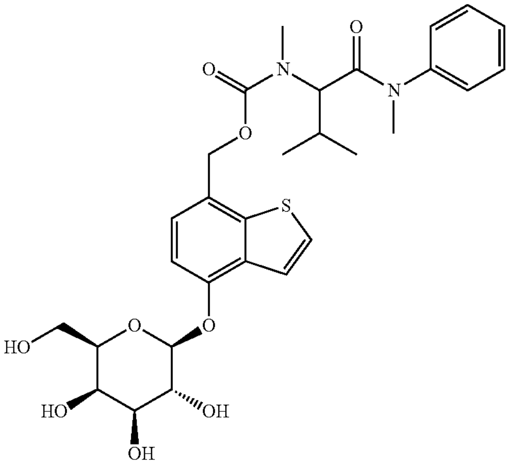

A-10

Step 1: Preparation of Compound A-10a

Core C-3 (160 mg, 0.89 mmol) was dissolved in ACN (12 mL) under a nitrogen atmosphere at 0° C., and then aceto-bromo-alpha-D-galactose (406 mg, 0.98 mmol), silver oxide (I) (520 mg, 2.22 mmol) and a molecular sieve (70 mg) were sequentially added, and the mixture was stirred at room temperature for 30 minutes. After completion of the reaction, the reaction solution was diluted with EA (100 mL), filtered using a Celite filter, and extracted by adding distilled water (100 mL) to the solution. The obtained organic layer was dried over anhydrous magnesium sulfate, filtered, and then concentrated under reduced pressure. The resulting residue was subjected to column chromatography to obtain Compound A-10a in the form of a solid (400 mg, 87.7%) $^1$H-NMR (400 MHz, $CDCl_3$) δ 10.13 (s, 1H), 7.84 (d, J=8 Hz, 1H), 7.59 (d, J 5.6 Hz, 1H), 7.49 (d, J 5.6 Hz, 1H), 7.09 (d, J 8 Hz, 1H), 5.67 (dd, J 10.4, 8 Hz, 1H), 5.52 (d, J=3.2 Hz, 2H), 5.30 (d, J=8 Hz, 1H), 5.19 (dd, J=10.4, 3.6 Hz, 2H), 4.29 (i, 1H), 4.21-4.17 (s, 2H), 2.21 (s, 3H), 2.10 (s, 3H), 2.04 (s, 6H).

Step 2: Preparation of Compound A-10b

Compound A-10a (183 mg, 0.36 mmol) was dissolved in THE (10 mL) under a nitrogen atmosphere at 09C, and then sodium borohydride (34 mg, 0.90 mmol) was added, and the mixture was stirred at 0° C. for 1 hour, and then the mixture was stirred at room temperature for 2.5 hours. After completion of the reaction, distilled water (50 mL) was added to terminate the reaction, and EA (50 mL) was added to extract the organic layer twice. The obtained organic layer was dried over anhydrous magnesium sulfate, filtered, and then concentrated under reduced pressure. The resulting residue was subjected to column chromatography to obtain Compound A-10b in the form of a white solid (137.2 mg, 75%).

$^1$H-NMR (400 MHz, $CDCl_3$) δ 7.45 (d, J=5.6 Hz, 1H), 7.40 (d, J=5.6 Hz, 1H), 7.28 (d, J=8 Hz, 1H), 6.95 (d, J=8 Hz, 1H), 5.63 (dd, J=10.4, 8 Hz, 1H), 5.50 (d, J=2.8 Hz, 1H), 5.17-5.14 (m, 2H), 4.92 (d, J=5.6 Hz, 2H), 4.29-4.11 (m, 3H), 2.20 (s, 3H), 2.08 (s, 3H), 2.05 (s, 3H), 2.03 (s, 3H), 1.79 (t, J=6 Hz, 1H).

Step 3: Preparation of Compound A-10c

Compound A-10b (137.2 mg, 0.18 mmol) was dissolved in MC (10 mL) under a nitrogen atmosphere at 0° C., and then 4-nitrophenyl chloroformate (81.2 mg, 0.40 mmol) and DIPEA (140 L, 0.81 mmol) were sequentially added, and the mixture was stirred for 16 hours while slowly raising the temperature from 0° C. to room temperature. After completion of the reaction, EA (50 mL) and distilled water (50 mL) were added to extract the organic layer. The obtained organic layer was dried over anhydrous magnesium sulfate, filtered, and then concentrated under reduced pressure. The residue thus obtained was subjected to column chromatography to obtain Compound A-10c in the form of a white solid (114.7 mg, 63%).

$^1$H-NMR (400 MHz, $CDCl_3$) δ 8.27 (d, J=9.2 Hz, 2H), 7.48 (d, J=5.6 Hz, 1H), 7.44 (d, J=5.6 Hz, 1H), 7.39-7.36 (m, 3H), 6.97 (d, J=8 Hz, 1H), 5.64 (dd, J=10.4, 8 Hz, 1H), 5.24 (s, 2H), 5.51 (d, J=3.2 Hz, 1H), 5.19-5.14 (m, 2H), 4.29-4.13 (m, 3H), 2.21 (s, 3H), 2.08 (s, 3H), 2.05 (s, 3H), 2.04 (s, 3H).

Step 4: Preparation of Compound A-10d

Compound A-10c (64 mg, 0.094 mmol) was dissolved in DMF (3 mL) under a nitrogen atmosphere at 0° C., and then Compound PL-1 (25 mg, 0.113 mmol), HOBt (20 mg, 0.141 mmol), pyridine (500 μL) and DIPEA (41 μL, 0.235 mmol) were sequentially added, and the mixture was stirred at room temperature for 12 hours. After completion of the reaction, extraction was performed using EA (50 mL) and 1N-hydrochloric acid aqueous solution (50 mL). The obtained organic layer was dried over anhydrous magnesium sulfate, filtered, and then concentrated under reduced pressure. The resulting residue was subjected to column chromatography to obtain Compound A-10d (49 mg, 68.3%).

$^1$H-NMR (400 MHz, $CDCl_3$) δ 7.46-7.39 (m, 2H), 7.34 (m, 1H), 7.28-7.22 (m, 2H), 7.16-7.03 (m, 3H), 7.01-6.65 (m, 2H), 5.63 (m, 1H), 5.50 (m, 1H), 5.17-4.93 (m, 4H), 4.63-4.09 (m, 4H), 3.26-3.22 (m, 3H), 2.88-3.87 (m, 3H), 2.32 (m, 1H), 2.20 (s, 3H), 2.08-2.07 (m, 3H), 2.05-2.03 (m, 6H), 0.90-0.87 (m, 3H), 0.72-0.55 (m, 3H); MS m/z: 757 $[M+H]^+$.

Step 5: Preparation of Compound A-10

Compound A-10d (49 mg, 0.065 mmol) was dissolved in methanol (2 mL) at 0° C., and then lithium hydroxide monohydrate (13.6 mg, 0.324 mmol) dissolved in distilled water (400 μL) was slowly added dropwise, and the mixture was stirred at 0° C. for 10 minutes. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and freeze-dried to obtain Compound A-10 in the form of a white solid (28.5 mg, 74%).

$^1$H-NMR (400 MHz, DMSO-$d_6$) δ 7.72 (m, 0.5H), 7.68-7.65 (m, 1H), 7.58 (m, 0.5H), 7.31-7.21 (m, 3H), 7.15-7.02 (m, 4H), 5.31 (m, 1H), 5.10-4.91 (m, 3H), 4.68 (m, 1H), 4.55 (m, 1H), 4.24 (m, 1H), 3.73-3.44 (m, 3H), 3.14 (s, 3H), 2.72 (m, 3H), 2.16 (m, 1H), 0.83-0.77 (m, 3H), 0.63-0.43 (m, 3H); EI-MS m/z: 589 $[M+H]^+$.

Example I-10: Preparation of Compound A-11

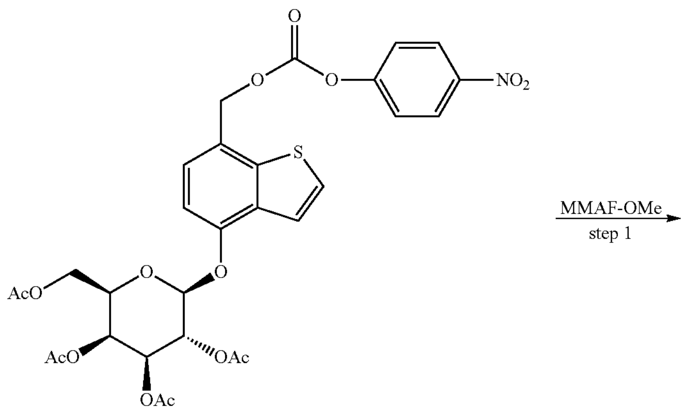

A-10c

MMAF-OMe
step 1

-continued
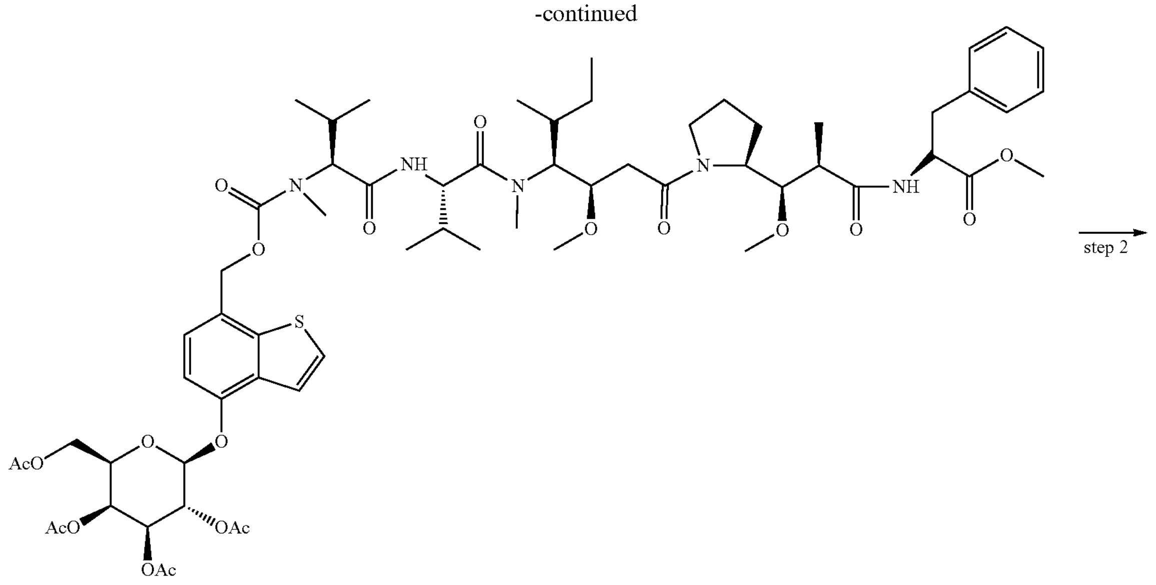
A-11a
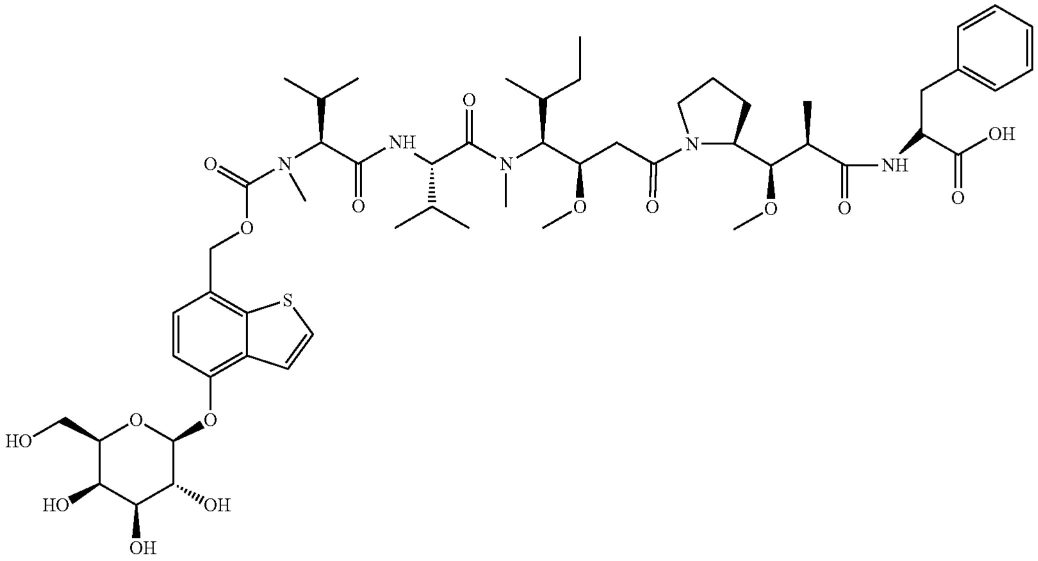
A-11
Compound A-11 was obtained in the form of a white solid in the same manner as in Example I-9, except that MMAF-OMe was used instead of Compound PL-1 in Step 4 of Example I-9 (10.4 mg, 65% n); EI-MS m/z: 1101 $[M+H]^+$.

Example I-11: Preparation of Compound A-12
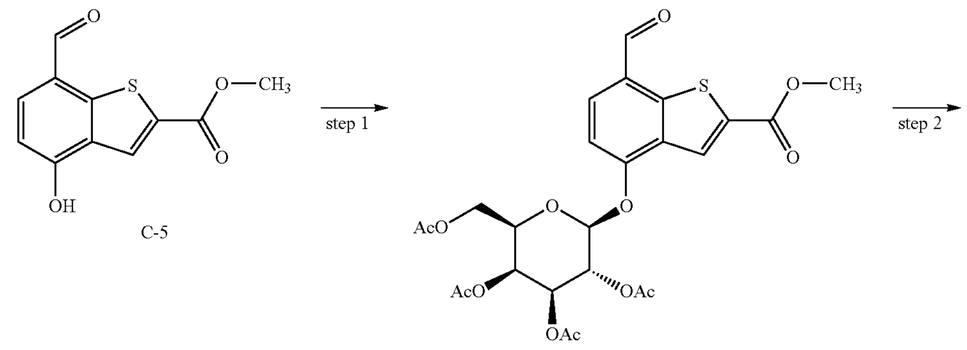
C-5 A-12a
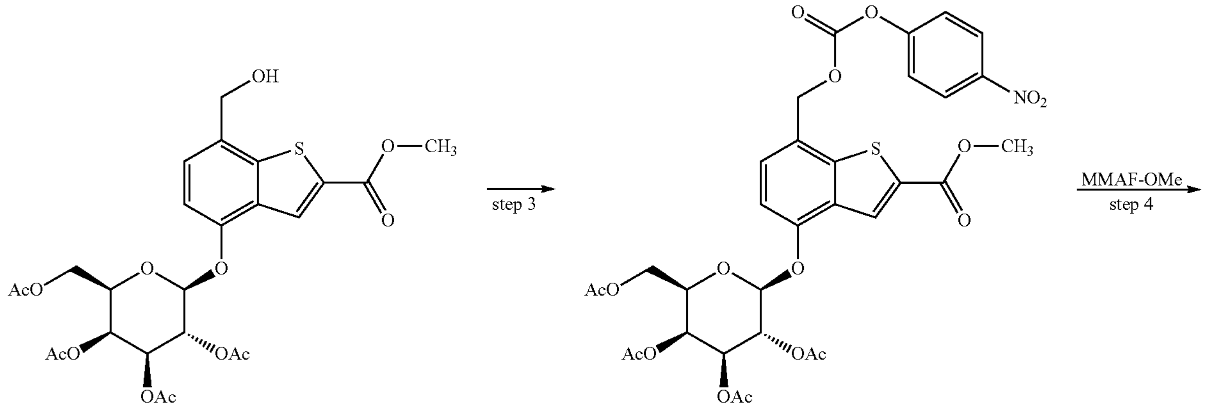
A-12b A-12c
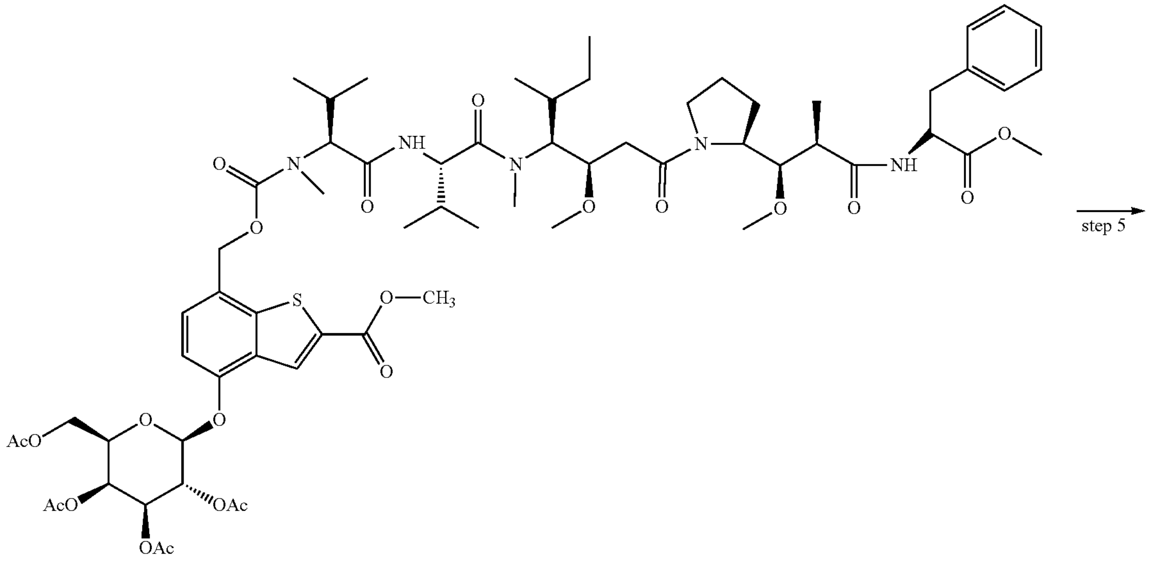
A-12d -continued
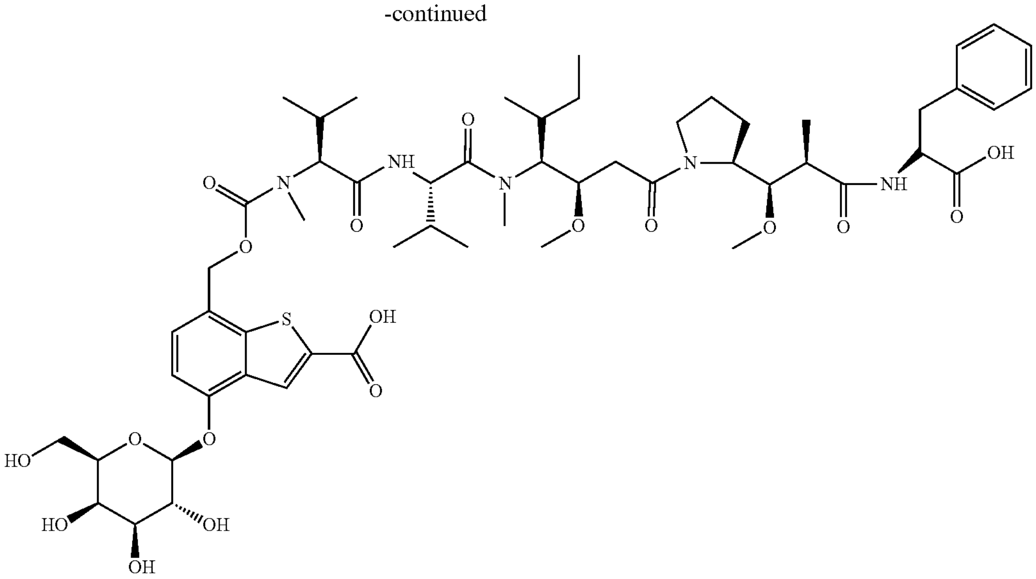
A-12
Compound A-12 was obtained in the form of a white solid using Core C-5 as a starting material in the same manner as in Example I-9, except that MMAF-OMe was used instead of Compound PL-1 in Step 4 of Example I-9 (11.7 mg, 64%); EI-MS m/z: 1145 $[M+H]^+$.
Example I-12: Preparation of Compound A-13
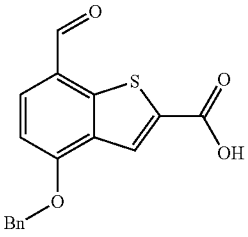
C-6
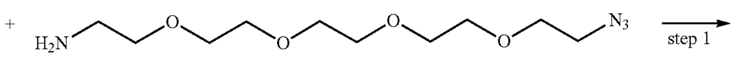
HCl salt.
P-4
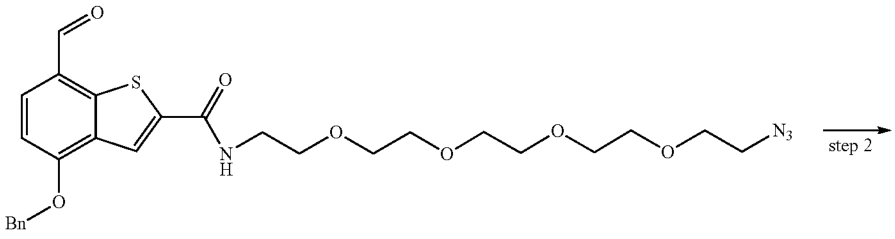
A-13a
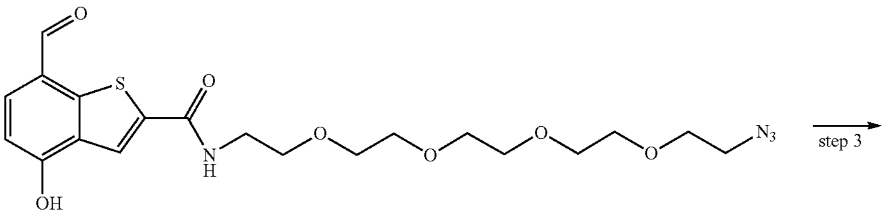
A-13b -continued
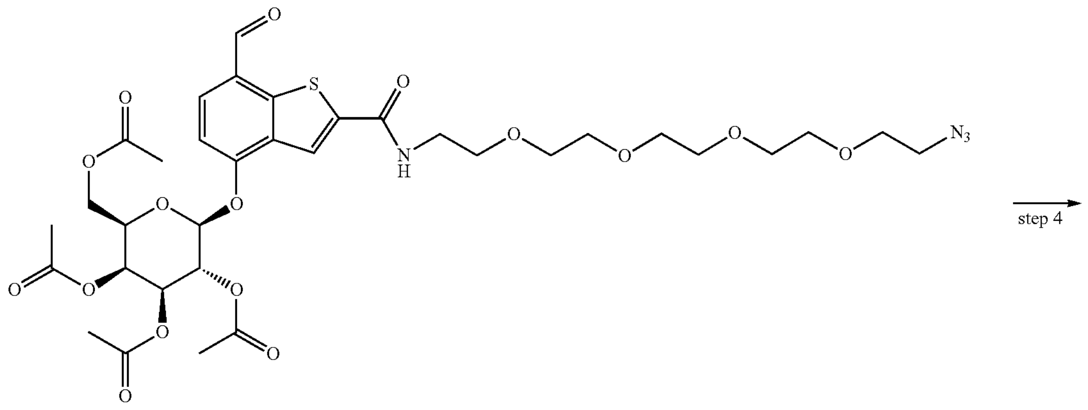
A-13c
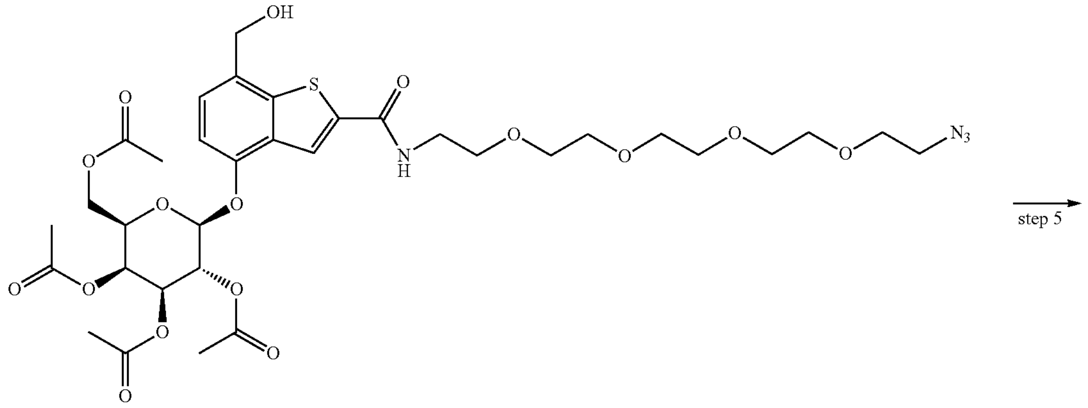
A-13d
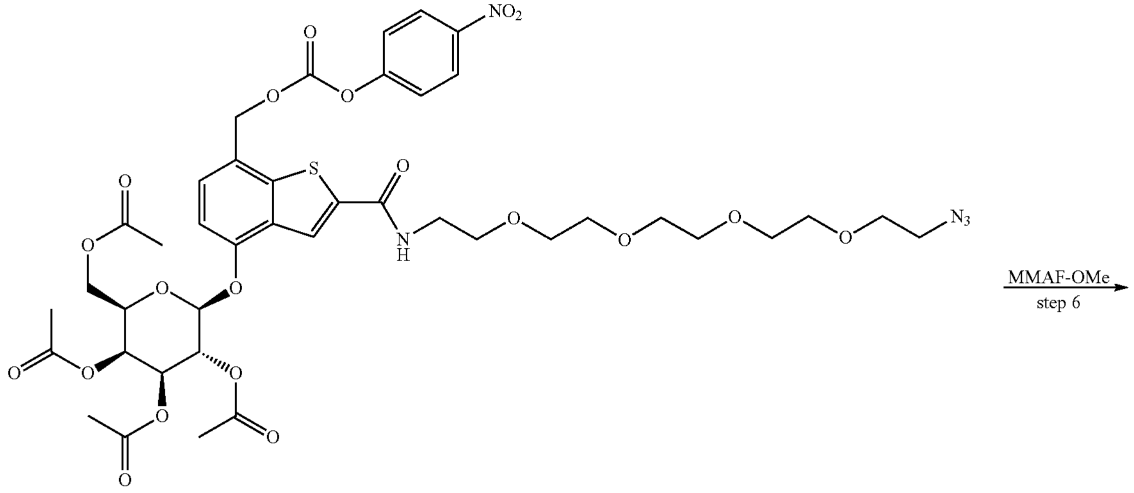
A-13e -continued

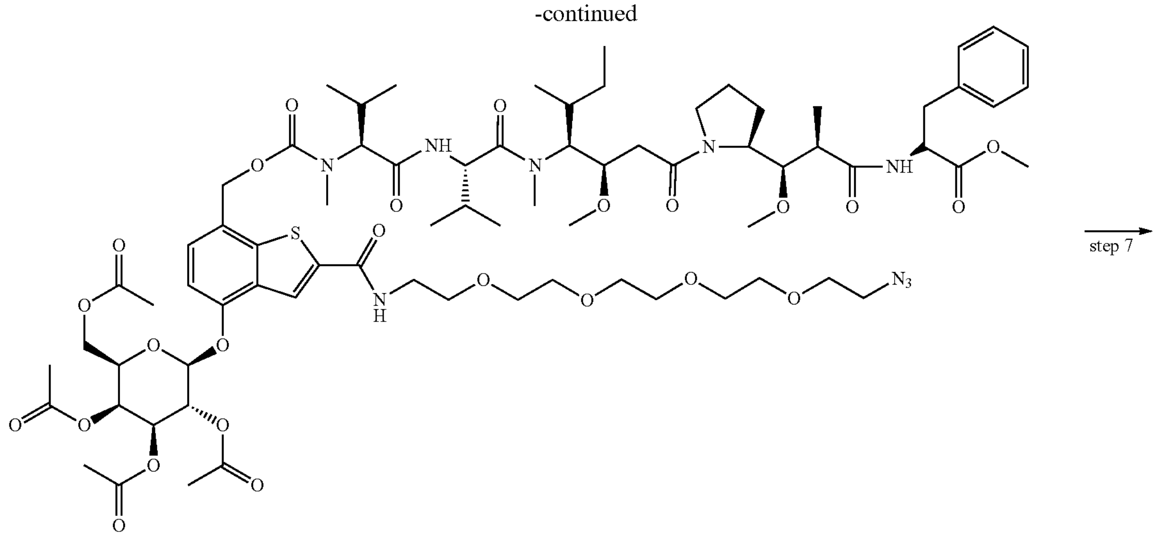

A-13f

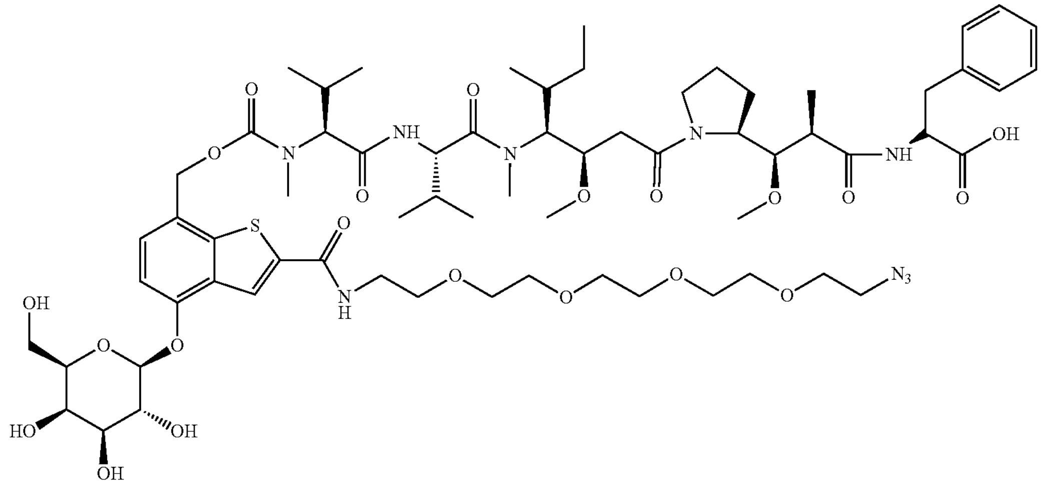

A-13

Step 1: Preparation of Compound A-13a

Core C-6 (192 mg, 0.61 mmol) was dissolved in DMF (5 mL) under a nitrogen atmosphere at 0° C., and then EDCI (177 mg, 0.92 mmol), HOBt (83.1 mg, 0.61 mmol), DMAP (7.5 mg, 0.06 mmol) and DIPEA (322 μL, 1.85 mmol) were sequentially added, and Linker P-4 (Azido-PEG4-Amine, TCI, CAS NO. 951671-92-4, 184 mg, 0.61 mmol) dissolved in DMF (3 mL) was added, and then the mixture was stirred at 0° C. for 3 hours. The mixture was stirred for an additional 16 hours while raising the temperature to room temperature. After completion of the reaction, the organic layer was extracted with EA (100 mL) and 2N-hydrochloric acid aqueous solution (100 mL). 2N-sodium hydroxide aqueous solution (5 mL) and distilled water (50 mL) were added to the obtained organic layer to extract the organic layer. The obtained organic layer was dried over anhydrous magnesium sulfate, filtered, and then concentrated under reduced pressure. The resulting residue was subjected to column chromatography to obtain Compound A-13a in the form of a brown oil (184.9 mg, 54%).

$^1$H-NMR (400 MHz, $CDCl_3$) δ 10.07 (s, 1H), 8.12 (s, 1H), 7.89 (d, J=8.4 Hz, 1H), 7.50-7.37 (m, 5H), 7.00 (d, J=8 Hz, 1H), 6.96 (m, 1H), 5.33 (s, 2H), 3.68-3.58 (m, 18H), 3.31 (t, J=5.2 Hz, 2H); EI-MS m/z. 557 $[M+H]^+$.

Step 2: Preparation of Compound A-13b

Compound A-13a (184.9 mg, 0.33 mmol) was dissolved in MC (10 mL) under a nitrogen atmosphere at −50° C., and then boron trichloride solution (1M-$BCl_3$ in MC, 2.99 mL, 2.99 mmol) was slowly added, and the mixture was stirred for 3.5 hours while slowly raising the temperature to −30° C. After completion of the reaction, distilled water (100 mL) was slowly added dropwise to terminate the reaction, and 2N-sodium hydroxide aqueous solution was added at 0° C. to neutralize it. MC (100 mL) was added to the mixture to extract the organic layer twice. The obtained organic layer was dried over anhydrous magnesium sulfate, filtered, and then concentrated under reduced pressure. The resulting residue was subjected to column chromatography to obtain Compound A-13b in the form of a light orange solid (75.9 mg, 49%).

$^1$H-NMR (400 MHz, $CDCl_3$) δ 10.02 (s, 1H), 8.41 (s, 1H), 7.84 (d, J=8 Hz, 1H), 7.32 (brs, 1H), 6.98 (d, J=8 Hz, 1H), 3.82-3.64 (m, 16H), 3.55 (t, J=5.2 Hz, 2H), 3.28 (t, J=5.2 Hz, 2H).

Steps 3 to 7: Preparation of Compound A-13

Compound A-13 was obtained in the form of a white solid in the same manner as in Example I-9, except that MMAF- OMe was used instead of Compound PL-1 in Step 4 of Example I-9 (25.7 mg, 66%); EI-MS m/z: 1389 $[M+H]^+$.
Example I-13: Preparation of Compound A-14
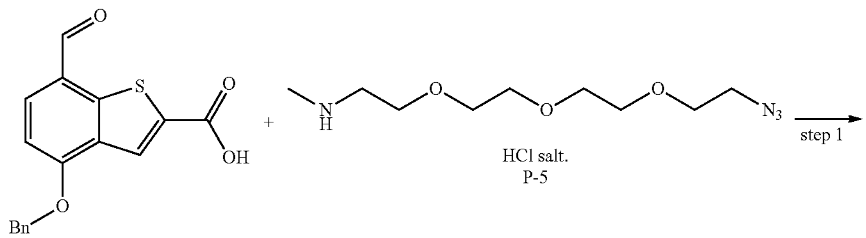
HCl salt.
P-5
C-6
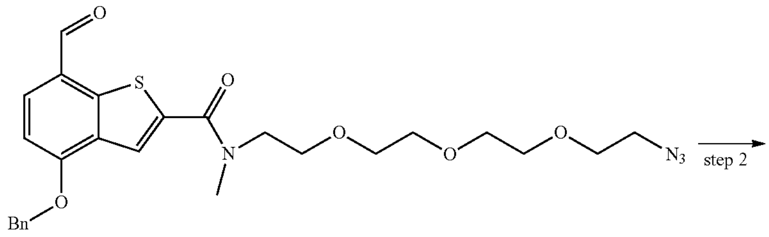
A-14a
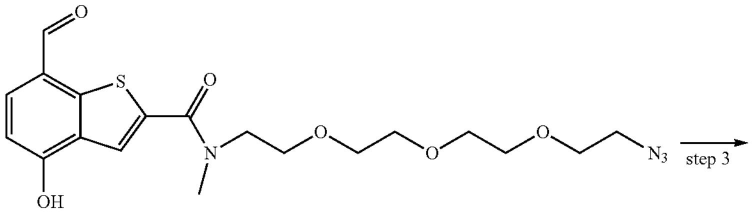
A-14b
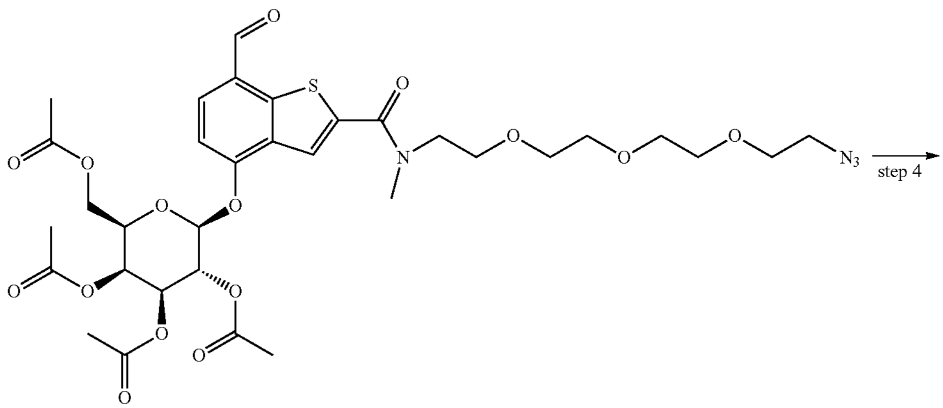
A-14c -continued
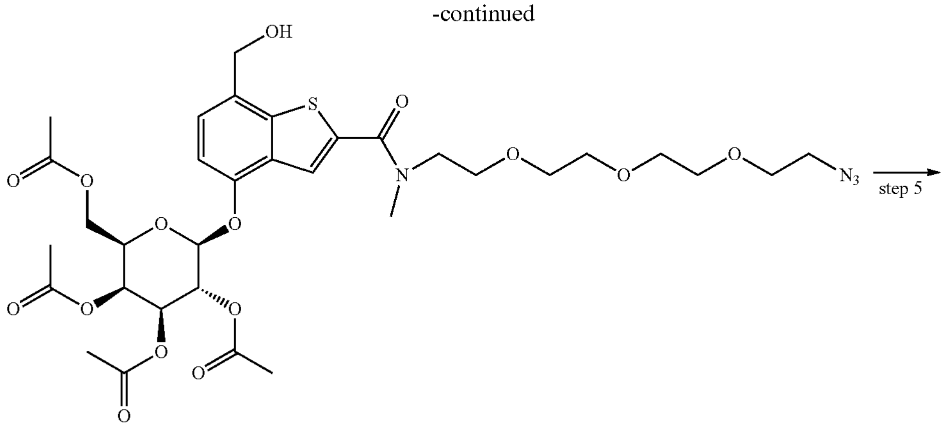
A-14d
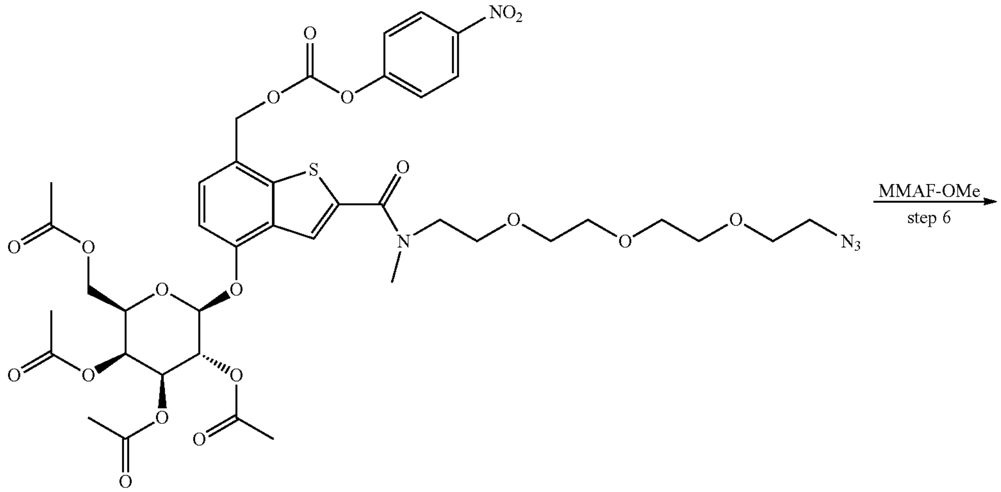
A-14e
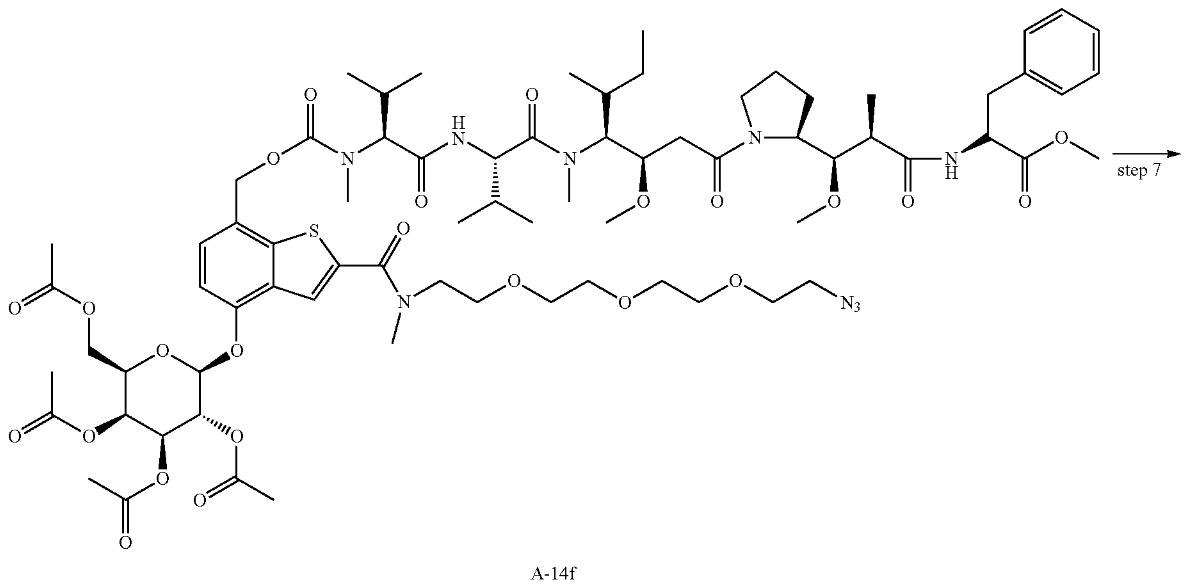
A-14f -continued
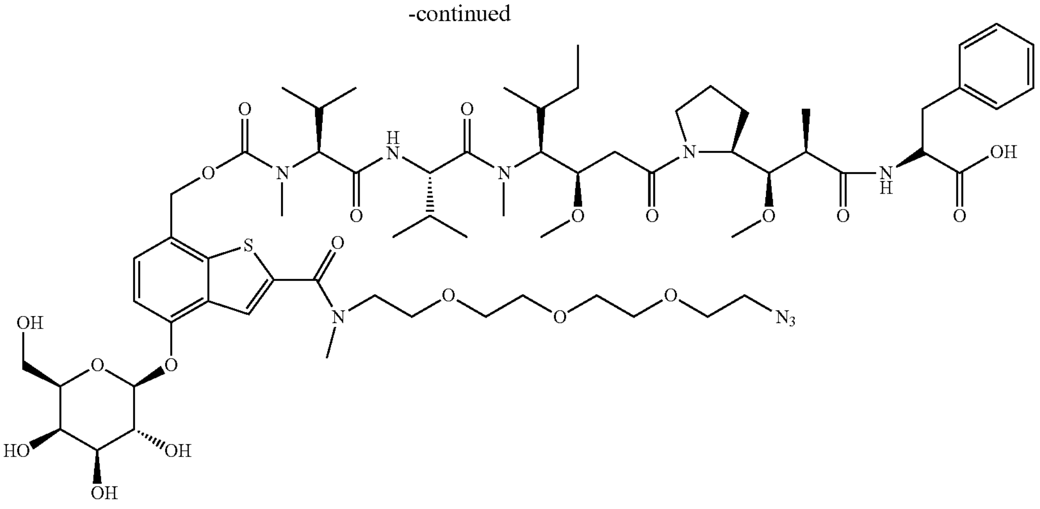
A-14
Compound A-14 was obtained in the form of a white solid in the same manner as in Example I-12, except that Linker P-5 was used instead of Linker P-4 in Step 1 of Example I-12 (22.4 mg, 67%); EI-MS m/z: 1358 [M+H]+.
Example I-14: Preparation of Compound A-15
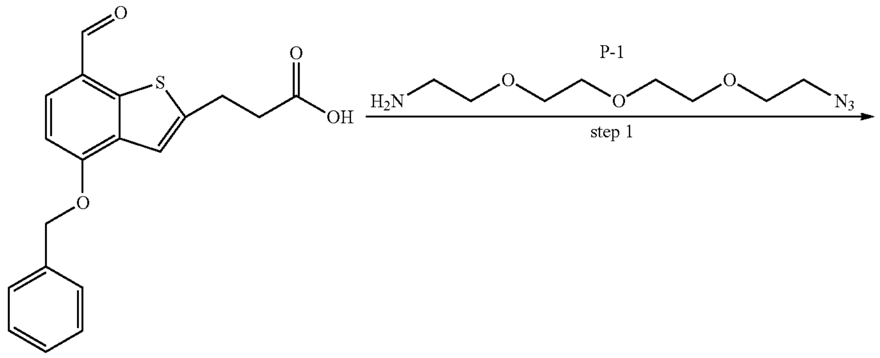
C-7
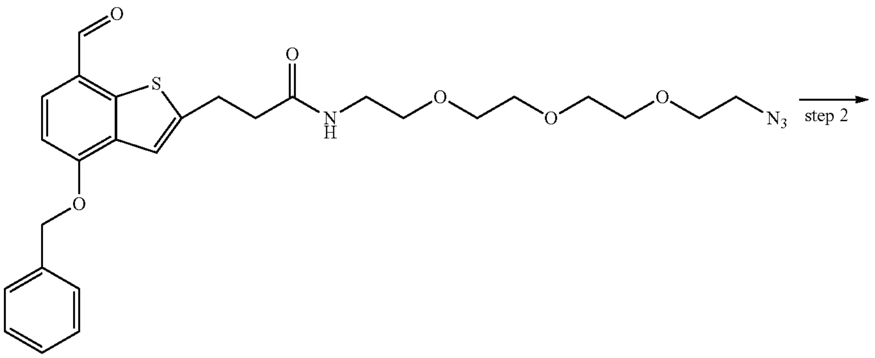
A-15a -continued
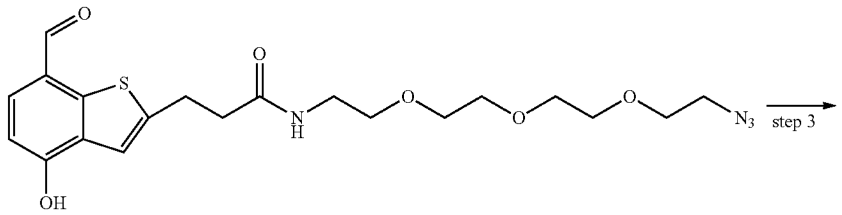
A-15b
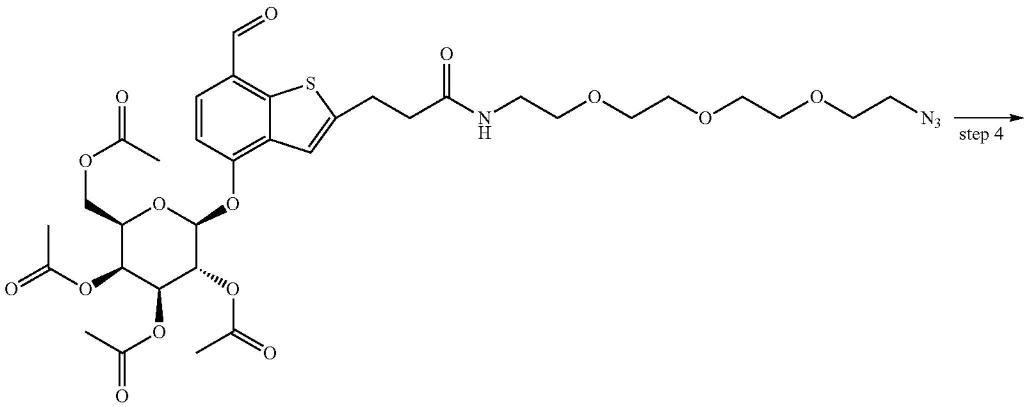
A-15c
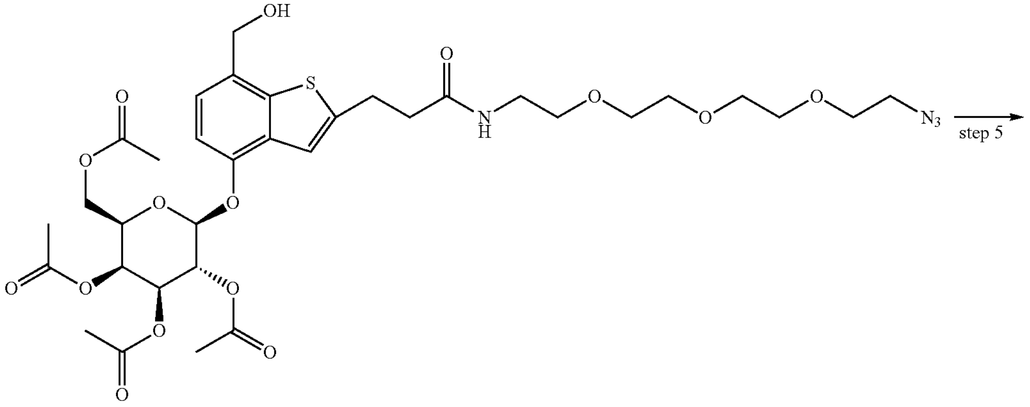
A-15d
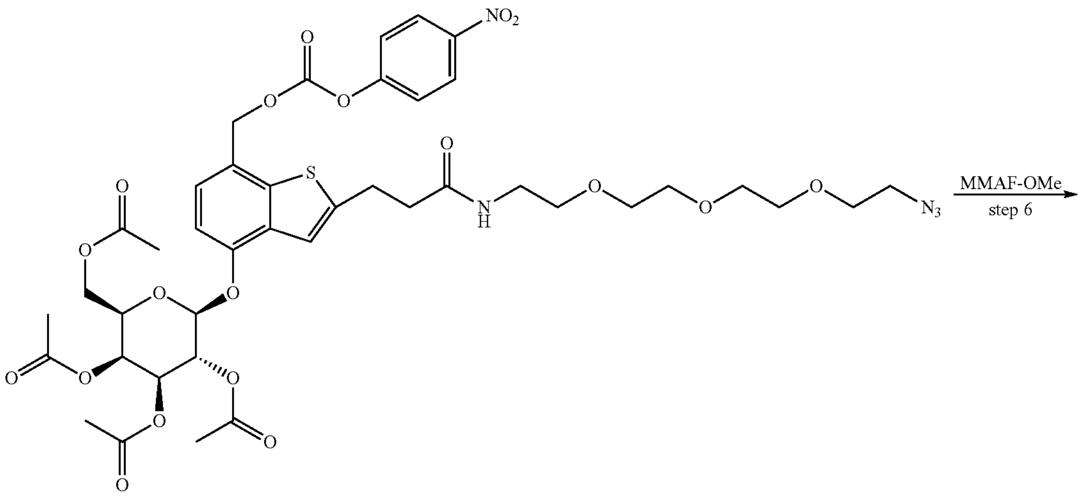
A-15e -continued

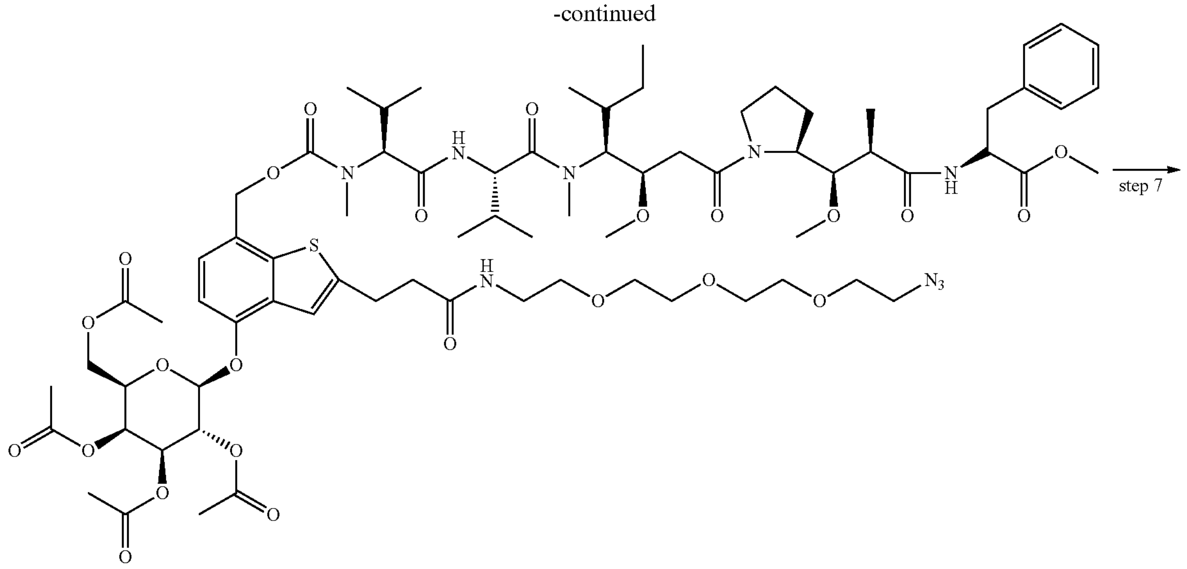

A-15f

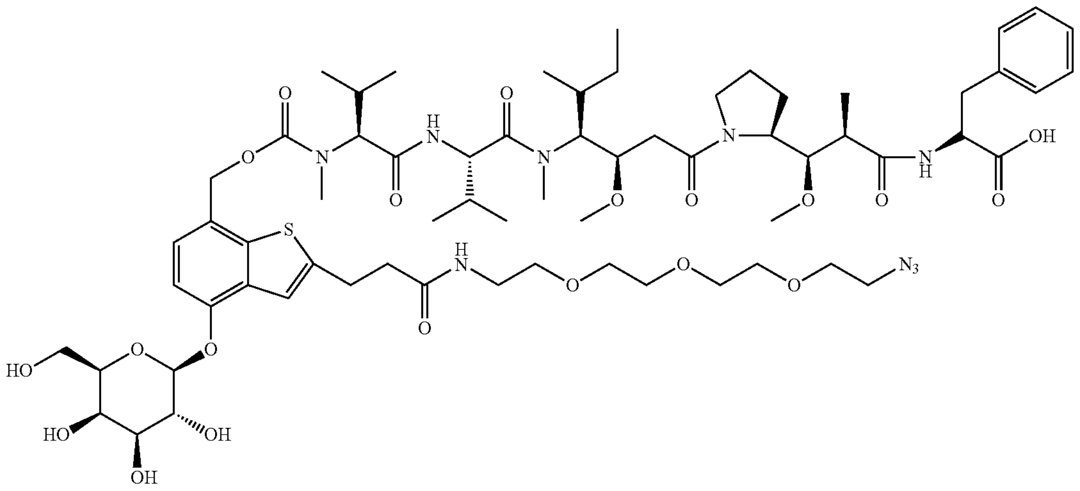

A-15

Step 1: Preparation of Compound A-15a

Core C-7 (278 mg, 0.81 mmol) and Linker P-i (208 mg, 0.81 mmol) were dissolved in DMF (5 mL) under a nitrogen atmosphere at 0° C., and then EDCI hydrochloride (235 mg, 1.22 mmol), DMAP (10 mg, 0.08 mmol) and DIPEA (430 μL, 2.45 mmol) were sequentially added, and the mixture was stirred for 16 hours while slowly raising the temperature to room temperature. After completion of the reaction, the organic layer was extracted twice with EA (250 mL) and 2N-hydrochloric acid aqueous solution (250 mL). A saturated aqueous sodium chloride solution (250 mL) was added to the obtained organic layer to extract the organic layer. The obtained organic layer was dried over anhydrous magnesium sulfate, filtered, and then concentrated under reduced pressure. The resulting residue was subjected to column chromatography to obtain Compound A-15a in the form of a yellow oil (207 mg, 47%).

$^1$H-NMR (400 MHz, $CDCl_3$) δ 10.03 (s, 1H), 7.74 (d, J=8 Hz, 1H), 7.49-7.34 (m, 6H), 6.94 (d, J=8 Hz, 1H), 6.18 (m, 1H), 5.30 (s, 2H), 3.65-3.60 (m, 6H), 3.57-3.55 (m, 2H), 3.52-3.48 (m, 4H), 3.44 (t, J=5.2 Hz, 2H), 3.35 (t, J 5.2 Hz, 2H), 3.31 (t, J=7.6 Hz, 2H), 2.64 (t, J=7.6 Hz, 2H); EI-MS m/z: 541 [M+H]$^+$.

Step 2: Preparation of Compound A-15b

Compound A-15a (207 mg, 0.38 mmol) was dissolved in MC (10 mL) under a nitrogen atmosphere at −55° C., and then boron trichloride solution (1M-$BCl_3$ in MC, 2.3 mL, 2.3 mmol) was slowly added, and the mixture was stirred for 2.5 hours while slowly raising the temperature to -40° C. After completion of the reaction, distilled water (100 mL) was slowly added dropwise to terminate the reaction, and 2N-sodium hydroxide aqueous solution was added at 0° C. to neutralize it. MC (100 mL) was added to the mixture to extract the organic layer twice. The obtained organic layer was dried over anhydrous magnesium sulfate, filtered, and then concentrated under reduced pressure. The resulting residue was subjected to column chromatography to obtain Compound A-15b in the form of a yellow sticky gum (97.5 mg, 56%).

$^1$H-NMR (400 MHz, $CDCl_3$) δ 9.98 (s, 1H), 7.66 (d, J=8 Hz, 1H), 7.44 (s, 1H), 6.89 (d, J=8 Hz, 1H), 6.36 (brs, 1H), 3.66 (m, 4H), 3.64-3.58 (m, 4H), 3.55-3.52 (m, 2H), 3.49-3.43 (m, 4H), 3.35-3.30 (m, 4H), 2.68 (t, J=7.2 Hz, 2H); EI-MS m/z: 451 [M+H]$^+$.

Step 3: Preparation of Compound A-15c

Compound A-15b (97.5 mg, 0.21 mmol) was dissolved in MC (7 mL) under a nitrogen atmosphere at 0° C., and then acetobromo-alpha-D-galactose (142 mg, 0.34 mmol) and benzyltributylammonium chloride (67.5 mg, 0.21 mmol) were added. 5N-sodium hydroxide aqueous solution (0.13 mL, 0.65 mmol) was slowly added to this reaction solution, and the mixture was stirred for 20 hours while slowly raising the temperature to room temperature. After completion of the reaction, MC (150 mL) and distilled water (150 mL) were added to extract the organic layer three times. The obtained organic layer was dried over anhydrous magnesium sulfate, filtered, and then concentrated under reduced pressure. The resulting residue was subjected to column chromatography to obtain Compound A-15c (42.3 mg, 25%).

$^1$H-NMR (400 MHz, $CDCl_3$) δ 10.08 (s, 1H), 7.75 (d, J=8.4 Hz, 1H), 7.18 (s, 1H), 6.05 (d, J=8.4 Hz, 1H), 6.14 (m, 1H), 5.59 (dd, J=10.4, 8 Hz, 1H), 5.52 (d, J=3.2 Hz, 1H), 5.27 (d, J=8 Hz, 1H), 5.18 (dd, J=10.4, 3.2 Hz, 1H), 4.27 (m, 1H), 4.20-4.15 (m, 2H), 3.67-3.65 (m, 6H), 3.61-3.59 (m, 2H), 3.57-3.52 (m, 4H), 3.48-3.45 (m, 2H), 3.37 (t, J=5.2 Hz, 2H), 3.16 (t, J=7.6 Hz, 2H), 2.63 (t, J=7.6 Hz, 2H), 2.21 (s, 3H), 2.09 (s, 3H), 2.06 (s, 3H), 2.04 (s, 3H).

Step 4: Preparation of Compound A-15d

Compound A-15c (42.3 mg, 0.054 mmol) was dissolved in THE (3 mL) under a nitrogen atmosphere at 0° C., and then sodium borohydride (5.1 mg, 0.135 mmol) was added, and the mixture was stirred for 2.5 hours while slowly raising the temperature from 0° C. to room temperature. After completion of the reaction, distilled water (50 mL) was added to terminate the reaction, and EA (50 mL) was added to extract the organic layer twice. The obtained organic layer was dried over anhydrous magnesium sulfate, filtered, and then concentrated under reduced pressure. The resulting residue was subjected to column chromatography to obtain Compound A-15d in the form of a white solid (30.6 mg, 72%); EI-MS m/z: 783 $[M+H]^+$.

Step 5: Preparation of Compound A-15e

Compound A-15d (30.6 mg, 0.039 mmol) was dissolved in MC (2 mL) under a nitrogen atmosphere at 0° C., and then 4-nitrophenyl chloroformate (11.8 mg, 0.058 mmol) and DIPEA (17 L, 0.098 mmol) were sequentially added, and the mixture was stirred for 16 hours while raising the temperature from 0° C. to room temperature. After completion of the reaction, MC (50 mL) and distilled water (50 mL) were added to extract the organic layer twice. The obtained organic layer was dried over anhydrous magnesium sulfate, filtered, and then concentrated under reduced pressure. The residue thus obtained was subjected to column chromatography to obtain Compound A-15e in the form of a white solid (22.2 mg, 60%); EI-MS m/z: 948 $[M+H]^+$.

Step 6: Preparation of Compound A-15f

Compound A-15e (22.2 mg, 0.023 mmol) was dissolved in DMF (0.5 mL) under a nitrogen atmosphere at 0° C., and then MMAF-OMe (17.5 mg, 0.023 mmol), HOBt (4.7 mg, 0.035 mmol), pyridine (500 μL), DIPEA (10.2 μL, 0.058 mmol) were sequentially added, and the mixture was stirred at room temperature for 16 hours. After completion of the reaction, the organic layer was extracted twice with EA (50 mL) and 2N-hydrochloric acid aqueous solution (50 mL). The obtained organic layer was dried over anhydrous magnesium sulfate, filtered, and then concentrated under reduced pressure. The resulting residue was subjected to column chromatography to obtain Compound A-15f in the form of a colorless solid (23.6 mg, 65%); EI-MS m/z: 1555 $[M+H]^+$.

Step 7: Preparation of Compound A-15

Compound A-15f (23.6 mg, 0.015 mmol) was dissolved in methanol (0.6 mL) and THE (0.3 mL) at 0° C., and then lithium hydroxide monohydrate (6.3 mg, 0.152 mmol) dissolved in distilled water (0.2 mL) was slowly added dropwise, and the mixture was stirred for 2.5 hours while slowly raising the temperature from 0° C. to room temperature. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and then freeze-dried to obtain Compound A-15 in the form of a white solid (10.1 mg, 48%); EI-MS m/z: 1373 $[M+H]^+$.

Example I-15: Preparation of Compound A-16

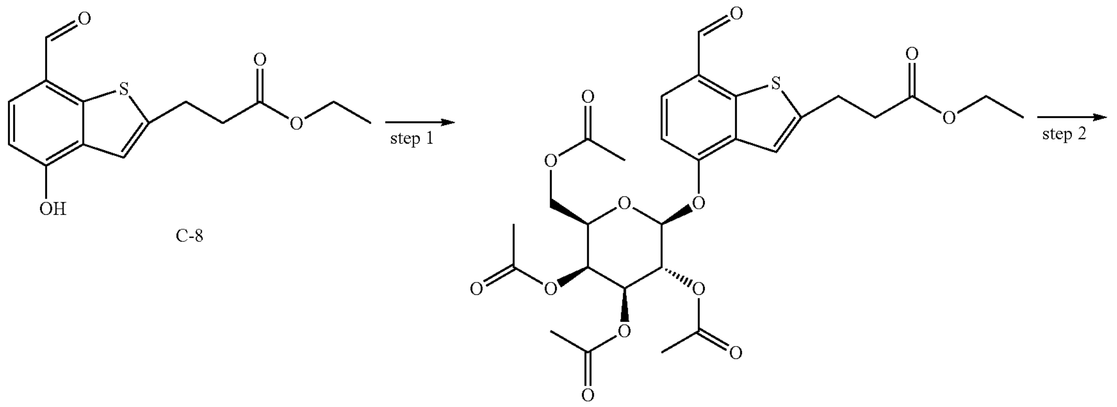

C-8

A-16a

-continued
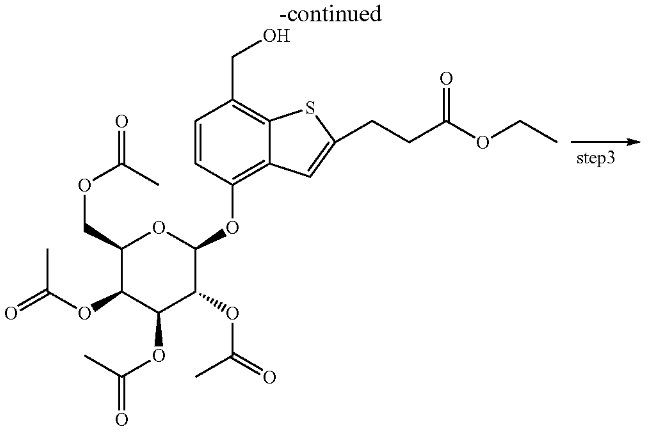
A-16b
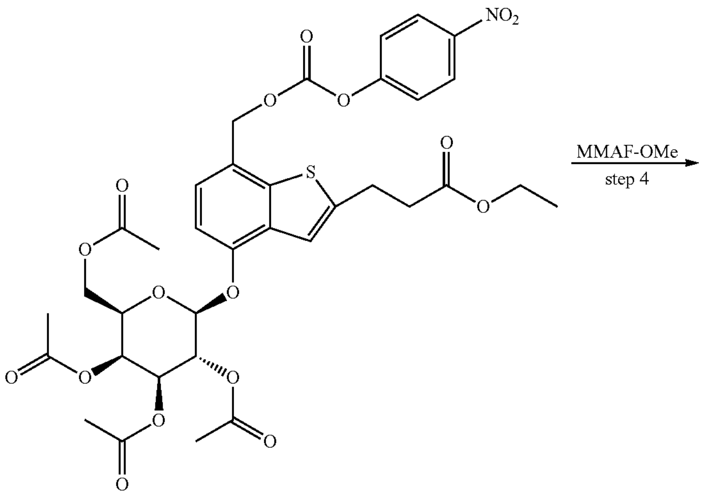
A-16c
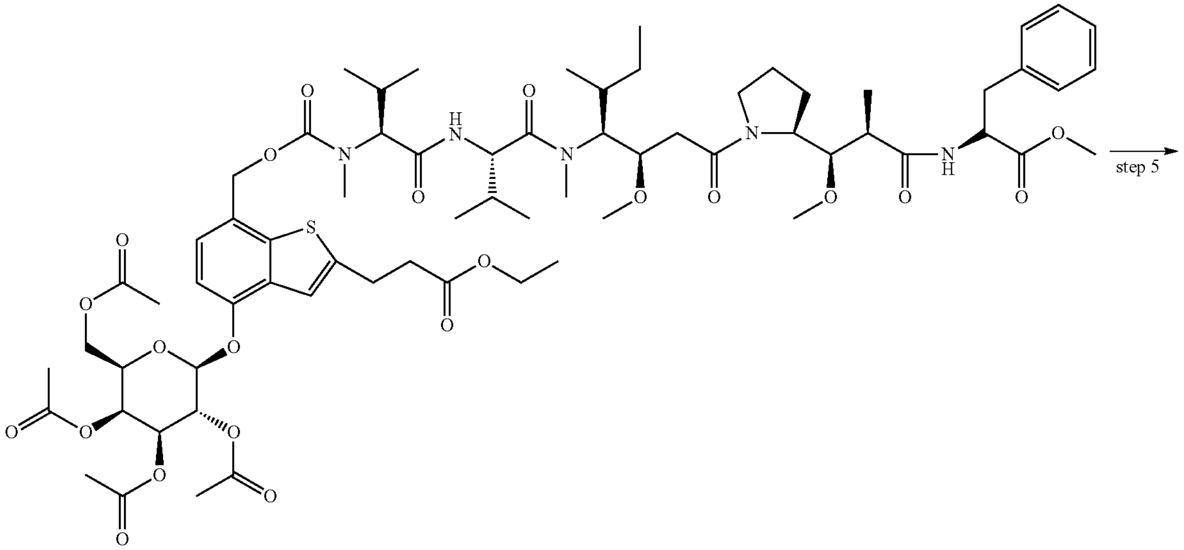
A-16d

-continued
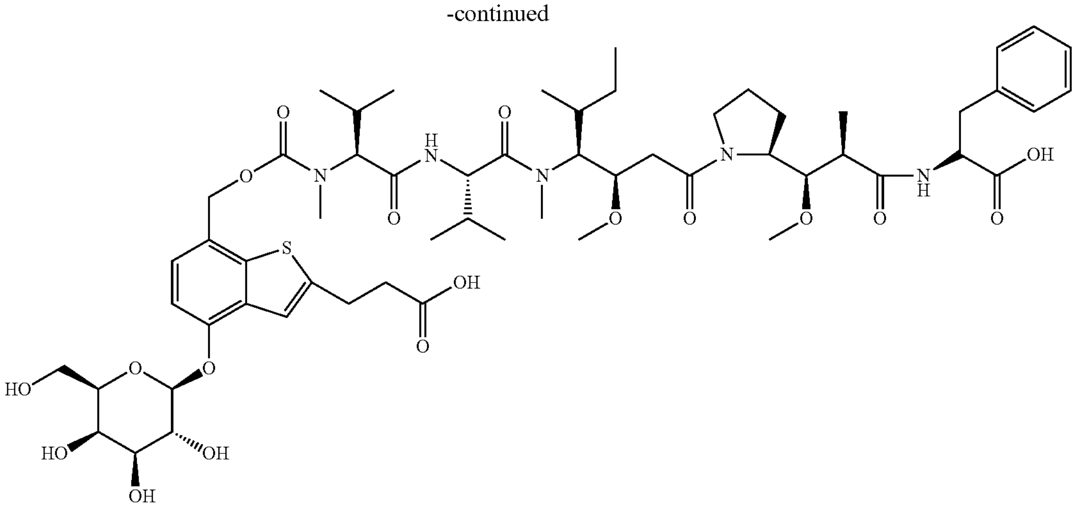
A-16
Compound A-16 was obtained in the form of a white solid using Core C-8 as a starting material in the same manner as in Example I-9, except that MMAF-OMe was used instead of Compound PL-1 in Step 4 of Example I-9 (7.7 mg, 60%); EI-MS m/z: 1172 $[M+H]^+$.
Example I-16: Preparation of Compound A-17
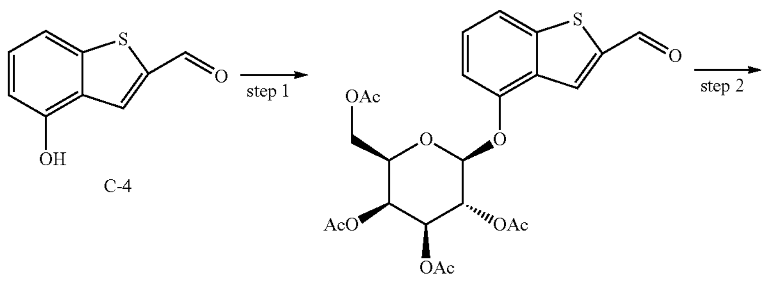
C-4
A-17a
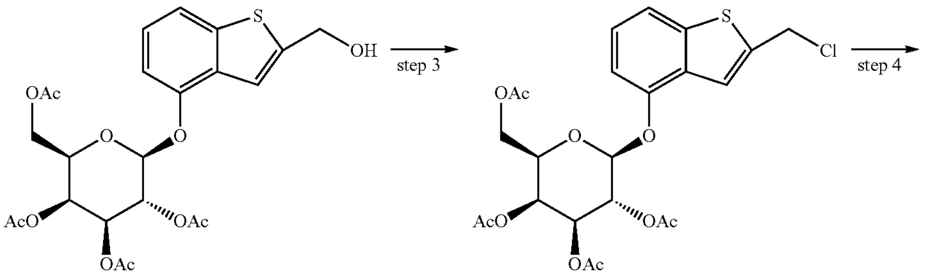
A-17b
A-17c -continued
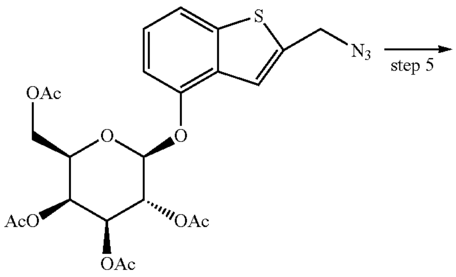
A-17d
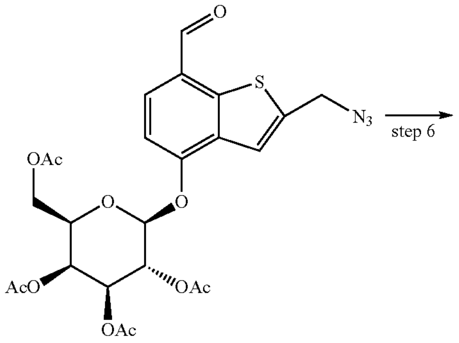
A-17e
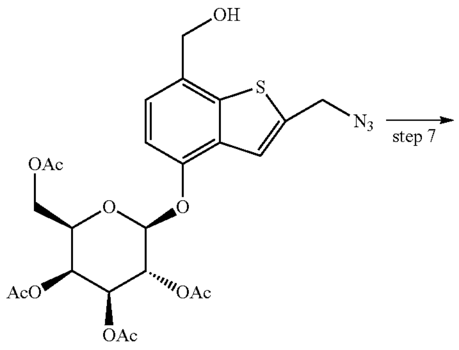
A-17f
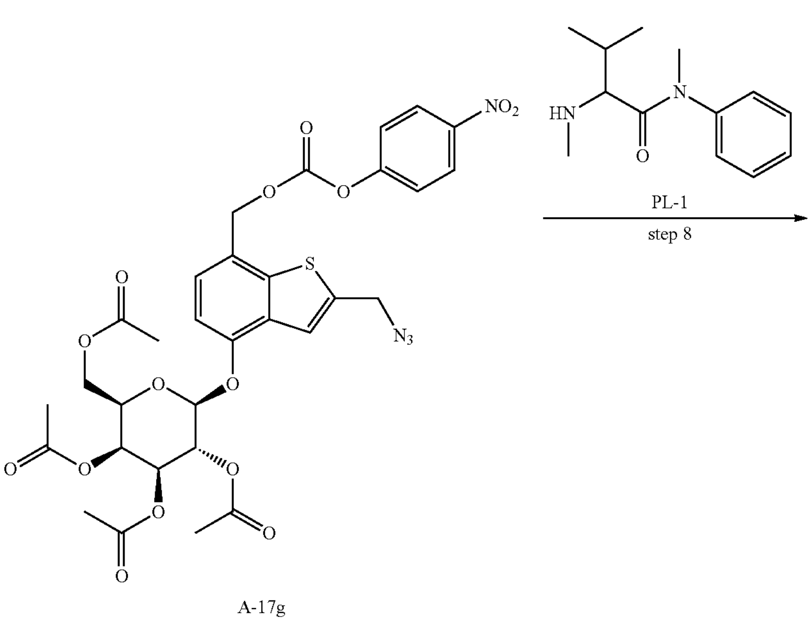
A-17g -continued

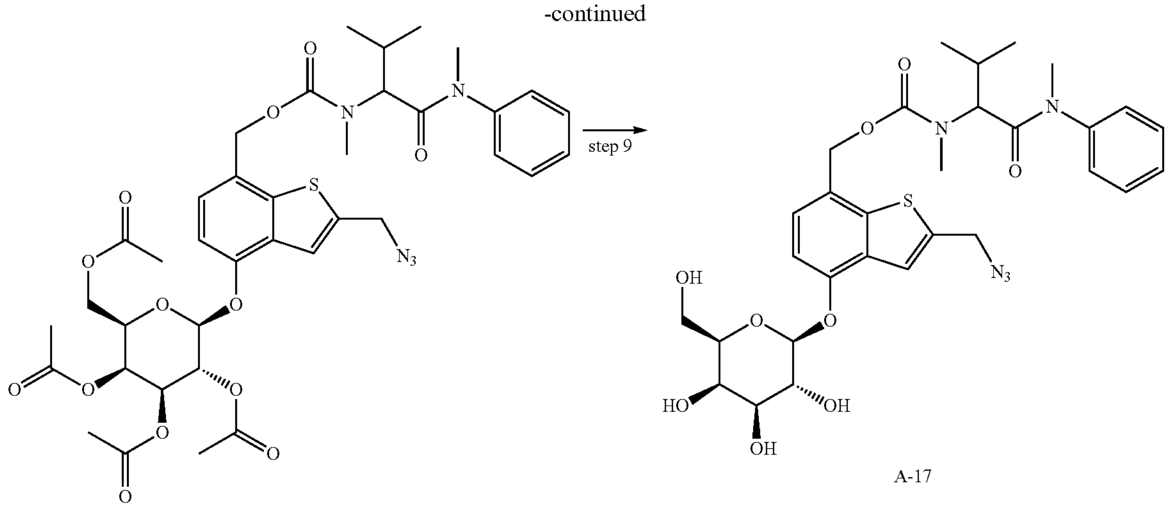

A-17h

A-17

Step 1: Preparation of Compound A-17a

Core C-4 (174 mg, 0.976 mmol) was dissolved in MC (30 mL) under a nitrogen atmosphere at room temperature, and then acetobromo-alpha-D-galactose (440 mg, 1.07 mmol) and benzyltributylammonium chloride (Sigma-Aldrich, CAS NO. 23616-79-7, 304 mg, 0.976 mmol) were sequentially added. 5N-sodium hydroxide aqueous solution (586 μL, 2.93 mmol) was added to this reaction solution, and the mixture was stirred for 5 hours. After completion of the reaction, MC (100 mL) and distilled water (100 mL) were added to extract the organic layer. The obtained organic layer was dried over anhydrous magnesium sulfate, filtered, and then concentrated under reduced pressure. The residue was subjected to column chromatography to obtain Compound A-17a (250 mg, 50.4%).

$^1$H-NMR (400 MHz, $CDCl_3$) δ 10.09 (s, 1H), 8.09 (s, 1H), 7.59 (d, J=8 Hz, 1H), 7.44 (t, J=8 Hz, 1H), 6.95 (d, J=8 Hz, 1H), 5.64 (dd, J=10.4, 8 Hz, 1H), 5.50 (d, J=3.2 Hz, 1H), 5.23 (d, J=8 Hz, 1H), 5.18 (dd, J=10.4, 8 Hz, 1H), 4.27 (m, 1H), 4.20-4.11 (m, 2H), 2.21 (s, 3H), 2.06 (s, 6H), 2.05 (s, 3H).

Step 2: Preparation of Compound A-17b

Compound A-17a (250 mg, 0.49 mmol) was dissolved in THE (10 mL) under a nitrogen atmosphere at 0° C., and then sodium borohydride (46.5 mg, 1.225 mmol) was added, and the mixture was stirred for 1 hour. After completion of the reaction, distilled water (50 mL) was added to terminate the reaction, and EA (50 mL) was added to extract the organic layer. The obtained organic layer was dried over anhydrous magnesium sulfate, filtered, and then concentrated under reduced pressure. The resulting residue was subjected to column chromatography to obtain Compound A-17b (230 mg, 92%).

$^1$H-NMR (400 MHz, $CDCl_3$) δ 7.53 (d, J=8 Hz, 1H), 7.28-7.22 (m, 2H), 6.93 (d, J=8 Hz, 1H), 5.60 (dd, J=10.4, 8 Hz, 1H), 5.48 (d, J=2.4 Hz, 1H), 5.16-5.12 (m, 2H), 4.91 (d, =5.2 Hz, 2H), 4.31 (dd, J=11.2, 7.2 Hz, 1H), 4.16-4.10 (m, 2H), 2.21 (s, 3H), 2.07 (s, 3H), 2.04 (s, 3H), 2.03 (s, 3H).

Step 3: Preparation of Compound A-17c

Compound A-17b (300 mg, 0.58 mmol) was dissolved in concentrated hydrochloric acid (8 mL) under a nitrogen atmosphere at 0° C., and then the mixture was stirred for 1 hour at 0° C. After completion of the reaction, EA (50 mL) and distilled water (50 mL) were added to extract the organic layer, and the obtained organic layer was dried over anhydrous magnesium sulfate, filtered, and then concentrated under reduced pressure to obtain Compound A-17c in the form of a white solid (300 mg, 96.7%); MS m/z: 529 $[M+H]^+$.

Step 4: Preparation of Compound A-17d

Compound A-17c (300 mg, 0.56 mmol) was dissolved in DMF (15 mL) under a nitrogen atmosphere at room temperature, and then sodium azide (55 mg, 0.84 mmol) was added, and the mixture was stirred at 60° C. for 2 hours. After completion of the reaction, EA (100 mL) and distilled water (200 mL) were added to extract the organic layer, and the obtained organic layer was dried over anhydrous magnesium sulfate, filtered, and then concentrated under reduced pressure. The resulting residue was subjected to column chromatography to obtain Compound A-17d (230 mg, 75.6%).

$^1$H-NMR (400 MHz, $CDCl_3$) δ 7.52 (d, J=8 Hz, 1H), 7.32 (s, 1H), 7.28 (t, J=8 Hz, 1H), 6.94 (d, J=8 Hz, 1H), 5.61 (dd, J=10.4, 8 Hz, 1H), 5.50 (d, J=2.4 Hz, 1H), 5.17-5.14 (m, 2H), 4.60 (d, J=14.4 Hz, 1H), 4.52 (d, J=14.4 Hz, 1H), 4.26 (dd, J=11.2, 6.8 Hz, 1H), 4.20-4.11 (m, 2H), 2.20 (s, 3H), 2.07 (s, 3H), 2.05 (s, 3H), 2.04 (s, 3H); MS m/z: 558 $[M+Na]^+$.

Step 5: Preparation of Compound A-17e

A-17d (230 mg, 0.42 mmol) was dissolved in MC (15 mL) under a nitrogen atmosphere at −78° C., and then dichloromethyl methyl ether (116 μL, 1.26 mmol) and titanium tetrachloride solution (1M-$TiCl_4$ in MC, 1.28 mL, 1.26 mmol) were sequentially and slowly added, and the mixture was stirred for 1 hour while maintaining the temperature. After completion of the reaction, cooled distilled water (100 mL) was slowly added dropwise to terminate the reaction, and EA (100 mL) was added to extract the organic layer. The obtained organic layer was dried over anhydrous magnesium sulfate, filtered, and then concentrated under reduced pressure. The resulting residue was subjected to column chromatography to obtain Compound A-17e in the form of a white solid (130 mg, 53.7%).

$^1$H-NMR (400 MHz, $CDCl_3$) δ 10.11 (s, 1H), 7.84 (d, J=8 Hz, 1H), 7.40 (s, 1H), 7.08 (d, J=8 Hz, 1H), 5.66 (dd, J=10.4, 8 Hz, 1H), 5.52 (d, J=3.2 Hz, 1H), 5.29 (d, J=8 Hz, 1H), 5.19 (dd, J=10.4, 3.2 Hz, 1H), 4.65 (d, J=14.4 Hz, 1H), 4.52 (d,

J=14.4 Hz, 1H), 4.31-4.17 (m, 3H), 2.21 (s, 3H), 2.09 (s, 3H), 2.05 (s, 6H); MS m/z: 586 $[M+Na]^+$.

Step 6: Preparation of Compound A-17f

Compound A-17e (130 mg, 0.23 mmol) was dissolved in THE (10 mL) under a nitrogen atmosphere at 0° C., and then sodium borohydride (22 mg, 0.575 mmol) was added, and the mixture was stirred for 1 hour. After completion of the reaction, distilled water (100 mL) was added to terminate the reaction, and EA (100 mL) was added to extract the organic layer. The obtained organic layer was dried over anhydrous magnesium sulfate, filtered, and then concentrated under reduced pressure. The resulting residue was subjected to column chromatography to obtain Compound A-17f (120 mg, 92.3%).

$^1$H-NMR (400 MHz, $CDCl_3$) δ 7.36 (s, 1H), 7.28 (d, J=8 Hz, 1H), 6.94 (d, J=8 Hz, 1H), 5.61 (dd, J=10.4, 8 Hz, 1H), 5.49 (d, J=2.8 Hz, 1H), 5.17-5.14 (m, 2H), 4.89 (d, J=5.6 Hz, 2H), 4.61 (d, J=14.4 Hz, 1H), 4.54 (d, J=14.4 Hz, 1H), 4.26 (dd, J=11.2, 6.8 Hz, 1H), 4.20-4.11 (m, 2H), 2.20 (s, 3H), 2.07 (s, 3H), 2.05 (s, 3H), 2.04 (s, 3H), 1.79 (t, J=5.6 Hz, 1H).

Step 7: Preparation of Compound A-17g

Compound A-17f (120 mg, 0.21 mmol) was dissolved in MC (3 mL) under a nitrogen atmosphere at 0° C., and then 4-nitrophenyl chloroformate (85 mg, 0.42 mmol), pyridine (51 μL, 0.63 mmol) and DIPEA (55 μL, 0.32 mmol) were sequentially added, and the mixture was stirred at 0° C. for 30 minutes and at room temperature for 2 hours. After completion of the reaction, the reaction solution was diluted with MC (50 mL), and 2N-hydrochloric acid aqueous solution (50 mL) was added to extract the organic layer twice. The obtained organic layer was dried over anhydrous magnesium sulfate, filtered, and then concentrated under reduced pressure. The residue thus obtained was subjected to column chromatography to obtain Compound A-17g (116.3 mg, 75%).

$^1$H-NMR (400 MHz, $CDCl_3$) δ 8.27 (d, J=9.2 Hz, 2H), 7.39-7.37 (m, 4H), 6.96 (d, J=8 Hz, 1H), 5.62 (dd, J=10.4, 8 Hz, 1H), 5.50 (d, J=3.2 Hz, 1H), 5.48 (s, 2H), 5.19-5.15 (m, 2H), 4.63 (d, J=14.4 Hz, 1H), 4.57 (d, J=14.4 Hz, 1H), 4.26 (m, 1H), 4.20-4.11 (m, 2H), 2.21 (s, 3H), 2.07 (s, 3H), 2.05 (s, 3H), 2.04 (s, 3H).

Step 8: Preparation of Compound A-17h

Compound A-17g (18.7 mg, 0.025 mmol) and Compound PL-1 (6.7 mg, 0.031 mmol) were dissolved in DMF (500 μL) under a nitrogen atmosphere at 0° C., and then HOBt (5.2 mg, 0.038 mmol), pyridine (500 μL) and DIPEA (11.1 μL, 0.064 mmol) were sequentially added, and the mixture was stirred at room temperature for 16 hours. After completion of the reaction, the organic layer was extracted twice with EA (50 mL) and 2N-hydrochloric acid aqueous solution (50 mL). The obtained organic layer was dried over anhydrous magnesium sulfate, filtered, and then concentrated under reduced pressure. The resulting residue was subjected to column chromatography to obtain Compound A-17h in the form of a white solid (17.9 mg, 86%).

$^1$H-NMR (400 MHz, $CDCl_3$) δ 7.37-7.32 (m, 1H), 7.28-7.22 (m, 2H), 7.19-6.85 (m, 5H), 5.61 (m, 1H), 5.50 (m, 1H), 5.18-5.09 (m, 4H), 4.64-4.48 (m, 3H), 4.39-4.13 (m, 3H), 3.25-3.23 (m, 3H), 2.90-2.88 (m, 3H), 2.32 (m, 1H), 2.20 (s, 3H), 2.07-2.04 (m, 9H), 0.98-0.83 (m, 3H), 0.72-0.55 (m, 3H); EI-MS m/z: 812 $[M+H]^+$.

Step 9: Preparation of Compound A-17

Compound A-17h (17.9 mg, 0.022 mmol) was dissolved in methanol (1 mL) and THE (0.5 mL) under a nitrogen atmosphere at 0° C., and then potassium carbonate (21.3 mg, 0.154 mmol) was added, and the mixture was stirred at 0° C. for 40 minutes. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and freeze-dried to obtain Compound A-17 in the form of a white solid (7.5 mg, 53%); EI-MS m/z: 644 $[M+H]^+$.

Example I-17: Preparation of Compound A-18

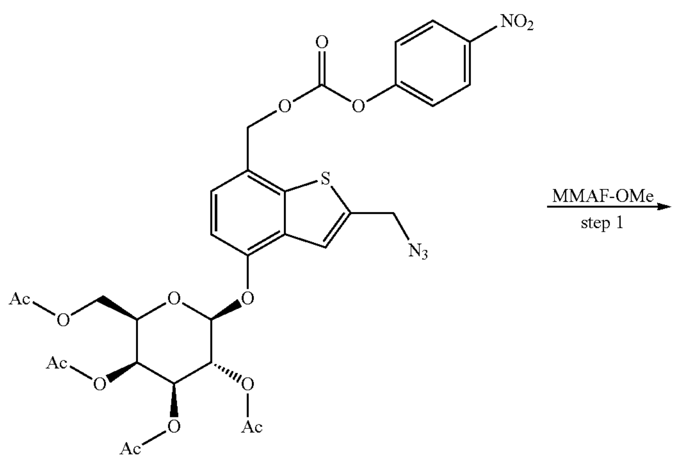

A-17g

-continued
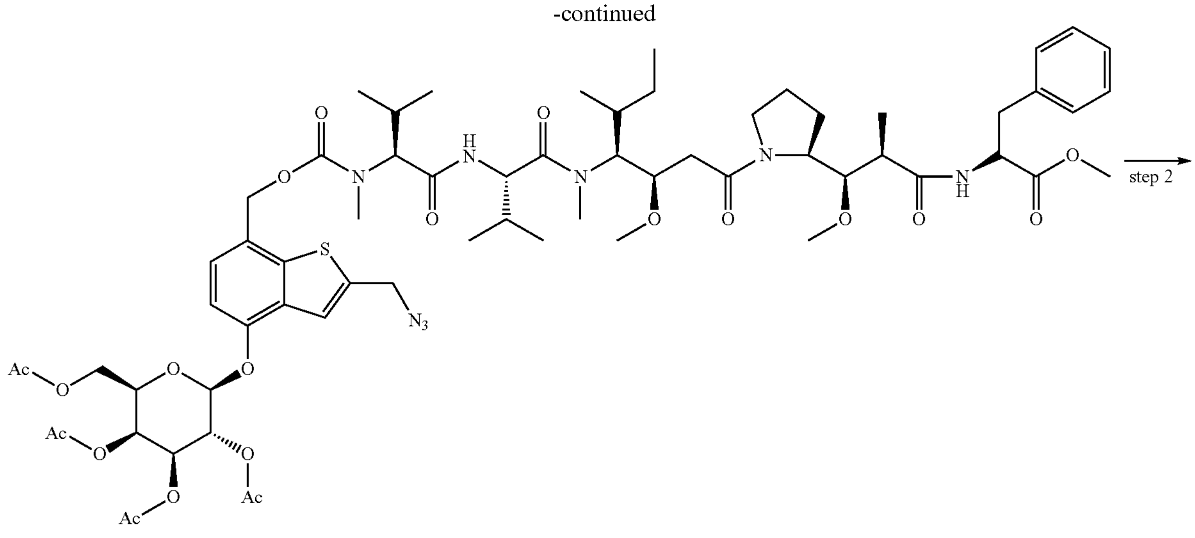
A-18a
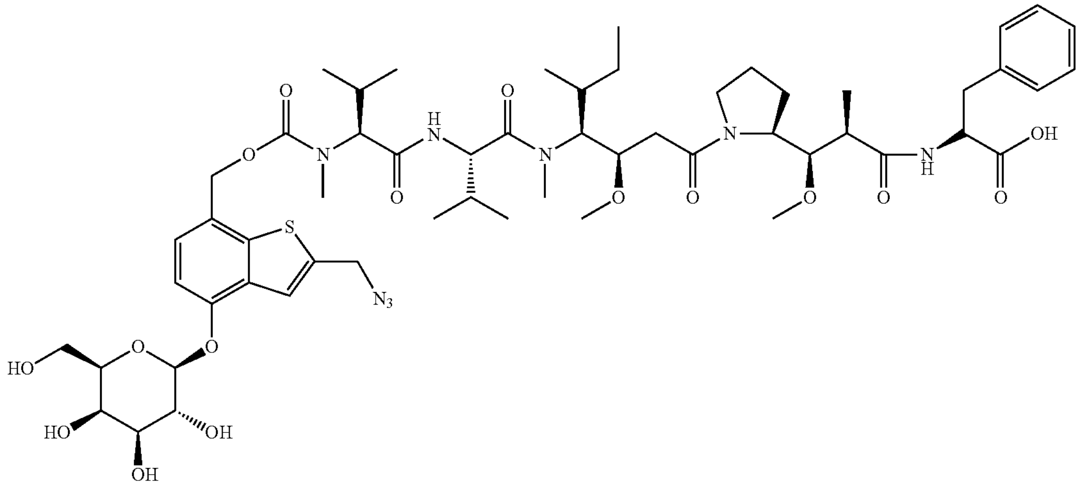
A-18
Compound A-18 was obtained as a white solid in the same manner as in Example I-16, except that MMAF-OMe was used instead of Compound PL-1 in Step 8 of Example I-16, and lithium hydroxide monohydrate was used instead of potassium carbonate in Step 9 (22 mg, 71%); EI-MS m/z: 1156 $[M+H]^+$.

Example I-18: Prep-18: Preparation Compound

A-19

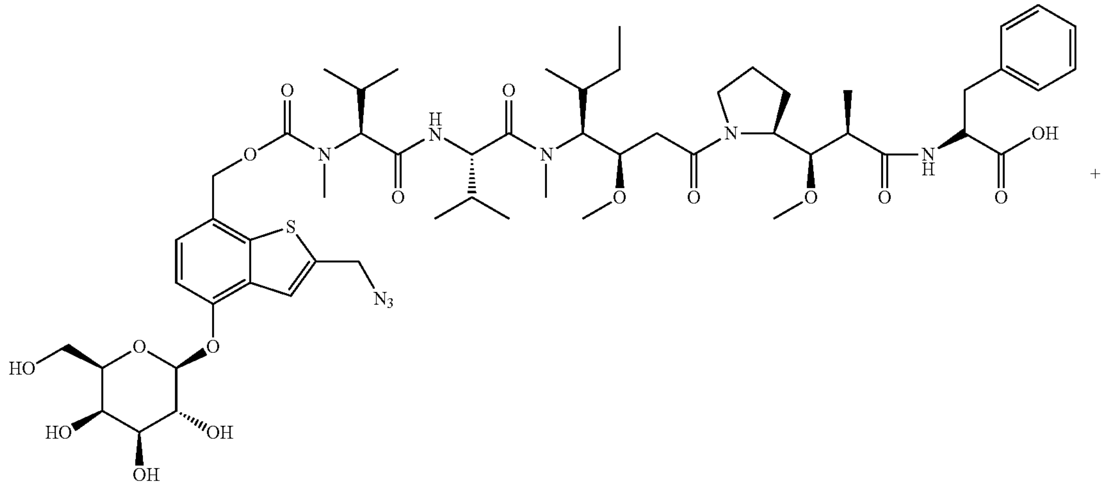

A-18

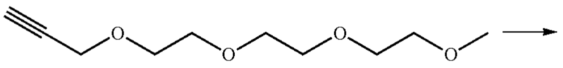

P-6

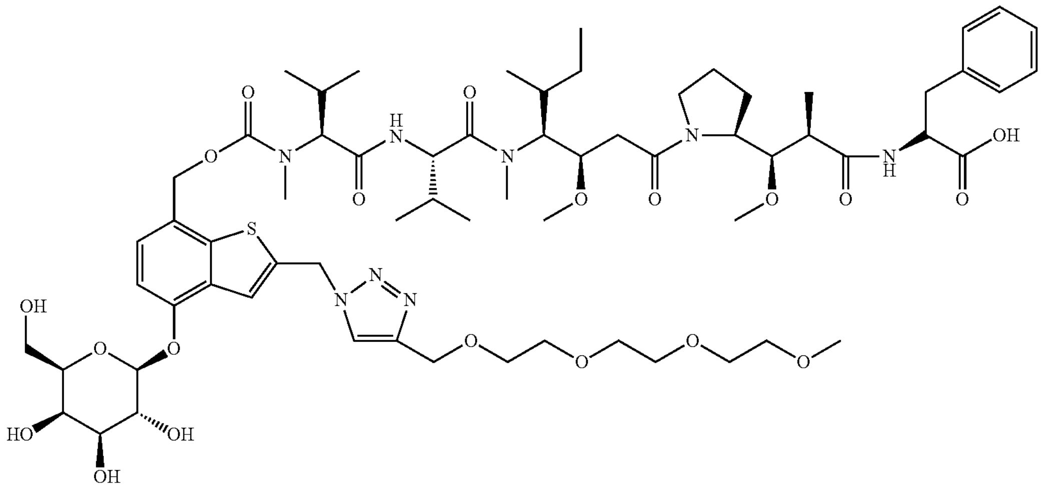

A-19

Compound A-18 (4.3 mg, 0.0037 mmol) was dissolved in DMO (200 IL) under a nitrogen atmosphere at 0° C., and then 70 μL of a solution of Linker P-6 (16.7 mg) dissolved in DMSO (1 mL) was taken and added to the reaction. Additionally, distilled water (2 mL), DMSO (0.4 mL), copper (II) sulfate pentahydrate ($CuSO_4.5H_2O$, 1 mg) and sodium ascorbate (1.47 mg) were sequentially added to the reaction solution, and then the mixture was stirred at room temperature for 30 minutes. After completion of the reaction, the reaction solution was diluted with distilled water (1 mL), separated and purified using Preparative-HPLC, and then freeze-dried to obtain Compound A-19 (3.6 mg, 72% n); MS m/z: 1358 $[M+H]^+$.

Example I-19: Preparation of Compound A-20

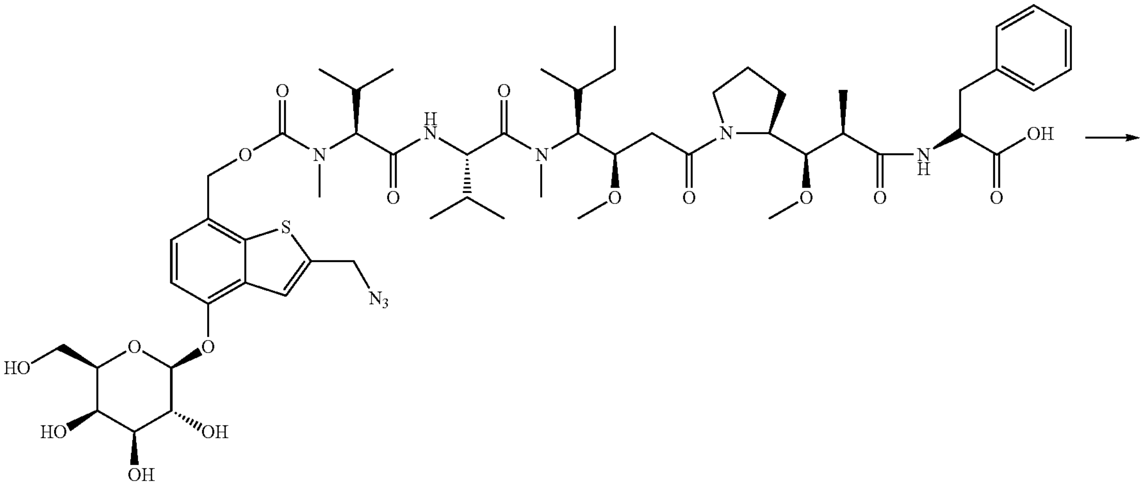

A-18

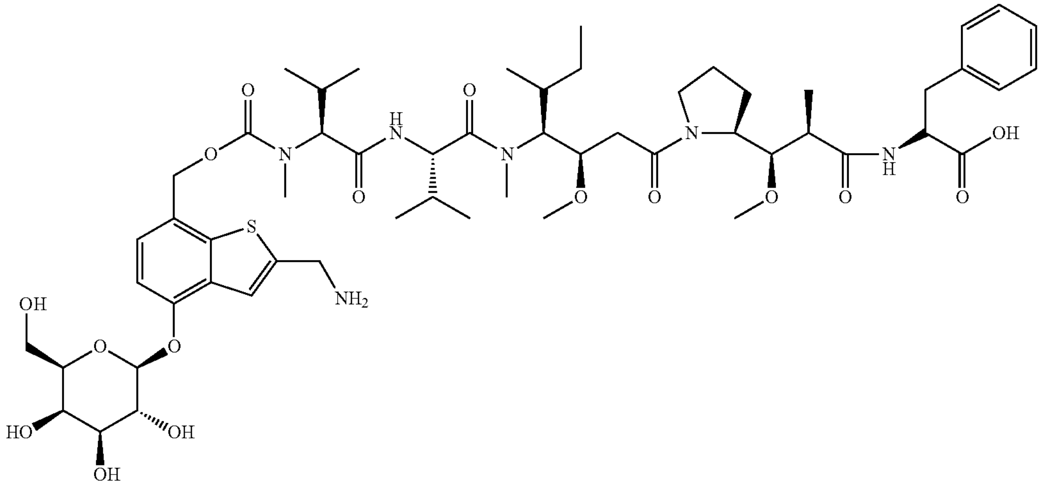

A-20

Compound A-18 (17.8 mg, 0.0154 mmol) was dissolved in THF (1 mL) under a nitrogen atmosphere at room temperature, and then triphenylphosphine (4.4 mg, 0.017 mmol) and distilled water (0.3 mL) were sequentially added, and the mixture was stirred for 12 hours. 2N-sodium hydroxide aqueous solution (10 μL) was added to the above reaction solution at room temperature, and the mixture was stirred for 30 minutes, and then 2N-hydrochloric acid aqueous solution was slowly added dropwise to adjust the pH of the reaction solution to 3, and the reaction solution was separated and purified using Preparative-HPLC, and then freeze-dried to obtain Compound A-20 was obtained (11.3 mg, 65% 7); MS m/z: 1130 $[M+H]^+$.

Example I-20: Preparation of Compound A-21

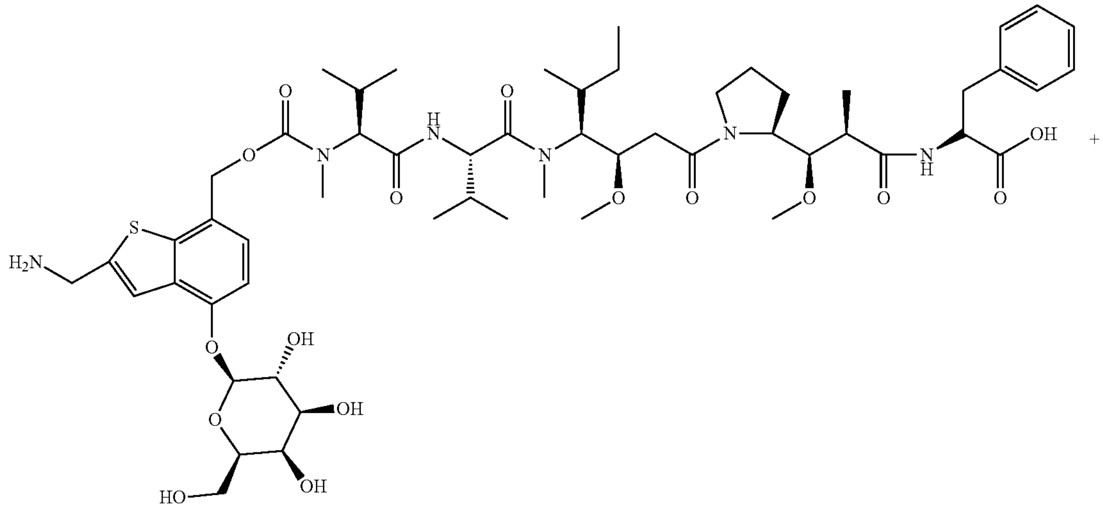

A-20

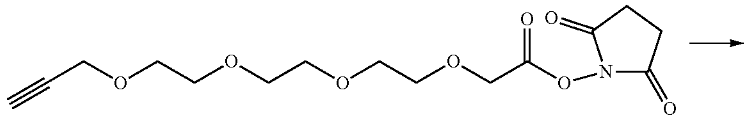

P-7

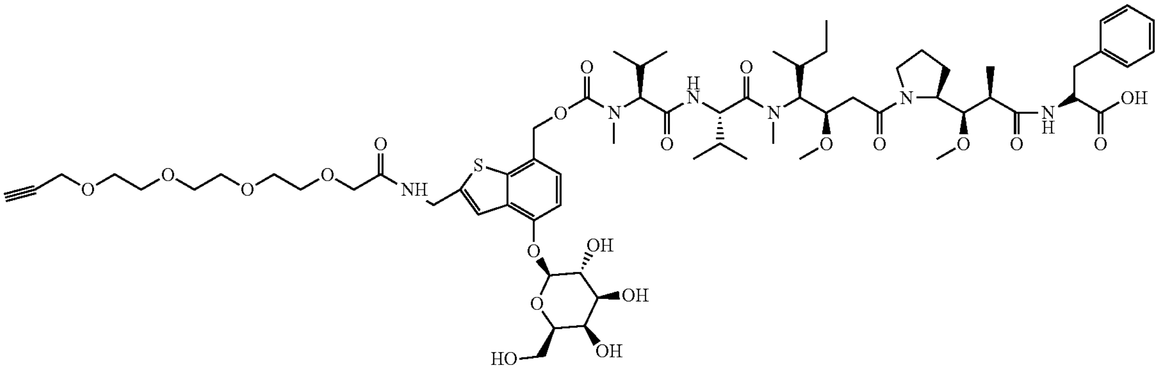

A-21

Compound A-20 (4.7 mg, 0.0041 mmol) was dissolved in THE (2 mL) under a nitrogen atmosphere at 0° C., and then Linker P-7 (2.7 mg, 0.0078 mmol), DIPEA (10 μL) and distilled water (200 μL) were sequentially added dropwise, and the mixture was stirred for 1 hour at room temperature. After completion of the reaction, the reaction solution was diluted with ACN (2 mL) containing 0.1% formic acid, separated and purified using Preparative-HPLC, and then freeze-dried to obtain Compound A-21 (2.9 mg, 51%); MS m/z: 1358 $[M+H]^+$.

Example I-21: Prep-21: Preparation Compound
A-22
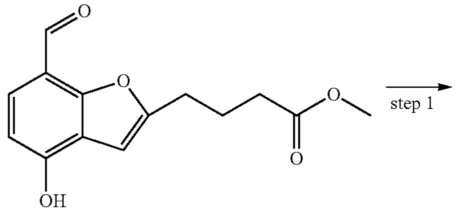
C-10
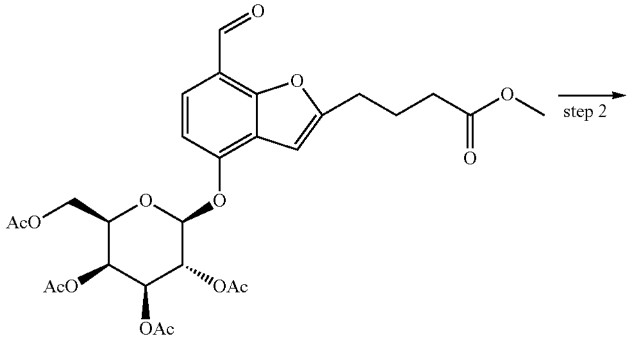
A-22a
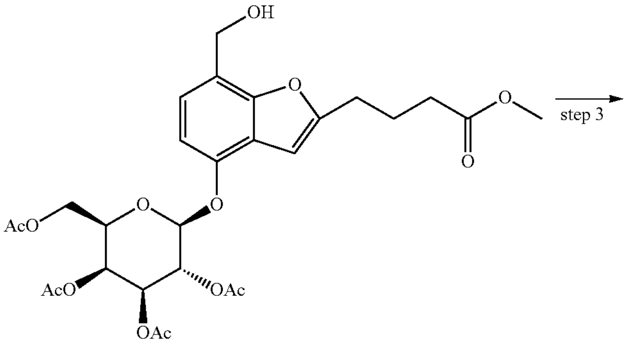
A-22b
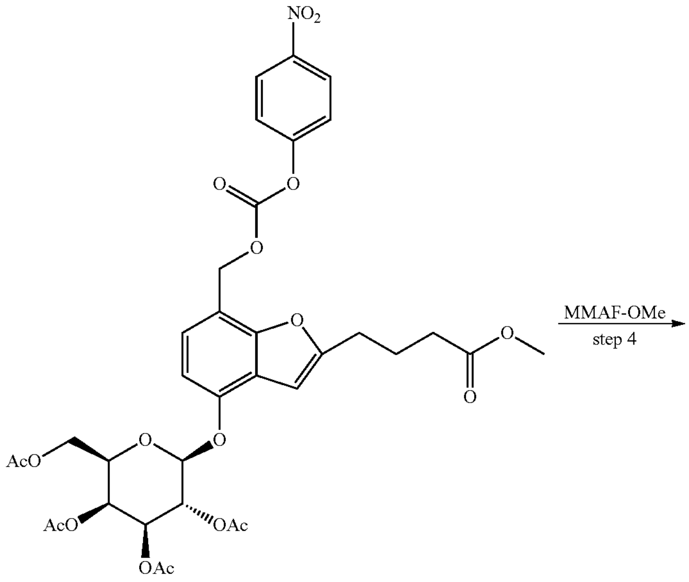
A-22c -continued
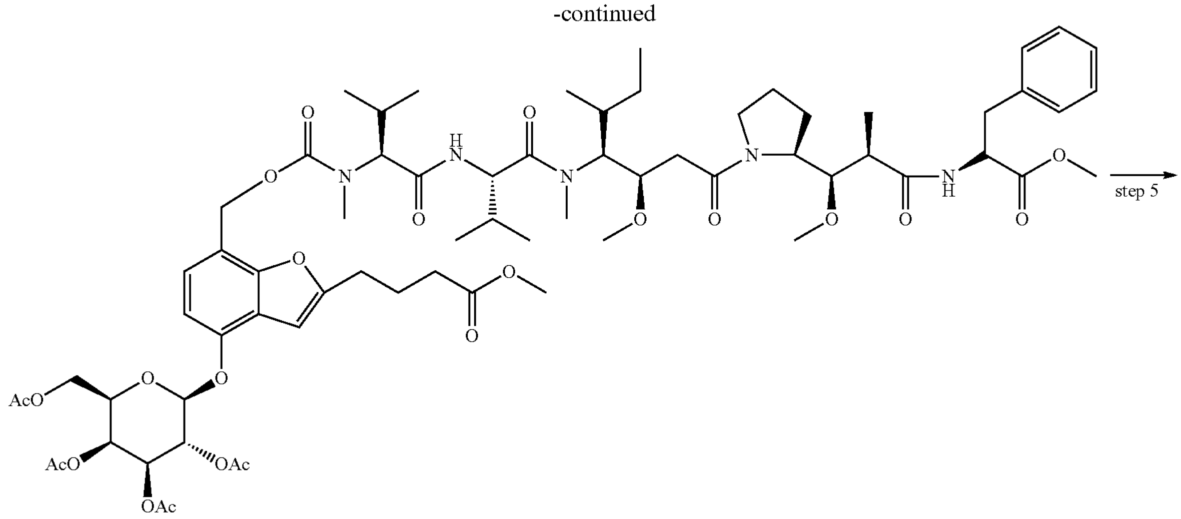
A-22d
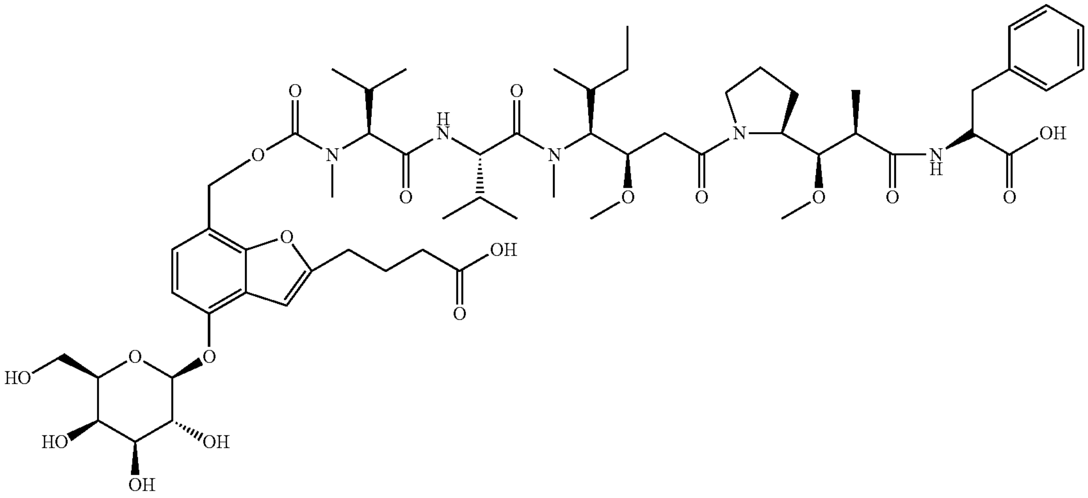
A-22
Compound A-22 was obtained in the form of a white solid using Core C-10 as a starting material in the same manner as in Example I-15 (8 mg, 58%); EI-MS m/z: 1171 $[M+H]^+$.
Example I-22: Preparation of Compound A-23
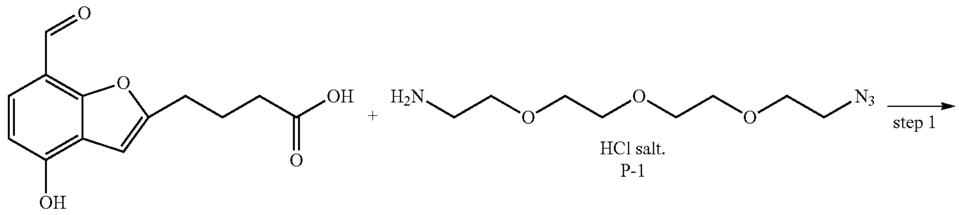
HCl salt.
P-1
C-11

-continued
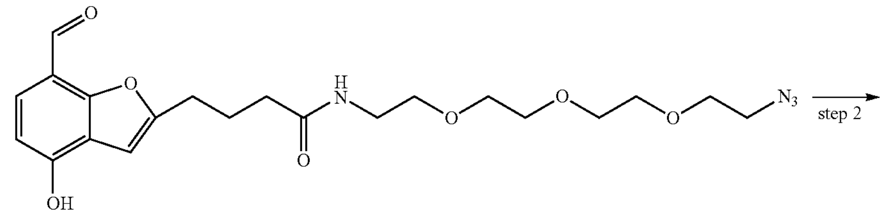
A-23a
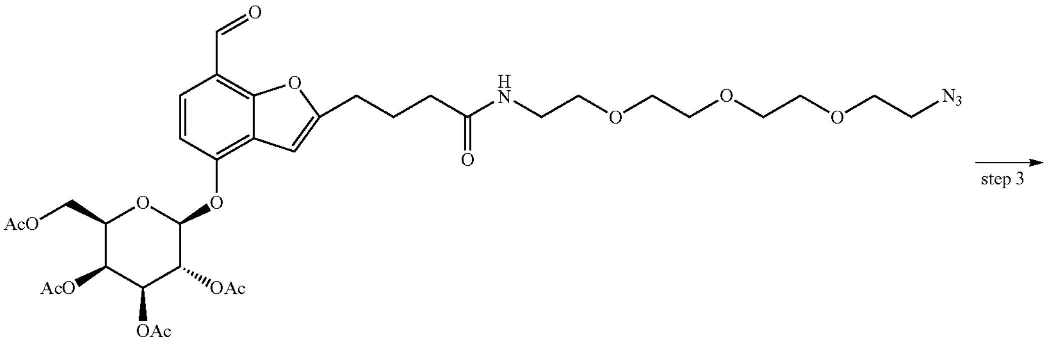
A-23b
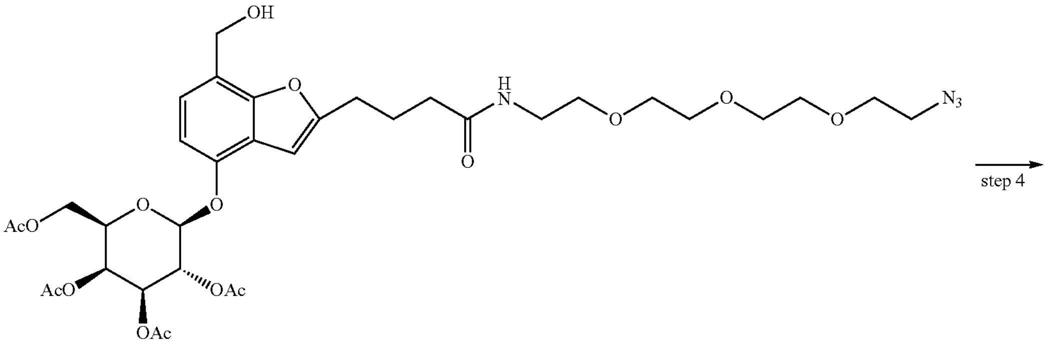
A-23c
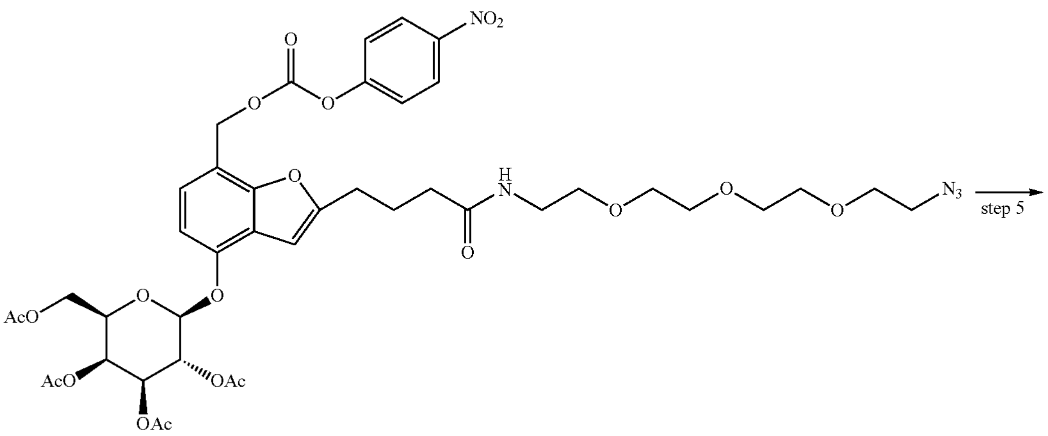
A-23d -continued

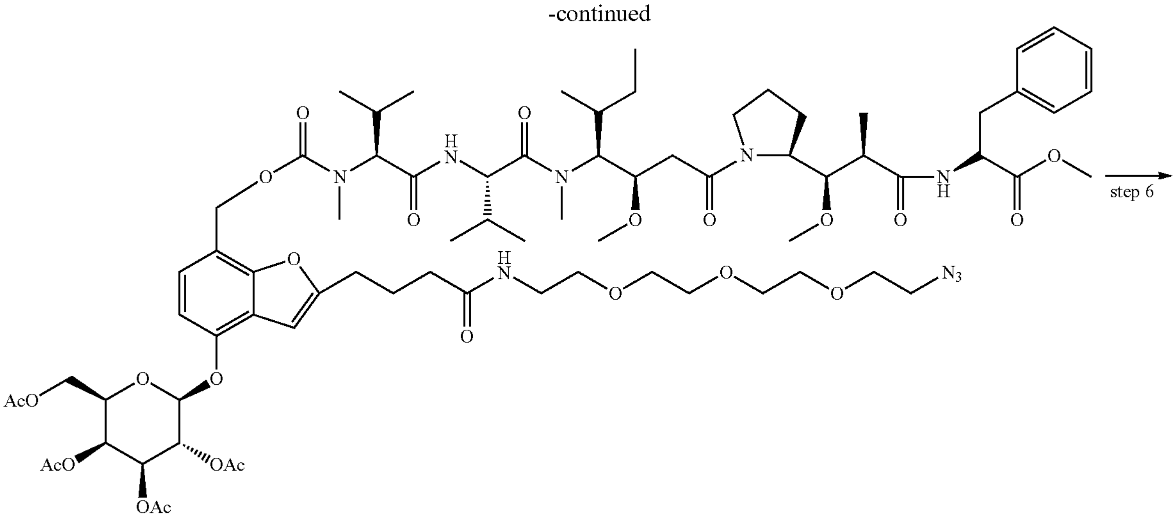

A-23e

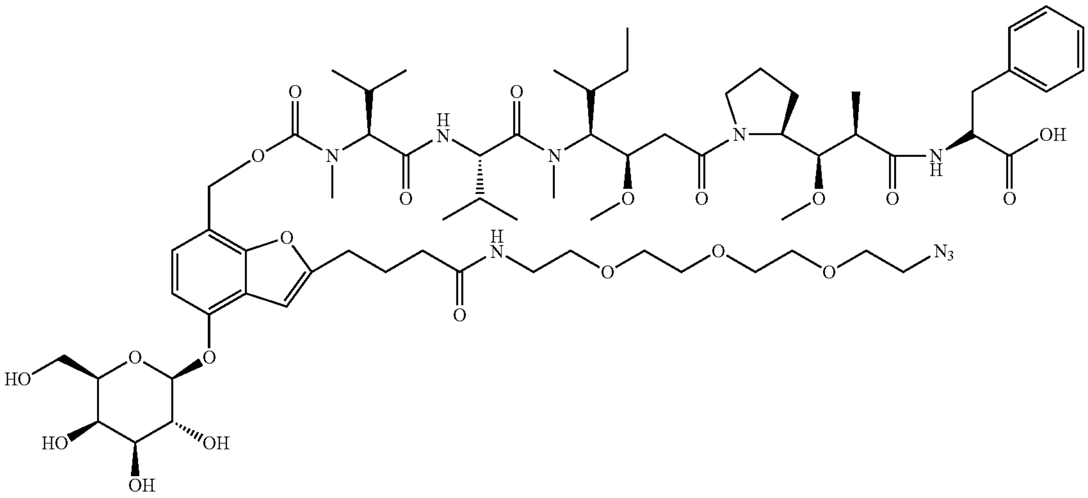

A-23

Step 1: Preparation of Compound A-23a

Core C-11 (189 mg, 0.76 mmol) and Linker P-1 (233 mg, 0.91 mmol) were dissolved in DMF (5 mL) under a nitrogen atmosphere at 0° C., and then EDCI hydrochloride (219 mg, 1.14 mmol), DMAP (9.3 mg, 0.07 mmol) and DIPEA (400 μL, 2.29 mmol) were sequentially added, and the mixture was stirred for 16 hours while slowly raising the temperature to room temperature. After completion of the reaction, the organic layer was extracted twice with EA (150 mL) and 2N-hydrochloric acid aqueous solution (150 mL). A saturated aqueous sodium chloride solution (100 mL) was added to the obtained organic layer to extract the organic layer. The obtained organic layer was dried over anhydrous magnesium sulfate, filtered, and then concentrated under reduced pressure. The resulting residue was subjected to column chromatography to obtain Compound A-23a in the form of an orange solid (47.5 mg, 14%); EI-MS m/z: 449 $[M+H]^+$.

Steps 2 to 6: Preparation of Compound A-23

Compound A-23 was obtained in the form of a white solid using Compound A-23a as a starting material in the same manner as in Example I-9, except that MMAF-OMe was used instead of Compound PL-1 in Step 4 of Example I-9 (16.8 mg, 69%); EI-MS m/z: 1371 $[M+H]^+$.

Example I-23: Preparation of Compound A-24
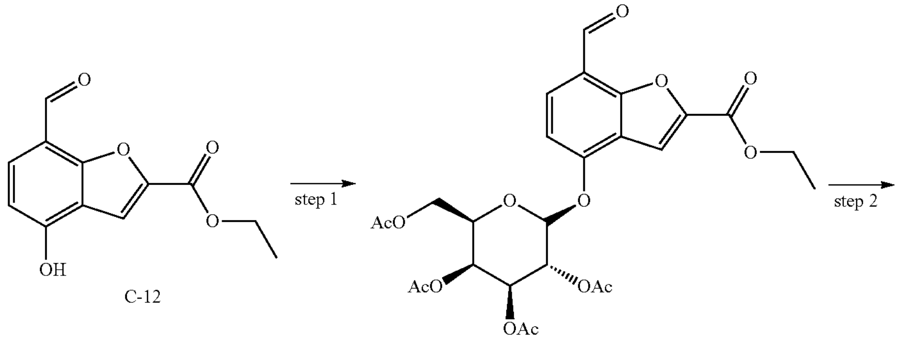
C-12
A-24a
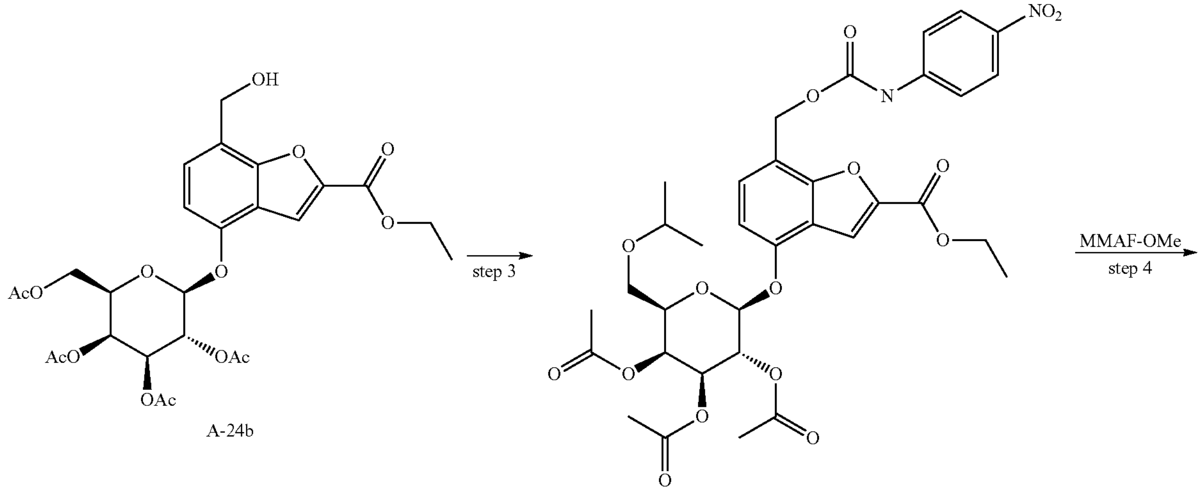
A-24b
A-24c
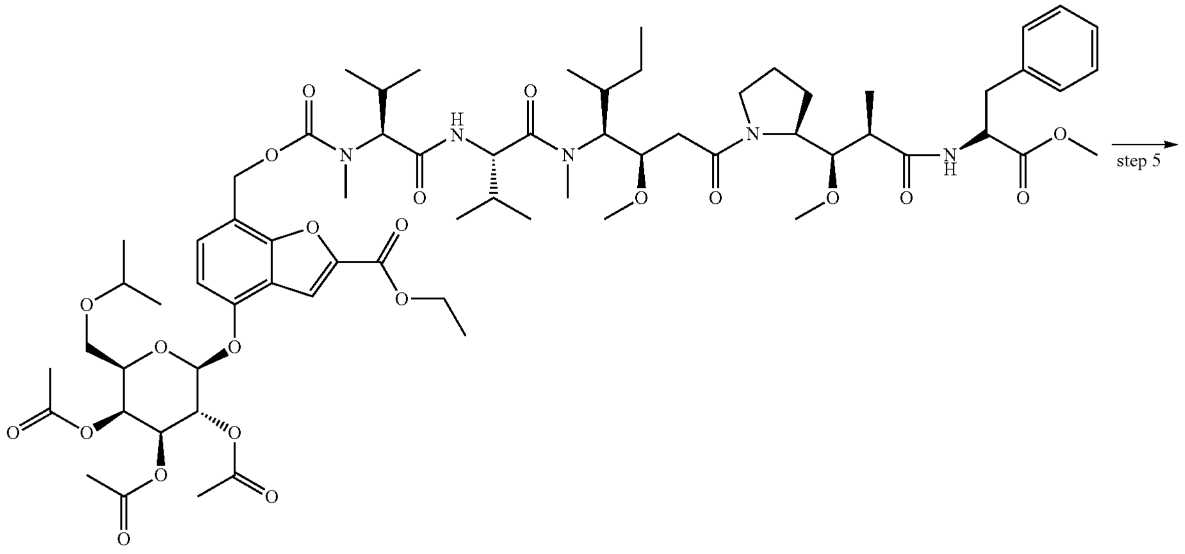
A-24d -continued
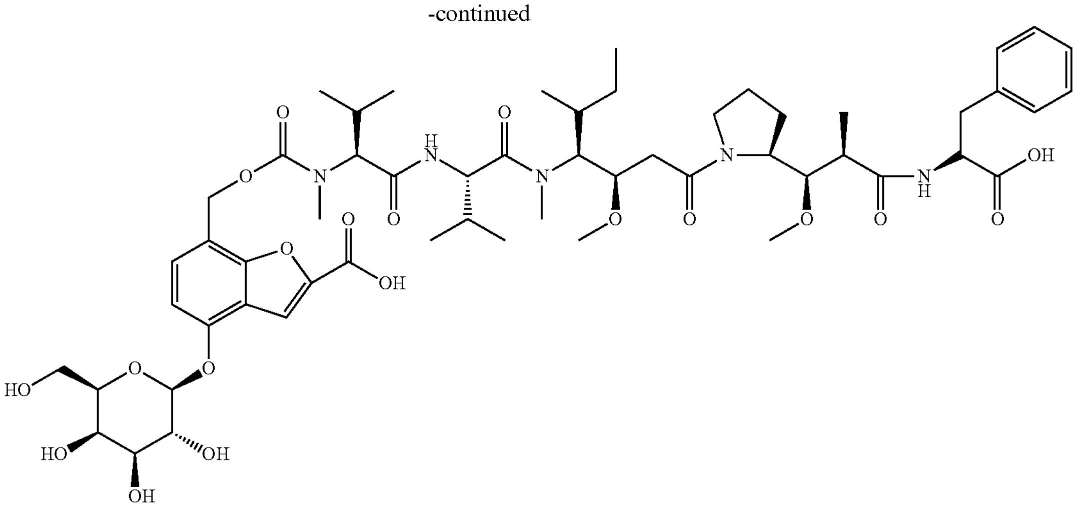
A-24
Compound A-24 was obtained in the form of a white solid using Core C-12 as a starting material in the same manner as in Steps 3 to 7 of Example I-1 (12.1 mg, 68%); EI-MS m/z: 1129 $[M+H]^+$.
Example I-24: Preparation of Compound A-25-2: Preparation of Compound A-25
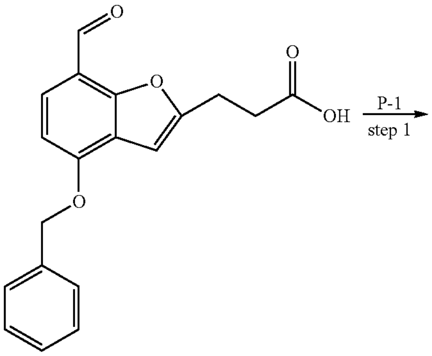
C-13
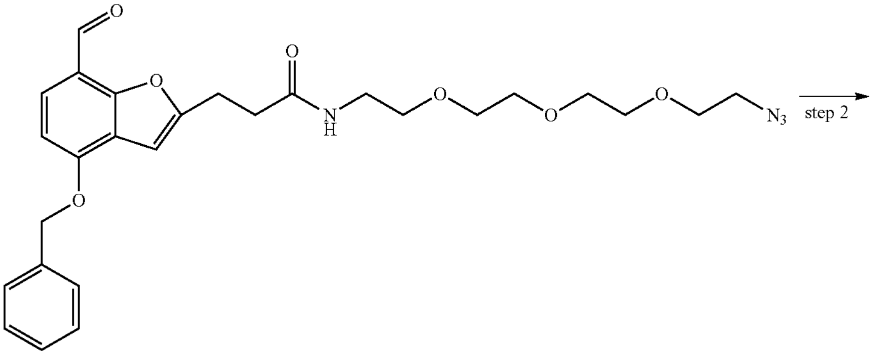
A-25a -continued
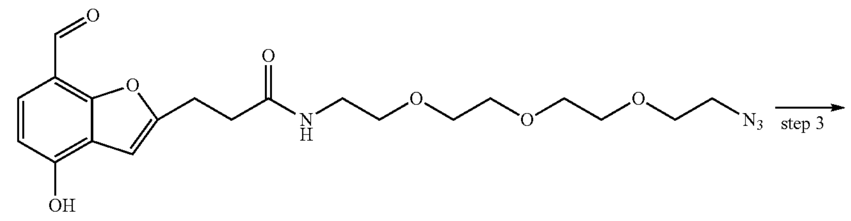
A-25b
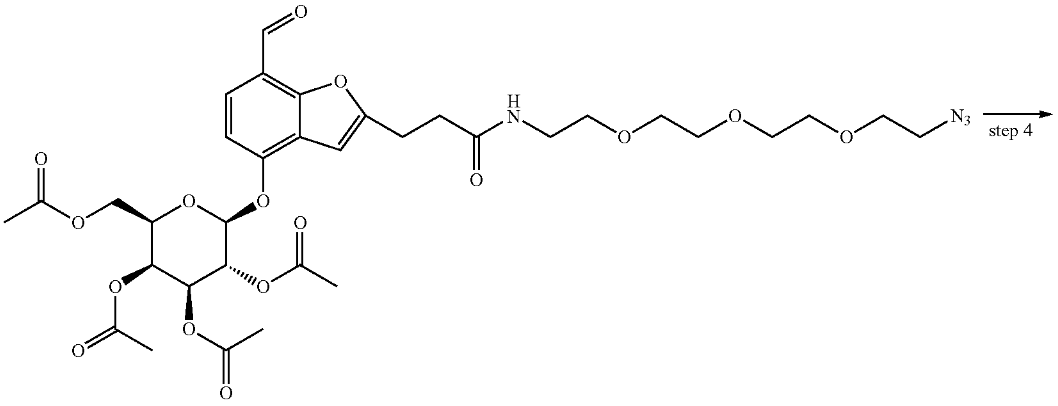
A-25c
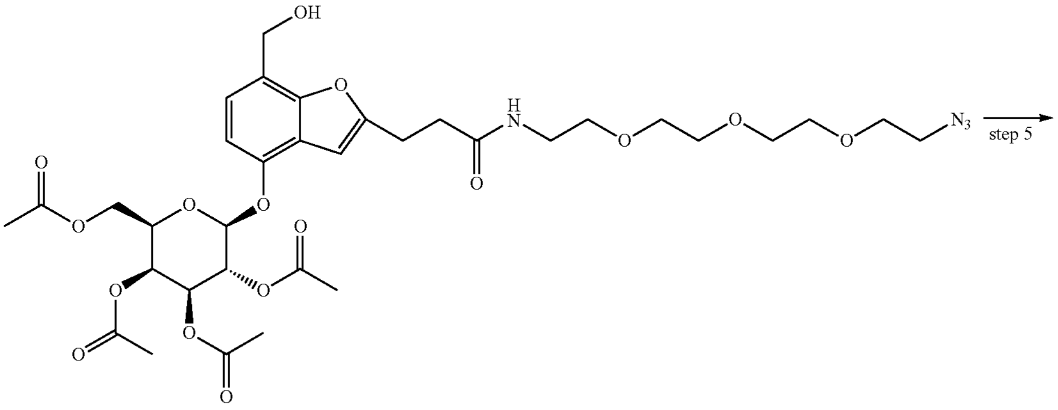
A-25d
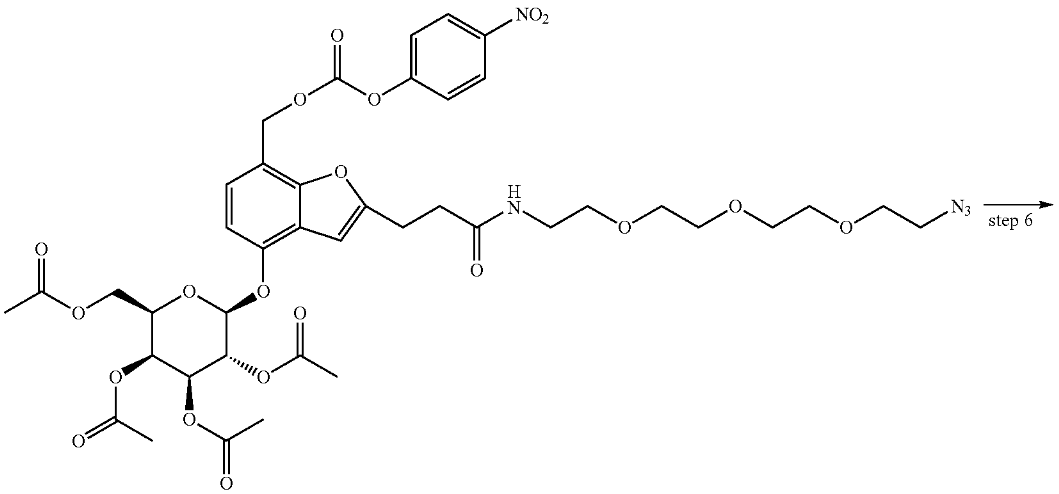
A-25e -continued
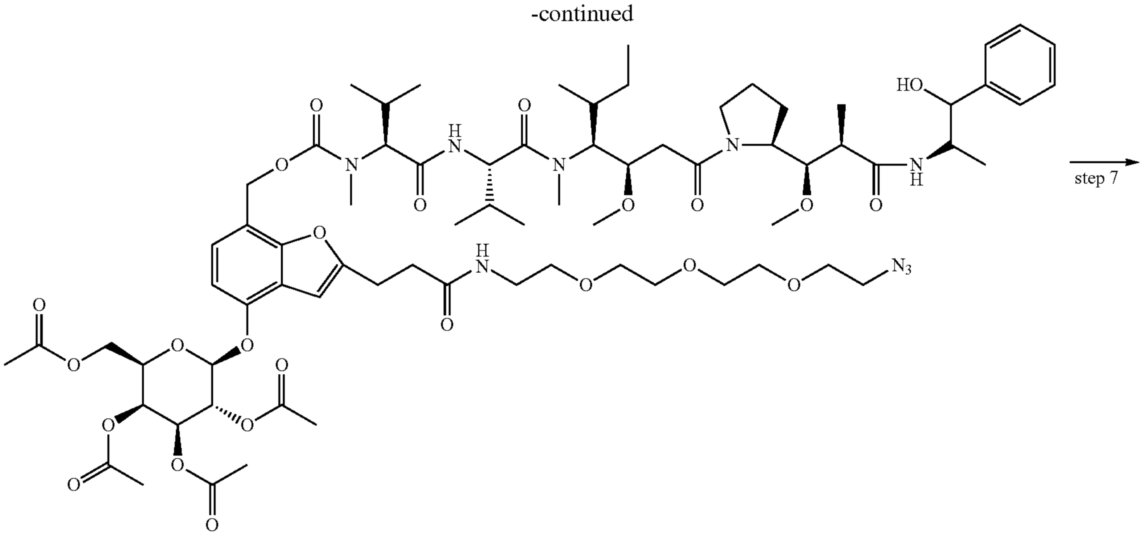
A-25f
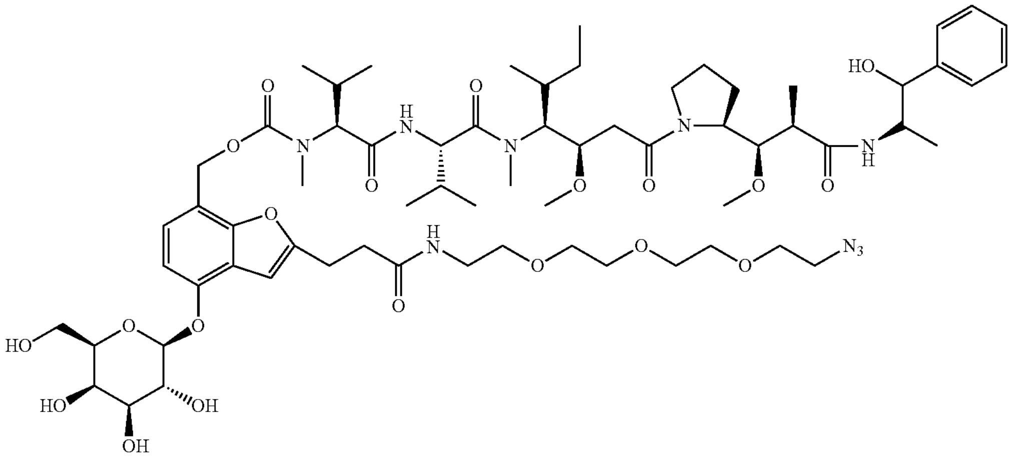
A-25
Compound A-25 was obtained in the form of a white solid using Core C-13 as a starting material in the same manner as in Example I-14 (18.6 mg, 65%); EI-MS m/z: 1342 $[M+H]^+$.
Example I-25: Preparation of Compound A-26
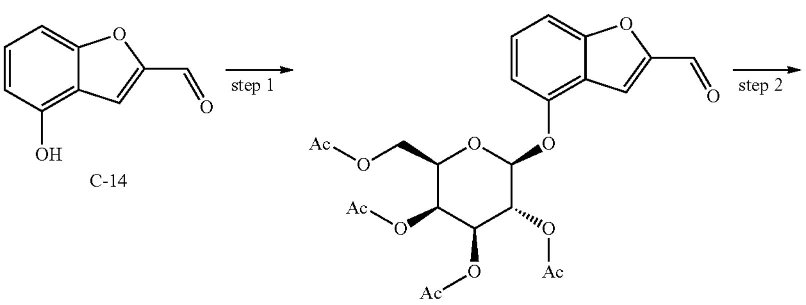
C-14
A-26a -continued
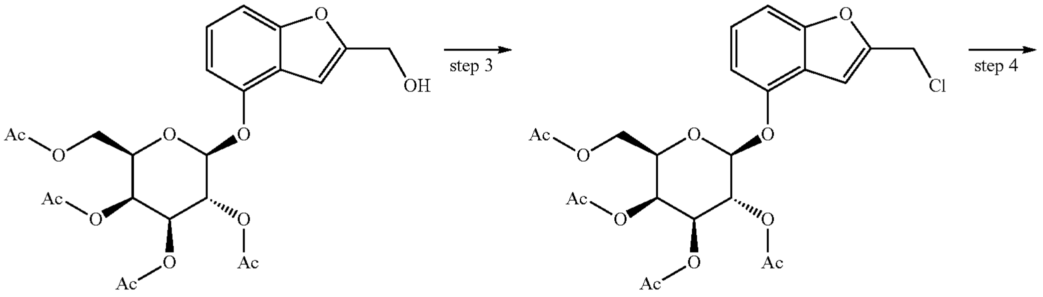
A-26b A-26c
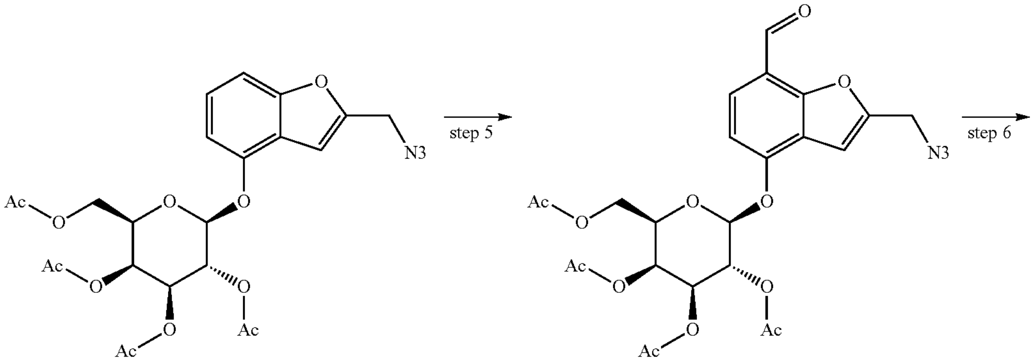
A-26d A-26e
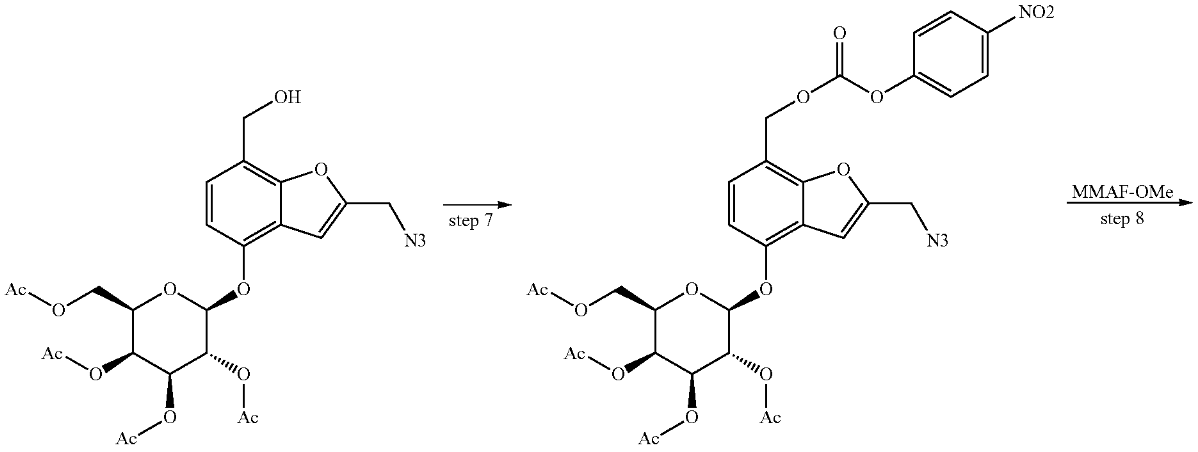
A-26f A-26g -continued
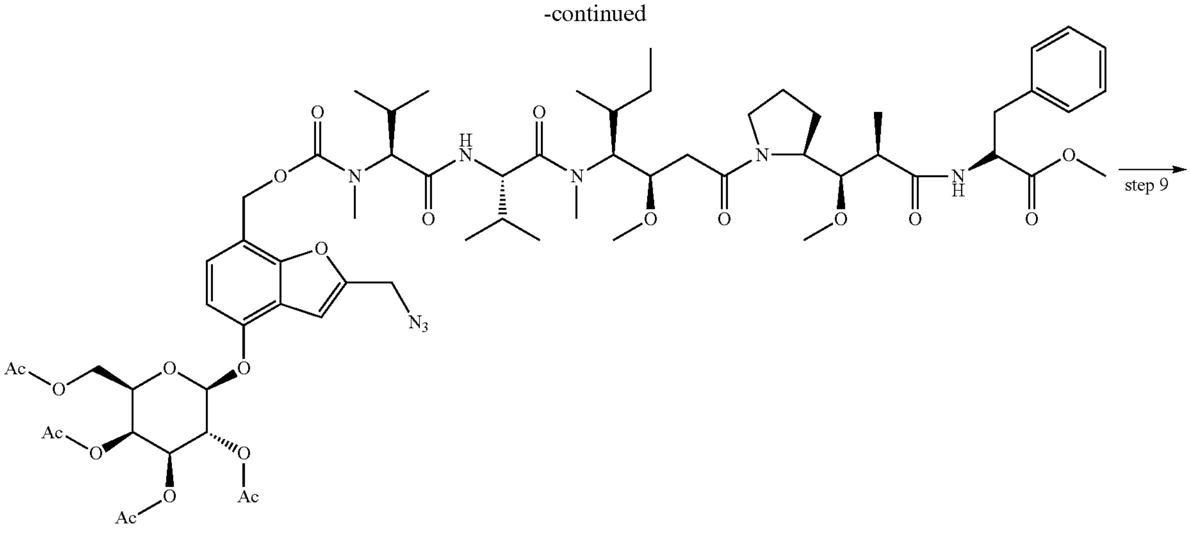
A-26h
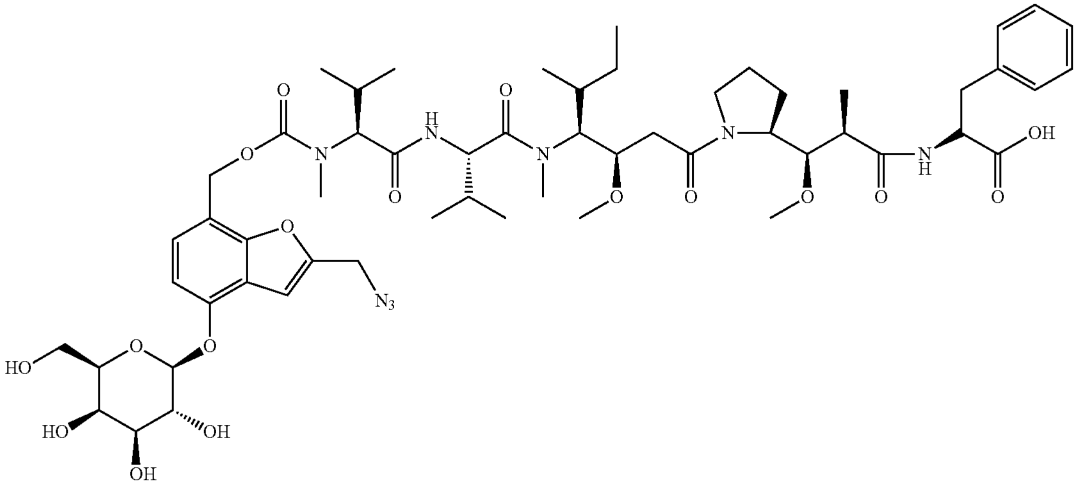
A-26
Compound A-26 was obtained in the form of a white solid using Core C-14 as a starting material in the same manner as in Example I-16, except that MMAF-OMe was used instead of Compound PL-1 in Step 8 of Example I-16, and lithium hydroxide monohydrate was used instead of potassium carbonate in Step 9 (21.3 mg, 61%); EI-MS m/z: 1140 $[M+H]^+$.

Example I-26: Preparation of Compound A-27

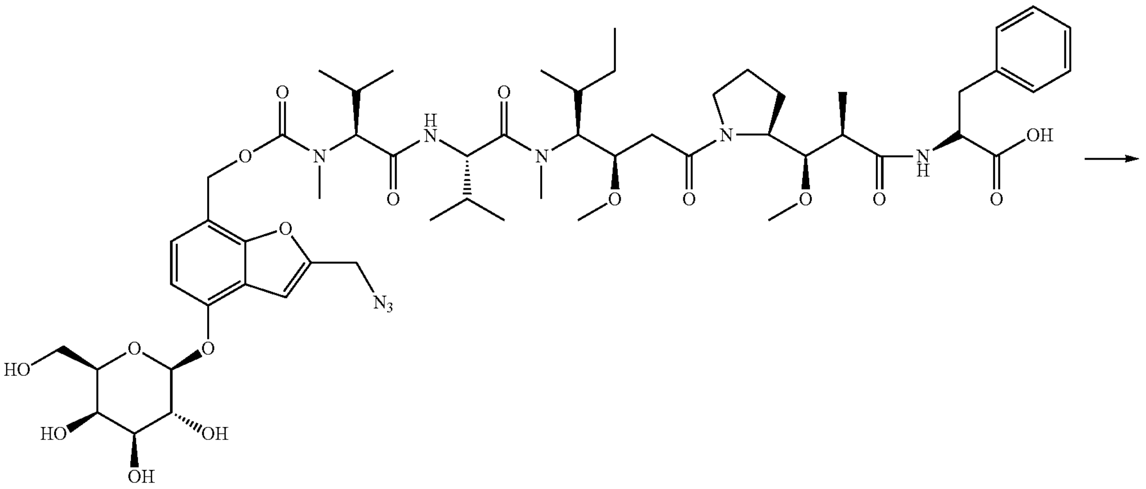

A-26

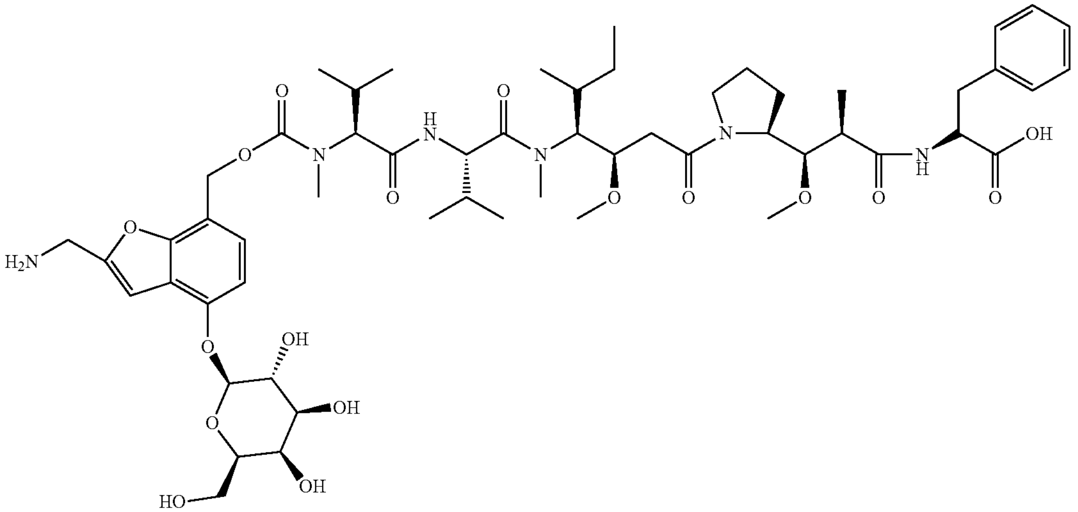

A-27

Compound A-26 (15.7 mg, 0.013 mmol) was dissolved in THE (1 mL) under a nitrogen atmosphere at room temperature, and then triphenylphosphine (5.4 mg, 0.0195 mmol) and distilled water (0.3 mL) were sequentially added, and the mixture was stirred for 16 hours. 2N-sodium hydroxide aqueous solution (10 μL) was added to the above reaction solution at room temperature, and the mixture was stirred for an additional 1 hour, and then 2N-hydrochloric acid aqueous solution was slowly added dropwise to adjust the pH of the reaction solution to 3, and the reaction solution was separated and purified using Preparative-HPLC, and then freeze-dried to obtain Compound A-27 in the form of a white solid (10.5 mg, 65%); MS m/z: 1113 $[M+H]^+$.

Example I-27: Preparation of Compound A-28

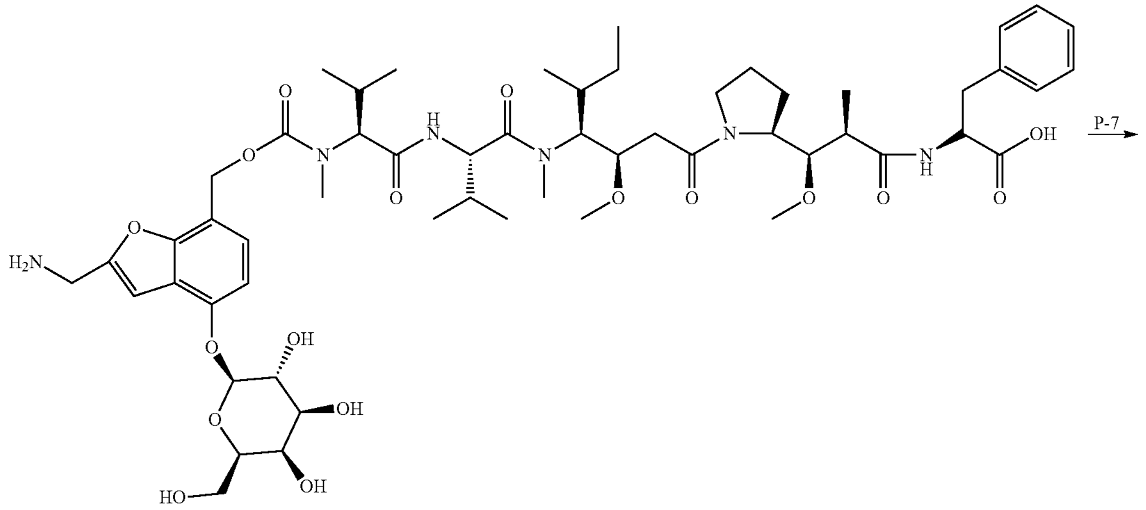

A-27

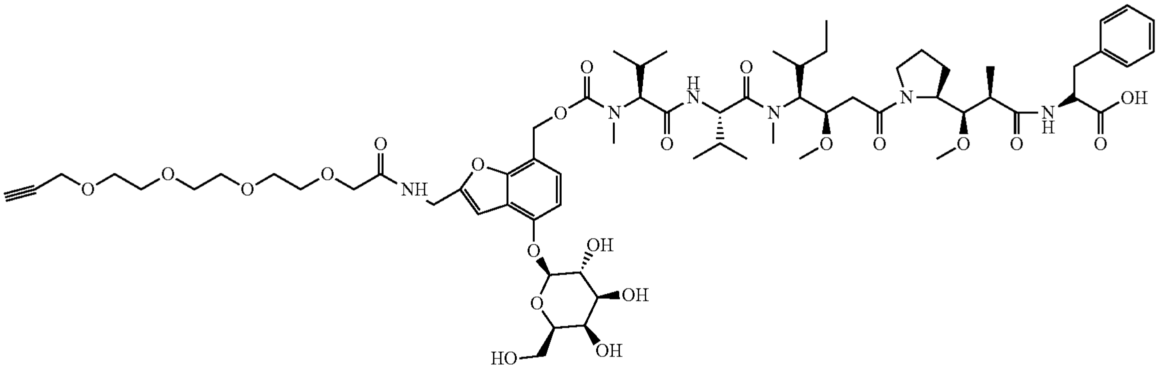

A-28

Compound A-27 (3 mg, 0.0026 mmol) was dissolved in THF (2 mL) under a nitrogen atmosphere at 0° C., and then Linker P-7 (1.4 mg, 0.0039 mmol), DIPEA (10 μL) and distilled water (200 μL) were sequentially added dropwise, and the mixture was stirred for 1 hour at room temperature. After completion of the reaction, 2N-hydrochloric acid aqueous solution (20 μL) was added, and the reaction solution was diluted with ACN (2 mL) containing 0.1% formic acid, separated and purified using Preparative-HPLC, and then freeze-dried to obtain Compound A-28 (2.2 mg, 61%); MS m/z: 1341 $[M+H]^+$.

Example I-28: Preparation of Compound A-29

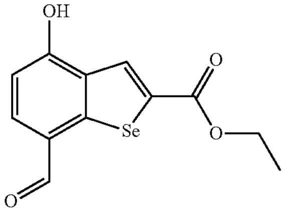

C-15

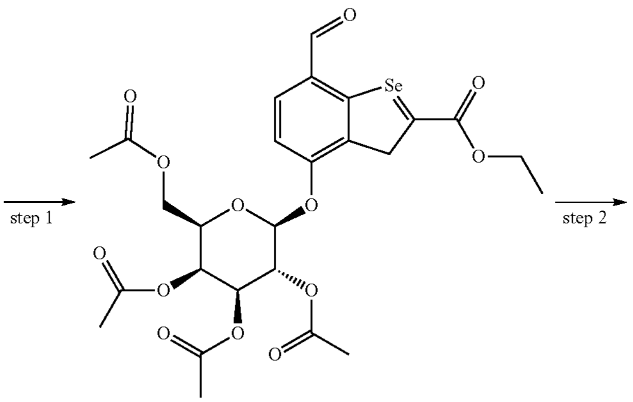

A-29a

-continued
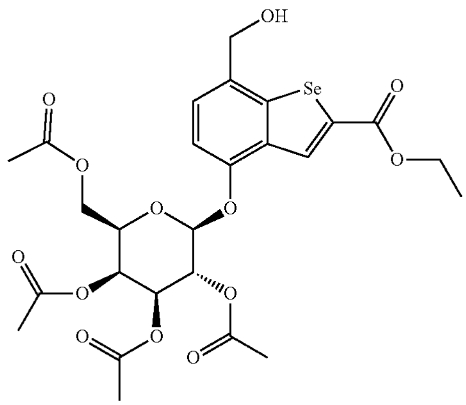
A-29b
step 3
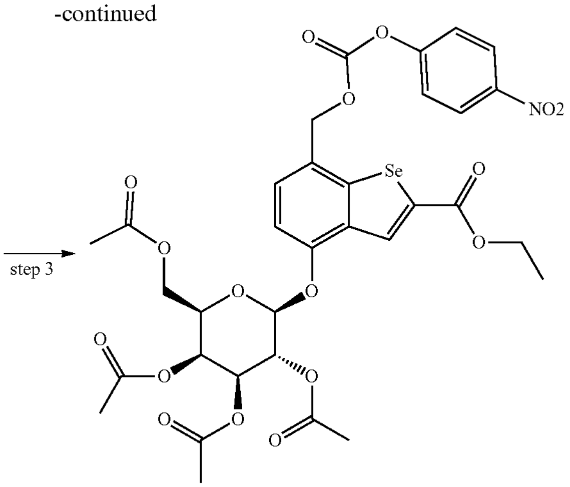
A-29c
step 4
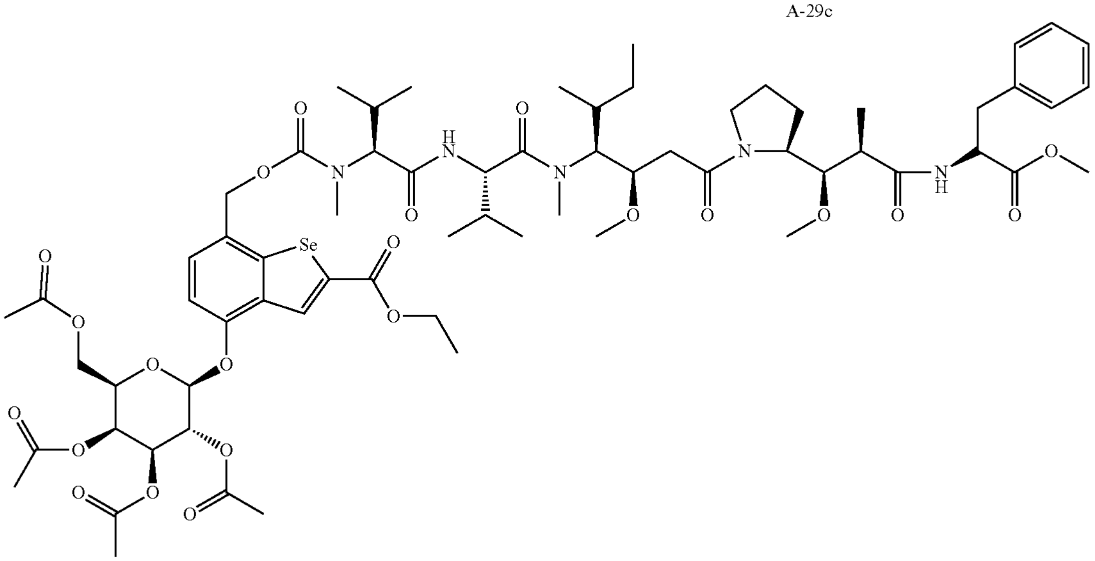
A-29d
step 5
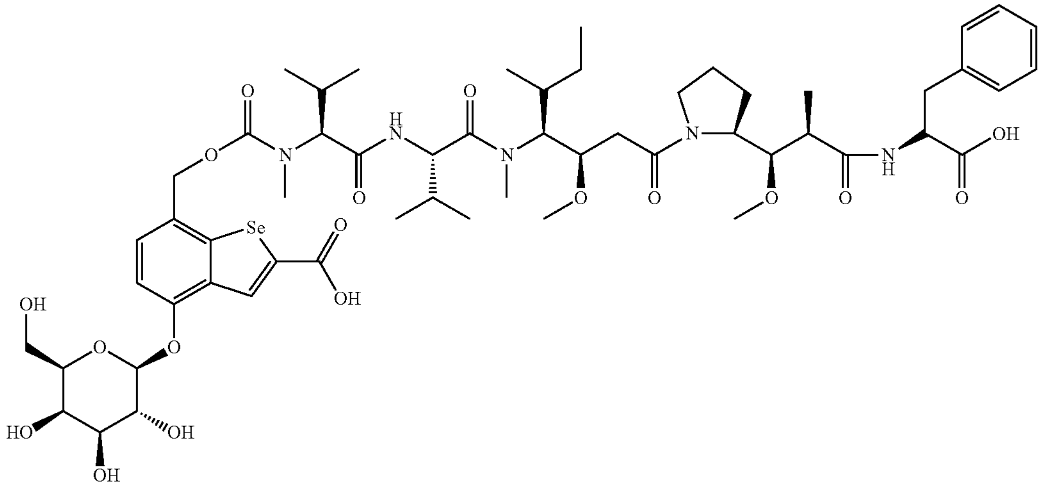
A-29
Compound A-29 was obtained in the form of a white solid using Core C-15 as a starting material in the same manner as in Example I-9, except that IPA and chloroform were used instead of THF as a solvent in Step 2 of Example I-9, silica gel was added with sodium borohydride, and MMAF-OMe was used instead of Compound PL-1 in Step 4 (15.9 mg, 64% n); EI-MS m/z: 1192 $[M+H]^+$.

Example I-29: Preparation of Compound A-33

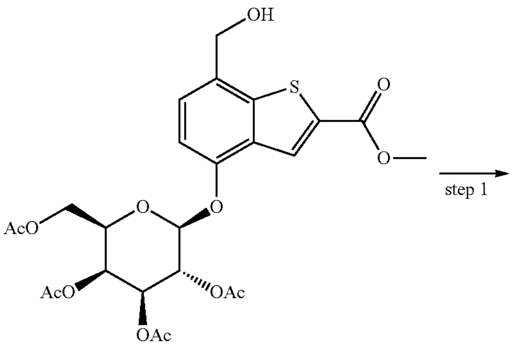

A-12b

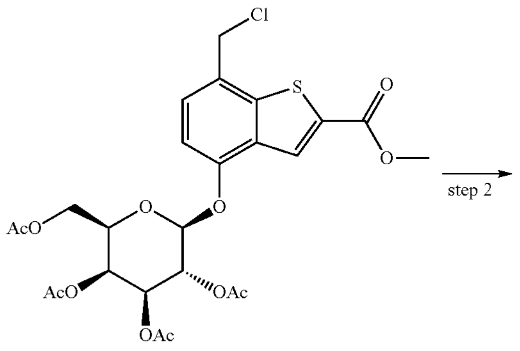

A-33a

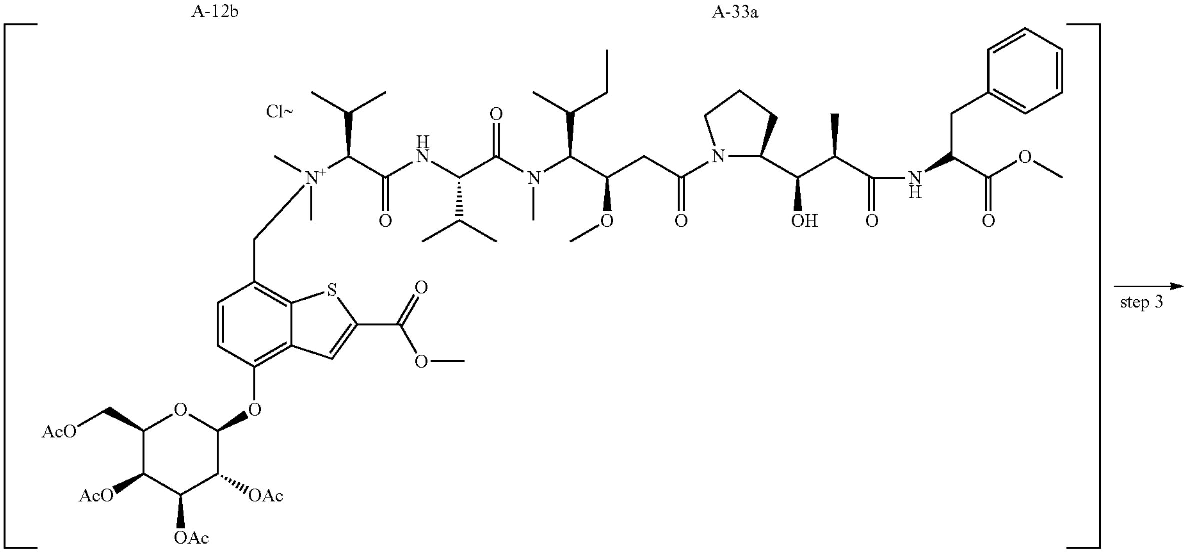

A-33b

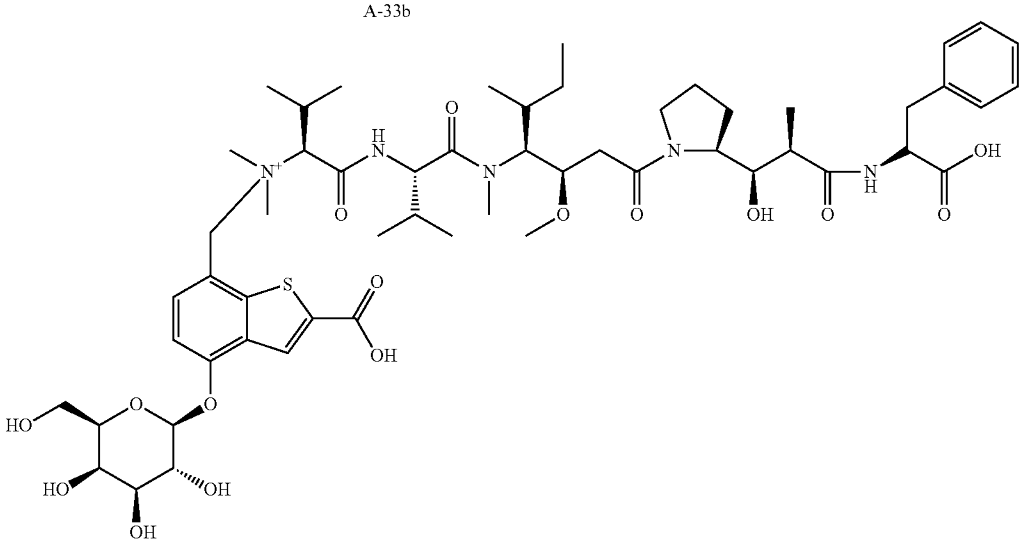

A-33

Step 1: Preparation of Compound A-33a

Compound A-12b (180 mg, 0.31 mmol) of Example I-11 was dissolved in MC (20 mL) under a nitrogen atmosphere at 0° C., and then thionyl chloride (48.2 μL, 0.65 mmol) was slowly added, and the mixture was stirred at 0° C. for 2 hours. After completion of the reaction, the mixture was diluted by adding MC (50 mL) and then concentrated under reduced pressure. The residue was solidified by adding n-hexane (50 mL) and then concentrated under reduced pressure to obtain Compound A-33a in the form of a white solid. The obtained compound was used in the next reaction without an additional purification process (185 mg, 99%).

$^1$H-NMR (400 MHz, $CDCl_3$) δ 8.12 (s, 1H), 7.41 (d, J=8 Hz, 1H), 6.98 (d, J=8 Hz, 1H), 5.62 (dd, J=10.8, 8 Hz, 1H), 5.48 (d, J=2.8 Hz, 1H), 5.17-5.13 (m, 2H), 4.80 (s, 2H), 4.22 (m, 1H), 4.18 (m, 1H), 4.12 (m, 1H), 3.96 (s, 3H), 2.21 (s, 3H), 2.08 (s, 3H), 2.07 (s, 3H), 2.04 (s, 3H); EI-MS m/z: 587 $[M+H]^+$.

Steps 2 and 3: Preparation of Compound A-33

Compound A-33a (30 mg, 0.051 mmol) was dissolved in DMF (3 mL) under a nitrogen atmosphere at 0° C., and then the compound auristatin F-OMe (42.7 mg, 0.056 mmol), DIPEA (26.7 L, 0.153 mmol) and TBAI (2 mg, 0.005 mmol) were sequentially added to the reaction, and the mixture was stirred at 40° C. for 16 hours. After completion of the reaction, the reaction solution containing the produced Compound A-33b (EI-MS m/z: 1311 $[M+H]^+$) was cooled to room temperature, and lithium hydroxide hydrate (21.4 mg, 0.51 mmol) was dissolved in distilled water (1 mL) and slowly added at 0° C., and the mixture was stirred for 2 hours. 2N-hydrochloric acid aqueous solution (0.3 mL) was slowly added dropwise to the reaction solution to terminate the reaction, and the reaction solution was diluted with ACN (1 mL) and distilled water (1 mL), then separated and purified using Preparative-HPLC, and then freeze-dried to obtain Compound A-33 (1.1 mg, 2%); EI-MS m/z: 1115 $[M+H]^+$.

Example I-30: Preparation of Compound A-34

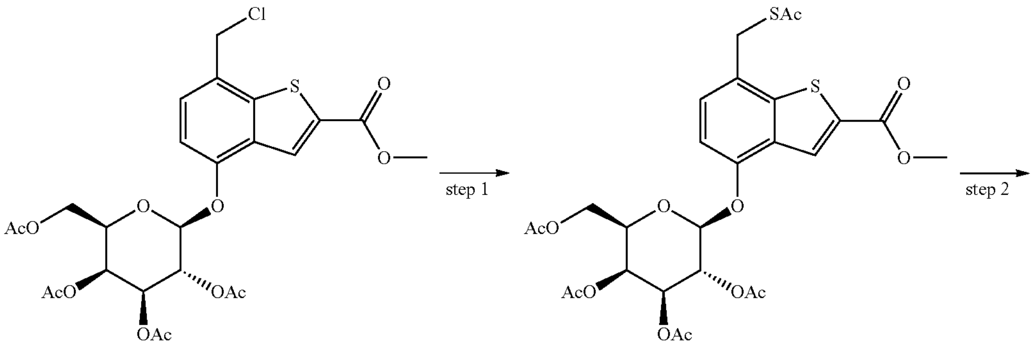

A-33a A-34a

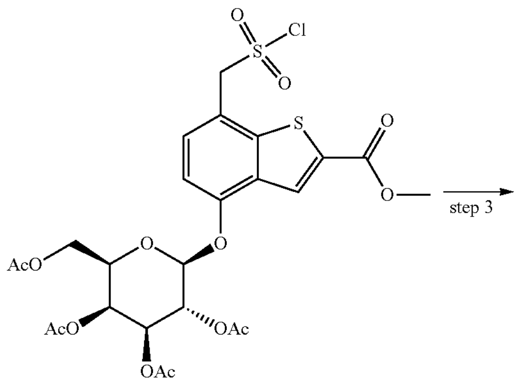

A-34b

-continued

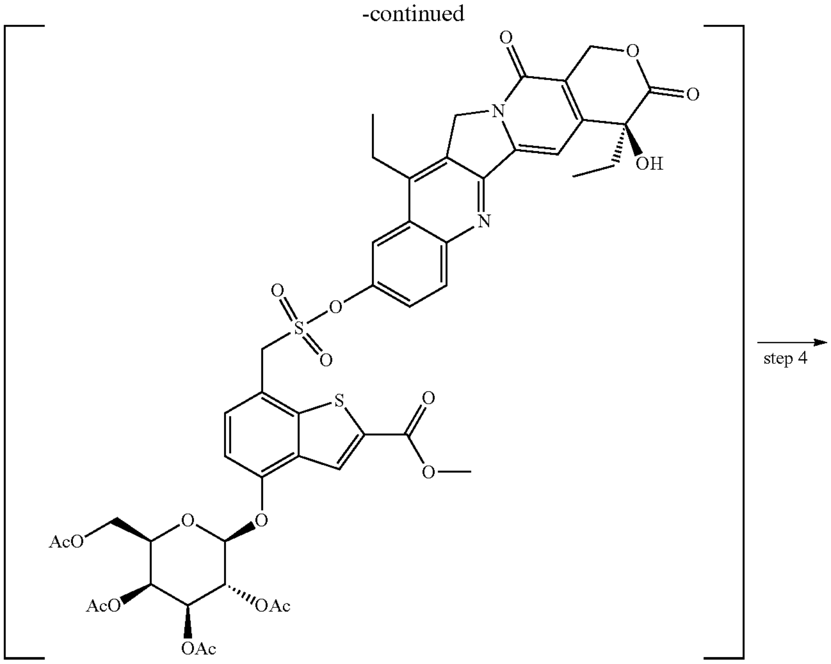

A-34c

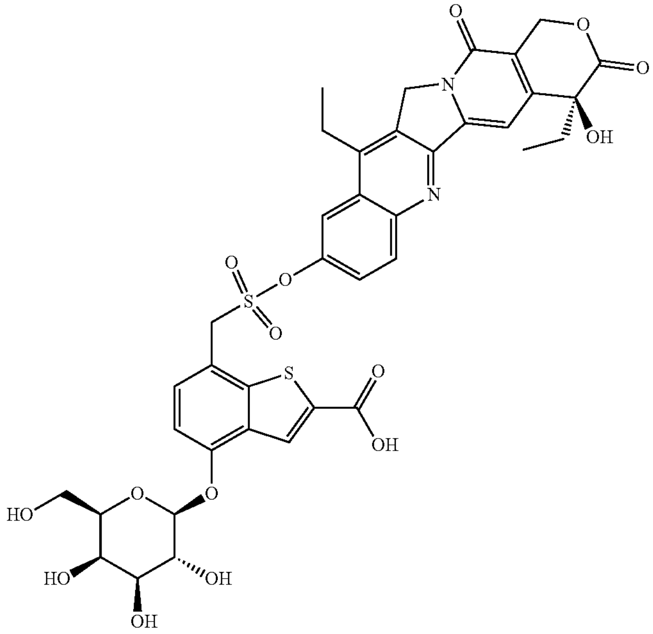

A-34

Step 1: Preparation of Compound A-34a

Compound A-33a (135 mg, 0.229 mmol) of Example 1-29 was dissolved in ACN (5 mL) under a nitrogen atmosphere at room temperature, and then potassium thioacetate (31.5 mg, 0.275 mmol) was added, and the mixture was stirred for 3 hours. After completion of the reaction, EA (50 mL) and distilled water (50 mL) were added to extract the organic layer. The obtained organic layer was dried over anhydrous magnesium sulfate, filtered, and then concentrated under reduced pressure. The resulting residue was subjected to column chromatography to obtain Compound A-34a (140 mg, 97%).

$^1$H-NMR (400 MHz, $CDCl_3$) δ 8.11 (s, 1H), 7.40 (d, J=8 Hz, 1H), 6.95 (d, J=8 Hz, 1H), 5.60 (dd, J=10.4, 8 Hz, 1H), 5.47 (d, J=2.8 Hz, 1H), 5.15-5.12 (m, 2H), 4.31 (d, J=5.2 Hz, 1H), 4.25-4.08 (m, 3H), 3.95 (s, 3H), 2.36 (s, 3H), 2.20 (s, 3H), 2.08 (s, 2H), 2.06 (s, 3H), 2.03 (s, 3H); EI-MS m/z: 627 $[M+H]^+$.

Step 2: Preparation of Compound A-34b

N-chlorosuccinimide (NCS, 120 mg, 0.88 mmol) was added to a mixed solution of 2N-hydrochloric acid aqueous solution (60 μL) and ACN (300 μL) under a nitrogen atmosphere at 0° C., and then Compound A-34a (140 mg, 0.22 mmol) was dissolved in ACN (100 μL) and added. The reaction solution was stirred at 0° C. for 3 hours, and after completion of the reaction, diethyl ether (100 mL) and distilled water (100 mL) were added to extract the organic layer. The obtained organic layer was dried over anhydrous magnesium sulfate, filtered, and then concentrated under reduced pressure to obtain Compound A-34b in the form of a white solid, which was used in the next reaction without an additional purification process (35 mg, 24%).

Steps 3 and 4: Preparation of Compound A-34

Compound A-34b (35 mg, 0.053 mmol) was dissolved in DMF (3 mL) under a nitrogen atmosphere at 0° C., and then SN-38 (CAS NO. 86639-52-3, 21 mg, 0.053 mmol) and TEA (18.7 L, 0.132 mmol) were sequentially added, and the mixture was stirred at 0° C. for 1 hour. After completion of the reaction, EA (50 mL) and 2N-hydrochloric acid aqueous solution (10 mL), distilled water (100 mL) were added to extract the organic layer. The obtained organic layer was dried over anhydrous magnesium sulfate, filtered, and then concentrated under reduced pressure to obtain Compound A-34c. The obtained Compound A-34c was dissolved by adding methanol (2 mL) and THE (1 mL), and then lithium hydroxide hydrate (22.5 mg, 0.53 mmol) was dissolved in distilled water (0.5 mL) and slowly added at 0° C., and the mixture was stirred for 30 minutes. The mixture was stirred at room temperature for an additional 30 minutes, and then 2N-hydrochloric acid aqueous solution (0.3 mL) was slowly added dropwise to terminate the reaction. The reaction solution was diluted with ACN (1 mL) and distilled water (1 mL), then separated and purified using Preparative-HPLC, and freeze-dried to obtain Compound A-34 (0.4 mg, 1%); EI-MS m/z: 825 [M+H]$^+$.

Example I-31: Preparation of Compound A-35

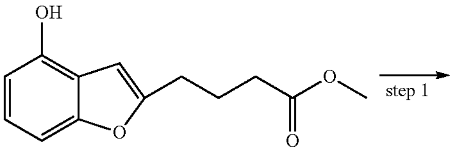

C-9

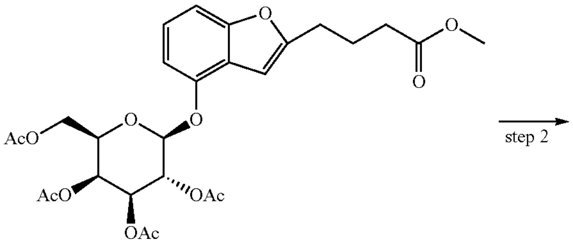

A-35a

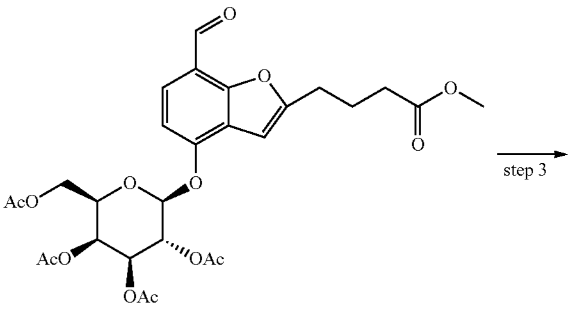

A-35b

-continued

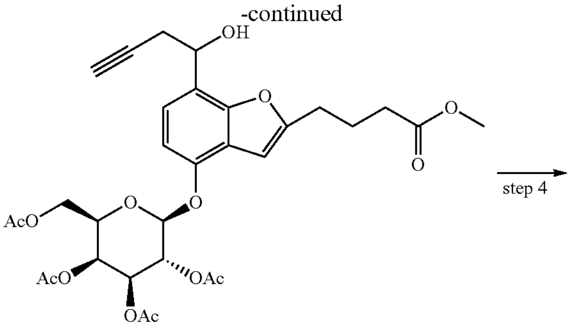

A-35c

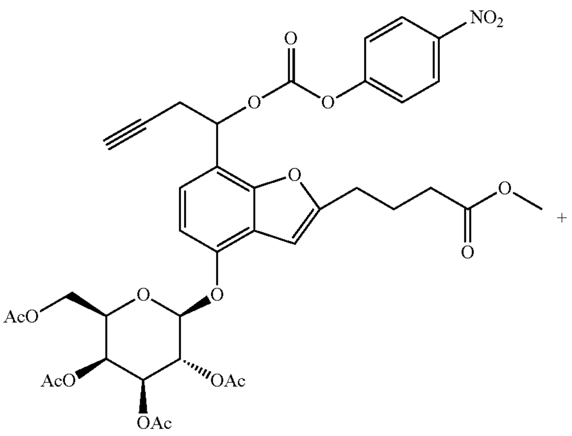

A-35d

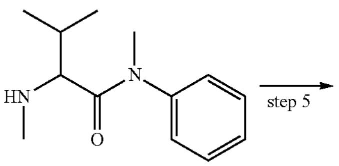

PL-1

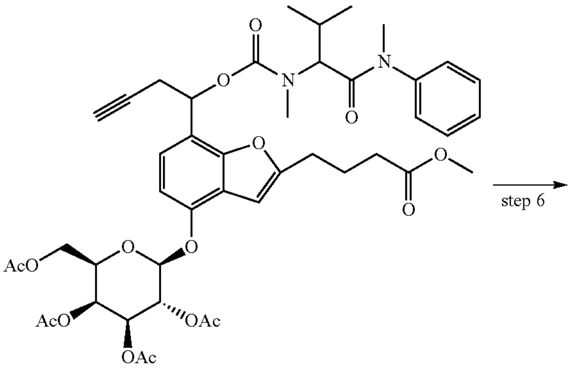

A-35e

-continued

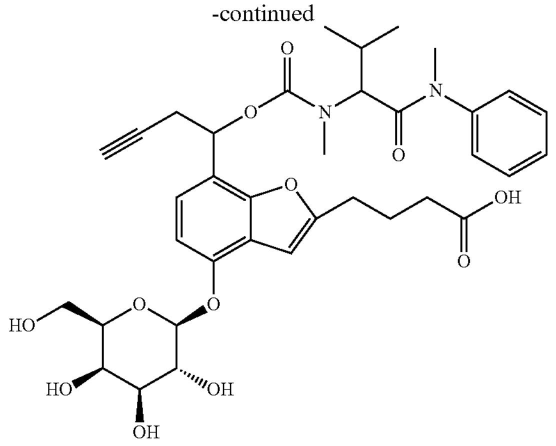

A-35

Step 1: Preparation of Compound A-35a

Core C-9 (572.6 mg, 2.44 mmol) was dissolved in MC (80 mL) under a nitrogen atmosphere at 0° C., and then aceto-bromo-alpha-D-galactose (1.1 g, 2.69 mmol) and benzyl-tributylammonium chloride (762.5 mg, 2.44 mmol) were added. 5N-sodium hydroxide aqueous solution (1.46 mL, 7.33 mmol) was slowly added to this reaction solution, and the mixture was stirred for 16 hours while slowly raising the temperature to room temperature. After completion of the reaction, MC (200 mL) and distilled water (200 mL) were added to extract the organic layer three times. The obtained organic layer was dried over anhydrous magnesium sulfate, filtered, and then concentrated under reduced pressure. The resulting residue was subjected to column chromatography to obtain Compound A-35a in the form of a solid (1.017 g, 74%).

$^1$H-NMR (400 MHz, $CDCl_3$) δ 7.17-7.10 (m, 2H), 6.80 (dd, J=7.6, 0.8 Hz, 1H), 6.42 (s, 1H), 5.57 (dd, J=10.4, 8 Hz, 1H), 5.48 (d, J=3.2 Hz, 1H), 5.15-5.10 (m, 2H), 4.28-4.23 (m, 1H), 4.20-4.16 (m, J=1H), 4.10-4.07 (m, 1H), 3.67 (s, 3H), 2.81 (t, J=7.2 Hz, 2H), 2.39 (t, J=7.2 Hz, 2H), 2.20 (s, 3H), 2.10-2.05 (m, 8H), 2.03 (s, 3H).

Step 2: Preparation of Compound A-35b

Compound A-35a (700 mg, 1.23 mmol) was dissolved in MC (40 mL) under a nitrogen atmosphere at −30° C., and then dichloromethyl methyl ether (450 μL, 4.92 mmol) and titanium tetrachloride solution (1M-$TiCl_4$ in MC, 4.9 mL, 4.92 mmol) were sequentially and slowly added, and the mixture was stirred for 2 hours while maintaining the temperature at −10° C. After completion of the reaction, distilled water (100 mL) was slowly added dropwise to terminate the reaction, and EA (100 mL) was added to extract the organic layer. The obtained organic layer was dried over anhydrous magnesium sulfate, filtered, and then concentrated under reduced pressure. The resulting residue was subjected to column chromatography to obtain Compound A-35b (190 mg, 25.8%).

$^1$H-NMR (400 MHz, $CDCl_3$) δ 10.33 (s, 1H), 7.69 (d, J=8.4 Hz, 1H), 6.88 (d, J=8.4 Hz, 1H), 6.49 (s, 1H), 5.59 (dd, J=10.4, 8 Hz, 1H), 5.49 (d, J=3.6 Hz, 1H), 5.23 (d, J=8 Hz, 1H), 5.16 (dd, J=10.4, 3.6 Hz, 1H), 4.27-4.14 (m, 3H), 3.68 (s, 3H), 2.89 (t, J=7.2 Hz, 2H), 2.42 (t, J=7.2 Hz, 2H), 2.20 (s, 3H), 2.11 (m, 2H), 2.07 (s, 3H), 2.06 (s, 3H), 2.03 (s, 3H).

Step 3: Preparation of Compound A-35c

Compound A-35b (190 mg, 0.32 mmol) was dissolved in anhydrous THE (3 mL) under a nitrogen atmosphere at room temperature, and then Zn powder (CAS NO. 7440-66-6, DAEJUNG, 105 mg, 3.2 mmol), 1,2-diiodoethane (CAS NO. 624-73-7, Alfa Aesar, 90.4 mg, 0.32 mmol), propargyl bromide (80% in toluene, 45.5 μL, 0.525 mmol) were sequentially added, and the mixture was reacted in an ultrasonic cleaner (powersonic 410) for 30 minutes through ultrasound. After completion of the reaction, the reaction solution was diluted with EA (50 mL), filtered using Celite, and extracted by adding distilled water (50 mL) and 2N-hydrochloric acid aqueous solution (0.7 mL). The obtained organic layer was dried over anhydrous magnesium sulfate, filtered, and then concentrated under reduced pressure. The resulting residue was subjected to column chromatography to obtain Compound A-35c in the form of a white solid (167 mg, 82.6%).

$^1$H-NMR (400 MHz, $CDCl_3$) δ 7.21 (m, 1H), 6.81-6.79 (m, 1H), 6.44 (s, 1H), 5.55 (dd, J=10.4, 8 Hz, 1H), 5.47 (d, J=3.2 Hz, 1H), 5.27 (m, 1H), 5.15-5.09 (m, 2H), 4.26-4.13 (m, 2H), 4.09 (m, 1H), 3.67 (s, 3H), 2.86-2.78 (m, 4H), 2.57 (dd, J=9.2, 4.8 Hz, 1H), 2.40 (m, 2H), 2.19 (s, 3H), 2.08-2.04 (m, 8H), 2.20 (s, 3H); MS m/z: 655 $[M+Na]^+$.

Step 4: Preparation of Compound A-35d

Compound A-35c (42 mg, 0.066 mmol) was dissolved in MC (2 mL) under a nitrogen atmosphere at 0° C., and then 4-nitrophenyl chloroformate (27 mg, 0.132 mmol) and pyridine (16 L, 0.2 mmol), DIPEA (11.6 μL, 0.066 mmol) were sequentially added, and the mixture was stirred for 1 hour. After completion of the reaction, the reaction solution was diluted with EA (50 mL), and distilled water (50 mL) and 2N-hydrochloric acid aqueous solution (2 mL) were added to extract the organic layer, and the extracted organic layer was dried over anhydrous magnesium sulfate, filtered, and then concentrated under reduced pressure. The residue thus obtained was subjected to column chromatography to obtain Compound A-35d (51 mg, 96.4%).

$^1$H-NMR (400 MHz, $CDCl_3$) δ 8.26 (d, J=9.2 Hz, 2H), 7.38 (d, J=9.2 Hz, 2H), 7.25 (m, 1H), 6.81 (dd, J=8.4, 2.4 Hz, 1H), 6.46 (s, 1H), 6.25 (m, 1H), 5.56 (dd, J=10.4, 8 Hz, 1H), 5.48 (d, J=2.8 Hz, 1H), 5.15-5.12 (m, 2H), 4.27-4.08 (m, 3H), 3.67 (s, 3H), 3.17-3.01 (m, 2H), 2.84 (t, J=7.2 Hz, 2H), 2.41 (t, J=7.2 Hz, 2H), 2.20 (s, 3H), 2.11-2.04 (m, 8H), 2.03 (s, 3H); MS m/z: 820 $[M+Na]^+$.

Step 5: Preparation of Compound A-35e

Compound A-35d (32 mg, 0.040 mmol) was dissolved in DMF (3 mL) under a nitrogen atmosphere at 0° C., and then Compound PL-1 (13.2 mg, 0.06 mmol), HOBt (5.4 mg, 0.04 mmol), pyridine (300 μL), DIPEA (14 μL, 0.08 mmol) were sequentially added, and the mixture was stirred for 30 minutes and then stirred at room temperature for an additional 12 hours. After completion of the reaction, extraction was performed using EA (50 mL) and 1N-hydrochloric acid aqueous solution (50 mL). The obtained organic layer was dried over anhydrous magnesium sulfate, filtered, and then concentrated under reduced pressure. The resulting residue was subjected to column chromatography to obtain Compound A-35e in the form of a white solid (27 mg, 77%); MS m/z: 901 $[M+Na]^+$.

Step 6: Preparation of Compound A-35

Compound A-35e (27 mg, 0.031 mmol) was dissolved in methanol (1 mL) and THE (0.5 mL) at 0° C., and then lithium hydroxide hydrate (19 mg, 0.461 mmol) dissolved in distilled water (0.2 mL) was added dropwise, and the mixture was stirred for 2.5 hours while slowly raising the temperature from 0° C. to room temperature. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and freeze-dried to obtain Compound A-35 in the form of a white solid (5.8 mg, 27%); EI-MS m/z: 719 $[M+Na]^+$.

Example I-32: Preparation of Compound A-36
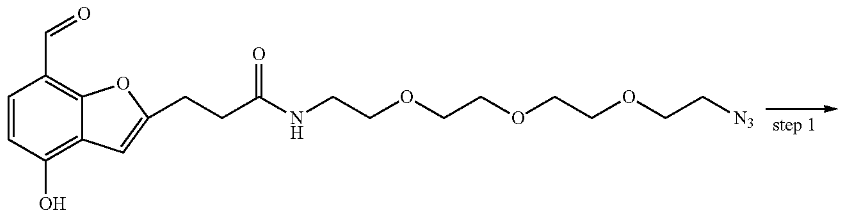
A-25b
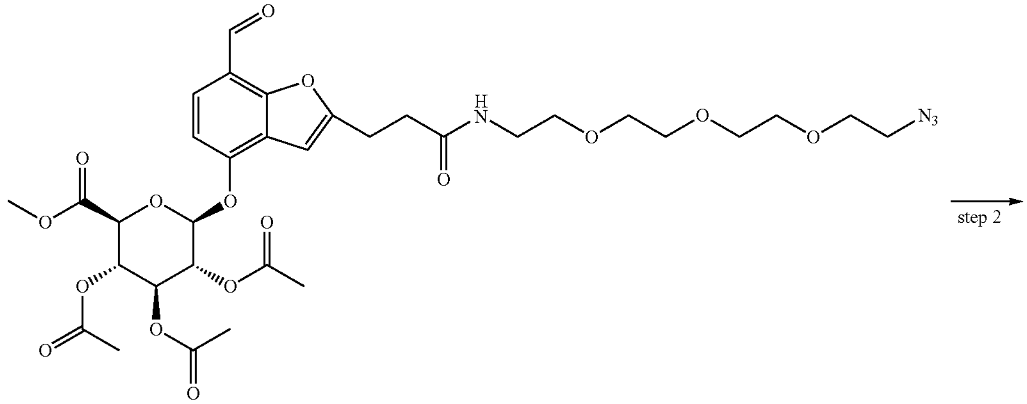
A-36a
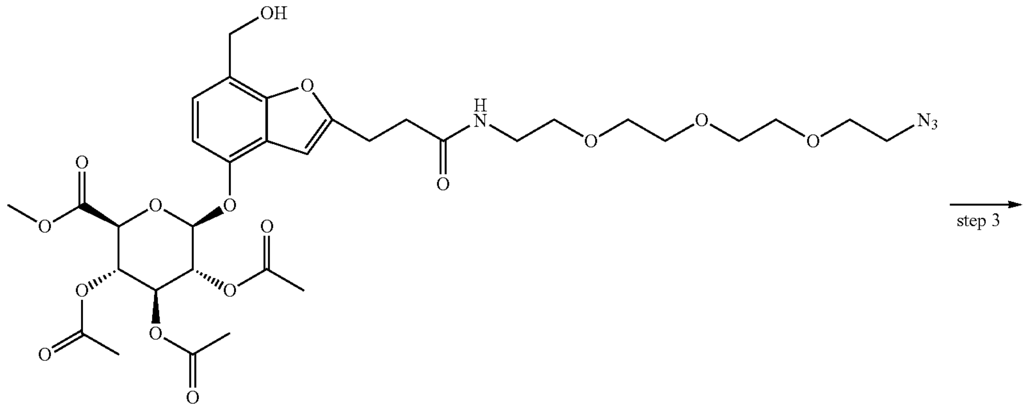
A-36b
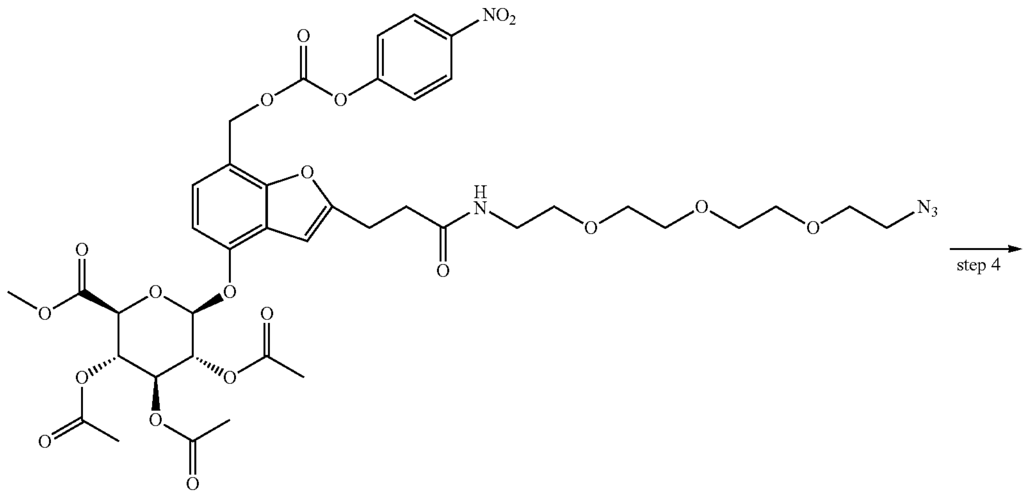
A-36c -continued

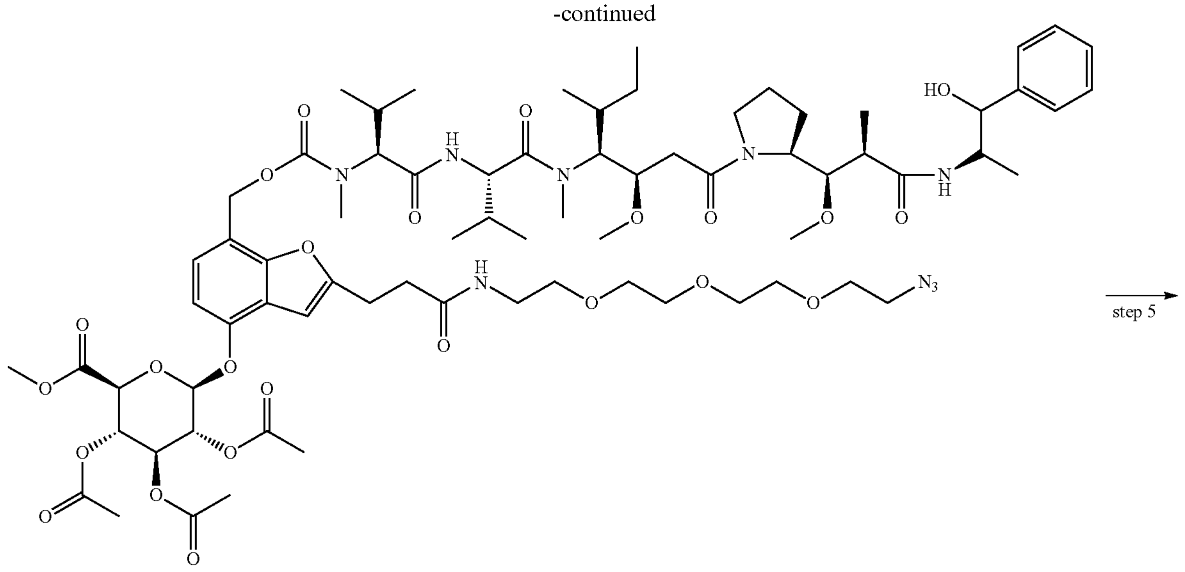

A-36d

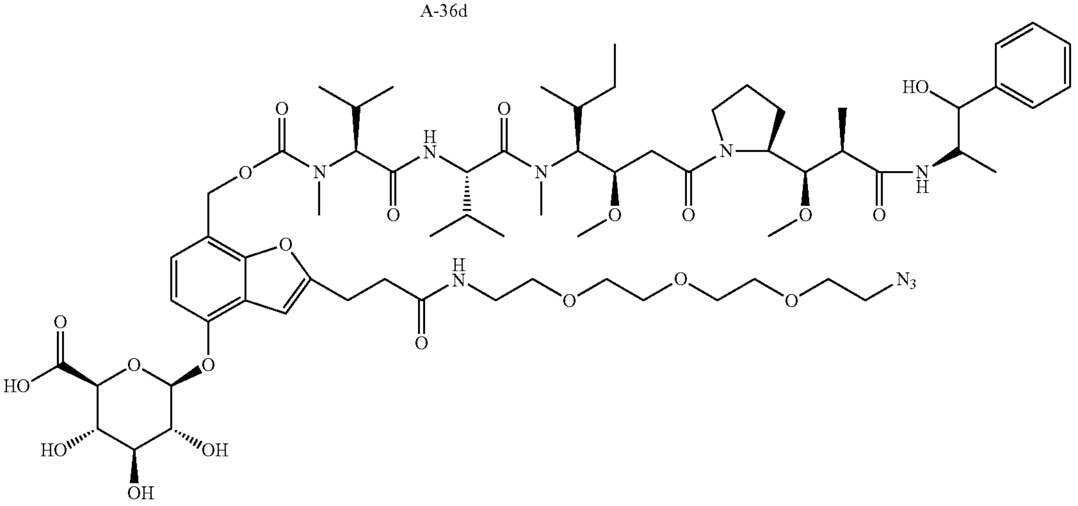

A-36

Step 1: Preparation of Compound A-36a

Compound A-25b (277 mg, 0.64 mmol) of Example I-24 was dissolved in MC (21 mL) under a nitrogen atmosphere at 0° C., and then acetobromo-a-D-glucuronic acid methyl ester (TCI, CAS No. 21085-72-3, 405 mg, 1.02 mmol), benzyltributylammonium chloride (199 mg, 0.64 mmol) and 5N-sodium hydroxide aqueous solution (0.53 mL, 2.55 mmol) were slowly added, and the mixture was stirred at 0° C. for 30 minutes and then stirred at room temperature for an additional 48 hours. After completion of the reaction, 2N-hydrochloric acid aqueous solution was added to the reaction solution to neutralize it, and MC (100 mL) and distilled water (100 mL) were added to extract the organic layer twice. The obtained organic layer was dried over anhydrous magnesium sulfate, filtered, and then concentrated under reduced pressure. The resulting residue was subjected to column chromatography to obtain Compound A-36a in the form of a yellow sticky gum (144 mg, 30%); EI-MS m/z: 751 $[M+H]^+$.

Step 2: Preparation of Compound A-36b

Compound A-36a (144 mg, 0.19 mmol) was dissolved in THE (10 mL) under a nitrogen atmosphere at 0° C., and then sodium borohydride (18 mg, 0.48 mmol) was added, and the mixture was stirred at 0° C. for 3 hours. After completion of the reaction, distilled water (50 mL) was added to terminate the reaction, and EA (50 mL) was added to extract the organic layer twice. The obtained organic layer was dried over anhydrous magnesium sulfate, filtered, and then concentrated under reduced pressure. The resulting residue was subjected to column chromatography to obtain Compound A-36b in the form of a colorless sticky gum (93.5 mg, 65%); EI-MS m/z: 753 $[M+H]^+$.

Step 3: Preparation of Compound A-36c

Compound A-36b (93.5 mg, 0.12 mmol) was dissolved in MC (5 mL) under a nitrogen atmosphere at 0° C., and then 4-nitrophenyl chloroformate (50.1 mg, 0.25 mmol), pyridine (30 μL, 0.37 mmol) and DIPEA (32.4 μL, 0.18 mmol) were sequentially added, and the mixture was stirred at 0° C. for 30 minutes and stirred at room temperature for an additional 2.5 hours. After completion of the reaction, the reaction solution was diluted with EA (50 mL), and 2N-hydrochloric acid aqueous solution (50 mL) was added to extract the organic layer. The obtained organic layer was dried over anhydrous magnesium sulfate, filtered, and then concentrated under reduced pressure. The residue thus obtained was subjected to column chromatography to obtain Compound A-36c (80.3 mg, 70%); EI-MS m/z: 918 [M+H]$^+$.

Step 4: Preparation of Compound A-36d

Compound A-36c (80.3 mg, 0.087 mmol) was dissolved in DMF (1 mL) under a nitrogen atmosphere at 0° C., and then MMAE (monomethyl auristatin E, CAS NO. 474645-27-7, 62.8 mg, 0.087 mmol), HOBt (17.7 mg, 0.131 mmol), DIPEA (38.1 μL, 0.218 mmol) and pyridine (1 mL) were sequentially added, and the mixture was stirred at room temperature for 16 hours. After completion of the reaction, the organic layer was extracted twice with EA (50 mL) and 2N-hydrochloric acid aqueous solution (50 mL). The obtained organic layer was dried over anhydrous magnesium sulfate, filtered, and then concentrated under reduced pressure. The resulting residue was separated and purified using Preparative-HPLC, and then freeze-dried to obtain Compound A-36d in the form of a white solid (42 mg, 32%); EI-MS m/z: 1497 [M+H]$^+$.

Step 5: Preparation of Compound A-36

Compound A-36d (42 mg, 0.028 mmol) was dissolved by mixing and adding methanol (0.7 mL), distilled water (0.35 mL) and THE (0.14 mL) at −20° C., and then lithium hydroxide (2.9 mg, 0.07 mmol) dissolved in distilled water (0.35 mL) was added dropwise, and the mixture was stirred for 1 hour while slowly raising the temperature from −20° C. to −5° C. After completion of the reaction, 2N-hydrochloric acid aqueous solution (0.2 mL) was added to terminate the reaction, and the reaction solution was diluted with ACN (1 mL) and distilled water (1 mL), then separated and purified using Preparative-HPLC, and freeze-dried to obtain Compound A-36 in the form of a white solid (29.1 mg, 76%); EI-MS m/z: 1357 [M+H]$^+$.

Example I-33: Preparation of Compound A-37

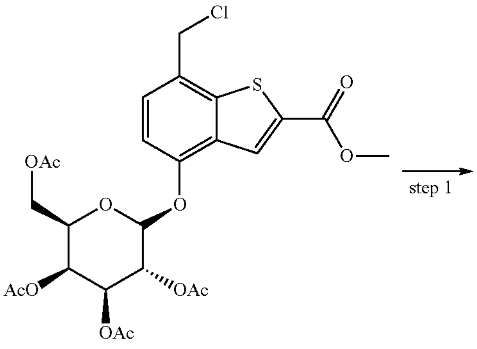

A-33a

-continued

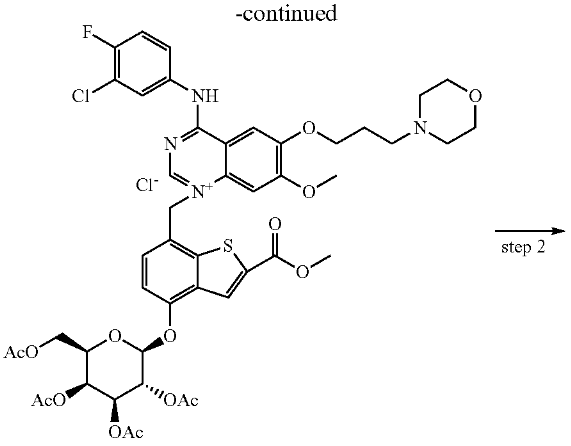

A-37a

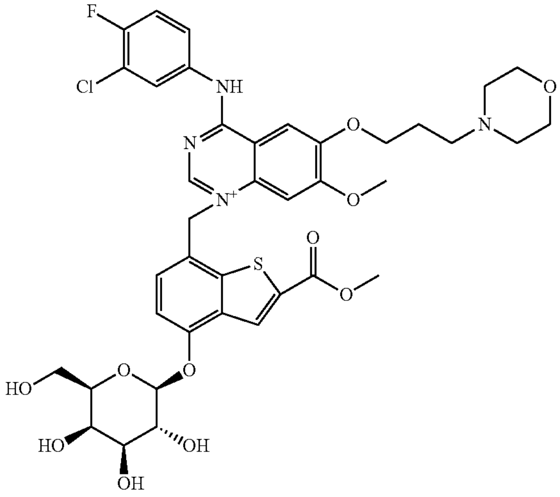

A-37

Step 1: Preparation of Compound A-37a

Compound A-33a (20 mg, 0.034 mmol) was dissolved in DMF (2 mL) under a nitrogen atmosphere at room temperature, and then Gefitinib (CAS No.: 18447535-2, 15.2 mg, 0.034 mmol), KI (potassium iodide, 1.7 mg, 0.01 mmol) and DIPEA (14.83 μL, 0.085 mmol) were sequentially added to the reaction, and the mixture was stirred at 60° C. for 15 hours. After completion of the reaction, 2N-hydrochloric acid aqueous solution (10 μL) was added to neutralize it, and the reaction solution was diluted with ACN (1 mL) and distilled water (1 mL), then separated and purified using Preparative-HPLC, and freeze-dried to obtain Compound A-37a (8.4 mg, 24%); EI-MS m/z: 998 [M+H]$^+$.

Step 2: Preparation of Compound A-37

Compound A-37a (3.6 mg, 0.0035 mmol) was dissolved in methanol (1 mL) and THF (0.5 mL) at 0° C., and then lithium hydroxide hydrate (1.5 mg, 0.035 mmol) dissolved in distilled water (0.3 mL) was added dropwise, and the mixture was stirred at 0° C. for 30 minutes. After completion of the reaction, 2N-hydrochloric acid aqueous solution (10 μL) was added to terminate the reaction, and the reaction solution was diluted with ACN (1 mL) and distilled water (1 mL), then separated and purified using Preparative-HPLC, and freeze-dried to obtain Compound A-37 (1.5 mg, 50%); EI-MS m/z: 830 [M+H]$^+$.

Example I-34: Preparation of Compound A-38
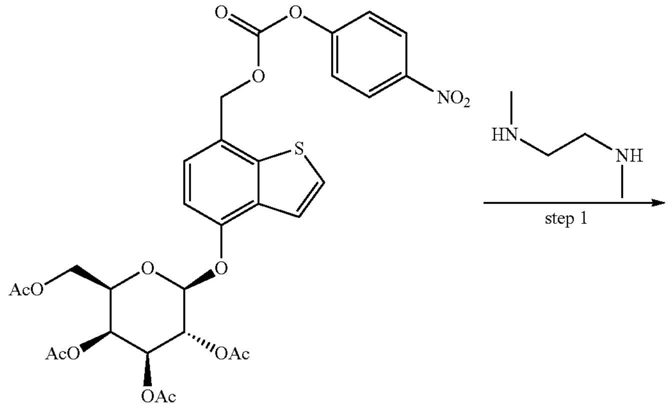
A-10c
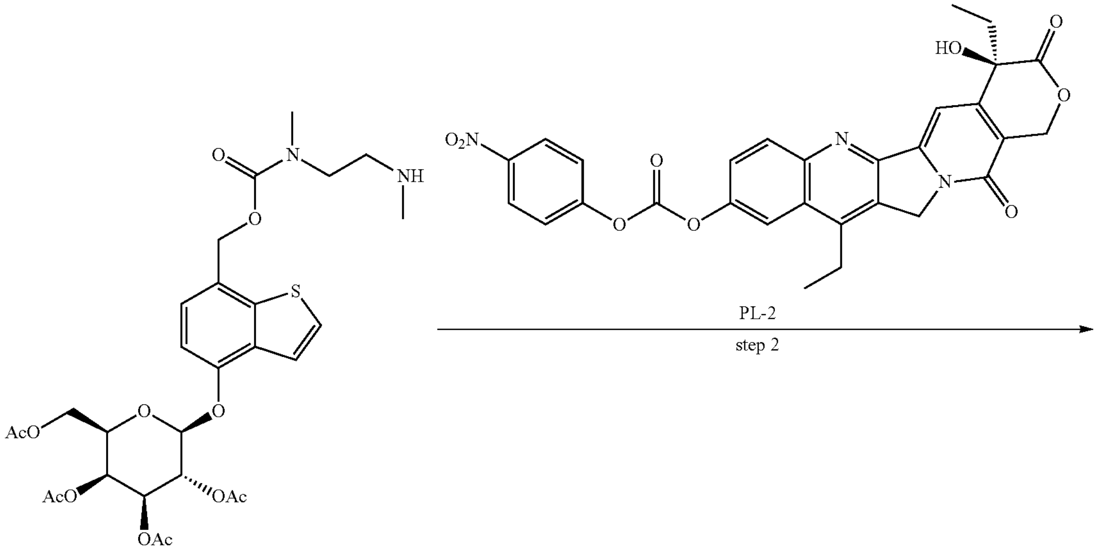
A-38a
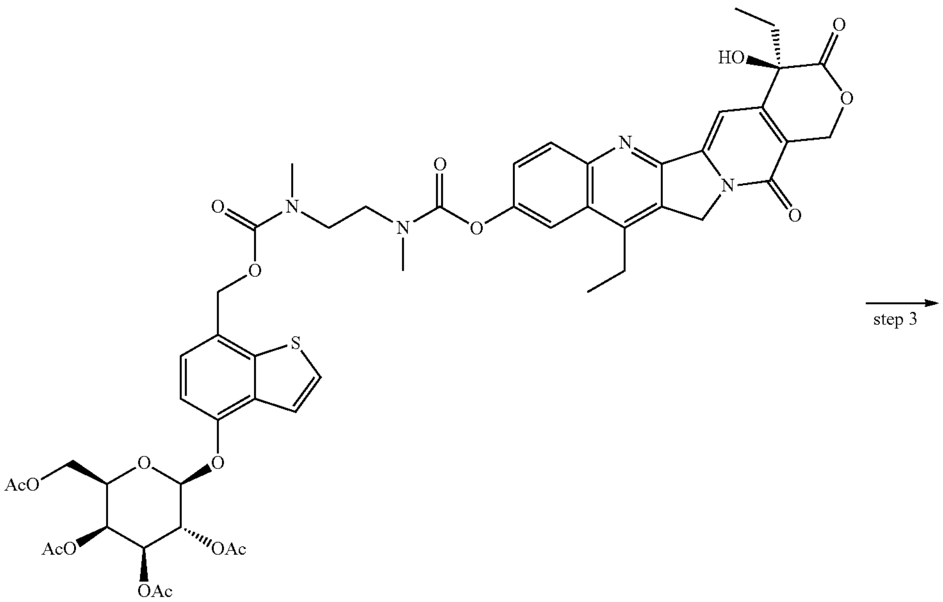
A-38b -continued

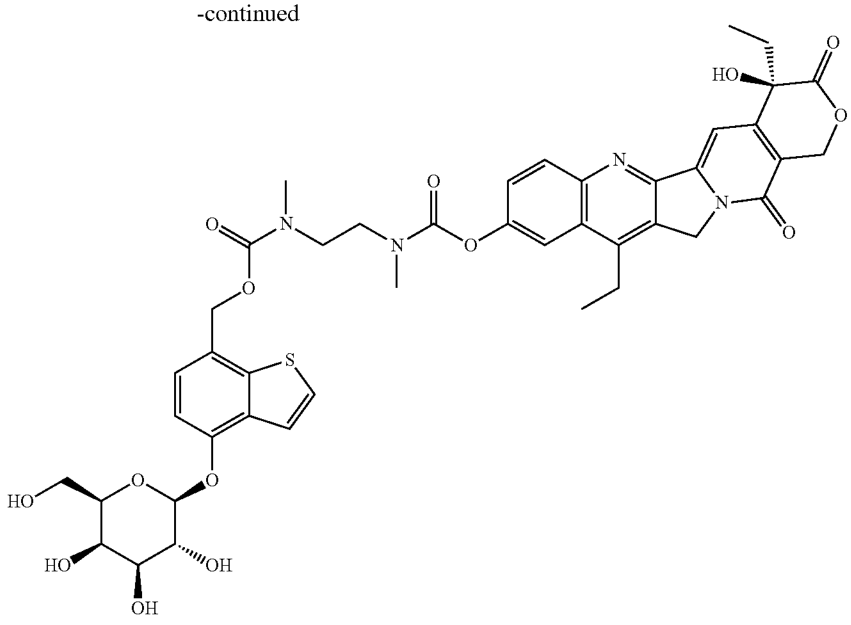

A-38

Step 1: Preparation of Compound A-38a

Compound A-38c (20.0 mg, 0.029 mmol) was dissolved in MC (3.0 mL) under a nitrogen atmosphere at 0° C., and then N,N'-dimethylethyl enediamine (TC, CAS NO. 110-70-3, 31 μL, 0.29 mmol) was added dropwise, and the mixture was stirred at room temperature for 1 hour. After completion of the reaction, 2N-hydrochloric acid aqueous solution was slowly added dropwise to adjust the pH of the reaction solution to 7, and then the reaction solution was separated and purified using Preparative-HPLC, and freeze-dried to obtain Compound A-38a in the form of a white solid (8.5 mg, 24%); EI-MS m/z: 625 $[M+H]^+$.

Step 2: Preparation of Compound A-38b

Compound A-38a (8.5 mg, 0.013 mmol) was dissolved in DMF (2.0 mL) under a nitrogen atmosphere at 01C, and then Compound PL-2 (7.5 mg, 0.013 mmol) and DTPEA (2.37 μL, 0.013 mmol) were sequentially added, and the mixture was stirred at room temperature for 2 hours. After completion of the reaction, EA (10 mL) and distilled water (10 mL) were added to extract the organic layer. The obtained organic layer was dried over anhydrous magnesium sulfate, filtered, and then concentrated under reduced pressure. The resulting residue was subjected to column chromatography to obtain Compound A-38b in the form of a transparent oil (10.0 mg, 71%~); EI-MS m/z: 1044 $[M+H]^+$.

Step 3: Preparation of Compound A-38

Compound A-38b (8.5 mg, 0.013 mmol) was dissolved in methanol (1.0 mL) under a nitrogen atmosphere at 0° C., and then potassium carbonate (9.27 mg, 0.067 mmol) dissolved in distilled water (500.0 μL) was slowly added dropwise, and the mixture was stirred at 0° C. for 2 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-38 in the form of a white solid (1.5 mg, 18%); EI-MS m/z: 875 $[M+H]^+$.

Example I-35: Preparation of Compound A-39

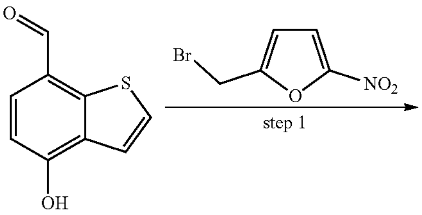

C-3

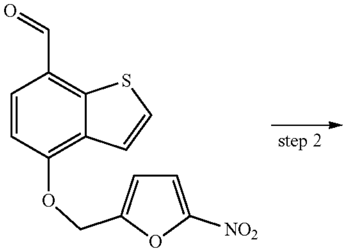

A-39a

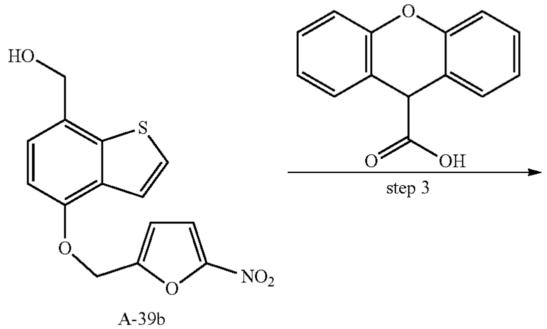

A-39b

-continued

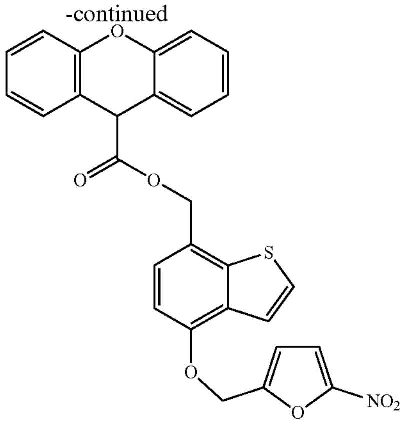

A-39

Step 1: Preparation of Compound A-39a

Core C-3 (55.0 mg, 0.308 mmol) was dissolved in ACN (5.0 mL) under a nitrogen atmosphere at 0° C., and then 2-(bromomethyl)-5-nitrofuran (Sigma Aldrich, CAS NO. 20782-91-6, 76.3 mg, 0.370 mmol) and potassium carbonate (85.1 mg, 0.616 mmol) were sequentially added, and the mixture was stirred at room temperature for 16 hours. After completion of the reaction, EA (10 mL) and distilled water (10 mL) were added to extract the organic layer. The obtained organic layer was dried over anhydrous magnesium sulfate, filtered, and then concentrated under reduced pressure. The resulting residue was subjected to column chromatography to obtain Compound A-39a in the form of a yellow solid (90.0 mg, 96%).

$^1$H-NMR (400 MHz, $CDCl_3$) δ 10.11 (s, 1H), 7.86 (d, J=8.0 Hz, 1H), 7.58 (s, 2H), 7.33 (d, J=3.6 Hz, 1H), 7.00 (d, J=8.0 Hz, 1H), 6.74 (d, J=3.6 Hz, 1H), 5.36 (s, 2H).

Step 2: Preparation of Compound A-39b

Compound A-39a (90.0 mg, 0.297 mmol) was dissolved in THE (10.0 mL) under a nitrogen atmosphere at 0° C., and then sodium borohydride (28.0 mg, 0.742 mmol) was added, and the mixture was stirred at 0° C. for 3 hours. After completion of the reaction, EA (30 mL) and distilled water (30 mL) were added to extract the organic layer. The obtained organic layer was dried over anhydrous magnesium sulfate, filtered, and then concentrated under reduced pressure. The resulting residue was subjected to column chromatography to obtain Compound A-39b in the form of a yellow solid (30.0 mg, 33%).

$^1$H-NMR (400 MHz, $CDCl_3$) δ 7.54 (d, J=5.6 Hz, 1H), 7.41 (d, J=5.6 Hz, 1H), 7.31-7.28 (m, 2H), 6.81 (d, J=8.0 Hz, 1H), 6.67 (d, J=3.6 Hz, 1H), 5.25 (s, 2H), 4.92 (d, J=5.6 Hz, 2H), 1.73 (t, J=5.6 Hz, 1H).

Step 3: Preparation of Compound A-39

Compound A-39b (20.0 mg, 0.065 mmol) and xanthene-9-carboxylic acid (Alfa Aesar, CAS NO. 82-07-5, 16.3 mg, 0.072 mmol) were dissolved in DMF (3.0 mL) under a nitrogen atmosphere at 0° C., and then EDCI hydrochloride (18.8 mg, 0.098 mmol), DMAP (0.8 mg, 0.006 mmol) and DIPEA (34.0 μL, 0.196 mmol) were sequentially added, and the mixture was stirred for 16 hours while slowly raising the temperature from 0° C. to room temperature. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-39 in the form of an ivory solid (2.3 mg, 6.8%).

$^1$H-NMR (400 MHz, DMSO) δ 7.73-7.71 (m, 2H), 7.51 (d, J=5.6 Hz, 1H), 7.39-7.32 (m, 4H), 7.26 (d, J=8.0 Hz, 1H), 7.18 (d, J=8.0 Hz, 2H), 7.15-7.04 (m, 4H), 5.43 (s, 2H), 5.30-5.26 (m, 3H); EI-MS m/z: 536 [M+Na]$^+$.

Example I-36: Preparation of Compound A-40

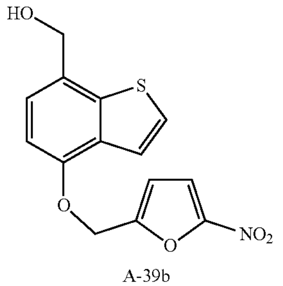

A-39b

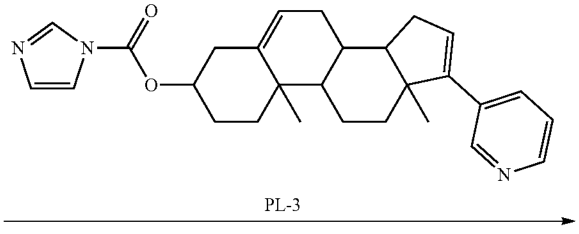

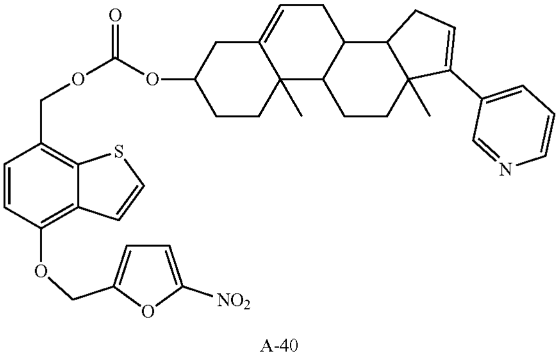

A-40

Compound A-39b (9.1 mg, 0.029 mmol) was dissolved in THE (2.0 mL) under a nitrogen atmosphere at 0° C., and then Compound PL-3 and sodium hydride (60% dispersion in mineral oil, 1.44 mg, 0.036 mmol) were sequentially added, and the mixture was stirred at 0° C. for 7 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-40 in the form of a white solid (5.1 mg, 2.5%).

$^1$H-NMR (400 MHz, $CDCl_3$) δ 8.49 (s, 1H), 8.33 (s, 1H), 7.51 (d, J=8.0 Hz, 1H), 7.41 (d, J=5.6 Hz, 1H), 7.28 (d, J=5.6 Hz, 1H), 7.22-7.18 (m, 2H), 7.13-7.09 (m, 1H), 6.68 (d, J=8.0 Hz, 1H), 6.55 (d, J=3.6 Hz, 1H), 5.86 (s, 1H), 5.31-5.30 (m, 1H), 5.24 (s, 2H), 5.12 (s, 2H), 4.40-4.37 (m, 1H), 2.17-2.11 (m, 3H), 1.97-1.73 (m, 5H), 1.67-1.30 (m, 10H), 0.93 (s, 3H), 0.91 (s, 3H); EI-MS m/z: 681 $[M+H]^+$.

Example I-37: Preparation of Compound A-41

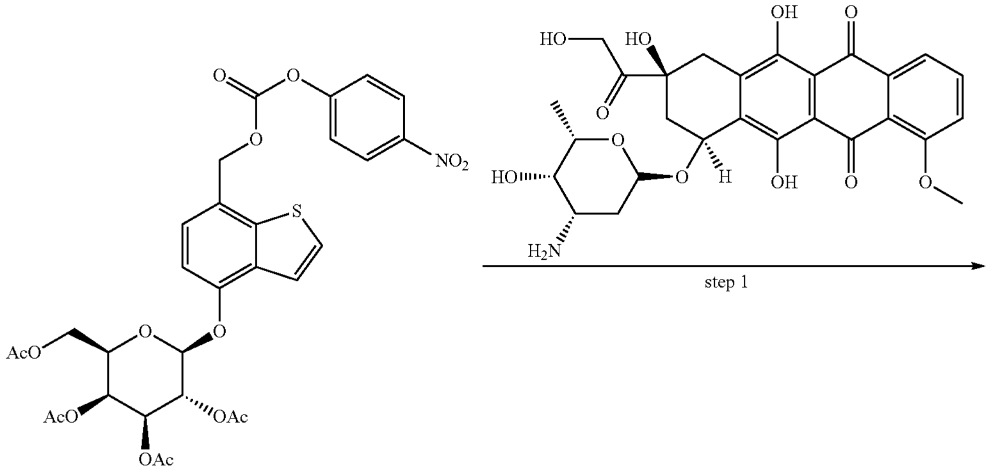

A-10c

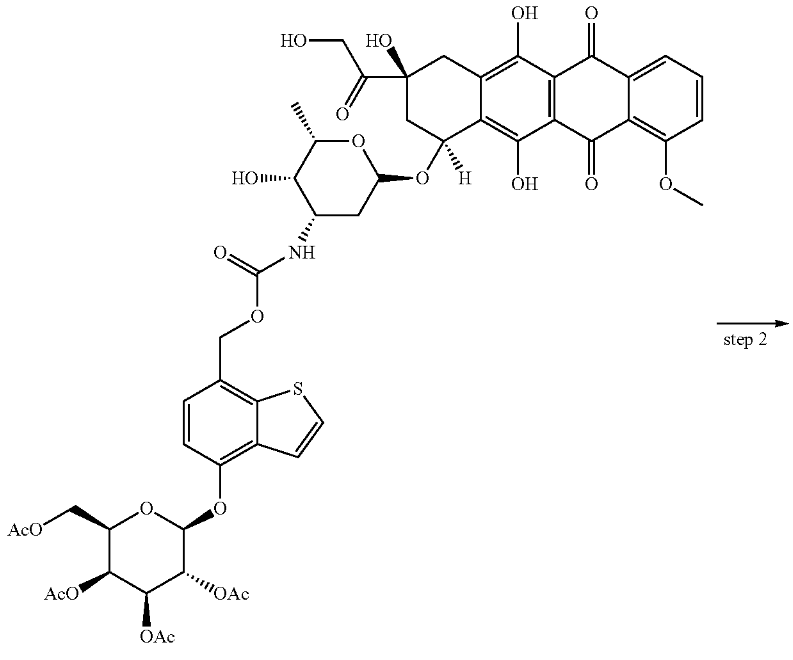

A-41a

-continued

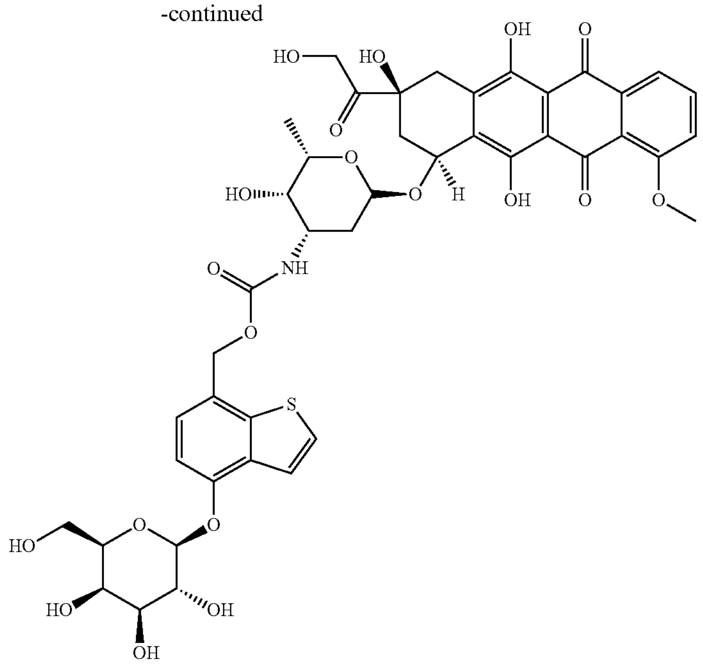

A-41

Step 1: Preparation of Compound A-41a

Compound A-10c (20.0 mg, 0.029 mmol) was dissolved in DMF (3.0 mL) under a nitrogen atmosphere at 0° C., and then Doxorubicin (Sigma Aldrich, CAS NO. 23214-92-8, 19.3 mg, 0.035 mmol) and DIPEA (7.6 μL, 0.043 mmol) were sequentially added, and the mixture was stirred at 0° C. for 4 hours. After completion of the reaction, EA (20 mL) and distilled water (20 mL) were added to extract the organic layer. The obtained organic layer was dried over anhydrous magnesium sulfate, filtered, and then concentrated under reduced pressure. The resulting residue was subjected to column chromatography to obtain Compound A-41a in the form of a red solid (12.0 mg, 38%); EI-MS m/z: 1102 $[M+Na]^+$.

Step 2: Preparation of Compound A-41

Compound A-41a (12.0 mg, 0.011 mmol) was dissolved in methanol (1.0 mL) and THE (0.5 mL) under a nitrogen atmosphere at 0° C., and then potassium carbonate (10.7 mg, 0.077 mmol) dissolved in distilled water (200.0 μL) was slowly added dropwise, and the mixture was stirred at 0° C. for 2 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-41 in the form of a red solid (0.3 mg, 2.9%); EI-MS m/z: 934 $[M+Na]^+$.

Example I-38: Preparation of Compound A-42

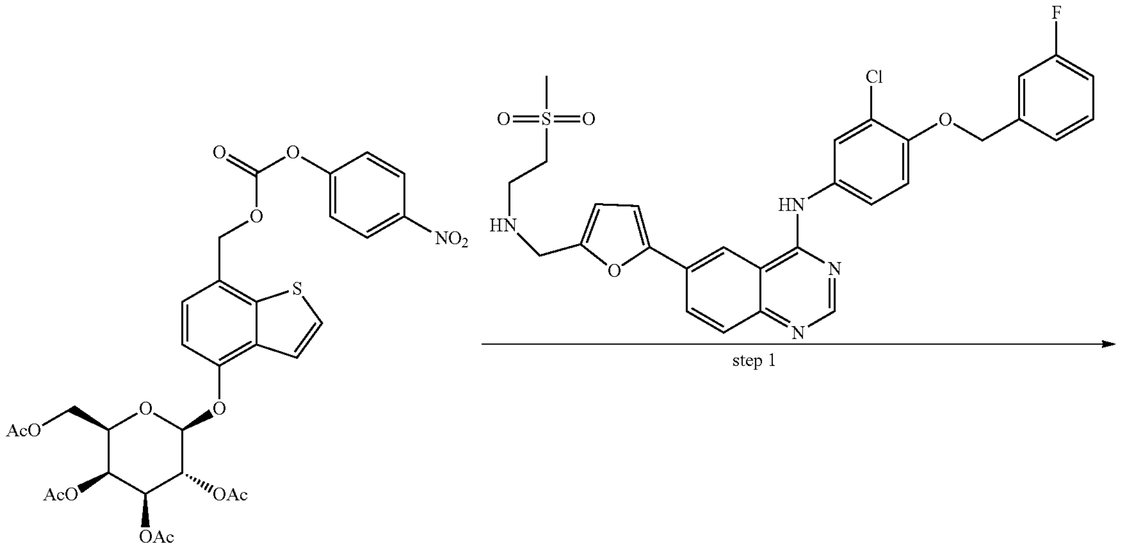

A-10c

-continued

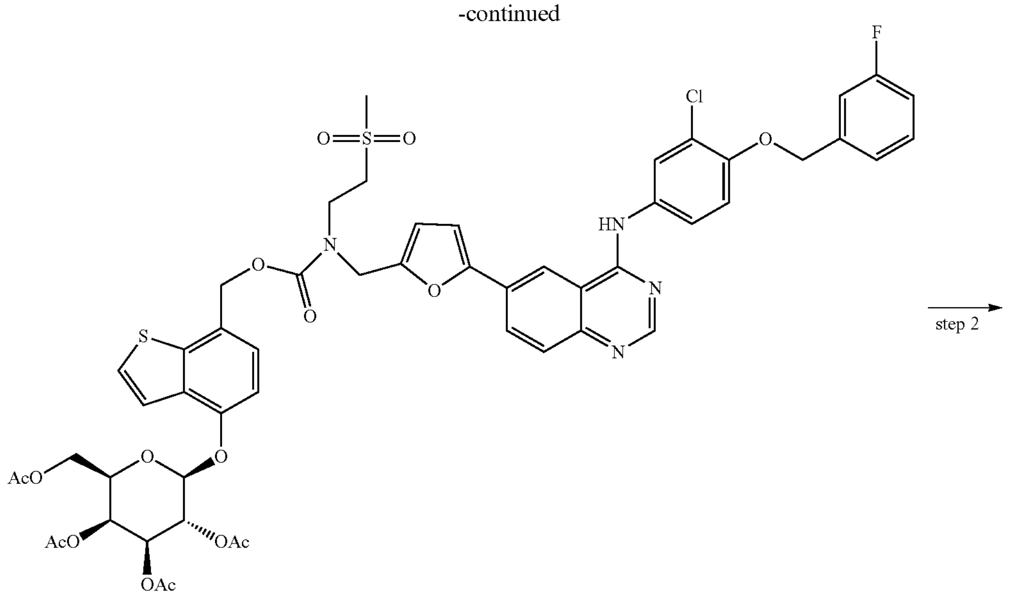

A-42a

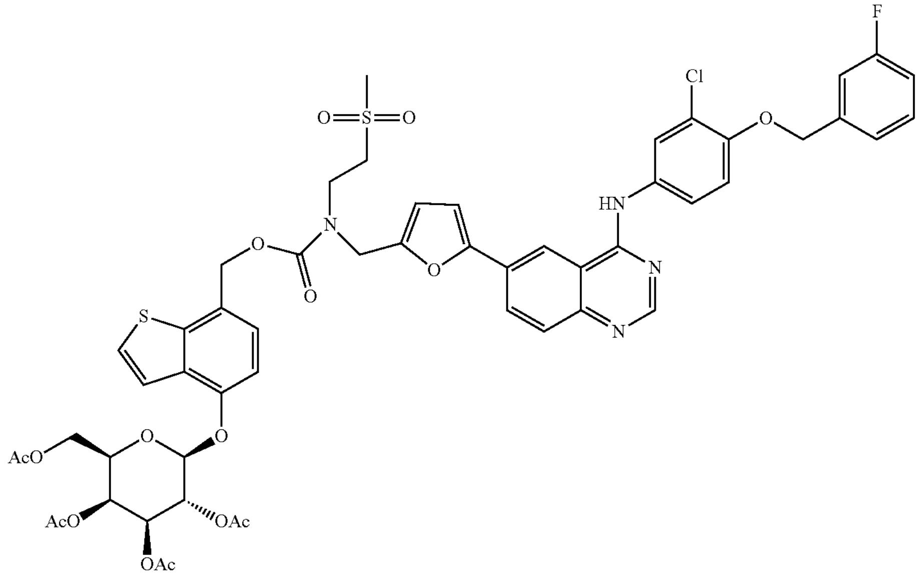

A-42

Step 1: Preparation of Compound A-42a

Compound A-10c (18.2 mg, 0.027 mmol) was dissolved in DMF (2.0 mL) under a nitrogen atmosphere, and then lapatinib (TCI, CAS NO. 231277-92-2, 15.6 mg, 0.027 mmol) and DIPEA (12.0 μL, 0.067 mmol) were sequentially added dropwise, and the mixture was stirred at room temperature for 48 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-42a in the form of a white solid (7.0 mg, 23%); EI-MS m/z: 1118 $[M+H]^+$.

Step 2: Preparation of Compound A-42

Compound A-42a (7.0 mg, 0.006 mmol) was dissolved in methanol (1.0 mL) and THF (0.5 mL) under a nitrogen atmosphere at 0° C., and then potassium carbonate (6.0 mg, 0.044 mmol) dissolved in distilled water (200.0 μL) was slowly added dropwise, and the mixture was stirred at 0° C. for 30 minutes. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-42 in the form of a white solid (3.7 mg, 62%); EI-MS m/z: 949 $[M+H]^+$.

Example I-39: Preparation of Compound A-43

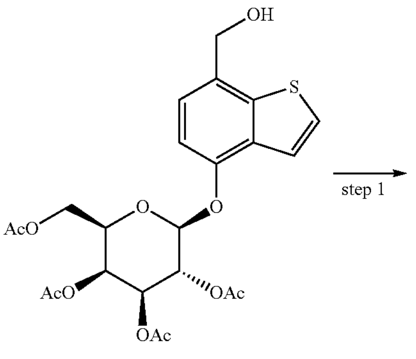

A-10b

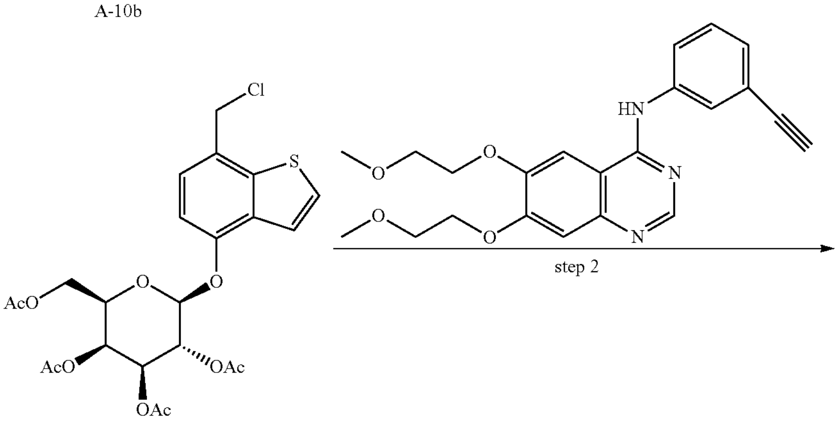

A-43a

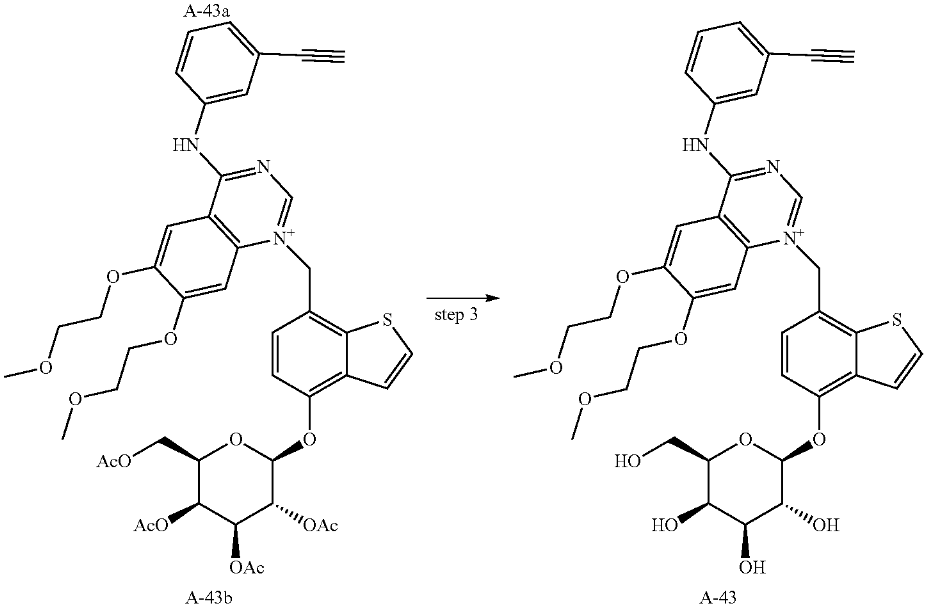

A-43b A-43

Step 1: Preparation of Compound A-43a

Compound A-10b (69.0 mg, 0.135 mmol) was dissolved in MC (2.0 mL) under a nitrogen atmosphere at 0° C., and then thionyl chloride (21.6 μL, 0.296 mmol) was slowly added dropwise, and the mixture was stirred at 0° C. for 3 hours. After completion of the reaction, MC (20 mL) and distilled water (20 mL) were added to extract the organic layer. The obtained organic layer was dried over anhydrous magnesium sulfate, filtered, and then concentrated under reduced pressure. The resulting residue was subjected to column chromatography to obtain Compound A-43a in the form of a white solid (62.0 mg, 87%).

$^1$H-NMR (400 MHz, $CDCl_3$) δ 7.46-7.42 (m, 2H), 7.30 (d, J=8.0 Hz, 1H), 6.93 (d, J=8.0 Hz, 1H), 5.63 (dd, J=10.4 Hz, J=8.0 Hz, 1H), 5.50 (d, J=3.2 Hz 1H), 5.17-5.13 (m, 2H), 4.83 (s, 2H), 4.28-4.24 (m, 1H), 4.21-4.18 (m, 1H), 4.16-4.11 (m, 1H), 2.20 (s, 3H), 2.08 (s, 3H), 2.04 (s, 3H), 2.03 (s, 3H).

Step 2: Preparation of Compound A-43b

Compound A-43a (21.0 mg, 0.040 mmol) was dissolved in DMF (1.0 mL) under a nitrogen atmosphere at 0° C., and then erlotinib (Sigma-Aldrich, CAS No. 183319-69-9, 20.6 mg 0.048 mmol) and potassium iodide (0.6 mg, 0.004 mmol) were sequentially added dropwise, and the mixture was stirred at 80° C. for 16 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-43b in the form of a white solid (2.2 mg, 62%).

$^1$H-NMR (400 MHz, DMSO) δ 8.25 (s, 1H), 7.80 (d, J=5.6 Hz, 1H), 7.64 (s, 1H), 7.40 (d, J=4.4 Hz, 1H), 7.27-7.23 (m, 2H), 7.12 (s, 1H), 7.07-7.04 (m, 3H), 6.77 (s, 1H), 5.57-5.53 (m, 3H), 5.39-5.31 (m, 3H), 4.47 (t, J=6.4 Hz, 1H), 4.13-4.12 (m, 4H), 4.07 (s, 1H), 3.94 (t, J=4.4 Hz, 2H), 3.66 (t, J=4.4 Hz, 2H), 3.42 (t, J=4.4 Hz, 2H), 3.29 (s, 3H), 3.16 (s, 3H), 2.15 (s, 3H), 2.00 (s, 6H), 1.96 (s, 3H); EI-MS m/z: 887 $[M+H]^+$.

Step 3: Preparation of Compound A-43

Compound A-43b (5.0 mg, 0.0056 mmol) was dissolved in methanol (1.0 mL) under a nitrogen atmosphere at 0° C., and then potassium carbonate (5.45 mg, 0.039 mmol) dissolved in distilled water (200.0 μL) was slowly added dropwise, and the mixture was stirred at 0° C. for 2 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-43 in the form of a white solid (2.2 mg, 54%).

$^1$H-NMR (400 MHz, DMSO) δ 8.29 (s, 1H), 8.26 (s, 1H), 7.71 (d, J=5.6 Hz, 1H), 7.66-7.63 (m, 2H), 7.34 (d, J=8.0 Hz, 1H), 5.67 (t, J=8.0 Hz, 1H), 7.13-7.09 (m, 2H), 7.08-7.03 (m, 2H), 6.81-6.77 (m, 1H), 5.55 (s, 2H), 4.89 (d, J=8.0 Hz, 1H), 4.11 (t, J=4.4 Hz, 2H), 4.06 (s, 1H), 3.93 (t, J=4.4 Hz, 2H), 3.73-3.44 (m, 9H), 3.29 (s, 3H), 3.18 (s, 3H); EI-MS m/z: 719 $[M+H]^+$.

Example I-40: Preparation of Compound A-44

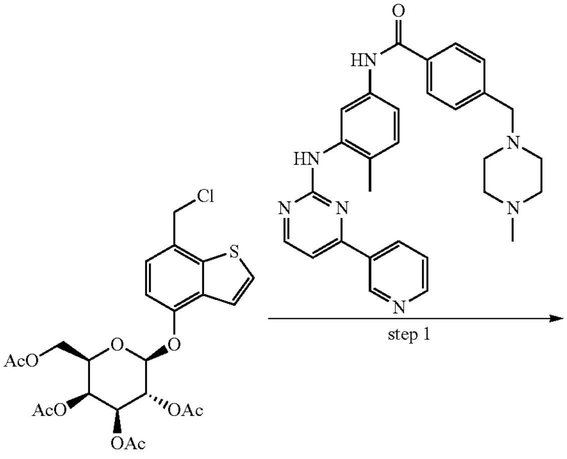

A-43a

-continued

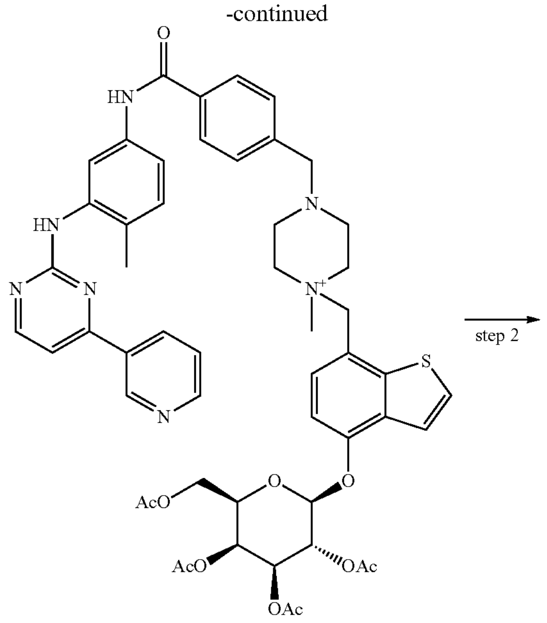

A-44a

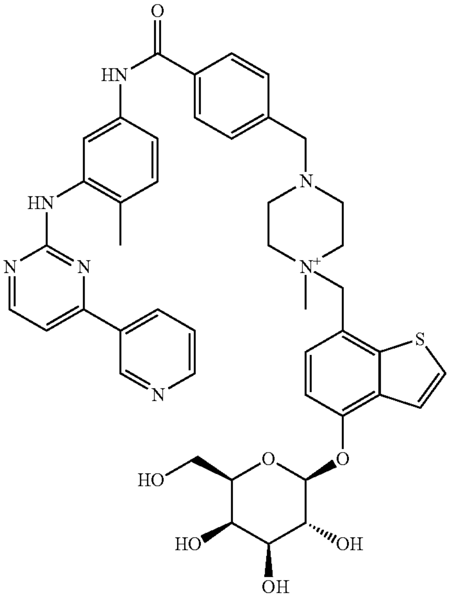

A-44

Step 1: Preparation of Compound A-44a

Compound A-43a (36.2 mg, 0.068 mmol) was dissolved in DMF (1.0 mL) under a nitrogen atmosphere at 0° C., and then imatinib (TCI, CAS No. 152459-95-5, 40.5 mg 0.082 mmol) and potassium iodide (1.1 mg, 0.006 mmol) were sequentially added dropwise, and the mixture was stirred at 80° C. for 16 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-44a in the form of a white solid (18.0 mg, 26%).

$^1$H-NMR (400 MHz, DMSO) δ 10.24 (s, 1H), 9.27 (d, J=3.2 Hz, 1H), 8.99 (s, 1H), 8.68 (dd, J=8.0 Hz, J=3.2 Hz 1H), 8.54 (s, 1H), 8.51 (d, J=5.6 Hz, 1H), 8.47 (dt, J=8.0 Hz, J=3.2 Hz, 1H), 8.08 (s, 1H), 7.96 (d, J=8.0 Hz, 2H), 7.89 (d,

J=5.6 Hz, 1H), 7.62 (d, J=8.4 Hz, 1H), 7.53-7.42 (m, 5H), 7.29 (d, J=5.6 Hz, 1H), 7.21 (d, J=8.4 Hz, 1H), 7.15 (d, J=8.4 Hz, 1H), 5.65 (d, J=10.8 Hz, 1H), 5.40-5.35 (m, 3H), 4.86 (s, 2H), 4.55 (t, J=6.4 Hz, 1H), 4.16-4.13 (m, 2H), 3.71 (s, 2H), 3.65-3.62 (m, 2H), 3.51-3.48 (m, 2H), 3.06 (s, 3H), 2.91-2.88 (m, 2H), 2.74-2.68 (m, 2H), 2.22 (s, 3H), 2.16 (s, 3H), 2.03 (s, 3H), 1.98 (s, 3H); EI-MS m/z: 988 $[M+H]^+$, 494 1/2 $[M+H]^+$.

Step 2: Preparation of Compound A-44

Compound A-44a (18.0 mg, 0.018 mmol) was dissolved in methanol (1.0 mL) under a nitrogen atmosphere at 0° C., and then potassium carbonate (17.6 mg, 0.127 mmol) dissolved in distilled water (200.0 μL) was slowly added dropwise, and the mixture was stirred at 0° C. for 30 minutes. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-44 in the form of a white solid (7.0 mg, 46%).

$^1$H-NMR (400 MHz, DMSO) δ 10.23 (s, 1H), 9.27 (d, J=1.6 Hz, 1H), 8.98 (s, 1H), 8.68 (dd, J=5.6 Hz, J=1.6 Hz, 1H), 8.51 (d, J=5.6 Hz, 1H), 8.48-8.46 (m, 2H), 8.08 (s, 1H), 7.96 (d, J=5.6 Hz, 2H), 7.80 (d, J=5.6 Hz, 1H), 7.66 (d, J=5.6 Hz, 1H), 7.56-7.42 (m, 5H), 7.23-7.18 (m, 2H), 4.99 (d, J=7.6 Hz, 1H), 4.85 (s, 2H), 3.76-3.46 (m, 15H), 3.05 (s, 3H), 2.91-2.88 (m, 2H), 2.74-2.69 (m, 2H), 2.22 (s, 3H), 3.17 (s, 2H), 3.65-3.62 (m, 2H), 3.51-3.48 (m, 2H), 3.06 (s, 3H), 2.91-2.88 (m, 2H), 2.74-2.68 (m, 2H), 2.22 (s, 3H); EI-MS m/z: 987 $[M+H]^+$, 494 1/2 $[M+H]^+$.

Example I-41: Preparation of Compounds A-45 and A-50

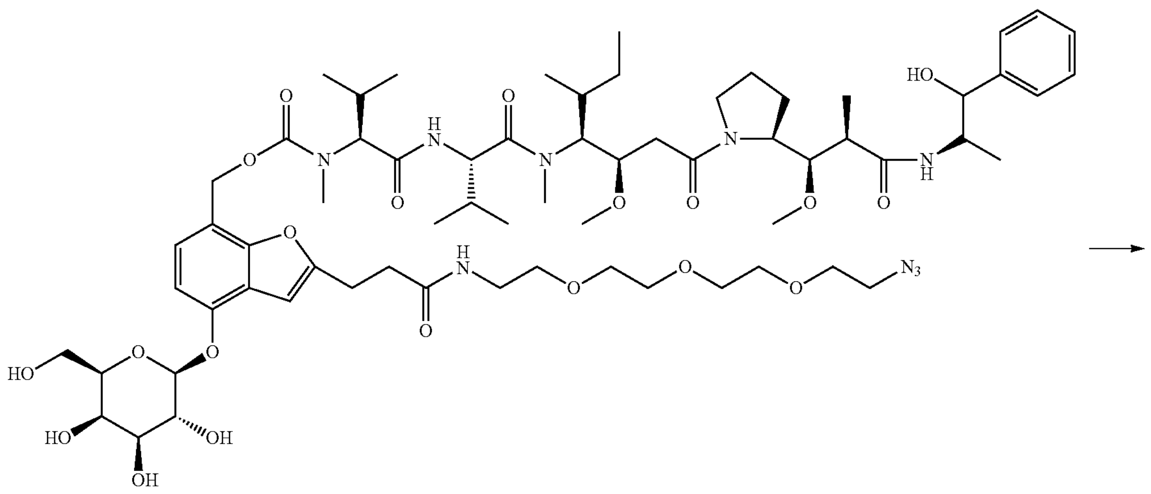

A-25

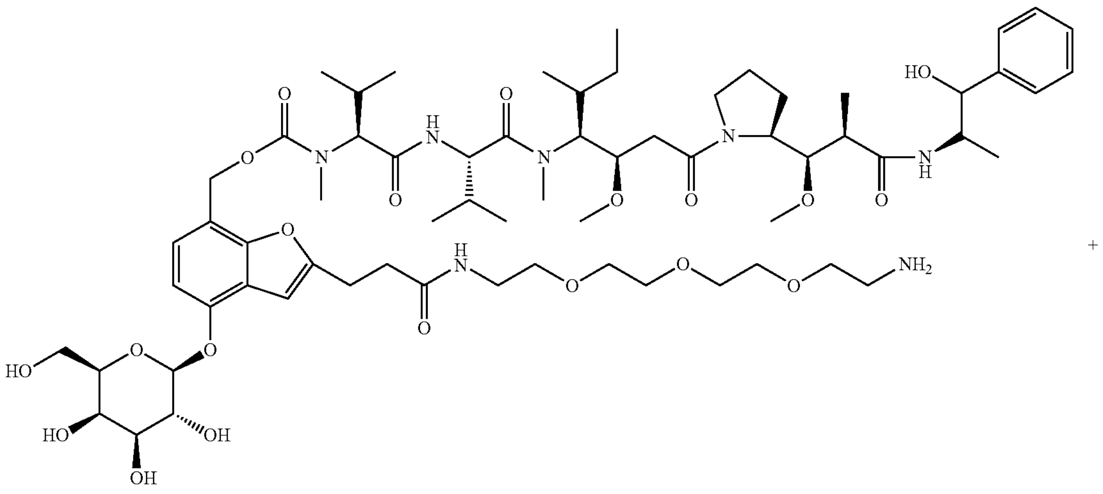

A-45

-continued

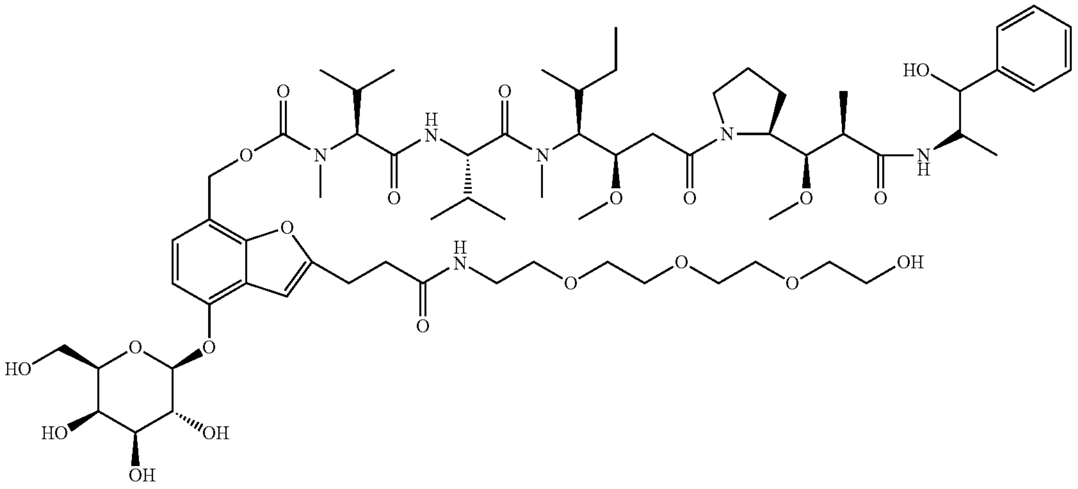

A-50

Compound A-25 (13.5 mg, 0.01 mmol) was dissolved in THF (1 mL) under a nitrogen atmosphere at room temperature, and then triphenylphosphine (3.95 mg, 0.015 mmol) and distilled water (0.3 mL) were sequentially added, and the mixture was stirred for 12 hours. 2N-sodium hydroxide aqueous solution (10 μL) was added to the above reaction solution at room temperature, and the mixture was stirred for 30 minutes, and then 2N-hydrochloric acid aqueous solution was slowly added dropwise to adjust the pH of the reaction solution to 3, and the reaction solution was separated and purified using Preparative-HPLC, and then freeze-dried to obtain Compounds A-45 and A-50, respectively (A-45: 1 mg, 7%, A-50: 7.8 mg, 59%); MS m/z: A-45=1317 $[M+H]^+$, A-50=1318 $[M+H]^+$.

Example I-42: Preparation of Compound A-46

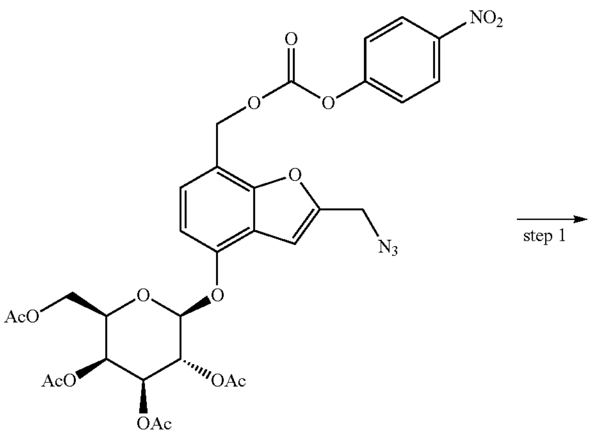

A-26g

-continued

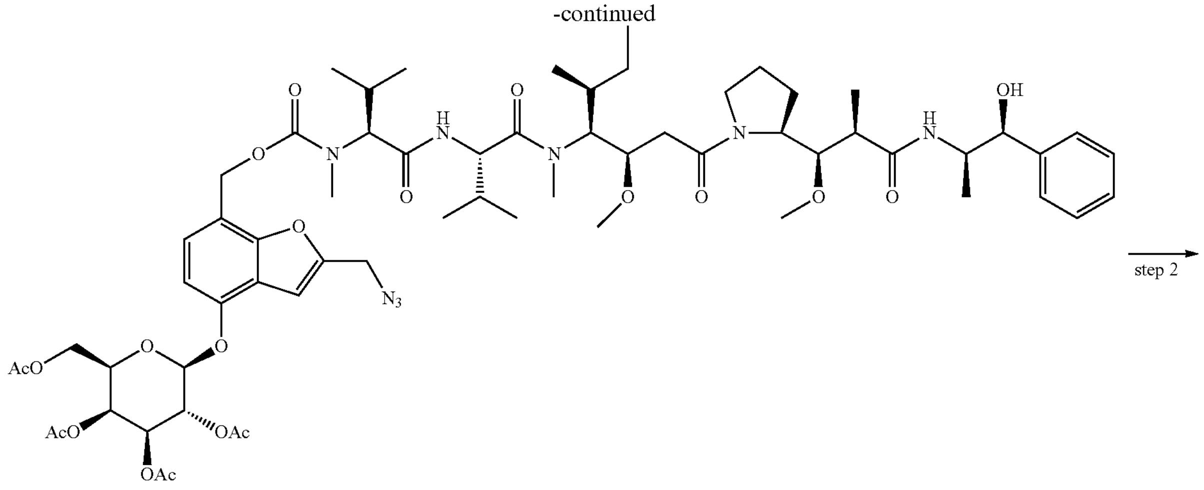

A-46a

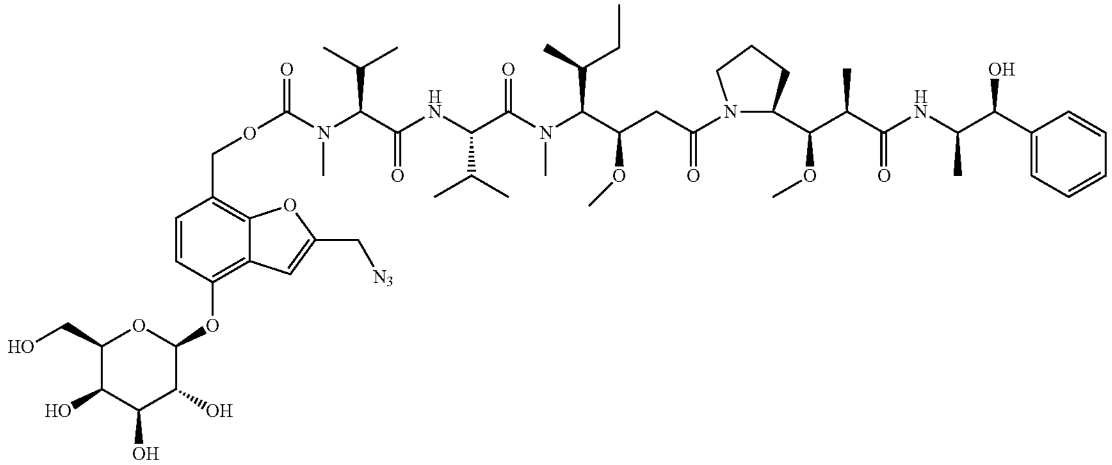

A-46

Step 1: Preparation of Compound A-46a

Compound A-26g (50.0 mg, 0.070 mmol) was dissolved in DMF (2.0 mL) under a nitrogen atmosphere at 0° C., and then MMAE (50.0 mg, 0.070 mmol), HOBt (14.0 mg, 0.105 mmol), DIPEA (30.0 μL, 0.175 mmol) and pyridine (1.0 mL) were sequentially added, and the mixture was stirred at room temperature for 16 hours. After completion of the reaction, extraction was performed using distilled water (50 mL), 2N-hydrochloric acid aqueous solution (50 mL) and EA (100 mL). The obtained organic layer was dried over anhydrous magnesium sulfate, filtered, and then concentrated under reduced pressure. The resulting residue was subjected to column chromatography to obtain Compound A-46a in the form of a white solid (75.0 mg, 83%); EI-MS m/z: 1294 $[M+H]^+$.

Step 2: Preparation of Compound A-46

Compound A-46a (62.0 mg, 0.048 mmol) was dissolved in methanol (1.0 mL) under a nitrogen atmosphere at 0° C., and then potassium carbonate (46.3 mg, 0.335 mmol) dissolved in distilled water (1.0 mL) was slowly added dropwise, and the mixture was stirred at 0° C. for 1 hour. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-46 in the form of a white solid (29.0 mg, 59%); EI-MS m/z: 1126 $[M+H]^+$.

Example I-43: Preparation of Compound A-47

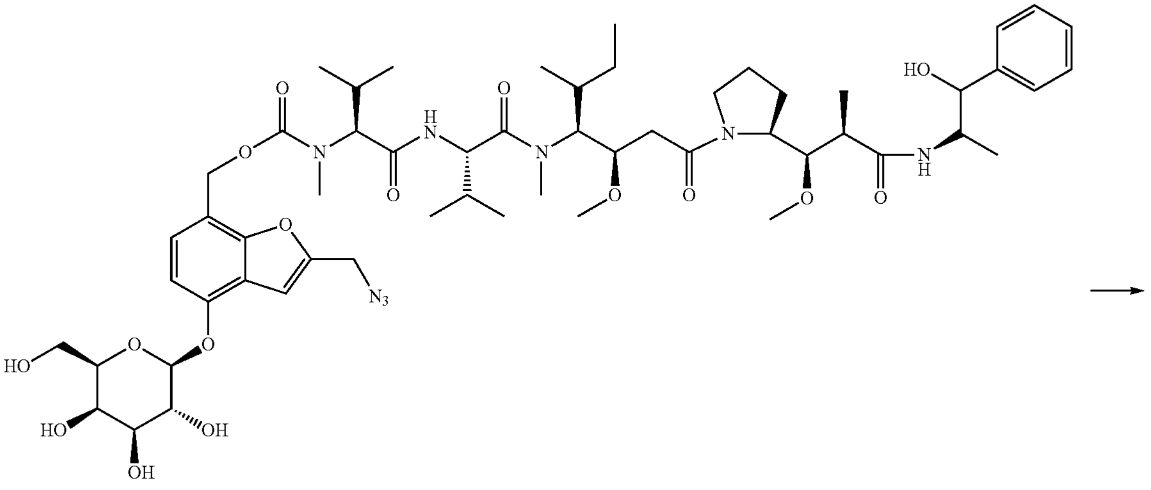

A-46

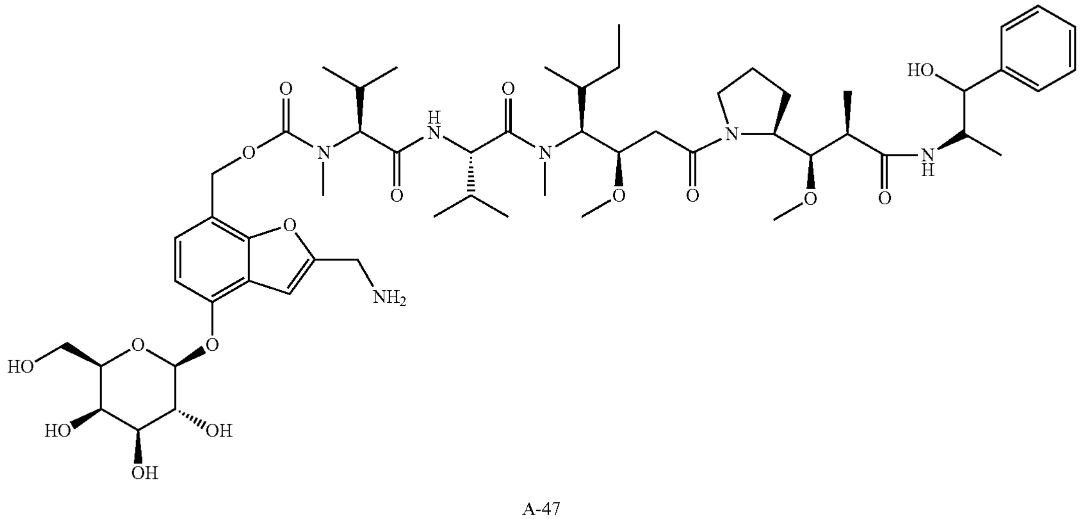

A-47

Compound A-46 (12.4 mg, 0.011 mmol) was dissolved in THF (2 mL) under a nitrogen atmosphere at room temperature, and then triphenylphosphine (4.33 mg, 0.0165 mmol) and distilled water (0.1 mL) were sequentially added, and the mixture was stirred for 48 hours. After completion of the reaction, the reaction solution was diluted with ACN (1 mL) and distilled water (1 mL), then separated and purified using Preparative-HPLC, and then freeze-dried to obtain Compound A-47 (3 mg, 24.8%); EI-MS m/z: 1100 $[M+H]^+$.

Example I-44: Preparation of Compound A-48
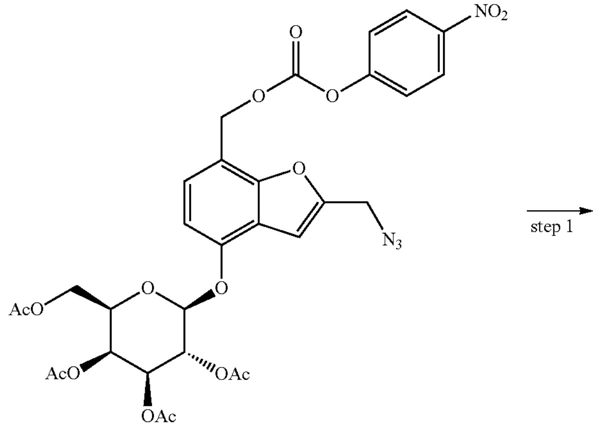
A-26g
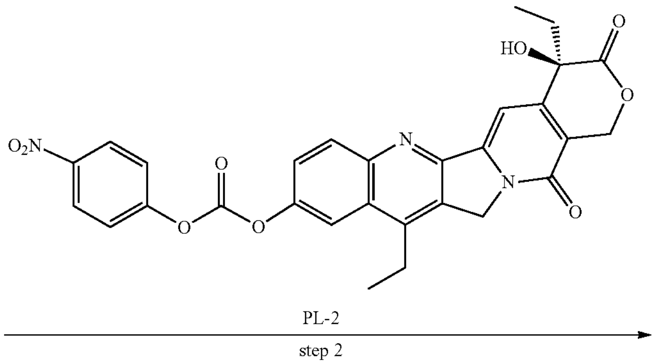
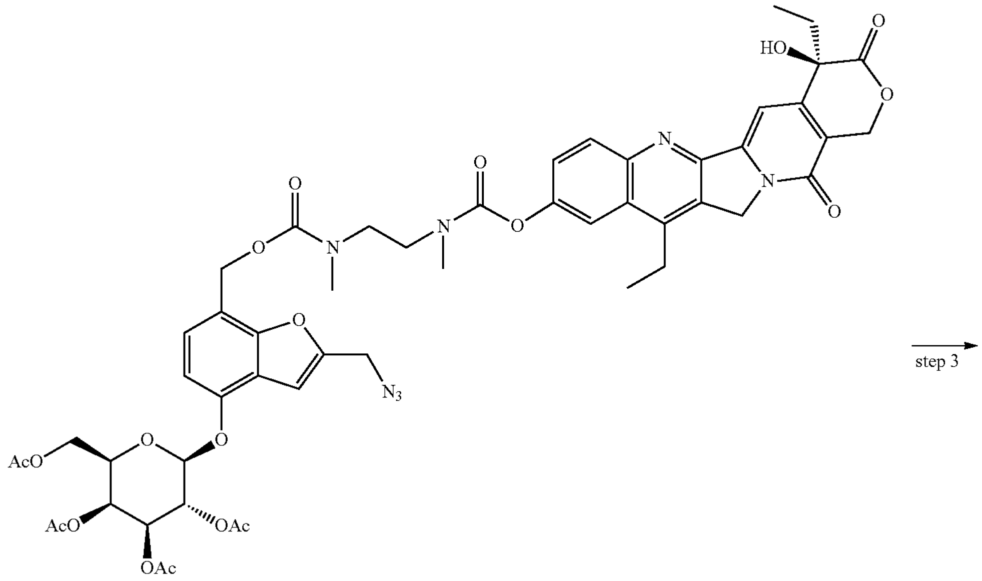
A-48b -continued

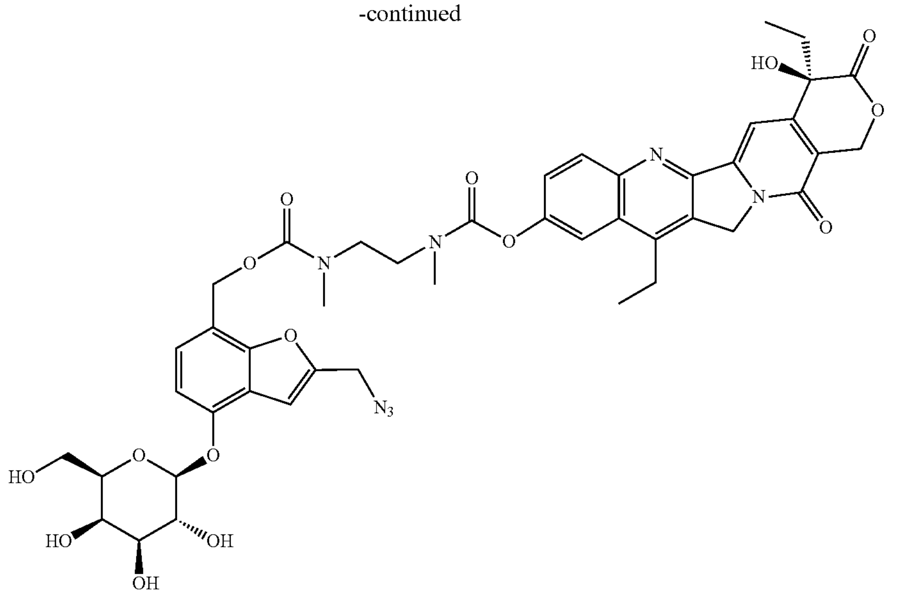

A-48

Step 1: Preparation of Compound A-48a

Compound A-26g (43.0 mg, 0.060 mmol) was dissolved in MC (6.0 mL) under a nitrogen atmosphere at 0° C., and then N,N'-dimethylethylenediamine (TCI, CAS NO. 110-70-3, 64 μL, 0.6 mmol) was added, and the mixture was stirred at room temperature for 1 hour. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-48a in the form of a white solid (28.5 mg, 71%); EI-MS m/z: 664 $[M+H]^+$.

Step 2: Preparation of Compound A-48b

Compound A-48a (28.5 mg, 0.043 mmol) was dissolved in DMF (1.0 mL) under a nitrogen atmosphere at 0° C., and then Compound PL-2 (24 mg, 0.043 mmol) and DIPEA (7.5 μL, 0.043 mmol) were sequentially added, and the mixture was stirred at room temperature for 4 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-48b in the form of a white solid (26.5 mg, 57%); EI-MS m/z: 1083 $[M+H]^+$.

Step 3: Preparation of Compound A-48

Compound A-48b (26.5 mg, 0.024 mmol) was dissolved in methanol (1.0 mL) and THE (0.5 mL) under a nitrogen atmosphere at 0° C., and then potassium carbonate (23.6 mg, 0.171 mmol) dissolved in distilled water (200.0 μL) was slowly added dropwise, and the mixture was stirred at 0° C. for 2 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-48 in the form of a white solid (16.5 mg, 73%); EI-MS m/z: 914 $[M+H]^+$.

Example I-45: Preparation of Compound A-49

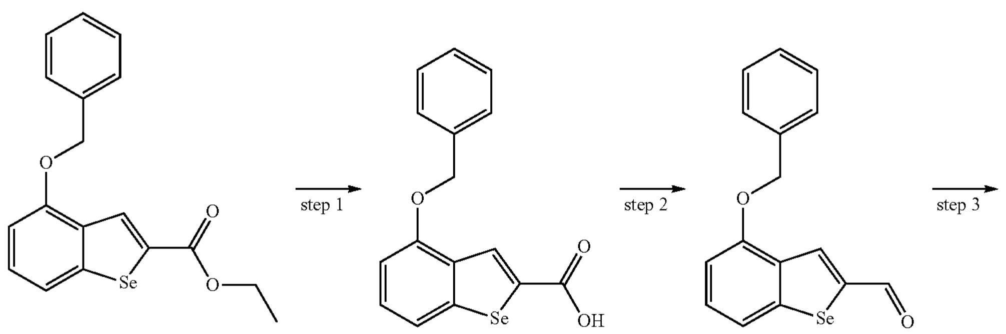

C-15e A-49a A-49b

-continued
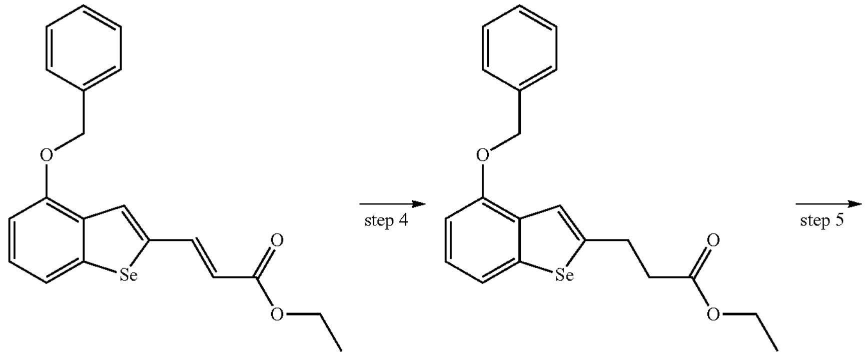
A-49c A-49d
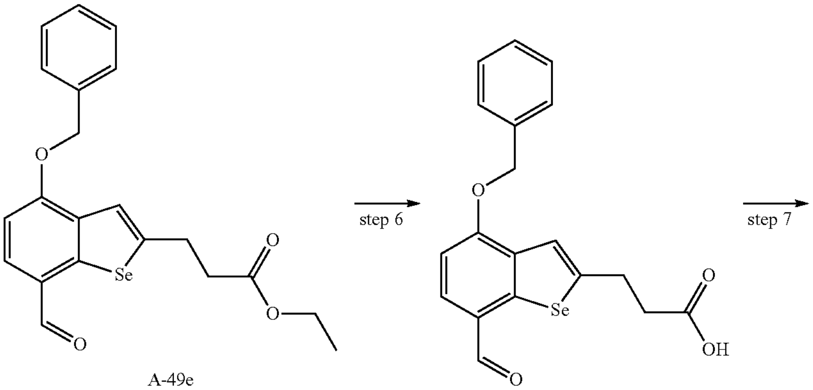
A-49e
A-49f
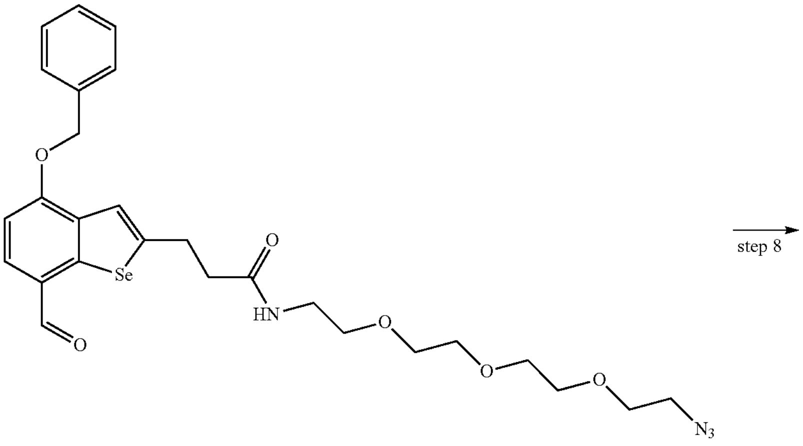
A-49g
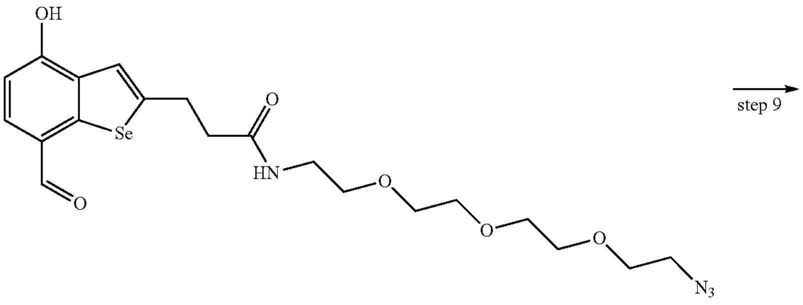
A-49h -continued
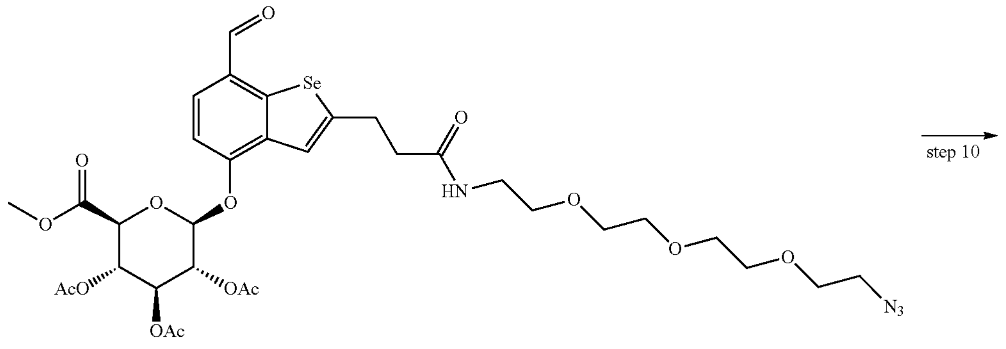
A-49i
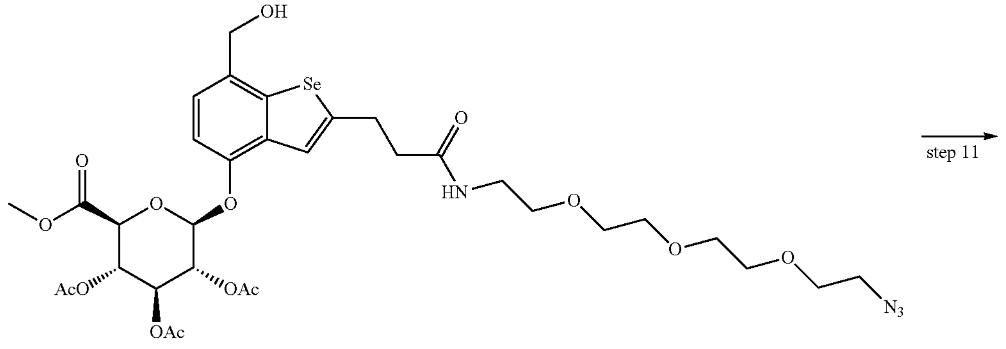
A-49j
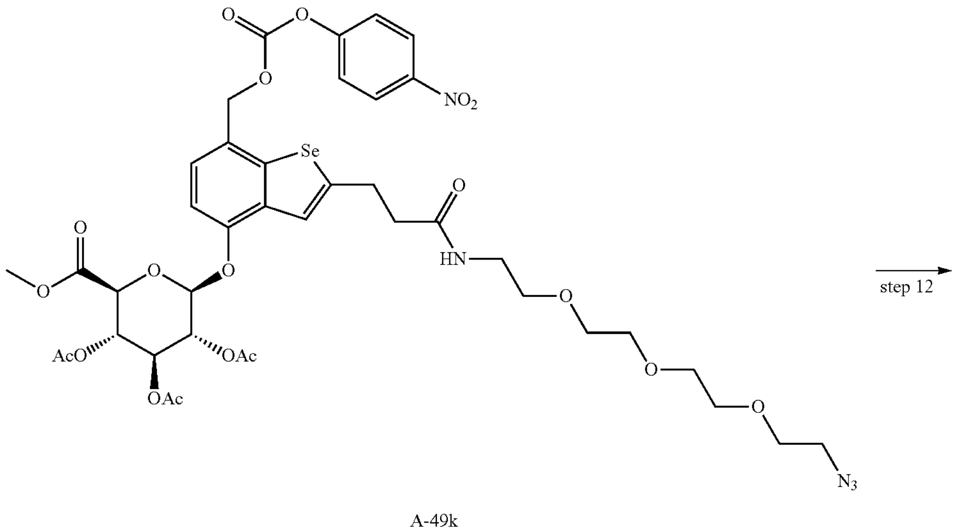
A-49k -continued

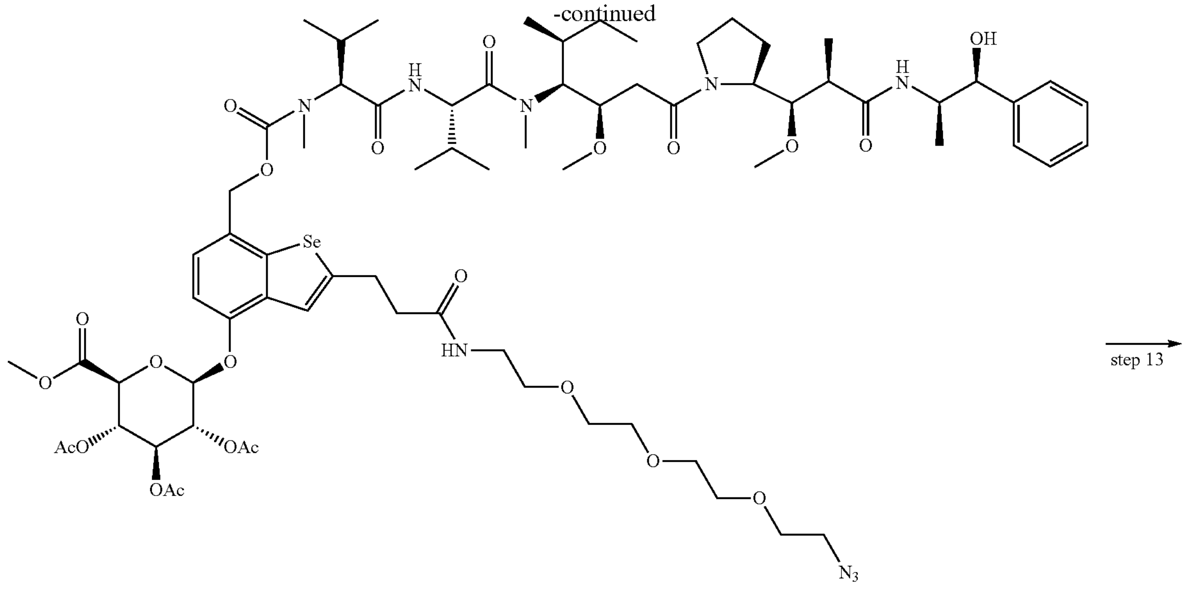

A-49L

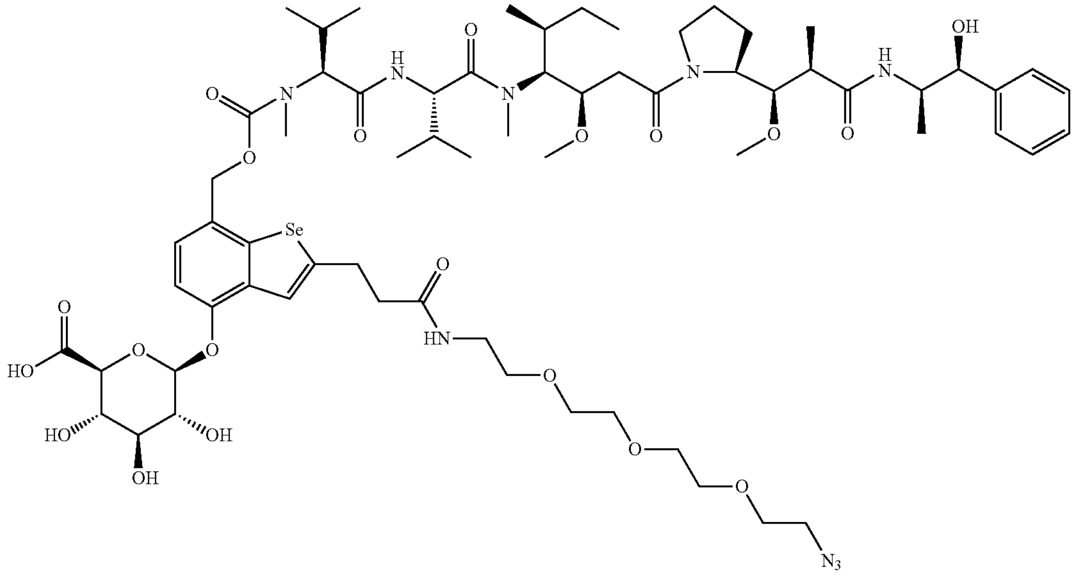

A-49

Step 1: Preparation of Compound A-49a LAH (2.25 g, 59.29 mmol) was added to THF (300 mL) under a nitrogen atmosphere at room temperature, and then the mixture was cooled to 0° C. Compound C-15e (8.53 g, 23.74 mmol) was dissolved in THF (75 mL) and slowly added, and the mixture was stirred at 0° C. for 5 minutes. After completion of the reaction, 2N-sodium hydroxide aqueous solution (36 mL) was added to terminate the reaction, and the reaction solution was diluted with THE (150 mL) and filtered using Celite. The obtained solution was concentrated under reduced pressure. The resulting residue was subjected to column chromatography to obtain Compound A-49a in the form of an ivory solid (7.2 g, 96%).

$^1$H-NMR (400 MHz, $CDCl_3$) δ 7.66 (s, 1H), 7.48-7.33 (m, 6H), 7.19 (t, J=8 Hz, 1H), 6.83 (d, J=8 Hz, 1H), 5.19 (s, 2H), 4.93 (d, J=6 Hz, 2H), 1.92 (t, J=6 Hz, 1H); EI-MS m/z: 318 $[M+H]^+$.

Step 2: Preparation of Compound A-49b

Compound A-49a (4.66 g, 14.69 mmol) was added to MC (93 mL) under a nitrogen atmosphere at room temperature, and then TEMPO (Alfa aesar, CAS NO. 2564-83-2, 230 mg, 1.47 mmol) and TBAI (543 mg, 1.47 mmol) were added. Then, sodium bicarbonate (4.2 g, 0.5 mol) and potassium carbonate (691 mg, 0.05 mol) were dissolved in 100 mL of water and added, and then NCS (N-Chlorosuccinimide, Merck, CAS NO. 128-09-6, 2.16 g, 16.18 mmol) was sequentially added, and the mixture was stirred at room temperature for 2 hours. After completion of the reaction, MC (100 mL) and distilled water (100 mL) were added to extract the organic layer twice. The organic layer was washed by adding a saturated aqueous sodium chloride solution (100 mL), and then the obtained organic layer was dried over anhydrous magnesium sulfate, filtered, and then concentrated under reduced pressure. The resulting residue was subjected to column chromatography to obtain Compound A-49b in the form of a yellow solid (4.35 g, 94%).

$^1$H-NMR (400 MHz, $CDCl_3$) δ 9.95 (s, 1H), 8.53 (s, 1H), 7.53-7.35 (m, 7H), 6.88 (d, J=8 Hz, 1H), 5.23 (s, 2H); EI-MS m/z: 316 $[M+H]^+$.

Step 3: Preparation of Compound A-49c

Compound A-49b (4.35 g, 13.80 mmol) was dissolved in MC (70 mL) under a nitrogen atmosphere at room temperature, and then (carbethoxymethylene)triphenylphosphorane (Merck, CAS No. 1099-45-2, 9.16 g, 27.59 mmol) was added, and the mixture was stirred at room temperature for 1.5 hours. After completion of the reaction, the reaction solution was concentrated under reduced pressure. The resulting residue was subjected to column chromatography to obtain Compound A-49c in the form of an ivory solid (5.12 g, 96%).

$^1$H-NMR (400 MHz, $CDCl_3$) δ 7.94 (s, 1H), 7.86 (d, J=15.2 Hz, 1H), 7.48-7.34 (m, 6H), 6.82 (d, J=8 Hz, 1H), 6.10 (d, J=15.2 Hz, 1H), 5.20 (s, 2H), 4.26 (q, J=7.2 Hz, 2H), 1.33 (t, J=7.2 Hz, 3H); EI-MS m/z: 386 $[M+H]^+$.

Step 4: Preparation of Compound A-49d

Compound A-49c (5.12 g, 13.29 mmol) was dissolved in EA (147 mL) and methanol (441 mL) under a nitrogen atmosphere at room temperature, and then 5% palladium charcoal (5% Pd/C, 5.12 g) was added, and the mixture was stirred under a hydrogen environment for 16 hours. After completion of the reaction, the reaction solution was diluted with MC (800 mL) and filtered using Celite. The filtered solution was concentrated under reduced pressure. The resulting residue was subjected to column chromatography to obtain Compound A-49d in the form of a beige oil (4.53 g, 88%).

$^1$H-NMR (400 MHz, $CDCl_3$) δ 7.50-7.3 (m, 7H), 7.14 (t, J=8 Hz, 1H), 6.81 (d, J=8 Hz, 1H), 5.12 (s, 2H), 4.16 (q, J=7.2 Hz, 2H), 3.25 (t, J=7.6 Hz, 2H), 2.73 (t, J=7.6 Hz, 2H), 1.26 (t, J=7.2 Hz, 3H); EI-MS m/z: 388 $[M+H]^+$.

Step 5: Preparation of Compound A-49e

Compound A-49d (3.88 g, 10.01 mmol) was dissolved in MC (287 mL) under a nitrogen atmosphere at −78° C., and then dichloromethyl methyl ether (Merck, CAS No. 4885-02-3, 2.72 mL, 30.01 mmol) and titanium tetrachloride solution (1M-$TiCl_4$ in MC, 30 mL, 30 mmol) were sequentially and slowly added, and the mixture was stirred for 2 hours while maintaining the temperature. After completion of the reaction, distilled water (250 mL) was slowly added dropwise to terminate the reaction, and MC (250 mL) was added to extract the organic layer twice. The organic layer was washed by adding a saturated aqueous sodium chloride solution (250 mL), and then the obtained organic layer was dried over anhydrous magnesium sulfate, filtered, and then concentrated under reduced pressure. The resulting residue was subjected to column chromatography to obtain Compound A-49e in the form of a yellow oil (2.59 g, 62%).

$^1$H-NMR (400 MHz, $CDCl_3$) δ 10.05 (s, 1H), 7.72 (d, J=8.4 Hz, 1H), 7.58 (s, 1H), 7.49-7.36 (m, 5H), 6.99 (d, J=8.4 Hz, 1H), 5.30 (s, 2H), 4.17 (q, J=7.2 Hz, 2H), 3.32 (t, J=7.6 Hz, 2H), 2.76 (t, J=7.6 Hz, 2H), 1.25 (t, J=7.2 Hz, 3H); EI-MS m/z: 416 $[M+H]^+$.

Step 6: Preparation of Compound A-49f

Compound A-49e (2.85 g, 6.86 mmol) was dissolved in ethanol (17 mL) and THE (17 mL) under a nitrogen atmosphere at 0° C., and then lithium hydroxide monohydrate (864 mg, 20.59 mmol) dissolved in distilled water (8.5 mL) was slowly added dropwise, and the mixture was stirred at room temperature for 1.5 hours. After completion of the reaction, 2N-hydrochloric acid aqueous solution (15 mL) was added to terminate the reaction, and EA (85 mL) and distilled water (85 mL) were added to extract the organic layer. The organic layer was washed by adding a saturated aqueous sodium chloride solution (250 mL), and then the obtained organic layer was dried over anhydrous magnesium sulfate, filtered, and then concentrated under reduced pressure. The resulting residue was subjected to column chromatography to obtain Compound A-49f in the form of an orange solid (2.56 g, 96%).

$^1$H-NMR (400 MHz, $CDCl_3$) δ 10.05 (s, 1H), 7.73 (d, J=8 Hz, 1H), 7.60 (s, 1H), 7.52-7.36 (m, 5H), 6.99 (d, J=8.4 Hz, 1H), 5.31 (s, 2H), 3.33 (t, J=7.6 Hz, 2H), 2.83 (t, J=7.6 Hz, 2H); EI-MS m/z: 388 $[M+H]^+$.

Step 7: Preparation of Compound A-49g

Compound A-49f (2.56 g, 6.61 mmol) was dissolved in DMF (22 mL) under a nitrogen atmosphere at 0° C., and then EDC (1.9 g, 9.91 mmol), HOBt (894 mg, 6.61 mmol), DMAP (81 mg, 0.66 mmol) and DIPEA (3.45 mL, 19.81 mmol) were sequentially added, and the mixture was stirred for 1.5 hours. Additionally, Linker P-1 (1.68 g, 6.60 mmol) dissolved in DMF (11 mL) was slowly added dropwise, and the reaction mixture was stirred at room temperature for 16 hours and then extracted with EA (100 mL) and distilled water (100 mL). The obtained organic layer was washed by adding a saturated aqueous sodium chloride solution (50 mL) and then dried over anhydrous magnesium sulfate, and the organic layer was filtered and then concentrated under reduced pressure. The resulting residue was subjected to column chromatography to obtain Compound A-49g in the form of a brown oil (2.24 g, 58%).

$^1$H-NMR (400 MHz, $CDCl_3$) δ 10.04 (s, 1H), 7.71 (d, J=8.4 Hz, 1H), 7.58 (s, 1H), 7.49 -7.36 (m, 5H), 6.98 (d, J=8 Hz, 1H), 6.14 (brs, 1H), 5.30 (s, 2H), 3.71-3.49 (m, 14H), 3.47-3.44 (m, 2H), 3.36-3.33 (m, 4H), 2.61 (t, J=7.6 Hz, 2H); EI-MS m/z: 588 $[M+H]^+$.

Step 8: Preparation of Compound A-49h

Compound A-49g (2.23 g, 3.80 mmol) was dissolved in MC (76 mL) under a nitrogen atmosphere at −78° C., and then pentamethylbenzene (Alfa aesar CAS NO. 700-12-9, 1.69 g, 11.40 mmol) was added, and boron trichloride solution (1M-$BCl_3$ in MC, 22.8 mL, 22.8 mmol) was slowly added, and then the mixture was stirred for 1 hour while slowly raising the temperature to −55° C. After completion of the reaction, distilled water (150 mL) was slowly added dropwise to terminate the reaction, and 2N-sodium hydroxide aqueous solution was added at 0° C. to neutralize it. MC (150 mL) and distilled water (150 mL) were added to the mixture to extract the organic layer twice. The obtained organic layer was washed by adding a saturated aqueous sodium chloride solution (150 mL), then dried over anhydrous magnesium sulfate, filtered, and then concentrated under reduced pressure. The resulting residue was subjected to column chromatography to obtain Compound A-49h in the form of a beige solid (1.33 g, 71%).

$^1$H-NMR (400 MHz, $CDCl_3$) δ 10.01 (s, 1H), 8.42 (brs, 1H), 7.66-7.64 (m, 2H), 6.94 (d, J=8 Hz, 1H), 6.32 (brs, 1H), 3.66-3.59 (m, 8H), 3.53-3.52 (m, 2H), 3.48-3.44 (m, 4H), 3.38-3.33 (m, 4H), 2.66 (t, J=7.2 Hz, 2H); EI-MS m/z: 498 $[M+H]^+$.

Step 9: Preparation of Compound A-49i

Compound A-49h (500 mg, 1.01 mmol) was dissolved in MC (33 mL) under a nitrogen atmosphere at 0° C., and then acetobromo-a-D-glucuronic acid methyl ester (TCI, 838 mg, 2.11 mmol), benzyltributylammonium chloride (314 mg, 1.01 mmol) and 5N-sodium hydroxide aqueous solution (1 mL, 5.00 mmol) were slowly added, and the mixture was stirred at 0° C. for 30 minutes and then stirred at room temperature for an additional 16 hours. After completion of the reaction, 2N-hydrochloric acid aqueous solution was added to the reaction solution to neutralize it, and MC (165 mL) and distilled water (165 mL) were added to extract it. The obtained organic layer was washed by adding a saturated aqueous sodium chloride solution (165 mL), then dried over anhydrous magnesium sulfate, filtered, and then concentrated under reduced pressure. The resulting residue was subjected to column chromatography to obtain Compound A-49i in the form of an ivory sticky gum (200 mg, 25%).

$^1$H-NMR (400 MHz, $CDCl_3$) δ 10.10 (s, 1H), 7.73 (d, J=8 Hz, 1H), 7.39 (s, 1H), 7.09 (d, J=8.4 Hz, 1H), 6.16 (brs, 1H), 5.44-5.37 (m, 4H), 4.29 (m, 1H), 3.72 (s, 3H), 3.67-3.46 (m, 14H), 3.38-3.33 (m, 4H), 2.61 (t, J=7.6 Hz, 2H), 2.09 (s, 3H), 2.07 (s, 6H); EI-MS m/z: 814 $[M+H]^+$.

Step 10: Preparation of Compound A-49j

Compound A-49i (198 mg, 0.24 mmol) was dissolved in THE (13.3 mL) under a nitrogen atmosphere at 0° C., and then sodium borohydride ($NaBH_4$, 27.6 mg, 0.73 mmol) was added, and the mixture was stirred at 0° C. for 5 hours. After completion of the reaction, distilled water (13 mL) was added to terminate the reaction, and EA (53 mL) and distilled water (27 mL) were added to extract the organic layer twice. The obtained organic layer was washed by adding a saturated aqueous sodium chloride solution (53 mL), then dried over anhydrous magnesium sulfate, filtered, and then concentrated under reduced pressure. The resulting residue was subjected to column chromatography to obtain Compound A-49j in the form of a white sticky gum (146 mg, 74%).

$^1$H-NMR (400 MHz, $CDCl_3$) δ 7.34 (s, 1H), 7.14 (d, J=8 Hz, 1H), 6.93 (d, J=8 Hz, 1H), 6.22 (brs, 1H), 5.39-5.35 (m, 3H), 5.19 (m, 1H), 4.81 (d, J=5.6 Hz, 2H), 4.20 (m, 1H), 3.74 (s, 3H), 3.65-3.43 (m, 14H), 3.38-3.28 (m, 4H), 2.61 (m, 2H), 2.07 (s, 3H), 2.05 (s, 6H); EI-MS m/z: 816 $[M+H]^+$.

Step 11: Preparation of Compound A-49k

Compound A-49j (171 mg, 0.21 mmol) was dissolved in MC (5.1 mL) under a nitrogen atmosphere at 0° C., and then 4-nitrophenyl chloroformate (85 mg, 0.42 mmol), pyridine (50.7 μL, 0.63 mmol) and DIPEA (54.8 μL, 0.32 mmol) were sequentially added, and the mixture was stirred at 0° C. for 30 minutes and stirred at room temperature for an additional 2.5 hours. After completion of the reaction, the reaction solution was diluted with EA (25 mL), and 2N-hydrochloric acid aqueous solution (25 mL) was added to extract the organic layer. The obtained organic layer was washed by adding a saturated aqueous sodium chloride solution (25 mL), then dried over anhydrous magnesium sulfate, filtered, and then concentrated under reduced pressure. The residue thus obtained was subjected to column chromatography to obtain Compound A-49k in the form of a transparent sticky foam (158 mg, 77%).

$^1$H-NMR (400 MHz, $CDCl_3$) δ 8.27 (d, J=8.8 Hz, 1H), 7.41-7.37 (m, 3H), 6.95 (d, J=8.4 Hz, 1H), 6.20 (brs, 1H), 5.43-5.37 (m, 5H), 5.24-5.23 (m, 1H), 4.23-4.21 (m, 1H), 3.73 (s, 3H), 3.66-3.54 (m, 12H), 3.51-3.47 (m, 2H), 3.37-3.34 (m, 4H), 2.60 (d, J=7.6 Hz, 2H), 2.08-2.06 (m, 9H); EI-MS m/z: 981 $[M+H]^+$.

Step 12: Preparation of Compound A-49L

Compound A-49k (41.1 mg, 0.042 mmol) was dissolved in DMF (1 mL) under a nitrogen atmosphere at 0° C., and then MMAE (30 mg, 0.042 mmol), HOBt (8.5 mg, 0.063 mmol), DIPEA (18.2 μL, 0.104 mmol) and pyridine (1 mL) were sequentially added, and the mixture was stirred at room temperature for 16 hours. After completion of the reaction, the organic layer was extracted twice with EA (20 mL) and 2N-hydrochloric acid aqueous solution (20 mL). The obtained organic layer was washed by adding a saturated aqueous sodium chloride solution (20 mL), then dried over anhydrous magnesium sulfate, filtered, and then concentrated under reduced pressure. The resulting residue was subjected to column chromatography to obtain Compound A-49L in the form of a white solid (47.7 mg, 73%); EI-MS m/z: 1560 $[M+H]^+$, 780 1/2 $[M+H]^+$.

Step 13: Preparation of Compound A-49

Compound A-49L (47.7 mg, 0.031 mmol) was dissolved by mixing and adding methanol (0.76 mL), distilled water (0.1 mL) and THE (0.48 mL) at −20° C., and then lithium hydroxide (5.1 mg, 0.12 mmol) dissolved in distilled water (0.44 mL) was added dropwise, and the mixture was stirred at −20° C. for 1 hour. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and freeze-dried to obtain Compound A-49 in the form of a white solid (28.2 mg, 65%); EI-MS m/z: 1420 $[M+H]^+$, 710 1/2 $[M+H]^+$.

Example I-46: Preparation of Compound A-51

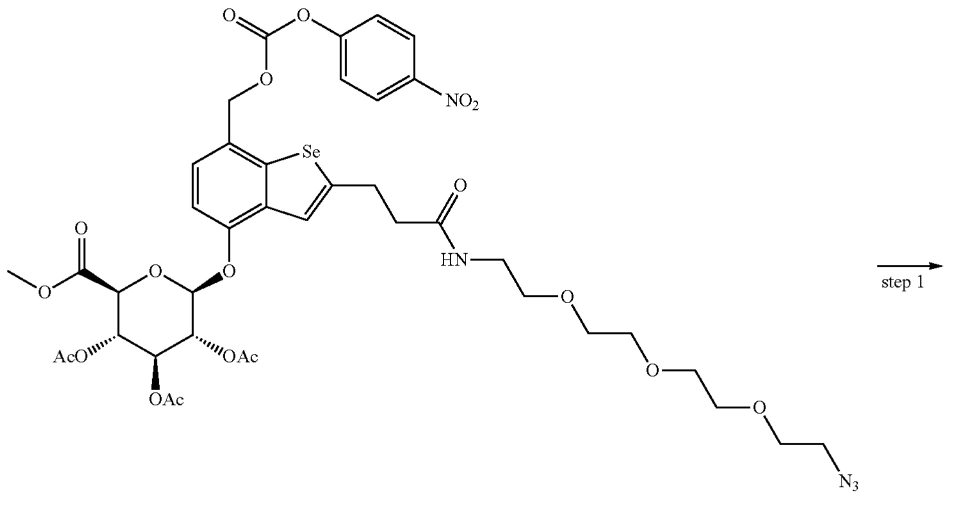

A-49k

-continued

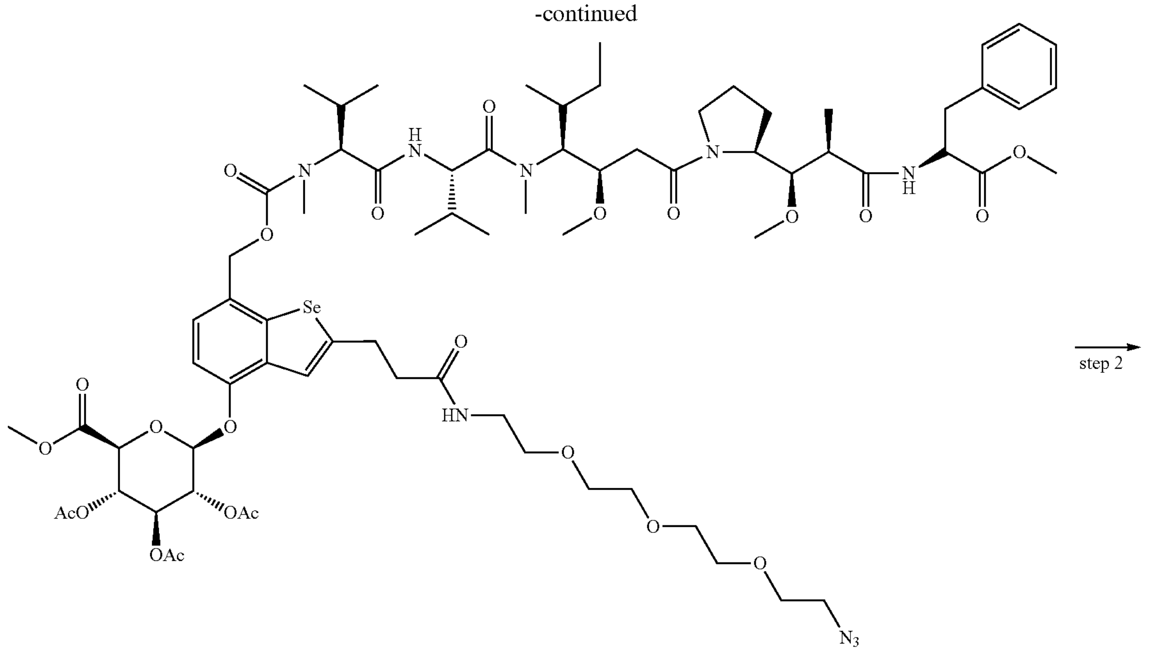

A-51a

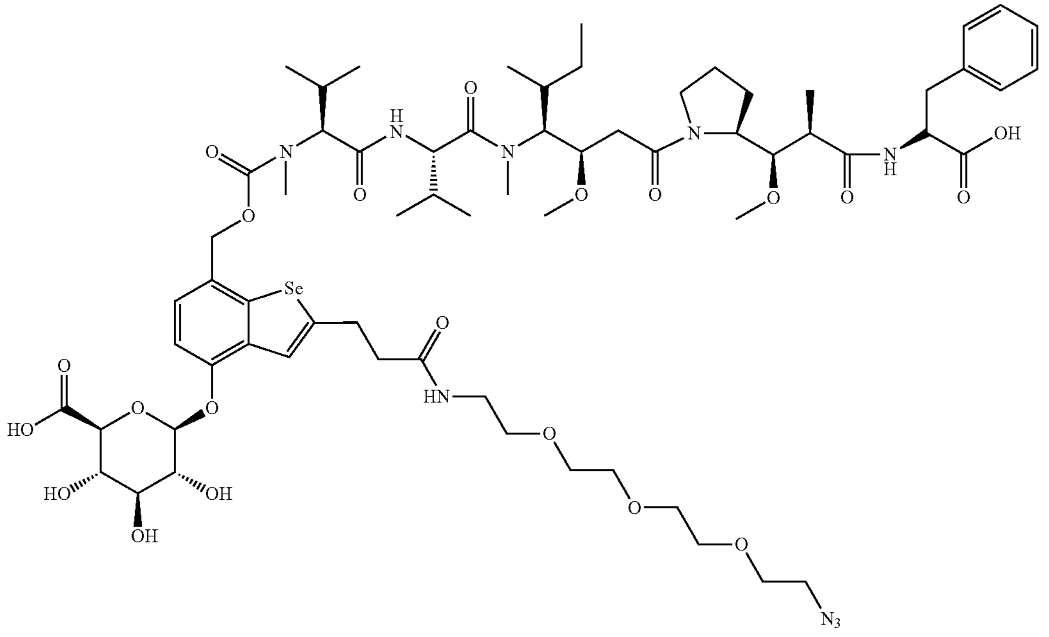

A-51

Step 1: Preparation of Compound A-51a

Compound A-49k (37 mg, 0.038 mmol) was dissolved in DMF (1 mL) under a nitrogen atmosphere at 0° C., and then MMAF-OMe (28 mg, 0.038 mmol), HOBt (7.6 mg, 0.056 mmol), DIPEA (16.4 μL, 0.094 mmol) and pyridine (1 mL) were sequentially added, and the mixture was stirred at room temperature for 16 hours. After completion of the reaction, the organic layer was extracted twice with EA (20 mL) and 2N-hydrochloric acid aqueous solution (20 mL). The obtained organic layer was washed by adding a saturated aqueous sodium chloride solution (20 mL), then dried over anhydrous magnesium sulfate, filtered, and then concentrated under reduced pressure. The resulting residue was subjected to column chromatography to obtain Compound A-51a in the form of a transparent sticky foam (45 mg, 75%); EI-MS m/z: 1588 $[M+H]^+$, 794 1/2 $[M+H]^+$.

Step 2: Preparation of Compound A-51

Compound A-51a (45 mg, 0.028 mmol) was dissolved by mixing and adding methanol (0.71 mL), distilled water (0.11 mL) and THE (0.14 mL) at −20° C., and then lithium hydroxide (8.9 mg, 0.212 mmol) dissolved in distilled water (0.6 mL) was added dropwise, and the mixture was stirred for 3 hours while slowly raising the temperature from −20° C. to −5° C. After completion of the reaction, 2N-hydrochloric acid aqueous solution (0.5 mL) was added to terminate the reaction, and the reaction solution was diluted with ACN (1 mL) and distilled water (1 mL), then separated and purified using Preparative-HPLC, and freeze-dried to obtain Compound A-51 in the form of a white solid (22.2 mg, 55%); EI-MS m/z: 1434 $[M+H]^+$, 717 1/2 $[M+H]^+$.
Example I-47: Preparation of Compound A-52
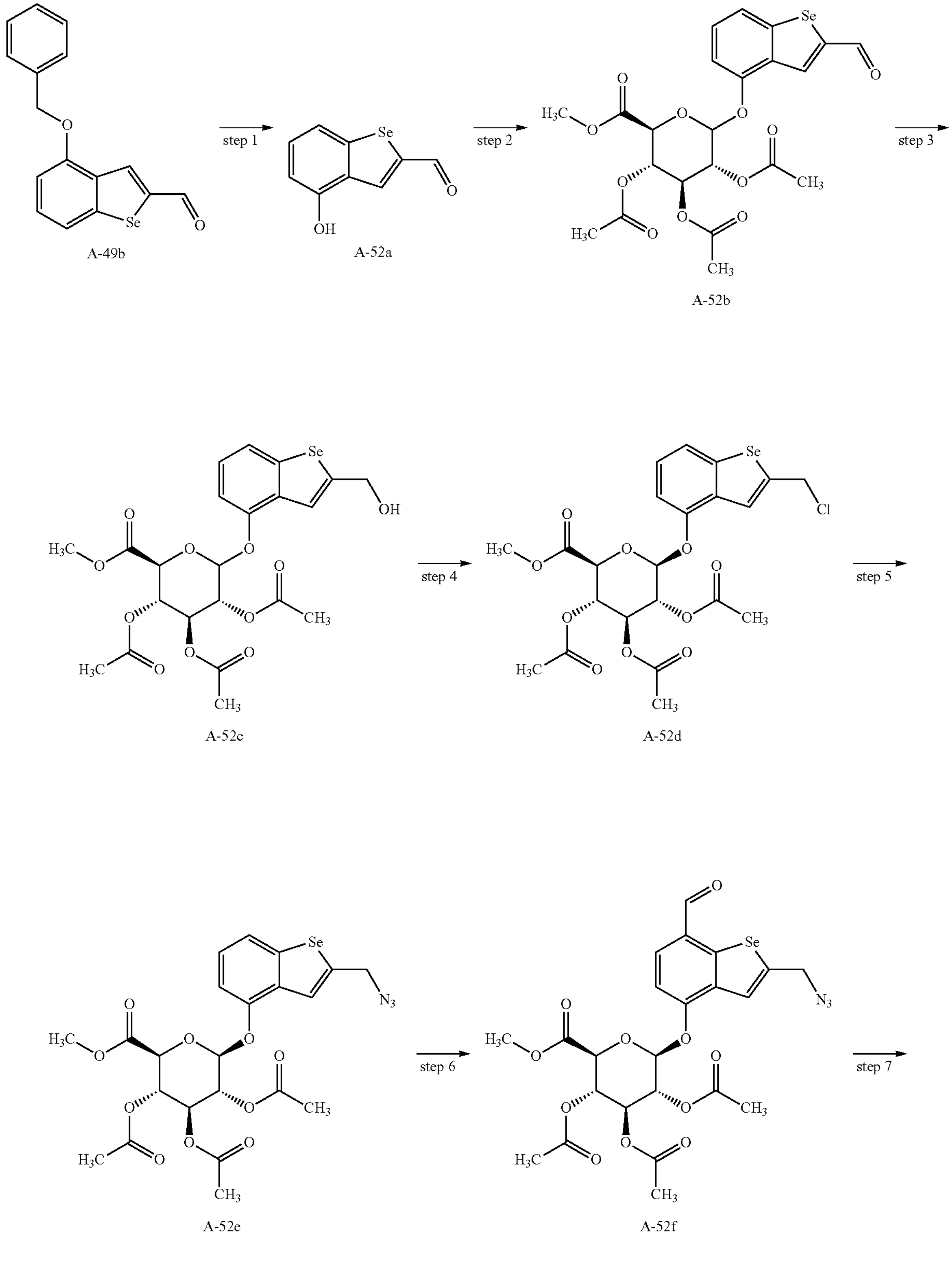

-continued

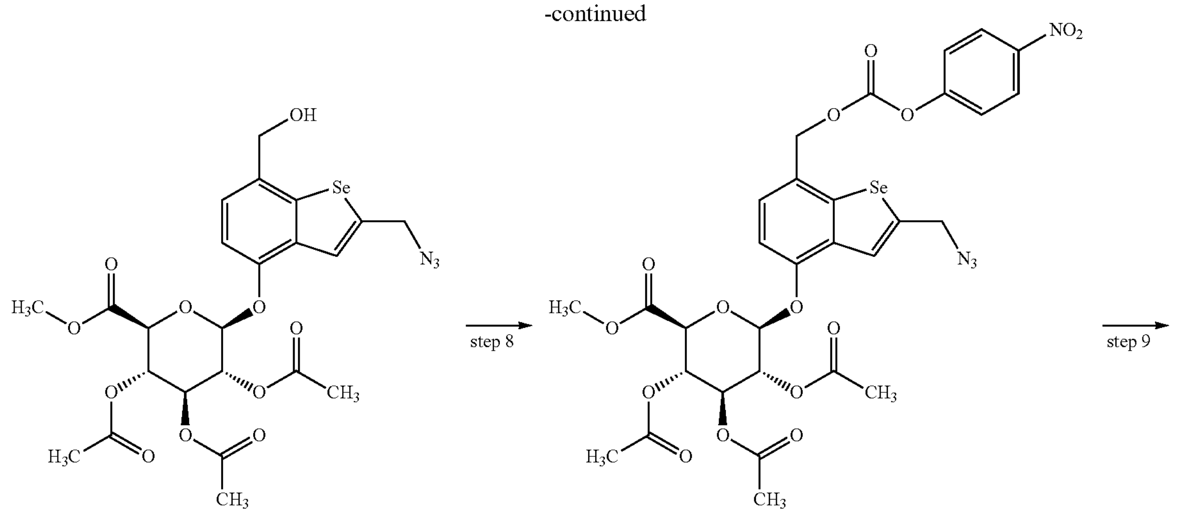

A-52g A-52h

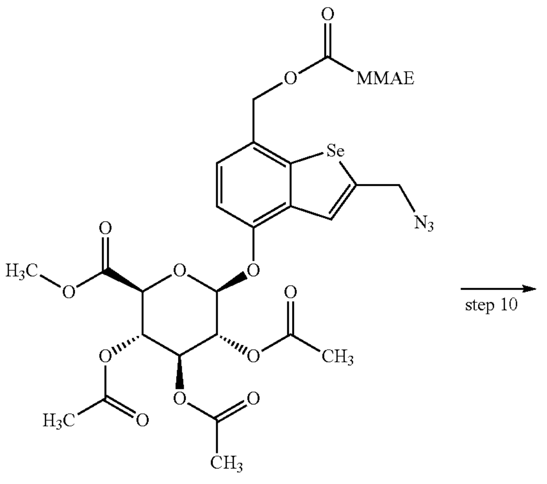

A-52i

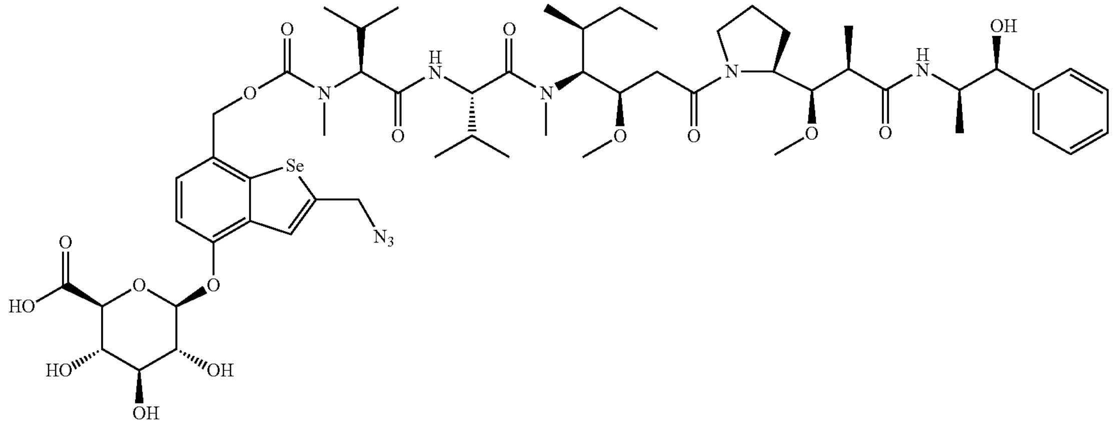

A-52

Step 1: Preparation of Compound A-52a

Compound A-49b (8 g, 25.38 mmol) was dissolved in MC (242 mL, 0.105 M) under a nitrogen atmosphere at −78° C., and then boron trichloride solution (1M-$BCl_3$ in MC, 76.14 mL, 76.14 mmol) was slowly added, and the mixture was stirred for 2 hours. After completion of the reaction, distilled water (200 mL) was added to terminate the reaction, and 2N-sodium hydroxide aqueous solution was added at 0° C. to neutralize it. 2N-hydrochloric acid aqueous solution was slowly added dropwise to the mixture to adjust the pH of the reaction solution to 7. MC (200 mL) was added to the mixture to extract the organic layer twice. The obtained organic layer was dried over anhydrous magnesium sulfate, filtered, and then concentrated under reduced pressure. The resulting residue was subjected to column chromatography to obtain Compound A-52a in the form of a yellowish green solid (4.9 g, 85.8%).

$^1$H-NMR (400 MHz, DMSO) δ 9.97 (s, 1H), 8.65 (s, 1H), 7.53 (d, J=8 Hz, 1H), 7.32 (t, J=8 Hz, 1H), 6.82 (d, J=8 Hz, 1H); EI-MS m/z: 226 $[M+H]^+$.

Step 2: Preparation of Compound A-52b

Silver carbonate (9.07 g, 32.9 mmol) and HMTTA (1,1,4,7,10,10-hexamethyltriethylenetetramine, 1.13 g, 4.88 mmol) were dissolved in ACN (80 mL) under a nitrogen atmosphere at room temperature, and then the mixture was stirred for 1 hour. The reaction solution was cooled to 0° C., and then a solution of Compound A-52a (2 g, 8.88 mmol) dissolved in ACN (30 mL) and a solution of acetobromo-a-D-glucuronic acid methyl ester (TCI, 8.82 g, 22.2 mmol) dissolved in ACN (20 mL) were sequentially and slowly added, and the mixture was stirred for 16 hours while slowly raising the temperature from 0° C. to room temperature. After completion of the reaction, the filtrate obtained through a Celite filter was concentrated under reduced pressure. EA (100 mL) and distilled water (100 mL) were added to the concentrate thus obtained to extract the organic layer twice. The obtained organic layer was washed by adding an aqueous sodium chloride solution. The washed organic layer was dried over anhydrous magnesium sulfate, filtered, and then concentrated under reduced pressure. The resulting residue was subjected to column chromatography to obtain Compound A-52b in the form of a yellow solid (0.82 g, 17%).

$^1$H-NMR (400 MHz, $CDCl_3$) δ 9.97 (s, 1H), 8.36 (s, 1H), 7.64 (d, J=8 Hz, 1H), 7.39 (t, J=8 Hz, 1H), 6.97 (d, J=8 Hz, 1H), 5.5-5.36 (m, 3H), 5.31 (m, 1H), 4.25 (m, 1H), 3.73 (s, 3H), 2.09 (s, 3H), 2.07 (s, 6H); EI-MS m/z: 542 $[M+H]^+$.

Step 3: Preparation of Compound A-52c

Compound A-52b (2.50 g, 4.61 mmol) was dissolved in THE (45 mL, 0.1 M) under a nitrogen atmosphere at 0° C., and then sodium borohydride (0.44 g) was added, and the mixture was stirred for 2 hours. After completion of the reaction, distilled water (30 mL) was added to terminate the reaction, and then EA (30 mL) was added to extract the organic layer twice. The obtained organic layer was dried over anhydrous magnesium sulfate, filtered, and then concentrated under reduced pressure. The resulting residue was subjected to column chromatography to obtain Compound A-52c in the form of a white solid (1.37 g, 54.6%).

$^1$H-NMR (400 MHz, $CDCl_3$) δ 7.58 (d, J=8 Hz, 1H), 7.47 (s, 1H), 7.2 (t, J=8 Hz, 1H), 6.94 (d, J=8 Hz, 1H), 5.41-5.35 (m, 3H), 5.23 (m, 1H), 4.93 (d, J=6 Hz, 2H), 4.21 (m, 1H), 3.73 (s, 3H), 2.07 (s, 3H), 2.06 (s, 3H), 2.05 (s, 3H), 1.99 (t, J=6 Hz, 1H); EI-MS m/z: 566 $[M+Na]^+$.

Step 4: Preparation of Compound A-52d

Compound A-52c (700 mg, 1.29 mmol) was dissolved in 37% hydrochloric acid aqueous solution (35 mL) under a nitrogen atmosphere at −10° C., and then the mixture was stirred for 2 hours at −10° C. After completion of the reaction, EA (40 mL) and distilled water (40 mL) were added to extract the organic layer twice. The obtained organic layer was dried over anhydrous magnesium sulfate, filtered, and then concentrated under reduced pressure to obtain Compound A-52d in the form of a white solid (700 mg, 97.2%).

$^1$H-NMR (400 MHz, $CDCl_3$) δ 7.6-7.54 (m, 2H), 7.23-7.2 (m, 1H), 6.95 (d, J=8 Hz, 1H), 5.5-5.35 (m, 3H), 5.22 (d, J=7.2 Hz, 1H), 4.88 (s, 2H), 4.23-4.2 (m, 1H), 3.73 (s, 3H), 2.08-2.04 (m, 9H); EI-MS m/z: 584 $[M+Na]^+$.

Step 5: Preparation of Compound A-52e

Compound A-52d (700 mg, 1.25 mmol) was dissolved in DMF (25 mL) under a nitrogen atmosphere at room temperature, and then sodium azide (121 mg, 1.87 mmol) was added, and the mixture was stirred at 60° C. for 16 hours. After completion of the reaction, EA (30 mL) and distilled water (60 mL) were added to extract the organic layer twice. The obtained organic layer was dried over anhydrous magnesium sulfate, filtered, and then concentrated under reduced pressure. The resulting residue was subjected to column chromatography to obtain Compound A-52e in the form of a white solid (428 mg, 58.4%).

$^1$H-NMR (400 MHz, $CDCl_3$) δ 7.58 (d, J=8 Hz, 1H), 7.52 (s, 1H), 7.25-7.2 (m, 1H), 6.95 (d, J=8 Hz, 1H), 5.46-5.34 (m, 3H), 5.24 (d, J=7.2 Hz, 1H), 4.63 (d, J=14.4 Hz, 1H), 4.57 (d, J=14.4 Hz, 1H) 4.26-4.19 (m, 1H), 3.73 (s, 3H), 2.08 (s, 3H), 2.06 (s, 6H); EI-MS m/z: 591 [M+Na]*.

Step 6: Preparation of Compound A-52f

A-52e (434 mg, 0.76 mmol) was dissolved in MC (24 mL) under a nitrogen atmosphere at −78° C., and then dichloromethyl methyl ether (210 μL, 2.3 mmol) and titanium tetrachloride solution (1M-$TiCl_4$ in MC, 2.3 mL, 2.3 mmol) were sequentially and slowly added, and the mixture was stirred for 4 hours while maintaining the temperature. After completion of the reaction, the distilled water (100 mL), which was cooled at −78° C., was slowly added dropwise to terminate the reaction, and MC (100 mL) was added to extract the organic layer twice. The obtained organic layer was washed by adding an aqueous sodium chloride solution. The washed organic layer was dried over anhydrous magnesium sulfate, filtered, and then concentrated under reduced pressure. The resulting residue was subjected to column chromatography to obtain Compound A-52f in the form of a white solid (208 mg, 45.6%).

$^1$H-NMR (400 MHz, $CDCl_3$) δ 10.13 (s, 1H), 7.82 (d, J=8 Hz, 1H), 7.6 (s, 1H), 7.12 (d, J=8 Hz, 1H), 5.5-5.38 (m, 4H), 4.7 (d, J=14.4 Hz, 1H), 4.63 (d, J=14.4 Hz, 1H), 4.35-4.27 (m, 1H), 3.72 (s, 3H), 2.09 (s, 3H), 2.07 (s, 3H), 2.05 (s, 3H); EI-MS m/z: 619 $[M+Na]^+$.

Step 7: Preparation of Compound A-52g

Compound A-52f (121 mg, 0.2 mmol) was dissolved in THE (8 mL) under a nitrogen atmosphere at 0° C., and then sodium borohydride (40 mg, 1.01 mmol) was added, and the mixture was stirred for 2 hours. After completion of the reaction, distilled water (50 mL) was added to terminate the reaction, and EA (50 mL) was added to extract the organic layer twice. The obtained organic layer was washed by adding an aqueous sodium chloride solution. The washed organic layer was dried over anhydrous magnesium sulfate, filtered, and then concentrated under reduced pressure. The resulting residue was subjected to column chromatography to obtain Compound A-52g in the form of a white solid (73 mg, 60.2%).

$^1$H-NMR (400 MHz, $CDCl_3$) δ 7.56 (s, 1H), 7.2 (d, J=8 Hz, 1H), 6.95 (d, J=7.6 Hz, 1H), 5.45-5.3 (m, 3H), 5.22 (d, J=6.8 Hz, 1H), 4.86 (d, J=5.6 Hz, 2H), 4.63 (d, J=14.4 Hz, 1H), 4.58 (d, J=14.4 Hz, 1H), 4.24-4.2 (m, 1H), 3.74 (s, 3H), 2.08 (s, 3H), 2.05 (s, 6H), 1.74 (t, J=6 Hz, 1H); EI-MS m/z: 621 $[M+Na]^+$.

Step 8: Preparation of Compound A-52h

Compound A-52g (423 mg, 0.71 mmol) was dissolved in MC (18.5 mL) under a nitrogen atmosphere at 0° C., and then 4-nitrophenyl chloroformate (285 mg, 1.41 mmol), pyridine (170 μL, 2.12 mmol) and DIPEA (180 μL, 1.06 mmol) were sequentially added, and the mixture was stirred at 0° C. for 30 minutes and at room temperature for 2 hours. After completion of the reaction, the reaction solution was diluted with MC (50 mL), and 2N-hydrochloric acid aqueous solution (50 mL) was added to extract the organic layer twice. The obtained organic layer was washed by adding an aqueous sodium chloride solution. The washed organic layer was dried over anhydrous magnesium sulfate, filtered, and then concentrated under reduced pressure. The resulting residue was subjected to column chromatography to obtain Compound A-52h in the form of a white solid (499.2 mg, 92.6%).

$^1$H-NMR (400 MHz, $CDCl_3$) δ 8.27 (d, J=9.2 Hz, 2H), 7.58 (s, 1H), 7.38 (d, J=9.2 Hz, 2H), 7.34 (d, J=8 Hz, 1H), 6.98 (d, J=8 Hz, 1H), 5.46-5.34 (m, 5H), 5.27 (d, J=7.2 Hz, 1H), 4.66 (d, J=14.4 Hz, 1H), 4.6 (d, J=14.4 Hz, 1H), 4.26-4.22 (m, 1H), 3.74 (s, 3H), 2.08 (s, 3H), 2.07-2.03 (m, 6H); EI-MS m/z: 786 $[M+Na]^+$.

Step 9: Preparation of Compound A-52i

Compound A-52h (100 mg, 0.13 mmol) was dissolved in DMF (2 mL) under a nitrogen atmosphere at 0° C., and then MMAE (94 mg, 0.13 mmol), HOBt (26 mg, 0.195 mmol), DIPEA (56 µL, 0.325 mmol) and pyridine (2 mL) were sequentially added, and the mixture was stirred at room temperature for 16 hours. After completion of the reaction, the organic layer was extracted twice with EA (50 mL) and 2N-hydrochloric acid aqueous solution (50 mL). The obtained organic layer was dried over anhydrous magnesium sulfate, filtered, and then concentrated under reduced pressure. The resulting residue was subjected to column chromatography to obtain Compound A-52i in the form of a white solid (125 mg, 70.9%); EI-MS m/z: 1343 $[M+H]^+$.

Step 10: Preparation of Compound A-52

Compound A-52i (40.4 mg, 0.03 mmol) was dissolved by mixing and adding methanol (2 mL) and THE (2 mL) at −20° C., and then lithium hydroxide (8 mg, 0.19 mmol) dissolved in distilled water (0.4 mL) was added dropwise, and the mixture was stirred at −20° C. for 2 hours and stirred at 0° C. for an additional 30 minutes. After completion of the reaction, 2N-hydrochloric acid aqueous solution (0.5 mL) was added to terminate the reaction, and the reaction solution was diluted with ACN (1 mL) and distilled water (1 mL), then separated and purified using Preparative-HPLC, and freeze-dried to obtain Compound A-52 in the form of a white solid (30.3 mg, 83.7%); EI-MS m/z: 1202 [M]+.

Example I-48: Preparation of Compound A-53

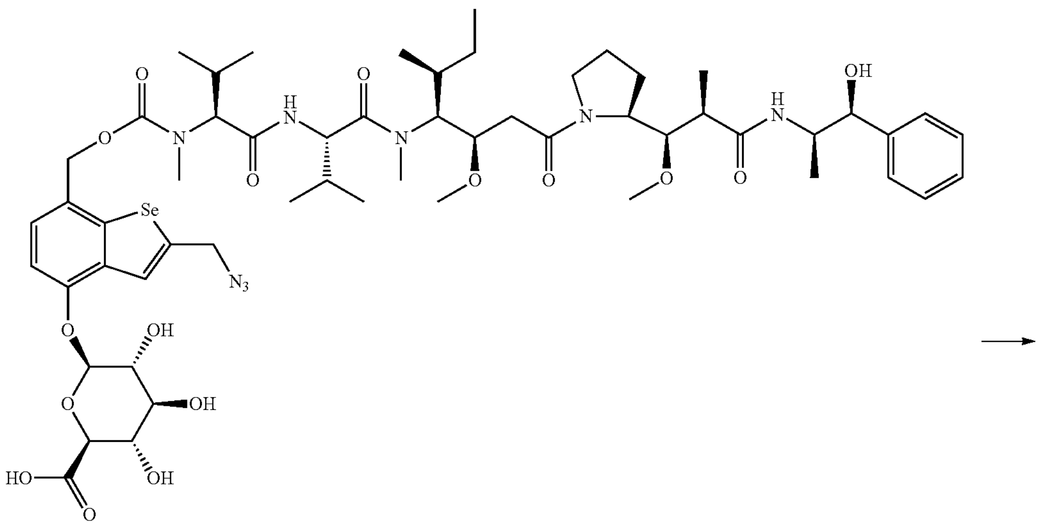

A-52

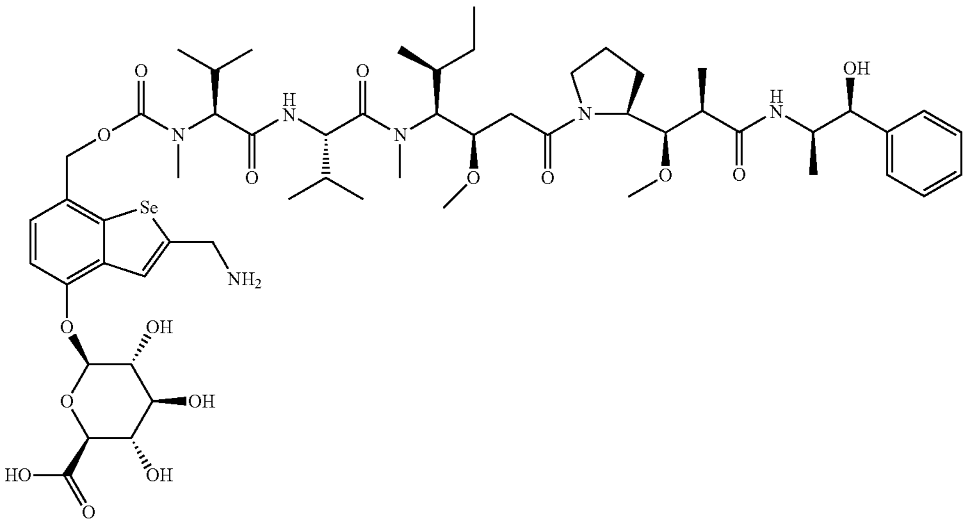

A-53

Compound A-52 (15.3 mg, 0.015 mmol) was dissolved in THE (1.0 mL) under a nitrogen atmosphere at room temperature, and then triphenylphosphine (5.9 mg, 0.022 mmol) and distilled water (200.0 μL) were sequentially added, and the mixture was stirred for 16 hours. 2N-sodium hydroxide aqueous solution (10.0 μL) was added to the above reaction solution, and the mixture was stirred for an additional 30 minutes, and then 2N-hydrochloric acid aqueous solution was slowly added dropwise to adjust the pH of the reaction solution to 3, and the reaction solution was separated and purified using Preparative-HPLC, and then freeze-dried to obtain Compound A-53 in the form of a white solid (11.4 mg, 76.2%); EI-MS m/z: 1177 $[M+H]^+$.

Example I-49: Preparation of Compound A-54

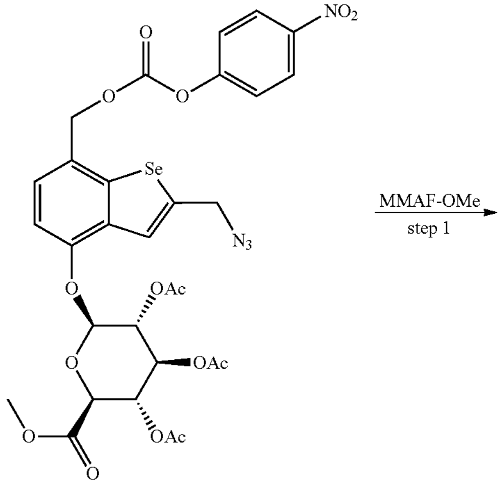

A-52h

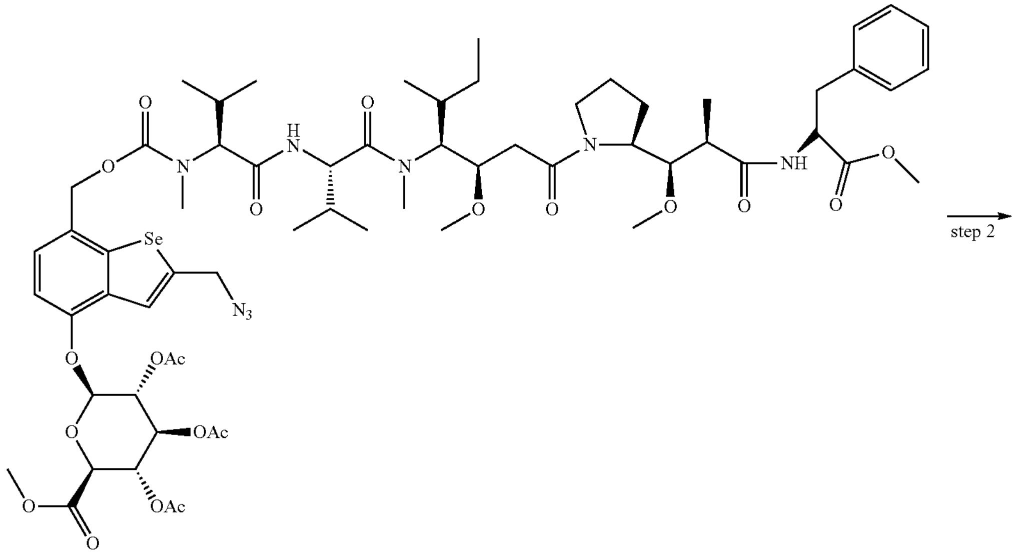

A-54a

-continued

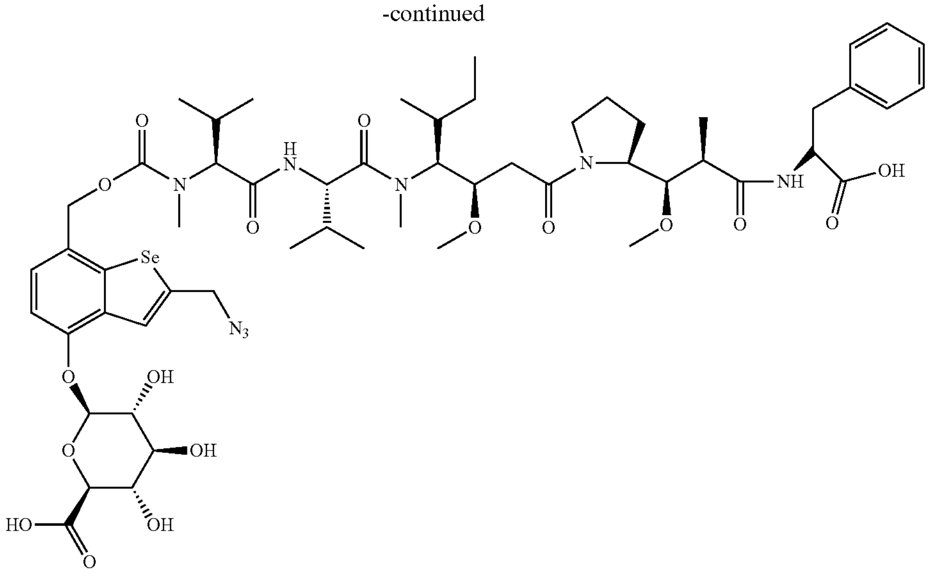

A-54

Step 1: Preparation of Compound A-54a

Compound A-52h (100.0 mg, 0.13 mmol) was dissolved in DMF (2.0 mL) under a nitrogen atmosphere at 0° C., and then MMAF-OMe (monomethyl auristatin F methyl ester, CAS NO. 863971-12-4, 97.7 mg, 0.13 mmol), HOBt (26.0 mg, 0.195 mmol), DIPEA (56.0 μL, 0.325 mmol) and pyridine (2.0 mL) were sequentially added, and the mixture was stirred at room temperature for 16 hours. After completion of the reaction, extraction was performed using distilled water (10 mL), 2N-hydrochloric acid aqueous solution (5 mL) and EA (15 mL). The obtained organic layer was dried over anhydrous magnesium sulfate, filtered, and then concentrated under reduced pressure. The resulting residue was subjected to column chromatography to obtain Compound A-54a in the form of a white solid (120.0 mg, 67%); EI-MS m/z: 1371 $[M+H]^+$.

Step 2: Preparation of Compound A-54

Compound A-54a (60.0 mg, 0.043 mmol) was dissolved in methanol (1.0 mL) under a nitrogen atmosphere at 0° C., and then lithium hydroxide (13.8 mg, 0.328 mmol) dissolved in distilled water (1.0 mL) was slowly added dropwise, and the mixture was stirred at room temperature for 3 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-54 in the form of a white solid (29.6 mg, 56%); EI-MS m/z: 1217 $[M+H]^+$.

Example I-50: Preparation of Compound A-55

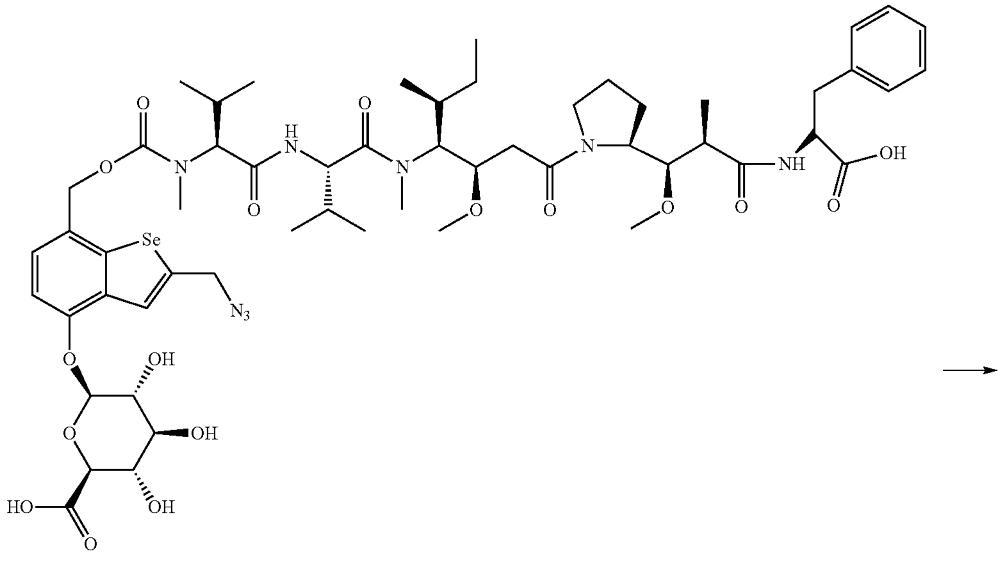

A-54

-continued

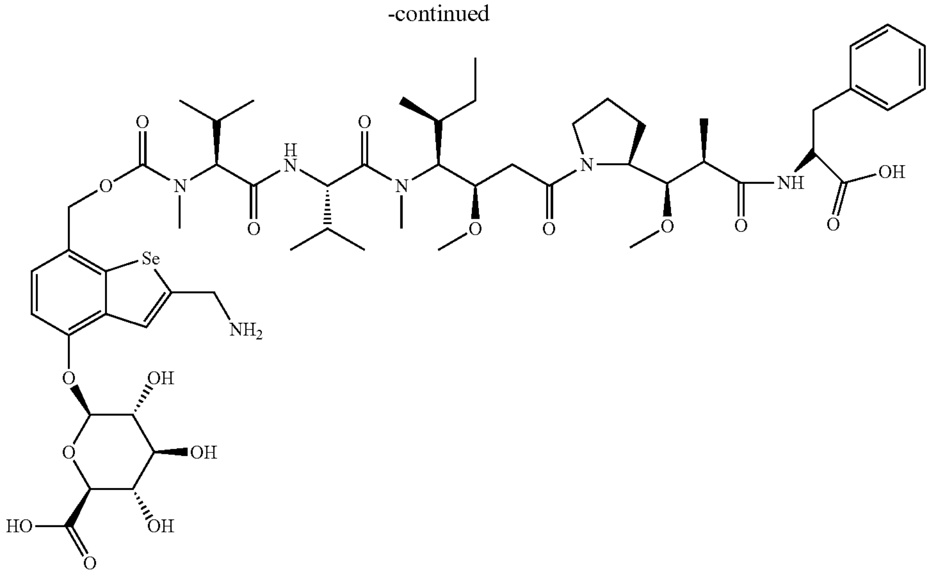

A-55

Compound A-54 (21.7 mg, 0.017 mmol) was dissolved in THE (1.5 mL) under a nitrogen atmosphere at room temperature, and then triphenylphosphine (5.1 mg, 0.019 mmol) and distilled water (0.15 mL) were sequentially added, and the mixture was stirred for 16 hours. 2N-hydrochloric acid aqueous solution (10.0 μL) was added to the above reaction solution, and after reaction for 4 hours, 2N-sodium hydroxide aqueous solution (20.0 μL) was added, and the mixture was stirred for an additional 1 hour. Then, 2N-hydrochloric acid aqueous solution was slowly added dropwise to adjust the pH of the reaction solution to 3, and the reaction solution was separated and purified using Preparative-HPLC, and then freeze-dried to obtain Compound A-55 in the form of a white solid (11.0 mg, 52%); EI-MS m/z: 1191 $[M+H]^+$.

Example I-51: Preparation of Compound A-56

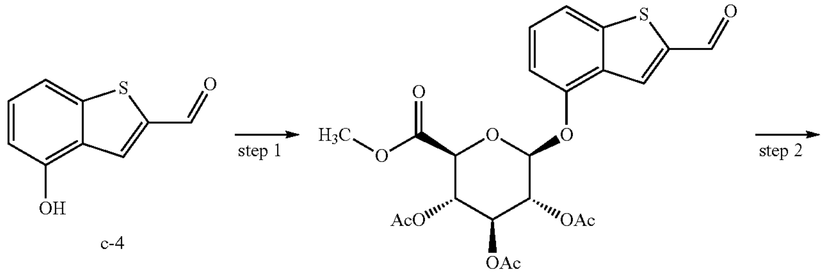

c-4

A-56a

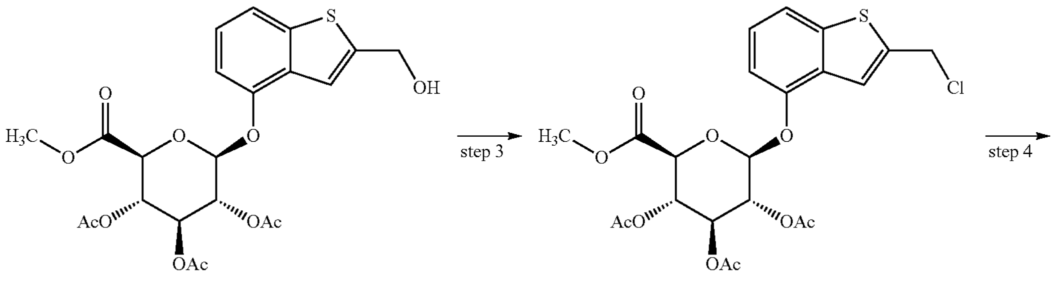

A-56b

A-56c

-continued
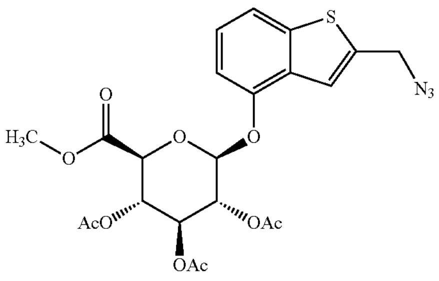
A-56d
step 5
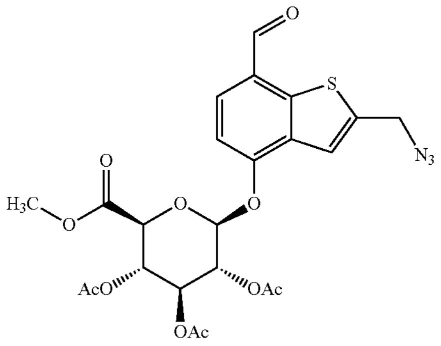
A-56e
step 6
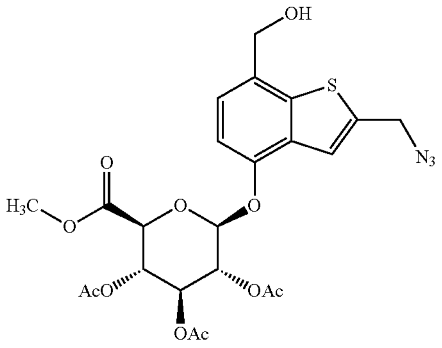
A-56f
step 7
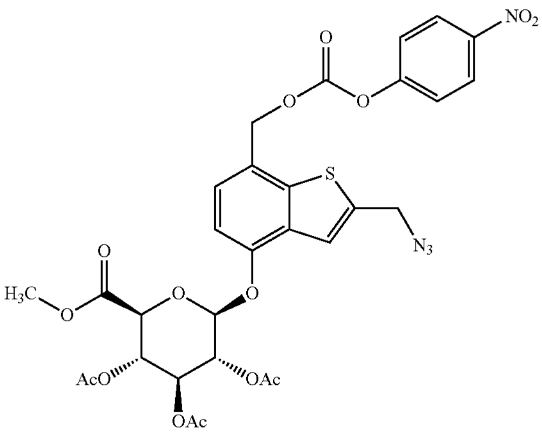
A-56g
step 8
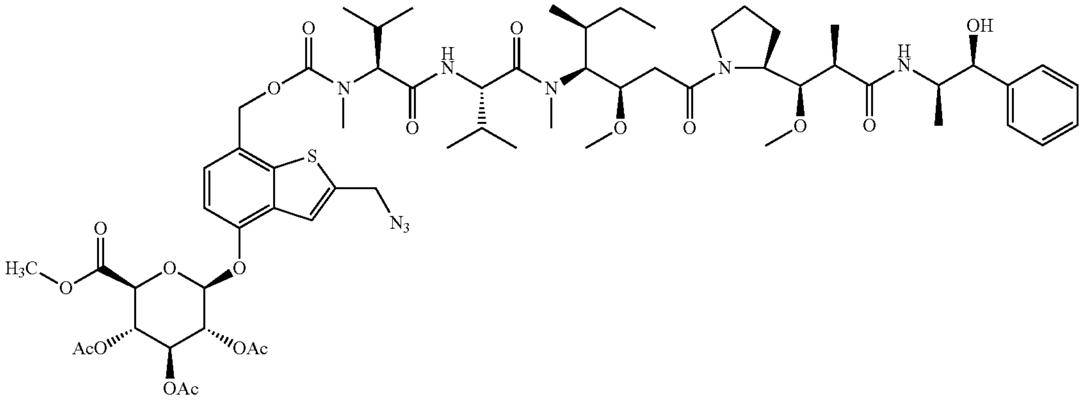
step 9
A-56h -continued

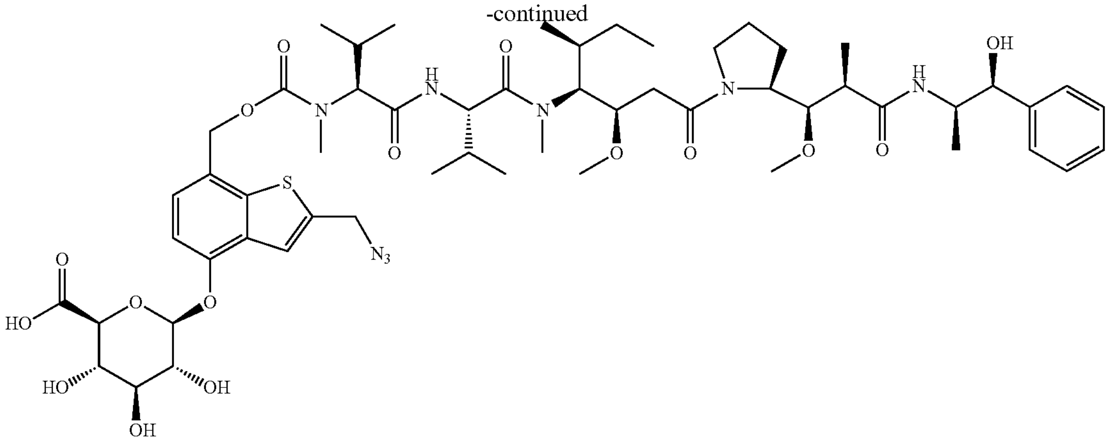

A-56

Step 1: Preparation of Compound A-56a

Silver carbonate (Alfa aesar, CAS NO. 534-16-7, 37.9 g, 137.44 mmol) was added to ACN (330 mL) under a nitrogen atmosphere at room temperature, and then HMTTA (Alfa aesar, CAS NO. 3083-10-1, 5.56 mL, 20.43 mmol) was added, and the mixture was stirred for 1 hour. Additionally, Core C-4 (6.62 g, 37.15 mmol) and acetobromo-a-D-glucuronic acid methyl ester (TCI, 36.88 g, 92.86 mmol) dissolved in ACN (100 mL) were slowly added, and the mixture was stirred for 16 hours while slowly raising the temperature from 0° C. to room temperature. After completion of the reaction, the reaction solution was diluted with EA (500 mL) and filtered using Celite. Distilled water (1000 mL) and 2N-hydrochloric acid aqueous solution (70 mL) were added to extract the filtered solution. The obtained organic layer was washed by adding a saturated aqueous sodium chloride solution (500 mL), then dried over anhydrous magnesium sulfate, filtered, and then concentrated under reduced pressure to obtain Compound A-56a, which was used in the next reaction without an additional purification process (11.93 g, 65%); EI-MS m/z: 517 [M+Na]*.

Step 2: Preparation of Compound A-56b

Compound A-56a (11.93 g, 24.13 mmol) was dissolved in THF (600 mL) under a nitrogen atmosphere at 0° C., and then sodium borohydride (2.28 g, 60.31 mmol) was added, and the mixture was stirred for 1.5 hours. After completion of the reaction, distilled water (600 mL) was added to terminate the reaction, and EA (1000 mL) and distilled water (500 mL) were added to extract the organic layer. The obtained organic layer was washed by adding a saturated aqueous sodium chloride solution (500 mL), then dried over anhydrous magnesium sulfate, filtered, and then concentrated under reduced pressure. The resulting residue was subjected to column chromatography to obtain Compound A-56b in the form of an ivory solid (3.42 g, 29%).

$^1$H-NMR (400 MHz, $CDCl_3$) δ 7.53 (d, J=8.4 Hz, 1H), 7.28 (s, 1H), 7.25 (m, 1H), 6.93 (d, J=8 Hz, 1H), 5.41-5.37 (m, 3H), 5.25 (d, J=6.8 Hz, 1H), 4.92 (d, J=6 Hz, 2H), 4.21 (m, 1H), 3.72 (s, 3H), 2.07 (s, 3H), 2.06 (s, 3H), 2.05 (s, 3H), 1.91 (t, J=6 Hz, 1H); EI-MS m/z: 518 $[M+Na]^+$.

Step 3: Preparation of Compound A-56c

Compound A-56b (3.42 g, 6.89 mmol) was dissolved in concentrated hydrochloric acid (172 mL) under a nitrogen atmosphere at −10° C., and then the mixture was stirred for 3 hours at -10° C. After completion of the reaction, EA (400 mL) and distilled water (400 mL) were added to extract the organic layer, and the obtained organic layer was washed by adding a saturated aqueous sodium chloride solution (200 mL), then dried over anhydrous magnesium sulfate, filtered, and then concentrated under reduced pressure to obtain Compound A-56c, which was used in the next reaction without an additional purification process (2.77 g, 78%); MS m/z: 536 $[M+Na]^+$.

Step 4: Preparation of Compound A-56d

Compound A-56c (2.78 g, 5.40 mmol) was dissolved in DMF (103 mL) under a nitrogen atmosphere at room temperature, and then sodium azide (526 mg, 8.09 mmol) was added, and the mixture was stirred at 60° C. for 16 hours. After completion of the reaction, EA (300 mL) and distilled water (300 mL) were added to extract the organic layer, and the obtained organic layer was washed by adding a saturated aqueous sodium chloride solution (150 mL), then dried over anhydrous magnesium sulfate, filtered, and then concentrated under reduced pressure. The resulting residue was subjected to column chromatography to obtain Compound A-56d in the form of a white solid (1.45 g, 52%).

$^1$H-NMR (400 MHz, $CDCl_3$) δ 7.53 (d, J=8.4 Hz, 1H), 7.32 (s, 1H), 7.28 (m, 1H), 6.94 (d, J=7.6 Hz, 1H), 5.45-5.37 (m, 3H), 5.25 (d, J=7.2 Hz, 1H), 4.60 (d, J=14.4 Hz, 1H), 4.53 (d, J=14.4 Hz, 1H), 4.23 (m, 1H), 3.73 (s, 3H), 2.07 (s, 3H), 2.05 (s, 6H); MS m/z: 543 $[M+Na]^+$.

Step 5: Preparation of Compound A-56e

Compound A-56d (1.45 g, 2.78 mmol) was dissolved in MC (80 mL) under a nitrogen atmosphere at −78° C., and then dichloromethyl methyl ether (1.51 mL, 16.68 mmol) and titanium tetrachloride solution (1M-$TiCl_4$ in MC, 16.7 mL, 16.7 mmol) were sequentially and slowly added, and the mixture was stirred for 2.5 hours while maintaining the temperature. After completion of the reaction, cooled distilled water (100 mL) was slowly added dropwise to terminate the reaction, and MC (200 mL) and distilled water (200 mL) were added to extract the organic layer. The obtained organic layer was washed by adding a saturated aqueous sodium chloride solution (100 mL), then dried over anhydrous magnesium sulfate, filtered, and then concentrated under reduced pressure. The resulting residue was subjected to column chromatography to obtain Compound A-56e in the form of a white solid (608 mg, 40%).

$^1$H-NMR (400 MHz, $CDCl_3$) δ 10.11 (s, 1H), 7.85 (d, J=8 Hz, 1H), 7.39 (s, 1H), 7.09 (d, J=8.4 Hz, 1H), 5.45-5.41 (m, 4H), 4.65 (d, J=14.4 Hz, 1H), 4.58 (d, J=14.4 Hz, 1H), 4.32 (m, 1H), 3.72 (s, 3H), 2.09 (s, 3H), 2.07 (s, 3H), 2.05 (s, 3H); MS m/z: 571 $[M+Na]^+$.

Step 6: Preparation of Compound A-56f

Compound A-56e (608 mg, 1.11 mmol) was dissolved in THE (56 mL) under a nitrogen atmosphere at 0° C., and then sodium borohydride (188 mg, 4.97 mmol) was added, and the mixture was stirred for 4 hours. After completion of the reaction, distilled water (60 mL) was added to terminate the reaction, and EA (100 mL) and distilled water (50 mL) were added to extract the organic layer. The obtained organic layer was washed by adding a saturated aqueous sodium chloride solution (100 mL), then dried over anhydrous magnesium sulfate, filtered, and then concentrated under reduced pressure. The resulting residue was subjected to column chromatography to obtain Compound A-56f in the form of a white solid (469 mg, 77%).

$^1$H-NMR (400 MHz, $CDCl_3$) δ 7.36 (s, 1H), 7.29 (d, J=8 Hz, 1H), 6.94 (d, J=8 Hz, 1H), 5.42-5.37 (m, 3H), 5.24 (d, J=6.8 Hz, 1H), 4.89 (d, J=6 Hz, 2H), 4.61 (d, J=14.4 Hz, 1H), 4.54 (d, J=14.4 Hz, 1H), 4.22 (m, 1H), 3.74 (s, 3H), 2.07 (s, 3H), 2.05 (s, 6H), 1.75 (t, J=6 Hz, 1H); MS m/z: 573 $[M+Na]^+$.

Step 7: Preparation of Compound A-56g

Compound A-56f (468 mg, 0.85 mmol) was dissolved in MC (14 mL) under a nitrogen atmosphere at 0° C., and then 4-nitrophenyl chloroformate (342 mg, 1.70 mmol), pyridine (20.5 μL, 2.54 mmol) and DIPEA (222 μL, 1.28 mmol) were sequentially added, and the mixture was stirred for 1.5 hours while slowly raising the temperature from 0° C. to room temperature. After completion of the reaction, the reaction solution was diluted with EA (70 mL), and 2N-hydrochloric acid aqueous solution (70 mL) was added to extract the organic layer. The obtained organic layer was washed by adding a saturated aqueous sodium chloride solution (70 mL), then dried over anhydrous magnesium sulfate, filtered, and then concentrated under reduced pressure. The residue thus obtained was subjected to column chromatography to obtain Compound A-56g in the form of a white solid (560 mg, 92%).

$^1$H-NMR (400 MHz, $CDCl_3$) δ 8.27 (d, J=8.8 Hz, 2H), 7.39-7.37 (m, 4H), 6.96 (d, J=8 Hz, 1H), 5.48 (s, 2H), 5.45-5.38 (m, 3H), 5.28 (d, J=6.8 Hz, 1H), 4.63 (d, J=14.4 Hz, 1H), 4.56 (d, J=14.4 Hz, 1H), 4.25 (m, 1H), 3.74 (s, 3H), 2.08 (s, 3H), 2.06 (s, 3H), 2.05 (s, 3H); MS m/z: 738 $[M+Na]^+$.

Step 8: Preparation of Compound A-56h

Compound A-56g (100 mg, 0.14 mmol) was dissolved in DMF (2 mL) under a nitrogen atmosphere at 0° C., and then MMAE (100 mg, 0.14 mmol), HOBt (28 mg, 0.21 mmol), DIPEA (60.8 μL, 0.35 mmol) and pyridine (2 mL) were sequentially added, and the mixture was stirred at room temperature for 16 hours. After completion of the reaction, the organic layer was extracted twice with EA (40 mL) and 2N-hydrochloric acid aqueous solution (40 mL). The obtained organic layer was washed by adding a saturated aqueous sodium chloride solution (40 mL), then dried over anhydrous magnesium sulfate, filtered, and then concentrated under reduced pressure. The resulting residue was subjected to column chromatography to obtain Compound A-56h in the form of a white solid (129 mg, 71%); EI-MS m/z: 1296 $[M+H]^+$.

Step 9: Preparation of Compound A-56

Compound A-56h (63.7 mg, 0.049 mmol) was dissolved by mixing and adding methanol (1.3 mL), distilled water (0.1 mL) and THE (0.25 mL) at −20° C., and then lithium hydroxide (10.3 mg, 0.246 mmol) dissolved in distilled water (0.8 mL) was added dropwise, and the mixture was stirred at −20° C. for 2 hours. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and freeze-dried to obtain Compound A-56 in the form of a white solid (46.2 mg, 91%); EI-MS m/z: 1156 $[M+H]^+$.

Example I-52: Preparation of Compound A-57

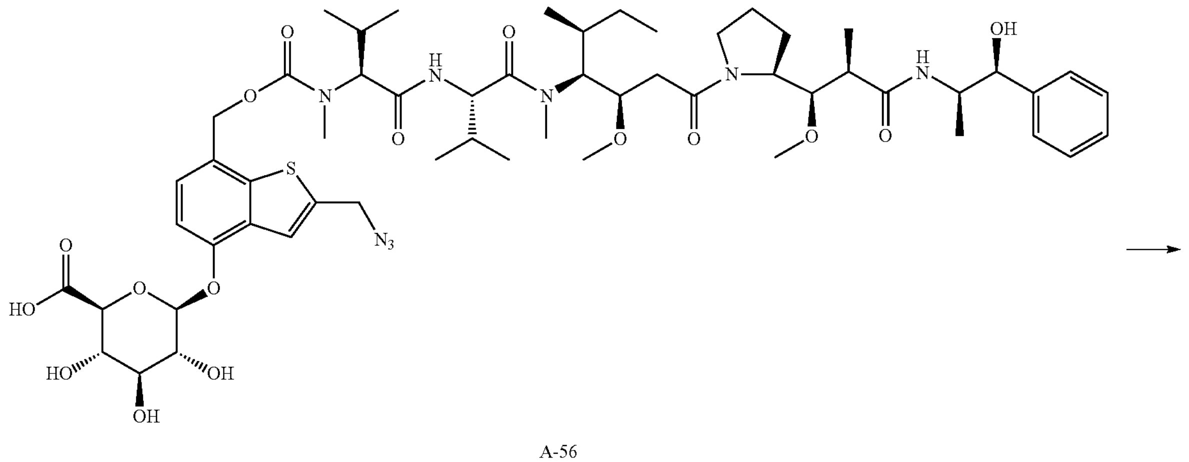

A-56

-continued

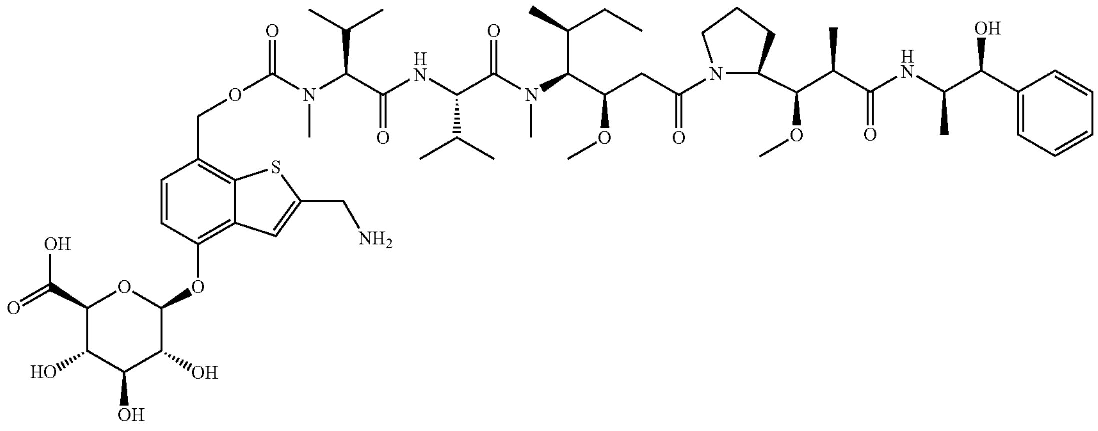

A-57

Compound A-56 (20 mg, 0.017 mmol) was dissolved in THE (1.5 mL) under a nitrogen atmosphere at room temperature, and then triphenylphosphine (5 mg, 0.019 mmol) and distilled water (0.15 mL) were sequentially added, and the mixture was stirred for 16 hours. 2N-sodium hydroxide aqueous solution (10 μL) was added to the above reaction solution at room temperature, and the mixture was stirred for an additional 4 hours, and then 2N-hydrochloric acid aqueous solution was slowly added dropwise to adjust the pH of the reaction solution to 3, and the reaction solution was separated and purified using Preparative-HPLC, and then freeze-dried to obtain Compound A-57 in the form of a white solid (13.7 mg, 70%); MS m/z: 1130 $[M+H]^+$.

Example I-53: Preparation of Compound A-58

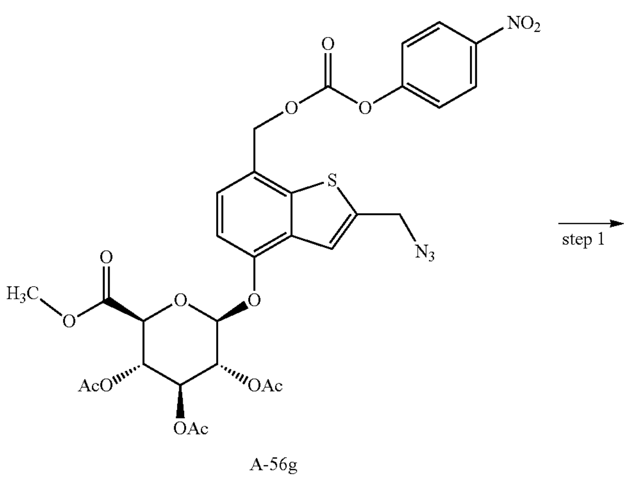

A-56g

-continued

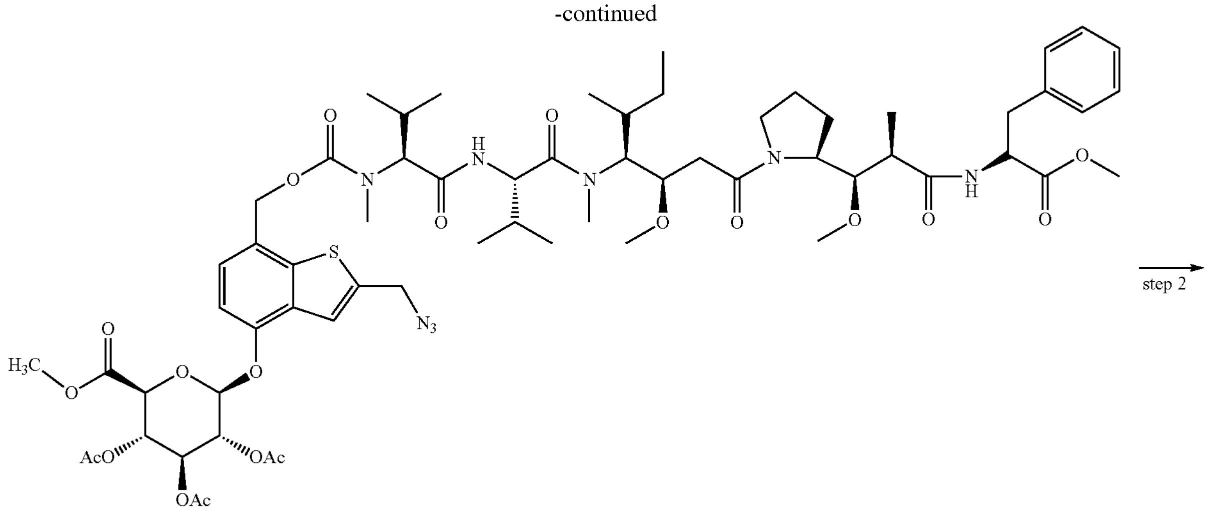

A-58a

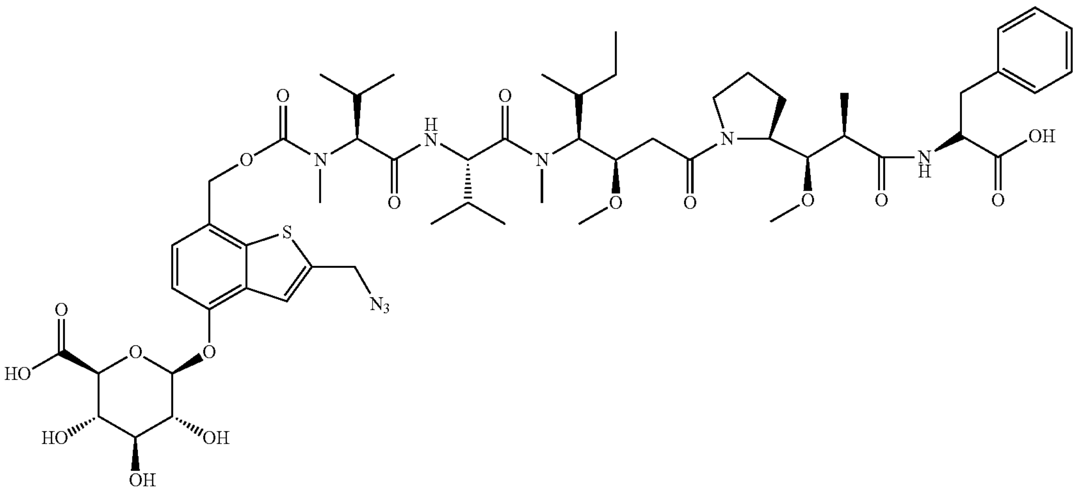

A-58

Step 1: Preparation of Compound A-58a

Compound A-56g (100 mg, 0.14 mmol) was dissolved in DMF (2 mL) under a nitrogen atmosphere at 0° C., and then MMAF-OMe (104 mg, 0.14 mmol), HOBt (28 mg, 0.21 mmol), DIPEA (60.8 μL, 0.35 mmol) and pyridine (2 mL) were sequentially added, and the mixture was stirred at room temperature for 16 hours. After completion of the reaction, the organic layer was extracted twice with EA (40 mL) and 2N-hydrochloric acid aqueous solution (40 mL). The obtained organic layer was washed by adding a saturated aqueous sodium chloride solution (40 mL), then dried over anhydrous magnesium sulfate, filtered, and then concentrated under reduced pressure. The resulting residue was subjected to column chromatography to obtain Compound A-58a in the form of a white solid (139 mg, 75%); EI-MS m/z: 1324 $[M+H]^+$.

Step 2: Preparation of Compound A-58

Compound A-58a (70.5 mg, 0.053 mmol) was dissolved by mixing and adding methanol (1.3 mL), distilled water (0.1 mL) and THE (0.25 mL) at −20° C., and then lithium hydroxide (22.4 mg, 0.533 mmol) dissolved in distilled water (1.6 mL) was added dropwise, and the mixture was stirred at −20° C. for 2.5 hours and then stirred for 2 hours while slowly raising the temperature to 0° C. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and freeze-dried to obtain Compound A-58 in the form of a white solid (35.1 mg, 56%); EI-MS m/z: 1170 $[M+H]^+$.

Example I-54: Preparation of Compound A-59

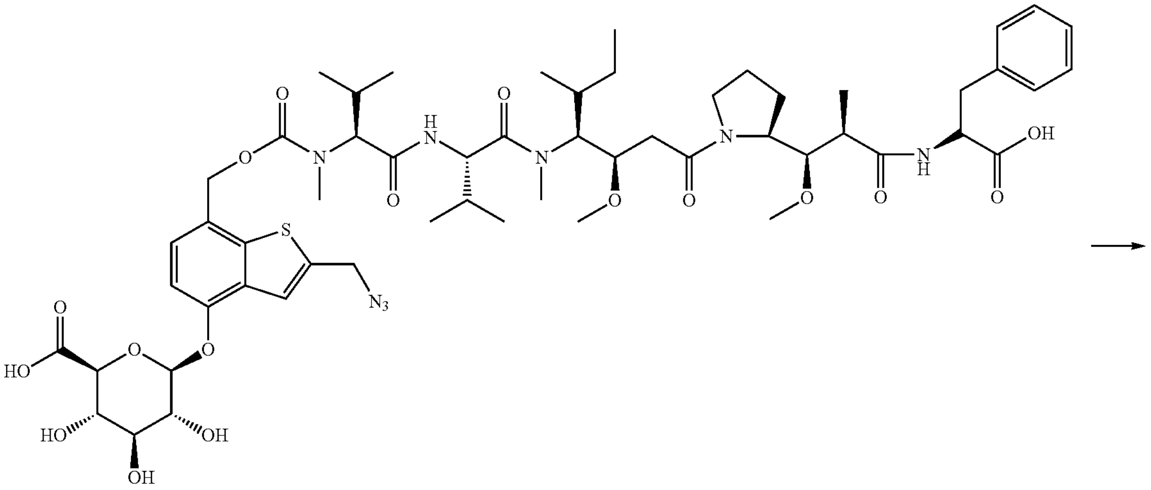

A-58

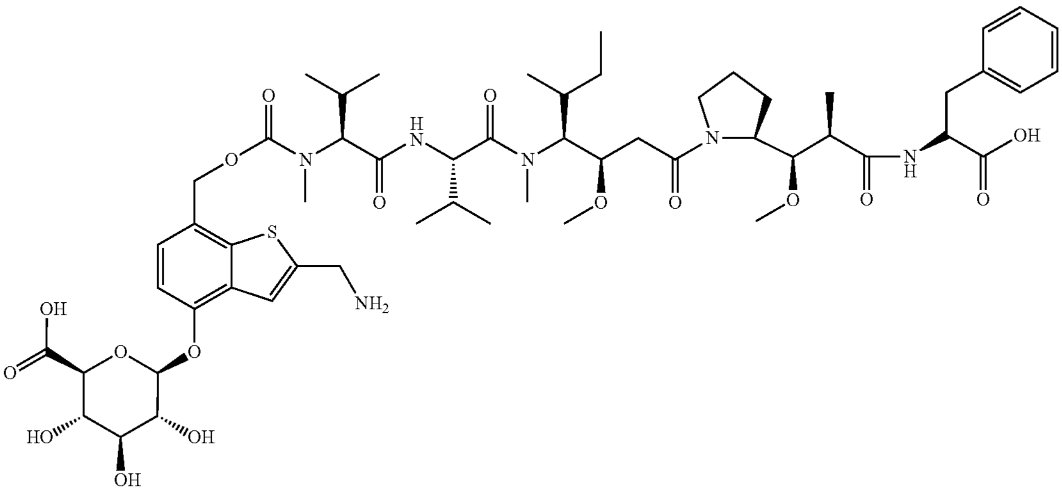

A-59

Compound A-58 (20 mg, 0.017 mmol) was dissolved in THF (1.5 mL) under a nitrogen atmosphere at room temperature, and then triphenylphosphine (5 mg, 0.019 mmol) and distilled water (0.15 mL) were sequentially added, and the mixture was stirred for 16 hours. 2N-hydrochloric acid aqueous solution (10 μL) was added to the above reaction solution at room temperature, and the mixture was stirred for 1 hour, and then 2N-sodium hydroxide aqueous solution (20 μL) was added, and the mixture was stirred for an additional 2 hours. After completion of the reaction, 2N-hydrochloric acid aqueous solution was slowly added dropwise to adjust the pH of the reaction solution to 3, and the reaction solution was separated and purified using Preparative-HPLC, and then freeze-dried to obtain Compound A-59 in the form of a white solid (14.3 mg, 73%); MS m/z: 1144 $[M+H]^+$.

Example I-55: Preparation of Compound A-60

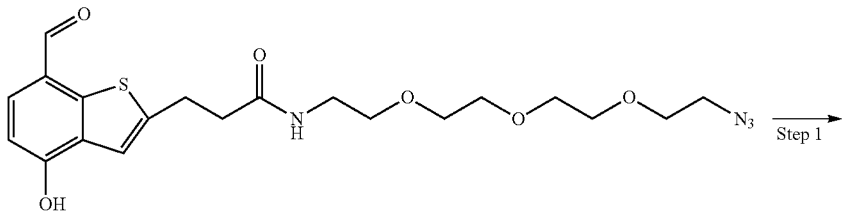

A-15b

-continued
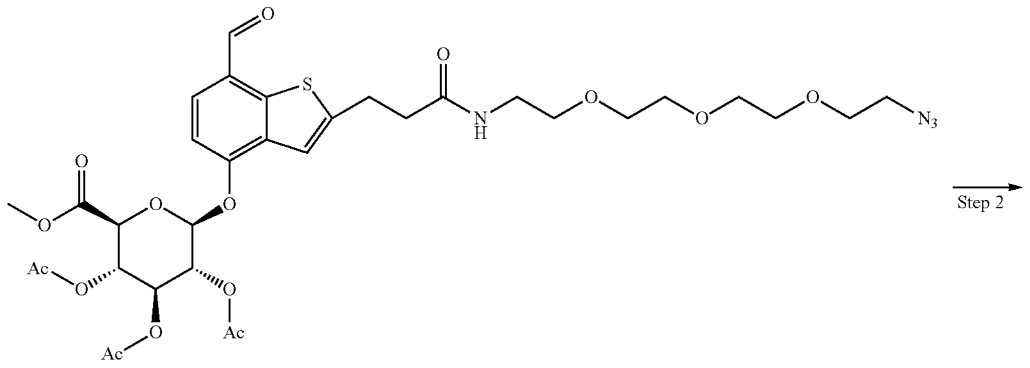
A-60a
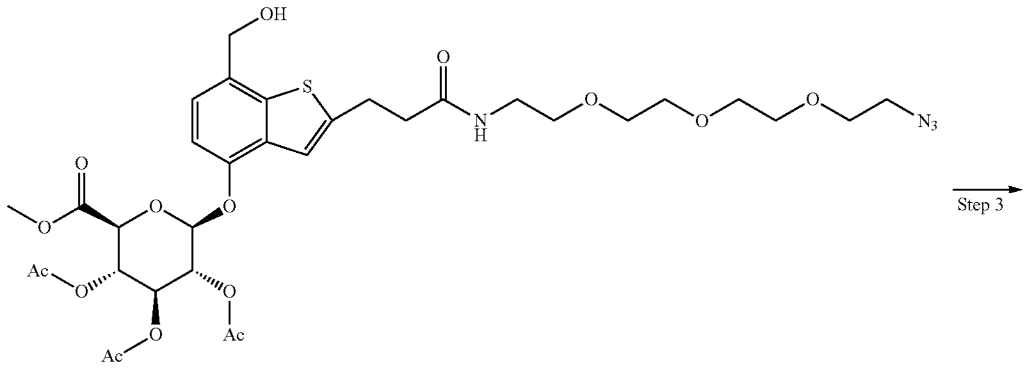
A-60b
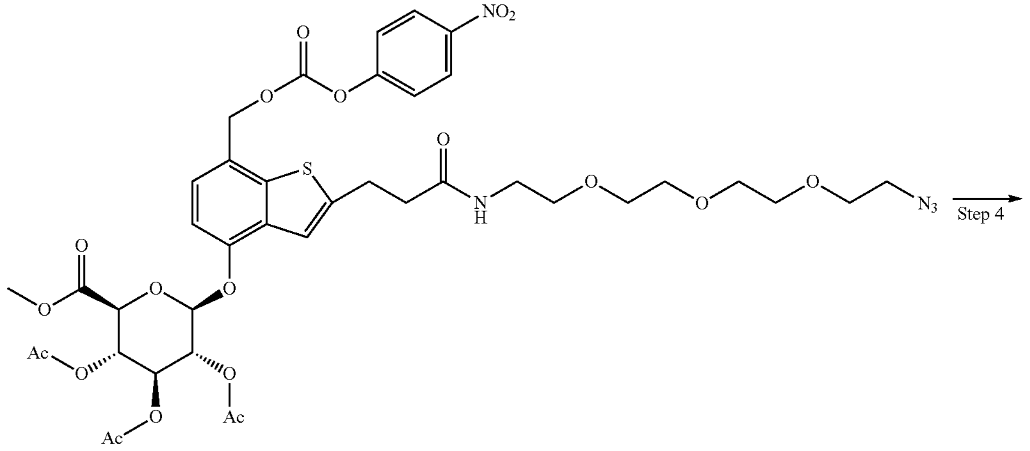
A-60c

-continued

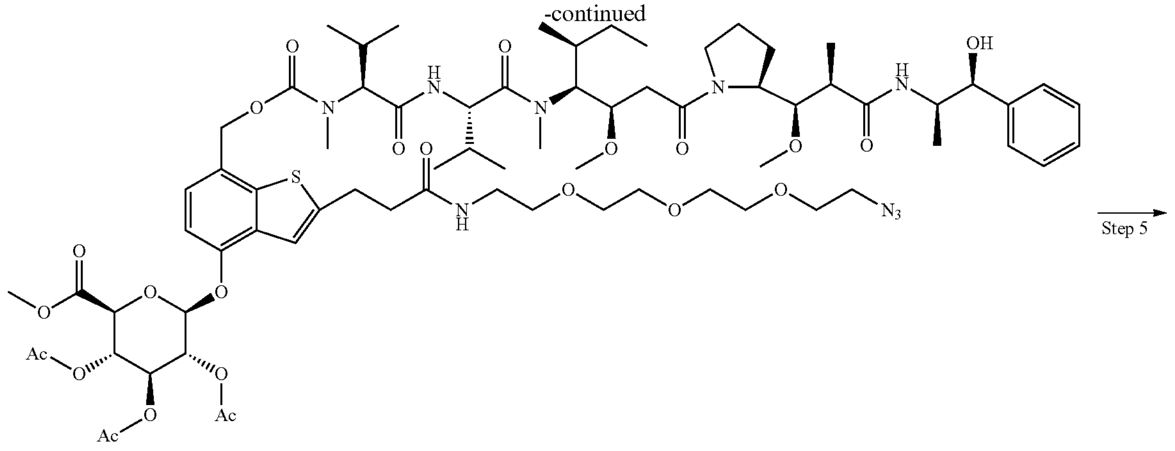

A-60d

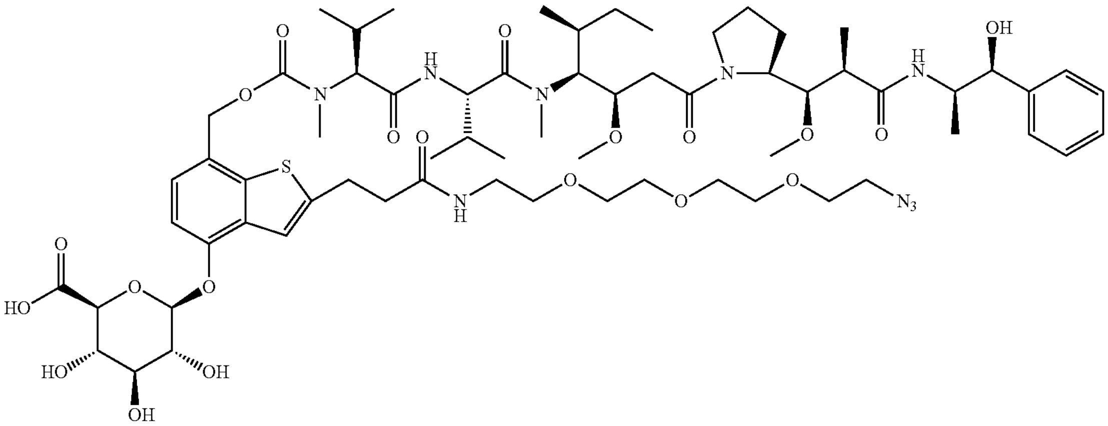

A-60

Step 1: Preparation of Compound A-60a

Compound A-15b (1.15 g, 2.56 mmol) was dissolved in MC (85 mL) under a nitrogen atmosphere at 0° C., and then acetobromo-a-D-glucuronic acid methyl ester (TCI, 1.63 g, 4.11 mmol), benzyltributyl ammonium chloride (801 mg, 2.56 mmol) and 5N-sodium hydroxide aqueous solution (1.54 mL, 7.70 mmol) were slowly added, and the mixture was stirred for 16 hours while slowly raising the temperature from 0° C. to room temperature. After completion of the reaction, 2N-hydrochloric acid aqueous solution was added to the reaction solution to neutralize it, and MC (150 mL) and distilled water (80 mL), a saturated aqueous sodium chloride solution (70 mL) were added to extract the organic layer twice. The obtained organic layer was dried over anhydrous magnesium sulfate, filtered, and then concentrated under reduced pressure. The resulting residue was subjected to column chromatography to obtain Compound A-60a in the form of a yellow sticky gum (348 mg, 18%).

$^1$H-NMR (400 MHz, $CDCl_3$) δ 10.08 (s, 1H), 7.76 (d, J=8 Hz, 1H), 7.16 (s, 1H), 7.05 (d, J=8 Hz, 1H), 6.14 (m, 1H), 5.47-5.35 (m, 4H), 4.30 (m, 1H), 3.71 (s, 3H), 3.69-3.62 (m, 6H), 3.62-3.58 (m, 2H), 3.58-3.51 (m, 4H), 3.51-3.43 (m, 2H), 3.40-3.35 (m, 2H), 3.31 (t, J=7.6 Hz, 2H), 2.63 (t, J=7.6 Hz, 2H), 2.09 (s, 3H), 2.07 (s, 6H); EI-MS m/z: 767 $[M+H]^+$.

Step 2: Preparation of Compound A-60b

Compound A-60a (415 mg, 0.54 mmol) was dissolved in THF (20 mL) under a nitrogen atmosphere at 0° C., and then sodium borohydride (71.2 mg, 1.88 mmol) was added, and the mixture was stirred for 4 hours while slowly raising the temperature from 0° C. to room temperature. After completion of the reaction, distilled water (100 mL) was added to terminate the reaction, and EA (100 mL) was added to extract the organic layer twice. The obtained organic layer was dried over anhydrous magnesium sulfate, filtered, and then concentrated under reduced pressure. The resulting residue was subjected to column chromatography to obtain Compound A-60b in the form of a colorless sticky gum (286 mg, 69%).

$^1$H-NMR (400 MHz, $CDCl_3$) δ 7.20 (d, J=8 Hz, 1H), 7.12 (s, 1H), 6.91 (d, J=8 Hz, 1H), 6.13 (m, 1H), 5.41-5.34 (m, 3H), 5.20 (m, 1H), 4.85 (d, J=6 Hz, 2H), 4.20 (m, 1H), 3.73 (s, 3H), 3.66-3.58 (m, 6H), 3.58-3.54 (m, 2H), 3.54-3.48 (m, 4H), 3.48-3.41 (m, 2H), 3.38-3.33 (m, 2H), 3.25 (t, J=7.6 Hz, 2H), 2.59 (t, J=7.6 Hz, 2H), 2.07 (s, 6H), 2.05 (s, 3H); EI-MS m/z: 769 $[M+H]^+$.

Step 3: Preparation of Compound A-60c

Compound A-60b (286 mg, 0.37 mmol) was dissolved in MC (10 mL) under a nitrogen atmosphere at 0° C., and then 4-nitrophenyl chloroformate (150 mg, 0.74 mmol), DIPEA (97.2 μL, 0.56 mmol) and pyridine (90 μL, 1.12 mmol) were sequentially added, and the mixture was stirred at 0° C. for 30 minutes and stirred at room temperature for an additional 2 hours. After completion of the reaction, the reaction solution was diluted with MC (50 mL), and 2N-hydrochloric acid aqueous solution (50 mL) was added to extract the organic layer. The obtained organic layer was dried over anhydrous magnesium sulfate, filtered, and then concentrated under reduced pressure. The residue thus obtained was subjected to column chromatography to obtain Compound A-60c in the form of a colorless sticky gum (136 mg, 39%).

$^1$H-NMR (400 MHz, $CDCl_3$) δ 8.27 (d, J=9.2 Hz, 2H), 7.39 (d, J=9.2 Hz, 2H), 7.30 (d, J=8 Hz, 1H), 7.15 (s, 1H), 6.92 (d, J=8 Hz, 1H), 6.26 (m, 1H), 5.45 (s, 2H), 5.42-5.34 (m, 3H), 5.25 (m, 1H), 4.22 (m, 1H), 3.73 (s, 3H), 3.67-3.59 (m, 8H), 3.59-3.51 (m, 4H), 3.51-3.45 (m, 2H), 3.36 (t, J=5.2 Hz, 2H), 3.28 (t, J=7.6 Hz, 2H), 2.62 (t, J=7.6 Hz, 2H), 2.08 (s, 3H), 2.07 (s, 3H), 2.06 (s, 3H); EI-MS m/z: 934 $[M+H]^+$.

Step 4: Preparation of Compound A-60d

Compound A-60c (57.4 mg, 0.061 mmol) was dissolved in DMF (1 mL) under a nitrogen atmosphere at 0° C., and then MMAE (44.1 mg, 0.061 mmol), HOBt (12.4 mg, 0.092 mmol), DIPEA (26.8 μL, 0.154 mmol) and pyridine (1 mL) were sequentially added, and the mixture was stirred at room temperature for 16 hours. After completion of the reaction, the organic layer was extracted twice with EA (50 mL) and 2N-hydrochloric acid aqueous solution (50 mL), and then the organic layer was washed with a saturated aqueous sodium chloride solution (50 mL). The obtained organic layer was dried over anhydrous magnesium sulfate, filtered, and then concentrated under reduced pressure. The resulting residue was subjected to column chromatography to obtain Compound A-60d in the form of a white sticky gum (60.9 mg, 65%); EI-MS m/z: 1513 $[M+H]^+$, 756 1/2 $[M+H]^+$.

Step 5: Preparation of Compound A-60

Compound A-60d (60.9 mg, 0.04 mmol) was dissolved by mixing and adding methanol (1 mL), distilled water (0.4 mL) and THE (0.4 mL) at −20° C., and then lithium hydroxide (8.4 mg, 0.201 mmol) dissolved in distilled water (0.6 mL) was added dropwise, and the mixture was stirred for 1.5 hours while slowly raising the temperature from −20° C. to −5° C. After completion of the reaction, 2N-hydrochloric acid aqueous solution (0.2 mL) was added to terminate the reaction, and the reaction solution was diluted with ACN (3 mL) and distilled water (3 mL), then separated and purified using Preparative-HPLC, and freeze-dried to obtain Compound A-60 in the form of a white solid (39.7 mg, 72%); EI-MS m/z: 1373 $[M+H]^+$, 686 1/2 $[M+H]^+$.

Example I-56: Preparation of Compound A-61

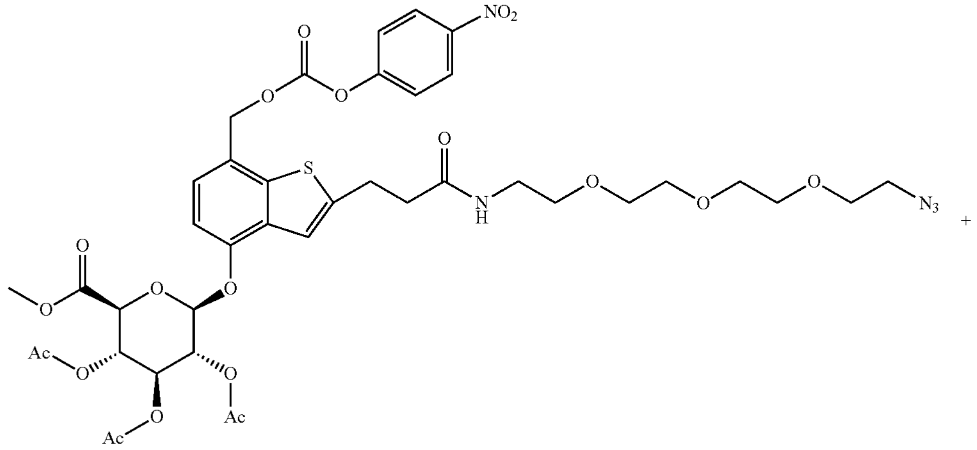

A-60c

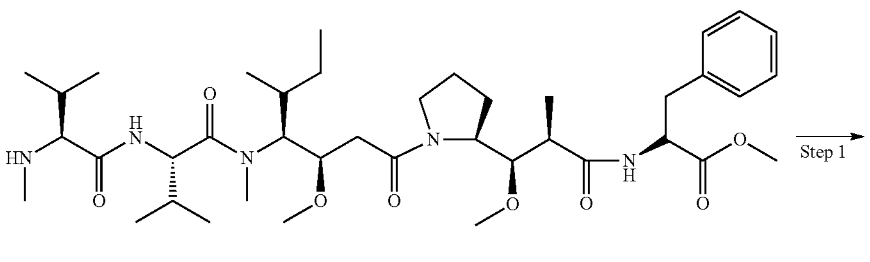

-continued

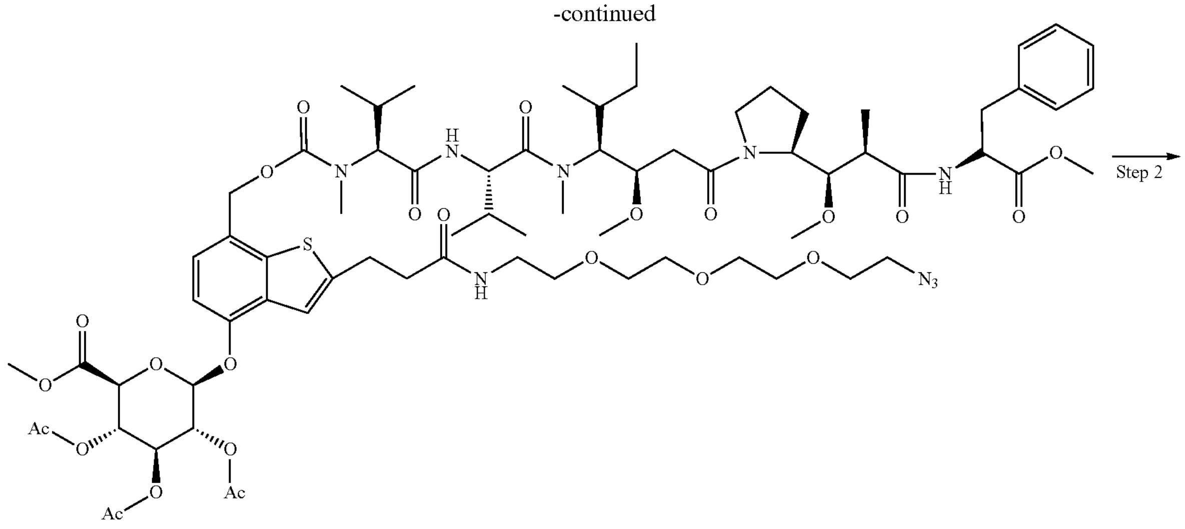

A-61a

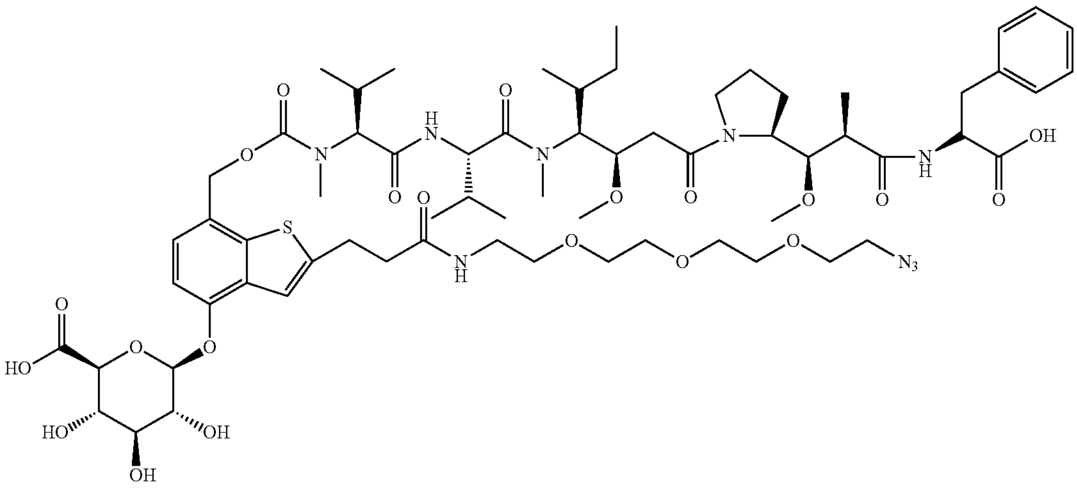

A-61

Step 1: Preparation of Compound A-61a

Compound A-60c (52.4 mg, 0.056 mmol) was dissolved in DMF (1 mL) under a nitrogen atmosphere at 0° C., and then MMAF-OMe (41.9 mg, 0.056 mmol), HOBt (11.4 mg, 0.084 mmol), DIPEA (24.4 μL, 0.14 mmol) and pyridine (1 mL) were sequentially added, and the mixture was stirred at room temperature for 16 hours. After completion of the reaction, the organic layer was extracted twice with EA (50 mL) and 2N-hydrochloric acid aqueous solution (50 mL), and then the organic layer was washed with a saturated aqueous sodium chloride solution (50 mL). The obtained organic layer was dried over anhydrous magnesium sulfate, filtered, and then concentrated under reduced pressure. The resulting residue was subjected to column chromatography to obtain Compound A-61a in the form of a colorless sticky gum (63.5 mg, 73%); EI-MS m/z: 1541 $[M+H]^+$, 770 1/2 $[M+H]^+$.

Step 2: Preparation of Compound A-61

Compound A-61a (63.5 mg, 0.041 mmol) was dissolved by mixing and adding methanol (1 mL), distilled water (0.4 mL) and THF (0.4 mL) at −20° C., and then lithium hydroxide (13 mg, 0.309 mmol) dissolved in distilled water (0.6 mL) was added dropwise, and the mixture was stirred for 4.5 hours while slowly raising the temperature from −20° C. to −5° C. After completion of the reaction, 2N-hydrochloric acid aqueous solution (0.3 mL) was added to terminate the reaction, and the reaction solution was diluted with ACN (3 mL) and distilled water (3 mL), then separated and purified using Preparative-HPLC, and freeze-dried to obtain Compound A-61 in the form of a white solid (40.1 mg, 70%); EI-MS m/z: 1387 $[M+H]^+$, 693 1/2 $[M+H]^+$.

Example I-57: Preparation of Compound A-62
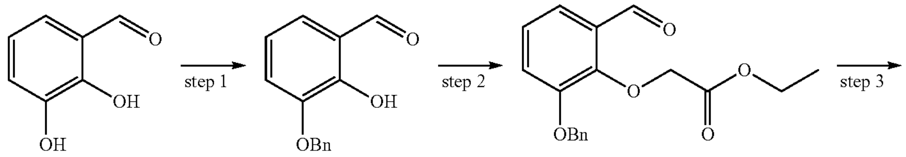
A-62a A-62b A-62c
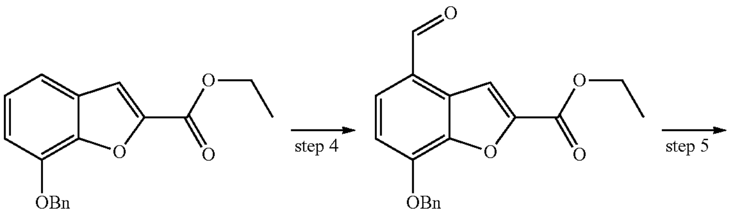
A-62d A-62e
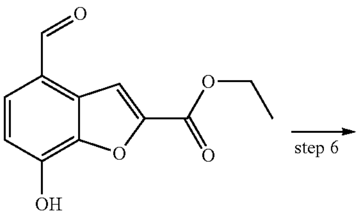
A-62f
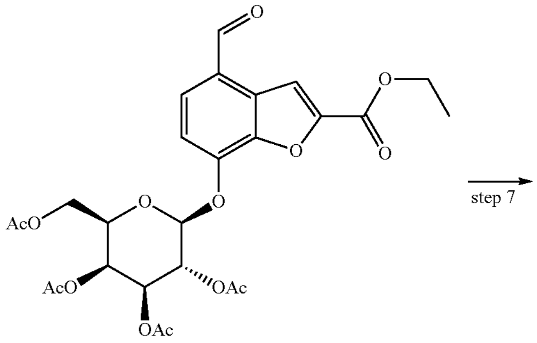
A-62g
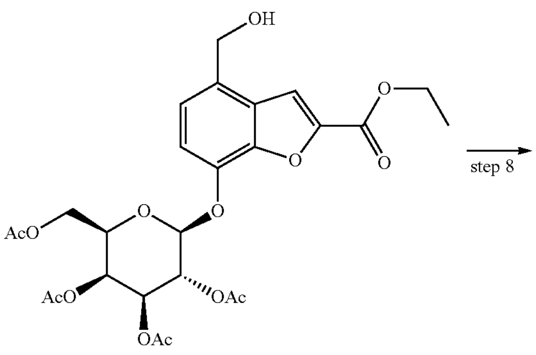
A-62h
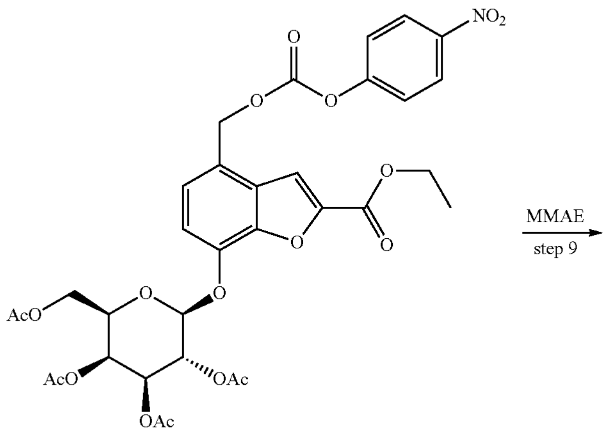
A-62i -continued

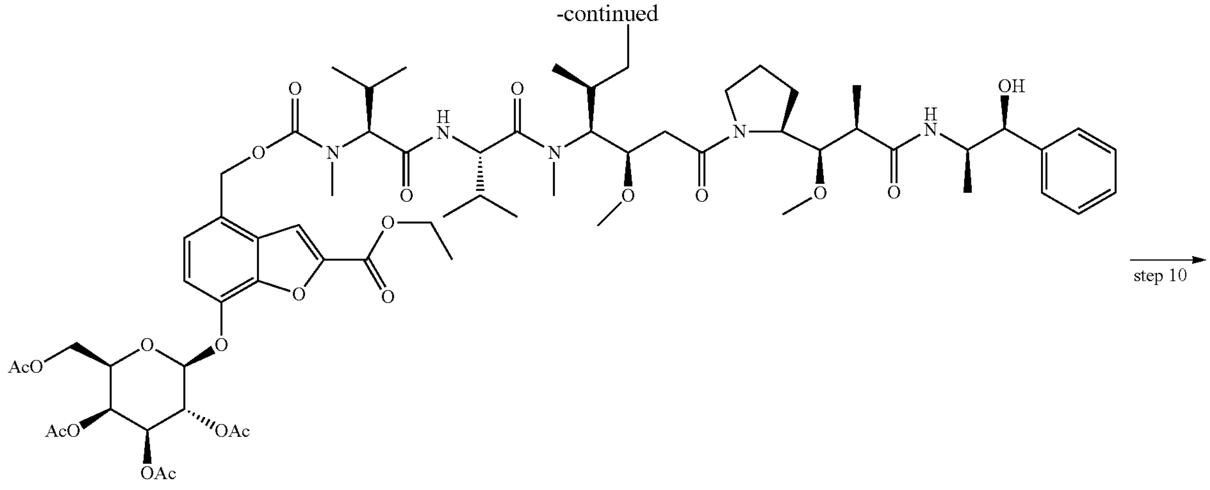

A-62j

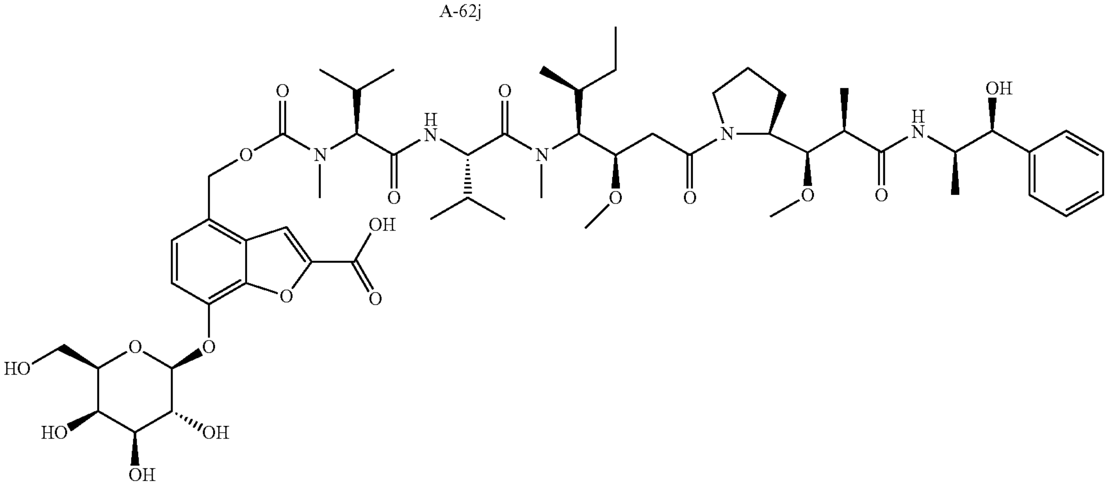

A-62

Step 1: Preparation of Compound A-62b

THF (12.0 mL) was added dropwise to sodium hydride (60% dispersion in mineral oil, 724.0 mg, 18.1 mmol) under a nitrogen atmosphere at 0° C., and Compound A-62a (2,3-dihydroxybenzaldehyde, Alfa Aesar, CAS No. 24677-78-9, 1.0 g, 7.24 mmol) dissolved in THE (8.0 mL) was slowly added to the reaction solution, and then the mixture was stirred at room temperature for 1 hour. Benzyl bromide (0.86 mL, 7.24 mmol) was slowly added to the reaction solution, and the mixture was stirred for an additional 16 hours. After completion of the reaction, distilled water (50 mL), 2N-hydrochloric acid aqueous solution (50 mL) and EA (100 mL) were added to extract the organic layer. The obtained organic layer was dried over anhydrous magnesium sulfate, filtered, and then concentrated under reduced pressure. Ethanol (30.0 mL) was added to the residue, and then the resulting solid was filtered to obtain Compound A-62b in the form of a yellow solid (680.0 mg, 41%).

$^1$H-NMR (400 MHz, $CDCl_3$) δ 11.07 (s, 1H), 9.92 (s, 1H), 7.45-7.31 (m, 5H), 7.19 (dd, J=7.6 Hz, J=1.2 Hz, 1H), 7.13 (d, J=7.6 Hz, 1H), 6.89 (t, J=7.6 Hz, 1H), 5.19 (s, 3H).

Step 2: Preparation of Compound A-62c

Compound A-62b (680.0 mg, 2.97 mmol) was dissolved in DMF (5.0 mL) under a nitrogen atmosphere, and then ethyl bromoacetate (0.38 mL, 3.57 mmol) and potassium carbonate (1.03 g, 7.44 mmol) were sequentially added, and then the mixture was stirred at 80° C. for 2 hours.

After completion of the reaction, distilled water (50 mL) and EA (50 mL) were added to extract the organic layer. The obtained organic layer was washed by adding a saturated aqueous sodium chloride solution (50 mL). The organic layer was dried over anhydrous magnesium sulfate, filtered, and then concentrated under reduced pressure. The residue was subjected to column chromatography to obtain Compound A-62c in the form of a white solid (870.0 mg, 93%).

$^1$H-NMR (400 MHz, $CDCl_3$) δ 10.63 (s, 1H), 7.47 (d, J=8.0 Hz, 1H), 7.44-7.34 (m, 5H), 7.19 (d, J=8.0 Hz, 1H), 7.11 (t, J=8.0 Hz, 1H), 5.13 (s, 2H), 4.85 (s, 2H) 4.15 (q, J=7.2 Hz, 2H), 1.22 (t, J=7.2 Hz, 3H).

Step 3: Preparation of Compound A-62d

Compound A-62c (870.0 mg, 2.76 mmol) was dissolved in DMF (10.0 mL) under a nitrogen atmosphere, and then potassium carbonate (1.03 g, 7.44 mmol) was added, and then the mixture was stirred at 100° C. for 3 hours. After completion of the reaction, distilled water (100 mL) and EA (100 mL) were added to extract the organic layer. The obtained organic layer was washed by adding a saturated aqueous sodium chloride solution (100 mL). The organic layer was dried over anhydrous magnesium sulfate, filtered, and then concentrated under reduced pressure. The residue was subjected to column chromatography to obtain Compound A-62d in the form of a white solid (640.0 mg, 78%); EI-MS m/z: 297 $[M+H]^+$. $^1$H-NMR (400 MHz, $CDCl_3$) δ 7.51-7.49 (m, 3H), 7.40-7.30 (m, 3H), 7.25-7.23 (m, 1H), 7.15 (t, J=8.0 Hz, 1H), 6.94 (d, J=8.0 Hz, 1H), 5.33 (s, 2H), 4.44 (q, J=7.2 Hz, 2H), 1.42 (t, J=7.2 Hz, 3H).

Step 4: Preparation of Compound A-62e

Compound A-62d (640.0 mg, 2.16 mmol) was dissolved in MC (20.0 mL) under a nitrogen atmosphere at −78° C., and then dichloromethyl methyl ether (0.57 mL, 6.48 mmol) and titanium tetrachloride solution (1M-$TiCl_4$ in MC, 6.48 mL, 6.48 mmol) were sequentially and slowly added, and the mixture was stirred for 2 hours while maintaining the temperature. After completion of the reaction, cooled distilled water (100 mL) was slowly added dropwise to terminate the reaction, and EA (100 mL) was added to extract the organic layer. The obtained organic layer was dried over anhydrous magnesium sulfate, filtered, and then concentrated under reduced pressure. The resulting residue was subjected to column chromatography to obtain Compound A-62e in the form of a white solid (420.0 mg, 60%); EI-MS m/z: 325 $[M+H]^+$.

$^1$H-NMR (400 MHz, $CDCl_3$) δ 10.03 (s, 1H), 8.22 (s, 1H), 7.69 (d, J=8.0 Hz, 1H), 7.50-7.48 (m, 2H), 7.42-7.34 (m, 3H), 7.04 (d, J=8.0 Hz, 1H), 5.42 (s, 2H), 4.45 (q, J=7.2 Hz, 2H), 1.43 (t, J=7.2 Hz, 3H).

Step 5: Preparation of Compound A-62f

Compound A-62e (420.0 mg, 1.29 mmol) was dissolved in MC (13.0 mL) under a nitrogen atmosphere at −78° C., and then boron trichloride solution (1M-$BCl_3$ in MC, 3.88 mL, 3.88 mmol) was slowly added, and the mixture was stirred for 2 hours while maintaining the temperature. After completion of the reaction, distilled water (50.0 mL) was slowly added dropwise at −50° C. to terminate the reaction, and EA (100 mL) and distilled water (100 mL) were further added at room temperature to extract the organic layer. The obtained organic layer was dried over anhydrous magnesium sulfate, filtered, and then concentrated under reduced pressure. The resulting residue was subjected to column chromatography to obtain Compound A-62f in the form of an ivory solid (145.0 mg, 47%).

$^1$H-NMR (400 MHz, $CDCl_3$) δ 10.05 (s, 1H), 8.23 (s, 1H), 7.73 (d, J=8.0 Hz, 1H), 7.10 (d, J=8.0 Hz, 1H), 6.51 (s, 1H), 4.46 (q, J=7.2 Hz, 2H), 1.44 (t, J=7.2 Hz, 3H).

Step 6: Preparation of Compound A-62g

Compound A-62f (140.0 mg 0.59 mmol) was dissolved in ACN (20.0 mL) under a nitrogen atmosphere at 0° C., and then acetobromo-alpha-D-galactose (295.0 mg, 0.71 mmol), a molecular sieve (50.0 mg) and silver oxide (I) (346.0 mg, 1.49 mmol) were sequentially added, and the mixture was stirred at room temperature for 2 hours. After completion of the reaction, the reaction solution was diluted with EA (100 mL), filtered using Celite, and washed by adding a saturated aqueous sodium chloride solution (100 mL) to the solution. The reaction solution was dried over anhydrous magnesium sulfate, filtered, and then concentrated under reduced pressure. The resulting residue was subjected to column chromatography to obtain Compound A-62g in the form of a white solid (303.0 mg, 89%); EI-MS m/z: 586 $[M+Na]^+$.

$^1$H-NMR (400 MHz, $CDCl_3$) δ 10.10 (s, 1H), 8.23 (s, 1H), 7.73 (d, J=8.0 Hz, 1H), 7.27 (d, J=8.0 Hz, 1H), 5.60-5.59 (m, 2H), 5.50 (d, J=3.2 Hz, 1H), 5.21-5.17 (m, 1H), 4.45 (q, J=7.2 Hz, 2H), 4.23-4.17 (m, 3H), 2.19 (s, 3H), 2.14 (s, 3H), 2.03 (s, 3H), 1.98 (s, 3H), 1.43 (t, J=7.2 Hz, 3H).

Step 7: Preparation of Compound A-62h

Compound A-62g (136.0 mg, 0.24 mmol) was dissolved in THE (10.0 mL) under a nitrogen atmosphere at 0° C., and then sodium borohydride (22.8 mg, 0.60 mmol) was added, and the mixture was stirred at 0° C. for 2 hours. After completion of the reaction, EA (50 mL) and distilled water (50 mL) were added to extract the organic layer. The obtained organic layer was dried over anhydrous magnesium sulfate, filtered, and then concentrated under reduced pressure. The resulting residue was subjected to column chromatography to obtain Compound A-62h in the form of a white solid (85.0 mg, 62%).

$^1$H-NMR (400 MHz, $CDCl_3$) δ 7.70 (s, 1H), 7.18 (s, 2H), 5.57 (dd, J=10.4 Hz, J=8.0 Hz, 1H), 5.47 (d, J=3.2 Hz, 1H), 5.27 (d, J=8.0 Hz, 1H), 5.14 (dd, J=10.4 Hz, J=3.2 Hz, 1H), 4.90 (d, J=5.6 Hz, 2H), 4.43 (q, J=7.2 Hz, 2H), 4.24-4.19 (m, 2H) 4.14-4.06 (m, 1H), 2.20 (s, 3H), 2.19 (s, 3H), 2.02 (s, 3H), 2.01 (s, 3H), 1.72 (t, J=5.6 Hz, 1H), 1.42 (t, J=7.2 Hz, 3H).

Step 8: Preparation of Compound A-62i

Compound A-62h (85.0 mg, 0.15 mmol) was dissolved in MC (3.0 mL) under a nitrogen atmosphere at 0° C., and then 4-nitrophenyl chloroformate (45.0 mg, 0.22 mmol) and DIPEA (40.0 L, 0.22 mmol) and pyridine (36.0 μL, 0.45 mmol) were sequentially added, and the mixture was stirred for 16 hours while slowly raising the temperature from 0° C. to room temperature. After completion of the reaction, EA (50 mL) and distilled water (50 mL) were added to extract the organic layer. The obtained organic layer was dried over anhydrous magnesium sulfate, filtered, and then concentrated under reduced pressure. The resulting residue was subjected to column chromatography to obtain Compound A-62i in the form of a white solid (54.0 mg, 49%).

$^1$H-NMR (400 MHz, $CDCl_3$) δ 8.27 (d, J=9.2 Hz, 2H), 7.68 (s, 1H), 7.37 (d, J=9.2 Hz, 2H), 7.32-7.20 (m, 2H), 5.58 (dd, J=10.4 Hz, J=8.0 Hz, 1H), 5.49 (s, 3H), 5.35 (d, J=8.0 Hz, 1H), 5.16 (dd, J=10.4 Hz, J=3.2 Hz, 1H), 4.45 (q, J=7.2 Hz, 2H), 4.25-4.15 (m, 2H), 4.14-4.09 (m, 1H), 2.20 (s, 3H), 2.18 (s, 3H), 2.03 (s, 3H), 2.01 (s, 3H), 1.43 (s, J=7.2 Hz, 3H).

Step 9: Preparation of Compound A-62j

Compound A-62i (54.0 mg, 0.073 mmol) was dissolved in DMF (2.0 mL) under a nitrogen atmosphere at 0° C., and then MMAE (53.0 mg, 0.073 mmol), HOBt (15.0 mg, 0.110 mmol), DIPEA (33.0 μL, 0.184 mmol) and pyridine (1.0 mL) were sequentially added, and the mixture was stirred at room temperature for 6 hours. After completion of the reaction, extraction was performed using distilled water (50 mL), 2N-hydrochloric acid aqueous solution (50 mL) and EA (100 mL). The obtained organic layer was dried over anhydrous magnesium sulfate, filtered, and then concentrated under reduced pressure. The resulting residue was subjected to column chromatography to obtain Compound A-62j in the form of a white solid (35.0 mg, 36%); EI-MS m/z: 1311 $[M+H]^+$.

Step 10: Preparation of Compound A-62

Compound A-62j (20.0 mg, 0.015 mmol) was dissolved in methanol (1.0 mL) under a nitrogen atmosphere at 0° C., and then lithium hydroxide (4.8 mg, 0.114 mmol) dissolved in distilled water (1.0 mL) was slowly added dropwise, and the mixture was stirred at 0° C. for 2 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-62 in the form of a white solid (9.2 mg, 54%); EI-MS m/z: 1115 $[M+H]^+$.

Example I-58: Preparation of Compound A-63
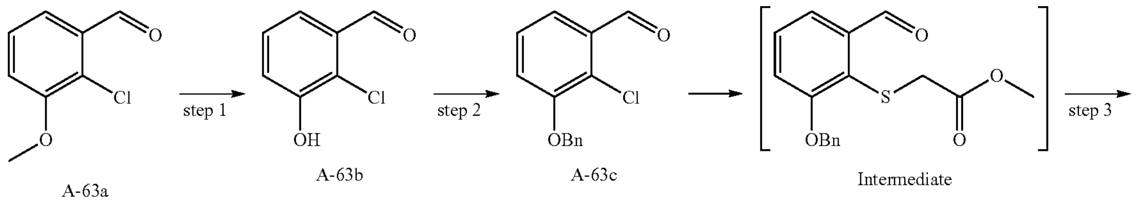
A-63a A-63b A-63c Intermediate
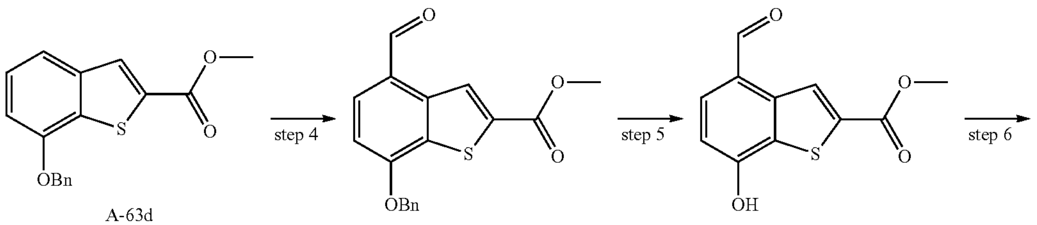
A-63d A-63e A-63f
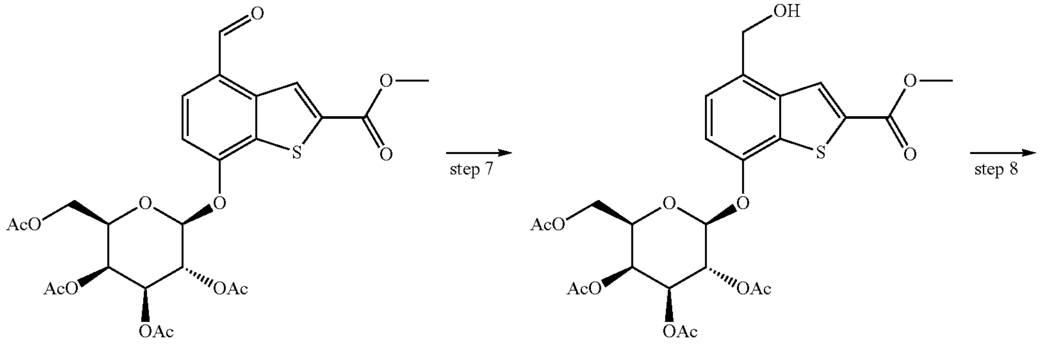
A-63g A-63h
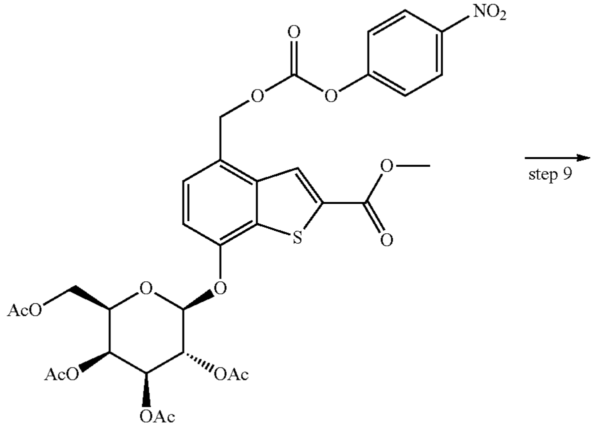
A-63i -continued

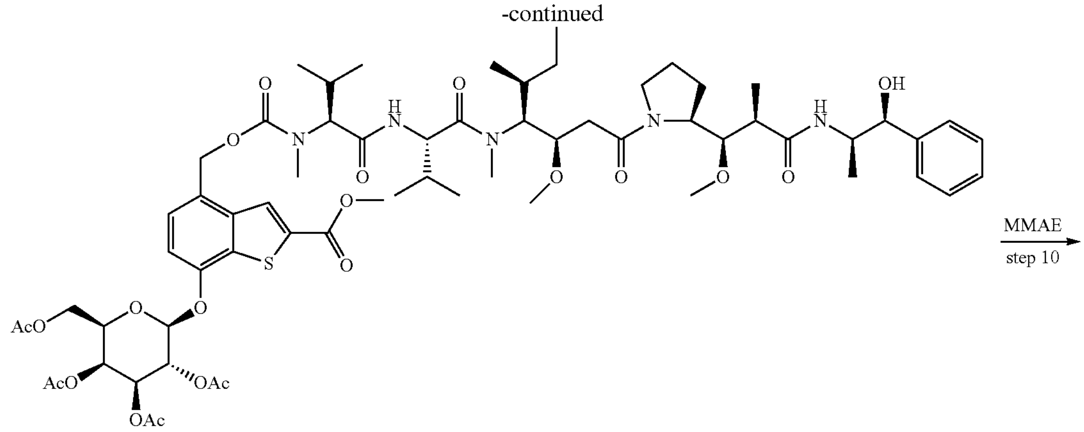

A-63j

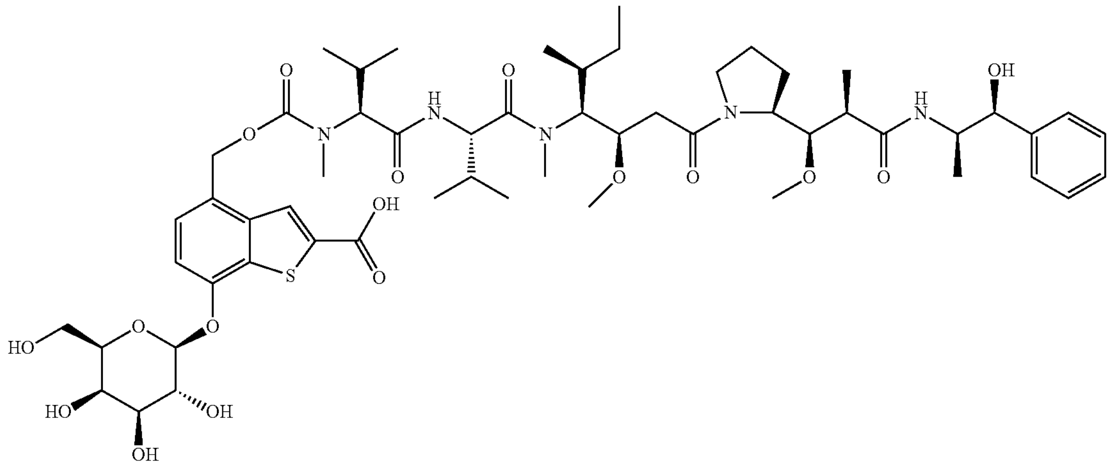

A-63

Step 1: Preparation of Compound A-63b

Compound A-63a (2-chloro-3-methoxybenzaldehyde, Sigma Aldrich, CAS NO. 54881-49-1, 3.0 g, 17.6 mmol) was dissolved in MC (60.0 mL) under a nitrogen atmosphere at −78° C., and then boron tribromide solution (1M-$BBr_3$ in MC, 53.0 mL, 53.0 mmol) was slowly added, and the mixture was stirred at room temperature for 16 hours. After completion of the reaction, distilled water (100 mL) was slowly added dropwise to terminate the reaction, and EA (500 mL) and distilled water (500 mL) were added to extract the organic layer. The obtained organic layer was dried over anhydrous magnesium sulfate, filtered, and then concentrated under reduced pressure. The resulting residue was subjected to column chromatography to obtain Compound A-63b in the form of a pink solid (1.8 g, 65%).

$^1$H-NMR (400 MHz, $CDCl_3$) δ 10.39 (s, 1H), 7.52 (dd, J=7.2 Hz, 2.0 Hz, 1H), 7.35-7.27 (m, 2H), 5.81 (s, 1H).

Step 2: Preparation of Compound A-63c

Compound A-63b (1.8 g, 11.5 mmol) was dissolved in ACN (60.0 mL) under a nitrogen atmosphere at 0° C., and then potassium carbonate (3.98 g, 28.7 mmol) and benzyl bromide (2.05 mL, 1.72 mmol) were slowly added, and the mixture was stirred at 0° C. for 10 minutes. The reaction temperature was raised to room temperature, and the mixture was stirred for an additional 16 hours. After completion of the reaction, EA (200 mL) and distilled water (200 mL) were added to extract the organic layer. The obtained organic layer was dried over anhydrous magnesium sulfate, filtered, and then concentrated under reduced pressure. The resulting residue was subjected to column chromatography to obtain Compound A-63c in the form of a white solid (2.0 g, 71%).

$^1$H-NMR (400 MHz, $CDCl_3$) δ 10.54 (s, 1H), 7.54 (dd, J=7.6 Hz, 1.2 Hz, 1H), 7.48-7.27 (m, 5H), 7.19 (dd, J=7.6 Hz, J=1.2 Hz, 1H), 5.21 (s, 2H).

Step 3: Preparation of Compound A-63d

Compound A-63c (650.0 mg, 2.63 mmol) was dissolved in DMF (25.0 mL) under a nitrogen atmosphere, and then methyl thioglycolate (Merck, 0.47 mL, 5.27 mmol) and potassium carbonate (728.0 mg, 5.27 mmol) were added, and the mixture was stirred at room temperature for 30 minutes. The reaction temperature was raised to 80° C., and the mixture was stirred for an additional 3 hours. After completion of the reaction, EA (250 mL) and distilled water (250 mL) were added to extract the organic layer. The obtained organic layer was washed by adding a saturated aqueous sodium chloride solution (250 mL). The organic layer was dried over anhydrous magnesium sulfate, filtered, and then concentrated under reduced pressure to obtain A-63d in the form of a yellow solid, which was used in the next reaction without an additional purification process (230.0 mg, 29%).

Step 4: Preparation of Compound A-63e

Compound A-63d (400.0 mg, 1.34 mmol) was dissolved in MC (30.0 mL) under a nitrogen atmosphere at −78° C., and then dichloromethyl methyl ether (0.71 mL, 8.04 mmol) and titanium tetrachloride solution (1M-$TiCl_4$ in MC, 8.04 mL, 8.04 mmol) were sequentially and slowly added, and the mixture was stirred for 2 hours while maintaining the temperature. After completion of the reaction, cooled distilled water (100 mL) was slowly added dropwise to terminate the reaction, and EA (150 mL) was added to extract the organic layer. The obtained organic layer was dried over anhydrous magnesium sulfate, filtered, and then concentrated under reduced pressure. The resulting residue was subjected to column chromatography to obtain Compound A-63e in the form of a white solid (125.0 mg, 28%).

$^1$H-NMR (400 MHz, $CDCl_3$) δ 10.08 (s, 1H), 9.01 (s, 1H), 7.84 (d, J=8.0 Hz, 1H), 7.53-7.35 (m, 5H), 7.04 (d, J=8.0 Hz, 1H), 5.38 (s, 2H), 3.97 (s, 3H).

Step 5: Preparation of Compound A-63f

Compound A-63e (400.0 mg, 1.34 mmol) was dissolved in MC (10.0 mL) under a nitrogen atmosphere at −78° C., and then boron trichloride solution (1M-$BCl_3$ in MC, 1.14 mL, 1.14 mmol) was slowly added, and the mixture was stirred for 1 hour while maintaining the temperature. After completion of the reaction, distilled water (50.0 mL) was slowly added dropwise at −50° C. to terminate the reaction, and EA (100 mL) and distilled water (50 mL) were further added at room temperature to extract the organic layer. The obtained organic layer was dried over anhydrous magnesium sulfate, filtered, and then concentrated under reduced pressure. The resulting residue was subjected to column chromatography to obtain Compound A-63f in the form of a white solid (40.0 mg, 44%).

$^1$H-NMR (400 MHz, $CDCl_3$) δ 10.09 (s, 1H), 9.03 (s, 1H), 7.81 (d, J=8.0 Hz, 1H), 6.96 (d, J=8.0 Hz, 1H), 5.93 (s, 1H), 3.98 (s, 3H).

Step 6: Preparation of Compound A-63g

Compound A-63f (40.0 mg 0.169 mmol) was dissolved in ACN (10.0 mL) under a nitrogen atmosphere at 0° C., and then acetobromo-alpha-D-galactose (83.0 mg, 0.203 mmol) and silver oxide (I) (98.0 mg, 0.423 mmol) were sequentially added, and the mixture was stirred at room temperature for 2 hours. After completion of the reaction, the reaction solution was diluted with EA (50 mL), filtered using Celite, and washed by adding a saturated aqueous sodium chloride solution (50 mL) to the solution. The reaction solution was dried over anhydrous magnesium sulfate, filtered, and then concentrated under reduced pressure. The resulting residue was subjected to column chromatography to obtain Compound A-63g in the form of a white solid (60.0 mg, 62%).

$^1$H-NMR (400 MHz, $CDCl_3$) δ 10.14 (s, 1H), 9.00 (s, 1H), 7.86 (d, J=8.0 Hz, 1H), 7.21 (d, J=8.0 Hz, 1H), 5.66 (dd, J=10.4 Hz, J=8.0 Hz, 1H), 5.51 (d, 3.2 Hz, 1H), 5.29 (d, 8.0 Hz, 1H), 5.17 (dd, J=10.4 Hz, J=3.2 Hz, 1H), 4.29-4.19 (m, 3H), 2.22 (s, 3H), 2.108 (s, 3H), 2.100 (s, 3H), 2.04 (s, 3H).

Step 7: Preparation of Compound A-63h

Compound A-63g (23.0 mg, 0.04 mmol) was dissolved in THE (3.0 mL) under a nitrogen atmosphere at 0° C., and then sodium borohydride (3.84 mg, 0.10 mmol) was added, and the mixture was stirred at 0° C. for 2 hours. After completion of the reaction, EA (50 mL) and distilled water (50 mL) were added to extract the organic layer. The obtained organic layer was dried over anhydrous magnesium sulfate, filtered, and then concentrated under reduced pressure. The resulting residue was subjected to column chromatography to obtain Compound A-63h in the form of a white solid (20.0 mg, 86%); EI-MS m/z: 590 $[M+Na]^+$.

$^1$H-NMR (400 MHz, $CDCl_3$) δ 8.27 (s, 1H), 7.34 (d, J=8.0 Hz, 1H), 7.11 (d, J=8.0 Hz, 1H), 5.62 (dd, J=10.4 Hz, J=8.0 Hz, 1H), 5.49 (d, J=3.2 Hz, 1H), 5.15-5.12 (m, 2H), 4.99 (d, J=5.6 Hz, 2H), 4.30-4.27 (m, 1H), 4.21-4.17 (m, 1H), 4.16-4.09 (m, 1H), 3.95 (s, 3H), 2.21 (s, 3H), 2.17 (s, 3H), 2.13 (s, 3H), 2.03 (s, 3H).

Step 8: Preparation of Compound A-63i

Compound A-63h (20.0 mg, 0.035 mmol) was dissolved in MC (1.0 mL) under a nitrogen atmosphere at 0° C., and then 4-nitrophenyl chloroformate (20 mg, 0.105 mmol) and DIPEA (18.0 L, 0.105 mmol) and pyridine (17.0 μL, 0.21 mmol) were sequentially added, and the mixture was stirred at room temperature for 6 hours. After completion of the reaction, EA (50 mL) and distilled water (50 mL) were added to extract the organic layer. The obtained organic layer was dried over anhydrous magnesium sulfate, filtered, and then concentrated under reduced pressure. The resulting residue was subjected to column chromatography to obtain Compound A-63i in the form of a white solid (24.0 mg, 90%).

$^1$H-NMR (400 MHz, $CDCl_3$) δ 8.27 (d, J=9.2 Hz, 2H), 8.24 (s, 1H), 7.45 (d, J=8.0 Hz, 2H), 7.37 (d, J=9.2 Hz, 2H), 7.12 (d, J=8.0 Hz, 1H), 5.63 (dd, J=10.4 Hz, J=3.2 Hz, 1H), 5.57 (s, 2H), 5.50 (d, J=3.2 Hz, 1H), 5.18 (d, J=8.0 Hz, 1H), 5.15 (dd, J=10.4 Hz, J=3.2 Hz, 1H), 4.28-4.25 (m, 1H), 4.21-4.09 (m, 2H), 2.21 (s, 3H), 2.12 (s, 3H), 2.08 (s, 3H), 2.04 (s, 3H); EI-MS m/z: 755 [M+Na]*.

Step 9: Preparation of Compound A-63j

Compound A-63i (24.0 mg, 0.032 mmol) was dissolved in DMF (1.0 mL) under a nitrogen atmosphere at 0° C., and then MMAE (23.4 mg, 0.032 mmol), HOBt (6.7 mg, 0.049 mmol), DIPEA (14.0 μL, 0.081 mmol) and pyridine (1.0 mL) were sequentially added, and the mixture was stirred at room temperature for 6 hours. After completion of the reaction, extraction was performed using distilled water (10 mL), 2N-hydrochloric acid aqueous solution (5 mL), EA (15 mL). The obtained organic layer was dried over anhydrous magnesium sulfate, filtered, and then concentrated under reduced pressure. The resulting residue was subjected to column chromatography to obtain Compound A-63j in the form of a white solid (19.0 mg, 44%); EI-MS m/z: 1313 $[M+H]^+$.

Step 10: Preparation of Compound A-63

Compound A-63j (19.0 mg, 0.014 mmol) was dissolved in methanol (1.0 mL) under a nitrogen atmosphere at 0° C., and then lithium hydroxide (9.0 mg, 0.214 mmol) dissolved in distilled water (1.0 mL) was slowly added dropwise, and the mixture was stirred at room temperature for 6 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-63 in the form of a white solid (6.7 mg, 41%); EI-MS m/z: 1131 $[M+H]^+$.

Example I-59: Preparation of Compound A-64
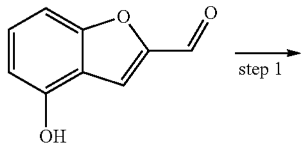
c-14
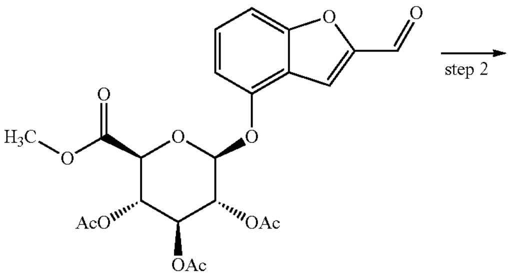
A-64a
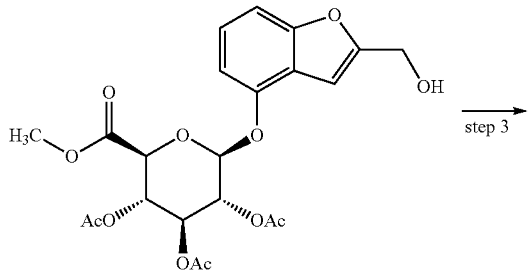
A-64b
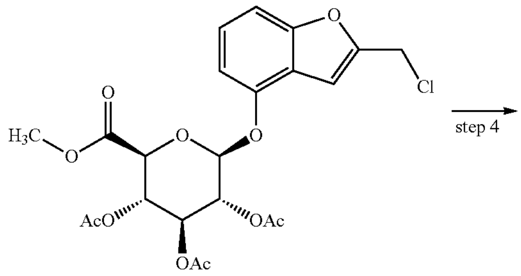
A-64c
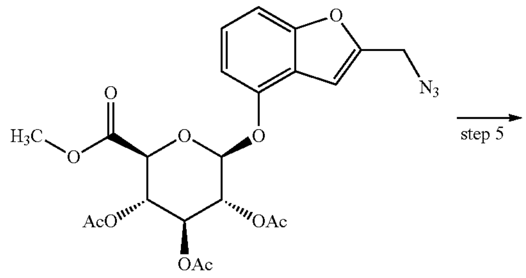
A-64d
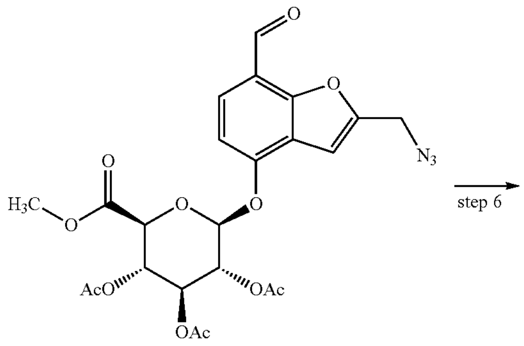
A-64e
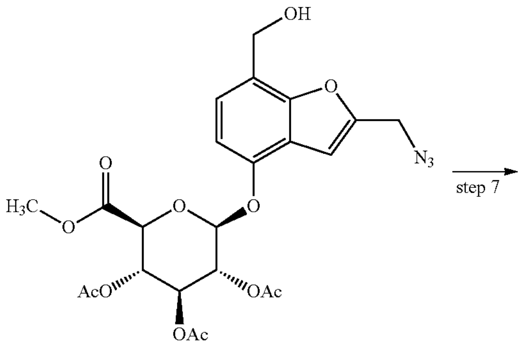
A-64f
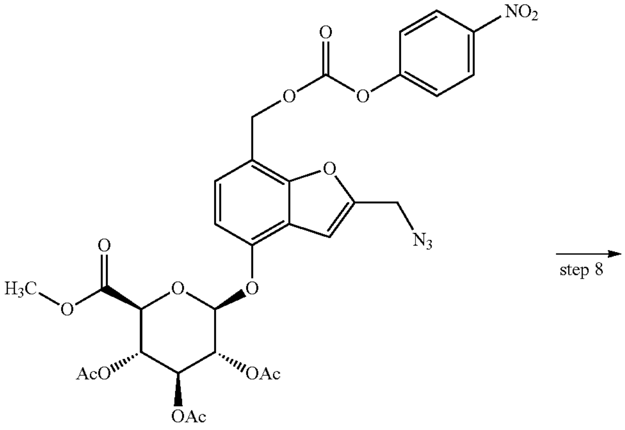
A-64g -continued

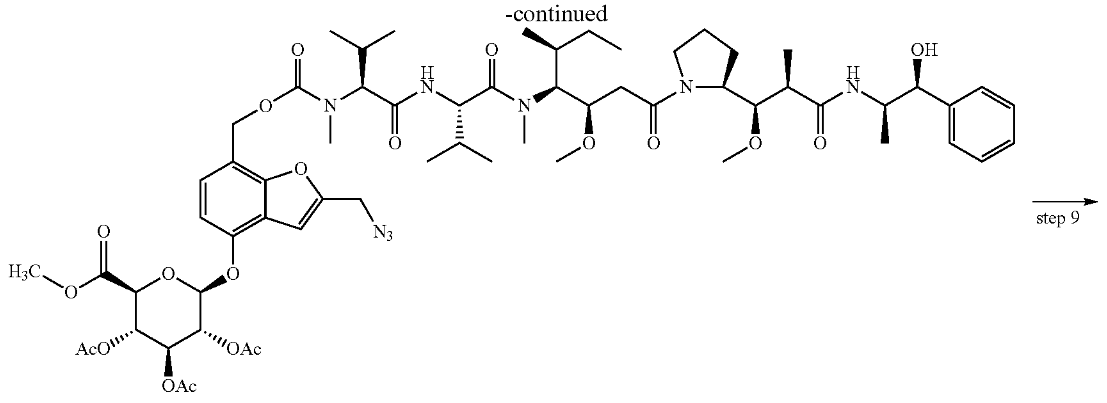

A-64h

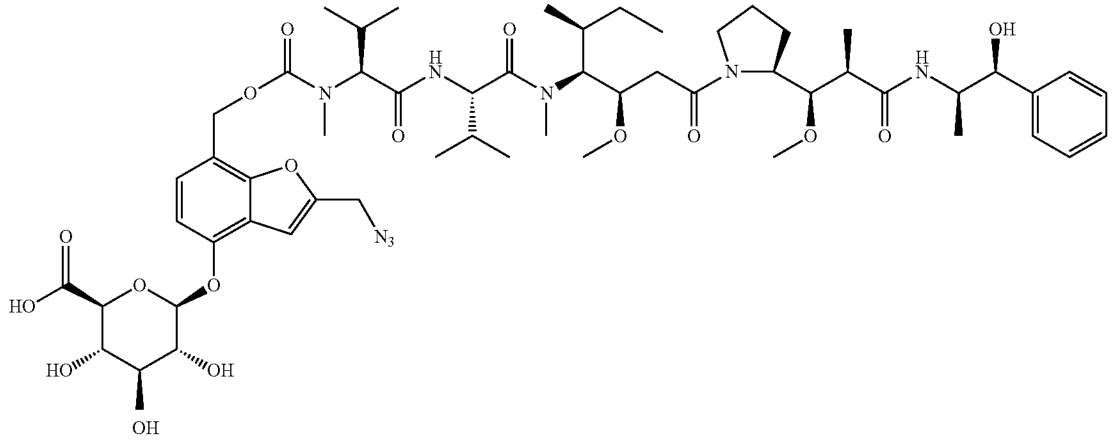

A-64

Step 1: Preparation of Compound A-64a

Silver carbonate (Alfa aesar, 25.0 g, 90.59 mmol) was added to ACN (200 mL) under a nitrogen atmosphere at room temperature, and then HMTTA (Alfa aesar, 3.66 mL, 13.47 mmol) was added, and the mixture was stirred for 1 hour. Additionally, Core C-14 (3.97 g, 24.49 mmol) and acetobromo-a-D-glucuronic acid methyl ester (TCI, 24.3 g, 61.21 mmol) dissolved in ACN (45 mL) were slowly added, and the mixture was stirred for 16 hours while slowly raising the temperature from 0° C. to room temperature. After completion of the reaction, the reaction solution was diluted with EA (400 mL) and filtered using Celite. The filtered solution was extracted by adding distilled water (800 mL) and 2N-hydrochloric acid aqueous solution (20 mL). The obtained organic layer was washed by adding a saturated aqueous sodium chloride solution (400 mL), then dried over anhydrous magnesium sulfate, filtered, and then concentrated under reduced pressure to obtain Compound A-64a, which was used in the next reaction without an additional purification process (2.73 g, 23%); EI-MS m/z: 500 [M+Na] *.

Step 2: Preparation of Compound A-64b

Compound A-64a (2.73 g, 5.71 mmol) was dissolved in THE (286 mL) under a nitrogen atmosphere at 0° C., and then sodium borohydride (540 mg, 14.27 mmol) was added, and the mixture was stirred for 1 hour. After completion of the reaction, distilled water (250 mL) was added to terminate the reaction, and EA (500 mL) and distilled water (250 mL) were added to extract the organic layer. The obtained organic layer was washed by adding a saturated aqueous sodium chloride solution (200 mL), then dried over anhydrous magnesium sulfate, filtered, and then concentrated under reduced pressure. The resulting residue was subjected to column chromatography to obtain Compound A-64b in the form of a white solid (1.37 g, 50%).

$^1$H-NMR (400 MHz, $CDCl_3$) δ 7.22-7.20 (m, 2H), 6.84-6.82 (m, 1H), 6.70 (s, 1H), 5.39-5.37 (m, 3H), 5.24-5.22 (m, 1H), 4.75 (d, J=6 Hz, 2H), 4.22-4.19 (m, 1H), 3.74 (s, 3H), 2.07 (s, 3H), 2.06 (s, 3H), 2.05 (s, 3H), 1.86 (t, J=6 Hz, 1H); EI-MS m/z: 502 [M+Na]*.

Step 3: Preparation of Compound A-64c

Compound A-64b (1.02 g, 2.12 mmol) was dissolved in MC (53 mL) under a nitrogen atmosphere at 0° C., and then MsCl (methanesulfonyl chloride, CAS NO. 124-63-0, Daejung Chemicals & Metals, 986 μL, 12.74 mmol) and TEA (888 μL, 6.37 mmol) were added, and the mixture was stirred for 7 hours at room temperature. After completion of the reaction, distilled water (55 mL) was added at 0° C. to terminate the reaction, and EA (130 mL) and distilled water (130 mL) were added to extract the organic layer, and the obtained organic layer was washed by adding a saturated aqueous sodium chloride solution (130 mL), then dried over anhydrous magnesium sulfate, filtered, and then concentrated under reduced pressure to obtain Compound A-64c, which was used in the next reaction without an additional purification process (1.45 g, quantitatively obtained); MS m/z: 520 $[M+Na]^+$.

Step 4: Preparation of Compound A-64d

Compound A-64c (1.45 g, 2.91 mmol) was dissolved in DMF (56 mL) under a nitrogen atmosphere at room temperature, and then sodium azide (283 mg, 4.36 mmol) was added, and the mixture was stirred at 60° C. for 16 hours. After completion of the reaction, EA (230 mL) and distilled water (230 mL) were added to extract the organic layer, and the obtained organic layer was washed by adding a saturated aqueous sodium chloride solution (180 mL), then dried over anhydrous magnesium sulfate, filtered, and then concentrated under reduced pressure. The resulting residue was subjected to column chromatography to obtain Compound A-64d in the form of a white solid (689 mg, 47%).

$^1$H-NMR (400 MHz, $CDCl_3$) δ 7.24-7.23 (m, 2H), 6.84 (t, J=4.4 Hz, 1H), 6.76 (s, 1H), 6.94 (d, J=7.6 Hz, 1H), 5.38-5.37 (m, 3H), 5.24-5.22 (m, 1H), 4.42 (s, 2H), 4.22-4.20 (m, 1H), 3.74 (s, 3H), 2.07 (s, 3H), 2.06 (s, 3H), 2.05 (s, 3H); MS m/z: 527 $[M+Na]^+$.

Step 5: Preparation of Compound A-64e

A-64d (689 mg, 1.36 mmol) was dissolved in MC (37 mL) under a nitrogen atmosphere at −78° C., and then dichloromethyl methyl ether (925 μL, 10.22 mmol) and titanium tetrachloride solution (1M-$TiCl_4$ in MC, 10.2 mL, 10.2 mmol) were sequentially and slowly added, and the mixture was stirred for 4 hours while maintaining the temperature. After completion of the reaction, cooled distilled water (60 mL) was slowly added dropwise to terminate the reaction, and EA (70 mL) and distilled water (70 mL) were added to extract the organic layer. The obtained organic layer was washed by adding a saturated aqueous sodium chloride solution (70 mL), then dried over anhydrous magnesium sulfate, filtered, and then concentrated under reduced pressure. The resulting residue was subjected to column chromatography to obtain Compound A-64e in the form of a white solid (145 mg, 20%).

$^1$H-NMR (400 MHz, $CDCl_3$) δ 10.35 (s, 1H), 7.81 (d, J=8.4 Hz, 1H), 6.93 (d, J=8.8 Hz, 1H), 6.82 (s, 1H), 5.40 (m, 4H), 4.51 (s, 2H), 4.30-4.27 (m, 1H), 3.73 (s, 3H), 2.08 (s, 3H), 2.07 (s, 3H), 2.06 (s, 3H); MS m/z: 534 $[M+H]^+$.

Step 6: Preparation of Compound A-64f

Compound A-64e (133 mg, 0.25 mmol) was dissolved in THE (12.5 mL) under a nitrogen atmosphere at 0° C., and then sodium borohydride (23.6 mg, 0.62 mmol) was added, and the mixture was stirred for 2.5 hours. After completion of the reaction, distilled water (20 mL) was added to terminate the reaction, and EA (30 mL) and distilled water (10 mL) were added to extract the organic layer. The obtained organic layer was washed by adding a saturated aqueous sodium chloride solution (20 mL), then dried over anhydrous magnesium sulfate, filtered, and then concentrated under reduced pressure. The resulting residue was subjected to column chromatography to obtain Compound A-64f in the form of a white solid (112.5 mg, 84%).

$^1$H-NMR (400 MHz, $CDCl_3$) δ 7.27-7.25 (m, 1H), 6.83 (d, J=8 Hz, 1H), 6.78 (s, 1H), 5.39-5.35 (m, 3H), 5.22-5.20 (m, 1H), 4.93 (d, J=6 Hz, 2H), 4.44 (s, 2H), 4.22-4.20 (m, 1H), 3.74 (s, 3H), 2.07 (s, 3H), 2.06 (s, 3H), 2.05 (s, 3H), 1.83 (t, J=6 Hz, 1H); MS m/z: 557 $[M+Na]^+$.

Step 7: Preparation of Compound A-64g

Compound A-64f (111 mg, 0.21 mmol) was dissolved in MC (3.3 mL) under a nitrogen atmosphere at 0° C., and then 4-nitrophenyl chloroformate (84 mg, 0.42 mmol), pyridine (50.1 μL, 0.62 mmol) and DIPEA (54.2 μL, 0.31 mmol) were sequentially added, and the mixture was stirred at 0° C. for 30 minutes. After completion of the reaction, the reaction solution was diluted with EA (15 mL), and 2N-hydrochloric acid aqueous solution (15 mL) was added to extract the organic layer. The obtained organic layer was washed by adding a saturated aqueous sodium chloride solution (15 mL), then dried over anhydrous magnesium sulfate, filtered, and then concentrated under reduced pressure. The residue thus obtained was subjected to column chromatography to obtain Compound A-64g in the form of a white solid (130 mg, 90%).

$^1$H-NMR (400 MHz, $CDCl_3$) δ 8.27 (d, J=9.2 Hz, 2H), 7.39 (d, J=9.2 Hz, 2H), 7.35 (d, J=8.4 Hz, 1H), 6.86 (d, J=8.4 Hz, 1H), 6.81 (s, 1H) 5.59-5.52 (m, 2H), 5.38-5.37 (m, 3H), 5.26-5.25 (m, 1H), 4.46 (s, 1H), 4.24-4.22 (m, 1H), 3.74 (s, 3H), 2.07 (s, 3H), 2.06 (s, 6H); MS m/z: 722 $[M+Na]^+$.

Step 8: Preparation of Compound A-64h

Compound A-64g (41.1 mg, 0.059 mmol) was dissolved in DMF (1 mL) under a nitrogen atmosphere at 0° C., and then MMAE (42.1 mg, 0.059 mmol), HOBt (12 mg, 0.089 mmol), DIPEA (25.5 μL, 0.147 mmol) and pyridine (1 mL) were sequentially added, and the mixture was stirred at room temperature for 16 hours. After completion of the reaction, the organic layer was extracted twice with EA (20 mL) and 2N-hydrochloric acid aqueous solution (20 mL). The obtained organic layer was washed by adding a saturated aqueous sodium chloride solution (20 mL), then dried over anhydrous magnesium sulfate, filtered, and then concentrated under reduced pressure. The resulting residue was subjected to column chromatography to obtain Compound A-64h in the form of a white solid (60 mg, 80%); EI-MS m/z: 1280 $[M+H]^+$.

Step 9: Preparation of Compound A-64

Compound A-64h (59 mg, 0.046 mmol) was dissolved by mixing and adding methanol (1.2 mL), distilled water (0.3 mL) and THE (0.25 mL) at −20° C., and then lithium hydroxide (9.7 mg, 0.231 mmol) dissolved in distilled water (0.6 mL) was added dropwise, and the mixture was stirred at −20° C. for 2.5 hours. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and freeze-dried to obtain Compound A-64 in the form of a white solid (40.9 mg, 78%); EI-MS m/z: 1140 $[M+H]^+$.

Example I-60: Preparation of Compound A-65

IDC-174$C_3$

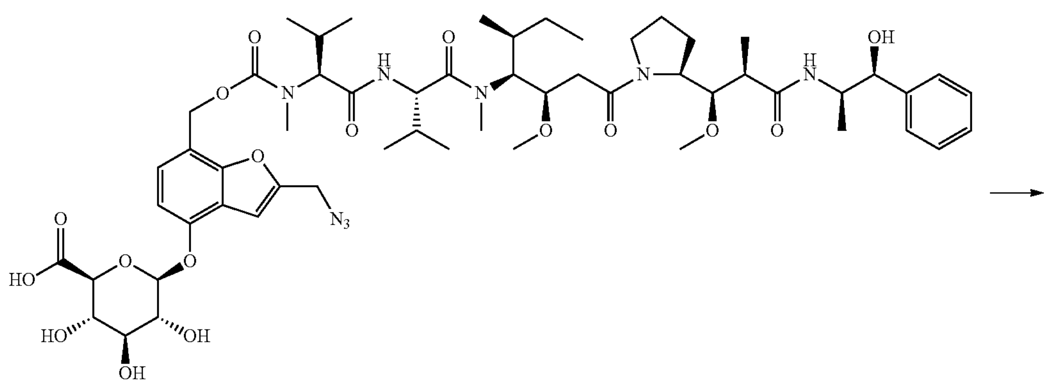

A-64

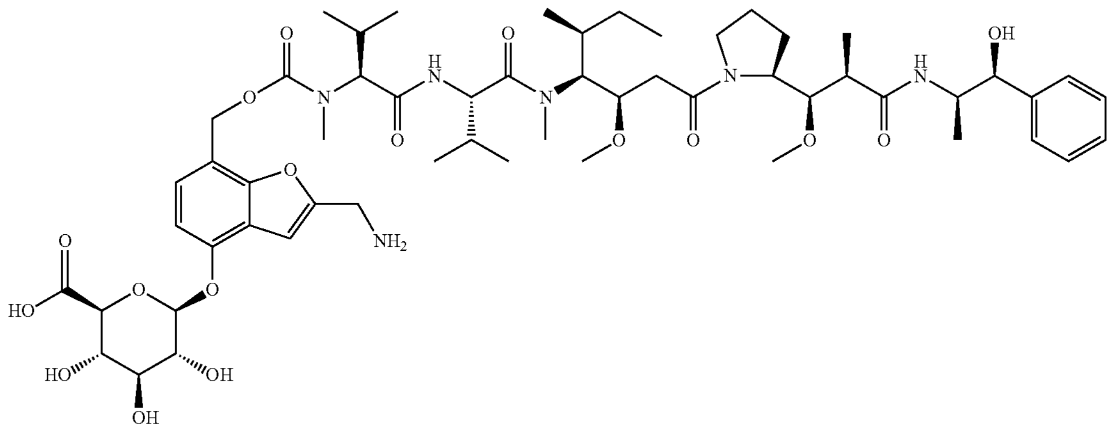

A-65

Compound A-64 (20.1 mg, 0.018 mmol) was dissolved in THF (1.5 mL) under a nitrogen atmosphere at room temperature, and then triphenylphosphine (5.1 mg, 0.019 mmol) and distilled water (0.15 mL) were sequentially added, and the mixture was stirred for 16 hours. 2N-hydrochloric acid aqueous solution (10 μL) was added to the above reaction solution at room temperature, and the mixture was stirred for 1 hour, and then 2N-sodium hydroxide aqueous solution (20 μL) was added, and the mixture was stirred for an additional 2 hours. After completion of the reaction, 2N-hydrochloric acid aqueous solution was slowly added dropwise to adjust the pH of the reaction solution to 3, and the reaction solution was separated and purified using Preparative-HPLC, and then freeze-dried to obtain Compound A-65 in the form of a white solid (13.6 mg, 69%); MS m/z: 1114 $[M+H]^+$.

Example I-61: Preparation of Compound A-66

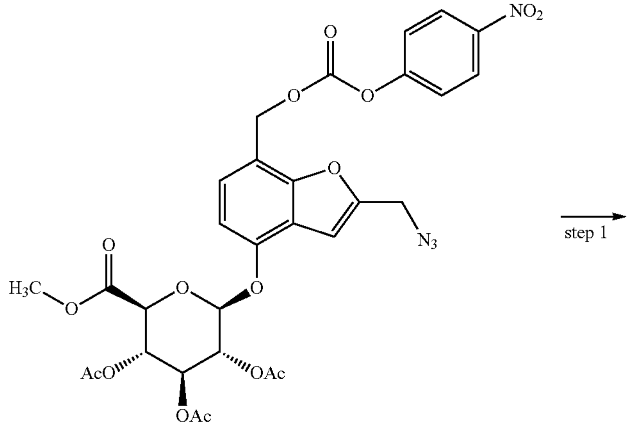

A-64g

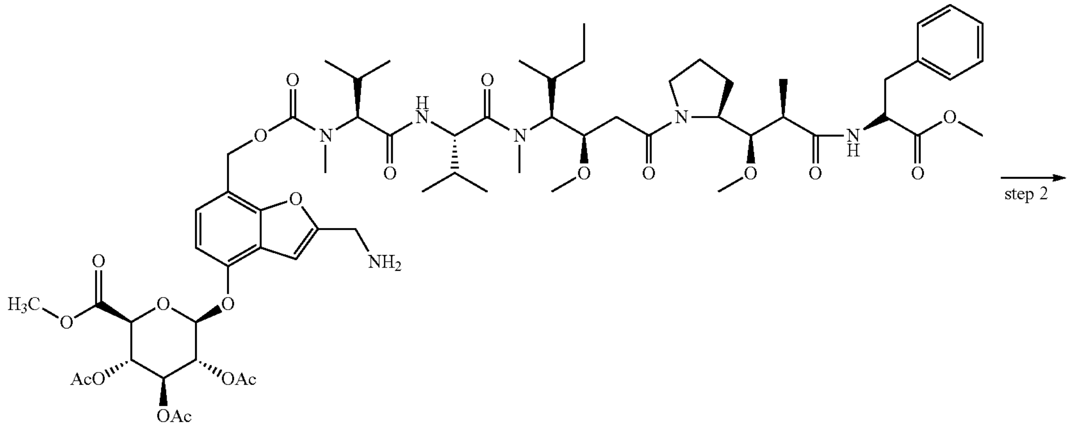

A-66a

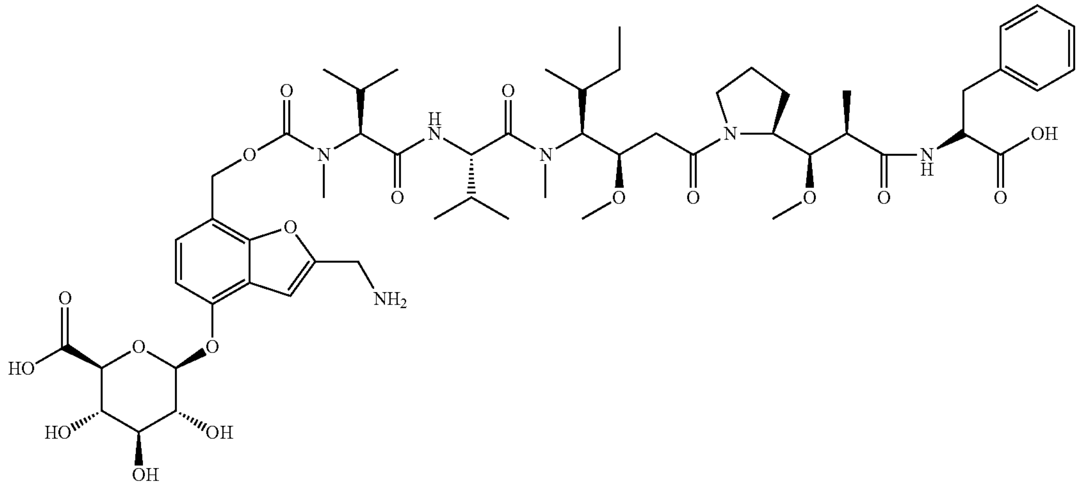

A-66

Step 1: Preparation of Compound A-66a

Compound A-64g (40 mg, 0.057 mmol) was dissolved in DMF (1 mL) under a nitrogen atmosphere at 0° C., and then MMAF-OMe (43 mg, 0.58 mmol), HOBt (12 mg, 0.089 mmol), DIPEA (24.9 μL, 0.142 mmol) and pyridine (1 mL) were sequentially added, and the mixture was stirred at room temperature for 16 hours. After completion of the reaction, the organic layer was extracted twice with EA (20 mL) and 2N-hydrochloric acid aqueous solution (20 mL). The obtained organic layer was washed by adding a saturated aqueous sodium chloride solution (20 mL), then dried over anhydrous magnesium sulfate, filtered, and then concentrated under reduced pressure. The resulting residue was subjected to column chromatography to obtain Compound A-66a in the form of a white solid (57.7 mg, 79%); EI-MS m/z: 1308 [M+H]$^+$.

Step 2: Preparation of Compound A-66

Compound A-66a (57.7 mg, 0.044 mmol) was dissolved by mixing and adding methanol (1.1 mL), distilled water (0.2 mL) and THF (0.22 mL) at −20° C., and then lithium hydroxide (13.9 mg, 0.331 mmol) dissolved in distilled water (0.9 mL) was added dropwise, and the mixture was stirred at −20° C. for 3.5 hours, and then the mixture was stirred for 2 hours while slowly raising the temperature to room temperature. After completion of the reaction, 2N-hydrochloric acid aqueous solution (1 mL) was added to terminate the reaction, and the reaction solution was diluted with ACN (1 mL) and distilled water (1 mL), then separated and purified using Preparative-HPLC, and freeze-dried to obtain Compound A-66 in the form of a white solid (38.8 mg, 76%); EI-MS m/z: 1154 [M+H]$^+$.

Example I-62: Preparation of Compounds A-67 and A-68

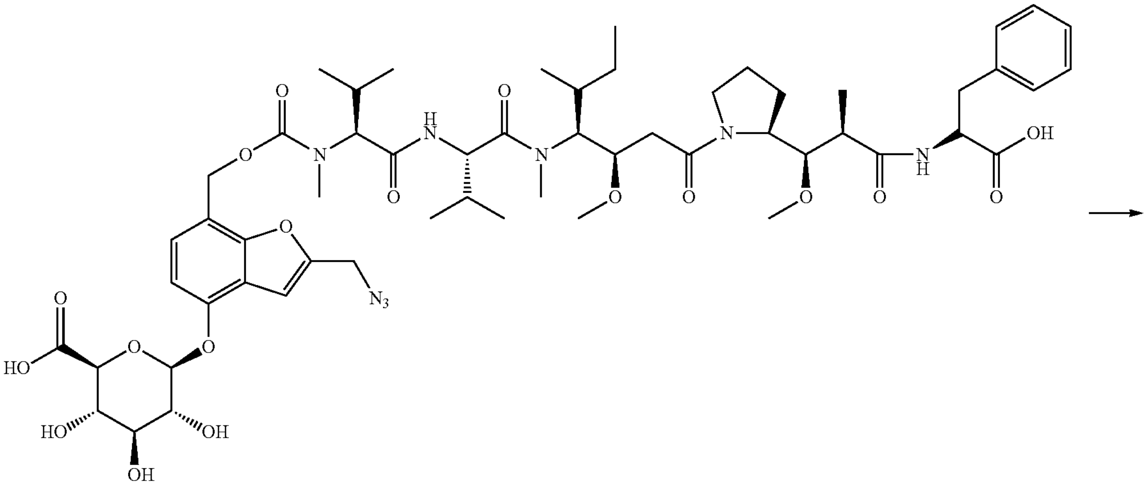

A-66

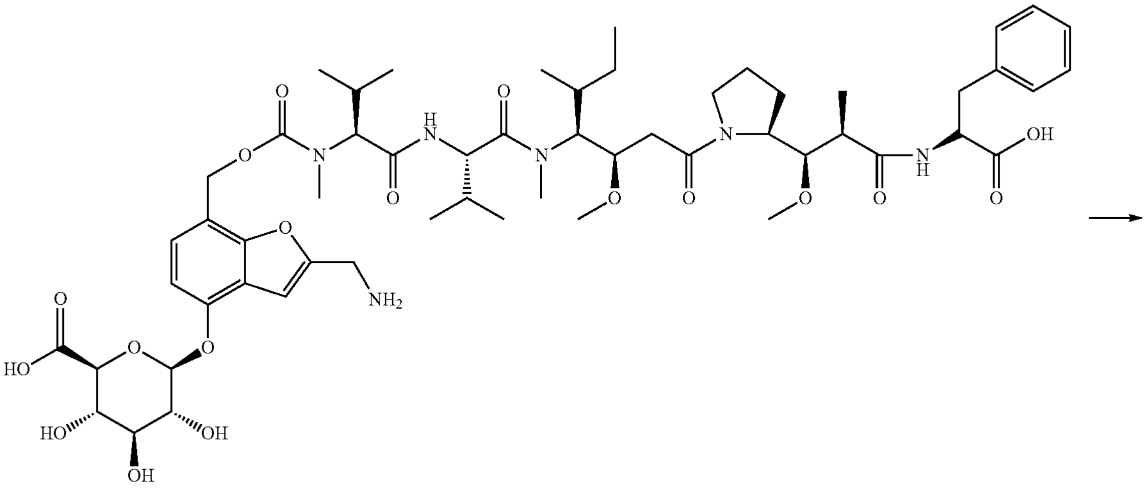

A-67

-continued

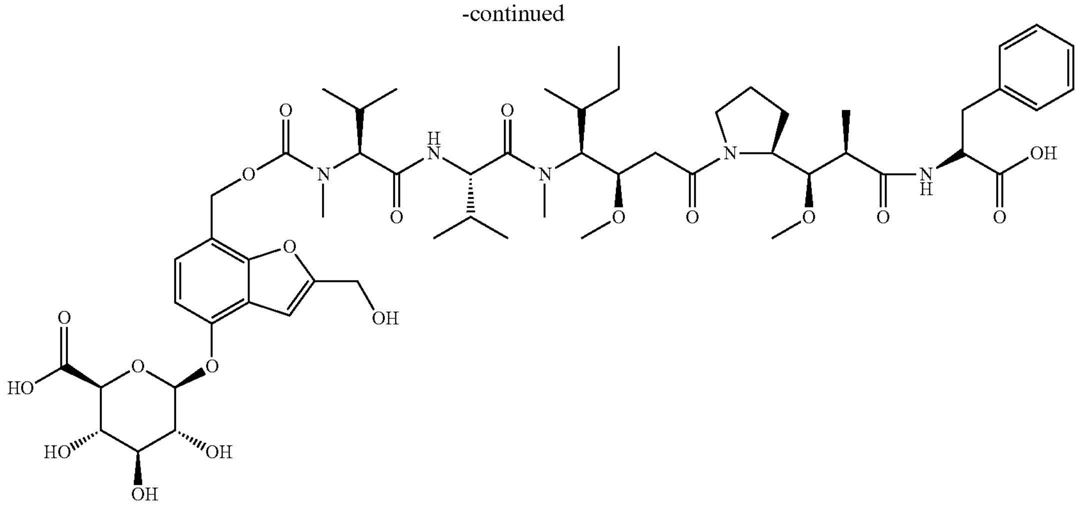

A-68

Compound A-66 (20 mg, 0.017 mmol) was dissolved in THE (1.5 mL) under a nitrogen atmosphere at room temperature, and then triphenylphosphine (7.3 mg, 0.028 mmol) and distilled water (0.15 mL) were sequentially added, and the mixture was stirred for 16 hours. 2N-hydrochloric acid aqueous solution (10 μL) was added to the above reaction solution at room temperature, and the mixture was stirred for an additional 16 hours, and then 2N-sodium hydroxide aqueous solution (20 μL) was added, and the mixture was stirred for 4.5 hours. After completion of the reaction, 2N-hydrochloric acid aqueous solution was slowly added dropwise to adjust the pH of the reaction solution to 3, and the reaction solution was separated and purified using Preparative-HPLC, and then freeze-dried to obtain Compounds A-67 and A-68, respectively, in the form of a white solid (A-67: 13.4 mg, 69%, A-68: 0.5 mg, 3%); EI-MS m/z: A-67=1128 $[M+H]^+$, A-68=1129 $[M+H]^+$.

Example I-63: Preparation of Compound A-69

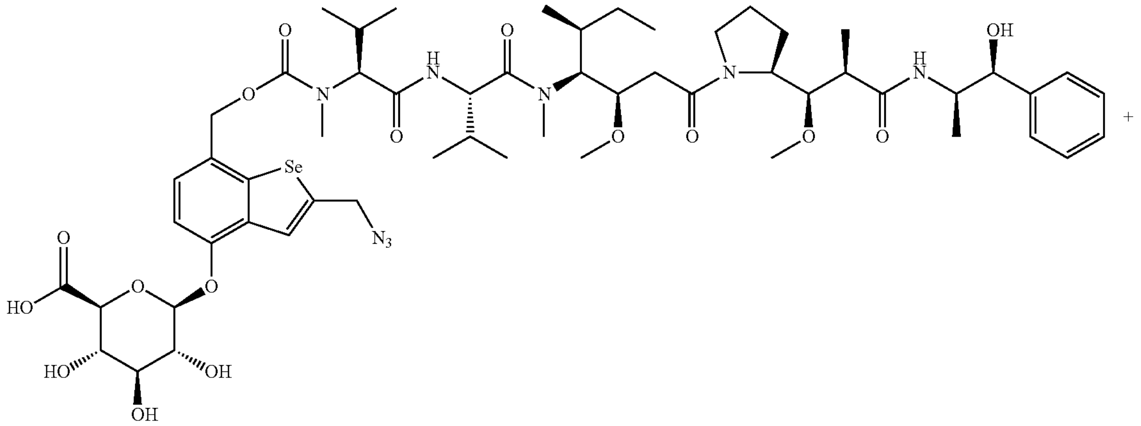

A-52

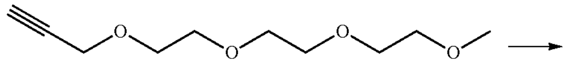

P-6

-continued

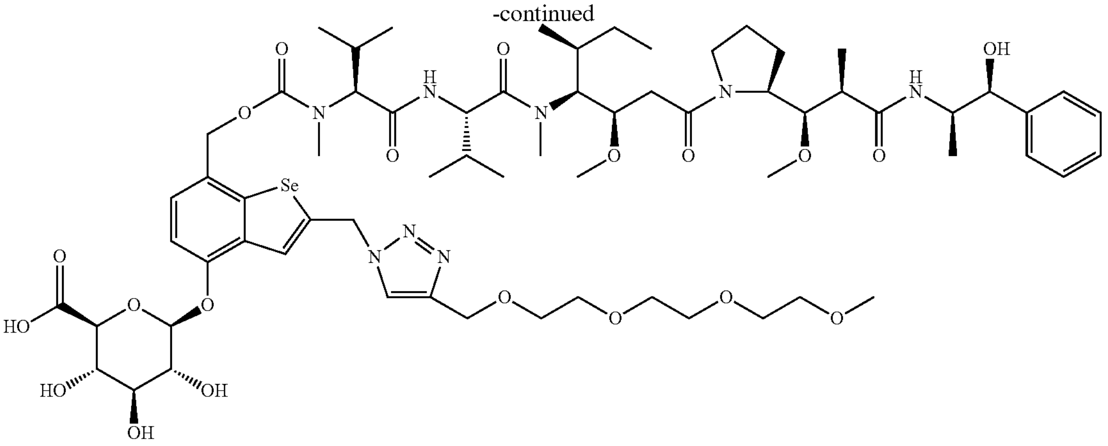

A-69

Compound A-52 (7.1 mg, 0.0059 mmol) was dissolved in DMSO (200 μL) under a nitrogen atmosphere at 0° C., and then 160 μL of a solution of Linker P-6 (15.6 mg) dissolved in DMSO (1.56 mL) was taken and added to the reaction. Additionally, distilled water (2 mL), DMSO (0.8 mL), copper (II) sulfate pentahydrate ($CuSO_4 \cdot 5H_2O$, 1.6 mg) and sodium ascorbate (2.34 mg) were sequentially added to the reaction solution, and then the mixture was stirred at room temperature for 10 minutes. After completion of the reaction, the reaction solution was diluted with distilled water (2 mL), separated and purified using Preparative-HPLC, and then freeze-dried to obtain Compound A-69 in the form of a white solid (7.8 mg, 94%); EI-MS m/z: 1404 $[M+H]^+$, 702 1/2 $[M+H]^+$.

Example I-64: Preparation of Compound A-70

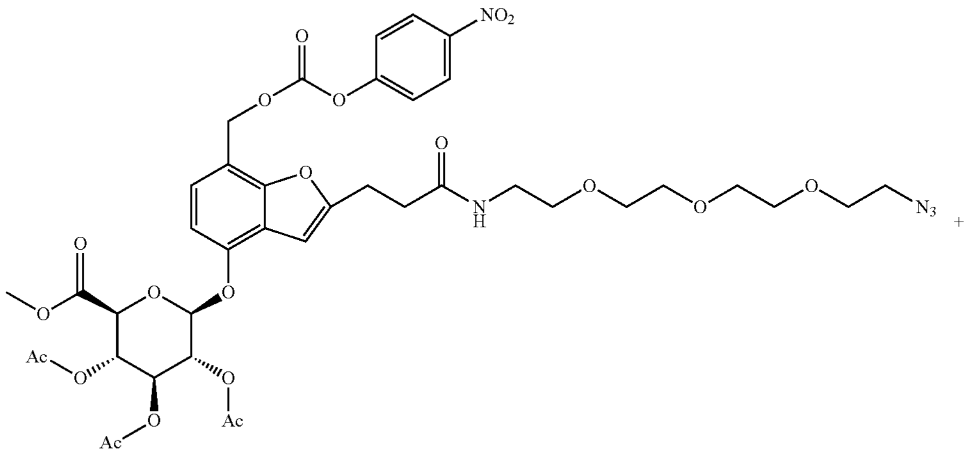

A-36c

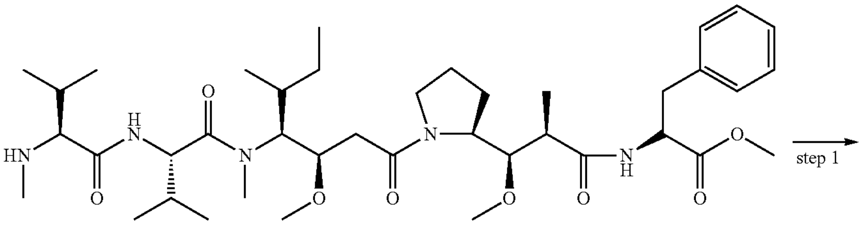

-continued

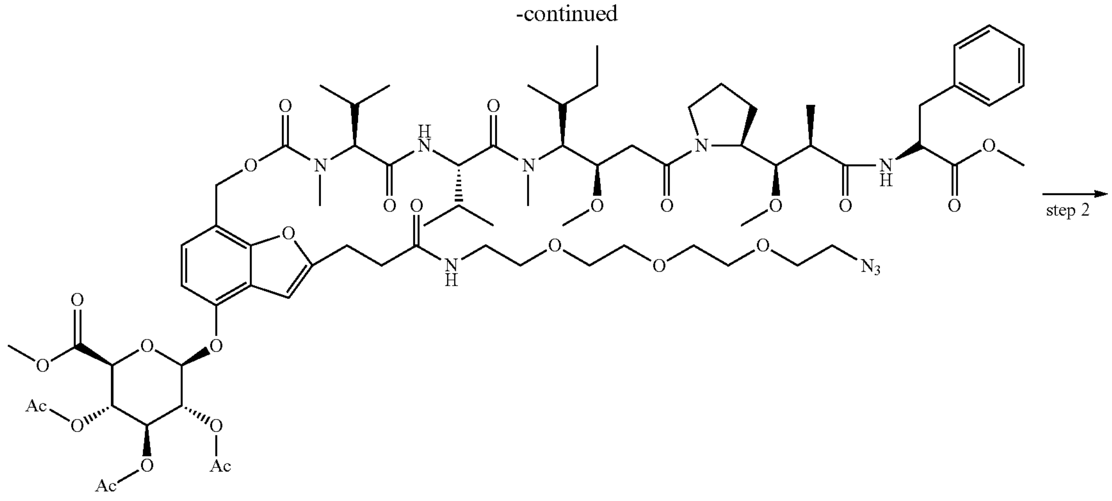

A-70a

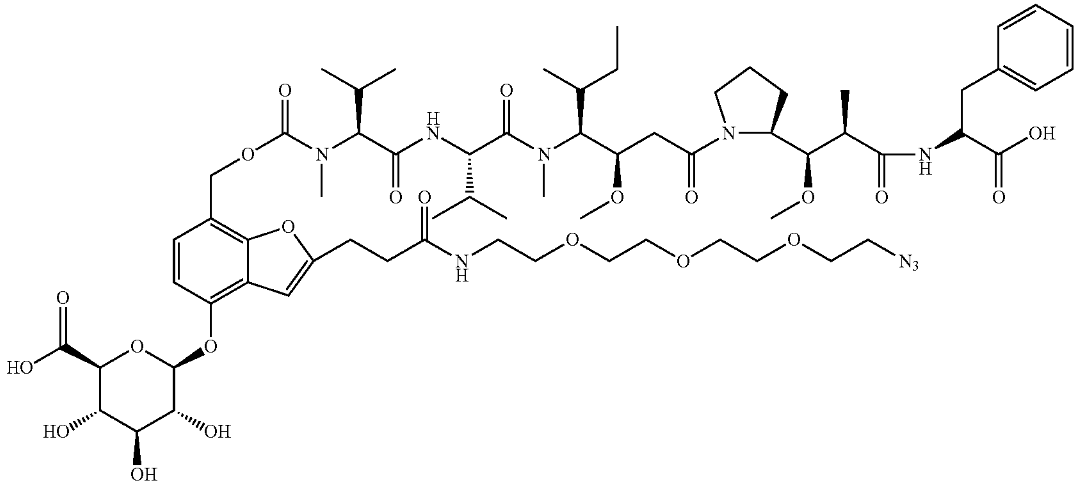

A-70

Step 1: Preparation of Compound A-70a

Compound A-36c (35.5 mg, 0.039 mmol) was dissolved in DMF (1 mL) under a nitrogen atmosphere at 0° C., and then MMAF-OMe (28.8 mg, 0.039 mmol), HOBt (7.8 mg, 0.058 mmol), DIPEA (16.8 μL, 0.097 mmol) and pyridine (1 mL) were sequentially added, and the mixture was stirred at room temperature for 16 hours. After completion of the reaction, the organic layer was extracted with EA (50 mL) and 2N-hydrochloric acid aqueous solution (50 mL), and then the organic layer was washed with a saturated aqueous sodium chloride solution (50 mL). The obtained organic layer was dried over anhydrous magnesium sulfate, filtered, and then concentrated under reduced pressure. The resulting residue was subjected to column chromatography to obtain Compound A-70a in the form of a colorless sticky gum (41.3 mg, 70%); EI-MS m/z: 1524 $[M+H]^+$, 762 1/2 $[M+H]^+$.

Step 2: Preparation of Compound A-70

Compound A-70a (41.3 mg, 0.027 mmol) was dissolved by mixing and adding methanol (0.7 mL), distilled water (0.25 mL) and THE (0.28 mL) at −20° C., and then lithium hydroxide (8.5 mg, 0.203 mmol) dissolved in distilled water (0.45 mL) was added dropwise, and the mixture was stirred for 3 hours while slowly raising the temperature from −20° C. to −5° C. After completion of the reaction, 2N-hydrochloric acid aqueous solution (0.2 mL) was added to terminate the reaction, and the reaction solution was diluted with ACN (2 mL) and distilled water (2 mL), then separated and purified using Preparative-HPLC, and freeze-dried to obtain Compound A-70 in the form of a white solid (28.5 mg, 77%); EI-MS m/z: 1371 $[M+H]^+$, 685 1/2 $[M+H]^+$.

Example I-65: Preparation of Compound A-71

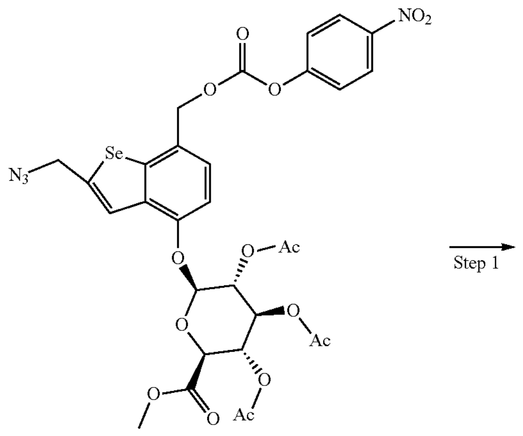

A-52h

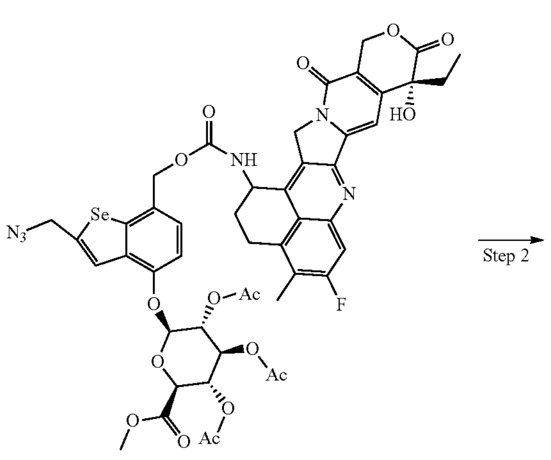

A-71a

-continued

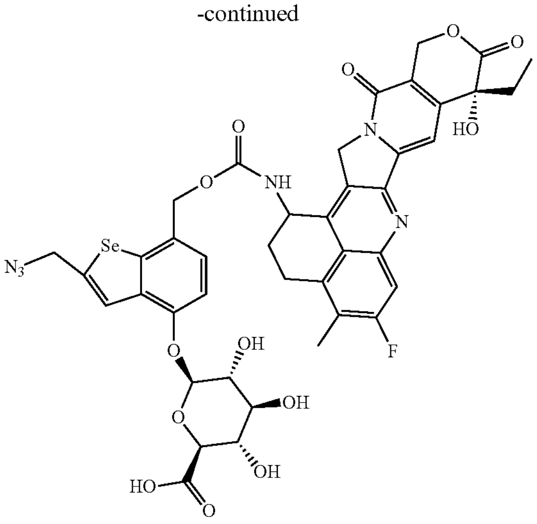

A-71

Step 1: Preparation of Compound A-71a

Compound A-52h (53.7 mg, 0.07 mmol) and Exatecan mesylate (CAS NO. 169869-90-3, 37.4 mg, 0.07 mmol) were dissolved in DMF (2 mL) under a nitrogen atmosphere at 0° C., and then HOBt (10.4 mg, 0.08 mmol), pyridine (0.3 mL) and DIPEA (24.5 μL, 0.14 mmol) were sequentially added, and the mixture was stirred at 0° C. for 30 minutes. Additionally, the reaction mixture was stirred at room temperature for 2 hours. After completion of the reaction, the organic layer was extracted with EA (50 mL) and 2N-hydrochloric acid aqueous solution (50 mL), and then the organic layer was washed with a saturated aqueous sodium chloride solution (50 mL). The obtained organic layer was dried over anhydrous magnesium sulfate, filtered, and then concentrated under reduced pressure. The resulting residue was subjected to column chromatography to obtain Compound A-71a in the form of a yellow solid (66.8 mg, 89%).

$^1$H-NMR (400 MHz, $CDCl_3$) δ 7.67 (m, 1H), 7.56 (s, 1H), 7.48 (s, 1H), 7.26 (m, 1H), 6.84 (d, J=8 Hz, 1H), 5.68 (m, 1H), 5.45-5.23 (m, 9H), 5.11 (m, 1H), 4.57 (s, 2H), 4.15 (m, 1H), 3.73 (s, 3H), 3.20-3.13 (m, 2H), 2.42 (s, 3H), 2.39-2.28 (m, 2H), 2.11-2.04 (m, 10H), 1.90 (q, J=7.2 Hz, 2H), 1.28-1.23 (m, 2H), 1.05 (t, J=7.2 Hz, 3H); EI-MS m/z: 1060 $[M+H]^+$.

Step 2: Preparation of Compound A-71

Compound A-71a (66.8 mg, 0.063 mmol) was dissolved by mixing and adding methanol (3.2 mL) and THE (3.2 mL) at −20° C., and then lithium hydroxide (13.2 mg, 0.315 mmol) dissolved in distilled water (0.64 mL) was added dropwise, and the mixture was stirred for 4 hours while slowly raising the temperature from −20° C. to −5° C. After completion of the reaction, 2N-hydrochloric acid aqueous solution (0.3 mL) was added to terminate the reaction, and the reaction solution was diluted with ACN (3 mL) and distilled water (3 mL), then separated and purified using Preparative-HPLC, and freeze-dried to obtain Compound A-71 in the form of an ivory solid (36.3 mg, 63%); EI-MS m/z: 920 $[M+H]^+$.

Example I-66: Preparation of Compound A-72
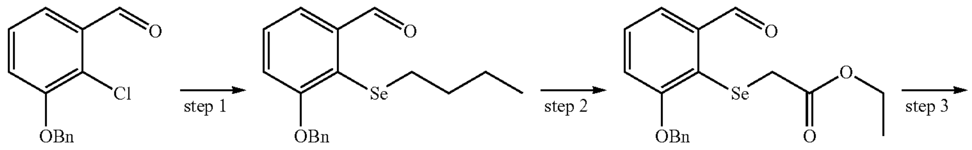
A-63c A-72a A-72b
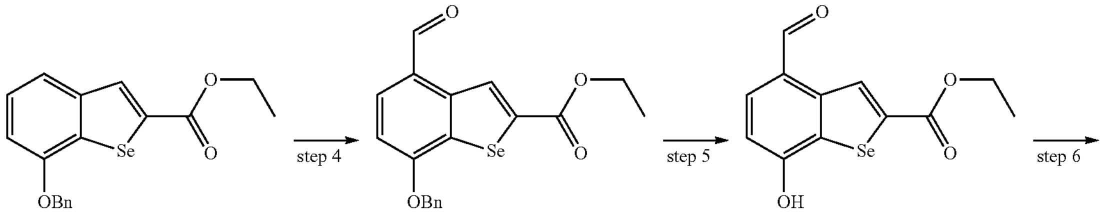
A-72c A-72d A-72e
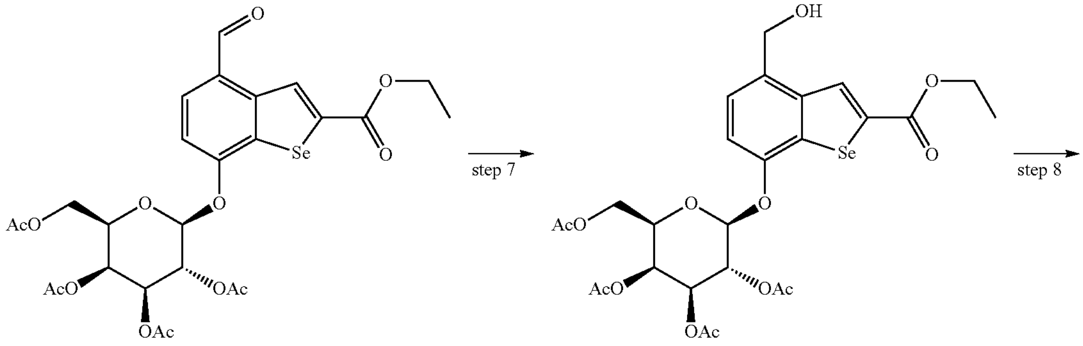
A-72f A-72g
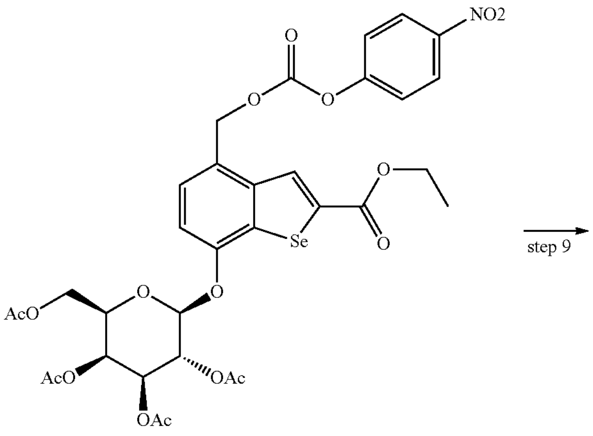
A-72h -continued

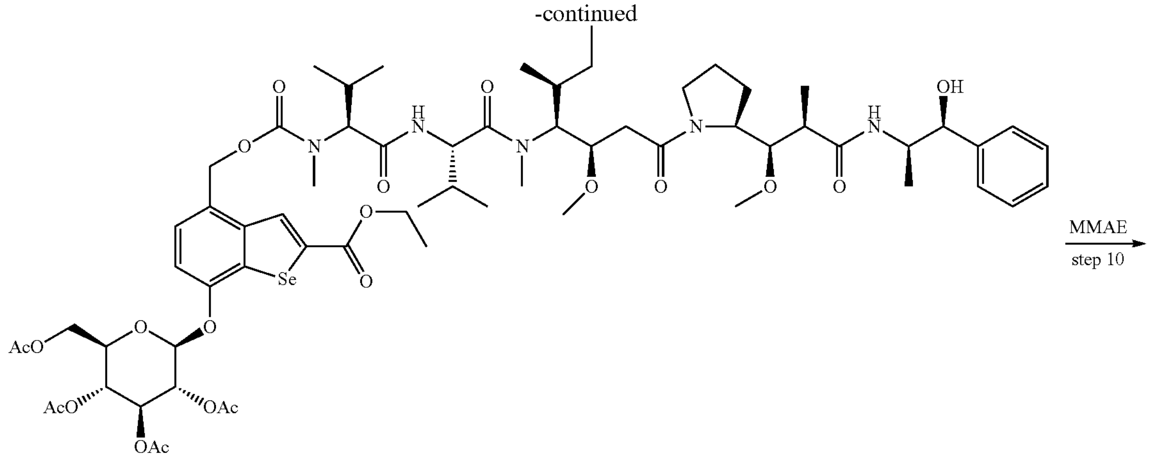

A-72i

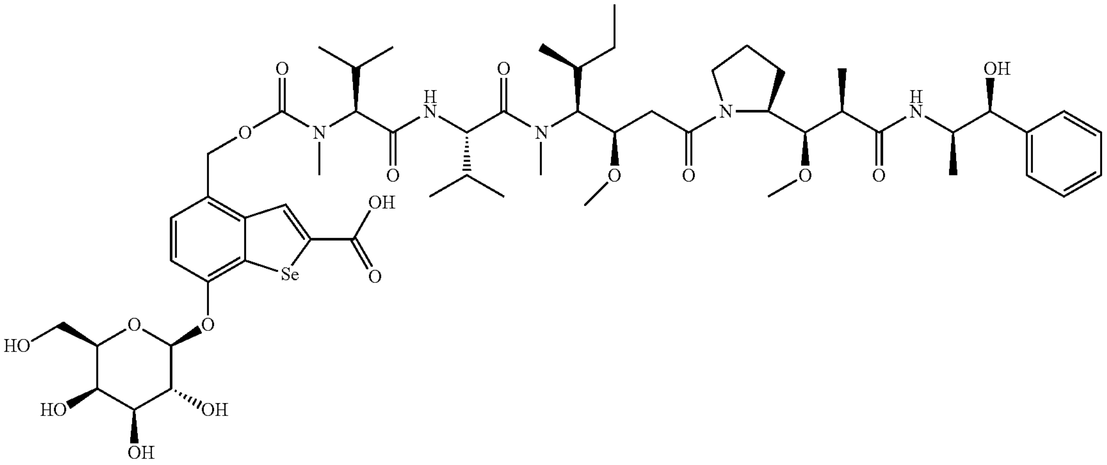

A-72

Step 1: Preparation of Compound A-72a

Selenium powder (TCI, CAS No. 7782-49-2, 640.0 mg, 8.10 mmol) was added to THE (27.0 mL) under a nitrogen atmosphere at room temperature, and the mixture was cooled to 0° C., and then n-butyl lithium solution (2.5M n-BuLi in hexane, 3.56 mL, 8.91 mmol) was slowly added dropwise. The mixture was stirred at 0° C. for 40 minutes, and then Compound A-63c (2.0 g, 8.10 mmol) was dissolved in DMF (5.4 mL) and added, and the mixture was stirred at room temperature for 3 hours. After completion of the reaction, distilled water (100 mL) was added dropwise to terminate the reaction. EA (100 mL) was added to the reaction solution, and then the organic layer was extracted. The obtained organic layer was dried over anhydrous magnesium sulfate, filtered, and then concentrated under reduced pressure. The resulting residue was subjected to column chromatography to obtain Compound A-72a in the form of a yellow liquid (2.03 g, 72%).

$^1$H-NMR (400 MHz, $CDCl_3$) δ 10.71 (s, 1H), 7.54 (d, J=8.0 Hz, 1H), 7.50-7.48 (m, 2H), 7.42-7.32 (m, 4H), 7.14 (d, J=8.0 Hz, 1H), 5.20 (s, 2H), 2.89 (t, J=7.6 Hz, 2H), 1.71-1.50 (m, 2H), 1.39-1.31 (m, 2H), 0.81 (t, J=7.6 Hz, 3H).

Step 2: Preparation of Compound A-72b

Compound A-72a (2.0 g, 5.75 mmol) was dissolved in DMF (25.0 mL) under a nitrogen atmosphere at room temperature, and then ethyl bromoacetate (1.6 mL, 13.4 mmol) and potassium carbonate (1.85 g, 13.4 mmol) were sequentially added, and then the mixture was stirred at 120° C. for 16 hours. After completion of the reaction, distilled water (250 mL) and EA (250 mL) were added to extract the organic layer. The obtained organic layer was washed by adding a saturated aqueous sodium chloride solution (250 mL). The organic layer was dried over anhydrous magnesium sulfate, filtered, and then concentrated under reduced pressure. The residue was subjected to column chromatography to obtain Compound A-72b in the form of a white solid (1.5 g, 69%).

$^1$H-NMR (400 MHz, $CDCl_3$) δ 10.63 (s, 1H), 7.56 (d, J=8.0 Hz, 1H), 7.50-7.49 (m, 2H), 7.44-7.39 (m, 3H), 7.37-7.33 (m, 1H), 7.18 (d, J=8.0 Hz, 1H), 5.22 (s, 1H), 3.95 (q, J=7.2 Hz, 2H), 3.53 (s, 2H), 1.05 (t, J=7.2 Hz, 3H).

Step 3: Preparation of Compound A-72c

Compound A-72b (1.5 g, 3.97 mmol) was dissolved in DMF (20.0 mL) under a nitrogen atmosphere at 0° C., and then potassium carbonate (824.0 mg, 5.96 mmol) was added, and the mixture was stirred at 120° C. for 2 hours. After completion of the reaction, EA (200 mL) and distilled water (200 mL) were added to extract the organic layer. The obtained organic layer was washed by adding a saturated aqueous sodium chloride solution (200 mL). The organic layer was dried over anhydrous magnesium sulfate, filtered, and then concentrated under reduced pressure. The resulting residue was subjected to column chromatography to obtain Compound A-72c in the form of a white solid (1.2 g, 84%).

$^1$H-NMR (400 MHz, $CDCl_3$) δ 8.30 (s, 1H), 7.51 (d, J=8.0 Hz, 1H), 7.48-7.46 (m, 2H), 7.42-7.38 (m, 2H), 7.35-7.32 (m, 2H), 6.87 (d, J=8.0 Hz, 1H), 5.27 (s, 2H), 4.38 (q, J=7.2 Hz, 2H), 4.38 (t, J=7.2 Hz, 3H); EI-MS m/z: 360 $[M+H]^+$.

Step 4: Preparation of Compound A-72d

Compound A-72c (1.2 g, 3.34 mmol) was dissolved in MC (30.0 mL) under a nitrogen atmosphere at 0° C., and then dichloromethyl methyl ether (1.19 mL, 13.36 mmol) and titanium tetrachloride solution (1M-$TiCl_4$ in MC, 13.36 mL, 13.36 mmol) were sequentially and slowly added, and the mixture was stirred for 3 hours while maintaining the temperature. After completion of the reaction, cooled distilled water (150 mL) was slowly added dropwise to terminate the reaction, and EA (150 mL) was added to extract the organic layer. The obtained organic layer was dried over anhydrous magnesium sulfate, filtered, and then concentrated under reduced pressure. The resulting residue was subjected to column chromatography to obtain Compound A-72d in the form of a white solid (1.09 g, 89%).

$^1$H-NMR (400 MHz, $CDCl_3$) δ 10.04 (s, 1H), 9.32 (s, 1H), 7.84 (d, J=8.0 Hz, 1H), 7.48-7.35 (m, 5H), 7.00 (d, J=8.0 Hz, 1H), 5.37 (s, 2H), 4.41 (q, J=7.2 Hz, 2H), 1.42 (t, J=7.2 Hz, 3H).

Step 5: Preparation of Compound A-72e

Compound A-72d (420.0 mg, 1.11 mmol) was dissolved in MC (20.0 mL) under a nitrogen atmosphere at −78° C., and then boron trichloride solution (1M-$BCl_3$ in MC, 3.33 mL, 3.33 mmol) was slowly added, and the mixture was stirred for 2 hours while maintaining the temperature. After completion of the reaction, distilled water (50 mL) was slowly added dropwise at −50° C. to terminate the reaction, and EA (150 mL) and distilled water (100 mL) were further added at room temperature to extract the organic layer. The obtained organic layer was dried over anhydrous magnesium sulfate, filtered, and then concentrated under reduced pressure. The resulting residue was subjected to column chromatography to obtain Compound A-72e in the form of a white solid (300.0 mg, 90%).

$^1$H-NMR (400 MHz, $CDCl_3$) δ 10.05 (s, 1H), 9.33 (s, 1H), 7.81 (d, J=8.0 Hz, 1H), 6.92 (d, J=8.0 Hz, 1H), 5.98 (s, 1H), 4.41 (q, J=7.2 Hz, 2H), 1.43 (t, J=7.2 Hz, 3H).

Step 6: Preparation of Compound A-72f

Compound A-72e (150.0 mg 0.50 mmol) was dissolved in ACN (30.0 mL) under a nitrogen atmosphere at 0° C., and then acetobromo-alpha-D-galactose (250.0 mg, 0.60 mmol) and silver oxide (I) (290.0 mg, 1.25 mmol) were sequentially added, and the mixture was stirred at room temperature for 2 hours. After completion of the reaction, the reaction solution was diluted with EA (50 mL), filtered using Celite, and washed by adding a saturated aqueous sodium chloride solution (80 mL) to the solution. The reaction solution was dried over anhydrous magnesium sulfate, filtered, and then concentrated under reduced pressure. The resulting residue was subjected to column chromatography to obtain Compound A-72f in the form of a white solid (290.0 mg, 91%).

$^1$H-NMR (400 MHz, $CDCl_3$) δ 10.11 (s, 1H), 9.30 (s, 1H), 7.87 (d, J=8.0 Hz, 1H), 7.15 (d, J=8.0 Hz, 1H), 5.63 (dd, J=10.4 Hz, 8.0 Hz, 1H), 7.52 (d, J=3.2 Hz, 1H), 5.28 (d, J=8.0 Hz, 1H), 5.17 (dd, J=10.4 Hz, 3.2 Hz, 1H), 4.42 (d, J=7.2 Hz, 1H), 4.31-4.26 (m, 1H), 4.22-4.14 (m, 2H), 2.22 (s, 3H), 2.10 (s, 6H), 2.04 (s, 3H), 1.43 (t, J=7.2 Hz, 3H).

Step 7: Preparation of Compound A-72g

Compound A-72f (90.0 mg, 0.143 mmol) was dissolved in THE (10.0 mL) under a nitrogen atmosphere at 0° C., and then sodium borohydride (13.5 mg, 0.358 mmol) was added, and the mixture was stirred at 0° C. for 2 hours. After completion of the reaction, EA (50 mL) and distilled water (50 mL) were added to extract the organic layer. The obtained organic layer was dried over anhydrous magnesium sulfate, filtered, and then concentrated under reduced pressure. The resulting residue was subjected to column chromatography to obtain Compound A-72g in the form of a white solid (72.0 mg, 80%).

$^1$H-NMR (400 MHz, $CDCl_3$) δ 8.52 (s, 1H), 7.36 (d, J=8.0 Hz, 1H), 7.03 (d, J=8.0 Hz, 1H), 5.60 (dd, J=10.4 Hz, 8.0 Hz, 1H), 5.49 (d, J=3.2 Hz, 1H), 5.16-5.12 (m, 2H), 4.99 (d, J=5.6 Hz, 2H), 4.39 (q, J=7.2 Hz, 2H), 4.30-4.25 (m, 1H), 4.21-4.17 (m, 1H), 4.14-4.11 (m, 1H), 2.21 (s, 3H), 2.11 (s, 3H), 2.09 (s, 3H), 2.03 (s, 3H), 1.41 (t, J=7.2 Hz, 3H).

Step 8: Preparation of Compound A-72h

Compound A-72g (70.0 mg, 0.111 mmol) was dissolved in MC (3.0 mL) under a nitrogen atmosphere at 0° C., and then 4-nitrophenyl chloroformate (44.0 mg, 0.222 mmol) and DIPEA (58.0 L, 0.333 mmol) and pyridine (31.0 μL, 0.388 mmol) were sequentially added, and the mixture was stirred at room temperature for 4 hours. After completion of the reaction, EA (50 mL) and distilled water (50 mL) were added to extract the organic layer. The obtained organic layer was dried over anhydrous magnesium sulfate, filtered, and then concentrated under reduced pressure. The resulting residue was subjected to column chromatography to obtain Compound A-72h in the form of a white solid (70.0 mg, 79%).

$^1$H-NMR (400 MHz, $CDCl_3$) δ 8.50 (s, 1H), 8.26 (d, J=9.2 Hz, 2H), 7.46 (d, J=8.0 Hz, 1H), 7.36 (d, J=9.2 Hz, 2H), 7.04 (d, J=8.0 Hz, 1H), 5.63-5.57 (m, 3H), 5.50 (d, J=3.2 Hz, 1H), 5.19-5.13 (m, 2H), 4.42 (q, J=7.2 Hz, 2H), 4.30-4.25 (m, 2H), 4.21-4.11 (m, 2H), 2.21 (s, 3H), 2.11 (s, 3H), 2.09 (s, 3H), 2.04 (s, 3H), 1.43 (t, J=7.2 Hz, 3H).

Step 9: Preparation of Compound A-72i

Compound A-72h (70.0 mg, 0.088 mmol) was dissolved in DMF (1.0 mL) under a nitrogen atmosphere at 0° C., and then MMAE (63.0 mg, 0.088 mmol), HOBt (18.0 mg, 0.132 mmol), DIPEA (38.4 μL, 0.22 mmol) and pyridine (1.0 mL) were sequentially added, and the mixture was stirred at room temperature for 16 hours. After completion of the reaction, extraction was performed using distilled water (20 mL), 2N-hydrochloric acid aqueous solution (5 mL) and EA (25 mL). The obtained organic layer was dried over anhydrous magnesium sulfate, filtered, and then concentrated under reduced pressure. The resulting residue was subjected to column chromatography to obtain Compound A-72i in the form of a white solid (60.0 mg, 50%); EI-MS m/z: 1374 $[M+H]^+$.

Step 10: Preparation of Compound A-72

Compound A-72i (60.0 mg, 0.043 mmol) was dissolved in methanol (1.0 mL) under a nitrogen atmosphere at 0° C., and then lithium hydroxide (19.2 mg, 0.458 mmol) dissolved in distilled water (1.0 mL) was slowly added dropwise, and the mixture was stirred at room temperature for 3 hours. After completion of the reaction, 2N-hydrochloric acid aqueous solution (1.0 mL) was added to terminate the reaction, and the reaction solution was diluted with ACN (1.0 mL) and distilled water (1.0 mL), then separated and purified using Preparative-HPLC, and freeze-dried to obtain Compound A-72 in the form of a white solid (40.6 mg, 78%); EI-MS m/z: 1178 $[M+H]^+$.

Example I-67: Preparation of Compound A-73

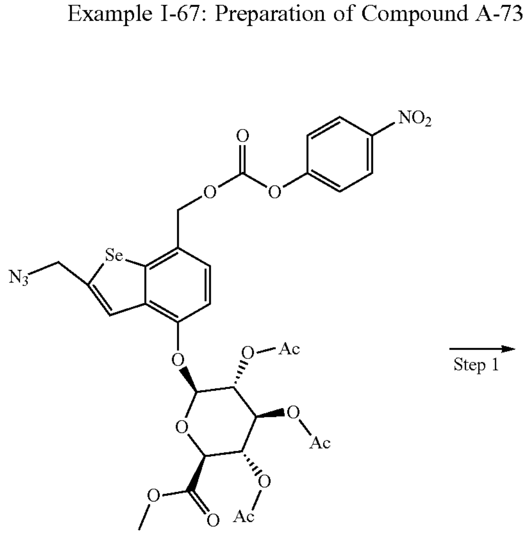

A-52h

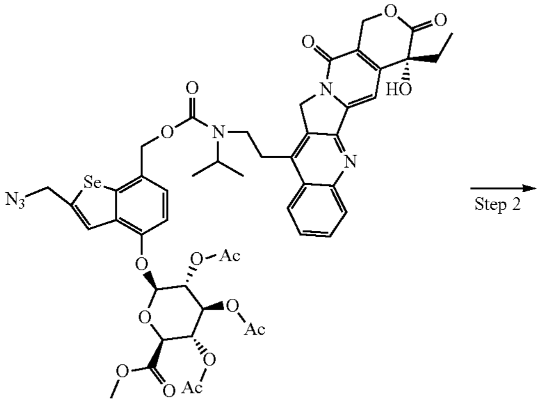

A-73a

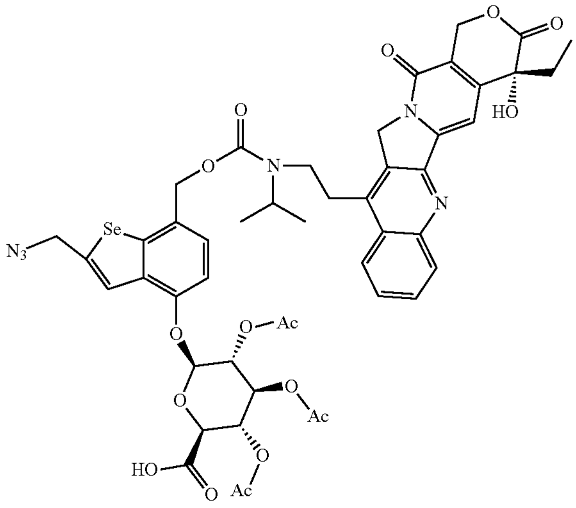

A-73

Step 1: Preparation of Compound A-73a

Compound A-52h (39.2 mg, 0.051 mmol) and Belotecan hydrochloride (CAS NO. 213819-48-8, 24.1 mg, 0.051 mmol) were dissolved in DMF (2 mL) under a nitrogen atmosphere at 0° C., and then HOBt (7.6 mg, 0.056 mmol), pyridine (0.3 mL) and DIPEA (17.9 μL, 0.102 mmol) were sequentially added, and the mixture was stirred at 0° C. for 30 minutes. Additionally, the reaction mixture was stirred at room temperature for 3 hours. After completion of the reaction, the organic layer was extracted with EA (50 mL) and 2N-hydrochloric acid aqueous solution (50 mL), and then the organic layer was washed with a saturated aqueous sodium chloride solution (50 mL). The obtained organic layer was dried over anhydrous magnesium sulfate, filtered, and then concentrated under reduced pressure. The resulting residue was subjected to column chromatography to obtain Compound A-73a in the form of a white solid (48.9 mg, 90%); EI-MS m/z: 1058 $[M+H]^+$.

Step 2: Preparation of Compound A-73

Compound A-73a (29 mg, 0.027 mmol) was dissolved by mixing and adding methanol (1.4 mL) and THE (1.4 mL) at −20° C., and then lithium hydroxide (5.7 mg, 0.137 mmol) dissolved in distilled water (0.28 mL) was added dropwise, and the mixture was stirred for 2 hours while slowly raising the temperature from −20° C. to −5° C. After completion of the reaction, 2N-hydrochloric acid aqueous solution (0.2 mL) was added to terminate the reaction, and the reaction solution was diluted with ACN (2 mL) and distilled water (2 mL), then separated and purified using Preparative-HPLC, and freeze-dried to obtain Compound A-73 in the form of a yellow solid (15.3 mg, 61%); EI-MS m/z: 918 $[M+H]^+$.

Example I-68: Preparation of Compound A-74

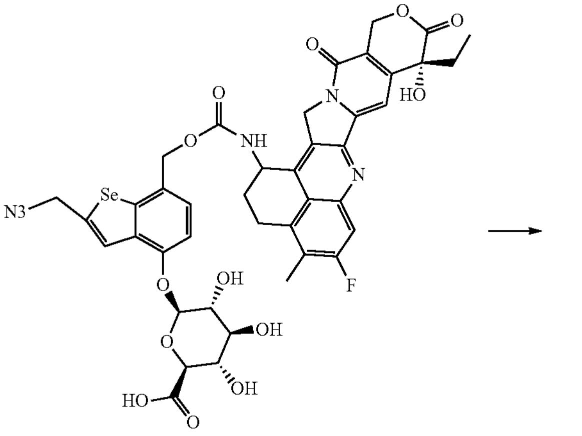

A-71

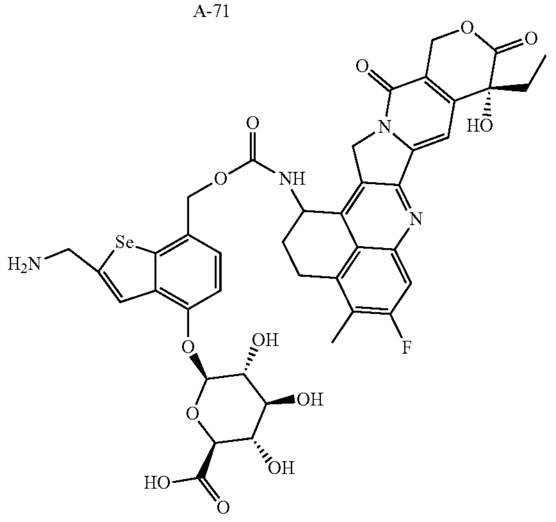

A-74

Compound A-71 (20.9 mg, 0.023 mmol) was dissolved in 1,4-dioxane (2 mL) and distilled water (0.4 mL) under a nitrogen atmosphere at room temperature, and then triphenylphosphine (8.9 mg, 0.034 mmol) was added, and the mixture was stirred for 12 hours. 2N-sodium hydroxide aqueous solution (20 μL) was added to the above reaction solution at room temperature, and the mixture was stirred for 3 hours, and then 2N-hydrochloric acid aqueous solution was slowly added dropwise to adjust the pH of the reaction solution to 3, and the reaction solution was separated and purified using Preparative-HPLC, and then freeze-dried to obtain Compound A-74 (11.5 mg, 56%); EI-MS m/z: 894 $[M+H]^+$.

Example I-69: Preparation of Compound A-75

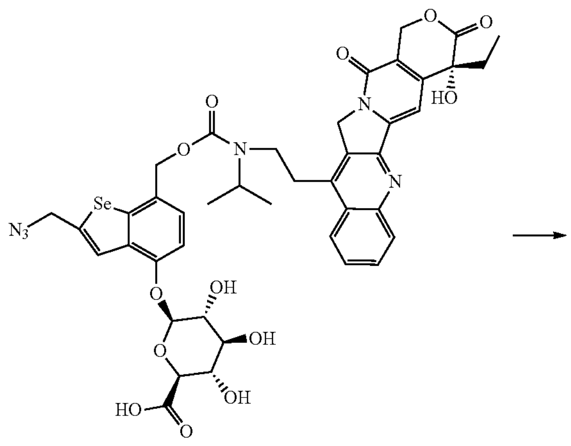

A-73

-continued

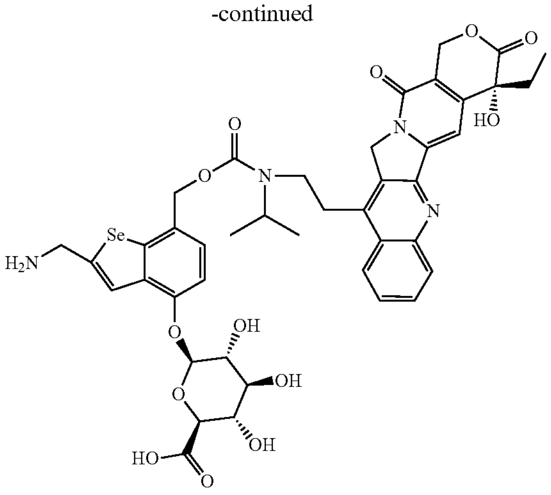

A-75

Compound A-73 (18.4 mg, 0.02 mmol) was dissolved in 1,4-dioxane (1 mL) and distilled water (0.2 mL) under a nitrogen atmosphere at room temperature, and then triphenylphosphine (7.9 mg, 0.03 mmol) was added, and the mixture was stirred for 12 hours. 2N-sodium hydroxide aqueous solution (20 μL) was added to the above reaction solution at room temperature, and the mixture was stirred for 3.5 hours, and then 2N-hydrochloric acid aqueous solution was slowly added dropwise to adjust the pH of the reaction solution to 3, and the reaction solution was separated and purified using Preparative-HPLC, and then freeze-dried to obtain Compound A-75 (8.2 mg, 46%); EI-MS m/z: 892 $[M+H]^+$.

Example I-70: Preparation of Compound A-76

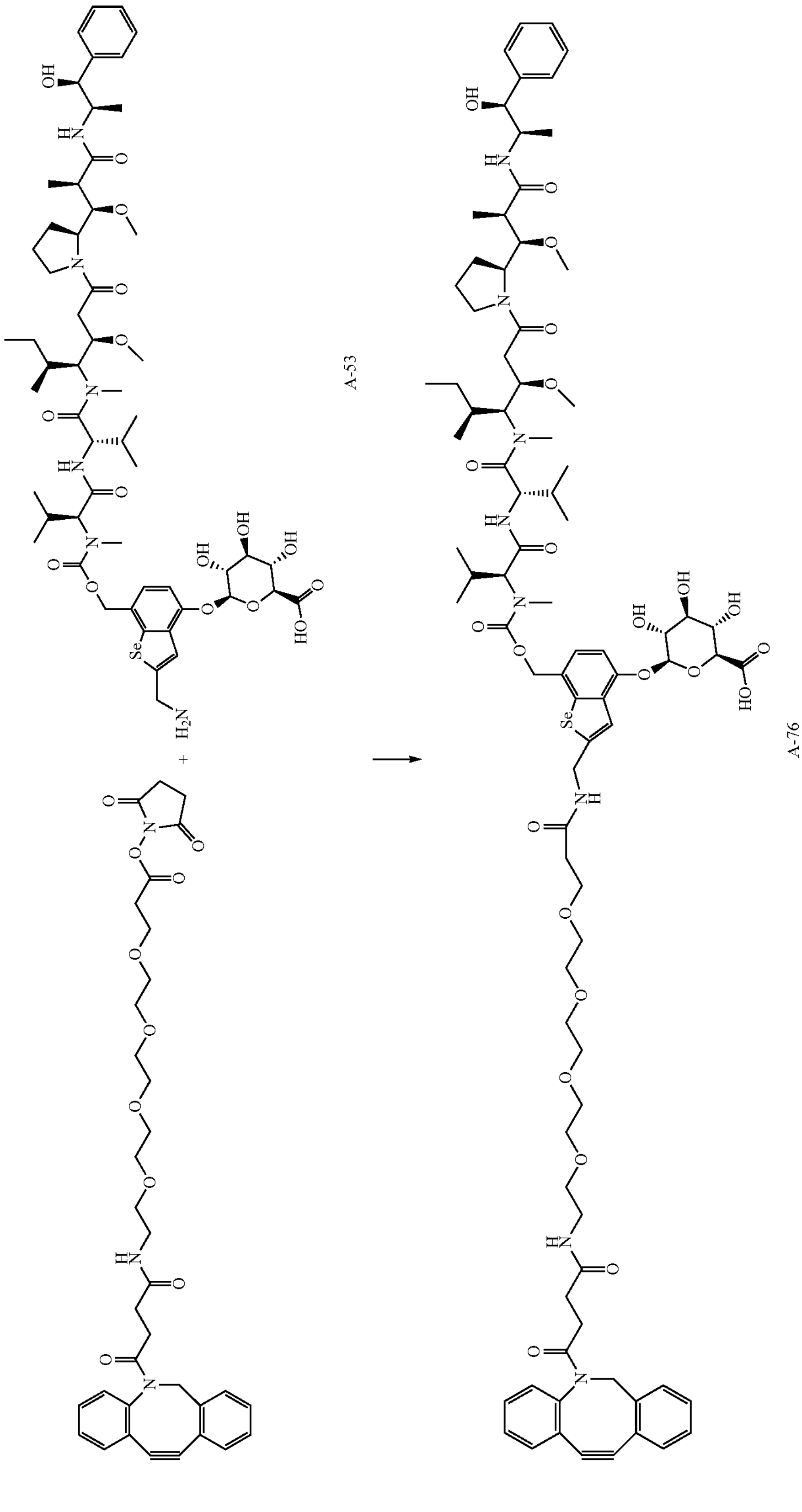
A-53
A-76

Compound A-53 (1 mg, 0.00085 mmol) was dissolved in THE (1 mL) under a nitrogen atmosphere at room temperature, and then DBCO-PEG4-NHS ester (TCI, CAS NO. 1427004-19-0, 0.5 mg, 0.00094 mmol), distilled water (200 μL), DIPEA (10 μL) and pyridine (10 μL) were sequentially added dropwise, and the mixture was stirred for 3 hours. After completion of the reaction, the reaction solution was diluted with ACN (1 mL) containing 0.1% formic acid, separated and purified using Preparative-HPLC, and then freeze-dried to obtain Compound A-76 in the form of a white solid (0.8 mg, 57%); MS m/z: 1711 $[M+H]^+$.

Example I-71: Preparation of Compound A-77

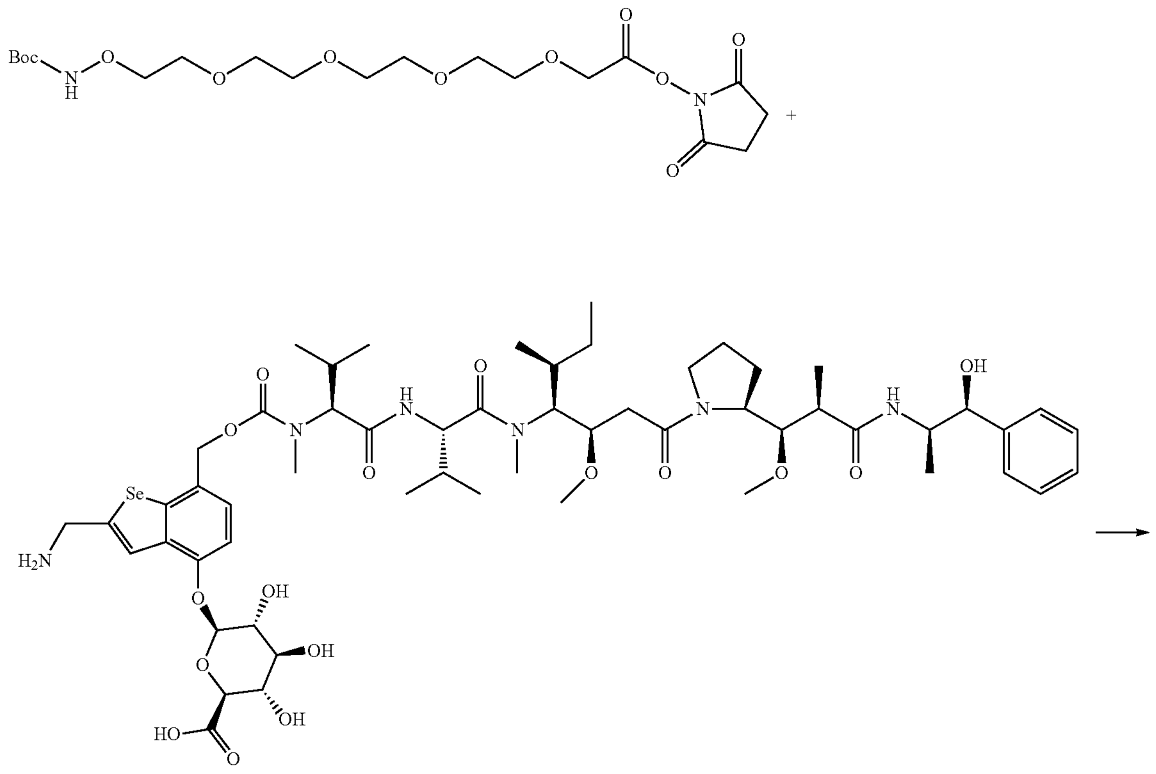

A-53

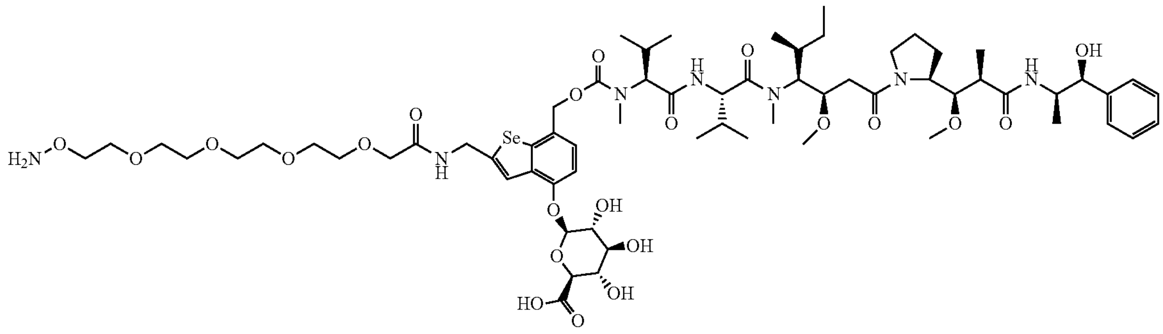

A-77

Compound A-77 was obtained in a manner similar to Example 70, using N-Boc-aminooxyacetic acid NHS ester (prepared by the method described in WO2015/182984, WO2018/090045) instead of DBCO-PEG4-NHS ester in Example I-70 (2 mg, 55%); MS m/z: 1426 $[M+H]^+$.

Example II-1: Preparation of Compound B-1

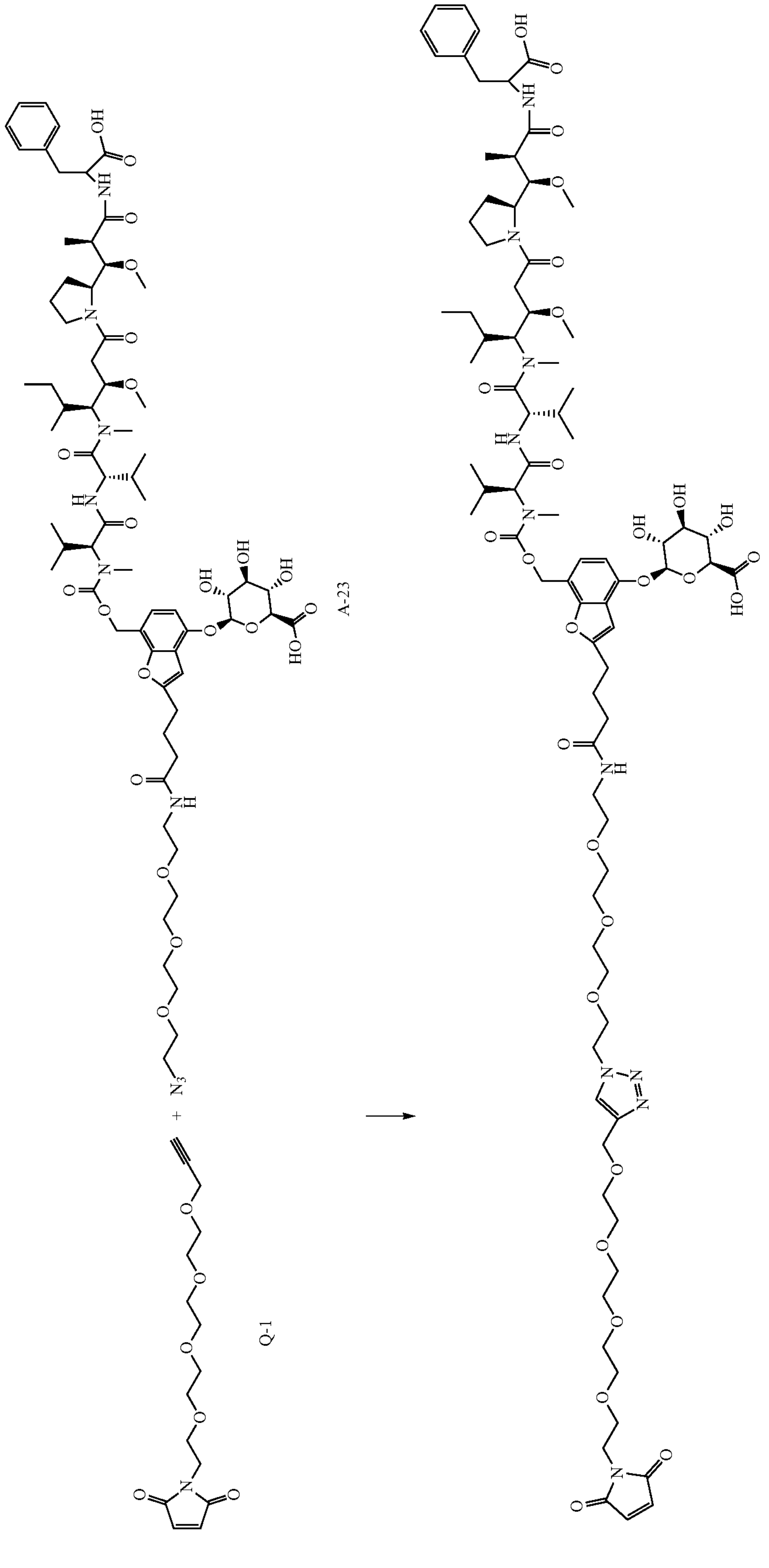
A-23
Q-1
B-1

Step 2: Preparation of Compound B-1 Compound A-23 (4.5 mg, 0.0032 mmol) was dissolved in DMSO (200 μL) under a nitrogen atmosphere at 0° C., and then 100 μL of a solution of Linker Q-1 (10 mg) dissolved in DMSO (1 mL) was taken and added to the reaction. Additionally, distilled water (2 mL), DMSO (0.4 mL), copper (II) sulfate pentahydrate ($CuSO_4 \cdot 5H_2O$, 1 mg), sodium ascorbate (1.3 mg) were sequentially added to the reaction solution, and then the mixture was stirred at room temperature for 30 minutes. After completion of the reaction, the reaction solution was diluted with distilled water (1 mL), separated and purified using Preparative-HPLC, and then freeze-dried to obtain Compound B-1 in the form of a white solid (4.5 mg, 81.8%); MS m/z: 1682 $[M+H]^+$.

Example II-2: Preparation of Compound B-2

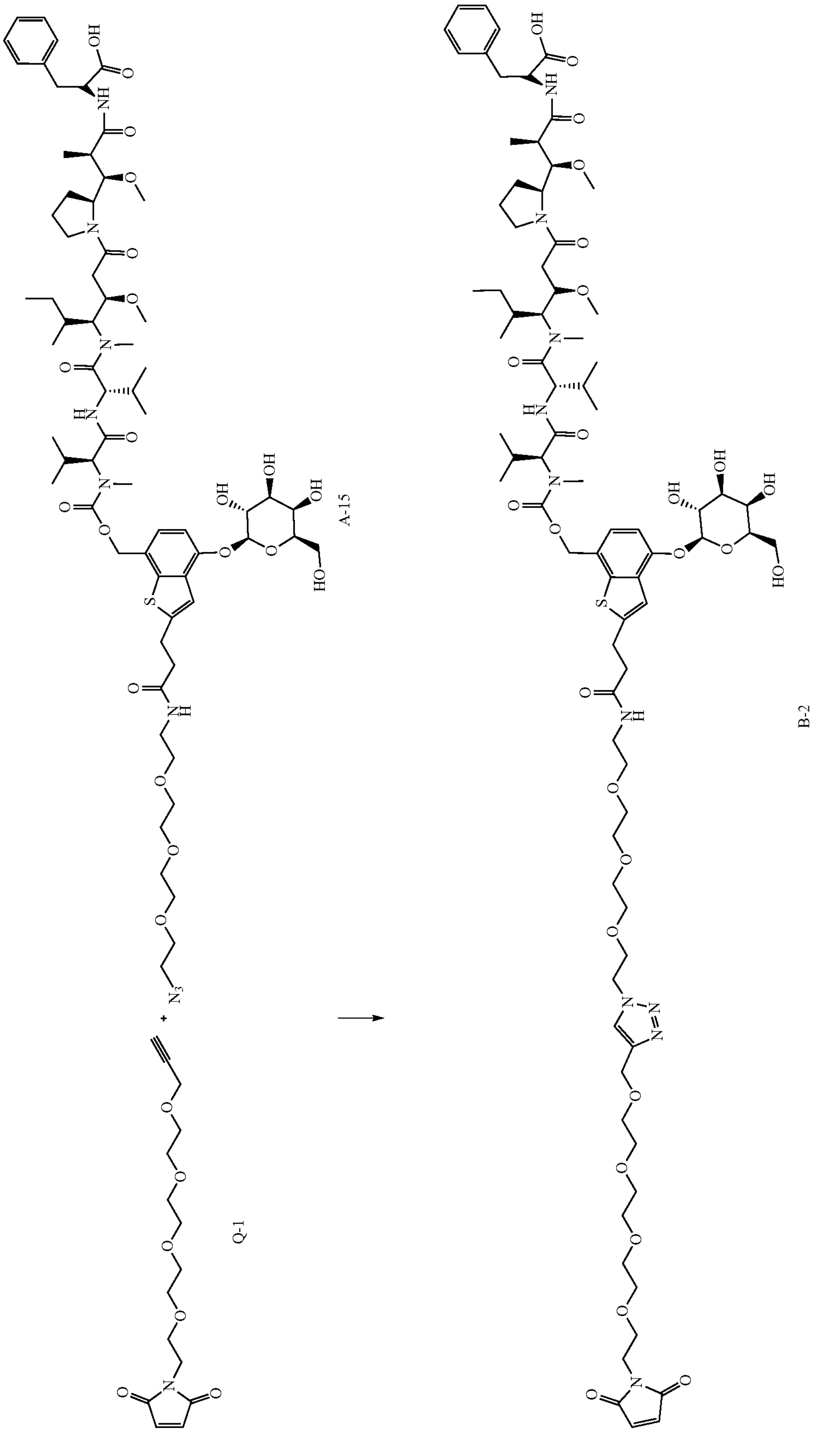
A-15
Q-1
B-2

Compound A-15 (4.5 mg, 0.0032 mmol) was dissolved in DMSO (200 μL) under a nitrogen atmosphere at 0° C., and then 150 μL of a solution of Linker Q-1 (10 mg) dissolved in DMSO (1 mL) was taken and added to the reaction. Additionally, distilled water (2 mL), ethanol (20 μL), copper (II) sulfate pentahydrate ($CuSO_4 \cdot 5H_2O$, 1 mg), sodium ascorbate (1.3 mg) were sequentially added to the reaction solution, and then the mixture was stirred at room temperature for 30 minutes. After completion of the reaction, the reaction solution was diluted with distilled water (1 mL), separated and purified using Preparative-HPLC, and then freeze-dried to obtain Compound B-2 in the form of a white solid (3.9 mg, 70.9%); MS m/z: 1684 $[M+H]^+$.

Example II-3: Preparation of Compound B-3

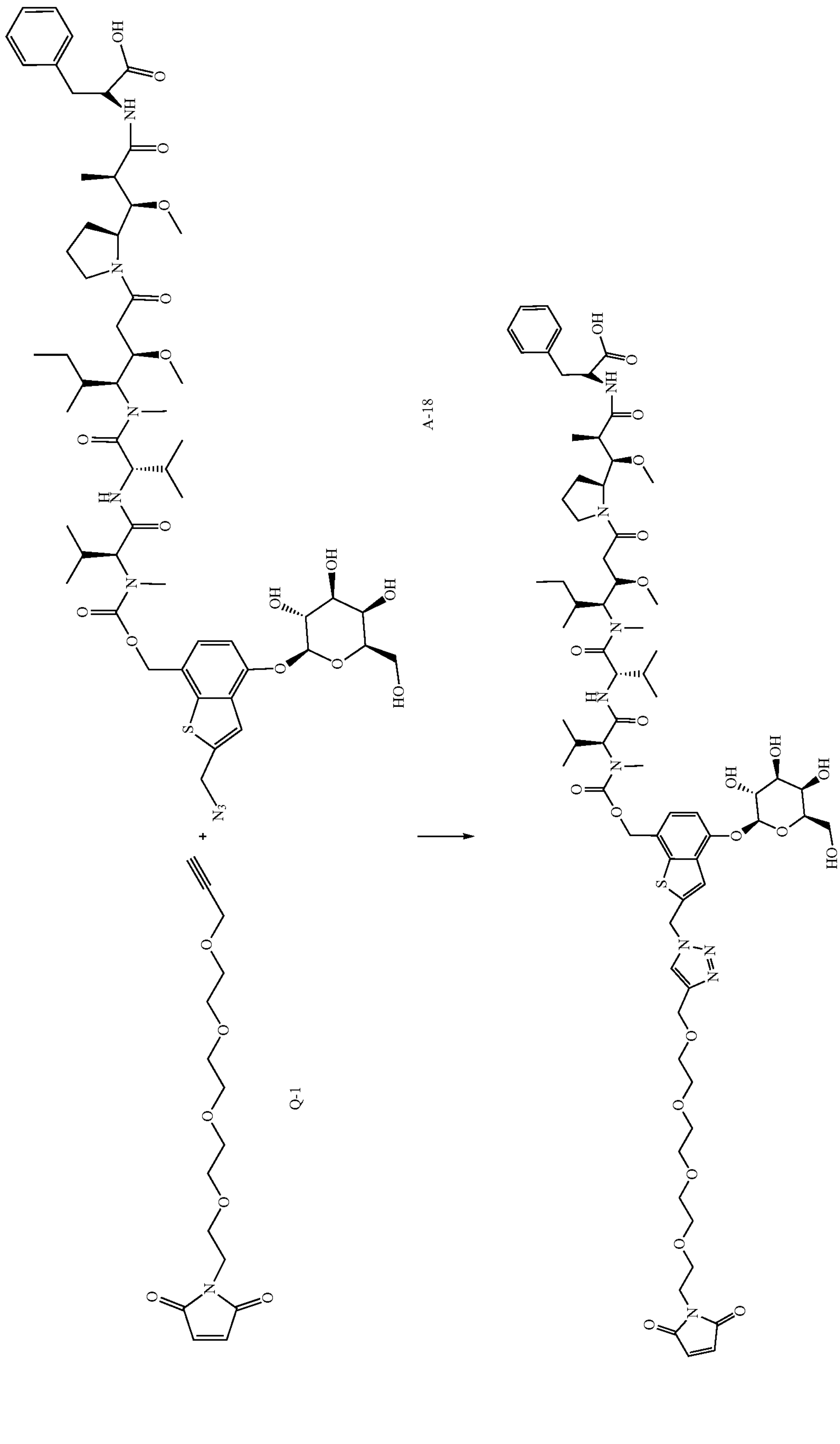
A-18
Q-1
B-3

Compound B-3 was obtained in the form of a white solid in the same manner as in Example II-2, except that Compound A-18 was used instead of Compound A-15 in Example II-2 (6.3 mg, 77.5%); MS m/z: 1466 $[M+H]^+$.

Example II-4: Preparation of Compound B-4

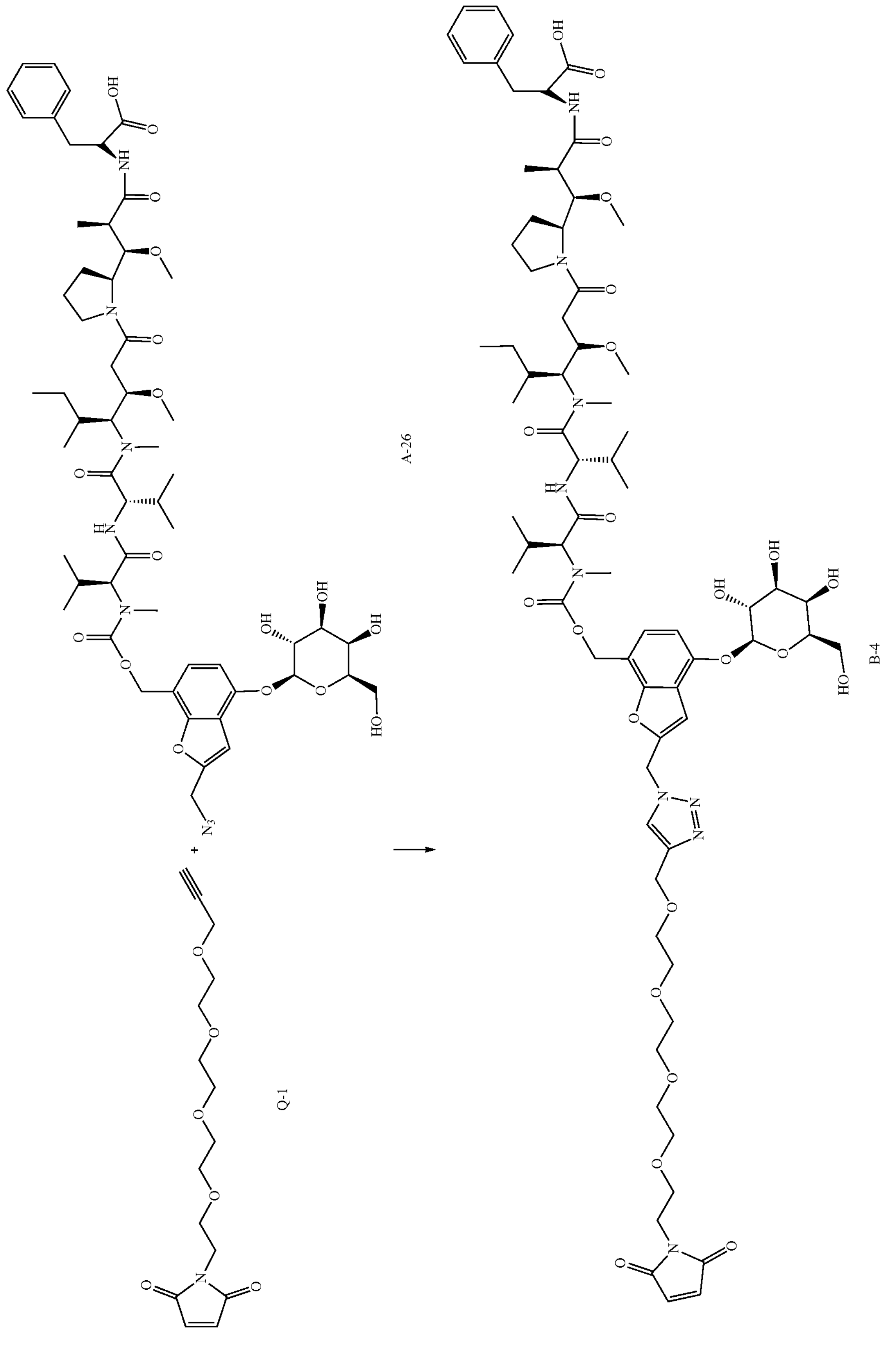
A-26
Q-1
B-4

Compound B-4 was obtained in the form of a white solid in the same manner as in Example II-2, except that Compound A-26 was used instead of Compound A-15 in Example II-2 (6.7 mg, 93.9%); MS m/z: 1450 $[M+H]^+$.

Example II-5: Preparation of Compound B-5

IDC-190 $C_3$

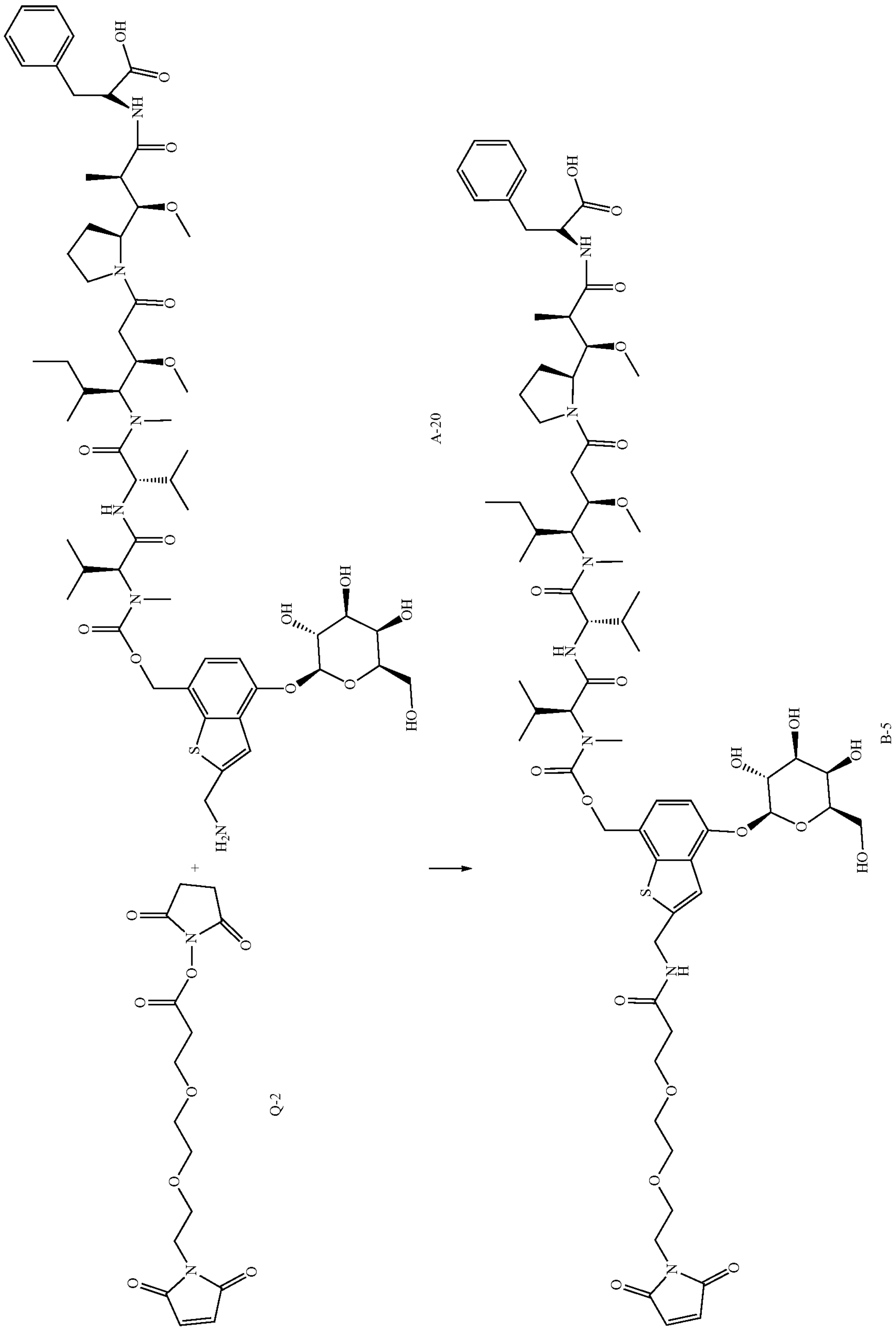
A-20
Q-2
B-5

Compound A-20 (6 mg, 0.0053 mmol) was dissolved in THE (2 mL) under a nitrogen atmosphere at 0° C., and then Linker Q-2 (2 mg, 0.0058 mmol), distilled water (200 μL), DIPEA (10 μL), pyridine (20 μL) were sequentially added dropwise, and the mixture was stirred for 1 hour at room temperature. After completion of the reaction, 2N-hydrochloric acid aqueous solution (20 L) was added, and the reaction solution was diluted with ACN (2 mL) containing 0.1% formic acid, separated and purified using Preparative-HPLC, and then freeze-dried to obtain Compound B-5 (5.6 mg, 77.7%); MS m/z: 1369 $[M+H]^+$.

Example II-6: Preparation of Compound B-6

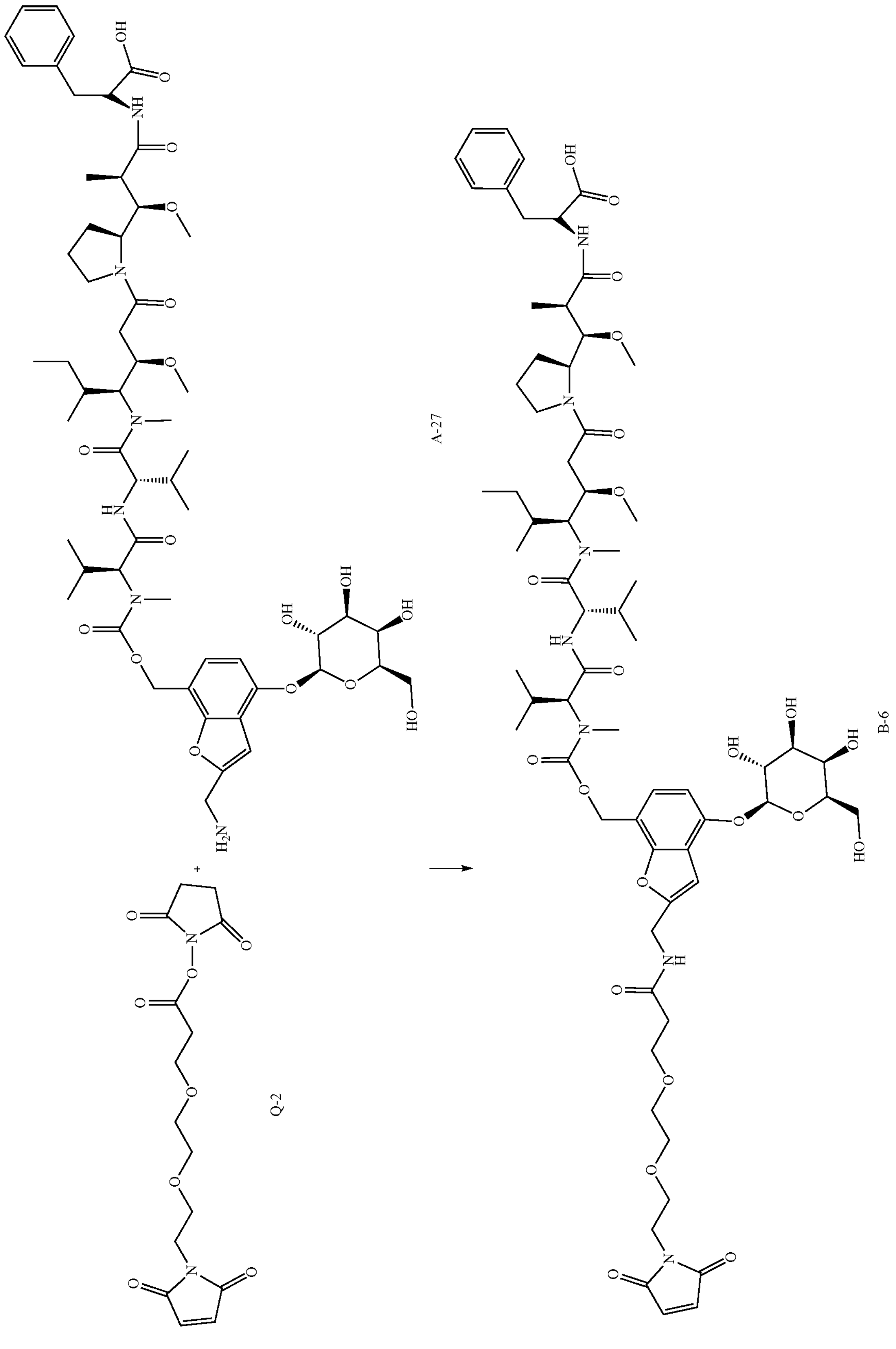
A-27
Q-2
B-6

Compound B-6 was obtained in the same manner as in Example II-5, except that Compound A-27 was used instead of Compound A-20 in Example II-5, and the addition of pyridine was omitted (4 mg, 54.9 0%); MS m/z: 1352 $[M+H]^+$.

Example II-7: Preparation of Compound B-7

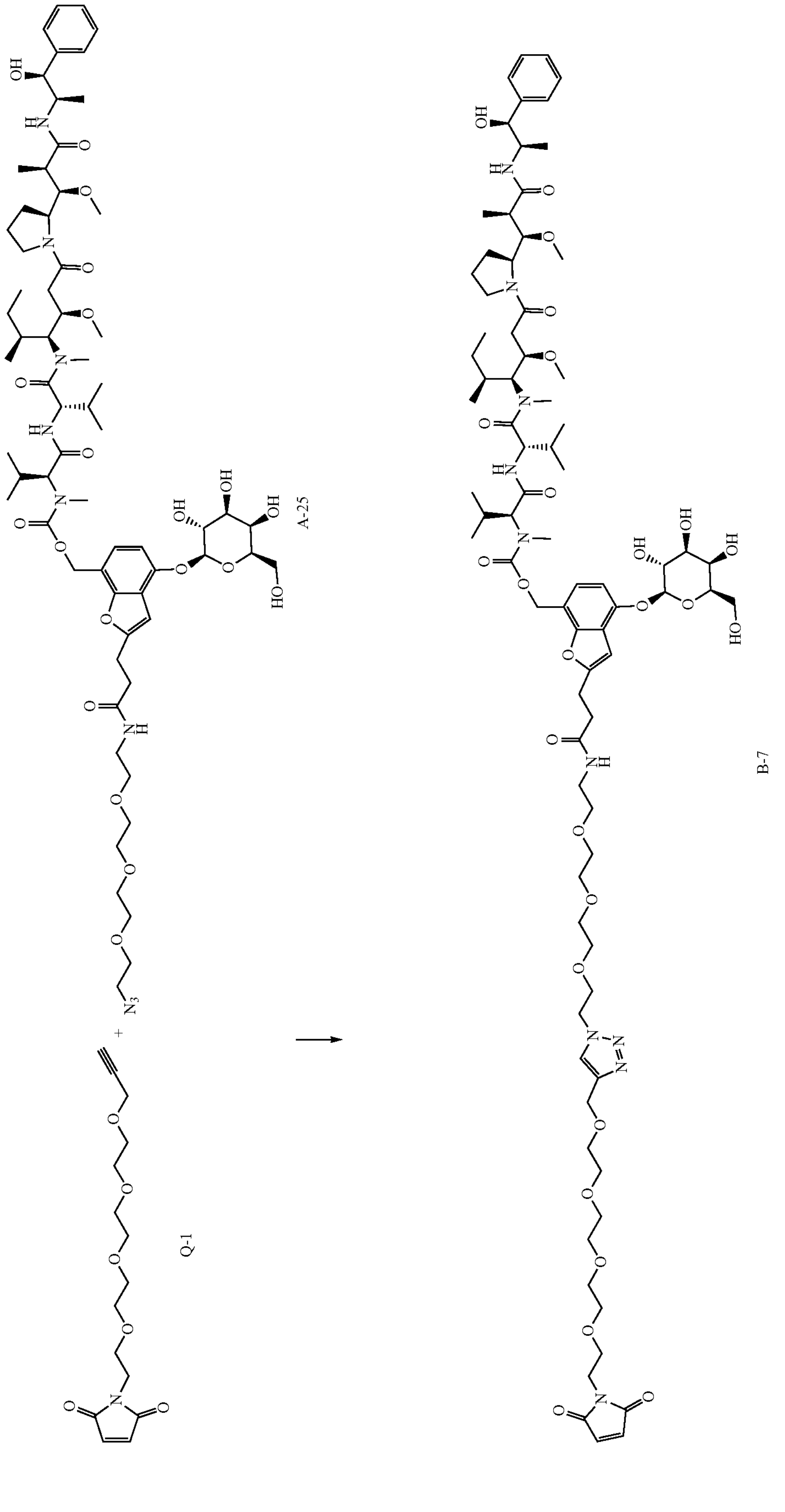
A-25
Q-1
B-7

Compound B-7 was obtained in the form of a white solid in the same manner as in Example II-2, except that Compound A-25 was used instead of Compound A-15 in Example II-2 (4.6 mg, 71.8%); MS m/z: 1654 [M+H]+

Example II-8: Preparation of Compound B-8

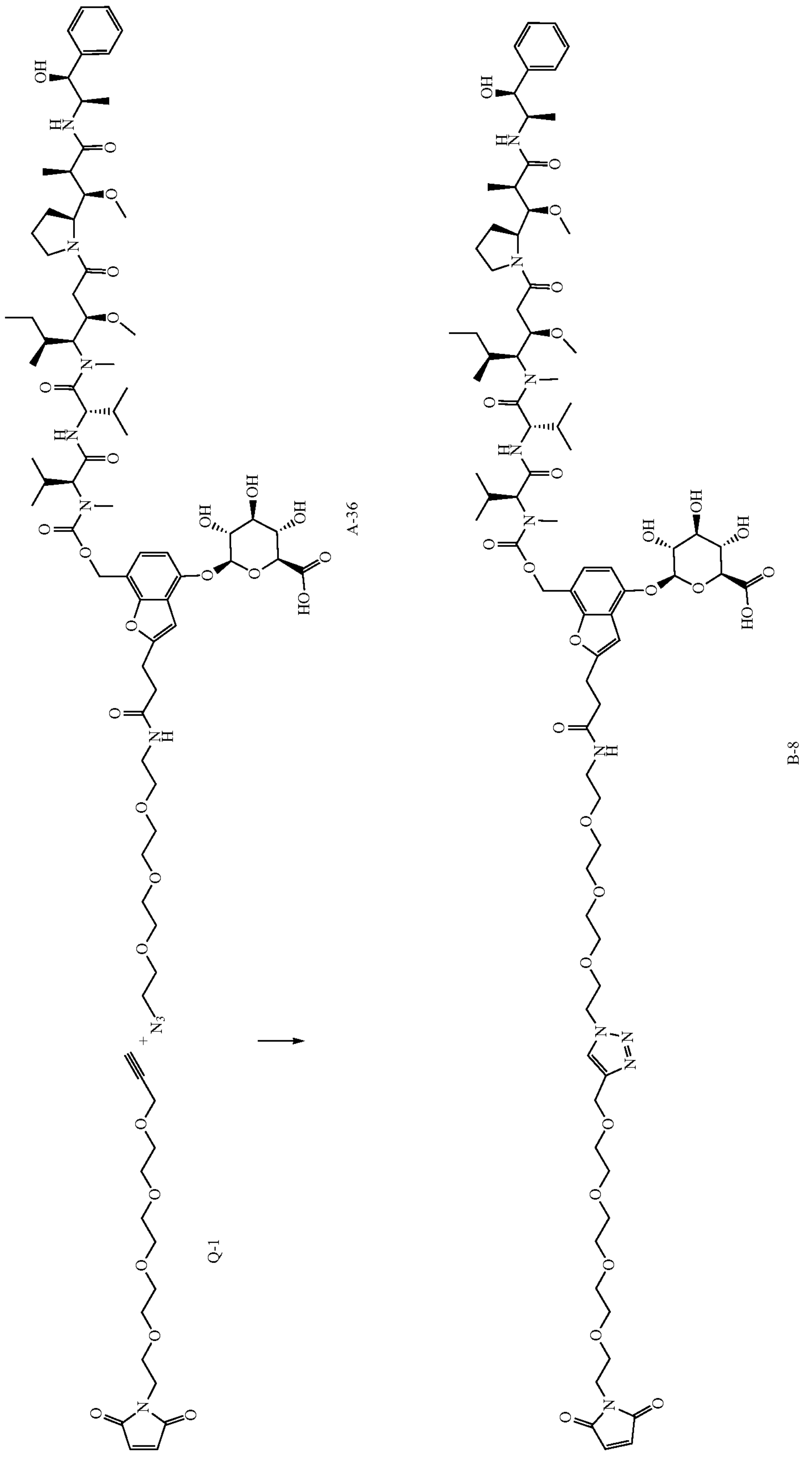
A-36
Q-1
B-8

Compound B-8 was obtained in the form of a white solid in the same manner as in Example II-2, except that Compound A-36 was used instead of Compound A-15 in Example II-2 (4.8 mg, 71%); MS m/z: 1668 $[M+H]^+$.

Example II-9: Preparation of Compound B-9

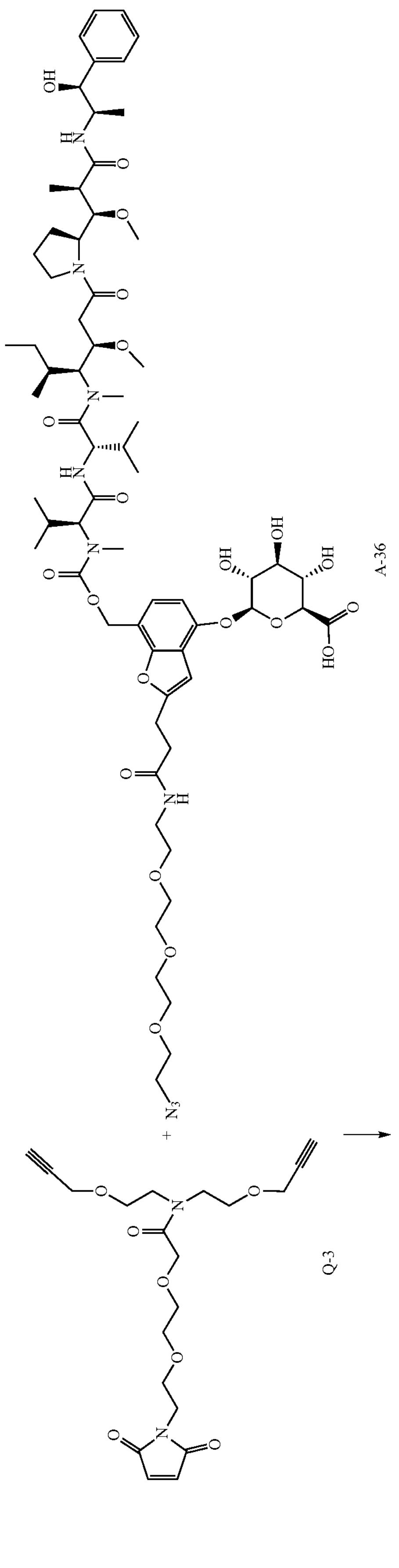
A-36
Q-3

-continued
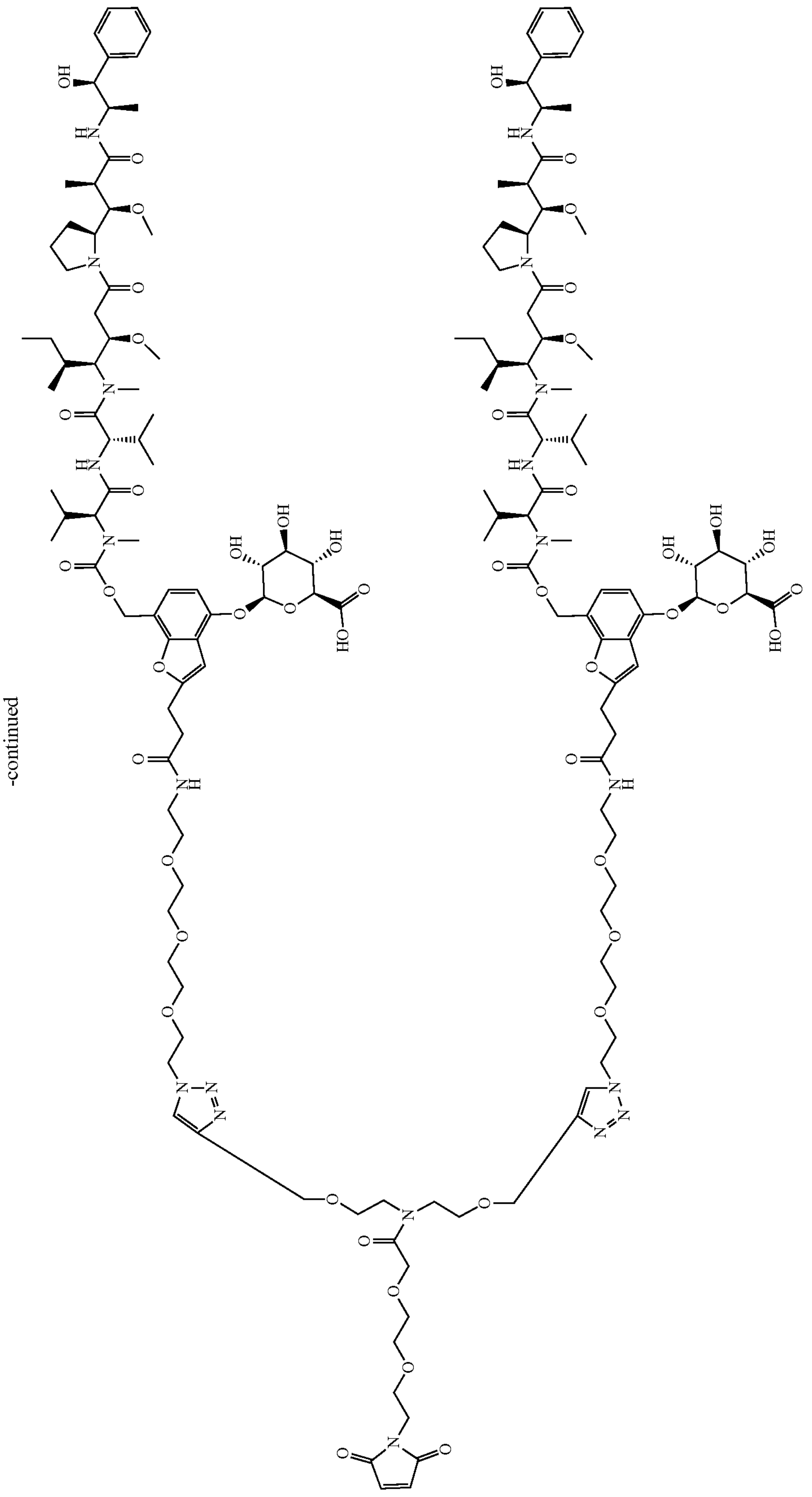
B-9

Compound B-9 was obtained in the form of a white solid in the same manner as in Example II-2, except that Linker Q-3 was used instead of Linker Q-1, and Compound A-36 was used instead of Compound A-15 in Example II-2 (5.6 mg, 73%); MS m/z: 3120 $[M+H]^+$.

Example II-10: Preparation of Compound B-10

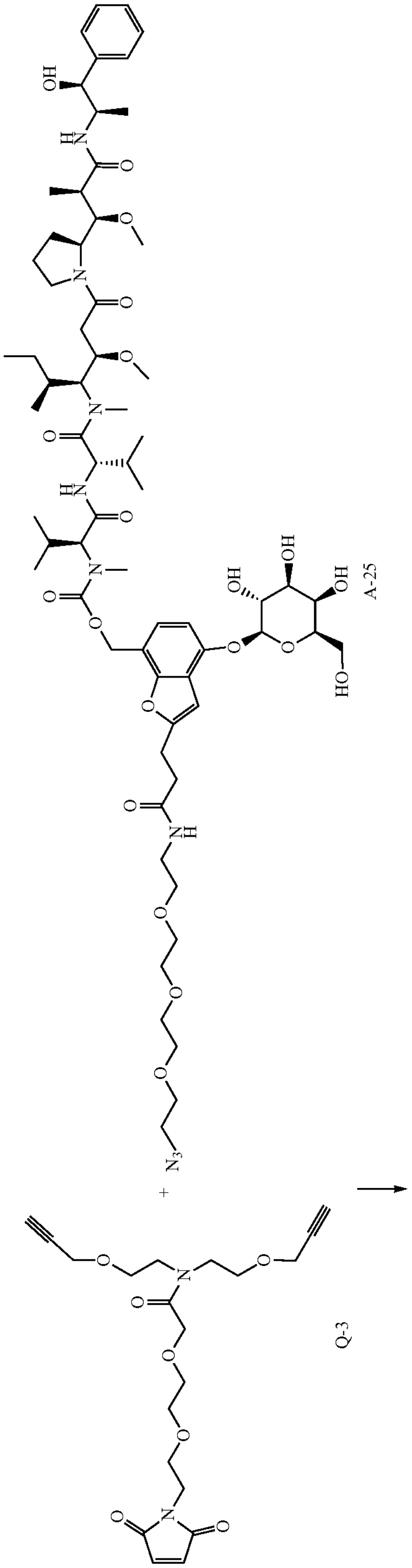
A-25
Q-3

-continued
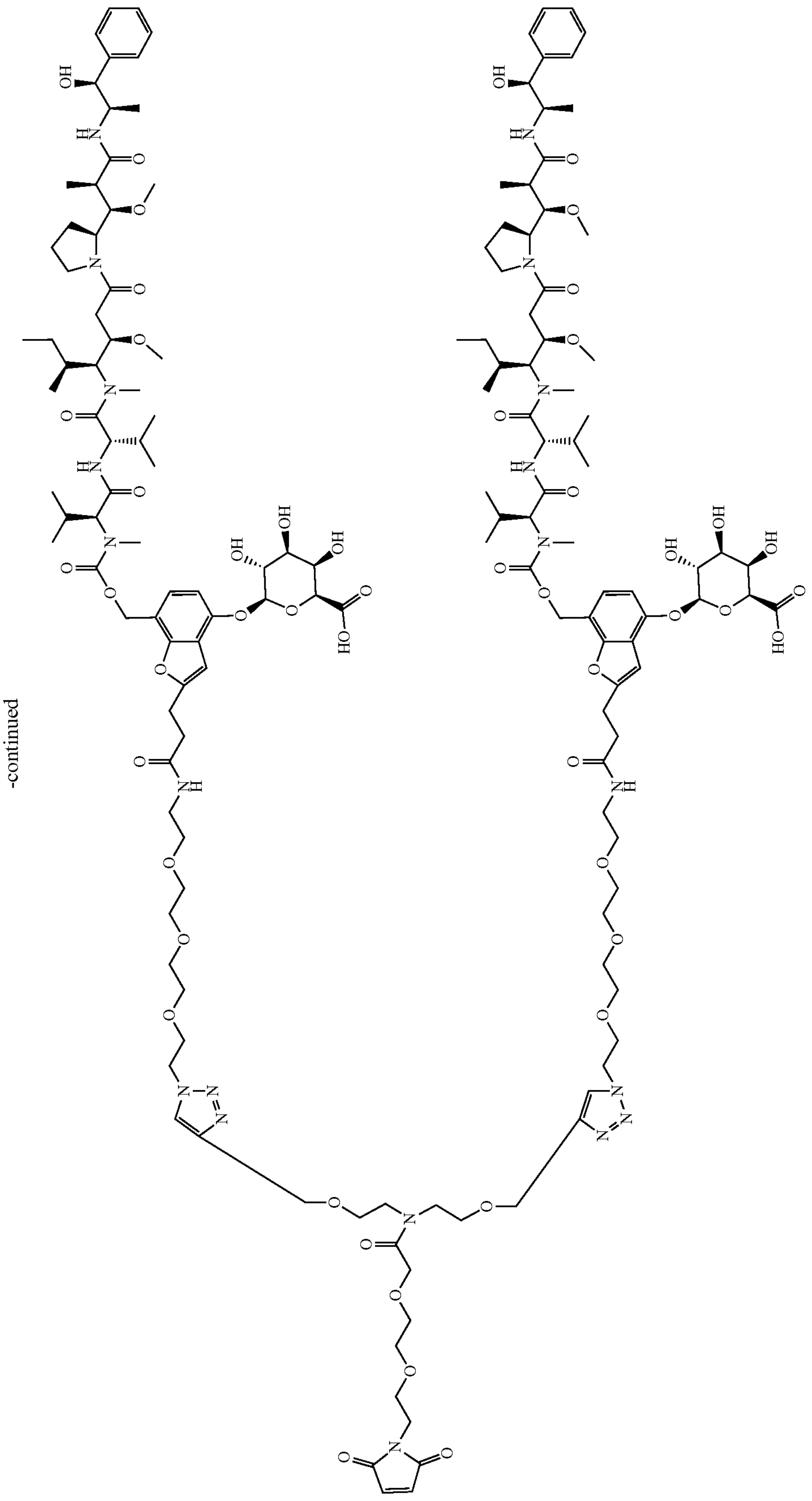
B-10

Compound B-10 was obtained in the form of a white solid in the same manner as in Example II-2, except that Linker Q-3 was used instead of Linker Q-1, and Compound A-25 was used instead of Compound A-15 in Example II-2 (6.9 mg, 90%); MS m/z: 3092 $[M+H]^+$.

Example II-11: Preparation of Compound B-11

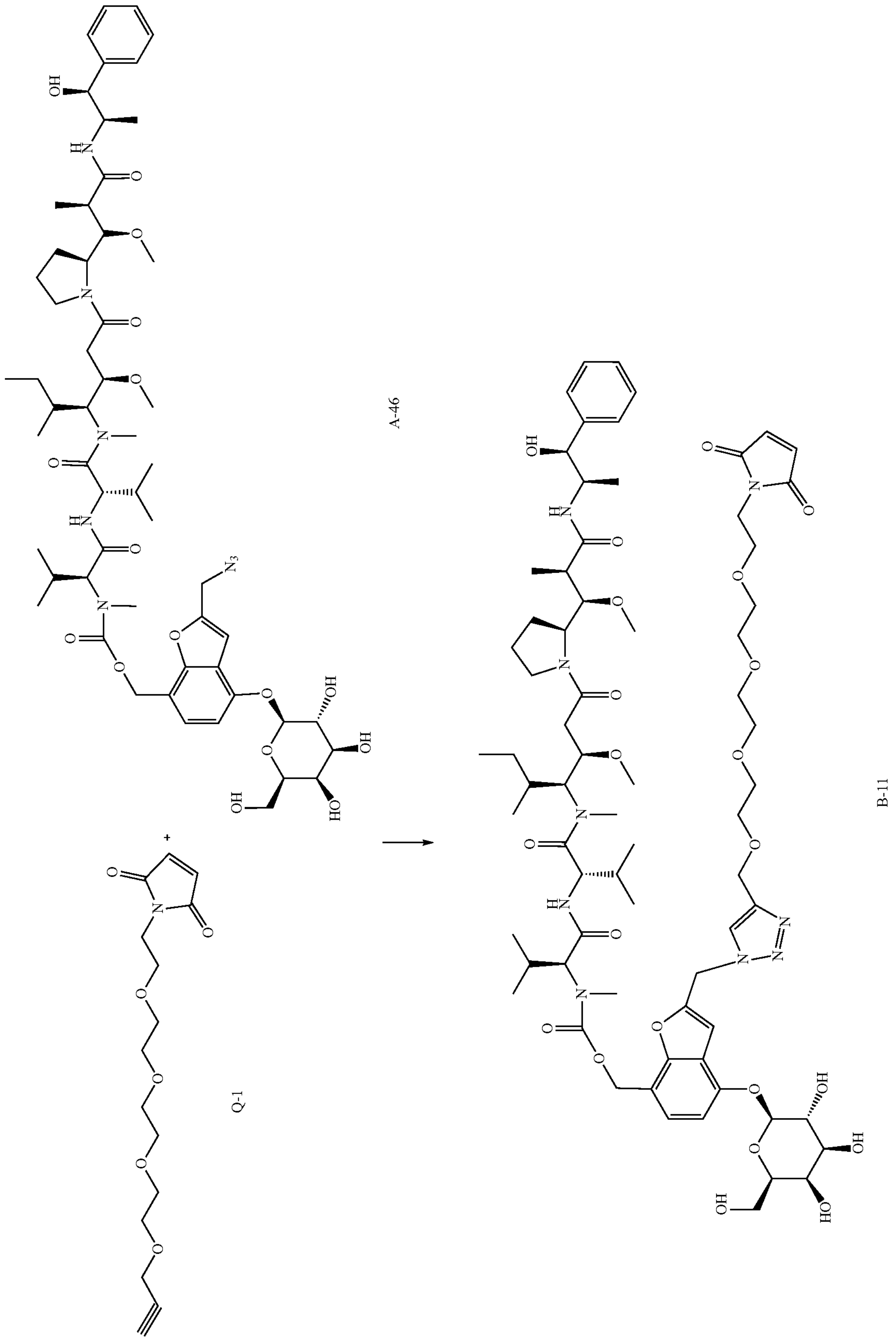
A-46
Q-1
B-11

Compound A-46 (4.2 mg, 0.0037 mmol) was dissolved in DMSO (200 μL) under a nitrogen atmosphere at 0° C., and then 100 μL of a solution of Linker Q-1 (7 mg) dissolved in DMSO (0.5 mL) was taken and added to the reaction. Additionally, distilled water (2 mL), copper (II) sulfate pentahydrate ($CuSO_4 \cdot 5H_2O$, 1 mg) and sodium ascorbate (1.3 mg) were sequentially added to the reaction solution, and then the mixture was stirred at room temperature for 30 minutes. After completion of the reaction, the reaction solution was diluted with distilled water (1 mL) and ACN (1 mL), separated and purified using Preparative-HPLC, and then freeze-dried to obtain Compound B-11 in the form of a white solid (4.8 mg, 89.5%); MS m/z: 1436 $[M+H]^+$ Example II-12: Preparation of Compound B-12

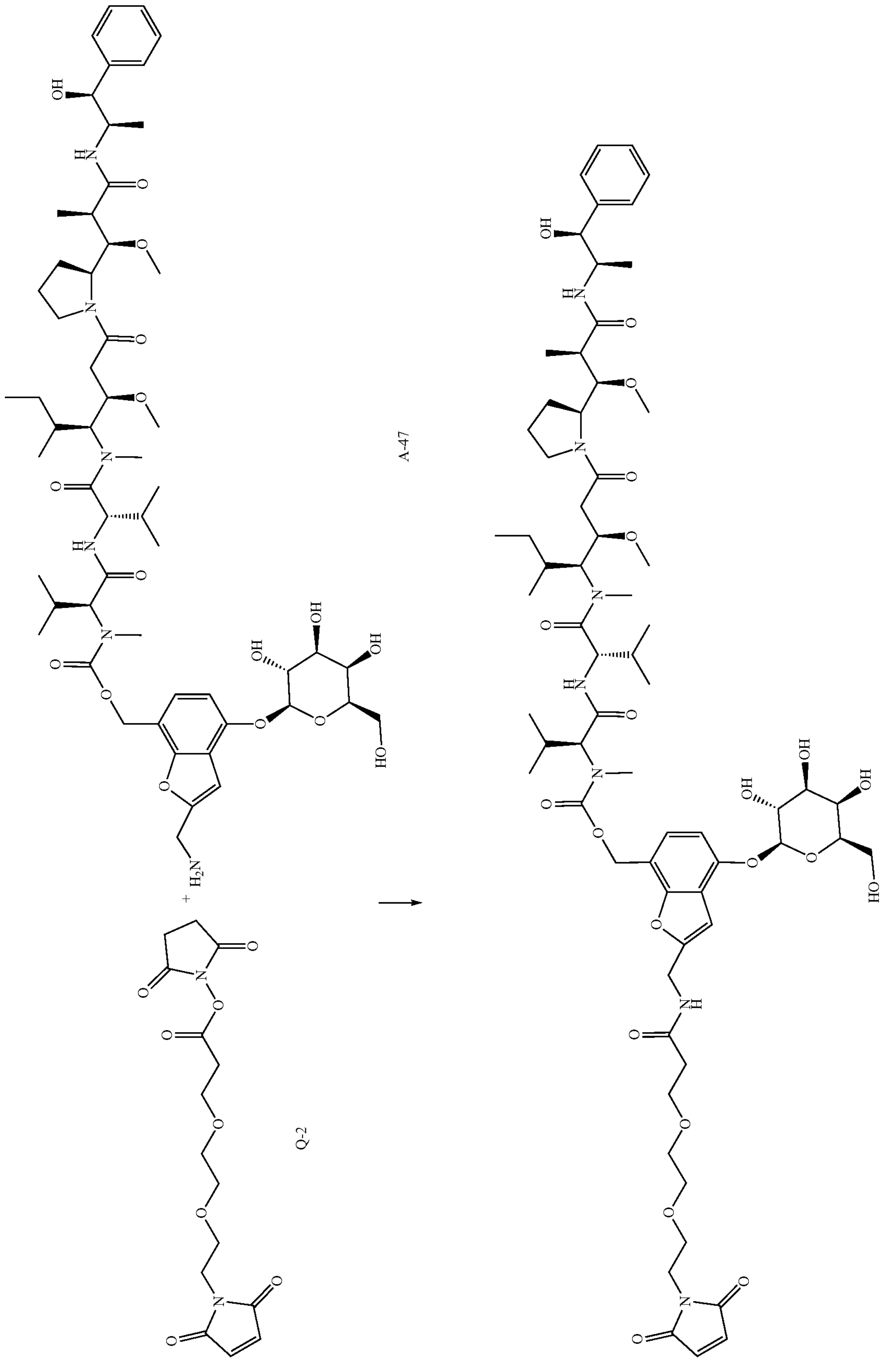
A-47
Q-2
B-12

Compound A-47 (3.1 mg, 0.0028 mmol) was dissolved in THE (2 mL) under a nitrogen atmosphere at 0° C., and then Linker Q-2 (1.5 mg, 0.0042 mmol), distilled water (100 μL) and DIPEA (5 μL) were sequentially added dropwise, and the mixture was stirred for 1 hour at room temperature. After completion of the reaction, the reaction solution was diluted with ACN (1 mL) containing 0.1% formic acid and distilled water (1 mL), separated and purified using Preparative-HPLC, and then freeze-dried to obtain Compound B-12 (2.4 mg, 63.6%); MS m/z: 1338 $[M+H]^+$.

Example II-13: Preparation of Compound B-13

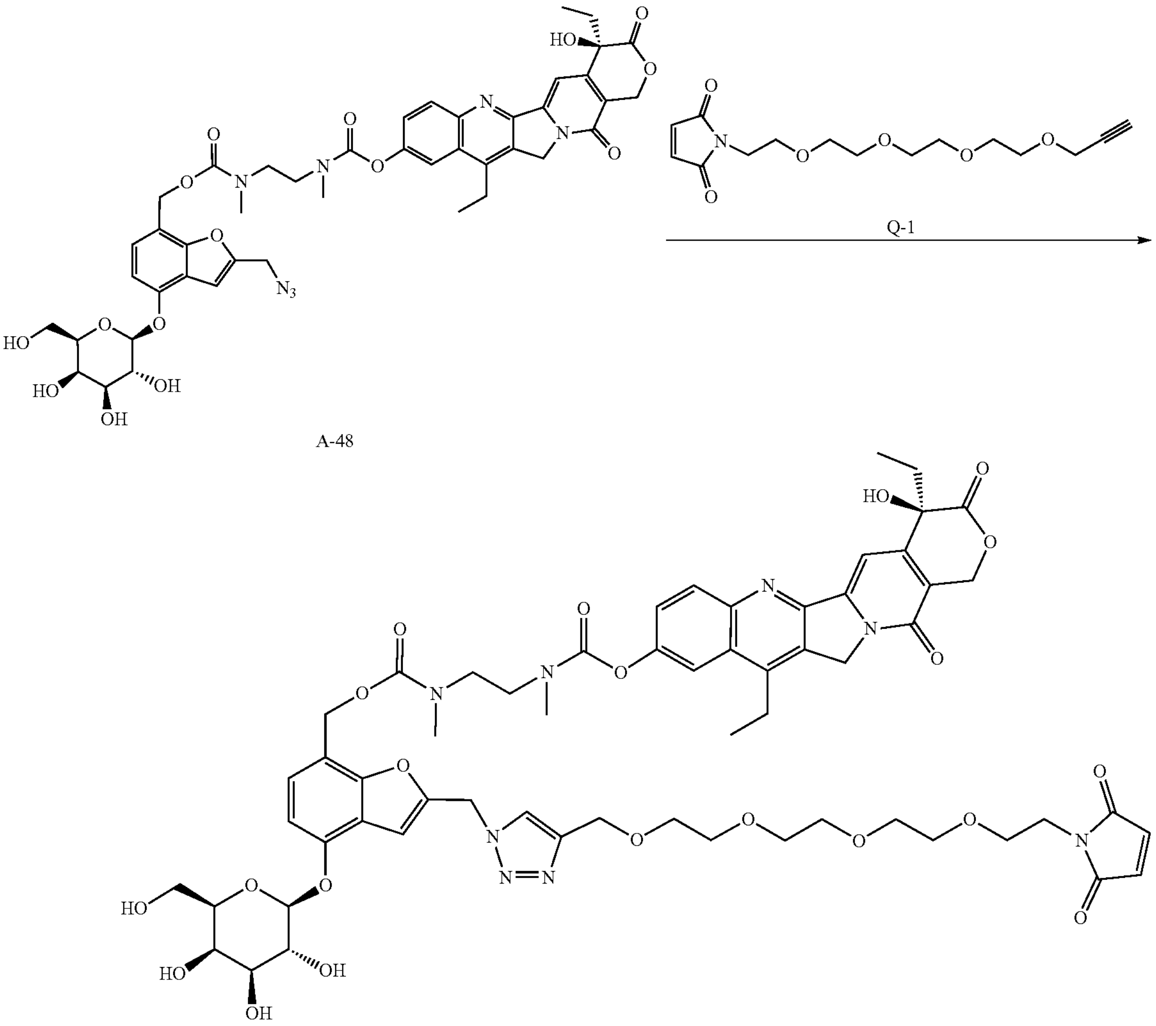

A-48

B-13

Compound A-48 (3.6 mg, 0.0039 mmol) was dissolved in DMSO (400.0 μL) under a nitrogen atmosphere at 0° C., and then 135 μL of a solution of Linker Q-1 (2.0 mg) dissolved in DMSO (200.0 μL) was taken and added to the reaction. Additionally, distilled water (2.0 mL), copper (II) sulfate pentahydrate ($CuSO_4 \cdot 5H_2O$, 1.0 mg) and sodium ascorbate (1.3 mg) were sequentially added to the reaction solution, and then the mixture was stirred at room temperature for 30 minutes. After completion of the reaction, the reaction solution was diluted with distilled water (1.0 mL), separated and purified using Preparative-HPLC, and then freeze-dried to obtain Compound B-13 in the form of a white solid (2.9 mg, 60%); EI-MS m/z: 1225 $[M]^+$, 613$[1/2\ M+H]^+$.

Example II-14: Preparation of Compound B-14

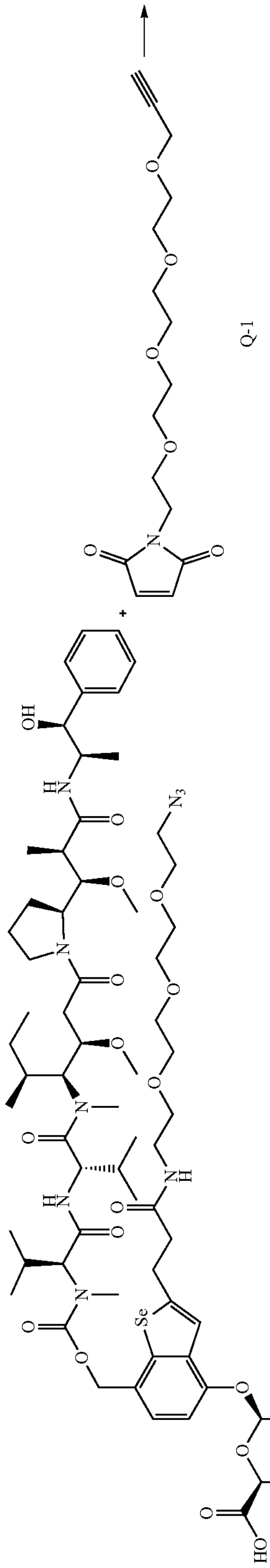
A-49
Q-1
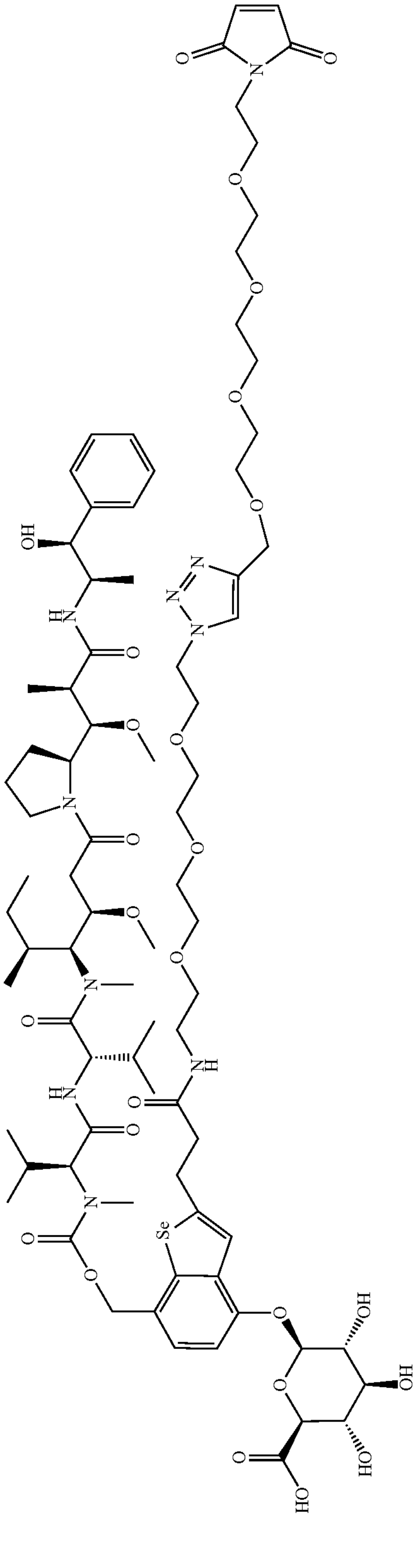
B-14

Compound A-49 (5.9 mg, 0.0041 mmol) was dissolved in DMSO (200 μL) under a nitrogen atmosphere at 0° C., and then 140 μL of a solution of Linker Q-1 (2.6 mg) dissolved in DMSO (0.26 mL) was taken and added to the reaction. Additionally, distilled water (2 mL), DMSO (1.8 mL), copper (II) sulfate pentahydrate ($CuSO_4 \cdot 5H_2O$, 1.14 mg) and sodium ascorbate (1.64 mg) were sequentially added to the reaction solution, and then the mixture was stirred at room temperature for 15 minutes. After completion of the reaction, the reaction solution was diluted with distilled water (2 mL), separated and purified using Preparative-HPLC, and then freeze-dried to obtain Compound B-14 in the form of a white solid (6.9 mg, 96%); EI-MS m/z: 1731 $[M+H]^+$, 865 1/2 $[M+H]^+$.

Example II-15: Preparation of Compound B-15

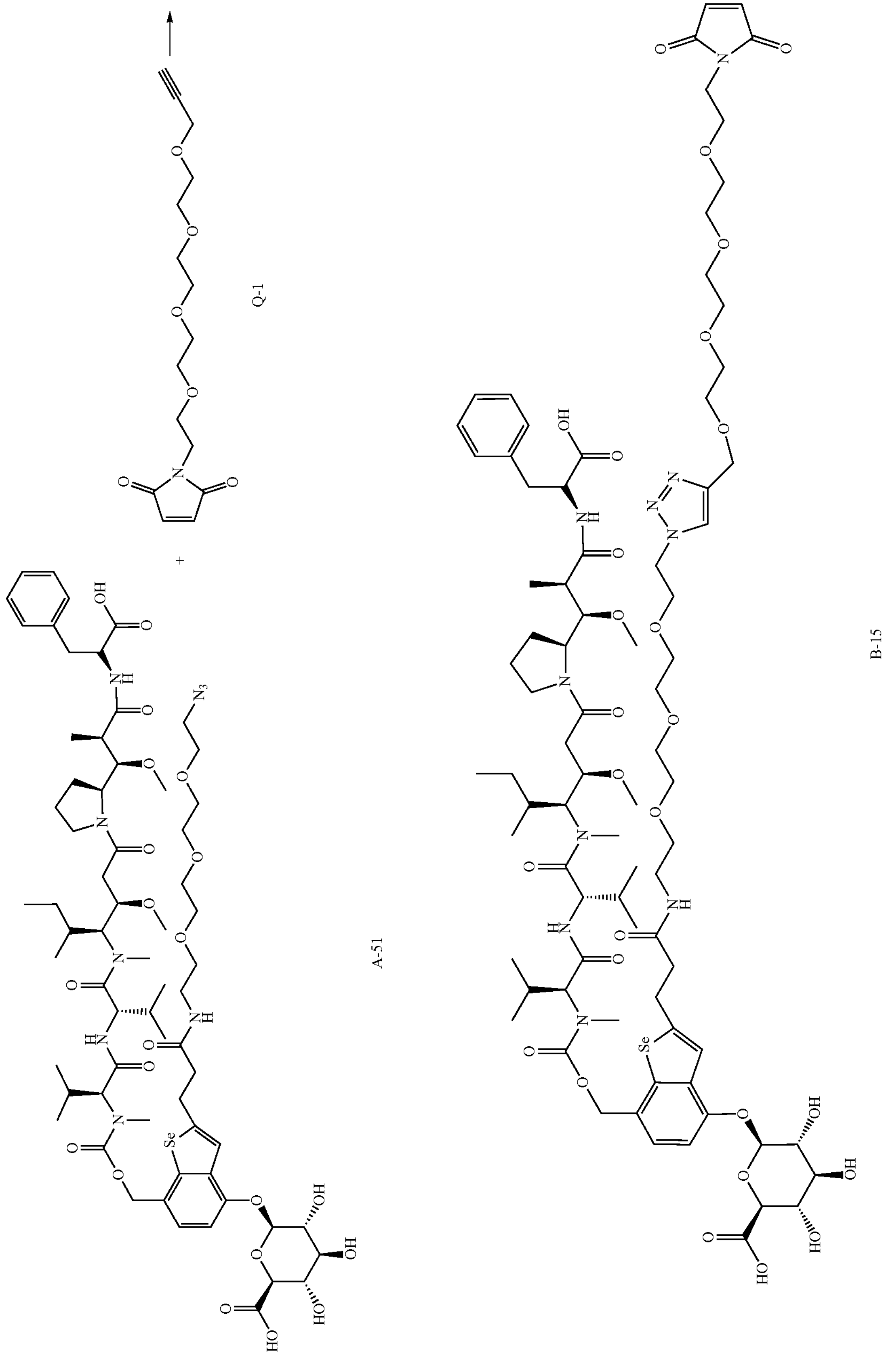
A-51
Q-1
B-15

Compound A-51 (5.7 mg, 0.004 mmol) was dissolved in DMSO (200 μL) under a nitrogen atmosphere at 0° C., and then 140 μL of a solution of Linker Q-1 (2.2 mg) dissolved in DMSO (0.22 mL) was taken and added to the reaction. Additionally, distilled water (2 mL), DMSO (1.8 mL), copper (II) sulfate pentahydrate ($CuSO_4 \cdot 5H_2O$, 1.1 mg) and sodium ascorbate (1.57 mg) were sequentially added to the reaction solution, and then the mixture was stirred at room temperature for 30 minutes. After completion of the reaction, the reaction solution was diluted with distilled water (2 mL), separated and purified using Preparative-HPLC, and then freeze-dried to obtain Compound B-15 in the form of a white solid (6.1 mg, 88%); EI-MS m/z: 1745 $[M+H]^+$, 873 1/2 $[M+H]^+$.

Example II-16: Preparation of Compound B-16

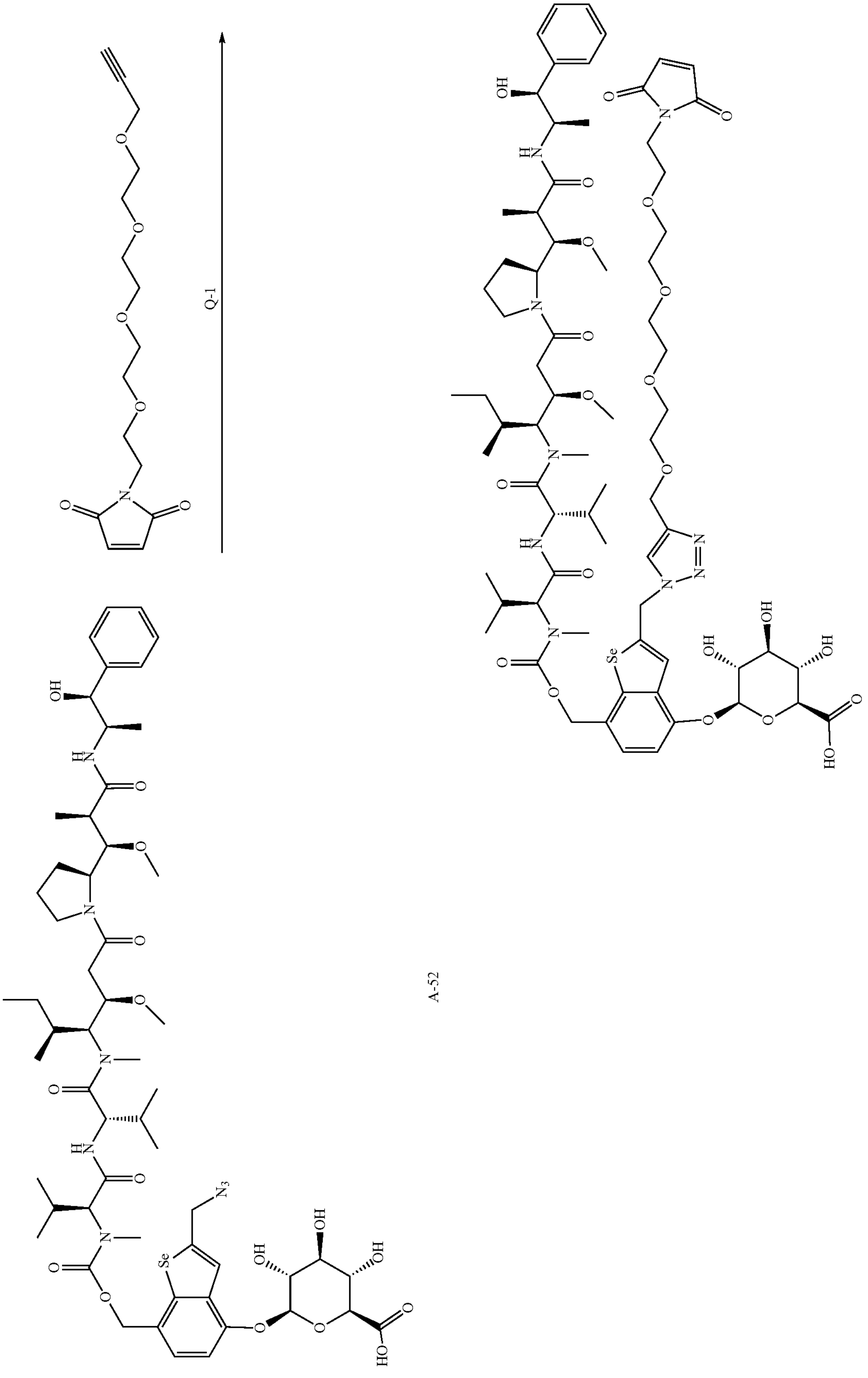
A-52
B-16

Compound A-52 (5.0 mg, 0.0041 mmol) was dissolved in DMSO (2.0 mL) under a nitrogen atmosphere at 0° C., and then 142 μL of a solution of Linker Q-1 (2.0 mg) dissolved in DMSO (200.0 μL) was taken and added to the reaction. Additionally, distilled water (2.0 mL), copper (II) sulfate pentahydrate ($CuSO_4 \cdot 5H_2O$, 1.0 mg) and sodium ascorbate (1.3 mg) were sequentially added to the reaction solution, and then the mixture was stirred at room temperature for 30 minutes. After completion of the reaction, the reaction solution was diluted with distilled water (1.0 mL), separated and purified using Preparative-HPLC, and then freeze-dried to obtain Compound B-16 in the form of a white solid (3.1 mg, 49%); EI-MS m/z: 1514 $[M+H]^+$, 757 1/2 $[M+H]^+$.

Example 11-17: Preparation of Compound B-17

Compound A-53 (5.3 mg, 0.0045 mmol) was dissolved in THE (2.0 mL) under a nitrogen atmosphere at 0° C., and then Linker Q-2 (2.39 mg, 0.0067 mmol), distilled water (200 μL), DIPEA (10.0 μL) and pyridine (20.0 μL) were sequentially added dropwise, and the mixture was stirred for 1 hour at room temperature. After completion of the reaction, 2N-hydrochloric acid aqueous solution (20.0 μL) was added, and the reaction solution was diluted with ACN (2.0 mL) containing 0.1% formic acid, separated and purified using Preparative-HPLC, and then freeze-dried to obtain Compound B-17 in the form of a white solid (3.5 mg, 54.9%); EI-MS m/z: 1416 $[M+H]^+$, 708 1/2 $[M+H]^+$.

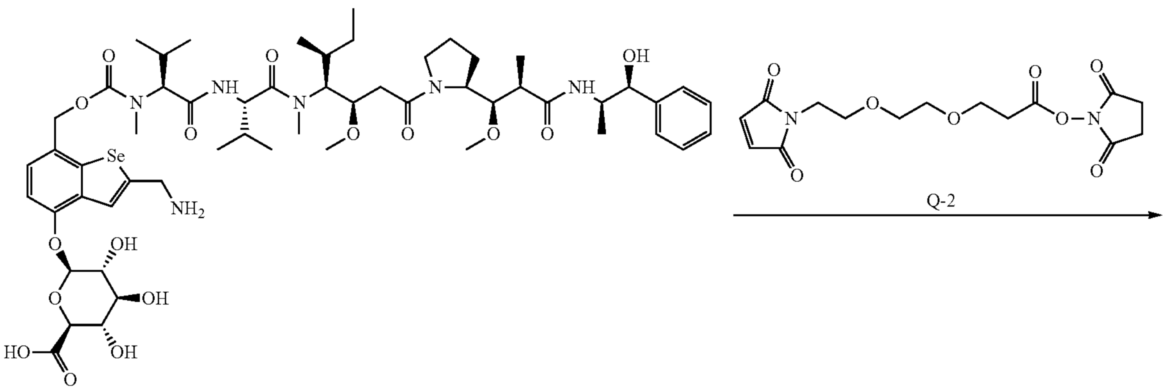

A-53

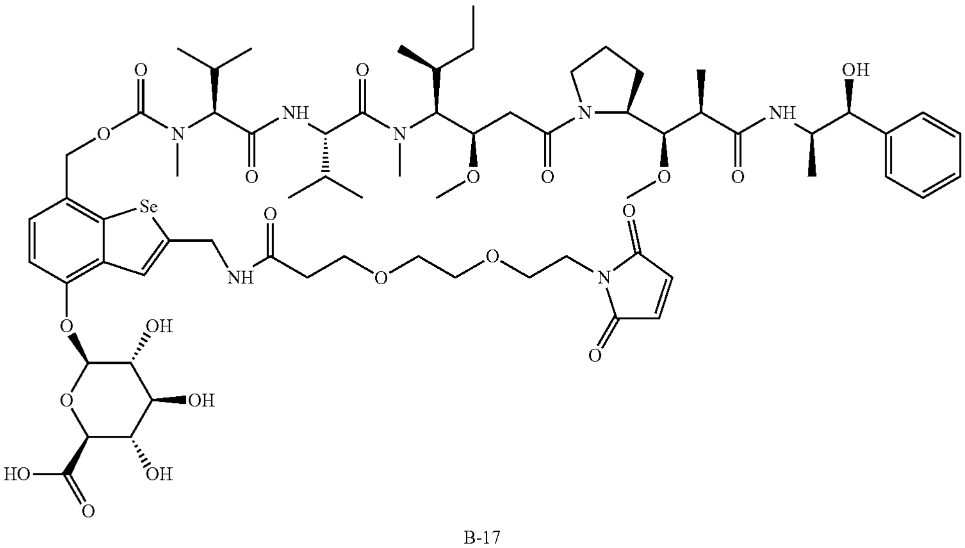

B-17

Example 11-18: Preparation of Compound B-18

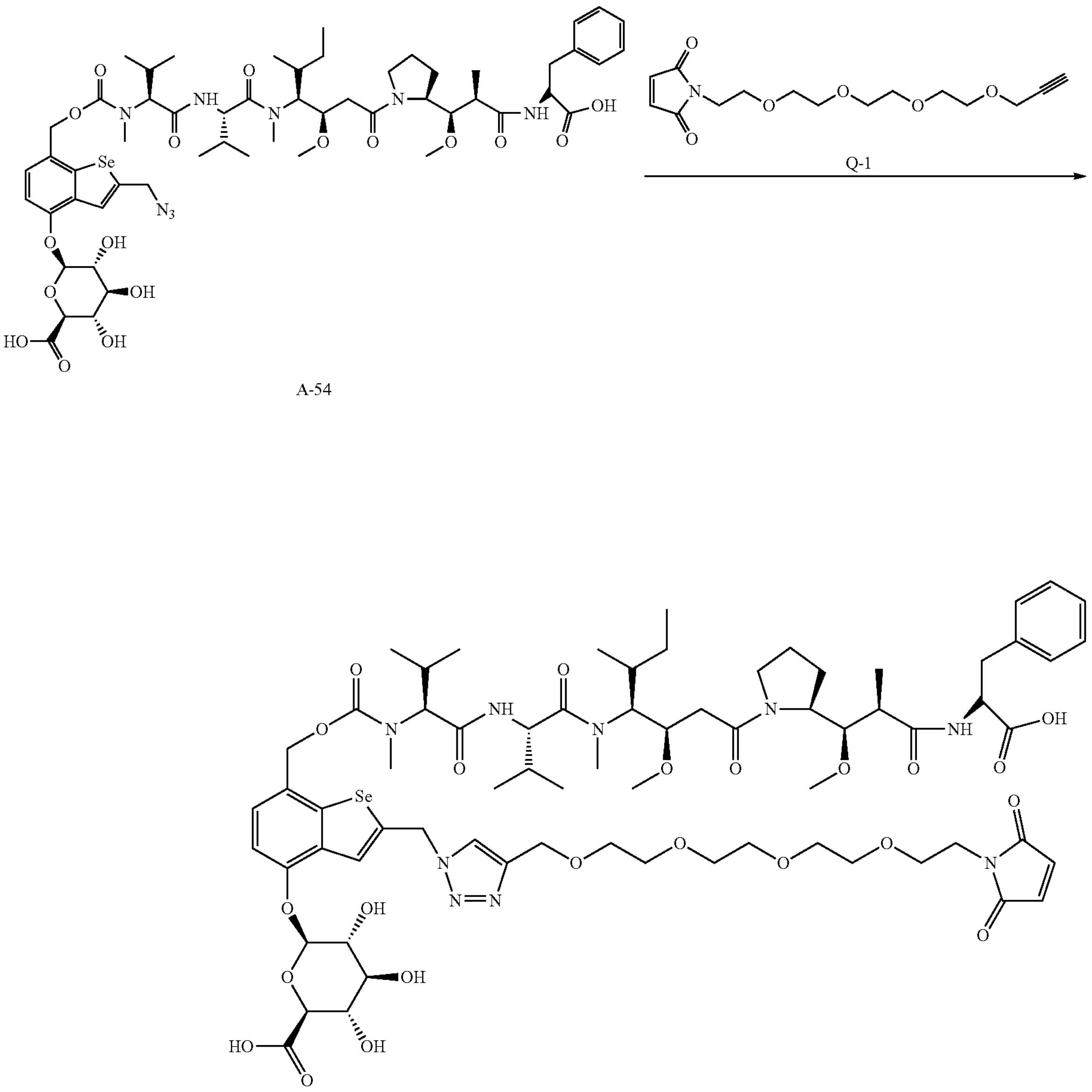

A-54

Q-1

B-18

Compound A-54 (7.1 mg, 0.0041 mmol) was dissolved in DMSO (2.0 mL) under a nitrogen atmosphere at 0° C., and then 199.0 μL of a solution of Linker Q-1 (2.0 mg) dissolved in DMSO (200.0 μL) was taken and added to the reaction. Additionally, distilled water (2.0 mL), copper (II) sulfate pentahydrate ($CuSO_4 \cdot 5H_2O$, 1.0 mg) and sodium ascorbate (1.3 mg) were sequentially added to the reaction solution, and then the mixture was stirred at room temperature for 30 minutes. After completion of the reaction, the reaction solution was diluted with distilled water (1.0 mL), separated and purified using Preparative-HPLC, and then freeze-dried to obtain Compound B-18 in the form of a white solid (3.1 mg, 49%); EI-MS m/z: 1528 $[M+H]^+$, 764 1/2 $[M+H]^+$.

Example II-19: Preparation of Compound B-19

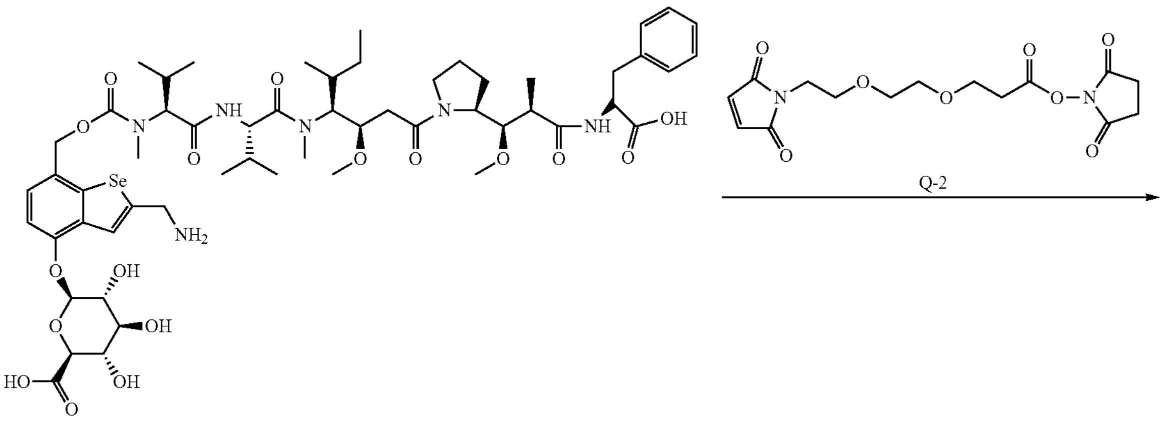

A-55

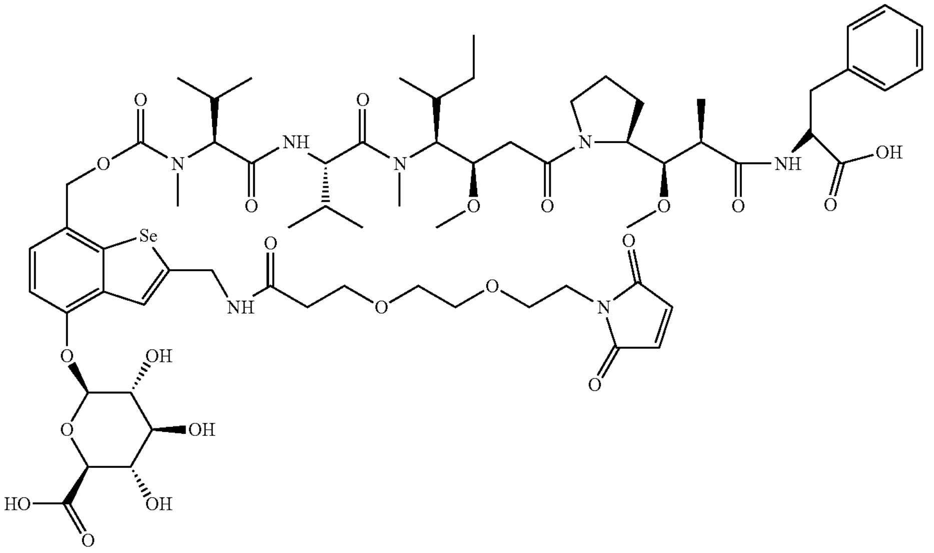

B-19

Compound A-55 (4.4 mg, 0.0037 mmol) was dissolved in THF (2.0 mL) under a nitrogen atmosphere at 0° C., and then Linker Q-2 (1.96 mg, 0.0055 mmol), distilled water (200.0 μL), DIPEA (1030 μL) and pyridine (20.0 μL) were sequentially added dropwise, and the mixture was stirred for 1 hour at room temperature. After completion of the reaction, 2N-hydrochloric acid aqueous solution (20.0 μL) was added, and the reaction solution was diluted with ACN (2.0 mL) containing 0.1% formic acid, separated and purified using Preparative-HPLC, and then freeze-dried to obtain Compound B-19 in the form of a white solid (2.5 mg, 47.3%); EI-MS m/z: 1430 $[M+H]^+$, 715 1/2 $[M+H]^+$.

Example II-20: Preparation of Compound B-20

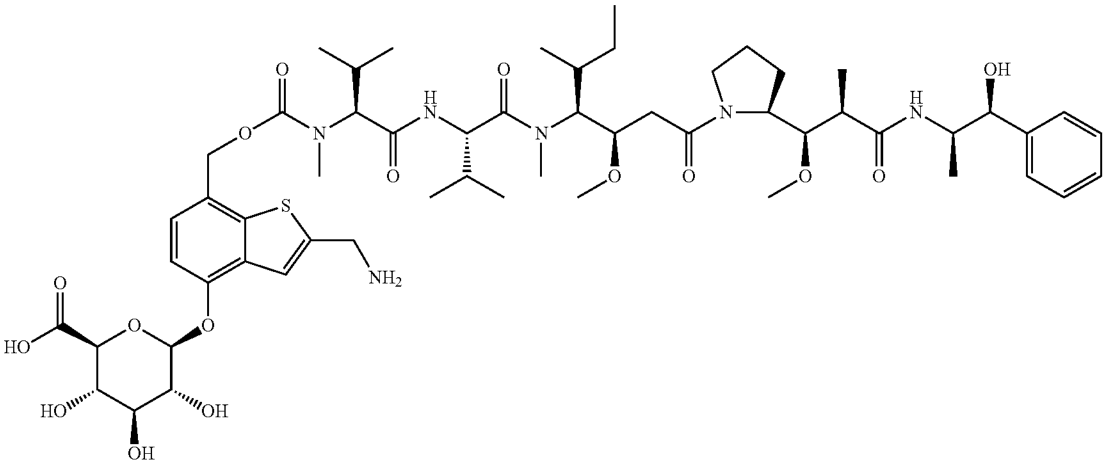

+

A-57

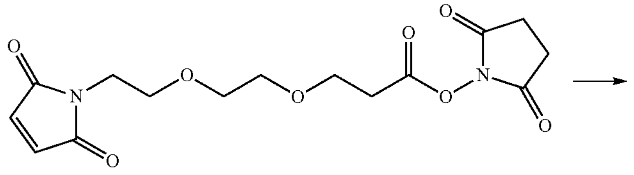

Q-2

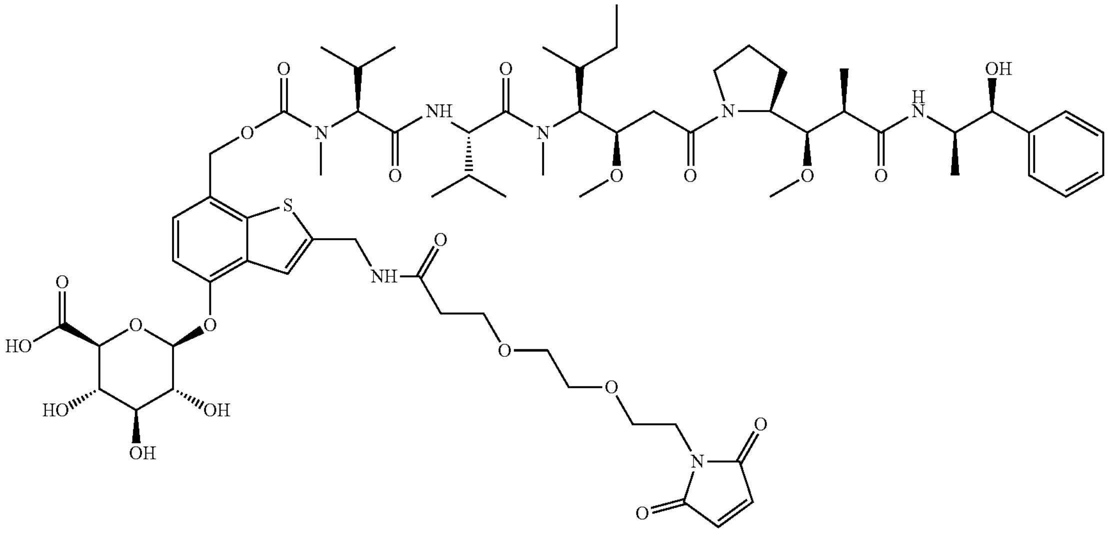

B-20

Compound A-57 (5 mg, 0.0044 mmol) was dissolved in THF (2.5 mL) under a nitrogen atmosphere at room temperature, and then Linker Q-2 (2.9 mg, 0.0082 mmol), distilled water (200 L), DIPEA (10 μL) and pyridine (10 μL) were sequentially added dropwise, and the mixture was stirred for 1.5 hours. After completion of the reaction, the reaction solution was diluted with ACN (2 mL) containing 0.1% formic acid, separated and purified using Preparative-HPLC, and then freeze-dried to obtain Compound B-20 in the form of a white solid (4.2 mg, 69%); MS m/z: 1369 $[M+H]^+$, 684 1/2 $[M+H]^+$.

Example II-21: Preparation of Compound B-21

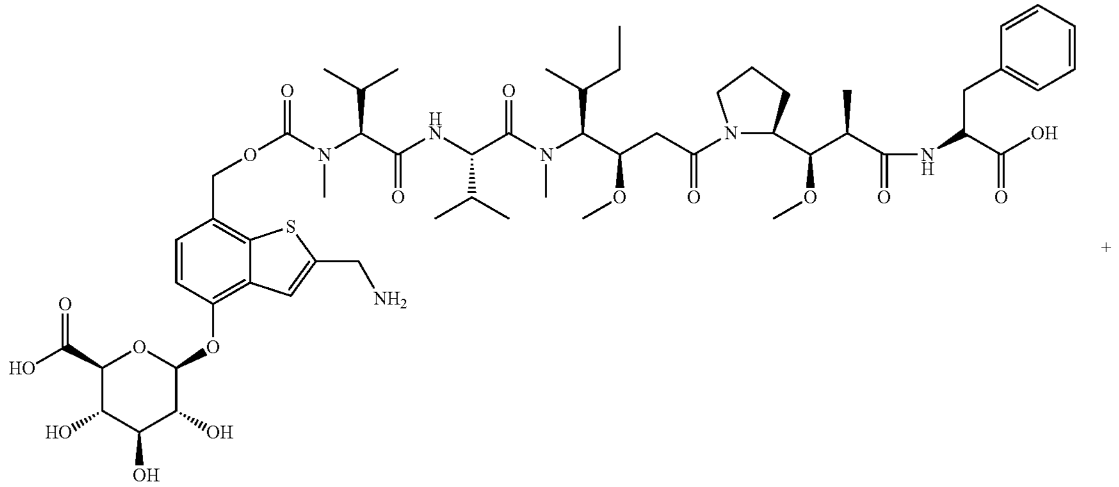

A-59

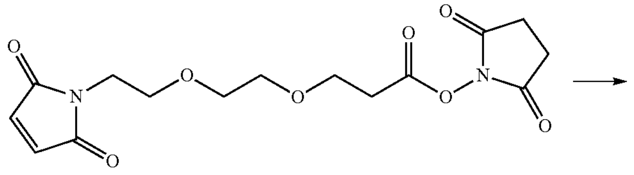

Q-2

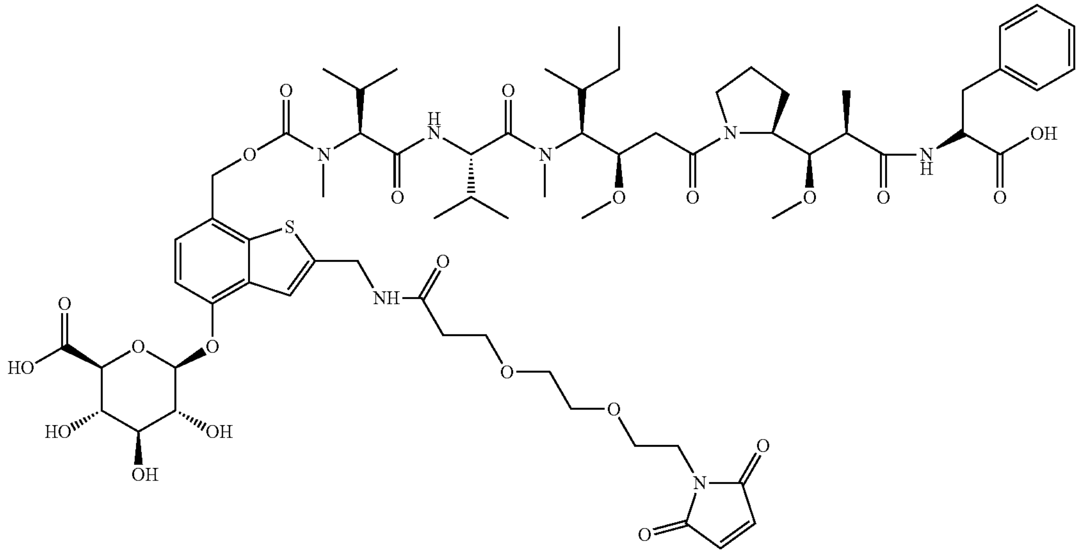

B-21

Compound A-59 (5.1 mg, 0.0045 mmol) was dissolved in THF (2.05 mL) under a nitrogen atmosphere at room temperature, and then Linker Q-2 (2.3 mg, 0.0079 mmol), distilled water (200 L), DIPEA (10 μL) and pyridine (10 μL) were sequentially added dropwise, and the mixture was stirred for 3 hours. After completion of the reaction, the reaction solution was diluted with ACN (2 mL) containing 0.1% formic acid, separated and purified using Preparative-HPLC, and then freeze-dried to obtain Compound B-21 in the form of a white solid (3.5 mg, 57%); MS m/z: 1383 $[M+H]^+$, 691 1/2 $[M+H]^+$.

Example II-22: Preparation of Compound B-22

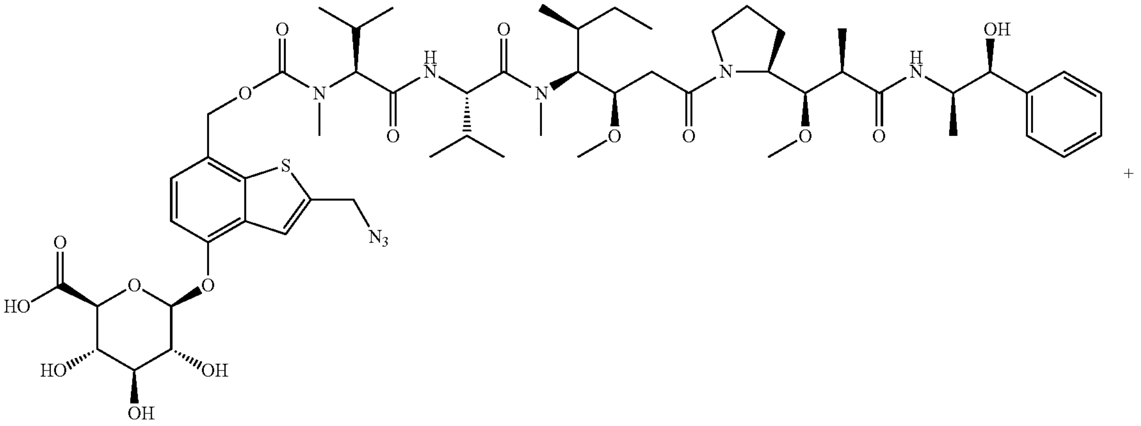

A-56

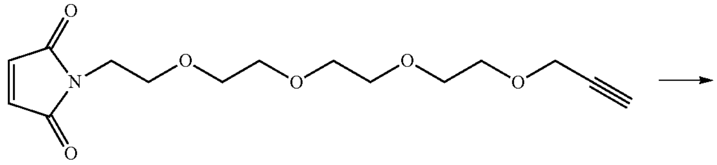

Q-1

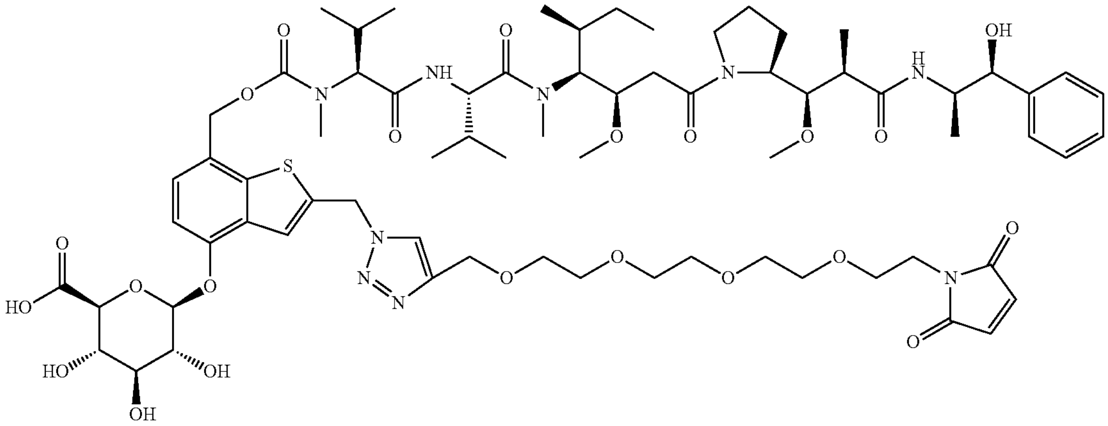

B-22

Compound A-56 (4.9 mg, 0.0042 mmol) was dissolved in DMSO (1 mL) under a nitrogen atmosphere at room temperature, and then a solution of Linker Q-1 (1.5 mg, 0.0048 mmol) dissolved in DMSO (1 mL) was added. Additionally, distilled water (200 μL), copper (II) sulfate pentahydrate ($CuSO_4 \cdot 5H_2O$, 0.74 mg, 0.0046 mmol) and sodium ascorbate (1.5 mg, 0.0085 mmol) were sequentially added to the reaction solution, and then the mixture was stirred for 2.5 hours. After completion of the reaction, the reaction solution was diluted with distilled water (1 mL), separated and purified using Preparative-HPLC, and then freeze-dried to obtain Compound B-22 in the form of a white solid (3.2 mg, 51%); MS m/z: 1467 $[M+H]^+$, 733 1/2 $[M+H]^+$.

Example II-23: Preparation of Compound B-23

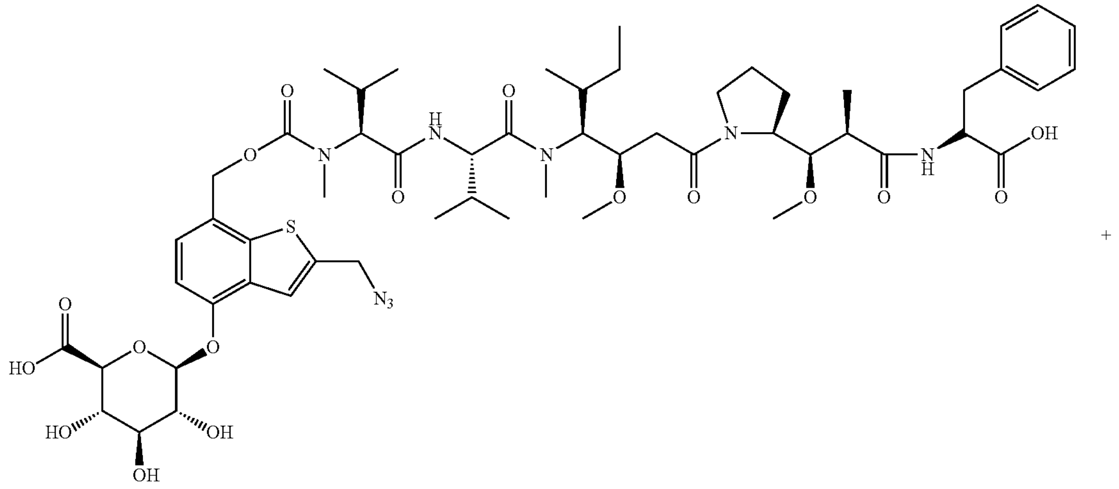

A-58

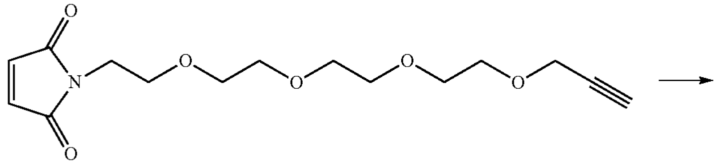

Q-1

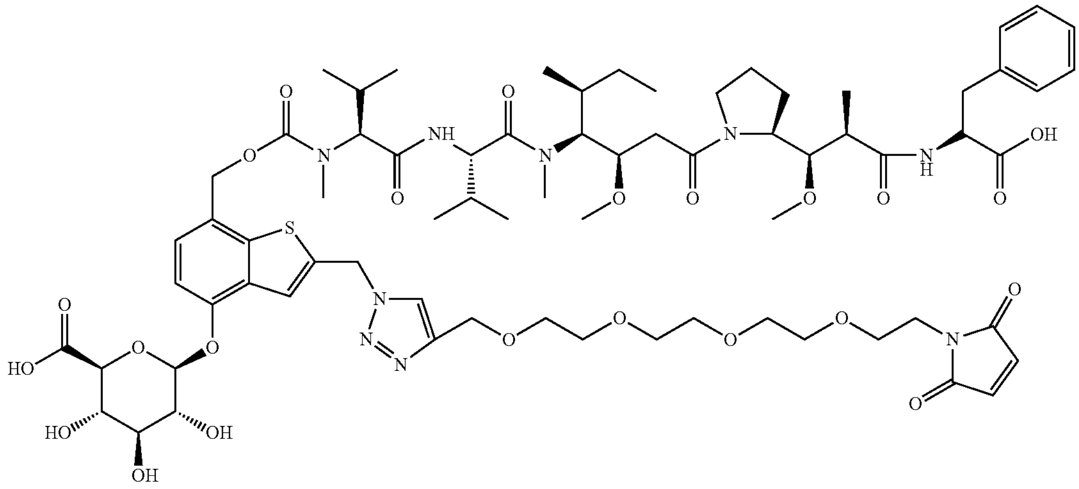

B-23

Compound A-58 (4.8 mg, 0.0041 mmol) was dissolved in DMSO (1 mL) under a nitrogen atmosphere at room temperature, and then a solution of Linker Q-1 (1.4 mg, 0.0045 mmol) dissolved in DMSO (1 mL) was added. Additionally, distilled water (200 μL), copper (II) sulfate pentahydrate ($CuSO_4 \cdot 5H_2O$, 0.72 mg, 0.0045 mmol) and sodium ascorbate (1.4 mg, 0.0079 mmol) were sequentially added to the reaction solution, and then the mixture was stirred for 5 hours. After completion of the reaction, the reaction solution was diluted with distilled water (1 mL), separated and purified using Preparative-HPLC, and then freeze-dried to obtain Compound B-23 in the form of a white solid (3.2 mg, 51%); MS m/z: 1481 $[M+H]^+$, 740 1/2 $[M+H]^+$.

Example II-24: Preparation of Compound B-24

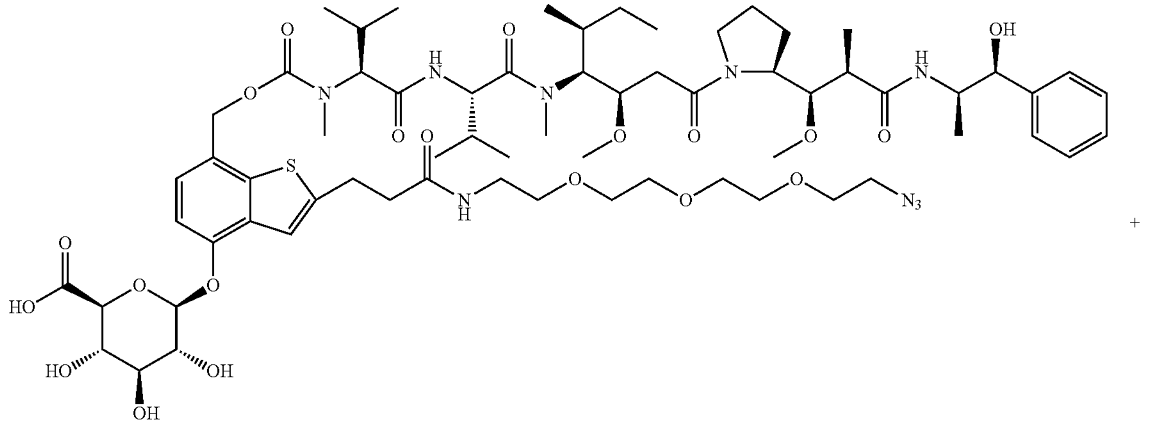

A-60

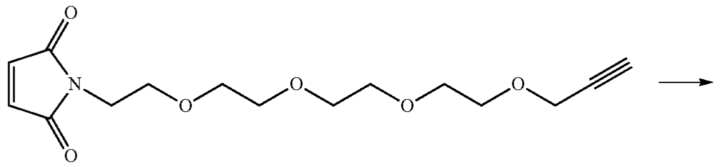

Q-1

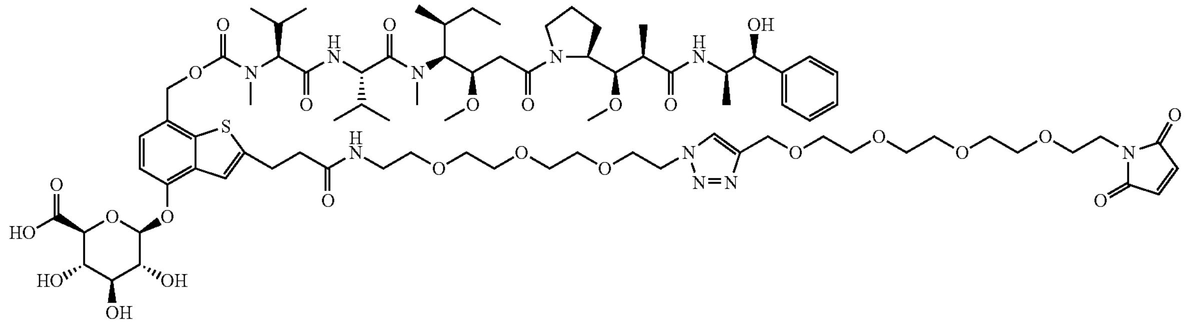

B-24

Compound A-60 (11.1 mg, 0.0081 mmol) was dissolved in DMSO (200 μL) under a nitrogen atmosphere at 0° C., and then 300 μL of a solution of Linker Q-1 (5.7 mg) dissolved in DMSO (0.57 mL) was taken and added to the reaction. Additionally, distilled water (2 mL), copper (II) sulfate pentahydrate ($CuSO_4 \cdot 5H_2O$, 2.22 mg) and sodium ascorbate (3.2 mg) were sequentially added to the reaction solution, and then the mixture was stirred at room temperature for 1.5 hours. After completion of the reaction, the reaction solution was diluted with distilled water (2 mL), separated and purified using Preparative-HPLC, and then freeze-dried to obtain Compound B-24 in the form of a white solid (11.6 mg, 85%); EI-MS m/z: 1683 $[M+H]^+$, 842 1/2 $[M+H]^+$.

Example II-25: Preparation of Compound B-25

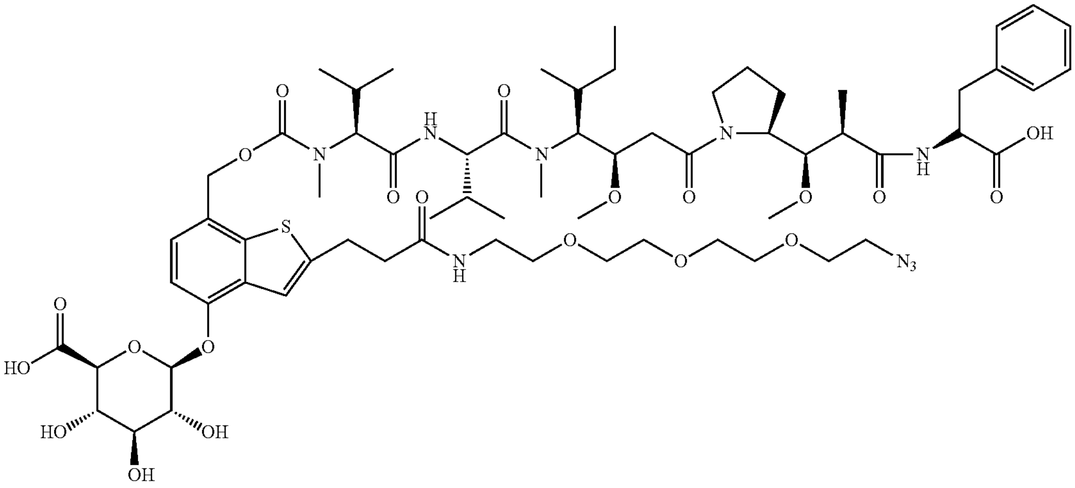

A-61

+

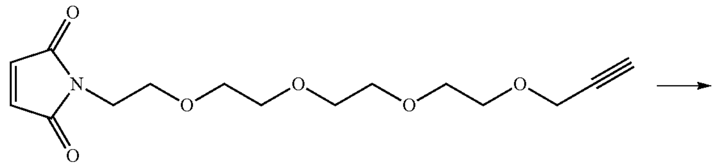

Q-1

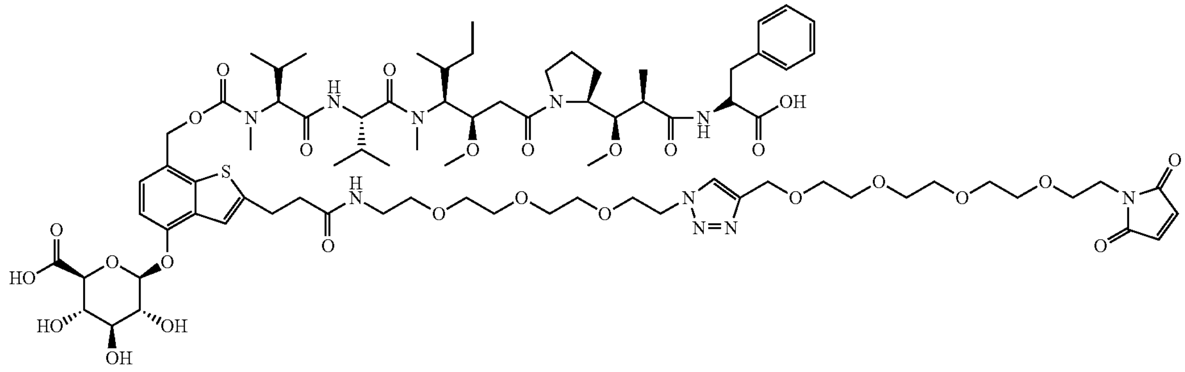

B-25

Compound A-61 (5.1 mg, 0.0037 mmol) was dissolved in DMSO (200 μL) under a nitrogen atmosphere at 0° C., and then 140 μL of a solution of Linker Q-1 (4.2 mg) dissolved in DMSO (0.42 mL) was taken and added to the reaction. Additionally, distilled water (2 mL), DMSO (0.4 mL), copper (II) sulfate pentahydrate ($CuSO_4 \cdot 5H_2O$, 1.01 mg) and sodium ascorbate (1.46 mg) were sequentially added to the reaction solution, and then the mixture was stirred at room temperature for 1.5 hours. After completion of the reaction, the reaction solution was diluted with distilled water (2 mL), separated and purified using Preparative-HPLC, and then freeze-dried to obtain Compound B-25 in the form of a white solid (3.8 mg, 61%); EI-MS m/z: 1697 $[M+H]^+$, 849 1/2 $[M+H]^+$.

Example II-26: Preparation of Compound B-26

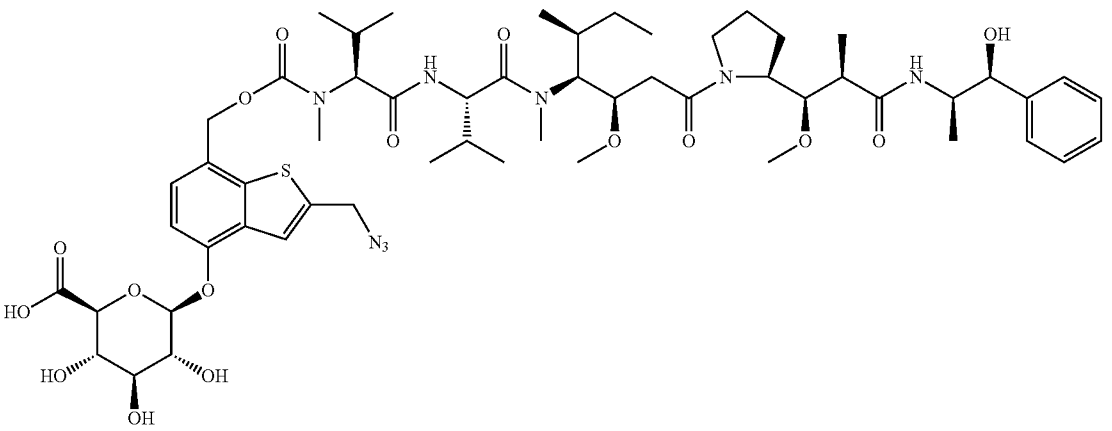

A-64

+

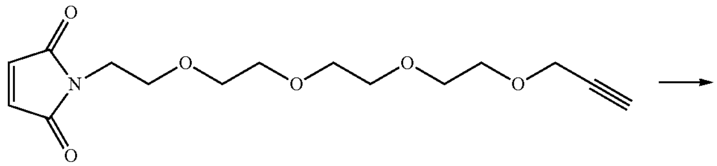

Q-1

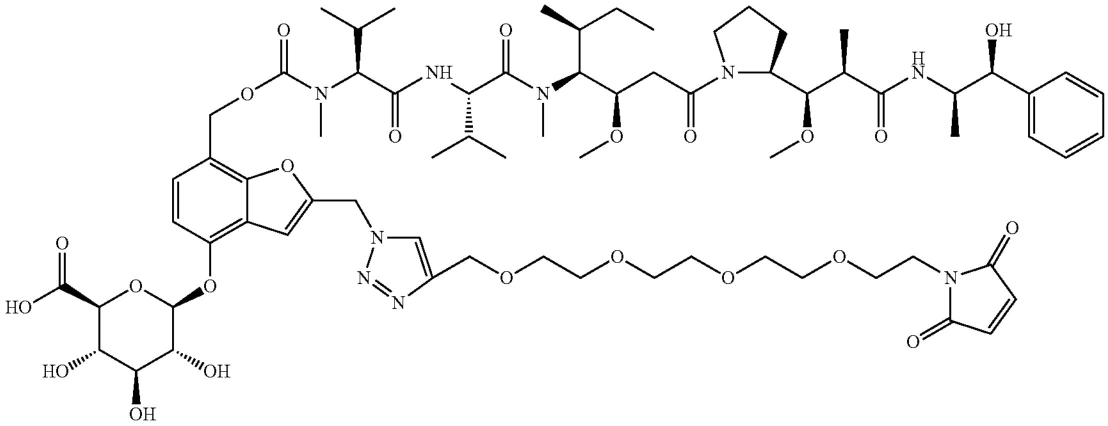

B-26

Compound A-64 (4.4 mg, 0.0039 mmol) was dissolved in DMSO (0.2 mL) under a nitrogen atmosphere at room temperature, and then 130 μL of a solution of Linker Q-1 (4.8 mg, 0.0154 mmol) dissolved in DMSO (480 μL) was taken and added to the reaction. Additionally, distilled water (2 mL), copper (II) sulfate pentahydrate ($CuSO_4 \cdot 5H_2O$, 0.68 mg, 0.0043 mmol) and sodium ascorbate (1.4 mg, 0.0079 mmol) were sequentially added to the reaction solution, and then the mixture was stirred for 3.5 hours. After completion of the reaction, the reaction solution was diluted with distilled water (1 mL), separated and purified using Preparative-HPLC, and then freeze-dried to obtain Compound B-26 in the form of a white solid (1.1 mg, 20%); MS m/z: 1451 $[M+H]^+$, 725 1/2 $[M+H]^+$.

Example II-27: Preparation of Compound B-27

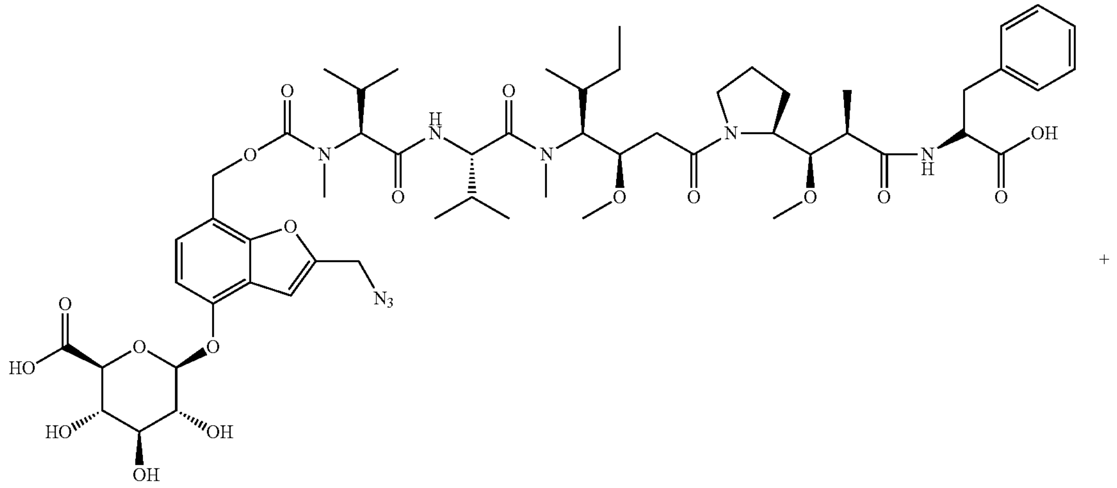

A-66

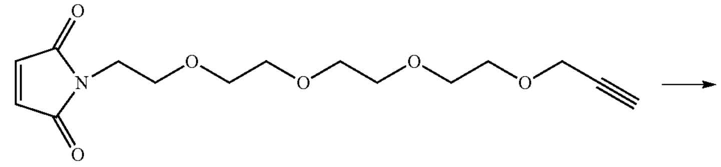

Q-1

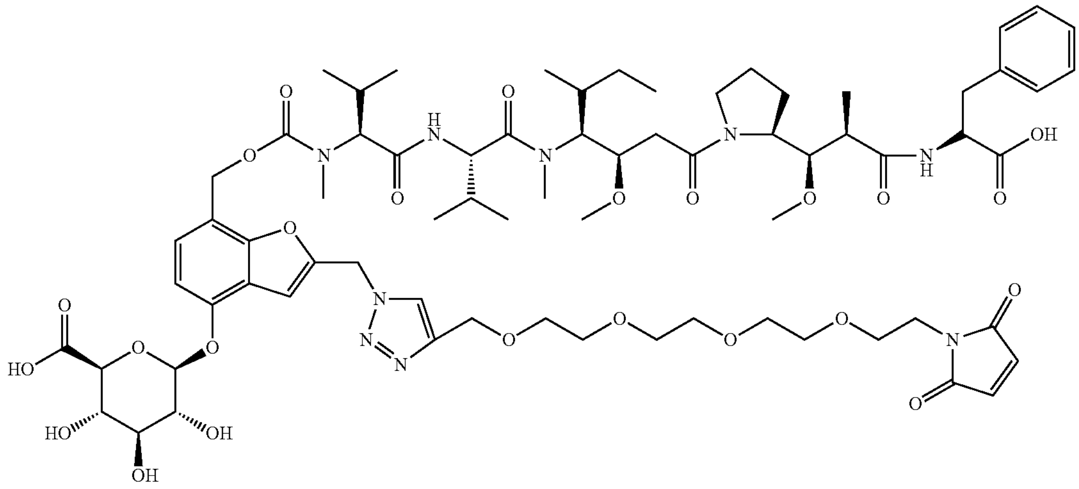

B-27

Compound A-66 (4.5 mg, 0.0039 mmol) was dissolved in DMSO (0.2 mL) under a nitrogen atmosphere at room temperature, and then 130 μL of a solution of Linker Q-1 (5.4 mg, 0.0173 mmol) dissolved in DMSO (540 μL) was taken and added to the reaction. Additionally, distilled water (2 mL), copper (II) sulfate pentahydrate ($CuSO_4 \cdot 5H_2O$, 0.69 mg, 0.0043 mmol) and sodium ascorbate (1.4 mg, 0.0079 mmol) were sequentially added to the reaction solution, and then the mixture was stirred for 4.5 hours. After completion of the reaction, the reaction solution was diluted with distilled water (1 mL), separated and purified using Preparative-HPLC, and then freeze-dried to obtain Compound B-27 in the form of a white solid (3.2 mg, 51%); MS m/z: 1465 $[M+H]^+$, 732 1/2 $[M+H]^+$.

Example II-28: Preparation of Compound B-28

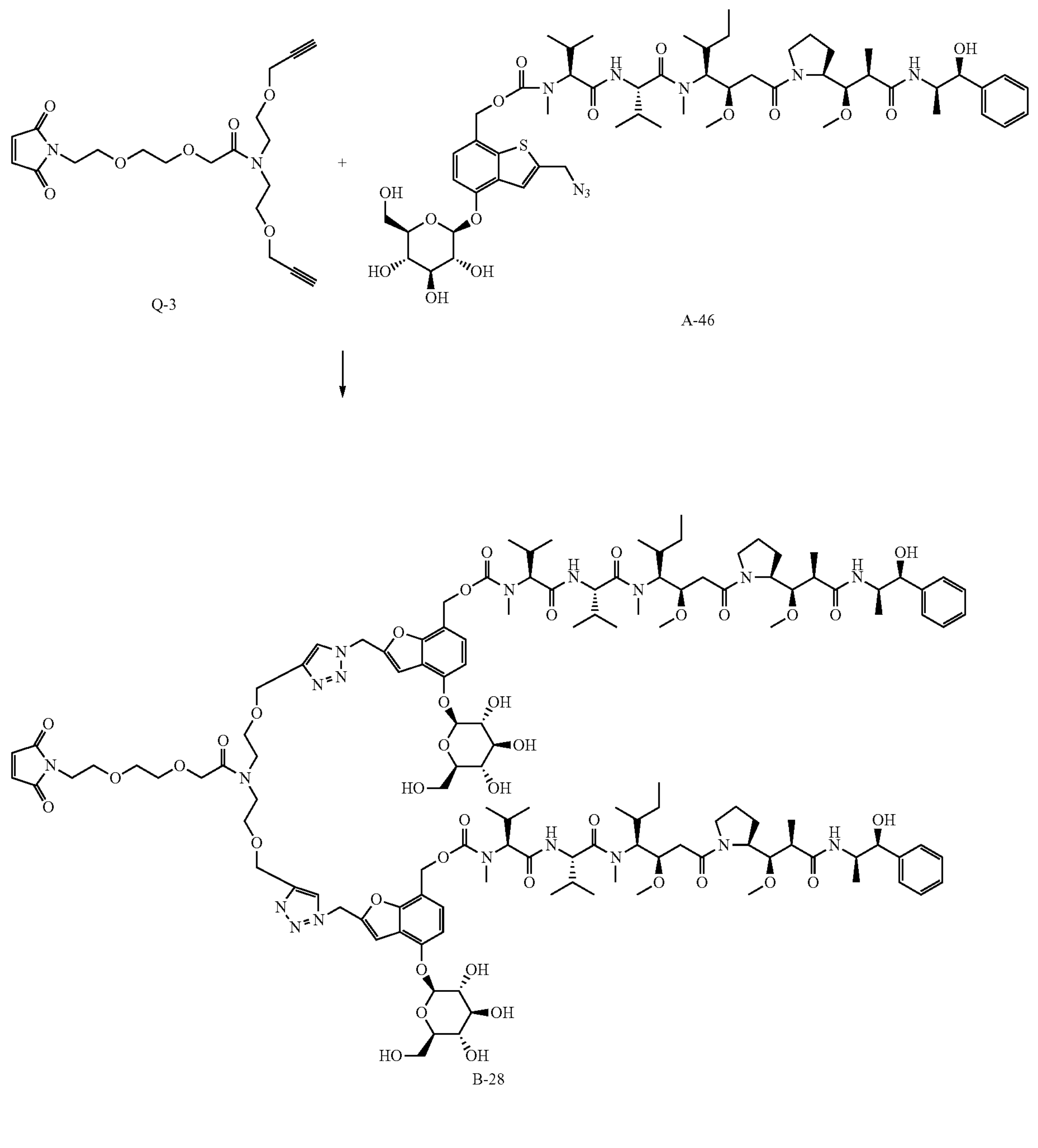

Q-3

A-46

B-28

Compound A-46 (6.7 mg, 0.0059 mmol) was dissolved in DMSO (200 μL) under a nitrogen atmosphere at 0° C., and then 100 μL of a solution of Linker Q-3 (4.8 mg) dissolved in DMSO (400 μL) was taken and added to the reaction. Additionally, distilled water (2 mL), copper (II) sulfate pentahydrate ($CuSO_4 \cdot 5H_2O$, 1 mg) and sodium ascorbate (1.3 mg) were sequentially added to the reaction solution, and then the mixture was stirred at room temperature for 30 minutes. After completion of the reaction, the reaction solution was diluted with distilled water (1 mL), separated and purified using Preparative-HPLC, and then freeze-dried to obtain Compound B-28 in the form of a white solid (6.4 mg, 81.6%); MS m/z: 2657 $[M+H]^+$, 1328 1/2 $[M+H]^+$, 886 1/3 $[M+H]^+$.

Example II-29: Preparation of Compound B-29

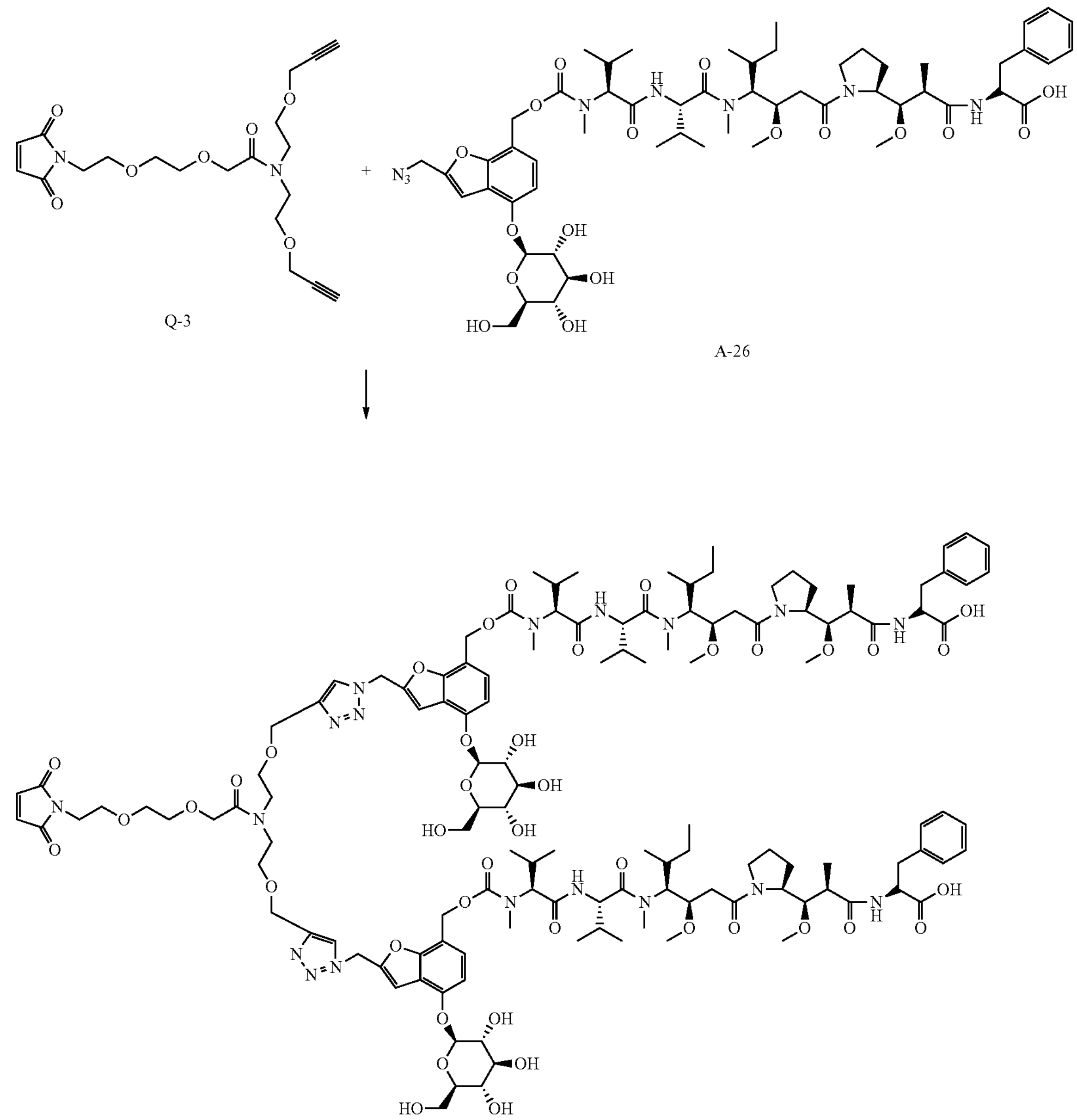

Q-3

A-26

B-29

Compound A-26 (6.4 mg, 0.0056 mmol) was dissolved in DMSO (400 μL) under a nitrogen atmosphere at 0° C., and then 100 μL of a solution of Linker Q-3 (4.8 mg) dissolved in DMSO (400 μL) was taken and added to the reaction. Additionally, distilled water (2 mL), copper (II) sulfate pentahydrate ($CuSO_4 \cdot 5H_2O$, 1 mg) and sodium ascorbate (1.2 mg) were sequentially added to the reaction solution, and then the mixture was stirred at room temperature for 20 minutes. After completion of the reaction, the reaction solution was diluted with distilled water (1 mL) and ACN (1 mL), separated and purified using Preparative-HPLC, and then freeze-dried to obtain Compound B-29 in the form of a white solid (5.7 mg, 75.7%); MS m/z: 2685 $[M+H]^+$, 1342 1/2 $[M+H]^+$, 895 1/3 $[M+H]^+$.

Example II-30: Preparation of Compound B-30

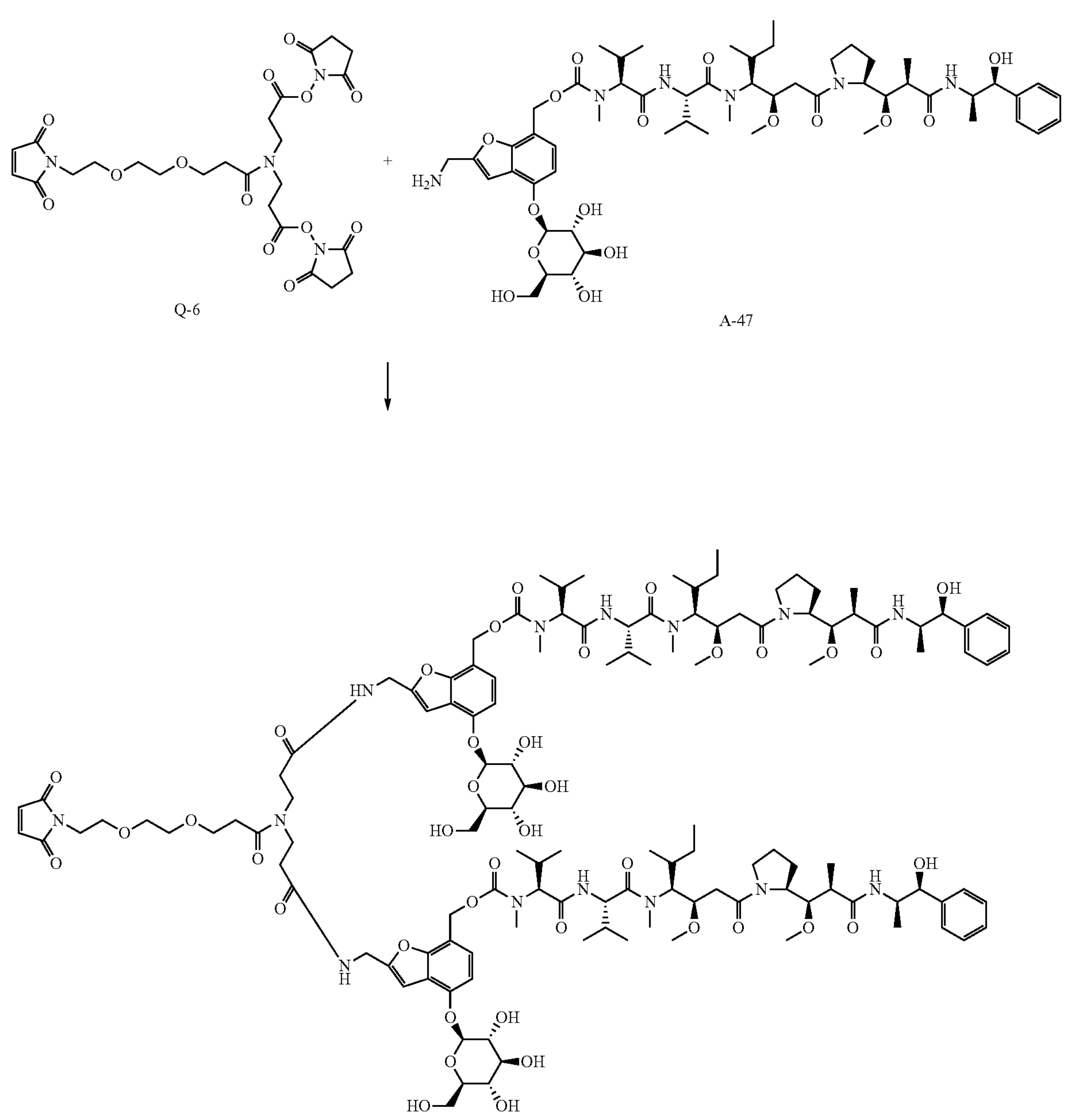

Q-6

A-47

B-30

Compound A-47 (2 mg, 0.0018 mmol) was dissolved in THF (1 mL) under a nitrogen atmosphere at 0° C., and then Linker Q-6 (0.54 mg, 0.0009 mmol) and DIPEA (5 μL) were sequentially added dropwise, and the mixture was stirred at 0° C. for 30 minutes. Additionally, the mixture was stirred at room temperature for 2 hours, and then the reaction solution was diluted with ACN (1 mL) containing 0.1% formic acid and distilled water (1 mL), separated and purified using Preparative-HPLC, and then freeze-dried to obtain Compound B-30 (1.4 mg, 60.8%); MS m/z: 2562 $[M+H]^+$, 1281 1/2 $[M+H]^+$, 854 $1/3^{[M+H]+}$.

Example 11-31: Preparation of Compound B-31

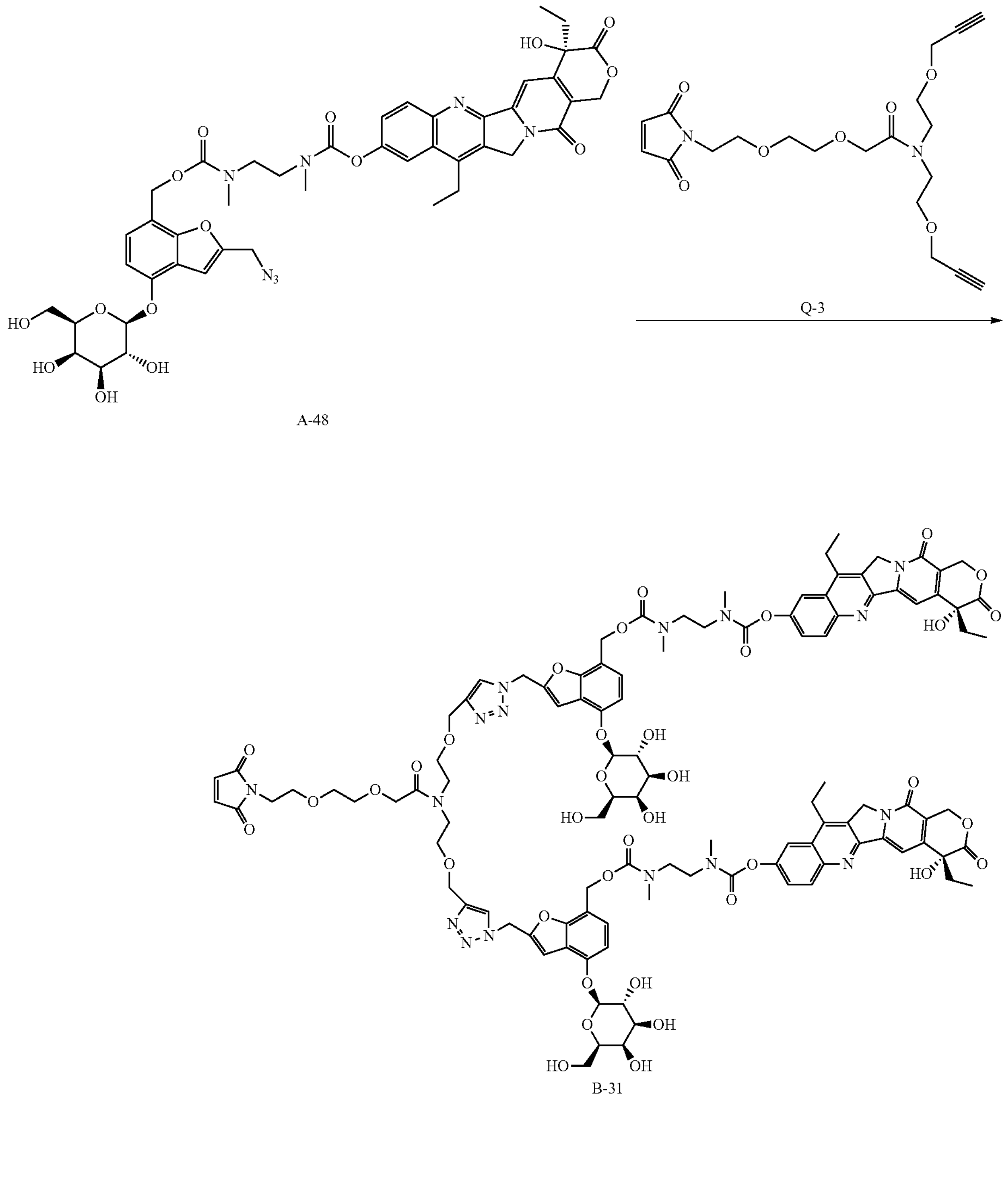

A-48

B-31

Compound A-48 (6.0 mg, 0.0065 mmol) was dissolved in DMSO (1.5 mL) under a nitrogen atmosphere at 0° C., and then 133 μL of a solution of Linker Q-3 (2.0 mg) dissolved in DMSO (200.0 μL) was taken and added to the reaction. Additionally, distilled water (2.0 mL), ACN (0.5 mL), copper (II) sulfate pentahydrate ($CuSO_4 \cdot 5H_2O$, 2.0 mg) and sodium ascorbate (2.6 mg) were sequentially added to the reaction solution, and then the mixture was stirred at room temperature for 1 hour. After completion of the reaction, the reaction solution was diluted with distilled water (1.0 mL), separated and purified using Preparative-HPLC, and then freeze-dried to obtain Compound B-31 in the form of a white solid (3.4 mg, 23%); EI-MS m/z: 2234 $[M+H]^+$, MS m/z: 1117 1/2 $[M+H]^+$.

Example II-32: Preparation of Compound B-32

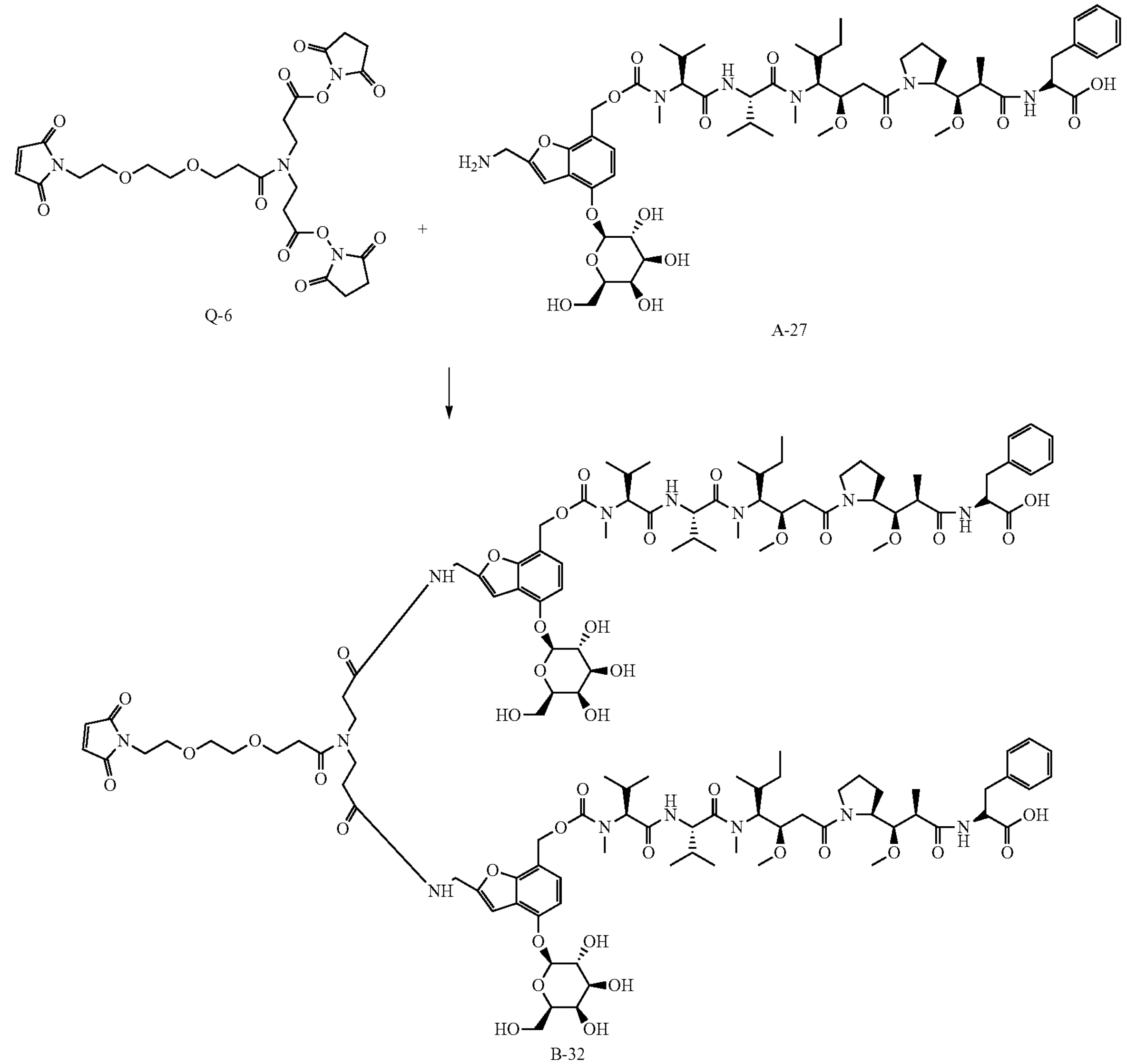

Q-6

A-27

B-32

Compound A-27 (3.1 mg, 0.0027 mmol) was dissolved in a mixed solvent of THE (1.5 mL), DMSO (200 μL) and distilled water (100 μL) under a nitrogen atmosphere at 0° C., and then 500 μL of a solution of Linker Q-6 (3 mg) dissolved in DMSO (2.5 mL) was taken and added to the reaction. Finally, DIPEA (5 μL) was added dropwise, and the mixture was stirred at 0° C. for 30 minutes. Additionally, the mixture was stirred at room temperature for 2 hours, and then the reaction solution was diluted with ACN (1 mL) containing 0.1% formic acid and distilled water (1 mL), separated and purified using Preparative-HPLC, and then freeze-dried to obtain Compound B-32 (1.4 mg, 60.8%); MS m/z: 2592 $[M+H]^+$, 1296 1/2 $[M+H]^+$, 864 1/3 $[M+H]^+$.

Example II-33: Preparation of Compound B-33

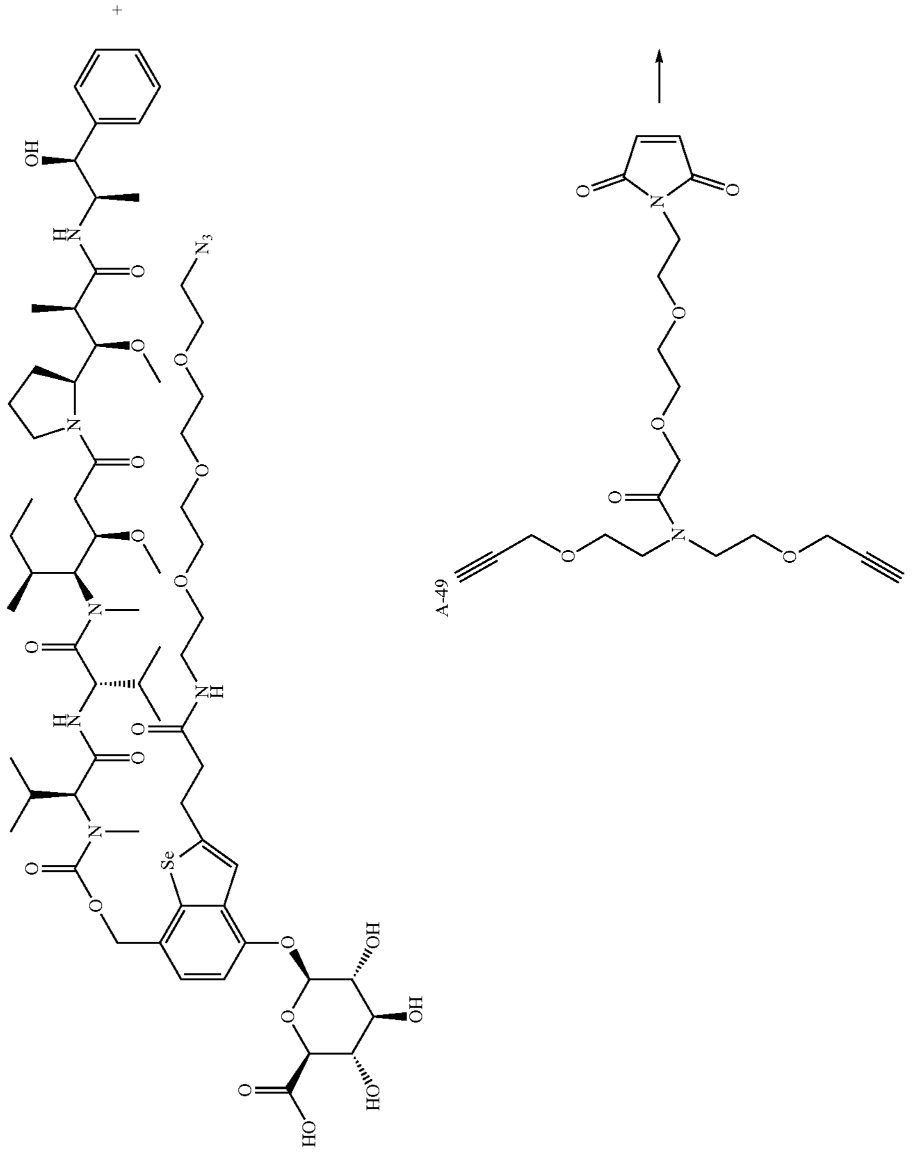
A-49
Q-3

-continued
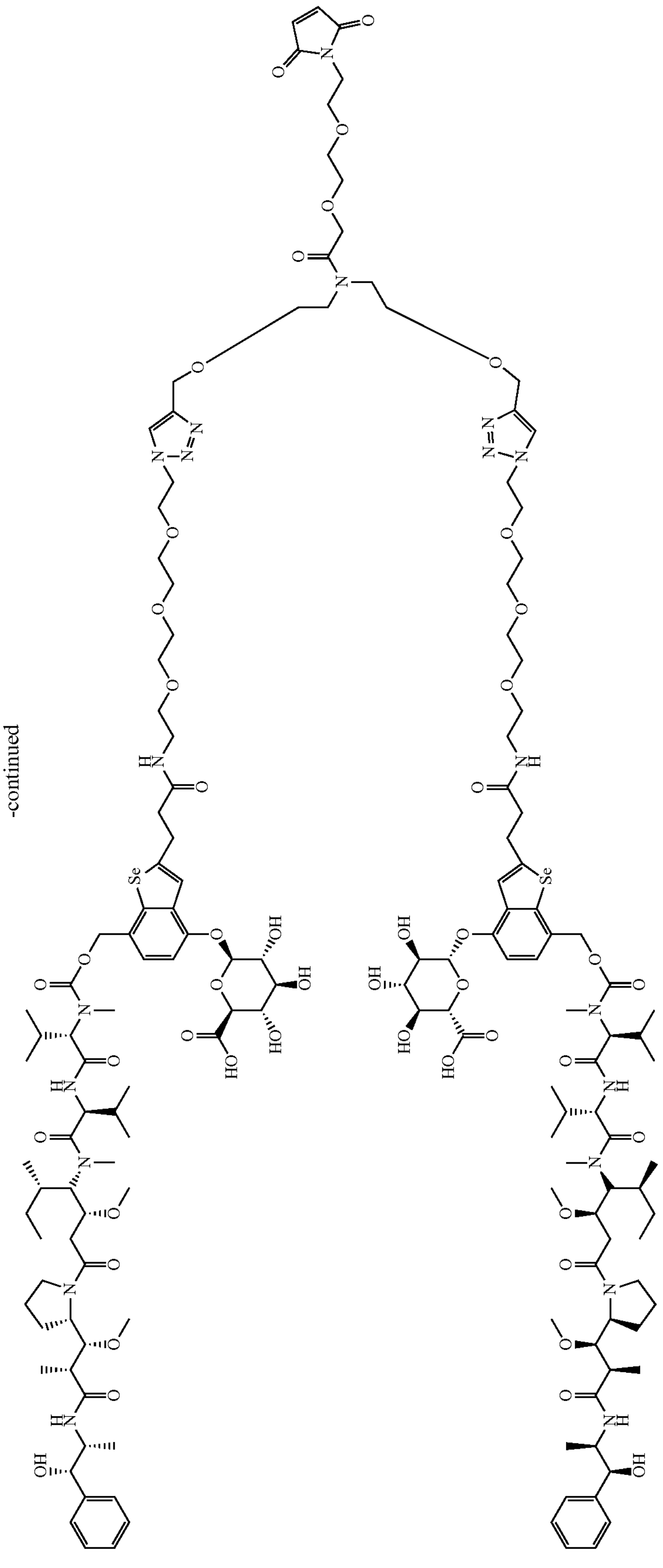
B-33

Compound A-49 (6.0 mg, 0.0042 mmol) was dissolved in DMSO (200 μL) under a nitrogen atmosphere at 0° C., and then 86 μL of a solution of Linker Q-3 (2.2 mg) dissolved in DMSO (0.22 mL) was taken and added to the reaction. Additionally, distilled water (2 mL), DMSO (1.8 mL), copper (II) sulfate pentahydrate ($CuSO_4 \cdot 5H_2O$, 1.16 mg) and sodium ascorbate (1.67 mg) were sequentially added to the reaction solution, and then the mixture was stirred at room temperature for 1 hour. After completion of the reaction, the reaction solution was diluted with distilled water (3 mL), separated and purified using Preparative-HPLC, and then freeze-dried to obtain Compound B-33 in the form of a white solid (3.8 mg, 55%); EI-MS m/z: 1623 1/2 $[M+H]^+$, 1082 1/3 $[M+H]^+$.

Example 11-34: Preparation of Compound B-34

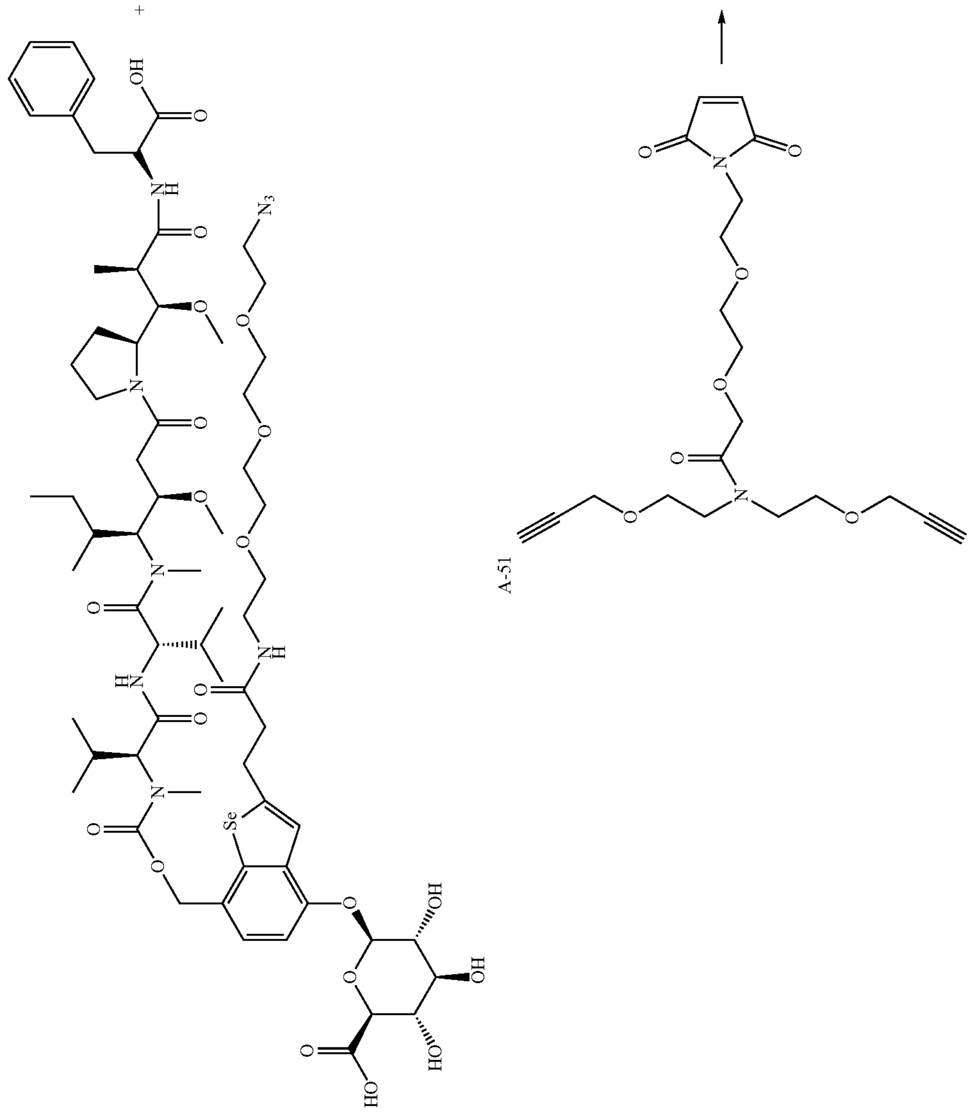
A-51
Q-3

-continued
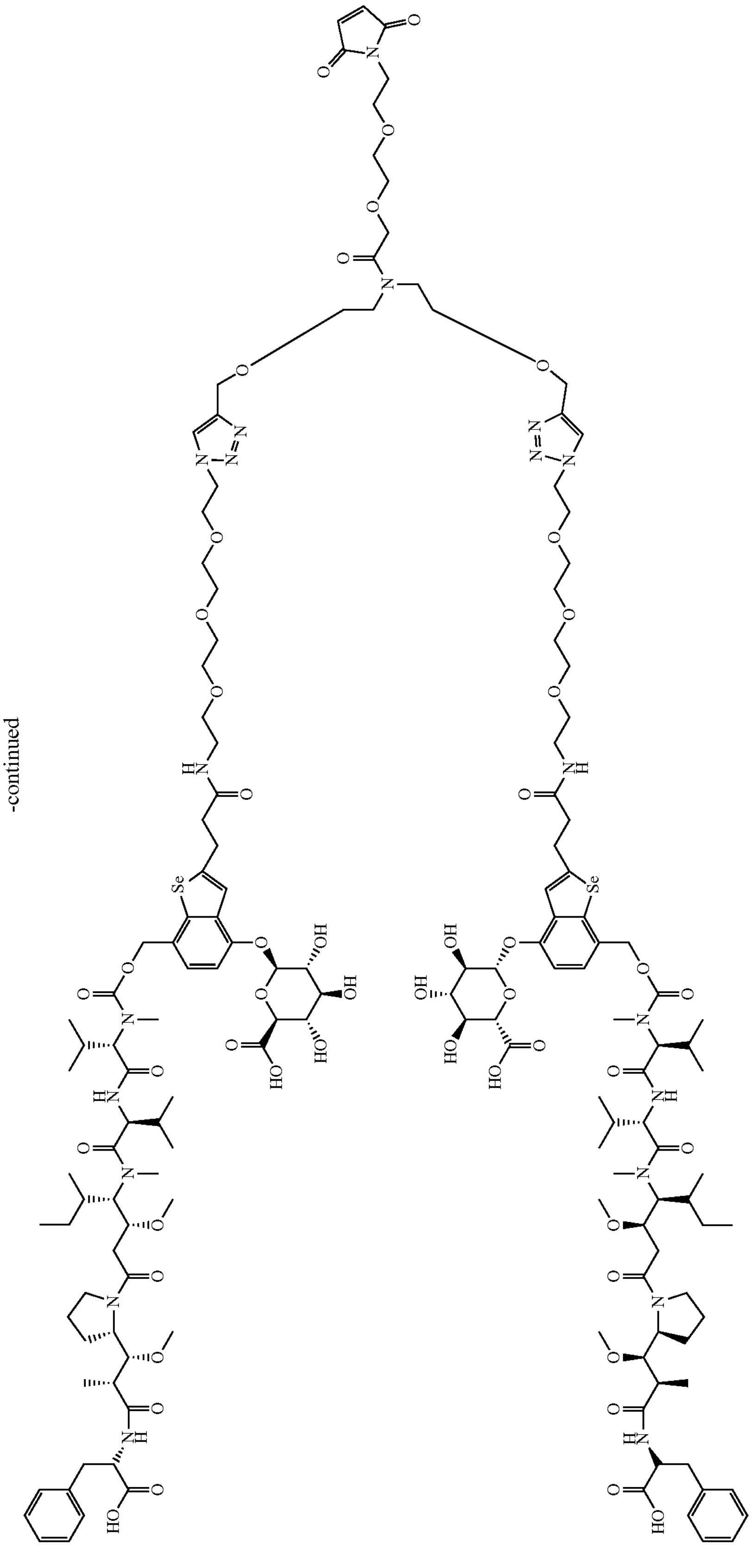
B-34

Compound A-51 (5.9 mg, 0.0041 mmol) was dissolved in DMSO (200 μL) under a nitrogen atmosphere at 0° C., and then 83 μL of a solution of Linker Q-3 (2.2 mg) dissolved in DMSO (0.22 mL) was taken and added to the reaction. Additionally, distilled water (2 mL), DMSO (1.8 mL), copper (II) sulfate pentahydrate ($CuSO_4 \cdot 5H_2O$, 1.13 mg) and sodium ascorbate (1.63 mg) were sequentially added to the reaction solution, and then the mixture was stirred at room temperature for 1.5 hours. After completion of the reaction, the reaction solution was diluted with distilled water (3 mL), separated and purified using Preparative-HPLC, and then freeze-dried to obtain Compound B-34 in the form of a white solid (2.2 mg, 33%); EI-MS m/z: 1637 1/2 $[M+H]^+$, 1091 1/3 $[M+H]^+$.

Example 11-35: Preparation of Compound B-35

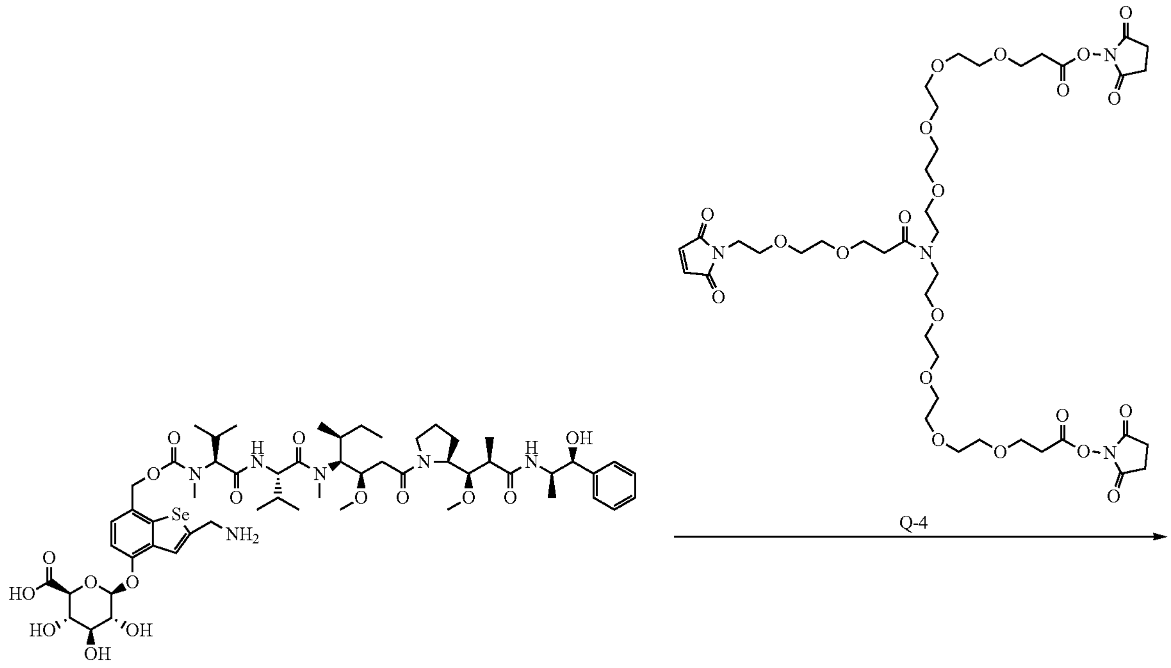

A-53

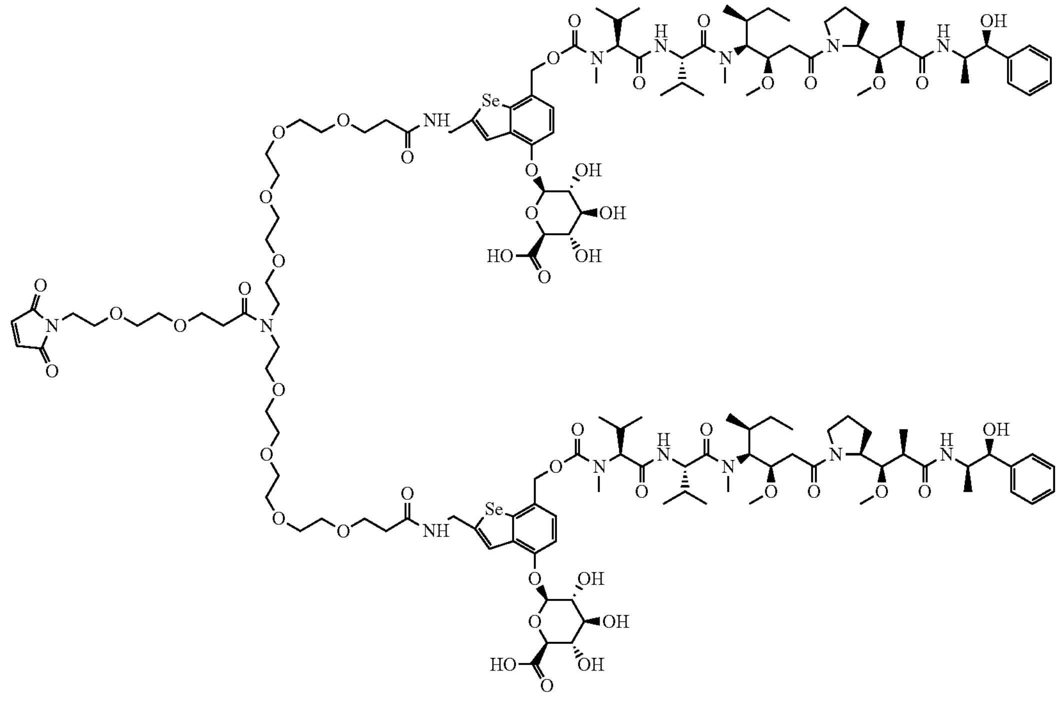

B-35

Compound A-53 (5.9 mg, 0.005 mmol) was dissolved in THE (1 mL) under a nitrogen atmosphere at room temperature, and then 2.5 mL of a solution of Linker Q-4 (3.1 mg) dissolved in THE (3.1 mL) was taken and added to the reaction. Additionally, distilled water (0.2 mL), pyridine (10 μL) and DIPEA (10 μL) were sequentially added to the reaction solution, and then the mixture was stirred at room temperature for 2.5 hours. After completion of the reaction, 2N-hydrochloric acid aqueous solution (20 μL) was added, and the reaction solution was diluted with ACN (3 mL) containing 0.1% formic acid, separated and purified using Preparative-HPLC, and then freeze-dried to obtain Compound B-35 (3.2 mg, 43%); EI-MS m/z: 1534 1/2 $[M+H]^+$, 1023 1/3 $[M+H]^+$.

Example II-36: Preparation of Compound B-36

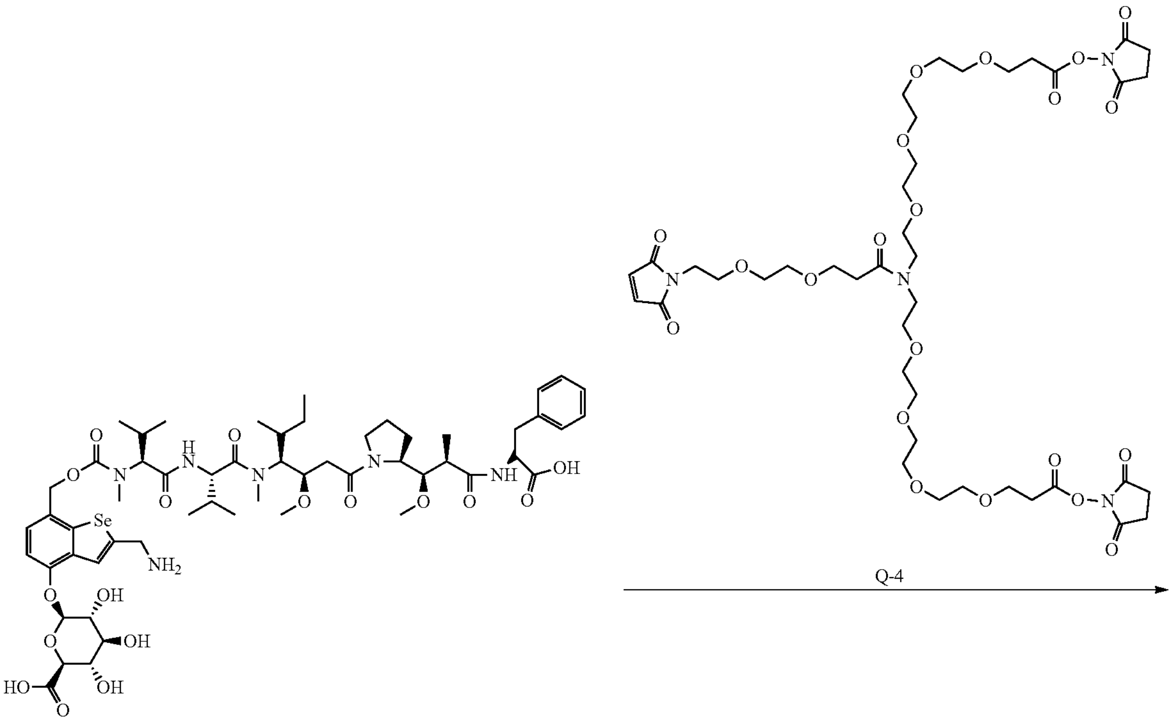

A-55

-continued

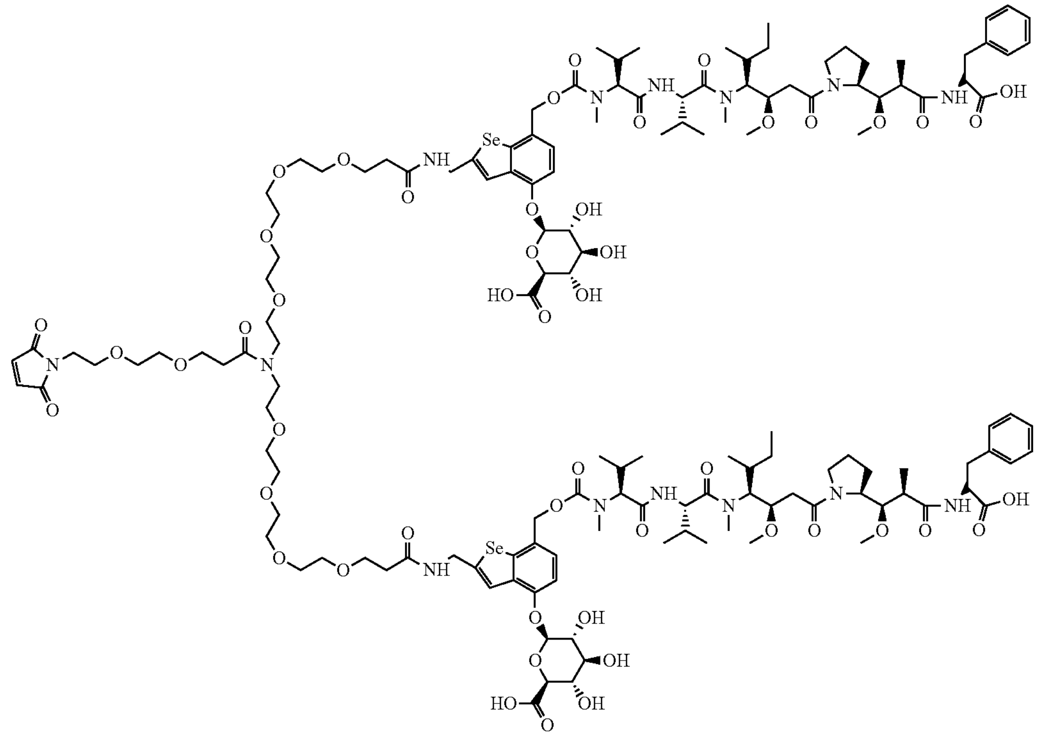

B-36

Compound A-55 (6.8 mg, 0.0057 mmol) was dissolved in THE (2.0 mL) under a nitrogen atmosphere at 0° C., and then Linker Q-4 (2.75 mg, 0.0027 mmol), distilled water (200.0 μL), DIPEA (10.0 μL) and pyridine (20.0 μL) were sequentially added dropwise, and the mixture was stirred for 2 hours at room temperature. After completion of the reaction, 2N-hydrochloric acid aqueous solution (20.0 μL) was added, and the reaction solution was diluted with ACN (2.0 mL) containing 0.1% formic acid, separated and purified using Preparative-HPLC, and then freeze-dried to obtain Compound B-36 in the form of a white solid (2.6 mg, 30.0%); EI-MS m/z: 1548 1/2 $[M+H]^+$, 1032 1/3 $[M+H]^+$.

Example II-37: Preparation of Compound B-37

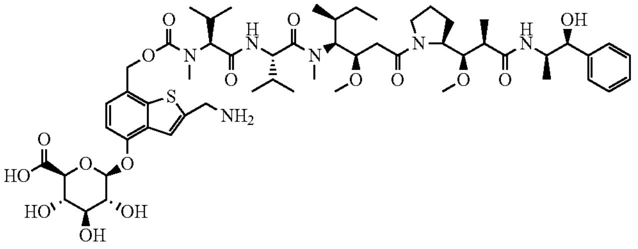

A-57

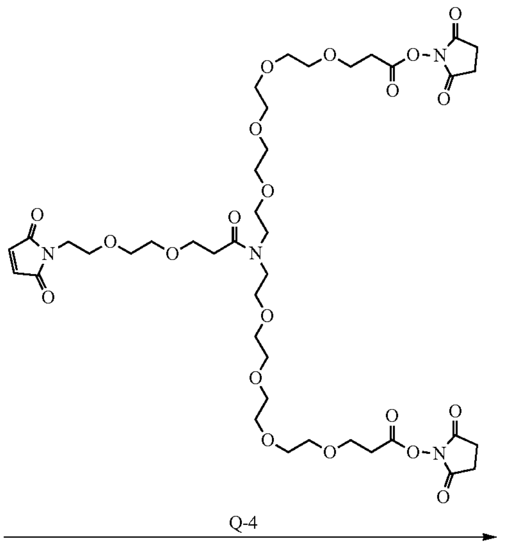

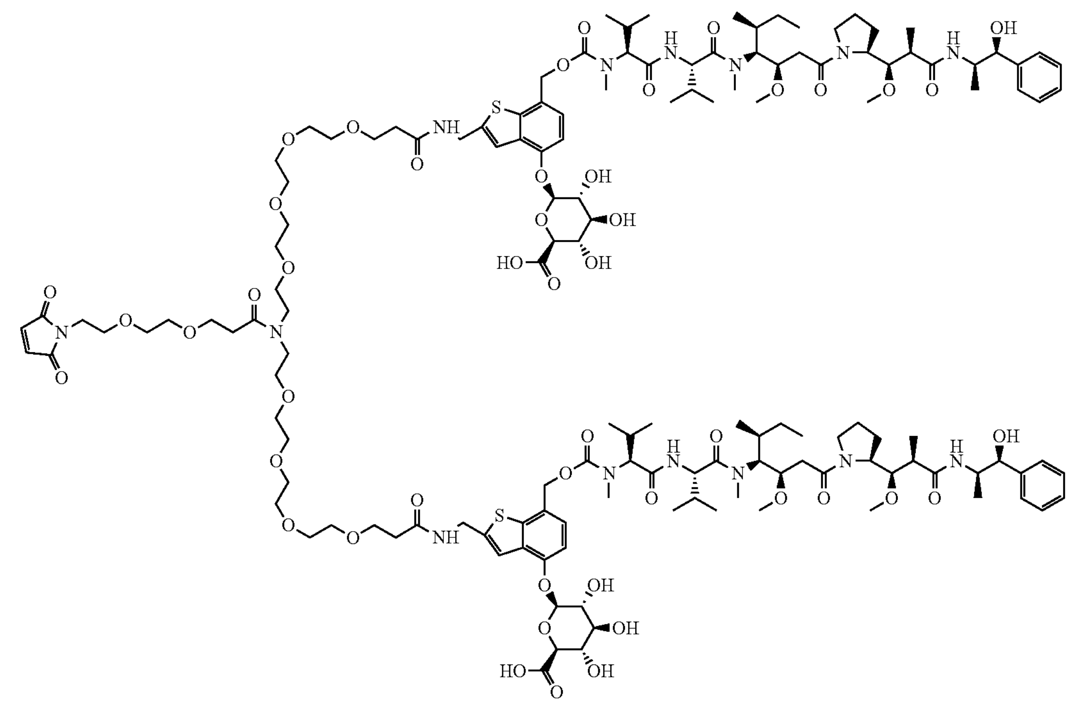

B-37

Compound A-57 (6.1 mg, 0.0054 mmol) was dissolved in THF (2.14 mL) under a nitrogen atmosphere at room temperature, and then Linker Q-4 (3.1 mg, 0.0033 mmol), distilled water (200 μL), DIPEA (10 μL) and pyridine (10 μL) were sequentially added dropwise, and the mixture was stirred for 3 hours. After completion of the reaction, the reaction solution was diluted with ACN (2 mL) containing 0.1% formic acid, separated and purified using Preparative-HPLC, and then freeze-dried to obtain Compound B-37 in the form of a white solid (3.7 mg, 23%); MS m/z: 2976 $[M+H]^+$, 1487 1/2 $[M+H]^+$, 991 1/3 $[M+H]^+$.

Example II-38: Preparation of Compound B-38

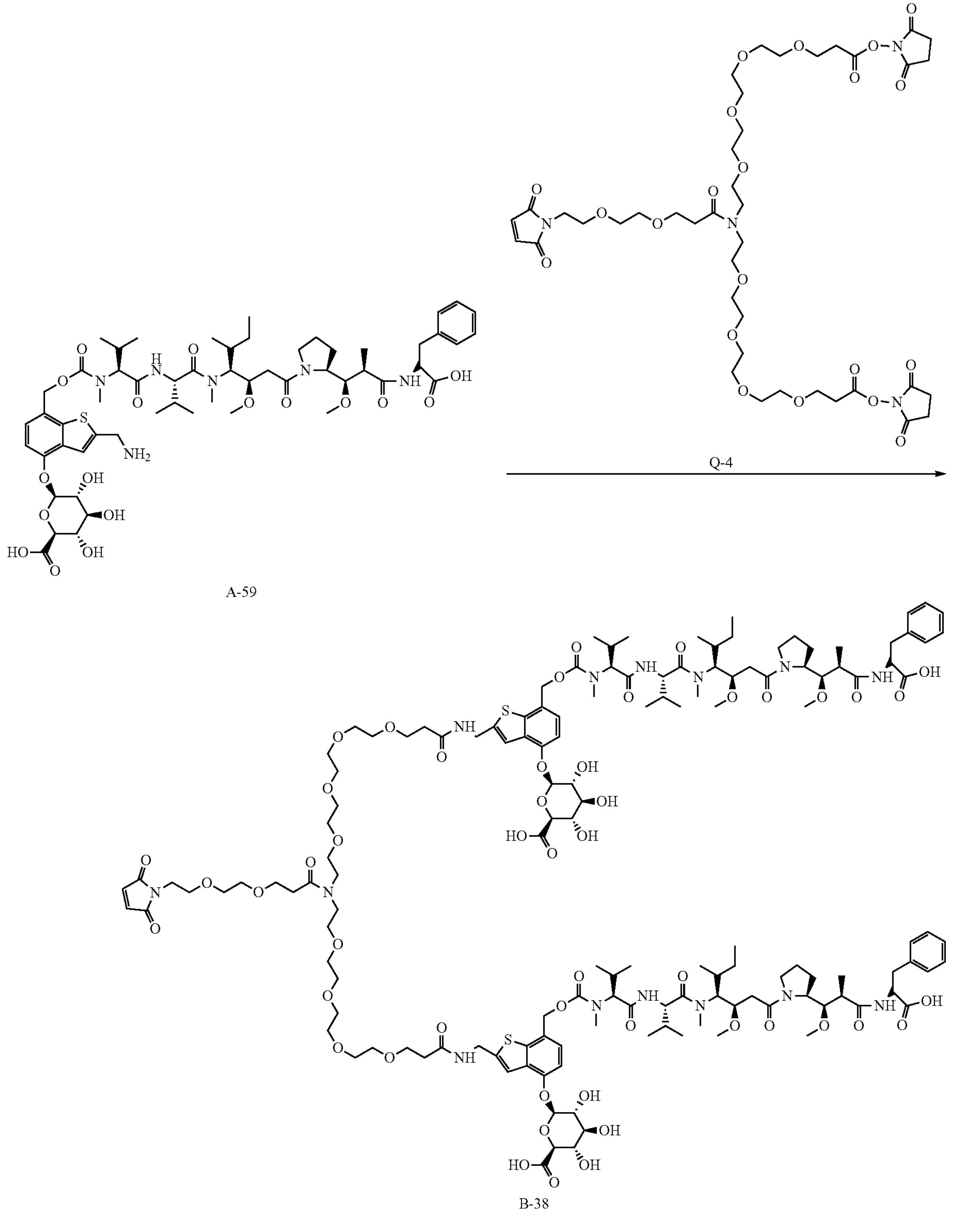

A-59

B-38

Compound A-59 (6.3 mg, 0.0055 mmol) was dissolved in THF (2.11 mL) under a nitrogen atmosphere at room temperature, and then Linker Q-4 (3 mg, 0.0032 mmol), distilled water (200 μL), DIPEA (10 μL) and pyridine (10 μL) were sequentially added dropwise, and the mixture was stirred for 4 hours. After completion of the reaction, the reaction solution was diluted with ACN (2 mL) containing 0.1% formic acid, separated and purified using Preparative-HPLC, and then freeze-dried to obtain Compound B-38 in the form of a white solid (4 mg, 24%); MS m/z: 3004 [M+H], 1501 1/2 [M+H], 1001 1/3 $[M+H]^+$.

Example II-39: Preparation of Compound B-39

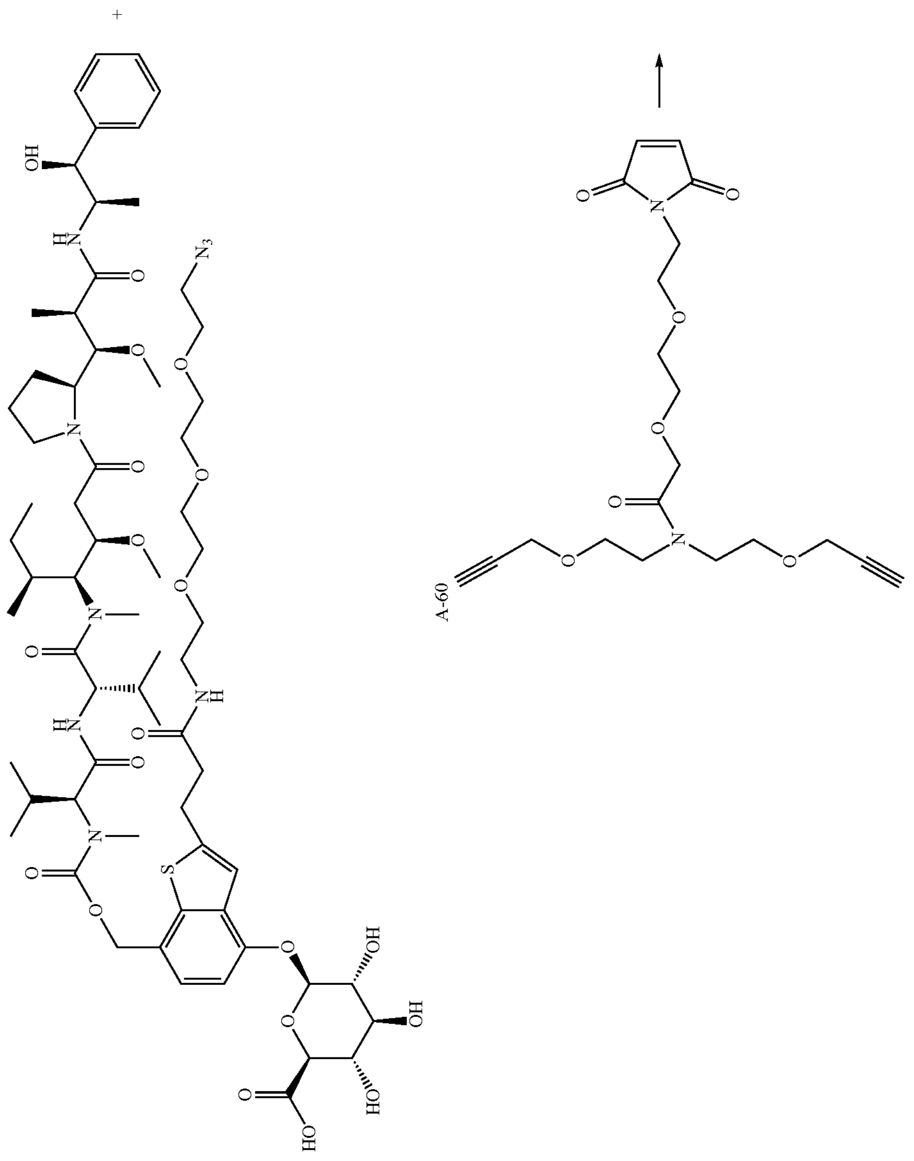
A-60
Q-3

-continued
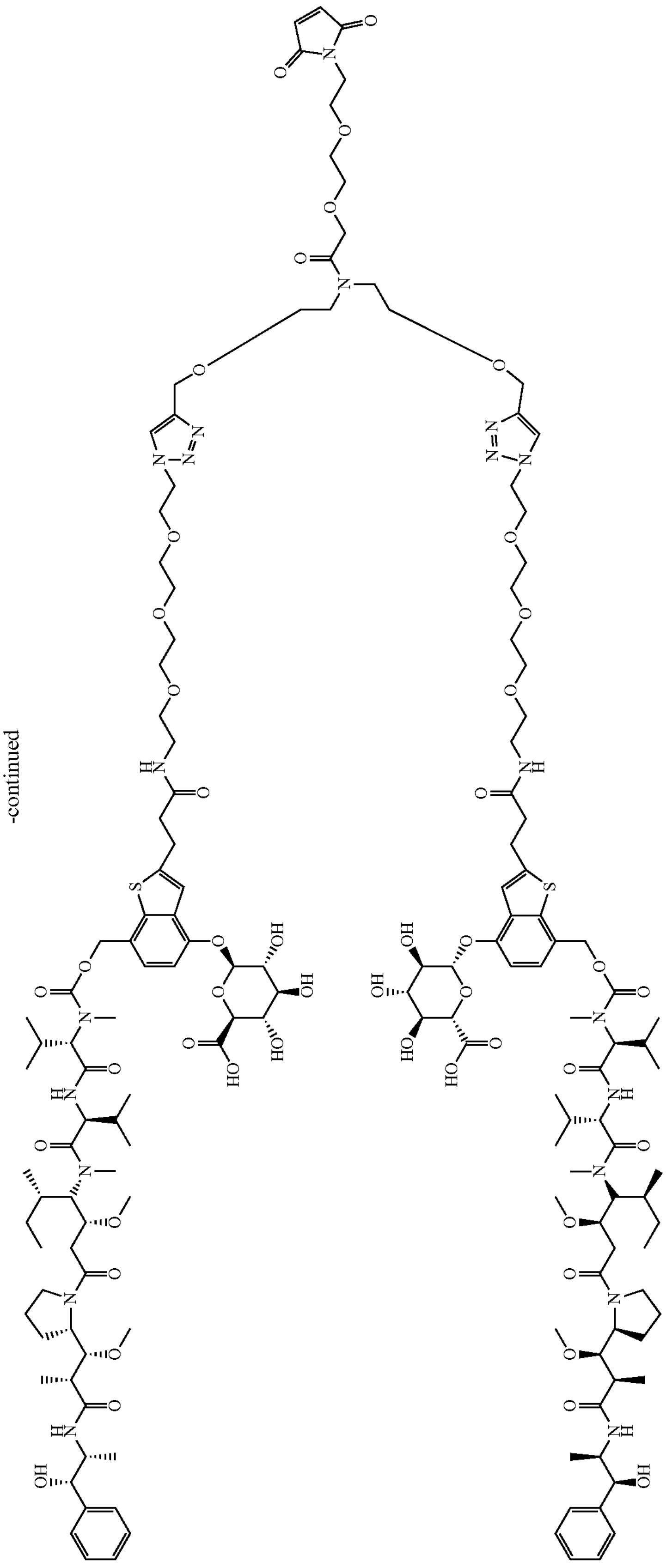
B-39

Compound A-60 (6.7 mg, 0.0049 mmol) was dissolved in DMSO (200 μL) under a nitrogen atmosphere at 0° C., and then 100 μL of a solution of Linker Q-3 (1.7 mg) dissolved in DMSO (0.17 mL) was taken and added to the reaction. Additionally, distilled water (2 mL), DMSO (0.4 mL), copper (II) sulfate pentahydrate ($CuSO_4 \cdot 5H_2O$, 1.34 mg) and sodium ascorbate (1.93 mg) were sequentially added to the reaction solution, and then the mixture was stirred at room temperature for 30 minutes. After completion of the reaction, the reaction solution was diluted with distilled water (3 mL), separated and purified using Preparative-HPLC, and then freeze-dried to obtain Compound B-39 in the form of a white solid (5.1 mg, 66%); EI-MS m/z: 1575 1/2 $[M+H]^+$, 1050 1/3 $[M+H]^+$.

Example II-40: Preparation of Compound B-40

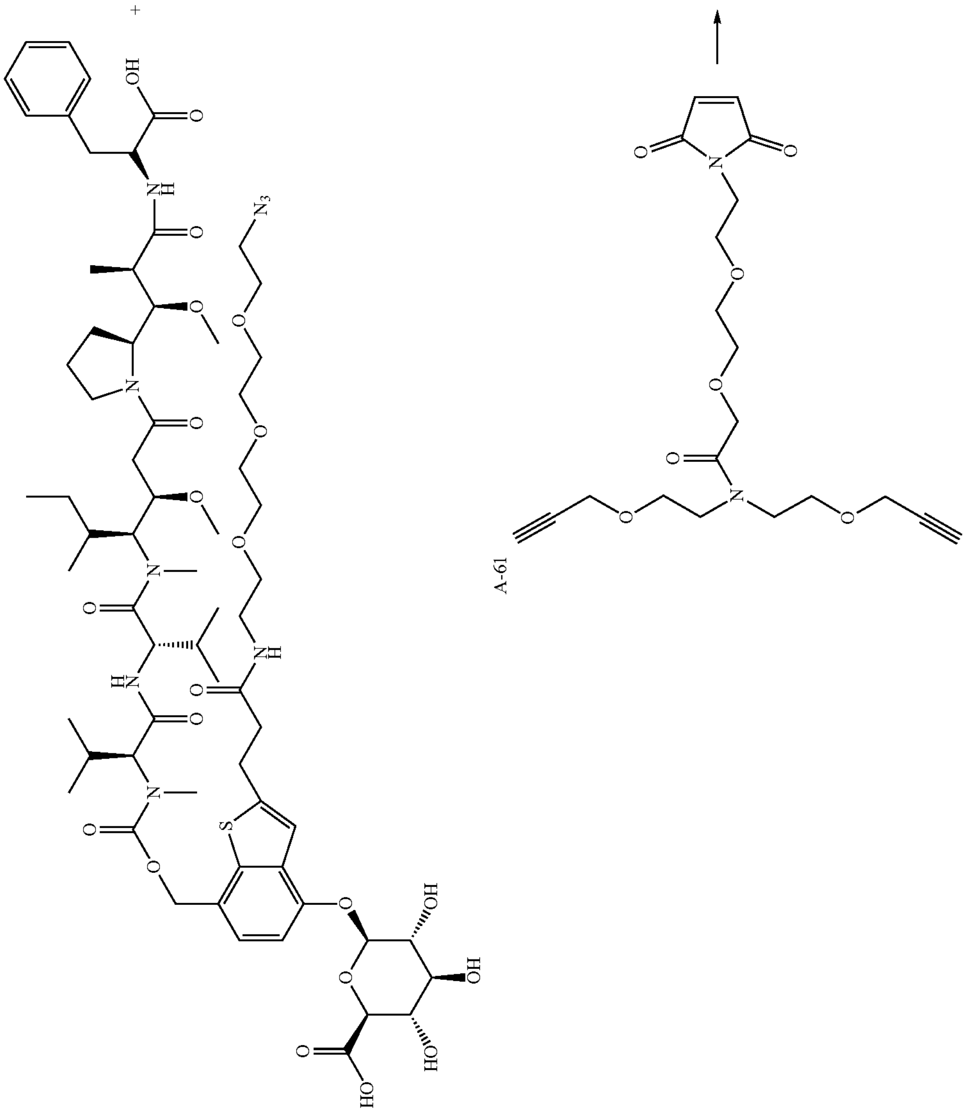
A-61
Q-3

-continued
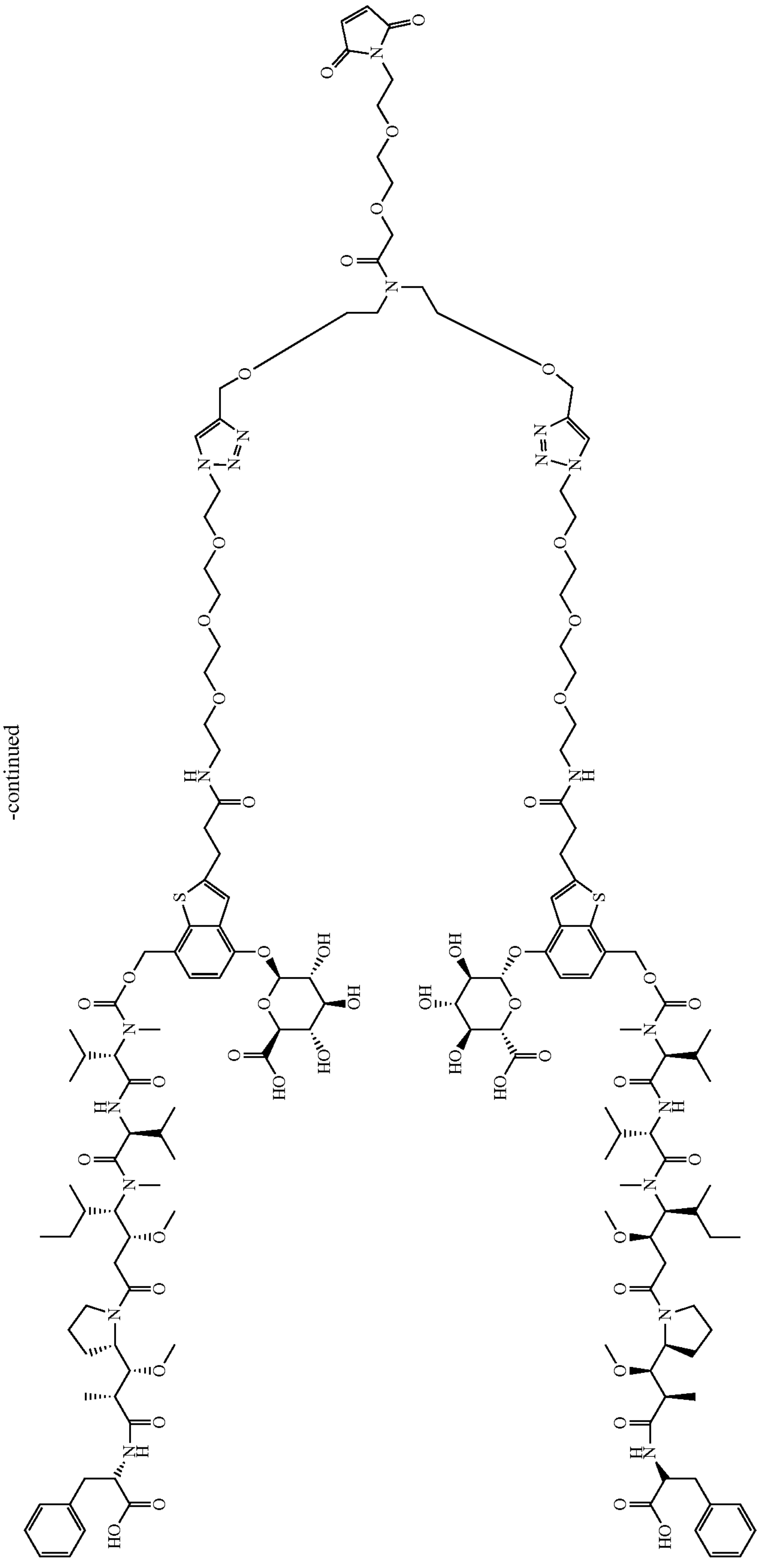
B-40

Compound A-61 (8.0 mg, 0.0058 mmol) was dissolved in DMSO (200 μL) under a nitrogen atmosphere at 0° C., and then 117 μL of a solution of Linker Q-3 (2.0 mg) dissolved in DMSO (0.2 mL) was taken and added to the reaction. Additionally, distilled water (2 mL), DMSO (0.8 mL), copper (II) sulfate pentahydrate ($CuSO_4 \cdot 5H_2O$, 1.58 mg) and sodium ascorbate (2.28 mg) were sequentially added to the reaction solution, and then the mixture was stirred at room temperature for 40 minutes. After completion of the reaction, the reaction solution was diluted with distilled water (3 mL), separated and purified using Preparative-HPLC, and then freeze-dried to obtain Compound B-40 in the form of a white solid (4.5 mg, 49%); EI-MS m/z: 1589 1/2 $[M+H]^+$, 1059 1/3 $[M+H]^+$.

Example II-41: Preparation of Compound B-41

Compound A-65 (5 mg, 0.0045 mmol) was dissolved in THE (2 mL) under a nitrogen atmosphere at room temperature, and then Linker Q-2 (2.4 mg, 0.0068 mmol), DIPEA (20 μL) and pyridine (10 μL) were sequentially added dropwise, and the mixture was stirred for 6.5 hours. After completion of the reaction, 2N-hydrochloric acid aqueous solution (10 μL) was added, and the reaction solution was diluted with ACN (2 mL) containing 0.1% formic acid, separated and purified using Preparative-HPLC, and then freeze-dried to obtain Compound B-41 in the form of a white solid (2.3 mg, 38%); MS m/z: 1353 $[M+H]^+$, 676 1/2 $[M+H]^+$.

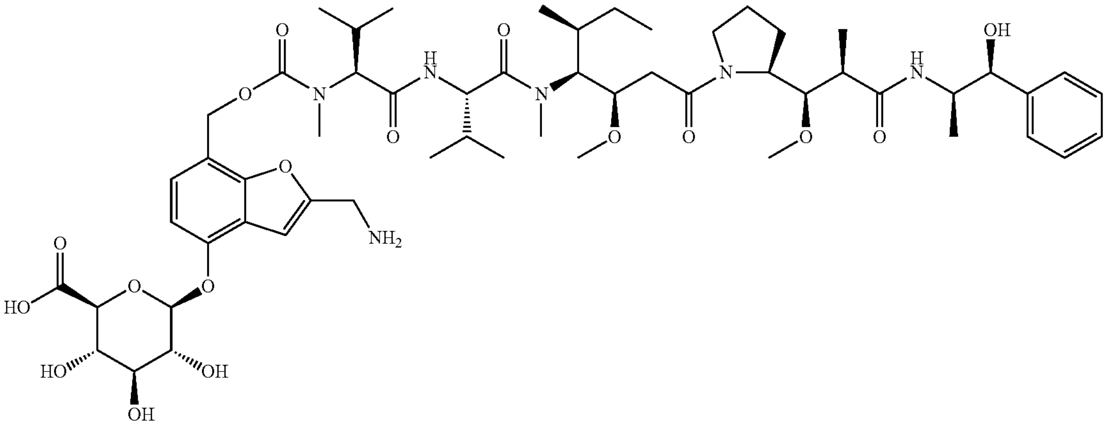

A-65

+

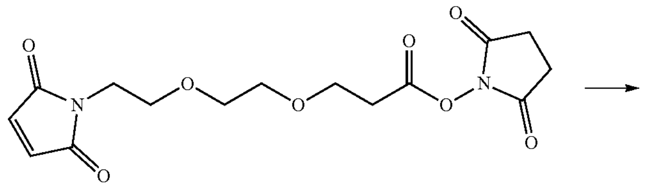

Q-2

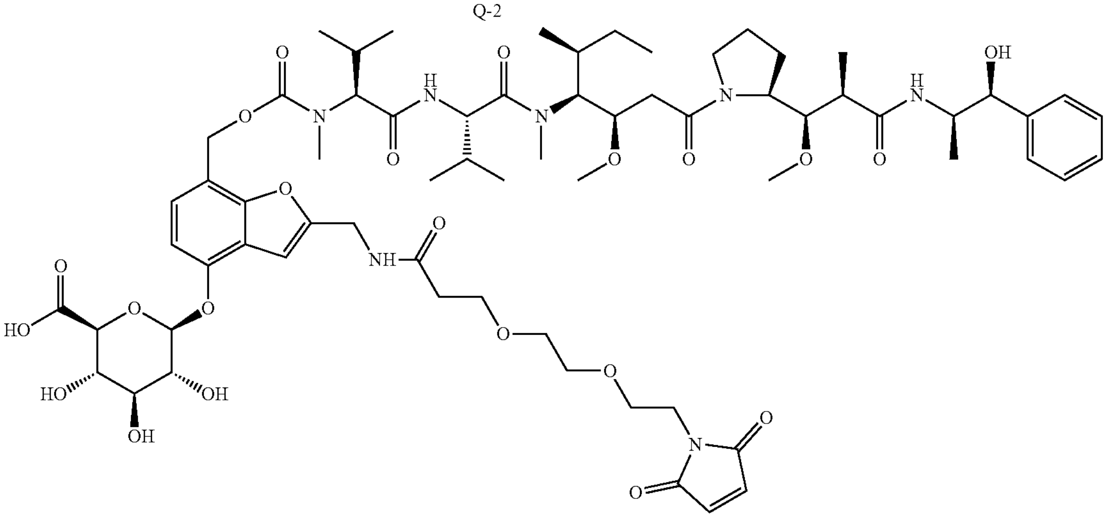

B-41

Example II-42: Preparation of Compound B-42

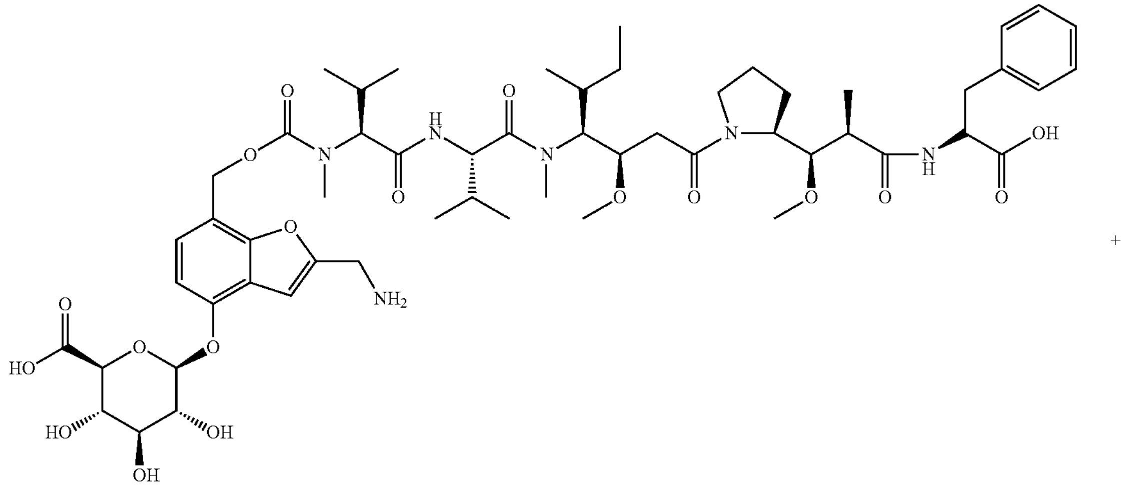

A-67

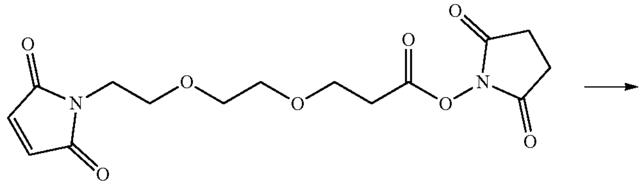

Q-2

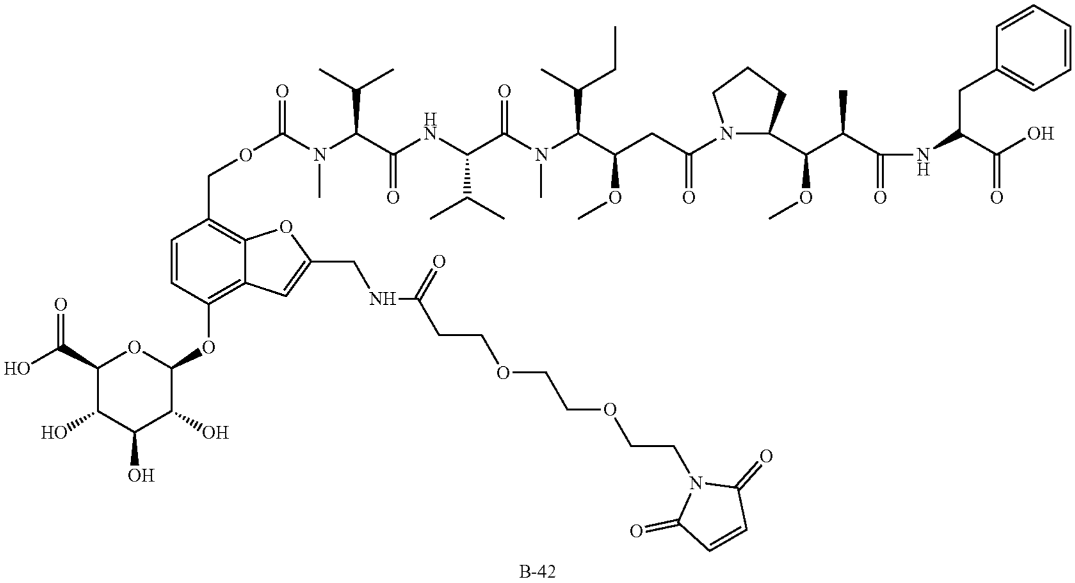

B-42

Compound A-67 (5.1 mg, 0.0045 mmol) was dissolved in THF (2 mL) under a nitrogen atmosphere at room temperature, and then Linker Q-2 (2.4 mg, 0.0068 mmol), distilled water (110 μL), DIPEA (10 μL) and pyridine (10 μL) were sequentially added dropwise, and the mixture was stirred for 6 hours. After completion of the reaction, 2N-hydrochloric acid aqueous solution (30 μL) was added, and the reaction solution was diluted with ACN (2 mL) containing 0.1% formic acid, separated and purified using Preparative-HPLC, and then freeze-dried to obtain Compound B-42 in the form of a white solid (2.5 mg, 40%); MS m/z: 1367 $[M+H]^+$, 683 1/2 $[M+H]^+$.

Example II-43: Preparation of Compound B-43
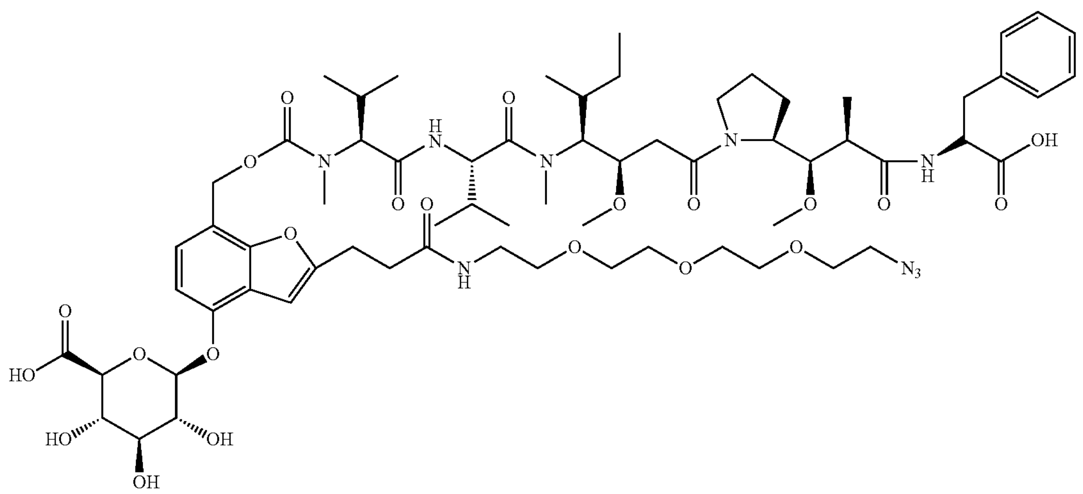
A-70
+
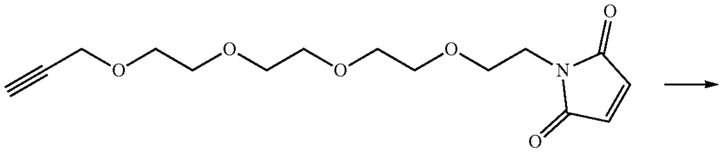
Q-1
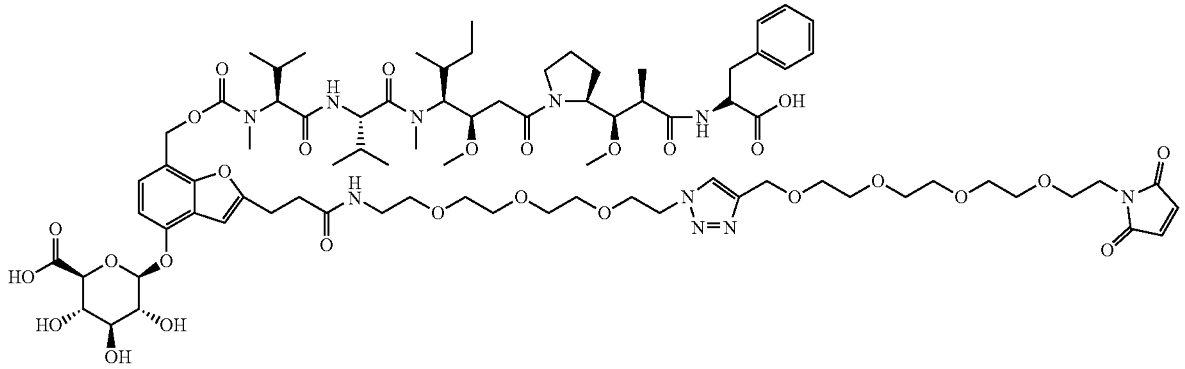
B-43

Compound A-70 (4.6 mg, 0.0033 mmol) was dissolved in DMSO (200 μL) under a nitrogen atmosphere at 0° C., and then 140 μL of a solution of Linker Q-1 (4.3 mg) dissolved in DMSO (0.43 mL) was taken and added to the reaction. Additionally, distilled water (2 mL), DMSO (0.4 mL), copper (II) sulfate pentahydrate ($CuSO_4 \cdot 5H_2O$, 0.92 mg) and sodium ascorbate (1.33 mg) were sequentially added to the reaction solution, and then the mixture was stirred at room temperature for 30 minutes. After completion of the reaction, the reaction solution was diluted with distilled water (3 mL), separated and purified using Preparative-HPLC, and then freeze-dried to obtain Compound B-43 in the form of a white solid (5.2 mg, 92%); EI-MS m/z: 1681 $[M+H]^+$, 841 1/2 $[M+H]^+$.

Example II-44: Preparation of Compound B-44

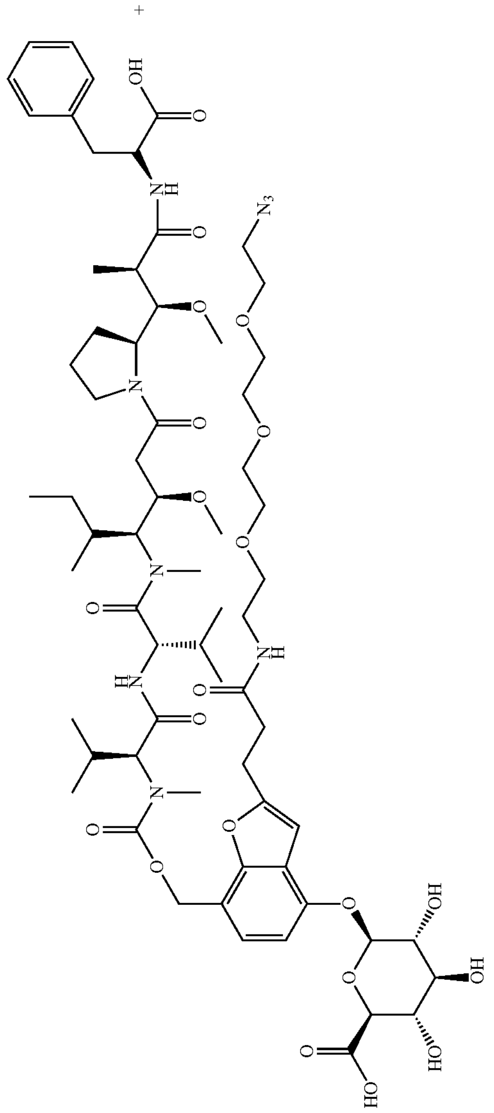
A-70
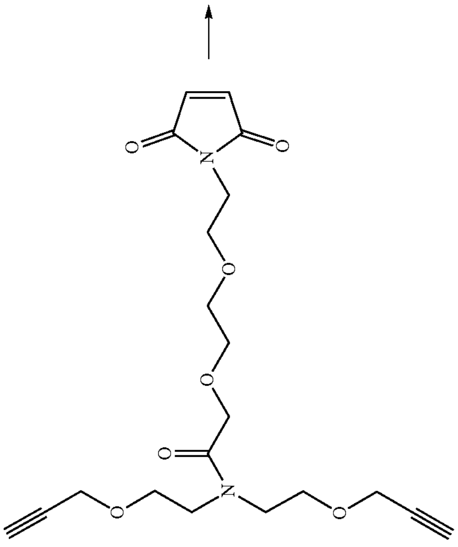
Q-3

-continued
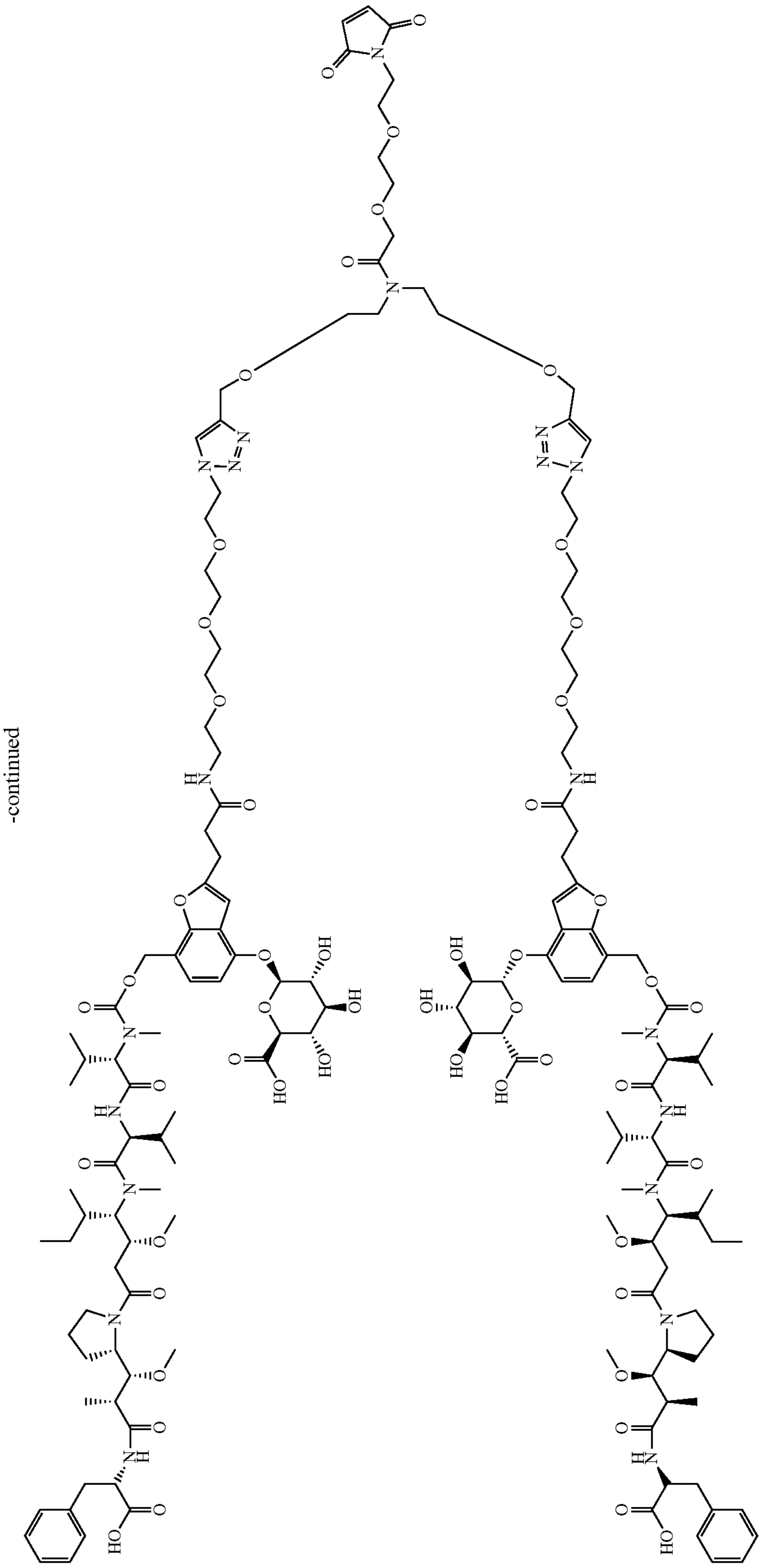
B-44

Compound A-70 (7.7 mg, 0.0056 mmol) was dissolved in DMSO (200 μL) under a nitrogen atmosphere at 0° C., and then 114 μL of a solution of Linker Q-3 (2.1 mg) dissolved in DMSO (0.21 mL) was taken and added to the reaction. Additionally, distilled water (2 mL), DMSO (0.8 mL), copper (II) sulfate pentahydrate ($CuSO_4 \cdot 5H_2O$, 1.54 mg) and sodium ascorbate (2.22 mg) were sequentially added to the reaction solution, and then the mixture was stirred at room temperature for 1 hour. After completion of the reaction, the reaction solution was diluted with distilled water (3 mL), separated and purified using Preparative-HPLC, and then freeze-dried to obtain Compound B-44 in the form of a white solid (6.1 mg, 69%); EI-MS m/z: 1573 1/2 $[M+H]^+$, 1049 1/3 $[M+H]^+$.

Example II-45: Preparation of Compound B-45

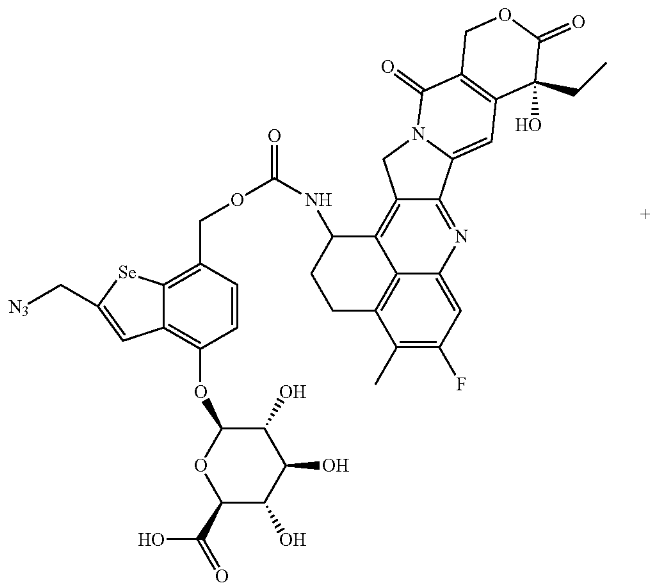

A-71

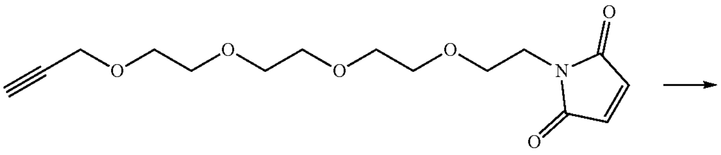

Q-1

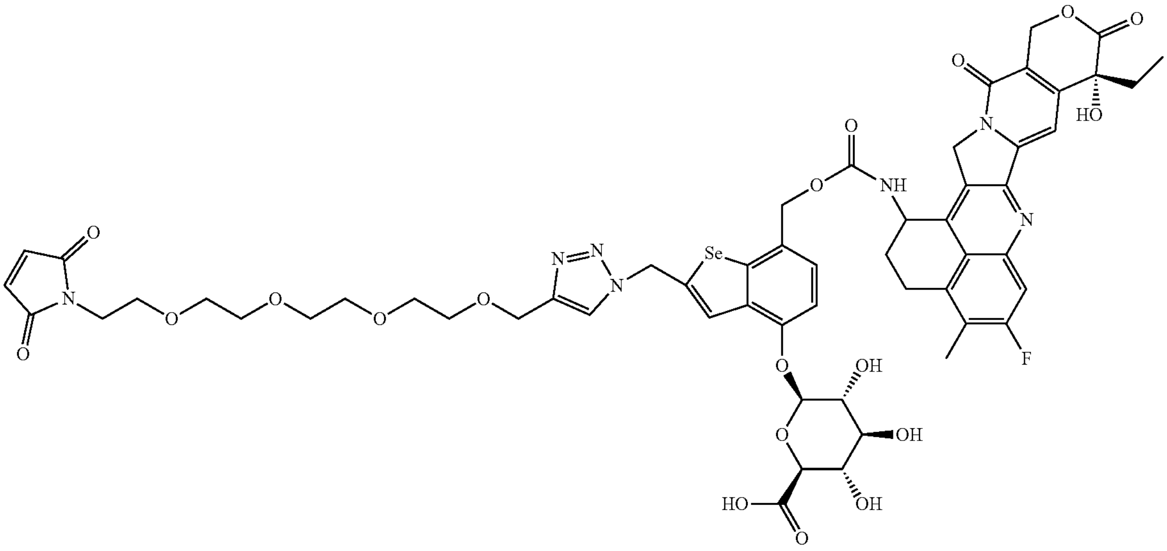

B-45

Compound A-71 (4.6 mg, 0.005 mmol) was dissolved in DMSO (600 μL) under a nitrogen atmosphere at 0° C., and then 200 μL of a solution of Linker Q-1 (4.3 mg) dissolved in DMSO (0.43 mL) was taken and added to the reaction. Additionally, distilled water (2 mL), DMSO (0.6 mL), copper (II) sulfate pentahydrate ($CuSO_4 \cdot 5H_2O$, 1.37 mg) and sodium ascorbate (1.98 mg) were sequentially added to the reaction solution, and then the mixture was stirred at room temperature for 30 minutes. After completion of the reaction, the reaction solution was diluted with distilled water (2 mL) and ACN (2 mL), separated and purified using Preparative-HPLC, and then freeze-dried to obtain Compound B-45 in the form of an ivory solid (4.7 mg, 76%); EI-MS m/z: 1231 $[M+H]^+$, 616 1/2 $[M+H]^+$.

Example 11-46: Preparation of Compound B-46

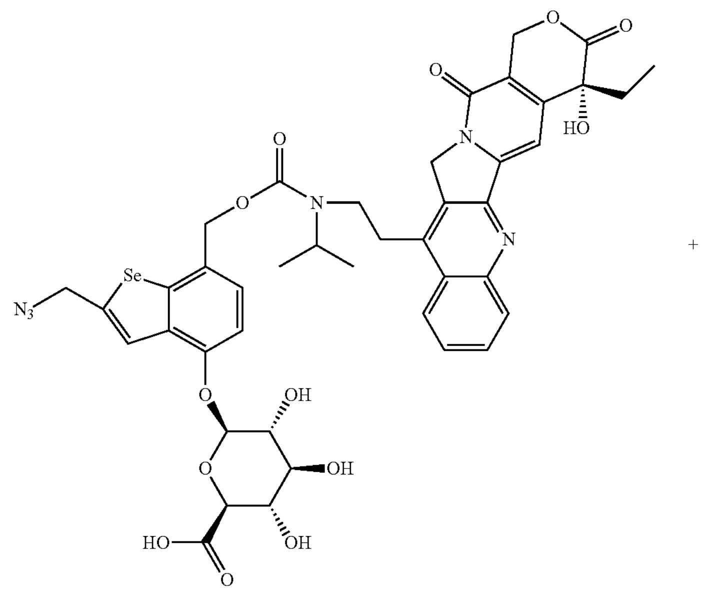

A-73

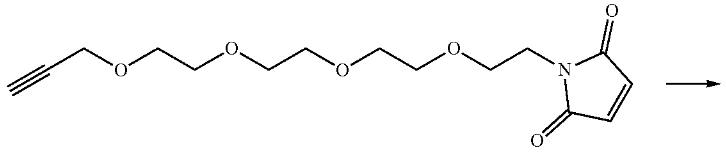

Q-1

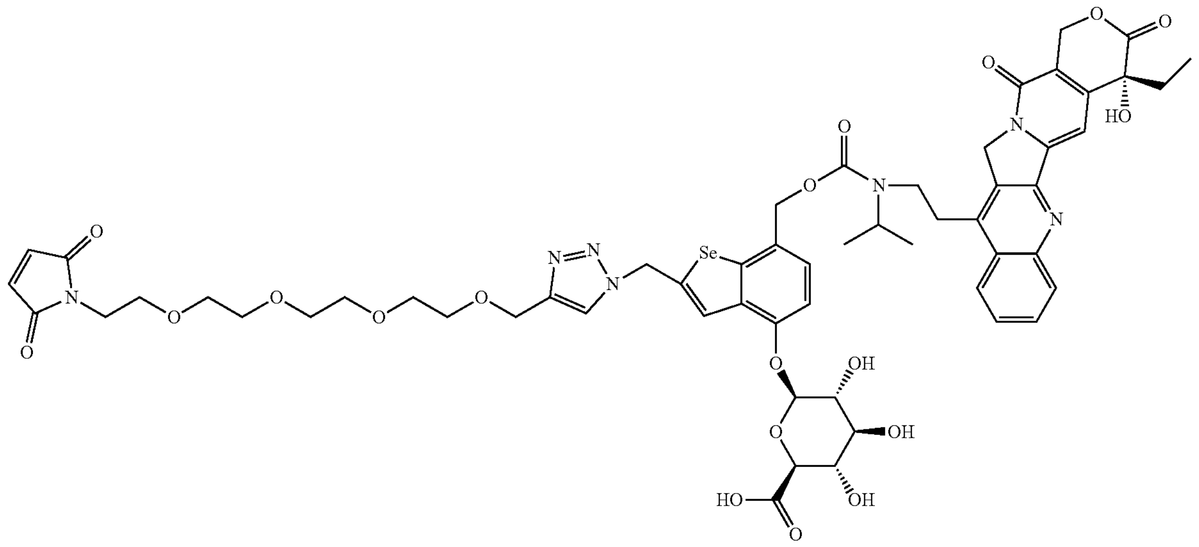

B-46

Compound A-73 (5.8 mg, 0.0063 mmol) was dissolved in DMSO (600 μL) under a nitrogen atmosphere at 0° C., and then 260 μL of a solution of Linker Q-1 (36.7 mg) dissolved in DMSO (3.67 mL) was taken and added to the reaction. Additionally, distilled water (2 mL), DMSO (0.8 mL), copper (II) sulfate pentahydrate ($CuSO_4 \cdot 5H_2O$, 1.73 mg) and sodium ascorbate (2.5 mg) were sequentially added to the reaction solution, and then the mixture was stirred at room temperature for 1 hour. After completion of the reaction, the reaction solution was diluted with distilled water (2 mL) and ACN (2 mL), separated and purified using Preparative-HPL C, and then freeze-dried to obtain Compound B-46 in the form of an ivory solid (5.8 mg, 740%) EI-MS m/z: 1229 $[M+H]^+$, 615 1/2 $[M+H]^+$.

Example II-47: Preparation of Compound B-47

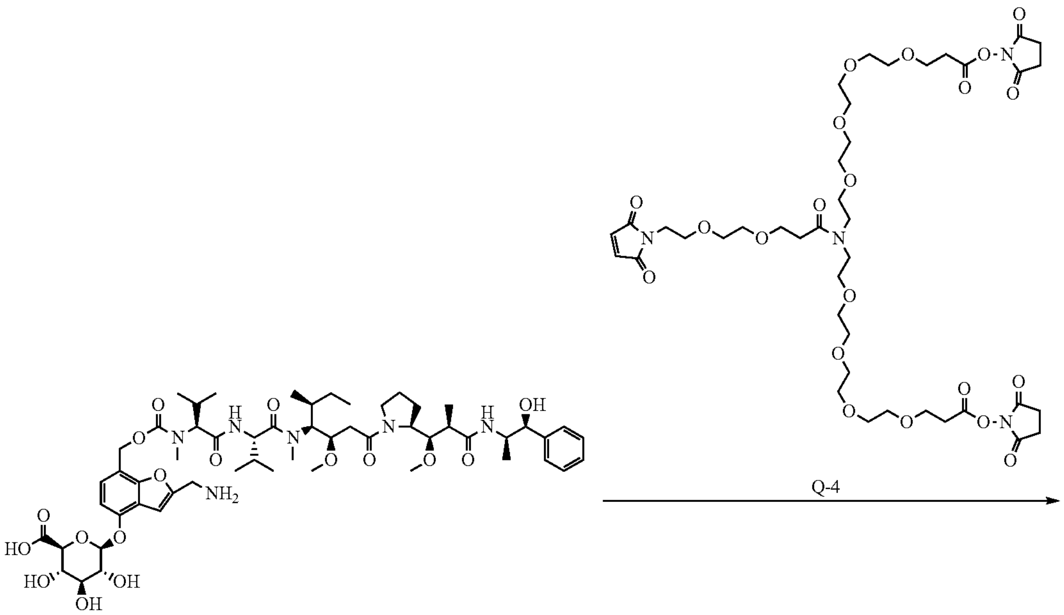

A-65

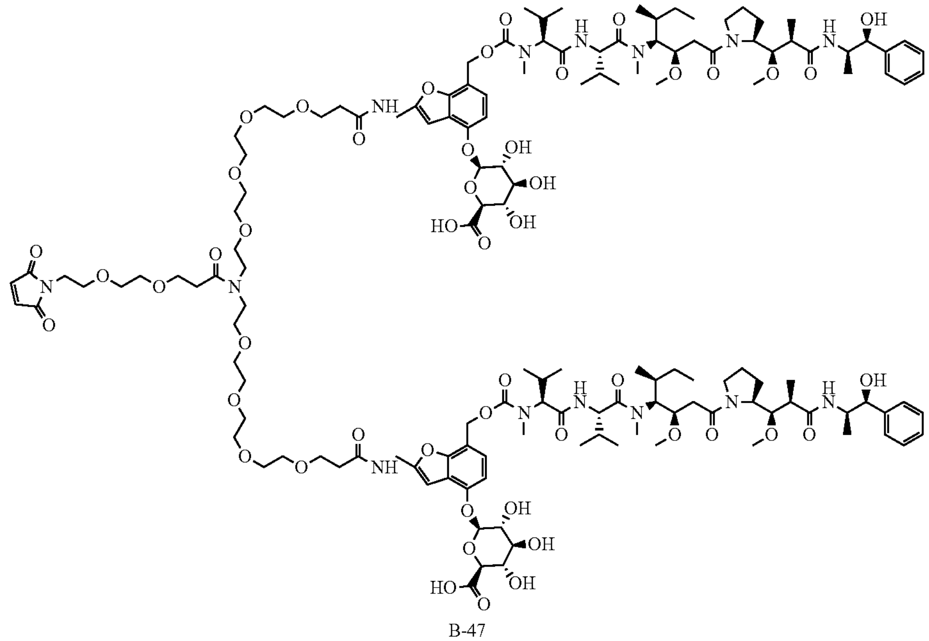

B-47

Compound A-65 (6.1 mg, 0.0055 mmol) was dissolved in THF (1.1 mL) under a nitrogen atmosphere at room temperature, and then Linker Q-4 (2.6 mg, 0.0027 mmol) dissolved in THF (0.9 mL), distilled water (200 μL), DIPEA (10 μL) and pyridine (10 μL) were sequentially added dropwise, and the mixture was stirred for 3 hours. After completion of the reaction, 2N-hydrochloric acid aqueous solution (20 μL) was added, and the reaction solution was diluted with ACN (2 mL) containing 0.1 % formic acid, separated and purified using Preparative-HPLC, and then freeze-dried to obtain Compound B-47 in the form of a white solid (2.1 mg, 13 %), MS m/z: 2944 $[M+H]^+$, 1471 1/2 $[M+H]^+$, 981 1/3 $[M+H]^+$.

Example II-48: Preparation of Compound B-48

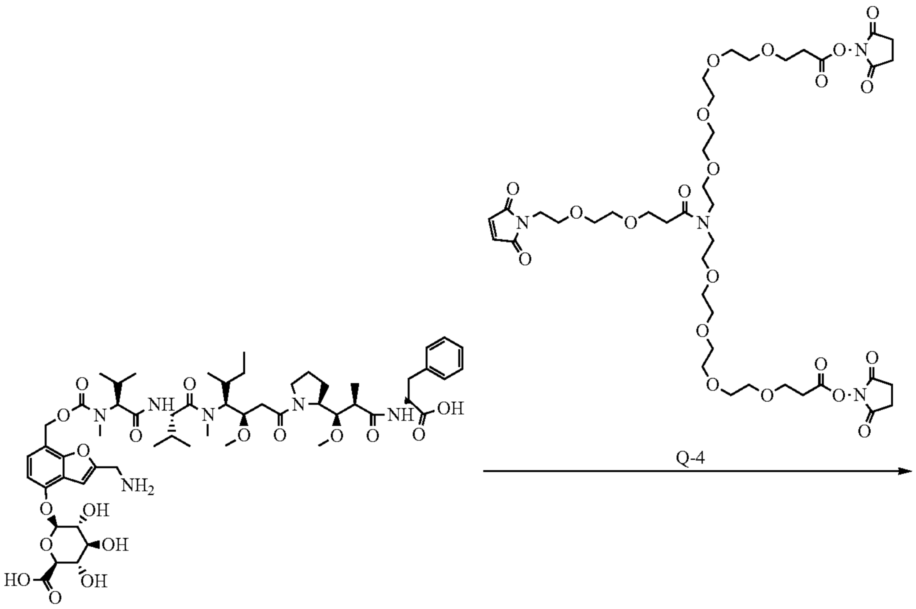

A-67

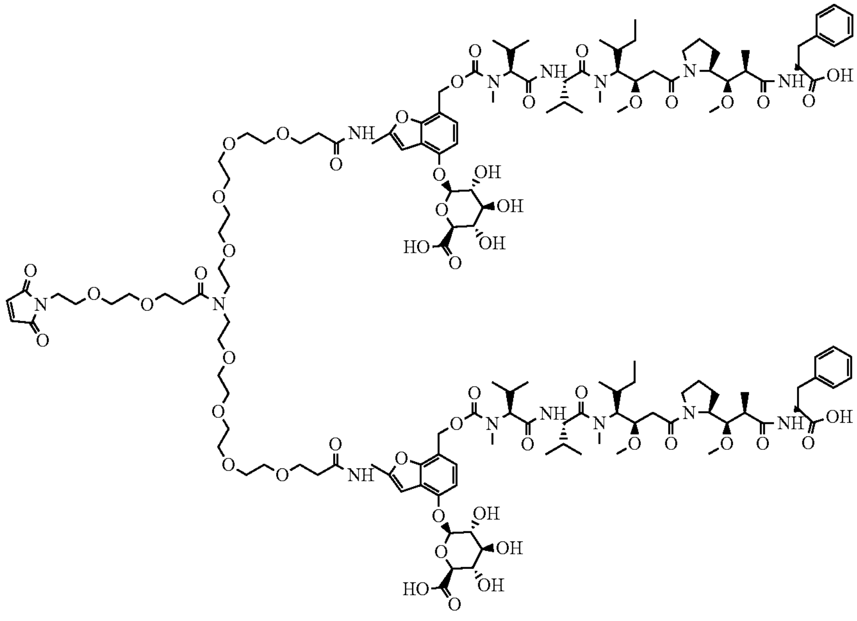

B-48

Compound A-67 (6.2 mg, 0.0055 mmol) was dissolved in THF (0.8 mL) under a nitrogen atmosphere at room temperature, and then Linker Q-4 (2.6 mg, 0.0027 mmol) dissolved in THF (1.2 mL), distilled water (200 μL), DIPEA (10 μL) and pyridine (10 μL) were sequentially added dropwise, and the mixture was stirred for 3 hours. After completion of the reaction, 2N-hydrochloric acid aqueous solution (20 μL) was added, and the reaction solution was diluted with ACN (2 mL) containing 0.1% formic acid, separated and purified using Preparative-HPLC, and then freeze-dried to obtain Compound B-48 in the form of a white solid (2.8 mg, 17%); MS m/z: 2972 $[M+H]^+$, 1485 1/2 $[M+H]^+$, 990 1/3 $[M+H]^+$.

Example II-49: Preparation of Compound B-49

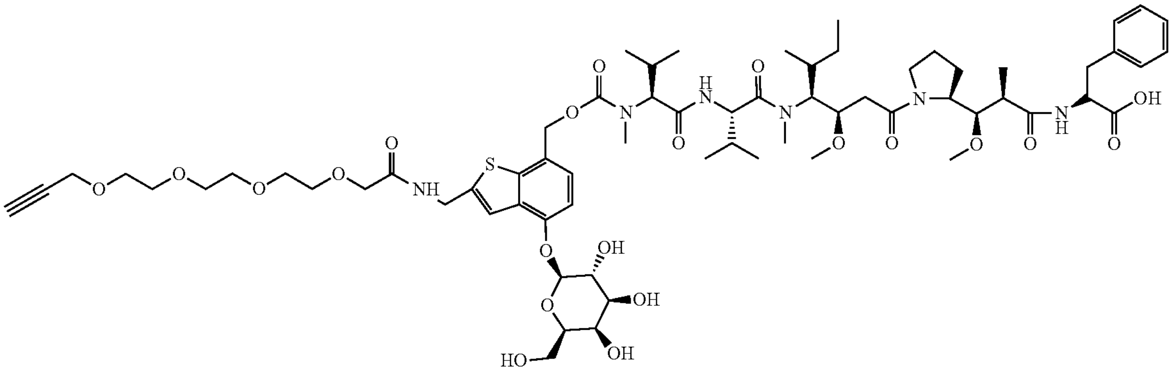

+

A-21

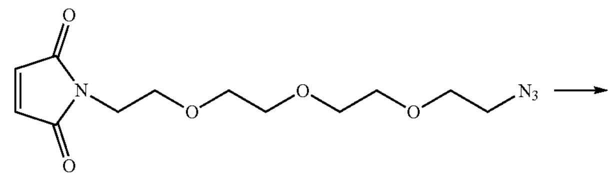

Q-5

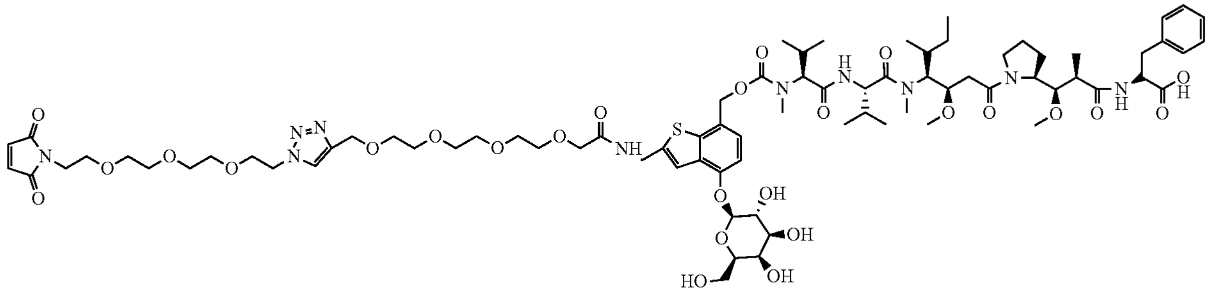

B-49

Compound A-21 (1.7 mg, 0.0012 mmol) was dissolved in DMSO (100 μL) under a nitrogen atmosphere at 0° C., and then 32 μL of a solution of Linker Q-5 (114 mg) dissolved in DMSO (5.7 mL) was taken and added to the reaction. Additionally, distilled water (1 mL), copper (II) sulfate pentahydrate ($CuSO_4 \cdot 5H_2O$, 0.3 mg) and sodium ascorbate (0.5 mg) were sequentially added to the reaction solution, and then the mixture was stirred at room temperature for 20 minutes. After completion of the reaction, the reaction solution was diluted with distilled water (2 mL) and ACN (2 mL), separated and purified using Preparative-HPLC, and then freeze-dried to obtain Compound B-49 in the form of a white solid (1.9 mg, 90%); EI-MS m/z: 1655 $[M+H]^+$, 828 1/2 $[M+H]^+$.

Example II-50: Preparation of Compound B-50

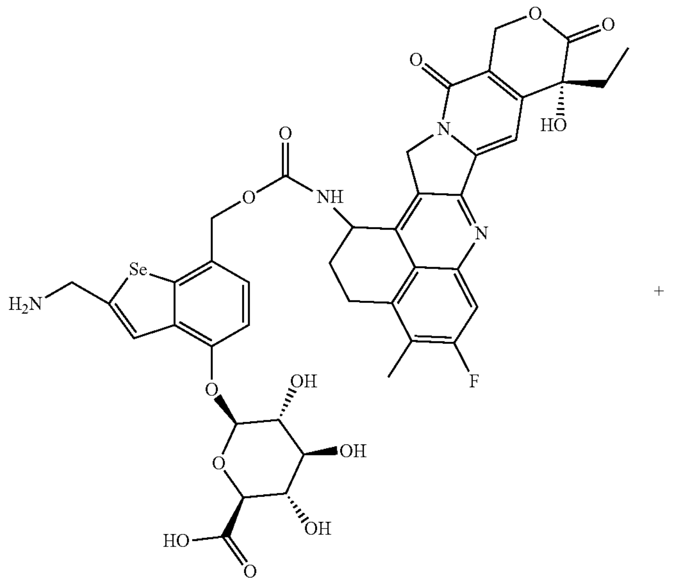

A-74

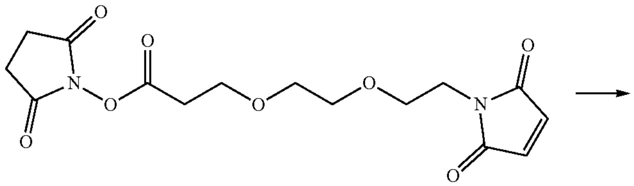

Q-2

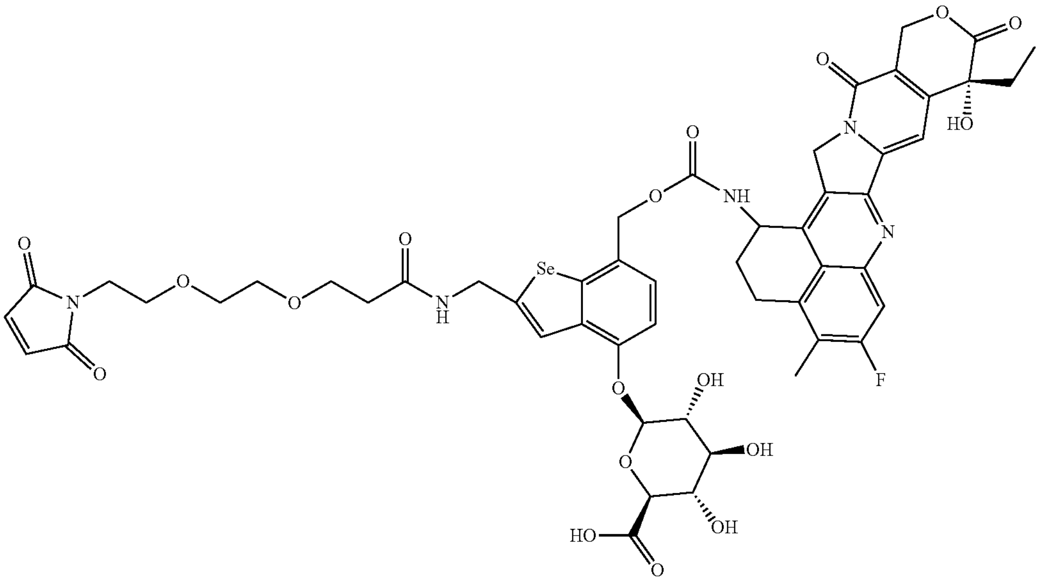

B-50

Compound A-74 (1.2 mg, 0.0013 mmol) was dissolved in THE (1 mL) under a nitrogen atmosphere at room temperature, and then 60 μL of a solution of Linker Q-2 (3.5 mg) dissolved in THE (0.35 mL) was taken and added to the reaction. Additionally, distilled water (0.1 mL), pyridine (10 μL) and DIPEA (10 μL) were sequentially added to the reaction solution, and then the mixture was stirred at room temperature for 1.5 hours. After completion of the reaction, 2N-hydrochloric acid aqueous solution (10 μL) was added, and the reaction solution was diluted with ACN (3 mL) containing 0.1% formic acid, separated and purified using Preparative-HPLC, and then freeze-dried to obtain Compound B-50 (0.2 mg, 13%); EI-MS m/z: 1133 $[M+H]^+$, 566 1/2 $[M+H]^+$.

Example II-51: Preparation of Compound B-51

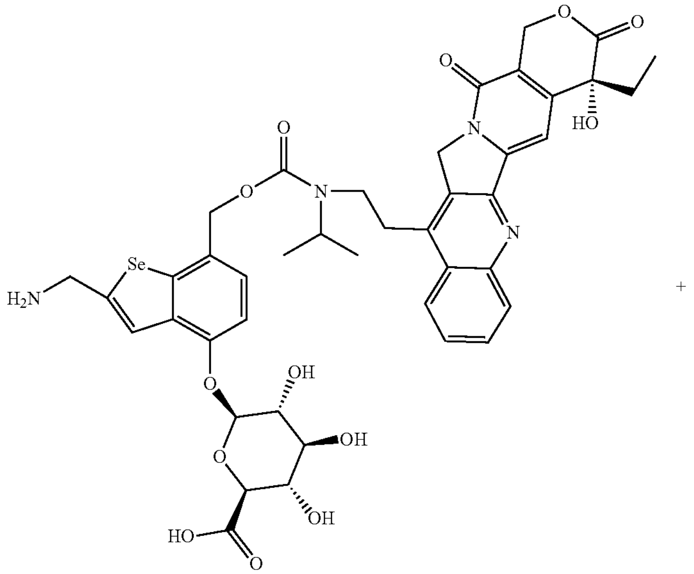

A-75

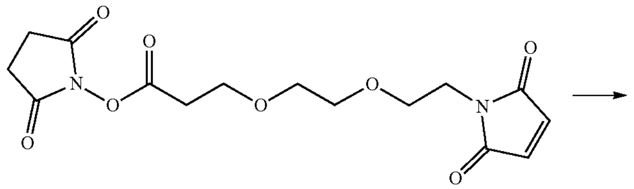

Q-2

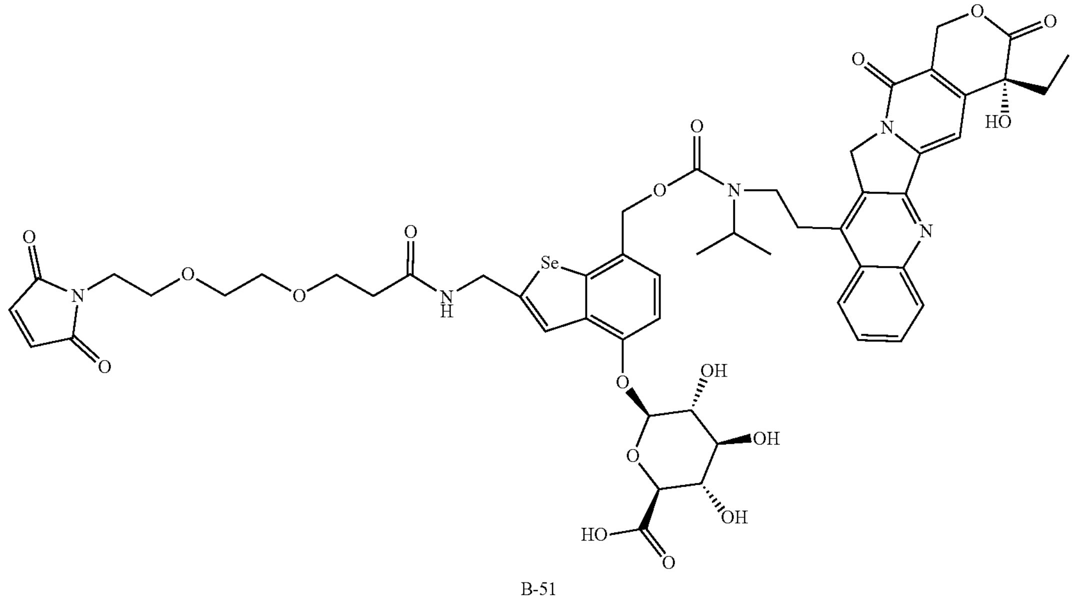

B-51

Compound A-75 (1.3 mg, 0.0014 mmol) was dissolved in THE (2 mL) under a nitrogen atmosphere at room temperature, and then 70 μL of a solution of Linker Q-2 (3.5 mg) dissolved in THE (0.35 mL) was taken and added to the reaction. Additionally, distilled water (0.2 mL), pyridine (10 μL) and DIPEA (10 μL) were sequentially added to the reaction solution, and then the mixture was stirred at room temperature for 1.5 hours. After completion of the reaction, 2N-hydrochloric acid aqueous solution (10 μL) was added, and the reaction solution was diluted with ACN (3 mL) containing 0.1% formic acid, separated and purified using Preparative-HPLC, and then freeze-dried to obtain Compound B-51 in the form of a white solid (0.5 mg, 30%); EI-MS m/z: 1131 $[M+H]^+$, 566 1/2 $[M+H]^+$.

Example II-52: Preparation of Compound B-52

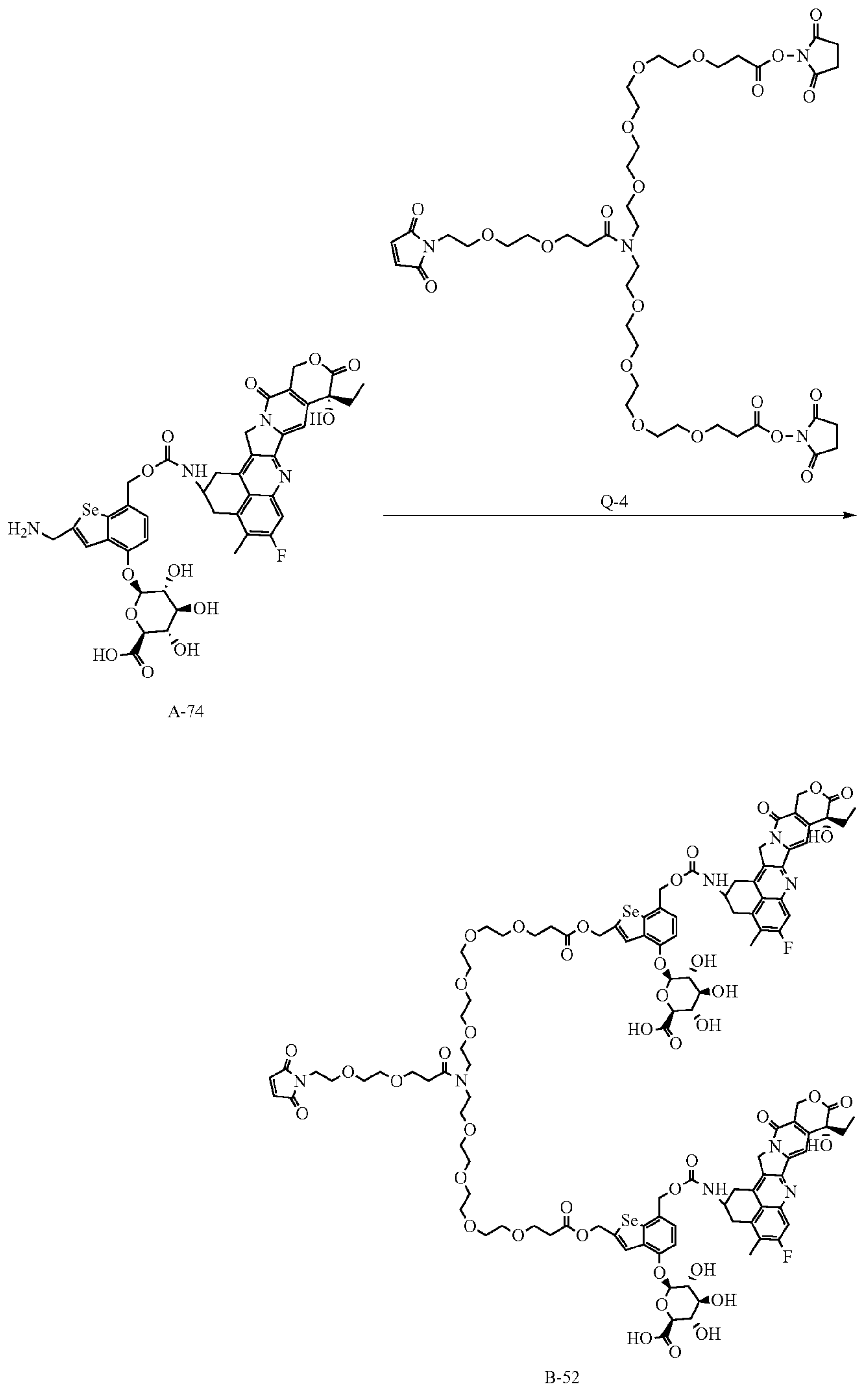

A-74

B-52

Compound A-74 (3.3 mg, 0.0036 mmol) was dissolved in DMF (0.5 mL) under a nitrogen atmosphere at 0° C., and then Linker Q-4 (1.75 mg, 0.0018 mmol) dissolved in DMF (0.5 mL) was added, and additionally, distilled water (20 μL) and TEA (10 μL) were sequentially added dropwise, and the mixture was stirred for 3 hours. After completion of the reaction, 2N-hydrochloric acid aqueous solution (20 μL) was added, and the reaction solution was diluted with distilled water (7 mL) containing 0.1% formic acid, separated and purified using Preparative-HPLC, and then freeze-dried to obtain Compound B-52 in the form of an ivory solid (0.9 mg, 20%); EI-MS m/z: 2505 [M+H]+.

Example II-53: Preparation of Compound B-53

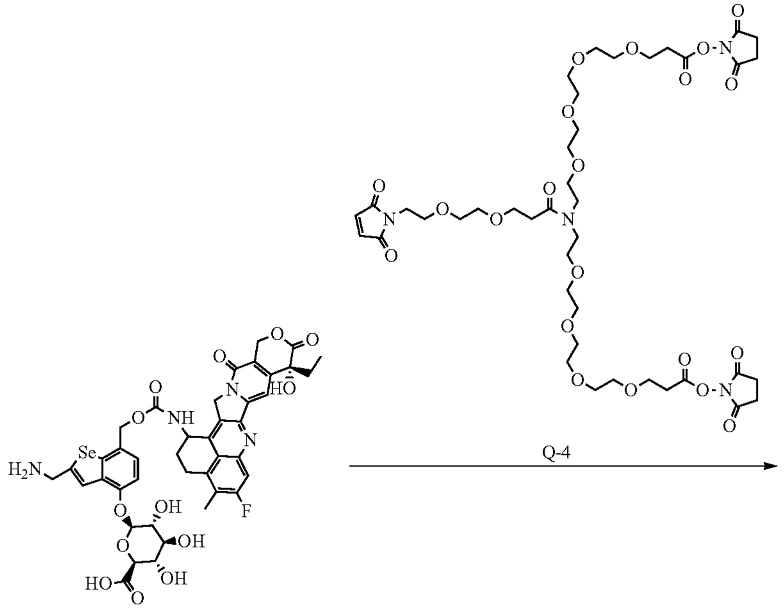

A-75

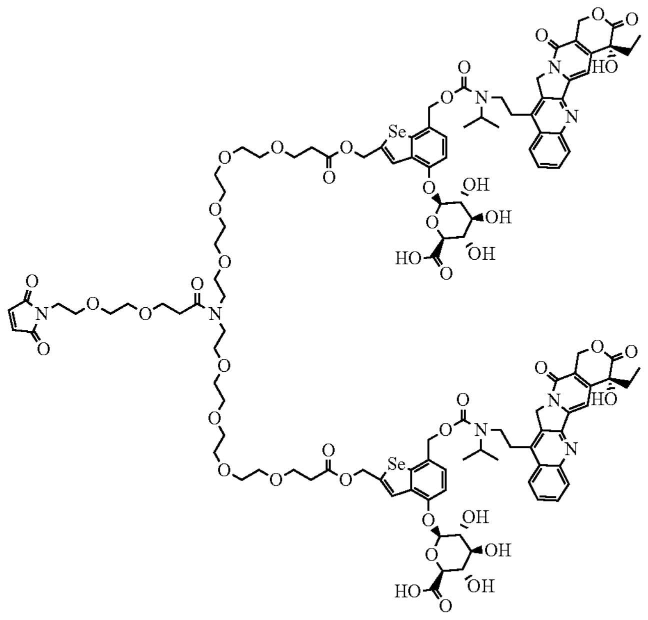

B-53

Compound A-75 (6.6 mg, 0.0074 mmol) was dissolved in THE (1.5 mL) under a nitrogen atmosphere at room temperature, and then Linker Q-4 (3.5 mg, 0.0037 mmol) dissolved in THE (0.5 mL) and distilled water (200 μL), DIPEA (10 μL), pyridine (10 μL), DMF (1 mL) were sequentially added dropwise, and the mixture was stirred for 5 hours. After completion of the reaction, 2N-hydrochloric acid aqueous solution (20 μL) was added, and the reaction solution was diluted with distilled water (7 mL) containing 0.1% formic acid, separated and purified using Preparative-HPLC, and then freeze-dried to obtain Compound B-53 in the form of an ivory solid (2.6 mg, 28%); MS m/z: 2501 $[M+H]^+$, 1250 1/2 $[M+H]^+$, 833 1/3 $[M+H]^+$.

Example 11-54: Preparation of Compound B-54

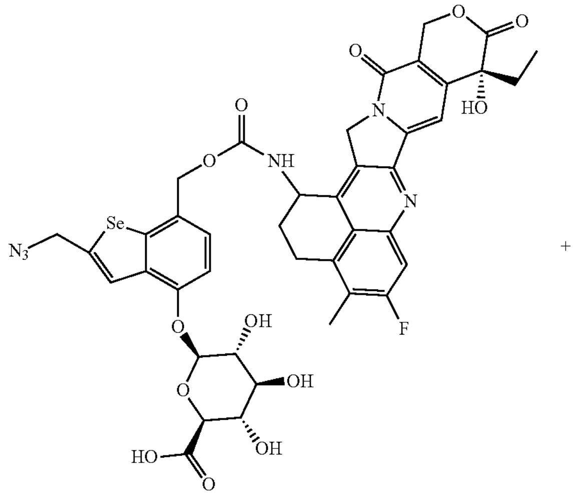

A-71

+

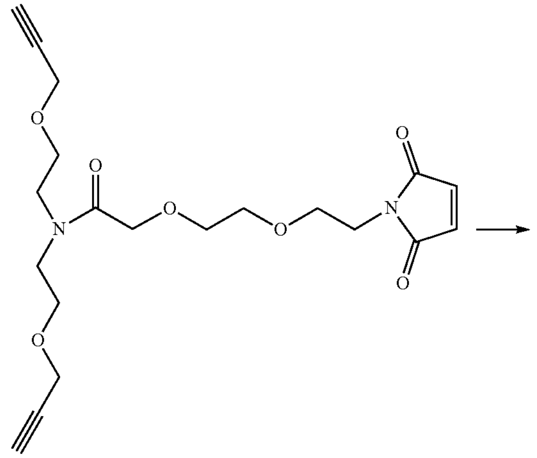

Q-3

-continued

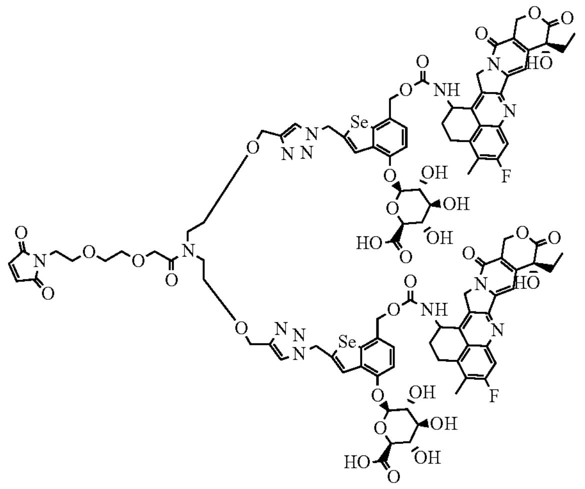

B-54

Compound A-71 (5.8 mg, 0.0063 mmol) was dissolved in DMSO (400 μL) under a nitrogen atmosphere at 0° C., and then 128 μL (3.15 μmol) of a solution of Linker Q-3 (2.4 mg) dissolved in DMSO (0.24 mL) was taken and added to the reaction. Additionally, distilled water (2 mL), DMSO (0.4 mL), copper (II) sulfate pentahydrate ($CuSO_4 \cdot 5H_2O$, 3.1 mg) and sodium ascorbate (4.9 mg) were sequentially added to the reaction solution, and then the mixture was stirred at room temperature for 2 hours. After completion of the reaction, the reaction solution was diluted with ACN (2 mL) and distilled water (6 mL), separated and purified using Preparative-HPLC, and then freeze-dried to obtain Compound B-54 in the form of an ivory solid (3 mg, 42%); EI-MS m/z: 2246 $[M+H]^+$, 1123 1/2 $[M+H]^+$, 749 1/3 $[M+H]^+$.

Example II-55: Preparation of Compound B-55

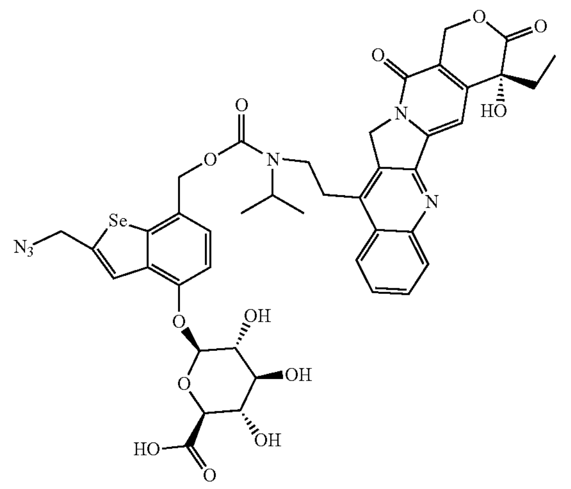

A-73

+

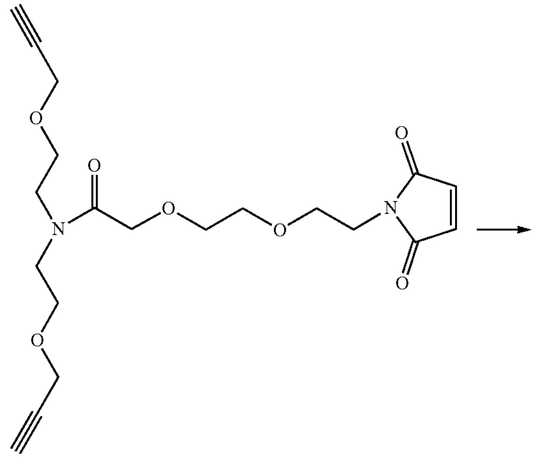

Q-3

-continued

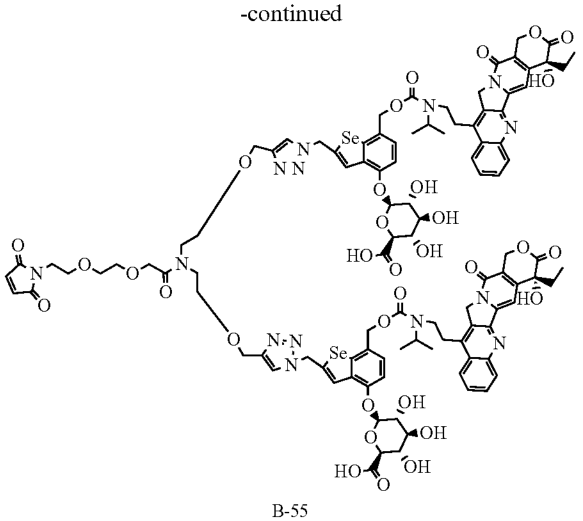

B-55

Compound A-73 (6.1 mg, 0.0066 mmol) was dissolved in DMSO (400 μL) under a nitrogen atmosphere at 0° C., and then 165 μL (4.0 μmol) of a solution of Linker Q-3 (2.4 mg) dissolved in DMSO (0.24 mL) was taken and added to the reaction. Additionally, distilled water (2 mL), DMSO (1 mL), copper (II) sulfate pentahydrate ($CuSO_4 \cdot 5H_2O$, 3.1 mg) and sodium ascorbate (5.2 mg) were sequentially added to the reaction solution, and then the mixture was stirred at room temperature for 2 hours. After completion of the reaction, the reaction solution was diluted with ACN (2 mL) and distilled water (6 mL), separated and purified using Preparative-HPLC, and then freeze-dried to obtain Compound B-55 in the form of an ivory solid (3.9 mg, 52%); EI-MS m/z: 2241 $[M+H]^+$, 1121 1/2 $[M+H]^+$, 748 1/3 $[M+H]^+$.

Example II-56: Preparation of Compound B-56

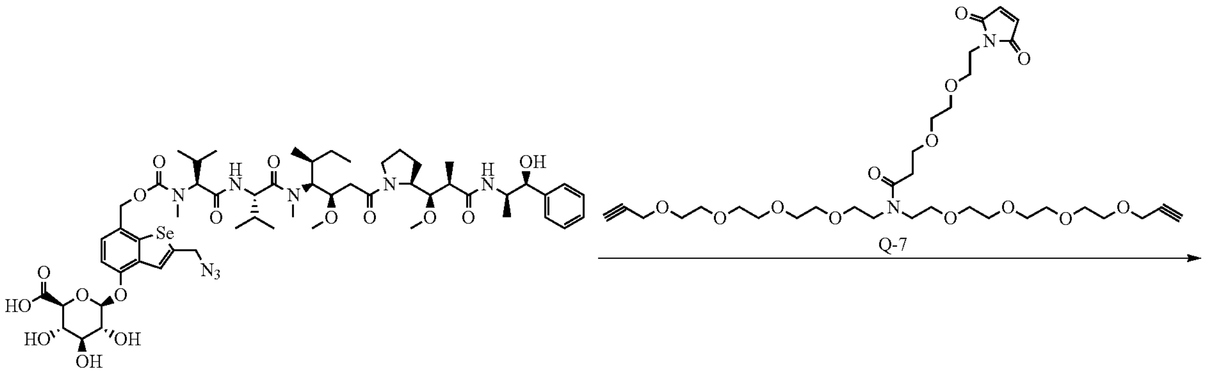

A-52

-continued

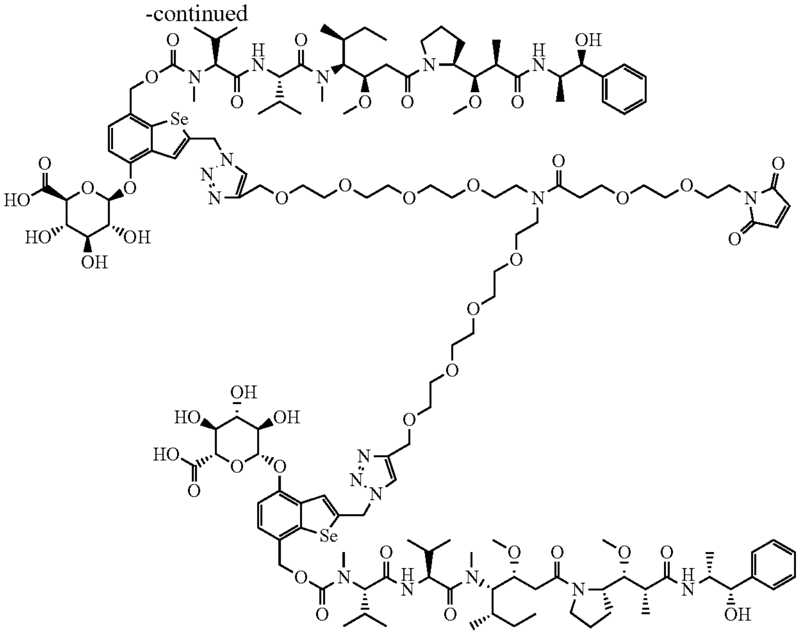

B-56

Compound A-52 (5.0 mg, 0.0041 mmol) was dissolved in DMSO (2 mL) under a nitrogen atmosphere at room temperature, and then 130 μL of a solution of Linker Q-7 (10.9 mg) dissolved in DMSO (1.0 mL) was taken and added to the reaction. Additionally, distilled water (2 mL), copper (II) sulfate pentahydrate ($CuSO_4 \cdot 5H_2O$, 1.0 mg), sodium ascorbate (1.3 mg) were sequentially added to the reaction solution, and then the mixture was stirred for 4 hours. After completion of the reaction, the reaction solution was diluted with distilled water (2 mL), separated and purified using Preparative-HPLC, and then freeze-dried to obtain Compound B-56 in the form of a white solid (2.0 mg, 31.2%); EI-MS m/z: 1544 1/2 $[M+H]^+$, 1030 1/3 $[M+H]^+$.

Example II-57: Preparation of Compound B-57

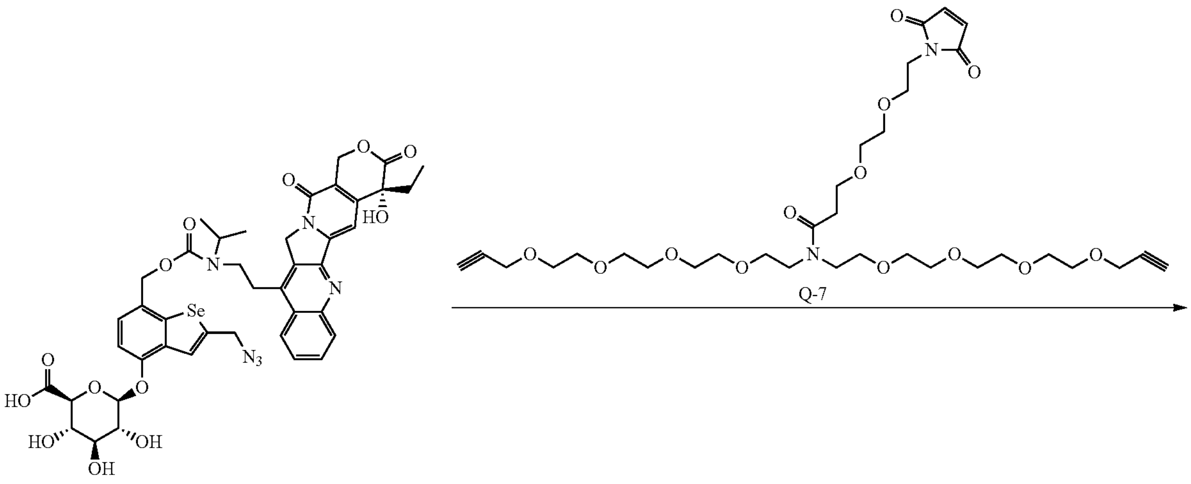

A-73

Q-7

-continued

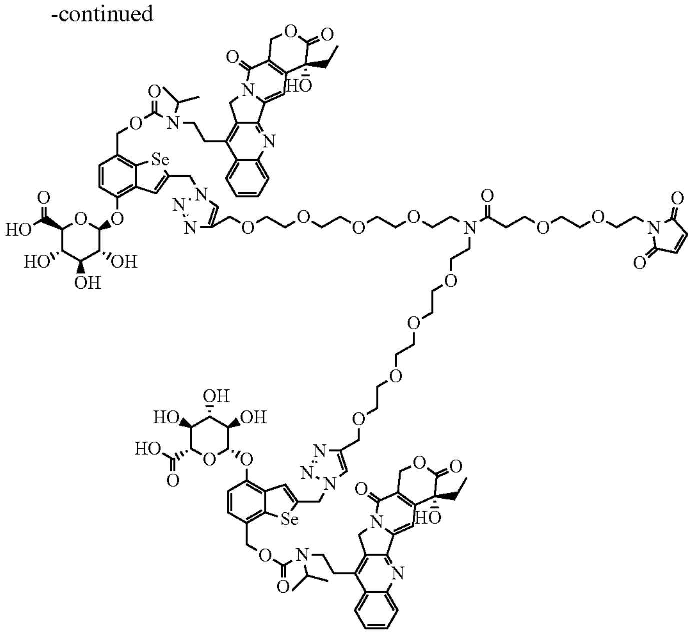

B-57

Compound A-73 (7.3 mg, 0.0079 mmol) was dissolved in DMSO (2 mL) under a nitrogen atmosphere at room temperature, and then 250 μL of a solution of Linker Q-7 (10.9 mg) dissolved in DMSO (1.0 mL) was taken and added to the reaction. Additionally, distilled water (2 mL), copper (II) sulfate pentahydrate ($CuSO_4 \cdot 5H_2O$, 1.0 mg), sodium ascorbate (1.3 mg) were sequentially added to the reaction solution, and then the mixture was stirred for 4 hours. After completion of the reaction, the reaction solution was diluted with distilled water (2 mL), separated and purified using Preparative-HPLC, and then freeze-dried to obtain Compound B-57 in the form of a white solid (2.8 mg, 28%); EI-MS m/z: 2521 $[M+H]^+$, 1260 1/2 $[M+H]^+$, 840 1/3 $[M+H]^+$.

Example II-58: Preparation of Compound B-58

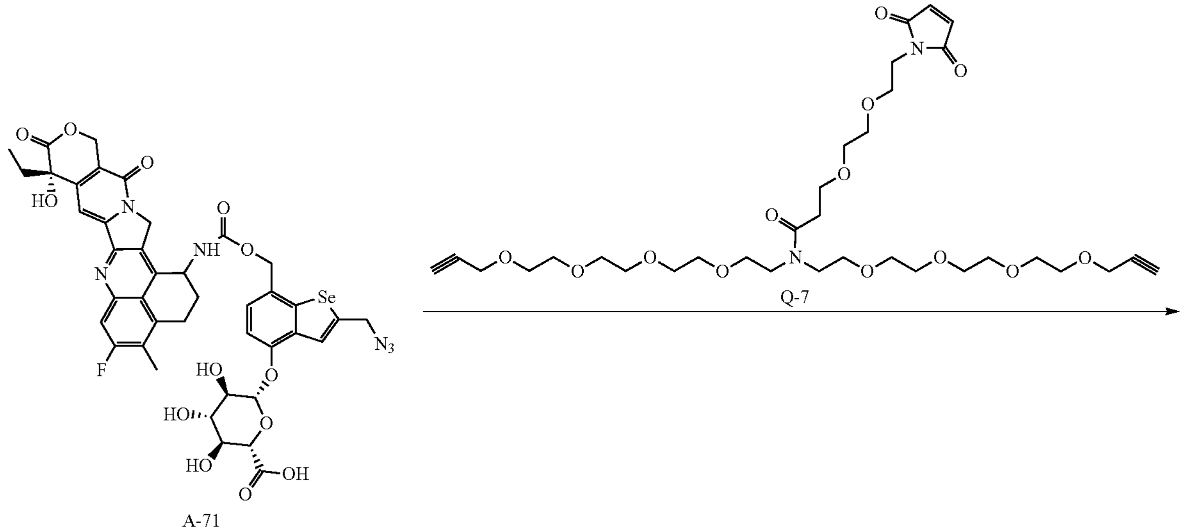

A-71

-continued

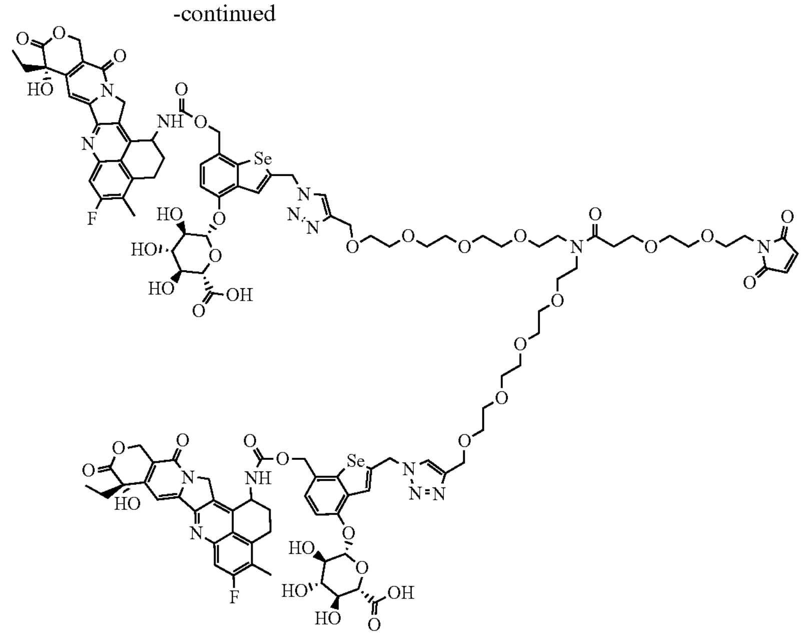

B-58

Compound A-71 (4.2 mg, 0.0045 mmol) was dissolved in DMSO (2 mL) under a nitrogen atmosphere at room temperature, and then 143 μL of a solution of Linker Q-7 (10.9 mg) dissolved in DMSO (1.0 mL) was taken and added to the reaction. Additionally, distilled water (2 mL), copper (II) sulfate pentahydrate ($CuSO_4 \cdot 5H_2O$, 1.0 mg), sodium ascorbate (1.3 mg) were sequentially added to the reaction solution, and then the mixture was stirred for 4 hours. After completion of the reaction, the reaction solution was diluted with distilled water (2 mL), separated and purified using Preparative-HPLC, and then freeze-dried to obtain Compound B-58 in the form of a white solid (1.2 mg, 21%); EI-MS m/z: 2524 $[M+H]^+$, 1263 1/2 $[M+H]^+$, 842 1/3 $[M+H]^+$.

Example III: Preparation of Antibody-Drug Conjugate (ADC)

Referring to the methods described in Nature Biotechnology, 2008, 26, 925-932; Bioconjugate Chem., 2013, 24, 1256-1263; Bioconjugate Chem., 2016, 27, 1324-1331; Bioconjugate Chem. 2014, 25, 460-469, etc., Compounds B-1 to B-10, B-15, B-14, B-30, B-33, B34, B-19, B-17, B-36, and B-35 were each specifically bound to Herceptin substituted with a thiol group at a specific position to produce ADC-1 to ADC-19, respectively, as a thiomab drug conjugate (TDC). The structures of ADC-1 to ADC-19 are shown in Tables D and E. At this time, the ratio of drug bound to the antibody (DAR, drug-antibody ratio) was measured using HPLC. Herceptin (Trastuzumab) used in this example was purchased from Y Biologics Co., Ltd., and this was produced by substituting alanine at position 149 of the antibody light chain with cysteine through a genetic recombination method, transiently injecting DNA into HEK293 cells using transient transfection, and purifying the antibody secreted into the culture solution.

Test Example 1: Kinetic Study of Enzymatic Reaction Rate Using Enzyme Cleavage Assay Method 1: *E. coli* β-Galactosidase Enzyme The compounds of the present invention (A-15, A-16, A-19, A-21, A-22, A-23, A-25, A-28 and A-29) were each dissolved in DMSO (dimethylsulfoxide: Sigma, SA-276855-1L) to a concentration of 10 mM, and then mixed with a PBS (pH 7.4; Hyclone, SH30256.01) buffer solution to prepare a solution having a concentration of 500 μM (5% DMSO). MPS (Methylphenylsulfoxide: Alfa aesar, A15009-5G), used as a standard material, was also prepared as a solution having a concentration of 500 μM in a PBS buffer solution. 415.8 μL of a PBS buffer solution and 140 μL of each of 500 μM compounds of the present invention and MPS were mixed, and then 4.2 μL of 3.36 mg/mL enzyme solution was added to prepare a total of 700 μL of enzymatic reaction solution. When comparing with human β-galactosidase, 21 μL of 1 mg/mL enzyme solution was added to achieve the same molar concentration, and 140 μL of each of the compound of the present invention and MPS were mixed with 399 μL of a PBS buffer solution.

The reaction of all conditions was initiated in a constant temperature incubator at 37° C. *E. coli* 3-galactosidase enzyme (Sigma, G4155) was used in the reaction mixture. The enzymatic reaction solution was aliquoted in an amount of 70 μL at 0 minutes before the reaction and at certain times after the reaction, and the remaining compounds of the present invention or MPS and substances liberated by the enzymatic reaction were quantitatively analyzed using the HPLC method.

Method 2: Human β-Galactosidase Enzyme

Compound A-22 was dissolved in DMSO to a concentration of 10 mM and then mixed with a PBS buffer solution to prepare as a solution having a concentration of 500 μM (5% DMSO). MPS, used as a standard material, was also prepared as a solution having a concentration of 500 M in a PBS buffer solution. 200 μL of 50 mM sodium citrate buffer solution (pH 4.5) and 100 L of each of 500 μM Compound A-22 of the present invention and MPS were mixed, and then 100 μL of 0.1 mg/mL enzyme solution was added to prepare a total of 500 μL of enzymatic reaction solution. The reaction of this solution was initiated in a constant temperature incubator at 37° C. Human β-galactosidase enzyme (R&D, 6464-GH-020) was used in the reaction mixture. The enzymatic reaction solution was aliquoted in an amount of 50 μL at 0 minutes before the reaction and at certain times after the reaction, and the remaining Compound A-22 or MPS and MMAF (monomethyl auristatin F) liberated by the enzymatic reaction were quantitatively analyzed using the HPLC method.

Method 3: *E. coli* β-Glucuronidase Enzyme

The compounds of the present invention (A-36 and A-69) were dissolved in DMSO to a concentration of 10 mM and then mixed with a PBS buffer solution to prepare as a solution having a concentration of 500 μM (5% DMSO). MPS, used as a standard material, was also prepared as a solution having a concentration of 500 μM in a PBS buffer solution. 406 μL of a PBS buffer solution (pH 7.4) and 140 μL of each of 500 μM compounds of the present invention and MPS were mixed, and then 14 μL of 1 mg/mL enzyme solution was added to prepare a total of 700 μL of enzymatic reaction solution. The reaction of this solution was initiated in a constant temperature incubator at 37° C. *E. coli* β-glucuronidase enzyme (Sigma G7396) was used in the reaction mixture. The enzymatic reaction solution was aliquoted in an amount of 70 μL at 0 minutes before the reaction and at certain times after the reaction, and the remaining compounds of the present invention or MPS and substances liberated by the enzymatic reaction were quantitatively analyzed using the HPLC method.

Method 4: Human β-Glucuronidase Enzyme

The compounds of the present invention (A-36 and A-69) were dissolved in DMSO to a concentration of 10 mM and then mixed with a PBS buffer solution to prepare as a solution having a concentration of 500 μM (5% DMSO). MPS, used as a standard material, was also prepared as a solution having a concentration of 500 μM in a PBS buffer solution. 200 μL of 50 mM sodium citrate buffer solution (pH 4.5) and 100 μL of each of 500 μM compounds of the present invention and MPS were mixed, and then 100 μL of 0.1 mg/mL enzyme solution was added to prepare a total of 500 μL of enzymatic reaction solution. The reaction of this solution was initiated in a constant temperature incubator at 37° C. Human β-glucuronidase enzyme (R&D Systems, 6144-GH-020) was used in the reaction mixture. The enzymatic reaction solution was aliquoted in an amount of 50 μL at 0 minutes before the reaction and at certain times after the reaction, and the remaining compounds of the present invention or MPS and MMAE (monomethyl auristatin E) liberated by the enzymatic reaction were quantitatively analyzed using the HPLC method.

The results of measuring the payload release half-life of the compounds of the present invention using Methods 1, 2, 3 and 4 above are shown in Table 1. In addition, the results of measuring the enzyme cleavage rates of Compounds A-15, A-23, A-36 and A-69 are shown in FIGS. 1 to 4, respectively.

TABLE 1

| Compounds of the present invention | Payload release $t_{1/2}$ (min) | Test method | pH condition |
|---|---|---|---|
| A-15 | 9.4 | Method 1 | 7.4 |
| A-16 | 22.5 | Method 1 | 7.4 |
| A-19 | 4.8 | Method 1 | 7.4 |
| A-21 | 4.7 | Method 1 | 7.4 |
| A-22 | 1.4 | Method 1 | 7.4 |
| | 6.4 | Method 2 | 4.5 |
| A-23 | 1.4 | Method 1 | 7.4 |
| A-25 | 0.7 | Method 1 | 7.4 |
| A-28 | 1.0 | Method 1 | 7.4 |
| A-29 | 27.5 | Method 1 | 7.4 |
| A-36 | 1.0 | Method 3 | 7.4 |
| | 6.5 | Method 4 | 4.5 |
| A-69 | 2.4 | Method 3 | 7.4 |
| | 13.2 | Method 4 | 4.5 |

From the results in Table 1 above and FIGS. 1 to 4, it was confirmed that the compounds of the present invention were rapidly degraded by β-galactosidase or β-glucuronidase and efficiently released the payload.

Test Example 2: Chemical Stability

The compounds of the present invention (A-15, A-16, A-19, A-21 to A-25, A-28, A-29, A-36 and A-69) were each dissolved in DMSO to a concentration of 10 mM and then mixed with a PBS buffer solution (pH 7.4) to prepare as a solution having a concentration of 500 μM (5% DMSO). MPS, used as a standard material, was also prepared as a solution having a concentration of 500 μM in a PBS buffer solution. 420 μL of a PBS buffer solution and 140 μL of each of 500 μM compounds of the present invention and MPS were mixed to prepare a total of 700 μL of reaction solution. The reaction of the mixed solution was initiated in a constant temperature incubator at 37° C. The reaction solution was aliquoted in an amount of 70 μL at 0 minutes before the reaction and at certain times after the reaction, and the remaining compounds of the present invention or MPS or the liberated MMAF or MMAE were quantitatively analyzed using the HPLC method. The results of measuring the half-life of the compounds of the present invention in a PBS buffer solution (pH 7.4) are shown in Table 2 below. In addition, the remaining amount of Compound A-69 in a PBS buffer solution (pH 7.4) according to the incubation time is shown in FIG. 5.

TABLE 2

| Compounds of the present invention | Chemical stability $t_{1/2}$ (day) |
|---|---|
| A-15 | >7 |
| A-16 | >7 |
| A-19 | >7 |
| A-21 | >7 |
| A-22 | >7 |
| A-23 | >7 |
| A-24 | >7 |
| A-25 | >7 |
| A-28 | >7 |
| A-29 | >7 |
| A-36 | >7 |
| A-69 | >7 |

Referring to Table 2 above and FIG. 5, it was confirmed that the compounds of the present invention are chemically stable in a neutral buffer solution for a long time.

Test Example 3: Plasma Stability Test

Method 1: Mouse Plasma Stability

The compounds of the present invention (A-16, A-22, A-25, A-36, A-69) and MPS, used as a standard material, were each dissolved in DMSO and a PBS buffer solution to a concentration of 30 mM, and then mixed in mouse plasma (Biochemed, 029-APSC-PMG) to a final concentration of 300 μM (final 1.0% DMSO) and 600 μM of the compounds and MPS, respectively. The reaction of the mixed solution in plasma was initiated in a constant temperature incubator at 37° C. Before the reaction and on certain days after the reaction, the above samples were aliquoted in an amount of 100 μL, and 200 μL of acetonitrile (ACN, Sigma, SA-271004-1L) was added to terminate the reaction, mixed, and then vortexed for about 1 minute, and then centrifuged (Beckman, B30150) at 4° C. for 15 minutes at 14,000 rpm to precipitate plasma proteins. Each supernatant obtained by centrifugation was collected and quantitatively analyzed using the HPLC method.

Method 2: Human Plasma Stability

The compounds of the present invention (A-19, A-22, A-25, A-36, A-69) and MPS, used as a standard material, were each dissolved in DMSO and a PBS buffer solution to a concentration of 30 mM, and then mixed in human plasma (Biochemed, 752PR-SC-PMG) to a final concentration of 300 μM (final 1.0% DMSO) and 600 μM of the compounds and MPS, respectively. The reaction of the mixed solution in plasma was initiated in a constant temperature incubator at 37° C. Before the reaction and on certain days after the reaction, the above samples were aliquoted in an amount of 100 μL, and 200 μL of ACN was added to terminate the reaction, mixed, and then vortexed for about 1 minute, and then centrifuged at 4° C. for 15 minutes at 14,000 rpm to precipitate plasma proteins. Each supernatant obtained by centrifugation was collected and quantitatively analyzed using the HPLC method.

Method 3: Rat Plasma Stability

The compounds of the present invention (A-22, A-69) and MPS, used as a standard material, were each dissolved in DMSO and a PBS buffer solution to a concentration of 30 mM, and then mixed in rat plasma (Biochemed, 031-APSC-PMG) to a final concentration of 300 μM (final 1.0% DMSO) and 600 μM of the compounds and MPS, respectively. The reaction of the mixed solution in plasma was initiated in a constant temperature incubator at 37° C. Before the reaction and on certain days after the reaction, the above samples were aliquoted in an amount of 100 μL, and 200 μL of ACN was added to terminate the reaction, mixed, and then vortexed for about 1 minute, and then centrifuged at 4° C. for 15 minutes at 14,000 rpm to precipitate plasma proteins. Each supernatant obtained by centrifugation was collected and quantitatively analyzed using the HPLC method.

Method 4: Beagle Dog Plasma Stability

The compounds of the present invention (A-22, A-69) and MPS, used as a standard material, were each dissolved in DMSO and a PBS buffer solution to a concentration of 30 mM, and then mixed in beagle dog plasma (Biochemed, 014-APSC-PMG) to a final concentration of 300 μM (final 1.0% DMSO) and 600 μM of the compounds and MPS, respectively. The reaction of the mixed solution in plasma was initiated in a constant temperature incubator at 37° C. Before the reaction and on certain days after the reaction, the above samples were aliquoted in an amount of 100 μL, and 200 μL of ACN was added to terminate the reaction, mixed, and then vortexed for about 1 minute, and then centrifuged at 4° C. for 15 minutes at 14,000 rpm to precipitate plasma proteins. Each supernatant obtained by centrifugation was collected and quantitatively analyzed using the HPLC method.

The results of measuring the plasma half-life of the compounds of the present invention using Methods 1 to 4 above are shown in Table 3. In addition, the remaining amount of Compound A-69 in plasma according to the incubation time is shown in FIG. 5.

TABLE 3

| Compounds of the present invention | Plasma stability $t_{1/2}$ (day) | Test method |
|---|---|---|
| A-16 | >7 | Method 1(mouse plasma) |
| A-19 | >7 | Method 2(human plasma) |
| A-22 | >7 | Method 1(mouse plasma) |
| | >7 | Method 2(human plasma) |
| | >7 | Method 3(rat plasma) |
| | >7 | Method 4 (beagle dog plasma) |
| A-25 | >7 | Method 1(mouse plasma) |
| | >7 | Method 2(human plasma) |
| A-36 | >7 | Method 1(mouse plasma |
| | >7 | Method 2(human plasma) |
| A-69 | >7 | Method 1(mouse plasma) |
| | >7 | Method 2(human plasma) |
| | >7 | Method 3(rat plasma) |
| | >7 | Method 4 (beagle dog plasma) |

Referring to Table 3 and FIG. 5, it was confirmed that the compounds of the present invention are stable in plasma for a long time.

Test Example 4: In Vitro Analysis of Antibody-Drug Conjugate

Method 1: Cell Cytotoxicity (JIMT-1) Experiment

JIMT-1 breast cancer cell line (DSMZ, ACC589) was prepared at a density of 40,000 cells per 1 mL of DMEM culture solution (Hyclone, SH30243.01) containing 10% fetal bovine serum (Hyclone, SH30919.03) and 1% antibiotic-antimycotic solution (Hyclone, SV30079.01), then dispensed into a 96-well plate (Sarstedt, 83.3924) at 100 mL (4,000 cells) per well, and cultured in a $CO_2$ constant temperature incubator (Forma, 51030303-TIF) for 24 hours. The cells were treated with 19 antibody-drug conjugates prepared in Example III, serially diluted in 1/3 from 41 nM to 0.0020 nM. In order to quantify living cells 96 hours later, 20 mL of MTS dye solution (Promega, G3581) was added to each well of the plate and left in a $CO_2$ constant temperature incubator for 4 hours. The absorbance of formazan formed by reduction of MTS (3-(4,5-dimethylthiazol-2-yl)-5-(3-carboxymethoxyphenyl)-2-(4-sulfophenyl)-2H-tetrazolium, inner salt) dye by mitochondrial oxidoreductase within the cell was measured at 490 nm using a spectrometer (Promega, GM3000) and then analyzed using the GraphPad Prism 7 program. The results of the cytotoxicity test of the antibody-drug conjugates are shown in Table 4 below.

Method 2: Cell Cytotoxicity (NCI-N87) Experiment

NCI-N87 gastric cancer cell line (Korean Cell Line Bank, 60113) was prepared at a density of 100,000 cells per 1 mL of RPMI1640 culture solution (Hyclone, SH30027.01) containing 10% fetal bovine serum (Hyclone, SH30919.03) and 1% antibiotic-antimycotic solution (Hyclone, SV30079.01), then dispensed into a 96-well plate (Sarstedt, 83.3924) at 100 mL (10,000 cells) per well, and cultured in a $CO_2$ constant temperature incubator (Forma, 51030303-TIF) for 24 hours. The cells were treated with 8 antibody-drug conjugates prepared in Example III, serially diluted in 1/2 from 4.5 nM to 0.0088 nM. In order to quantify living cells 96 hours later, 20 mL of MTS dye solution (Promega, G3581) was added to each well of the plate and left in a $CO_2$ constant temperature incubator for 4 hours. The absorbance of formazan formed by reduction of MTS (3-(4,5-dimethylthiazol-2-yl)-5-(3-carboxymethoxyphenyl)-2-(4-sulfophenyl)-2H-tetrazolium, inner salt) dye by mitochondrial oxidoreductase within the cell was measured at 490 nm using a spectrometer (Promega, GM3000) and then analyzed using the GraphPad Prism 7 program. The results of the cytotoxicity test of the antibody-drug conjugates are shown in Table 4 below.

Method 3: Cell Cytotoxicity (SK-BR3) Experiment

SK-BR3 breast cancer cell line (Korean Cell Line Bank, 30030) was prepared at a density of 80,000 cells per 1 mL of RPMI1640 culture solution (Hyclone, SH30027.01) containing 10% fetal bovine serum (Hyclone, SH30919.03) and 1% antibiotic-antimycotic solution (Hyclone, SV30079.01), then dispensed into a 96-well plate (Sarstedt, 83.3924) at 100 mL (8,000 cells) per well, and cultured in a $CO_2$ constant temperature incubator (Forma, 51030303-TIF) for 24 hours. The cells were treated with 4 antibody-drug conjugates prepared in Example III, serially diluted in 1/2 from 0.5 nM to 0.00098 nM. In order to quantify living cells 96 hours later, 20 mL of MTS dye solution (Promega, G3581) was added to each well of the plate and left in a $CO_2$ constant temperature incubator for 4 hours. The absorbance of formazan formed by reduction of MTS (3-(4,5-dimethylthiazol-2-yl)-5-(3-carboxymethoxyphenyl)-2-(4-sulfophenyl)-2H-tetrazolium, inner salt) dye by mitochondrial oxidoreductase within the cell was measured at 490 nm using a spectrometer (Promega, GM3000) and then analyzed using the GraphPad Prism 7 program. The results of the cytotoxicity test of the antibody-drug conjugates are shown in Table 4 below.

Method 4: Cell Cytotoxicity (BT-474) Experiment

BT-474 breast cancer cell line (Korean Cell Line Bank, 60062) was prepared at a density of 100,000 cells per 1 mL of RPMI1640 culture solution (Hyclone, SH30027.01) containing 10% fetal bovine serum (Hyclone, SH30919.03) and 1% antibiotic-antimycotic solution (Hyclone, SV30079.01), then dispensed into a 96-well plate (Sarstedt, 83.3924) at 100 mL (10,000 cells) per well, and cultured in a $CO_2$ constant temperature incubator (Forma, 51030303-TIF) for 24 hours. The cells were treated with 4 antibody-drug conjugates prepared in Example III, serially diluted in 1/2 from 1.5 nM to 0.0029 nM. In order to quantify living cells 96 hours later, 20 mL of MTS dye solution (Promega, G3581) was added to each well of the plate and left in a $CO_2$ constant temperature incubator for 4 hours. The absorbance of formazan formed by reduction of MTS (3-(4,5-dimethylthiazol-2-yl)-5-(3-carboxymethoxyphenyl)-2-(4-sulfophenyl)-2H-tetrazolium, inner salt) dye by mitochondrial oxidoreductase within the cell was measured at 490 nm using a spectrometer (Promega, GM3000) and then analyzed using the GraphPad Prism 7 program. The results of the cytotoxicity test of the antibody-drug conjugates are shown in Table 4 below.

Method 5: Cell Cytotoxicity (MCF-7) Experiment

MCF-7 breast cancer cell line (Korean Cell Line Bank, 30022) was prepared at a density of 40,000 cells per 1 mL of RPMI1640 culture solution (Hyclone, SH30027.01) containing 10% fetal bovine serum (Hyclone, SH30919.03) and 1% antibiotic-antimycotic solution (Hyclone, SV30079.01), then dispensed into a 96-well plate (Sarstedt, 83.3924) at 100 mL (4,000 cells) per well, and cultured in a $CO_2$ constant temperature incubator (Forma, 51030303-TIF) for 24 hours. The cells were treated with 4 antibody-drug conjugates prepared in Example III, diluted at a concentration of 50 nM and 3.125 nM. In order to quantify living cells 96 hours later, 20 mL of MTS dye solution (Promega, G3581) was added to each well of the plate and left in a $CO_2$ constant temperature incubator for 4 hours. The absorbance of formazan formed by reduction of MTS (3-(4,5-dimethylthiazol-2-yl)-5-(3-carboxymethoxyphenyl)-2-(4-sulfophenyl)-2H-tetrazolium, inner salt) dye by mitochondrial oxidoreductase within the cell was measured at 490 nm using a spectrometer (Promega, GM3000) and then analyzed using the GraphPad Prism 7 program. The results of the cytotoxicity test of the antibody-drug conjugates are shown in Table 4 below.

TABLE 4

| | | $IC_{50}$(nM) | | | | |
|---|---|---|---|---|---|---|
| ADC | DAR | JIMT-1 | NCI-N87 | SK-BR3 | BT-474 | MCF-7 |
| ADC-1 | 1.9 | 0.294 | | | | |
| ADC-2 | 2.0 | 0.274 | | | | |
| ADC-3 | 1.9 | 0.258 | | | | |
| ADC-4 | 1.9 | 0.189 | | | | |
| ADC-5 | 1.9 | 0.177 | | | | |
| ADC-6 | 1.9 | 0.162 | | | | |
| ADC-7 | 1.9 | 0.893 | 0.246 | 0.090 | 0.107 | >50 |
| ADC-8 | 1.9 | 1.249 | 0.282 | 0.091 | 0.110 | >50 |
| ADC-9 | 3.6 | 0.303 | 0.185 | 0.045 | 0.063 | >50 |
| ADC-10 | 3.6 | 0.312 | 0.191 | 0.047 | 0.076 | >50 |
| ADC-11 | 1.9 | 0.199 | 0.226 | | | |
| ADC-12 | 1.9 | 0.533 | 0.276 | | | |
| ADC-14 | 3.8 | 0.164 | 0.145 | | | |
| ADC-15 | 3.8 | 0.074 | 0.082 | | | |
| ADC-16 | 2.0 | 0.333 | | | | |
| ADC-17 | 2.0 | 0.496 | | | | |
| ADC-18 | 3.8 | 0.115 | | | | |
| ADC-19 | 3.8 | 0.215 | | | | |

From the results in Table 4 above, the excellent anticancer activity of the antibody-drug conjugate of the present invention was confirmed through in vitro experiments.

Test Example 5: In Vivo Analysis of Antibody-Drug Conjugate

The in vivo activity of the antibody-drug conjugates (ADC-1 to ADC-7, ADC-11 to ADC-15) prepared in Example III was measured in a tumor xenograft mouse model. JIMT-1 breast cancer cell line was cultured in DMEM culture solution containing 10% fetal bovine serum and 1% antibiotic-antimycotic solution (Gibco, 15240-062) at 37° C., 5% $CO_2$ conditions for 3 to 4 days. When the viability was 97% or higher, the cell line was harvested using trypsin-EDTA, then mixed with a DPBS (Hyclone, SH30028.02) buffer solution to obtain a concentration of $1.59\times10^8$ cells/mL. Thereafter, this was diluted 1:1 with matrigel (Corning, 356235) to obtain a concentration of $7.14\times10^7$ cells/mL. The cell suspension was injected subcutaneously into athymic nude mice (6-week, female) at a dose of 0.07 mL ($5\times10^6$ cells/mouse) using a disposable syringe (1 mL). When the tumor volume was 80 to 120 $mm^3$, the mice were separated into groups such that the average tumor volume was distributed as evenly as possible and drug administration was then initiated. Kadcyla® (T-DM1, Roche, CAS No. 1018448-65-1) and the antibody-drug conjugate of the present invention were each administered intravenously at a single dose of 5 mg/kg, and the tumor volume was measured twice a week at intervals of 3 to 4 days. The tumor volume was calculated by the following formula: volume=($a^2b$)/2, where a is the short diameter and b is the long diameter). All measurement results obtained in the experiments were statistically processed using SPSS (Version 27.0, IBM corporation, U.S.A.). The results of in vivo activity analysis of Kadcyla®, used as a control drug, and the antibody-drug conjugate of the present invention are shown in FIGS. 6 to 8.

Referring to FIGS. 6 to 8, it was confirmed that the antibody-drug conjugate of the present invention exhibits significantly excellent anticancer activity compared to the control drug Kadcyla® or the untreated control group.

TABLE A

Exemplary compounds of Formula 1

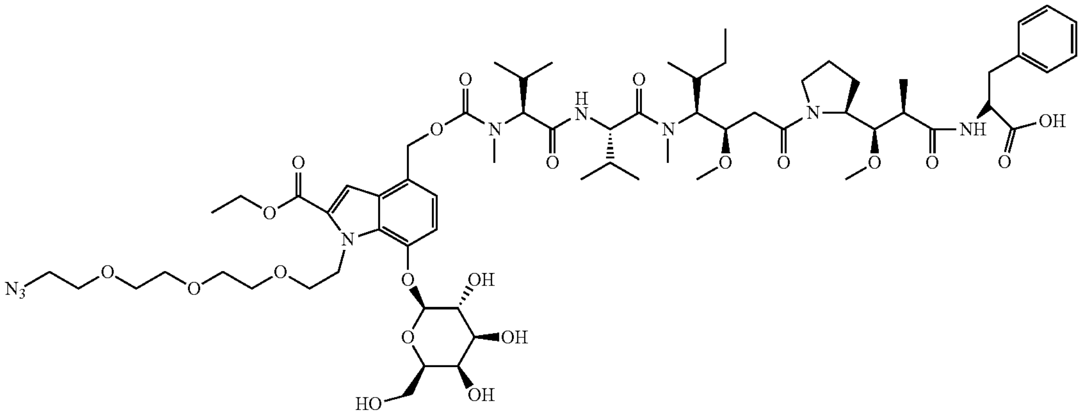

A-1

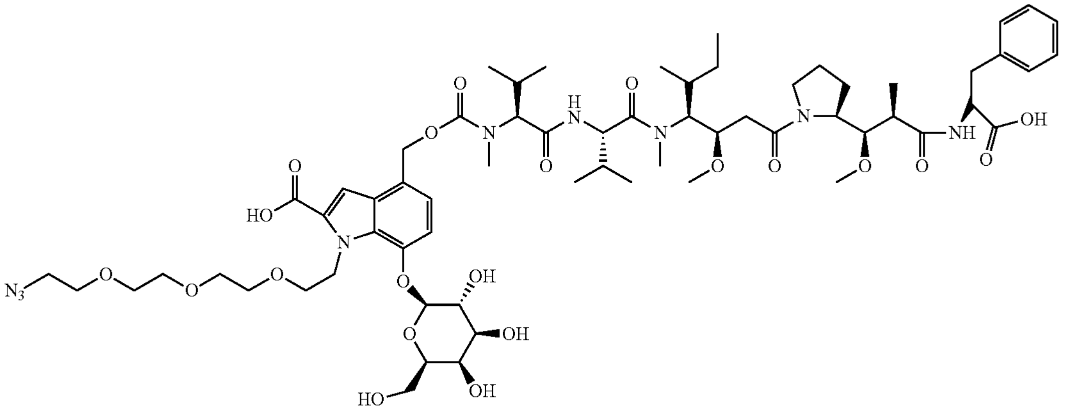

A-2

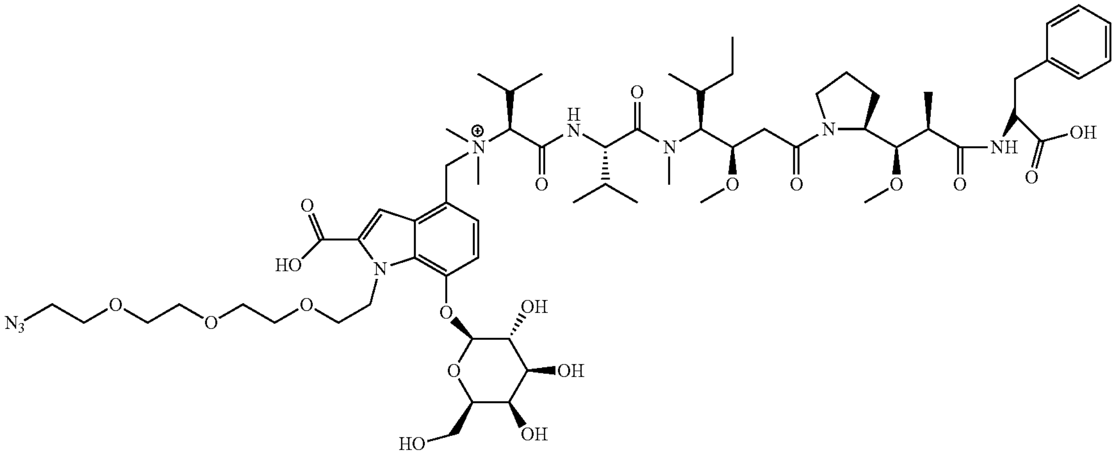

A-3

TABLE A-continued
Exemplary compounds of Formula 1
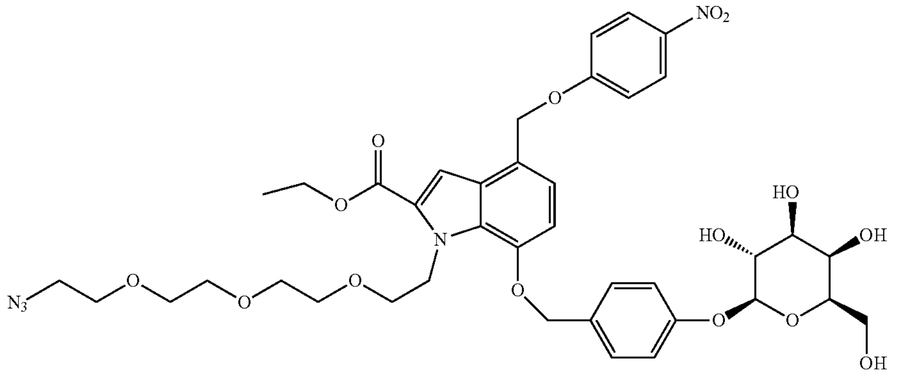 [SMILES: CCOC(=O)c1cc2c(COc3ccc([N+](=O)[O-])cc3)ccc(OCc3ccc(O[C@@H]4O[C@H](CO)[C@H](O)[C@H](O)[C@H]4O)cc3)c2n1CCOCCOCCOCCN=[N+]=[N-]]
A-4
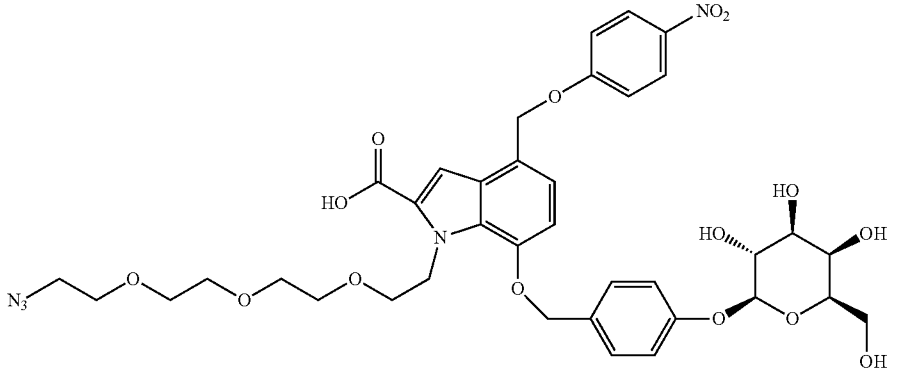 [SMILES: [N-]=[N+]=NCCOCCOCCOCCn1c(C(=O)O)cc2c(COc3ccc([N+](=O)[O-])cc3)ccc(OCc3ccc(O[C@@H]4O[C@H](CO)[C@H](O)[C@H](O)[C@H]4O)cc3)c21]
A-5
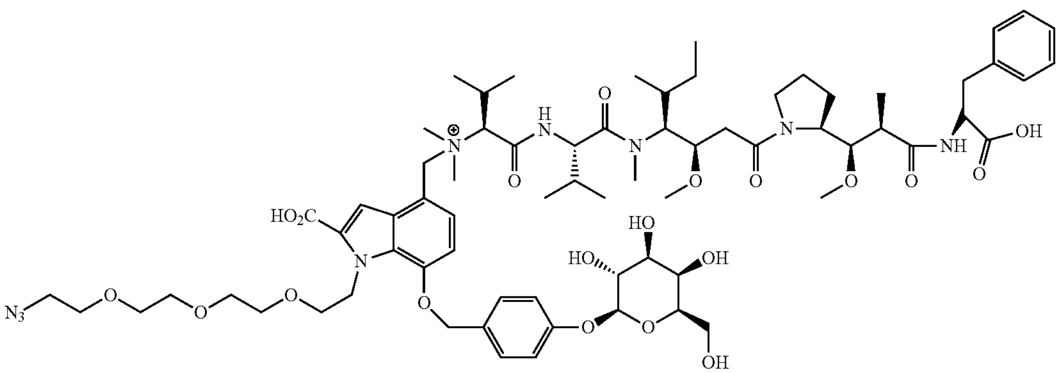
A-6
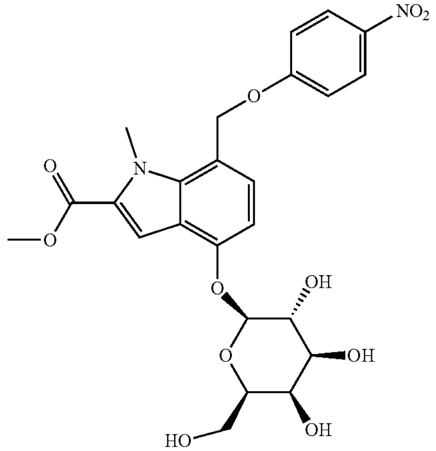 [SMILES: COC(=O)c1cc2c(O[C@@H]3O[C@H](CO)[C@H](O)[C@H](O)[C@H]3O)ccc(COc3ccc([N+](=O)[O-])cc3)c2n1C]
A-7

TABLE A-continued
Exemplary compounds of Formula 1
A-8
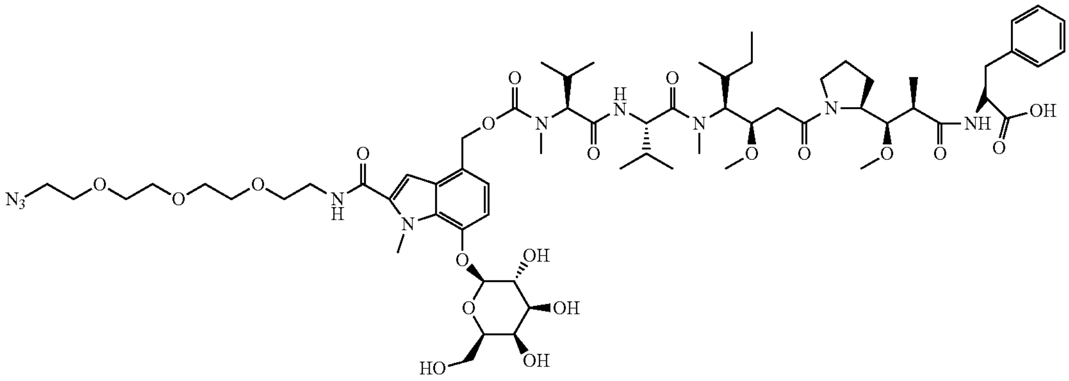
A-9
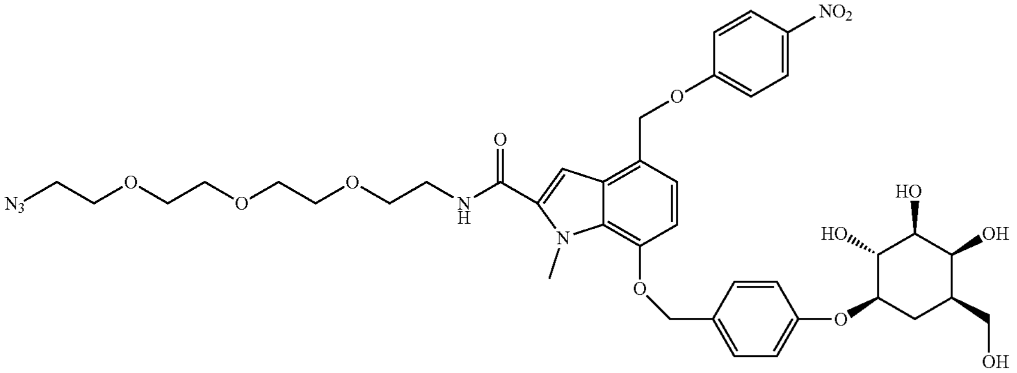 [SMILES: Cn1c(C(=O)NCCOCCOCCOCCN=[N+]=[N-])cc2c(COc3ccc([N+](=O)[O-])cc3)ccc(OCc3ccc(O[C@@H]4C[C@H](CO)[C@H](O)[C@H](O)[C@H]4O)cc3)c21]
A-10
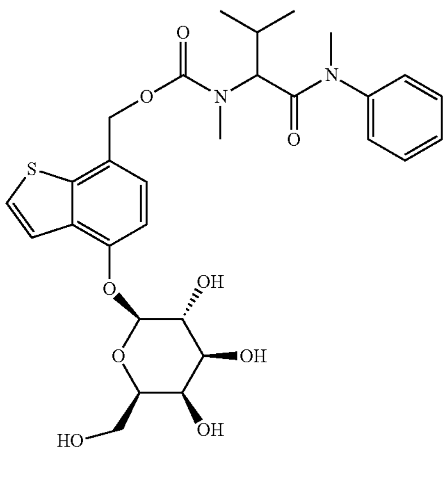 [SMILES: CC(C)C(C(=O)N(C)c1ccccc1)N(C)C(=O)OCc1ccc(O[C@@H]2O[C@H](CO)[C@H](O)[C@H](O)[C@H]2O)c2ccsc12]

TABLE A-continued
Exemplary compounds of Formula 1
A-11
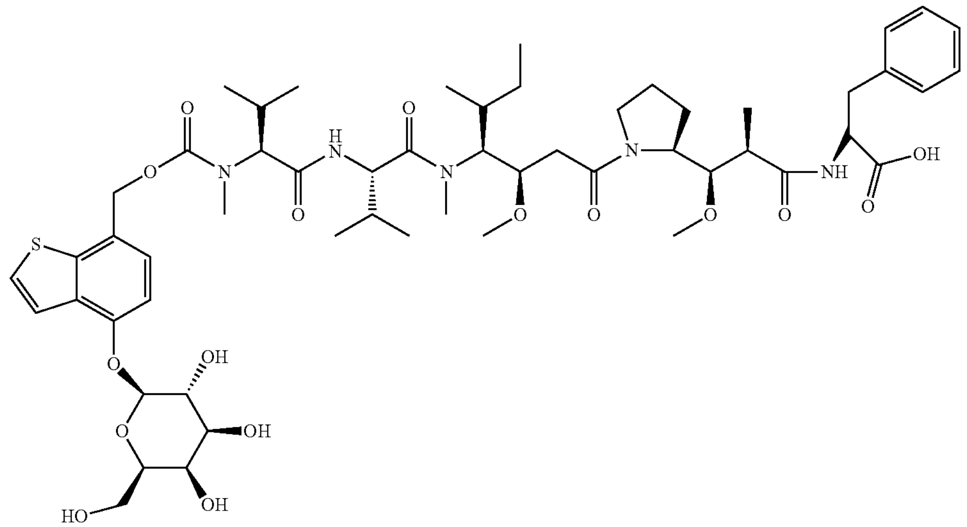
A-12
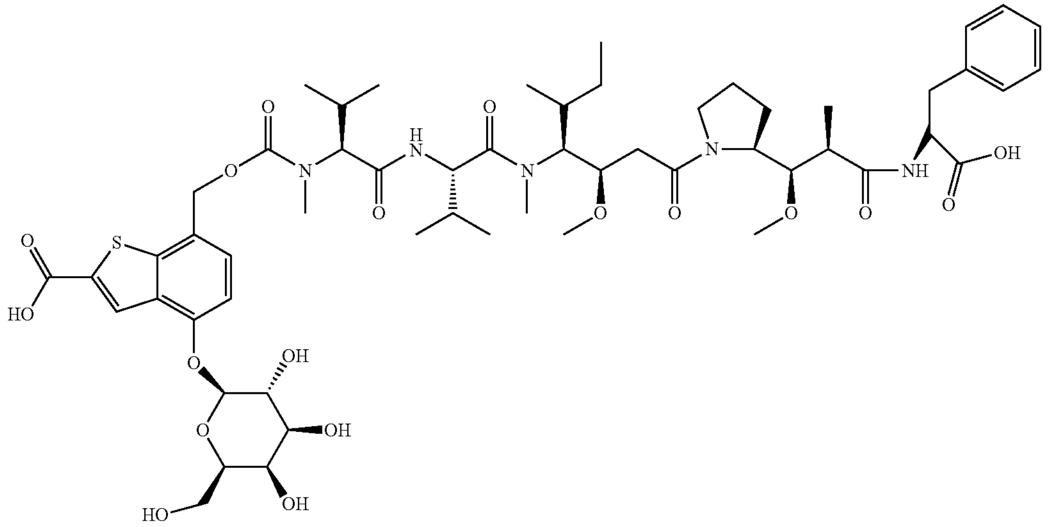
A-13
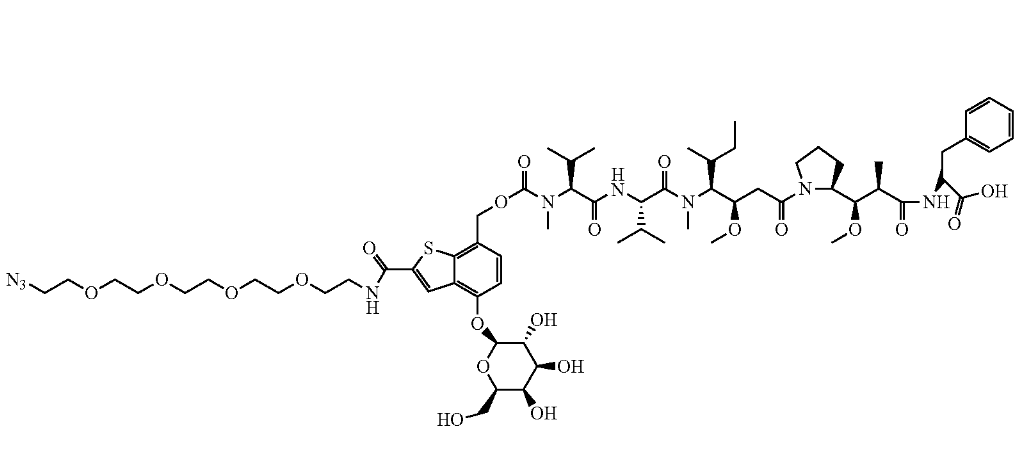

TABLE A-continued
Exemplary compounds of Formula 1
A-14
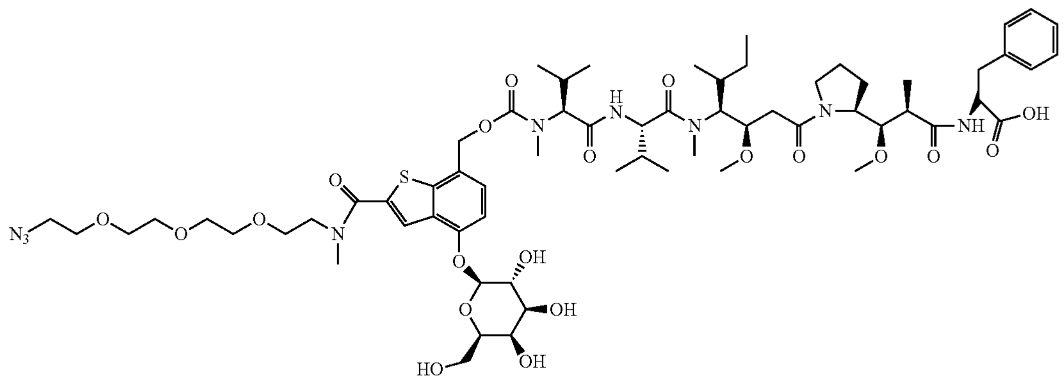
A-15
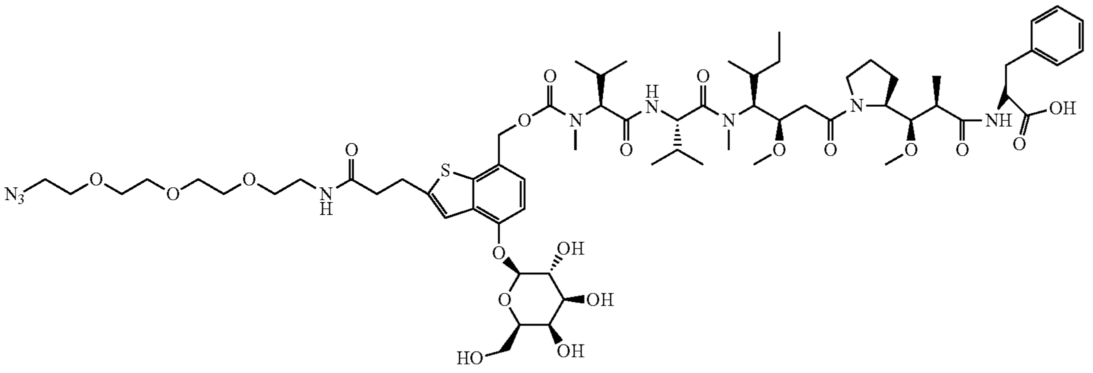
A-16
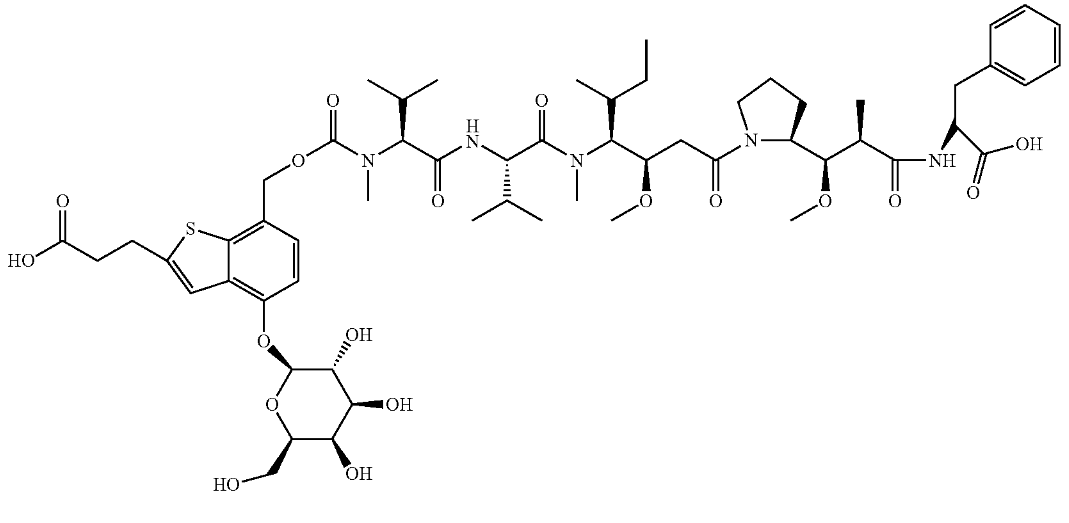

TABLE A-continued
| Exemplary compounds of Formula 1 |
|---|
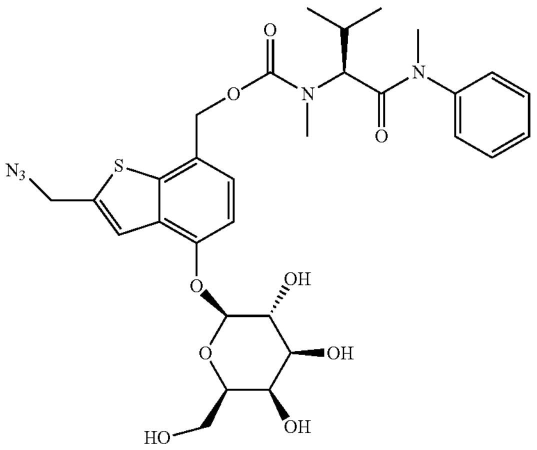 [SMILES: CC(C)[C@@H](C(=O)N(C)c1ccccc1)N(C)C(=O)OCc1ccc(O[C@@H]2O[C@H](CO)[C@H](O)[C@H](O)[C@H]2O)c2cc(CN=[N+]=[N-])sc12]
A-17
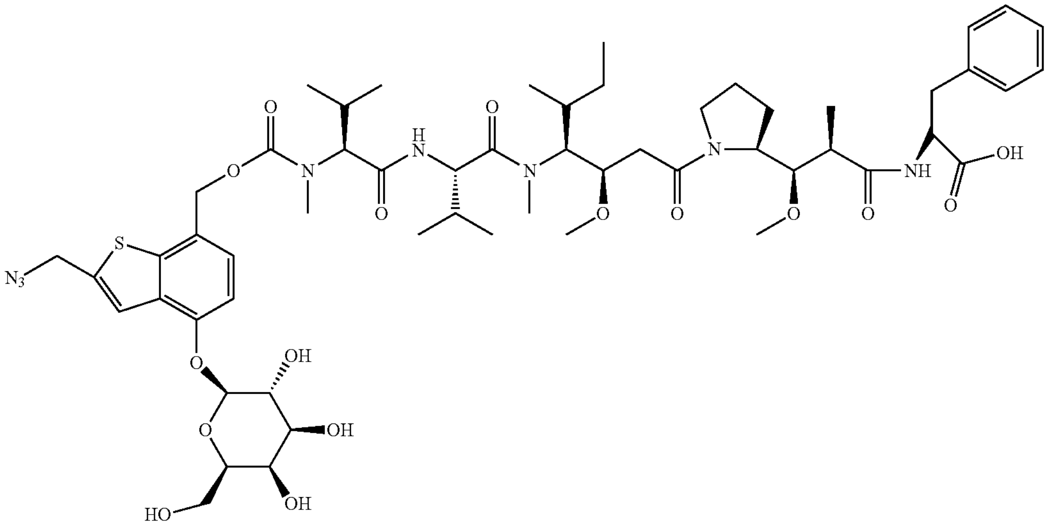
A-18
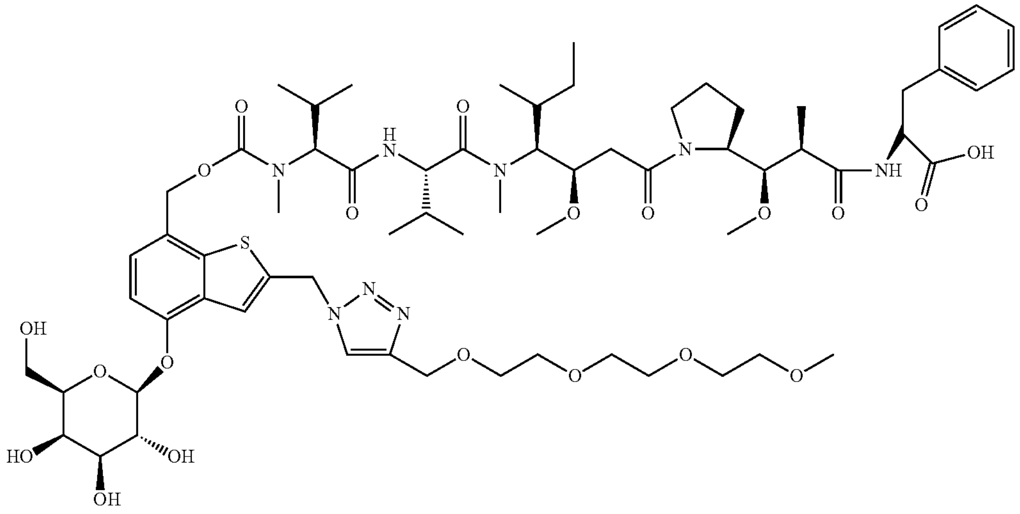
A-19

TABLE A-continued
| Exemplary compounds of Formula 1 |
|---|
A-20
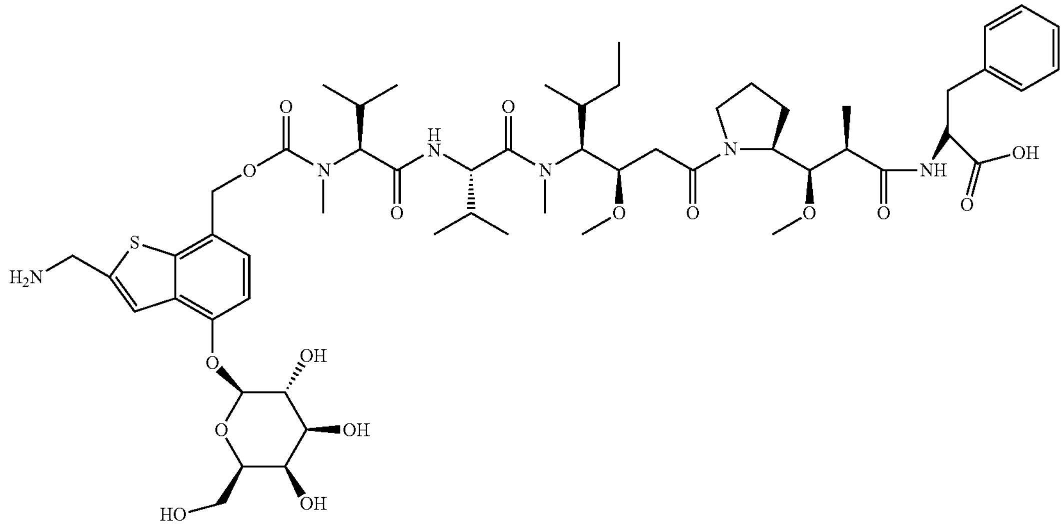
A-21
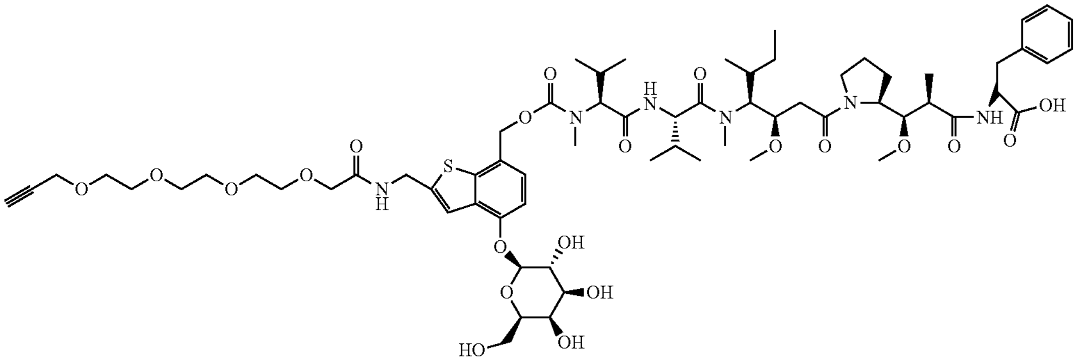
A-22
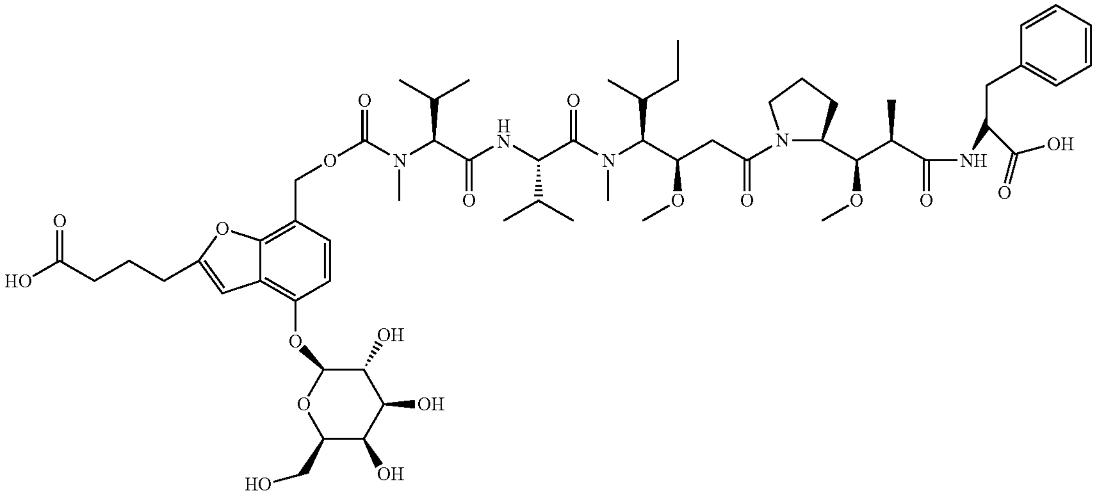

TABLE A-continued
| Exemplary compounds of Formula 1 |
| --- |
A-23
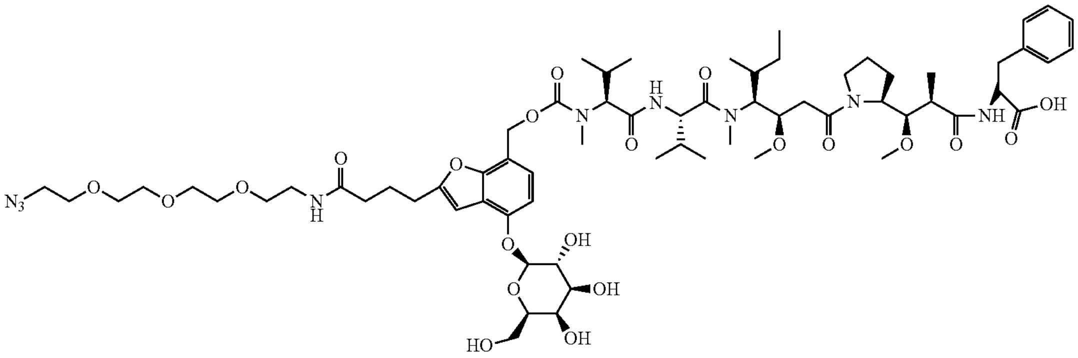
A-24
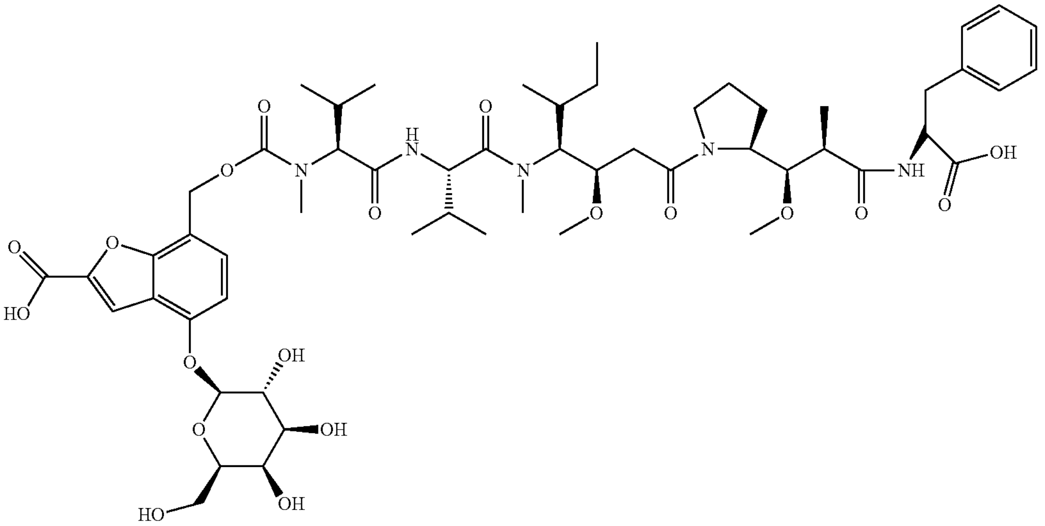
A-25
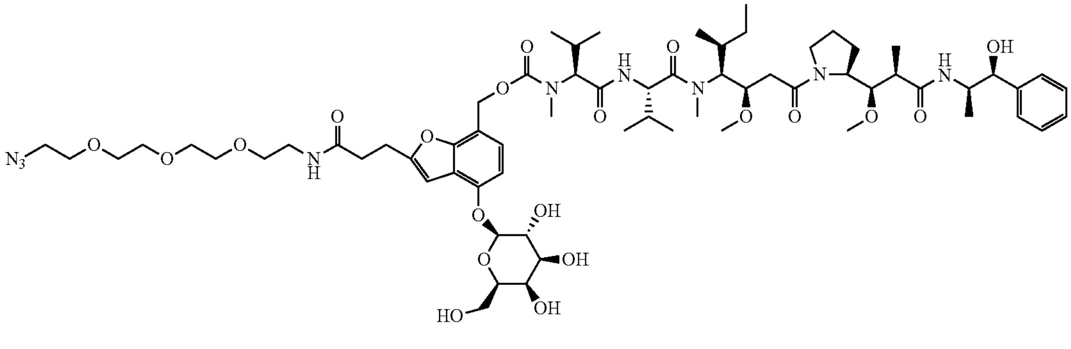 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](CO)[C@H](O)[C@H](O)[C@H]2O)c2cc(CCC(=O)NCCOCCOCCOCCN=[N+]=[N-])oc12)C(C)C]

TABLE A-continued
| Exemplary compounds of Formula 1 |
| --- |
| A-26 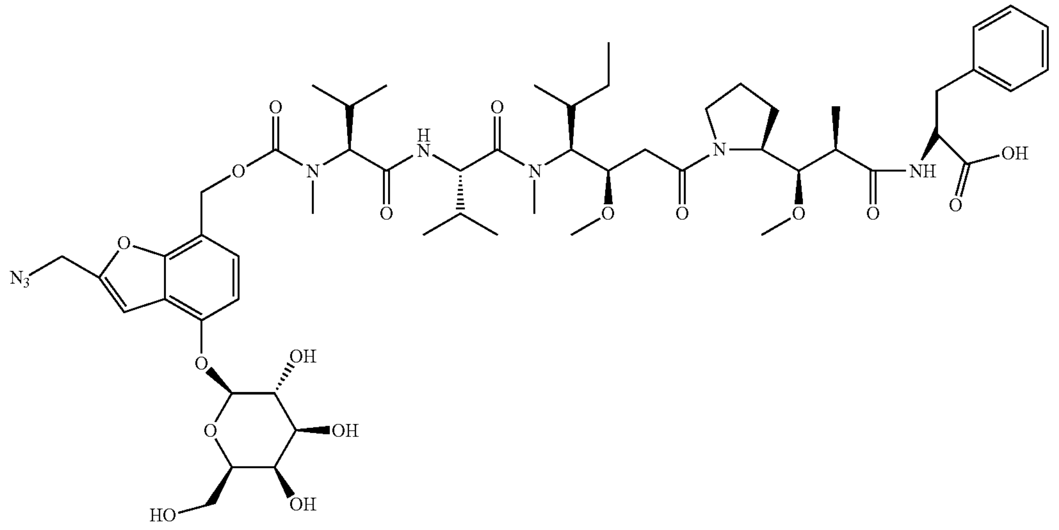 |
| A-27 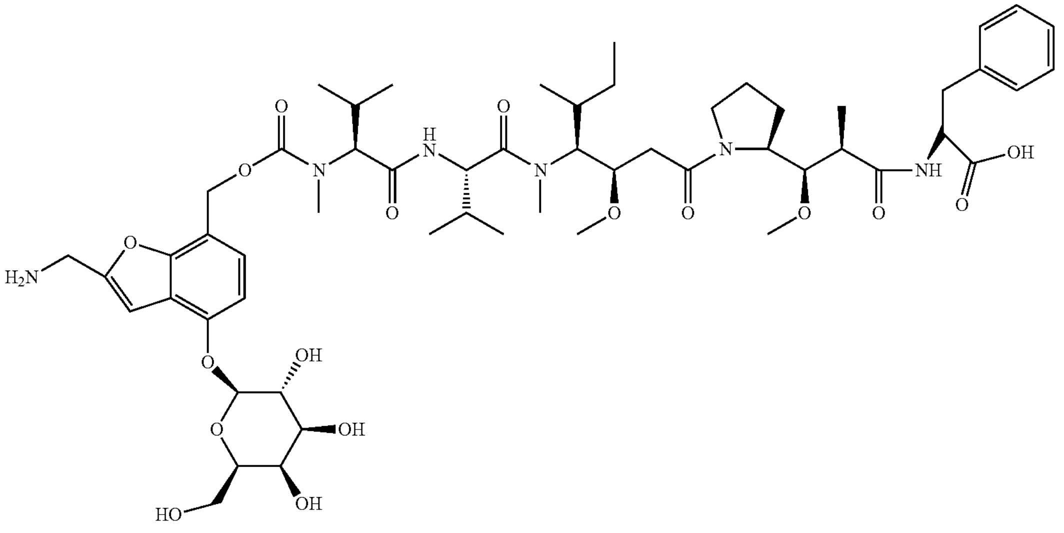 |
| A-28 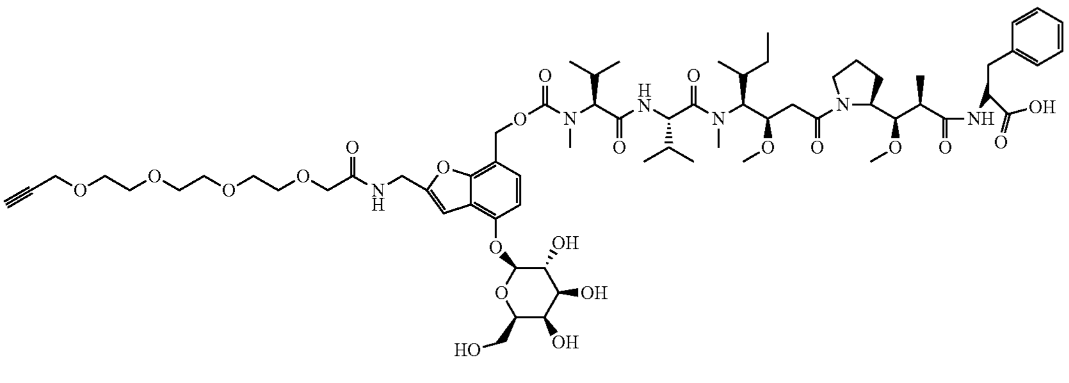 |

TABLE A-continued
| Exemplary compounds of Formula 1 |
| --- |
A-29
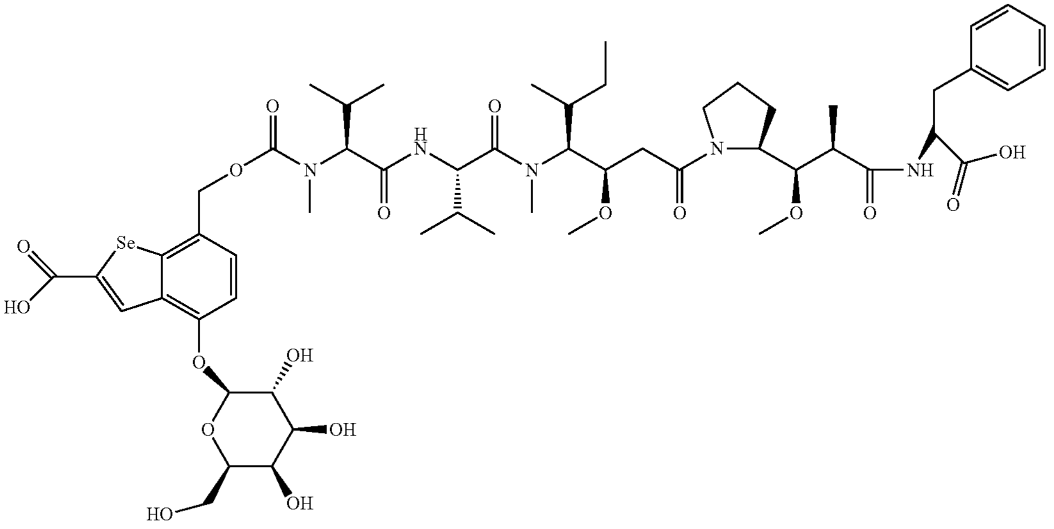
A-33
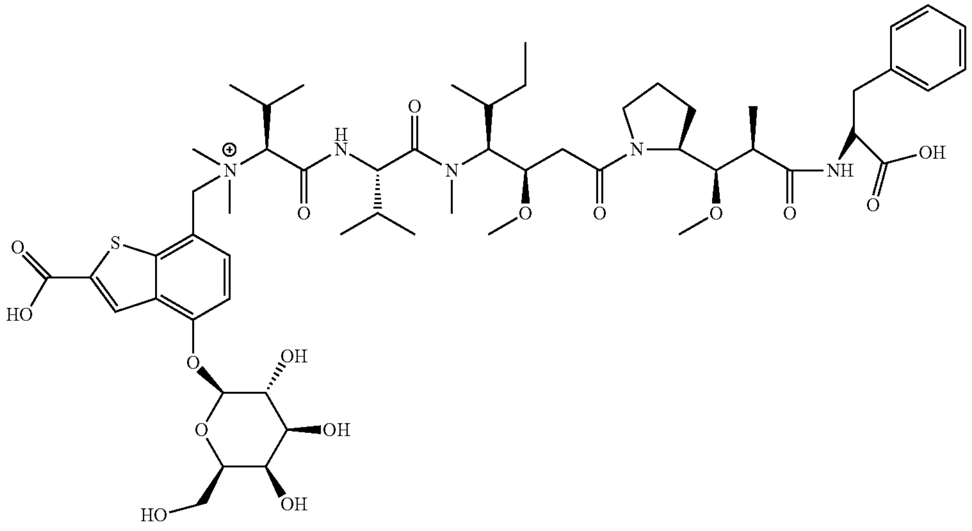
A-34
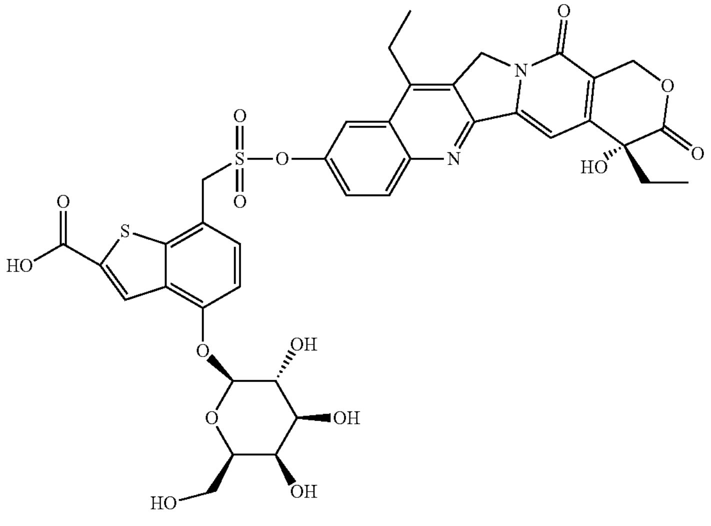 [SMILES: CCc1c2c(nc3ccc(OS(=O)(=O)Cc4ccc(O[C@@H]5O[C@H](CO)[C@H](O)[C@H](O)[C@H]5O)c5cc(C(=O)O)sc45)cc13)-c1cc3c(c(=O)n1C2)COC(=O)[C@@]3(O)CC]

TABLE A-continued
| Exemplary compounds of Formula 1 |
| --- |
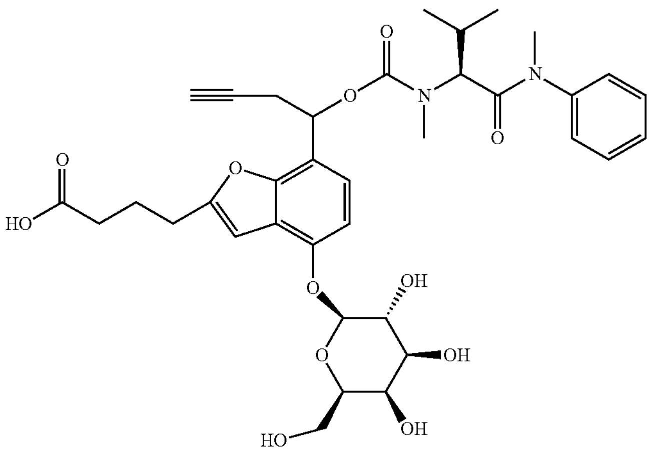 [SMILES: C#CCC(OC(=O)N(C)[C@H](C(=O)N(C)c1ccccc1)C(C)C)c1ccc(O[C@@H]2O[C@H](CO)[C@H](O)[C@H](O)[C@H]2O)c2cc(CCCC(=O)O)oc12]
A-35
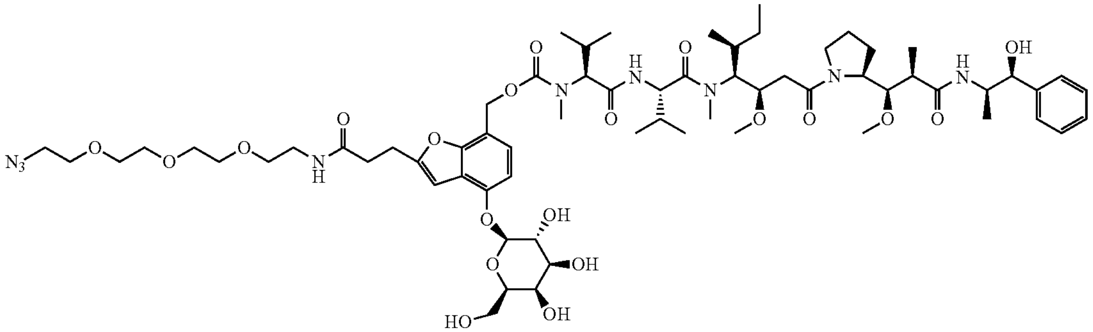 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](CO)[C@H](O)[C@H](O)[C@H]2O)c2cc(CCC(=O)NCCOCCOCCOCCN=[N+]=[N-])oc12)C(C)C]
A-36
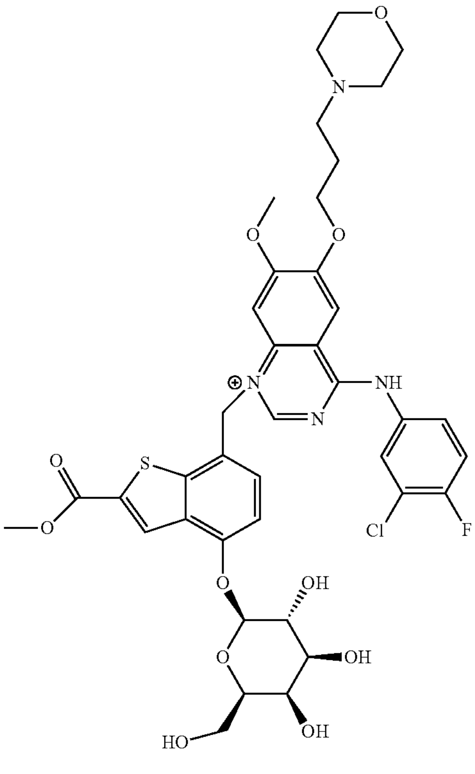 [SMILES: COC(=O)c1cc2c(O[C@@H]3O[C@H](CO)[C@H](O)[C@H](O)[C@H]3O)ccc(C[n+]3cnc(Nc4ccc(F)c(Cl)c4)c4cc(OCCCN5CCOCC5)c(OC)cc43)c2s1]
A-37

TABLE A-continued
| Exemplary compounds of Formula 1 |
| --- |
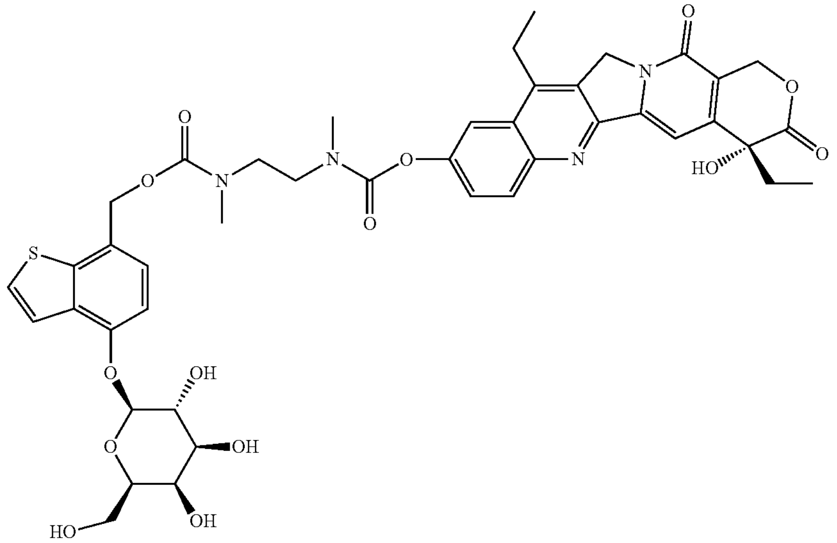 [SMILES: CCc1c2c(nc3ccc(OC(=O)N(C)CCN(C)C(=O)OCc4ccc(O[C@@H]5O[C@H](CO)[C@H](O)[C@H](O)[C@H]5O)c5ccsc45)cc13)-c1cc3c(c(=O)n1C2)COC(=O)[C@@]3(O)CC]
A-38
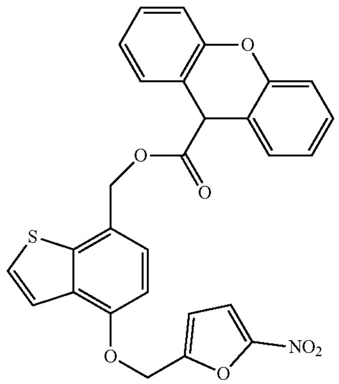 [SMILES: O=C(OCc1ccc(OCc2ccc([N+](=O)[O-])o2)c2ccsc12)C1c2ccccc2Oc2ccccc21]
A-39
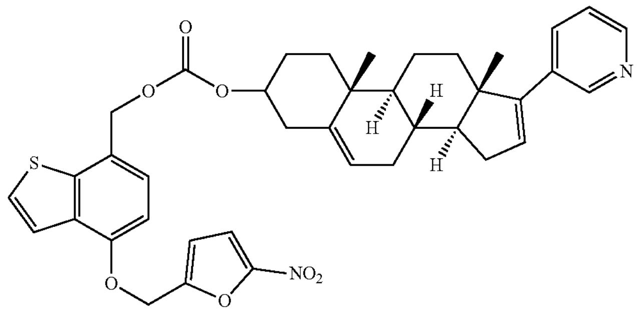
A-40

TABLE A-continued
| Exemplary compounds of Formula 1 |
| --- |
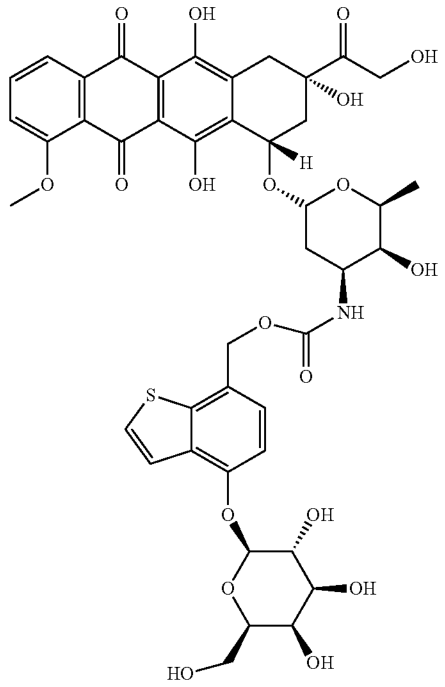
A-41
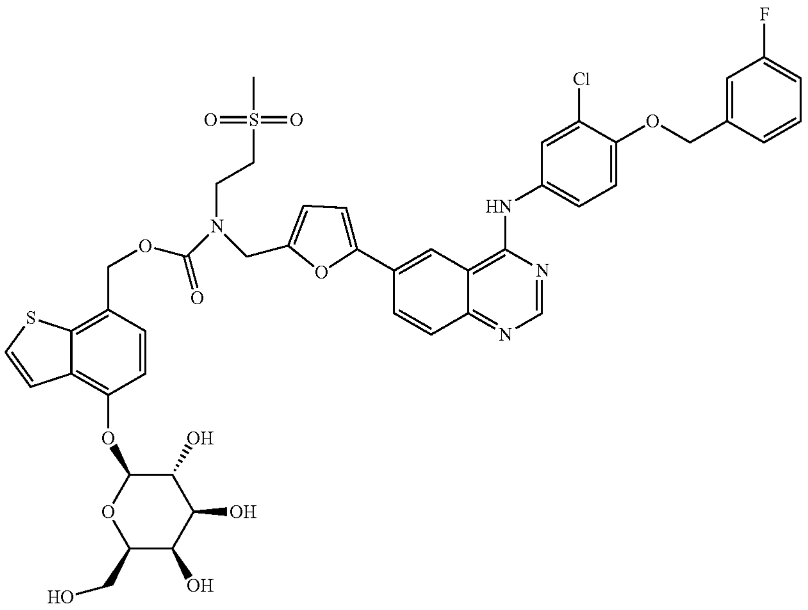 [SMILES: CS(=O)(=O)CCN(Cc1ccc(-c2ccc3ncnc(Nc4ccc(OCc5cccc(F)c5)c(Cl)c4)c3c2)o1)C(=O)OCc1ccc(O[C@@H]2O[C@H](CO)[C@H](O)[C@H](O)[C@H]2O)c2ccsc12]
A-42

TABLE A-continued
| Exemplary compounds of Formula 1 |
|---|
| 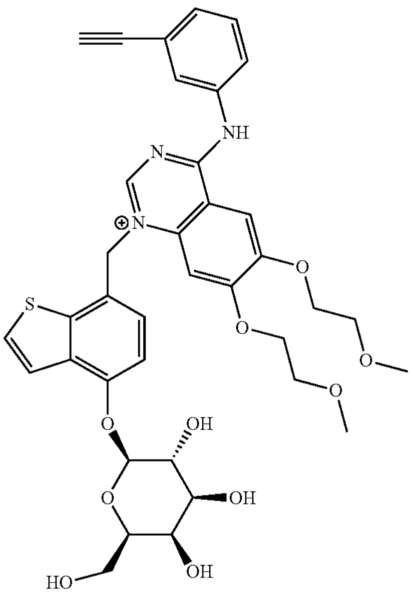 [SMILES: C#Cc1cccc(Nc2nc[n+](Cc3ccc(O[C@@H]4O[C@H](CO)[C@H](O)[C@H](O)[C@H]4O)c4ccsc34)c3cc(OCCOC)c(OCCOC)cc23)c1] A-43 |
| 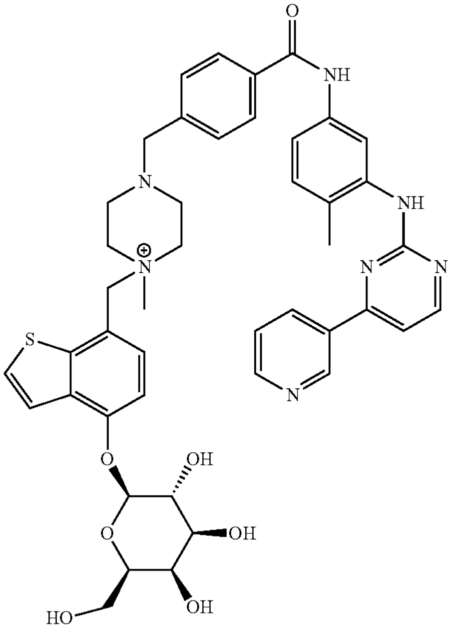 [SMILES: Cc1ccc(NC(=O)c2ccc(CN3CC[N+](C)(Cc4ccc(O[C@@H]5O[C@H](CO)[C@H](O)[C@H](O)[C@H]5O)c5ccsc45)CC3)cc2)cc1Nc1nccc(-c2cccnc2)n1] A-44 |
| 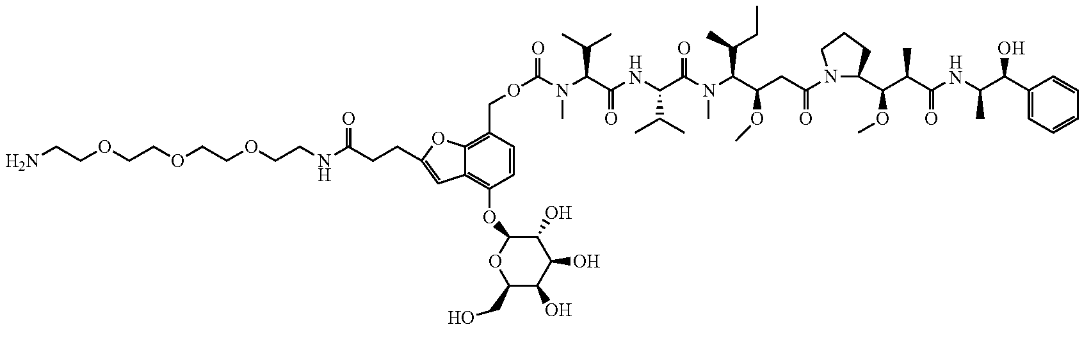 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](CO)[C@H](O)[C@H](O)[C@H]2O)c2cc(CCC(=O)NCCOCCOCCOCCN)oc12)C(C)C] A-45 |

TABLE A-continued
| Exemplary compounds of Formula 1 |
| --- |
A-46
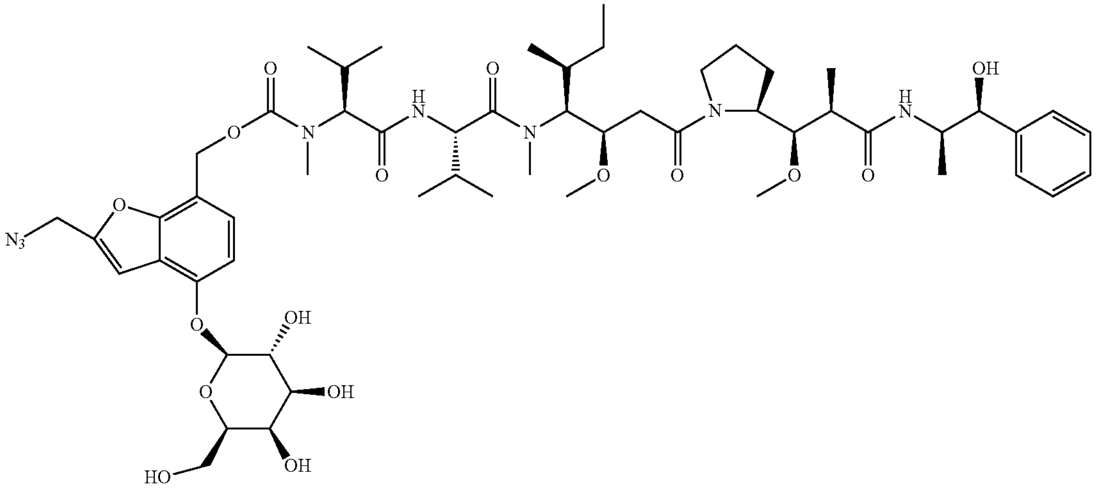 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](CO)[C@H](O)[C@H](O)[C@H]2O)c2cc(CN=[N+]=[N-])oc12)C(C)C]
A-47
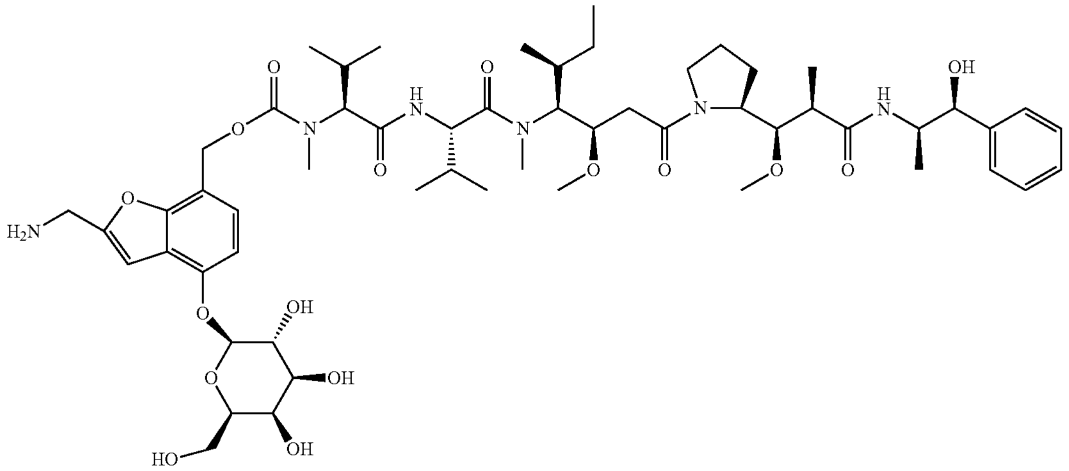 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](CO)[C@H](O)[C@H](O)[C@H]2O)c2cc(CN)oc12)C(C)C]
A-48
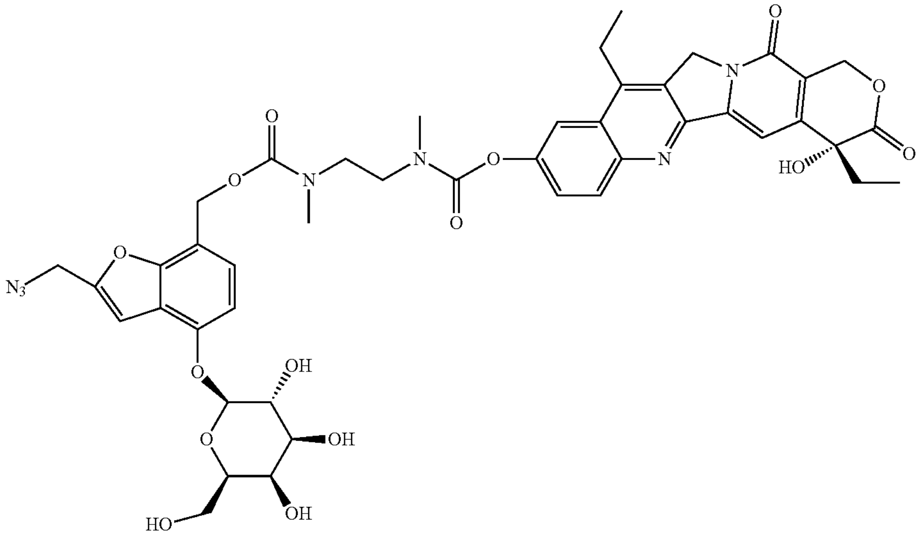 [SMILES: CCc1c2c(nc3ccc(OC(=O)N(C)CCN(C)C(=O)OCc4ccc(O[C@@H]5O[C@H](CO)[C@H](O)[C@H](O)[C@H]5O)c5cc(CN=[N+]=[N-])oc45)cc13)-c1cc3c(c(=O)n1C2)COC(=O)[C@@]3(O)CC]

TABLE A-continued
Exemplary compounds of Formula 1
A-49
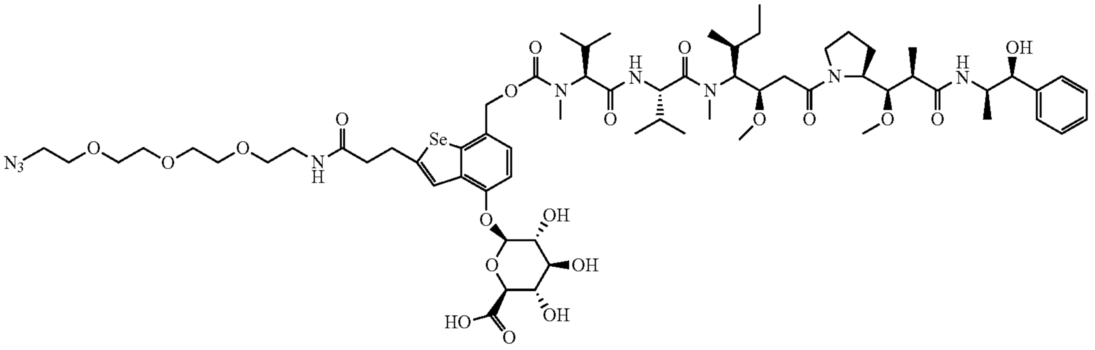
A-50
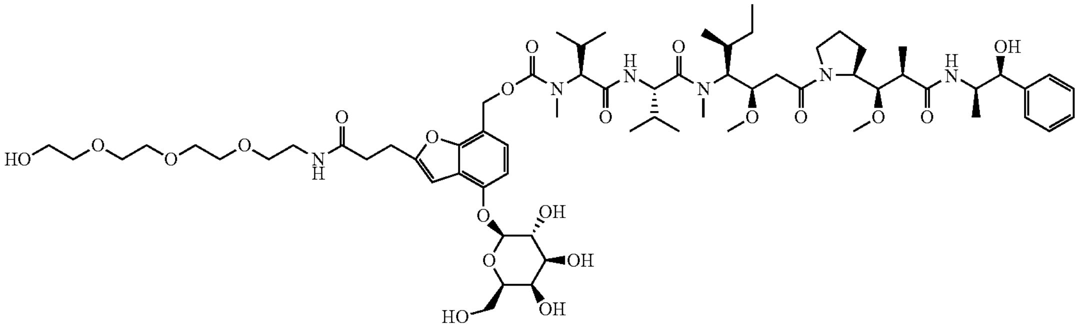 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](CO)[C@H](O)[C@H](O)[C@H]2O)c2cc(CCC(=O)NCCOCCOCCOCCO)oc12)C(C)C]
A-51
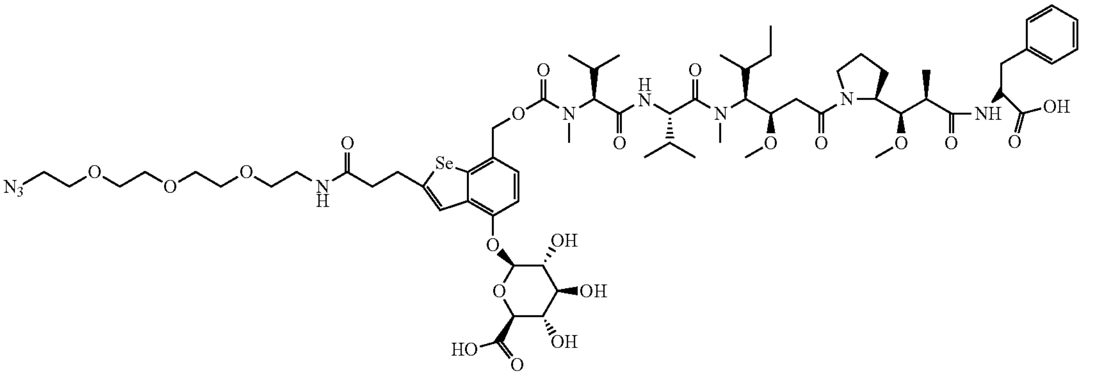
A-52
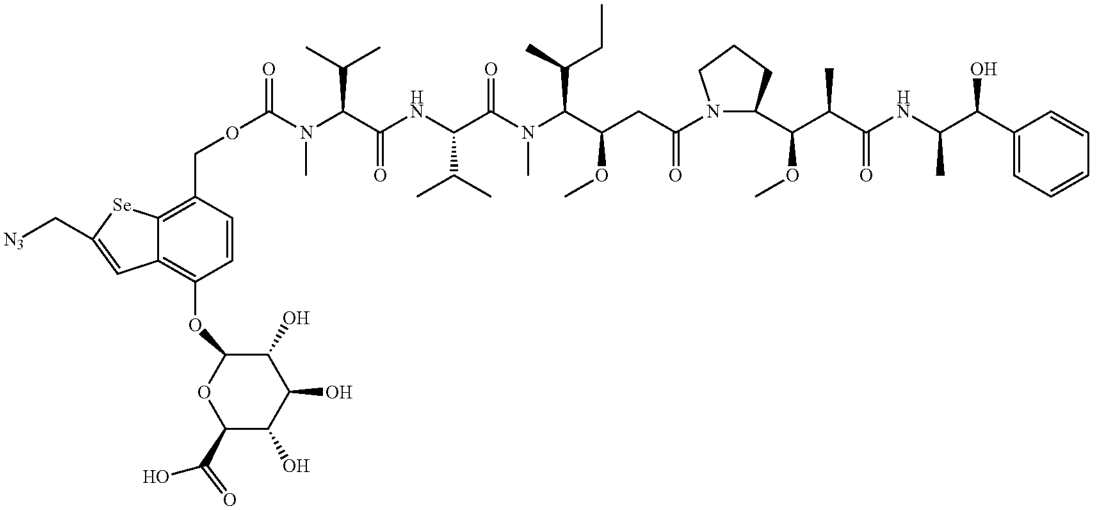

TABLE A-continued
Exemplary compounds of Formula 1
A-53
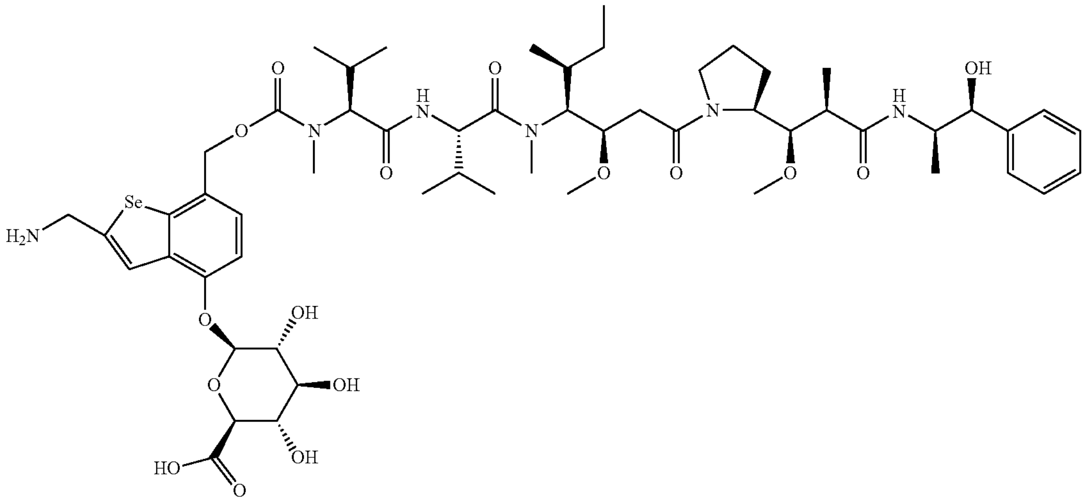 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c2cc(CN)[se]c12)C(C)C]
A-54
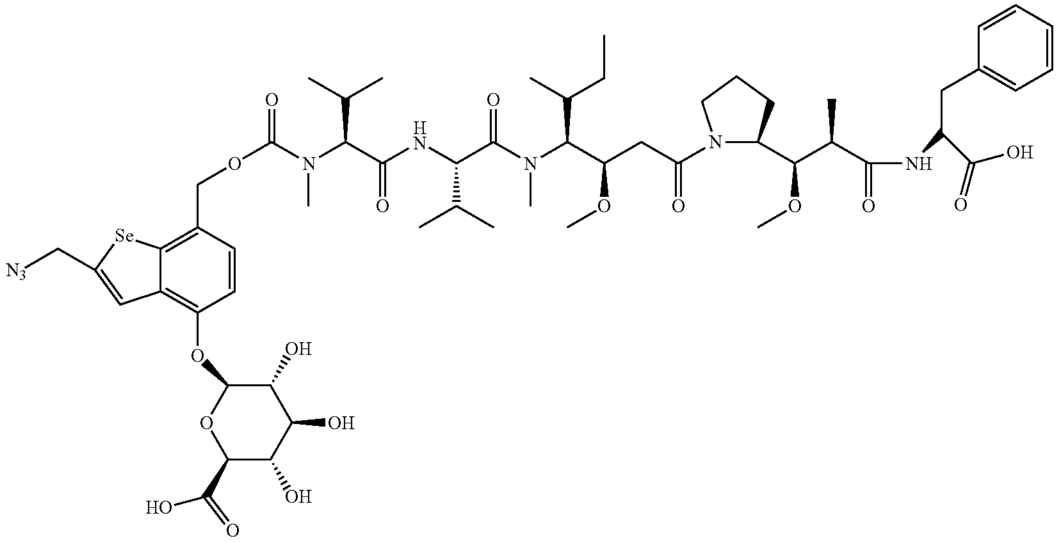
A-55
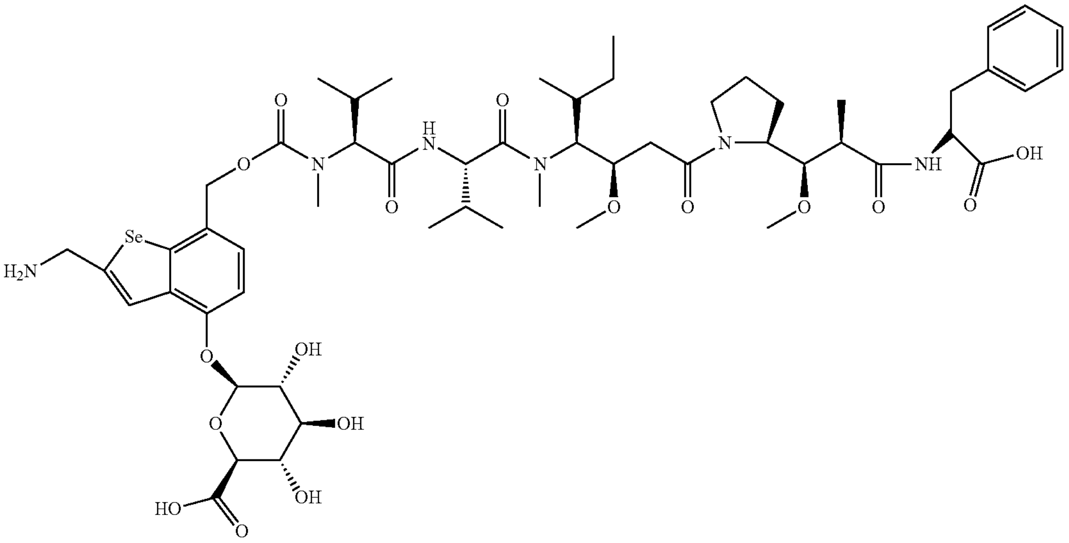

TABLE A-continued
Exemplary compounds of Formula 1
A-56
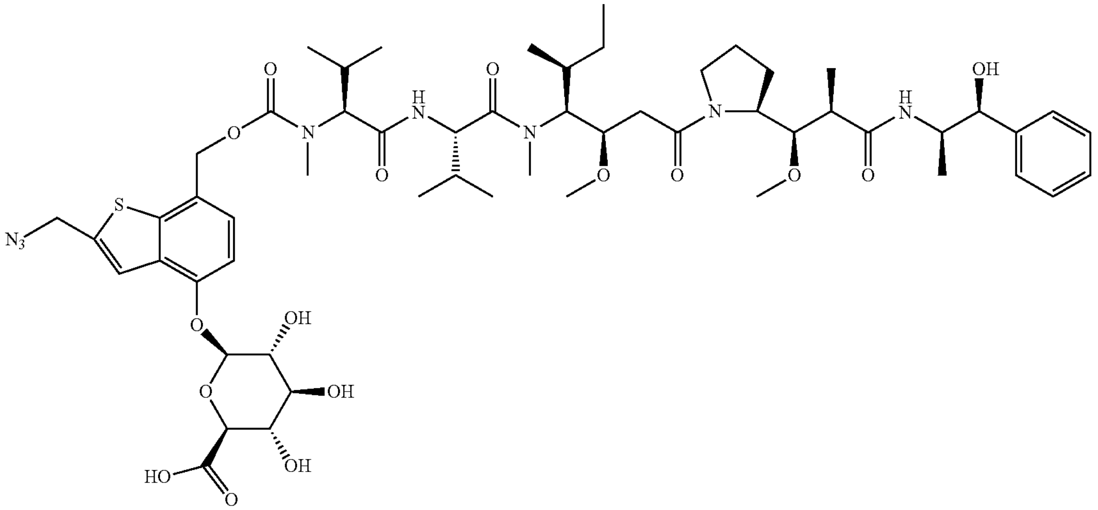 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c2cc(CN=[N+]=[N-])sc12)C(C)C]
A-57
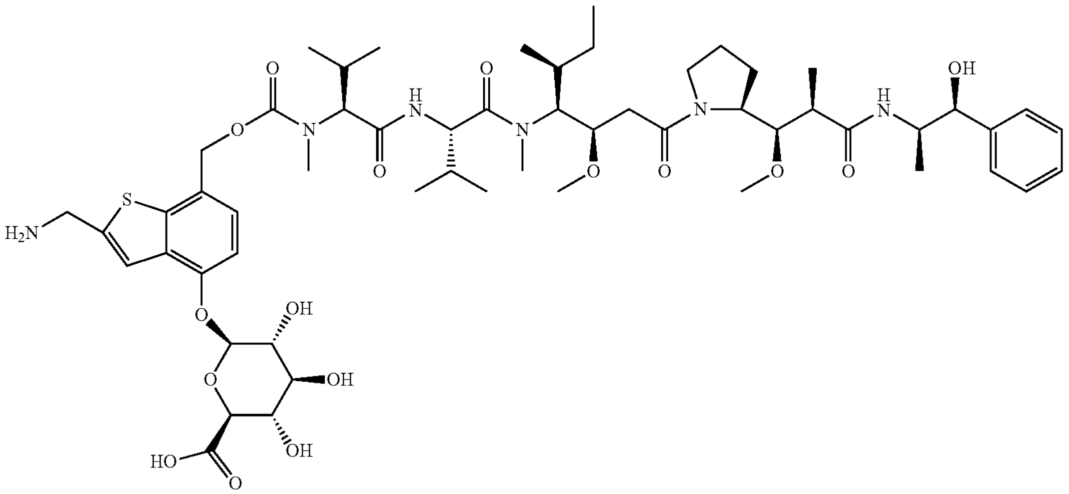
A-58
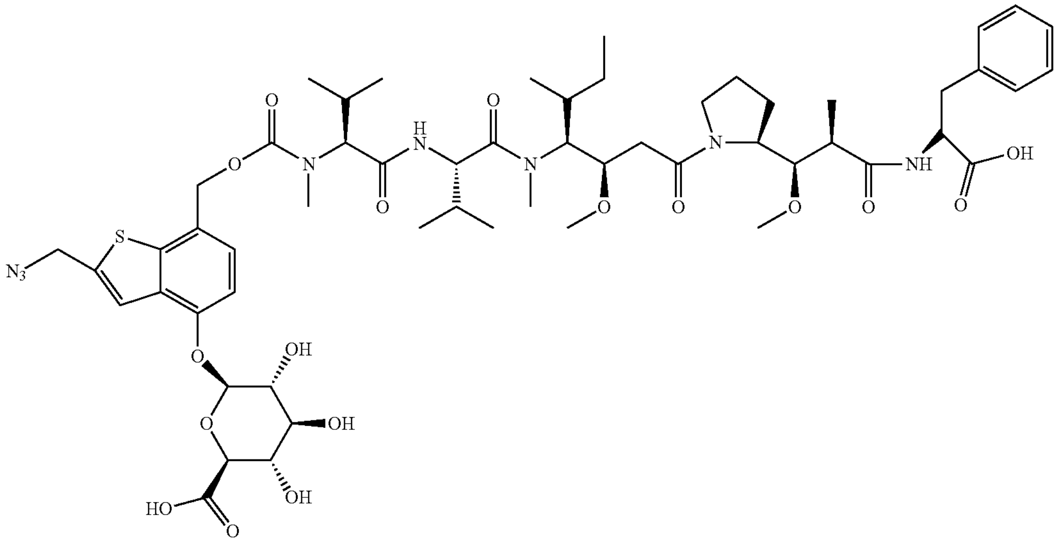

TABLE A-continued
Exemplary compounds of Formula 1
A-59
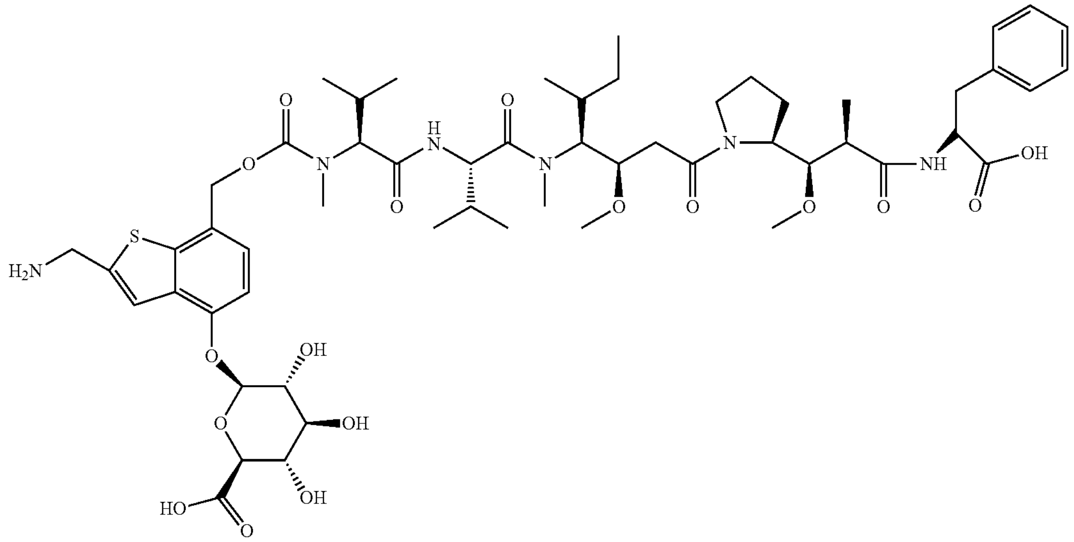
A-60
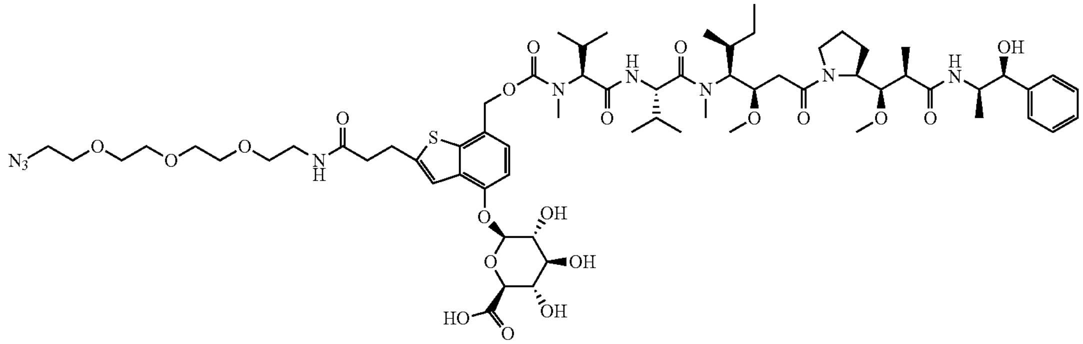 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c2cc(CCC(=O)NCCOCCOCCOCCN=[N+]=[N-])sc12)C(C)C]
A-61
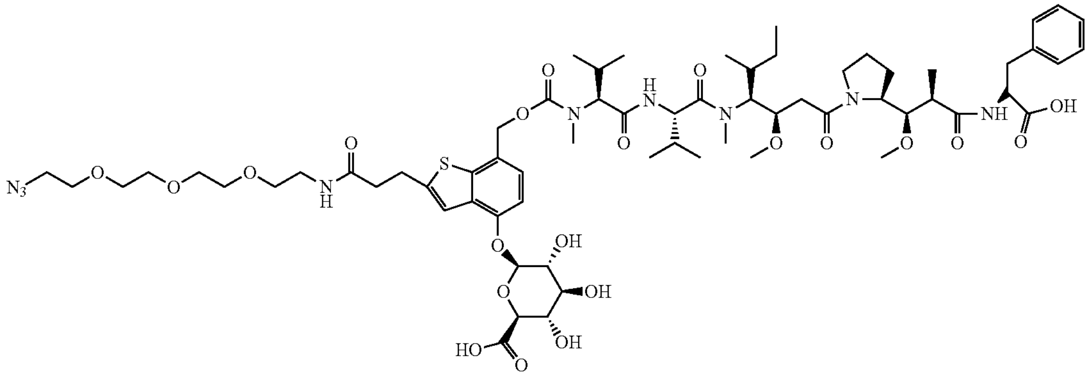

TABLE A-continued
| Exemplary compounds of Formula 1 |
| --- |
| A-62 |
| 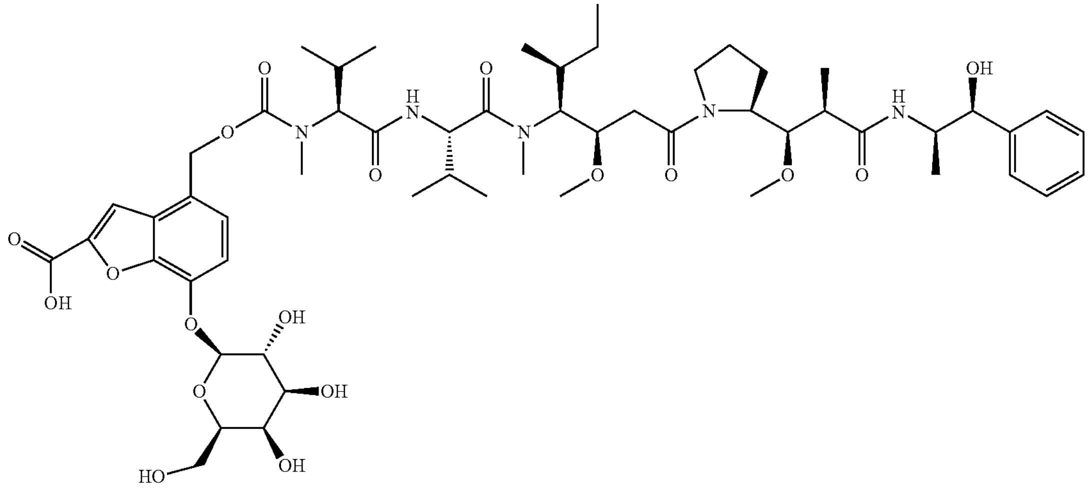 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](CO)[C@H](O)[C@H](O)[C@H]2O)c2oc(C(=O)O)cc12)C(C)C] |
| A-63 |
| 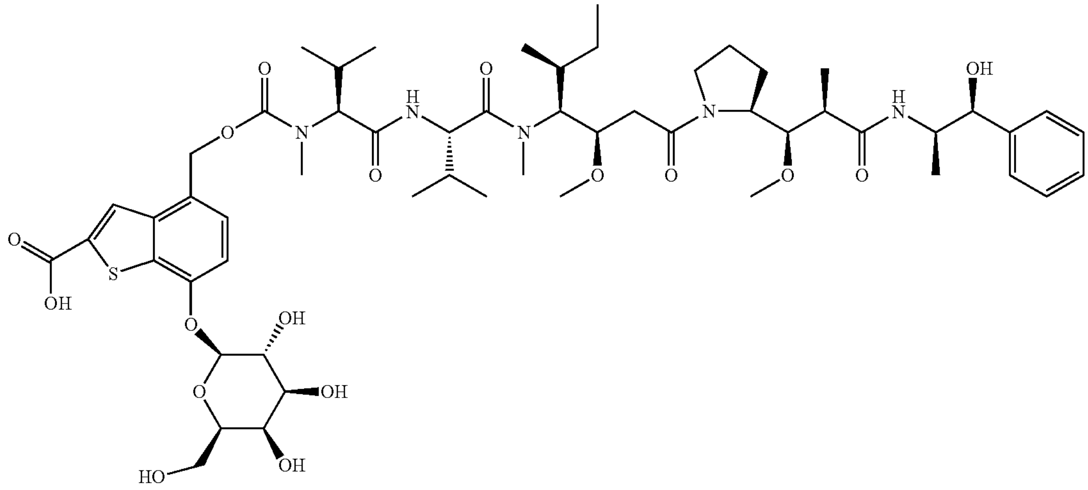 |
| A-64 |
| 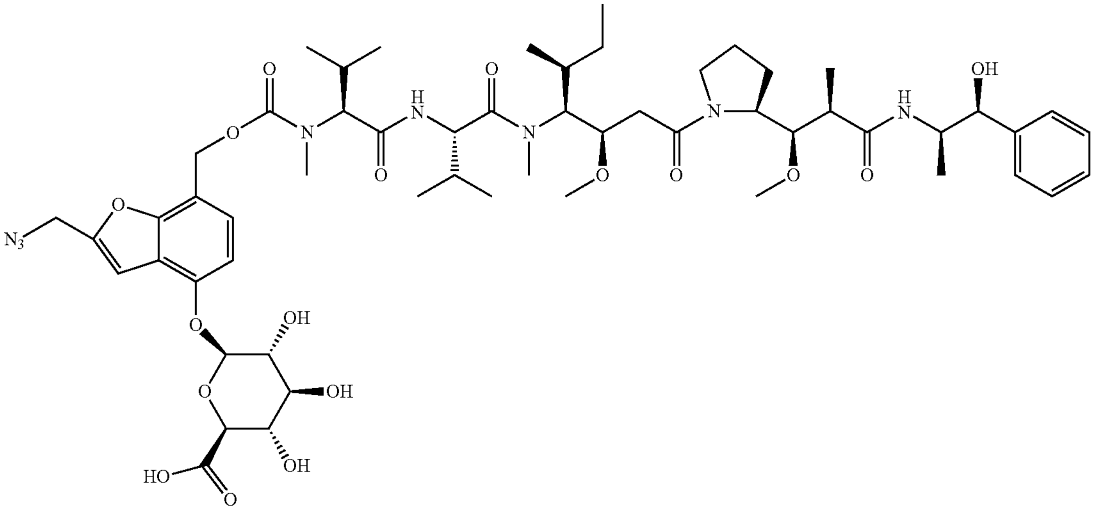 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c2cc(CN=[N+]=[N-])oc12)C(C)C] |

TABLE A-continued
Exemplary compounds of Formula 1
A-65
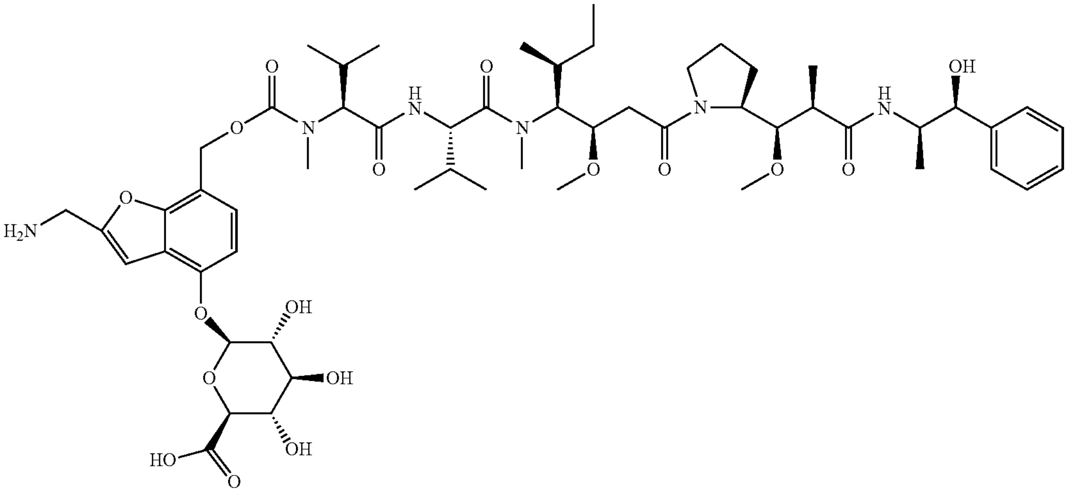
A-66
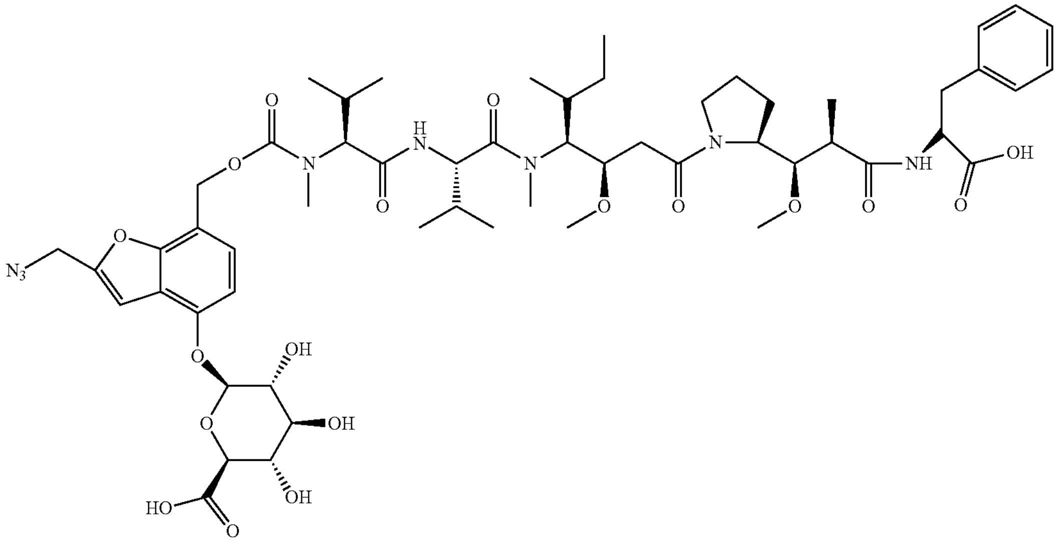
A-67
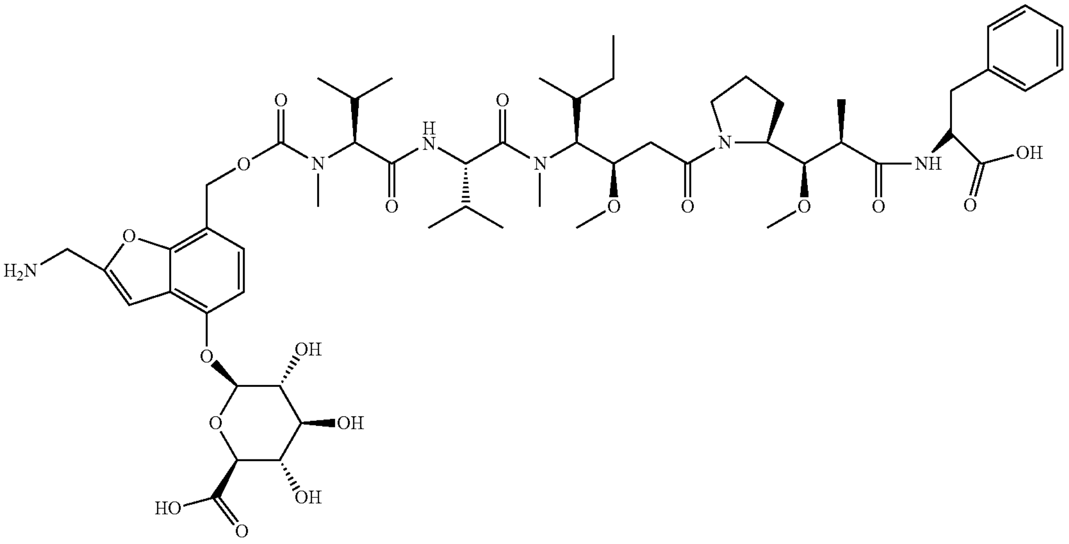

TABLE A-continued
Exemplary compounds of Formula 1
A-68
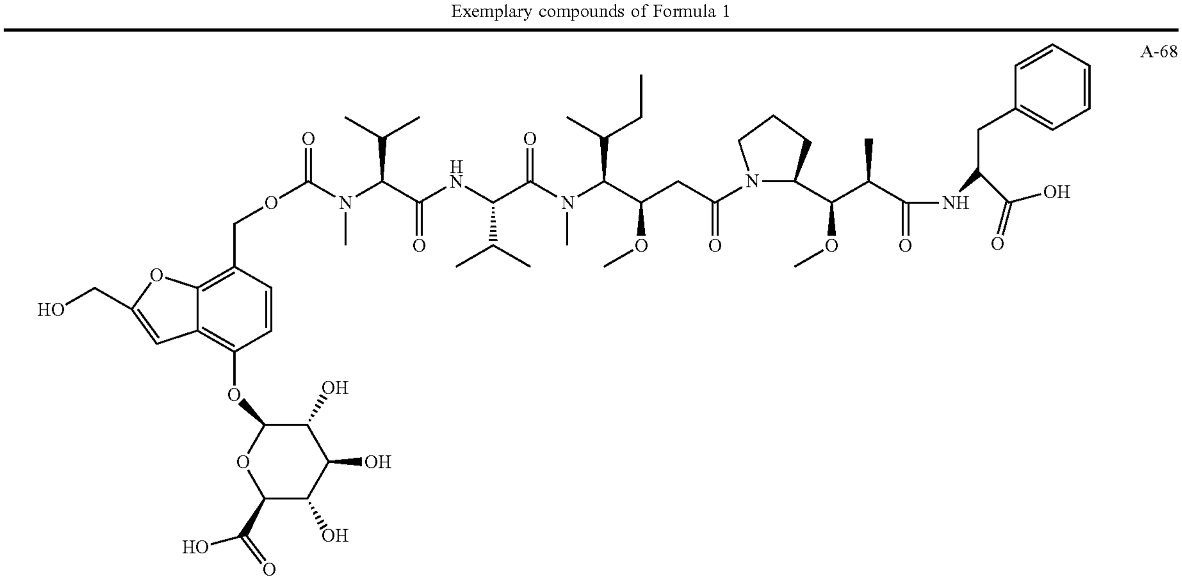
A-69
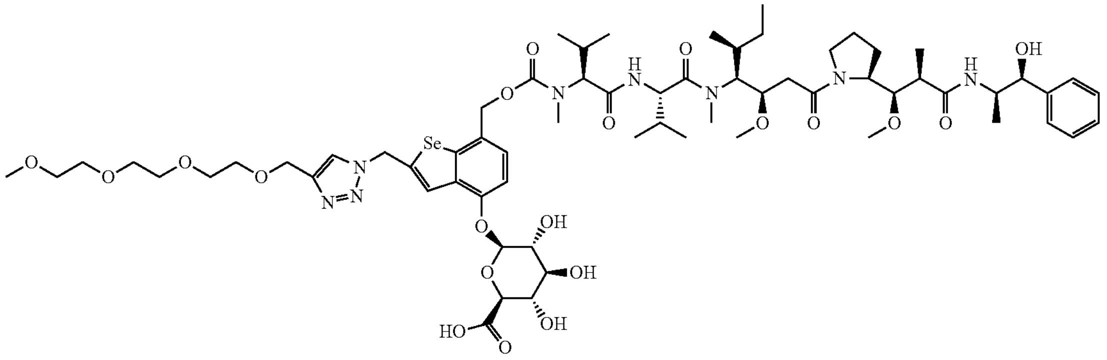 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c2cc(Cn3cc(COCCOCCOCCOC)nn3)[se]c12)C(C)C]
A-70
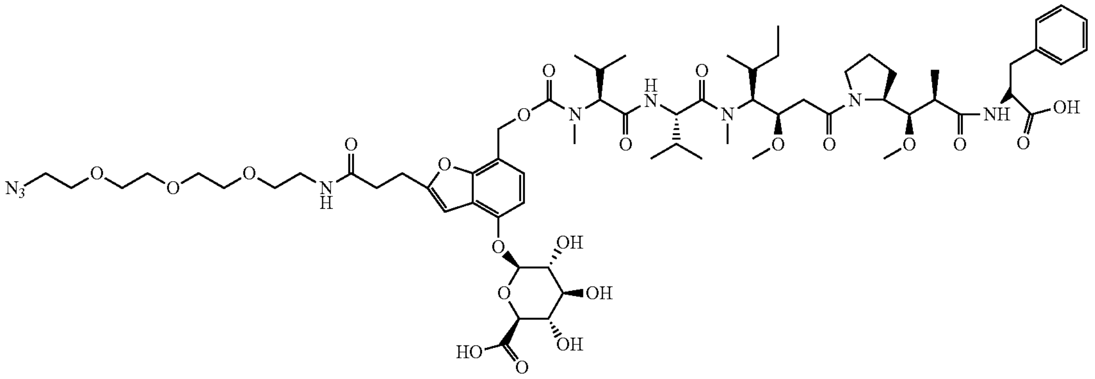

TABLE A-continued
Exemplary compounds of Formula 1
A-71
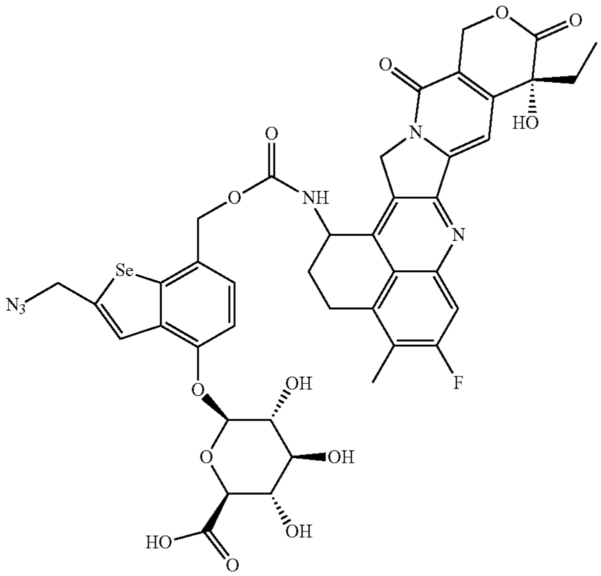 [SMILES: CC[C@]1(O)C(=O)OCc2c1cc1n(c2=O)Cc2c-1nc1cc(F)c(C)c3c1c2C(NC(=O)OCc1ccc(O[C@@H]2O[C@H](C(=O)O)[C@@H](O)[C@H](O)[C@H]2O)c2cc(CN=[N+]=[N-])[se]c12)CC3]
A-72
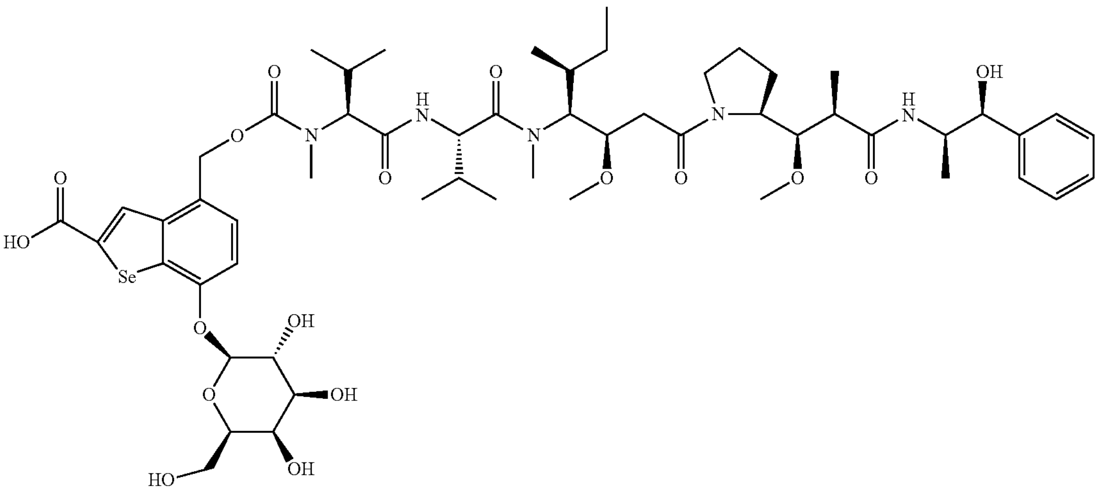 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](CO)[C@H](O)[C@H](O)[C@H]2O)c2[se]c(C(=O)O)cc12)C(C)C]

TABLE A-continued
| Exemplary compounds of Formula 1 |
| --- |
| 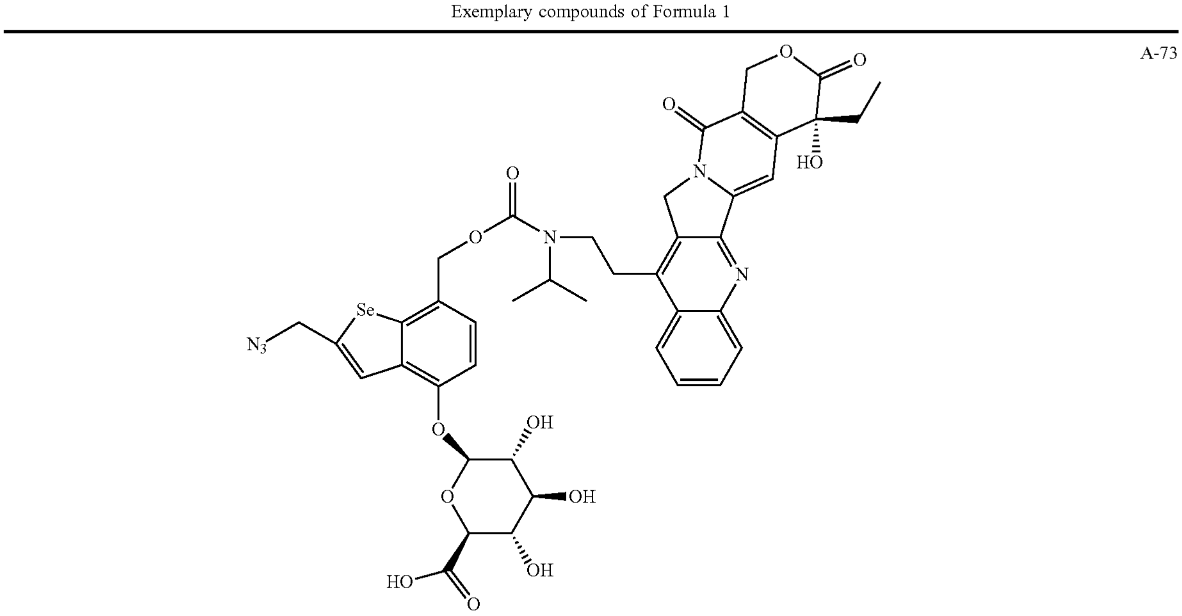 A-73 |
| 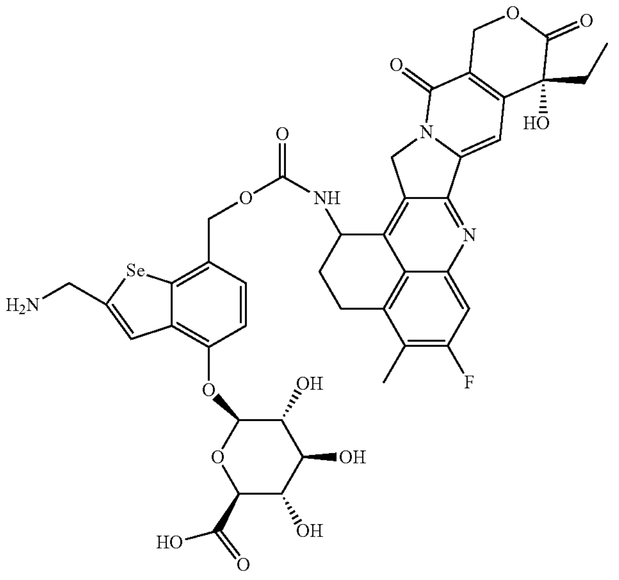 [SMILES: CC[C@]1(O)C(=O)OCc2c1cc1n(c2=O)Cc2c-1nc1cc(F)c(C)c3c1c2C(NC(=O)OCc1ccc(O[C@@H]2O[C@H](C(=O)O)[C@@H](O)[C@H](O)[C@H]2O)c2cc(CN)[se]c12)CC3] A-74 |

TABLE A-continued
Exemplary compounds of Formula 1
A-75
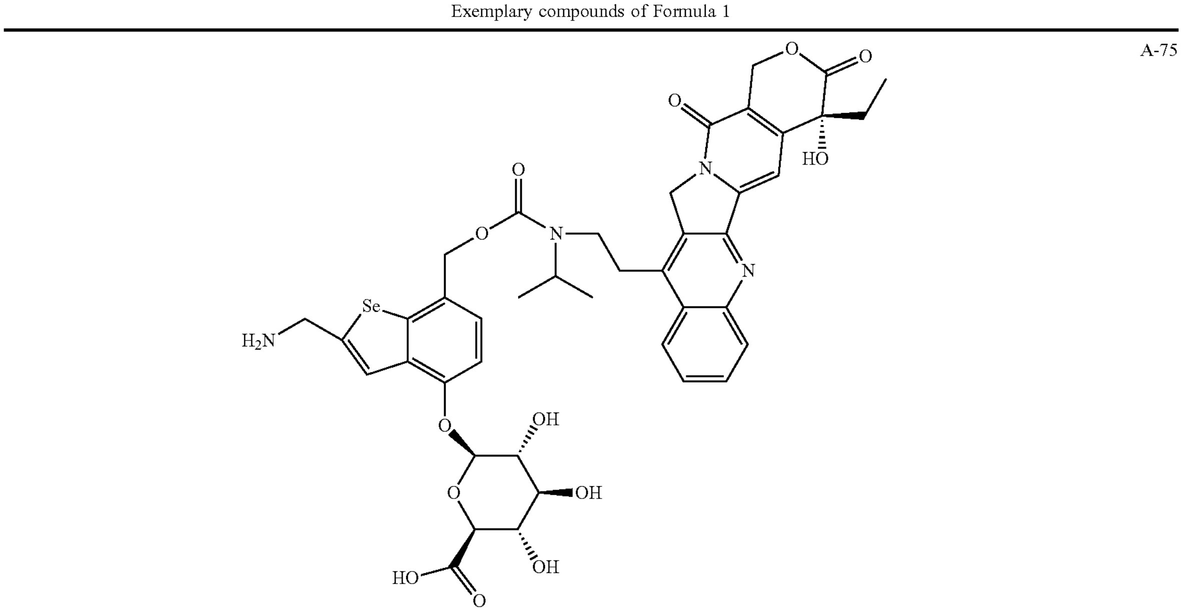
A-76
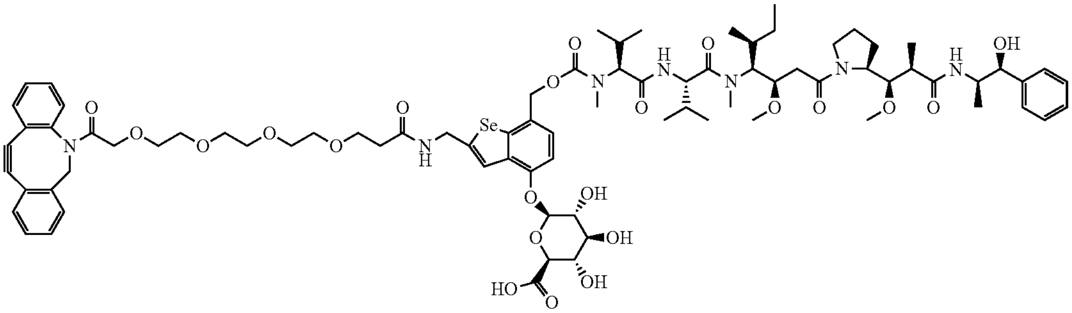 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c2cc(CNC(=O)CCOCCOCCOCCOCC(=O)N3Cc4ccccc4C#Cc4ccccc43)[se]c12)C(C)C]
A-77
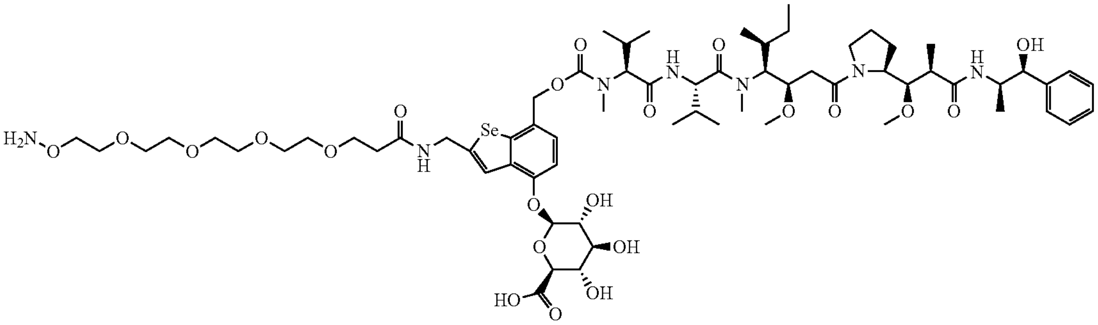 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c2cc(CNC(=O)CCOCCOCCOCCOCCON)[se]c12)C(C)C]

TABLE B
| Exemplary compounds having a maleimide functional group of Formula 1 (DAR2 type) |
|---|
| 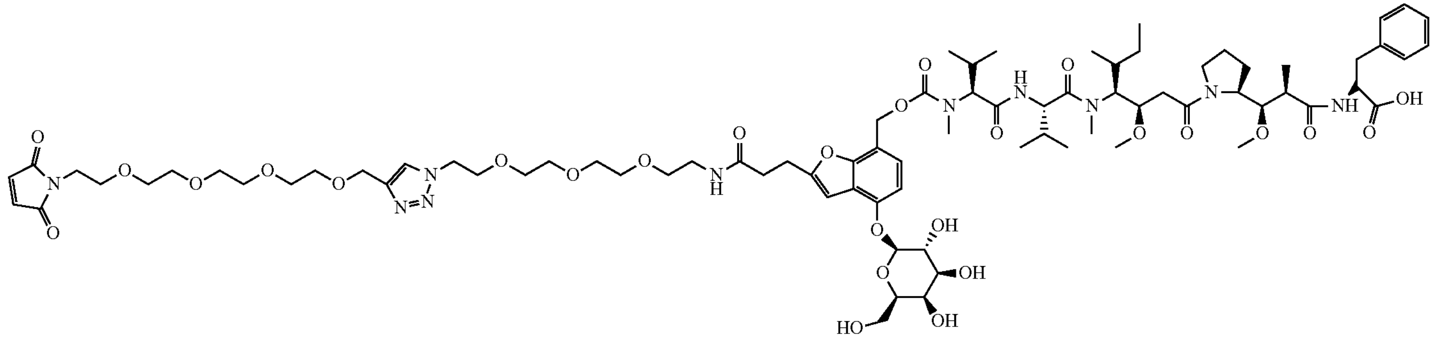 B-1 |
| 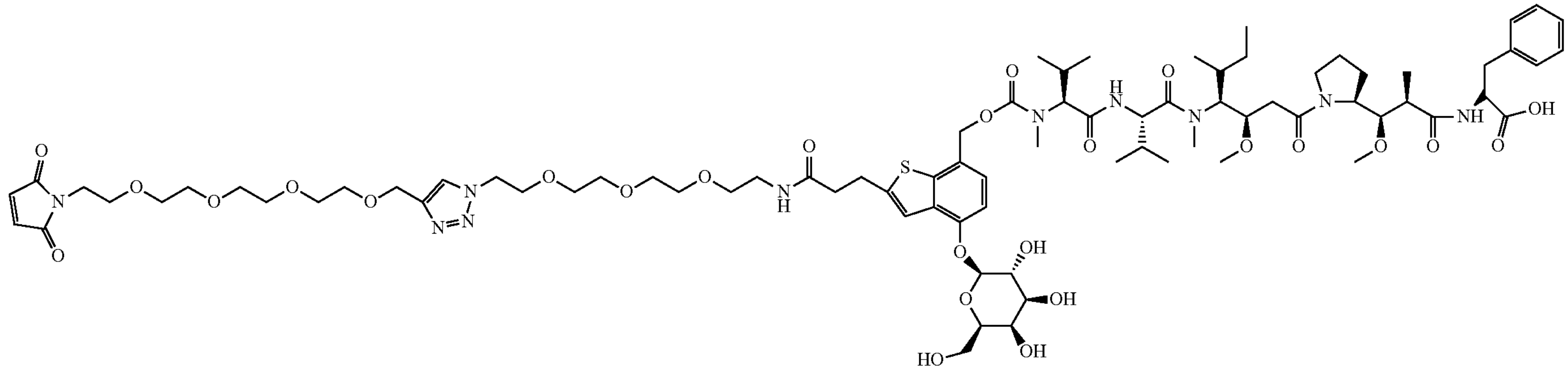 B-2 |

TABLE B-continued
Exemplary compounds having a maleimide functional group of Formula 1 (DAR2 type)
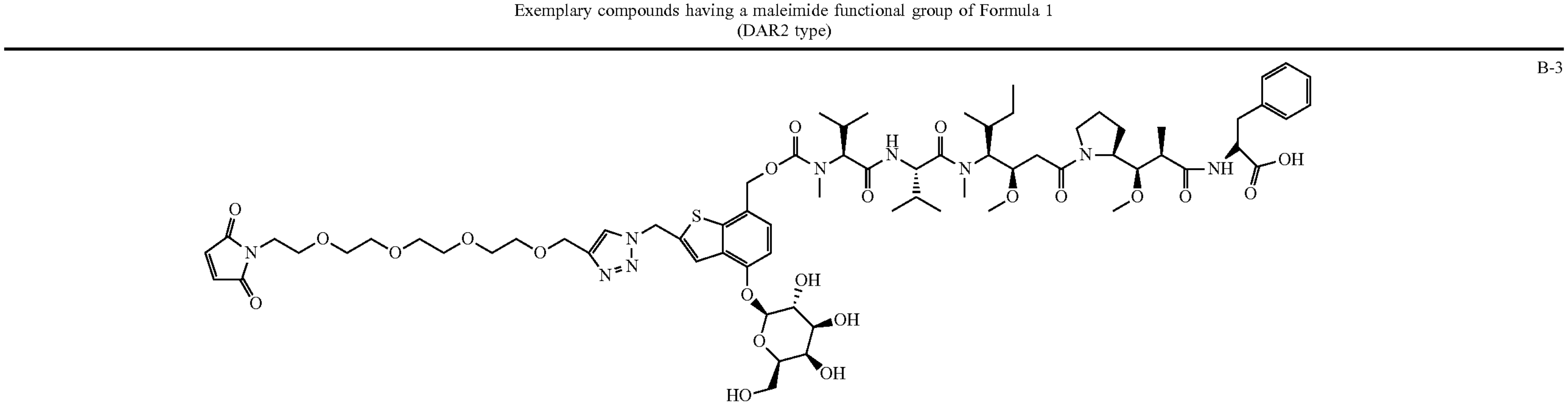
B-3
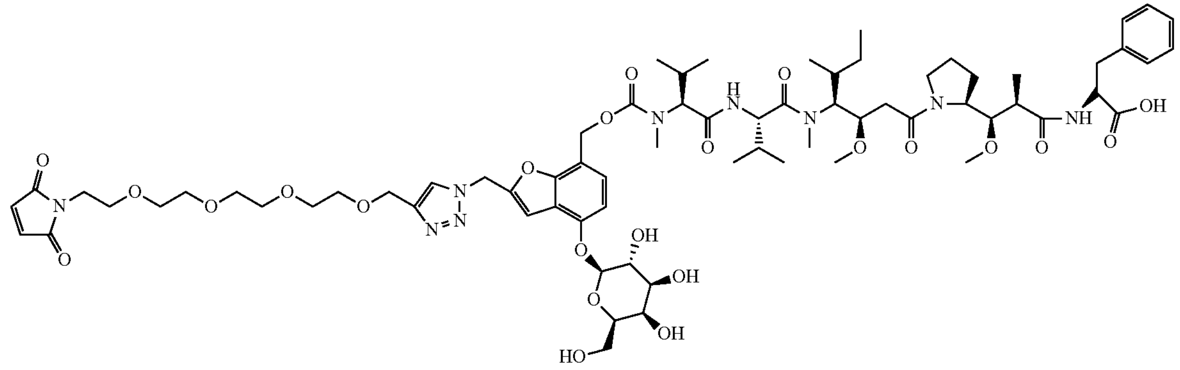
B-4

TABLE B-continued
| Exemplary compounds having a maleimide functional group of Formula 1 (DAR2 type) | |
|---|---|
| 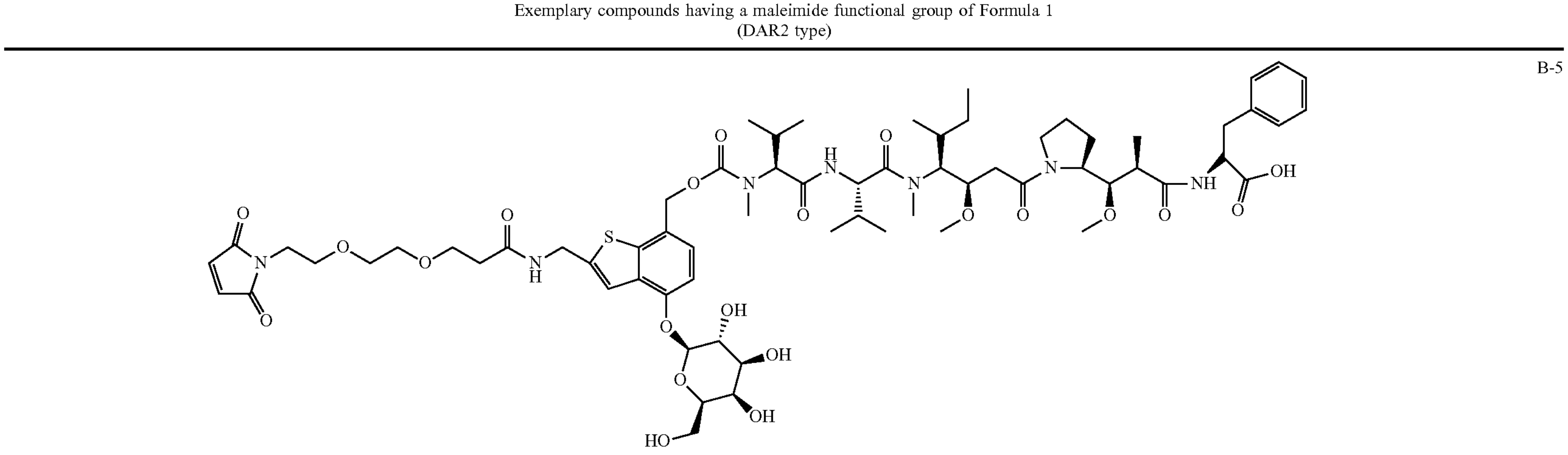 | B-5 |
| 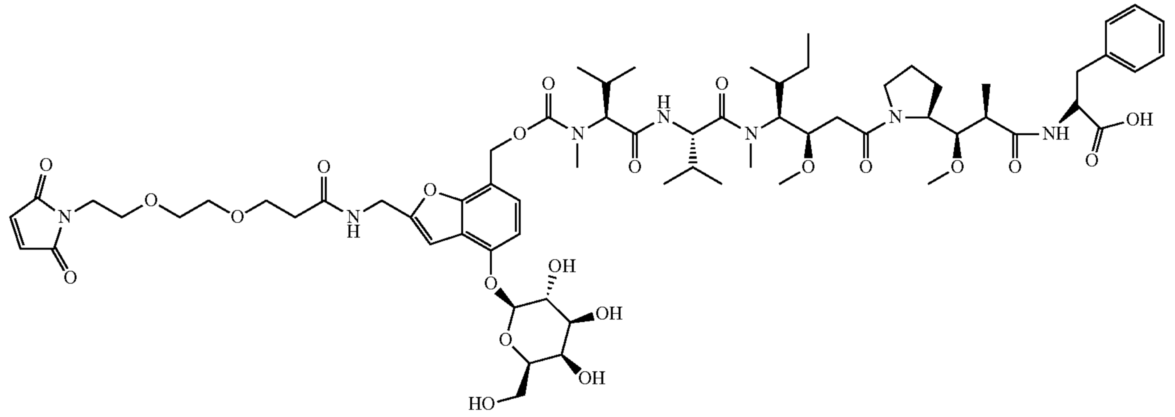 | B-6 |

TABLE B-continued
| Exemplary compounds having a maleimide functional group of Formula 1 (DAR2 type) | |
|---|---|
| 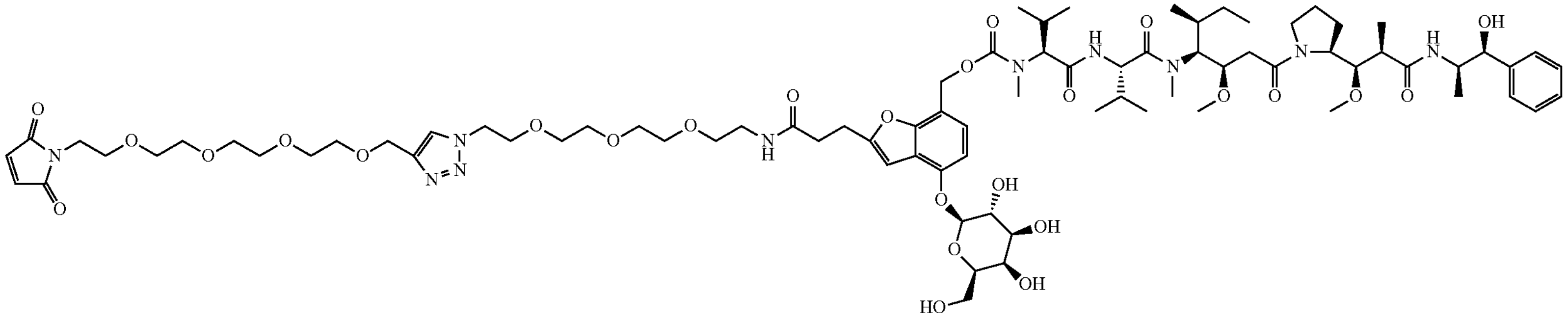 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](CO)[C@H](O)[C@H](O)[C@H]2O)c2cc(CCC(=O)NCCOCCOCCOCCn3cc(COCCOCCOCCOCCN4C(=O)C=CC4=O)nn3)oc12)C(C)C] | B-7 |
| 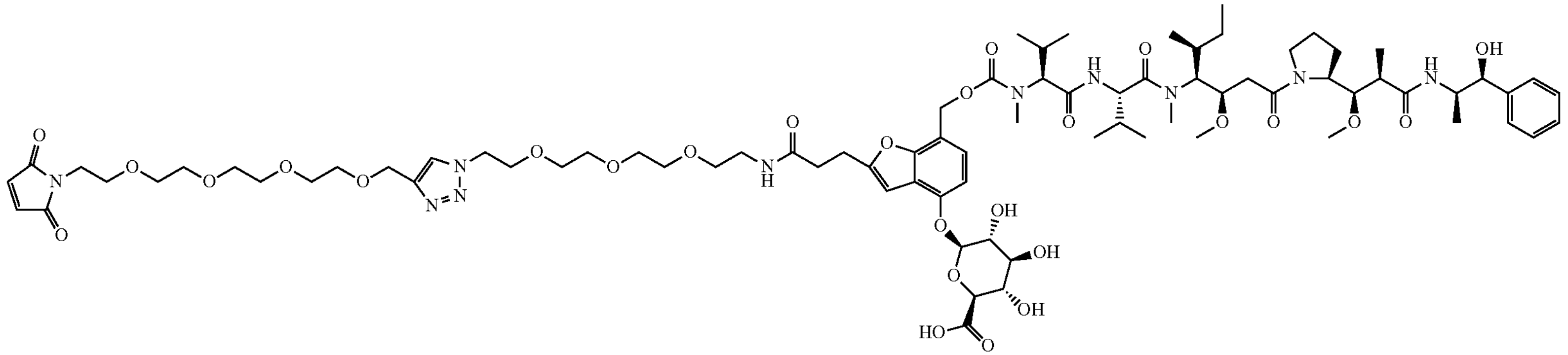 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c2cc(CCC(=O)NCCOCCOCCOCCn3cc(COCCOCCOCCOCCN4C(=O)C=CC4=O)nn3)oc12)C(C)C] | B-8 |
| 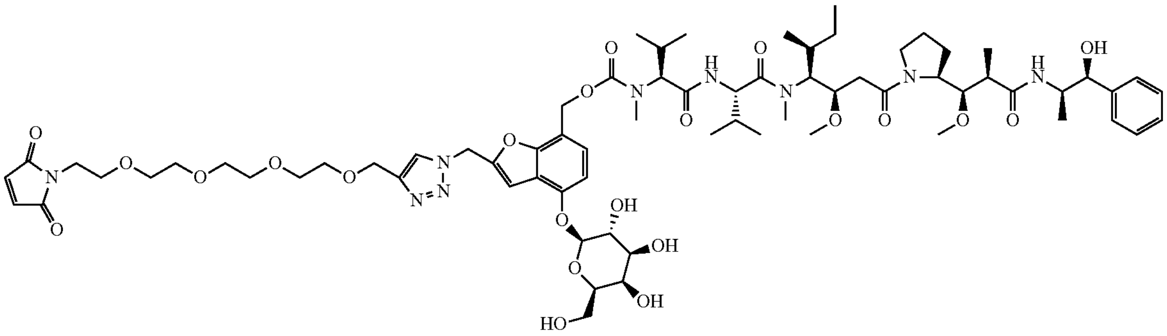 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](CO)[C@H](O)[C@H](O)[C@H]2O)c2cc(Cn3cc(COCCOCCOCCOCCN4C(=O)C=CC4=O)nn3)oc12)C(C)C] | B-11 |

TABLE B-continued
Exemplary compounds having a maleimide functional group of Formula 1 (DAR2 type)
B-12
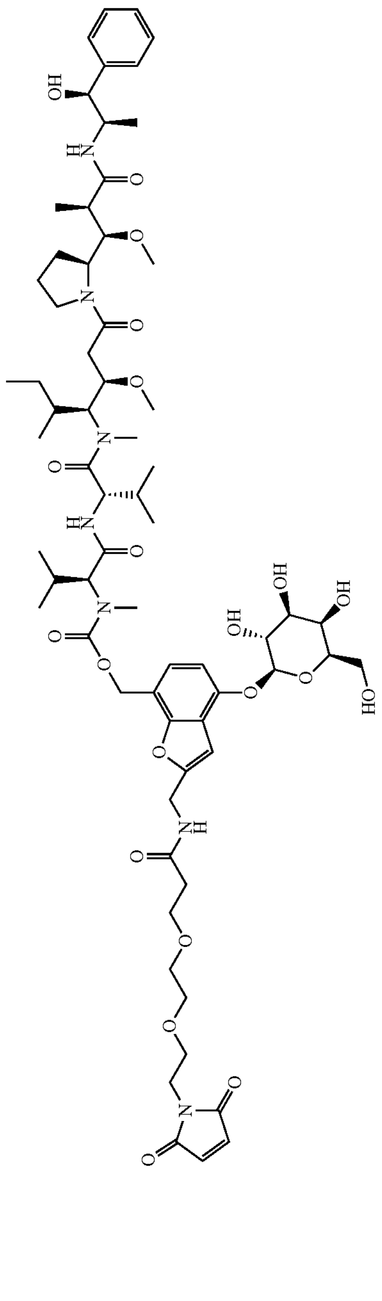
B-13
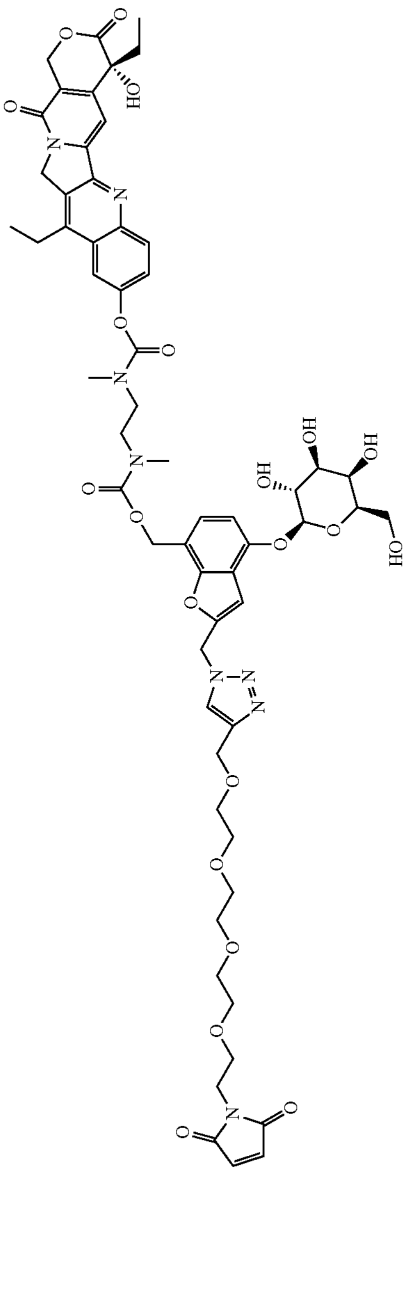

TABLE B-continued
| Exemplary compounds having a maleimide functional group of Formula 1 (DAR2 type) |
| --- |
| 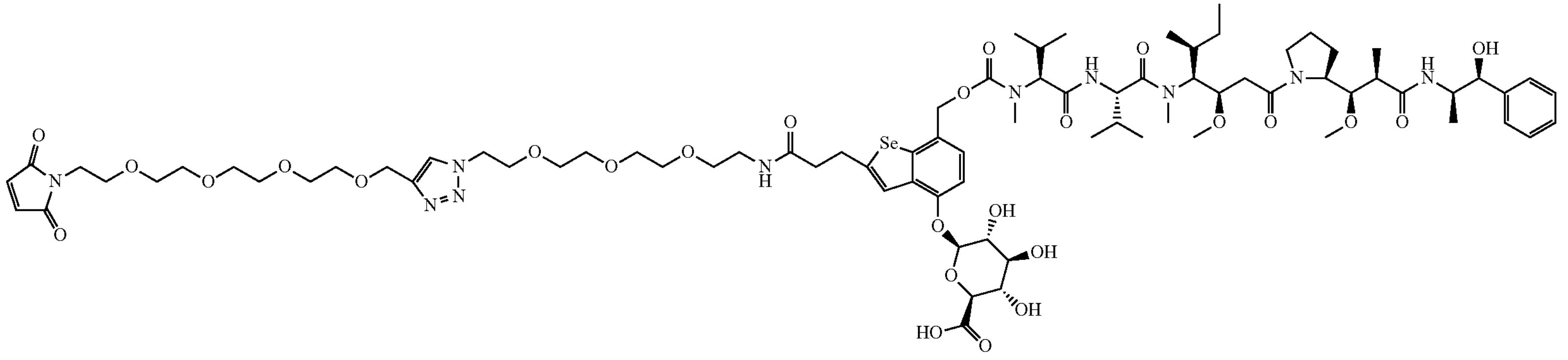 B-14 |
| 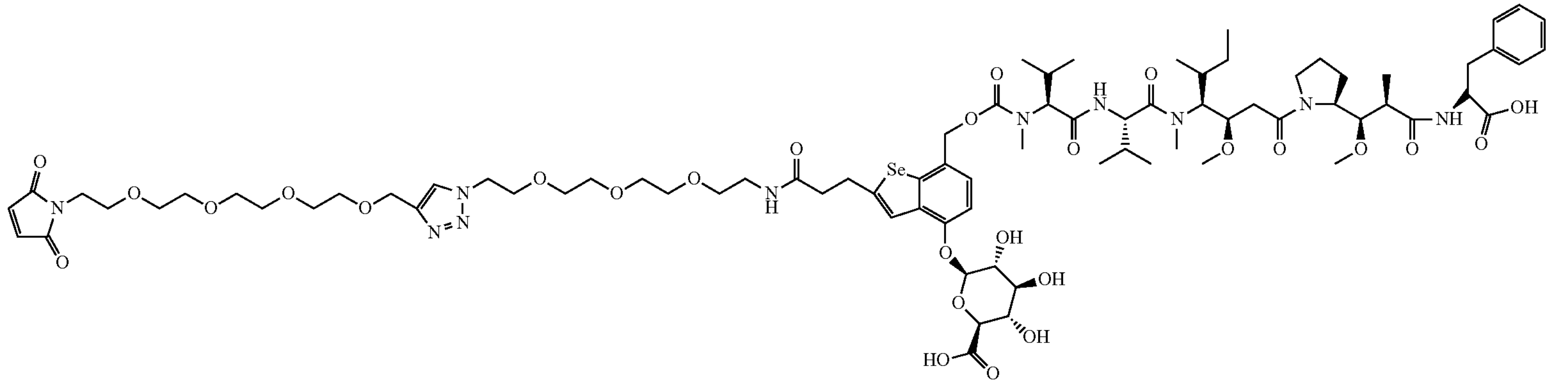 B-15 |

TABLE B-continued
| Exemplary compounds having a maleimide functional group of Formula 1 (DAR2 type) | |
|---|---|
| 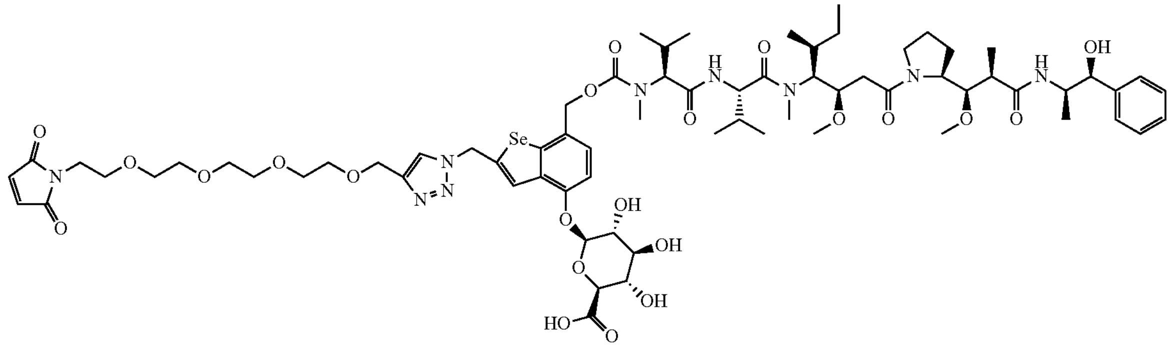 | B-16 |
| 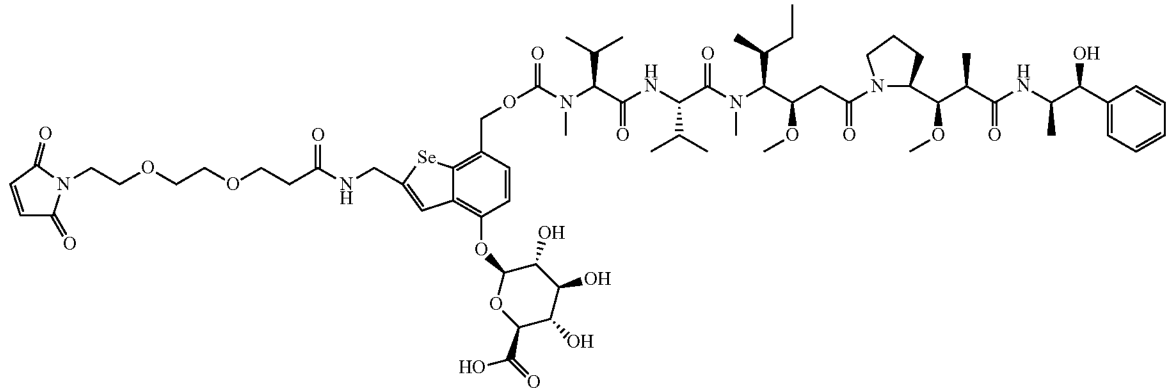 | B-17 |

TABLE B-continued
| Exemplary compounds having a maleimide functional group of Formula 1 (DAR2 type) | |
|---|---|
| 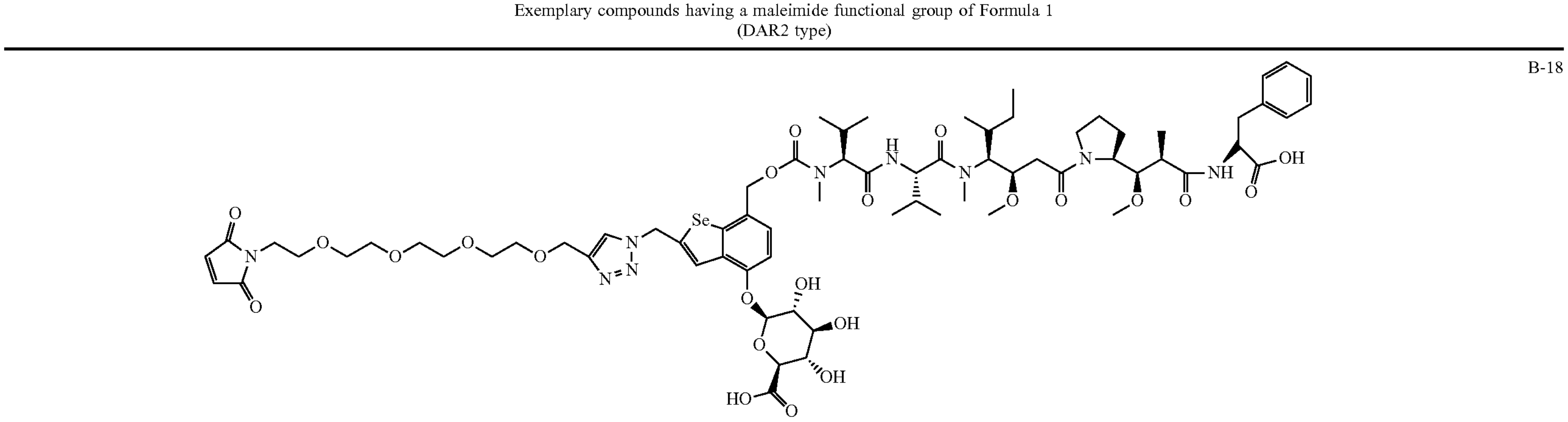 | B-18 |
| 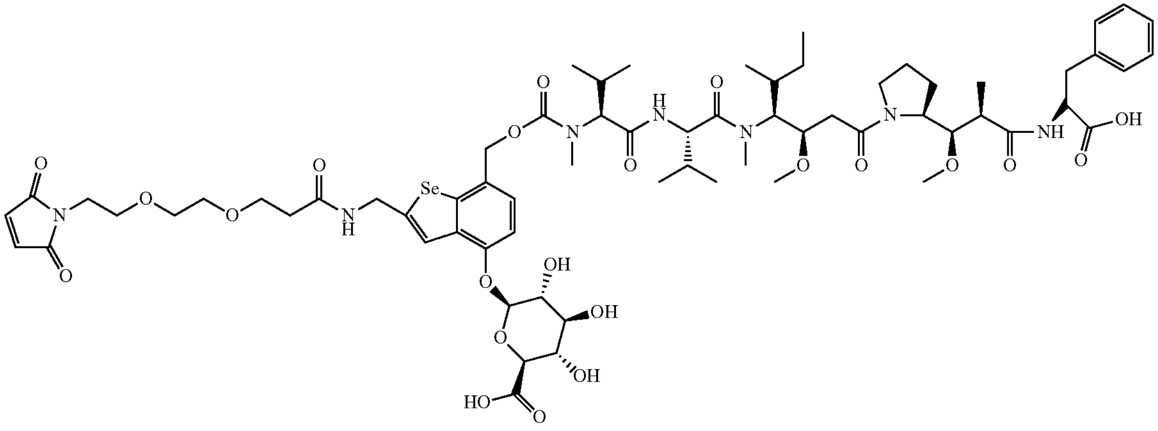 | B-19 |

TABLE B-continued
| Exemplary compounds having a maleimide functional group of Formula 1 (DAR2 type) | |
|---|---|
| 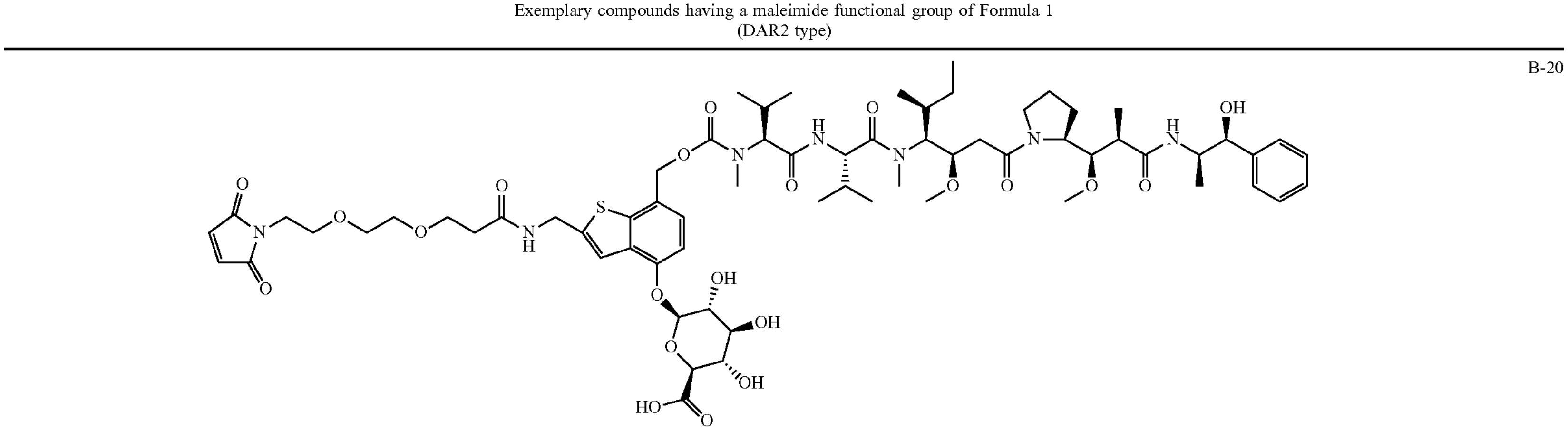 | B-20 |
| 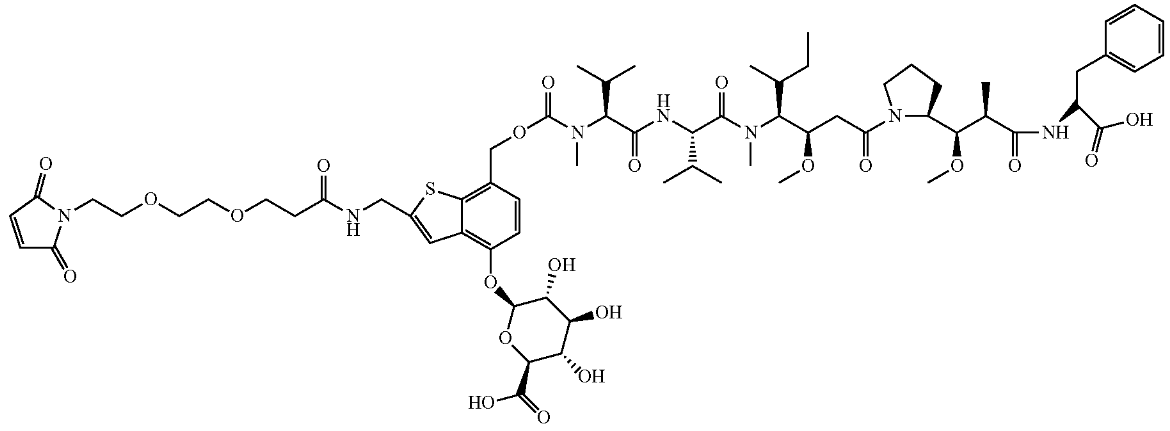 | B-21 |

TABLE B-continued
Exemplary compounds having a maleimide functional group of Formula 1
(DAR2 type)
B-22
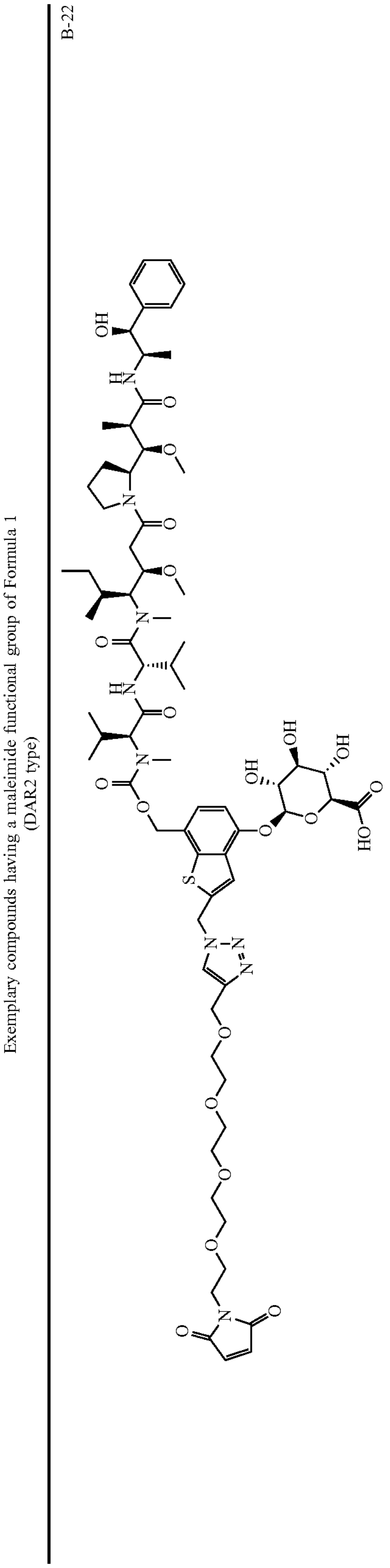
B-23
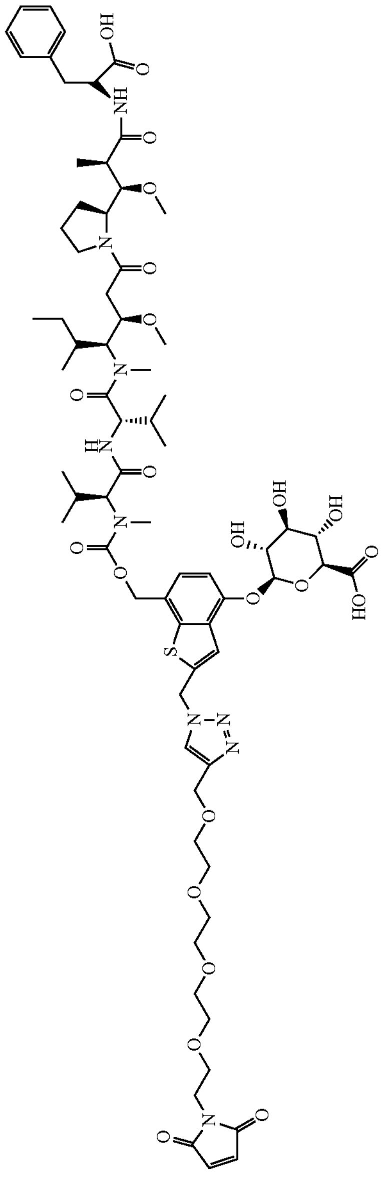

TABLE B-continued
Exemplary compounds having a maleimide functional group of Formula 1
(DAR2 type)
B-24
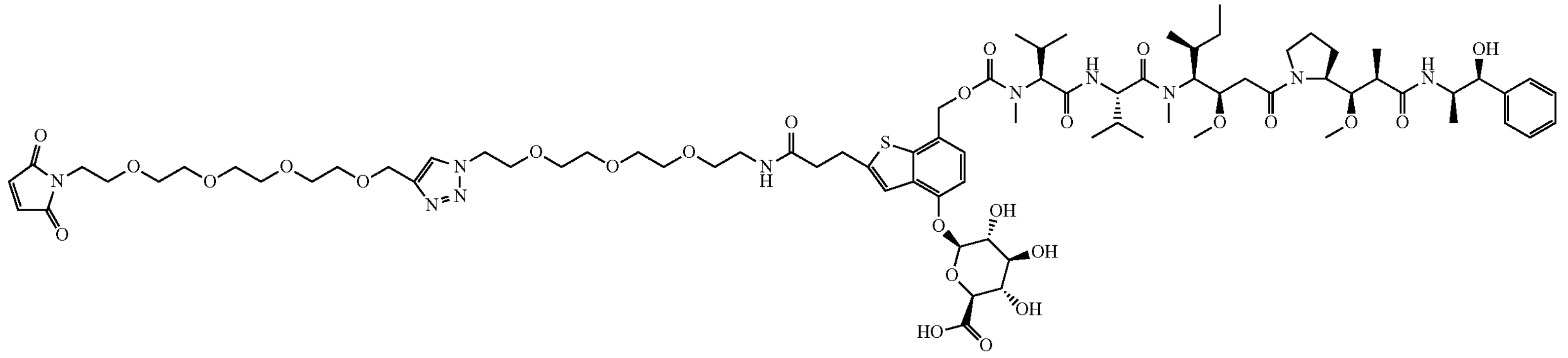
B-25
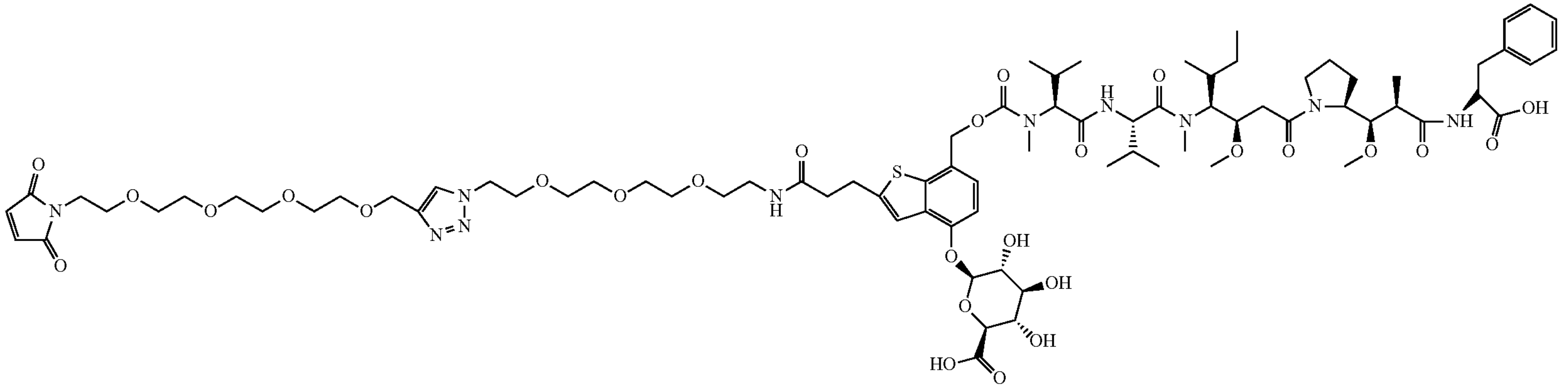

TABLE B-continued
| Exemplary compounds having a maleimide functional group of Formula 1 (DAR2 type) | |
|---|---|
| 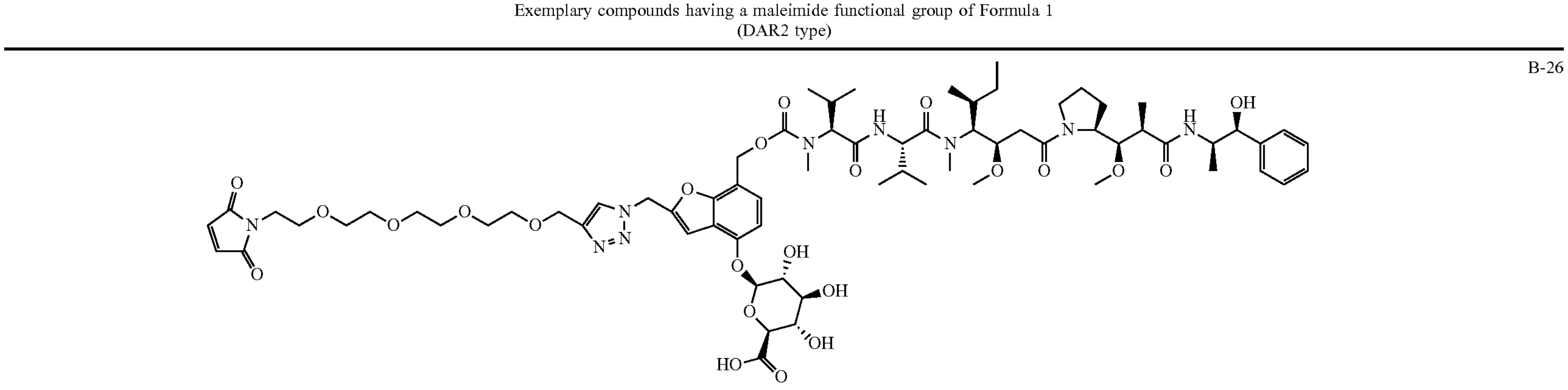 | B-26 |
| 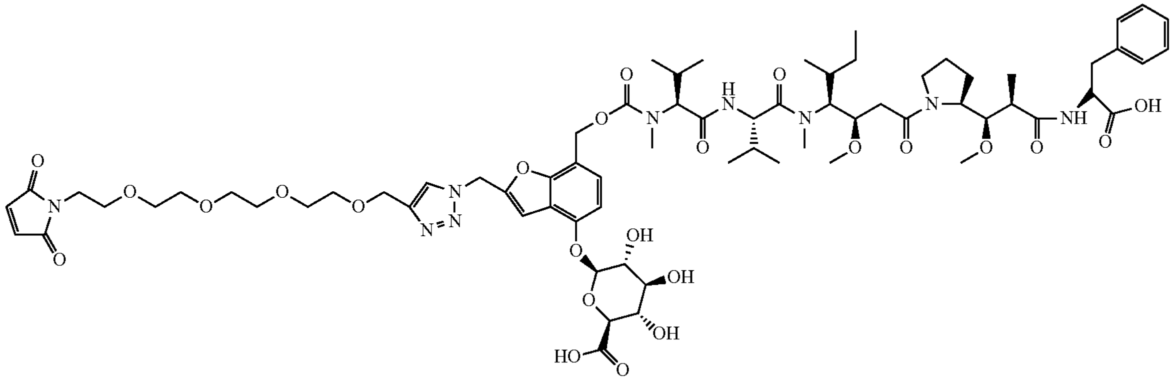 | B-27 |

TABLE B-continued
| Exemplary compounds having a maleimide functional group of Formula 1 (DAR2 type) | |
|---|---|
| 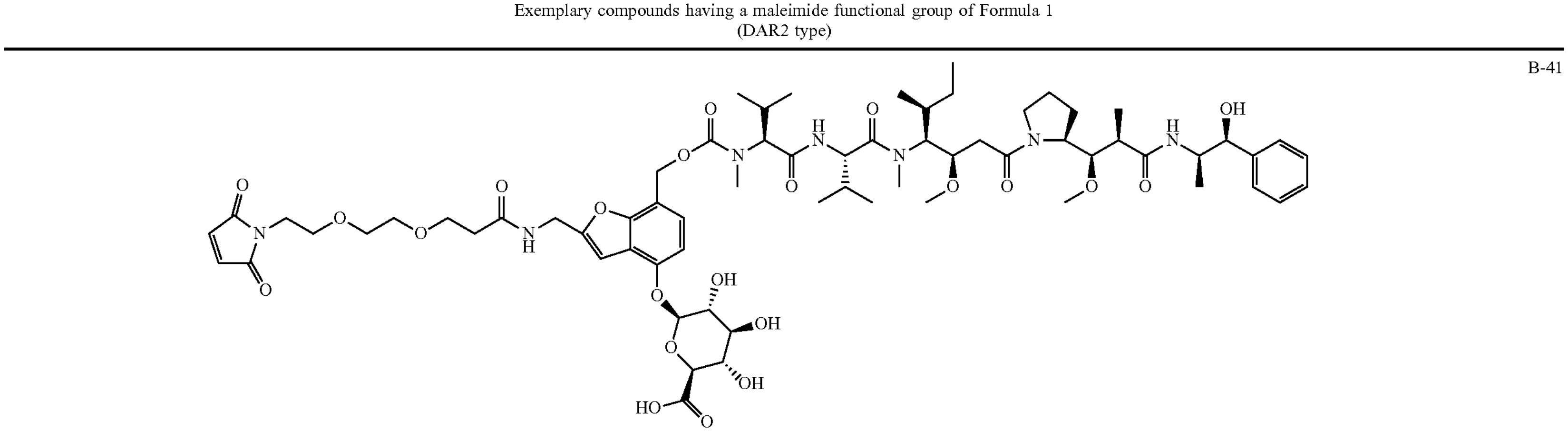 | B-41 |
| 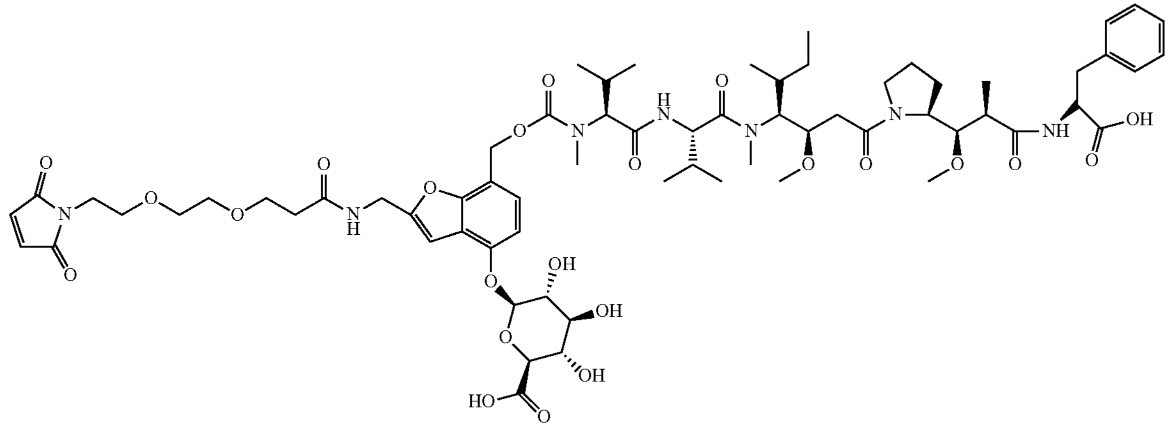 | B-42 |

TABLE B-continued
| Exemplary compounds having a maleimide functional group of Formula 1 (DAR2 type) | |
|---|---|
| 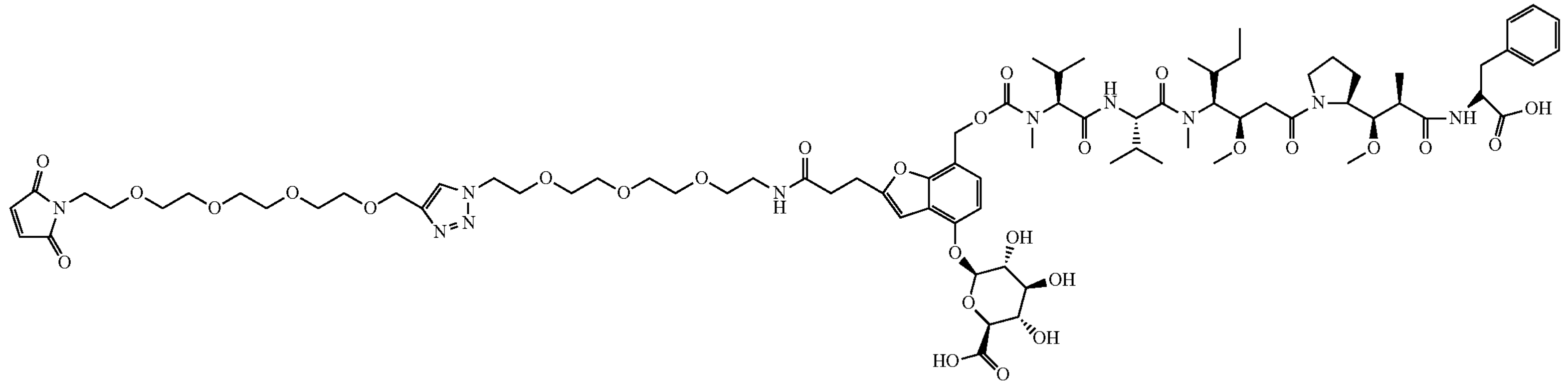 | B-43 |
| 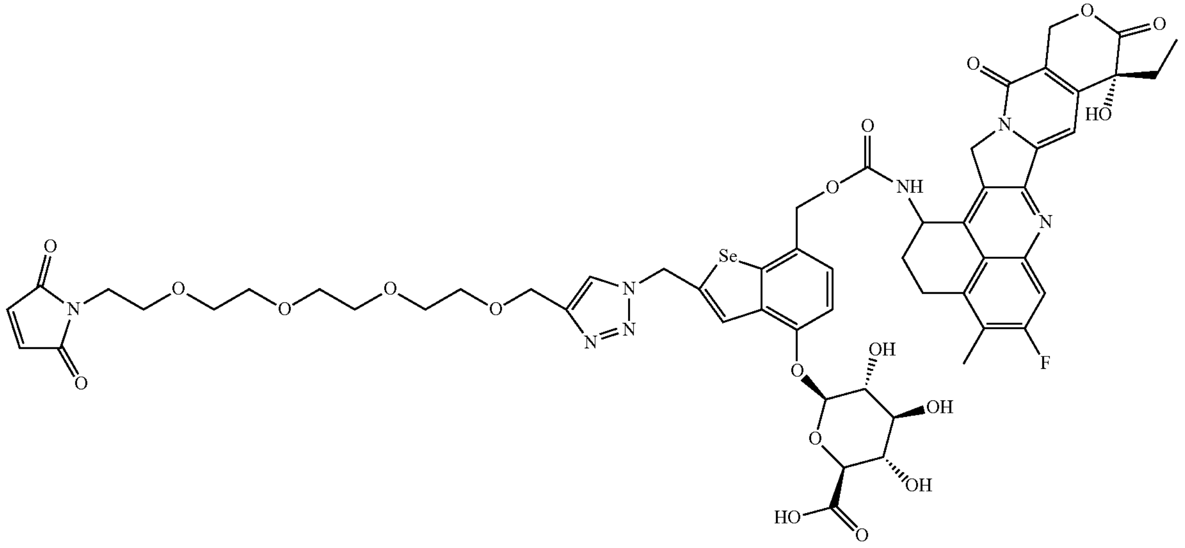 [SMILES: CC[C@]1(O)C(=O)OCc2c1cc1n(c2=O)Cc2c-1nc1cc(F)c(C)c3c1c2C(NC(=O)OCc1ccc(O[C@@H]2O[C@H](C(=O)O)[C@@H](O)[C@H](O)[C@H]2O)c2cc(Cn4cc(COCCOCCOCCOCCN5C(=O)C=CC5=O)nn4)[se]c12)CC3] | B-45 |

TABLE B-continued
Exemplary compounds having a maleimide functional group of Formula 1
(DAR2 type)
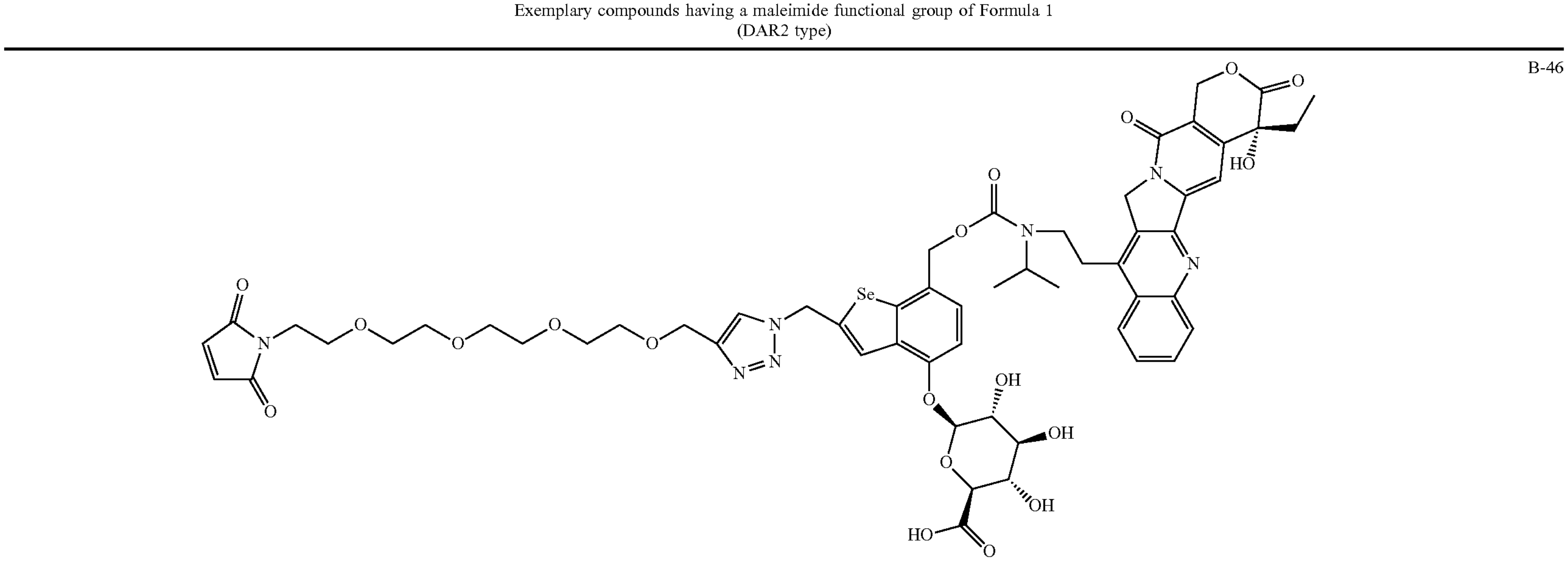
B-46
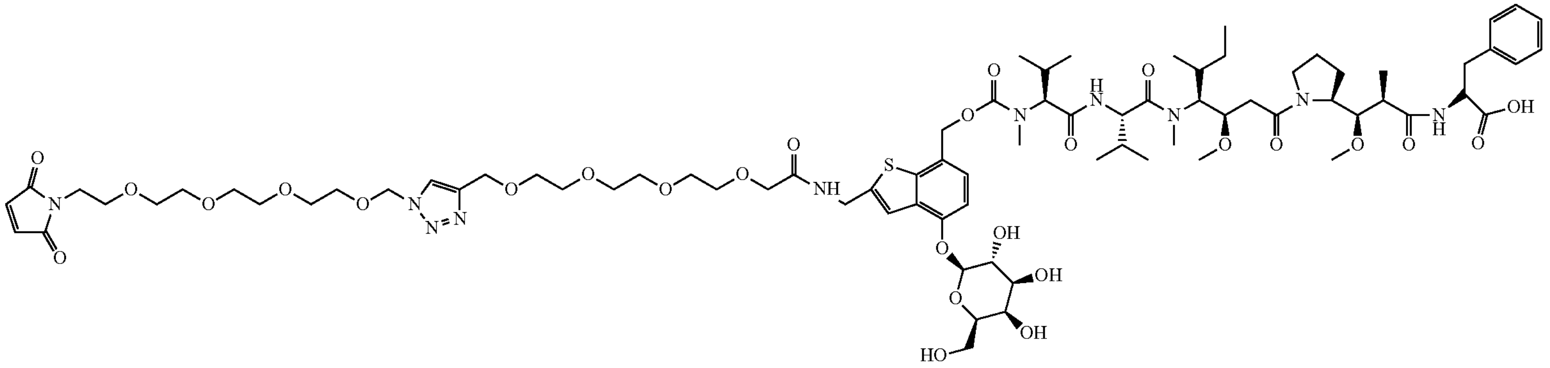
B-49

TABLE B-continued
| Exemplary compounds having a maleimide functional group of Formula 1 (DAR2 type) |
| --- |
| B-50 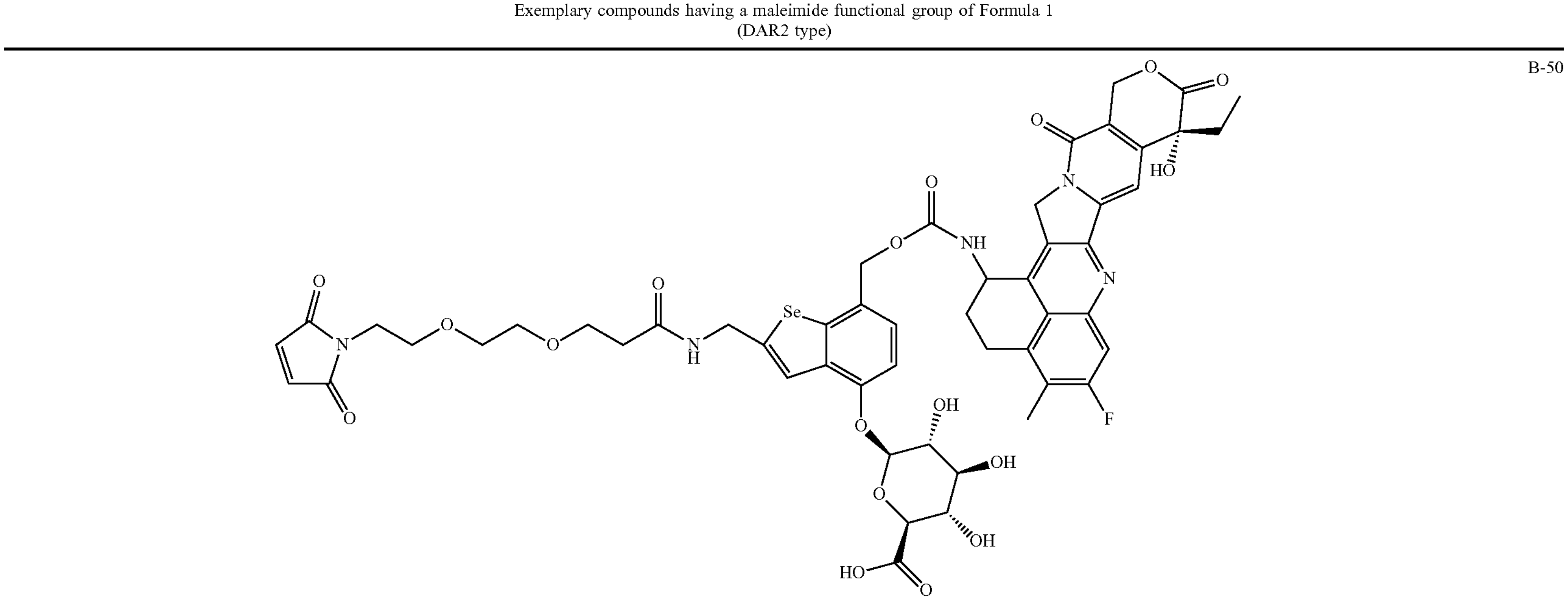 |

TABLE B-continued
| Exemplary compounds having a maleimide functional group of Formula 1 (DAR2 type) | |
|---|---|
| 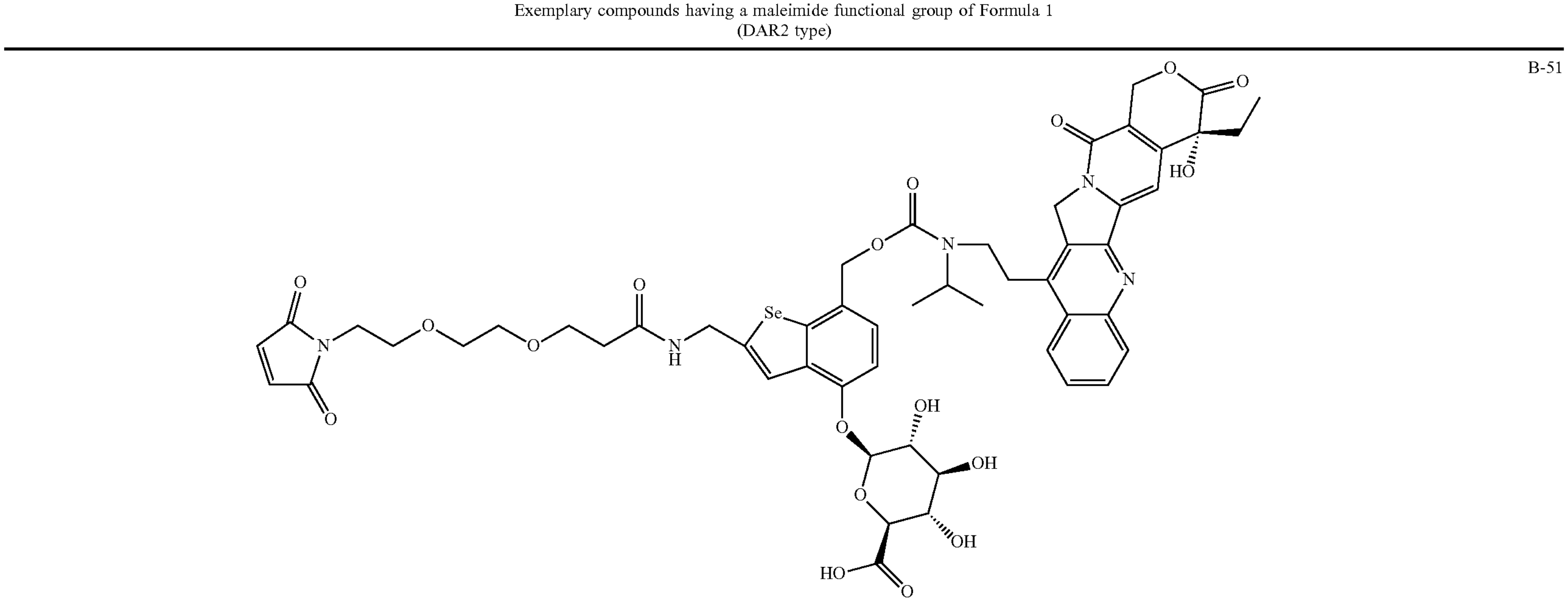 | B-51 |

TABLE C
| Exemplary compounds of DAR4 type | |
|---|---|
| 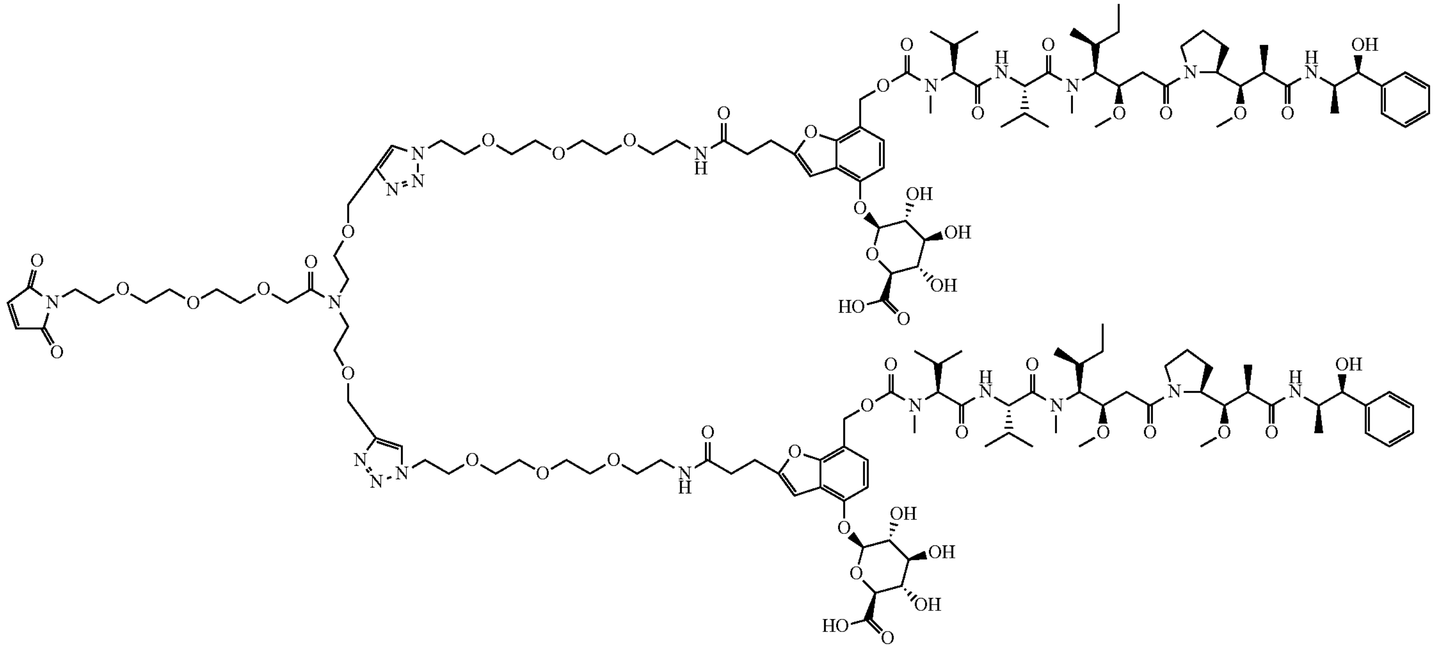 | B-9 |

TABLE C-continued
| Exemplary compounds of DAR4 type |
| --- |
| 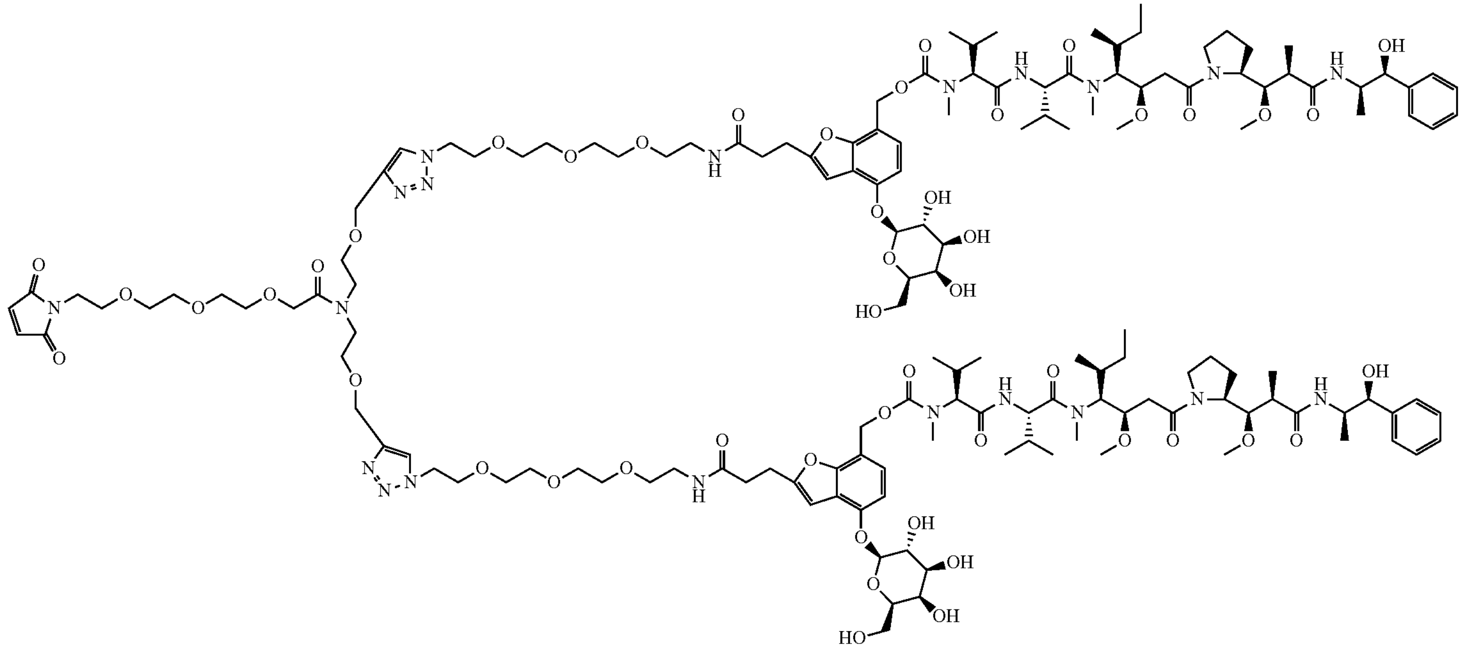 B-10 |

TABLE C-continued
| Exemplary compounds of DAR4 type |
| --- |
| B-28 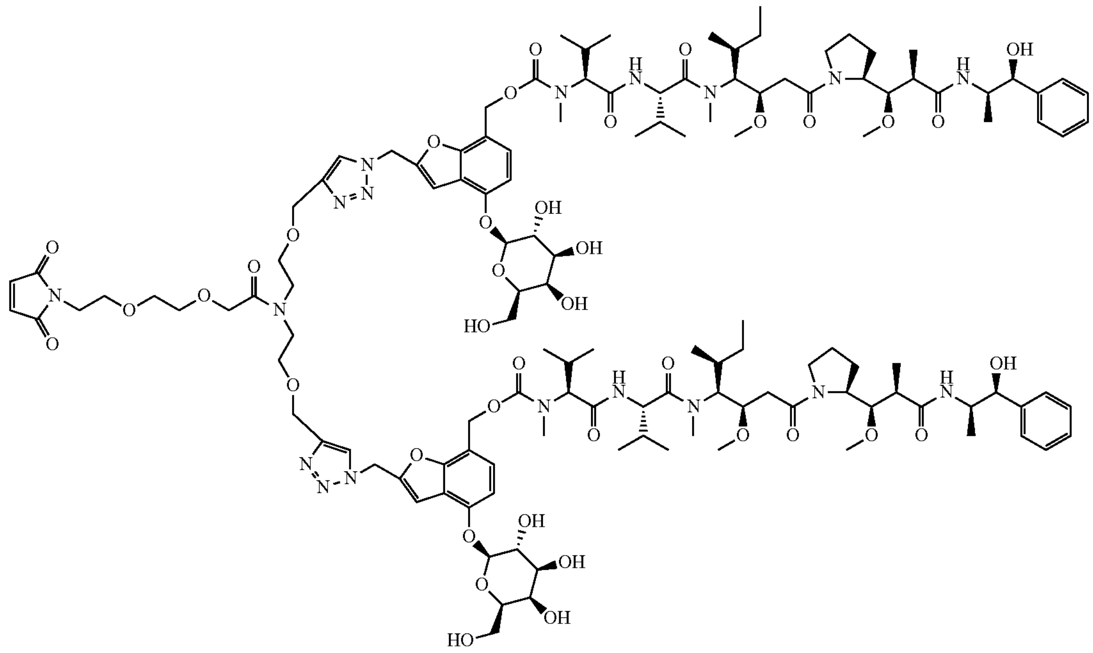 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](CO)[C@H](O)[C@H](O)[C@H]2O)c2cc(Cn3cc(COCCN(CCOCc4cn(Cc5cc6c(O[C@@H]7O[C@H](CO)[C@H](O)[C@H](O)[C@H]7O)ccc(COC(=O)N(C)[C@H](C(=O)N[C@H](C(=O)N(C)[C@@H]([C@@H](C)CC)[C@@H](CC(=O)N7CCC[C@H]7[C@H](OC)[C@@H](C)C(=O)N[C@H](C)[C@@H](O)c7ccccc7)OC)C(C)C)C(C)C)c6o5)nn4)C(=O)COCCOCCN4C(=O)C=CC4=O)nn3)oc12)C(C)C] |

TABLE C-continued
| Exemplary compounds of DAR4 type |
|---|
| B-29 |
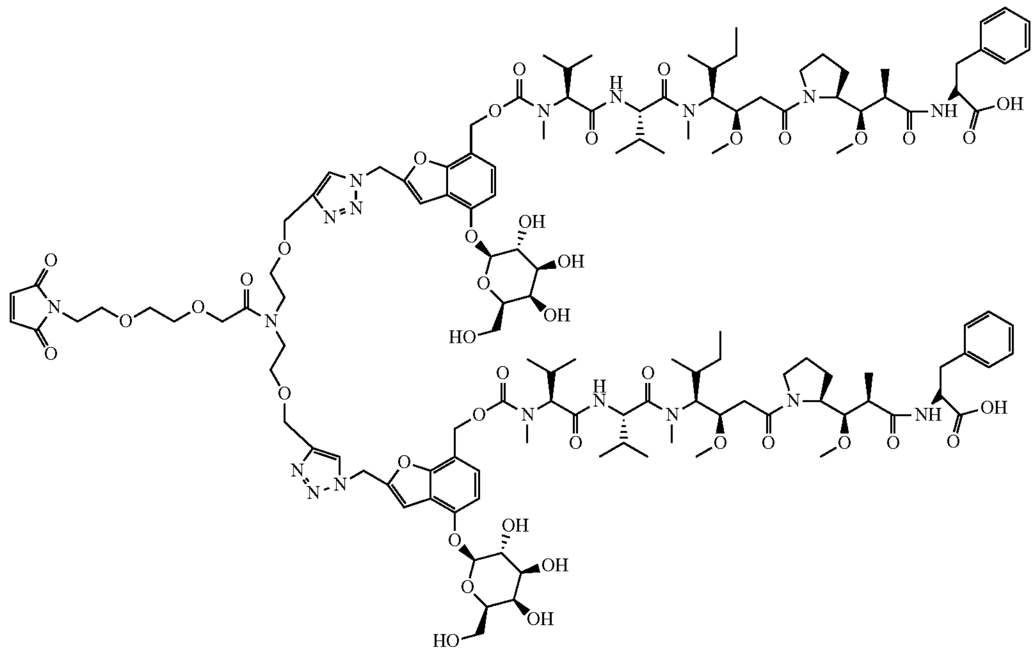

TABLE C-continued
| Exemplary compounds of DAR4 type | |
|---|---|
| 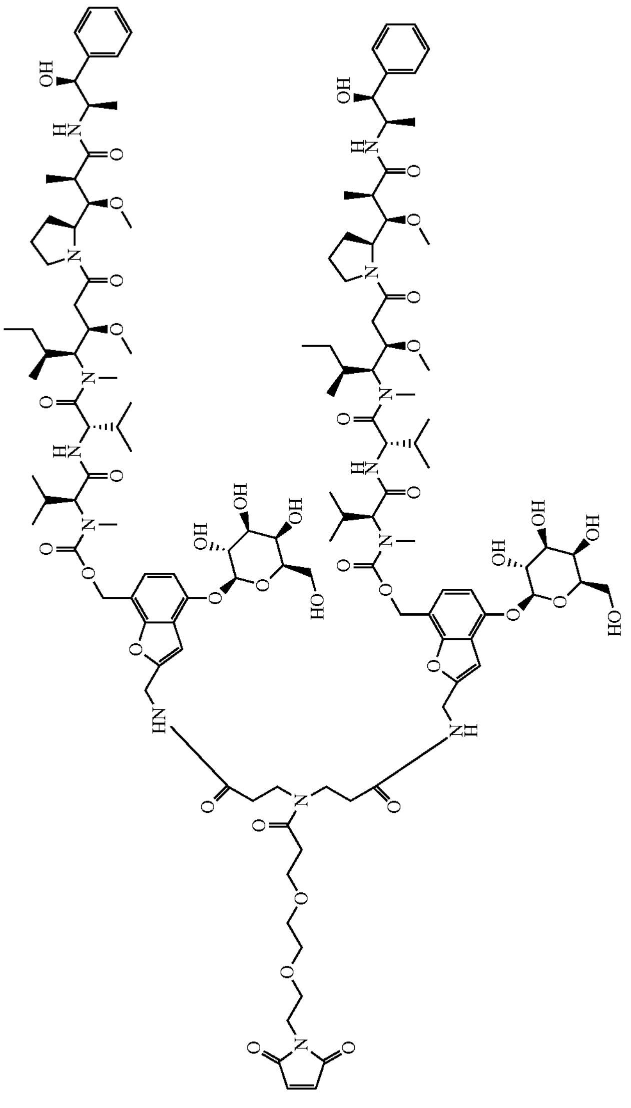 | B-30 |

TABLE C-continued
| Exemplary compounds of DAR4 type | |
|---|---|
| 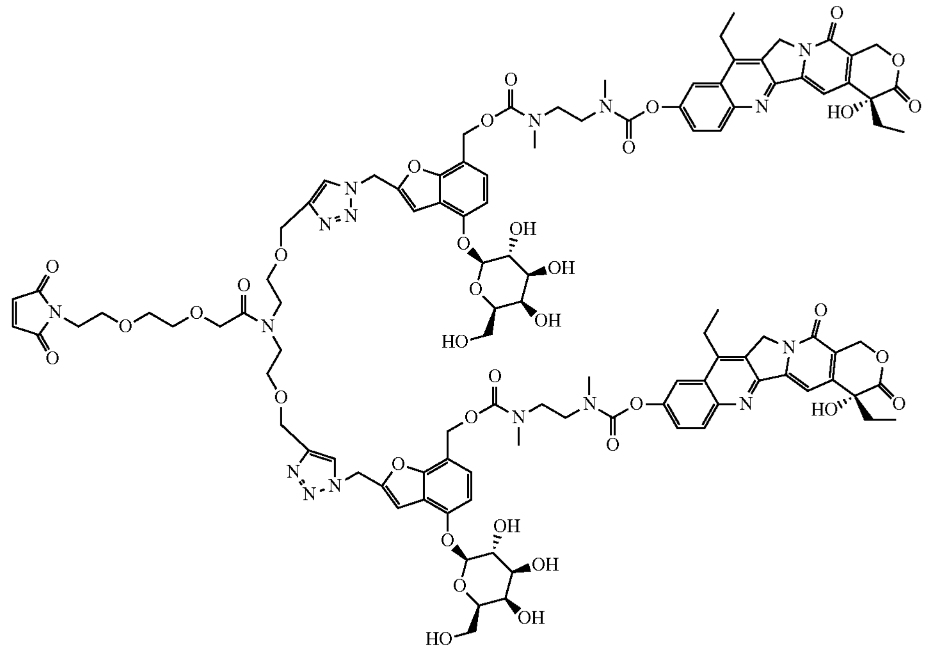 [SMILES: CCc1c2c(nc3ccc(OC(=O)N(C)CCN(C)C(=O)OCc4ccc(O[C@@H]5O[C@H](CO)[C@H](O)[C@H](O)[C@H]5O)c5cc(Cn6cc(COCCN(CCOCc7cn(Cc8cc9c(O[C@@H]%10O[C@H](CO)[C@H](O)[C@H](O)[C@H]%10O)ccc(COC(=O)N(C)CCN(C)C(=O)Oc%10ccc%11nc%12c(c(CC)c%11c%10)Cn%10c-%12cc%11c(c%10=O)COC(=O)[C@@]%11(O)CC)c9o8)nn7)C(=O)COCCOCCN7C(=O)C=CC7=O)nn6)oc45)cc13)-c1cc3c(c(=O)n1C2)COC(=O)[C@@]3(O)CC] | B-31 |

TABLE C-continued
| Exemplary compounds of DAR4 type |
|---|
| B-32 |
| 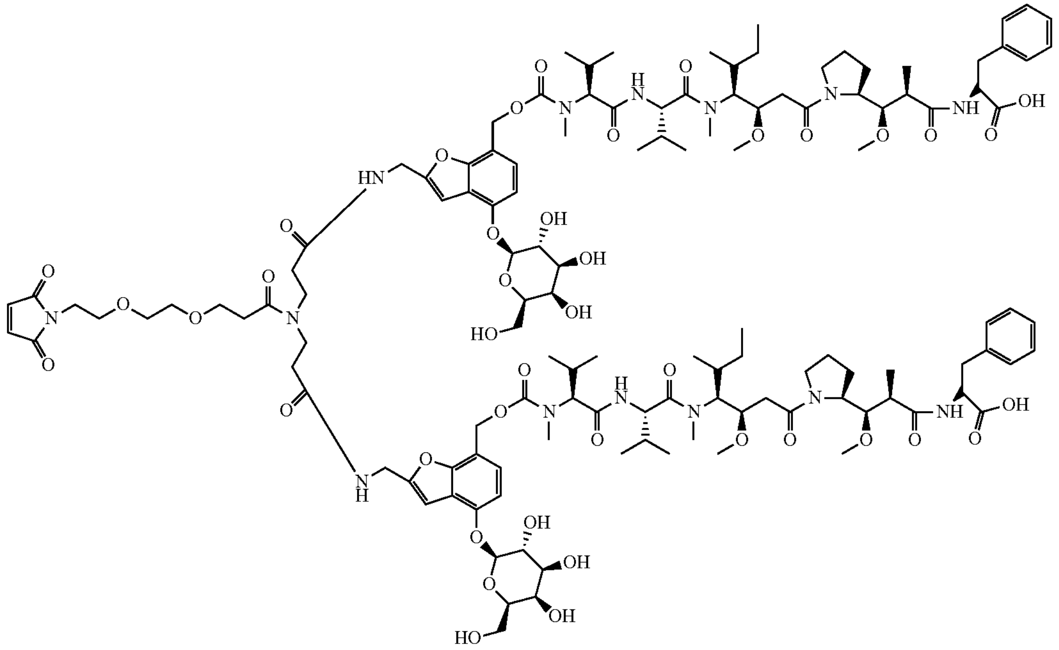 |

TABLE C-continued
Exemplary compounds of DAR4 type
B-33
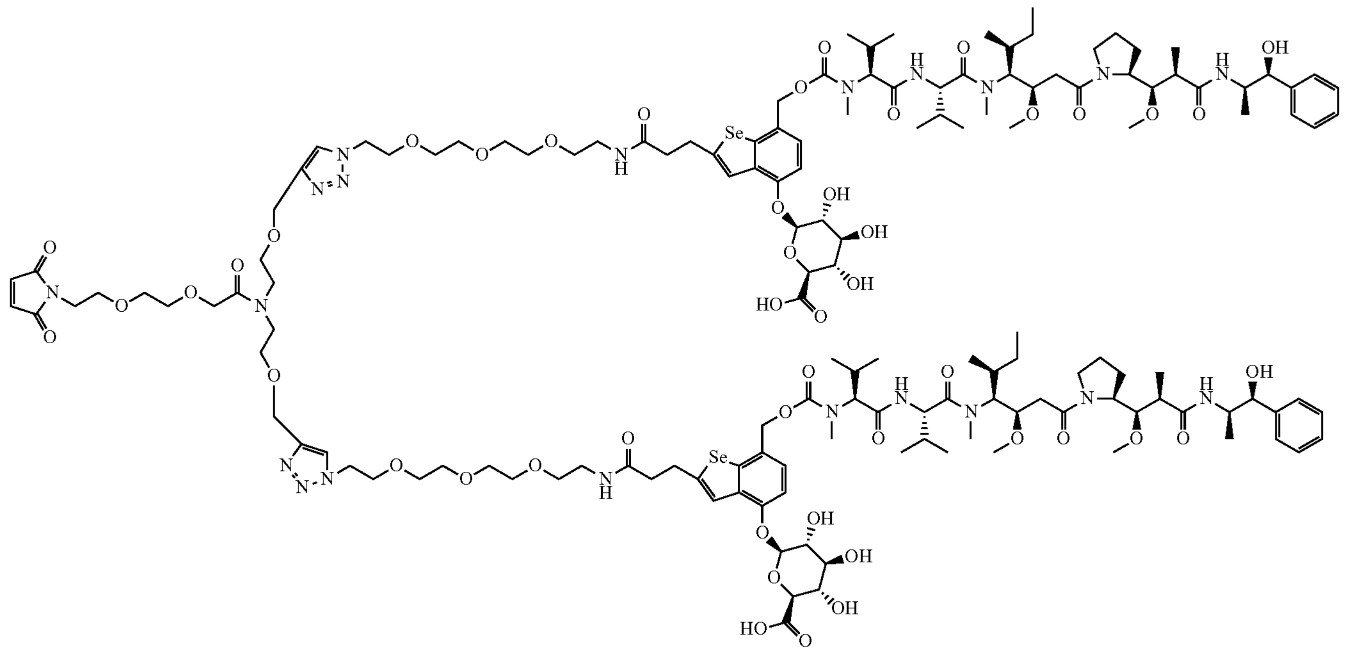

TABLE C-continued
| Exemplary compounds of DAR4 type |
| --- |
| 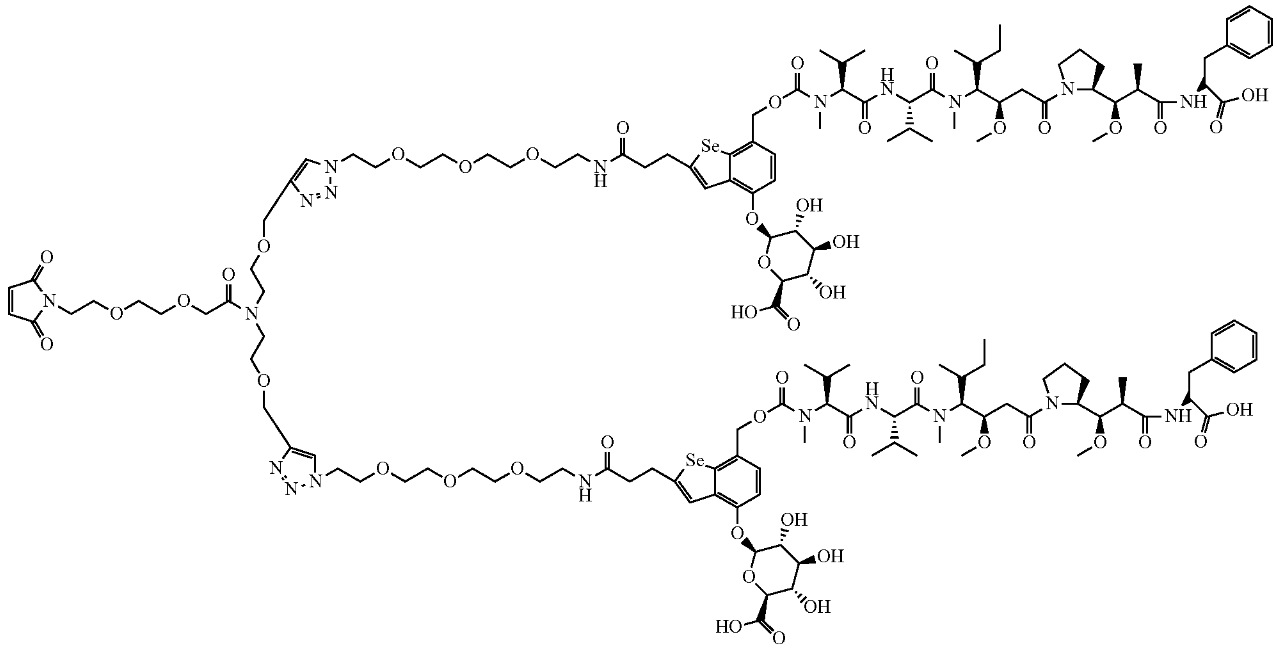 B-34 |

TABLE C-continued
| Exemplary compounds of DAR4 type |
| --- |
| B-35 |
| 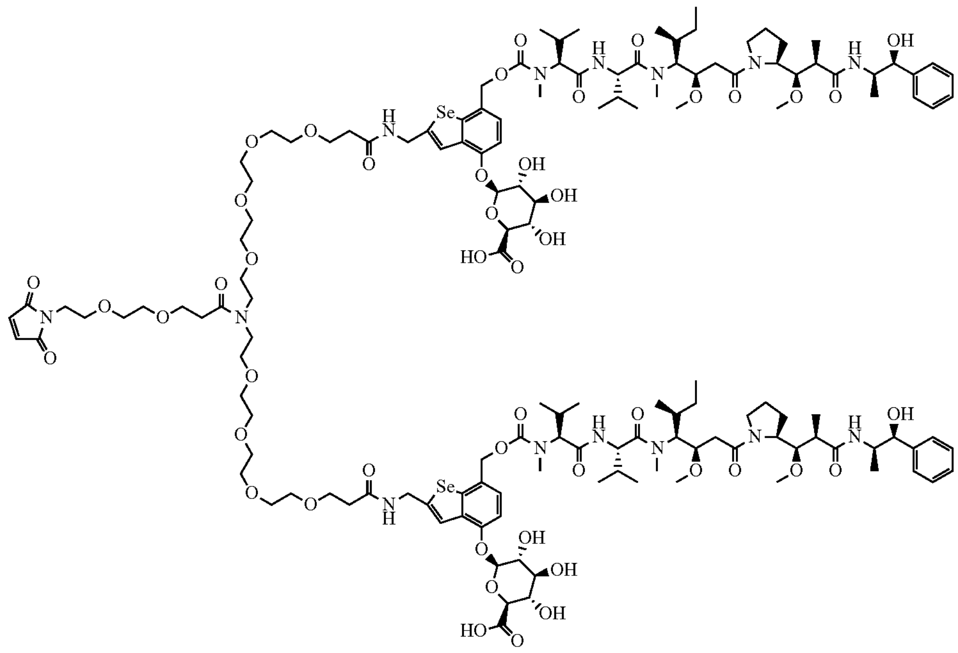 |

TABLE C-continued
| Exemplary compounds of DAR4 type |
|---|
| B-36 |
| 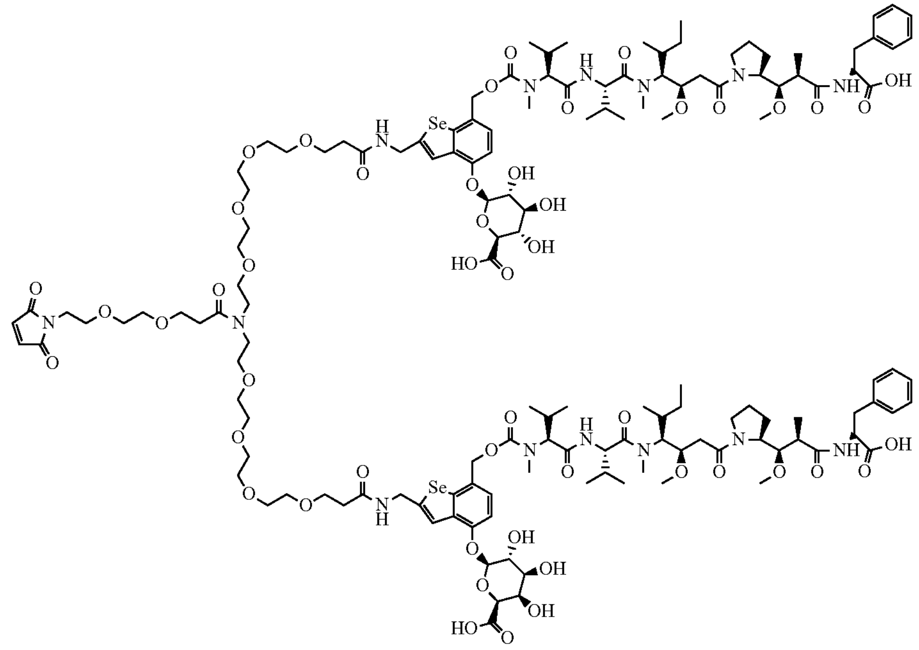 |

TABLE C-continued
| Exemplary compounds of DAR4 type |
| --- |
| B-37 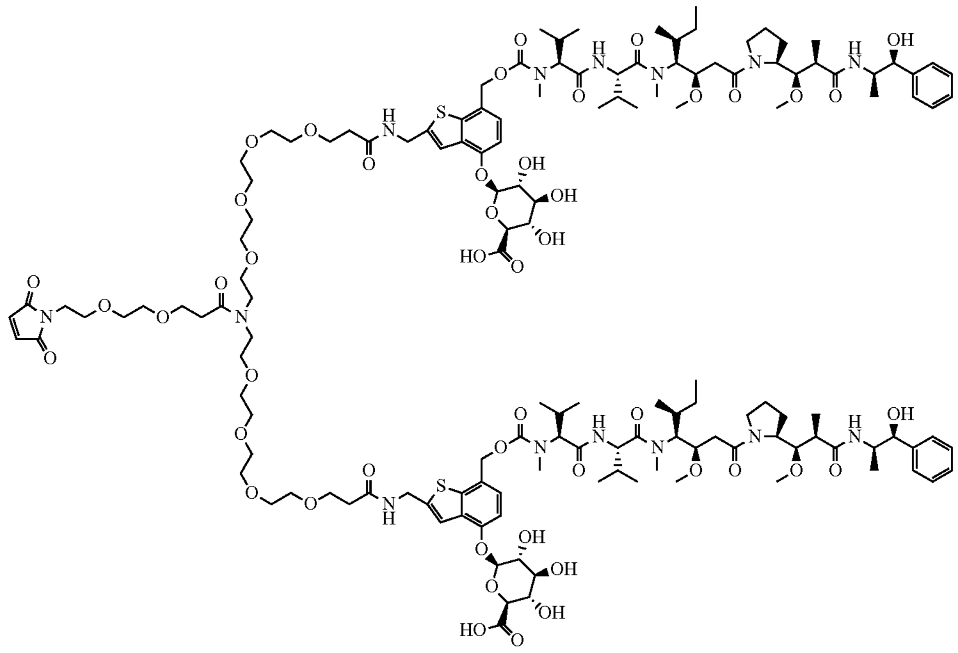 |

TABLE C-continued
| Exemplary compounds of DAR4 type |
| --- |
| B-38 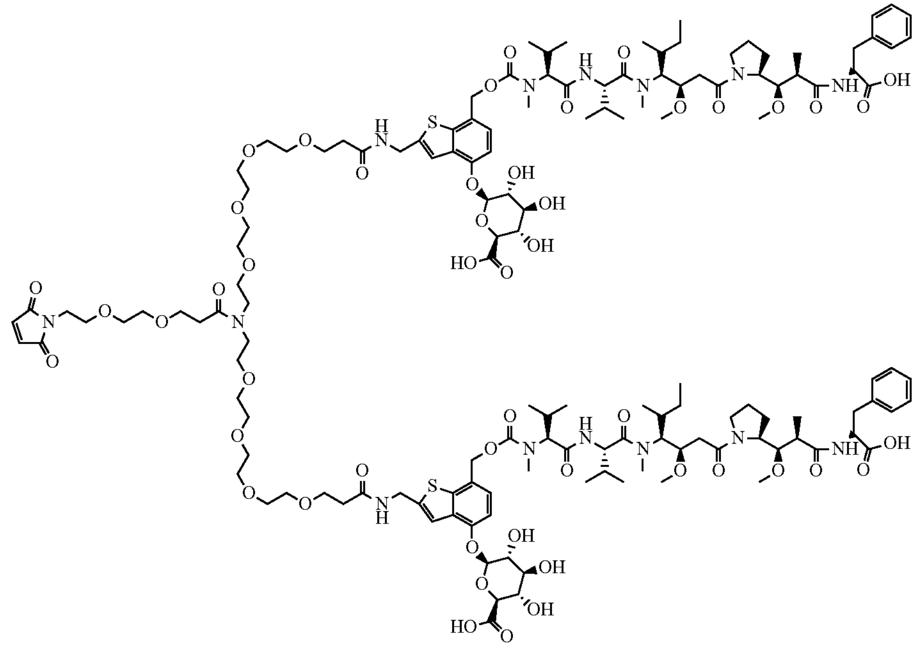 |

TABLE C-continued
Exemplary compounds of DAR4 type
B-39
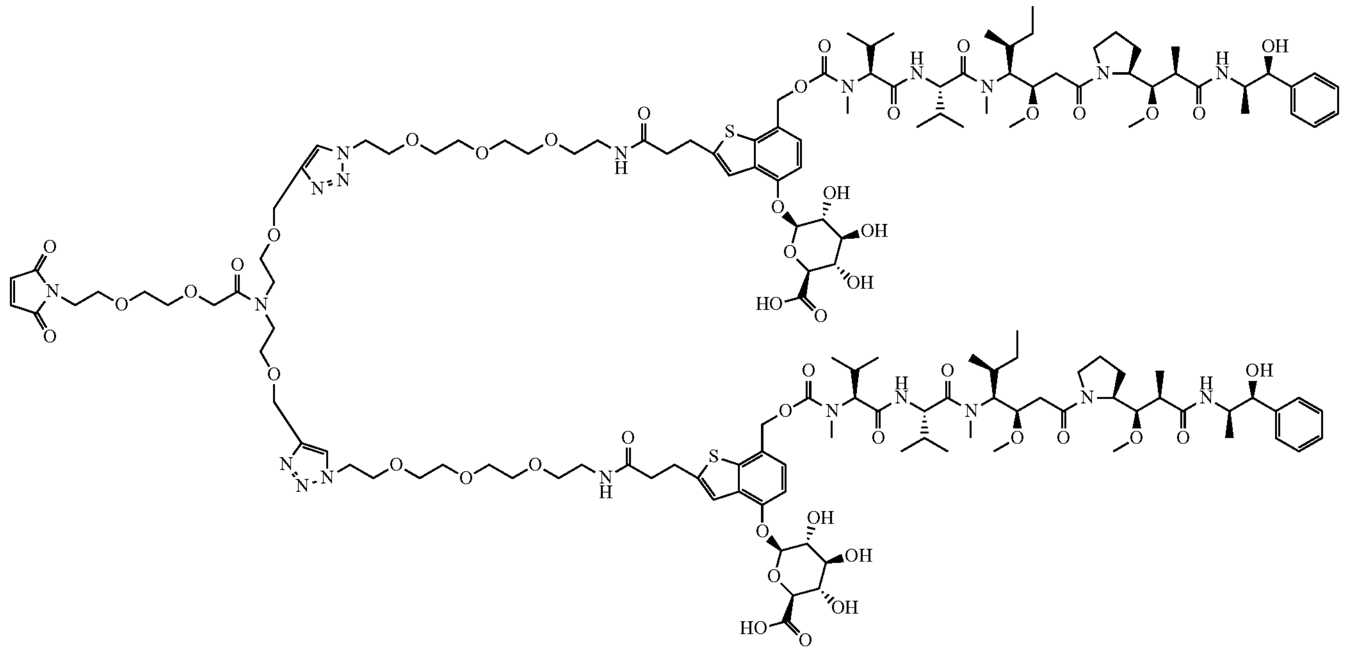

TABLE C-continued
| Exemplary compounds of DAR4 type |
| --- |
| B-40<br>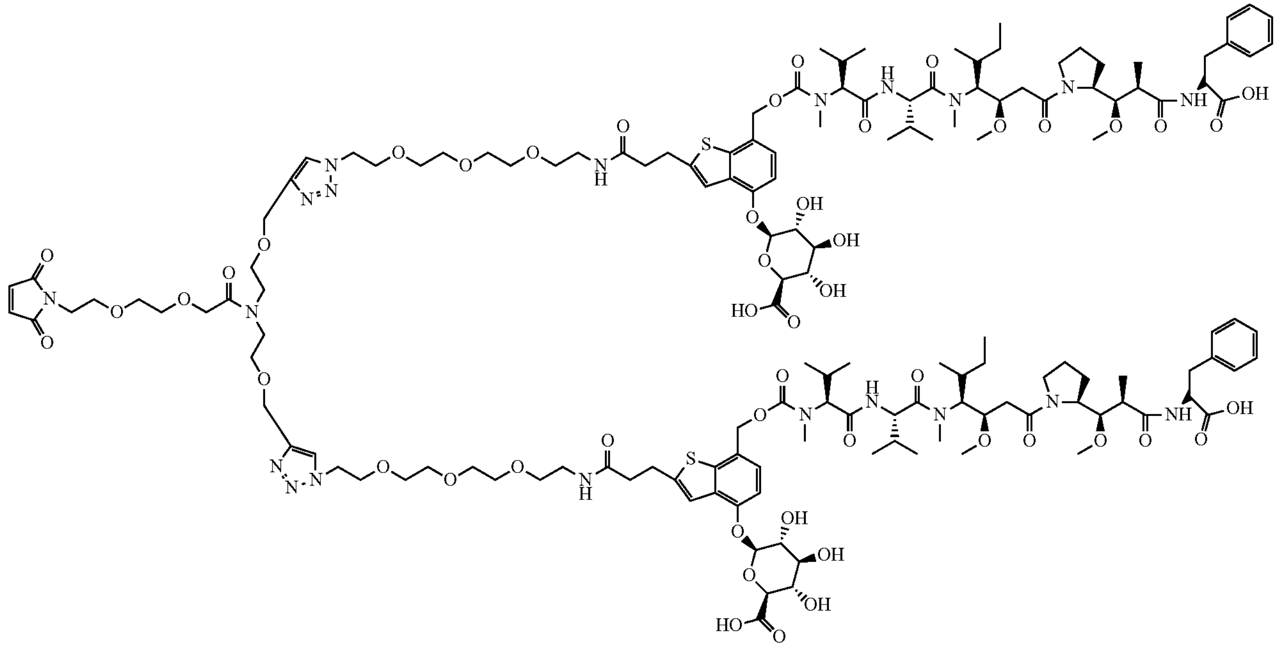 |

TABLE C-continued
Exemplary compounds of DAR4 type
B-44
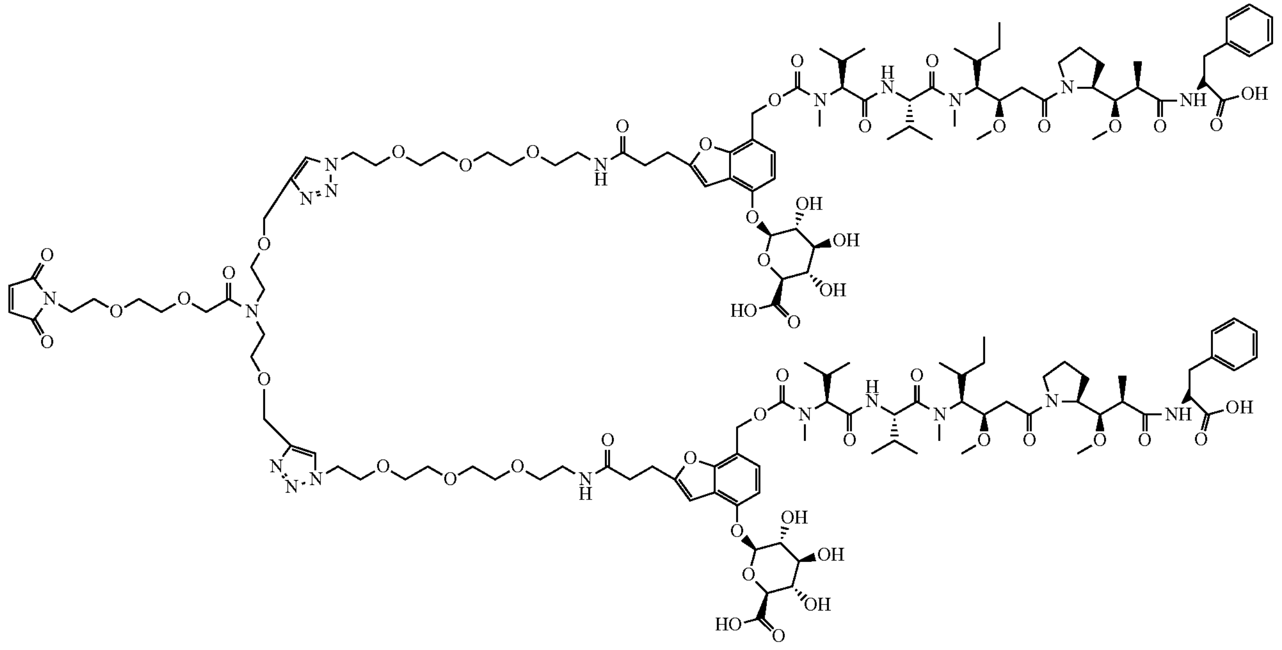

TABLE C-continued
| Exemplary compounds of DAR4 type |
| --- |
| B-47 |
| 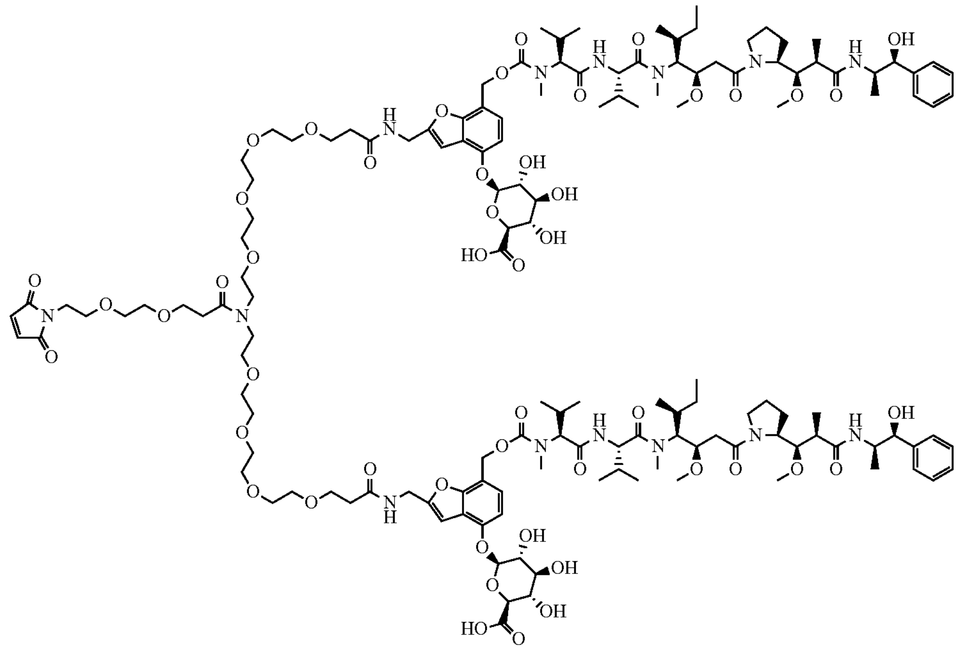 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c2cc(CNC(=O)CCOCCOCCOCCOCCN(CCOCCOCCOCCOCCC(=O)NCc3cc4c(O[C@@H]5O[C@H](C(=O)O)[C@@H](O)[C@H](O)[C@H]5O)ccc(COC(=O)N(C)[C@H](C(=O)N[C@H](C(=O)N(C)[C@@H]([C@@H](C)CC)[C@@H](CC(=O)N5CCC[C@H]5[C@H](OC)[C@@H](C)C(=O)N[C@H](C)[C@@H](O)c5ccccc5)OC)C(C)C)C(C)C)c4o3)C(=O)CCOCCOCCN3C(=O)C=CC3=O)oc12)C(C)C] |

TABLE C-continued
Exemplary compounds of DAR4 type
B-48
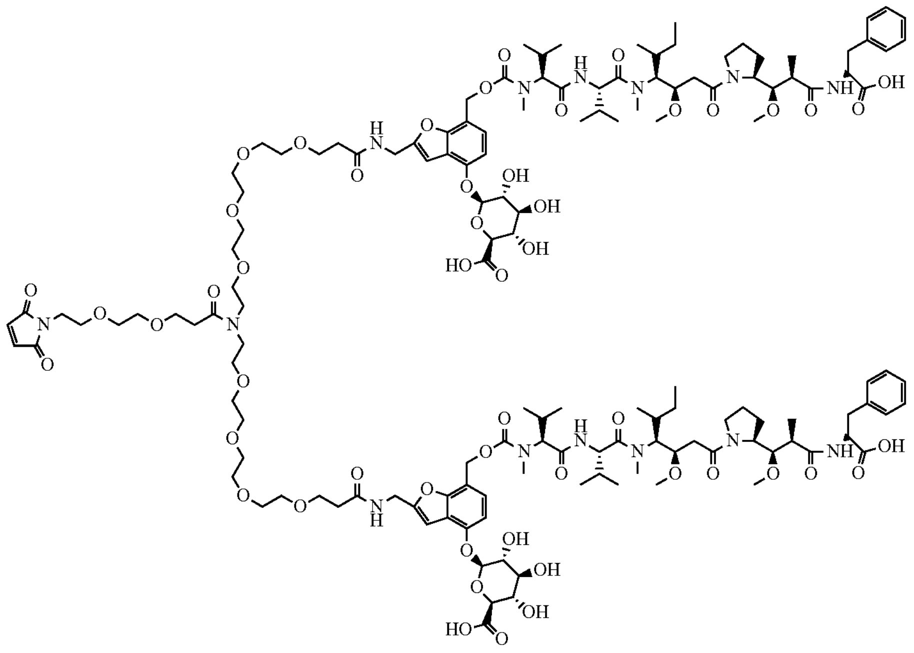

TABLE C-continued
| Exemplary compounds of DAR4 type |
| --- |
| B-52 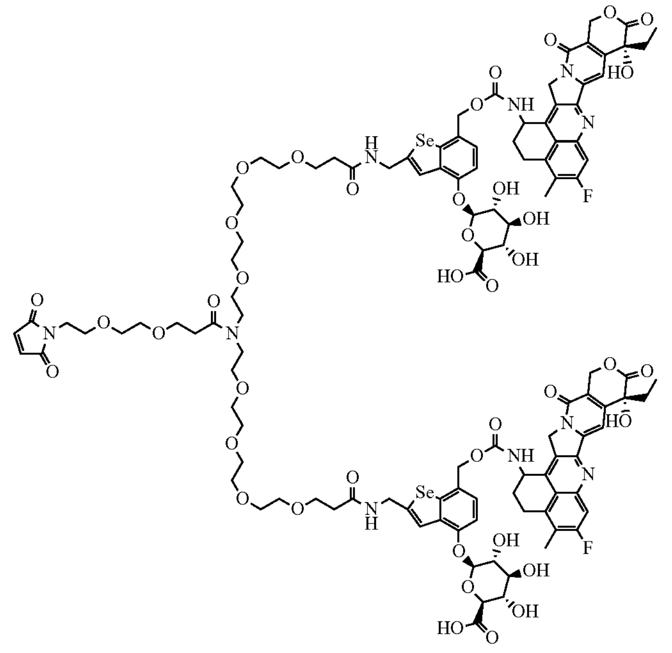 [SMILES: CC[C@]1(O)C(=O)OCc2c1cc1n(c2=O)Cc2c-1nc1cc(F)c(C)c3c1c2C(NC(=O)OCc1ccc(O[C@@H]2O[C@H](C(=O)O)[C@@H](O)[C@H](O)[C@H]2O)c2cc(CNC(=O)CCOCCOCCOCCOCCN(CCOCCOCCOCCOCCC(=O)NCc4cc5c(O[C@@H]6O[C@H](C(=O)O)[C@@H](O)[C@H](O)[C@H]6O)ccc(COC(=O)NC6CCc7c(C)c(F)cc8nc9c(c6c78)Cn6c-9cc7c(c6=O)COC(=O)[C@@]7(O)CC)c5[se]4)C(=O)CCOCCOCCN4C(=O)C=CC4=O)[se]c12)CC3] |

TABLE C-continued
| Exemplary compounds of DAR4 type |
|---|
| B-53 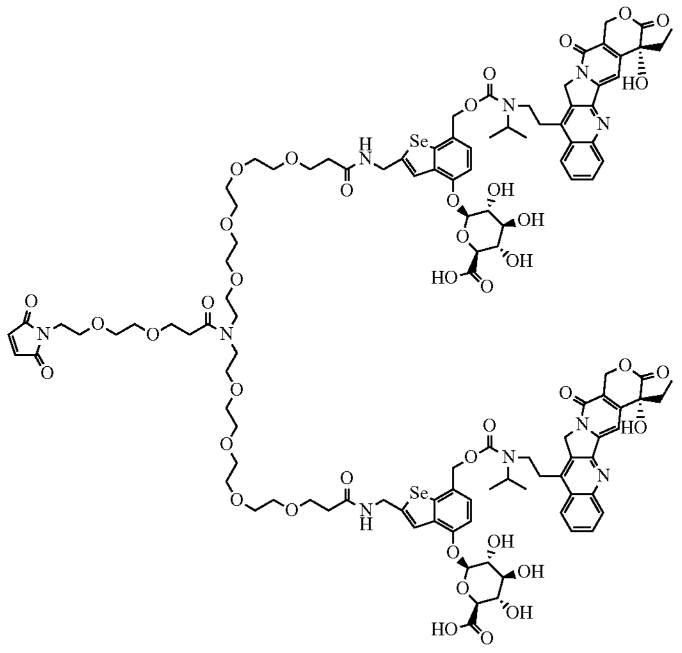 [SMILES: CC[C@]1(O)C(=O)OCc2c1cc1n(c2=O)Cc2c-1nc1ccccc1c2CCN(C(=O)OCc1ccc(O[C@@H]2O[C@H](C(=O)O)[C@@H](O)[C@H](O)[C@H]2O)c2cc(CNC(=O)CCOCCOCCOCCOCCN(CCOCCOCCOCCOCCC(=O)NCc3cc4c(O[C@@H]5O[C@H](C(=O)O)[C@@H](O)[C@H](O)[C@H]5O)ccc(COC(=O)N(CCc5c6c(nc7ccccc57)-c5cc7c(c(=O)n5C6)COC(=O)[C@@]7(O)CC)C(C)C)c4[se]3)C(=O)CCOCCOCCN3C(=O)C=CC3=O)[se]c12)C(C)C] |

TABLE C-continued
| Exemplary compounds of DAR4 type |
| --- |
| 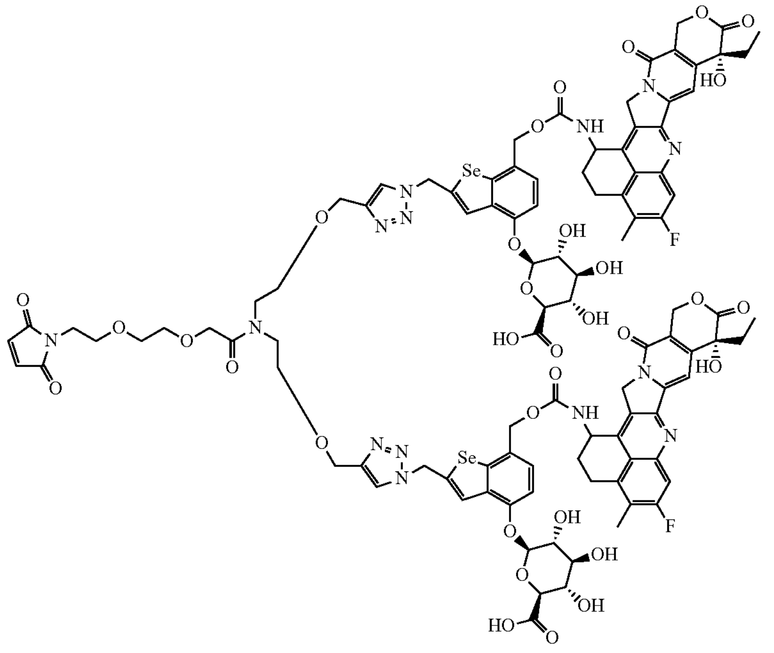 [SMILES: CC[C@]1(O)C(=O)OCc2c1cc1n(c2=O)Cc2c-1nc1cc(F)c(C)c3c1c2C(NC(=O)OCc1ccc(O[C@@H]2O[C@H](C(=O)O)[C@@H](O)[C@H](O)[C@H]2O)c2cc(Cn4cc(COCCN(CCOCc5cn(Cc6cc7c(O[C@@H]8O[C@H](C(=O)O)[C@@H](O)[C@H](O)[C@H]8O)ccc(COC(=O)NC8CCc9c(C)c(F)cc%10nc%11c(c8c9%10)Cn8c-%11cc9c(c8=O)COC(=O)[C@@]9(O)CC)c7[se]6)nn5)C(=O)COCCOCCN5C(=O)C=CC5=O)nn4)[se]c12)CC3] B-54 |

TABLE C-continued
| Exemplary compounds of DAR4 type |
|---|
| B-55 |
| 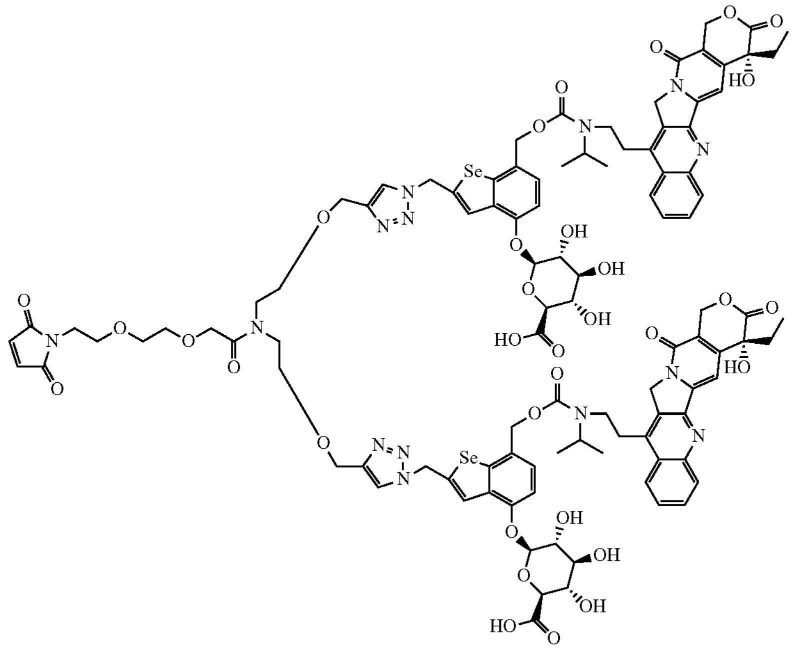 [SMILES: CC[C@]1(O)C(=O)OCc2c1cc1n(c2=O)Cc2c-1nc1ccccc1c2CCN(C(=O)OCc1ccc(O[C@@H]2O[C@H](C(=O)O)[C@@H](O)[C@H](O)[C@H]2O)c2cc(Cn3cc(COCCN(CCOCc4cn(Cc5cc6c(O[C@@H]7O[C@H](C(=O)O)[C@@H](O)[C@H](O)[C@H]7O)ccc(COC(=O)N(CCc7c8c(nc9ccccc79)-c7cc9c(c(=O)n7C8)COC(=O)[C@@]9(O)CC)C(C)C)c6[se]5)nn4)C(=O)COCCOCCN4C(=O)C=CC4=O)nn3)[se]c12)C(C)C] |

TABLE C-continued
| Exemplary compounds of DAR4 type |
| --- |
| B-56 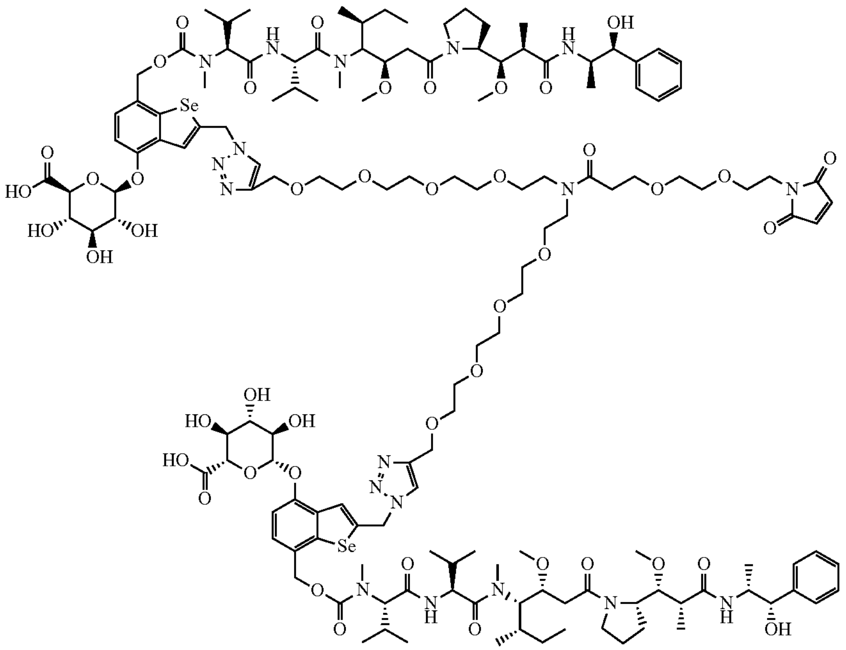 [SMILES: CC[C@H](C)C([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c2cc(Cn3cc(COCCOCCOCCOCCN(CCOCCOCCOCCOCc4cn(Cc5cc6c(O[C@@H]7O[C@H](C(=O)O)[C@@H](O)[C@H](O)[C@H]7O)ccc(COC(=O)N(C)[C@H](C(=O)N[C@H](C(=O)N(C)[C@@H]([C@@H](C)CC)[C@@H](CC(=O)N7CCC[C@H]7[C@H](OC)[C@@H](C)C(=O)N[C@H](C)[C@@H](O)c7ccccc7)OC)C(C)C)C(C)C)c6[se]5)nn4)C(=O)CCOCCOCCN4C(=O)C=CC4=O)nn3)[se]c12)C(C)C] |

TABLE C-continued
| Exemplary compounds of DAR4 type |
| --- |
| B-57 |
| 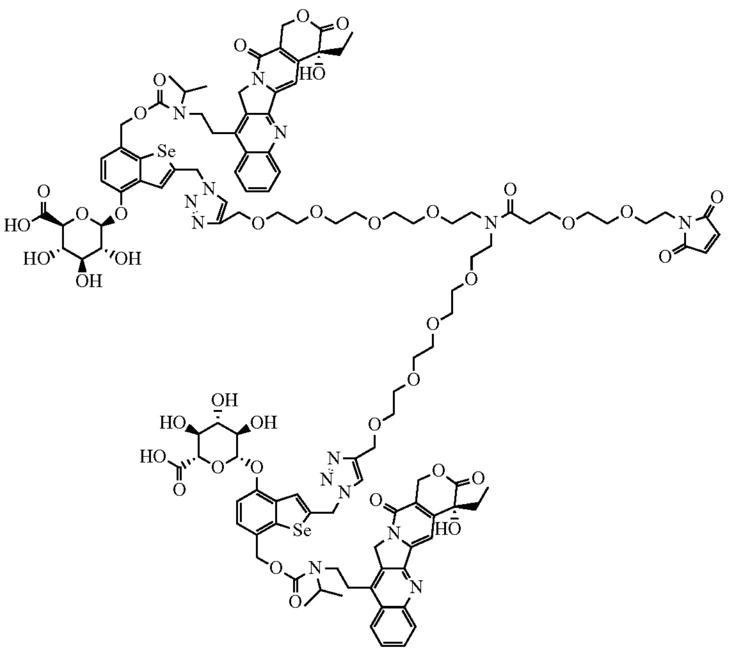 [SMILES: CC[C@]1(O)C(=O)OCc2c1cc1n(c2=O)Cc2c-1nc1ccccc1c2CCN(C(=O)OCc1ccc(O[C@@H]2O[C@H](C(=O)O)[C@@H](O)[C@H](O)[C@H]2O)c2cc(Cn3cc(COCCOCCOCCOCCN(CCOCCOCCOCCOCc4cn(Cc5cc6c(O[C@@H]7O[C@H](C(=O)O)[C@@H](O)[C@H](O)[C@H]7O)ccc(COC(=O)N(CCc7c8c(nc9ccccc79)-c7cc9c(c(=O)n7C8)COC(=O)[C@@]9(O)CC)C(C)C)c6[se]5)nn4)C(=O)CCOCCOCCN4C(=O)C=CC4=O)nn3)[se]c12)C(C)C] |

TABLE C-continued
| Exemplary compounds of DAR4 type | |
| --- | --- |
| 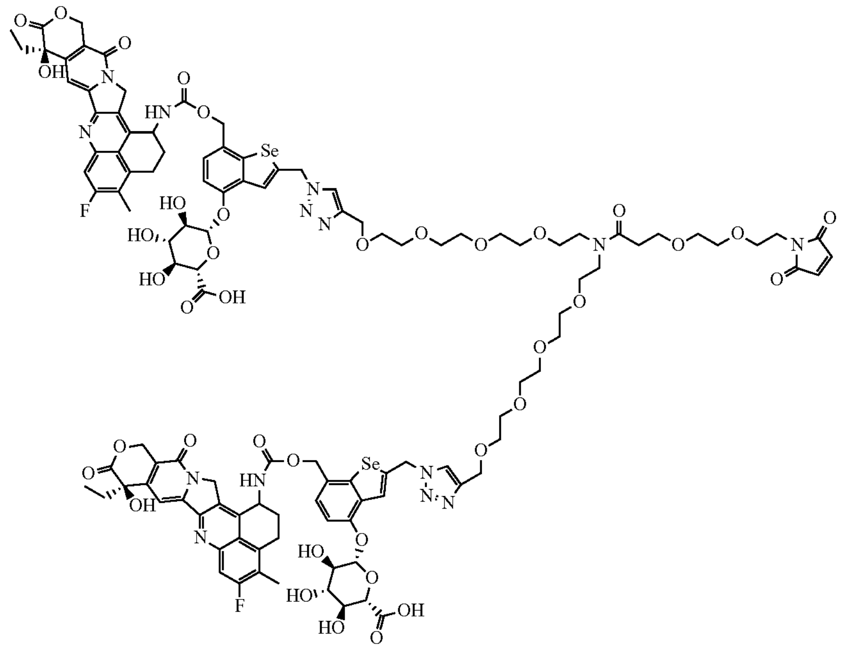 [SMILES: CC[C@]1(O)C(=O)OCc2c1cc1n(c2=O)Cc2c-1nc1cc(F)c(C)c3c1c2C(NC(=O)OCc1ccc(O[C@@H]2O[C@H](C(=O)O)[C@@H](O)[C@H](O)[C@H]2O)c2cc(Cn4cc(COCCOCCOCCOCCN(CCOCCOCCOCCOCc5cn(Cc6cc7c(O[C@@H]8O[C@H](C(=O)O)[C@@H](O)[C@H](O)[C@H]8O)ccc(COC(=O)NC8CCc9c(C)c(F)cc%10nc%11c(c8c9%10)Cn8c-%11cc9c(c8=O)COC(=O)[C@@]9(O)CC)c7[se]6)nn5)C(=O)CCOCCOCCN5C(=O)C=CC5=O)nn4)[se]c12)CC3] | B-58 |

TABLE D
| Exemplary ligand-drug conjugates (DAR2 type) | |
| --- | --- |
| 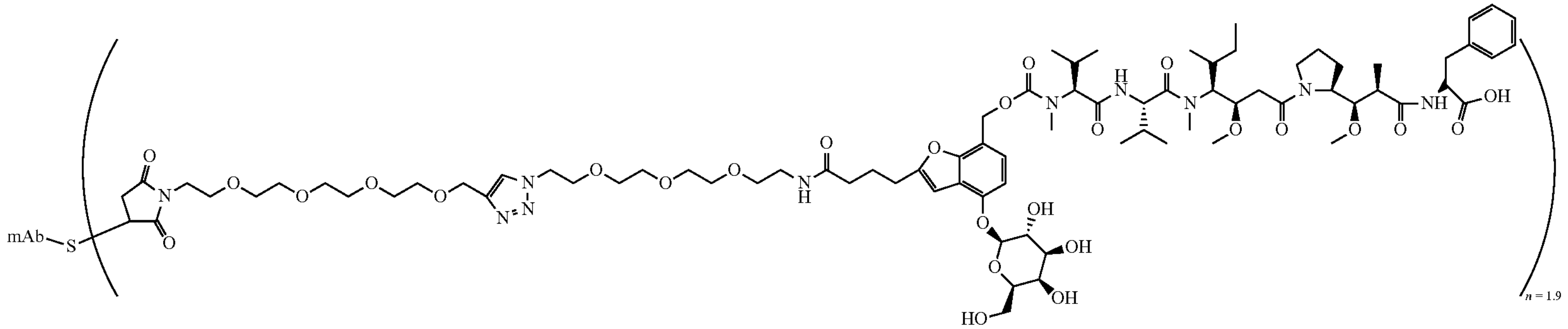 | ADC-1 |
| 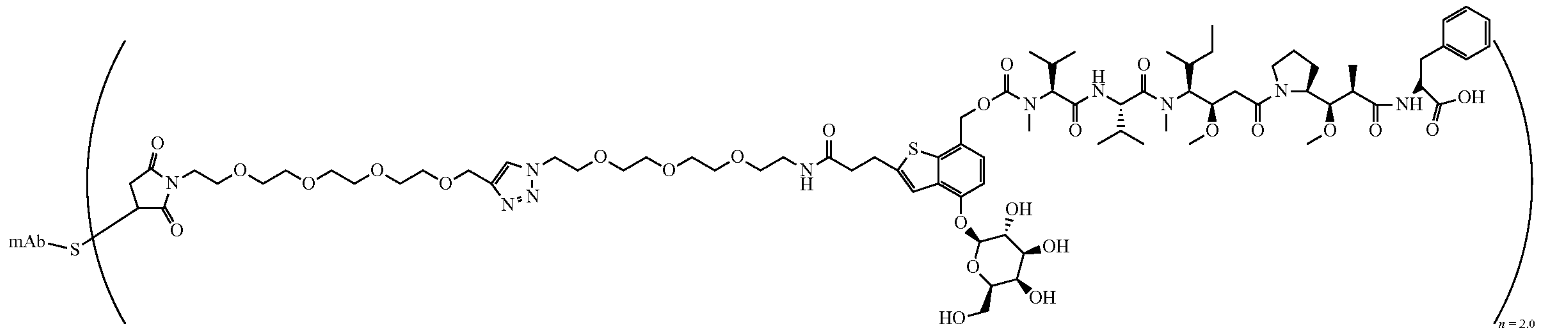 | ADC-2 |

TABLE D-continued
| Exemplary ligand-drug conjugates (DAR2 type) | |
|---|---|
| 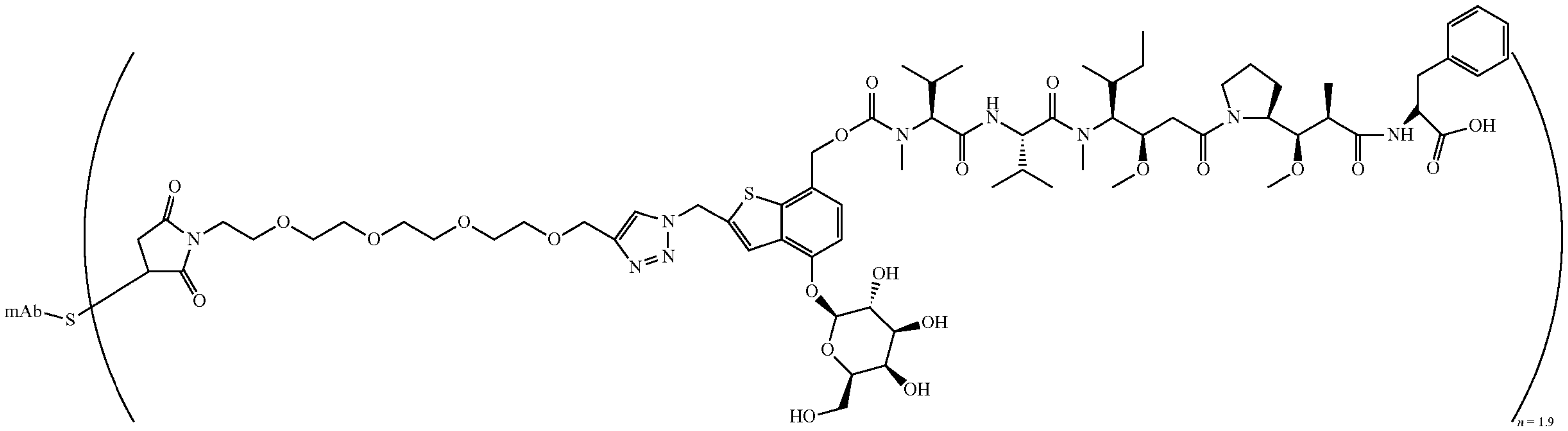 | ADC-3 |
| 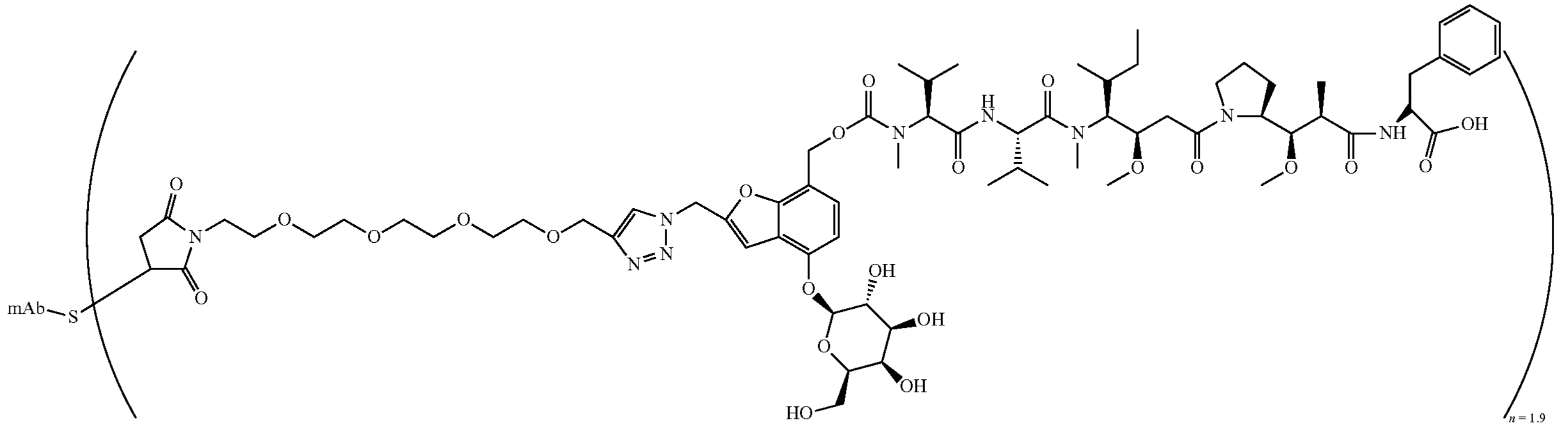 | ADC-4 |

TABLE D-continued
Exemplary ligand-drug conjugates (DAR2 type)
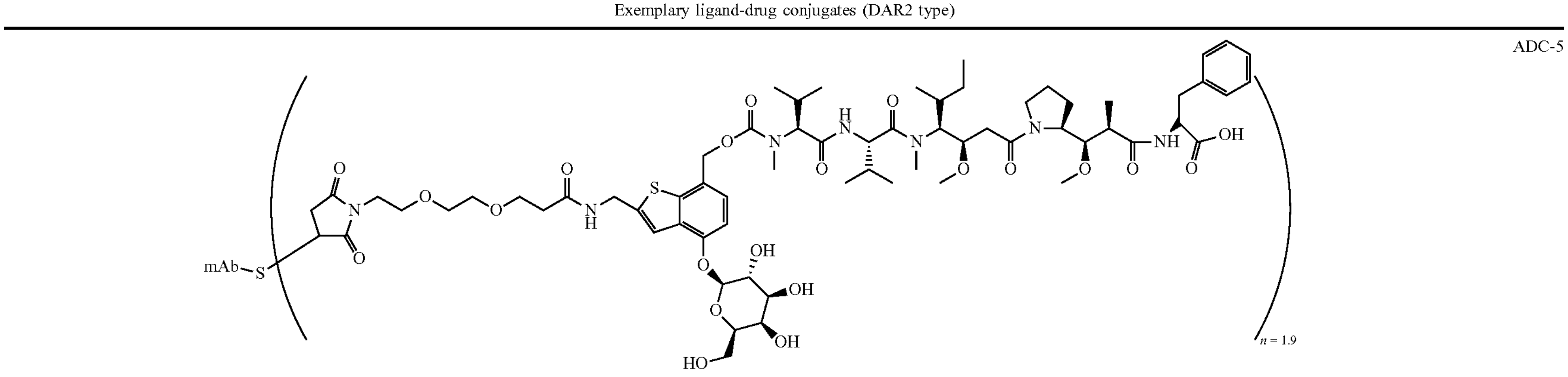
ADC-5
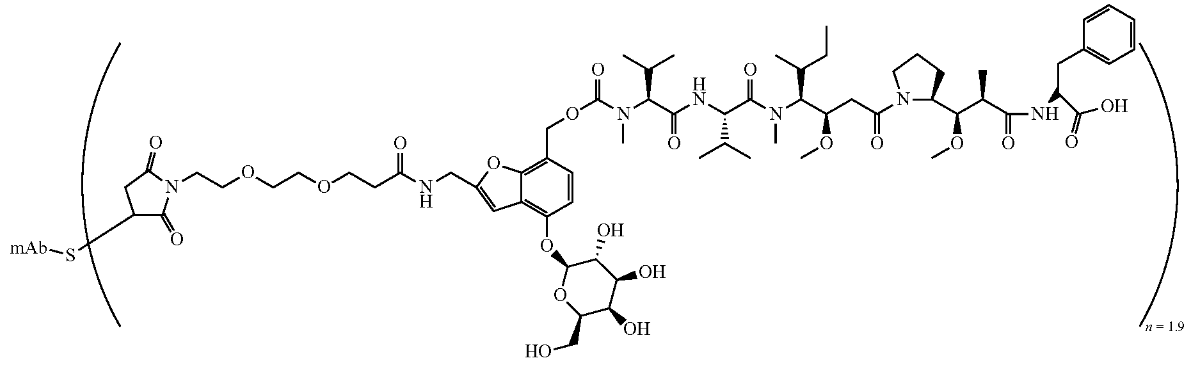
ADC-6
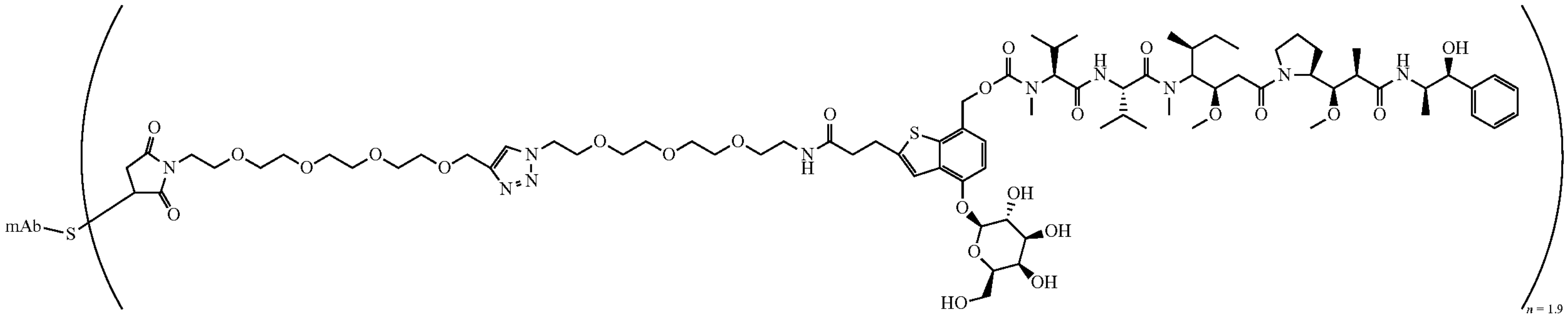
ADC-7

TABLE D-continued
| Exemplary ligand-drug conjugates (DAR2 type) |
|---|
| ADC-8<br>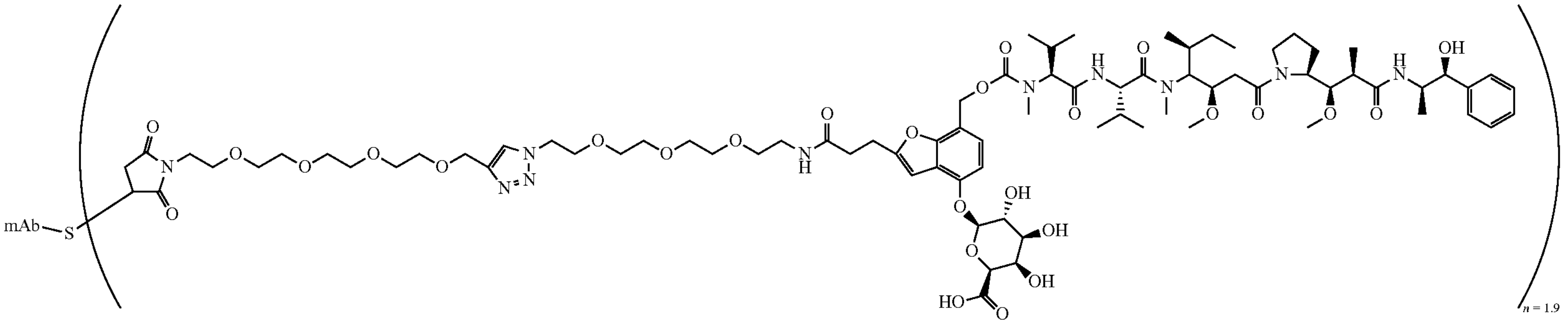 |
| ADC-11<br>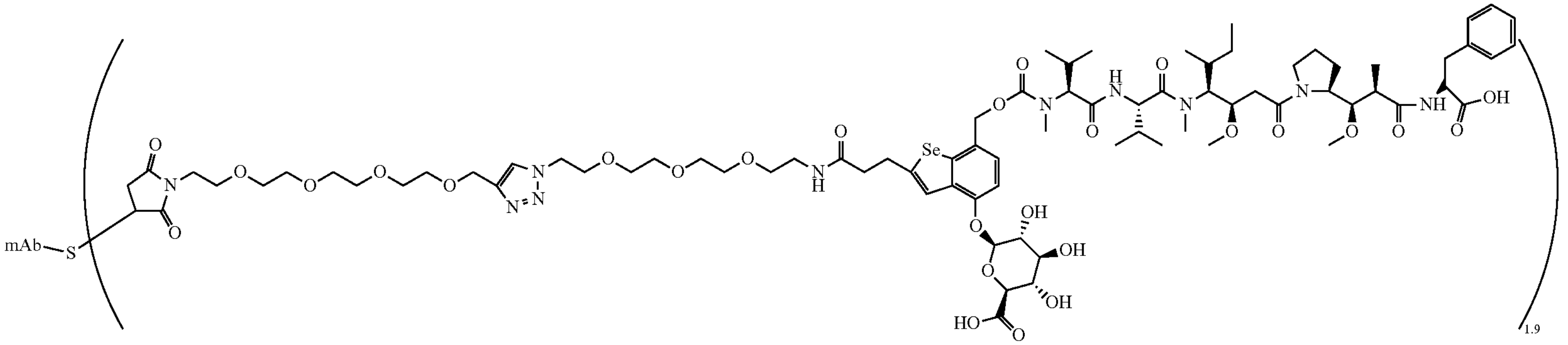 |

TABLE D-continued
Exemplary ligand-drug conjugates (DAR2 type)
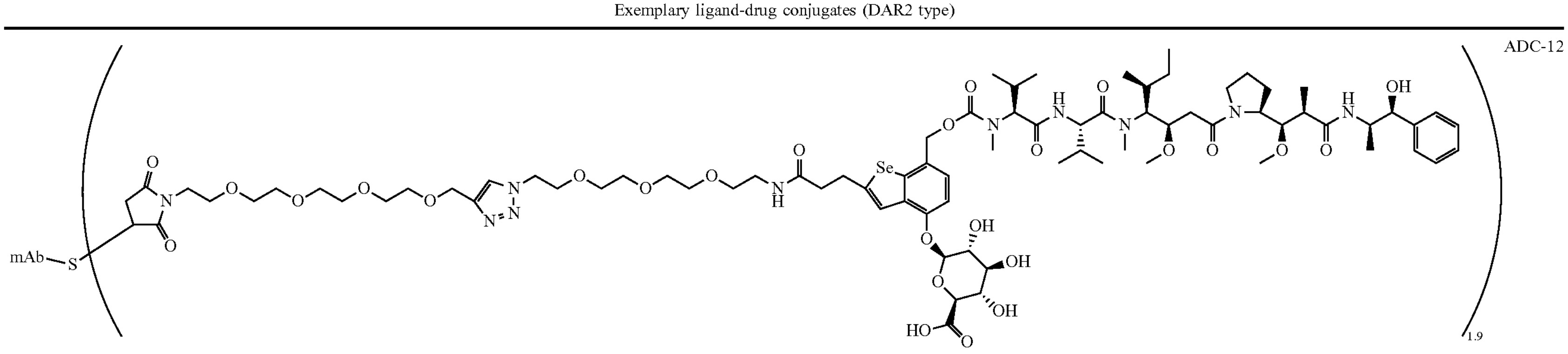
ADC-12
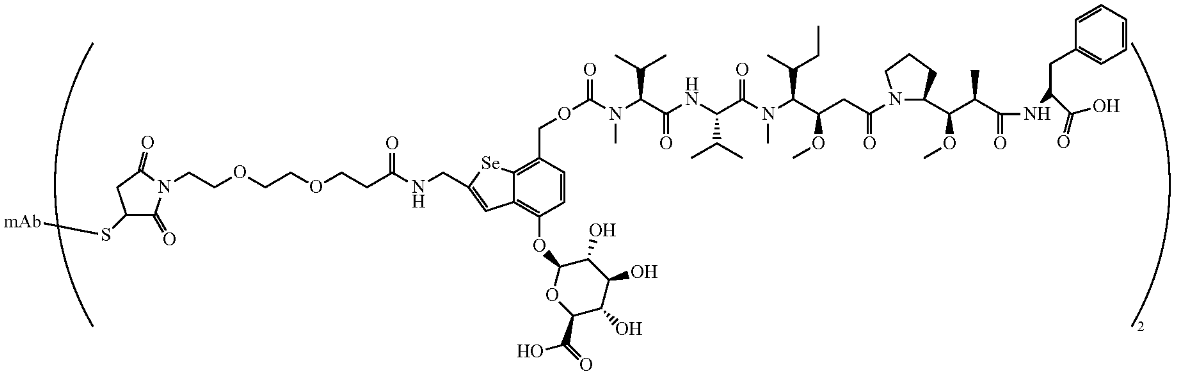
ADC-16

TABLE D-continued
| Exemplary ligand-drug conjugates (DAR2 type) |
| --- |
| ADC-17 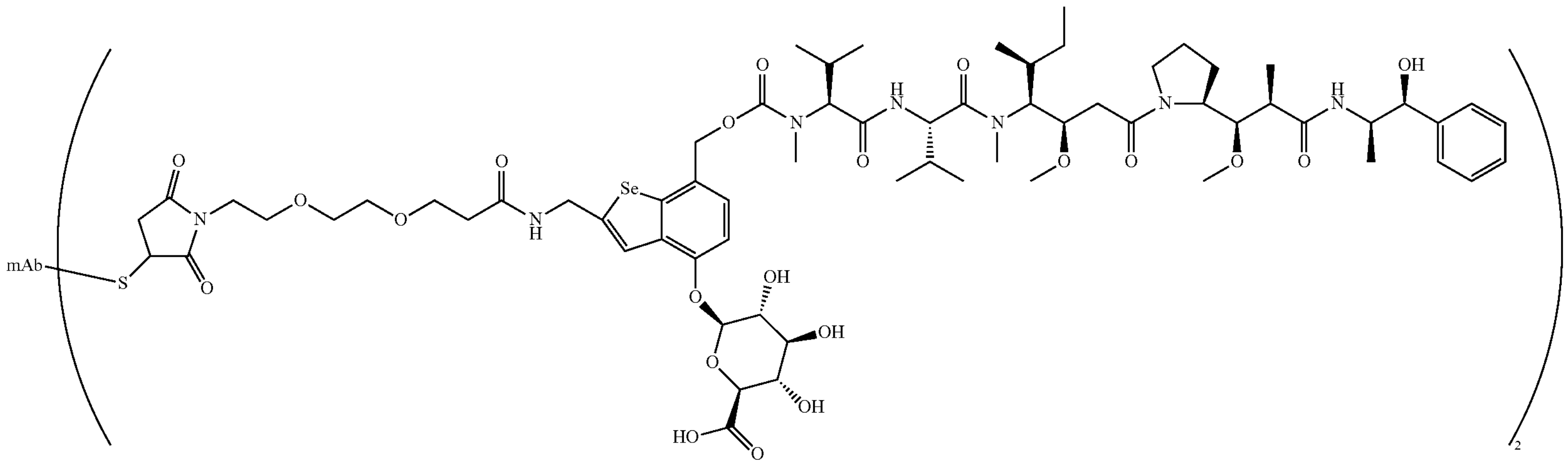 |

TABLE E
| Examplary ligand-drug conjugates (DAR4 type) |
| --- |
| 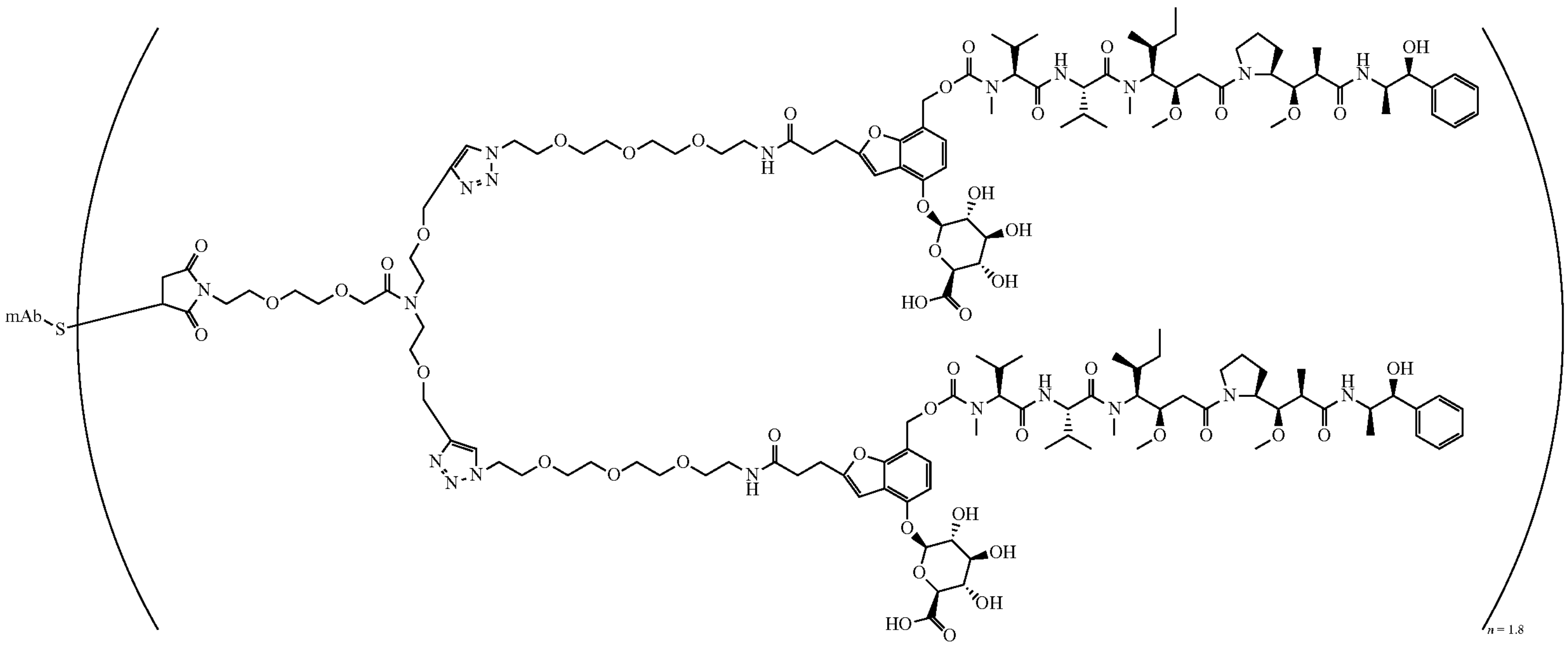 ADC-9 |

TABLE E-continued
| Examplary ligand-drug conjugates (DAR4 type) |
| --- |
| ADC-10 |
| 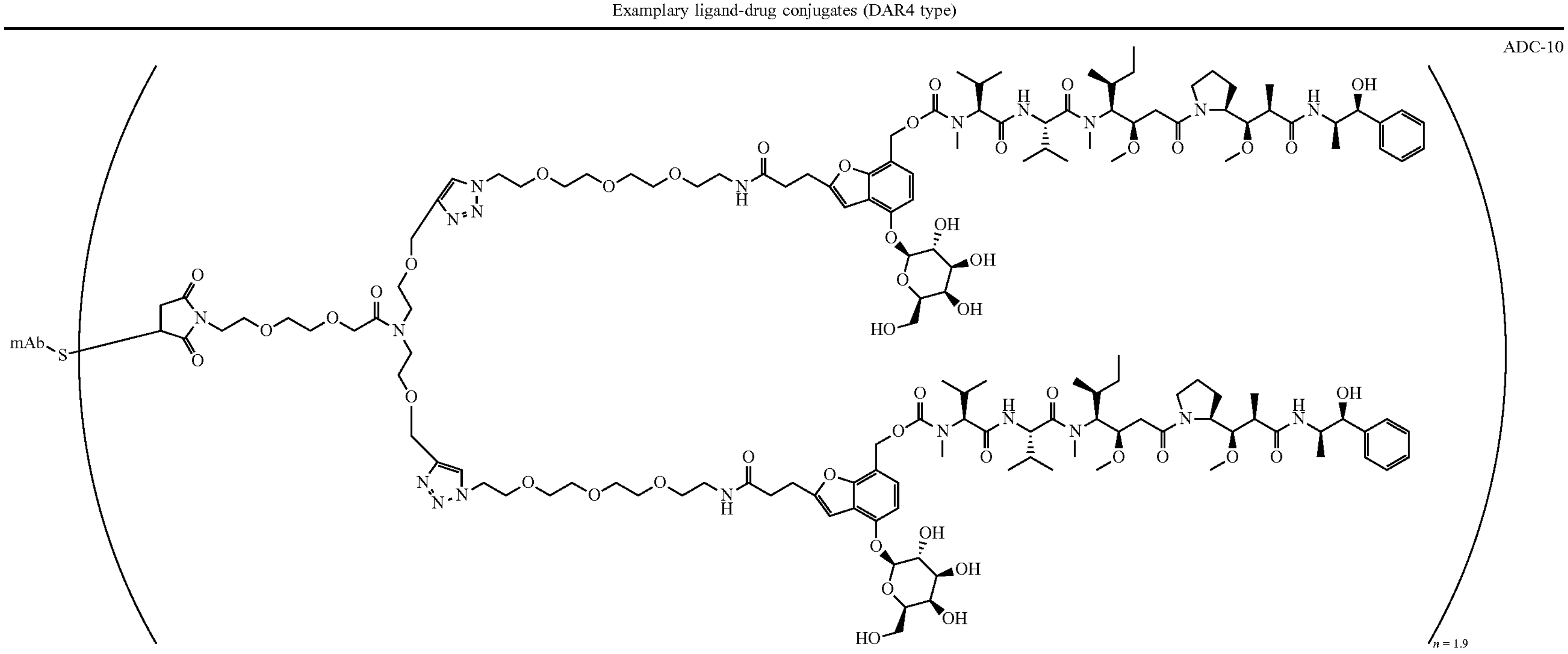 |

TABLE E-continued
| Examplary ligand-drug conjugates (DAR4 type) |
| --- |
| ADC-13 |
| 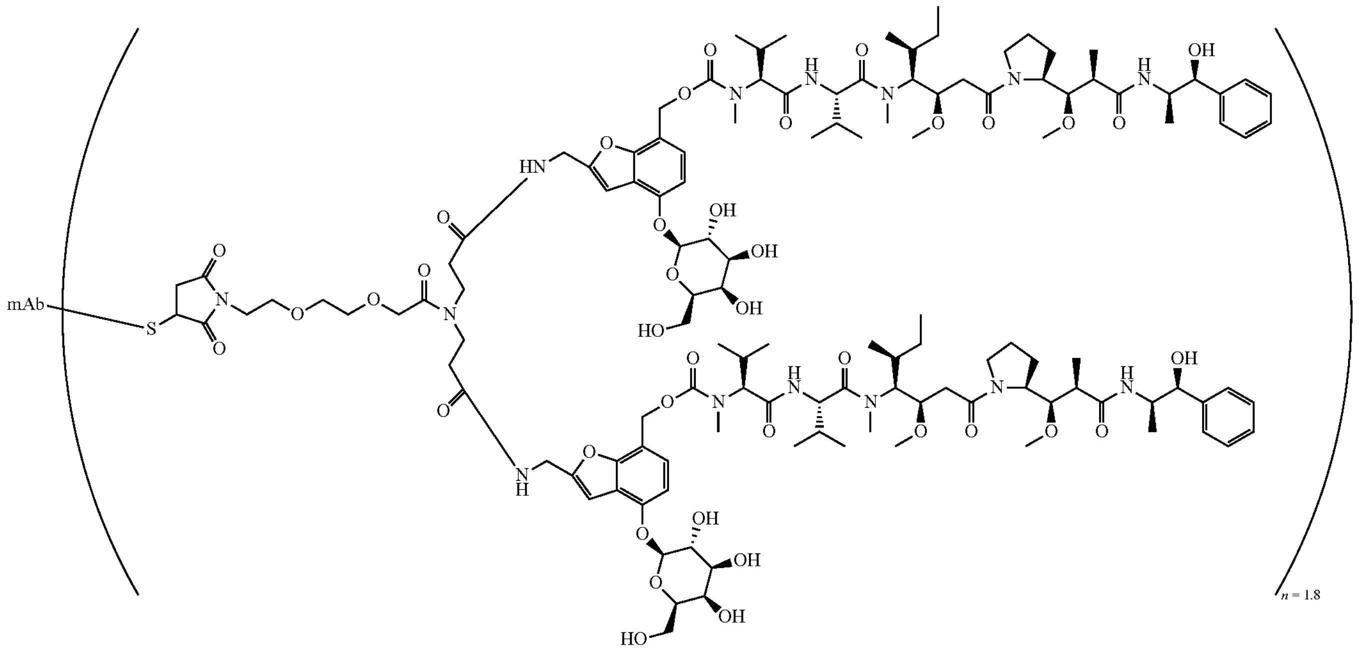 |

TABLE E-continued
| Examplary ligand-drug conjugates (DAR4 type) |
|---|
| 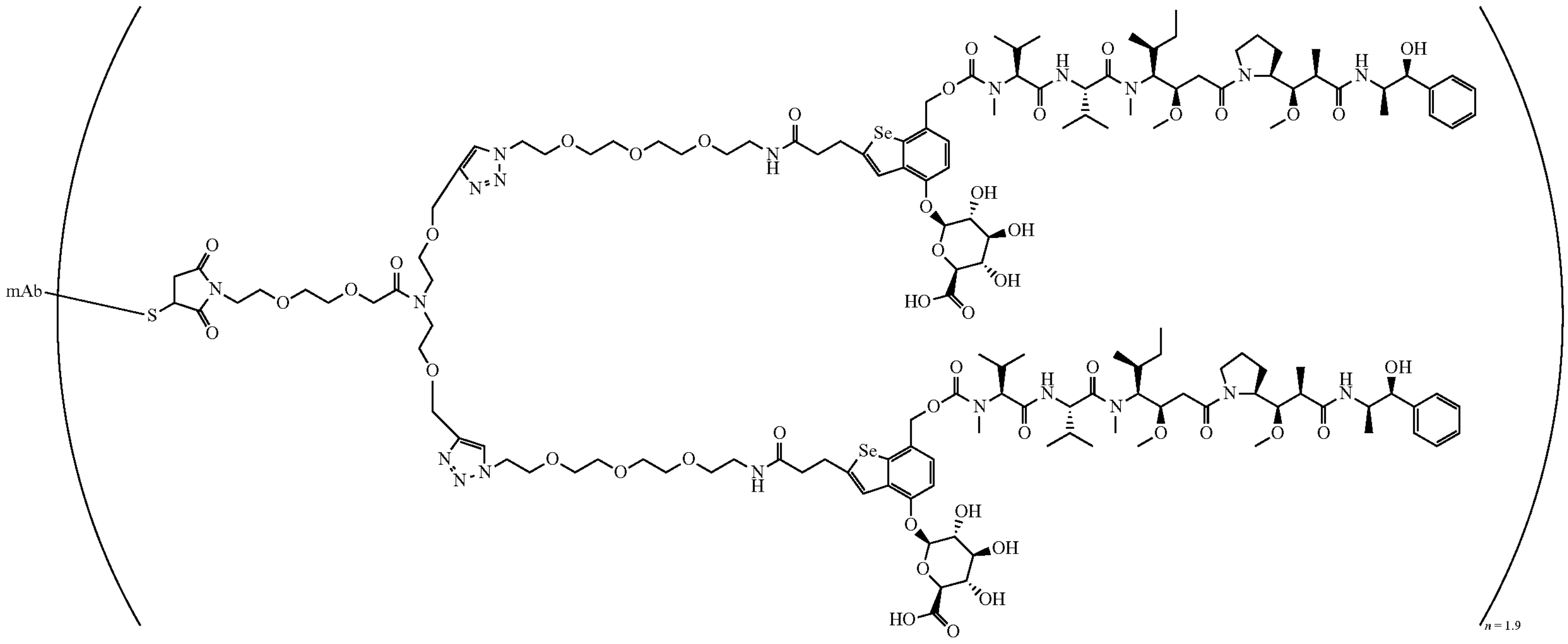 ADC-14 |

TABLE E-continued
| Examplary ligand-drug conjugates (DAR4 type) |
| --- |
| ADC-15 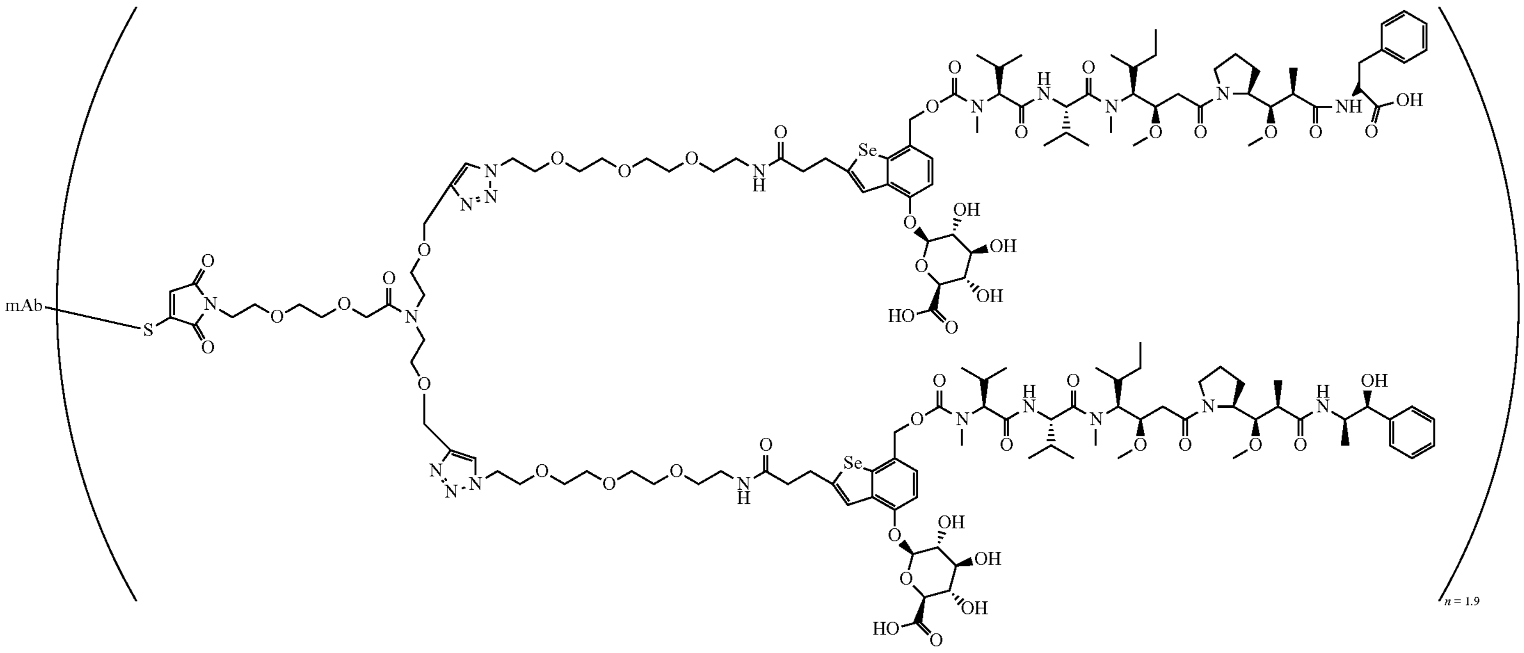 |

TABLE E-continued
| Examplary ligand-drug conjugates (DAR4 type) |
| --- |
| ADC-18 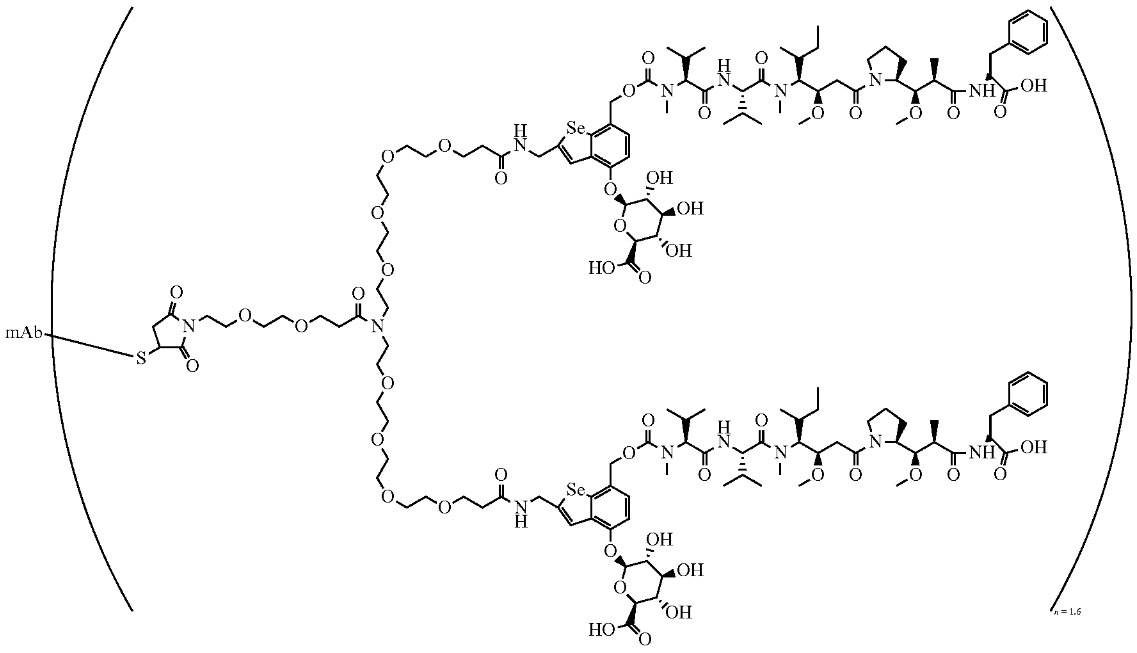 |

TABLE E-continued
| Examplary ligand-drug conjugates (DAR4 type) |
|---|
| ADC-19 |
| 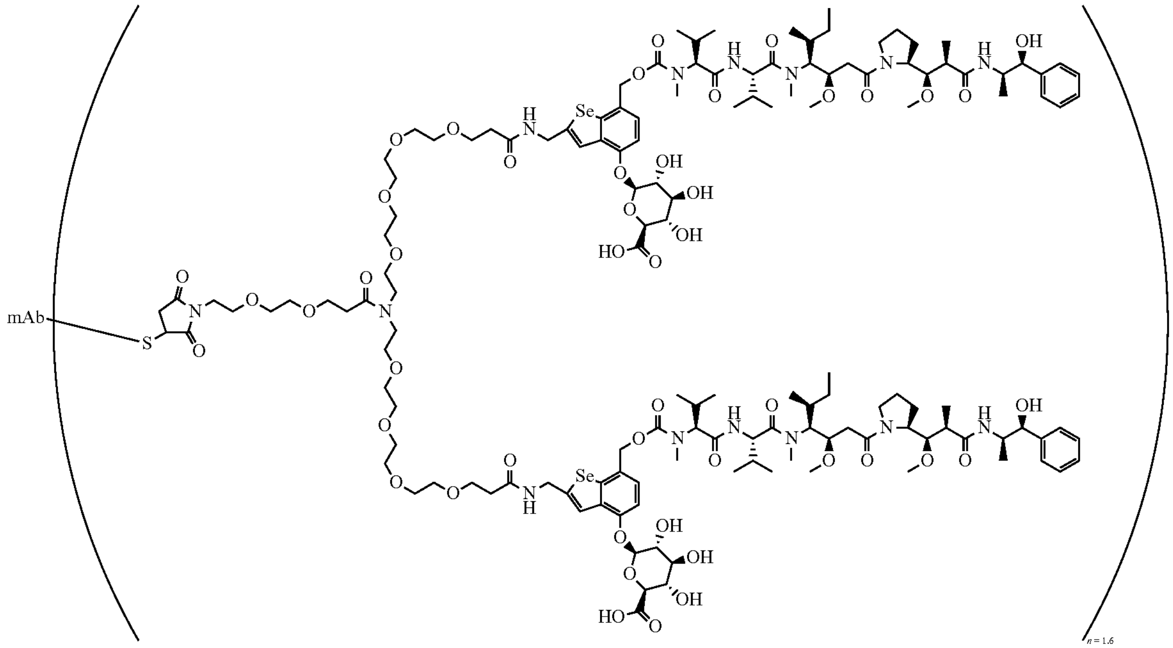 |

The invention claimed is:

1. A compound comprising a self-immolative group represented by Formula 1 below, or a pharmaceutically acceptable salt thereof:

$A\text{-}(L^1)_k\text{-}U_j$ [Formula 1]

in Formula 1, $L^1$ is a divalent or multivalent linking group, wherein (i) $L^1$ is —$(CH_2)_{na}$—; —$(CH_2CH_2O)_{ma}$—; —$(CH_2OCH_2)_{mb}$—; —$(OCH_2CH_2)_{mc}$—; —C(═O)—;

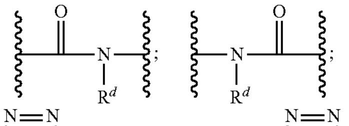

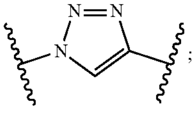 ; and 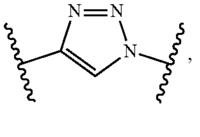 , or a combination thereof and $R^d$ is H or $C_{1-8}$ alkyl, and na, ma, mb and me are each independently an integer from 0 to 10 or (ii) $L^1$ is a $C_{1-200}$ alkylene optionally substituted with a divalent or multivalent functional group selected from the group consisting of amide, sulfonamide, amino, ether, carbonyl, triazole, tetrazole, and sulfo ester in the middle of the $C_{1-200}$ alkylene chain;

k is 0 or 1, and j is 1 to 10;

A is absent, H or a binding functional group, wherein the binding functional group is selected from the group consisting of OH, $C_{1-8}$ alkoxy, carboxy, $C_{1-8}$ alkoxycarbonyl, amino, mono-$C_{1-8}$ alkylamino, $N_3$, maleimidyl,

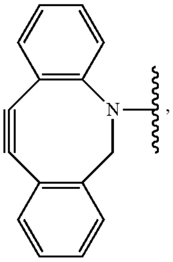 [SMILES: *N1Cc2ccccc2C#Cc2ccccc21] , and $C_{2-8}$ alkynyl; and

U is a moiety represented by Formula A below:

[Formula A]

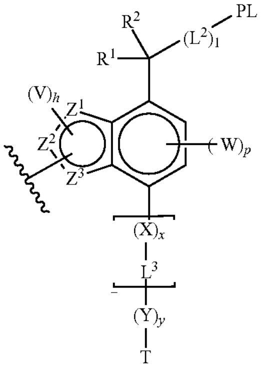

in Formula A, $R^1$ and $R^2$ are each independently H or $C_{1-8}$ saturated or unsaturated hydrocarbyl;

PL is an active agent linked to $L^2$ or the carbon atom to which $R^1$ and $R^2$ are bound by a heteroatom selected from N, O and S;

$L^2$ is a self-eliminating linker selected such that cleavage of the bond between $L^2$ and the carbon atom to which $R^1$ and $R^2$ are bound promotes cleavage of the bond between $L^2$ and PL, wherein $L^2$ is selected from the group consisting of —OC(═O)—, —$S(═O)_2$—, and

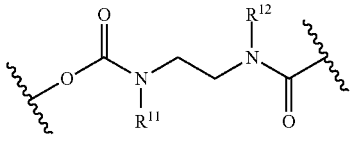 , and $R^{11}$ and $R^{12}$ are each independently H, $C_{1-8}$ alkyl, amino-$C_{1-8}$ alkyl, $C_{1-8}$ alkyl substituted with mono- or di-($C_{1-8}$ alkyl)amino, or —$(CH_2CH_2O)_gR^{13}$, wherein $R^{13}$ is H or $C_{1-4}$ alkyl, and g is an integer from 1 to 10;

one of $Z^1$ and $Z^3$ is selected from the group consisting of N, $NR^3$, O, S and Se, and the other one of $Z^1$ and $Z^3$ and $Z^2$ are each independently CH or N, and $\text{-}(L^1)_k\text{-}A$, and if present $\text{-}(V)_h$, each independently replace H of NH or CH;

represents a bond with $A\text{-}(L^1)_k\text{-}$;

$R^3$ is H or $C_{1-8}$ hydrocarbyl;

V is an electron withdrawing group or an electron donating group;

T is a triggering group capable of initiating the release of PL, and if present $L^2$, by a 1,6-elimination reaction upon cleavage;

$L^3$ is an optional self-immolative spacer group that is cleaved sequentially upon cleavage of T, if present; and h, i, 1, x and y are each independently 0 or 1;

$\text{-}(Y)_y\text{-}T$ is selected from the group consisting of moieties represented by

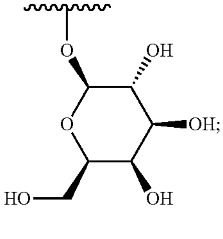 ; 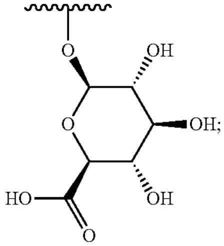 ;

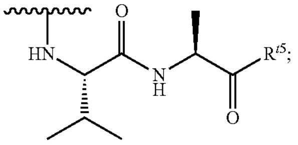 ; and

-continued

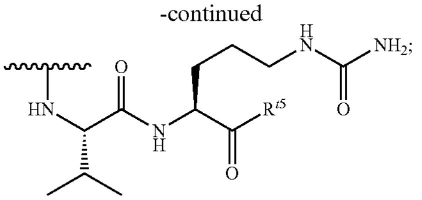

wherein

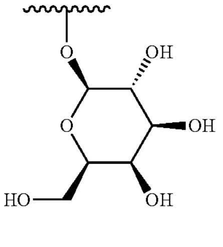 and 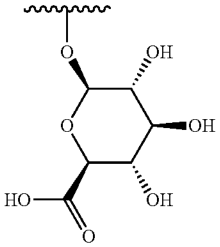

may include a form in which the —OH group is protected by a protecting group or substituted with a substituent;

$R^{t5}$ is OH, mono-$C_{1-8}$ alkylamino, di-$C_{1-8}$ alkylamino or —$NH(CH_2CH_2O)_fR^{t6}$, wherein $R^{t6}$ is H or $C_{1-4}$ alkyl; and f is an integer from 1 to 10, and r and s are each an integer from 1 to 5; and -$(X)_x$-$L^3$- is

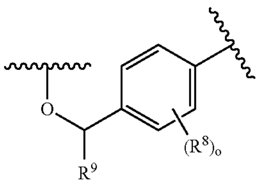

or —O—$CH_2$—, and $R^8$ and $R^9$ are each independently selected from the group consisting of H, halogen, $C_{1-8}$ alkyl, CN and $NO_2$, and o is an integer from 0 to 2.

2. The compound comprising a self-immolative group, or a pharmaceutically acceptable salt thereof, according to claim 1, wherein the ring

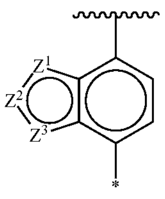

in Formula A above is selected from the following group:

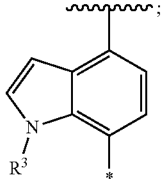; 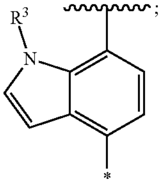; 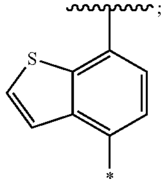; 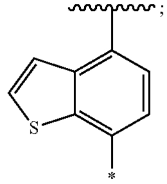; 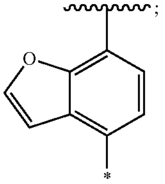; 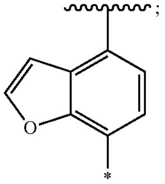; 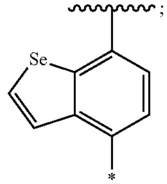; 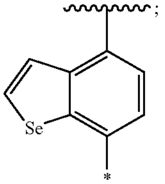; 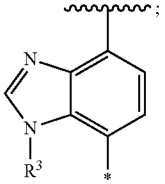; 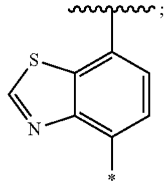; 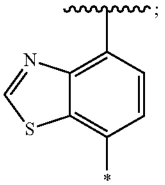; 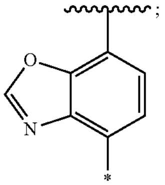; 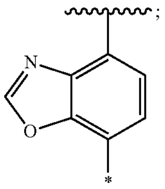; 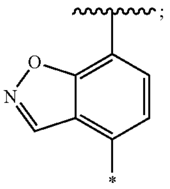; 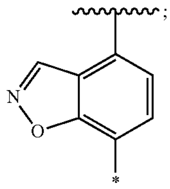; and 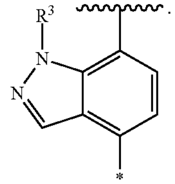.

3. The compound comprising a self-immolative group according to claim 1, wherein V is selected from the group consisting of halogen, CN, $NO_2$, formyl, $C_{1-8}$ alkylcarbonyl, carboxy, $C_{1-8}$ alkoxy-carbonyl, carboxy-$C_{1-8}$ alkyl, carbamoyl, mono-$C_{1-8}$ alkylcarbamoyl, di-$C_{1-8}$ alkylcarbamoyl, $C_{1-8}$ alkyl, $C_{1-8}$ alkenyl, OH, $C_{1-8}$ alkoxy, SH, $C_{1-8}$ alkylsulfanyl, $NH_2$, mono-$C_{1-8}$ alkylamino, di-$C_{1-8}$ alkylamino and $C_{6-18}$ aryl.

4. The compound comprising a self-immolative group according to claim 1, wherein PL is an active agent selected from a drug, a toxin, a fluorophore, an affinity ligand, a diagnostic substance or a detection probe.

5. The compound comprising a self-immolative group according to claim 4, wherein the drug is selected from cytokines, immunomodulatory compounds, anticancer agents, antiviral agents, anti-bacterial agents, antifungal agents, anthelmintic agents or a combination thereof.

6. The compound comprising a self-immolative group according to claim 1, wherein
PL is selected from the group consisting of
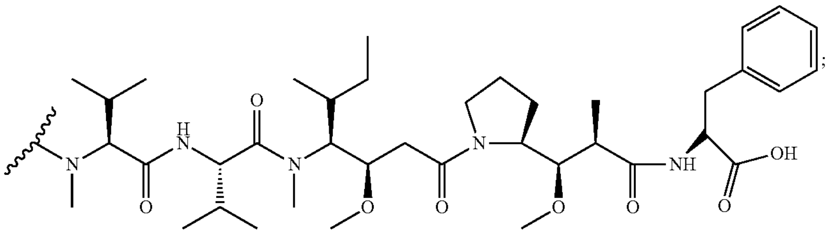
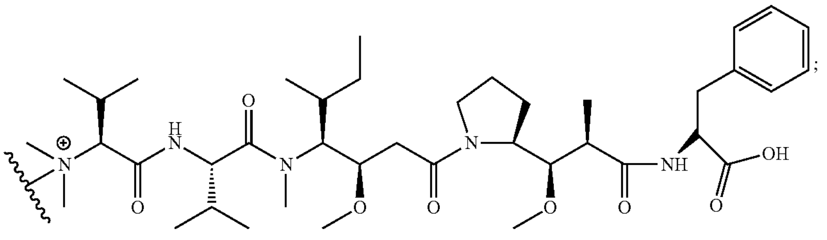
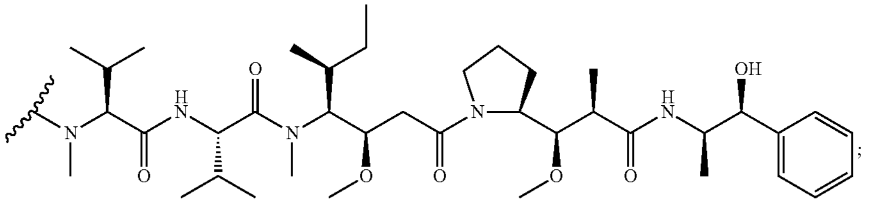
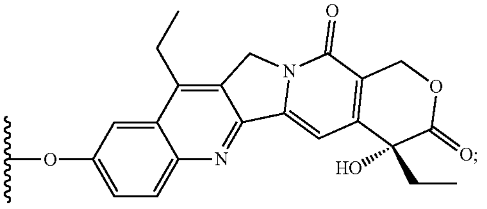
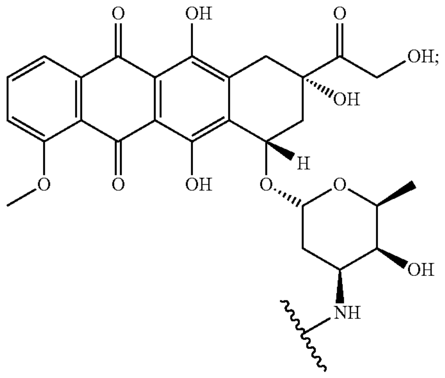
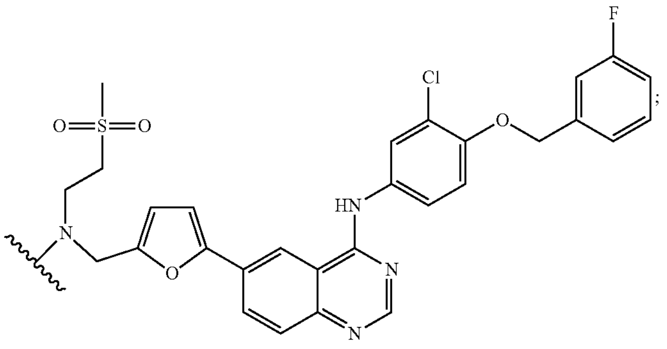
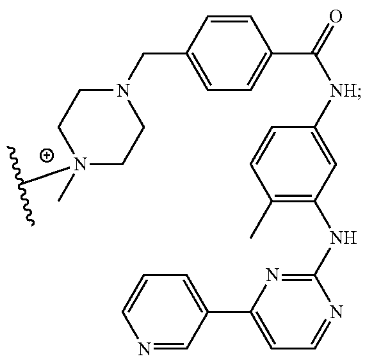

-continued
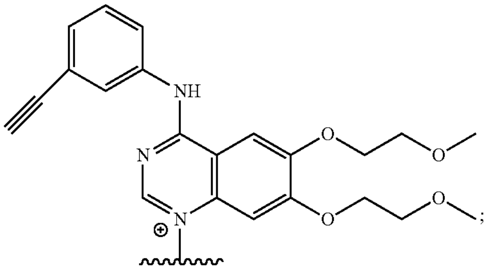
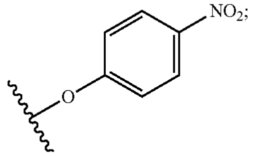
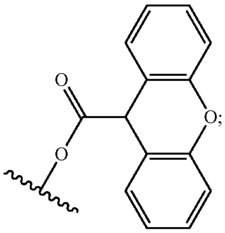
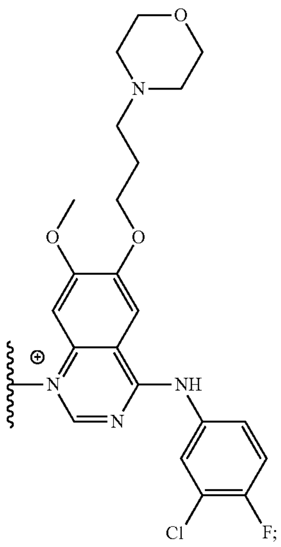
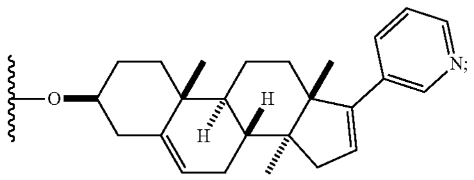
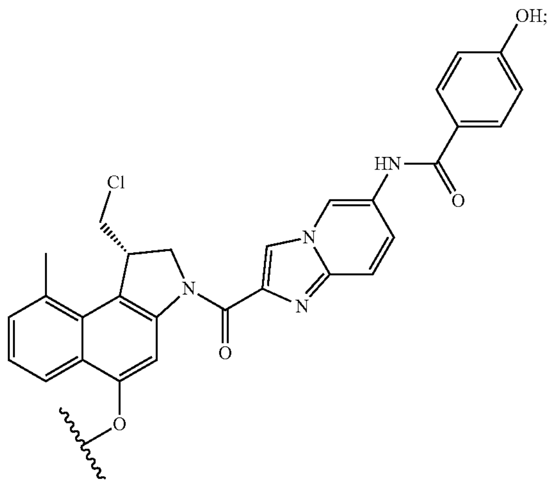
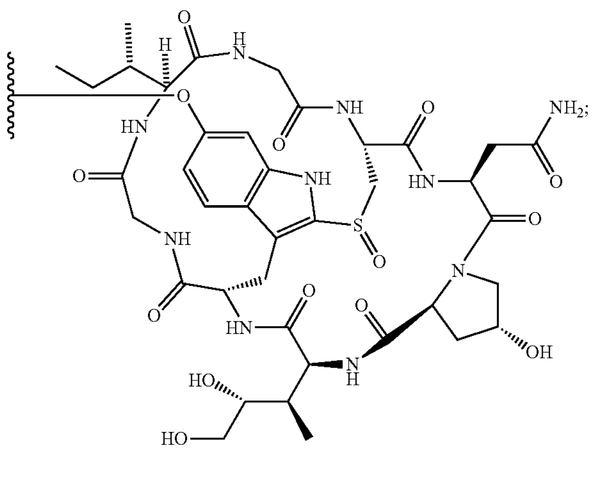

-continued
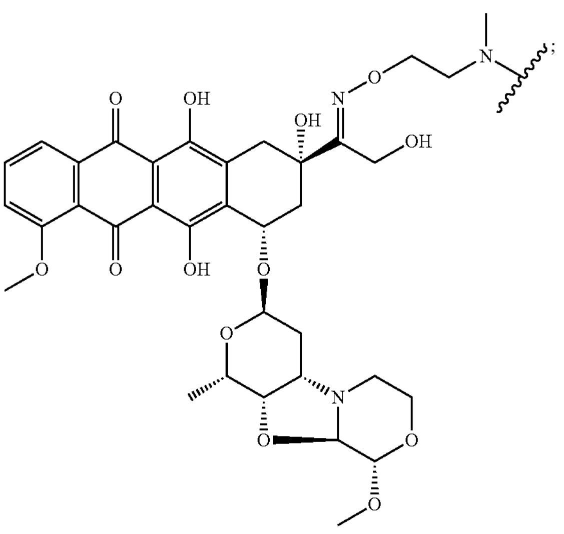
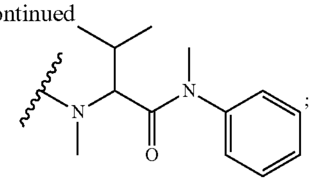
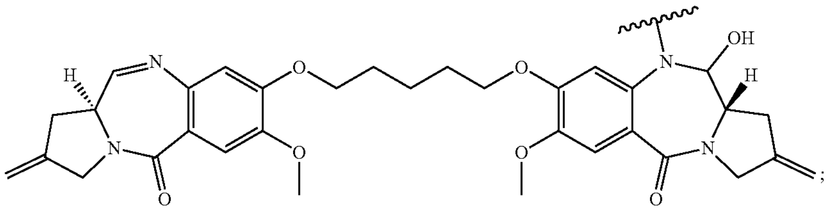
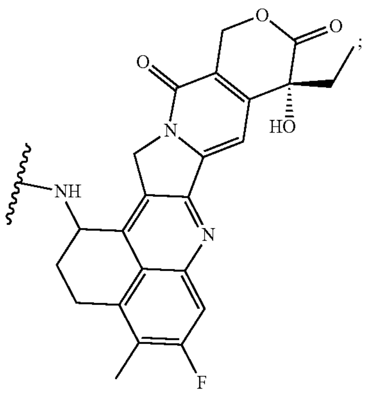
and
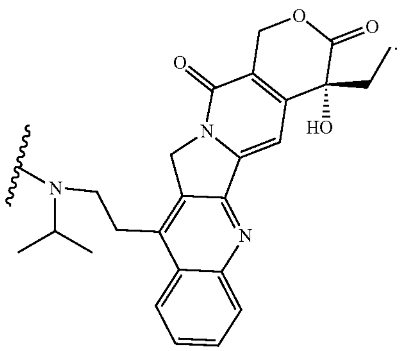
7. The compound comprising a self-immolative group according to claim 1, wherein
A-$L^1$- is selected from the group consisting of $N_3$—$(CH_2)_{n1}$—; $N_3$—$(CH_2CH_2O)_{m1}$—$(CH_2)_{n2}$—; HO—$(CH_2CH_2O)_{m1}$—$(CH_2)_{n2}$—; $H_2N$—$(CH_2CH_2O)_{m1}$—$(CH_2)_{n2}$—; $H_2N$—O—$(CH_2CH_2O)_{m1}$—$(CH_2)_{n2}$—; $N_3$—$(CH_2CH_2O)_{m2}$—$(CH_2)_{n3}$—$NR^{d1}$CO—$(CH_2)_{n4}$—; $R^{a1}$NH—$(CH_2)_{n5}$—; $R^{b1}$OC(=O)—$(CH_2)_{n6}$—; $R^{c1}C \equiv C$—$(CH_2OCH_2)_{m3}$—$CONR^{d2}$—$(CH_2)_{n7}$—;
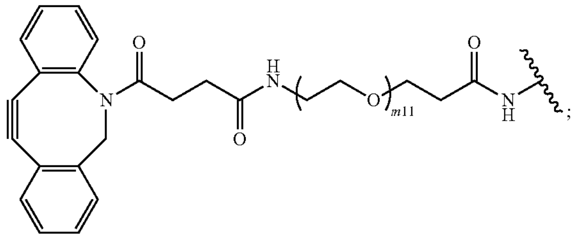

-continued
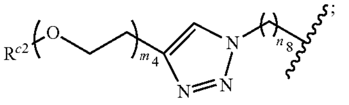
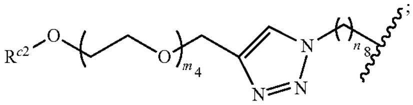
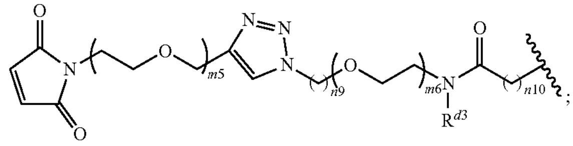
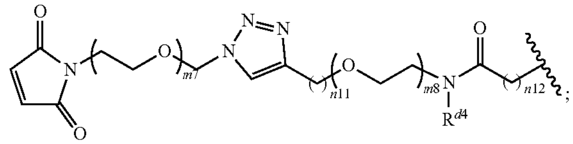
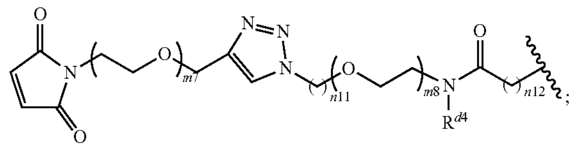
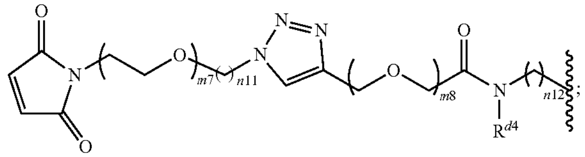
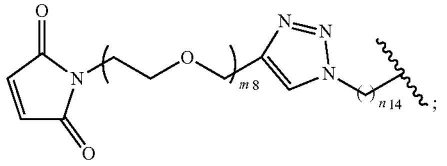
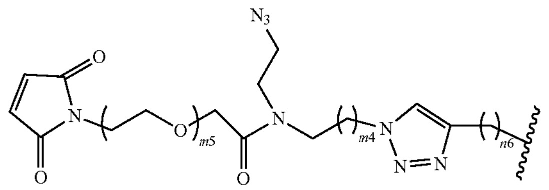
and
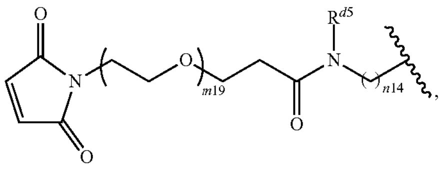
$R^{a1}$, $R^{b1}$, $R^{c1}$, $R^{c2}$ and $R^{d1}$ to $R^{d5}$ are each independently H or $C_{1-8}$ alkyl, and
n1 to n1 and m1 to m11 are each independently an integer from 0 to 10.
8. The compound comprising a self-immolative group according to claim 1, wherein
the compound represented by Formula 1 is selected from the group consisting of compounds represented by the following formulas:
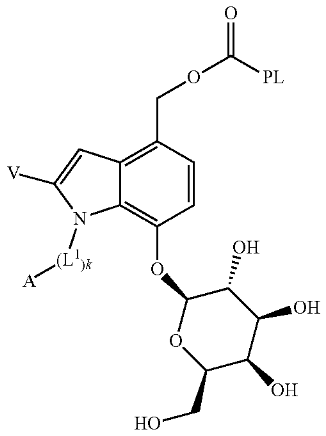
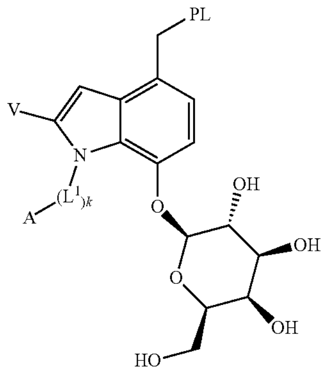
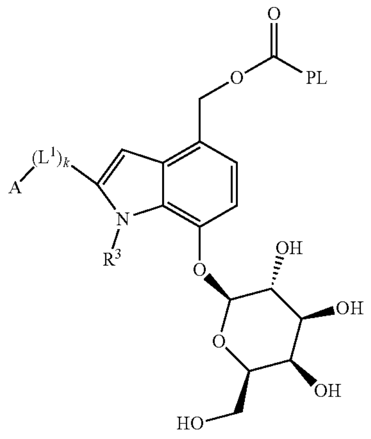
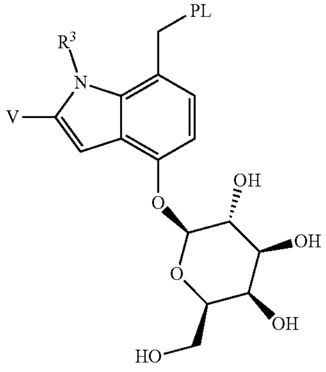

-continued
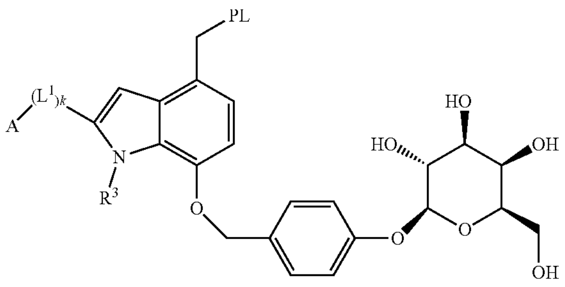
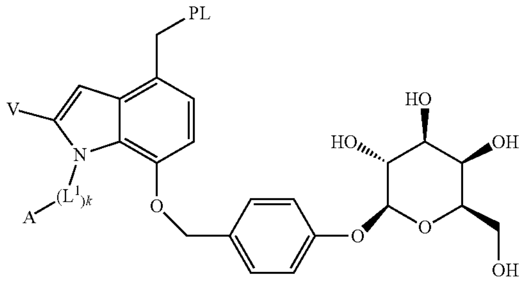
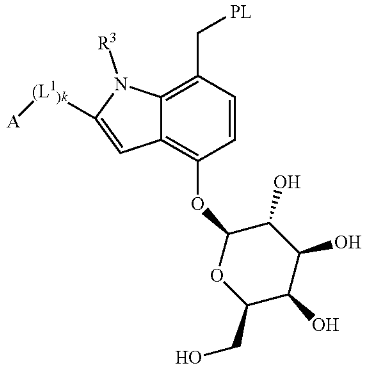
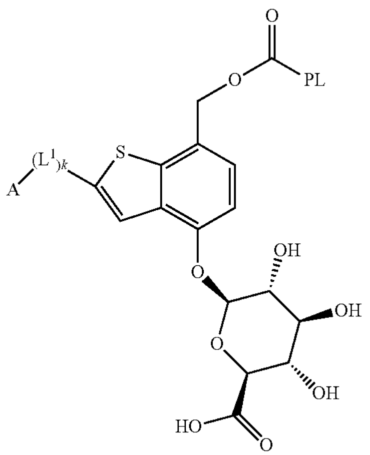
-continued
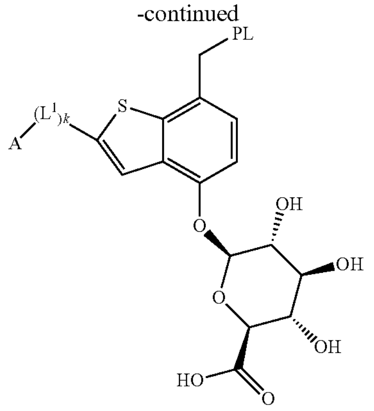
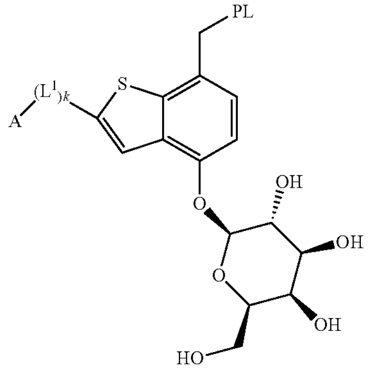
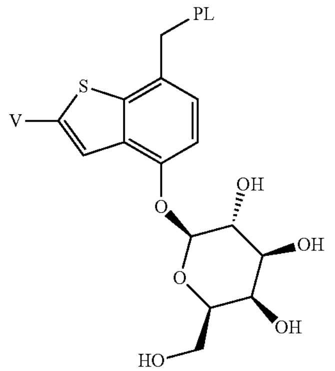
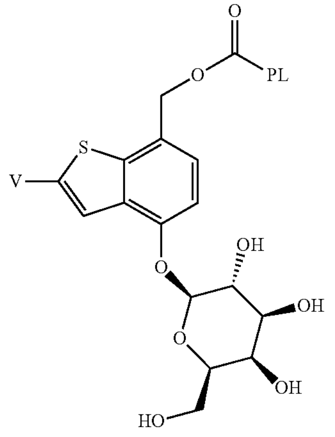

-continued
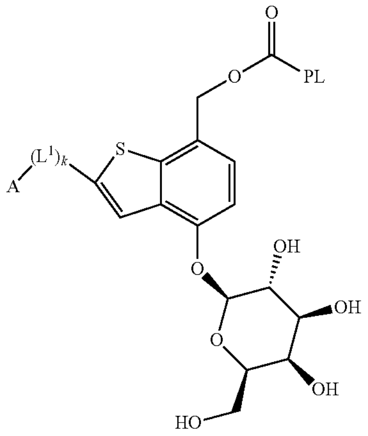
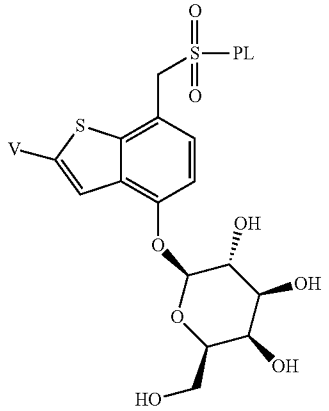
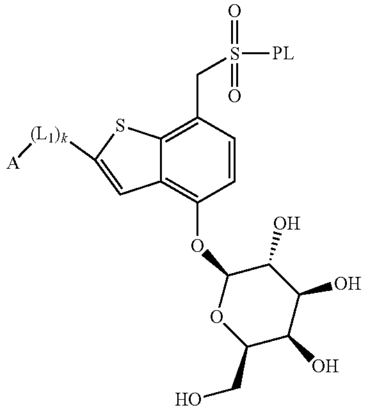
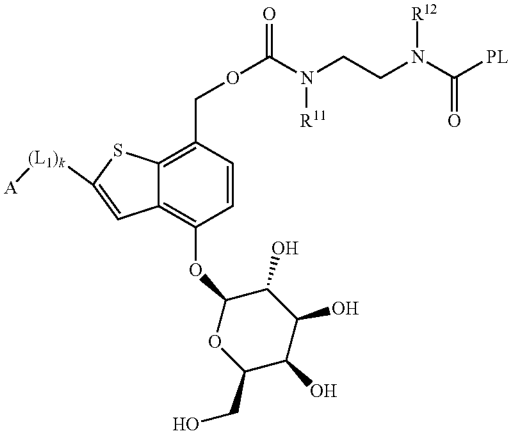
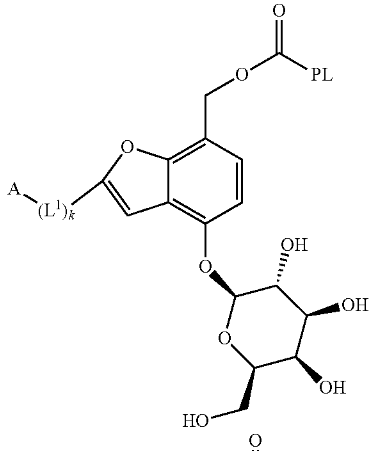
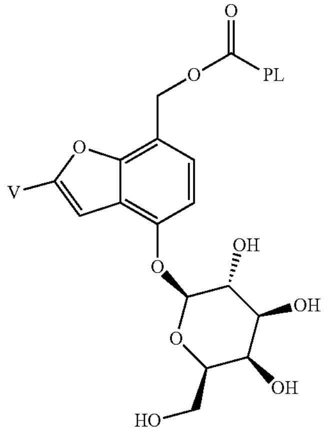
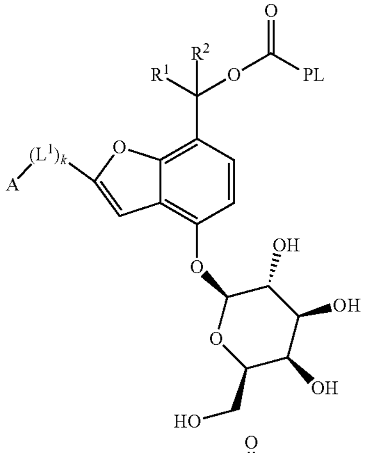
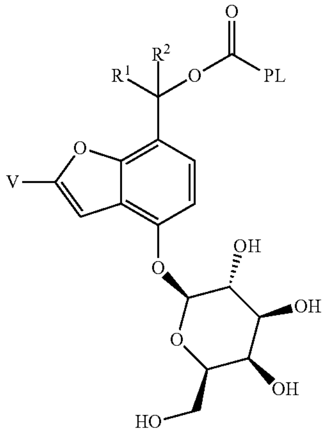
-continued -continued
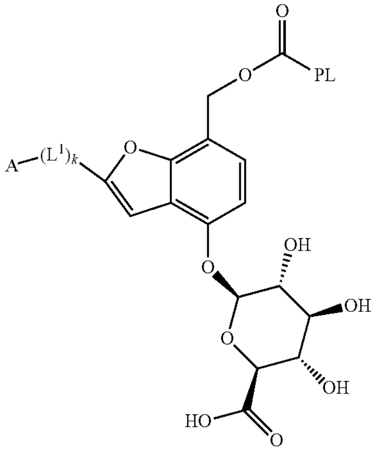
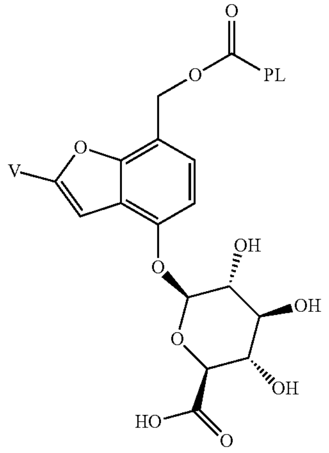
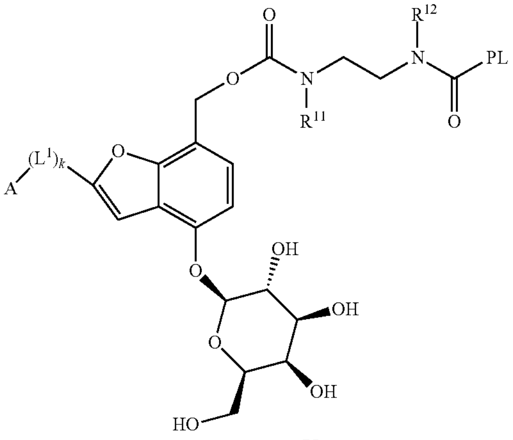
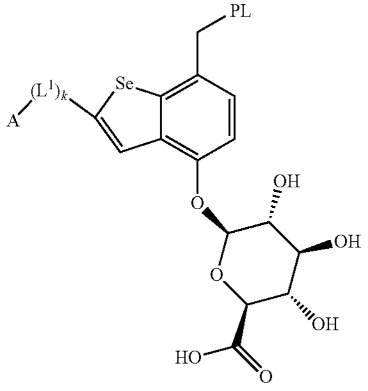
-continued
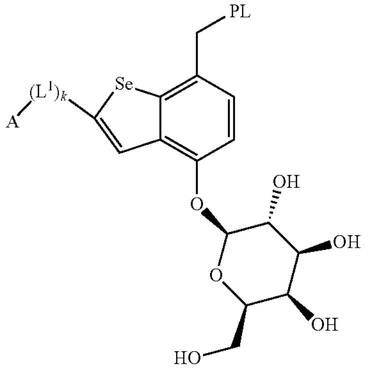
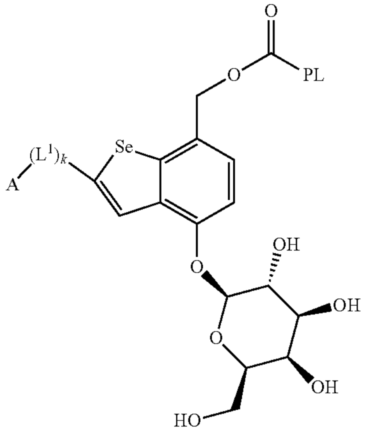
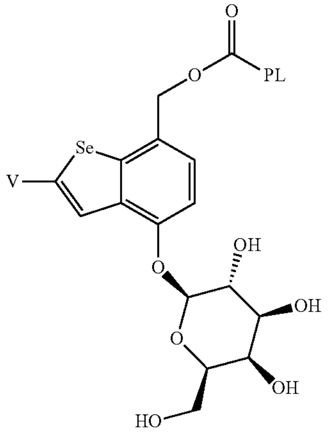
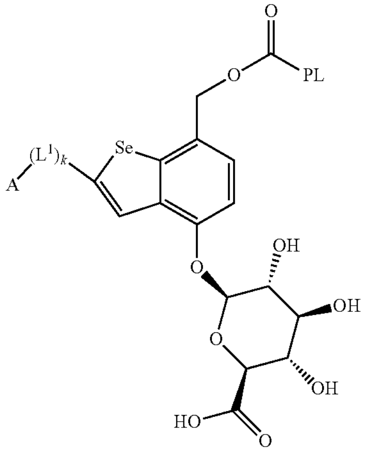

-continued
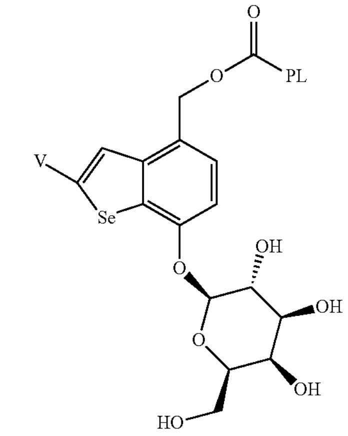
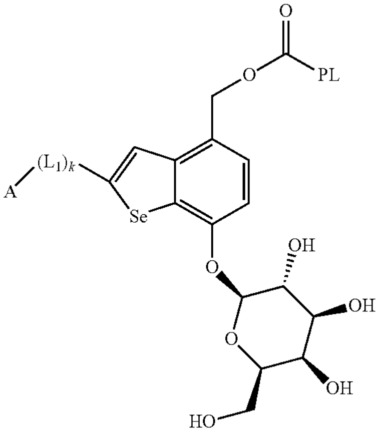
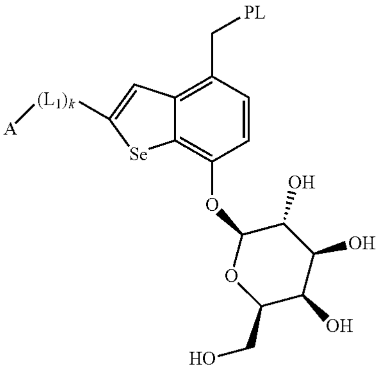
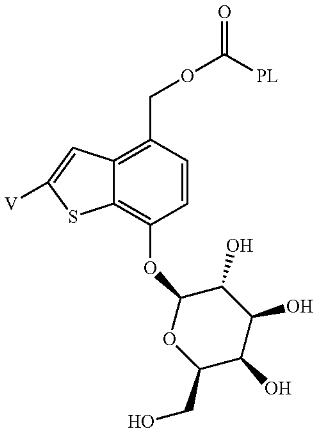
-continued
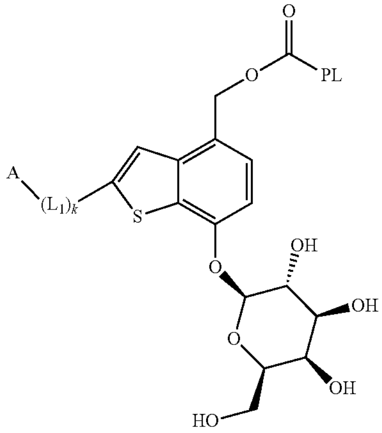
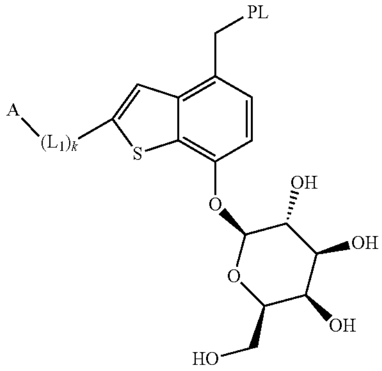
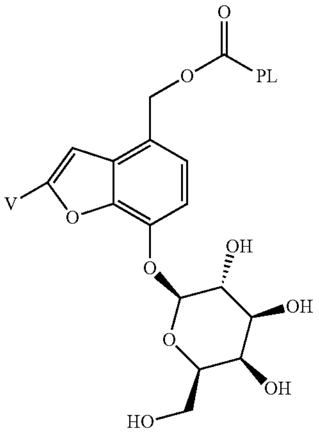
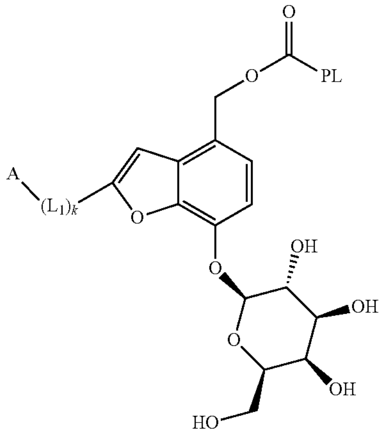

-continued

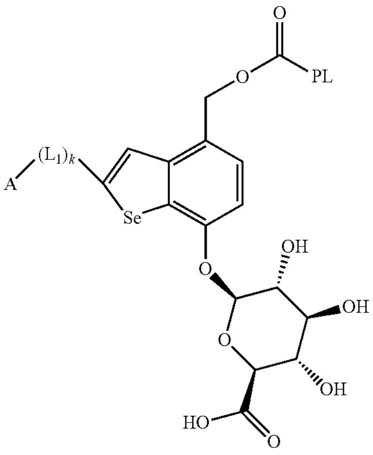

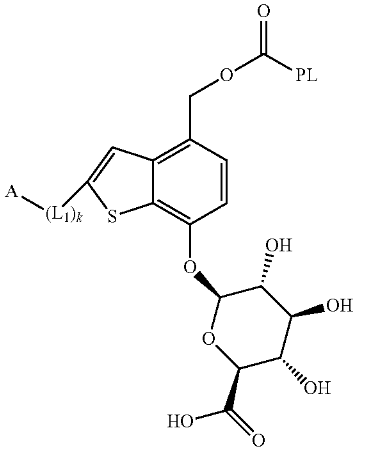

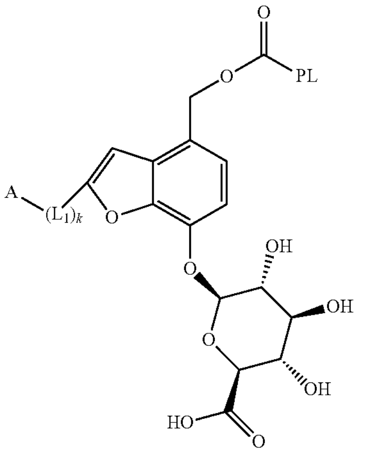

wherein, A, $L^1$, k, V, $R^1$, $R^2$, $R^3$, $R^{11}$, $R^{12}$ and PL are as defined in claim 1.

9. The compound comprising a self-immolative group according to claim 1, wherein the compound represented by Formula 1 is a compound represented by Formula 1-1 below:

[Formula 1-1]

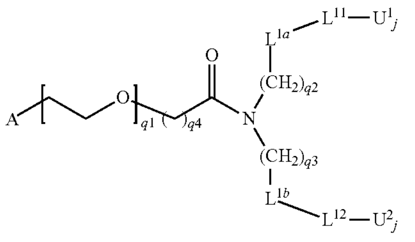

in Formula 1-1,

A has the same meaning as A defined in claim 1;

$U^1$ and $U^2$ each have the same meaning as U defined in claim 1, wherein $U^1$ and $U^2$ are the same or different from each other;

j is 1 to 10;

$L^{11}$ and $L^{12}$ are the same or different from each other and are (i) $-(CH_2)_{na}-$; $-(CH_2CH_2O)_{ma}-$; $-(CH_2OCH_2)_{mb}-$; $-(OCH_2CH_2)_{mc}-$; $-C(=O)-$;

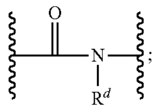;
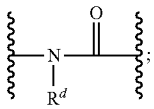;
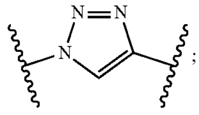; and 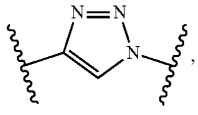, a combination thereof, and $R^d$ is H or $C_{1-8}$ alkyl, and na, ma, mb and mc are each independently an integer from 0 to 10 or (ii) a $C_{1-200}$ alkylene optionally substituted with a divalent or multivalent functional group selected from the group consisting of amide, sulfonamide, amino, ether, carbonyl, triazole, tetrazole, and sulfo ester in the middle of the $C_{1-200}$ alkylene chain;

$L^{1a}$ and $L^{1b}$ are each independently selected from a direct bond;

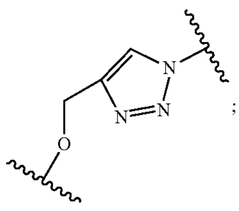;
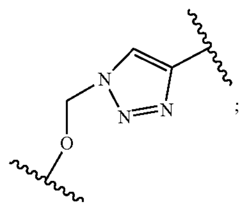;
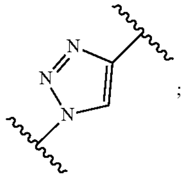;
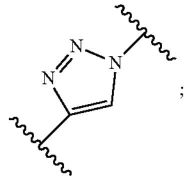;

-continued

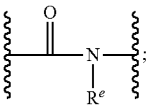

and

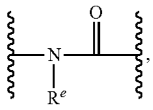

, and $R^e$ is H or $C_{1-8}$ alkyl; and q1, q2 and q3 are each independently an integer from 0 to 10, and q4 is an integer from 1 to 10;

provided that, if $L^{1a}$ is

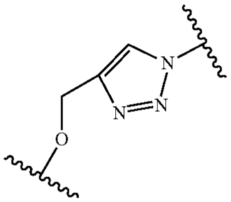

or

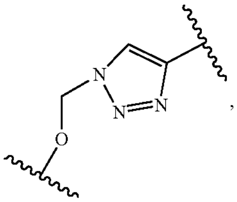

, q2 is not 0, and if $L^{1b}$ is

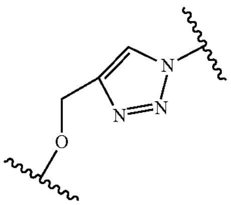

or

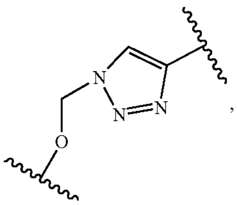

, q3 is not 0.

10. The compound according to claim 9, wherein

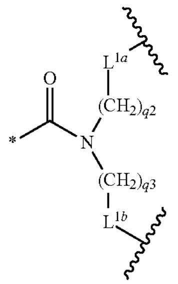

in Formula 1-1 above is selected from the following structures:

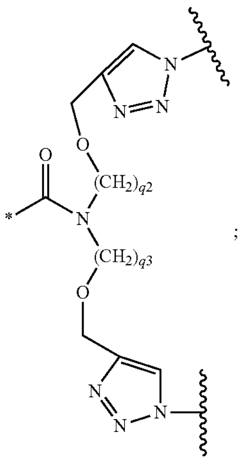

;

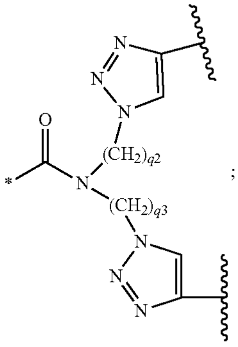

;

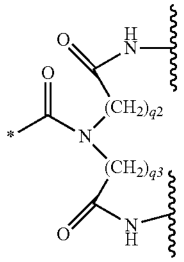

and

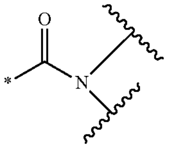

in the above formulas, the definitions of q2 and q3 are as defined in claim 9.

11. The compound according to claim 9, wherein $L^{11}$ and $L^{12}$ are each independently selected from $-(CH_2)_{n1}-$; $-(CH_2CH_2O)_{m1}-(CH_2)_{n2}-$; $-(CH_2CH_2O)_{m2}-(CH_2)_{n3}-NR^{d1}CO-(CH_2)_{n4}-$; $-(CH_2CH_2O)_{m10}-(CH_2)_{n15}-CONR^{d5}-(CH_2)_{n14}-$ and

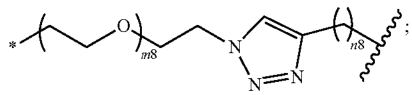

;

$R^{d1}$ and $R^{d5}$ are each independently H or $C_{1-8}$ alkyl, and $n_1$, n2, n3, n4, n8, n14 and n15, and m1, m2, m8 and m10 are each independently an integer from 1 to 8.

12. The compound according to claim 9, wherein the compound represented by Formula 1-1 is selected from the group consisting of compounds represented by the following formulas:

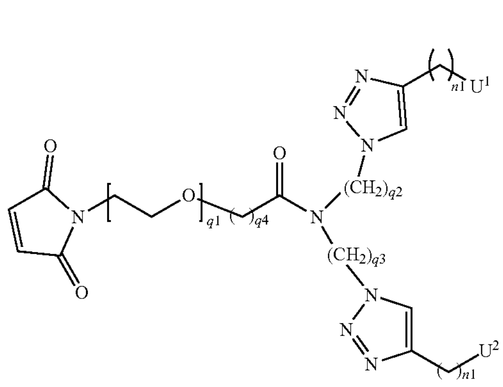
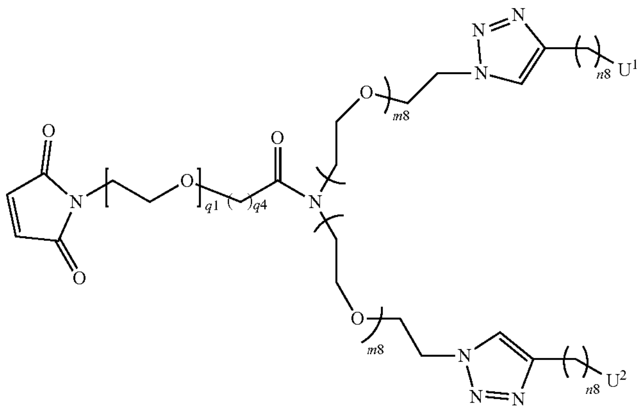
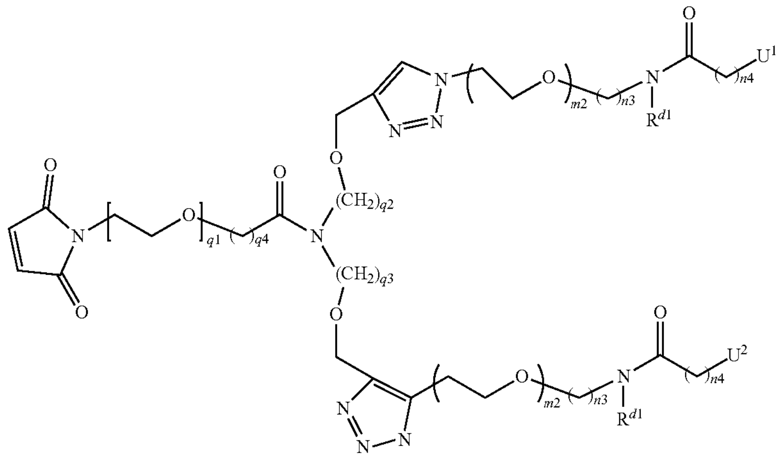
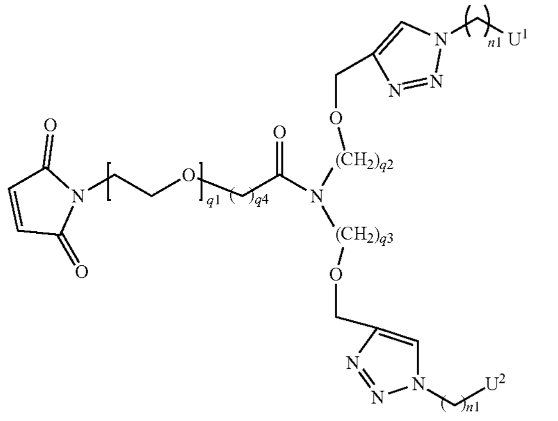
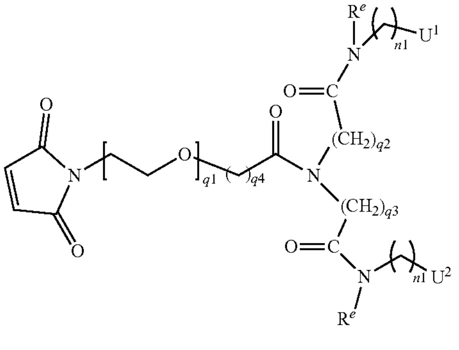

-continued

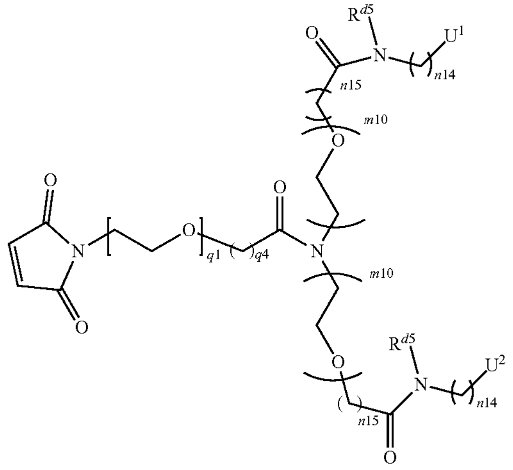

in the above formulas, q1 to q4, $U^1$ and $U^2$ are as defined in claim 9, $R^{d1}$, $R^{d5}$ and $R^e$ are each independently H or $C_{1-8}$ alkyl, and n1, n3, n4, n8, n14 and n15, m2, m8 and m10 are each independently an integer from 1 to 8.

13. A ligand-drug conjugate represented by Formula 2 below, or a pharmaceutically acceptable salt thereof:

[Formula 2]

$$E{-}\left[A'{-}(L^1)_k{-}U_j\right]_n$$

in Formula 2,

E is an antibody;

A' is a divalent linking group derived from the binding functional group of A;

the E-A' binding structure in Formula 2 includes

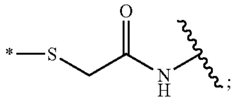;
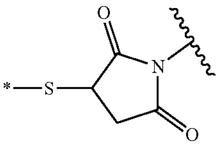;
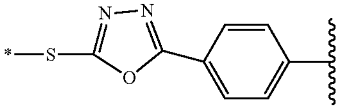;
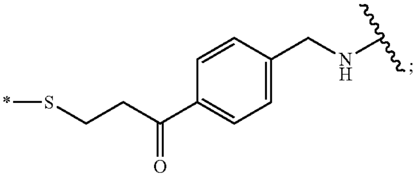;
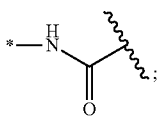;
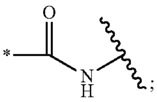;

-continued

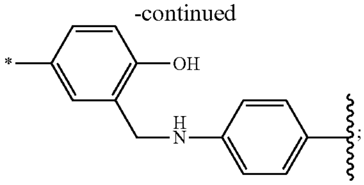;
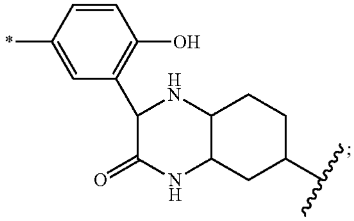;
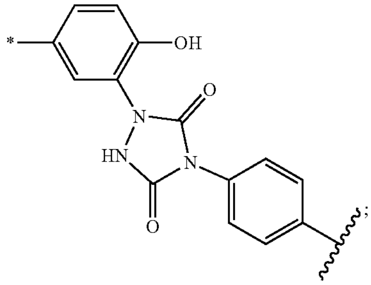;
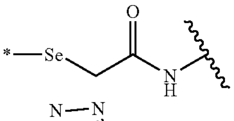;
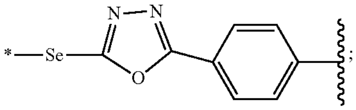;
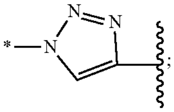 and 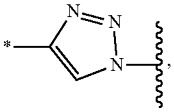, wherein * is the remaining moiety of the antibody;

n is a real number from 1 to 10; and wherein:

$L^1$ is a divalent or multivalent linking group, wherein (i) $L^1$ is $-(CH_2)_{na}-$; $-(CH_2CH_2O)_{ma}-$; $-(CH_2OCH_2)_{mb}-$; $-(OCH_2CH_2)_{mc}-$; $-C(=O)-$;

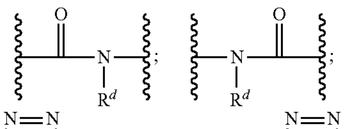

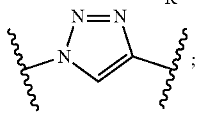

and

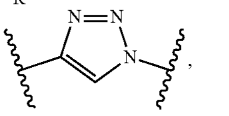

or a combination thereof, and $R^d$ is H or $C_{1-8}$ alkyl, and na, ma, mb and me are each independently an integer from 0 to 10 or (ii) L is a $C_{1-20}$ alkylene optionally substituted with a divalent or multivalent functional group selected from the group consisting of amide, sulfonamide, amino, ether, carbonyl, triazole, tetrazole, and sulfo ester in the middle of the $C_{1-200}$ alkylene chain;

k is 0 or 1, and j is 1 to 10;

A is absent, H or a binding functional group, wherein the binding functional group is selected from the group consisting of OH $C_{1-8}$ alkoxy, carboxy, $C_{1-8}$ alkoxycarbonyl, amino, mono-$C_{1-8}$ alkylamino, $N_3$, maleimidyl,

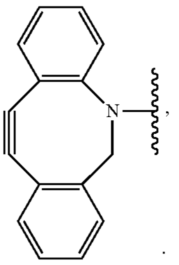 [SMILES: *N1Cc2ccccc2C#Cc2ccccc21]

and $C_{2-8}$ alkynyl; and

U is a moiety represented by Formula A below:

[Formula A]

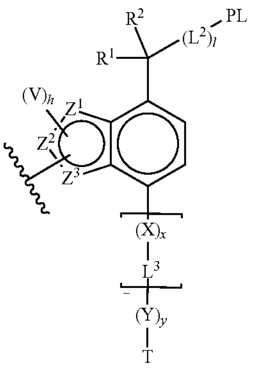

in Formula A, $R^1$ and $R^2$ are each independently H or $C_{1-8}$ saturated or unsaturated hydrocarbyl;

PL is an active agent linked to $L^2$ or the carbon atom to which $R^1$ and $R^2$ are bound by a heteroatom selected from N, O and S;

$L^2$ is a self-eliminating linker selected such that cleavage of the bond between $L^2$ and the carbon atom to which $R^1$ and $R^2$ are bound promotes cleavage of the bond between $L^2$ and PL, wherein $L^2$ is selected from the group consisting of —OC(=O)—, —S(=O)$_2$—, and

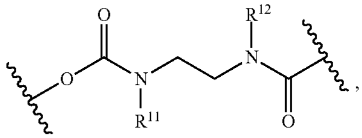

and $R_{11}$ and $R^{12}$ are each independently H, $C_{1-8}$ alkyl, amino-$C_{1-8}$ alkyl, $C_{1-8}$ alkyl substituted with mono- or di-($C_{1-8}$ alkyl)amino, or —$(CH_2CH_2O)_gR^{13}$, wherein $R^{13}$ is H or $C_{1-4}$ alkyl, and g is an integer from 1 to 10;

one of $Z^1$ and $Z^3$ is selected from the group consisting of N, $NR^3$, O, S and Se, and the other one of $Z^1$ and $Z^3$ and $Z^2$ are each independently CH or N, and -$(L^1)_k$-A, and if present -$(V)_h$, each independently replace H of NH or CH;

represents a bond with A-$(L^1)_k$-;

$R^3$ is H or $C_{1-8}$ hydrocarbyl;

V is an electron withdrawing group or an electron donating group;

T is a triggering group capable of initiating the release of PL, and if present $L^2$, by a 1,6-elimination reaction upon cleavage;

$L^3$ is an optional self-immolative spacer group that is cleaved sequentially upon cleavage of T, if present; and h, i, 1, x and y are each independently 0 or 1;

-$(Y)_y$-T is selected from the group consisting of moieties represented by

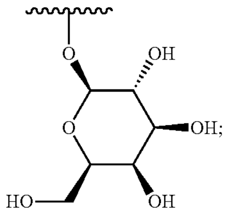

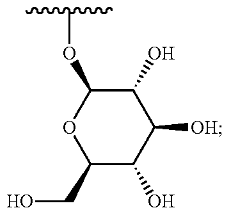

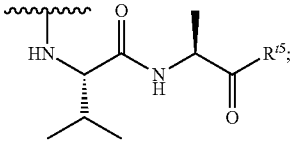

and

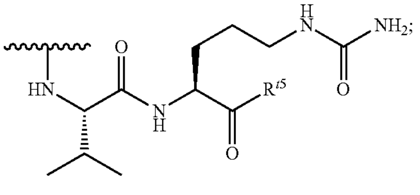

wherein

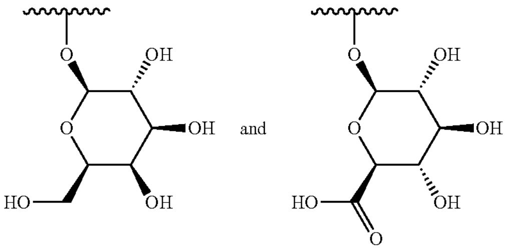 [SMILES: *O[C@@H]1O[C@H](CO)[C@H](O)[C@H](O)[C@H]1O ; "and" ; *O[C@@H]1O[C@H](C(=O)O)[C@@H](O)[C@H](O)[C@H]1O]

may include a form in which the —OH group is protected by a protecting group or substituted with a substituent;

$R^5$ is OH, mono-$C_{1-8}$ alkylamino, di-$C_{1-8}$ alkylamino or —$NH(CH_2CH_2O)_fR^{t6}$, wherein $R^{t6}$ is H or $C_{1-4}$ alkyl; and f is an integer from 1 to 10, and r and s are each an integer from 1 to 5; and $-(X)_x-L^3-$ is

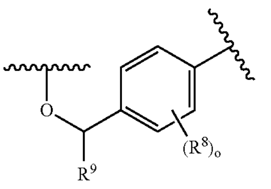

or —O—$CH_2$—, and $R^8$ and $R^9$ are each independently selected from the group consisting of H, halogen, $C_{1-8}$ alkyl, CN and $NO_2$, and o is an integer from 0 to 2.

14. The ligand-drug conjugate according to claim 13, wherein the antibody is selected from the group consisting of tumor cell-specific monoclonal or polyclonal antibodies, antibody fragments, and artificial antibody.

15. The ligand-drug conjugate according to claim 13, wherein the conjugate represented by Formula 2 is selected from the following conjugates:

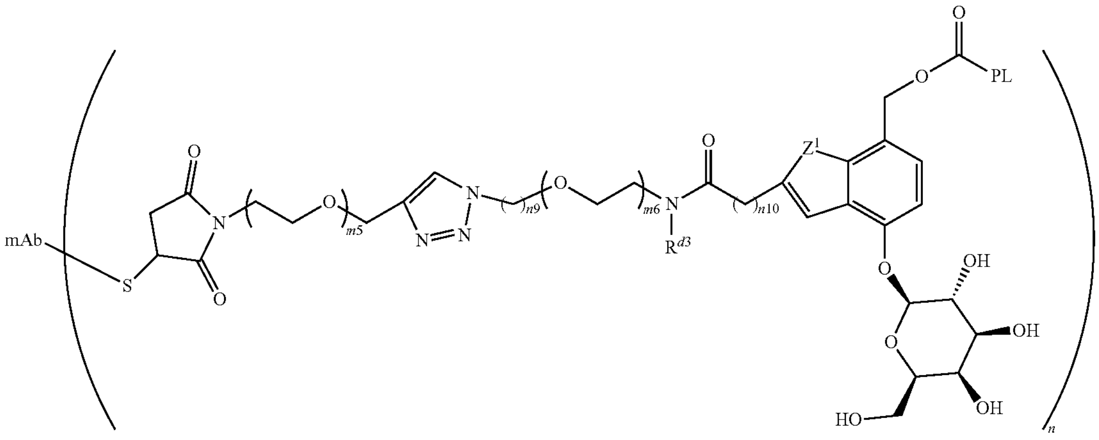

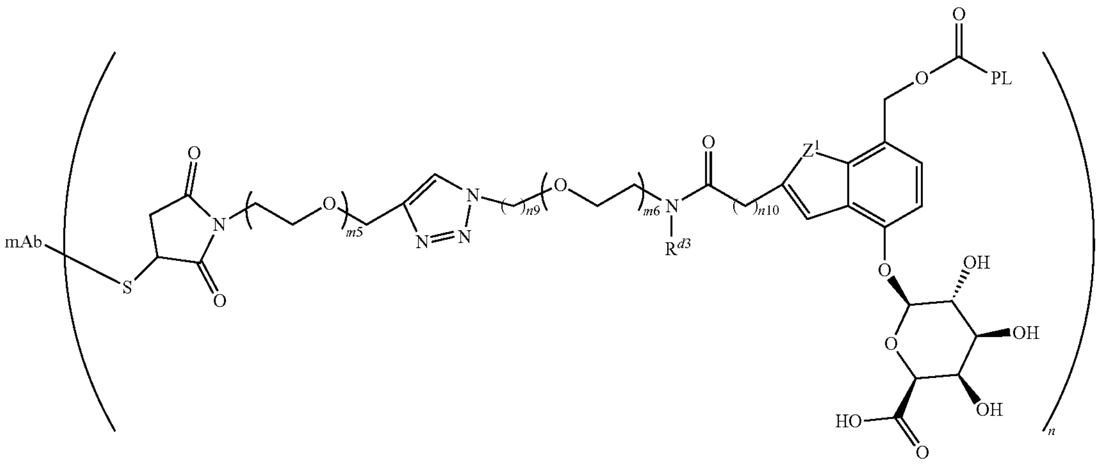

-continued
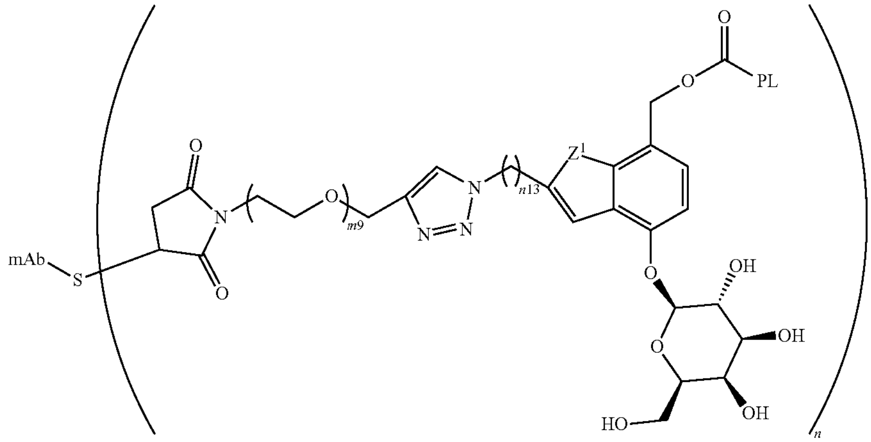
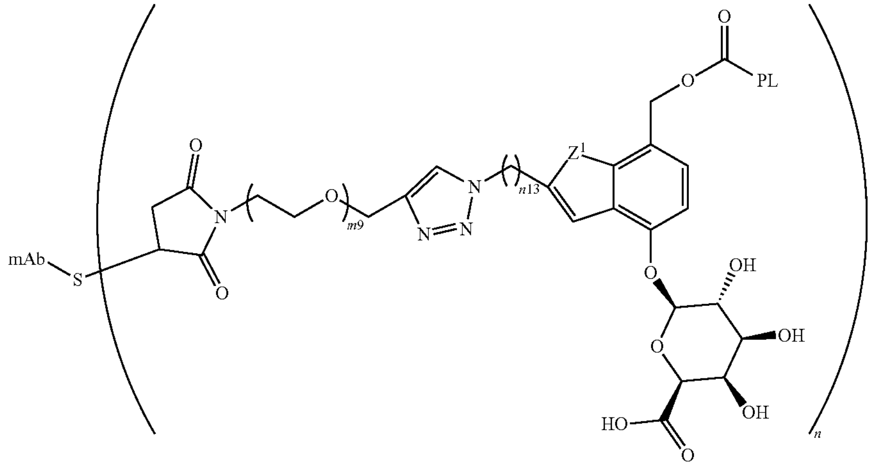
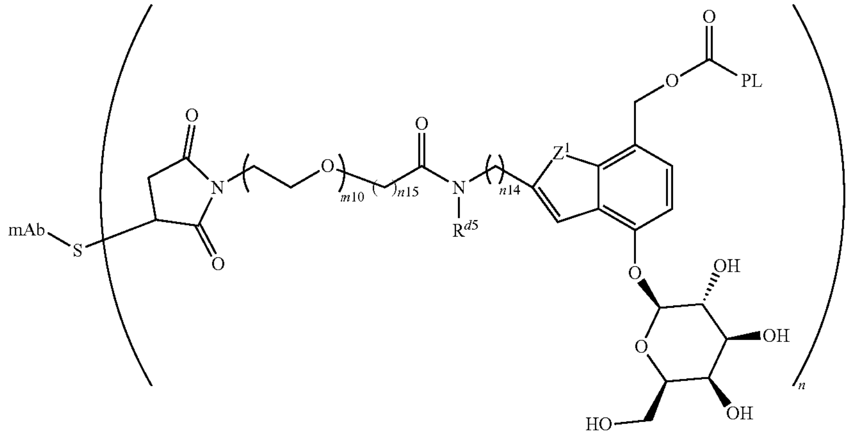

-continued

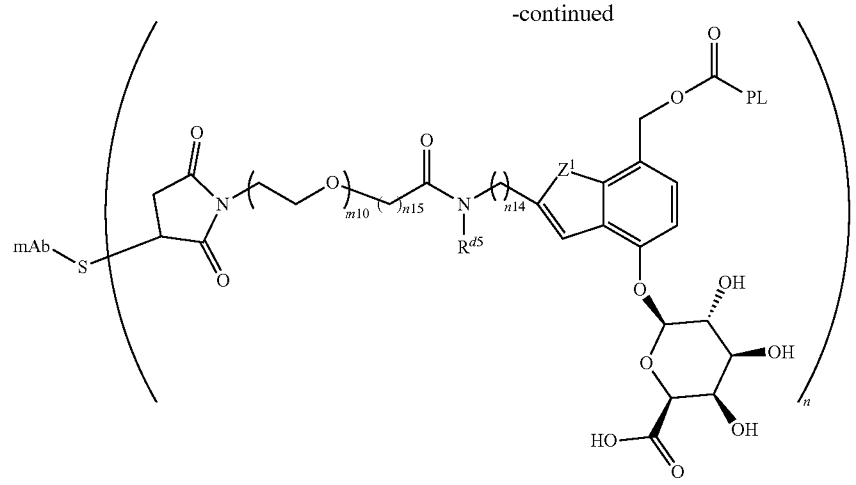

in the above formulas, mAb represents the moiety of the antibody;

m5, m6, m9, m10, n9, n10, n13, n14 and n15 are each independently an integer from 1 to 10;

$R^{d3}$ and $R^{d5}$ are each independently H or $C_{1-8}$ alkyl;

$Z^1$ is a heteroatom selected from $NR^3$, O, S and Se, and $R^3$ is H or $C_{1-8}$ hydrocarbyl;

PL is the moiety of the active agent; and n is a real number from 1 to 10.

16. The ligand-drug conjugate according to claim 15, wherein the ligand-drug conjugate represented by Formula 2 is selected from the group consisting of conjugates represented by the following formulas:

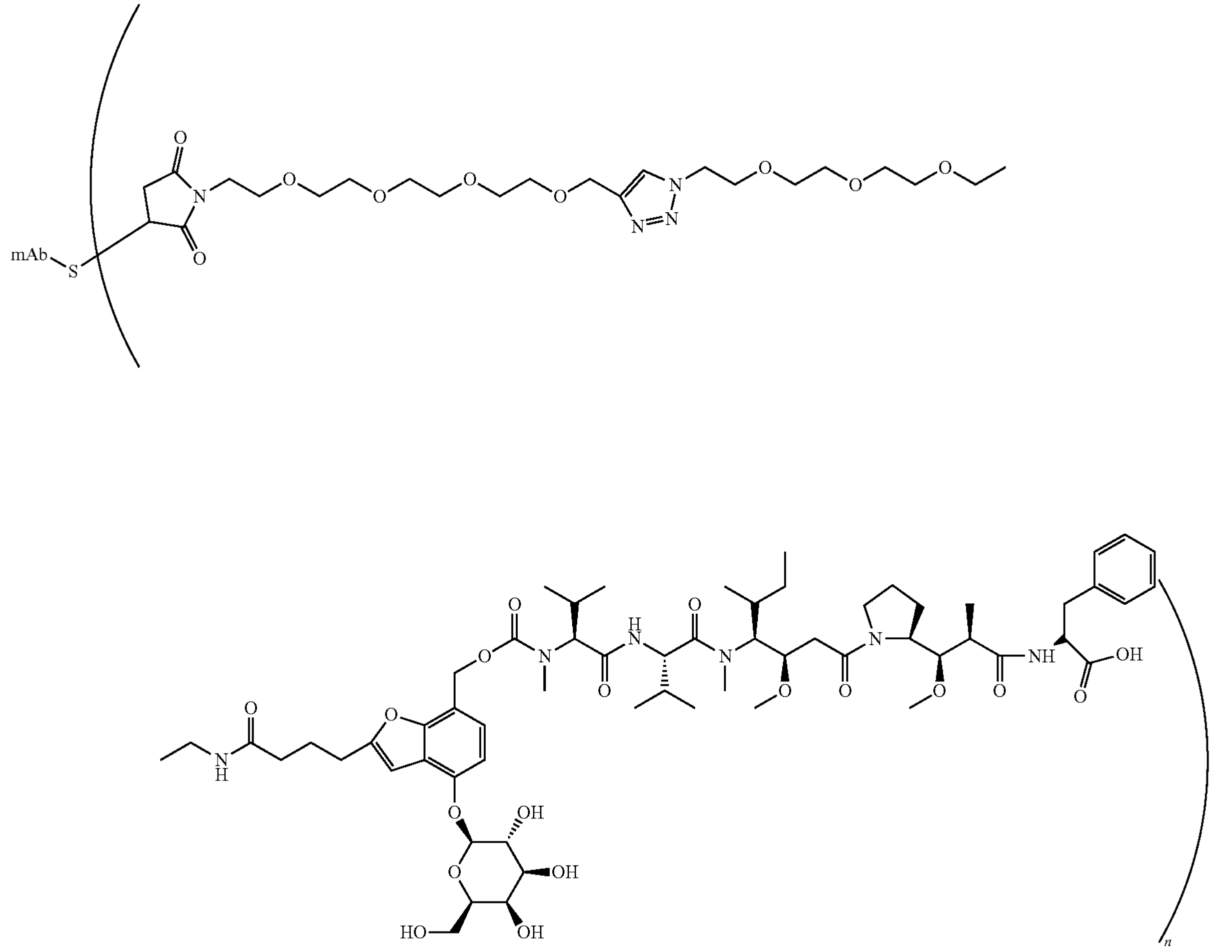

-continued
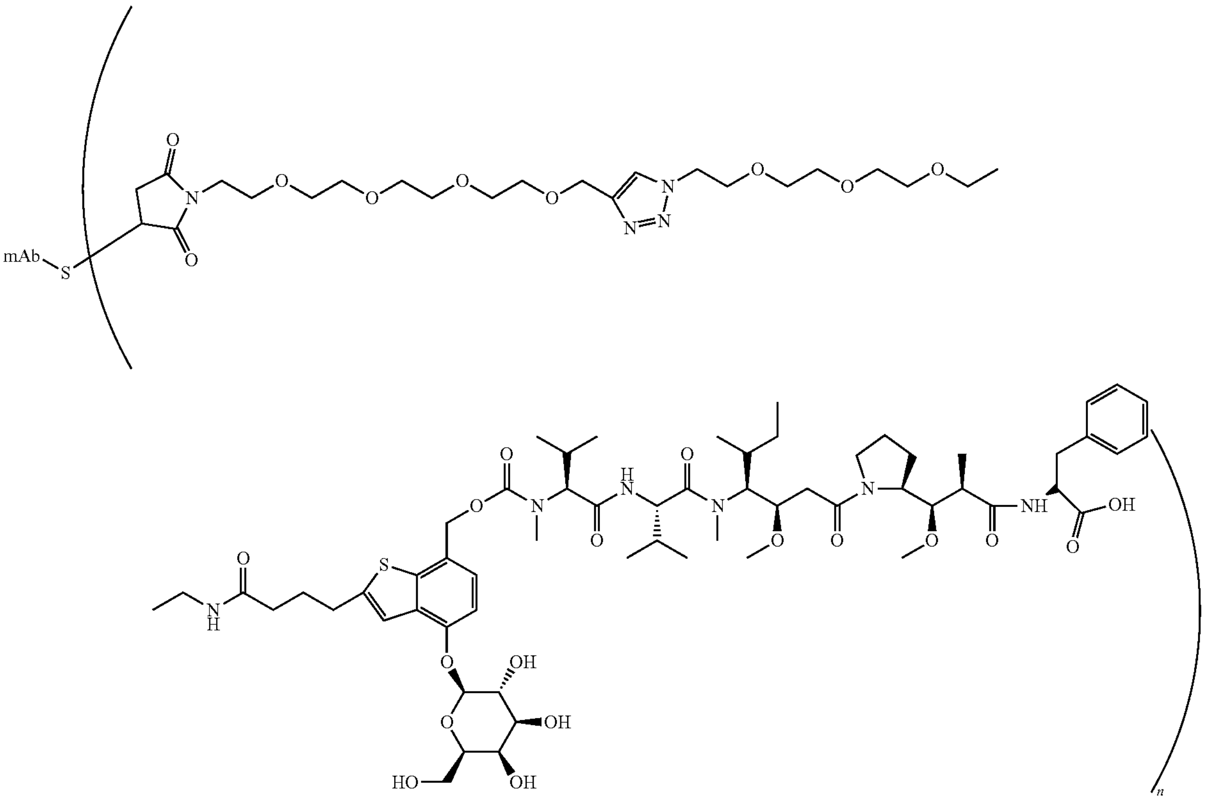
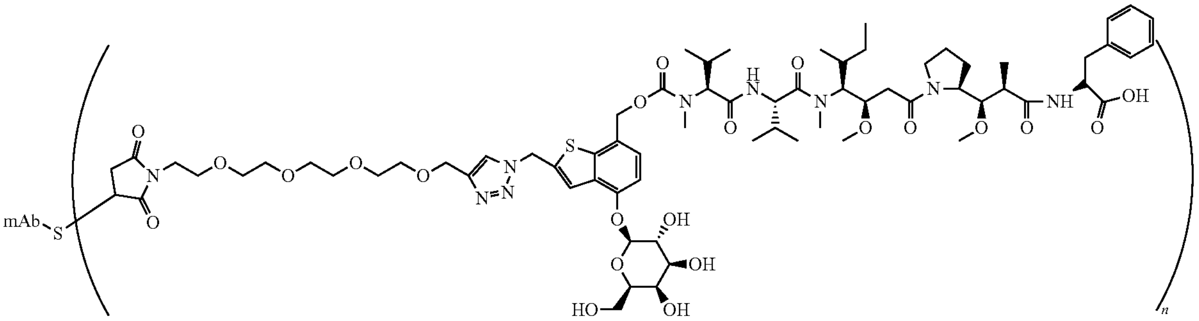
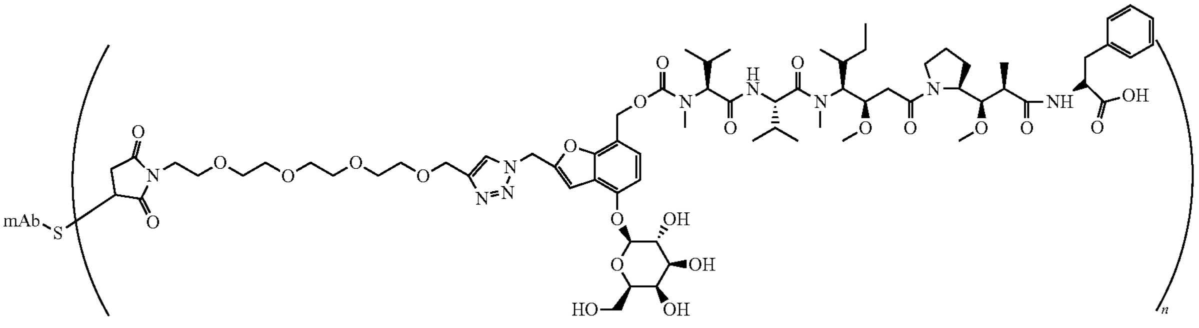

-continued
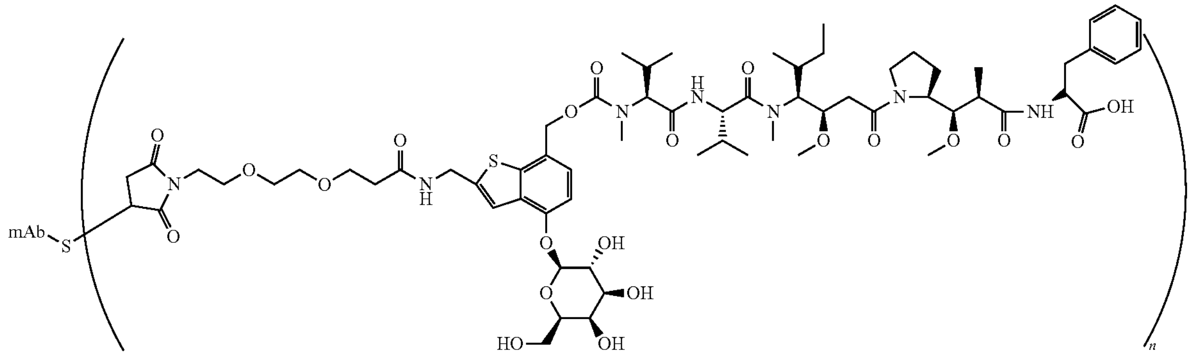
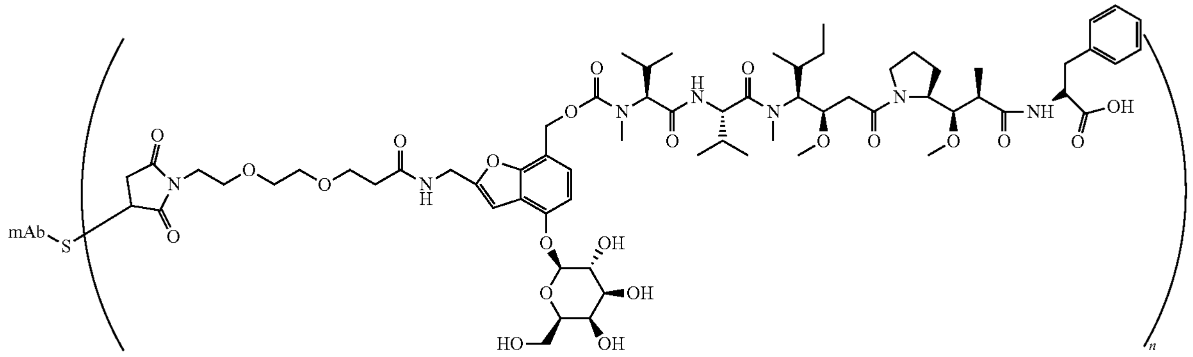
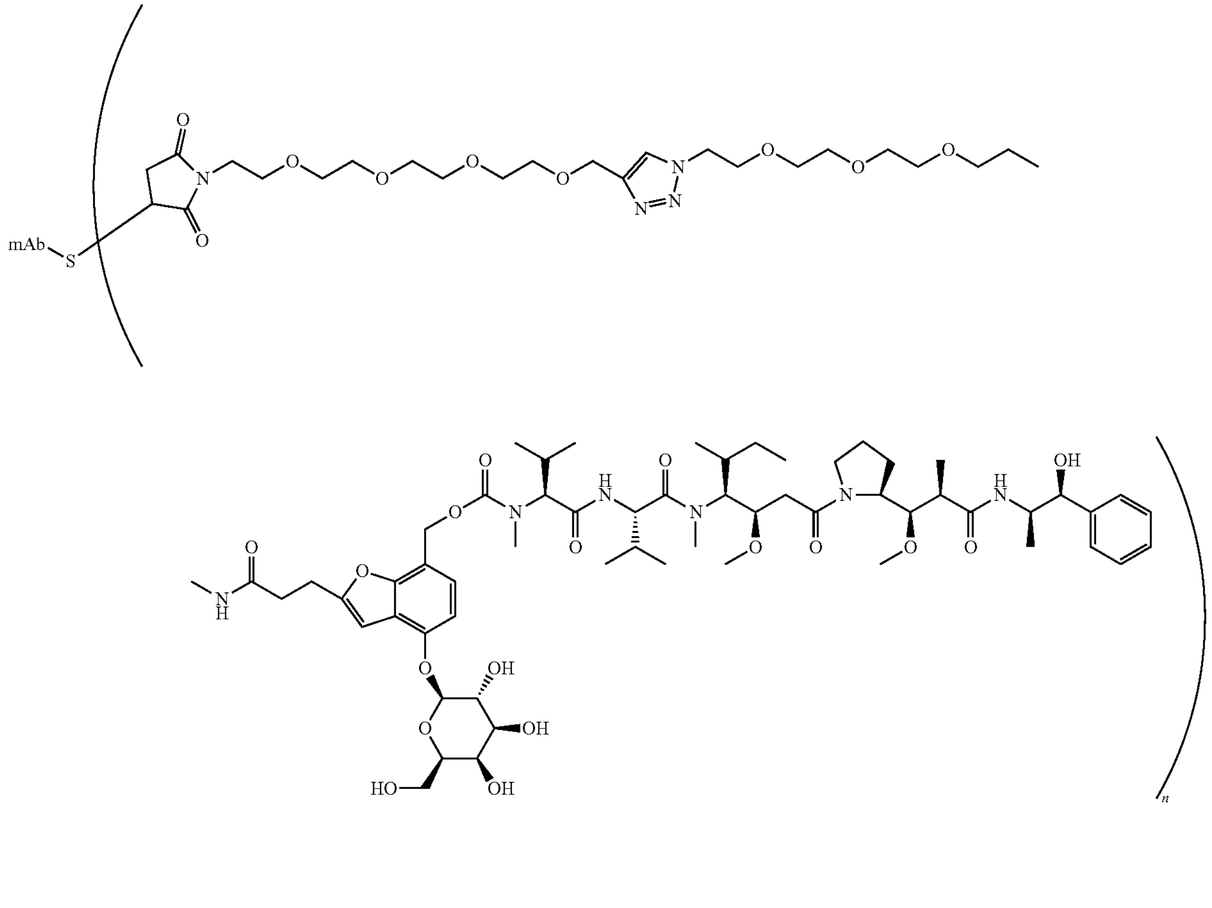

-continued
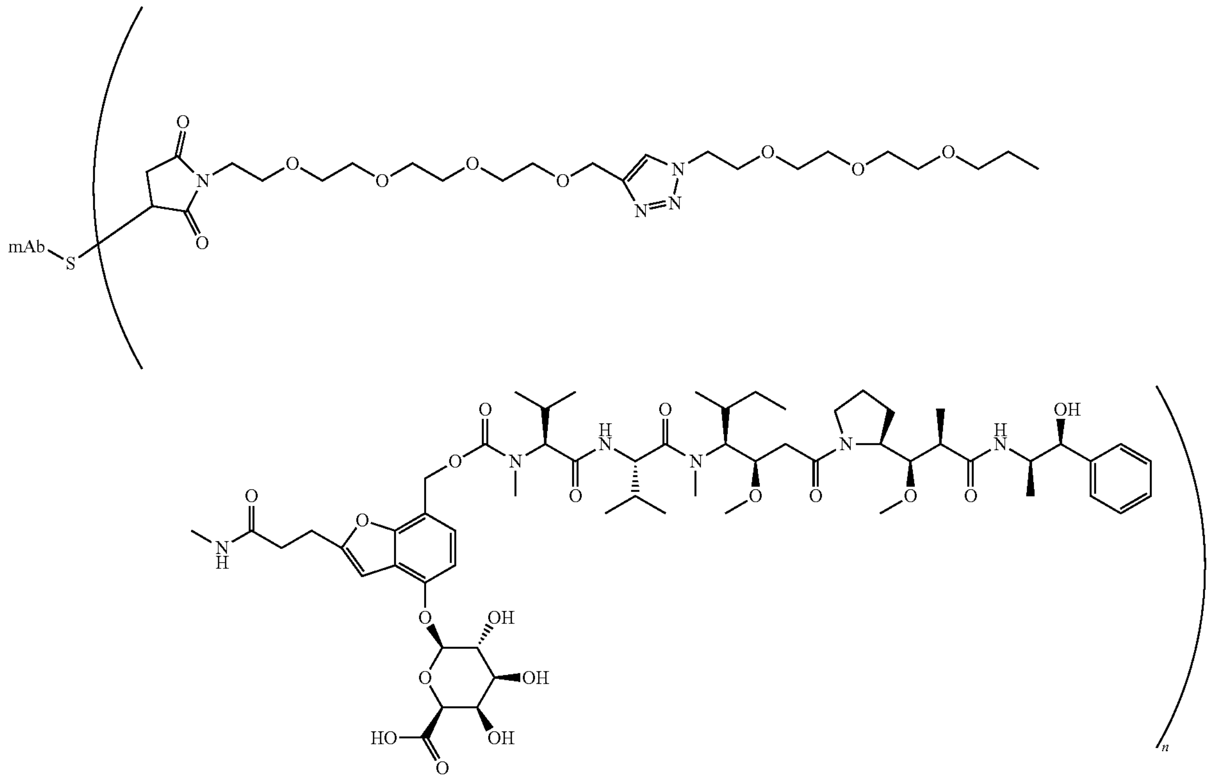
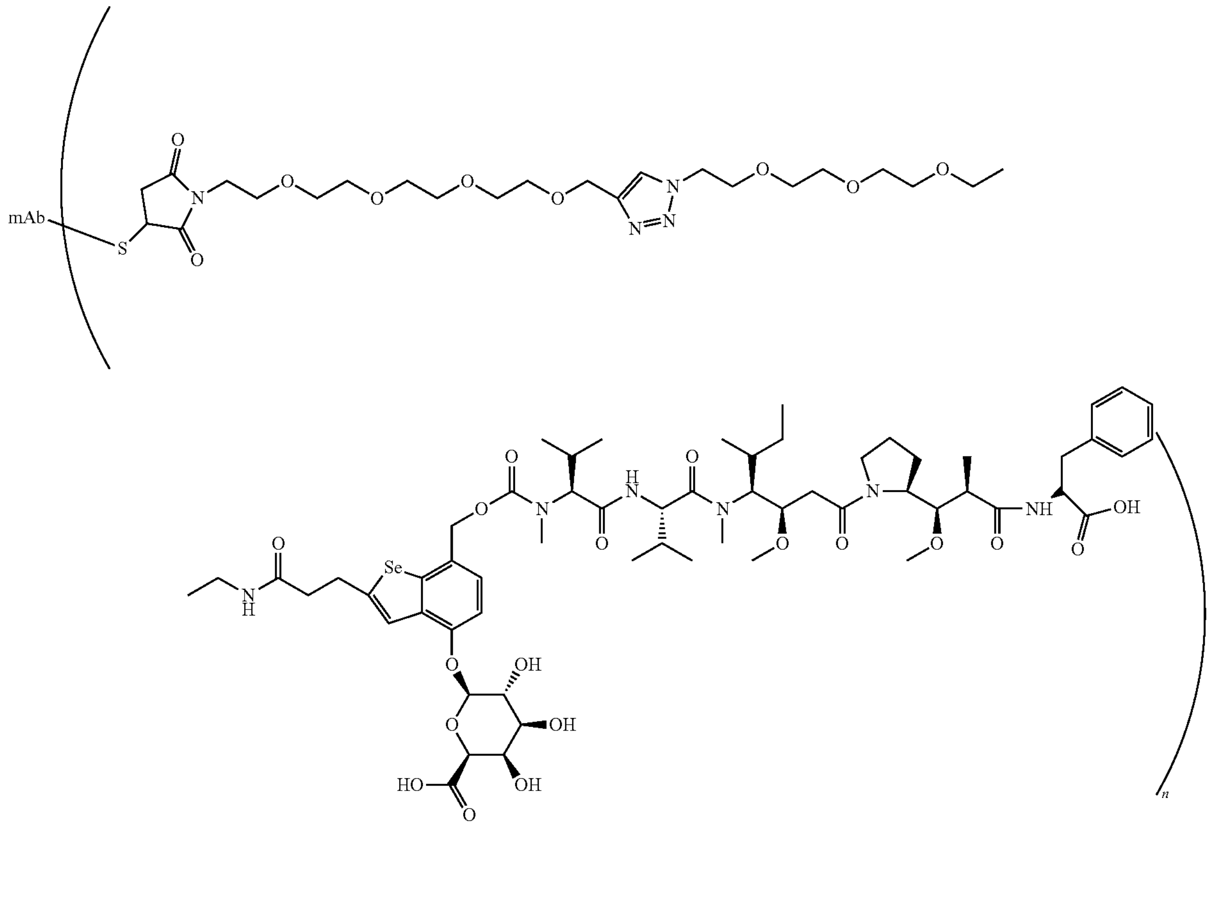

-continued
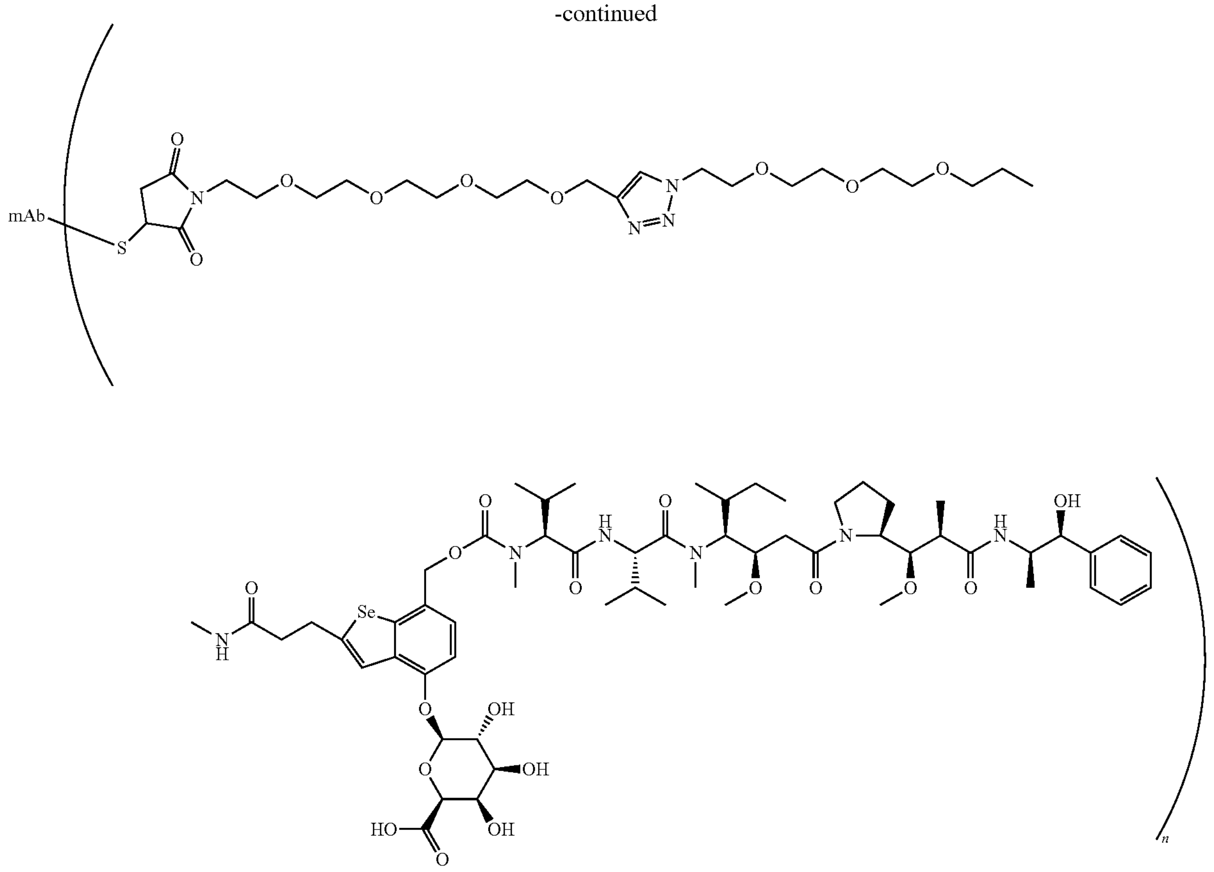
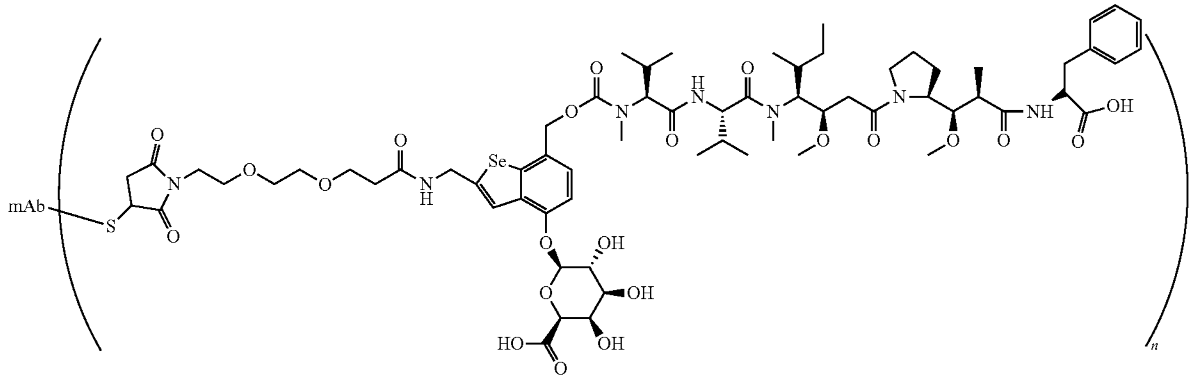
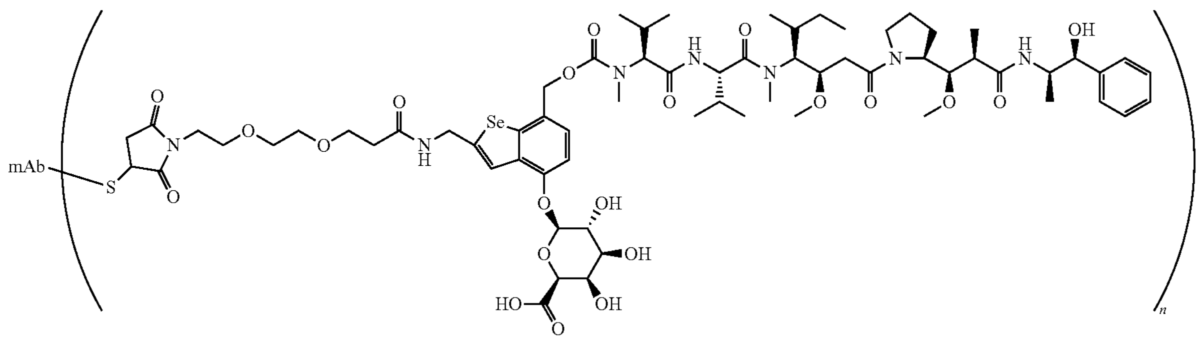
in the above formulas, mAb is the moiety of the antibody, and n is a real number from 1 to 10.

17. The ligand-drug conjugate according to claim 13, wherein the compound represented by Formula 2 is a compound represented by Formula 2-1 below:

[Formula 2-1]

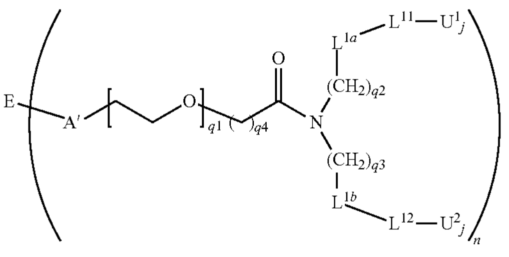

in Formula 2-1,

E is a ligand or protein having a receptor binding property;

A' is a divalent linking group derived from the binding functional group of A defined in claim 1;

$U^1$ and $U^2$ each have the same meaning as U defined in claim 1, wherein $U^1$ and $U^2$ are the same or different from each other;

j is 1 to 10;

$L^{11}$ and $L^{12}$ each have the same meaning as $L^1$ defined in claim 1, wherein $L^{11}$ and $L^{12}$ are the same or different from each other;

$L^{1a}$ and $L^{1b}$ are each independently selected from a direct bond;

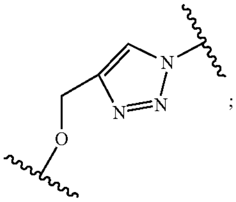
;
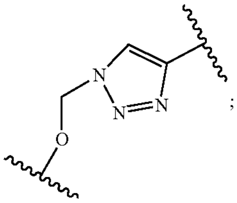
;
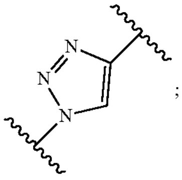
;
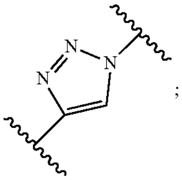
;

-continued

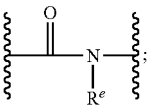
;
and
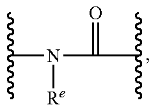
, and $R^e$ is H or $C_{1-8}$ alkyl; and q1, q2 and q3 are each independently an integer from 0 to 10, and q4 is an integer from 1 to 10;

provided that, if $L^{1a}$ is

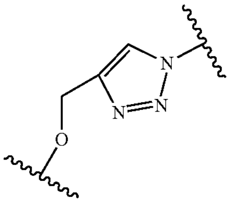
or
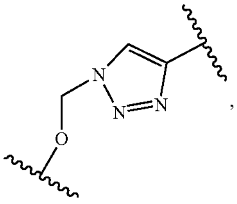
, q2 is not 0, and if $L^{1b}$ is

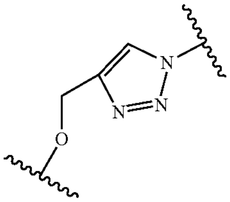
or
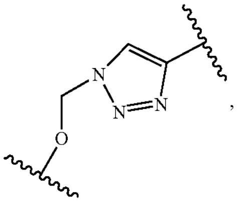
, q3 is not 0; and n is a real number from 1 to 10.

18. The ligand-drug conjugate according to claim 17, wherein the conjugate represented by Formula 2-1 is selected from the group consisting of conjugates represented by the following formulas:

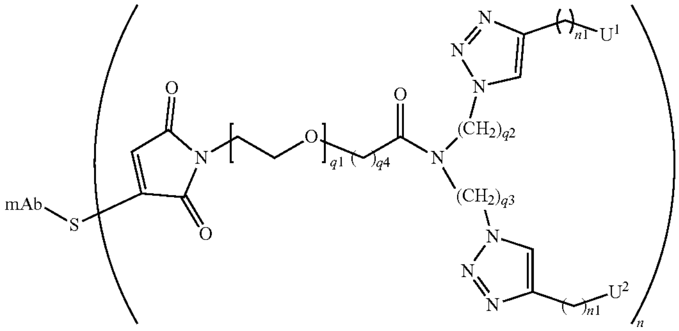

-continued
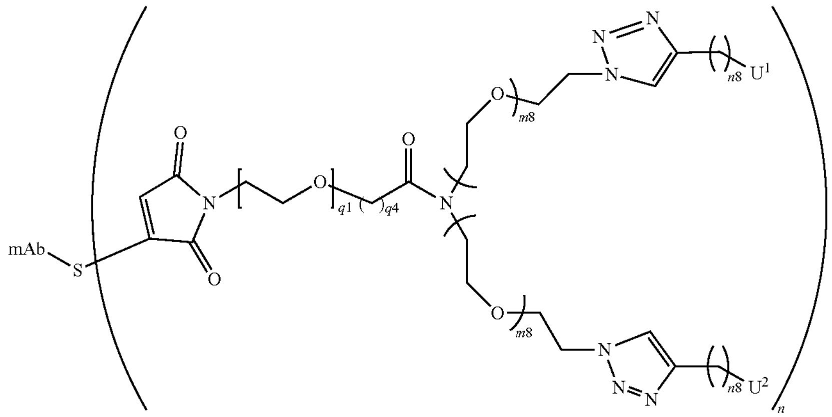
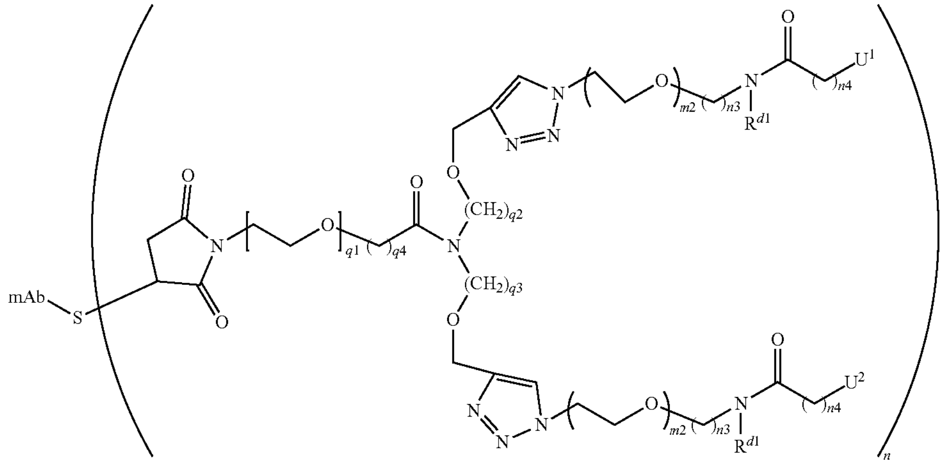
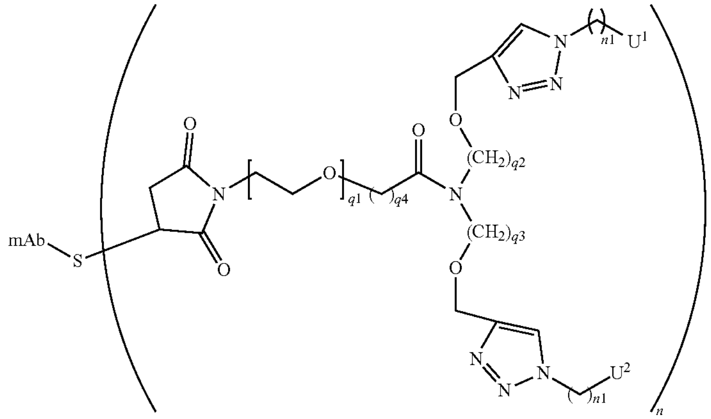
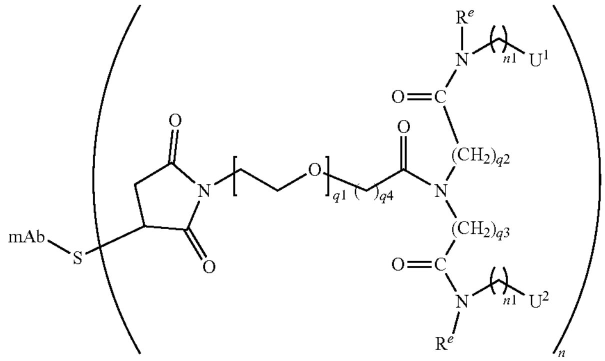

-continued

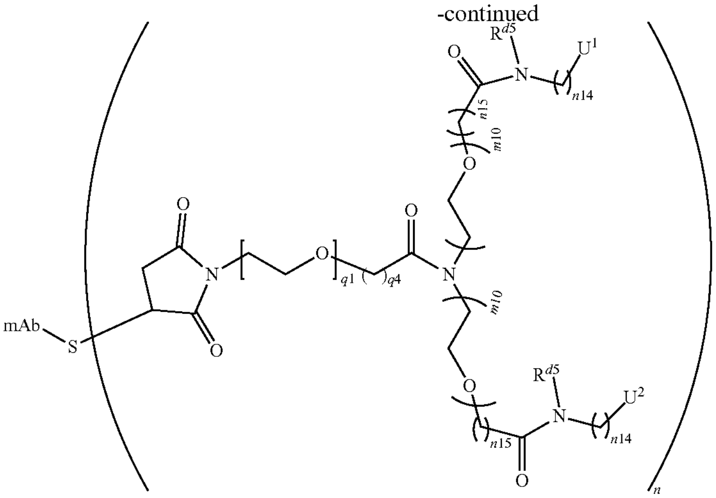

in the above formulas, mAb is the moiety of the antibody;

q1 to q4, n, $U^1$ and $U^2$ are as defined in claim 17, $R^{d1}$, $R^{d5}$ and $R^e$ are each independently H or $C_{1-8}$ alkyl, and n1, n3, n4, n8, n14 and n15, m2, m8 and m10 are each independently an integer from 1 to 8.

19. The ligand-drug conjugate according to claim 5, wherein the conjugate represented by Formula 2-1 is selected from the group consisting of conjugates represented by the following formulas:

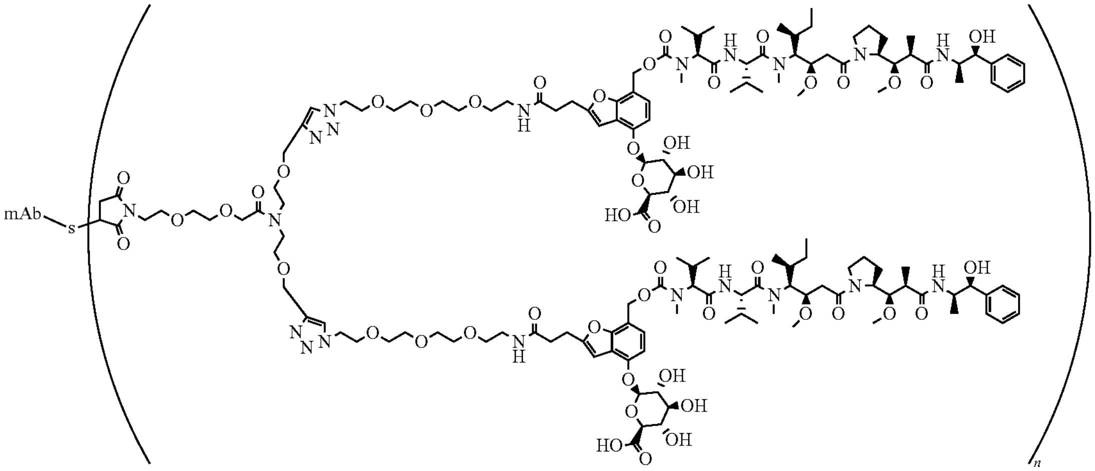

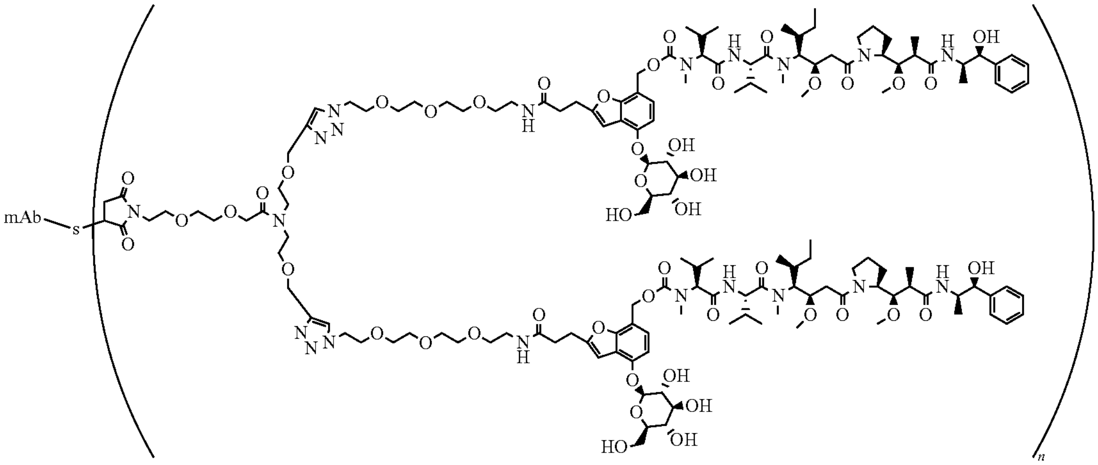

-continued
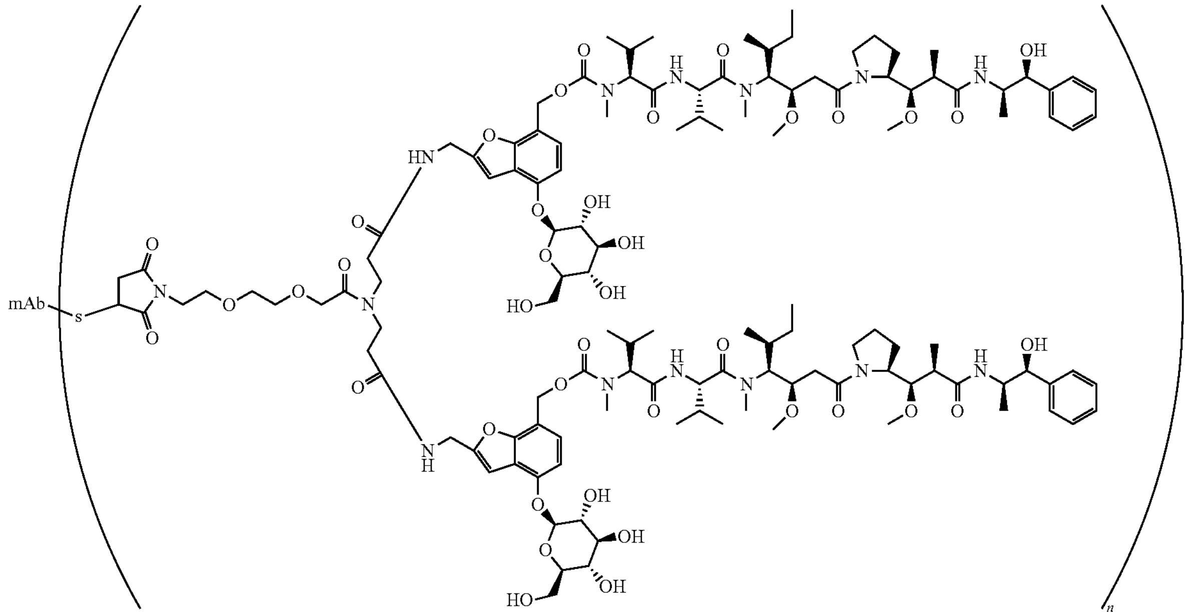
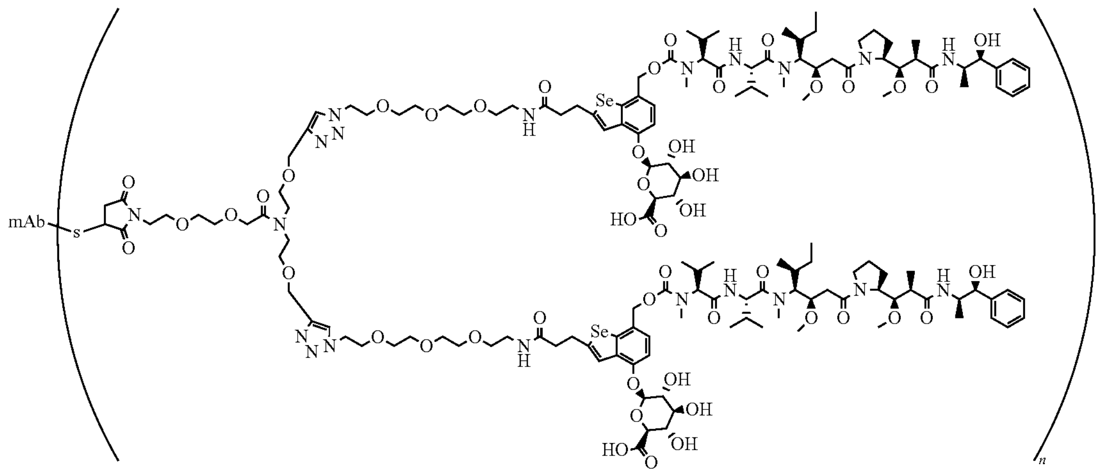
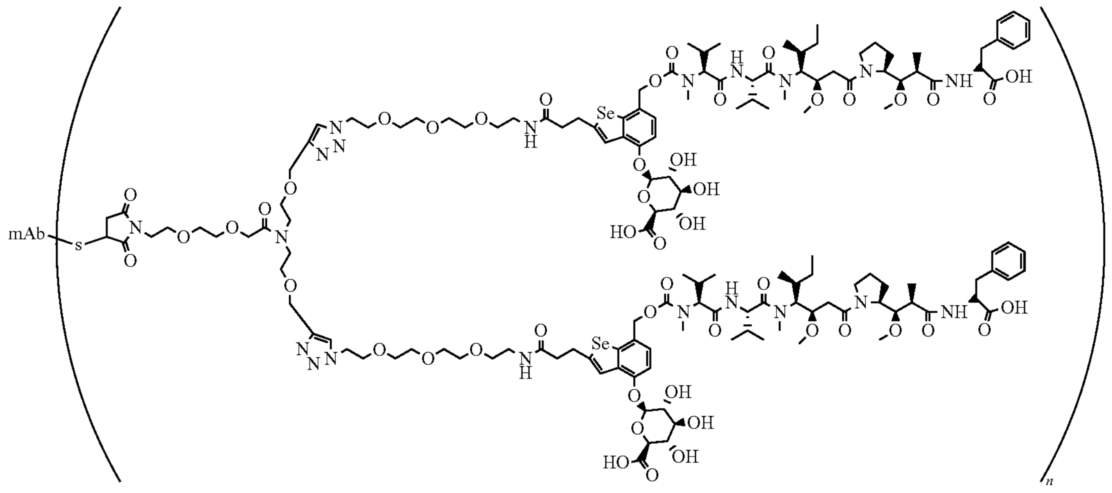

-continued
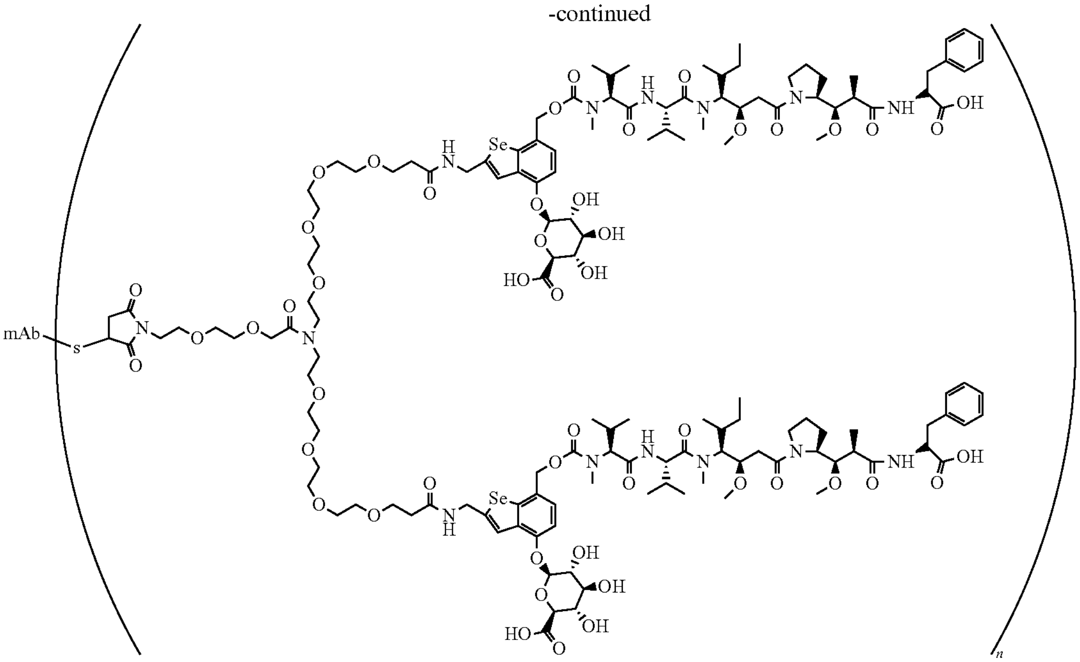
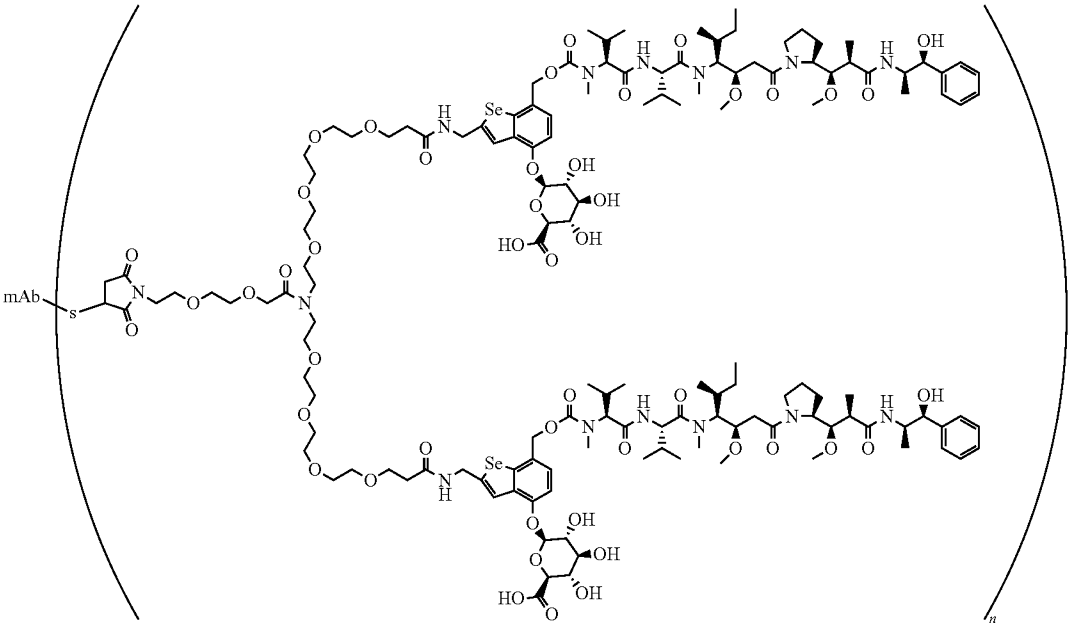
in the above formulas, mAb is the moiety of the antibody; and n is a real number from 1 to 10.
20. A pharmaceutical composition comprising the ligand-drug conjugate according to claim 13 and a pharmaceutically acceptable carrier or excipient.
* * * * *